US011479556B1

(12) United States Patent
Robbins et al.

(10) Patent No.: US 11,479,556 B1
(45) Date of Patent: Oct. 25, 2022

(54) BIFUNCTIONAL COMPOUNDS FOR DEGRADING BTK VIA UBIQUITIN PROTEOSOME PATHWAY

(71) Applicant: NURIX THERAPEUTICS, INC., San Francisco, CA (US)

(72) Inventors: Daniel W. Robbins, San Francisco, CA (US); Arthur T. Sands, San Francisco, CA (US); Joel McIntosh, San Francisco, CA (US); Jeffrey Mihalic, San Francisco, CA (US); Jeffrey Wu, San Francisco, CA (US); Daisuke Kato, San Francisco, CA (US); Dahlia Weiss, San Francisco, CA (US); Ge Peng, San Francisco, CA (US)

(73) Assignee: NURIX THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 15/734,774

(22) PCT Filed: Oct. 14, 2019

(86) PCT No.: PCT/US2019/056112
§ 371 (c)(1),
(2) Date: Dec. 3, 2020

(87) PCT Pub. No.: WO2020/018450
PCT Pub. Date: Apr. 23, 2020

Related U.S. Application Data

(60) Provisional application No. 62/901,984, filed on Sep. 18, 2019, provisional application No. 62/887,812, filed on Aug. 16, 2019, provisional application No. 62/836,398, filed on Apr. 19, 2019, provisional application No. 62/767,819, filed on Nov. 15, 2018, provisional application No. 62/745,786, filed on Oct. 15, 2018.

(51) Int. Cl.
| | |
|---|---|
| *C07D 487/10* | (2006.01) |
| *C07D 401/14* | (2006.01) |
| *C07D 471/10* | (2006.01) |
| *C07D 417/14* | (2006.01) |
| *C07D 413/14* | (2006.01) |
| *C07D 491/107* | (2006.01) |
| *C07D 498/10* | (2006.01) |
| *C07D 487/04* | (2006.01) |

(52) U.S. Cl.
CPC ......... *C07D 487/10* (2013.01); *C07D 401/14* (2013.01); *C07D 413/14* (2013.01); *C07D 417/14* (2013.01); *C07D 471/10* (2013.01); *C07D 487/04* (2013.01); *C07D 491/107* (2013.01); *C07D 498/10* (2013.01)

(58) Field of Classification Search
None
See application file for complete search history.

(56) References Cited

U.S. PATENT DOCUMENTS

| | | | |
|---|---|---|---|
| 10,130,659 B2 | 11/2018 | Wardell et al. |
| 10,166,257 B2 | 1/2019 | Wardell et al. |
| 10,272,113 B2 | 4/2019 | Wardell et al. |
| 10,363,273 B2 | 7/2019 | Wardell et al. |
| 10,398,734 B2 | 9/2019 | Wardell et al. |
| 10,415,015 B2 | 9/2019 | Veerapathran et al. |
| 10,420,799 B2 | 9/2019 | Wardell et al. |
| 10,463,697 B2 | 11/2019 | Wardell et al. |
| 10,517,894 B2 | 12/2019 | Frank et al. |
| 10,537,595 B2 | 2/2020 | Wardell et al. |
| 10,639,330 B2 | 5/2020 | Wardell et al. |
| 10,646,517 B2 | 5/2020 | Wardell et al. |
| 10,653,723 B1 | 5/2020 | Wardell et al. |
| 10,695,372 B2 | 6/2020 | Wardell et al. |
| 10,894,063 B2 | 1/2021 | Wardell et al. |
| 10,918,666 B2 | 2/2021 | Wardell et al. |
| 10,933,094 B2 | 3/2021 | Wardell et al. |
| 10,946,044 B2 | 3/2021 | Wardell et al. |
| 10,946,045 B2 | 3/2021 | Wardell et al. |
| 10,953,046 B2 | 3/2021 | Wardell et al. |
| 10,953,047 B2 | 3/2021 | Wardell et al. |
| 11,007,226 B2 | 5/2021 | Wardell et al. |
| 11,013,770 B1 | 5/2021 | Wardell et al. |
| 11,026,974 B2 | 6/2021 | Wardell et al. |
| 11,040,070 B2 | 6/2021 | Wardell et al. |
| 11,052,115 B2 | 7/2021 | Wardell et al. |
| 11,052,116 B2 | 7/2021 | Wardell et al. |
| 11,058,728 B1 | 7/2021 | Frank et al. |

(Continued)

FOREIGN PATENT DOCUMENTS

| | | |
|---|---|---|
| WO | WO 2007/072225 A2 | 6/2007 |
| WO | WO 2008/033403 A2 | 3/2008 |

(Continued)

OTHER PUBLICATIONS

International Search Report and Written Opinion for International Patent Application PCT/US2019/015250, 10 pages, dated Jun. 11, 2019.

International Search Report and Written Opinion for International Patent Application PCT/US2020/016489, 8 pages, dated May 27, 2020.

International Search Report and Written Opinion for International Patent Application PCT/US2020/033274, 19 pages, dated Oct. 23, 2020.

(Continued)

*Primary Examiner* — Samantha L Shterengarts
(74) *Attorney, Agent, or Firm* — Squire Patton Boggs (US) LLP

(57) ABSTRACT

The present invention relates to compounds useful for degrading BTK via a ubiquitin proteolytic pathway. The invention also provides pharmaceutically acceptable compositions comprising said compounds and methods of using the compositions in the treatment of various disease, conditions, or disorders.

106 Claims, No Drawings

(56) References Cited

U.S. PATENT DOCUMENTS

| | | | |
|---|---|---|---|
| 11,083,752 | B2 | 8/2021 | Wardell et al. |
| 11,123,371 | B2 | 9/2021 | Wardell et al. |
| 2007/0054355 | A1 | 3/2007 | Reiss et al. |
| 2017/0015655 | A1 | 1/2017 | Kaieda et al. |
| 2020/0323904 | A1 | 10/2020 | Sands et al. |
| 2021/0053961 | A1 | 2/2021 | Sands et al. |
| 2021/0053986 | A1 | 2/2021 | Sands et al. |
| 2021/0087259 | A1 | 3/2021 | Gosling et al. |
| 2021/0085717 | A1 | 4/2021 | Gosling et al. |
| 2021/0198280 | A1 | 7/2021 | Kelly et al. |

FOREIGN PATENT DOCUMENTS

| | | |
|---|---|---|
| WO | WO 2009/073905 A2 | 6/2009 |
| WO | WO 2012/089736 A1 | 7/2012 |
| WO | WO 2013/1066543 A2 | 7/2013 |
| WO | WO 2015/084998 A1 | 6/2015 |
| WO | WO 2016/196776 A2 | 12/2016 |
| WO | WO 2018/098275 A1 | 5/2018 |
| WO | WO 2019/148005 A1 | 8/2019 |
| WO | WO 2020/081450 A1 | 4/2020 |
| WO | WO 2020/167518 A1 | 8/2020 |
| WO | WO 2020/210508 A1 | 10/2020 |
| WO | WO 2020/236654 A1 | 11/2020 |
| WO | WO 2020/264398 A1 | 12/2020 |
| WO | WO 2021/021761 A1 | 2/2021 |
| WO | WO 2021/061853 A1 | 4/2021 |
| WO | WO 2021/061870 A1 | 4/2021 |
| WO | WO 2021/113557 A1 | 6/2021 |

OTHER PUBLICATIONS

International Search Report and Written Opinion for International Patent Application PCT/US2020/027492, 21 pages, dated Aug. 11, 2020.

International Search Report and Written Opinion for International Patent Application PCT/US2020/039957, 16 pages, dated Oct. 5, 2020.

International Search Report and Written Opinion for International Patent Application PCT/US2020/043788, 16 pages, dated Oct. 23, 2020.

International Search Report and Written Opinion for International Patent Application PCT/US2020/063176, 12 pages, dated Mar. 5, 2021.

International Search Report and Written Opinion for International Patent Application PCT/US2020/052317, 12 pages, dated Apr. 1, 2021.

International Search Report and Written Opinion for International Patent Application PCT/US2020/052335, 12 pages, dated Apr. 1, 2021.

Riling et al.: "Abstract A206: Small-molecule Cbl-b inhibitors as novel intracellular checkpoint inhibitors for cancer immunotherapy I Molecular Cancer Therapeutics", Jan. 1, 2018 (Jan. 1, 2018), XP055700949, Retrieved from the Internet:URL:https:// mct.aacrjournals.org/content/17/1_Supplement/A206 [retrieved on Jun. 4, 2020].

Gosling et al.: "Abstract 2696: Genetic and pharmacologic evaluation of the ubiquitin ligase CBL-B as a small-molecule, tumor immunotherapy target I Cancer Research", Apr. 3, 2019 (Apr. 3, 2019), XP055701108, Retrieved from the Internet:U RL:https:// cancerres.aacrjournals.org/content/79/13_Supplement/2696 [retrieved on Jun. 4, 2020].

International Search Report and Written Opinion of PCT/US2019/056112 dated Dec. 6, 2019.

Marshall et al., "Superior Activity of the Type C Class of ISS In Vitro and In Vivo Across Multiple Species", DNA and Cell Biology, vol. 24, No. 2, 2005, pp. 63-72.

Yang et al., "Exploiting Synthetic Lethality for the Therapy of ABC Diffuse Large B Cell Lymphoma", Cancer Cell, 21, 2012, pp. 723-737, DOI 10.1016/j.ccr.2012.05.024.

Bondeson et al., "Catalytic in vivo protein knockdown by small-molecule PROTACs", Nature Chemical Biology, published online Jun. 10, 2015; DOI: 10.1038/NCHEMBIO.1858.

Ye et al., "Engineered Artificial Antigen Presenting Cells Facilitate Direct and Efficient Expansion of Tumor Infiltrating Lymphocytes", Journal of Translation Medicine 2011, 9:131, 13 pages.

Good et al., Proliferative tracing with single-cell mass cytometry optimizes generation of stem cell memory-like T cells, Nature Biotechnology Mar. 2019; 37(3): 259-266. DOI:10.1038/s41587-019-0033-2.

Howe et al., "Models of Energy in the Human Jurkat T Cell Line", Assay and Drug Development Technologies, vol. 1, No. 4, 2003, pp. 537-544.

Stewart et al., "Efforts toward elucidating Thalidomide's molecular target: an expedient synthesis of the first Thalidomide biotin analogue", Org. Biomol. Chem., 2010, 8:4059-4062.

Tigno-Aranjuez et al., "Inhibition of RIP2's tyrosine kinase activity limits NOD2-driven cytokine responses", Genes & Development, 2010, 24:2666-2677; http://www.genesdev.org/cgi/doi/10.1101/gad.964410.

Hines et al., "Posttranslational protein knockdown coupled to receptor tyrosine kinase activation with phophoPROTACs", 2013, PNAS, 110(22):8942-8947.

BIFUNCTIONAL COMPOUNDS FOR DEGRADING BTK VIA UBIQUITIN PROTEOSOME PATHWAY

CROSS REFERENCE TO RELATED APPLICATION

This PCT application claims the benefit of U.S. provisional application No. 62/745,786, filed on Oct. 15, 2018; U.S. provisional application No. 62/767,819, filed on Nov. 15, 2018; U.S. provisional application No. 62/836,398, filed on Apr. 19, 2019; U.S. provisional application No. 62/887,812, filed on Aug. 16, 2019; and U.S. provisional application No. 62/901,984, filed on Sep. 18, 2019. Each of these documents is hereby incorporated by reference in its entirety.

FIELD OF THE INVENTION

The present invention provides novel bifunctional compounds for proteolytically degrading targeted Bruton's tyrosine kinases (BTK) and methods for treating diseases modulated by BTK.

BACKGROUND

B cell receptor (BCR) signaling controls B cell development, as well as mature B cell activation, signaling and survival. Mis-regulation of the BCR signaling pathway is associated with numerous disease indications involving B cell function, and targeting B cells and BCR signaling has clear therapeutic potential (Woyach, et al.; *Blood.* 120(6); 1175-1184. 2012). For example, depletion of B cells with monoclonal antibodies targeting CD20 has significant effects in treatment of B cell malignancies and auto-immune and inflammatory diseases (Cang, et al.; *J Hematolo Oncol.* 5; 64, 2012).

BTK is a member of the TEC family of kinases and is a crucial signaling hub in the BCR pathway. Mutations in BTK result in X-linked agammaglobulinaemia (XLA), in which B cell maturation is impaired, resulting in reduced immunoglobulin production (Hendriks, et al.; *Expert Opin Ther Targets* 15; 1002-1021, 2011). The central role of BTK in B cell signaling and function makes BTK an attractive therapeutic target for B cell malignancies as well as auto-immune and inflammatory diseases. Ibrutinib, a covalent inhibitor of BTK, has been approved to treat chronic lymphocytic leukemia (CLL), mantle cell lymphoma (MCL) and other B cell malignancies, as well as graft-versus-host disease (GvHD) (Miklos, et al.; *Blood.* 120(21); 2243-2250. 2017). Currently, ibrutinib and second-generation BTK inhibitors are being investigated for oncology and immune-related indications such as rheumatoid arthritis (Akinleye, et al.; *J of Hematolo Oncol.* 6: 59, 2013; Liu, et al.; *J Pharm and Exper Ther.* 338(1): 154-163. 2011; Di Paolo, et al.; *Nat Chem Biol.* 7(1): 41-50. 2011).

As an alternative to stoichiometric inhibition, proteolytic degradation of BTK could have dramatic consequences for B cell function by effectively blocking BCR signaling. Removal of BTK protein would eliminate BTK kinase activity as well as any protein interaction or scaffolding function of BTK. Specific degradation of BTK could be accomplished using heterobifunctional small molecules to recruit BTK to a ubiquitin ligase and thus promoting ubiquitylation and proteasomal degradation of BTK. Thalidomide derivatives, such as lenalidomide or pomalidomide, can be used to recruit potential substrates to cereblon (CRBN), a component of a ubiquitin ligase complex. This unique therapeutic approach could present a mechanism of action for interfering with BTK activity and BCR signaling that is distinct from the mechanism of stoichiometric BTK inhibition. Furthermore, this degradative approach could effectively target the C481S mutated form of BTK, which mutation has been clinically observed and confers resistance to inhibition by ibrutinib (Woyach, et al.; *Blood.* 120(6): 1175-1184. 2012).

Presently, there remains a need for bifunctional molecules that can induce the proteolytic degradation of BTK via a ubiquitin proteolytic pathway.

SUMMARY OF THE INVENTION

The present invention provides bifunctional compounds that induce the proteolytic degradation of BTK via a ubiquitin proteolysis pathway.

The present invention provides a compound of Formula (A)

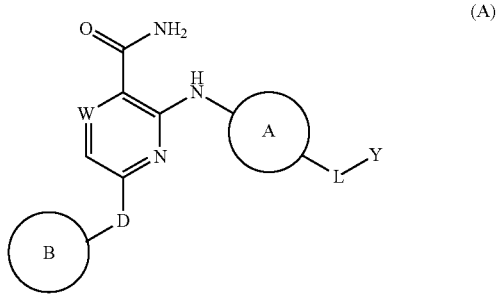

or a pharmaceutically acceptable salt thereof, wherein W is CH or N; D is a bond or —NH—; ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S, wherein ring A is optionally and independently substituted with up to 3 substituents selected from halo, —CN, —COOH, NH$_2$, and optionally substituted C$_{1-6}$ alkyl; ring B is a phenyl, a 5-6 membered heteroaryl, a 4-6 membered heterocycloalkyl, or a 8-10 membered (e.g., 8-9 membered or 9-10 membered) spiro bicyclic heterocycle, wherein ring B is optionally substituted, and wherein the heteroaryl and heterocycloalkyl of ring B has 1-3 heteroatoms independently selected from N, O, or S; L is —X$^1$—X$^2$—X$^3$—X$^4$—X$^5$—; X$^1$ is a bond, —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of X$^1$ is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S; X$^3$ is a bond, —C$_{1-8}$ alkyl-, —C≡C—, 4-6 membered cycloalkyl, —N(R)—, —N(R)—C(O)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; X$^4$ is a bond, —CH$_2$—CH$_2$—N(R)—, —N(R)—, —C$_{1-4}$ alkyl-, —(O—CH$_2$—CH$_2$—CH$_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S; X$^5$ is a bond, —C$_{1-4}$ alkyl-, —N(R)—, —O—, —C(O)—, or —C(O)—N(R)—; each R is independently —H or —C$_{1-3}$ alkyl; and each of m, n, and p is independently an integer from 1 to 3 (e.g., 1, 2, or 3); and Y is

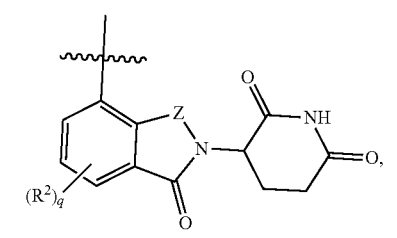

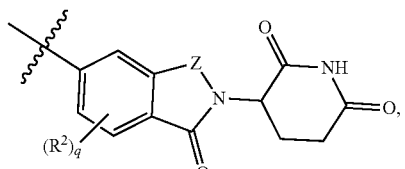

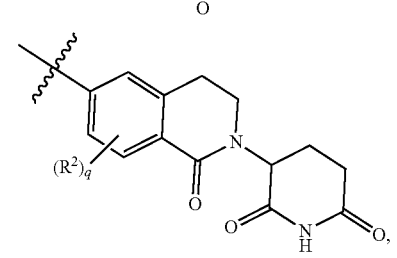

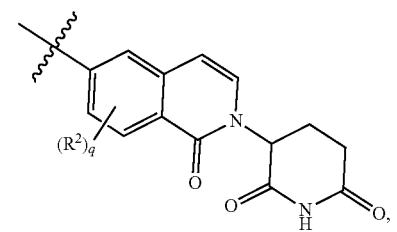

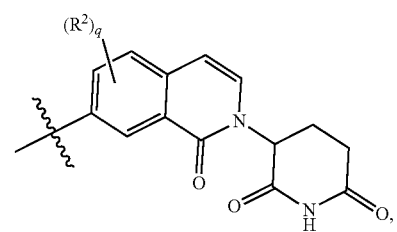

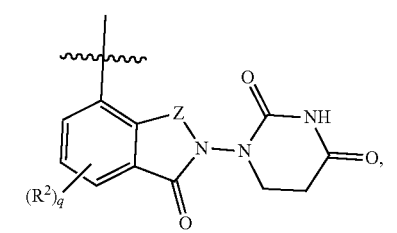

-continued

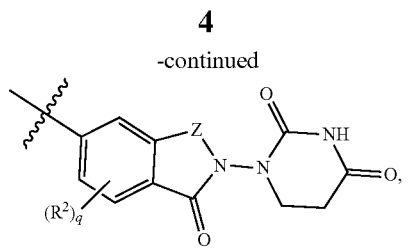

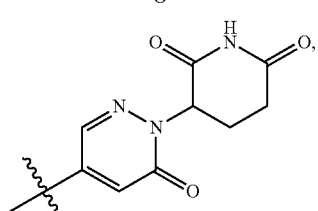

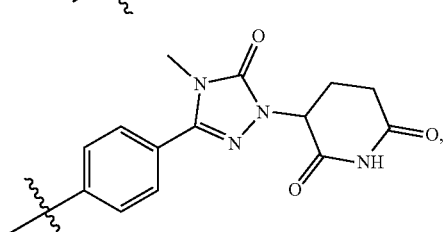

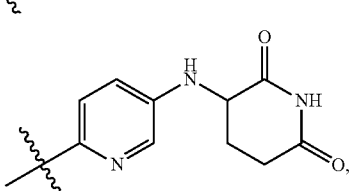

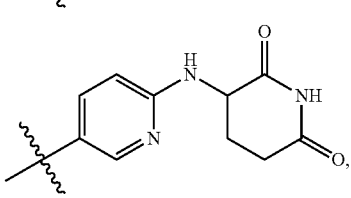

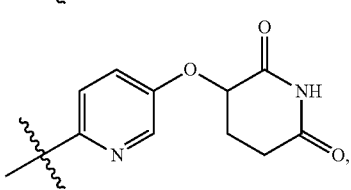

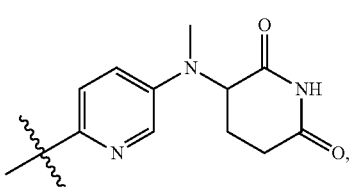

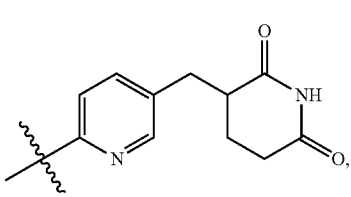

-continued

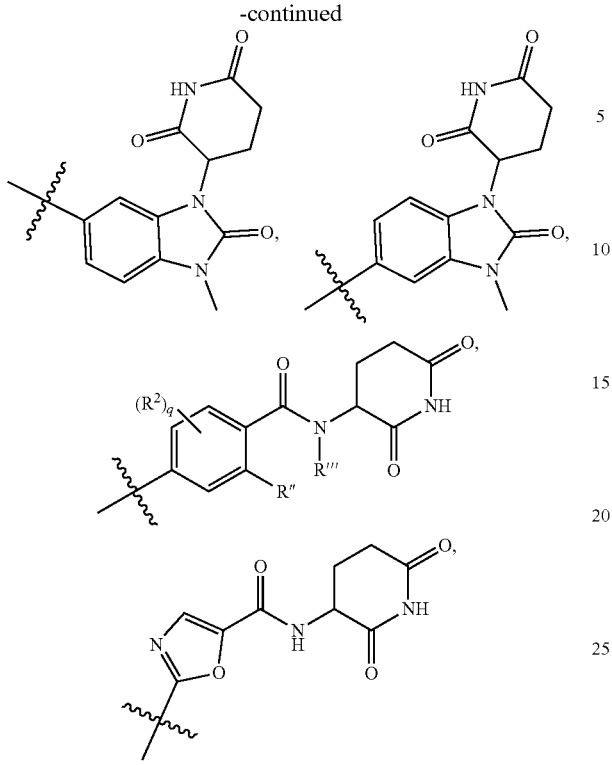

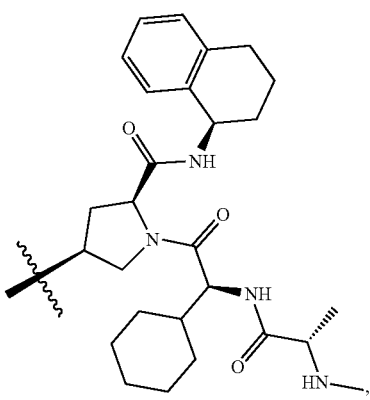

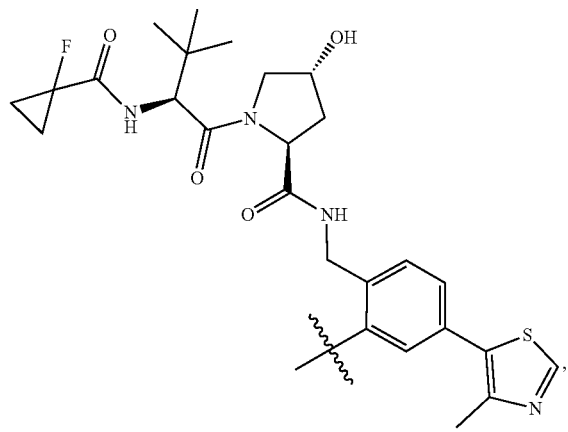

-continued

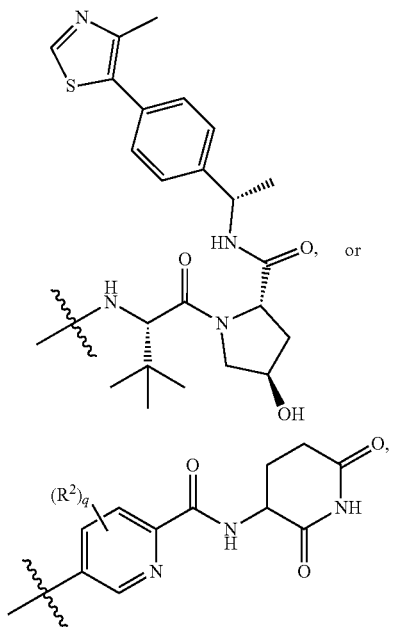

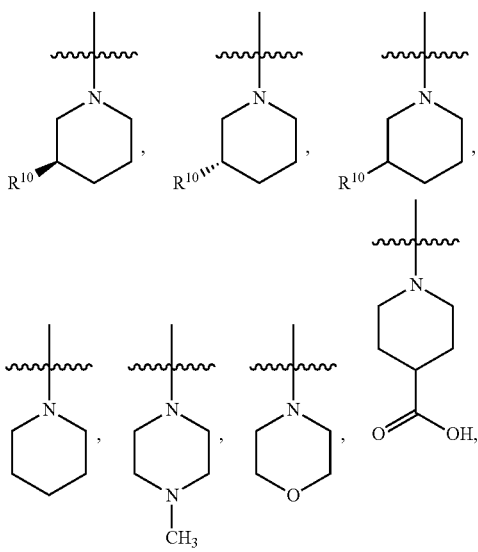

wherein each R² is independently halo, —CN, or C₁₋₄ alkyl, wherein each C₁₋₄ alkyl is optionally and independently substituted with up to three instances of halo, —CN, —COOH, —COONH₂, —NH₂, or —CF₃; each R″ and R‴ are independently H or, together with the atoms to which they are attached, form a 5-6 membered partially unsaturated or fully unsaturated benzofuzed heterocycle; each Z is —C(R^A)₂— or —C(O)—; each R^A is independently —H or C₁₋₄ alkyl; and q is 0, 1, or 2.

In some embodiments, ring B is an optionally substituted 5-6 membered heterocycloalkyl having 1-2 nitrogen atoms.

In some embodiments, ring B is an optionally substituted 5-6 membered heteroaryl having 1-2 heteroatoms independently selected from N and S.

In some embodiments, ring B is

-continued
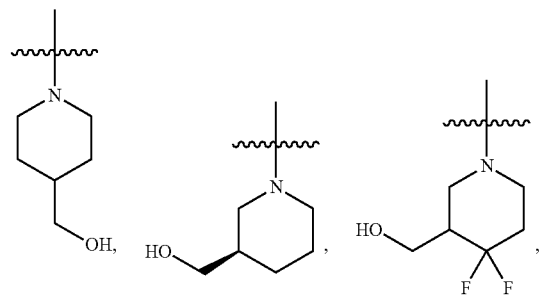
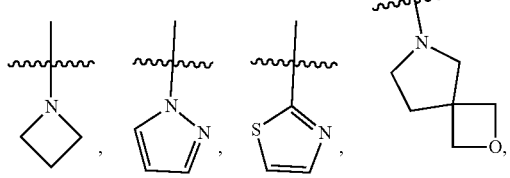
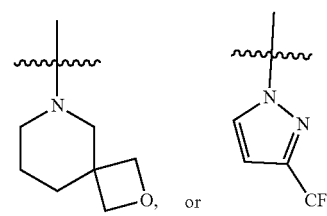
wherein R[10] is
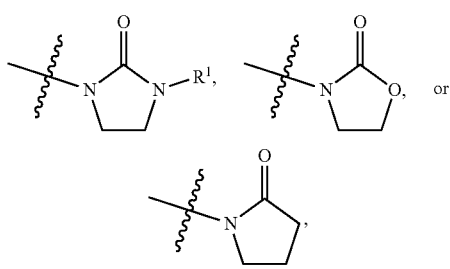
and wherein R[1] is a C[1-4] alkyl group. For example, ring B is
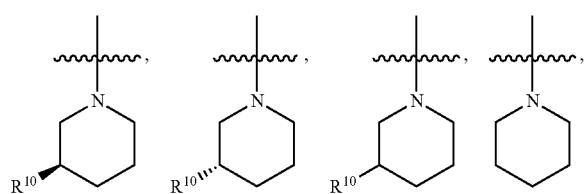
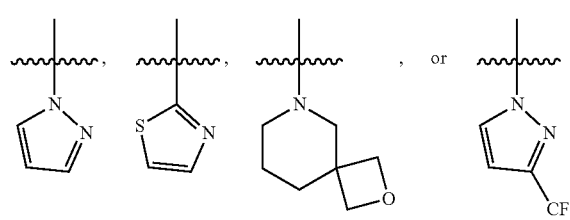
wherein R[10] is
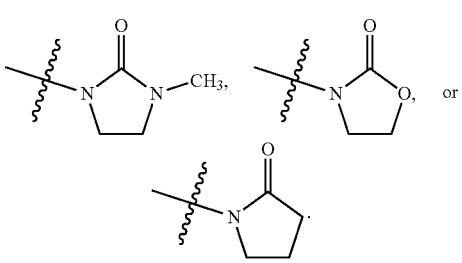
And, in some instances, ring B is
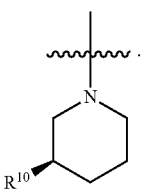
In other instances, R[10] is
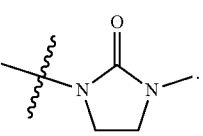
In some embodiments, ring A is
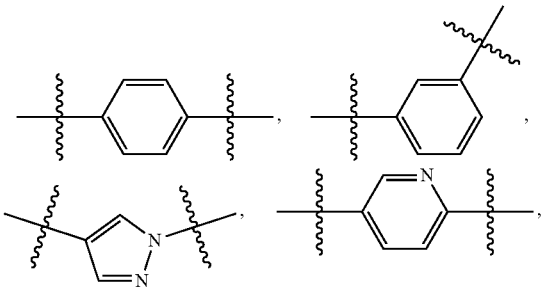
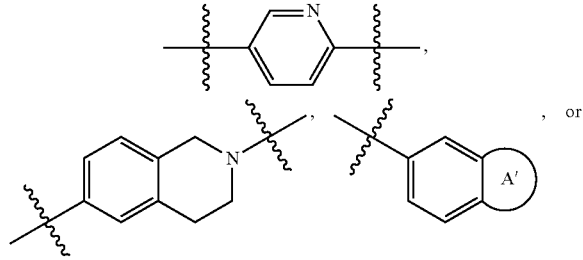
wherein ring A' together with the phenyl ring to which it is fused form a 9-10 membered bicyclic aryl or a 9-10 membered bicyclic heteroaryl wherein the bicyclic heteroaryl (i.e., the bicyclic heteroaryl including ring A') has 1-3 heteroatoms independently selected from N, O, or S. For example, ring A is

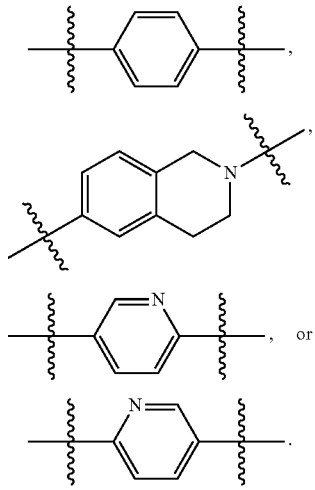

In some embodiments, at least one of $X^1$, $X^2$, and $X^5$ is —N(R)—, —C(O)—N(R)—, or —CH$_2$—.

In some embodiments, $X^1$ is —C(O)—N(R)—.

In some embodiments, $X^2$ is —(O—CH$_2$—CH$_2$)$_n$—, —(CH$_2$—CH$_2$—O)$_n$—, or —C$_{1-5}$ alkyl-.

In some embodiments, $X^3$ is a bond, —C≡C—, —C$_{1-4}$ alkyl-, or —N(R)—.

In some embodiments, $X^4$ is a bond, —CH$_2$—, or —N(R)—.

In some embodiments, $X^5$ is a bond.

In some embodiments, $X^1$ is —(O—CH$_2$—CH$_2$—CH$_2$)$_m$—, m is 1, and $X^2$ is —C(O)—N(R)—.

In some embodiments, $X^1$ is —CH$_2$—, —C(O)—,

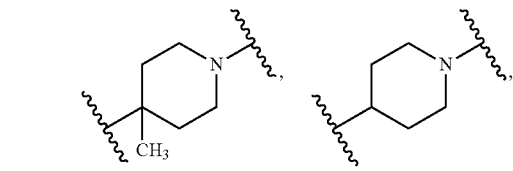

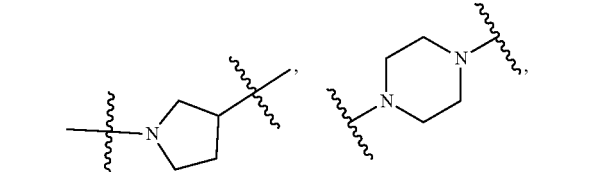

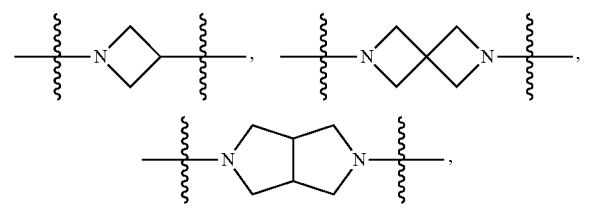

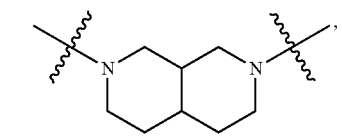

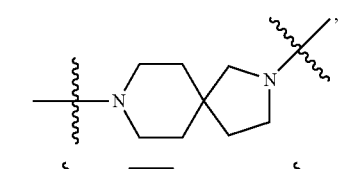

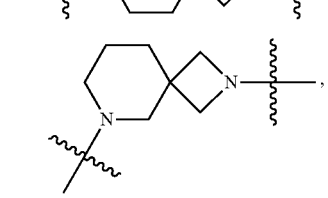

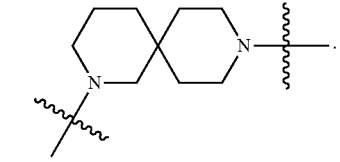

In some embodiments, $X^2$ is a bond, —C(O)—, —C$_{1-5}$ alkyl-,

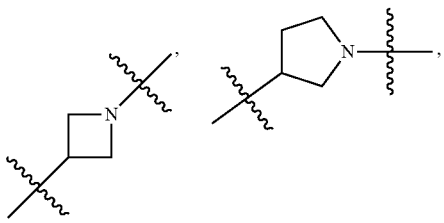

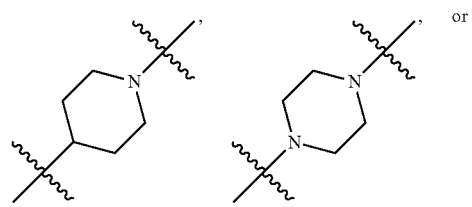

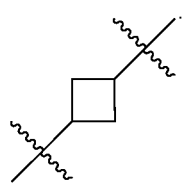

In some embodiments, $X^3$ is bond, —$C_{1-4}$ alkyl-, 4-6 membered cycloalkyl, or —N(R)—.
In some embodiments, $X^3$ is a bond, —$C_{1-4}$ alkyl-, —NH—,
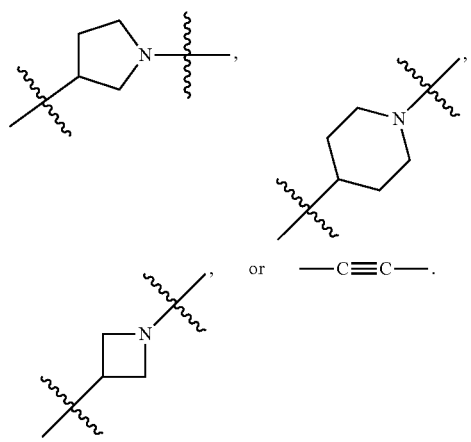
In some embodiments, $X^4$ is a bond,
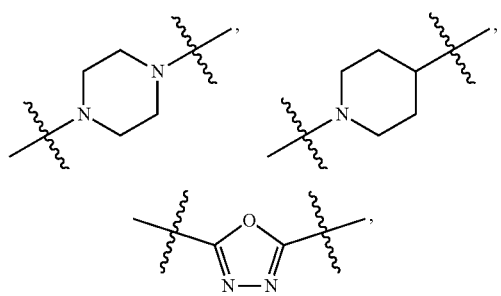
—$C_{1-4}$ alkyl-, —$CH_2$—$CH_2$—N(R)—, or —N(R)—.
In some embodiments, $X^5$ is a bond, —$C_{1-4}$ alkyl-, —N(R)—, or —C(O)—N(R)—.
In some embodiments, L is
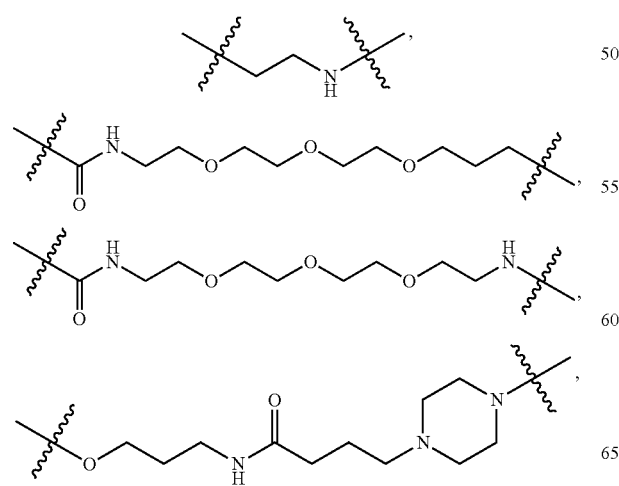
-continued
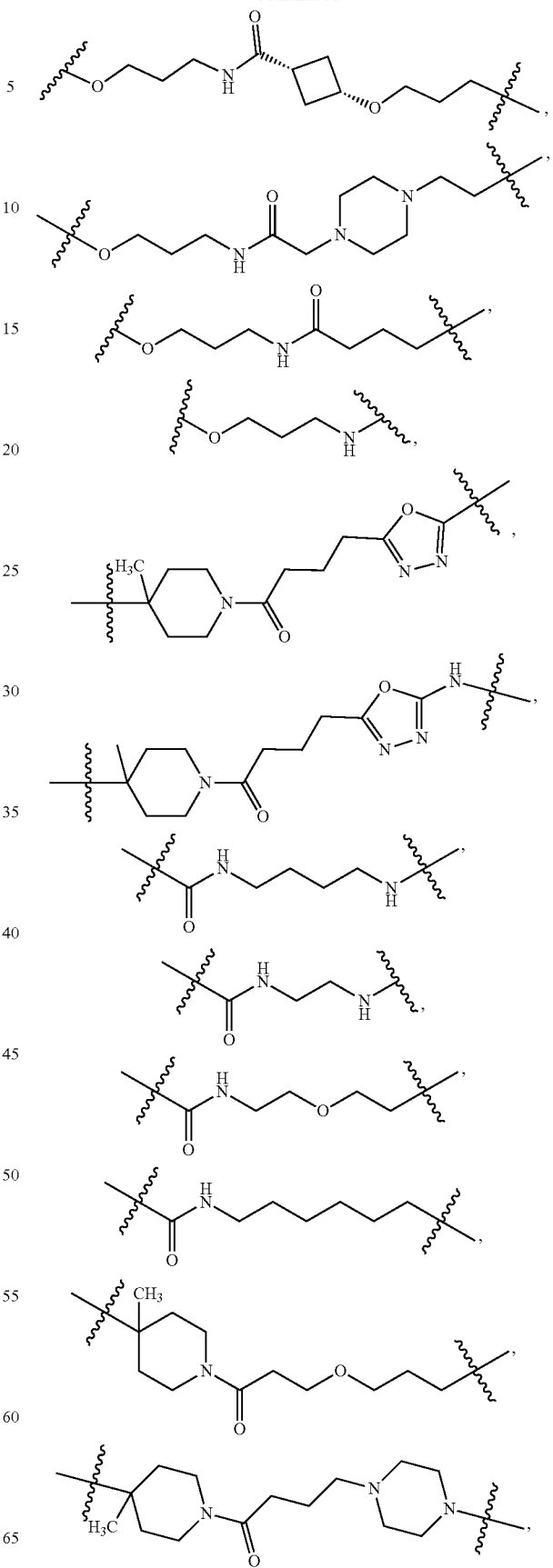

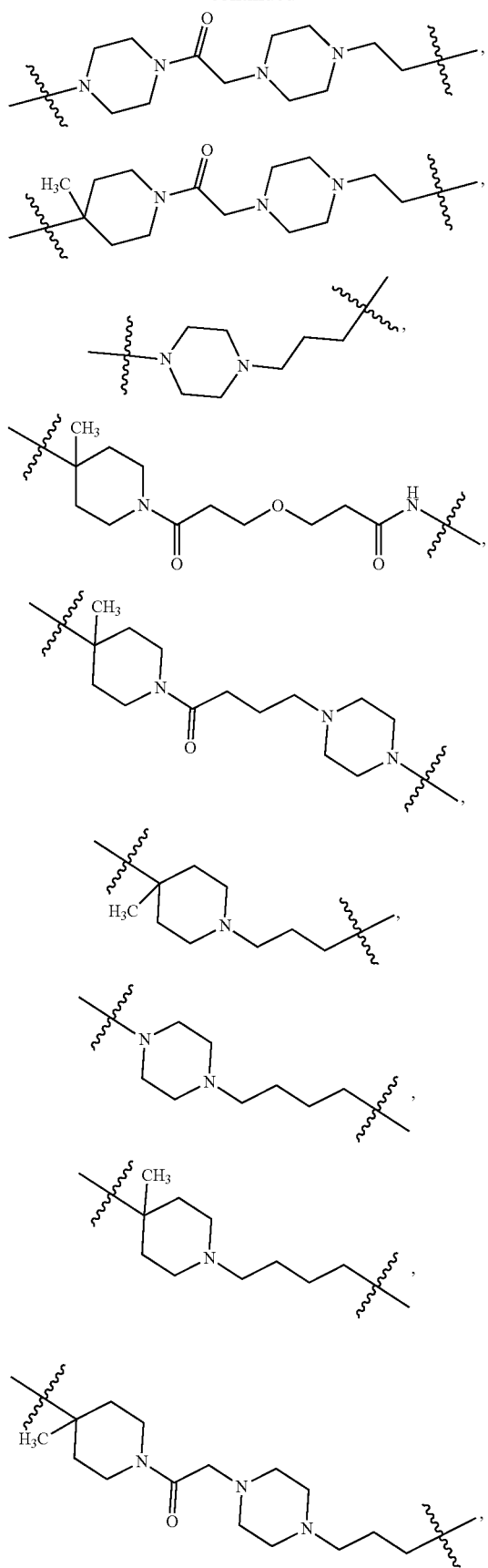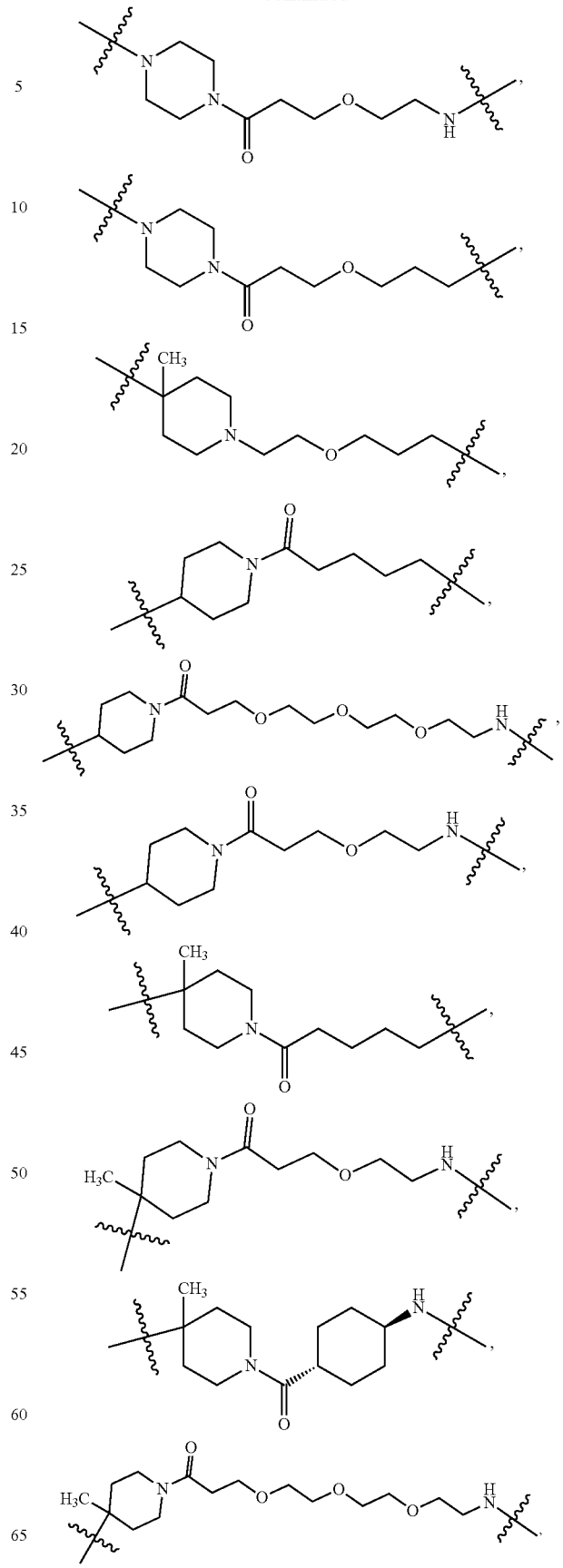

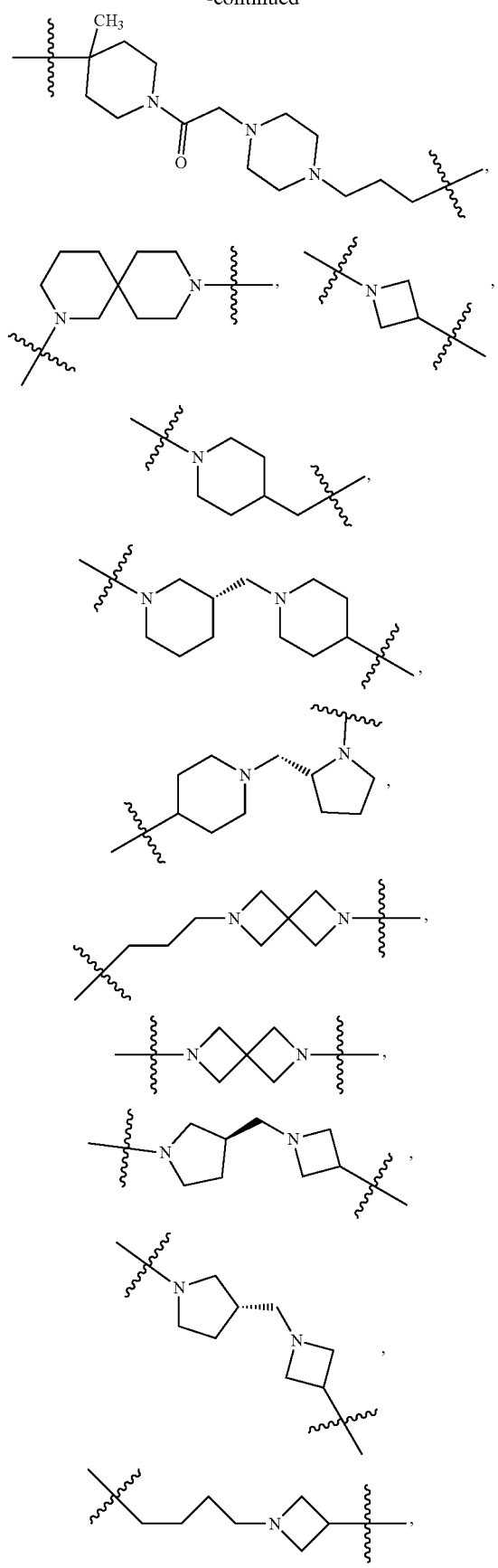
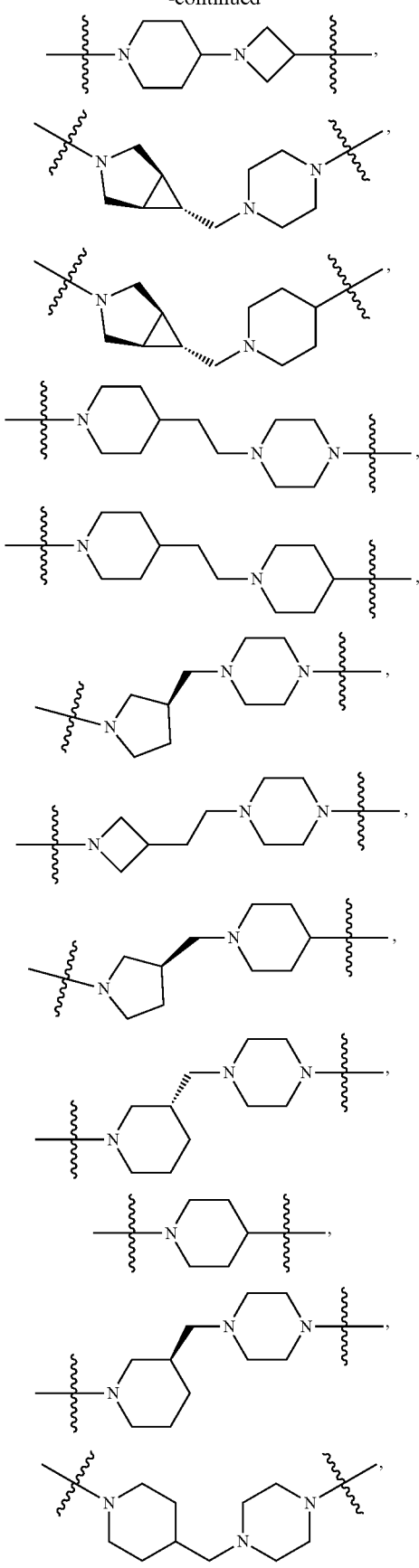

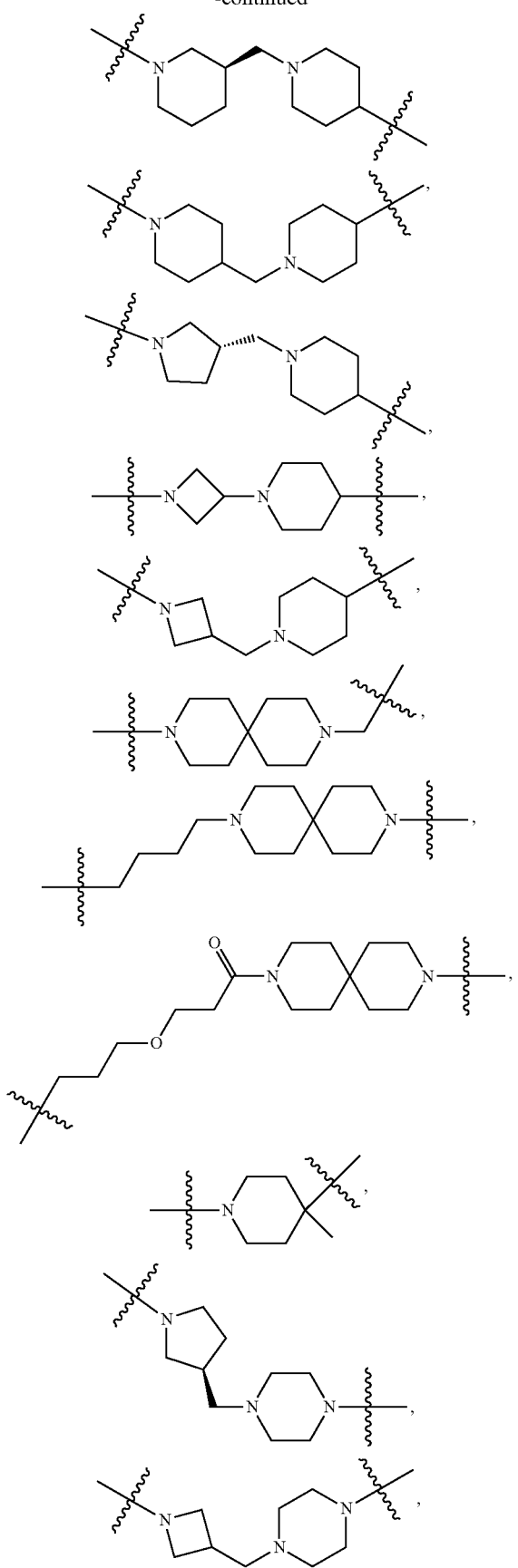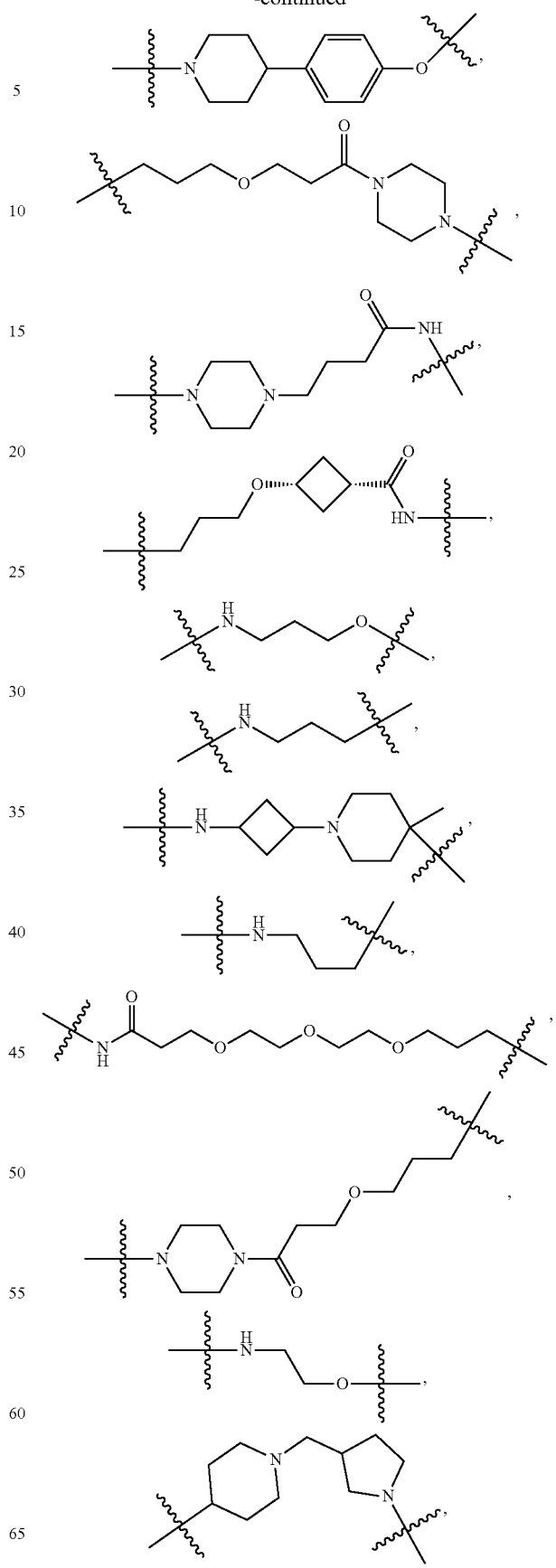

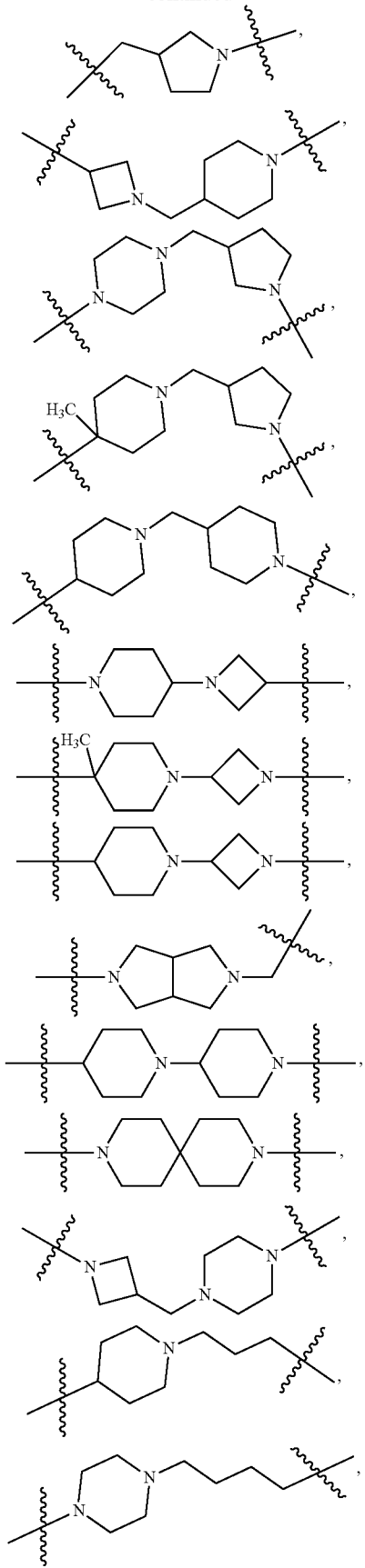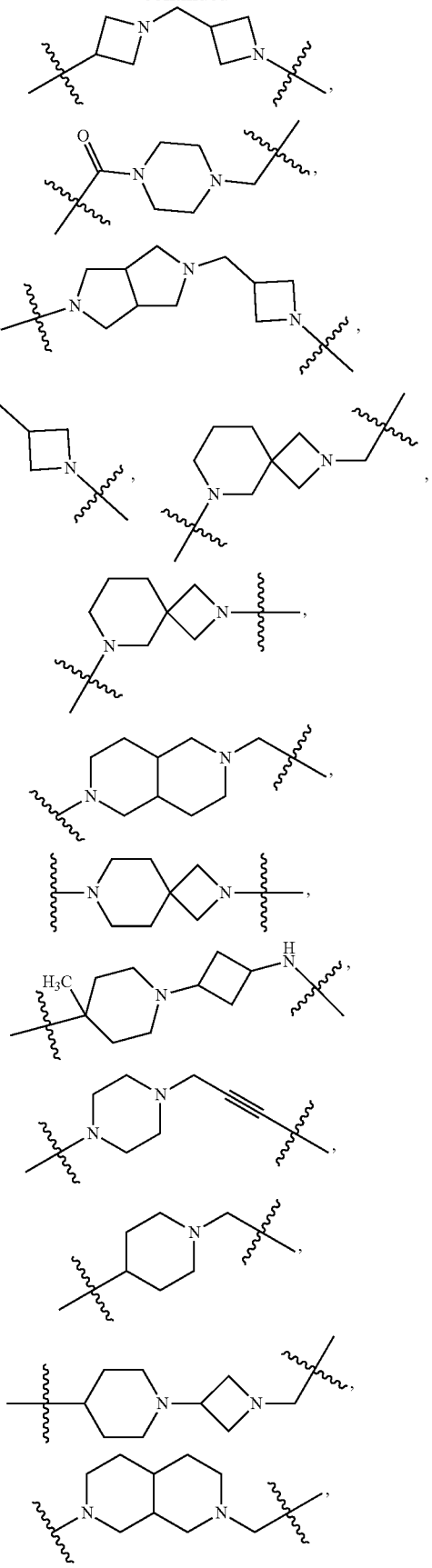

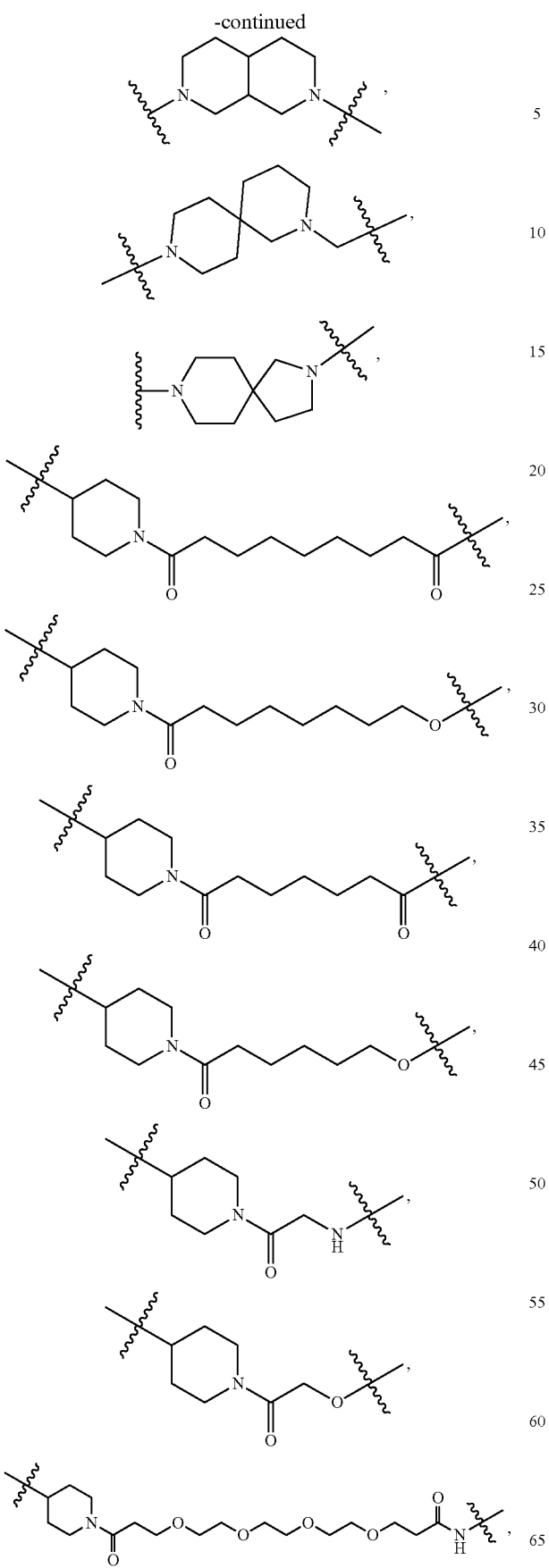
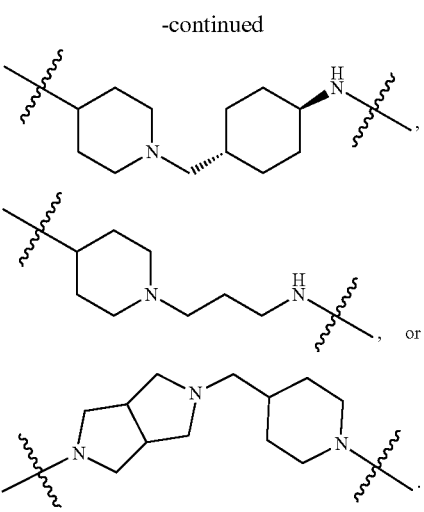
In some embodiments, Y is
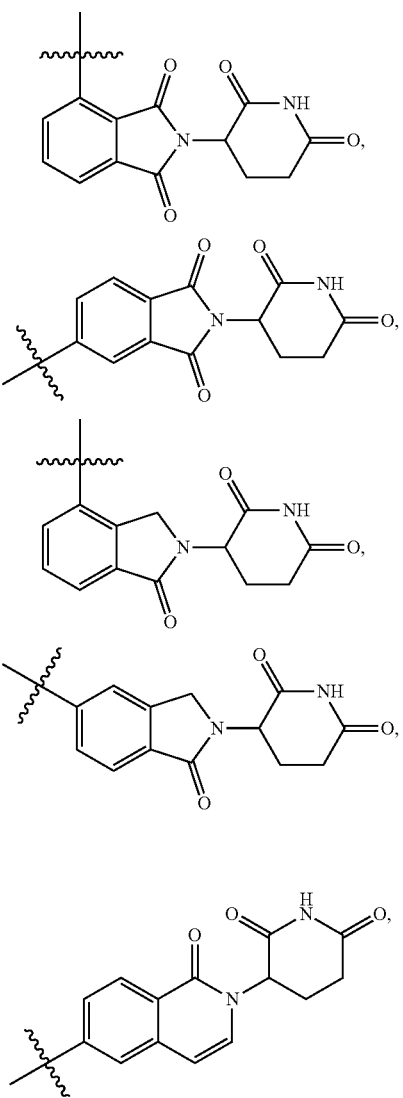

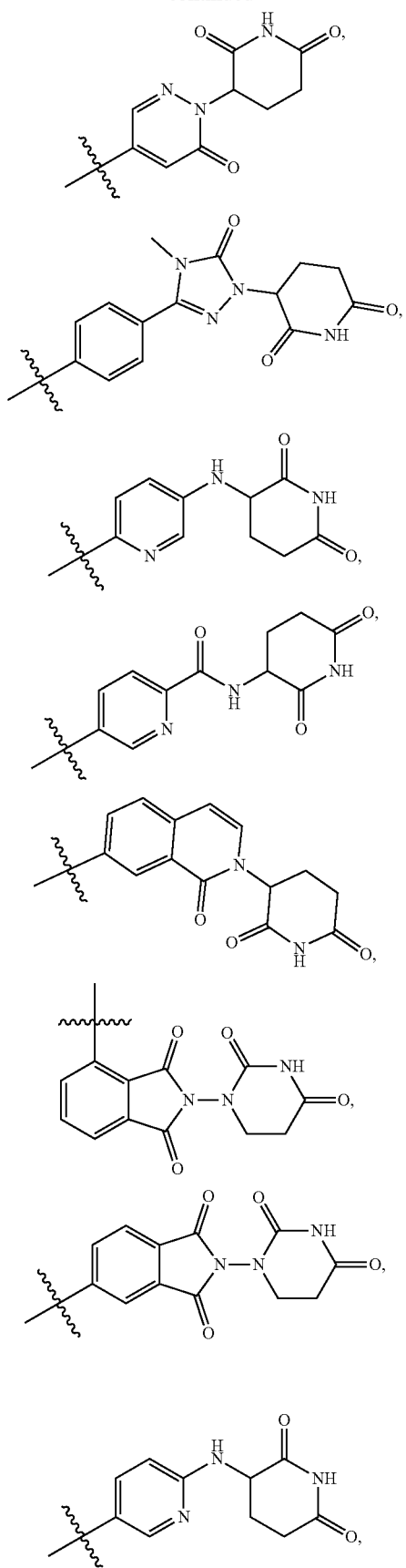
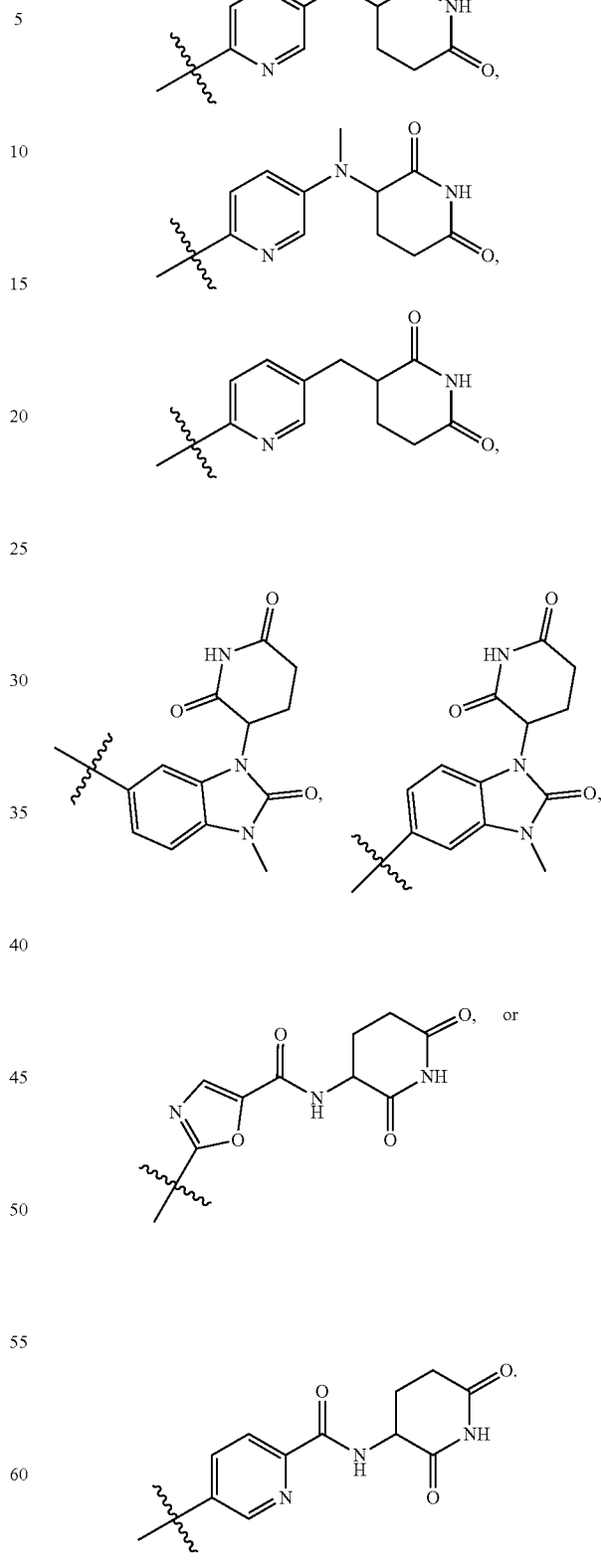
In some embodiments, W is N.
In some embodiments, D is a bond.

The present invention also provides a compound of Formula (B)

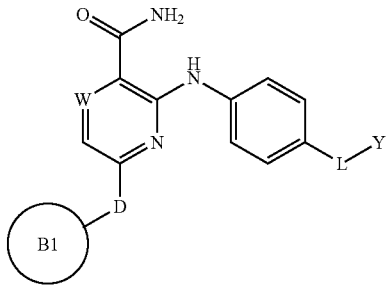

or a pharmaceutically acceptable salt thereof, wherein W is CH or N; D is a bond or —NH—; ring B1 is a 4-6 membered, fully saturated, partially unsaturated, or fully unsaturated monocyclic heterocycle or a 8-10 membered fully saturated spiro bicyclic heterocycle, wherein ring B1 has 1-3 heteroatoms independently selected from N, O, or S, and is optionally substituted with 1-3 groups selected from halo, —CH$_3$, —CF$_3$, —C(O)OH, —CH$_2$OH, or a 5 membered heterocycloalkyl optionally substituted with oxo and having 1-2 heteroatoms independently selected from N or O; L is —X$^1$—X$^2$—X$^3$—; X$^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of X$^1$ is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S; X$^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; each R is independently —H or —C$_{1-3}$ alkyl; each of m, n, and p is independently an integer from 1 to 3; and Y is

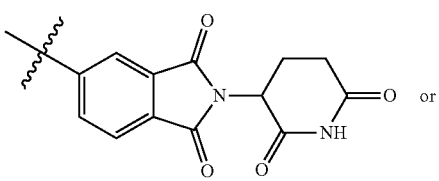 or

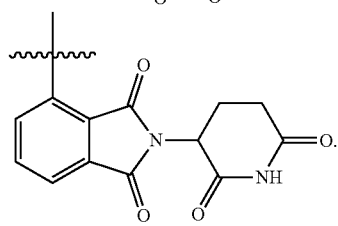

In some embodiments, ring B1 is

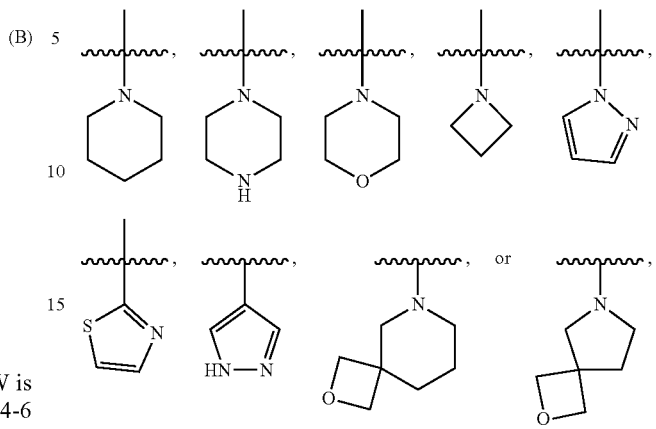

and ring B1 is optionally substituted 1-3 groups selected from —CH$_3$, —CH$_2$OH, —C(O)OH, —CF$_3$, —F,

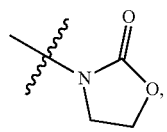 [SMILES: *N1CCOC1=O]

and

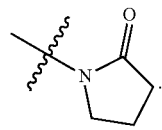 [SMILES: *N1CCCC1=O]

For example, ring B1 is

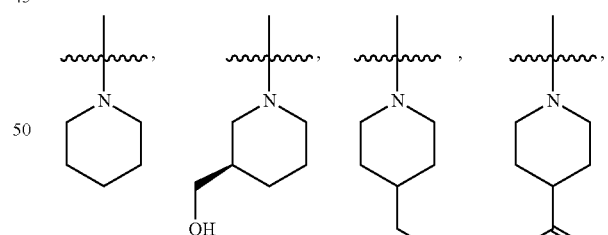

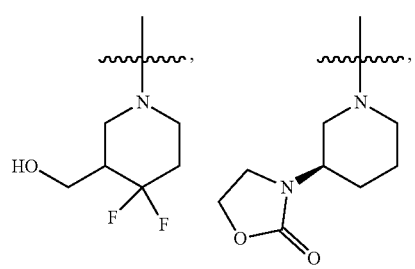

-continued

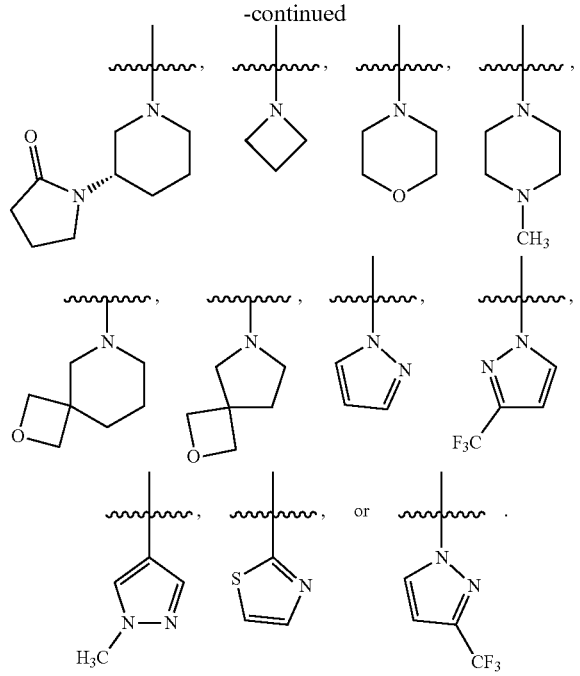

In other examples, ring B1 is

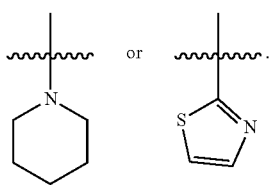 [SMILES: *N1CCCCC1 ; *c1nccs1]

In some embodiments, $X^1$ is

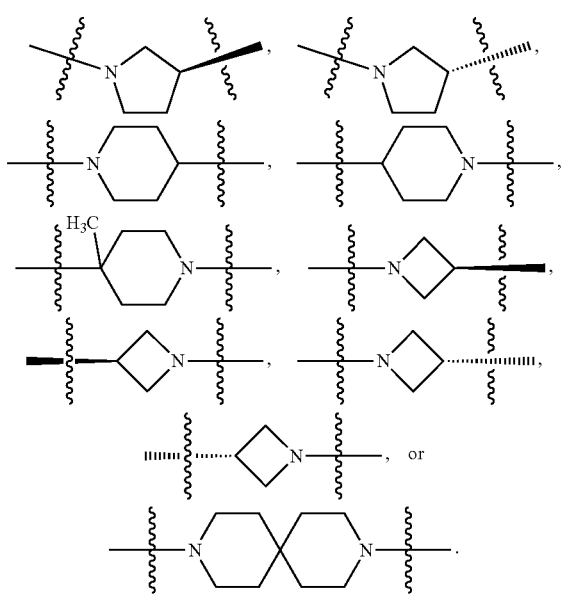

In some embodiments, $X^2$ is a bond, —$C_{1-5}$ alkyl-, 4-6 membered monocyclic cycloalkyl, or 4-6 membered mono- cyclic heterocycloalkyl having 1-2 heteroatoms independently selected from N, O, or S. For example, $X^2$ is a bond, —$C_{1-3}$ alkyl-, —C(O)—,

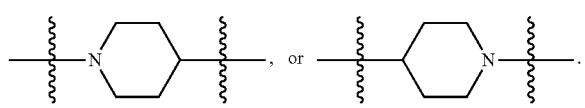

In some embodiments, $X^3$ is a bond, —$C_{1-4}$ alkyl-, —N(R)—, —(O—CH$_2$—CH$_2$)$_p$—, —(CH$_2$—CH$_2$—O)$_p$—, or a 4-6 membered heterocycloalkyl having 1-2 heteroatoms independently selected from N, O, or S wherein the heterocycloalkyl is optionally substituted with —CH$_3$. For example, $X^3$ is a bond,

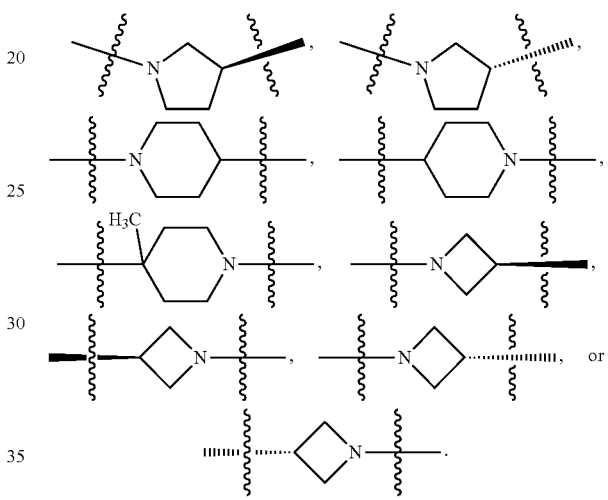

In some embodiments L is

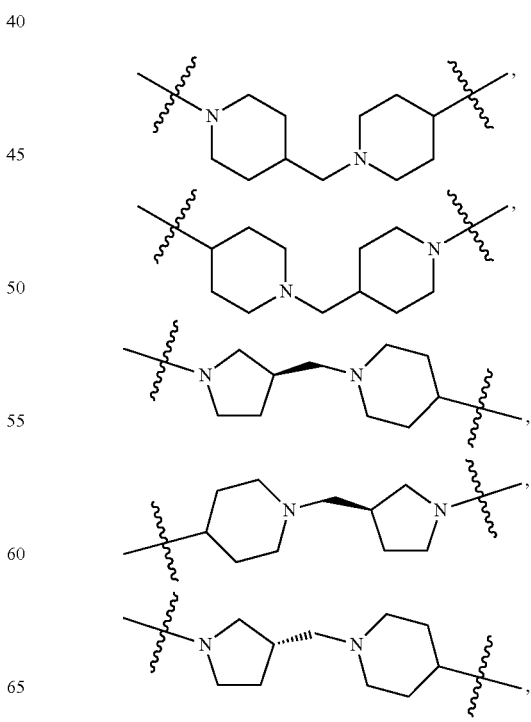

-continued

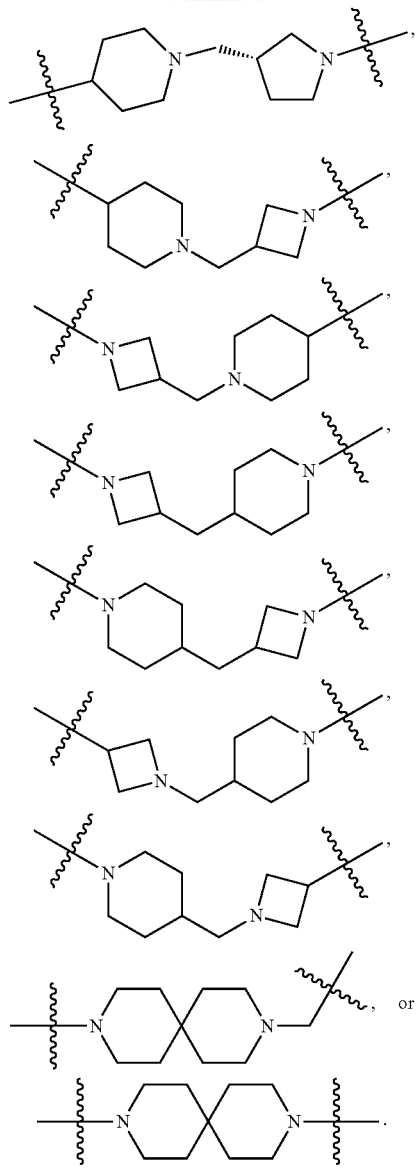

In some embodiments, W is N and D is a bond.

The present invention also provides a compound of Formula (C)

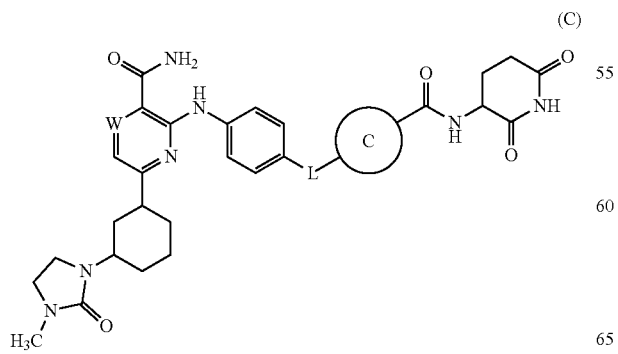

(C)

or a pharmaceutically acceptable salt thereof, wherein W is CH or N; ring C is phenyl or a saturated, partially unsaturated, or fully unsaturated 5-6 membered monocyclic heterocycle having 1-2 heteroatoms independently selected from N, O, or S, wherein each of the phenyl and heterocycle of ring C is optionally substituted; L is —X$^1$—X$^2$—X$^3$—; X$^1$ is —C(O)—N(R)—, —N(R)—C(O)—, —(O—CH$_2$—CH$_2$)$_m$—, —O—(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the bicyclic heterocycloalkyl and the monocyclic heterocycloalkyl of X$^1$ is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S; X$^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; each R is independently —H or —C$_{1-3}$ alkyl; and each of m, n, and p is independently an integer from 1 to 3.

In some embodiments, ring C is

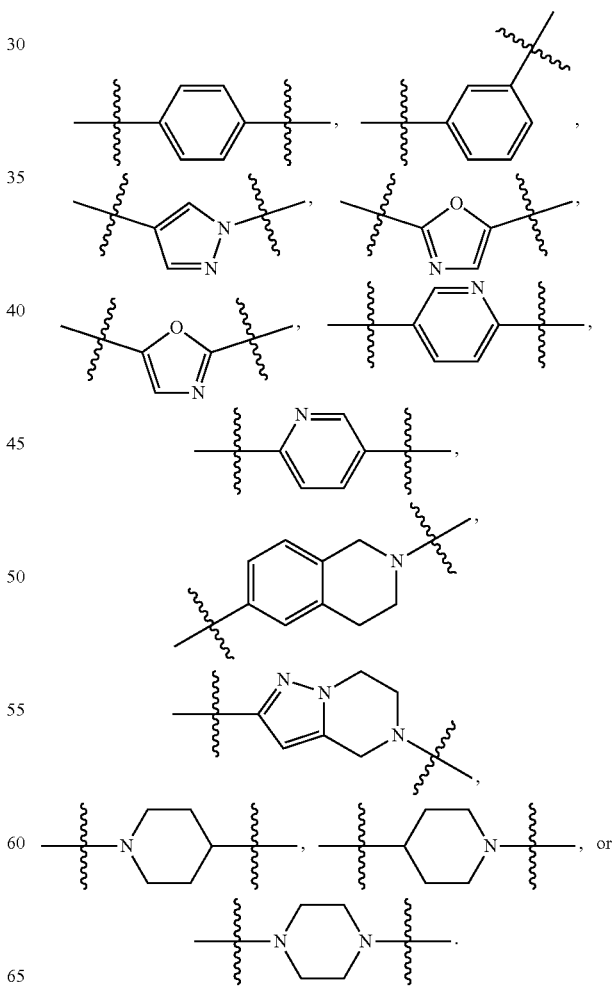

For example, ring C is

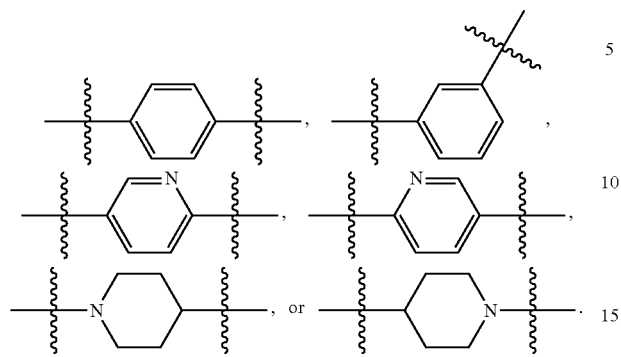

In some embodiments, $X^1$ is a 4-6 membered monocyclic heterocycloalkyl having 1-2 heteroatoms independently selected from N, O, or S. For example, $X^1$ is

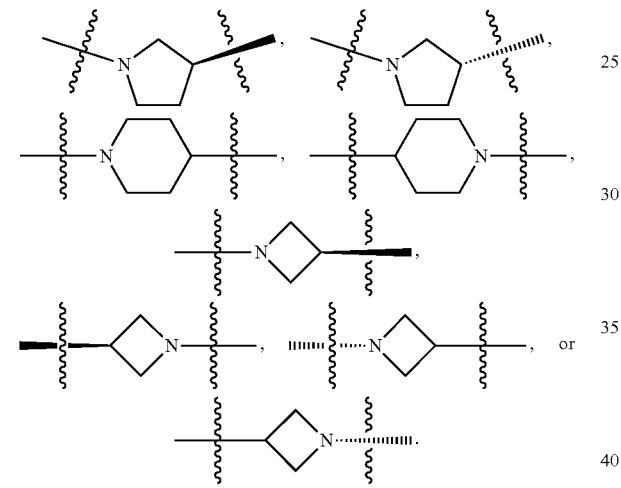

In some embodiments, $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —$C_{1-3}$ alkyl-.

In some embodiments, $X^3$ is a 4-6 membered cycloalkyl, —N(R)—, or a 4-6 membered heterocycloalkyl having 1-2 heteroatoms independently selected from N, O, or S wherein the heterocycloalkyl is optionally substituted with —$CH_3$. For example, $X^3$ is

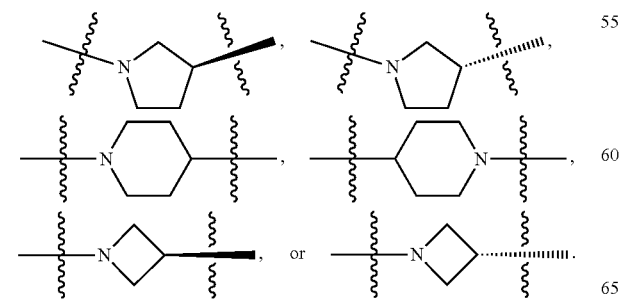

In some embodiments, L is

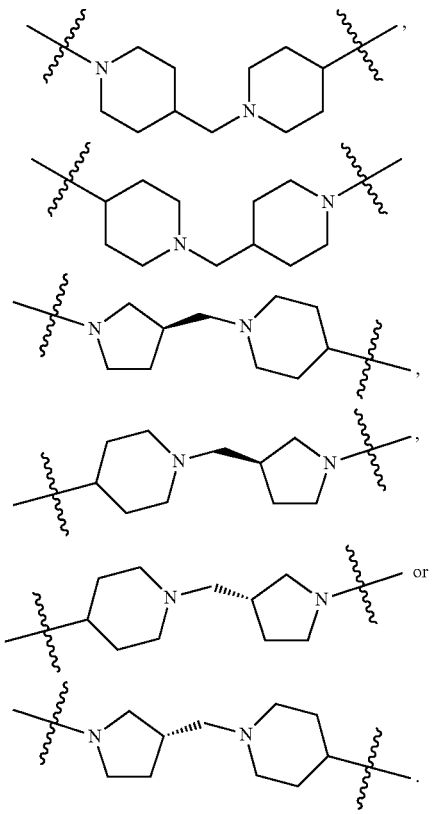

The present invention also provides a compound of Formula (D)

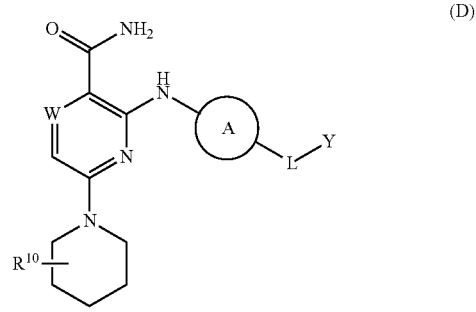

or a pharmaceutically acceptable salt thereof, wherein W is CH or N; ring A is

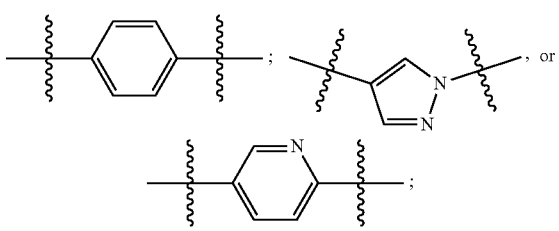

L is —X¹—X²—X³—; X¹ is —$C_{1-5}$ alkyl- or 4-6 membered monocyclic heterocycloalkyl having 1-2 heteroatoms independently selected from N, O, or S wherein the monocyclic heterocycloalkyl of X¹ is optionally substituted with —$CH_3$; X² is a bond, —$C_{1-5}$ alkyl-, or 4-6 membered monocyclic heterocycloalkyl having 1-2 heteroatoms independently selected from N, O, or S wherein the monocyclic heterocycloalkyl of X¹ is optionally substituted with —$CH_3$; X³ is a bond, —$C_{1-4}$ alkyl-, 4-6 membered monocyclic cycloalkyl, or 4-6 membered heterocycloalkyl having 1-2 heteroatoms independently selected from N, O, or S wherein the heterocycloalkyl is optionally substituted with —$CH_3$; Y is

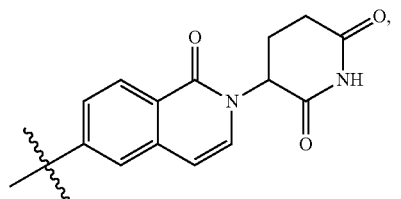

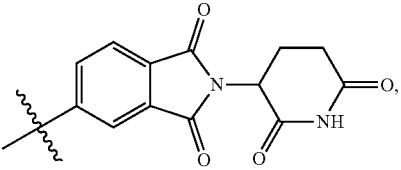

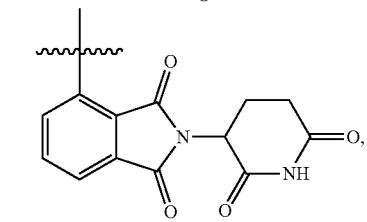

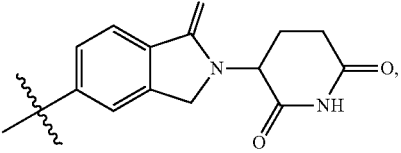

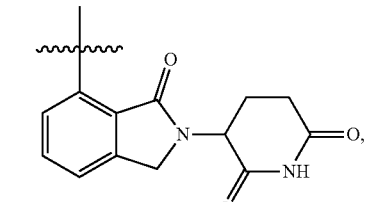

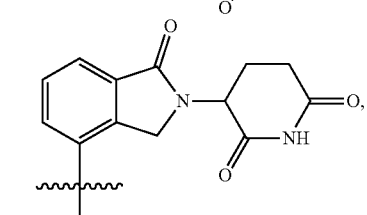

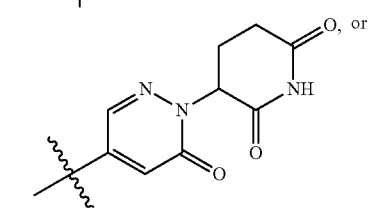

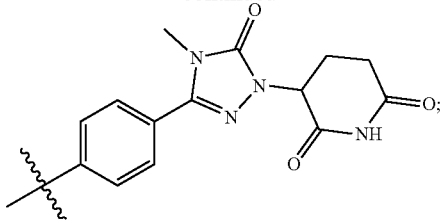

and $R^{10}$ is halo, —H, —$C_{1-5}$ alkyl, -3-6 membered cycloalkyl, 5-6 membered heterocycloalkyl, —CN, —OH, —$CF_3$, —$CH_2OH$, —$CH_2CH_2OH$,

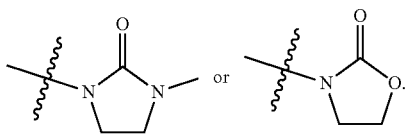

The present invention also provides a compound of Formula (D-1)

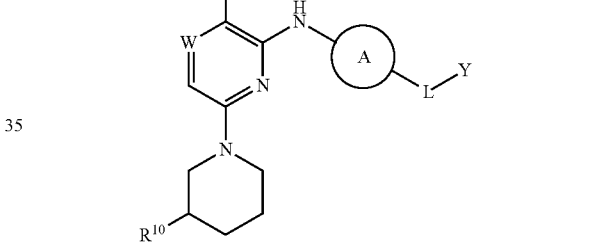

(D-1)

or a pharmaceutically acceptable salt thereof, wherein W is CH or N; ring A is

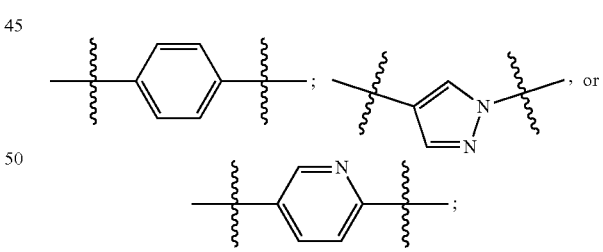

L is —X¹—X²—X³—; X¹ is —$C_{1-5}$ alkyl- or 4-6 membered monocyclic heterocycloalkyl having 1-2 heteroatoms independently selected from N, O, or S wherein the monocyclic heterocycloalkyl of X¹ is optionally substituted with —$CH_3$; X² is a bond, —$C_{1-5}$ alkyl-, or 4-6 membered monocyclic heterocycloalkyl having 1-2 heteroatoms independently selected from N, O, or S wherein the monocyclic heterocycloalkyl of X¹ is optionally substituted with —$CH_3$; X³ is a bond, —$C_{1-4}$ alkyl-, 4-6 membered monocyclic cycloalkyl, or 4-6 membered heterocycloalkyl having 1-2 heteroatoms independently selected from N, O, or S wherein the heterocycloalkyl is optionally substituted with —$CH_3$; Y is

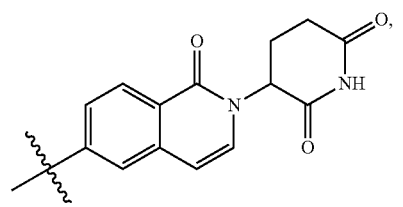

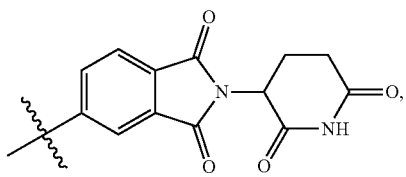

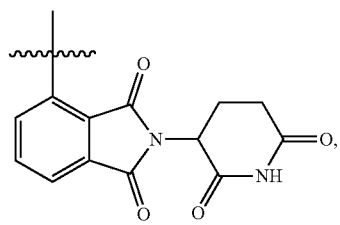

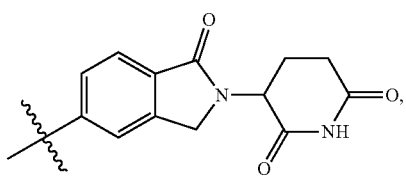

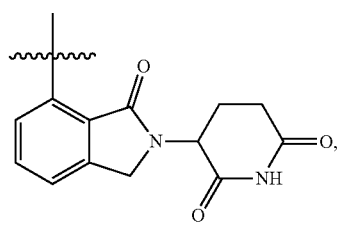

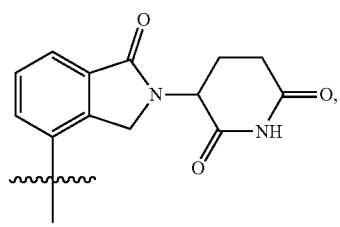

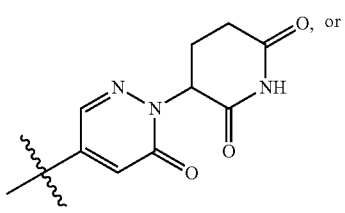

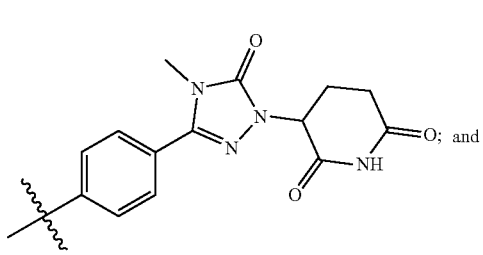

-continued

R¹⁰ is 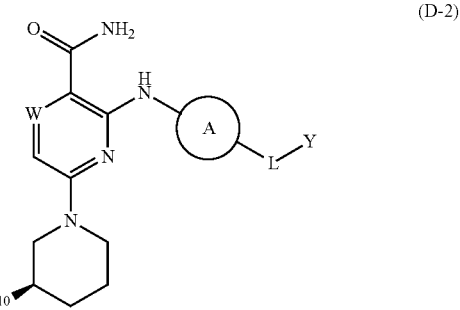

In some embodiments, the compound of Formula (D) is a compound of Formula (D-2):

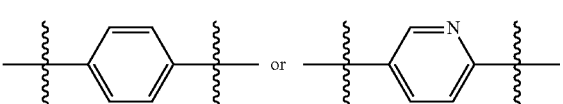
(D-2)

or a pharmaceutically acceptable salt thereof, wherein the terms ring A, L, Y, and R¹⁰ are as defined in the compound of Formula (A), (B), (C), (D), and (D-1).

In some embodiments, ring A is

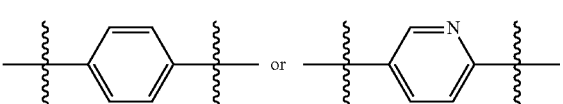

In some embodiments, $X^1$ is a 4-6 membered monocyclic heterocycloalkyl having 1-2 heteroatoms independently selected from N, O, or S wherein the monocyclic heterocycloalkyl of $X^1$ is optionally substituted with —CH₃. For example, $X^1$ is

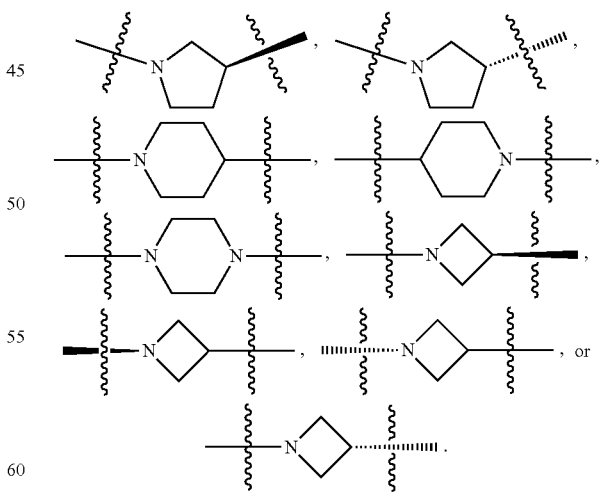

In some embodiments, $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having 1-2 heteroatoms independently selected from N, O, or S. For example, $X^3$ is
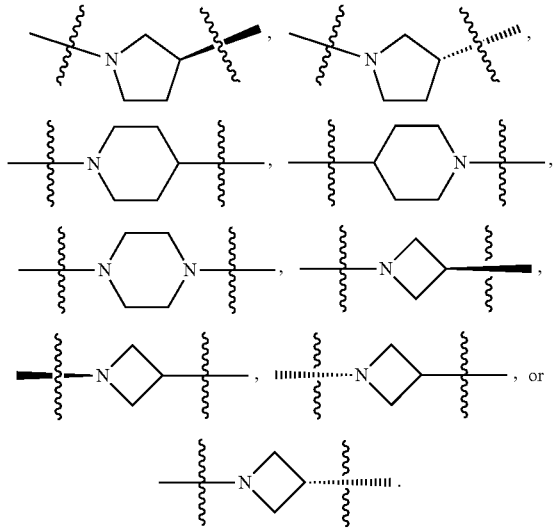
In some embodiments, L is
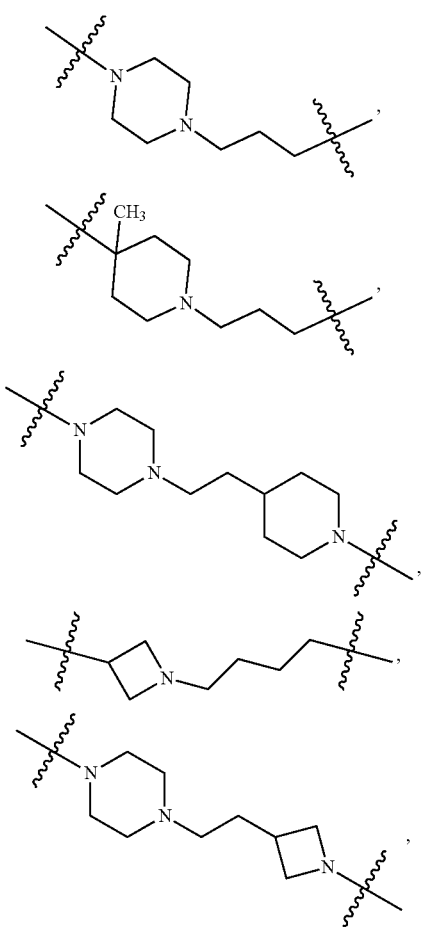
-continued
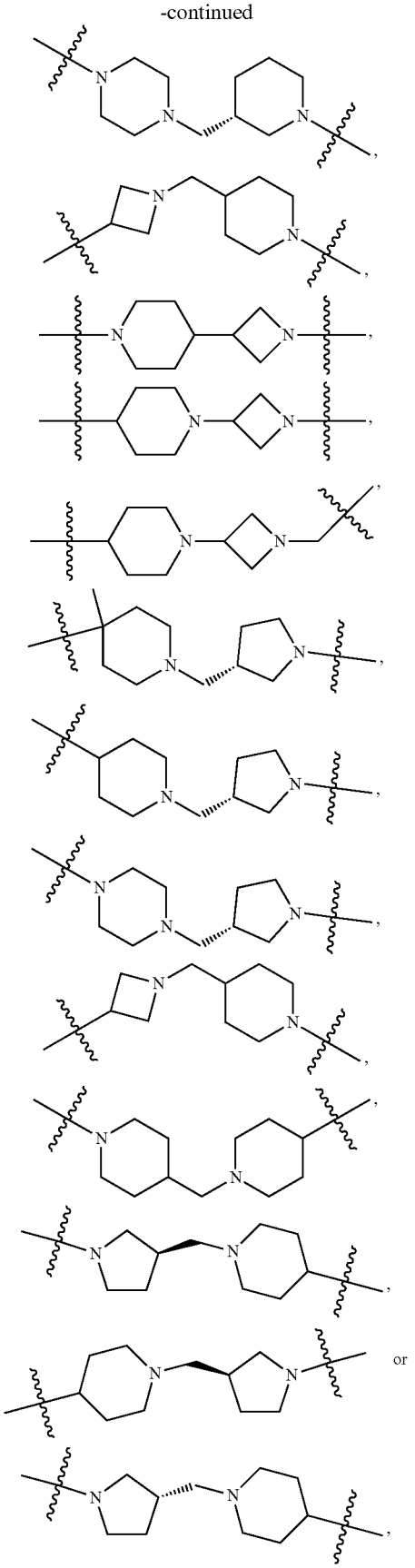

39

In some embodiments, $R^{10}$ is

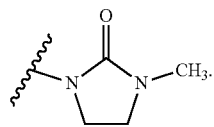 [SMILES: *N1CCN(C)C1=O]

In some embodiments, $R^{10}$ is

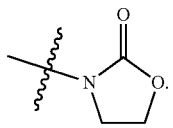 [SMILES: *N1CCOC1=O]

The present invention also provides a compound of Formula (E)

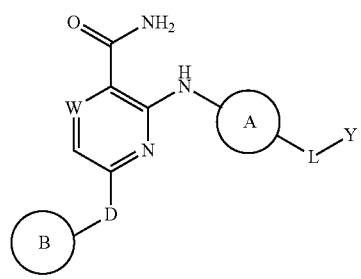

(E)

or a pharmaceutically acceptable salt thereof, wherein D is a bond or —NH—; W is N or CH; ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S; ring B is an optionally substituted 5-6 membered saturated, partially unsaturated, or fully unsaturated monocyclic heterocycle, or an optionally substituted 8-10 membered (e.g., 8-9 membered or 9-10 membered) spiro bicyclic heterocycle, wherein ring B has 1-3 heteroatoms independently selected from N, O, or S; L is —$X^1$—$X^2$—$X^3$—$X^4$—$X^5$—; $X^1$ is a bond, —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—

40

$CH_2$—$CH_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S; $X^5$ is a bond, —N(R)—, or —C(O)—N(R)—; each R is independently —H or —$C_{1-3}$ alkyl; each of m, n, and p is independently an integer from 1 to 3 (e.g., 1, 2, or 3); and Y is

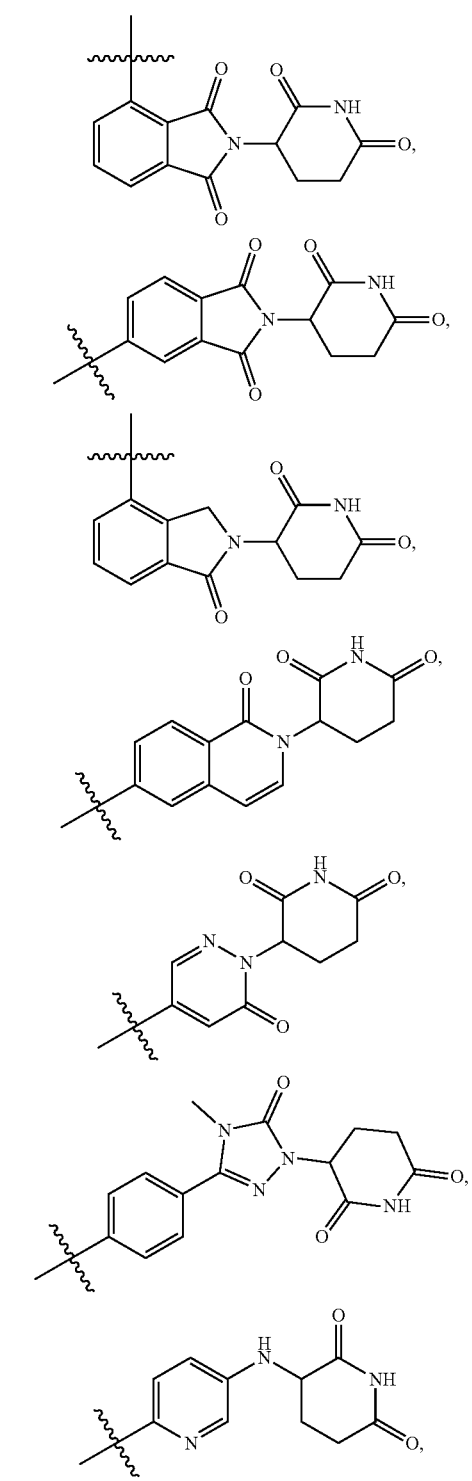

41
-continued
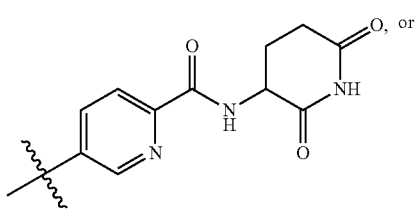
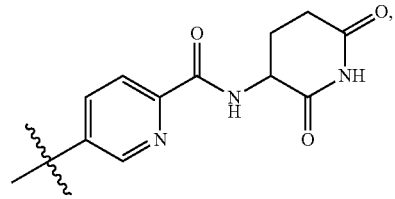
wherein at least one of $X^1$, $X^2$, $X^3$, $X^4$, and $X^5$ has a nitrogen atom, and Y is directly bonded to L at a nitrogen atom of $X^1$, $X^2$, $X^3$, $X^4$, or $X^5$.
In some embodiments, ring B is
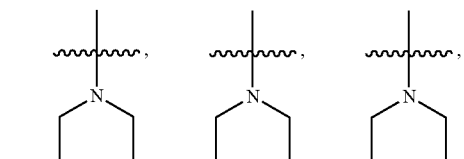
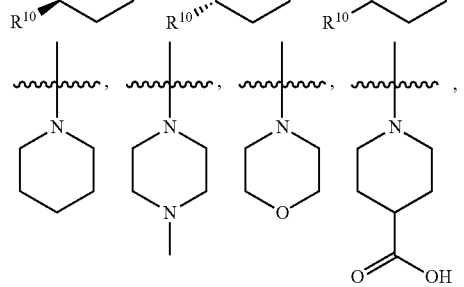
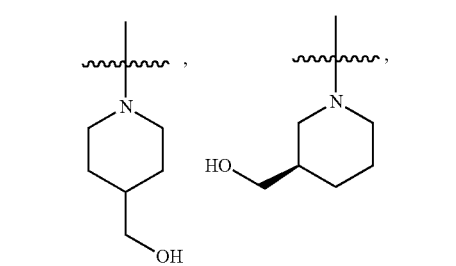
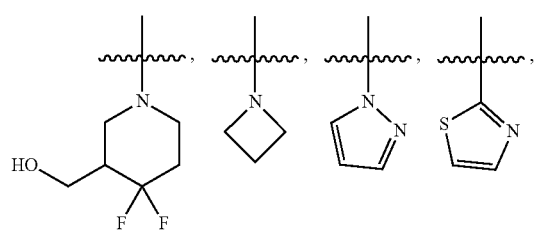
42
-continued
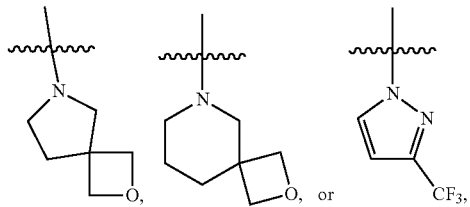
wherein $R^{10}$ is
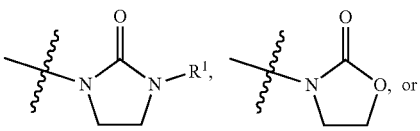
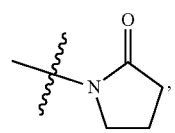
and wherein $R^1$ is a $C_{1-4}$ alkyl group. For example, ring B is
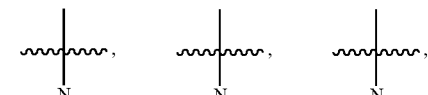
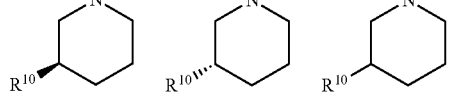
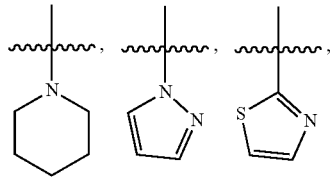
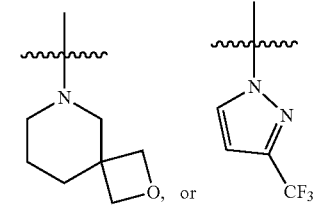
wherein $R^{10}$ is
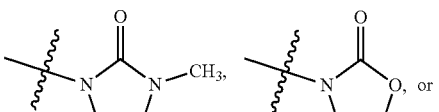

In other examples, ring B is
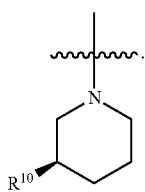
In some embodiments, $R^{10}$ is
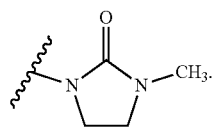 [SMILES: *N1CCN(C)C1=O]
In some embodiments, ring A is
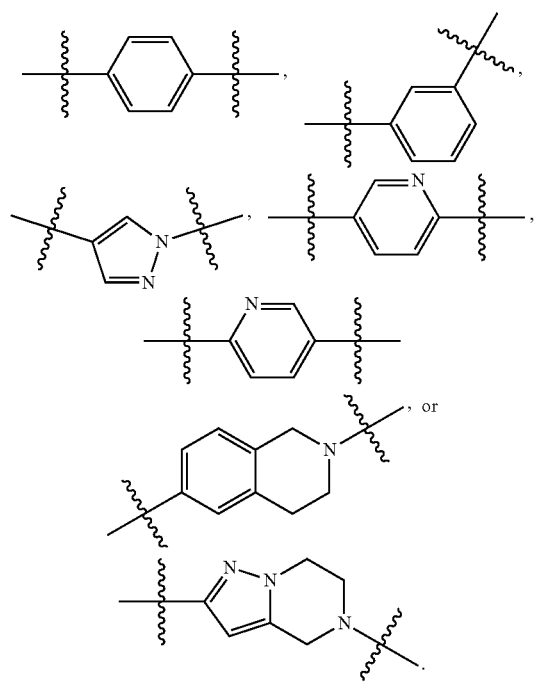
In some embodiments, $X^5$ is —N(R)—.
In some embodiments, $X^5$ is —C(O)—N(R)—.
In some embodiments, $X^5$ is a bond.
In some embodiments, L is
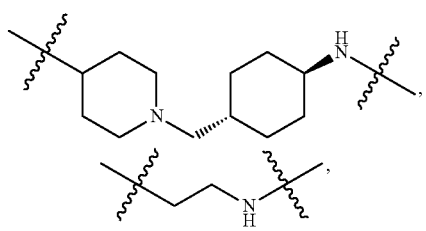
-continued
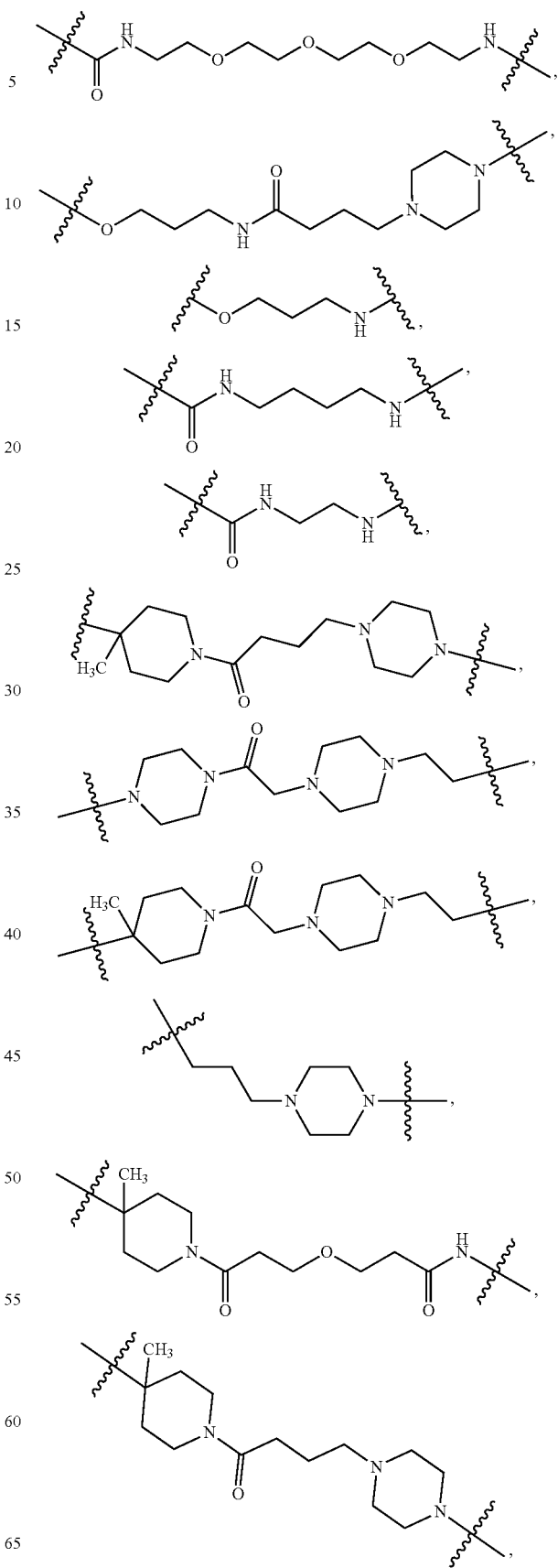

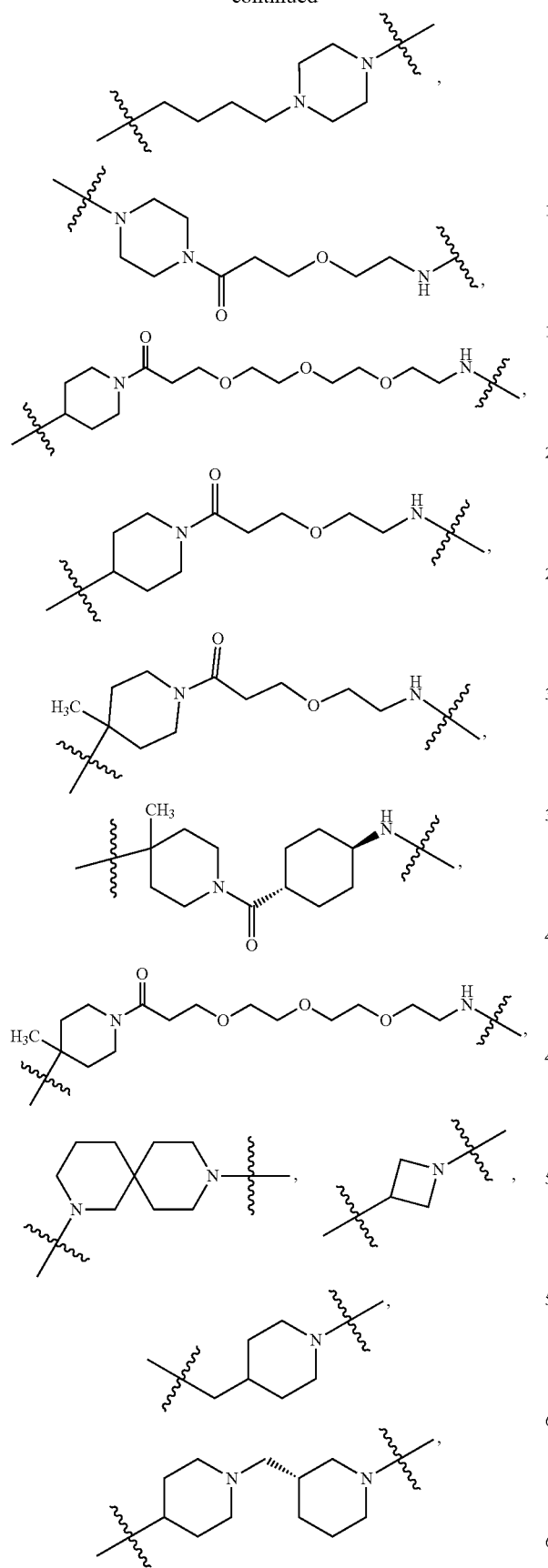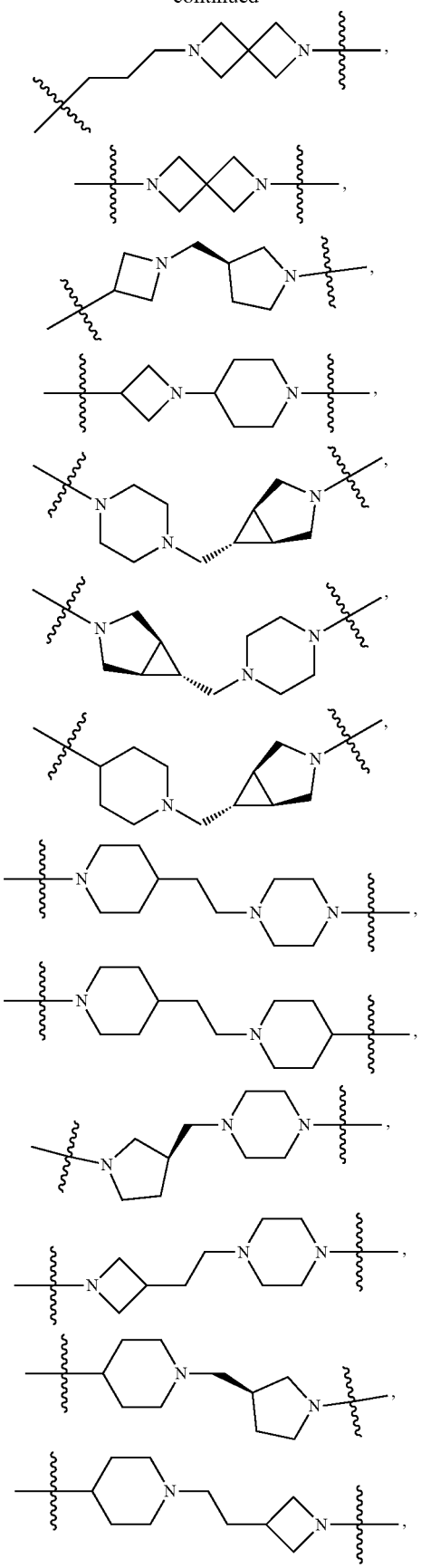

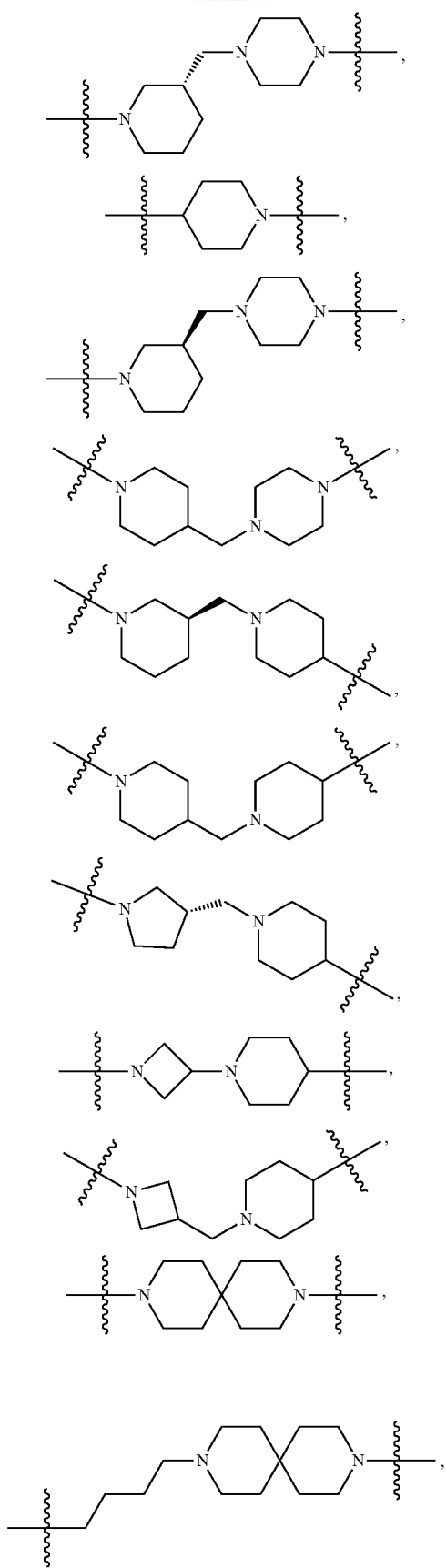
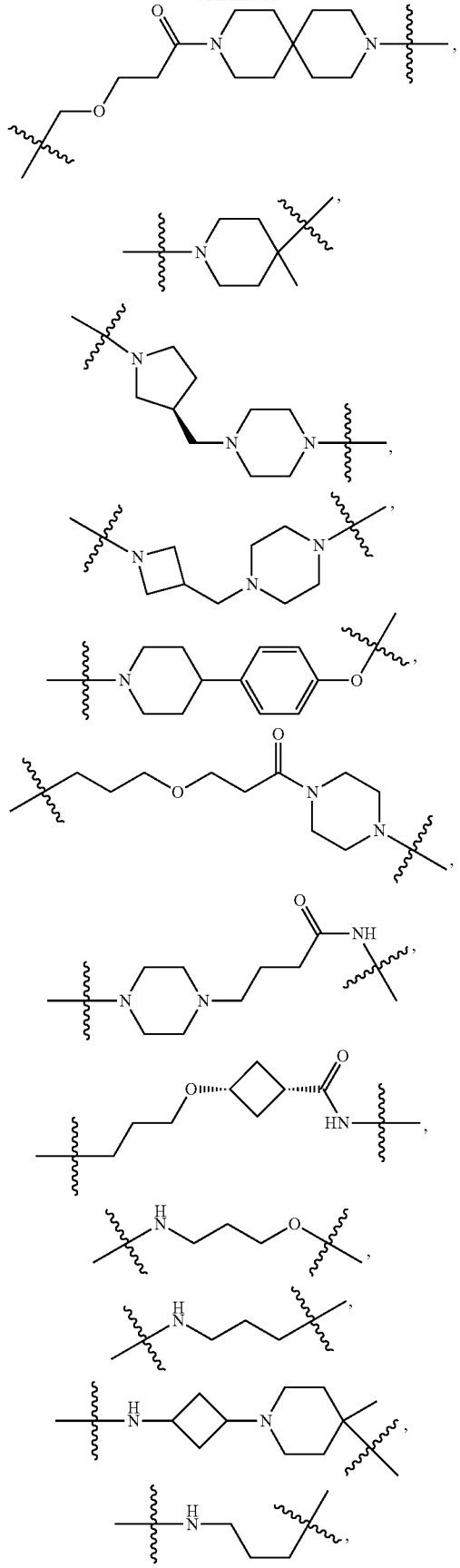

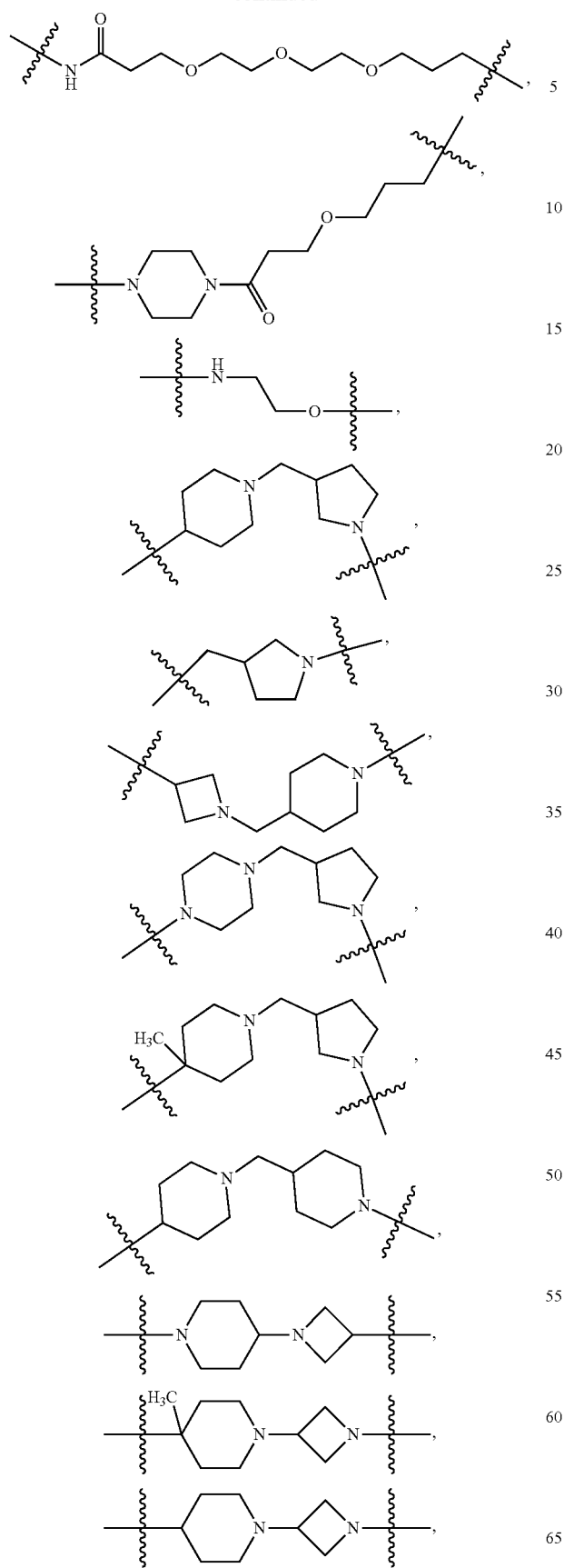
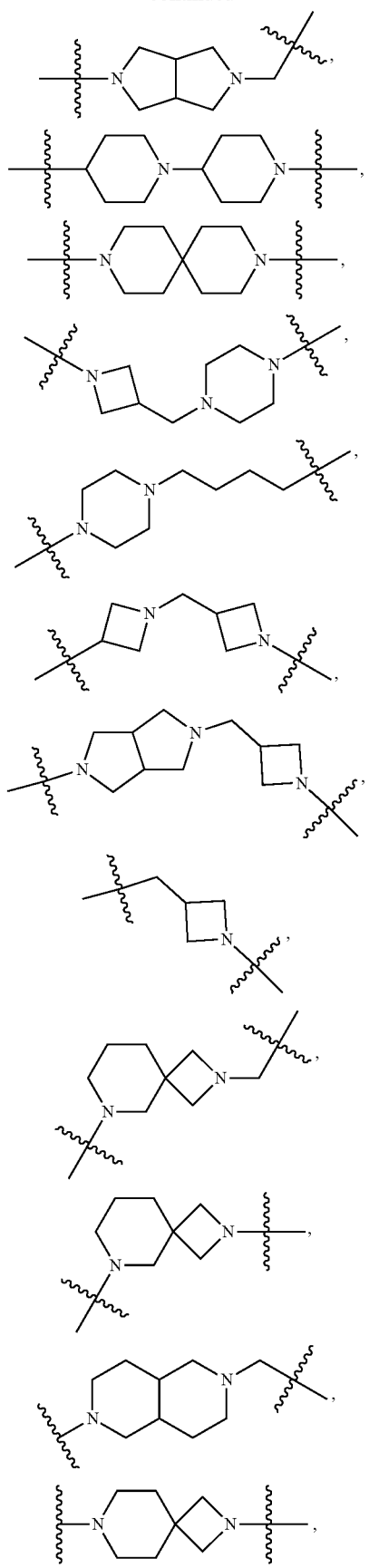

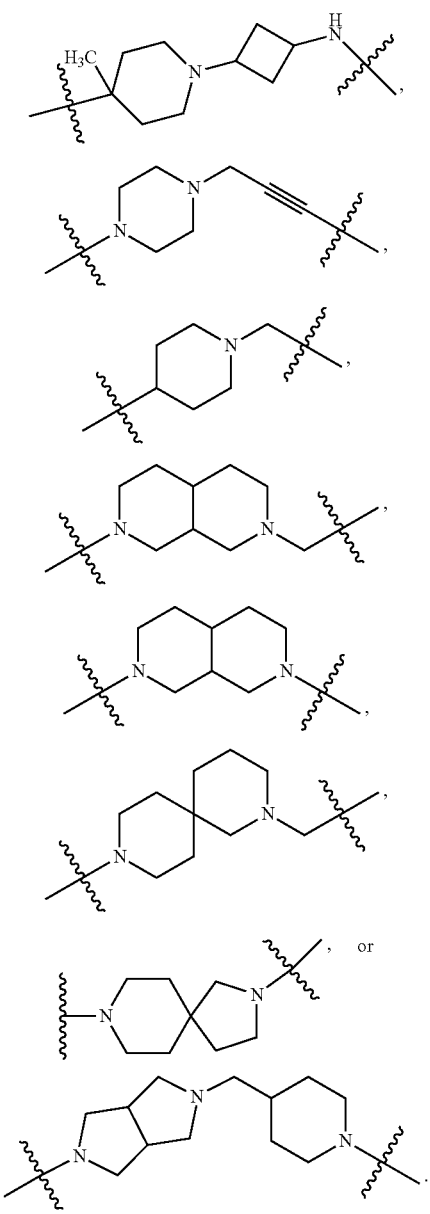

In some embodiments, Y is

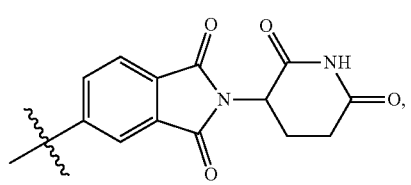

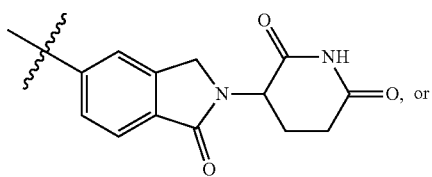

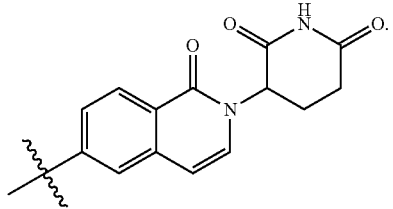

The present invention also provides a compound of Formula (F)

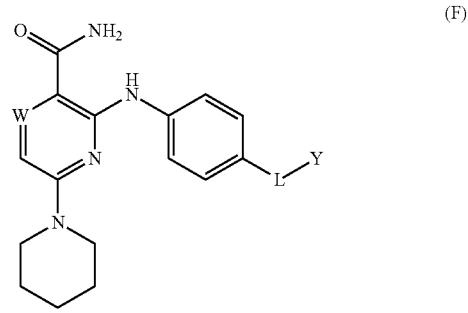

(F)

or a pharmaceutically acceptable salt thereof, wherein W is CH or N; L is —$X^1$—$X^2$—$X^3$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —CH$_3$; $X^2$ is a bond, —C$_{1-5}$ alkyl-, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; each R is independently —H or —C$_{1-3}$ alkyl; each of m, n, and p is independently an integer from 1 to 3; and Y is

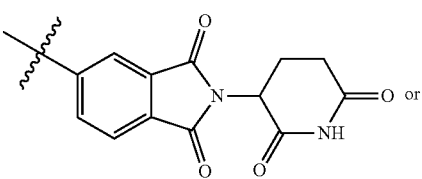

-continued

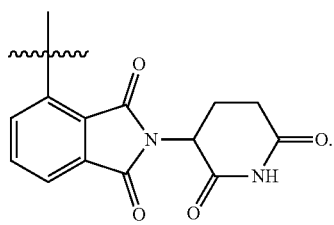

In some embodiments, W is N.

In some embodiments, Y is

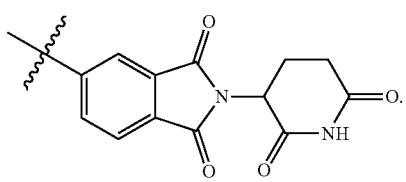 [SMILES: *c1ccc2c(c1)C(=O)N(C1CCC(=O)NC1=O)C2=O]

In some embodiments, $X^1$ is a 4-6 membered monocyclic heterocycloalkyl having 1-2 heteroatoms independently selected from N, O, or S, wherein each of the monocyclic heterocycloalkyl of $X^1$ is optionally substituted with —CH$_3$. For example, $X^1$ is

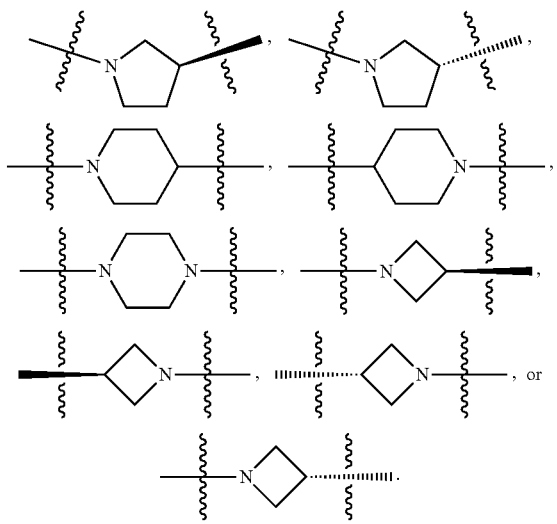

In some instances, $X^1$ is

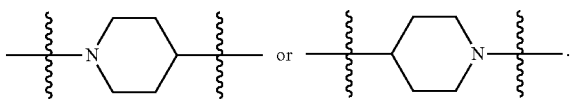 [SMILES: *C1CCN(*)CC1 ; *C1CCN(*)CC1]

In some embodiments, $X^2$ is a bond or —$C_{1-5}$ alkyl-.

In some embodiments, $X^3$ is a 4-6 membered monocyclic heterocycloalkyl having 1-2 heteroatoms independently selected from N, O, or S. For example, $X^3$ is

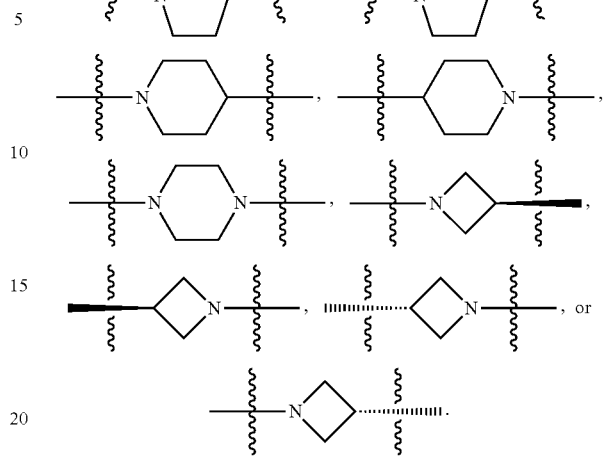

In some instances, $X^3$ is

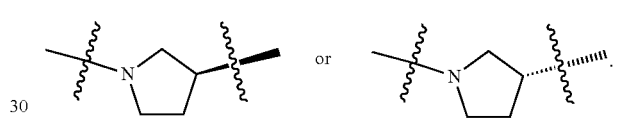

In some embodiments, L is

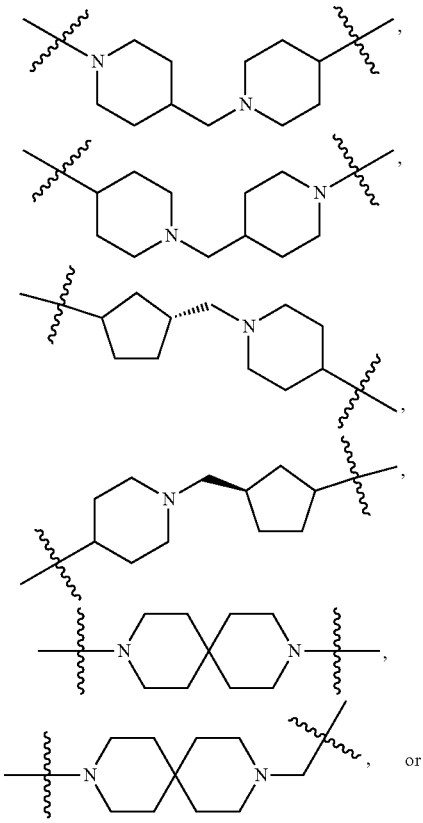

-continued

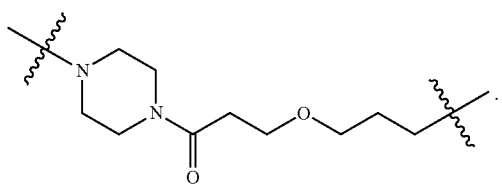

The present invention also provides a compound of Formula (G)

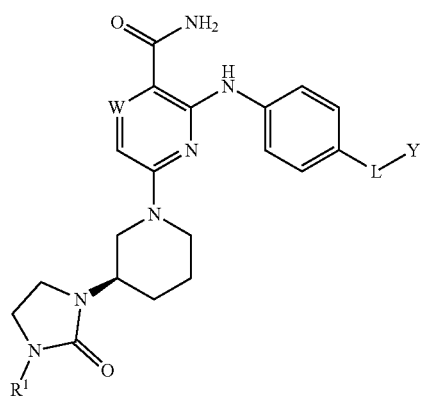

(G)

or a pharmaceutically acceptable salt thereof, wherein $R^1$, L, and Y are as defined for compounds of Formula (A), (B), (C), (D), (E), (F), (X), and (I).

In some embodiments, $R^1$ is methyl.

In some embodiments, Y is

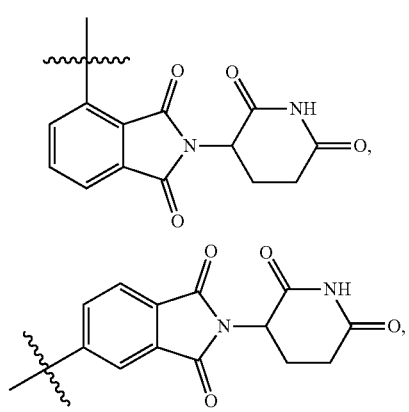

-continued

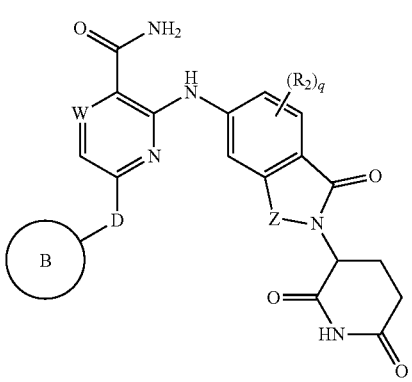

In some embodiments, W is N.

The present invention also provides a compound of Formula (H)

(H)

or a pharmaceutically acceptable salt thereof, wherein ring B, $R^2$, Z, W, D, and q are as defined in the compound of Formula (A), (B), (C), (D), (E), (F), (G), (X), and (I).

In some embodiments, q is 0.

The present invention also provides a compound of Formula (J)

(J)

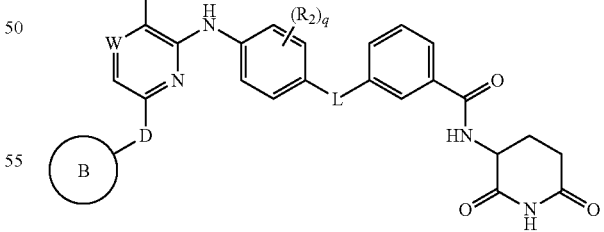

or a pharmaceutically acceptable salt thereof, wherein ring B, D, W, $R^2$, q, and L are as defined in the compound of Formula (A), (B), (C), (D), (E), (F), (H), (X), and (I).

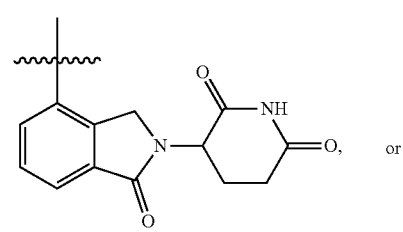 or

The present invention also provides a compound of Formula (K)

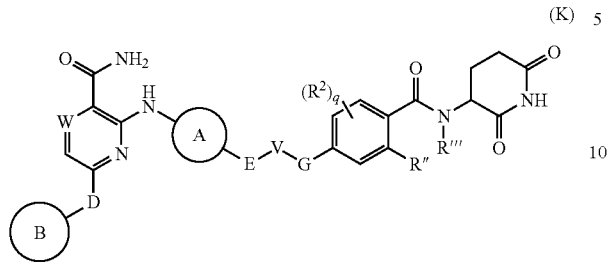

or a pharmaceutically acceptable salt thereof, wherein ring A is

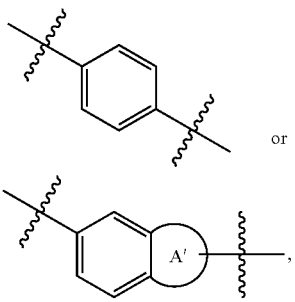

wherein ring A is optionally and independently substituted with up to 3 substituents selected from halo, CN, carboxyl, $NH_2$, and optionally substituted $C_{1-6}$ alkyl; V is a bond or $-CH_2-$; and E and G are each independently a 5-6 membered heterocycloalkyl, wherein each heterocycloalkyl contains at least one nitrogen atom. Ring B, W, $R^2$, q, R", R''', and ring A' are as defined in the compound of Formula (A).

In some embodiments, D is a bond and W is a nitrogen atom.

The present invention also provides a compound of Formula (M)

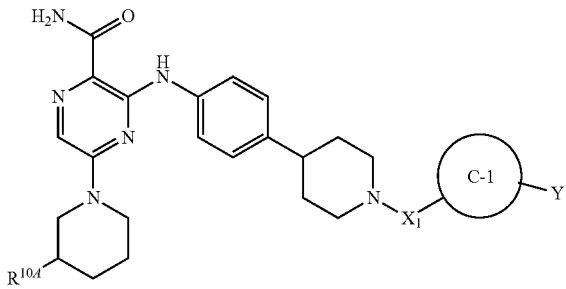

or a pharmaceutically acceptable salt thereof, wherein $R^{10A}$ is —H,

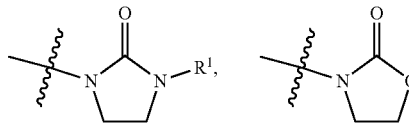

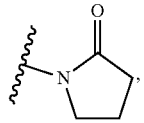

wherein $R^1$ is $C_{1-4}$ alkyl; $X^1$ is $-C_{1-5}$ alkyl-; ring C-1 is a 5-6 membered heterocycloalkyl having 1 nitrogen atom; and Y is

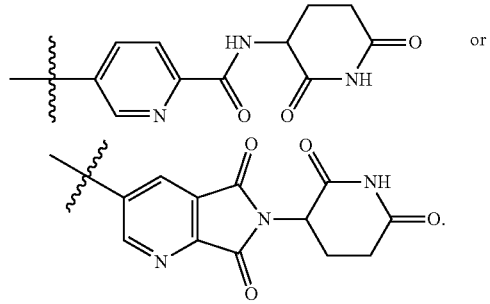

In some embodiments, $R^{10A}$ is —H or

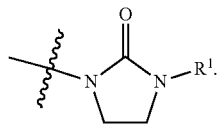

In some embodiments, $R^{10A}$ is

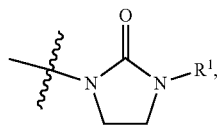

and $R^1$ is methyl, ethyl, propyl, iso-propyl, butyl, sec-butyl, or iso-butyl. For example, $R^1$ is methyl.

In some embodiments, $X^1$ is methylene, ethylene, or propylene. For instance, $X^1$ is methylene.

In some embodiments, ring C-1 is

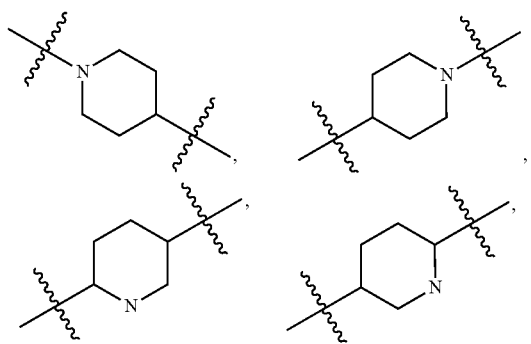

-continued

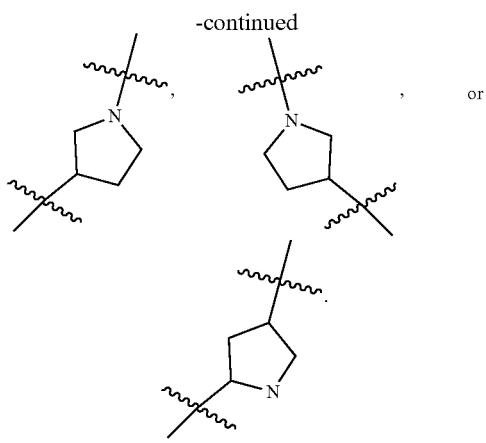

For instance, ring C-1 is

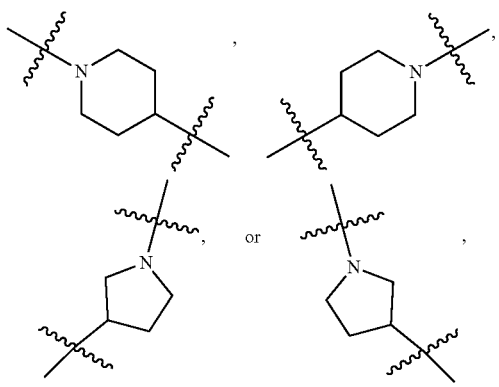

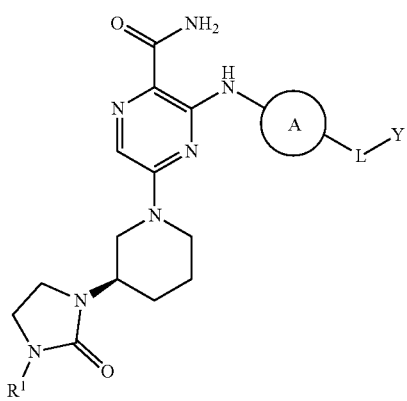

The present invention also provides a compound of Formula (X)

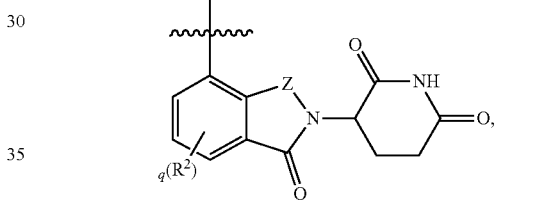
(X)

or a pharmaceutically acceptable salt thereof, wherein $R^1$ is $C_{1-3}$ alkyl; ring A is phenyl, 5-6 membered partially or fully unsaturated monocyclic heterocycle, 9-10 membered bicyclic aryl, or 9-10 membered bicyclic heteroaryl, wherein the heterocycle and the bicyclic heteroaryl of ring A each independently have 1-3 heteroatoms independently selected from N, O, or S; L is —$X^1$—$X^2$—$X^3$—$X^4$—$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —$C_{1-5}$ alkyl-, 7-12 membered spiro bicyclic heterocycloalkyl having 1-3 heteroatoms independently selected from N, O, or S wherein the bicyclic heterocycloalkyl of $X^1$ is optionally substituted with —CH$_3$, or 4-6 membered monocyclic heterocycloalkyl having 1-2 heteroatoms independently selected from N, O, or S wherein the monocyclic heterocycloalkyl of $X^1$ is optionally substituted with —CH$_3$; $X^2$ is a bond, —(O—CH$_2$—CH$_2$)$_n$—, —(CH$_2$—CH$_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; $X^4$ is a bond, —CH$_2$—CH$_2$—N(R)—, —N(R)—, —$C_{1-4}$ alkyl-, —(O—CH$_2$—CH$_2$—CH$_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S; $X^5$ is a bond, —$C_{1-4}$ alkyl-, —N(R)—, or —C(O)—N(R)—; each R is independently —H or —$C_{1-3}$ alkyl; each of m, n, and p is independently an integer from 1 to 3; Y is

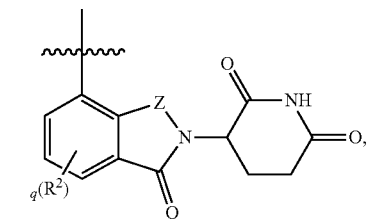

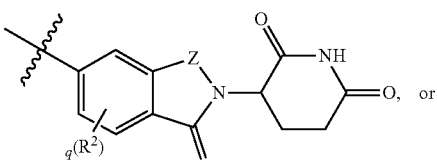

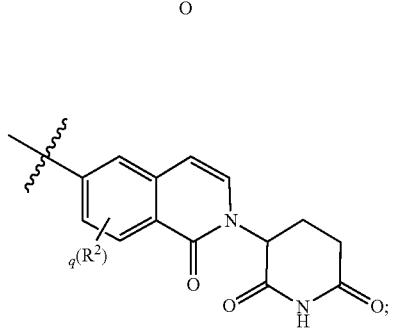

wherein each $R^2$ is independently halo or $C_{1-4}$ alkyl; each Z is —C($R^4$)$_2$— or —C(O)—; each $R^4$ is independently —H or $C_{1-4}$ alkyl; and q is 0, 1, or 2.

In some embodiments, q is 0. In other embodiments, q is 1 and $R^2$ is —F.

In some embodiments, Z is —CH— or —C(O)—.

In some embodiments, Y is

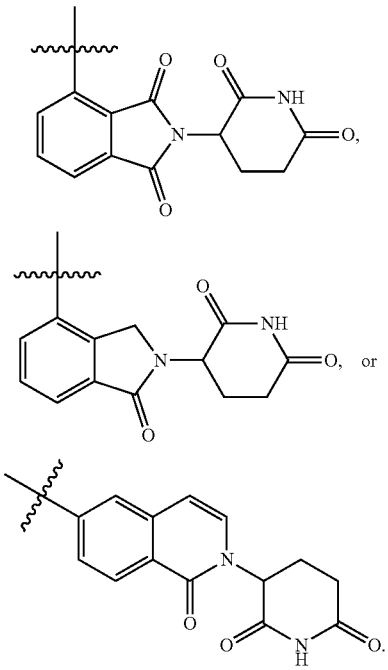

In some embodiments, Y is

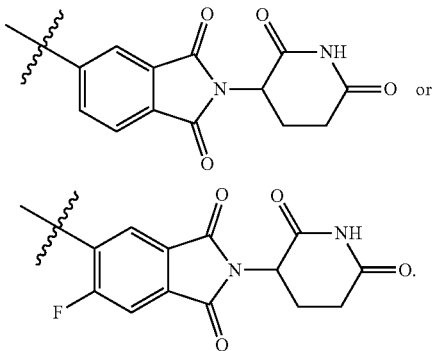

In some embodiments, R$^1$ is methyl, ethyl, or propyl. For example, R$^1$ is methyl.

In some embodiments, each R is independently —H or —CH$_3$.

In some embodiments, ring A is selected from

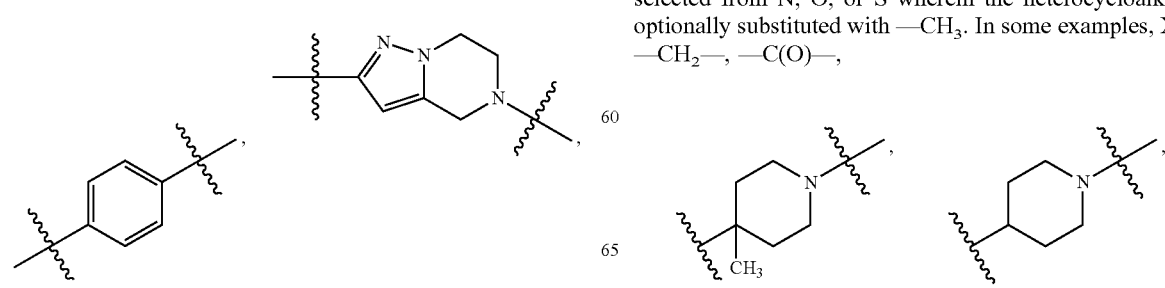

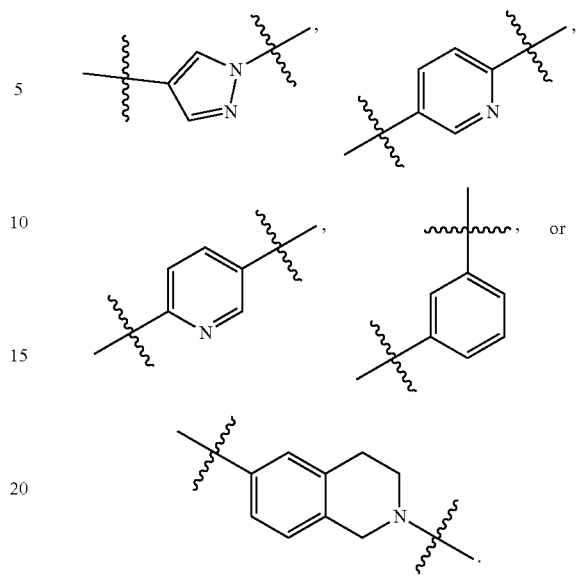

For example, ring A is selected from

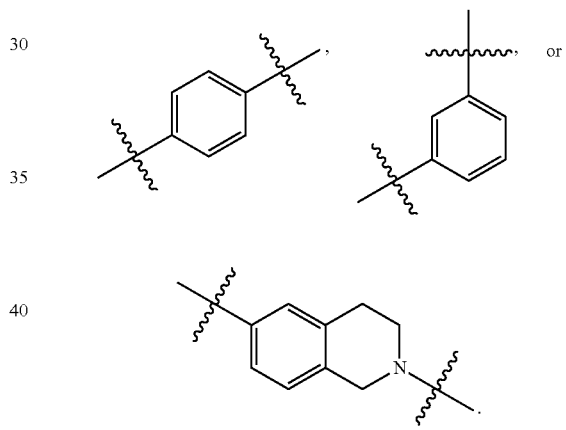

In some embodiments, at least one of X$^1$, X$^2$, and X$^5$ is —C(O)—N(R)— or —CH$_2$—.

In some embodiments, X$^1$ is —C(O)—N(R)—. In other examples, X$^1$ is —C$_{1-5}$ alkyl-; 7-12 membered spiro bicyclic heterocycloalkyl having 1-3 heteroatoms independently selected from N, O, or S wherein the heterocycloalkyl is optionally substituted with —CH$_3$; or 4-6 membered heterocycloalkyl having 1-2 heteroatoms independently selected from N, O, or S wherein the heterocycloalkyl is optionally substituted with —CH$_3$. In some examples, X$^1$ is —CH$_2$—, —C(O)—,

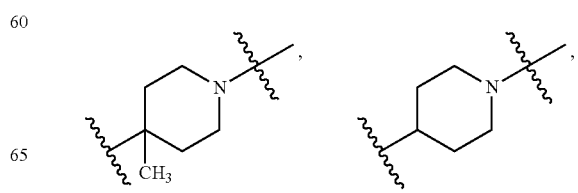

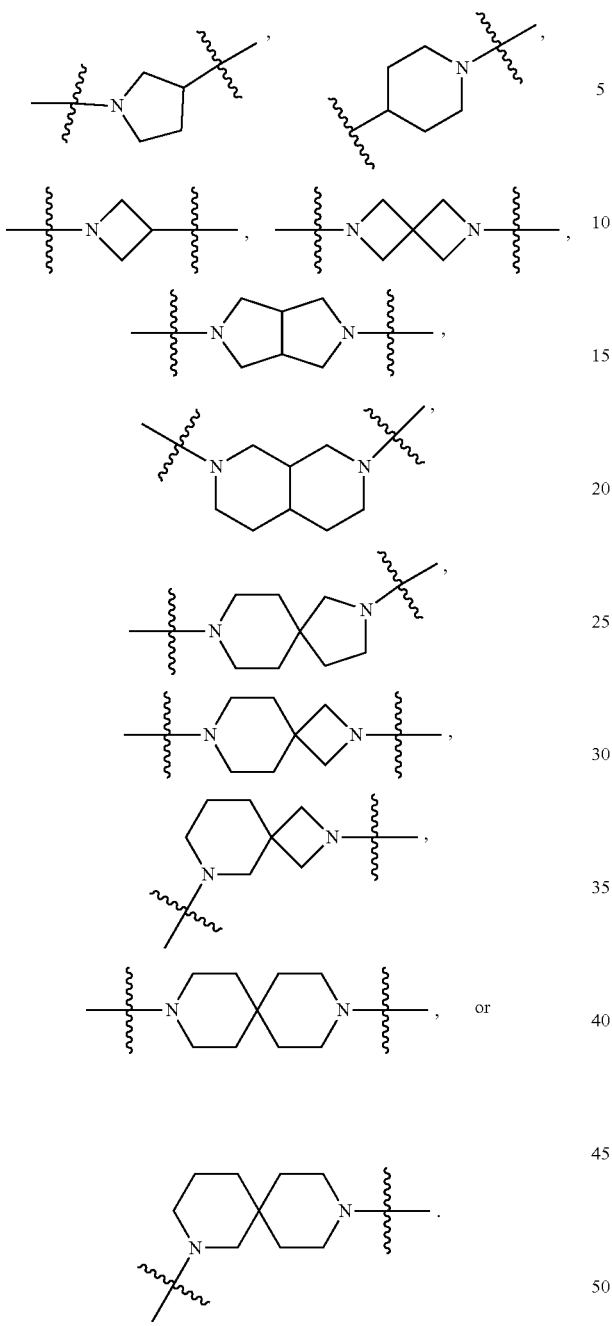

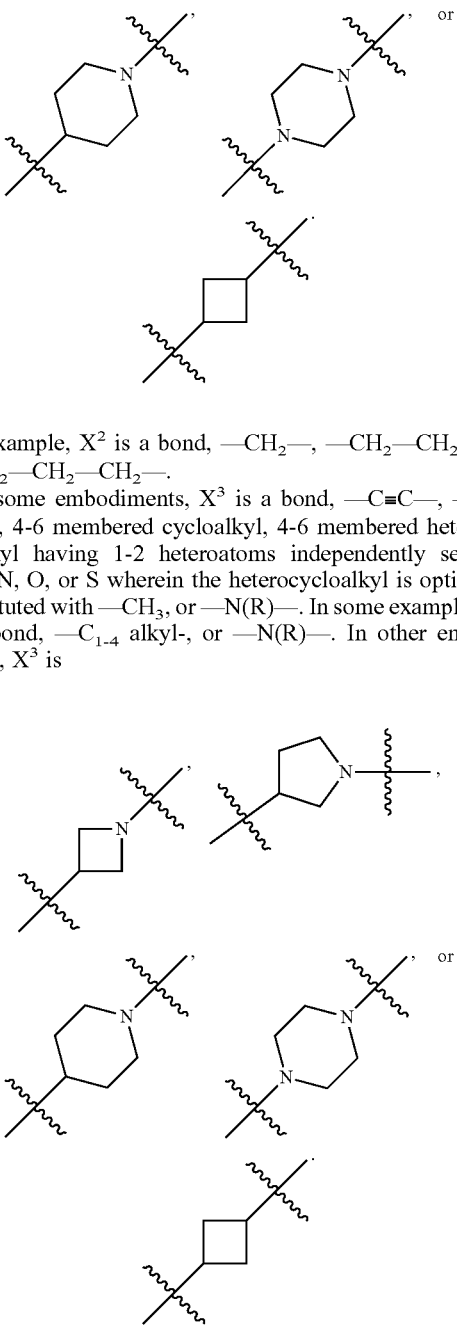

For example, $X^2$ is a bond, —$CH_2$—, —$CH_2$—$CH_2$—, or —$CH_2$—$CH_2$—$CH_2$—.

In some embodiments, $X^3$ is a bond, —C≡C—, —$C_{1-4}$ alkyl-, 4-6 membered cycloalkyl, 4-6 membered heterocycloalkyl having 1-2 heteroatoms independently selected from N, O, or S wherein the heterocycloalkyl is optionally substituted with —$CH_3$, or —N(R)—. In some examples, $X^3$ is a bond, —$C_{1-4}$ alkyl-, or —N(R)—. In other embodiments, $X^3$ is In some embodiments, $X^2$ is —(O—$CH_2$—$CH_2$)$_n$—, —($CH_2$—$CH_2$—O)$_n$—, or —$C_{1-5}$ alkyl-. In other embodiment, $X^2$ is a bond, —C(O)—, —$C_{1-5}$ alkyl-,

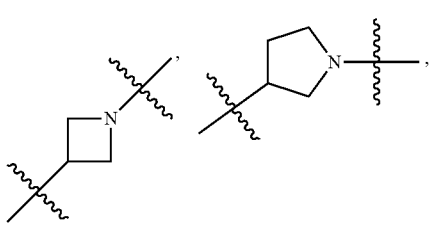

In some embodiments, $X^4$ is a bond, —$C_{1-4}$ alkyl-, —(O—$CH_2$—$CH_2$—$CH_2$)$_m$—, or 5-6 membered saturated, partially unsaturated, or fully unsaturated carbocycle having 0-3 heteroatoms independently selected from N, O, or S. For example, $X^4$ is a bond,

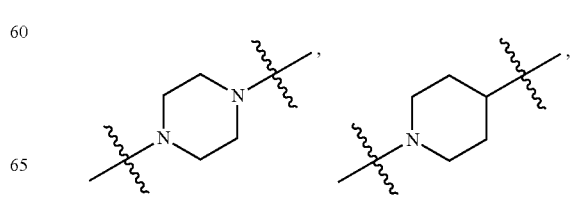

-continued
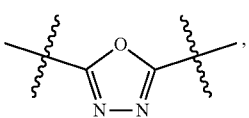
—C$_{1-4}$ alkyl-, —CH$_2$—CH$_2$—N(R)—, or —N(R)—. In other examples, X$^4$ is a bond, —CH$_2$—, or —N(R)—.
In some embodiments, X$^5$ is a bond, —C$_{1-4}$ alkyl-, —N(R)—, or —C(O)—N(R)—. For example, X$^5$ is a bond.
In some embodiments, X$^1$ is —(O—CH$_2$—CH$_2$—CH$_2$)$_m$—, m is 1, and X$^2$ is —C(O)—N(R)—.
In some embodiments, L is
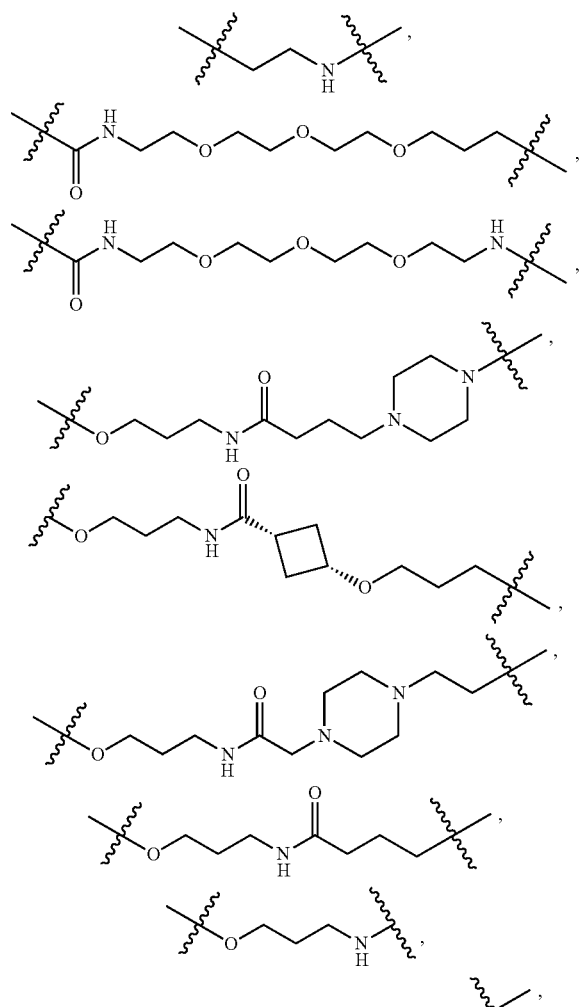
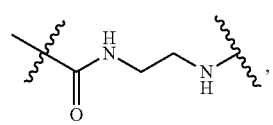
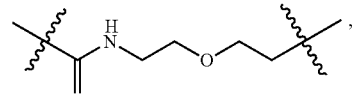
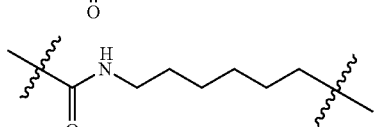
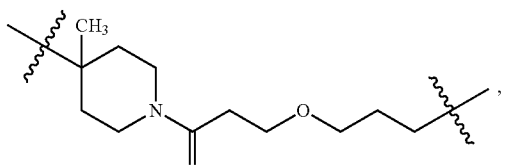
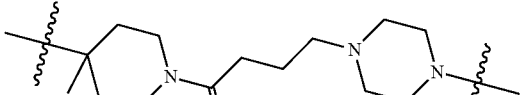
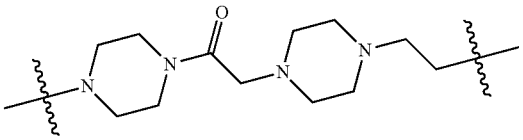
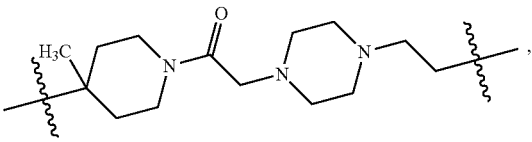
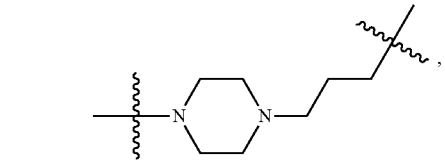
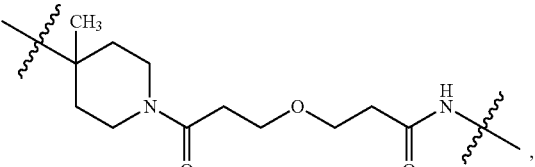
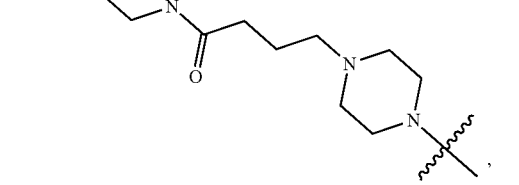

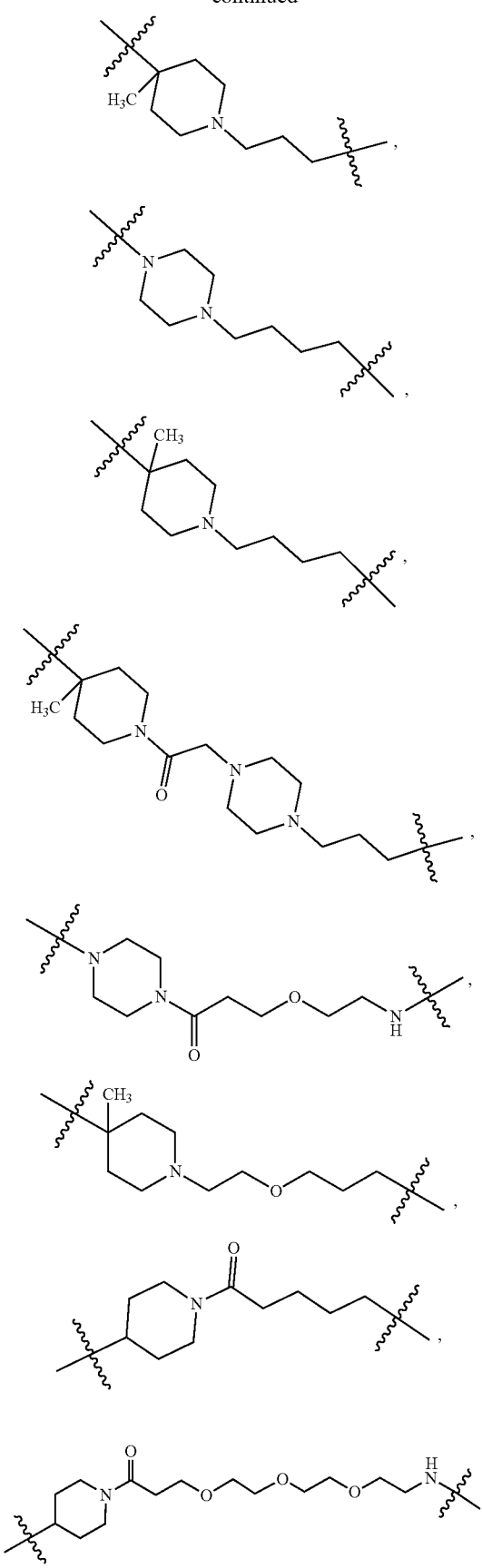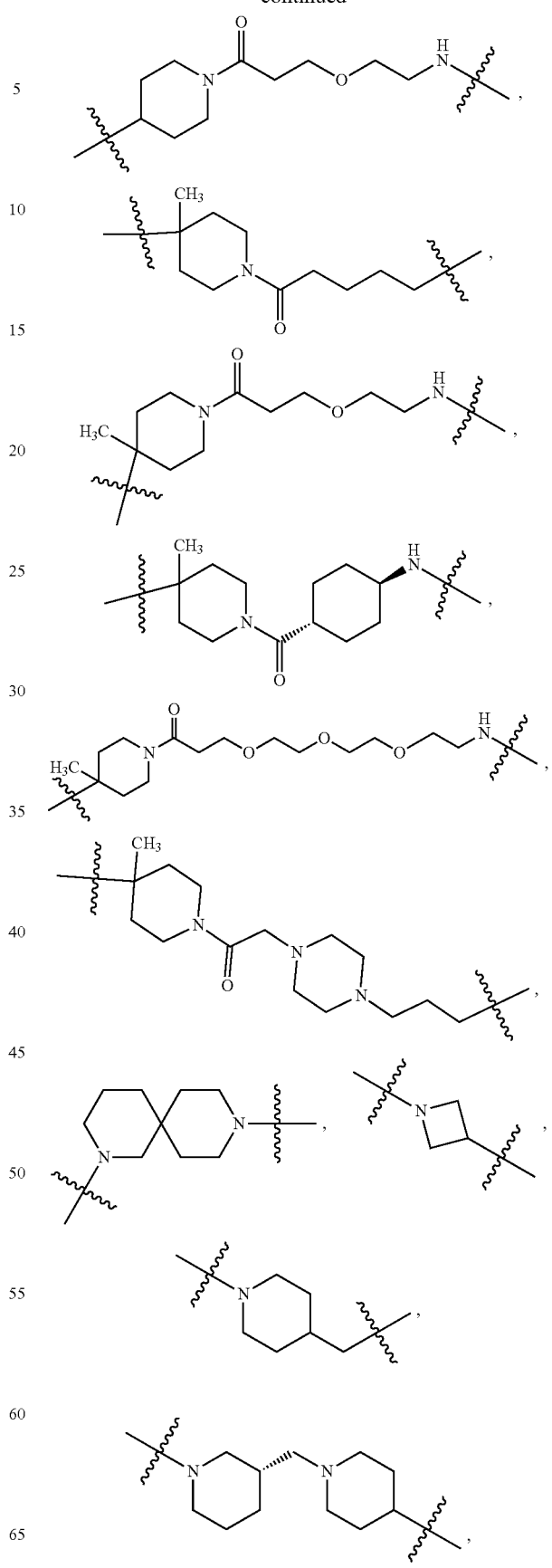

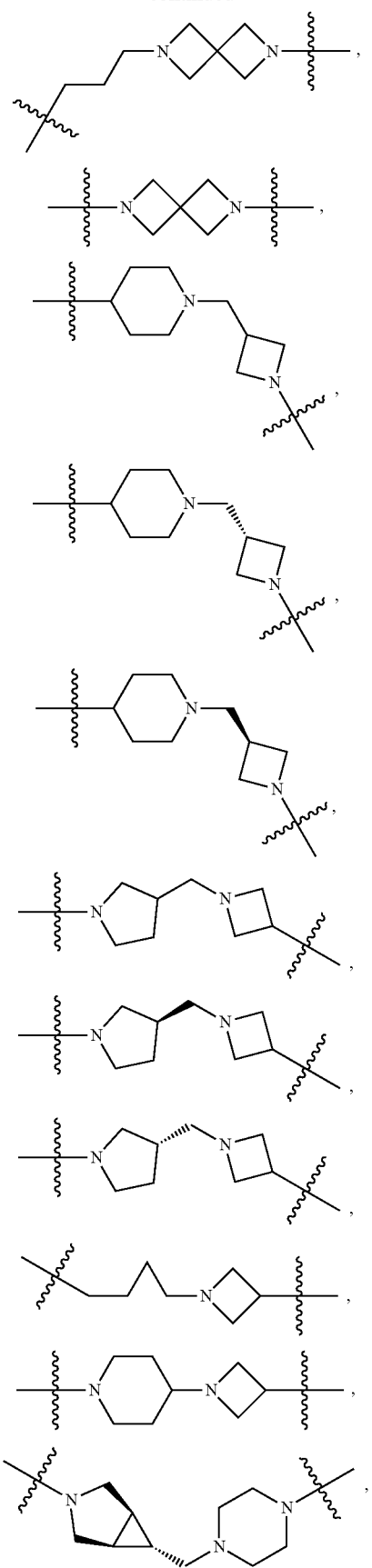
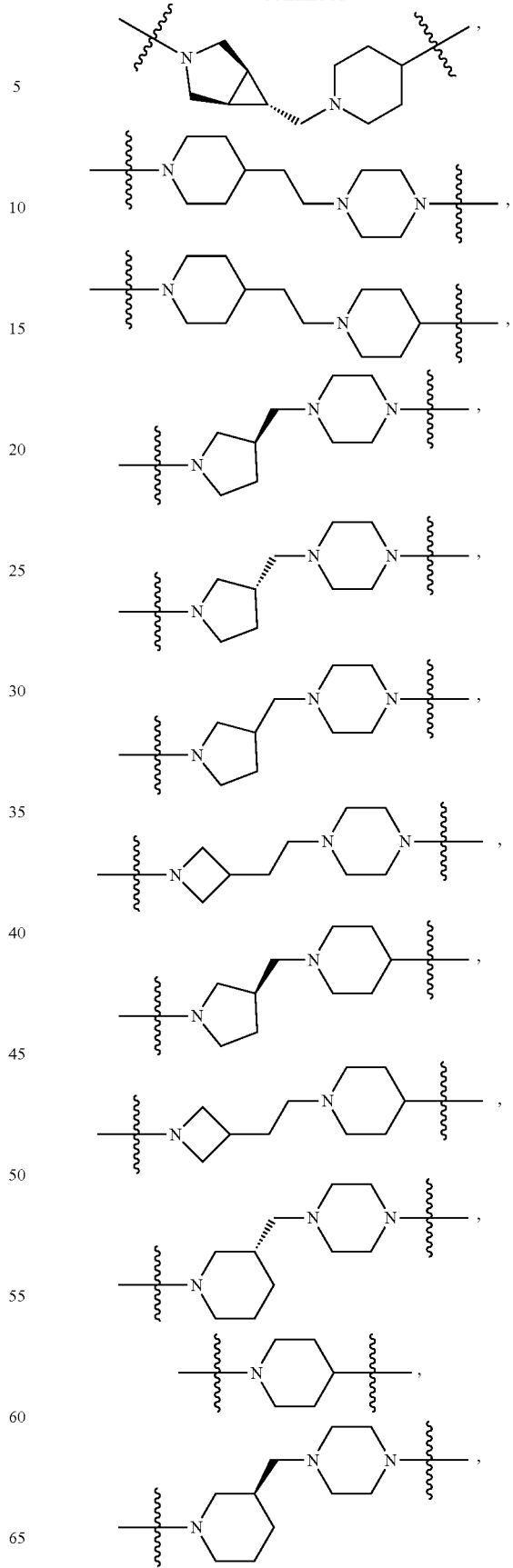

-continued
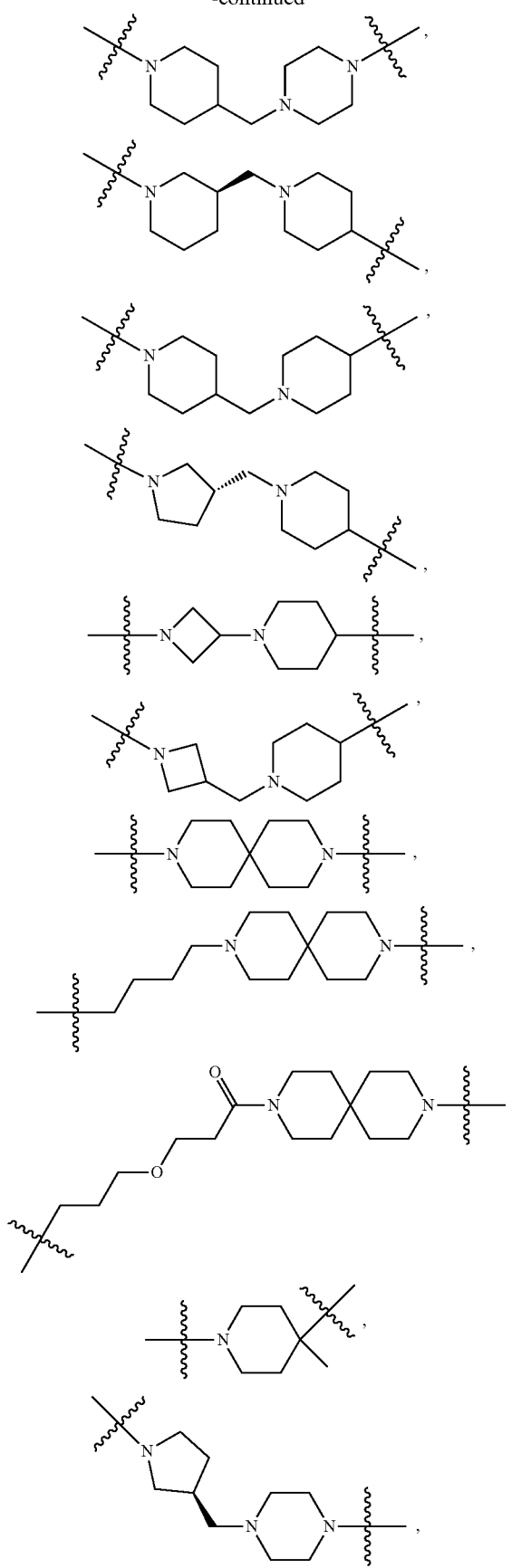
-continued
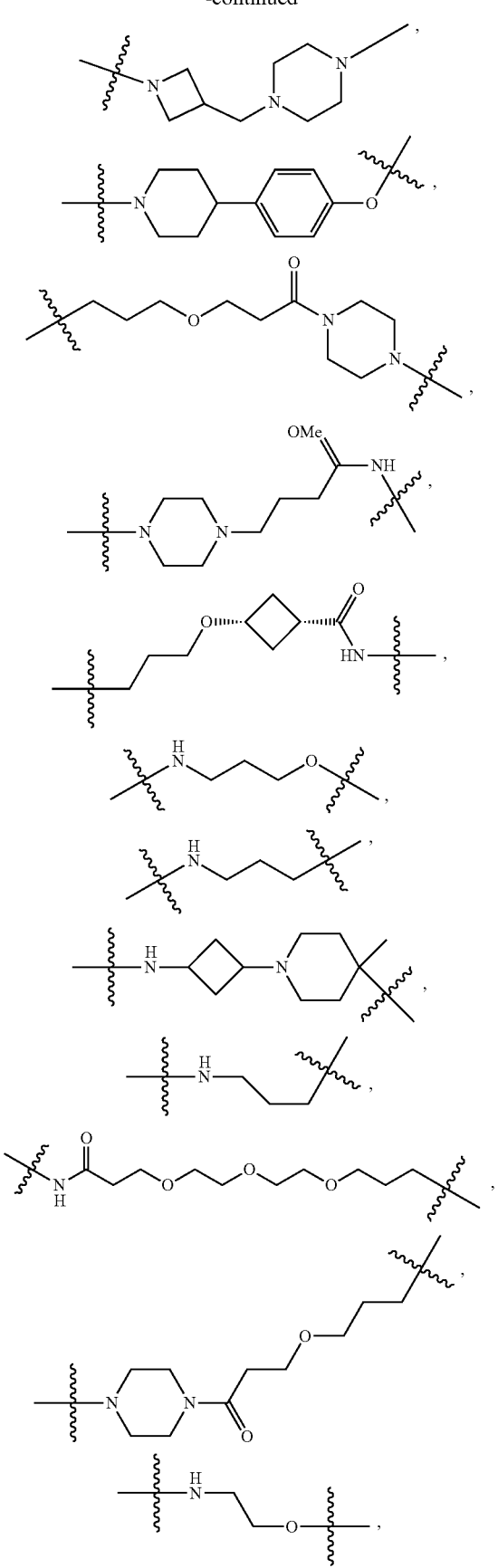

73
-continued
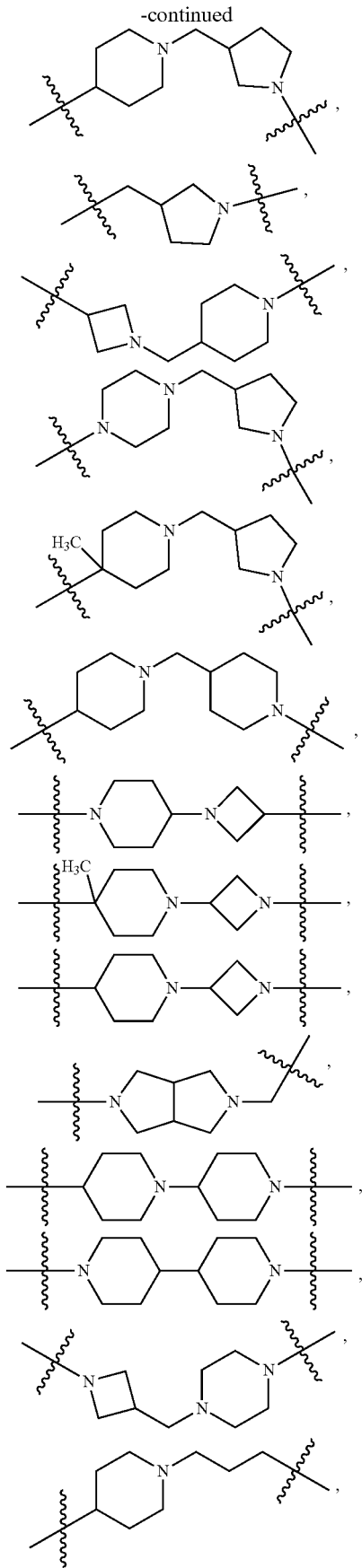
74
-continued
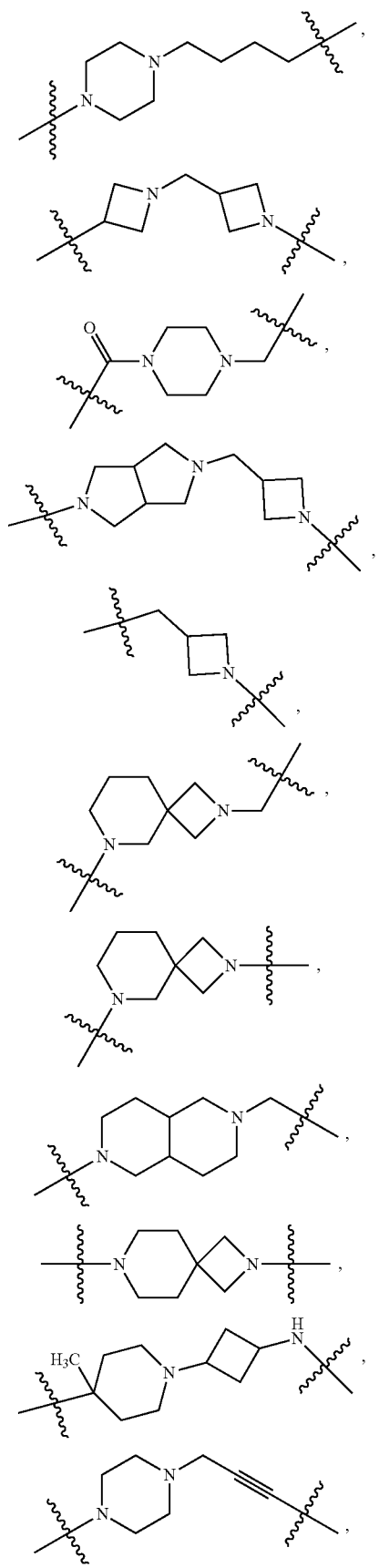

-continued

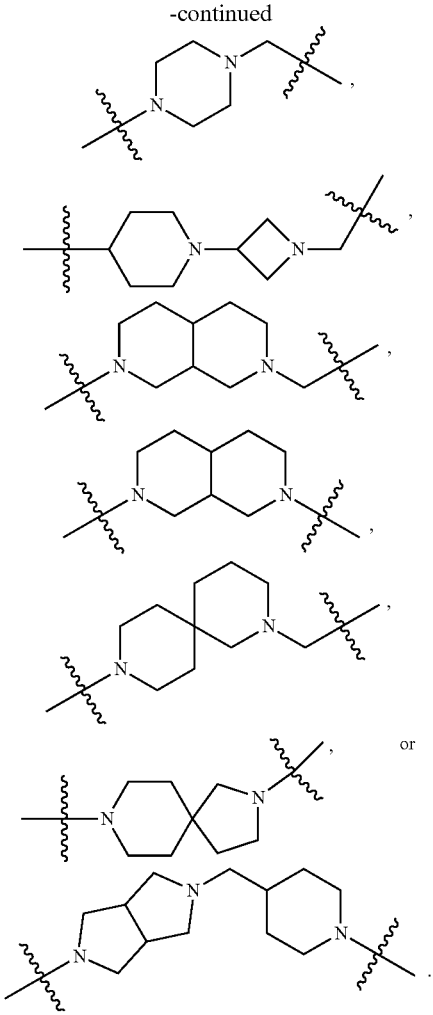

Another aspect of the present invention provides a compound of Formula (I)

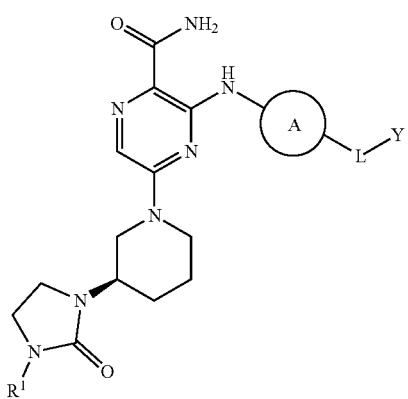

(I)

or a pharmaceutically acceptable salt thereof, wherein $R^1$ is $C_{1-3}$ alkyl; ring A is phenyl, 9-10 membered bicyclic aryl, or 9-10 membered bicyclic heteroaryl having 1-3 heteroatoms independently selected from N, O, or S; L is —$X^1$—$X^2$—$X^3$—$X^4$—$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S wherein the heterocycloalkyl is optionally substituted with —CH$_3$, or 4-6 membered heterocycloalkyl having 1-2 heteroatoms independently selected from N, O, or S wherein the heterocycloalkyl is optionally substituted with —CH$_3$; $X^2$ is a bond, —O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered cycloalkyl, or 4-6 membered heterocycloalkyl having 1-2 heteroatoms independently selected from N, O, or S; $X^3$ is a bond, —C$_{1-4}$ alkyl-, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; $X^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated heterocycle having 1-3 heteroatoms independently selected from N, O, or S; $X^5$ is a bond, —C$_{1-4}$ alkyl-, —N(R)—, or —C(O)—N(R)—; each R is independently —H or —C$_{1-3}$ alkyl; each of m, n, and p is independently an integer from 1 to 3; Y is

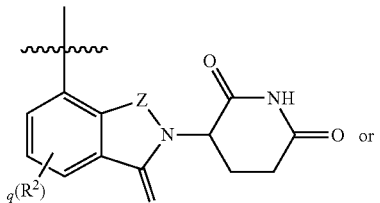

or

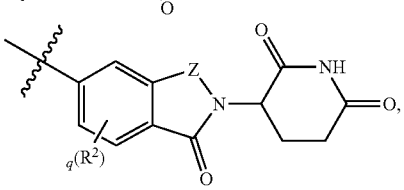

wherein each $R^2$ is independently halo or $C_{1-4}$ alkyl; each Z is —C($R^A$)$_2$— or —C(O)—; each $R^A$ is independently —H or $C_{1-4}$ alkyl; and q is 0, 1, or 2.

In some embodiments, the compound of Formula (I) is a compound of Formula (I-A)

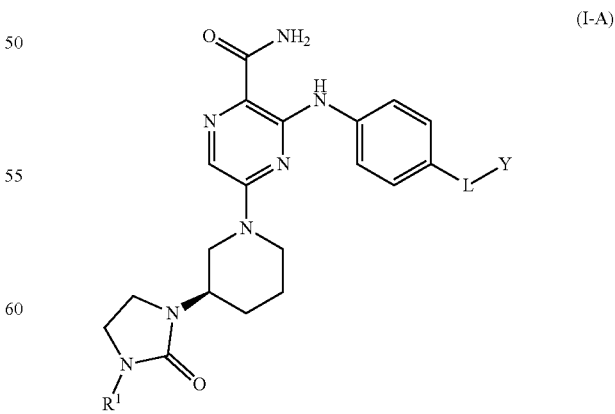

(I-A)

or a pharmaceutically acceptable salt thereof, wherein $R^1$ is $C_{1-3}$ alkyl; L is —$X^1$—$X^2$—$X^3$—$X^4$—$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S wherein the heterocycloalkyl is optionally substituted with —CH$_3$, or 4-6 membered heterocycloalkyl having 1-2 heteroatoms independently selected from N, O, or S wherein the heterocycloalkyl is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered cycloalkyl, or 4-6 membered heterocycloalkyl having 1-2 heteroatoms independently selected from N, O, or S; X$^3$ is a bond, —C$_{1-4}$ alkyl-, 4-6 membered cycloalkyl, —N(R)—, —(O—CH$_2$—CH$_2$)$_p$—, —(CH$_2$—CH$_2$—O)$_p$—, or 4-6 membered heterocycloalkyl having 1-2 heteroatoms independently selected from N, O, or S wherein the heterocycloalkyl is optionally substituted with —CH$_3$; X$^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated heterocycle having 1-3 heteroatoms independently selected from N, O, or S; X$^5$ is a bond, —C$_{1-4}$ alkyl-, —N(R)—, or —C(O)—N(R)—; each R is independently —H or —C$_{1-3}$ alkyl; each of m, n, and p is independently an integer from 1 to 3; Y is or a pharmaceutically acceptable salt thereof, wherein R$^1$ is C$_{1-3}$ alkyl; L is —X$^1$—X$^2$—X$^3$—X$^4$—X$^5$—; X$^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl ring having 1-3 heteroatoms independently selected from N, O, or S wherein the heterocycloalkyl is optionally substituted with —CH$_3$, or 4-6 membered heterocycloalkyl having 1-2 heteroatoms independently selected from N, O, or S wherein the heterocycloalkyl is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered cycloalkyl, or 4-6 membered heterocycloalkyl having 1-2 heteroatoms independently selected from N, O, or S; X$^3$ is a bond, —C$_{1-4}$ alkyl-, 4-6 membered cycloalkyl, —N(R)—, —(O—CH$_2$—CH$_2$)$_p$—, —(CH$_2$—CH$_2$—O)$_p$—, or 4-6 membered heterocycloalkyl having 1-2 heteroatoms independently selected from N, O, or S wherein the heterocycloalkyl is optionally substituted with —CH$_3$; X$^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated heterocycle having 1-3 heteroatoms independently selected from N, O, or S; X$^5$ is a bond, —C$_{1-4}$ alkyl-, —N(R)—, or —C(O)—N(R)—; each R is independently —H or —C$_{1-3}$ alkyl; each of m, n, and p is independently an integer from 1 to 3; Y is

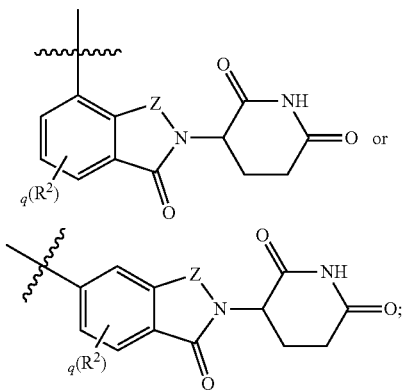
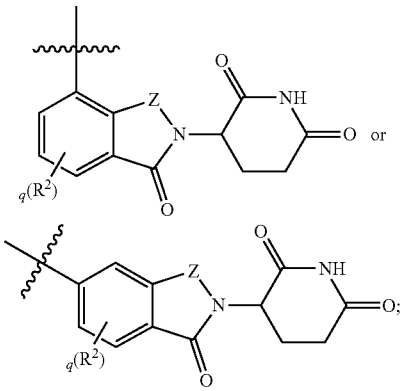

wherein each R$^2$ is independently halo or C$_{1-4}$ alkyl; each Z is —C(R$^A$)$_2$— or —C(O)—; each R$^A$ is independently —H or C$_{1-4}$ alkyl; and q is 0, 1, or 2.

In some embodiments, the compound of Formula (I) is a compound of Formula (I-B)

(I-B)

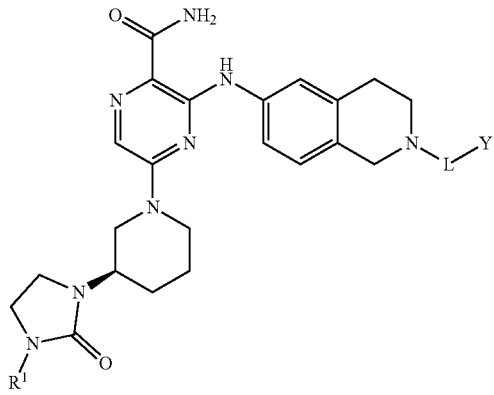

wherein each R$^2$ is independently halo or C$_{1-4}$ alkyl; each Z is —C(R$^A$)$_2$— or —C(O)—; each R$^A$ is independently —H or C$_{1-4}$ alkyl; and q is 0, 1, or 2.

In some embodiments, the compound of Formula (I) is a compound of Formula (II)

(II)

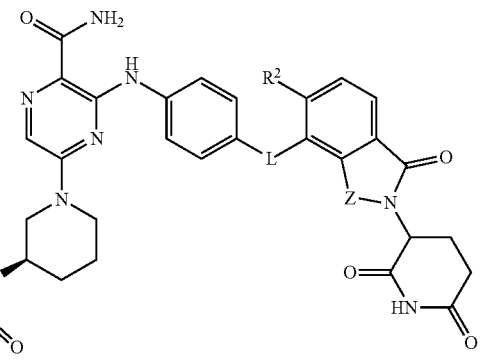

or a pharmaceutically acceptable salt thereof, wherein each of $R^1$, $R^2$, L, and Z are as defined in the compound of Formula (I).

In some embodiments, the compound of Formula (II) is a compound of Formulae (II-A) or (II-B)

cycloalkyl is optionally substituted with —$CH_3$, or 4-6 membered heterocycloalkyl having 1-2 heteroatoms independently selected from N, O, or S wherein the heterocycloalkyl is optionally substituted with —$CH_3$; $X^2$ is a bond or —$C_{1-5}$ alkyl-; $X^3$ is a bond, —$C_{1-4}$ alkyl-, or 4-6 mem-

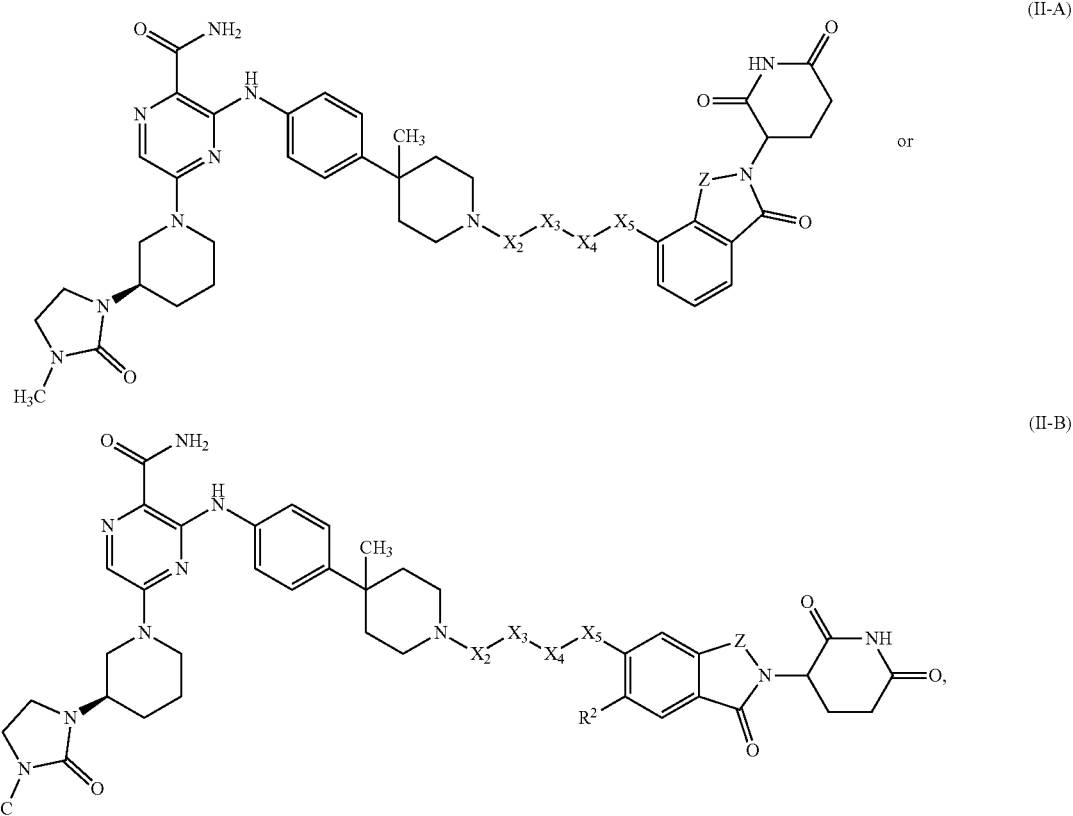

or a pharmaceutically acceptable salt thereof, wherein each of $X^2$, $X^3$, $X^4$, $X^5$ and $R^2$ are as defined in the compound of Formula (I).

In some embodiments, the compound of Formula (I) is a compound of Formula (III)

bered heterocycloalkyl having 1-2 heteroatoms independently selected from N, O, or S wherein the heterocycloalkyl is optionally substituted with —$CH_3$; Y is

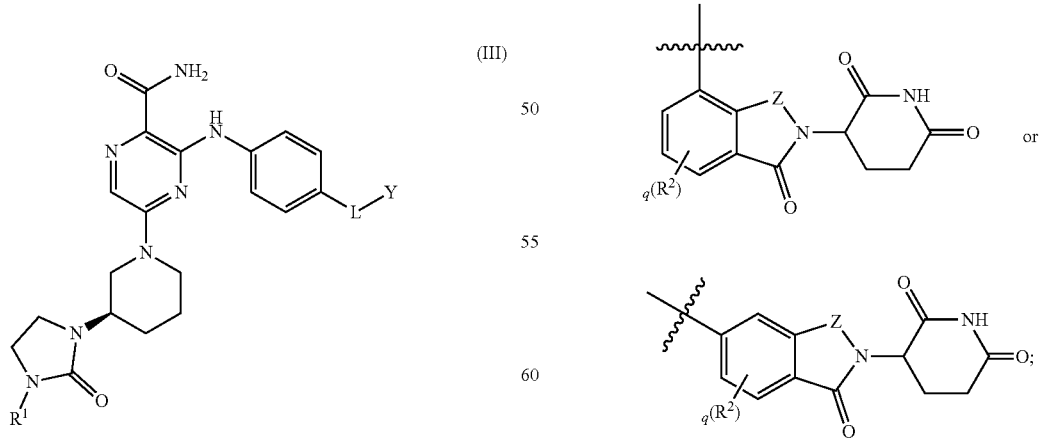

or a pharmaceutically acceptable salt thereof, wherein $R^1$ is $C_{1-3}$ alkyl; L is —$X^1$—$X^2$—$X^3$—; $X^1$ is 7-12 membered spiro bicyclic heterocycloalkyl having 1-3 heteroatoms independently selected from N, O, or S wherein the heterowherein each $R^2$ is independently halo or $C_{1-4}$ alkyl; each Z is —$C(R^4)_2$— or —C(O)—; each $R^4$ is independently —H; and q is 0, 1, or 2.

In some embodiments, the compound of Formula (I) is a compound of Formula (IV)

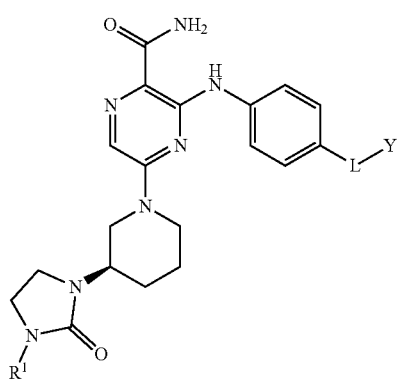

(IV)

or a pharmaceutically acceptable salt thereof, wherein $R^1$ is $C_{1-3}$ alkyl; L is —$X^1$—$X^2$—$X^3$—$X^4$—$X^5$—; $X^1$ is —C(O)—N(R)—, —N(R)—C(O)—, —(O—$CH_2$—$CH_2)_m$—, —O($C_6H_4$)—, —(O—$CH_2$—$CH_2$—$CH_2)_m$—, —$C_{1-5}$ alkyl-, 7-12 membered spiro bicyclic heterocycloalkyl having 1-3 heteroatoms independently selected from N, O, or S wherein the heterocycloalkyl is optionally substituted with —$CH_3$, or 4-6 membered heterocycloalkyl having 1-2 heteroatoms independently selected from N, O, or S wherein the heterocycloalkyl is optionally substituted with —$CH_3$; $X^2$ is a bond, —(O—$CH_2$—$CH_2)_n$—, —($CH_2$—$CH_2$—O)_n—, —N(R)—C(O)—, —N(R)—, —C(O)—, —$C_{1-5}$ alkyl-, 4-6 membered cycloalkyl, or 4-6 membered heterocycloalkyl having 1-2 heteroatoms independently selected from N, O, or S; $X^3$ is a bond, —$C_{1-4}$ alkyl-, 4-6 membered cycloalkyl, —N(R)—, —(O—$CH_2$—$CH_2)_p$—, —($CH_2$—$CH_2$—O)_p—, or 4-6 membered heterocycloalkyl having 1-2 heteroatoms independently selected from N, O, or S wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—$CH_2$—$CH_2)_m$—, or 5-6 membered saturated, partially unsaturated, or fully unsaturated heterocycle having 1-3 heteroatoms independently selected from N, O, or S; $X^5$ is a bond, —$C_{1-4}$ alkyl-, —N(R)—, or —C(O)—N(R)—; each R is independently —H or —$C_{1-3}$ alkyl; each of m, n, and p is independently an integer from 1 to 3; Y is

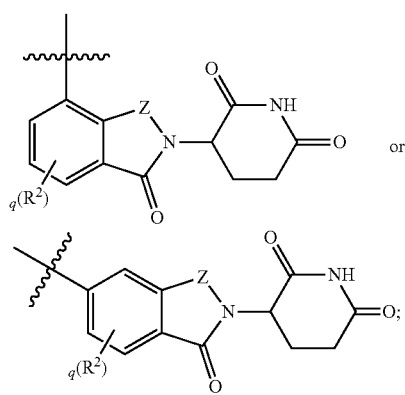

wherein each $R^2$ is independently halo or $C_{1-4}$ alkyl; each Z is —C($R^A$)_2— or —C(O)—; each $R^A$ is independently —H or $C_{1-4}$ alkyl; and q is 0, 1, or 2.

In some embodiments, ring A is selected from

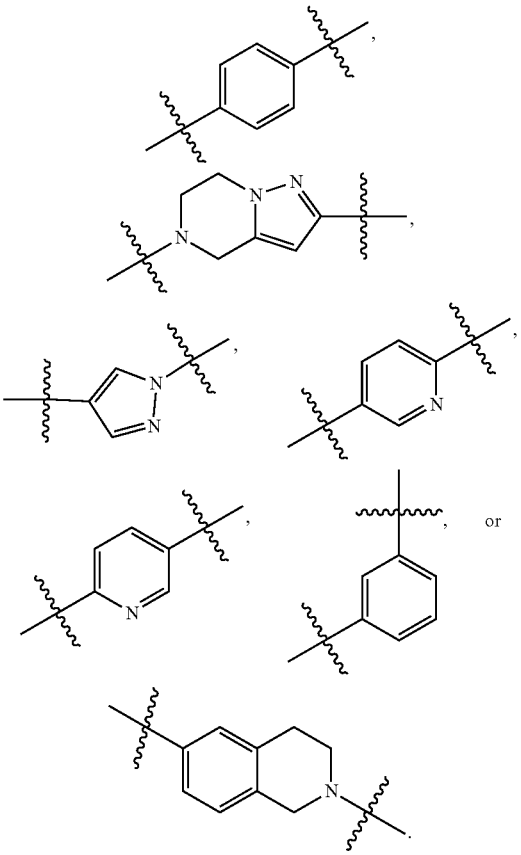

In some embodiments, Z is —CH— or —C(O)—.
In some embodiments, Y is

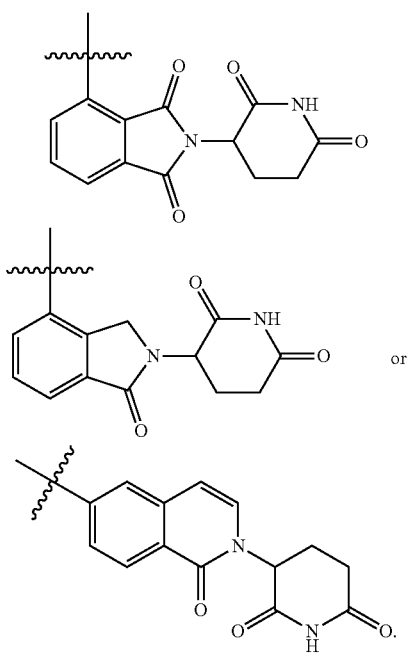

In some embodiments, Y is

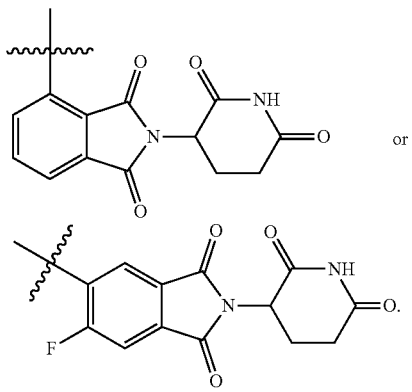 or

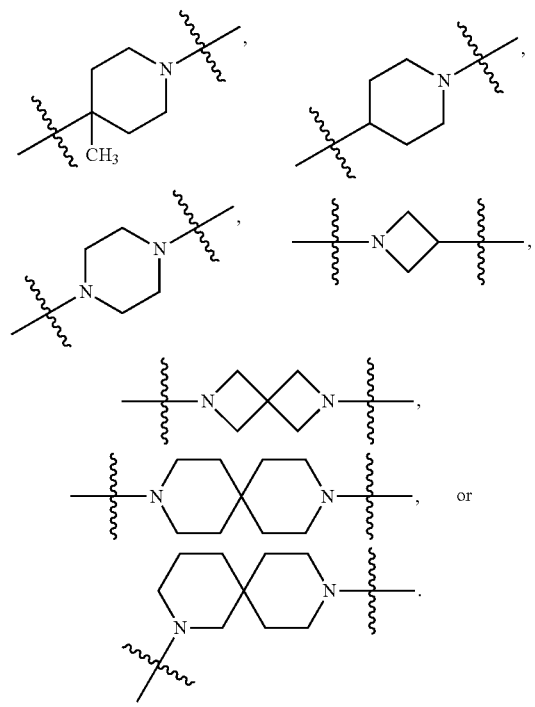

In some embodiments, $R^1$ is methyl, ethyl, or propyl.

In some embodiments, each R is independently —H or —CH$_3$.

In some embodiments, at least one of $X^1$, $X^2$, and $X^5$ is —C(O)—N(R)—. For example, $X^1$ is —C(O)—N(R)—. In other examples, $X^2$ is —(O—CH$_2$—CH$_2$)$_n$—, —(CH$_2$—CH$_2$—O)$_n$—, or —C$_{1-5}$ alkyl-. And, in some examples, $X^3$ is a bond, —C$_{1-4}$ alkyl-, or —N(R)—. In other examples, $X^4$ is a bond or —N(R)—.

In some embodiments, $X^1$ is —(O—CH$_2$—CH$_2$—CH$_2$)$_m$—, m is 1, and $X^2$ is —C(O)—N(R)—.

In some embodiments, $X^3$ is bond, —C$_{1-4}$ alkyl-, 4-6 membered cycloalkyl, or —N(R)—.

In some embodiments, $X^1$ is

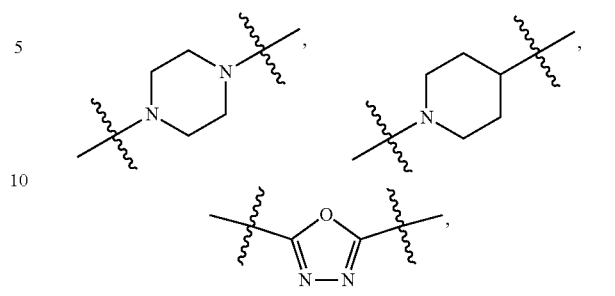

In some of these embodiments, $X^2$ is —C(O)—, —C$_{1-5}$ alkyl-, or 4-6 membered cycloalkyl. And, in some of these embodiments, $X^3$ is a bond, —C$_{1-4}$ alkyl-, or —(CH$_2$—CH$_2$—O)$_p$—.

In some embodiments, $X^4$ is a bond,

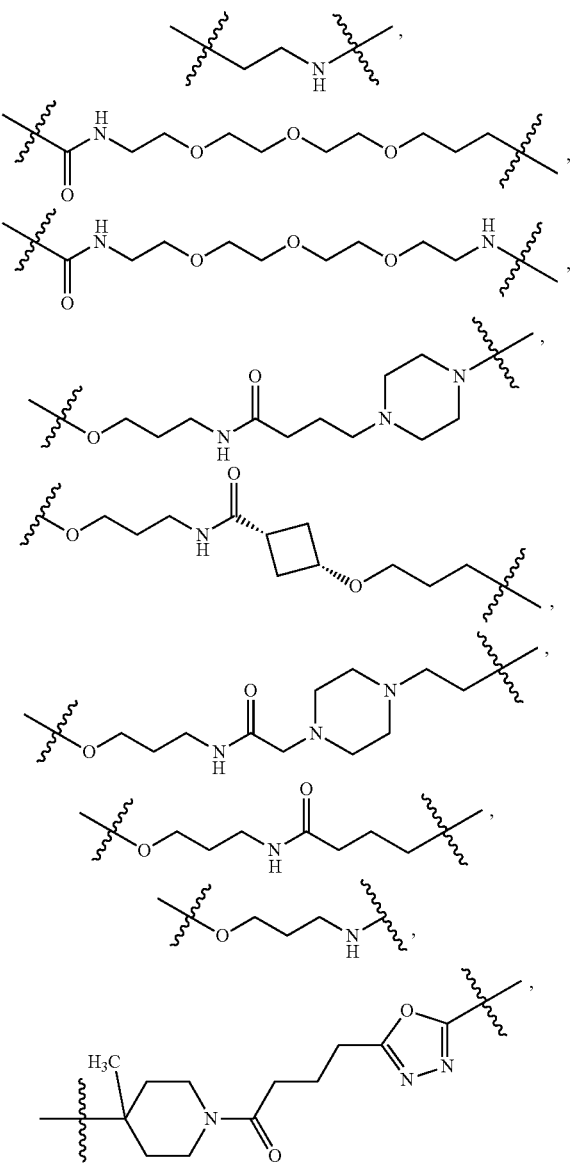

—C$_{1-4}$ alkyl-, —CH$_2$—CH$_2$—N(R)—, or —N(R)—.

In some embodiments, $X^5$ is a bond, —C$_{1-4}$ alkyl-, —N(R)—, or —C(O)—N(R)—.

In some embodiments, L is

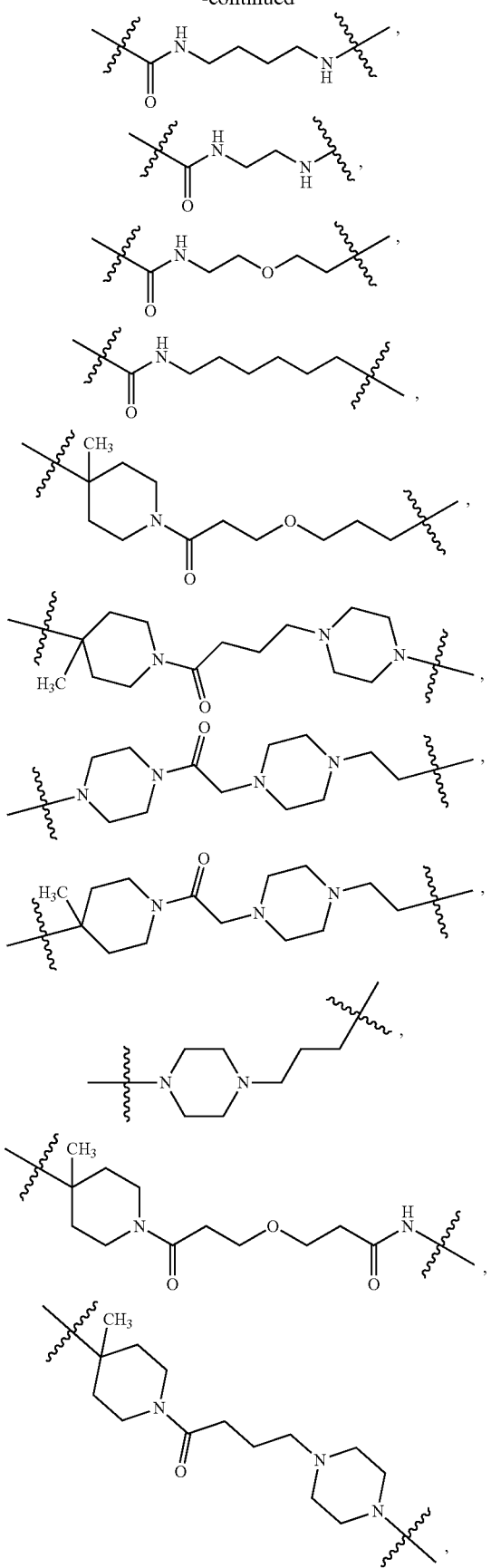
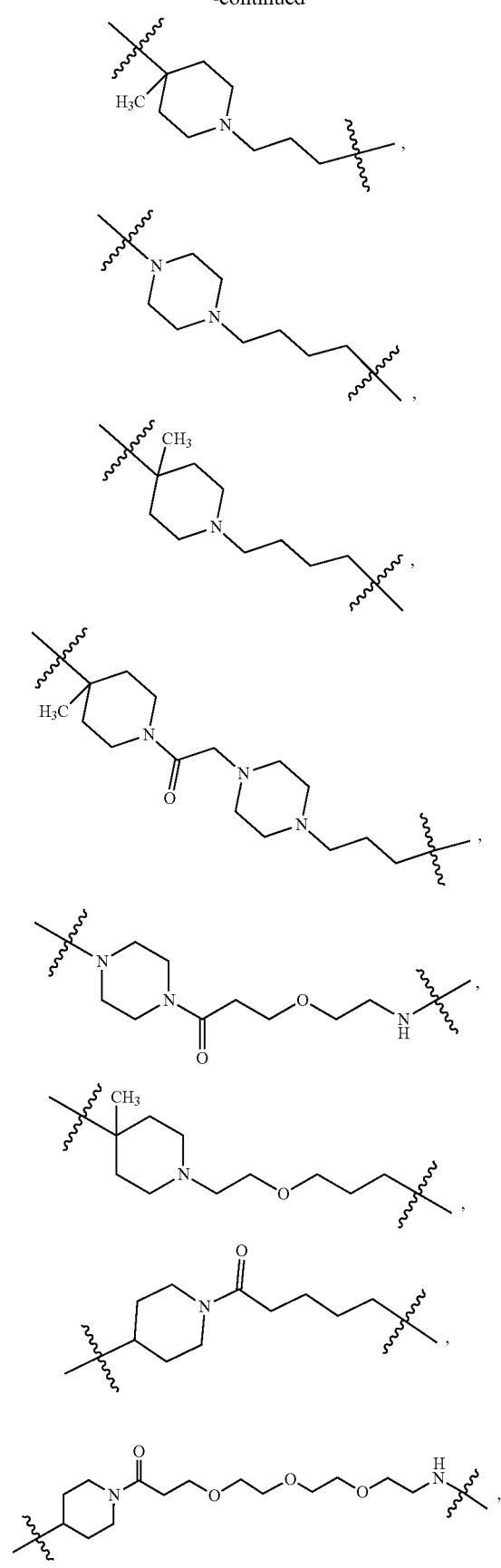

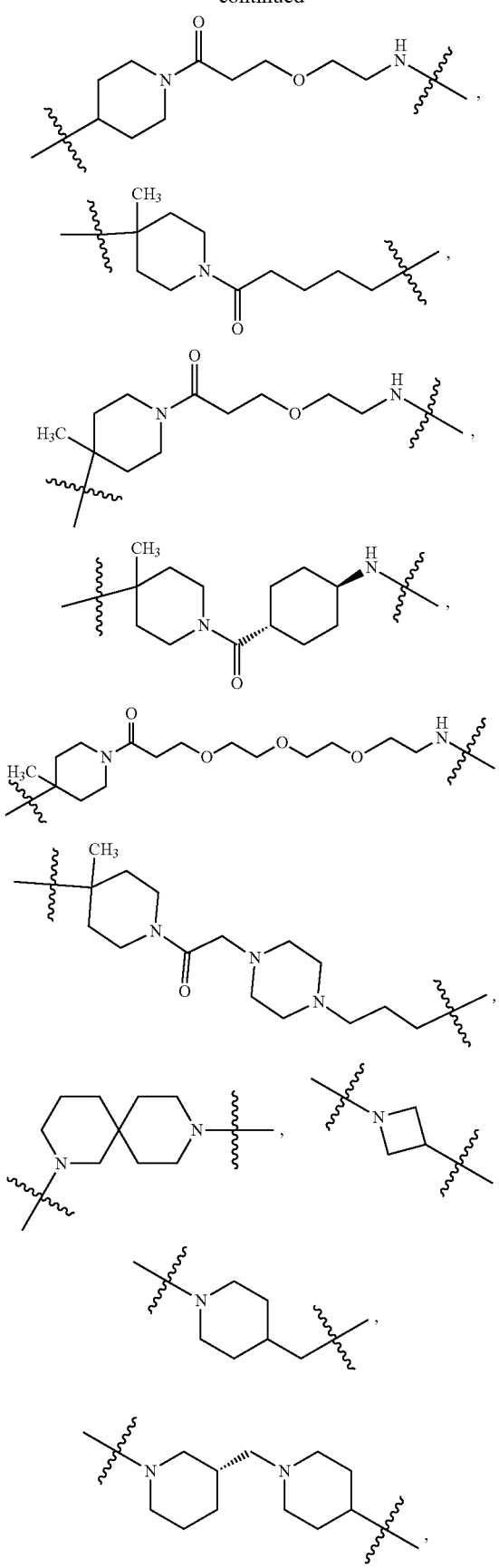
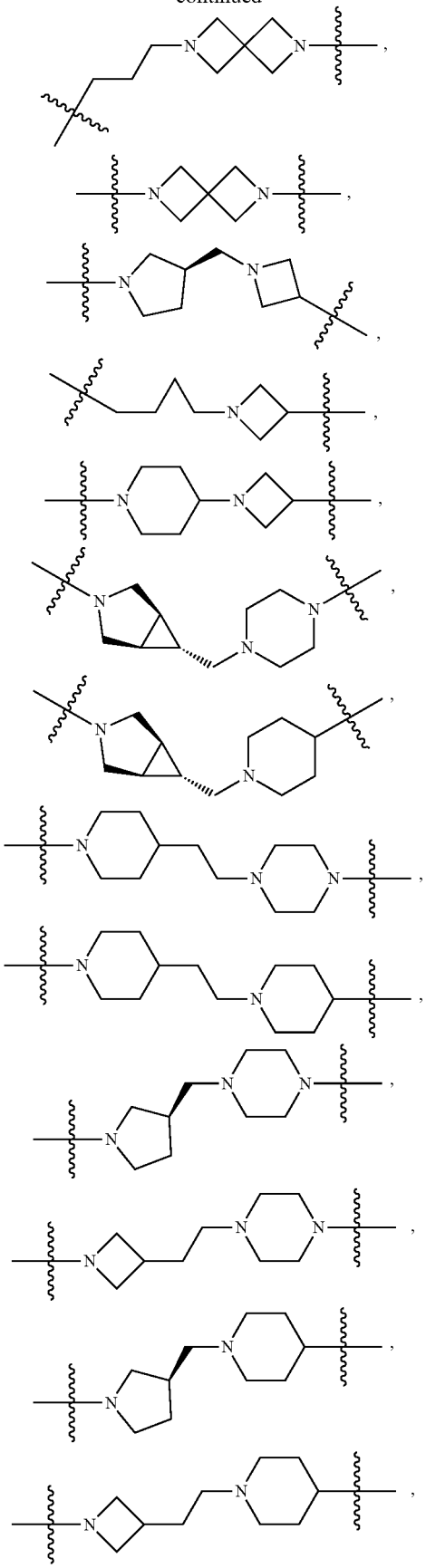

-continued
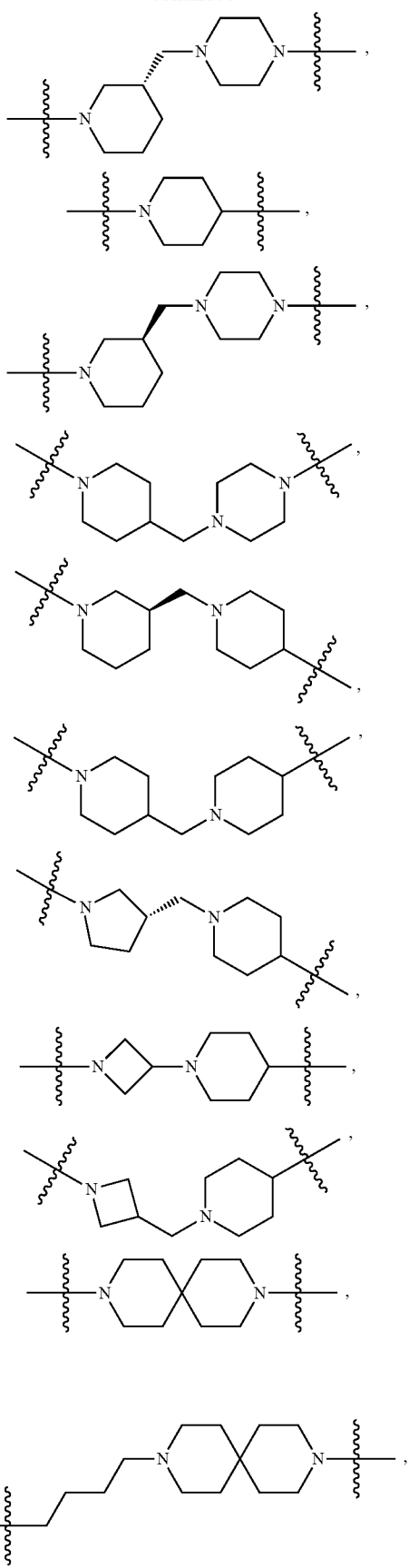
-continued
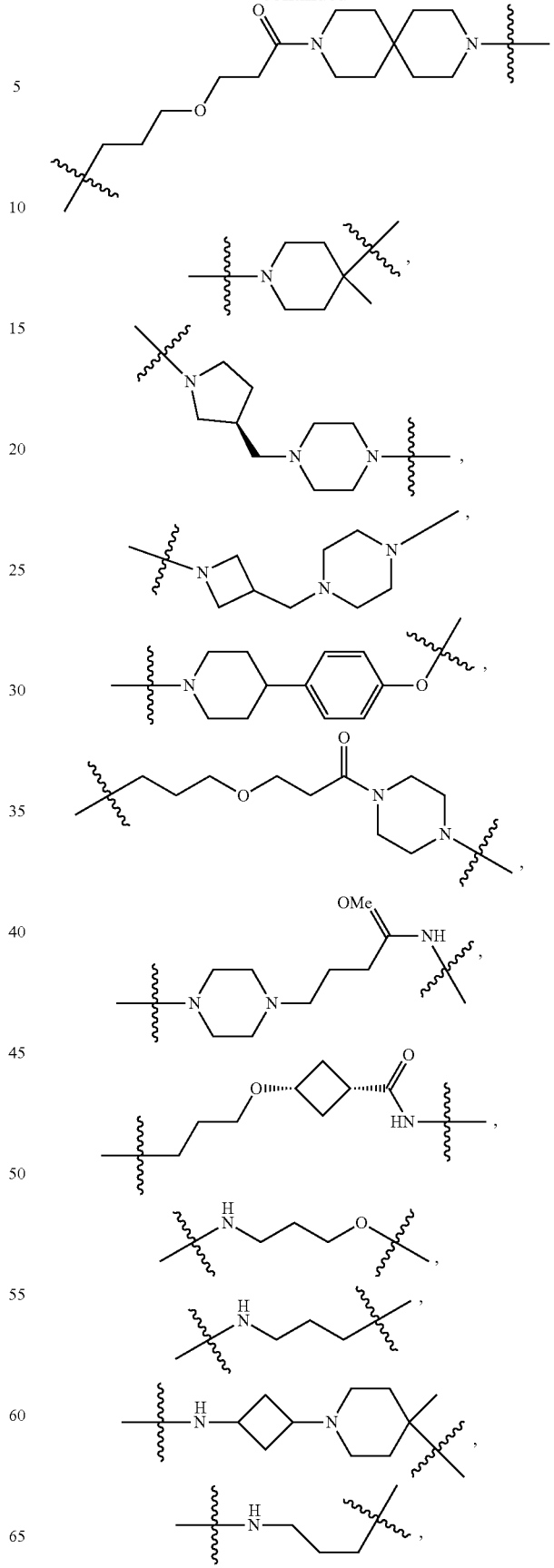

91
-continued
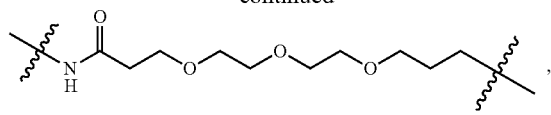
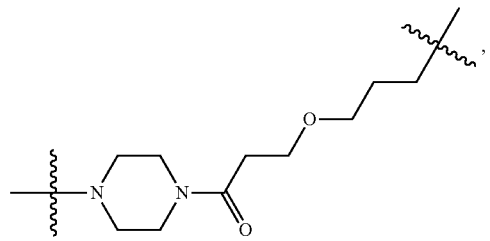
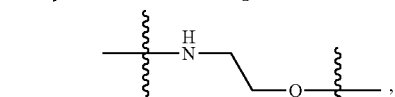
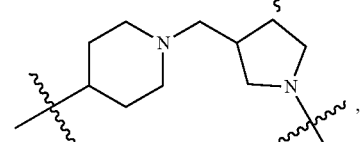
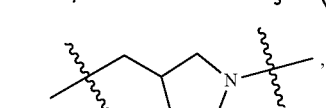
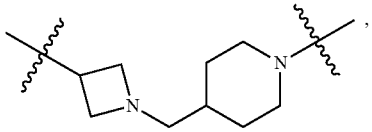
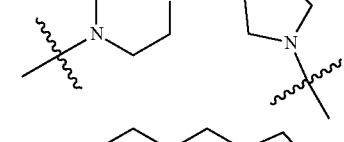
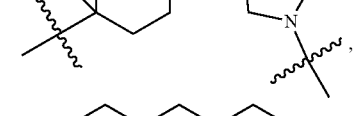
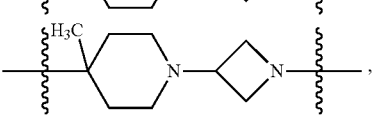
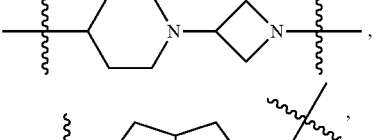
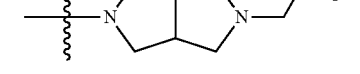
92
-continued
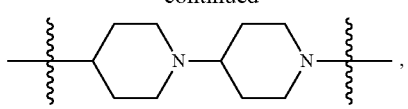
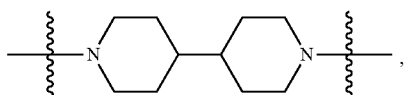
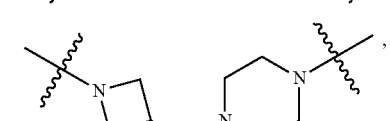
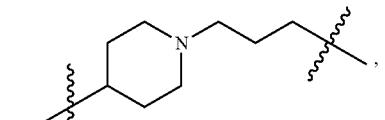
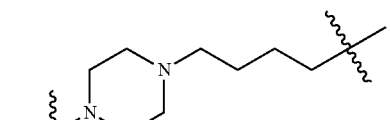
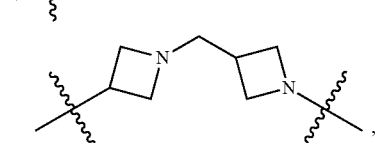
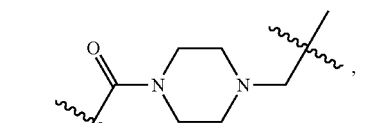
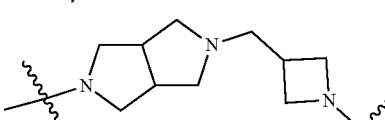
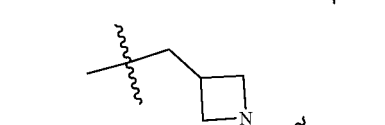
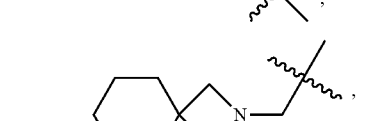
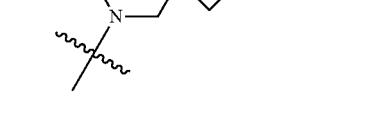
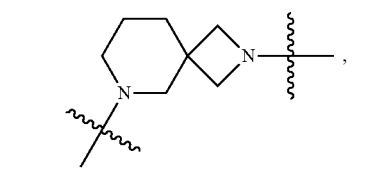

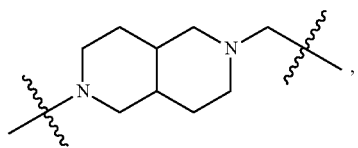,

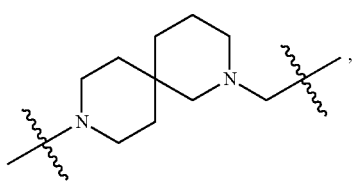, or

,

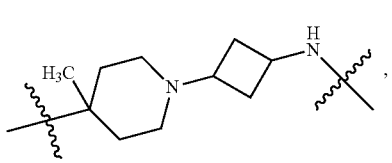,

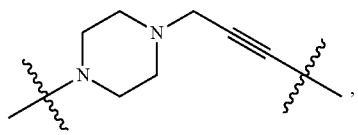,

In some embodiments, the compound of Formula (I) is a compound of Formula (I-A)

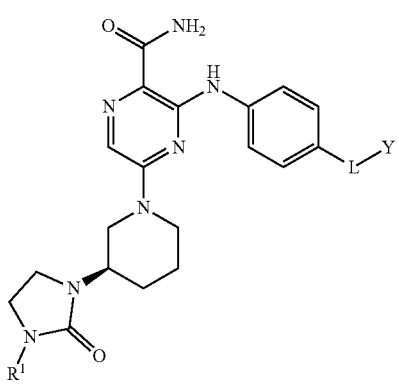

(I-A)

or a pharmaceutically acceptable salt thereof, wherein $R^1$ is $C_{1-3}$ alkyl; L is $-X^1-X^2-X^3-X^4-X^5-$; $X^1$ is $-C(O)-N(R)-$, $-N(R)-C(O)-$, $-(O-CH_2-CH_2)_m-$, $-O(C_6H_4)-$, $-(O-CH_2-CH_2-CH_2)_m-$, $-C_{1-5}$ alkyl-, 7-12 membered spiro bicyclic heterocycloalkyl having 1-3 heteroatoms independently selected from N, O, or S wherein the heterocycloalkyl is optionally substituted with $-CH_3$, or 4-6 membered heterocycloalkyl having 1-2 heteroatoms independently selected from N, O, or S wherein the heterocycloalkyl is optionally substituted with $-CH_3$; $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having 1-2 heteroatoms independently selected from N, O, or S; $X^3$ is a bond, $-C_{1-4}$ alkyl-, 4-6 membered cycloalkyl, $-N(R)-$, $-(O-CH_2-CH_2)_p-$, $-(CH_2-CH_2-O)_p-$, or 4-6 membered heterocycloalkyl having 1-2 heteroatoms independently selected from N, O, or S wherein the heterocycloalkyl is optionally substituted with $-CH_3$; $X^4$ is a bond, $-CH_2-CH_2-N(R)-$, $-N(R)-$, $-C_{1-4}$ alkyl-, $-(O-CH_2-CH_2-CH_2)_m-$, or 5-6 membered saturated, partially unsaturated, or fully unsaturated heterocycle having 1-3 heteroatoms independently selected from N, O, or S; $X^5$ is a bond, —$C_{1-4}$ alkyl-, —N(R)—, or —C(O)—N(R)—; each R is independently —H or —$C_{1-3}$ alkyl; each of m, n, and p is independently an integer from 1 to 3; Y is

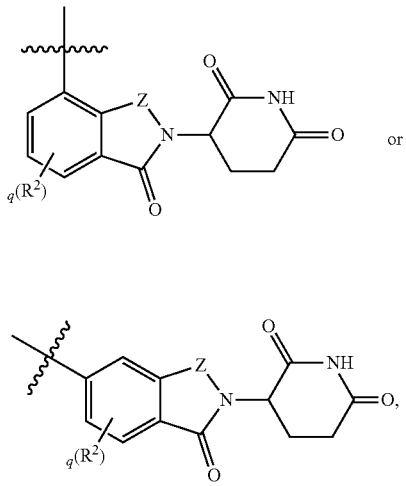
or

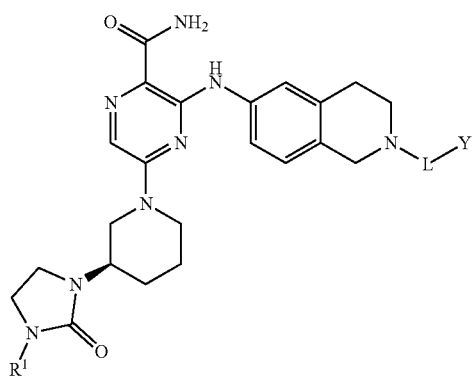

wherein each $R^2$ is independently halo or $C_{1-4}$ alkyl; each Z is —C($R^A$)$_2$— or —C(O)—; each $R^A$ is independently —H or $C_{1-4}$ alkyl; and q is 0, 1, or 2.

In some embodiments, the compound of Formula (I) is a compound of Formula (I-B)

(I-B)

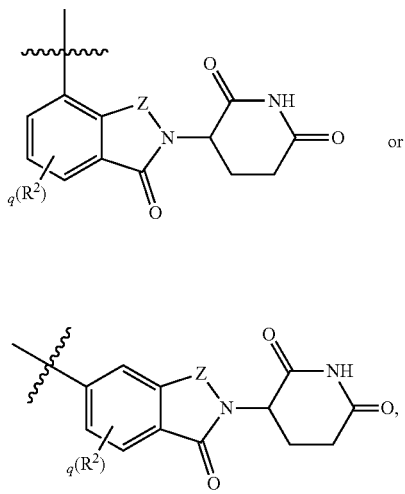

or a pharmaceutically acceptable salt thereof, wherein $R^1$ is $C_{1-3}$ alkyl; L is —$X^1$—$X^2$—$X^3$—$X^4$—$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —$C_{1-5}$ alkyl-, 7-12 membered spiro bicyclic heterocycloalkyl ring having 1-3 heteroatoms independently selected from N, O, or S wherein the heterocycloalkyl is optionally substituted with —CH$_3$, or 4-6 membered heterocycloalkyl having 1-2 heteroatoms independently selected from N, O, or S wherein the heterocycloalkyl is optionally substituted with —CH$_3$; $X^2$ is a bond, —(O—CH$_2$—CH$_2$)$_n$—, —(CH$_2$—CH$_2$—O)$_n$—, —N(R)—C(O)—, —N(R)—, —C(O)—, —$C_{1-5}$ alkyl-, 4-6 membered cycloalkyl, or 4-6 membered heterocycloalkyl having 1-2 heteroatoms independently selected from N, O, or S; $X^3$ is a bond, —$C_{1-4}$ alkyl-, 4-6 membered cycloalkyl, —N(R)—, —(O—CH$_2$—CH$_2$)$_p$—, —(CH$_2$—CH$_2$—O)$_p$—, or 4-6 membered heterocycloalkyl having 1-2 heteroatoms independently selected from N, O, or S wherein the heterocycloalkyl is optionally substituted with —CH$_3$; $X^4$ is a bond, —CH$_2$—CH$_2$—N(R)—, —N(R)—, —$C_{1-4}$ alkyl-, —(O—CH$_2$—CH$_2$—CH$_2$)$_m$—, or 5-6 membered saturated, partially unsaturated, or fully unsaturated heterocycle having 1-3 heteroatoms independently selected from N, O, or S; $X^5$ is a bond, —$C_{1-4}$ alkyl-, —N(R)—, or —C(O)—N(R)—; each R is independently —H or —$C_{1-3}$ alkyl; each of m, n, and p is independently an integer from 1 to 3; Y is

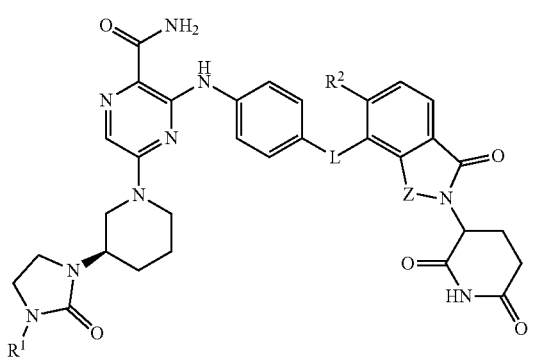

wherein each $R^2$ is independently halo or $C_{1-4}$ alkyl; each Z is —C($R^A$)$_2$— or —C(O)—; each $R^A$ is independently —H or —$C_{1-4}$ alkyl; and q is 0, 1, or 2.

In some embodiments, the compound of Formula (I) is a compound of Formula (II)

(II)

or a pharmaceutically acceptable salt thereof, wherein each of $R^1$, $R^2$, L, and Z are as defined herein for the compound of Formula (I), (I-A), or (I-B).

In some embodiments, the compound of Formula (I) is a compound of Formulae (II-A) or (II-B)

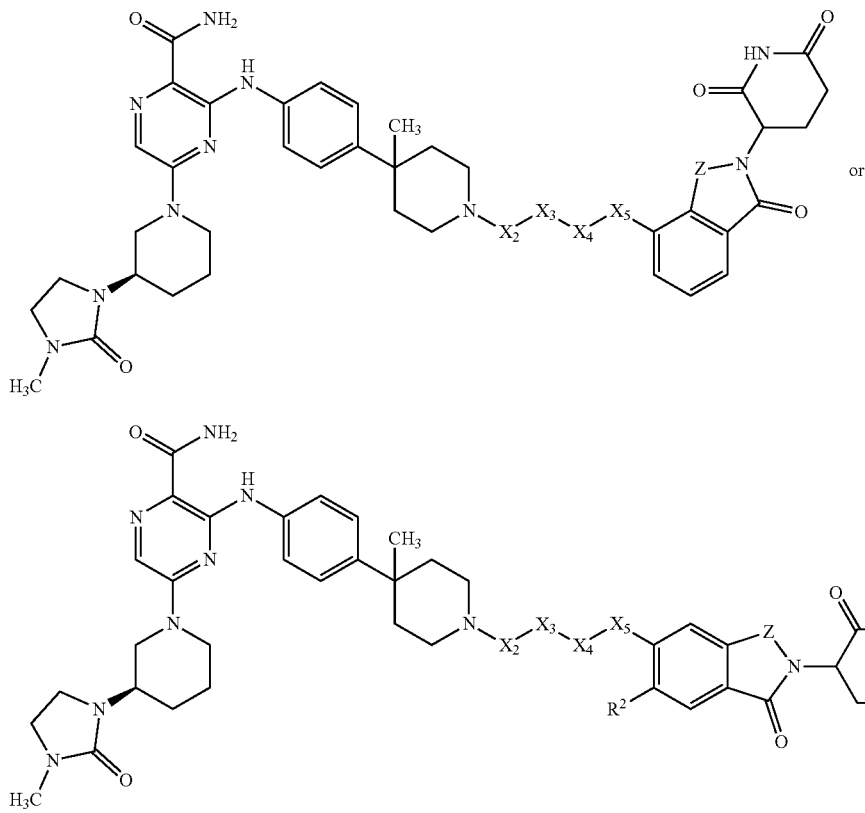

or a pharmaceutically acceptable salt thereof, wherein each of $X^2$, $X^3$, $X^4$, and $X^5$ are as defined herein for the compound of Formula (I), (I-A), or (I-B).

In some embodiments, the compound of Formula (I) is a compound of Formula (III)

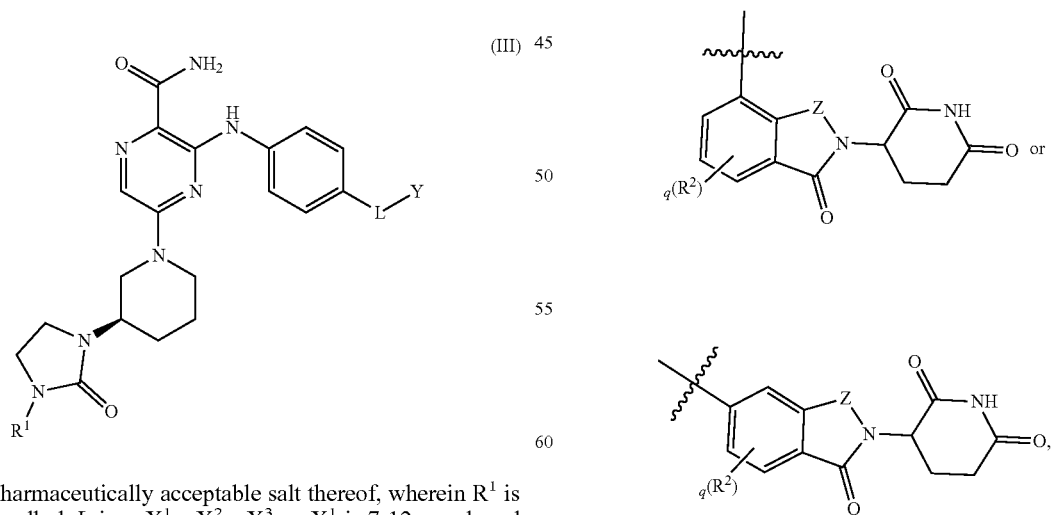

or a pharmaceutically acceptable salt thereof, wherein $R^1$ is —$C_{1-3}$ alkyl; L is —$X^1$—$X^2$—$X^3$—; $X^1$ is 7-12 membered spiro bicyclic heterocycloalkyl having 1-3 heteroatoms independently selected from N, O, or S wherein the heterocycloalkyl is optionally substituted with —$CH_3$, or 4-6 membered heterocycloalkyl having 1-2 heteroatoms independently selected from N, O, or S wherein the heterocycloalkyl is optionally substituted with —$CH_3$; $X^2$ is a bond or —$C_{1-5}$ alkyl-; $X^3$ is a bond, —$C_{1-4}$ alkyl-,4-6 membered heterocycloalkyl having 1-2 heteroatoms independently selected from N, O, or S wherein the heterocycloalkyl is optionally substituted with —$CH_3$; Y is wherein each $R^2$ is independently halo or —$C_{1-4}$ alkyl; each Z is —$C(R^4)_2$— or —$C(O)$—; each $R^4$ is independently —H; and q is 0, 1, or 2.

In some embodiments, the compound of Formula (I) is a compound of Formula (IV)

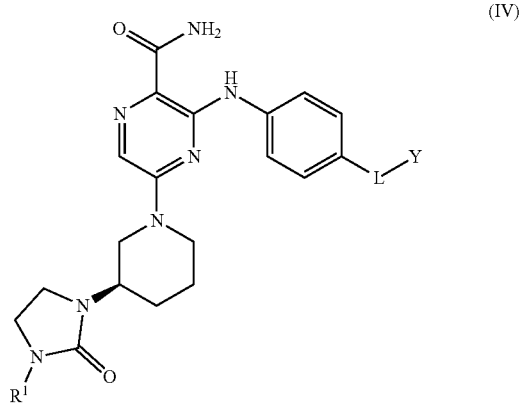

(IV)

or a pharmaceutically acceptable salt thereof, wherein $R^1$ is $C_{1-3}$ alkyl; L is $-X^1-X^2-X^3-X^4-X^5-$; $X^1$ is $-C(O)-N(R)-$, $-N(R)-C(O)-$, $-O-CH_2-CH_2)_m-$, $-O(C_6H_4)-$, $-(O-CH_2-CH_2-CH_2)_m-$, $-C_{1-5}$ alkyl-, 7-12 membered spiro bicyclic heterocycloalkyl having 1-3 heteroatoms independently selected from N, O, or S wherein the heterocycloalkyl is optionally substituted with $-CH_3$, or 4-6 membered heterocycloalkyl having 1-2 heteroatoms independently selected from N, O, or S wherein the heterocycloalkyl is optionally substituted with $-CH_3$; $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having 1-2 heteroatoms independently selected from N, O, or S; $X^3$ is a bond, $-C_{1-4}$ alkyl-, 4-6 membered cycloalkyl, $-N(R)-$, $-(O-CH_2-CH_2)_p-$, $-(CH_2-CH_2-O)_p-$, or 4-6 membered heterocycloalkyl having 1-2 heteroatoms independently selected from N, O, or S wherein the heterocycloalkyl is optionally substituted with $-CH_3$; $X^4$ is a bond, $-CH_2-CH_2-N(R)-$, $-N(R)-$, $-C_{1-4}$ alkyl-, $-(O-CH_2-CH_2-CH_2)_m-$, or 5-6 membered saturated, partially unsaturated, or fully unsaturated heterocycle having 1-3 heteroatoms independently selected from N, O, or S; $X^5$ is a bond, $-C_{1-4}$ alkyl-, $-N(R)-$, or $-C(O)-N(R)-$; each R is independently $-H$ or $-C_{1-3}$ alkyl; each of m, n, and p is independently an integer from 1 to 3; Y is

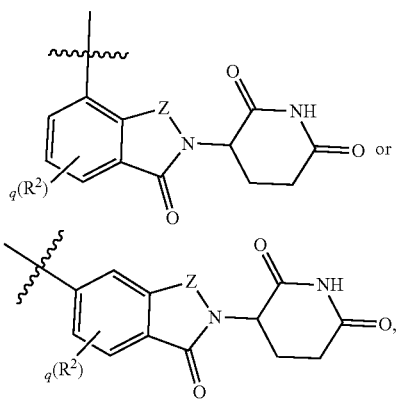

wherein each $R^2$ is independently halo or $C_{1-4}$ alkyl; each Z is $-C(R^4)_2-$ or $-C(O)-$; each $R^4$ is independently $-H$ or $-C_{1-4}$ alkyl; and q is 0, 1, or 2.

The present invention also provides a method of treating a disease or disorder mediated by BTK, comprising administering to a patient or biological sample a compound of Formula (A) or pharmaceutically acceptable salt thereof, or a pharmaceutical composition as described herein, wherein each of the variables contained therein are defined herein.

The present invention also provides a method of synthesizing a compound of Formula (A) or a pharmaceutically acceptable salt thereof.

DETAILED DESCRIPTION

The present invention provides bifunctional compounds that induce the proteolytic degradation of BTK via a ubiquitin proteolysis pathway. The present invention also provides a compound of Formula (A) or a pharmaceutically acceptable salt thereof.

As used herein, the following definitions shall apply unless otherwise indicated.

I. DEFINITIONS

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis," 4th Ed, Wuts, P.G.M. and Greene, T.W., Wiley-Interscience, New York: 2006.

As described herein, compounds of the invention optionally may be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, and alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic) carbonyl, (cycloaliphatic)carbonyl, or (heterocycloaliphatic) carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic) alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heterocarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino." These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl," "aralkoxy," or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused, bridged, or spiro) (e.g., 5- to 10-membered mono- or bicyclic) saturated ring structure, in which one or more of the ring atoms is a heteroatom (e.g., N, O, S, or combinations thereof). Non-limiting examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, decahydro-2,7-naphthyridine, 2,8-diazaspiro[4.5]decane, 2,7-diazaspiro[3.5]nonane, octahydropyrrolo[3,4-c]pyrrole, octahydro-1H-pyrrolo[3,4-b]pyridine, and 2,6-dioxa-tricyclo[3.3.1.0$^{3,7}$]nonyl. A monocyclic heterocycloalkyl group can be fused with a phenyl moiety to form structures, such as tetrahydroisoquinoline, that would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic) carbonylamino, (aryl)carbonylamino, (araliphatic)carbonylamino, (heterocycloaliphatic)carbonylamino, ((heterocycloaliphatic) aliphatic)carbonylamino, (heteroaryl) carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl. Other examples of heteroaryls include 1,2,3,4-tetrahydroisoquinoline and 4,5,6,7-tetrahydropyrazolo[1,5-a]pyrazine.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

As used herein, a "heteroaraliphatic" (such as a heteroaralkyl group) refers to an aliphatic group (e.g., a $C_{1-4}$ alkyl group) that is substituted with a heteroaryl group. "Aliphatic," "alkyl," and "heteroaryl" have been defined above.

As used herein, a "heteroaralkyl" group refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1] octyl, bicyclo[2.2.2]octyl, bicyclo[3.3.1]nonyl, bicyclo [3.3.2]decyl, 2-oxabicyclo[2.2.2]octyl, 1-azabicyclo[2.2.2] octyl, 3-azabicyclo[3.2.1]octyl, and 2,6-dioxa-tricyclo $[3.3.1.0^{3,7}]$nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—

O—$R^Z$, wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —$COOR^X$, —OC(O)H, —OC(O)$R^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —O—$S(O)_2$—$NR^YR^Z$ wherein $R^Y$ and $R^Z$ have been defined above.

As used herein, a "sulfonamide" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include aliphatic-S—, cycloaliphatic-S—, aryl-S—, or the like.

As used herein a "sulfinyl" group refers to —S(O)—$R^X$ when used terminally and —S(O)— when used internally, wherein $R^X$ has been defined above. Examples of sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —$S(O)_2$—$R^X$ when used terminally and —$S(O)_2$— when used internally, wherein $R^X$ has been defined above. Examples of sulfonyl groups include aliphatic-$S(O)_2$—, aryl-$S(O)_2$—, (cycloaliphatic(aliphatic))-$S(O)_2$—, cycloaliphatic-$S(O)_2$—, heterocycloaliphatic-$S(O)_2$—, heteroaryl-$S(O)_2$—, (cycloaliphatic(amido(aliphatic)))-$S(O)_2$— or the like.

As used herein, a "sulfoxy" group refers to —O—S(O)—$R^X$ or —S(O)—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, the term "phospho" refers to phosphinates and phosphonates. Examples of phosphinates and phosphonates include —P(O)($R^P$)$_2$, wherein $R^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure ($R^X$)$_2$N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidine" group refers to the structure —N=C(N($R^XR^Y$))N($R^XR^Y$) or —$NR^X$—C(=$NR^X$)$NR^XR^Y$ wherein $R^X$ and $R^Y$ have been defined above.

As used herein, the term "amidino" group refers to the structure —C=($NR^X$)N($R^XR^Y$) wherein $R^X$ and $R^Y$ have been defined above.

As used herein, the term "vicinal" generally refers to the placement of substituents on a group that includes two or more carbon atoms, wherein the substituents are attached to adjacent carbon atoms.

As used herein, the term "geminal" generally refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl, is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[$CH_2$]$_v$—, where v is 1-12. A branched aliphatic chain is a straight aliphatic chain that is substituted with one or more aliphatic groups. A branched aliphatic chain has the structure —[CQQ]$_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used herein interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables R, $R^1$, $R^2$, L, Y, and Z, and other variables contained in Formula (A), (B), (C), (D), (E), (F), (G), (H), (J), (K), (M), (X), (I), (I-A), (I-B), (II), (II-A), (II-B), (III), and (IV) described herein encompass specific groups, such as alkyl and aryl. Unless otherwise noted, each of the specific groups for the variables R, $R^{10}$, $R^4$, $R^1$, $R^2$, L, $L^1$, D, W, E, V, G, Y, and Z, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl) carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

As used herein, the term "substituted," whether preceded by the term "optionally" or not, refers generally to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. Non-limiting examples of spiro heterocycloalkyls include

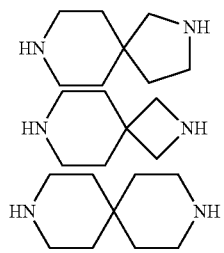

2,8-diazaspiro[4.5]decane; 2,7-diazaspiro[3.5]nonane; 3,9-diazaspiro[5.5]undecane;

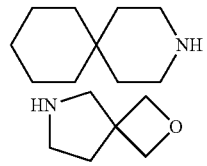

3-azaspiro[5.5]undecane; and 2-oxa-6-azaspiro[3.4]octane.

As one of ordinary skill in the art will recognize, combinations of substituents envisioned by this invention are those combinations that result in the formation of stable or chemically feasible compounds.

As used herein, the phrase "stable or chemically feasible" refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein also are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein also are meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

It is noted that the use of the descriptors "first," "second," "third," or the like is used to differentiate separate elements (e.g., solvents, reaction steps, processes, reagents, or the like) and may or may not refer to the relative order or relative chronology of the elements described.

II. BIFUNCTIONAL COMPOUNDS OF THE PRESENT INVENTION

The present invention provides bifunctional compounds that induce the proteolytic degradation of targeted BTK via a ubiquitin proteosome pathway. Certain compounds of the invention also degrade the ubiquitin ligase (e.g., E3 ligase).

A. Bifunctional Compounds

The present invention provides a compound of Formula (A)

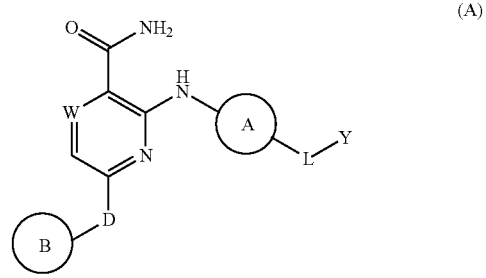

or a pharmaceutically acceptable salt thereof, wherein W is CH or N; D is a bond or —NH—; ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S, wherein ring A is optionally and independently substituted with up to 3 substituents selected from halo, —CN, —COOH, NH$_2$, and optionally substituted C$_{1-6}$ alkyl; ring B is a phenyl, a 5-6 membered heteroaryl, a 4-6 membered heterocycloalkyl, or a 8-10 membered (e.g., 8-9 membered or 9-10 membered) spiro bicyclic heterocycle, wherein ring B is optionally substituted, and wherein the heteroaryl and heterocycloalkyl of ring B has 1-3 heteroatoms independently selected from N, O, or S; L is —$X^1$—$X^2$—$X^3$—$X^4$—$X^5$—; $X^1$ is a bond, —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-8}$ alkyl-, —C≡C—, 4-6 membered cycloalkyl, —N(R)—, —N(R)—C(O)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—$CH_2$—$CH_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S; $X^5$ is a bond, —$C_{1-4}$ alkyl-, —N(R)—, —O—, —C(O)—, or —C(O)—N(R)—; each R is independently —H or —$C_{1-3}$ alkyl (e.g., methyl, ethyl, propyl, or isopropyl); and each of m, n, and p is independently an integer from 1 to 3 (e.g., 1, 2, or 3); and Y is

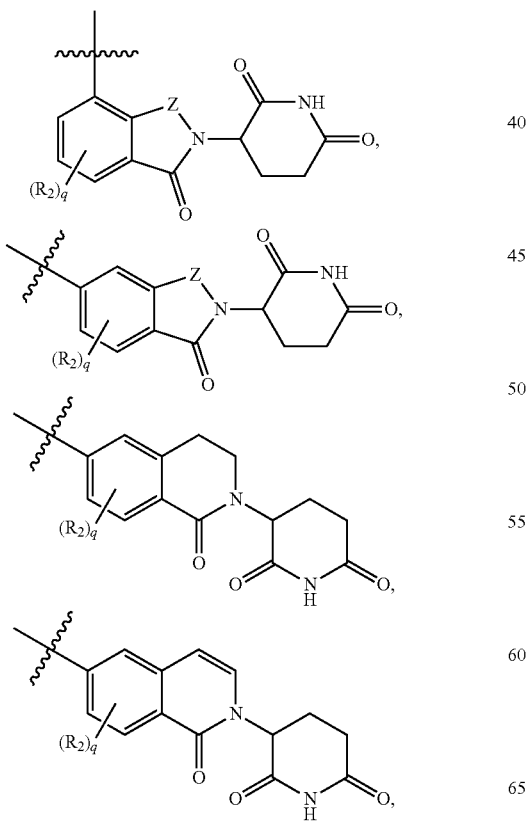

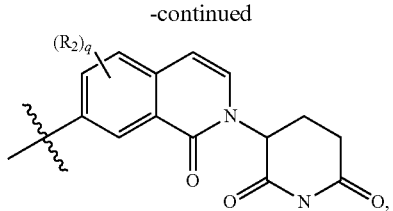

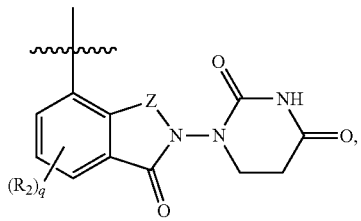

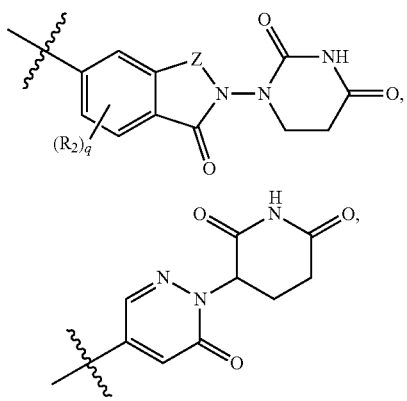

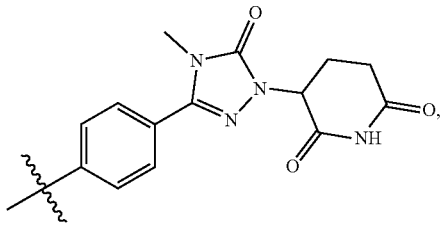

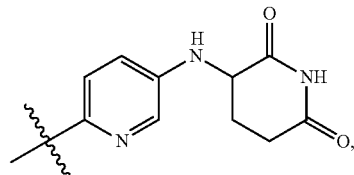

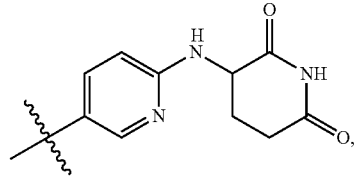

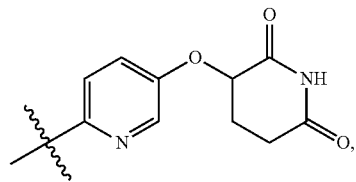

113
-continued

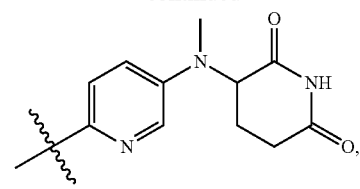

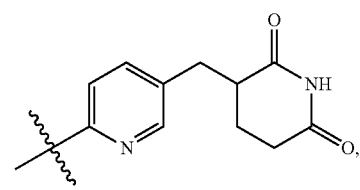

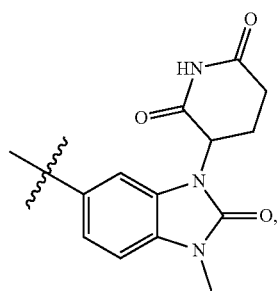

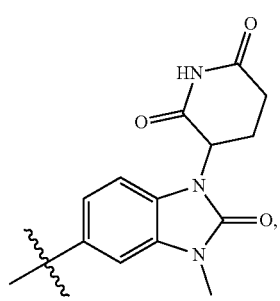

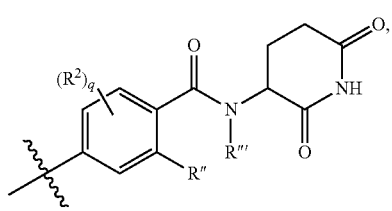

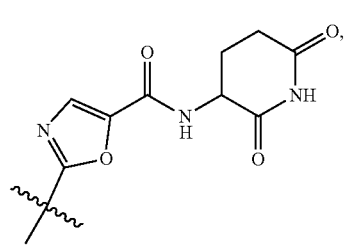

114
-continued

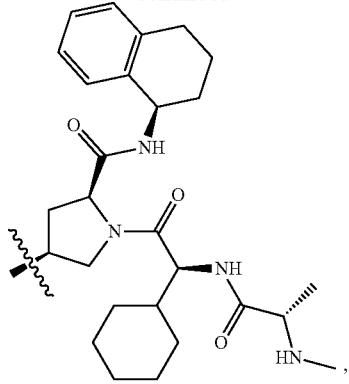

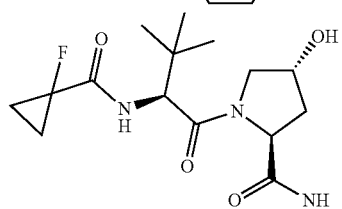

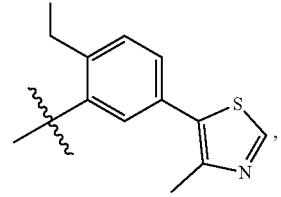

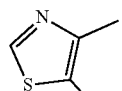 or

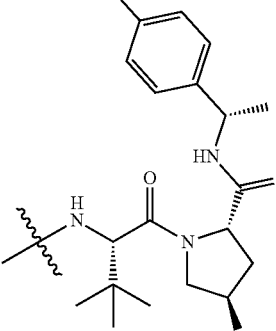

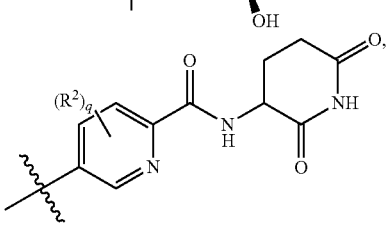

wherein each $R^2$ is independently halo, —CN, or —$C_{1-4}$ alkyl, wherein each $C_{1-4}$ alkyl is optionally and independently substituted with up to three instances of halo, —CN, —COOH, —COONH$_2$, —NH$_2$, or —CF$_3$; each R" and R'" are independently H or, together with the atoms to which they are attached, form a 5-6 membered partially unsaturated or fully unsaturated benzofuzed heterocycle; each Z is —C(R$^A$)$_2$— or —C(O)—; each R$^A$ is independently —H or —C$_{1-4}$ alkyl; and q is 0, 1, or 2.

With the exception of the moieties of group R, all moieties of the linking group L as defined in the compound of Formula (A) are bivalent moieties unless otherwise specified. For example any alkyl (e.g., n-propyl, n-butyl, n-hexyl, and the like), aryl (e.g., phenyl), cycloalkyl (e.g., cyclopropyl, cyclohexyl, and the like), aryl, heteroaryl, heterocylcoalkyl (e.g., piperidine, piperazine, and the like) that is present in L is bivalent unless otherwise specified.

In some embodiments, ring B is an optionally substituted 5-6 membered heterocycloalkyl having 1-2 nitrogen atoms. For example, ring B is piperidine-yl, piperizine-yl, or pyrrolidine-yl, any of which is optionally substituted.

In some embodiments, ring B is an optionally substituted 5-6 membered heteroaryl having 1-2 heteroatoms independently selected from N and S. For example, ring B is pyridine-yl, pyrazine-yl, or pyrimidine, any of which is optionally substituted.

In some embodiments, ring B is

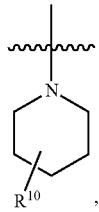

wherein $R^{10}$ is halo, —H, —$C_{1-5}$ alkyl (e.g., —$C_{1-3}$ alkyl), -3-6 membered cycloalkyl, 5-6 membered heterocycloalkyl, —CN, —OH, —$CF_3$, —$CH_2OH$, —$CH_2CH_2OH$, —C(O)OH,

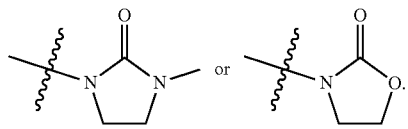

In some embodiments, ring B is

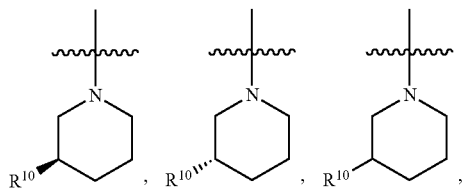

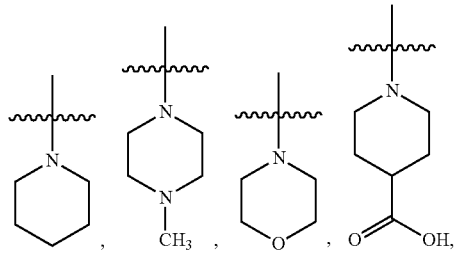

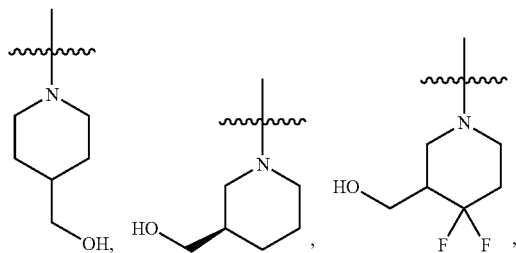

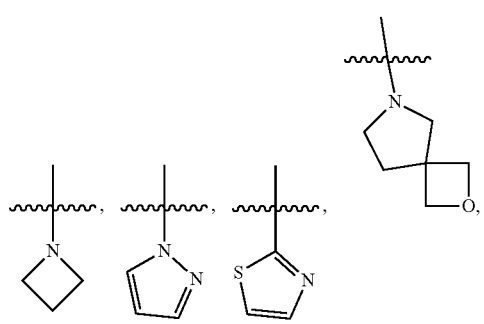

wherein $R^{10}$ is

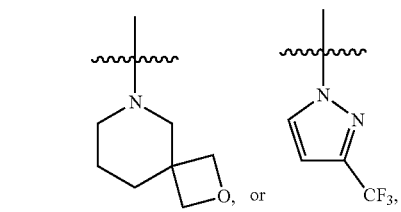

and wherein $R^1$ is a $C_{1-4}$ alkyl group. For example, ring B is

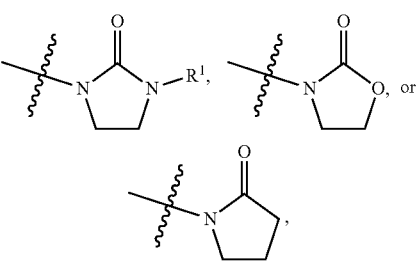

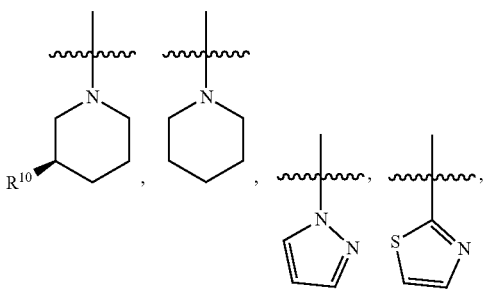

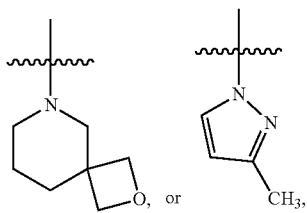

wherein $R^{10}$ is

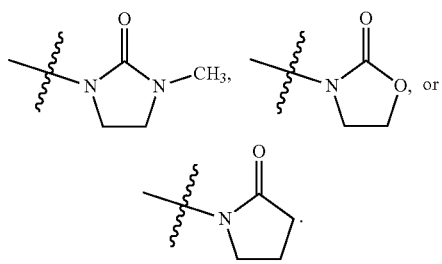

And, in some instances, ring B is

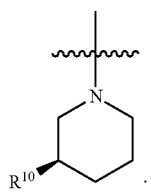

In other instances, $R^{10}$ is

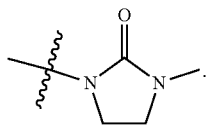 [SMILES: *N1CCN(C)C1=O]

In some embodiments, ring A is

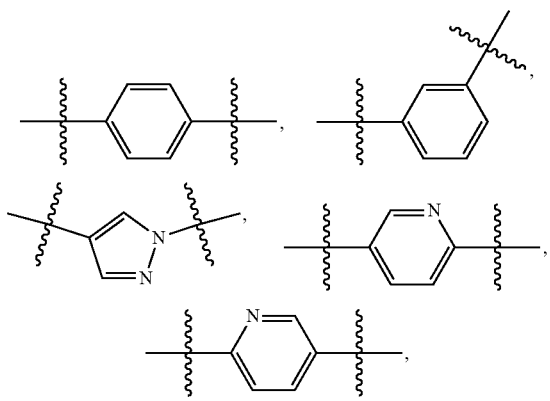

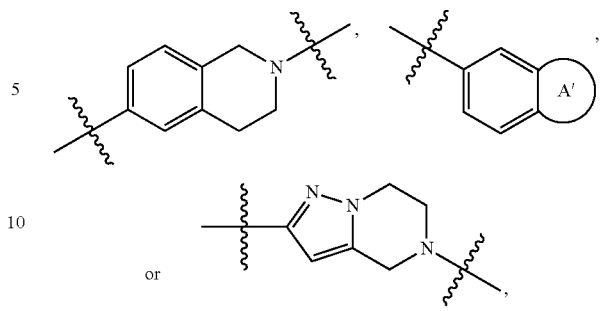

or

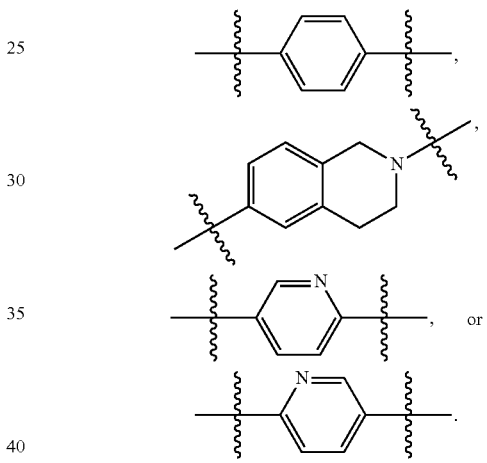

wherein ring A' together with the phenyl ring to which it is fused form a 9-10 membered bicyclic aryl or a 9-10 membered bicyclic heteroaryl wherein the bicyclic heteroaryl (i.e., the bicyclic heteroaryl including ring A') has 1-3 heteroatoms independently selected from N, O, or S. For example, ring A is In some embodiments, at least one of $X^1$, $X^2$, and $X^5$ is —N(R)—, —C(O)—N(R)—, or —CH$_2$—.

In some embodiments, $X^1$ is —C(O)—N(R)—.

In some embodiments, $X^2$ is —(O—CH$_2$—CH$_2$)$_n$—, —(CH$_2$—CH$_2$—O)$_n$—, or —C$_{1-5}$ alkyl-.

In some embodiments, $X^3$ is a bond, —C≡C—, —C$_{1-4}$ alkyl-, or —N(R)—.

In some embodiments, $X^4$ is a bond, —CH$_2$—, or —N(R)—.

In some embodiments, $X^5$ is a bond.

In some embodiments, $X^1$ is —(O—CH$_2$—CH$_2$—CH$_2$)$_m$—, m is 1, and $X^2$ is —C(O)—N(R)—.

In some embodiments, $X^1$ is —CH$_2$—, —C(O)—,

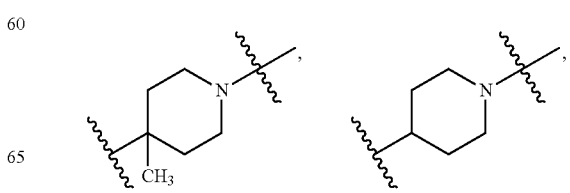

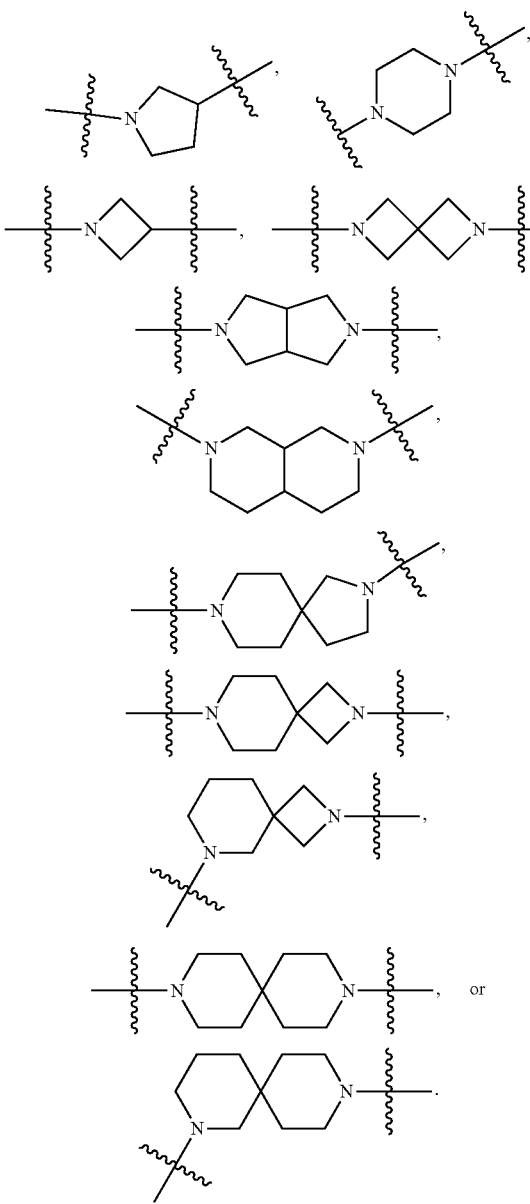
In some embodiments, $X^2$ is a bond, —C(O)—, —$C_{1-5}$ alkyl-,
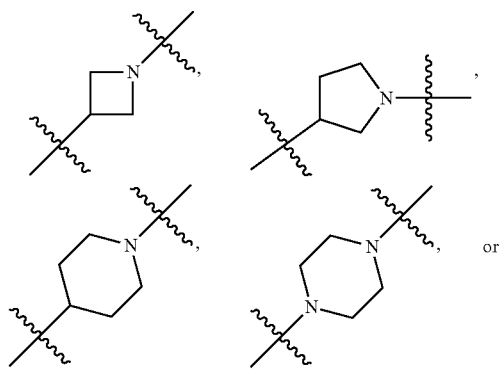
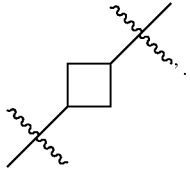
In some embodiments, $X^3$ is bond, —$C_{1-4}$ alkyl-, 4-6 membered cycloalkyl, or —N(R)—.
In some embodiments, $X^3$ is a bond, —$C_{1-4}$ alkyl-, —NH—,
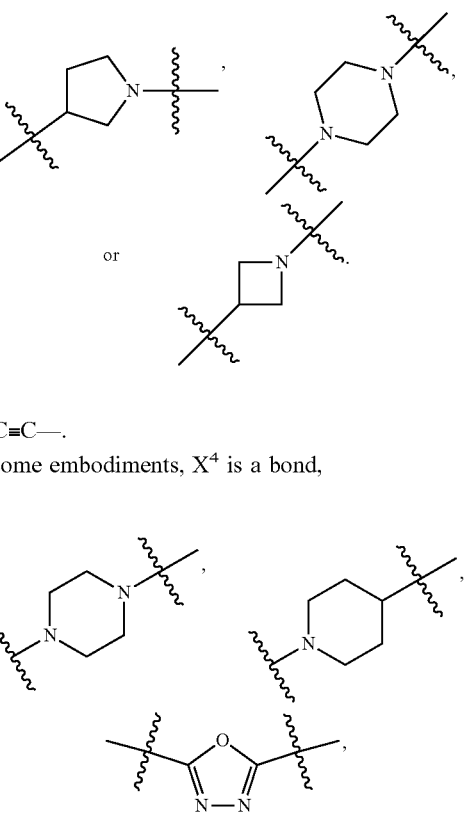
or —C≡C—.
In some embodiments, $X^4$ is a bond,
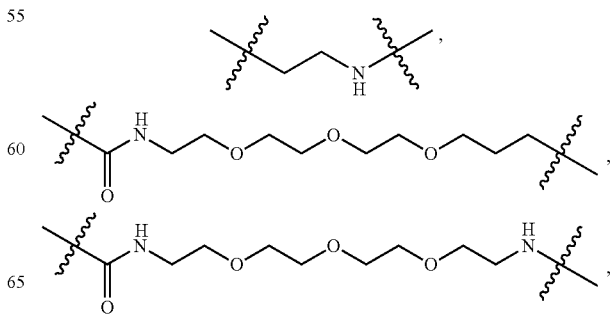
—$C_{1-4}$ alkyl-, —$CH_2$—$CH_2$—N(R)—, or —N(R)—.
In some embodiments, $X^5$ is a bond, —$C_{1-4}$ alkyl-, —N(R)—, or —C(O)—N(R)—.
In some embodiments, L is

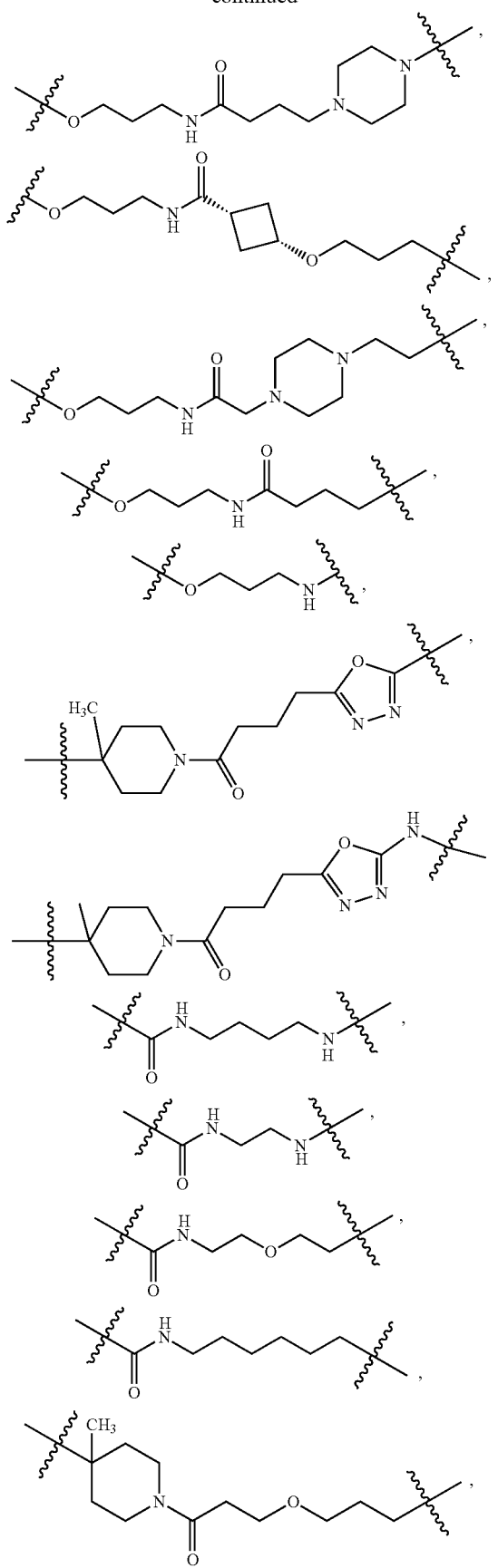
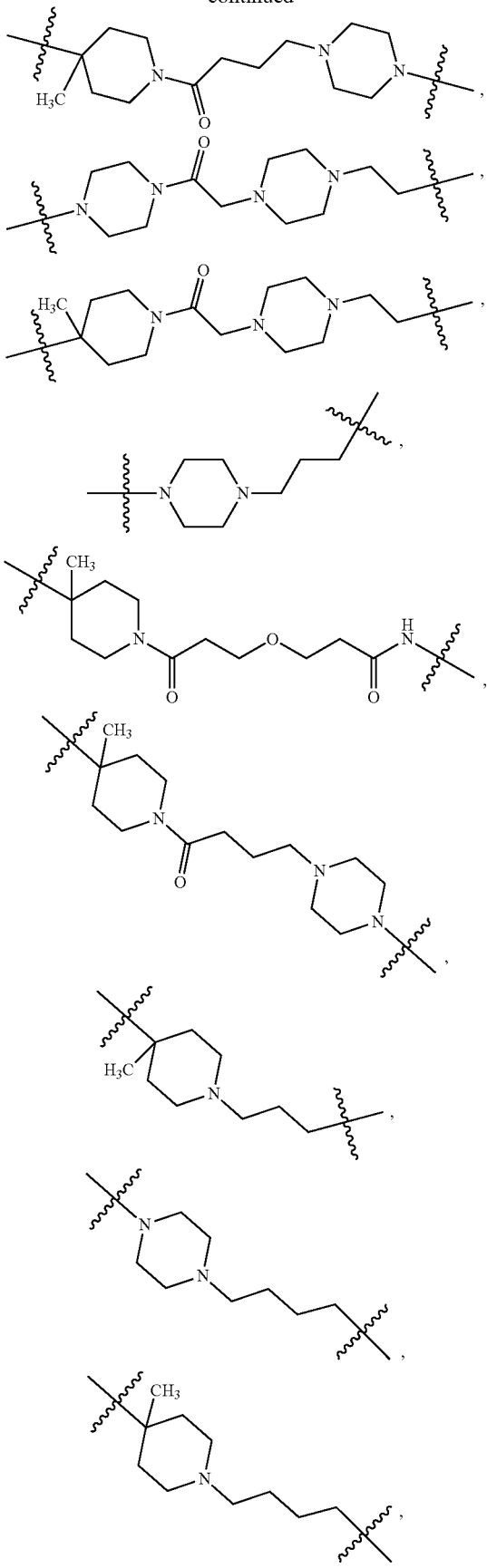

123
-continued
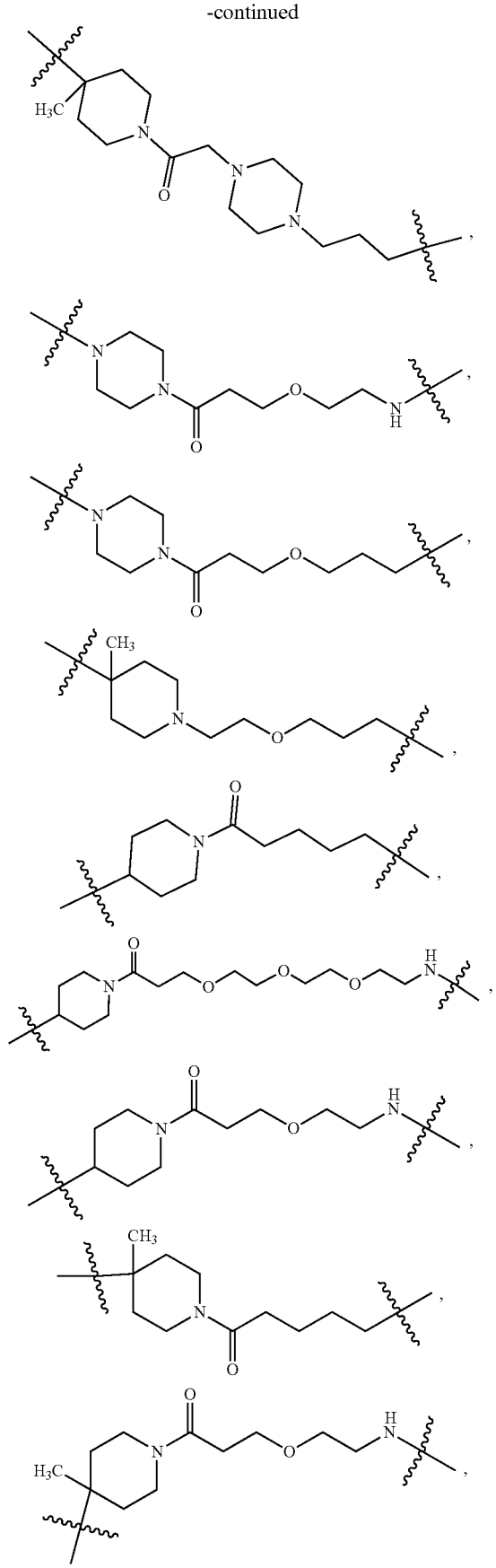
124
-continued
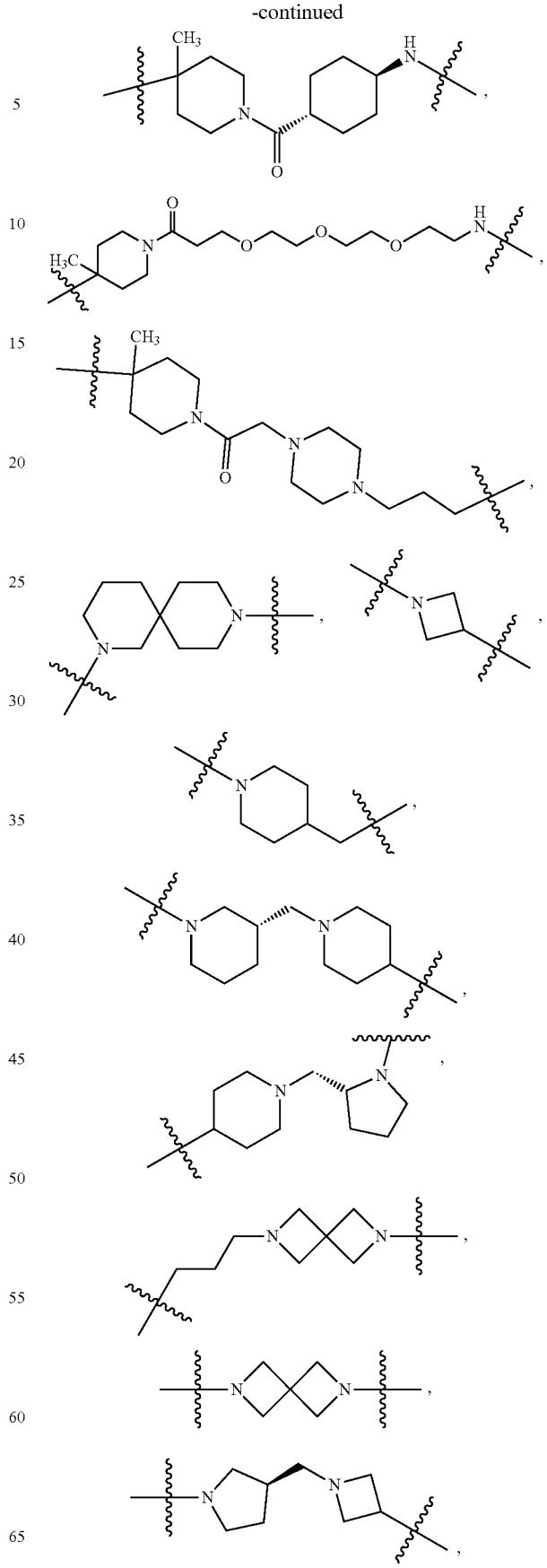

125
-continued
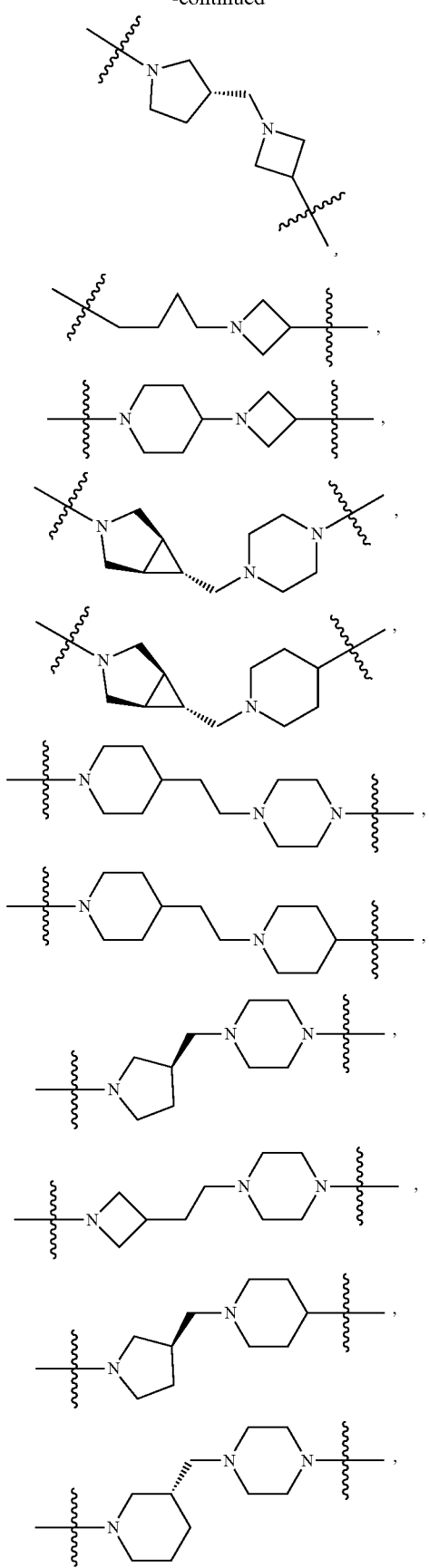
126
-continued
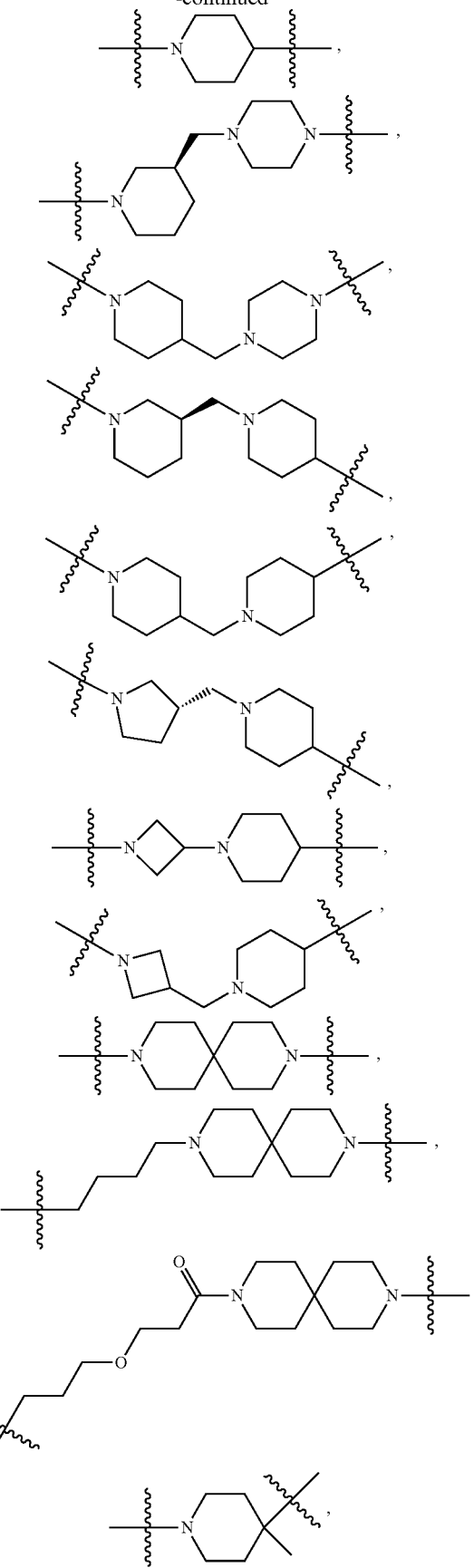

127
-continued
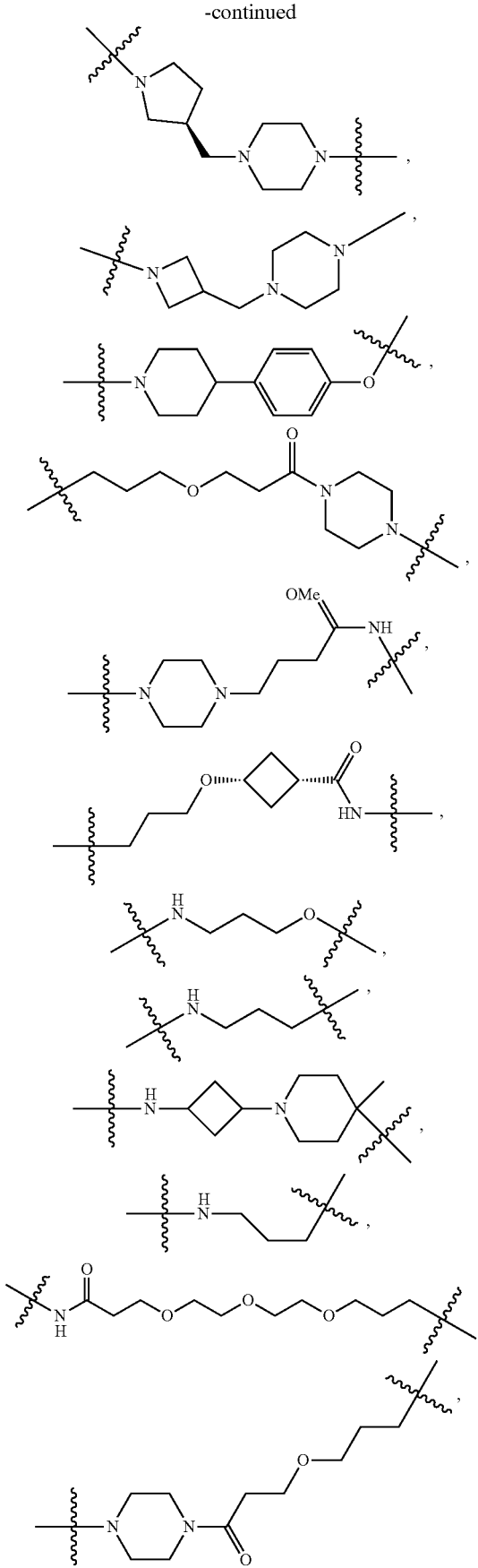
128
-continued
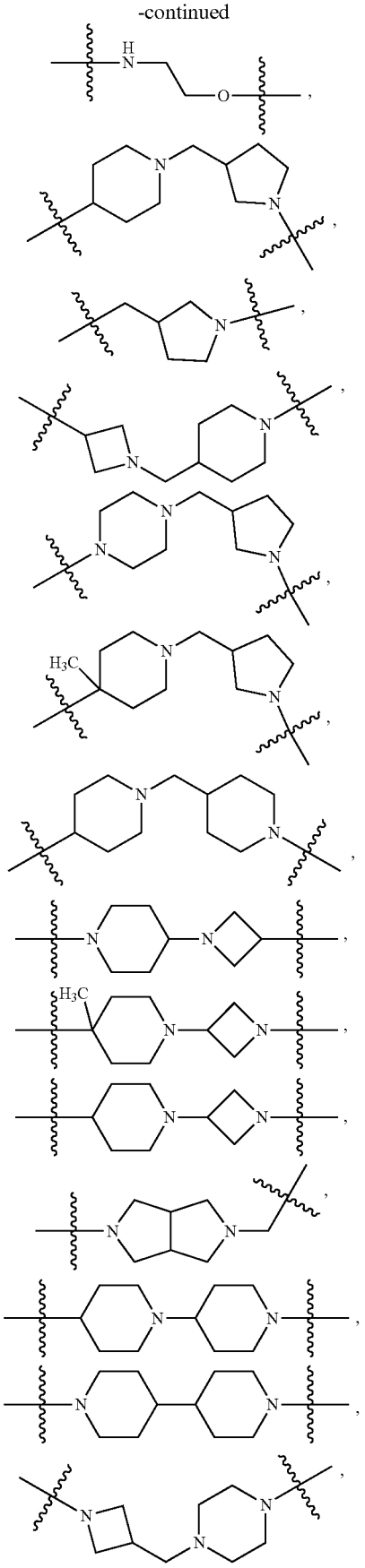

129
-continued
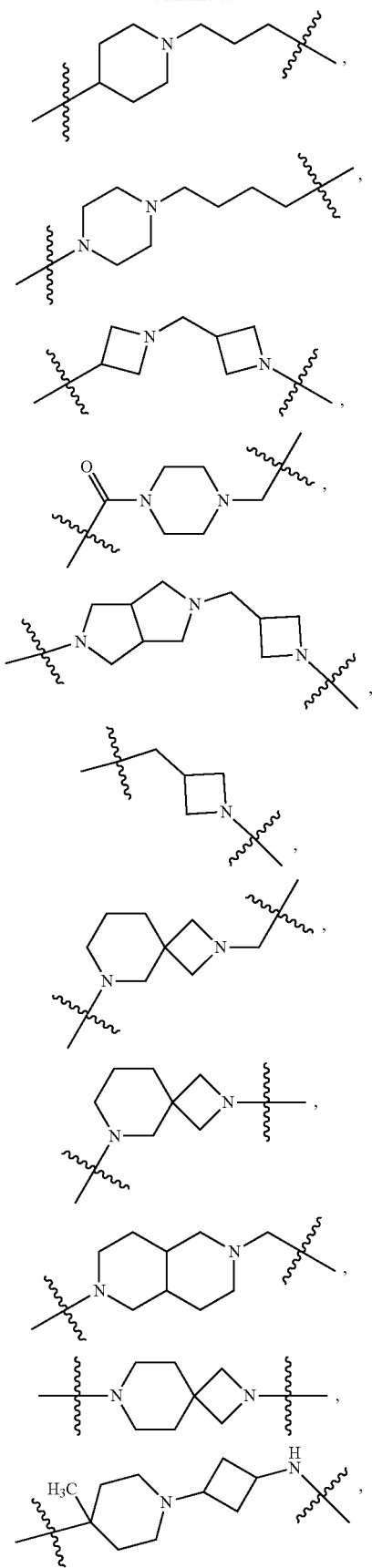
130
-continued
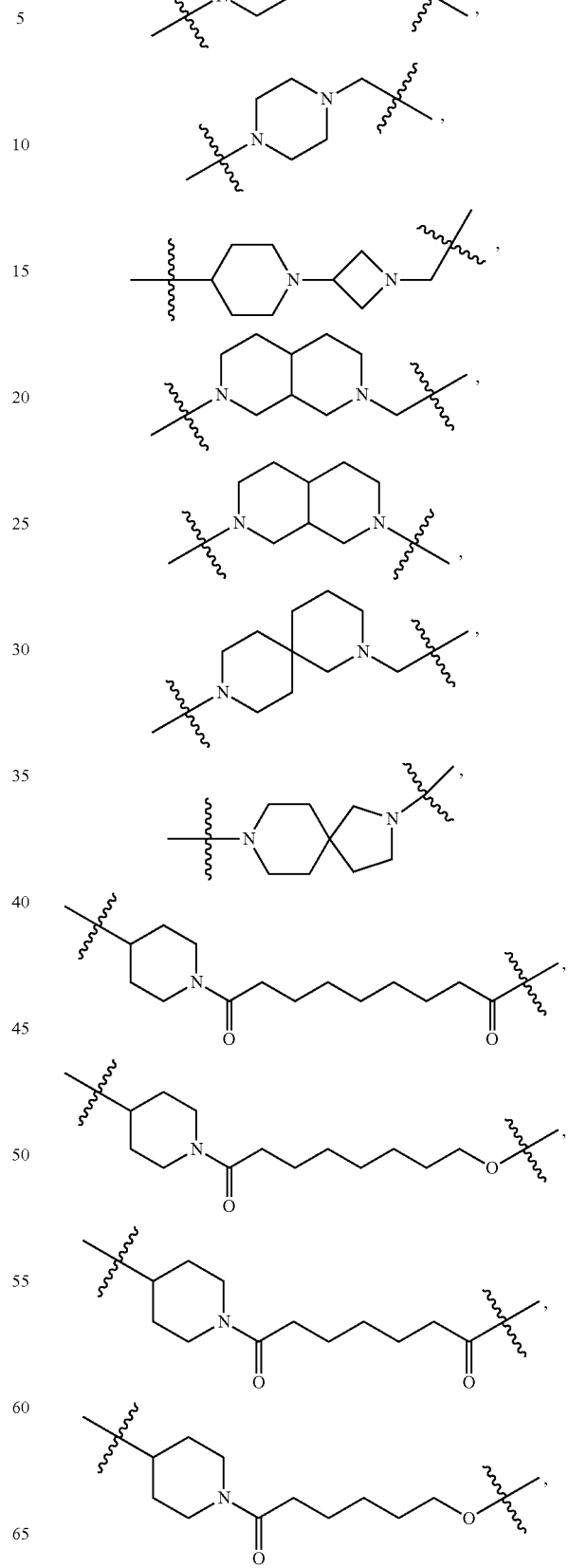

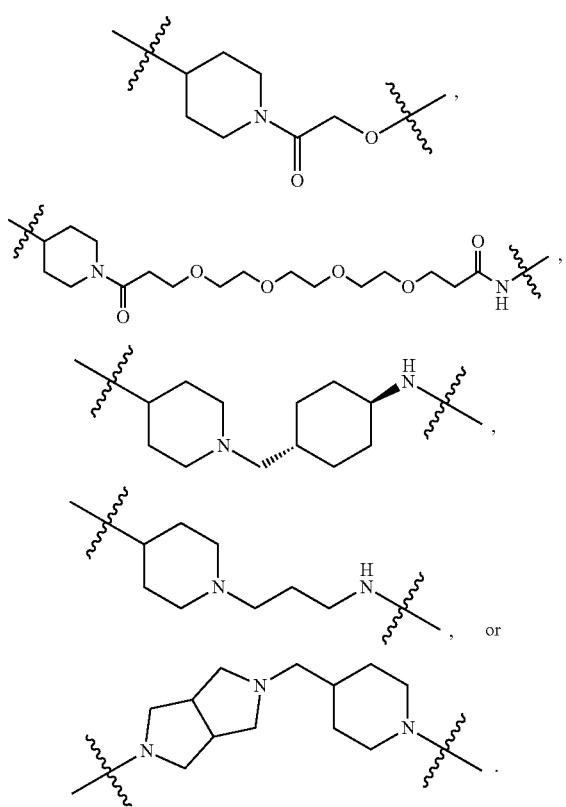
In some embodiments, Y is
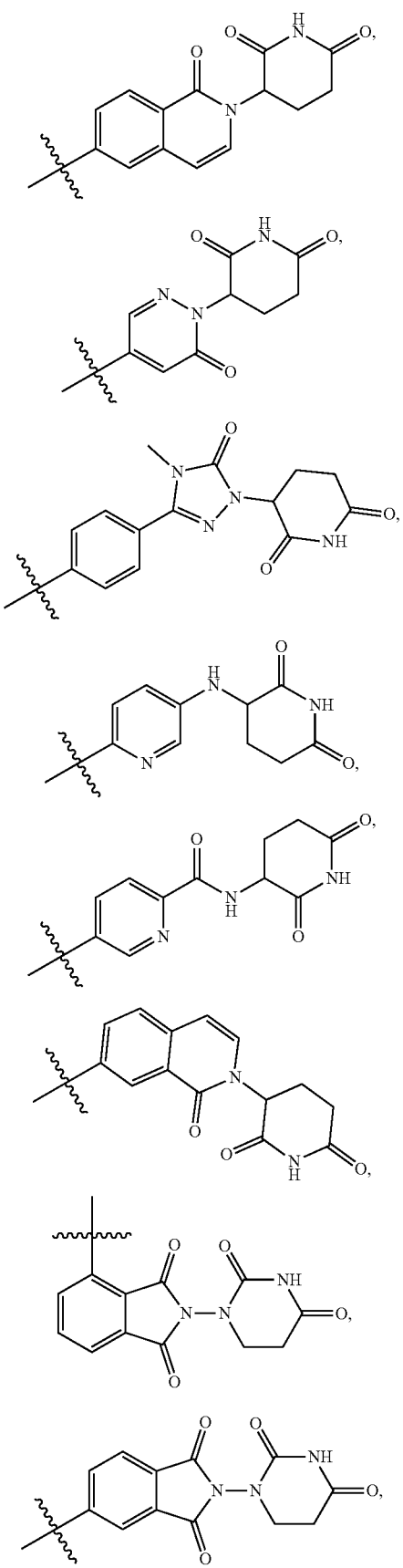

133
-continued

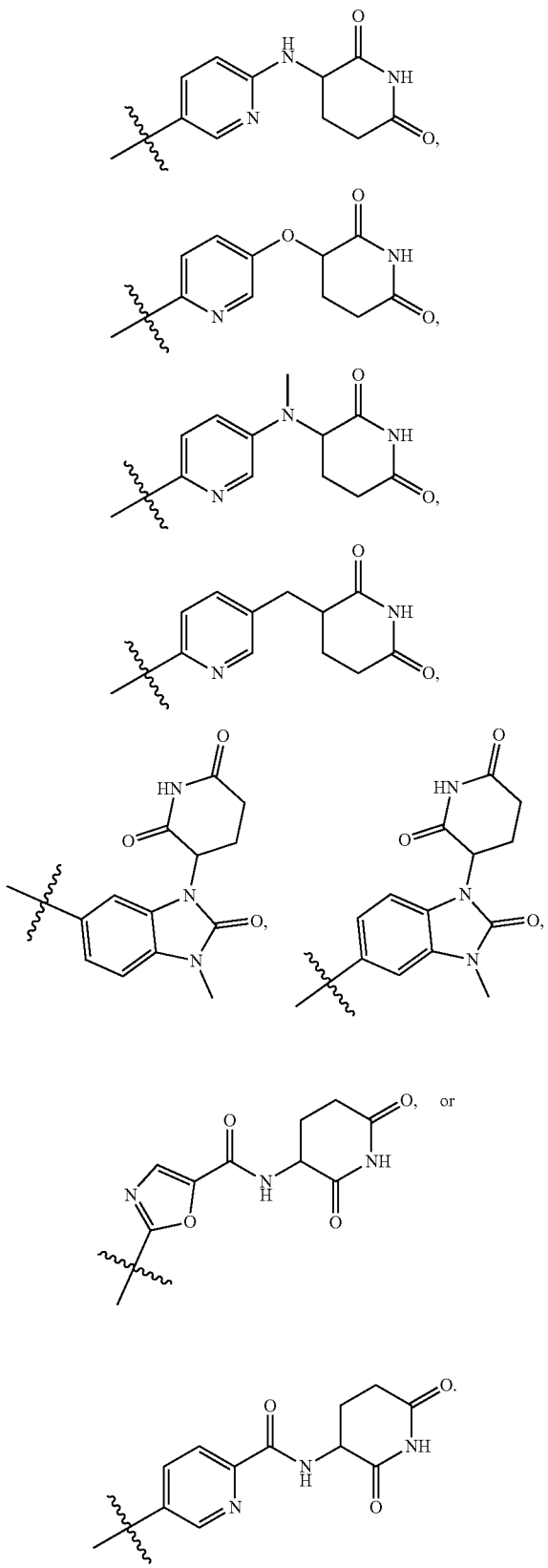

In some embodiments, W is N.
In some embodiments, D is a bond.

134

The present invention also provides a compound of Formula (B)

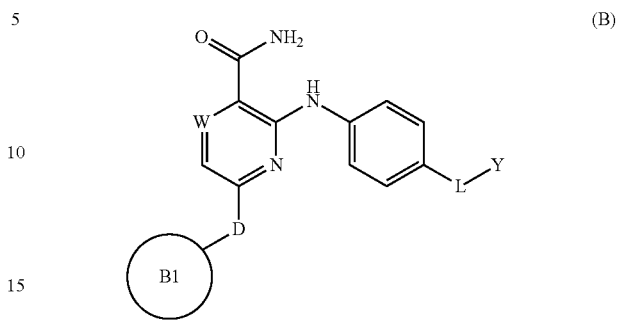

or a pharmaceutically acceptable salt thereof, wherein W is CH or N; D is a bond or —NH—; ring B1 is a 4-6 membered, fully saturated, partially unsaturated, or fully unsaturated monocyclic heterocycle or a 8-10 membered, fully saturated, spiro bicyclic heterocycle, wherein ring B1 has 1-3 heteroatoms independently selected from N, O, or S, and is optionally substituted with 1-3 groups selected from halo, —CH$_3$, —CF$_3$, —C(O)OH, —CH$_2$OH, or a 5 membered heterocycloalkyl optionally substituted with oxo and having 1-2 heteroatoms independently selected from N or 0; L is —X$^1$—X$^2$—X$^3$—; X$^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of X$^1$ is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S; X$^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$; each R is independently —H or —C$_{1-3}$ alkyl; each of m, n, and p is independently an integer from 1 to 3; and Y is

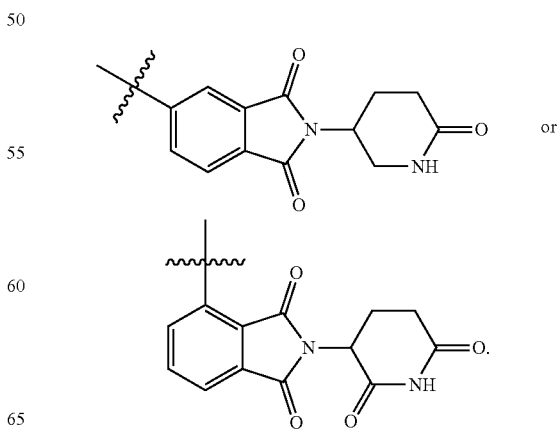

In some embodiments, ring B1 is

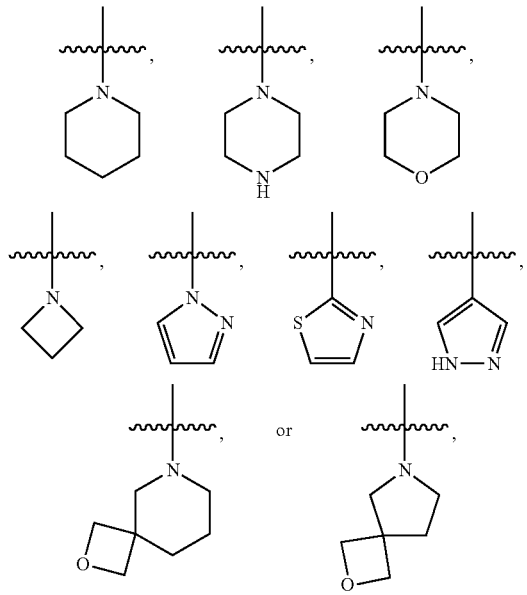

and ring B1 is optionally substituted 1-3 groups selected from —CH$_3$, —CH$_2$OH, —CH$_2$CH$_2$OH, —C(O)OH, —CF$_3$, —F,

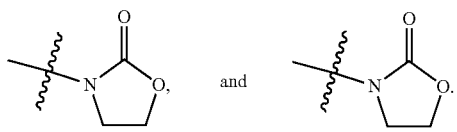 [SMILES: *N1CCOC1=O ; *N1CCOC1=O]

For example, ring B1 is

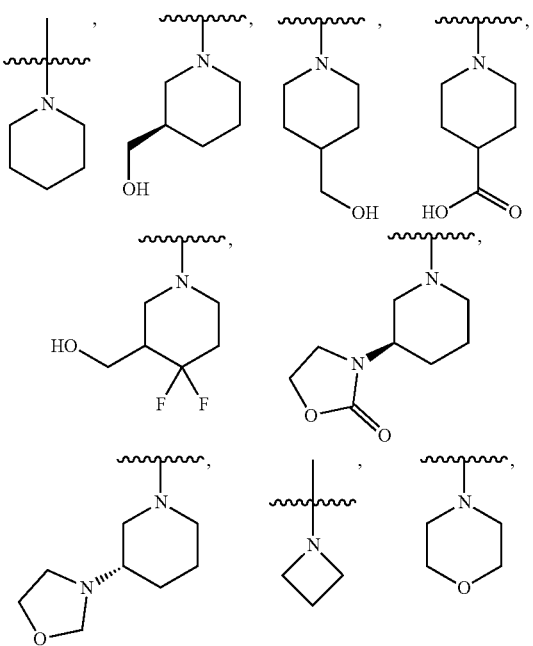

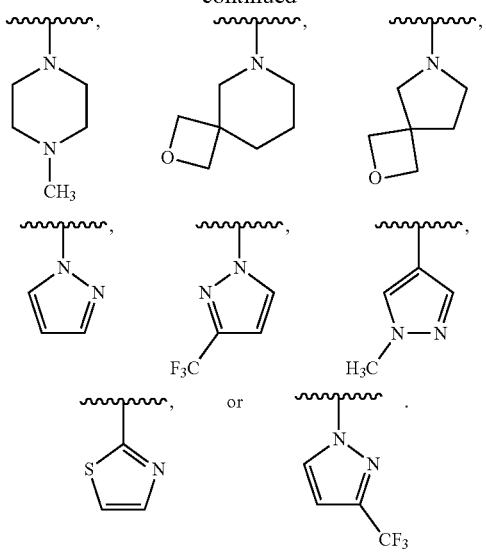

In other examples, ring B1 is

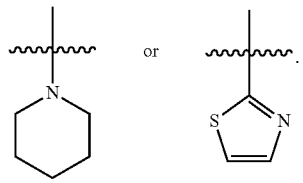 [SMILES: *N1CCCCC1 ; *c1nccs1]

In some embodiments, X$^1$ is

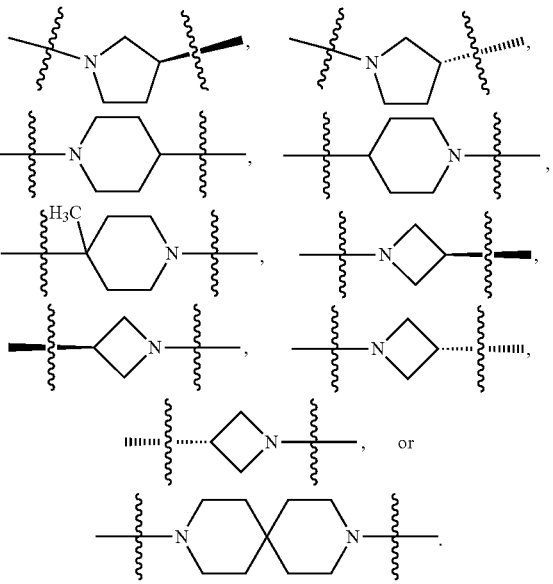

In some embodiments, X$^2$ is a bond, —C$_{1-5}$ alkyl-, 4-6 membered monocyclic cycloalkyl, or 4-6 membered monocyclic heterocycloalkyl having 1-2 heteroatoms independently selected from N, O, or S. For example, X$^2$ is a bond, —C$_{1-3}$ alkyl-, —C(O)—,

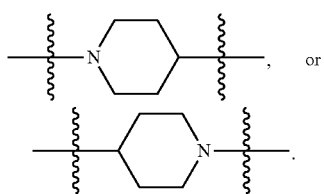

In some embodiments, $X^3$ is a bond, —$C_{1-4}$ alkyl-, —N(R)—, —(O—CH$_2$—CH$_2$)$_p$—, —(CH$_2$—CH$_2$—O)$_p$—, or a 4-6 membered heterocycloalkyl having 1-2 heteroatoms independently selected from N, O, or S wherein the heterocycloalkyl is optionally substituted with —CH$_3$. For example, $X^3$ is a bond,

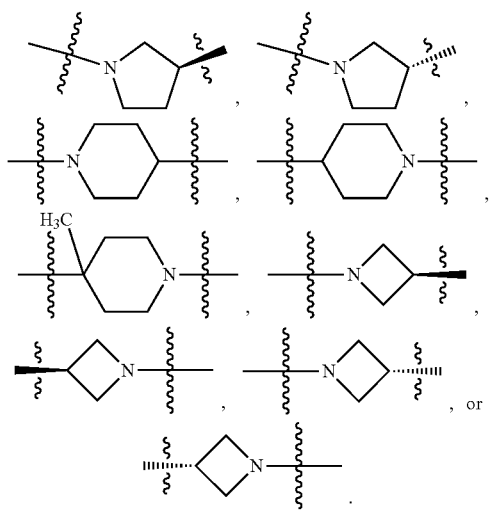

In some embodiments, L is

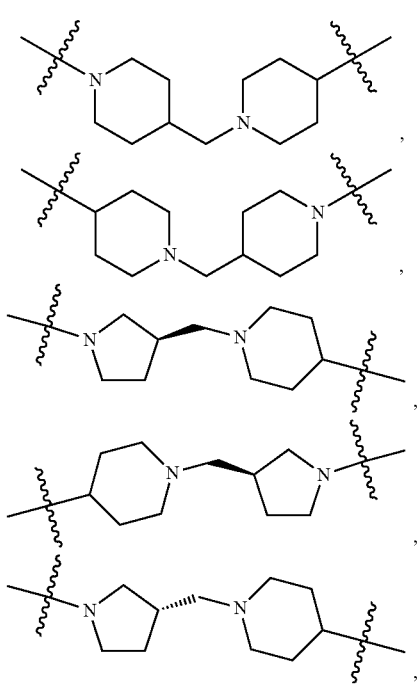

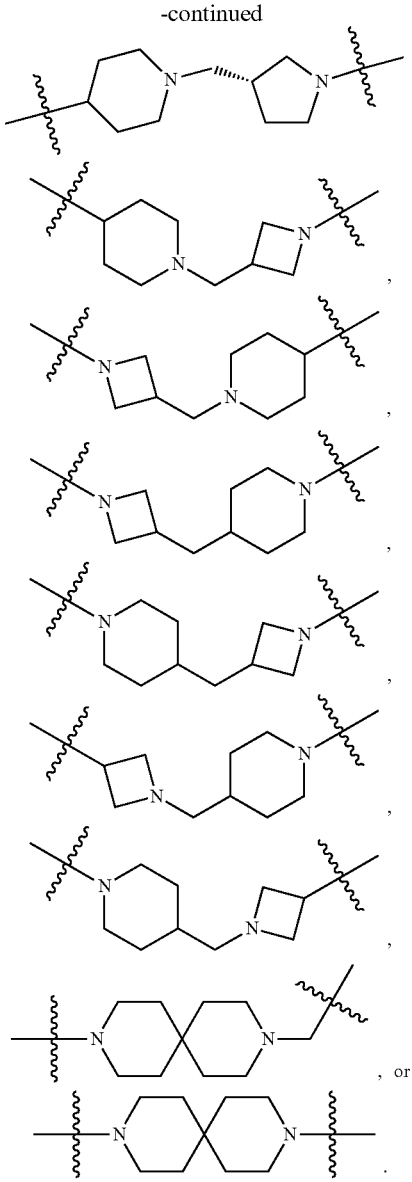

In some embodiments, W is N and D is a bond.

The present invention also provides a compound of Formula (C)

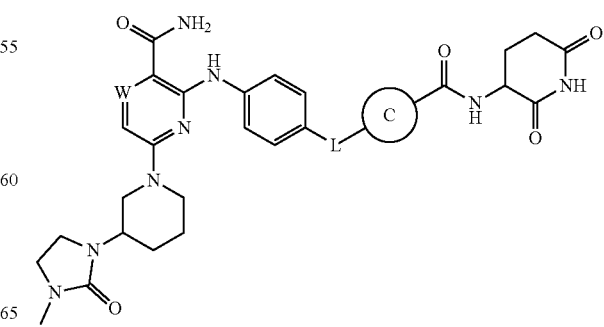

or a pharmaceutically acceptable salt thereof, wherein W is CH or N; ring C is phenyl or a saturated, partially unsaturated, or fully unsaturated 5-6 membered monocyclic heterocycle having 1-2 heteroatoms independently selected from N, O, or S, wherein each of the phenyl and heterocycle of ring C is optionally substituted; L is —$X^1$—$X^2$—$X^3$—; $X^1$ is —C(O)—N(R)—, —N(R)—C(O)—, —(O—$CH_2$—$CH_2$)$_m$—, —O—($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the bicyclic heterocycloalkyl and the monocyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; each R is independently —H or —$C_{1-3}$ alkyl; and each of m, n, and p is independently an integer from 1 to 3.

In some embodiments, W is N.

In some embodiments, ring C is

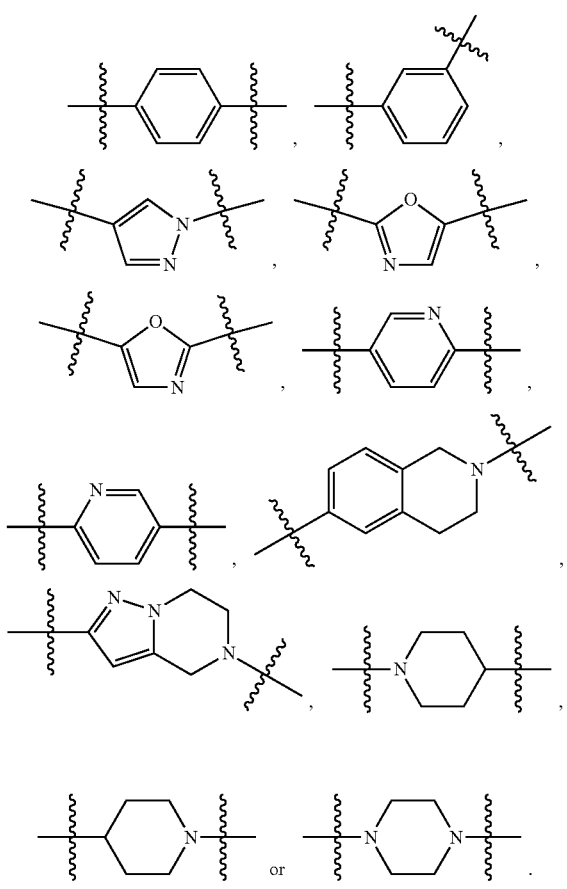

For example, ring C is

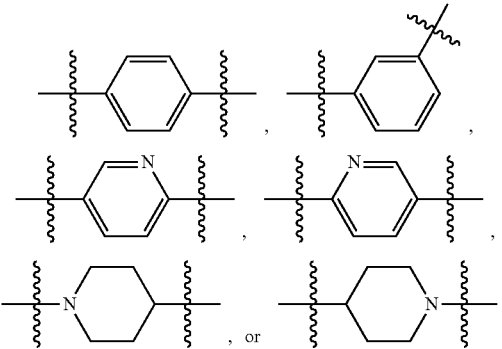

In other examples, ring C is or

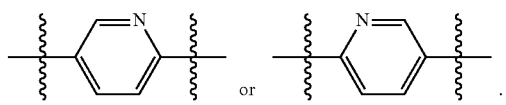 [SMILES: *c1ccc(*)nc1 ; *c1ccc(*)nc1]

In some embodiments, $X^1$ is a 4-6 membered monocyclic heterocycloalkyl having 1-2 heteroatoms independently selected from N, O, or S. For example, $X^1$ is

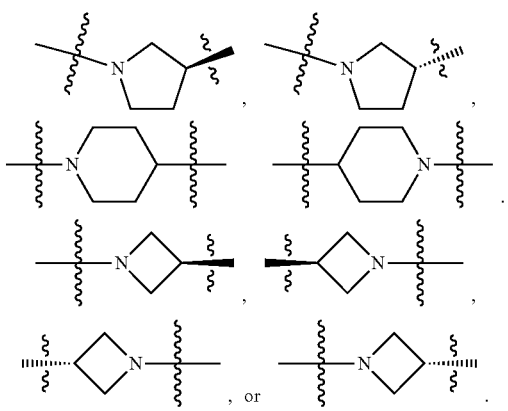

In some examples, $X^1$ is

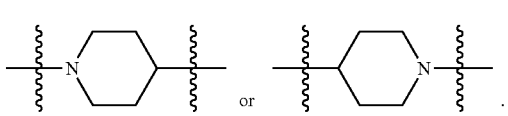

In some embodiments, $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —$C_{1-3}$ alkyl- (e.g., —$CH_2$—).

In some embodiments, $X^3$ is a 4-6 membered cycloalkyl, —N(R)—, or a 4-6 membered heterocycloalkyl having 1-2 heteroatoms independently selected from N, O, or S wherein the heterocycloalkyl is optionally substituted with —$CH_3$. For example, $X^3$ is

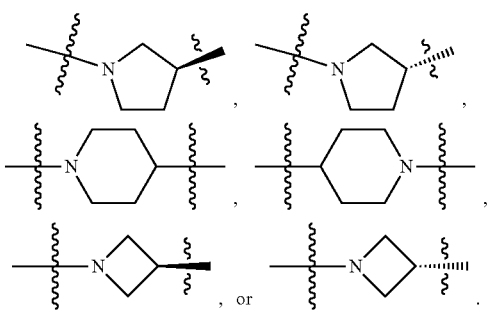

In other examples, $X^3$ is

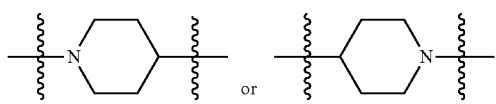

In some embodiments, L is

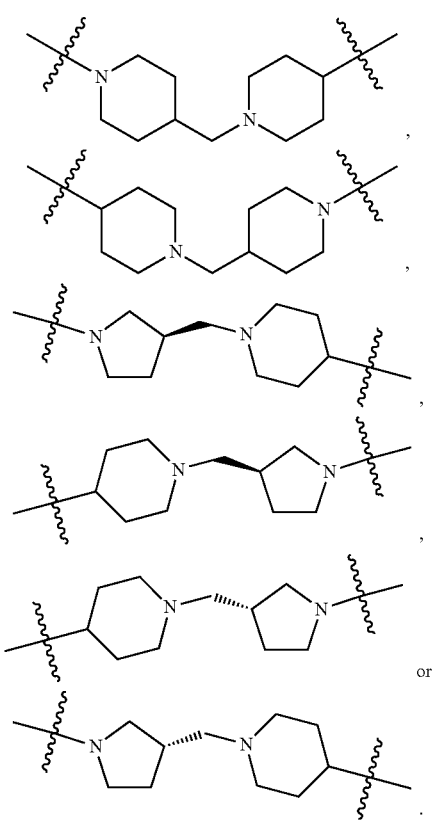

For example, L is

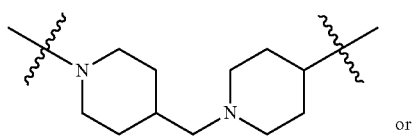

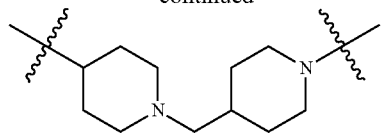

The present invention also provides a compound of Formula (D)

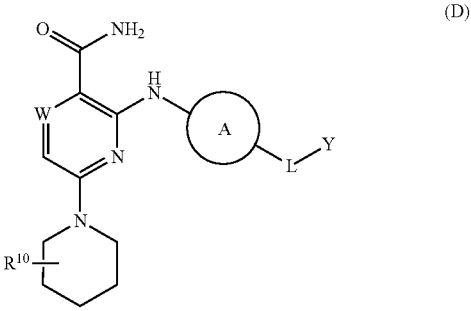

or a pharmaceutically acceptable salt thereof, wherein W is CH or N; ring A is

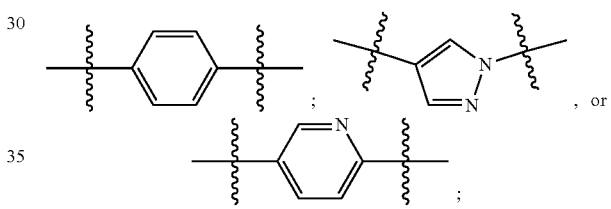

L is —$X^1$—$X^2$—$X^3$—; $X^1$ is —$C_{1-5}$ alkyl- or 4-6 membered monocyclic heterocycloalkyl having 1-2 heteroatoms independently selected from N, O, or S wherein the monocyclic heterocycloalkyl of $X^1$ is optionally substituted with —$CH_3$; $X^2$ is a bond, —$C_{1-5}$ alkyl-, or 4-6 membered monocyclic heterocycloalkyl having 1-2 heteroatoms independently selected from N, O, or S wherein the monocyclic heterocycloalkyl of $X^1$ is optionally substituted with —$CH_3$; $X^3$ is a bond, —$C_{1-4}$ alkyl-, 4-6 membered monocyclic cycloalkyl, or 4-6 membered heterocycloalkyl having 1-2 heteroatoms independently selected from N, O, or S wherein the heterocycloalkyl is optionally substituted with —$CH_3$; Y is

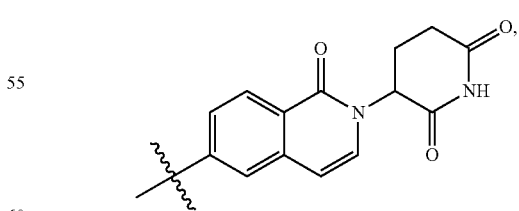

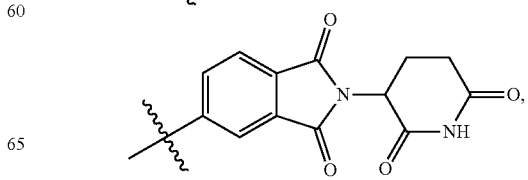

-continued

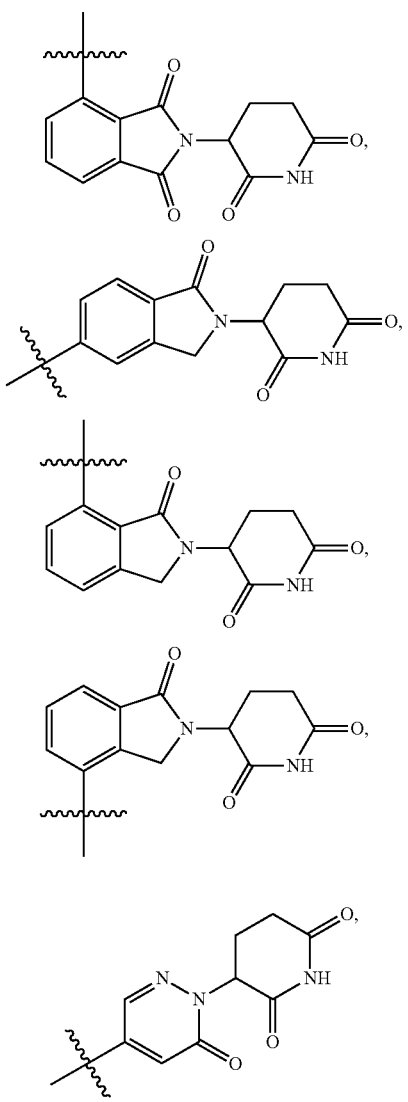

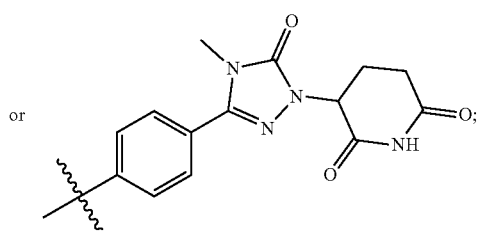

and R¹⁰ is halo, —H, —$C_{1-5}$ alkyl, -3-6 membered cycloalkyl, 5-6 membered heterocycloalkyl, —CN, —OH, —$CF_3$, —$CH_2OH$, —$CH_2CH_2OH$, —C(O)OH,

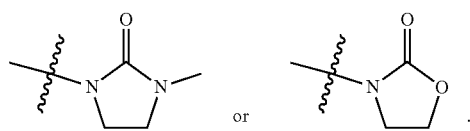

In some embodiments, ring A is

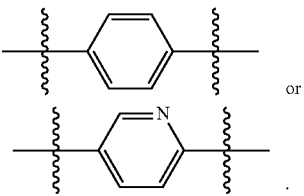

or

In some embodiments, $X^1$ is a 4-6 membered monocyclic heterocycloalkyl having 1-2 heteroatoms independently selected from N, O, or S wherein the monocyclic heterocycloalkyl of $X^1$ is optionally substituted with —$CH_3$. For example, $X^1$ is

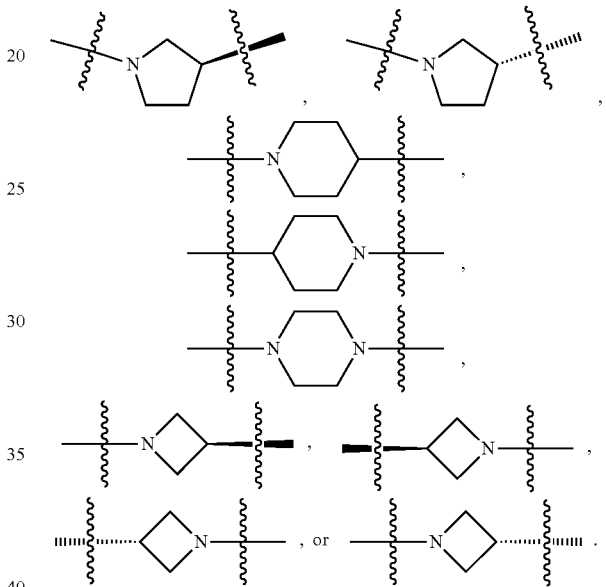

In some embodiments, $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having 1-2 heteroatoms independently selected from N, O, or S. For example, $X^3$ is

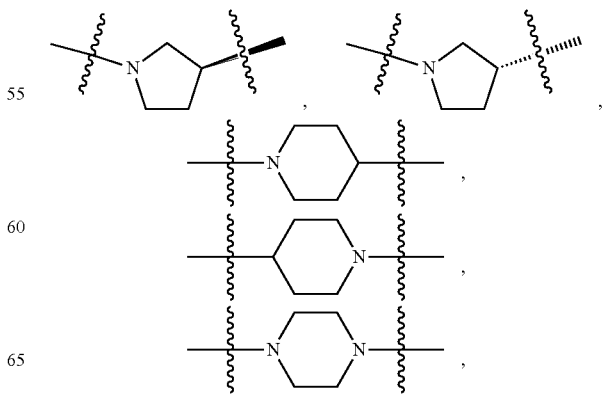

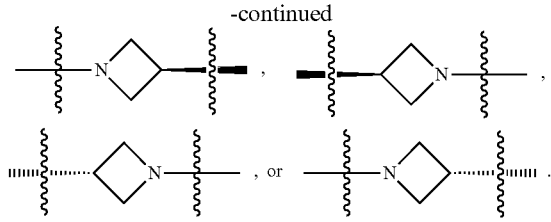
In some embodiments, L is
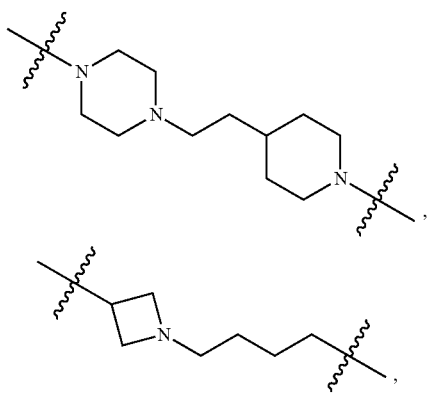
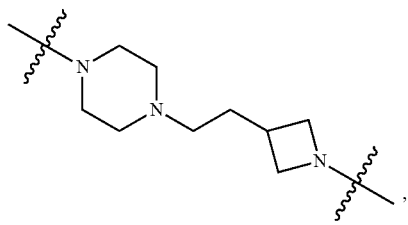
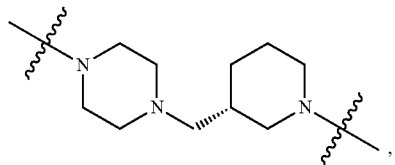
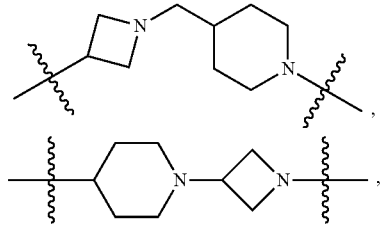
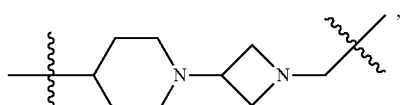
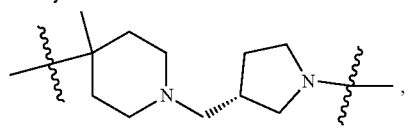
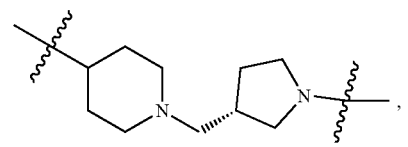
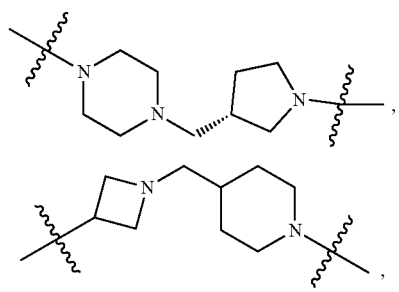
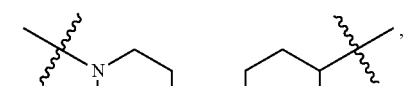
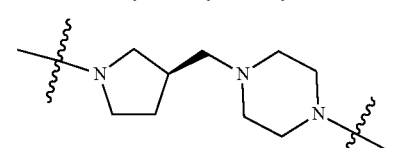
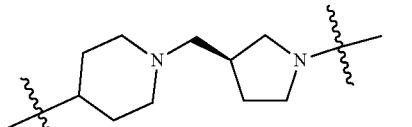
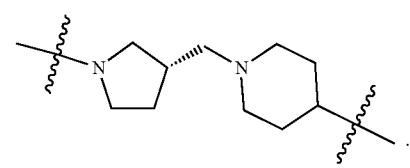
In some embodiments, $R^{10}$ is halo, —H, —$C_{1-5}$ alkyl (e.g., —$C_{1-3}$ alkyl), -3-6 membered cycloalkyl, 5-6 membered heterocycloalkyl, —CN, —OH, —$CF_3$, —$CH_2OH$, —C(O)OH, or —$CH_2CH_2OH$. For instance, $R^{10}$ is halo, —H, $C_{1-3}$ alkyl, $CF_3$, —$CH_2OH$, —C(O)OH, or —$CH_2CH_2OH$. In other instances, $R^{10}$ is
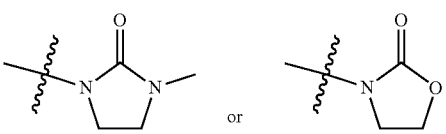
In some embodiments, $R^{10}$ is
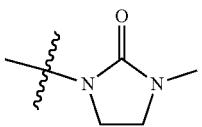

In some embodiments, $R^{10}$ is

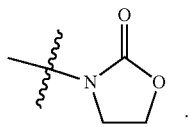

In some embodiments, the compound of Formula (D) is a compound of (D-1)

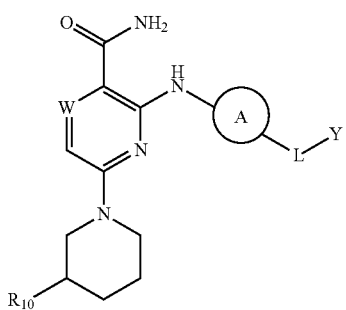

(D-1)

or a pharmaceutically acceptable salt thereof, wherein W is CH or N; ring A is

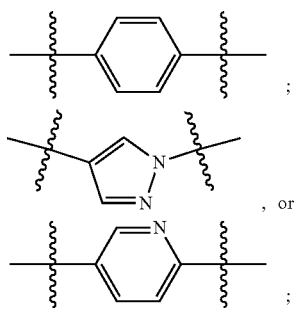

, or

L is —$X^1$—$X^2$—$X^3$—; $X^1$ is —$C_{1-5}$ alkyl- or 4-6 membered monocyclic heterocycloalkyl having 1-2 heteroatoms independently selected from N, O, or S wherein the monocyclic heterocycloalkyl of $X^1$ is optionally substituted with —$CH_3$; $X^2$ is a bond, —$C_{1-5}$ alkyl-, or 4-6 membered monocyclic heterocycloalkyl having 1-2 heteroatoms independently selected from N, O, or S wherein the monocyclic heterocycloalkyl of $X^1$ is optionally substituted with —$CH_3$; $X^3$ is a bond, —$C_{1-4}$ alkyl-, 4-6 membered monocyclic cycloalkyl, or 4-6 membered heterocycloalkyl having 1-2 heteroatoms independently selected from N, O, or S wherein the heterocycloalkyl is optionally substituted with —$CH_3$; Y is

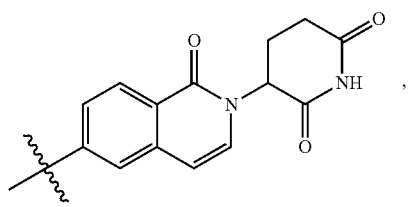

,

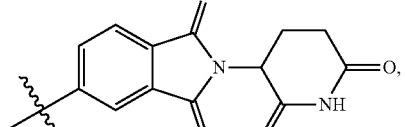

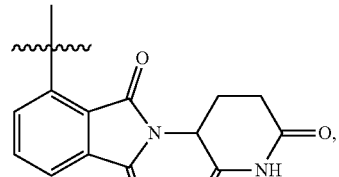

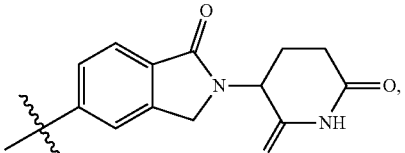

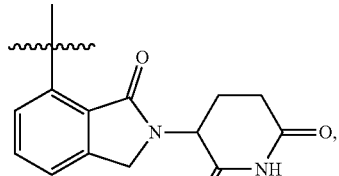

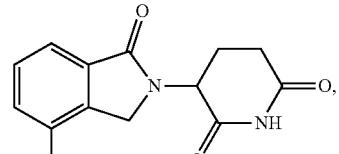

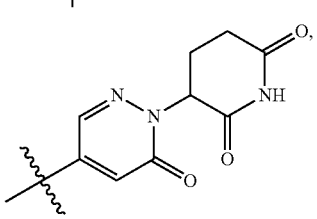

or

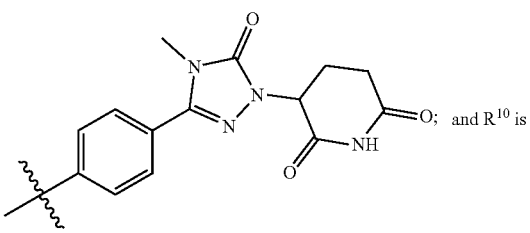

; and $R^{10}$ is

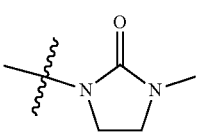 or 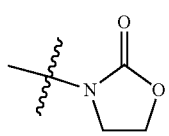

.

In some embodiments, ring A is

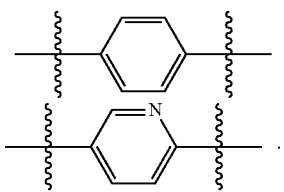

In some embodiments, $X^1$ is a 4-6 membered monocyclic heterocycloalkyl having 1-2 heteroatoms independently selected from N, O, or S wherein the monocyclic heterocycloalkyl of $X^1$ is optionally substituted with —CH$_3$. For example, $X^1$ is

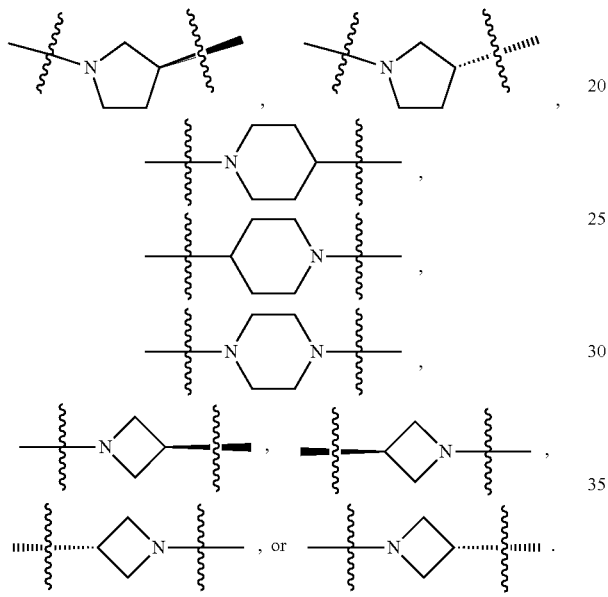

In some embodiments, $X^2$ is a bond, —C$_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —C$_{1-4}$ alkyl-.

In some embodiments, $X^3$ is a bond, a 4-6 membered monocyclic cycloalkyl, or 4-6 membered monocyclic heterocycloalkyl having 1-2 heteroatoms independently selected from N, O, or S. For example, $X^3$ is

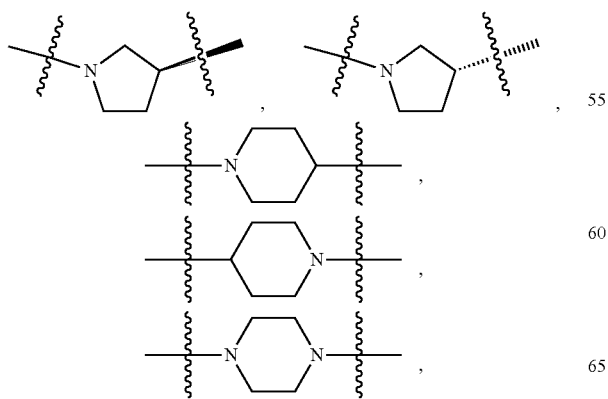

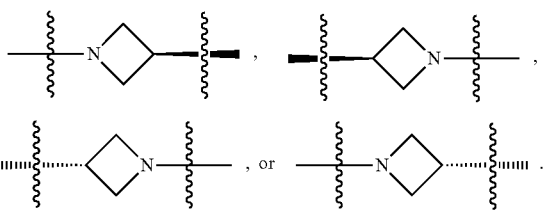

In some embodiments, L is

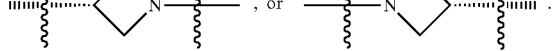

-continued

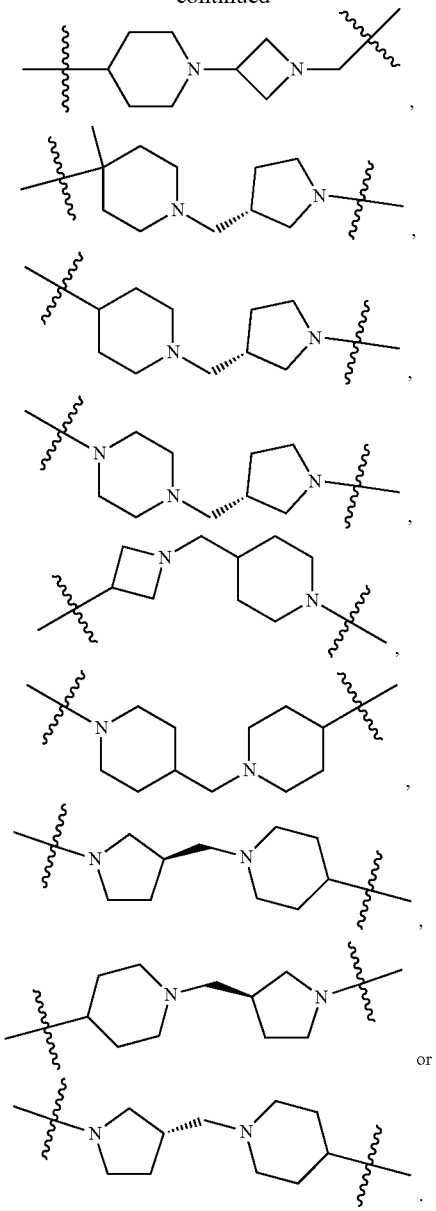

, or

.

In some embodiments, $R^{10}$ is

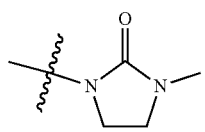

In some embodiments, $R^{10}$ is

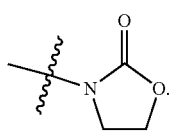 [SMILES: *N1CCOC1=O]

In some embodiments, the compound of Formula (D) or the compound of Formula (D-1) is a compound of Formula (D-2):

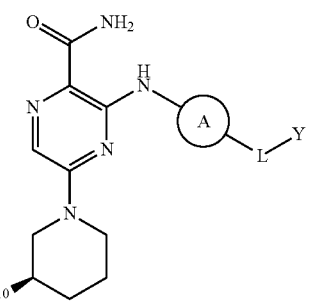

(D-2)

or a pharmaceutically acceptable salt thereof, wherein the terms ring A, L, Y, and $R^{10}$ are as defined in the compound of Formula (A), the compound of Formula (D), and the compound of Formula (D-1).

In some embodiments, ring A is

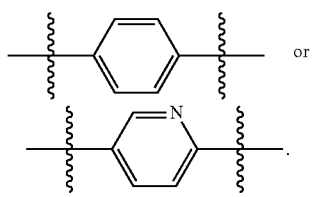

or

.

In some embodiments, $X^1$ is a 4-6 membered monocyclic heterocycloalkyl having 1-2 heteroatoms independently selected from N, O, or S wherein the monocyclic heterocycloalkyl of $X^1$ is optionally substituted with —$CH_3$. For example, $X^1$ is

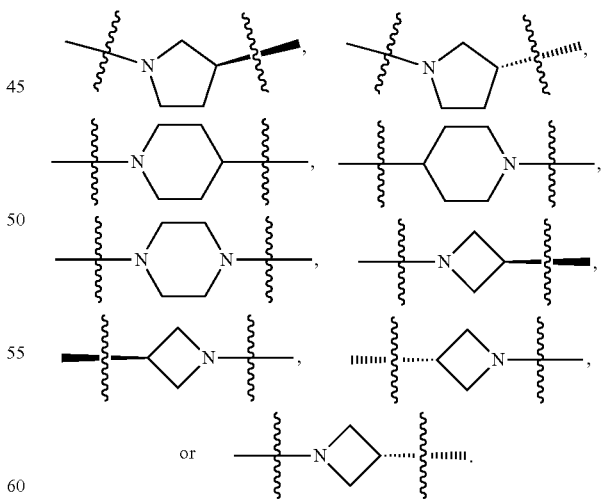

In some embodiments, $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having 1-2 heteroatoms independently selected from N, O, or S. For example, $X^3$ is
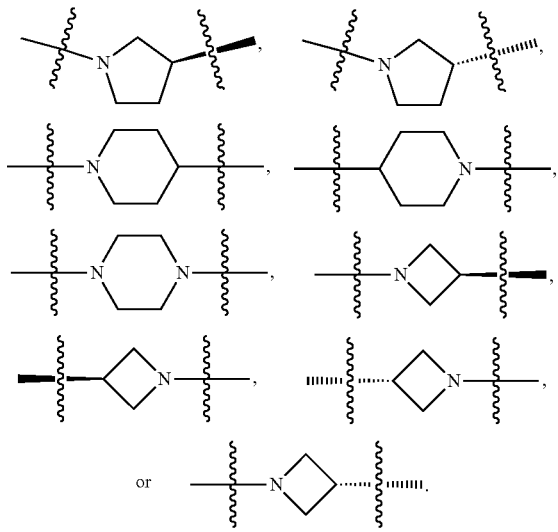
In some embodiments, L is
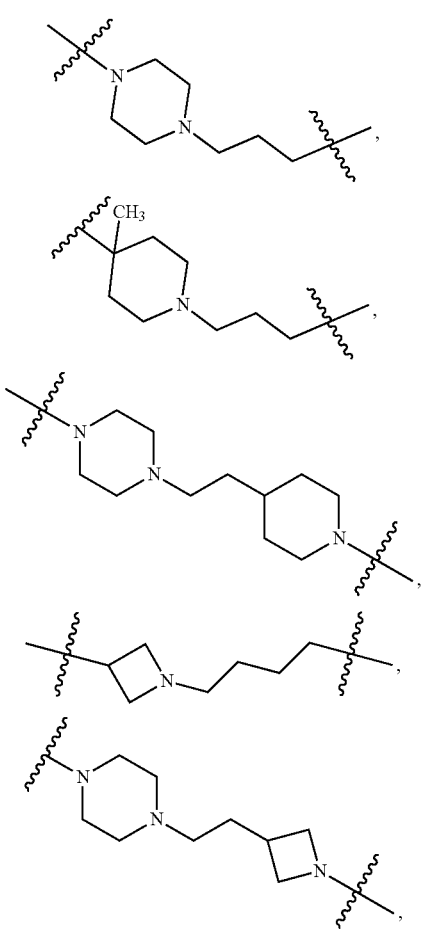
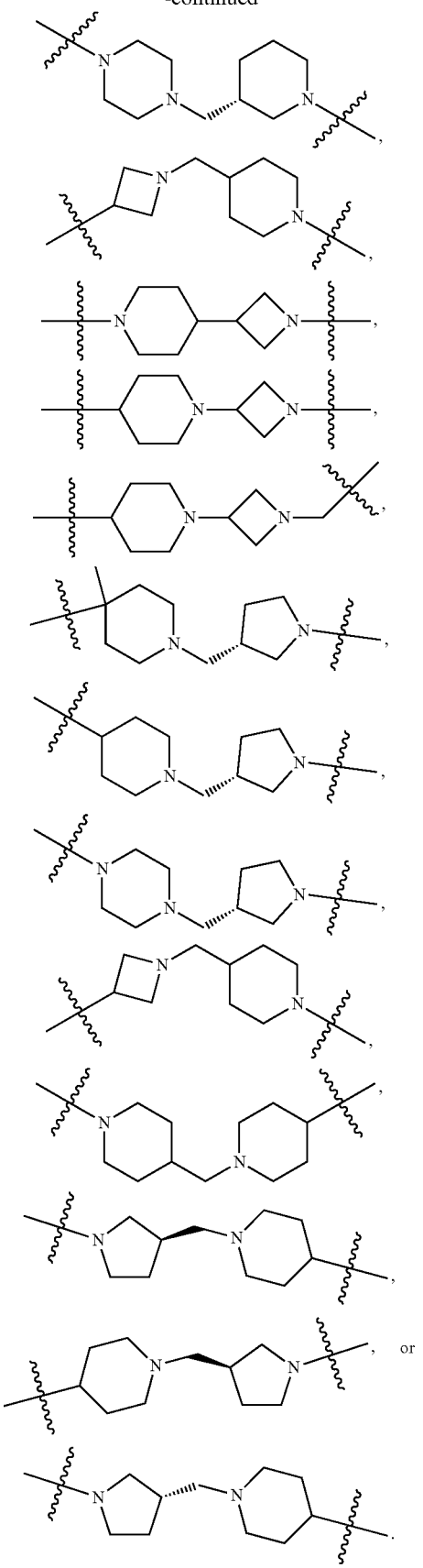

In some embodiments, $R^{10}$ is

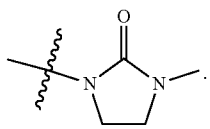 [SMILES: *N1CCN(C)C1=O]

In some embodiments, $R^{10}$ is

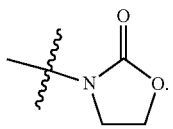 [SMILES: *N1CCOC1=O]

The present invention also provides a compound of Formula (E)

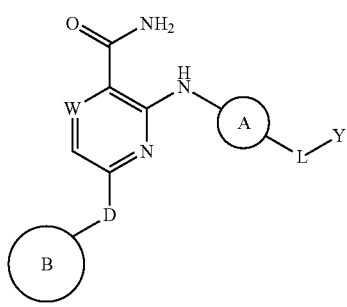

(E)

or a pharmaceutically acceptable salt thereof, wherein D is a bond or —NH—; W is N or CH; ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S; ring B is an optionally substituted 5-6 membered saturated, partially unsaturated, or fully unsaturated monocyclic heterocycle, or an optionally substituted 8-10 membered (e.g., 8-9 membered or 9-10 membered) spiro bicyclic heterocycle, wherein ring B has 1-3 heteroatoms independently selected from N, O, or S; L is —$X^1$—$X^2$—$X^3$—$X^4$—$X^5$—; $X^1$ is a bond, —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; $X^4$ is a bond, —$CH_2$— $CH_2$—N(R)—, —N(R)—, —$C_{1-4}$ alkyl-, —(O—$CH_2$— $CH_2$—$CH_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S; $X^5$ is a bond, —N(R)—, or —C(O)—N (R)—; each R is independently —H or —$C_{1-3}$ alkyl; each of m, n, and p is independently an integer from 1 to 3; and Y is

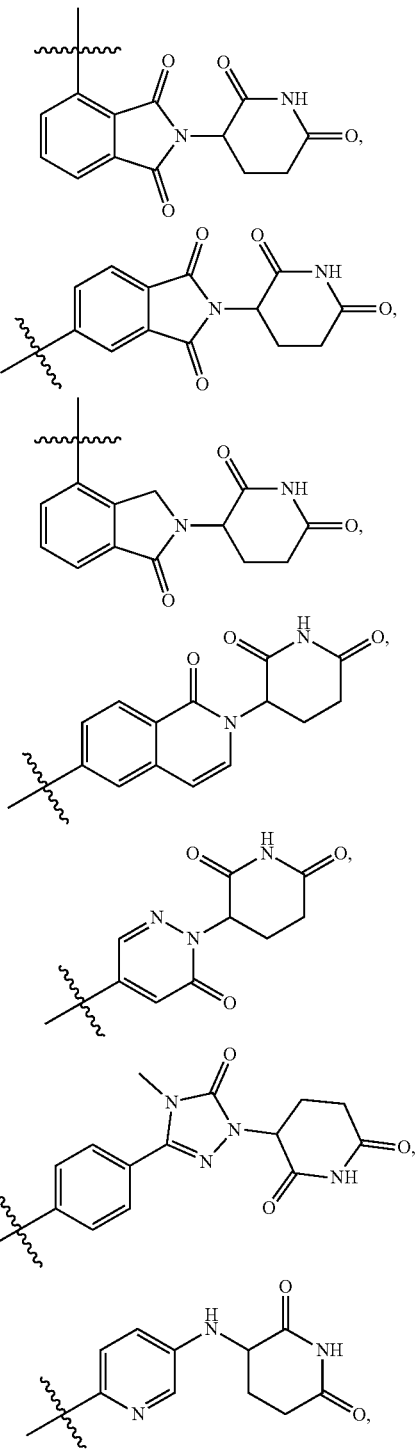

157
-continued
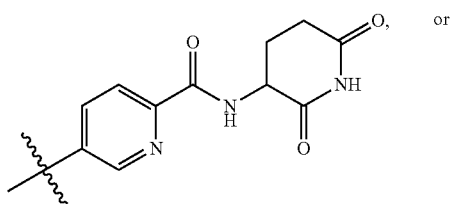
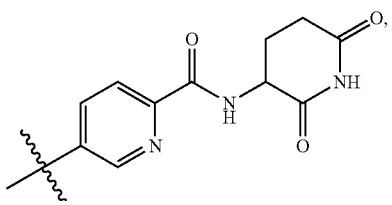
wherein at least one of $X^1$, $X^2$, $X^3$, $X^4$, and $X^5$ has a nitrogen atom, and Y is directly bonded to L at a nitrogen atom of $X^1$, $X^2$, $X^3$, $X^4$, or $X^5$.
In some embodiments, ring B is
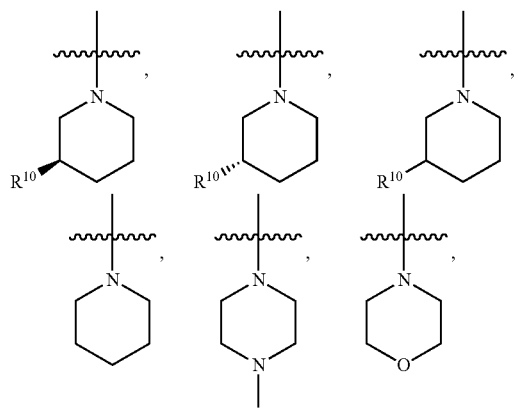
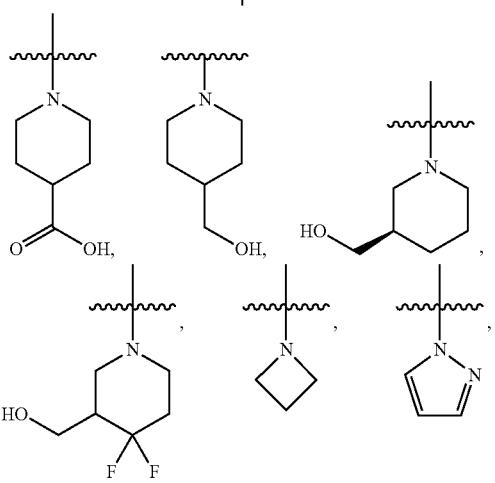
158
-continued
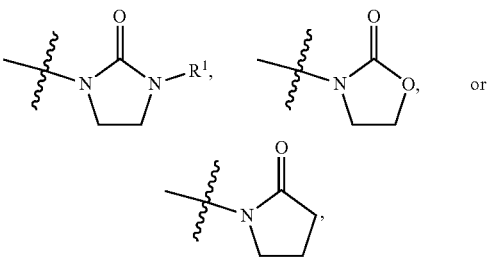
wherein $R^{10}$ is
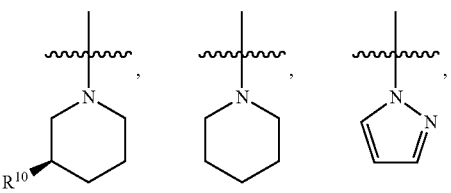
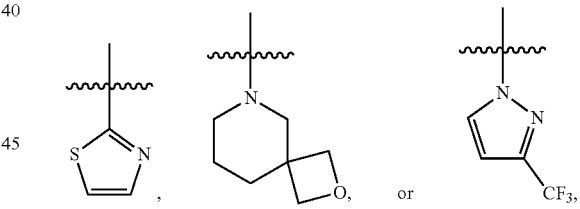
and wherein $R^1$ is a $C_{1-4}$ alkyl group. For example, ring B is
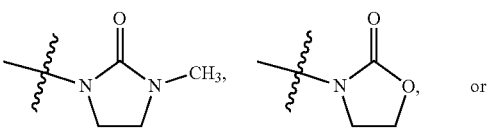
wherein $R^{10}$ is
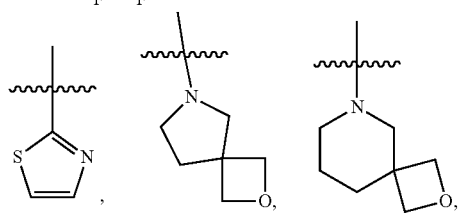
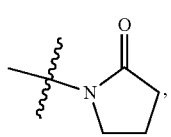

In other examples, ring B is
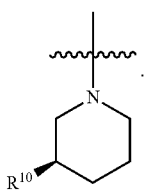
In some embodiments, $R^{10}$ is
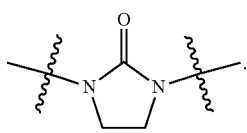 [SMILES: *N1CCN(*)C1=O]
In some embodiments, ring A is
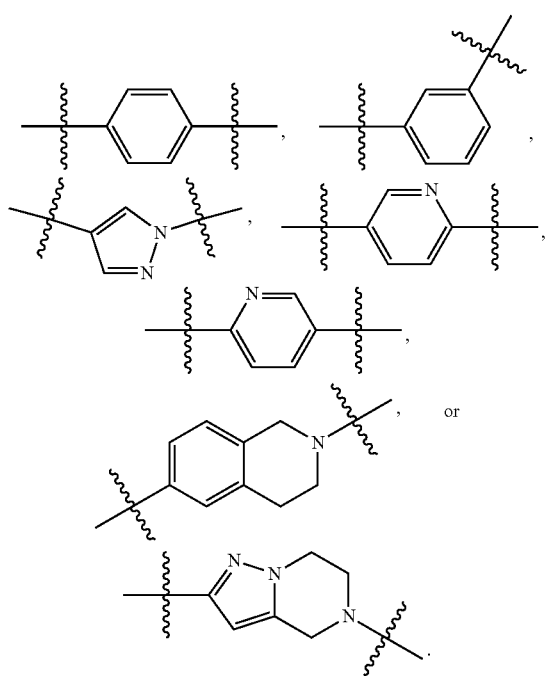
In some embodiments, $X^5$ is —N(R)—.
In some embodiments, $X^5$ is —C(O)—N(R)—.
In some embodiments, $X^5$ is a bond.
In some embodiments, L is
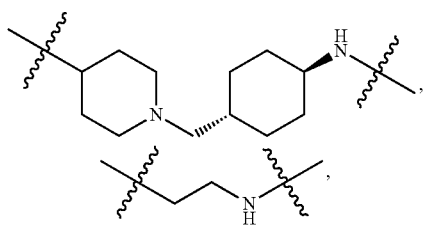
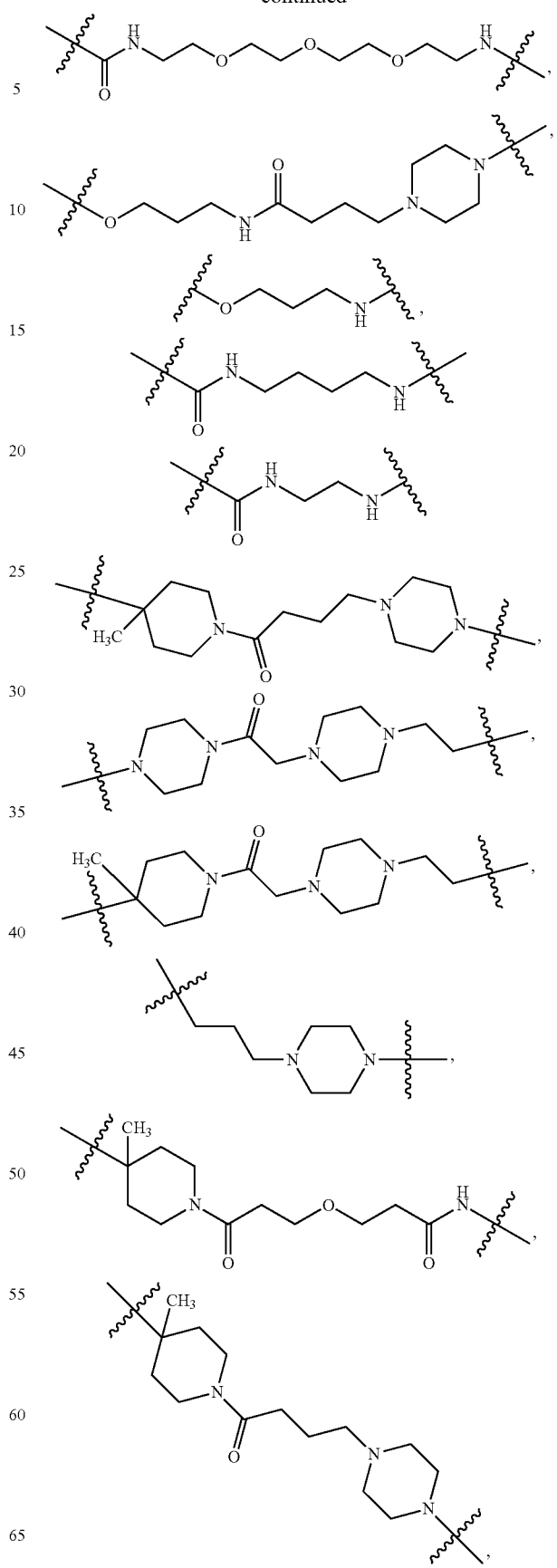

161
-continued
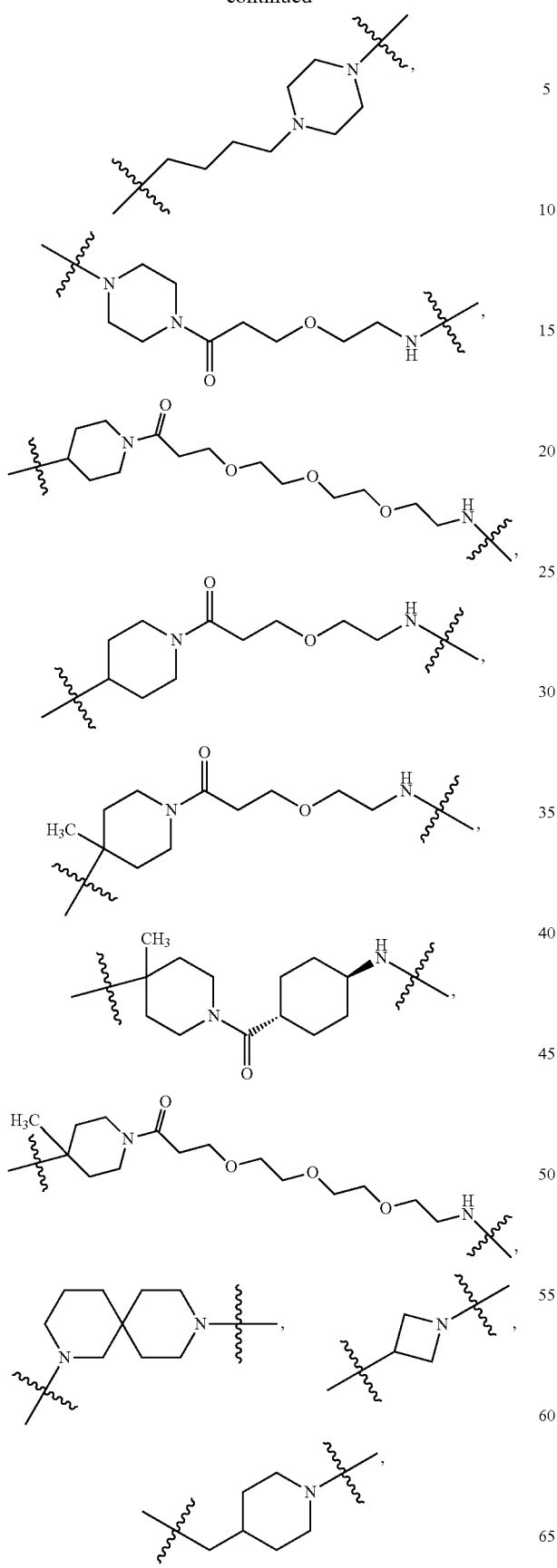
162
-continued
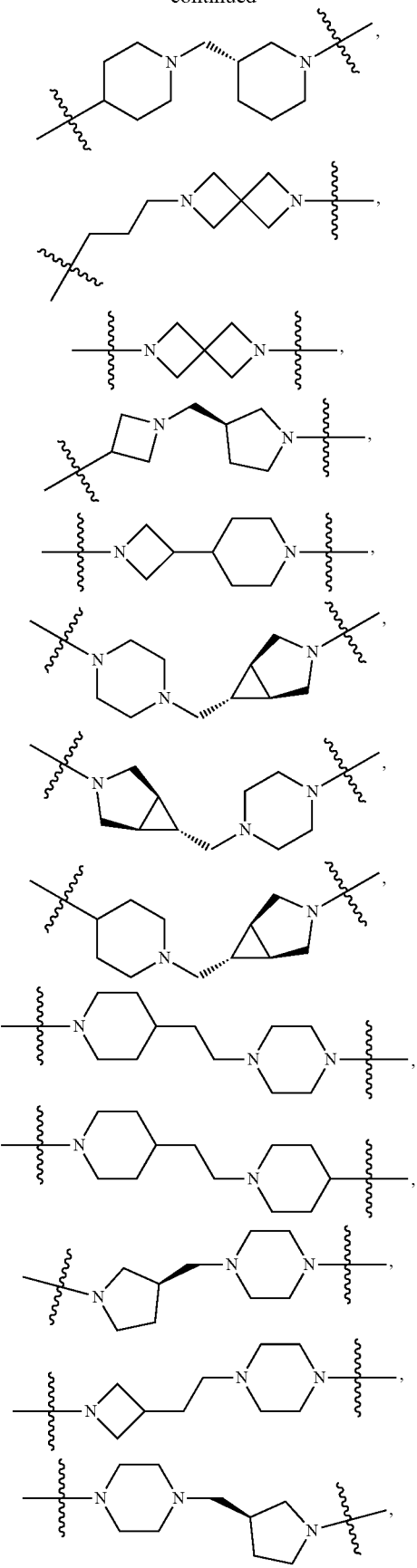

-continued
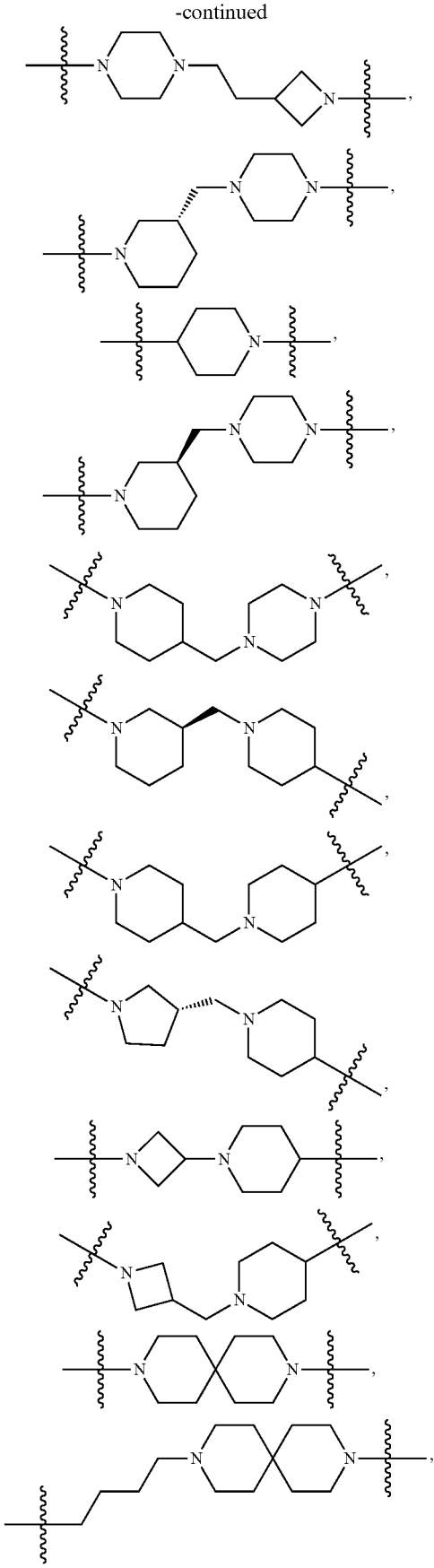
-continued
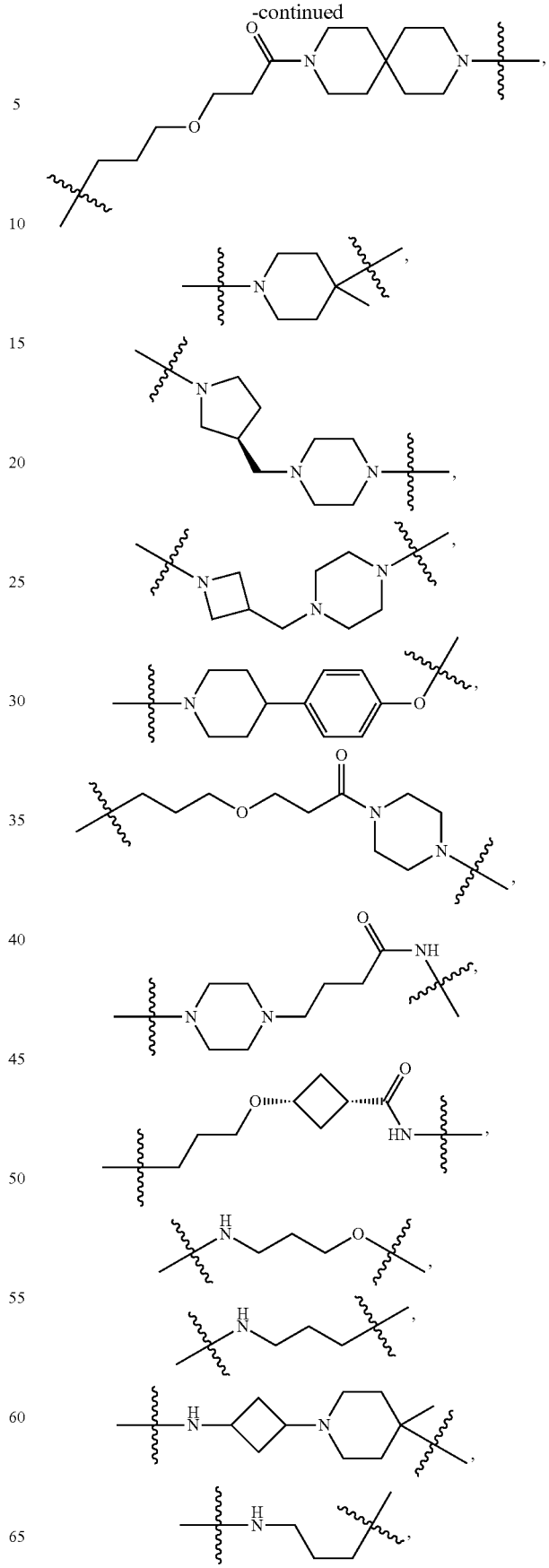

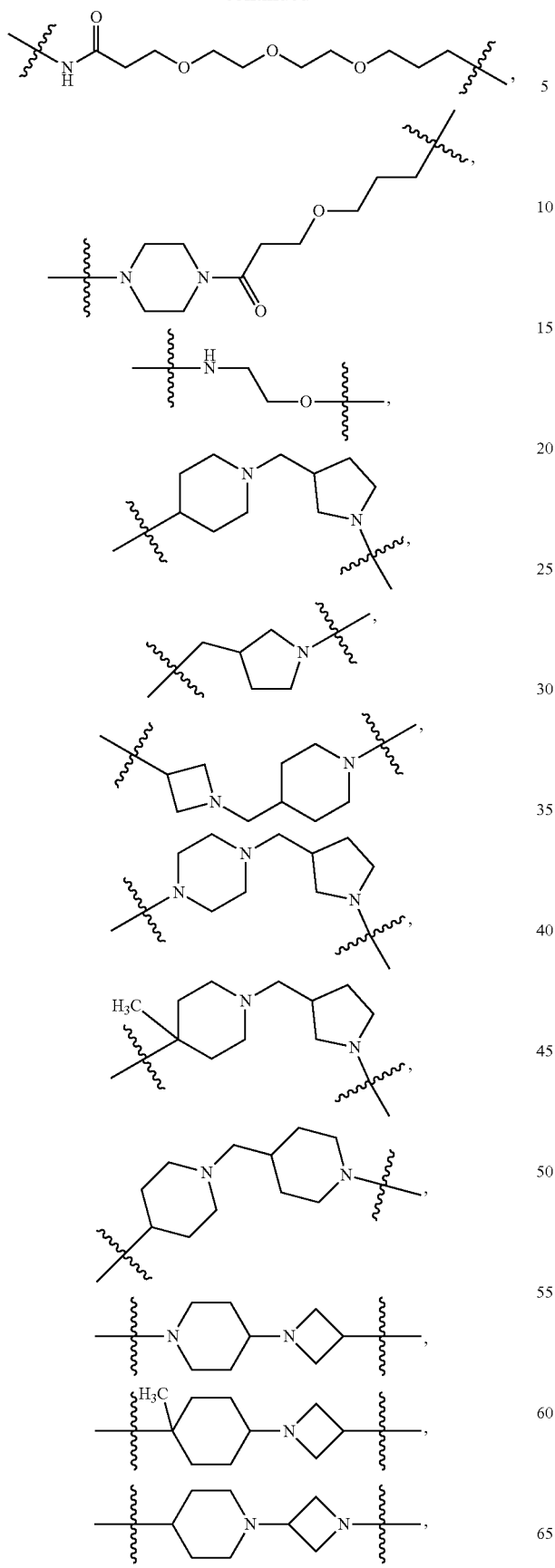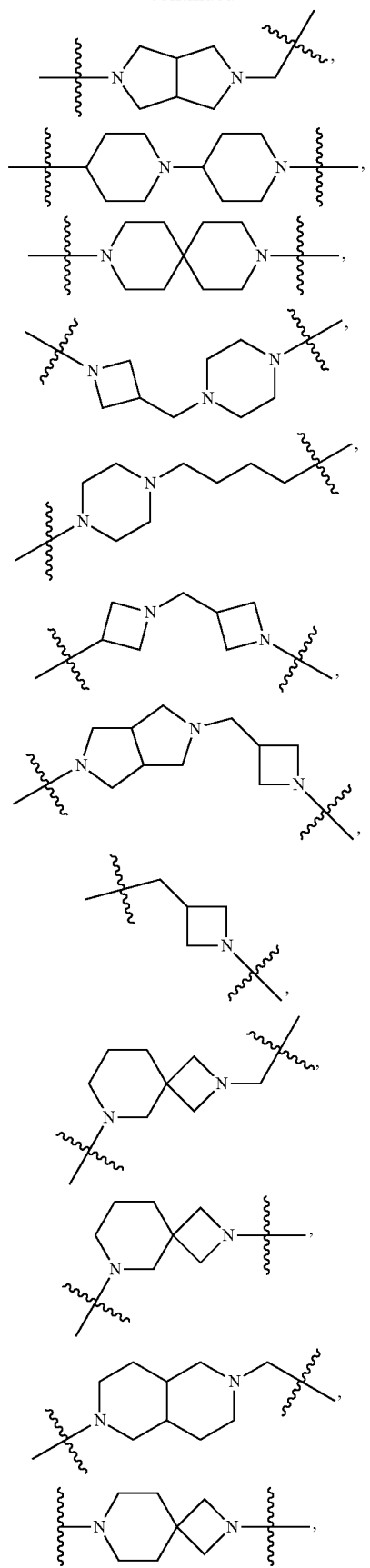

167
-continued

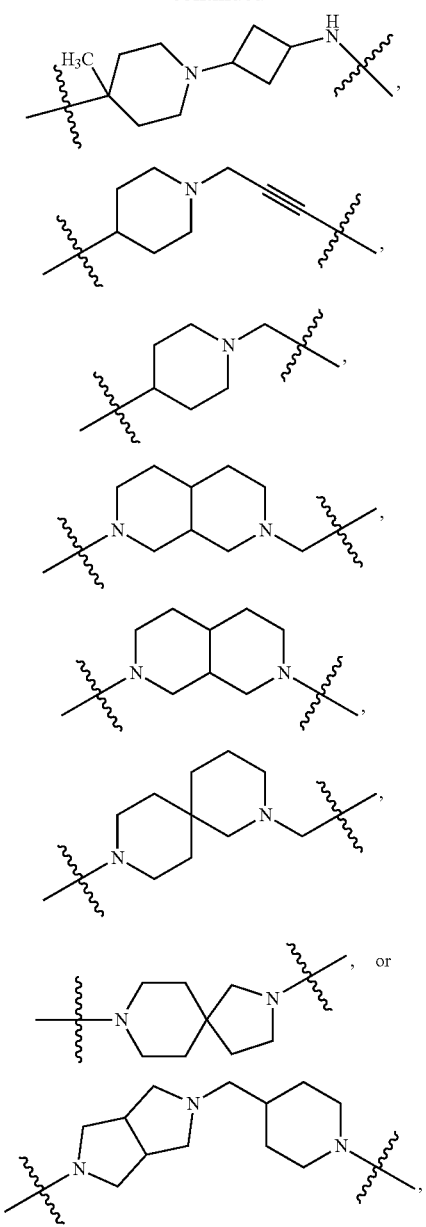

In some embodiments, Y is

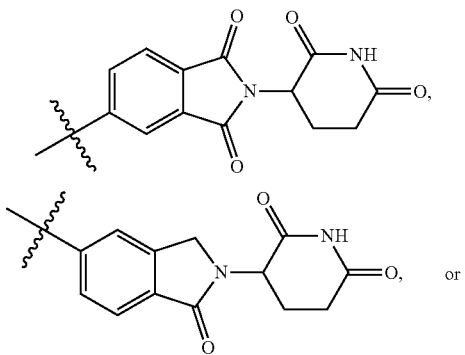

168
-continued

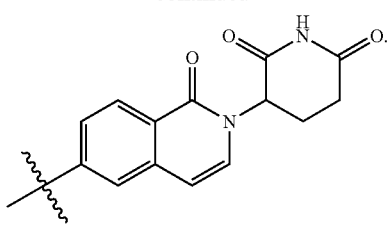

The present invention also provides a compound of Formula (F)

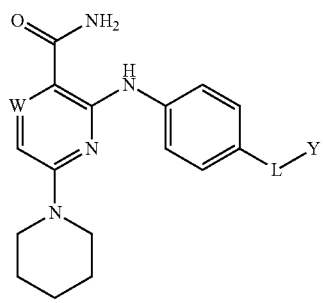

or a pharmaceutically acceptable salt thereof, wherein W is CH or N; L is —$X^1$—$X^2$—$X^3$—; $X^1$ is —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —$CH_3$; $X^2$ is a bond, —$C_{1-5}$ alkyl-, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; each R is independently —H or —$C_{1-3}$ alkyl; each of m, n, and p is independently an integer from 1 to 3; and Y is

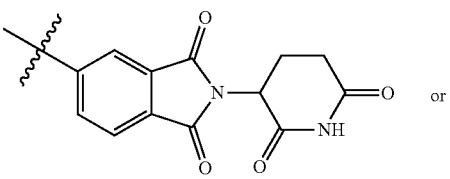

-continued

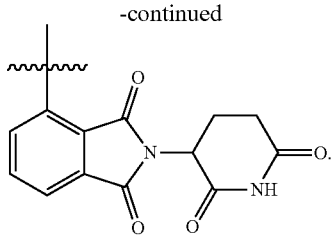

In some embodiments, W is N.

In some embodiments, Y is

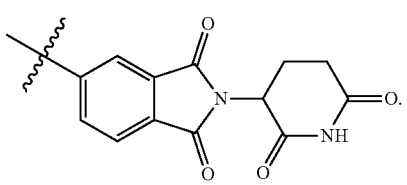 [SMILES: *c1ccc2c(c1)C(=O)N(C1CCC(=O)NC1=O)C2=O]

In some embodiments, $X^1$ is a 4-6 membered monocyclic heterocycloalkyl having 1-2 heteroatoms independently selected from N, O, or S, wherein each of the monocyclic heterocycloalkyl of $X^1$ is optionally substituted with —CH$_3$. For example, $X^1$ is

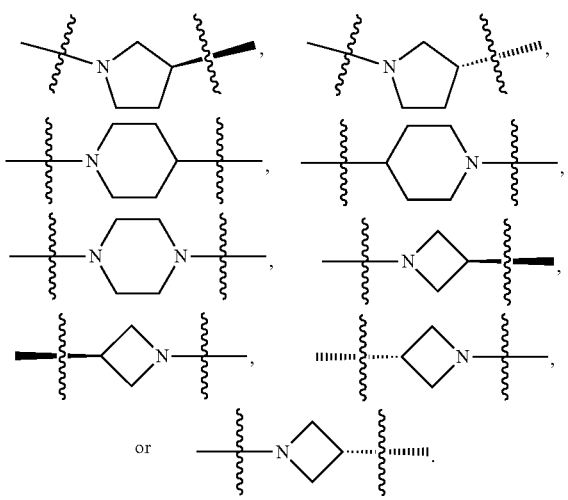

In some instances, $X^1$ is

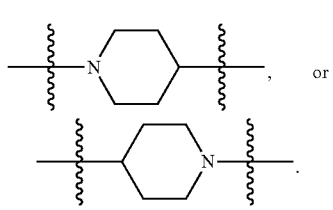

In some embodiments, $X^2$ is a bond or —C$_{1-5}$ alkyl-.

In some embodiments, $X^3$ is a 4-6 membered monocyclic heterocycloalkyl having 1-2 heteroatoms independently selected from N, O, or S. For example, $X^3$ is

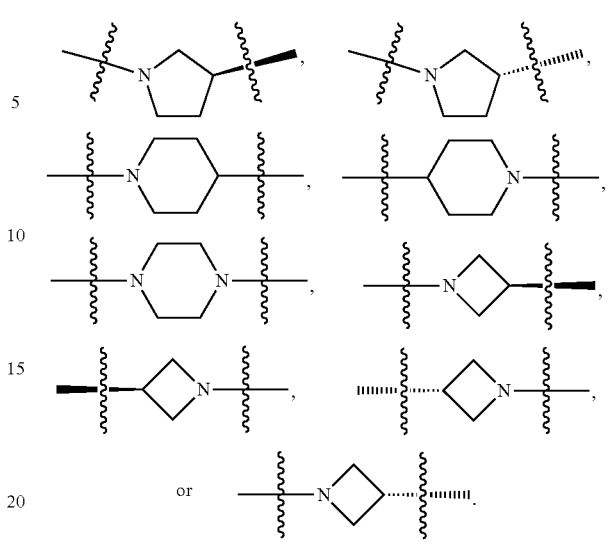

In some instances, $X^3$ is

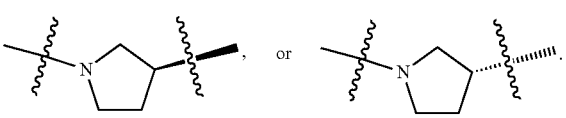

In some embodiments, L is

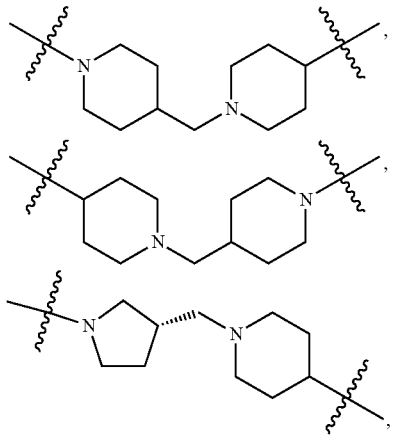

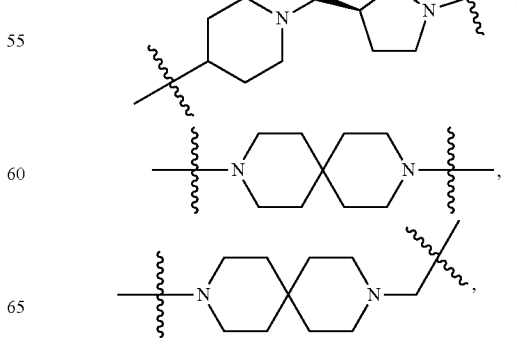

-continued

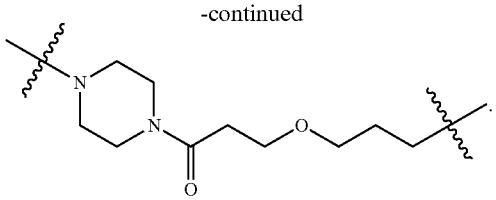

In some embodiments, L is

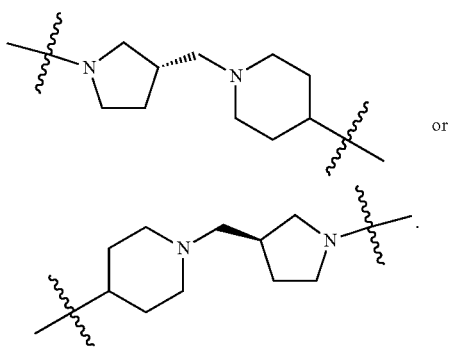

or

In some embodiments, W is N and L is

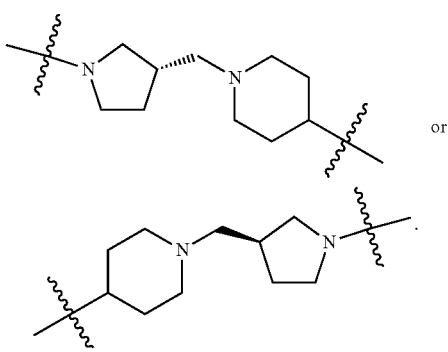

or

The present invention also provides a compound of Formula (G)

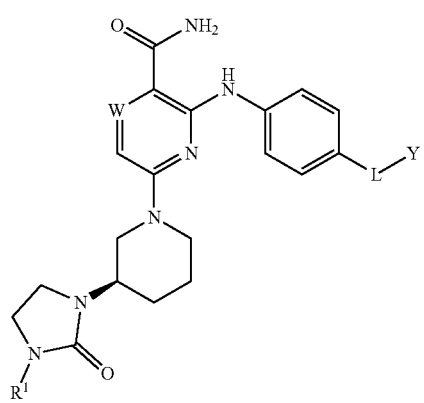

or a pharmaceutically acceptable salt thereof, wherein $R^1$, L, and Y are as defined for compounds of Formula (A).

In some embodiments, $R^1$ is methyl.

In some embodiments, Y is

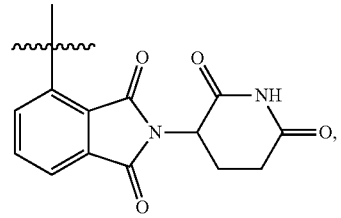

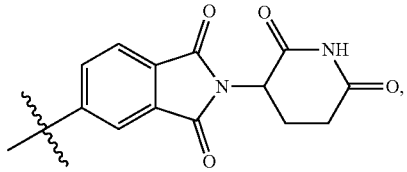

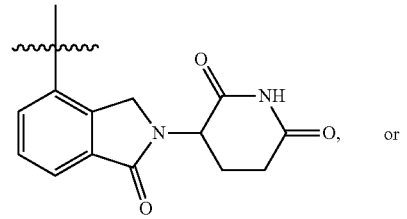

or

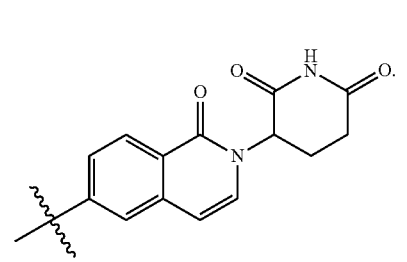

In some embodiments, W is N.

The present invention also provides a compound of Formula (H)

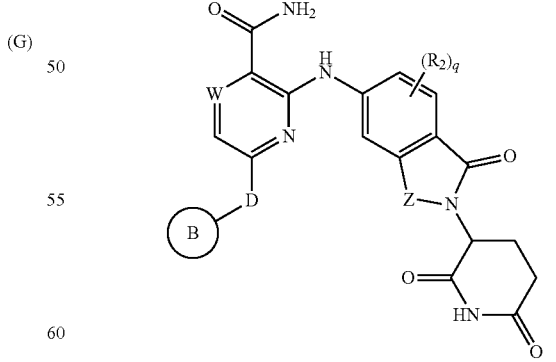

(H)

or a pharmaceutically acceptable salt thereof, wherein ring B, $R^2$, Z, W, D, and q are as defined in the compound of Formula (A).

In some embodiments, q is 0.

The present invention also provides a compound of Formula (J)

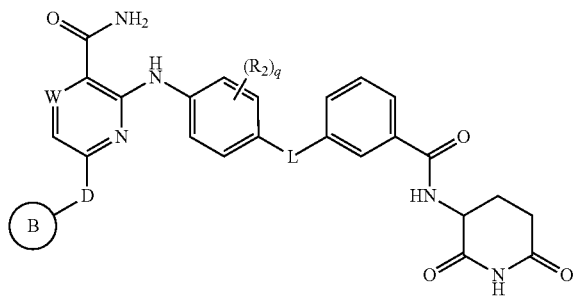

(J)

or a pharmaceutically acceptable salt thereof, wherein ring B, D, W, R², q, and L are as defined in the compound of Formula (A).

The present invention also provides a compound of Formula (K)

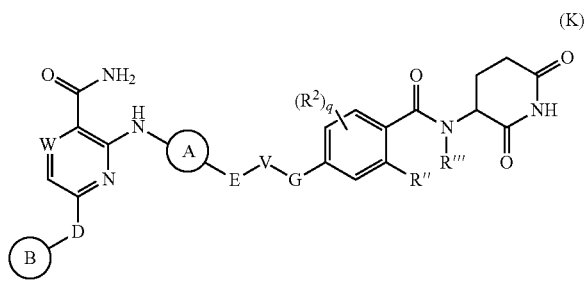

(K)

or a pharmaceutically acceptable salt thereof, wherein ring A is

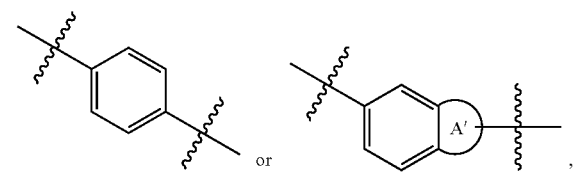

wherein ring A is optionally and independently substituted with up to 3 substituents selected from halo, —CN, -carboxyl, —NH₂, and optionally substituted —C$_{1-6}$ alkyl (e.g., optionally substituted —C$_{1-3}$ alkyl); V is a bond or —CH₂—; and E and G are each independently a 5-6 membered heterocycloalkyl, wherein each heterocycloalkyl contains at least one nitrogen atom. Ring B, W, R², q, R'', R''', and ring A' are as defined in the compound of Formula (A). In some embodiments, ring A' together with the phenyl ring to which it is fused form a 9-10 membered bicyclic aryl or a 9-10 membered bicyclic heteroaryl wherein the bicyclic heteroaryl has 1-3 heteroatoms independently selected from N, O, or S.

In some embodiments, D is a bond and W is a nitrogen atom.

The present invention also provides a compound of Formula (M)

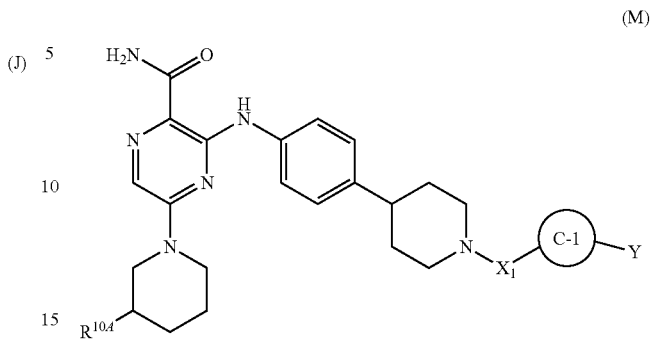

(M)

or a pharmaceutically acceptable salt thereof, wherein R$^{10A}$ is —H,

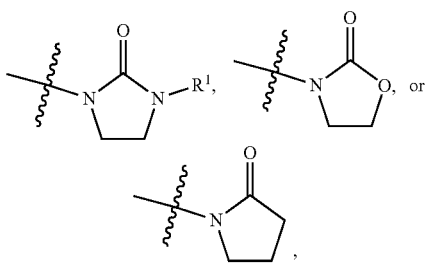

wherein R¹ is C$_{1-4}$ alkyl; X¹ is —C$_{1-5}$ alkyl-; ring C-1 is a 5-6 membered heterocycloalkyl having 1 nitrogen atom; and Y is

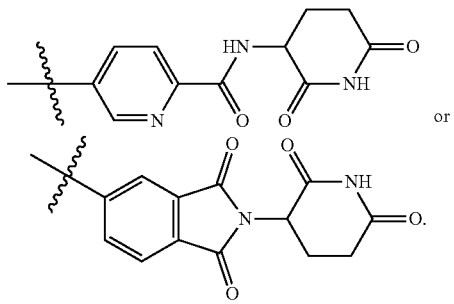

In some embodiments, R$^{10A}$ is —H or

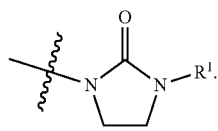

In some embodiments, R$^{10A}$ is

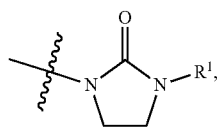

and R¹ is methyl, ethyl, propyl, iso-propyl, butyl, sec-butyl, or iso-butyl. For example, R¹ is methyl.

In some embodiments, X¹ is methylene, ethylene, or propylene. For instance, X¹ is methylene.

In some embodiments, ring C-1 is

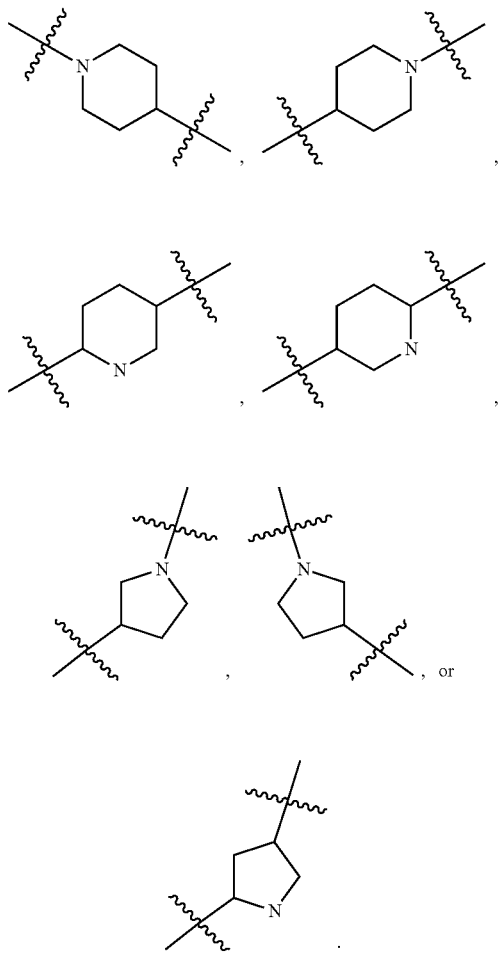

For instance, ring C-1 is

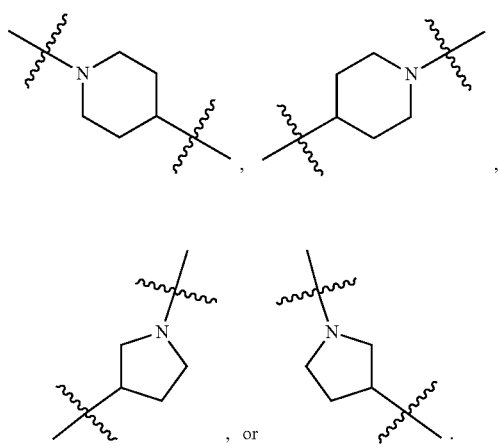

The present invention provides a compound of Formula (X)

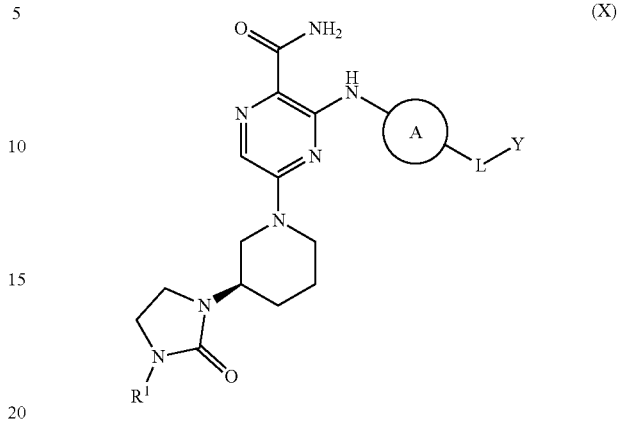

(X)

or a pharmaceutically acceptable salt thereof, wherein R¹ is $C_{1-3}$ alkyl; ring A is phenyl, 5-6 membered partially or fully unsaturated monocyclic heterocycle, 9-10 membered bicyclic aryl, or 9-10 membered bicyclic heteroaryl, wherein the heterocycle and the bicyclic heteroaryl of ring A each independently have 1-3 heteroatoms independently selected from N, O, or S; L is —X¹—X²—X³—X⁴—X⁵—; X¹ is —C(O)—N(R)—, —N(R)—C(O)—, —(O—CH₂—CH₂)$_m$—, —O(C₆H₄)—, —(O—CH₂—CH₂—CH₂)$_m$—, —$C_{1-5}$ alkyl-, 7-12 membered spiro bicyclic heterocycloalkyl having 1-3 heteroatoms independently selected from N, O, or S wherein the bicyclic heterocycloalkyl of X¹ is optionally substituted with —CH₃, or 4-6 membered monocyclic heterocycloalkyl having 1-2 heteroatoms independently selected from N, O, or S wherein the monocyclic heterocycloalkyl of X¹ is optionally substituted with —CH₃; X² is a bond, —(O—CH₂—CH₂)$_n$—, —(CH₂—CH₂—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S; X³ is a bond, —$C_{1-4}$ alkyl-, —C≡C—, 4-6 membered cycloalkyl, —N(R)—, —(O—CH₂—CH₂)$_p$—, —(CH₂—CH₂—O)$_p$—, 4-6 membered heterocycloalkyl having 1-2 heteroatoms independently selected from N, O, or S wherein the heterocycloalkyl is optionally substituted with —CH₃; X⁴ is a bond, —CH₂—CH₂—N(R)—, —N(R)—, —$C_{1-4}$ alkyl-, —(O—CH₂—CH₂—CH₂)$_m$—, or 5-6 membered saturated, partially unsaturated, or fully unsaturated carbocycle having 0-3 heteroatoms independently selected from N, O, or S; X⁵ is a bond, —$C_{1-4}$ alkyl-, —N(R)—, or —C(O)—N(R)—; each R is independently —H or —$C_{1-3}$ alkyl; each of m, n, and p is independently an integer from 1 to 3; Y is

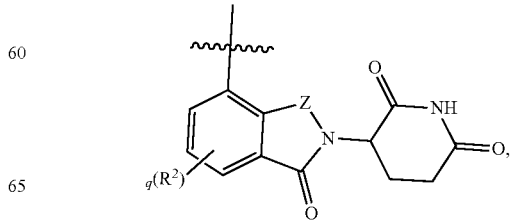

heteroatoms independently selected from N, O, or S; $X^5$ is a bond, —$C_{1-4}$ alkyl-, —N(R)—, or —C(O)—N(R)—; each R is independently —H or —$C_{1-3}$ alkyl; each of m, n, and p is independently an integer from 1 to 3 (e.g., 1, 2, or 3); Y is

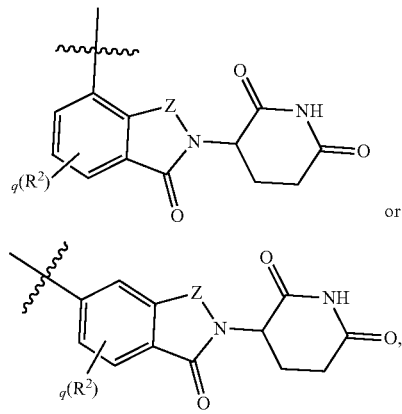

or wherein each $R^2$ is independently halo or —$C_{1-4}$ alkyl; each Z is —$C(R^A)_2$— or —C(O)—; each $R^A$ is independently —H or —$C_{1-4}$ alkyl; and q is 0, 1, or 2.

In some embodiments, q is 0. In other embodiments, q is 1 and $R^2$ is —F.

In some embodiments, Z is —$CH_2$— or —C(O)—.

In some embodiments, Y is

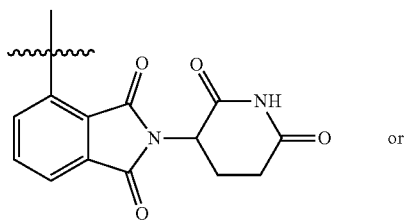

or

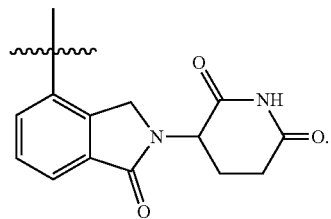

In other embodiments, Y is

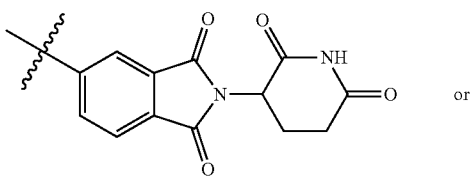

or

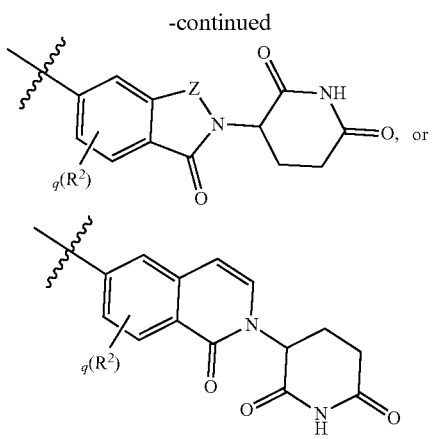

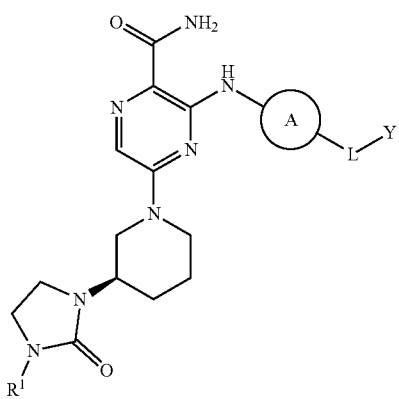

wherein; each $R^2$ is independently halo or $C_{1-4}$ alkyl; each Z is —$C(R^A)_2$— or —C(O)—; each $R^A$ is independently —H or $C_{1-4}$ alkyl; and q is 0, 1, or 2.

In some instances, the compound of Formula (X) is a compound of Formula (I)

(I)

or a pharmaceutically acceptable salt thereof, wherein $R^1$ is $C_{1-3}$ alkyl; ring A is phenyl, 9-10 membered bicyclic aryl, or 9-10 membered bicyclic heteroaryl having 1-3 heteroatoms independently selected from N, O, or S; L is —$X^1$—$X^2$—$X^3$—$X^4$—$X^5$—; $X^1$ is —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S wherein the heterocycloalkyl is optionally substituted with —$CH_3$, or 4-6 membered heterocycloalkyl having 1-2 heteroatoms independently selected from N, O, or S wherein the heterocycloalkyl is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered cycloalkyl, or 4-6 membered heterocycloalkyl having 1-2 heteroatoms independently selected from N, O, or S; $X^3$ is a bond, —$C_{1-4}$ alkyl-, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—$CH_2$)$_m$—, or 5-6 membered saturated, partially unsaturated, or fully unsaturated heterocycle having 1-3

-continued

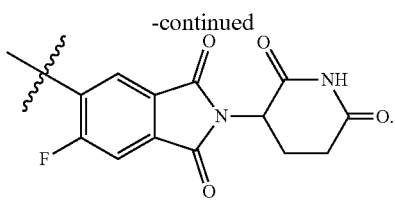

In some embodiments, $R^1$ is —$C_{1-3}$ alkyl. For example, $R^1$ is methyl, ethyl, propyl, or iso-propyl. In other examples, $R^1$ is methyl.

In some embodiments, each R is independently —H or —$CH_3$. For instance, each R is —H.

In some embodiments, $X^1$ is —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered heterocycloalkyl having 1-2 heteroatoms independently selected from N, O, or S wherein the heterocycloalkyl is optionally substituted with —$CH_3$. In some embodiments, $X^1$ is —C(O)—N(R)—. For example, $X^1$ is —C(O)—N(H)—, —C(O)—N($CH_3$)—, or —C(O)—N($CH_2CH_3$)—. In other embodiments, $X^1$ is a 5-6 membered heterocycloalkyl having 1-2 heteroatoms independently selected from N, O, or S wherein the heterocycloalkyl is optionally substituted with —$CH_3$. For example, $X^1$ is,

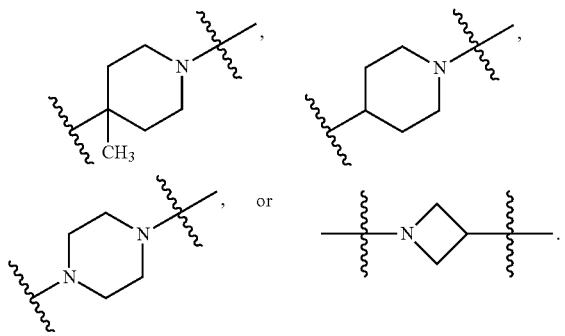

In other examples, $X^1$ is a 7-10 membered spiro bicyclic heterocycloalkyl ring having 1-3 heteroatoms independently selected from N, O, or S (e.g., N). For example, $X^1$ is

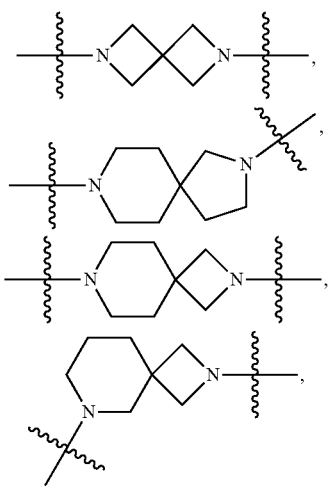

-continued

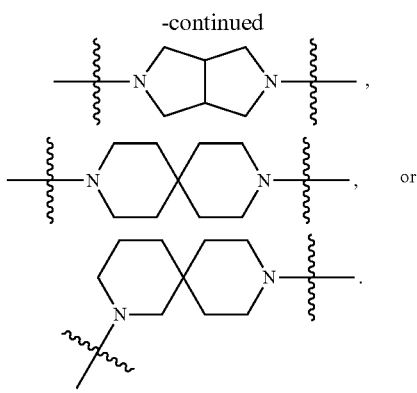

In other embodiments, $X^1$ is —(O—$CH_2$—$CH_2$)$_m$— or —(O—$CH_2$—$CH_2$—$CH_2$)$_m$—, wherein m is 1, 2, or 3. For example, $X^1$ is —(O—$CH_2$—$CH_2$)$_m$— or —(O—$CH_2$—$CH_2$—$CH_2$)$_m$—, and m is 1. In another example, $X^1$ is —(O—$CH_2$—$CH_2$)$_m$— or —(O—$CH_2$—$CH_2$—$CH_2$)$_m$—, and m is 2. In some embodiments, $X^1$ is —$C_{1-5}$ alkyl-. For example, $X^1$ is methylene, ethylene, propylene, butylene, or the like. In some embodiments, $X^1$ is —$CH_2$—, —C(O)—,

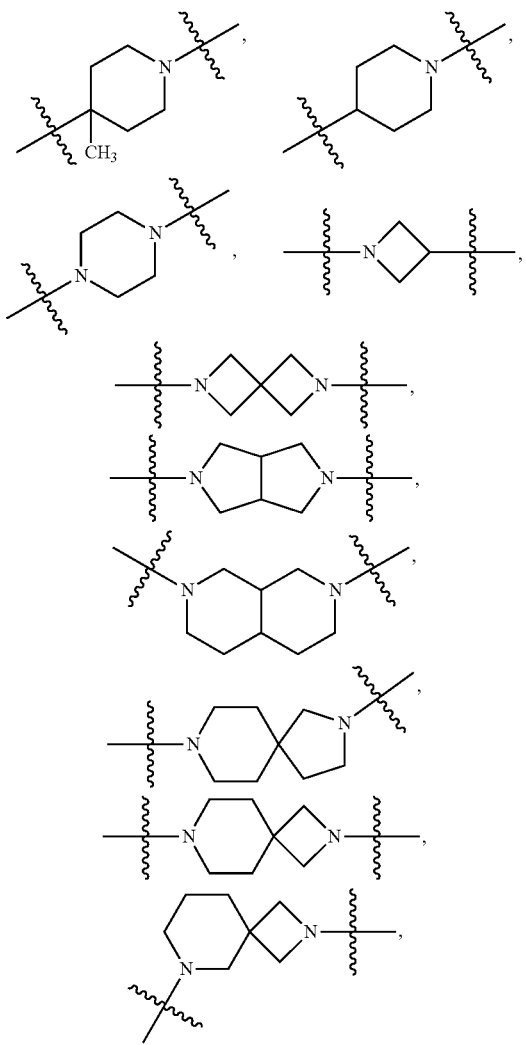

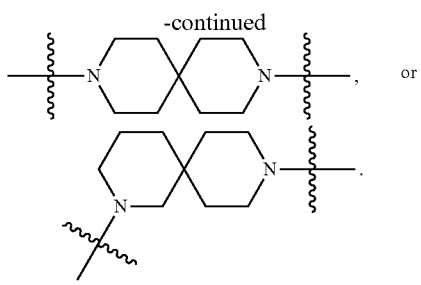

In some embodiments, $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having 1-2 heteroatoms independently selected from N, O, or S. In some embodiments, $X^2$ is a bond. In some embodiments, $X^2$ is $-(O-CH_2-CH_2)_n-$, $-(CH_2-CH_2-O)_n-$, or $-C_{1-5}$ alkyl-, wherein n is 1, 2, or 3. For example, $X^1$ is $-C(O)-N(R)-$, and $X^2$ is $-(O-CH_2-CH_2)_n-$, $-(CH_2-CH_2-O)_n-$, or $-C_{1-5}$ alkyl-. In some examples, $X^2$ is $-(O-CH_2-CH_2)_n-$ or $-(CH_2-CH_2-O)_n-$, where n is 1 or 2. In other examples, $X^2$ is $-C_{1-5}$ alkyl-. For instance, $X^2$ is methylene, ethylene, propylene, butylene, or the like. In other examples, $X^2$ is a bond, $-CH_2-$, $-CH_2-CH_2-$, or $-CH_2-CH_2-CH_2-$. In some examples, $X^2$ is 4-6 membered cycloalkyl. For instance, $X^2$ is

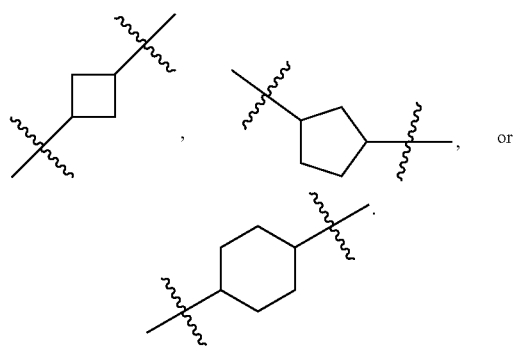

In other examples $X^2$ is 4-6 membered heterocycloalkyl having 1-2 heteroatoms independently selected from N, O, or S. For instance, $X^2$ is

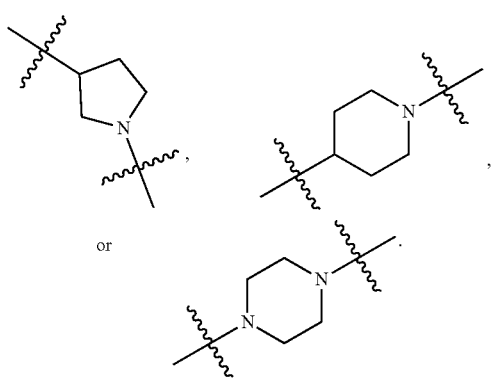

In some embodiments, $X^3$ is a bond, $-C_{1-4}$ alkyl-, 4-6 membered cycloalkyl, $-N(R)-$, $-(O-CH_2-CH_2)_p-$, $-(CH_2-CH_2-O)_p-$, 4-6 membered heterocycloalkyl having 1-2 heteroatoms independently selected from N, O, or S wherein the heterocycloalkyl is optionally substituted with $-CH_3$. In some embodiments, $X^3$ is a bond. In some embodiment, $X^3$ is methyl, ethyl, propyl, iso-propyl, butyl, or the like. In some embodiments, $X^3$ is cyclopently or cyclohexyl. In some embodiments, $X^3-N(H)-$. And, in other embodiments, $X^3$ is $-(O-CH_2-CH_2)_p-$ or $-(CH_2-CH_2-O)_p-$, wherein p is 1 or 2.

In some embodiments, $X^4$ is a bond, $-CH_2-CH_2-N(R)-$, $-N(R)-$, $-C_{1-4}$ alkyl-, $-(O-CH_2-CH_2-CH_2)_m-$, or 5-6 membered saturated, partially unsaturated, or fully unsaturated heterocycle having 1-3 heteroatoms independently selected from N, O, or S. In some embodiments, $X^4$ is a bond,

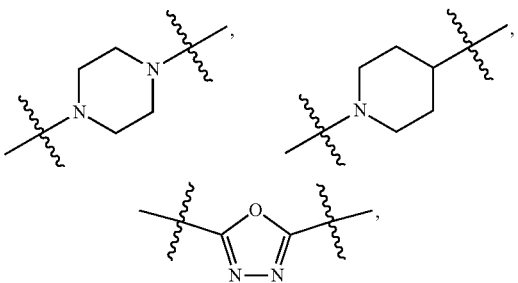

$-C_{1-4}$ alkyl-, $-CH_2-CH_2-N(R)-$, or $-N(R)-$. For example, $X^4$ is $-CH_2-CH_2-N(H)-$, or $-N(H)-$. In other examples, $X^4$ is methyl, ethyl, propyl, iso-propyl, butyl, sec-butyl, or the like.

In some embodiments, $X^5$ is a bond, $-C_{1-4}$ alkyl-, $-N(R)-$, or $-C(O)-N(R)-$. In some embodiments, $X^5$ is a bond. In some embodiments, $X^5$ is methyl, ethyl, propyl, iso-propyl, butyl, or the like. In some embodiments, $X^5$ is $-N(H)-$ or $-C(O)-N(H)-$.

In some embodiments, L is selected from

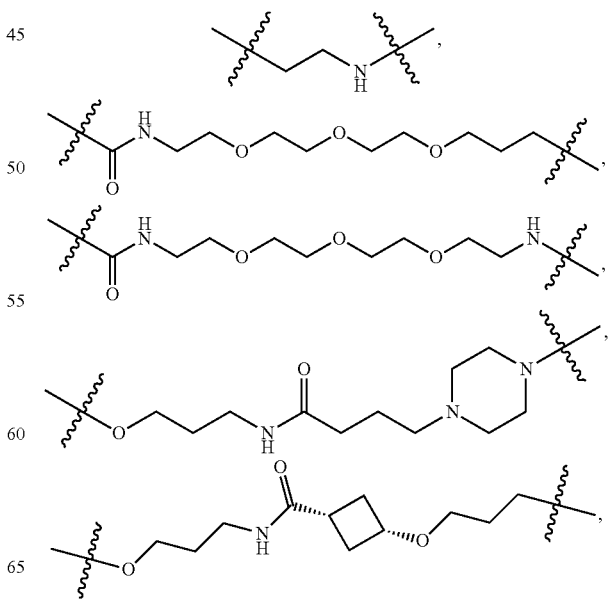

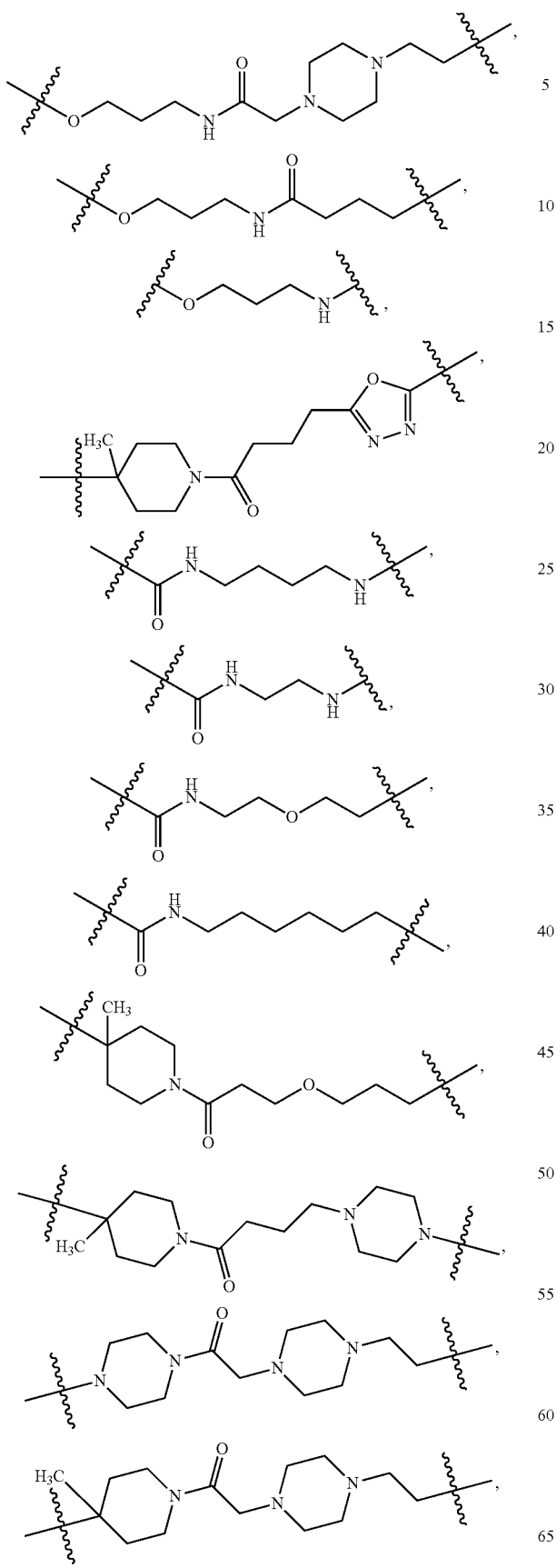
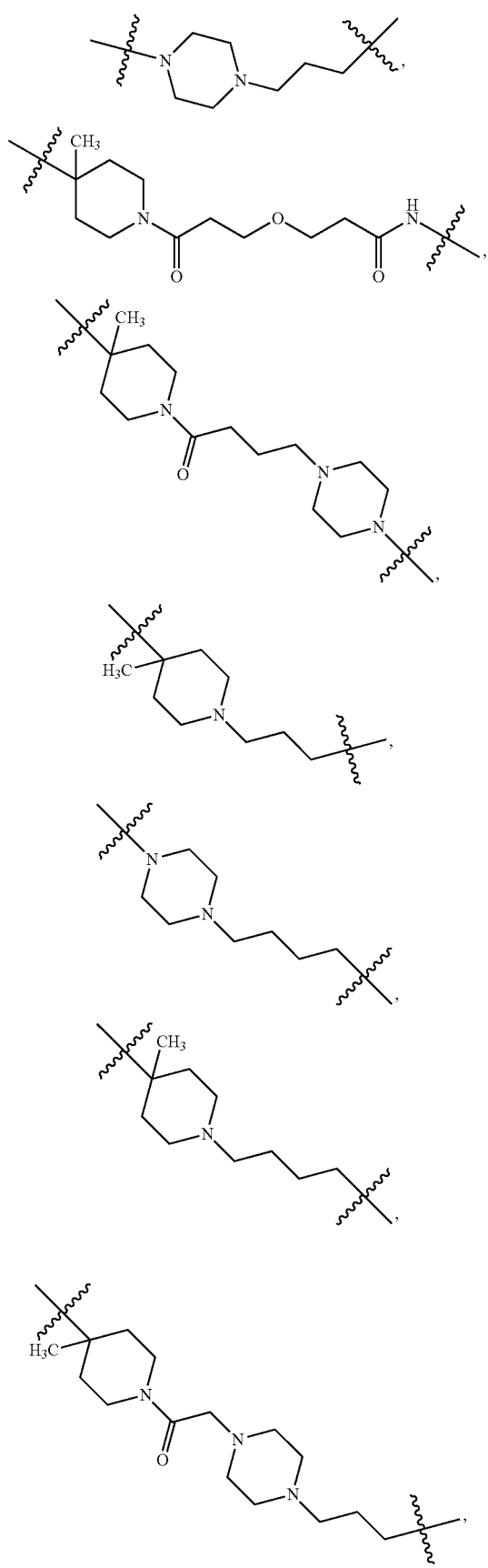

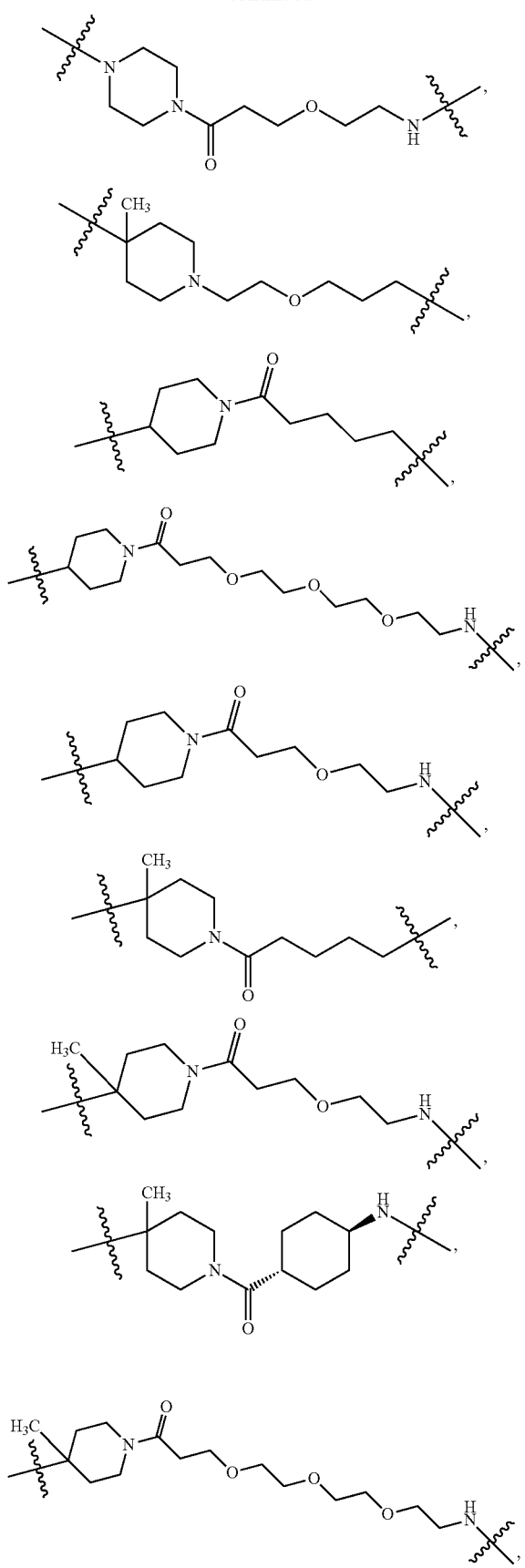
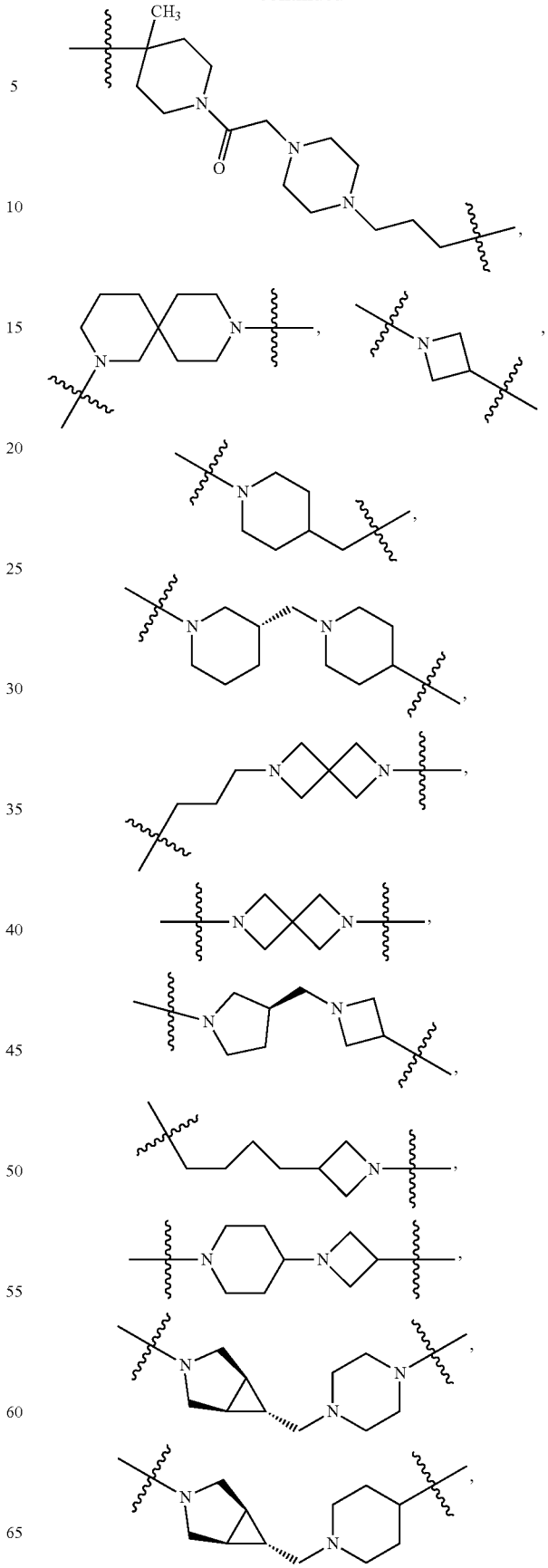

187
-continued
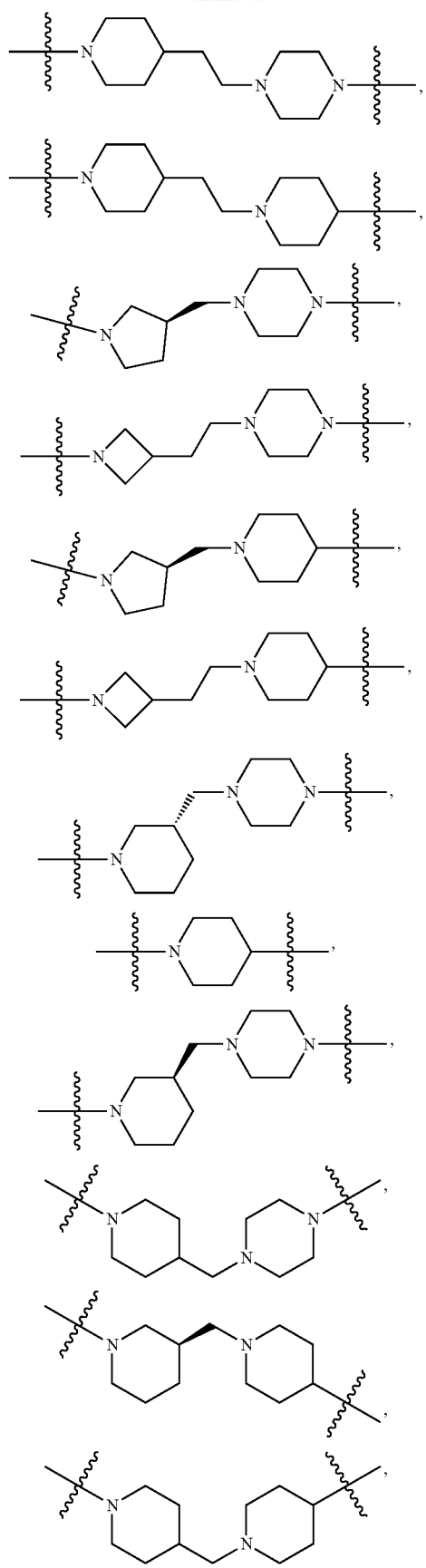
188
-continued
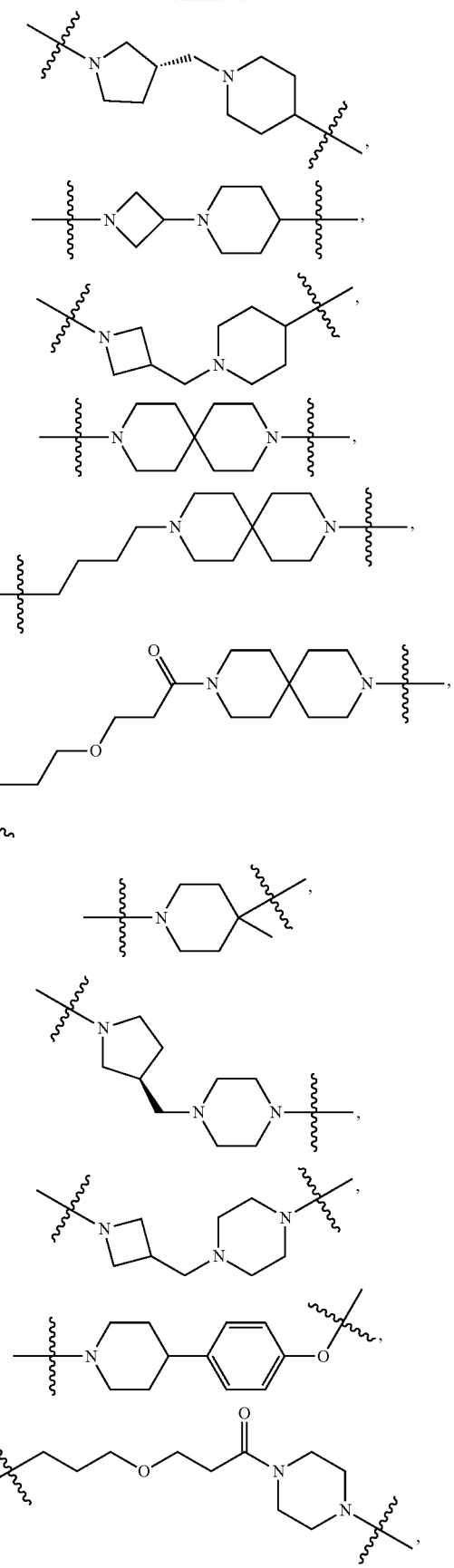

189
-continued
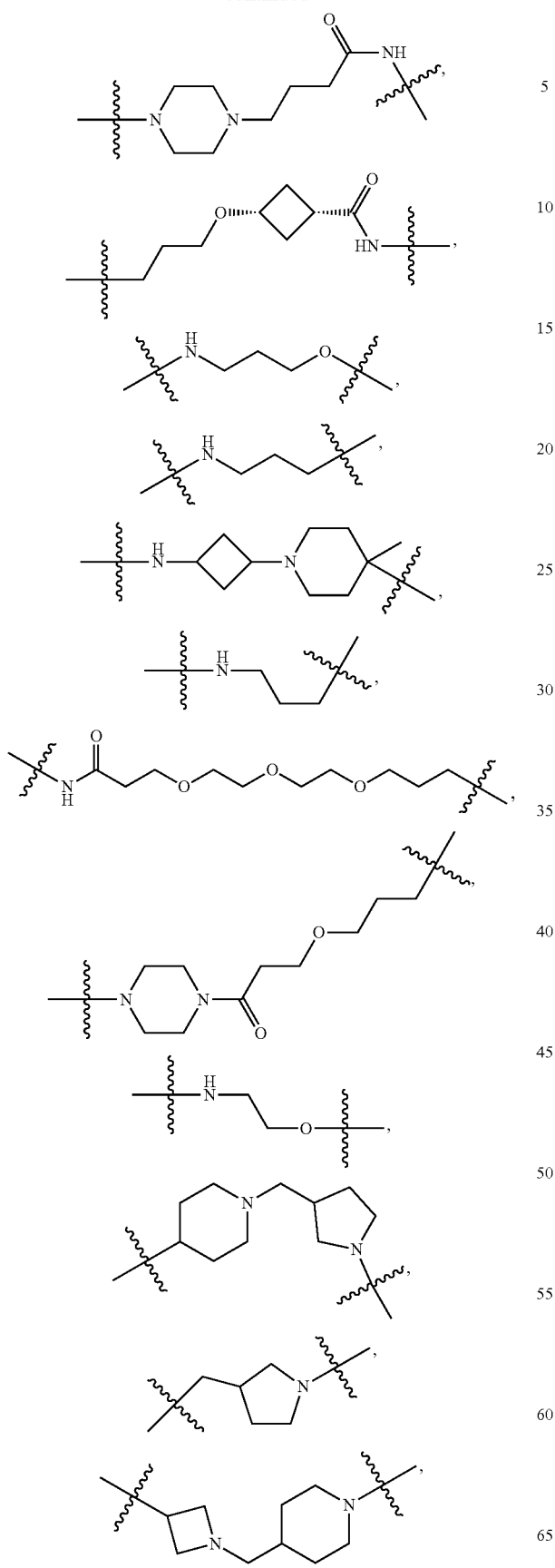
190
-continued
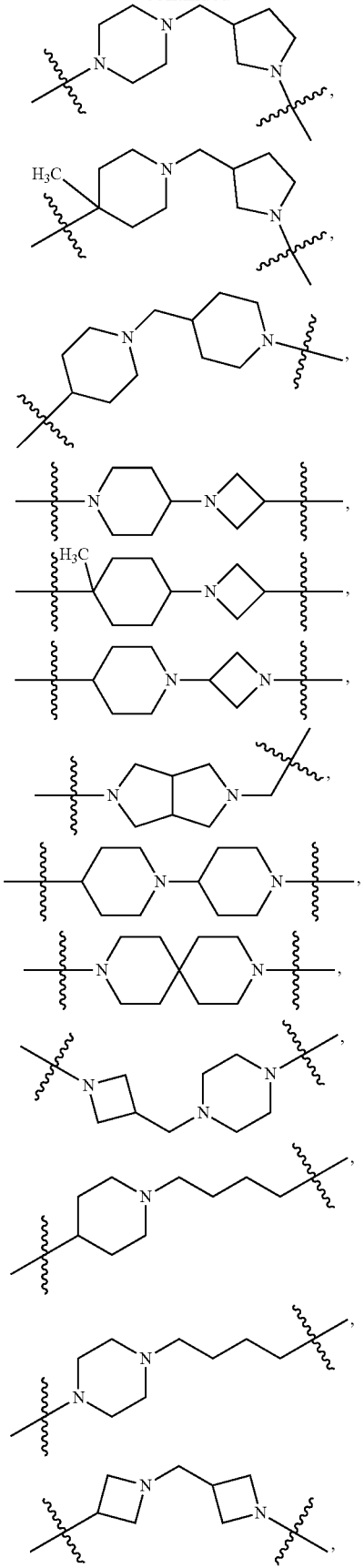

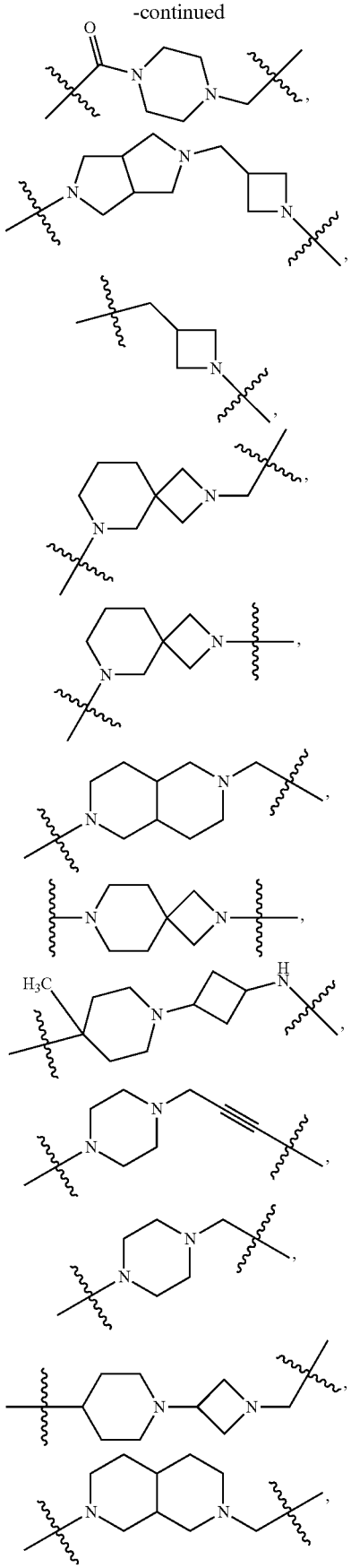

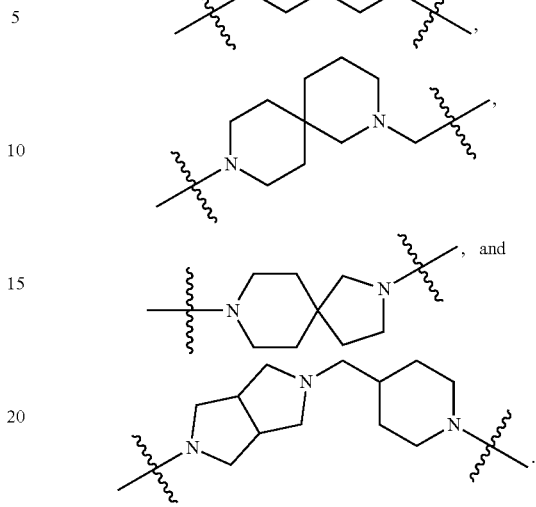

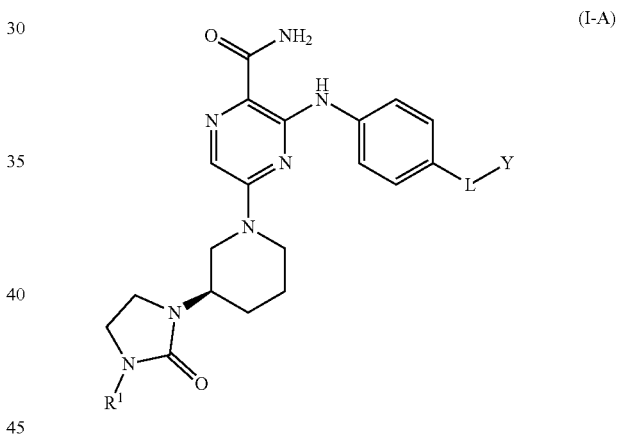

The present invention also provides a compound of Formula (I-A):

(I-A)

or a pharmaceutically acceptable salt thereof, wherein $R^1$ is $C_{1-3}$ alkyl; L is $-X^1-X^2-X^3-X^4-X^5-$; $X^1$ is $-C(O)-N(R)-$, $-N(R)-C(O)-$, $-(O-CH_2-CH_2)_m-$, $-O(C_6H_4)-$, $-(O-CH_2-CH_2-CH_2)_m-$, $-C_{1-5}$ alkyl-, 7-12 membered spiro bicyclic heterocycloalkyl having 1-3 heteroatoms independently selected from N, O, or S wherein the heterocycloalkyl is optionally substituted with $-CH_3$, or 4-6 membered heterocycloalkyl having 1-2 heteroatoms independently selected from N, O, or S wherein the heterocycloalkyl is optionally substituted with $-CH_3$; $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having 1-2 heteroatoms independently selected from N, O, or S; $X^3$ is a bond, $-C_{1-4}$ alkyl-, 4-6 membered cycloalkyl, $-N(R)-$, $-(O-CH_2-CH_2)_p-$, $-(CH_2-CH_2-O)_p-$, or 4-6 membered heterocycloalkyl having 1-2 heteroatoms independently selected from N, O, or S wherein the heterocycloalkyl is optionally substituted with $-CH_3$; $X^4$ is a bond, $-CH_2-CH_2-N(R)-$, $-N(R)-$, $-C_{1-4}$ alkyl-, $-(O-CH_2-CH_2-CH_2)_m-$, or 5-6 membered saturated, partially unsaturated, or fully unsaturated heterocycle having 1-3 heteroatoms independently selected from N, O, or S; X⁵ is a bond, —C₁₋₄ alkyl-, —N(R)—, or —C(O)—N(R)—; each R is independently —H or —C₁₋₃ alkyl; each of m, n, and p is independently an integer from 1 to 3; Y is

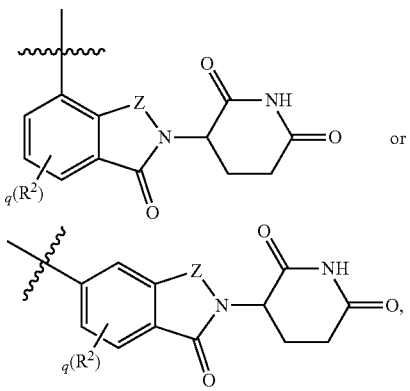

or wherein each R² is independently halo or —C₁₋₄ alkyl; each Z is —C(Rᴬ)₂— or —C(O)—; each Rᴬ is independently —H or —C₁₋₄ alkyl; and q is 0, 1, or 2.

In other embodiments, each of the variables in Formula (I-A) is as defined herein for the compound of Formula (X) or (I).

The present invention also provides a compound of Formula (I-B)

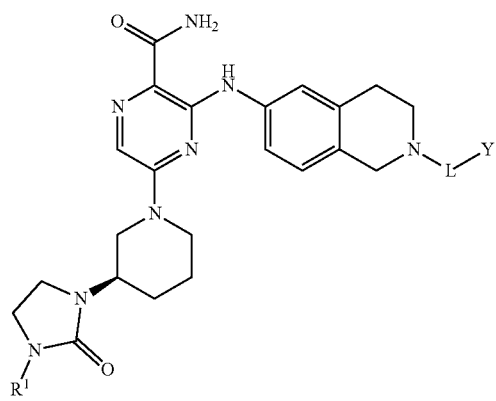

(I-B)

or a pharmaceutically acceptable salt thereof, wherein R¹ is C₁₋₃ alkyl; L is —X¹—X²—X³—X⁴—X⁵—; X¹ is —C(O)—N(R)—, —N(R)—C(O)—, —(O—CH₂—CH₂)ₘ—, —O(C₆H₄)—, —(O—CH₂—CH₂—CH₂)ₘ—, —C₁₋₅ alkyl-, 7-12 membered spiro bicyclic heterocycloalkyl ring having 1-3 heteroatoms independently selected from N, O, or S wherein the heterocycloalkyl is optionally substituted with —CH₃, or 4-6 membered heterocycloalkyl having 1-2 heteroatoms independently selected from N, O, or S wherein the heterocycloalkyl is optionally substituted with —CH₃; X² is a bond, —(O—CH₂—CH₂)ₙ—, —(CH₂—CH₂—O)ₙ—, —N(R)—C(O)—, —N(R)—, —C(O)—, —C₁₋₅ alkyl-, 4-6 membered cycloalkyl, or 4-6 membered heterocycloalkyl having 1-2 heteroatoms independently selected from N, O, or S; X³ is a bond, —C₁₋₄ alkyl-, 4-6 membered cycloalkyl, —N(R)—, —(O—CH₂—CH₂)ₚ—, —(CH₂—CH₂—O)ₚ—, or 4-6 membered heterocycloalkyl having 1-2 heteroatoms independently selected from N, O, or S wherein the heterocycloalkyl is optionally substituted with —CH₃; X⁴ is a bond, —CH₂—CH₂—N(R)—, —N(R)—, —C₁₋₄ alkyl-, —(O—CH₂—CH₂—CH₂)ₘ—, or 5-6 membered saturated, partially unsaturated, or fully unsaturated heterocycle having 1-3 heteroatoms independently selected from N, O, or S; X⁵ is a bond, —C₁₋₄ alkyl-, —N(R)—, or —C(O)—N(R)—; each R is independently —H or —C₁₋₃ alkyl; each of m, n, and p is independently an integer from 1 to 3; Y is

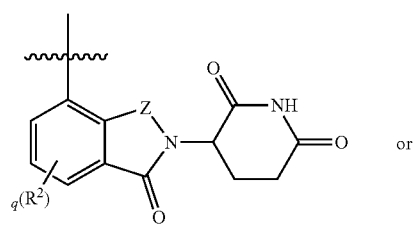

or

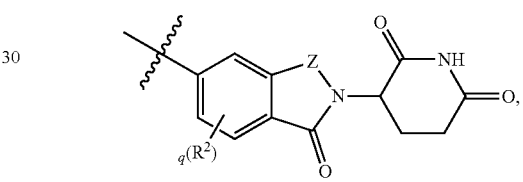

wherein each R² is independently halo or C₁₋₄ alkyl; each Z is —C(Rᴬ)₂— or —C(O)—; each Rᴬ is independently —H or C₁₋₄ alkyl; and q is 0, 1, or 2.

In other embodiments, each of the variables in Formula (I-B) is as defined herein for the compound of Formula (X) or (I).

The present invention also provides a compound of Formula (II):

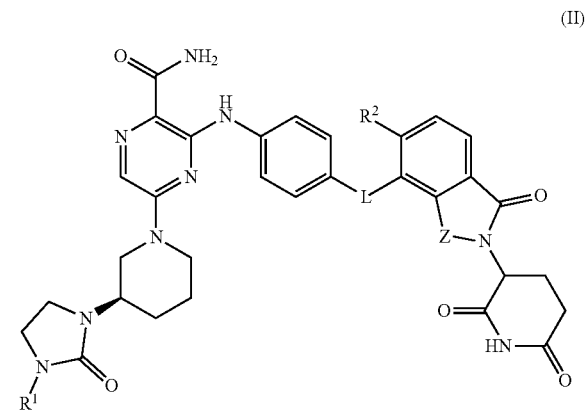

(II)

or a pharmaceutically acceptable salt thereof, wherein each of R¹, R², L, and Z are as defined herein for the compound of Formula (X), (I), (I-A), or (I-B).

In some embodiments, the compound of Formula (II) is a compound of Formulae (II-A) or (II-B)

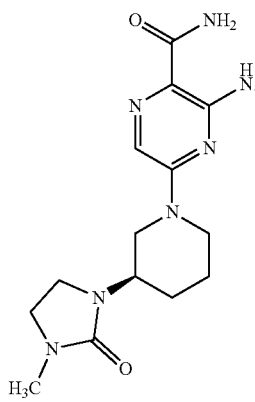

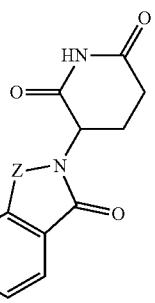

(II-A)

or

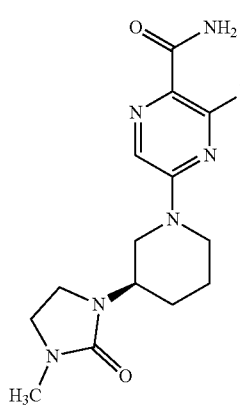

(II-B)

or a pharmaceutically acceptable salt thereof, wherein each of $X^2$, $X^3$, $X^4$, and $X^5$ are as defined herein for the compound of Formula (X), (I), (I-A), (I-B), or (II).

The present invention also provides a compound of Formula (III)

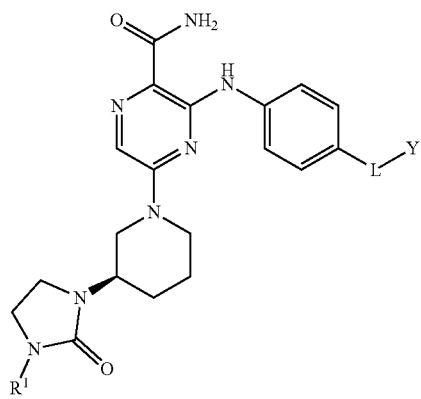

(III)

or a pharmaceutically acceptable salt thereof, wherein $R^1$ is $C_{1-3}$ alkyl; L is —$X^1$—$X^2$—$X^3$—; $X^1$ is 7-12 membered spiro bicyclic heterocycloalkyl having 1-3 heteroatoms independently selected from N, O, or S wherein the heterocycloalkyl is optionally substituted with —$CH_3$, or 4-6 membered heterocycloalkyl having 1-2 heteroatoms independently selected from N, O, or S wherein the heterocycloalkyl is optionally substituted with —$CH_3$; $X^2$ is a bond or —$C_{1-5}$ alkyl-; $X^3$ is a bond, —$C_{1-4}$ alkyl-,4-6 membered heterocycloalkyl having 1-2 heteroatoms independently selected from N, O, or S wherein the heterocycloalkyl is optionally substituted with —$CH_3$; Y is

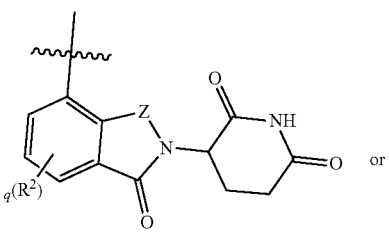

or

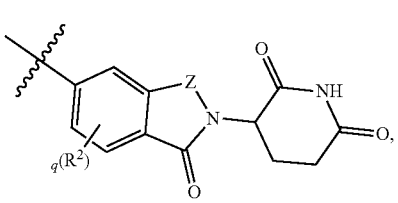

wherein each $R^2$ is independently halo or —$C_{1-4}$ alkyl; each Z is —$C(R^4)_2$— or —$C(O)$—; each $R^4$ is independently —H; and q is 0, 1, or 2.

The present invention also provides a compound of Formula (IV)

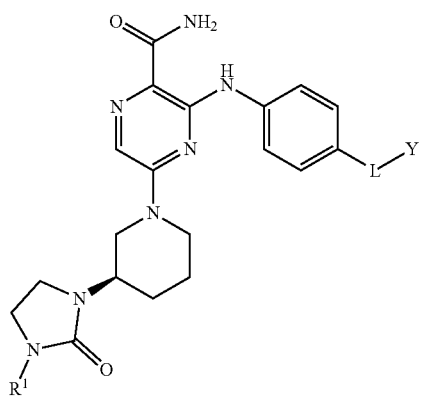

(IV)

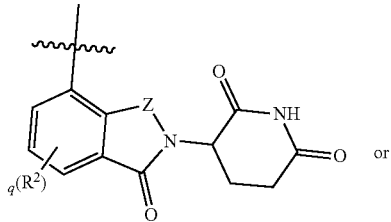

or

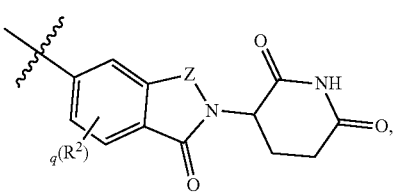

or a pharmaceutically acceptable salt thereof, wherein $R^1$ is $C_{1-3}$ alkyl; L is —$X^1$—$X^2$—$X^3$—$X^4$—$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S wherein the heterocycloalkyl is optionally substituted with —CH$_3$, or 4-6 membered heterocycloalkyl having 1-2 heteroatoms independently selected from N, O, or S wherein the heterocycloalkyl is optionally substituted with —CH$_3$; $X^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered cycloalkyl, or 4-6 membered heterocycloalkyl having 1-2 heteroatoms independently selected from N, O, or S; $X^3$ is a bond, —C$_{1-4}$ alkyl-, 4-6 membered cycloalkyl, —N(R)—, —(O—CH$_2$—CH$_2$)$_p$—, —(CH$_2$—CH$_2$—O)$_p$—, or 4-6 membered heterocycloalkyl having 1-2 heteroatoms independently selected from N, O, or S wherein the heterocycloalkyl is optionally substituted with —CH$_3$; $X^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated heterocycle having 1-3 heteroatoms independently selected from N, O, or S; $X^5$ is a bond, —C$_{1-4}$ alkyl-, —N(R)—, or —C(O)—N(R)—; each R is independently —H or —C$_{1-3}$ alkyl; each of m, n, and p is independently an integer from 1 to 3; Y is wherein each $R^2$ is independently halo or —C$_{1-4}$ alkyl; each Z is —C($R^4$)$_2$— or —C(O)—; each $R^4$ is independently —H or —C$_{1-4}$ alkyl; and q is 0, 1, or 2.

B. General Synthetic Schemes
General Procedure 1: Amide Coupling.

A mixture of amine (0.03 mmol), acid (0.03 mmol), HATU (0.04 mmol), DIPEA (0.15 mmol) and DMF was allowed to stir at r.t. for 30 minutes. The mixture was purified by HPLC (H$_2$O/MeCN with 0.1% TFA) to afford the amide product. An exemplary amide coupling is provided in the Scheme 1 below where 3-(3-(2-(2,6-dioxopiperidin-3-yl)-1-oxoisoindolin-4-yl)propoxy)propanoic acid, and (R)-3-((4-(3,9-diazaspiro[5.5]undecan-3-yl)phenyl)amino)-5-(3-(3-methyl-2-oxoimidazolidin-1-yl)piperidin-1-yl) pyrazine-2-carboxamide were reacted as described above to provide 3-((4-(9-(3-(3-(2-(2,6-dioxopiperidin-3-yl)-1-oxoisoindolin-4-yl)propoxy)propanoyl)-3,9-diazaspiro[5.5]undecan-3-yl)phenyl)amino)-5-((R)-3-(3-methyl-2-oxoimidazolidin-1-yl)piperidin-1-yl)pyrazine-2-carboxamide (Compound 57).

Scheme 1: Synthesis of Compound 57 Via Amide Formation.

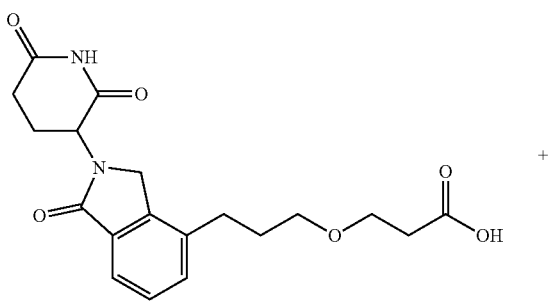

+

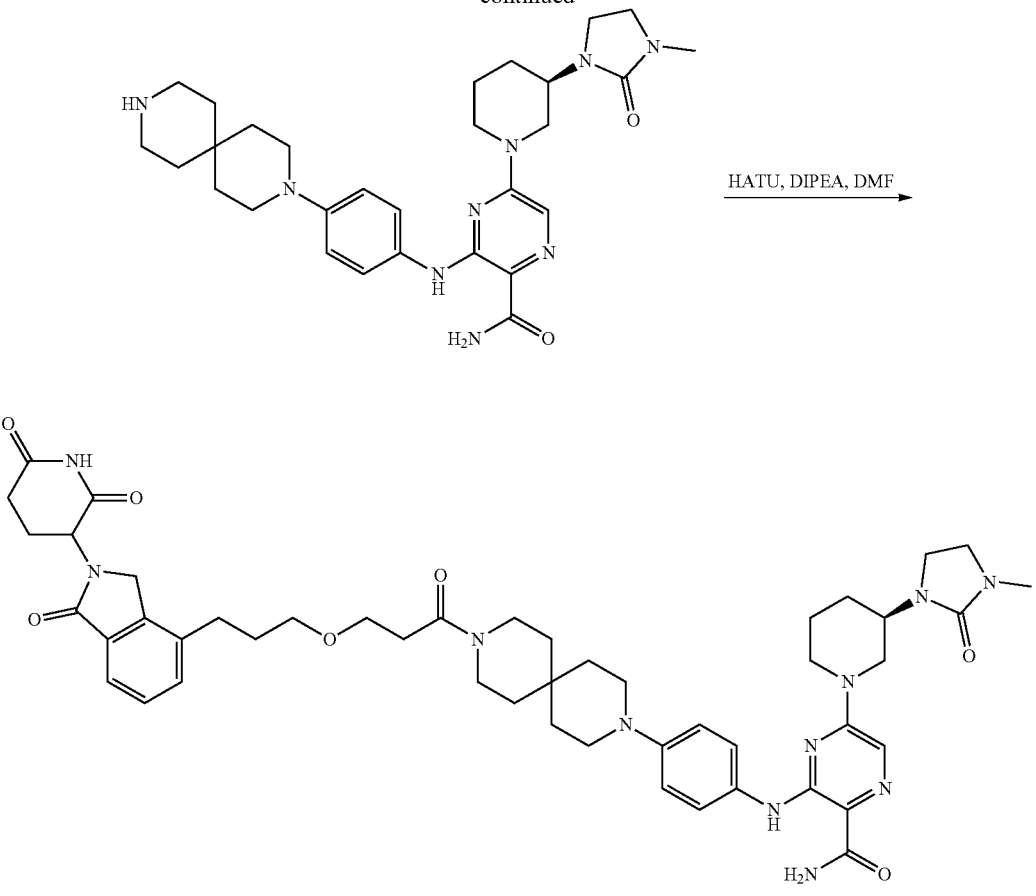

Compound 57

Other amide containing compounds of the invention synthesized by using general procedure 1 are Compounds 2-9, 10-14, 19, 20, 22-28, 61, 62, 63, and 67.

General Procedure 2: Reductive Amination.

A mixture of amine TFA salt (0.07 mmol), aldehyde (0.1 mmol), triethylamine (0.28 mmol), and DCE were allowed to stir at r.t. for 10 minutes. NaBH(OAc)$_3$ (0.14 mmol) was added and the mixture was allowed to stir at r.t. for 2 h. The mixture was filtered through celite, washing with CH$_2$Cl$_2$, concentrated, and purified by HPLC (H$_2$O/MeCN with 0.1% TFA) to afford the amine product. An exemplary reductive amination is provided in Scheme 2 where (R)-5-(3-(3-methyl-2-oxoimidazolidin-1-yl)piperidin-1-yl)-3-((4-(piperidin-4-yl)phenyl)amino)pyrazine-2-carboxamide was reacted as described above with (3R)-1-(2-(2,6-dioxopiperidin-3-yl)-1,3-dioxoisoindolin-5-yl)piperidine-3-carbaldehyde to provide 3-((4-(1-(((3S)-1-(2-(2,6-dioxopiperidin-3-yl)-1,3-dioxoisoindolin-5-yl)piperidin-3-yl)methyl)piperidin-4-yl)phenyl)amino)-5-((R)-3-(3-methyl-2-oxoimidazolidin-1-yl)piperidin-1-yl)pyrazine-2-carboxamide (Compound 32).

Scheme 2: Synthesis of Compound 32 Via Reductive Amination.

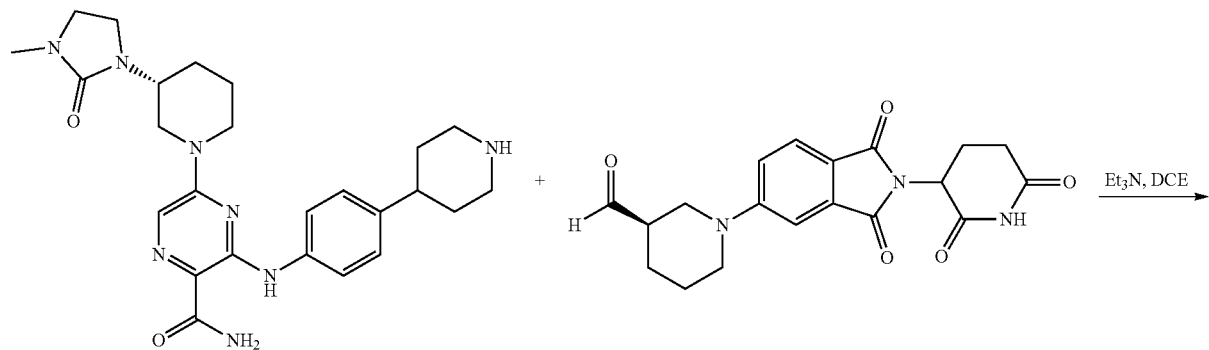

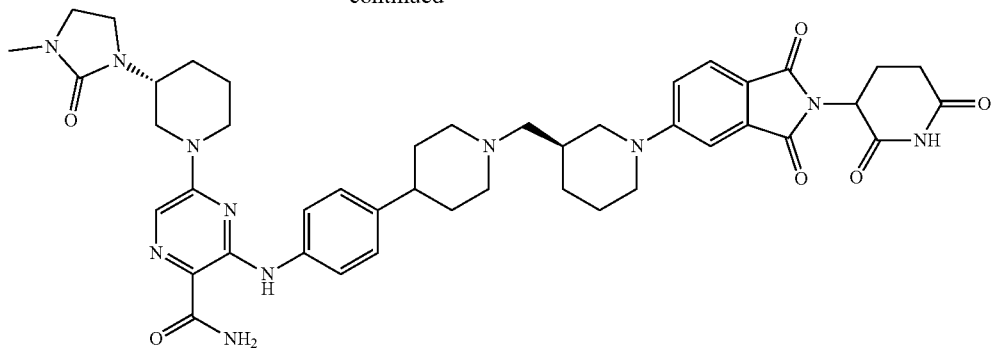

Compound 32

Other amine containing compounds of the invention synthesized by using general procedure 2 are Compounds 33, 46, 56, 15-18, 21, 31, 48-52, 54, 59, 60, 35, 36, and 38-45.

Scheme 3: Synthesis of Compounds of the Present Invention.

to stir at 90° C. for 16 h. The mixture was purified by HPLC (H₂O/MeCN with 0.1% TFA) to afford the desired product. An exemplary aryl fluoride displacement is provided in Scheme 3, where (R)-3-((4-(2,6-diazaspiro[3.3]heptan-2-yl) phenyl)amino)-5-(3-(3-methyl-2-oxoimidazolidin-1-yl)pip-

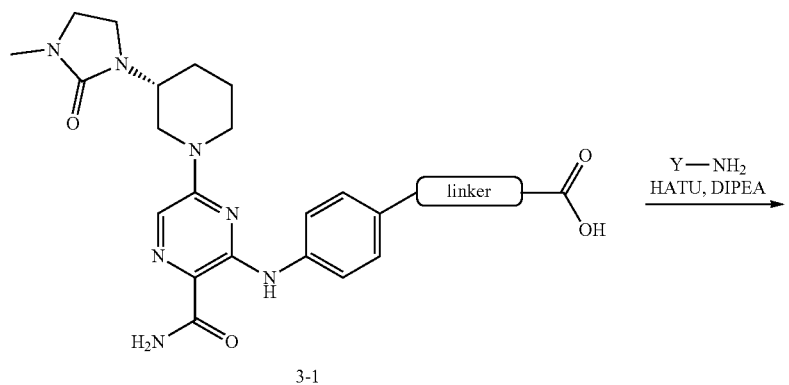

3-1

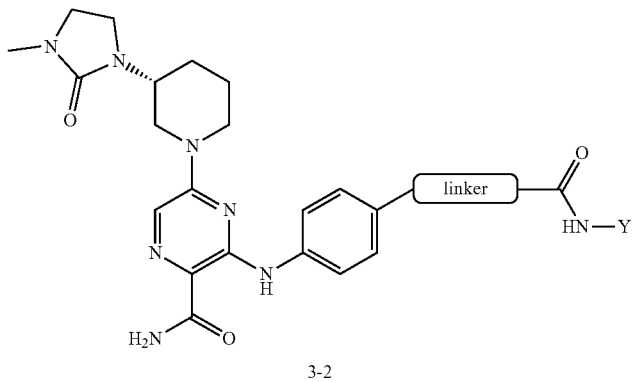

3-2

Intermediate (3-1), which can be generated by de-esterifying intermediate (1-6), is treated with amine, Y—NH₂, under coupling conditions to generate compounds of the present invention (3-2), wherein the terminal linking group of L is an amide.

General Procedure 3: Aryl Fluoride Displacement.

A mixture of amine (0.22 mmol), aryl fluoride (0.22 mmol), DIPEA (0.88 mmol) and DMF (1 mL) was allowed eridin-1-yl)pyrazine-2-carboxamide is reacted as described above with 2-(2,6-dioxopiperidin-3-yl)-5-fluoroisoindoline-1,3-dione to provide 3-((4-(6-(2-(2-(2,6-dioxopiperidin-3-yl)-1,3-dioxoisoindolin-5-yl)-2,6-diazaspiro[3.3]heptan-2-yl) phenyl)amino)-5-((R)-3-(3-methyl-2-oxoimidazolidin-1-yl) piperidin-1-yl)pyrazine-2-carboxamide (Compound 34).

Scheme 3: Synthesis of Compound 34 Via Aryl Fluoride Displacement
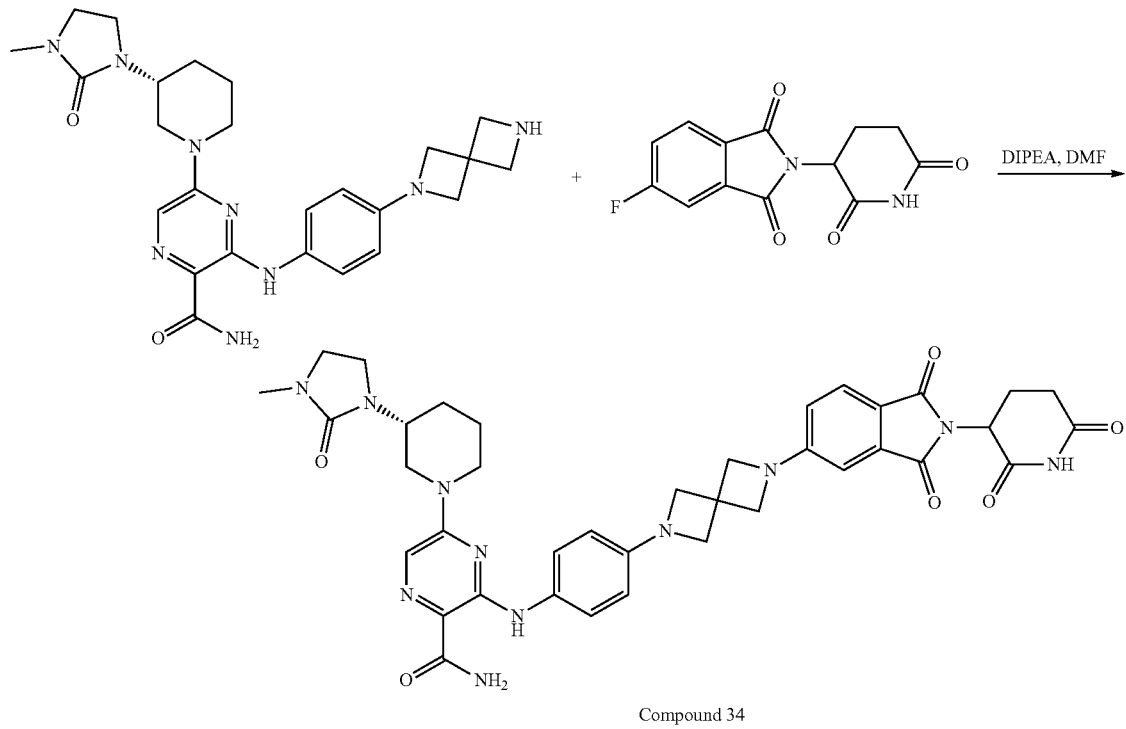
Compound 34
Other aryl amine containing compounds of the invention synthesized by using general procedure 3 are Compounds 55, 29, 47, 53, 58, 64-66, 37, and 30.
The abovementioned synthetic schemes were used to synthesize the compounds in Table 1.
TABLE 1
Example compounds of the present invention.
| Compound Number | Structure |
|---|---|
| 1 | 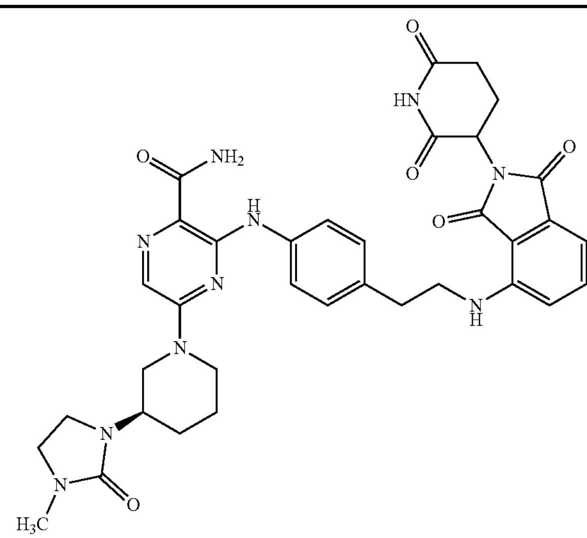 |

TABLE 1-continued
Example compounds of the present invention.
| Compound Number | Structure |
|---|---|
| 2 | 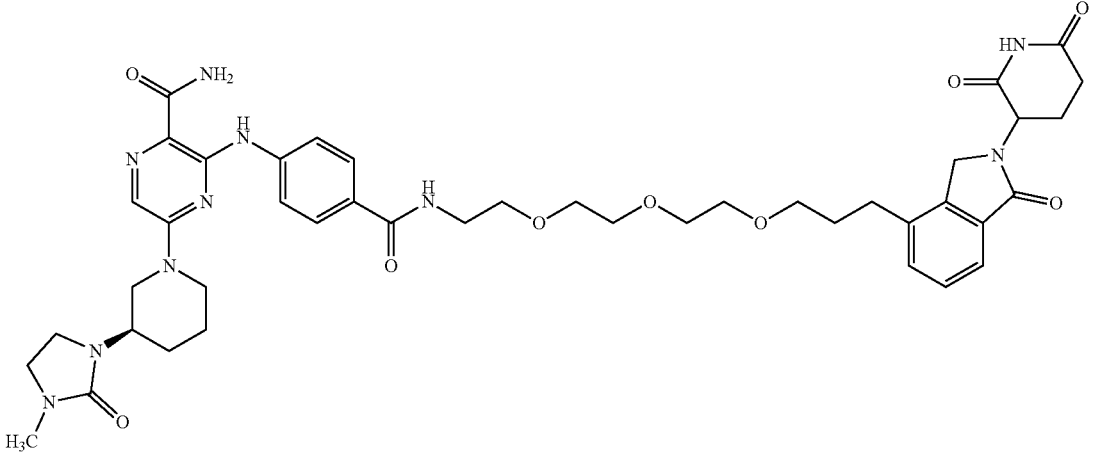 [SMILES: CN1CCN([C@@H]2CCCN(c3cnc(C(N)=O)c(Nc4ccc(C(=O)NCCOCCOCCOCCCc5cccc6c5CN(C5CCC(=O)NC5=O)C6=O)cc4)n3)C2)C1=O] |
| 3 | 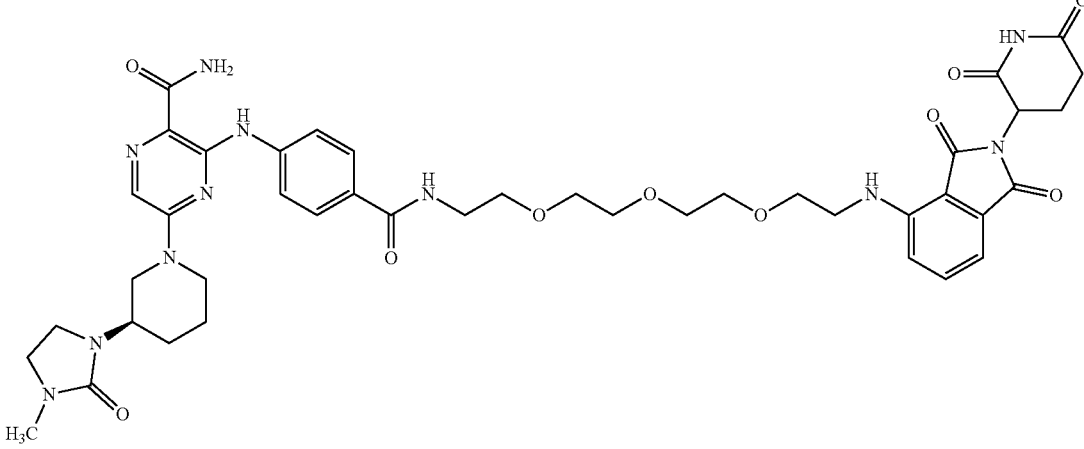 |
| 4 | 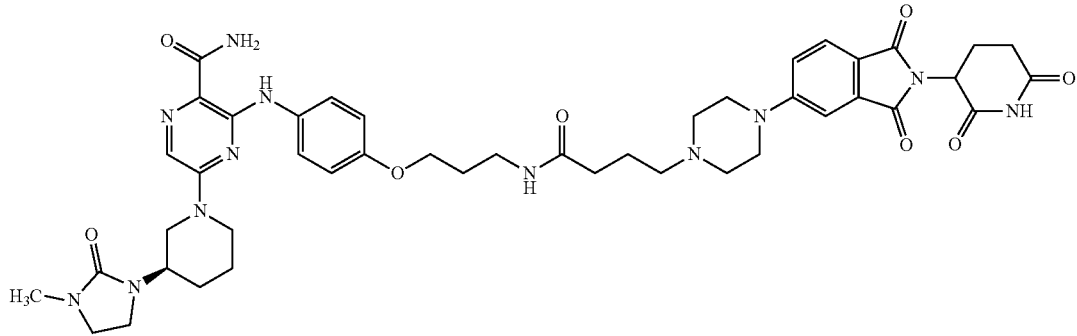 [SMILES: CN1CCN([C@@H]2CCCN(c3cnc(C(N)=O)c(Nc4ccc(OCCCNC(=O)CCCN5CCN(c6ccc7c(c6)C(=O)N(C6CCC(=O)NC6=O)C7=O)CC5)cc4)n3)C2)C1=O] |

TABLE 1-continued

Example compounds of the present invention.

| Compound Number | Structure |
|---|---|
| 5 | 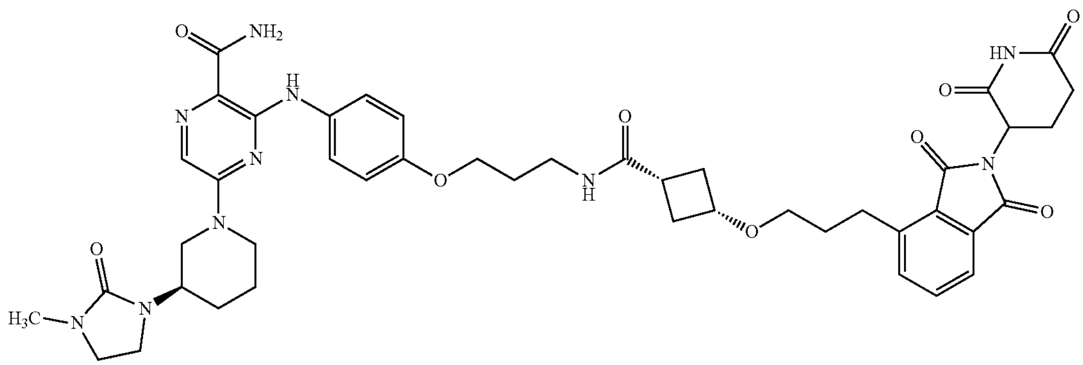 [SMILES: CN1CCN([C@@H]2CCCN(c3cnc(C(N)=O)c(Nc4ccc(OCCCNC(=O)[C@H]5C[C@@H](OCCCc6cccc7c6C(=O)N(C6CCC(=O)NC6=O)C7=O)C5)cc4)n3)C2)C1=O] |
| 6 | 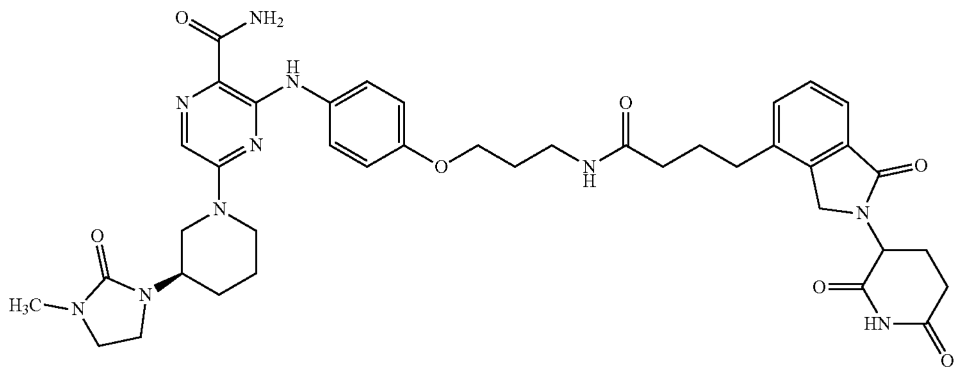 [SMILES: CN1CCN([C@@H]2CCCN(c3cnc(C(N)=O)c(Nc4ccc(OCCCNC(=O)CCCc5cccc6c5CN(C5CCC(=O)NC5=O)C6=O)cc4)n3)C2)C1=O] |
| 7 | 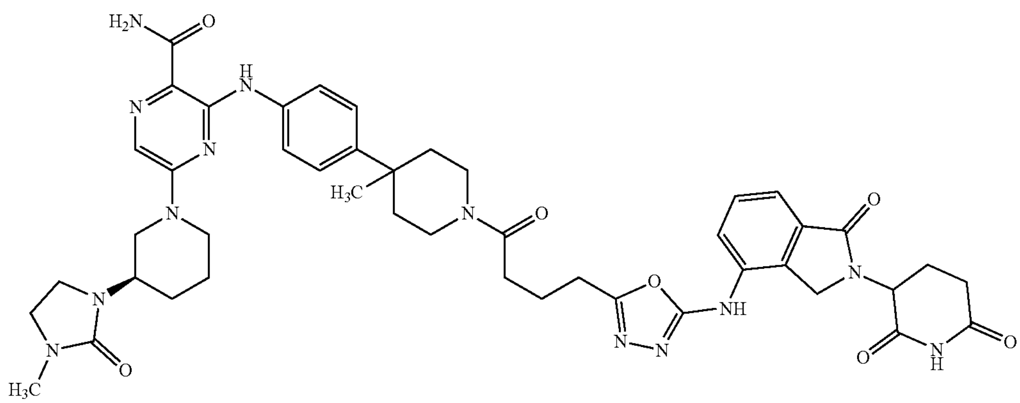 [SMILES: CN1CCN([C@@H]2CCCN(c3cnc(C(N)=O)c(Nc4ccc(C5(C)CCN(C(=O)CCCc6nnc(Nc7cccc8c7CN(C7CCC(=O)NC7=O)C8=O)o6)CC5)cc4)n3)C2)C1=O] |
| 8 | 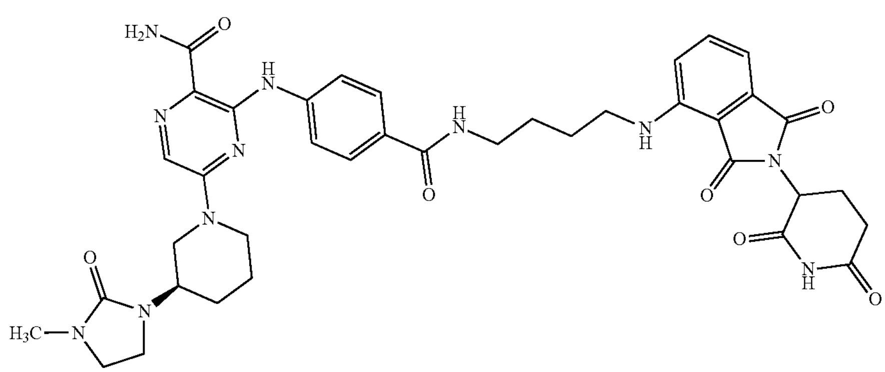 [SMILES: CN1CCN([C@@H]2CCCN(c3cnc(C(N)=O)c(Nc4ccc(C(=O)NCCCCNc5cccc6c5C(=O)N(C5CCC(=O)NC5=O)C6=O)cc4)n3)C2)C1=O] |

TABLE 1-continued
Example compounds of the present invention.
| Compound Number | Structure |
|---|---|
| 9 | 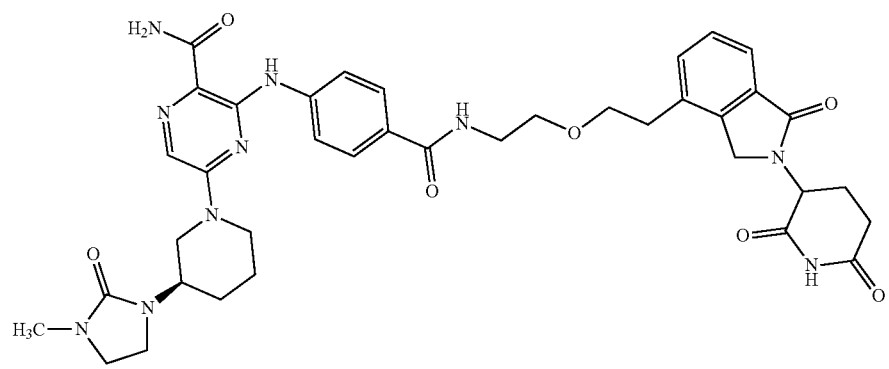 [SMILES: CN1CCN([C@@H]2CCCN(c3cnc(C(N)=O)c(Nc4ccc(C(=O)NCCOCCc5cccc6c5CN(C5CCC(=O)NC5=O)C6=O)cc4)n3)C2)C1=O] |
| 10 | 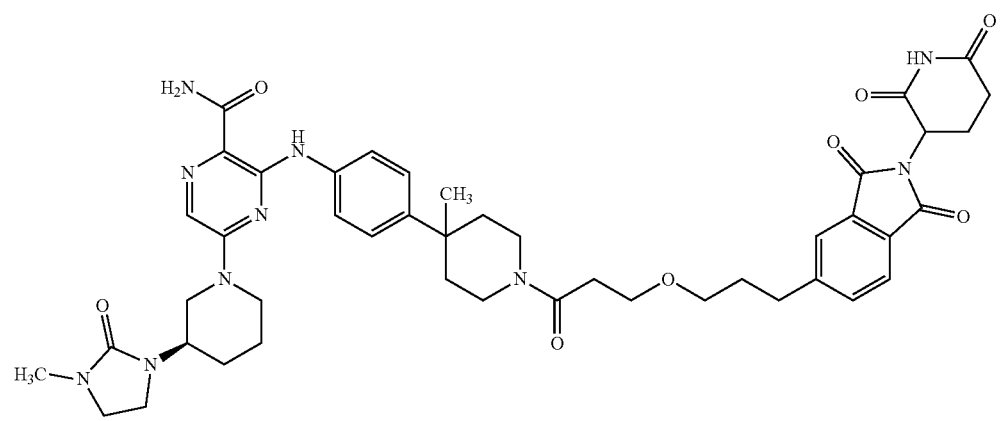 [SMILES: CN1CCN([C@@H]2CCCN(c3cnc(C(N)=O)c(Nc4ccc(C5(C)CCN(C(=O)CCOCCCc6ccc7c(c6)C(=O)N(C6CCC(=O)NC6=O)C7=O)CC5)cc4)n3)C2)C1=O] |
| 11 | 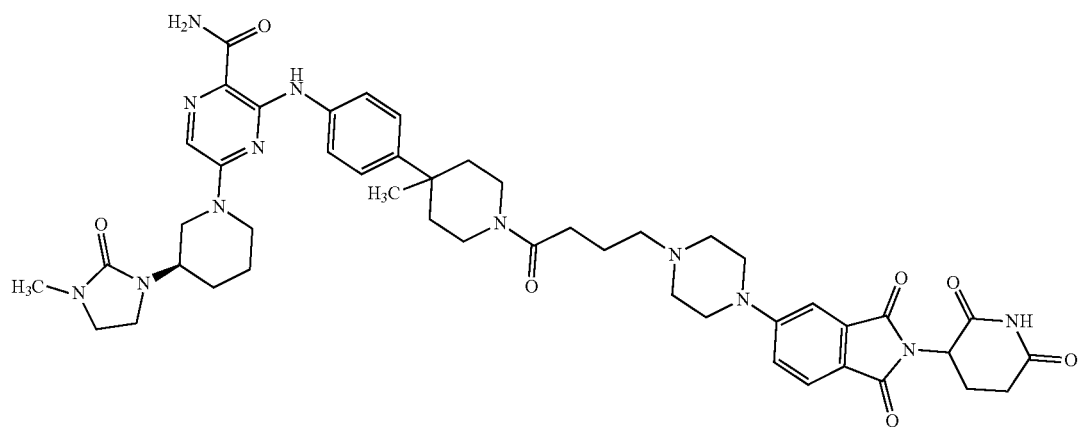 [SMILES: CN1CCN([C@@H]2CCCN(c3cnc(C(N)=O)c(Nc4ccc(C5(C)CCN(C(=O)CCCN6CCN(c7ccc8c(c7)C(=O)N(C7CCC(=O)NC7=O)C8=O)CC6)CC5)cc4)n3)C2)C1=O] |

TABLE 1-continued
Example compounds of the present invention.
| Compound Number | Structure |
|---|---|
| 12 | 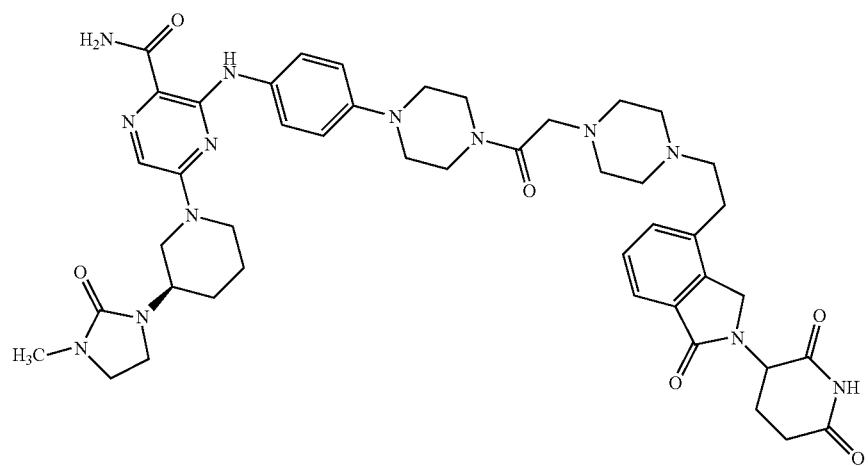 [SMILES: CN1CCN([C@@H]2CCCN(c3cnc(C(N)=O)c(Nc4ccc(N5CCN(C(=O)CN6CCN(CCc7cccc8c7CN(C7CCC(=O)NC7=O)C8=O)CC6)CC5)cc4)n3)C2)C1=O] |
| 13 | 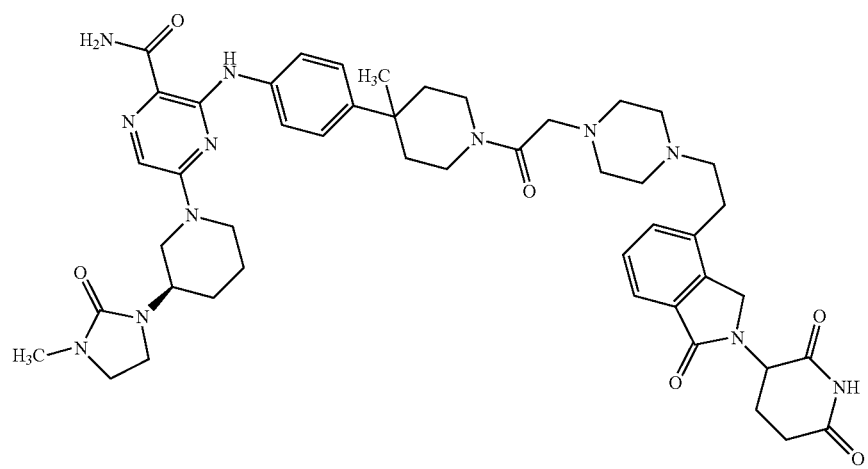 [SMILES: CN1CCN([C@@H]2CCCN(c3cnc(C(N)=O)c(Nc4ccc(C5(C)CCN(C(=O)CN6CCN(CCc7cccc8c7CN(C7CCC(=O)NC7=O)C8=O)CC6)CC5)cc4)n3)C2)C1=O] |
| 14 | 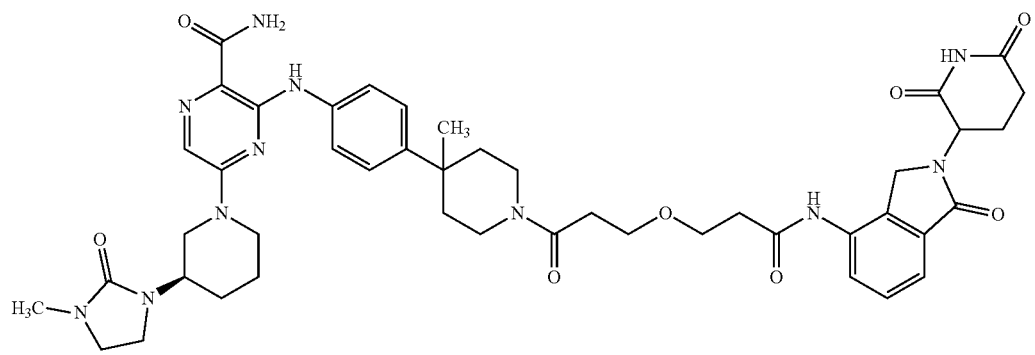 [SMILES: CN1CCN([C@@H]2CCCN(c3cnc(C(N)=O)c(Nc4ccc(C5(C)CCN(C(=O)CCOCCC(=O)Nc6cccc7c6CN(C6CCC(=O)NC6=O)C7=O)CC5)cc4)n3)C2)C1=O] |

TABLE 1-continued

Example compounds of the present invention.

| Compound Number | Structure |
|---|---|
| 15 | 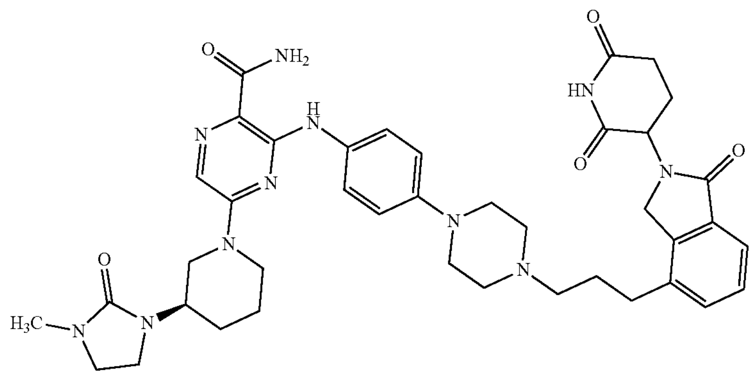 [SMILES: CN1CCN([C@@H]2CCCN(c3cnc(C(N)=O)c(Nc4ccc(N5CCN(CCCc6cccc7c6CN(C6CCC(=O)NC6=O)C7=O)CC5)cc4)n3)C2)C1=O] |
| 16 | 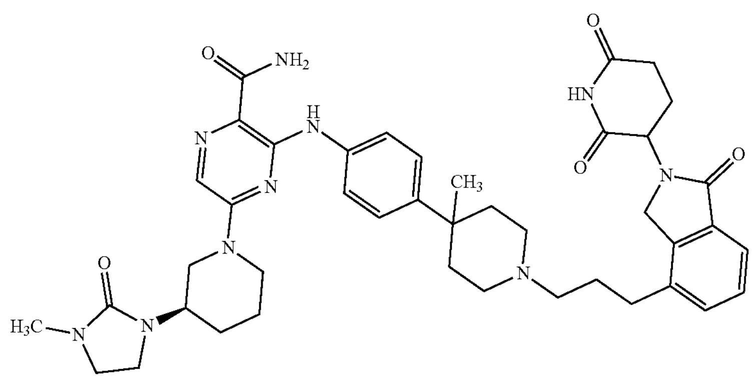 [SMILES: CN1CCN([C@@H]2CCCN(c3cnc(C(N)=O)c(Nc4ccc(C5(C)CCN(CCCc6cccc7c6CN(C6CCC(=O)NC6=O)C7=O)CC5)cc4)n3)C2)C1=O] |
| 17 | 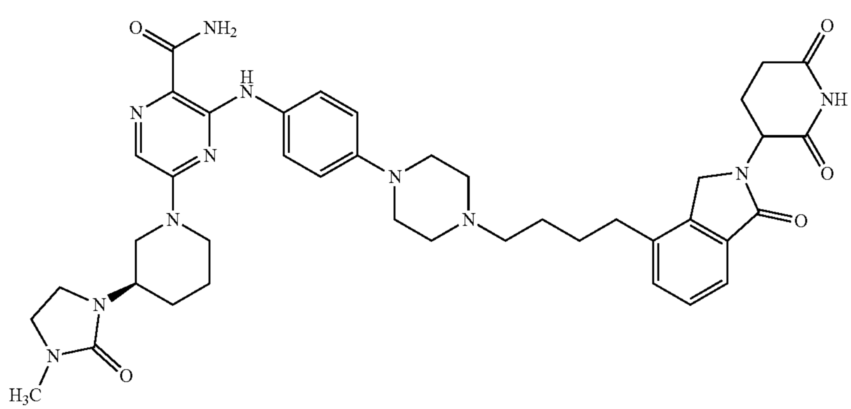 [SMILES: CN1CCN([C@@H]2CCCN(c3cnc(C(N)=O)c(Nc4ccc(N5CCN(CCCCc6cccc7c6CN(C6CCC(=O)NC6=O)C7=O)CC5)cc4)n3)C2)C1=O] |

TABLE 1-continued

Example compounds of the present invention.

| Compound Number | Structure |
|---|---|
| 18 | (chemical structure) |
| 19 | (chemical structure) |
| 20 | (chemical structure) |

TABLE 1-continued

Example compounds of the present invention.

| Compound Number | Structure |
|---|---|
| 21 | 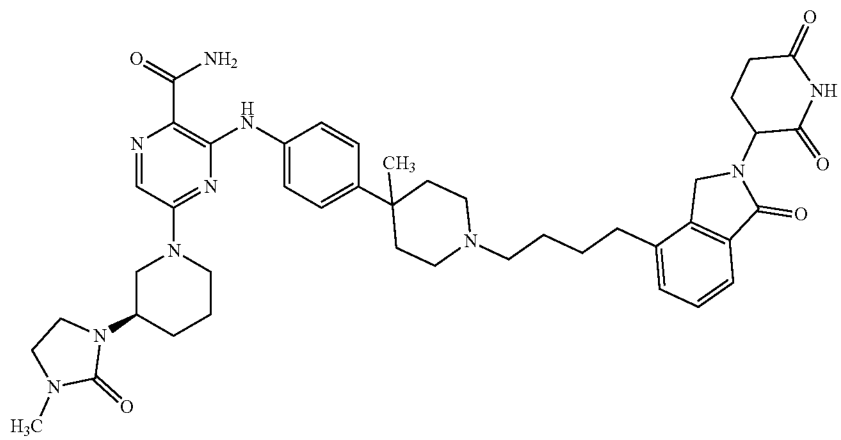 [SMILES: CN1CCN([C@@H]2CCCN(c3cnc(C(N)=O)c(Nc4ccc(C5(C)CCN(CCCCc6cccc7c6CN(C6CCC(=O)NC6=O)C7=O)CC5)cc4)n3)C2)C1=O] |
| 22 | 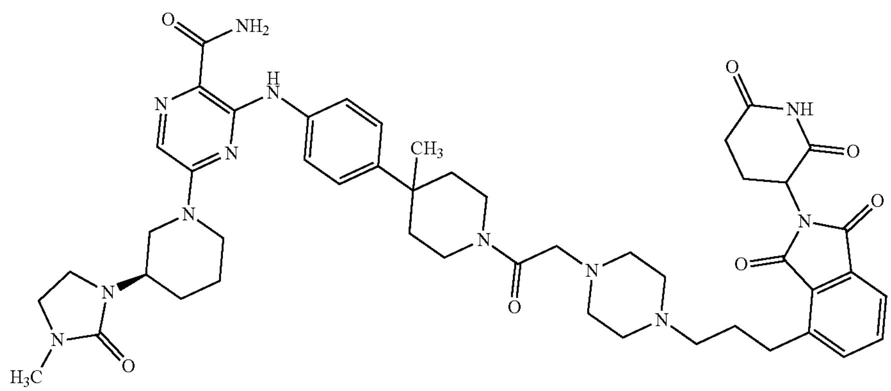 [SMILES: CN1CCN([C@@H]2CCCN(c3cnc(C(N)=O)c(Nc4ccc(C5(C)CCN(C(=O)CN6CCN(CCCc7cccc8c7C(=O)N(C7CCC(=O)NC7=O)C8=O)CC6)CC5)cc4)n3)C2)C1=O] |
| 23 | 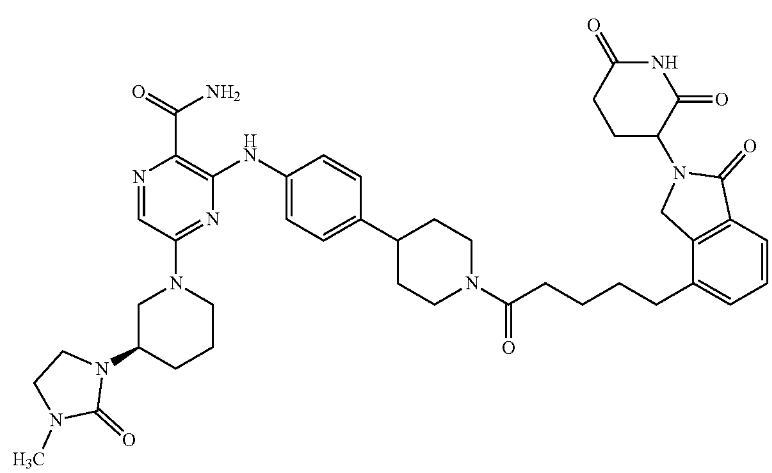 [SMILES: CN1CCN([C@@H]2CCCN(c3cnc(C(N)=O)c(Nc4ccc(C5CCN(C(=O)CCCCc6cccc7c6CN(C6CCC(=O)NC6=O)C7=O)CC5)cc4)n3)C2)C1=O] |

TABLE 1-continued

Example compounds of the present invention.

| Compound Number | Structure |
|---|---|
| 24 | 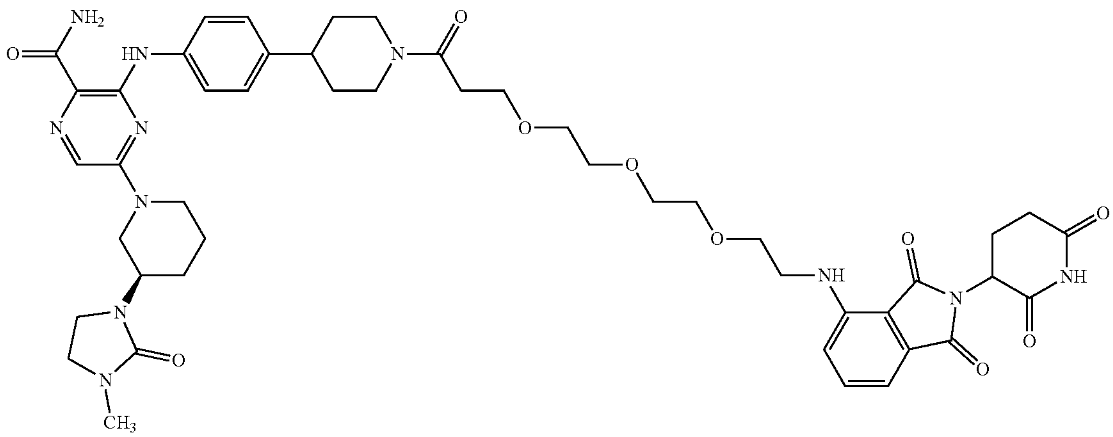 [SMILES: CN1CCN([C@@H]2CCCN(c3cnc(C(N)=O)c(Nc4ccc(C5CCN(C(=O)CCOCCOCCOCCNc6cccc7c6C(=O)N(C6CCC(=O)NC6=O)C7=O)CC5)cc4)n3)C2)C1=O] |
| 25 | 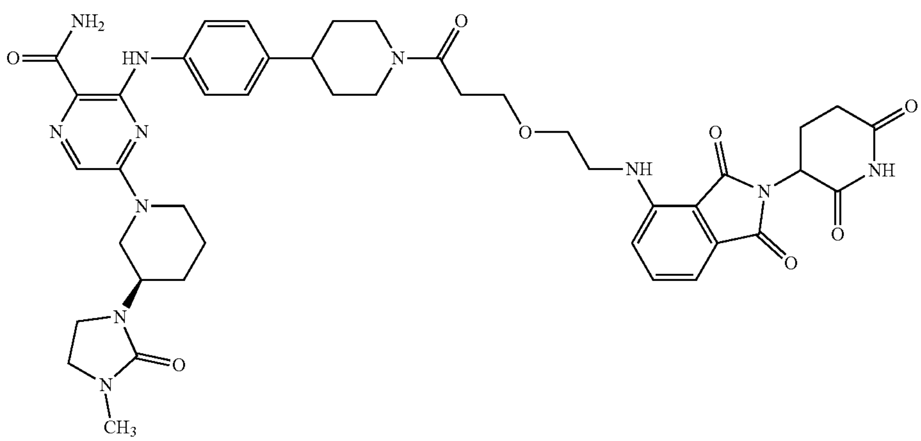 [SMILES: CN1CCN([C@@H]2CCCN(c3cnc(C(N)=O)c(Nc4ccc(C5CCN(C(=O)CCOCCNc6cccc7c6C(=O)N(C6CCC(=O)NC6=O)C7=O)CC5)cc4)n3)C2)C1=O] |
| 26 | 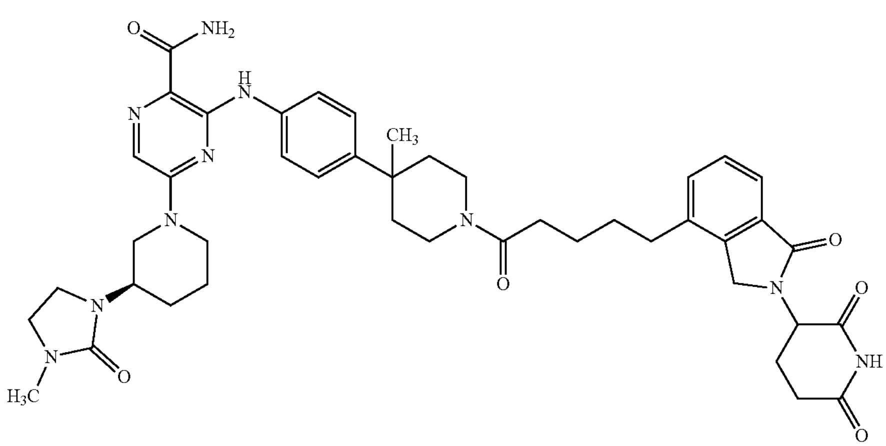 [SMILES: CN1CCN([C@@H]2CCCN(c3cnc(C(N)=O)c(Nc4ccc(C5(C)CCN(C(=O)CCCCc6cccc7c6CN(C6CCC(=O)NC6=O)C7=O)CC5)cc4)n3)C2)C1=O] |

TABLE 1-continued

Example compounds of the present invention.

| Compound Number | Structure |
| --- | --- |
| 27 | 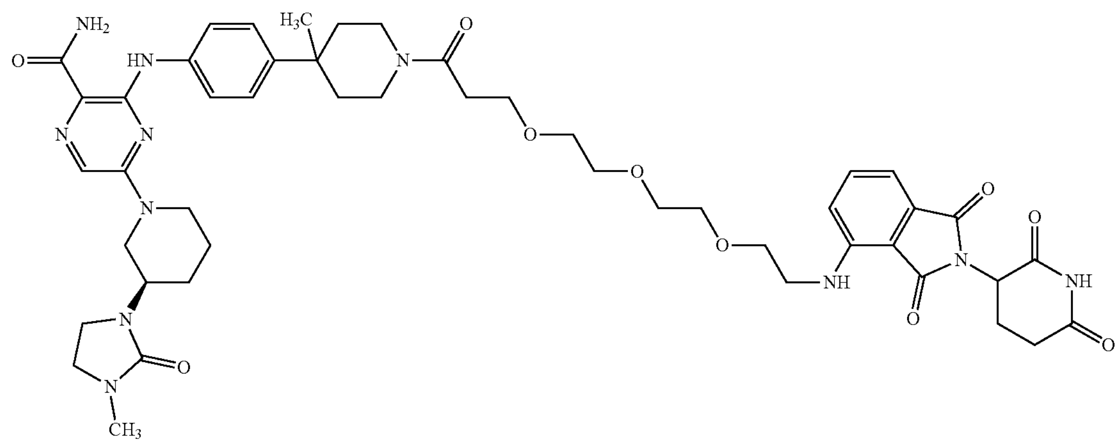 [SMILES: CN1CCN([C@@H]2CCCN(c3cnc(C(N)=O)c(Nc4ccc(C5(C)CCN(C(=O)CCOCCOCCOCCNc6cccc7c6C(=O)N(C6CCC(=O)NC6=O)C7=O)CC5)cc4)n3)C2)C1=O] |
| 28 | 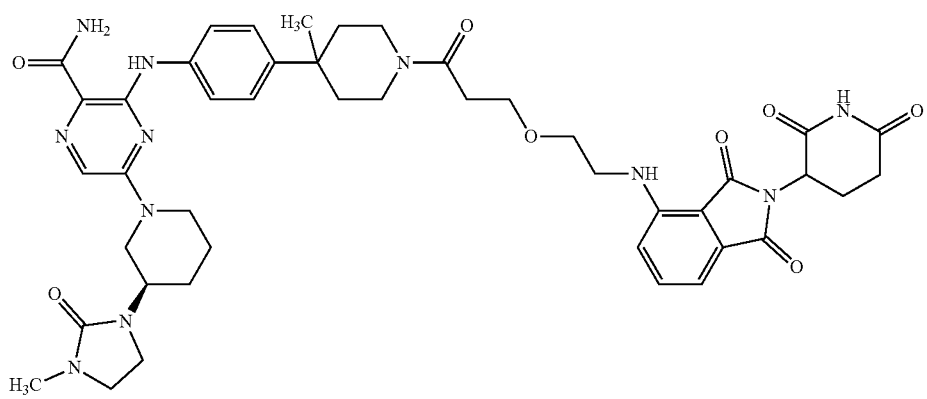 [SMILES: CN1CCN([C@@H]2CCCN(c3cnc(C(N)=O)c(Nc4ccc(C5(C)CCN(C(=O)CCOCCNc6cccc7c6C(=O)N(C6CCC(=O)NC6=O)C7=O)CC5)cc4)n3)C2)C1=O] |
| 29 | 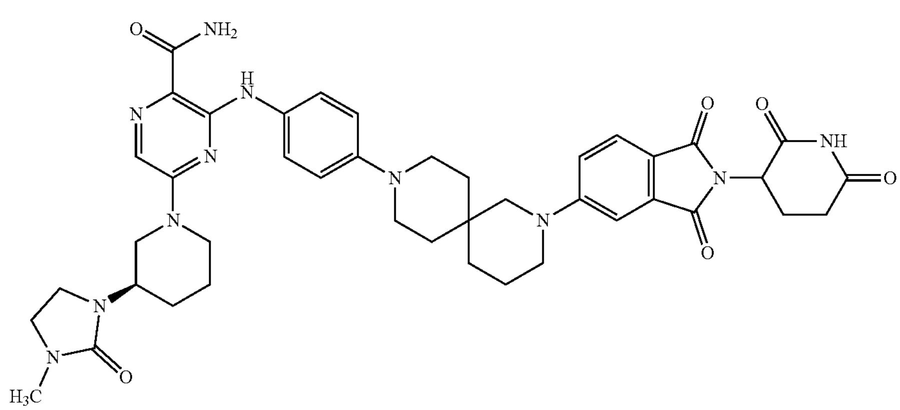 |

TABLE 1-continued

Example compounds of the present invention.

| Compound Number | Structure |
| --- | --- |
| 30 | 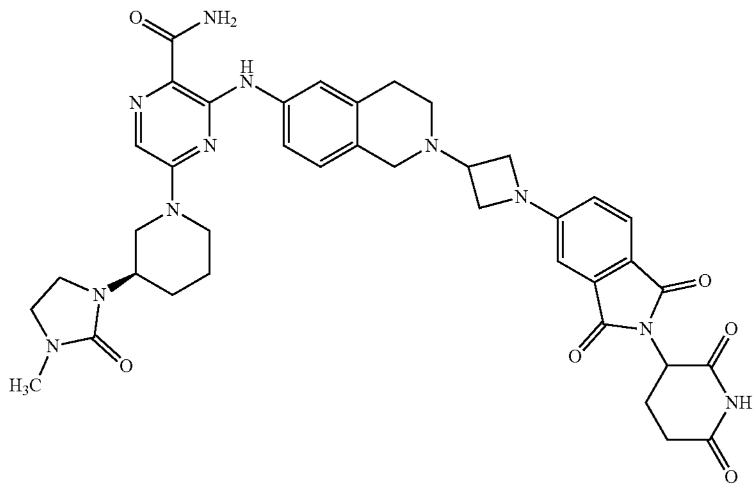 |
| 31 | 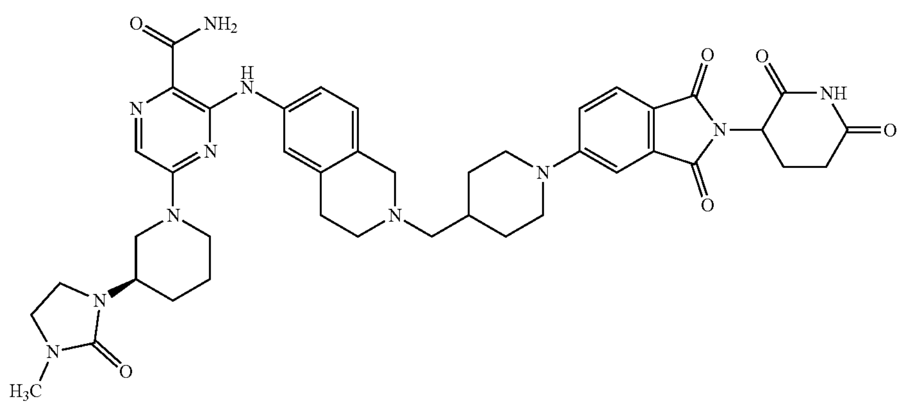 [SMILES: CN1CCN([C@@H]2CCCN(c3cnc(C(N)=O)c(Nc4ccc5c(c4)CCN(CC4CCN(c6ccc7c(c6)C(=O)N(C6CCC(=O)NC6=O)C7=O)CC4)C5)n3)C2)C1=O] |
| 32 | 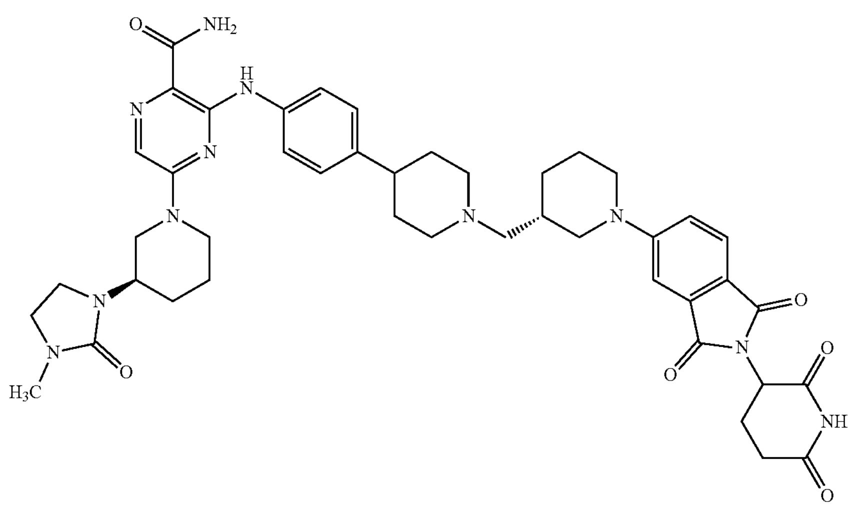 [SMILES: CN1CCN([C@@H]2CCCN(c3cnc(C(N)=O)c(Nc4ccc(C5CCN(C[C@@H]6CCCN(c7ccc8c(c7)C(=O)N(C7CCC(=O)NC7=O)C8=O)C6)CC5)cc4)n3)C2)C1=O] |

TABLE 1-continued
Example compounds of the present invention.
| Compound Number | Structure |
|---|---|
| 33 | 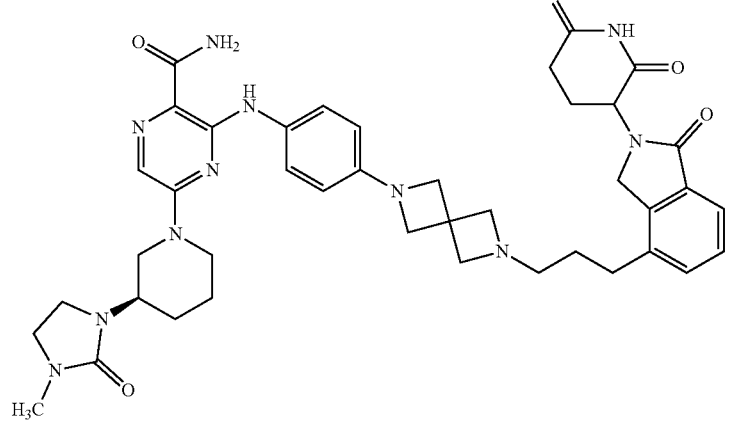 |
| 34 | 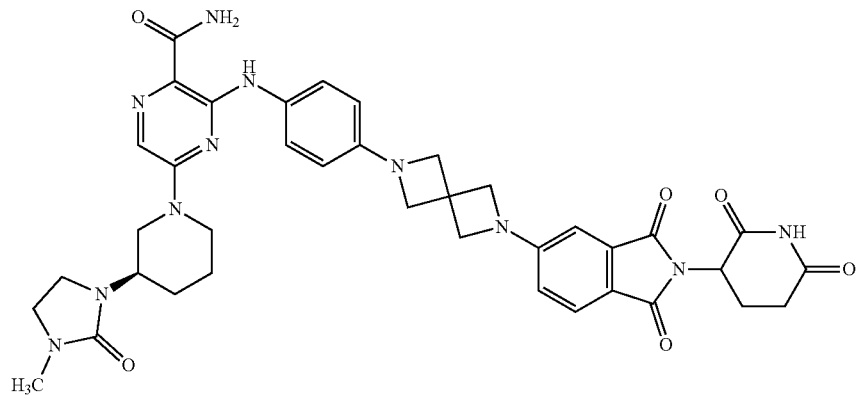 |
| 35 | 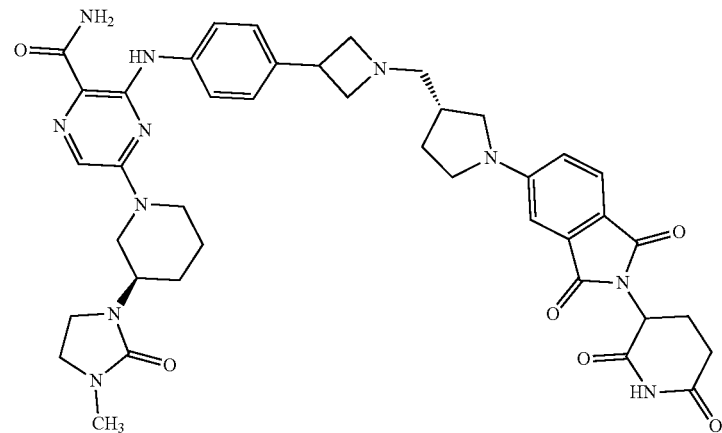 [SMILES: CN1CCN([C@@H]2CCCN(c3cnc(C(N)=O)c(Nc4ccc(C5CN(C[C@H]6CCN(c7ccc8c(c7)C(=O)N(C7CCC(=O)NC7=O)C8=O)C6)C5)cc4)n3)C2)C1=O] |

TABLE 1-continued
Example compounds of the present invention.
| Compound Number | Structure |
| --- | --- |
| 36 | 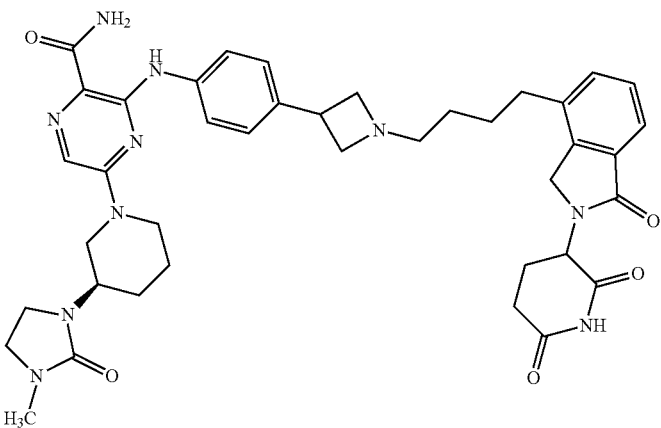 [SMILES: CN1CCN([C@@H]2CCCN(c3cnc(C(N)=O)c(Nc4ccc(C5CN(CCCCc6cccc7c6CN(C6CCC(=O)NC6=O)C7=O)C5)cc4)n3)C2)C1=O] |
| 37 | 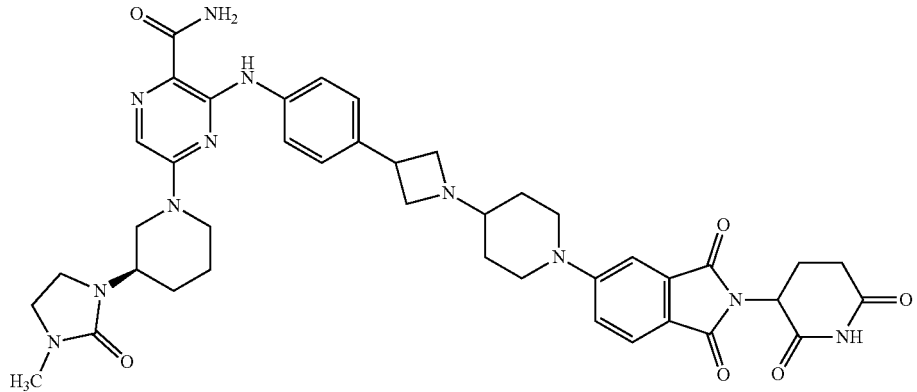 |
| 38 | 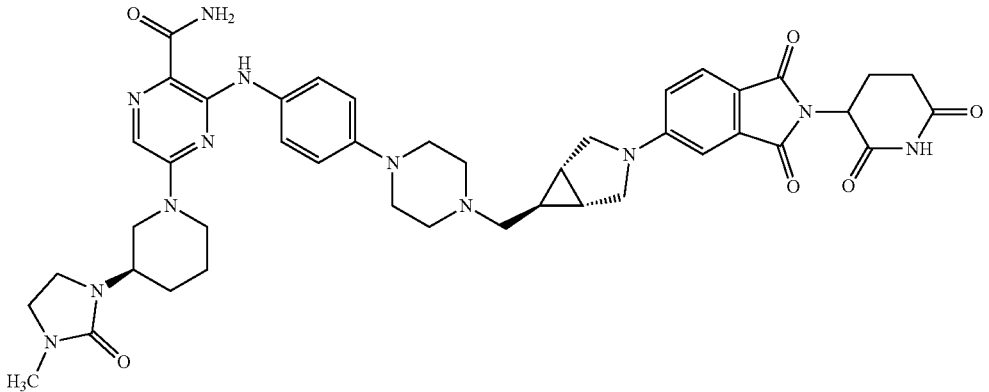 [SMILES: CN1CCN([C@@H]2CCCN(c3cnc(C(N)=O)c(Nc4ccc(N5CCN(C[C@@H]6[C@H]7CN(c8ccc9c(c8)C(=O)N(C8CCC(=O)NC8=O)C9=O)C[C@@H]67)CC5)cc4)n3)C2)C1=O] |

TABLE 1-continued
Example compounds of the present invention.
| Compound Number | Structure |
|---|---|
| 39 | 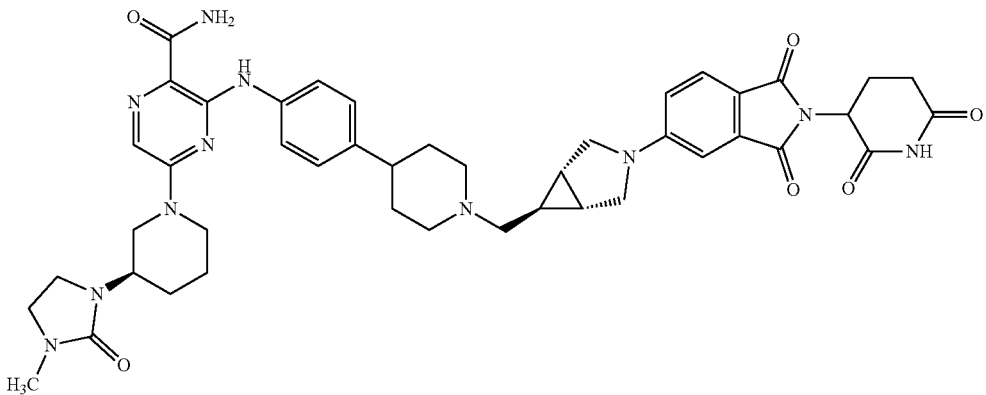 [SMILES: CN1CCN([C@@H]2CCCN(c3cnc(C(N)=O)c(Nc4ccc(C5CCN(C[C@@H]6[C@H]7CN(c8ccc9c(c8)C(=O)N(C8CCC(=O)NC8=O)C9=O)C[C@@H]67)CC5)cc4)n3)C2)C1=O] |
| 40 | 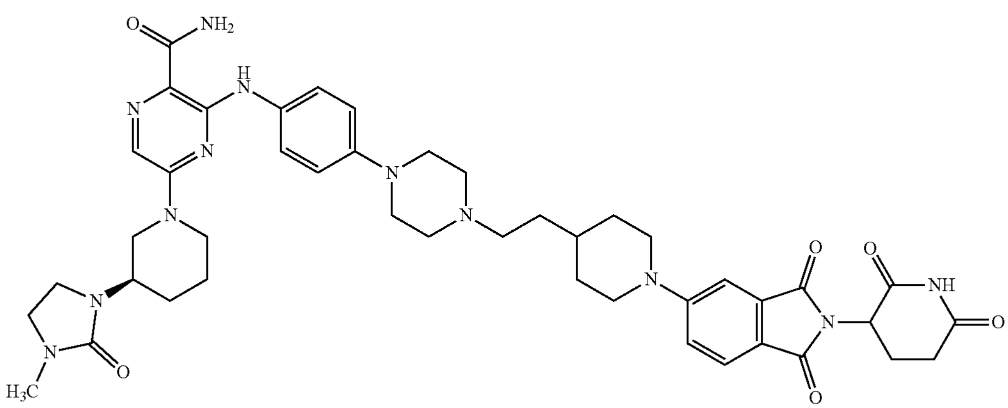 [SMILES: CN1CCN([C@@H]2CCCN(c3cnc(C(N)=O)c(Nc4ccc(N5CCN(CCC6CCN(c7ccc8c(c7)C(=O)N(C7CCC(=O)NC7=O)C8=O)CC6)CC5)cc4)n3)C2)C1=O] |
| 41 | 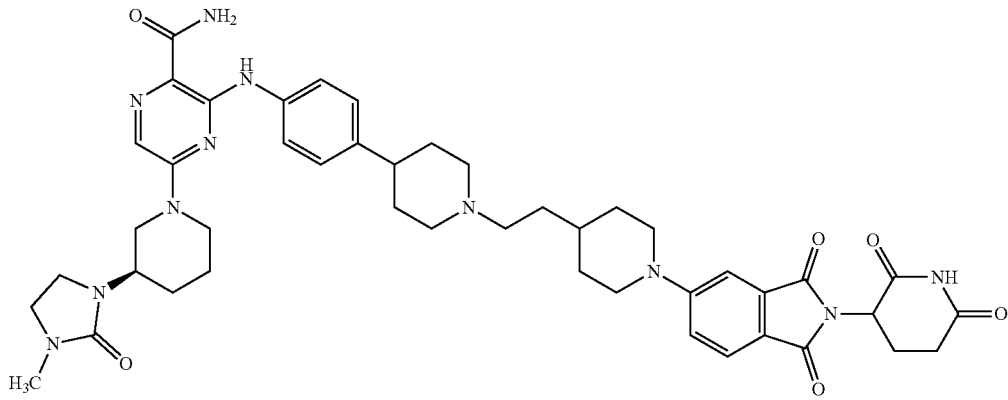 [SMILES: CN1CCN([C@@H]2CCCN(c3cnc(C(N)=O)c(Nc4ccc(C5CCN(CCC6CCN(c7ccc8c(c7)C(=O)N(C7CCC(=O)NC7=O)C8=O)CC6)CC5)cc4)n3)C2)C1=O] |

TABLE 1-continued
Example compounds of the present invention.
| Compound Number | Structure |
|---|---|
| 42 | 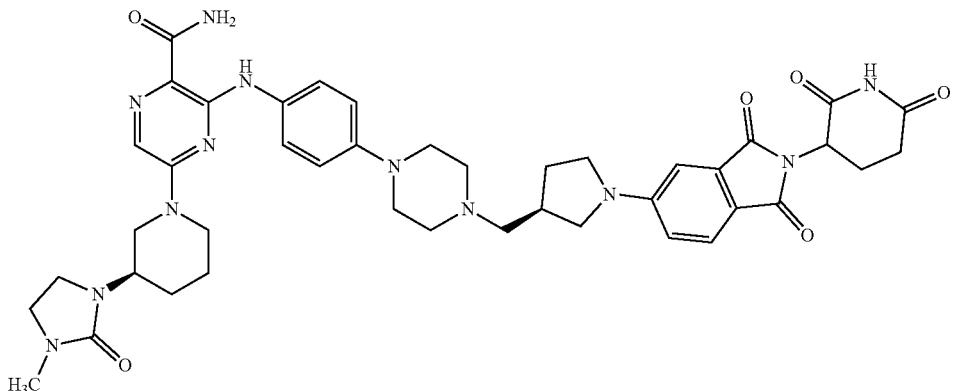 |
| 43 | 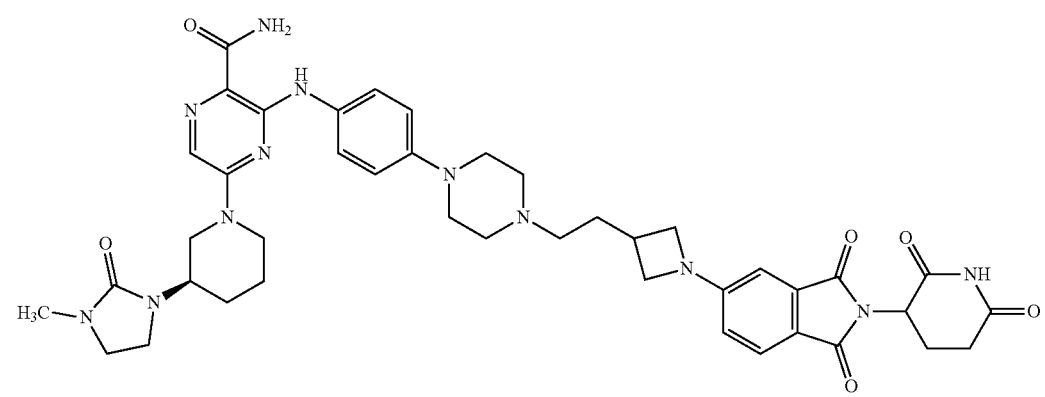 [SMILES: CN1CCN([C@@H]2CCCN(c3cnc(C(N)=O)c(Nc4ccc(N5CCN(CCC6CN(c7ccc8c(c7)C(=O)N(C7CCC(=O)NC7=O)C8=O)C6)CC5)cc4)n3)C2)C1=O] |
| 44 | 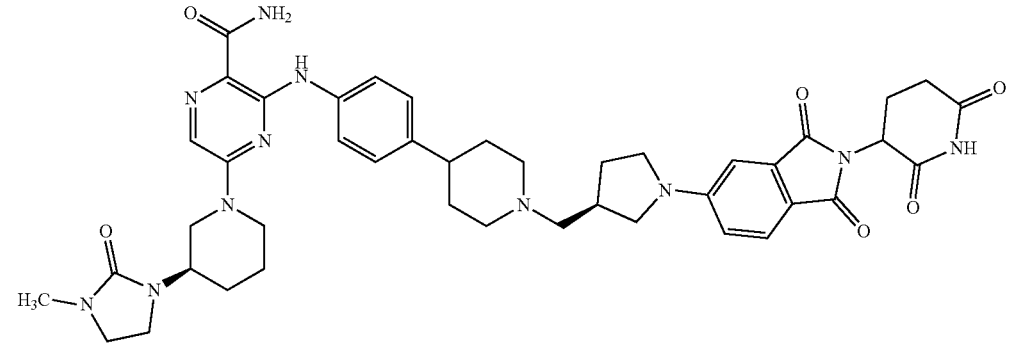 [SMILES: CN1CCN([C@@H]2CCCN(c3cnc(C(N)=O)c(Nc4ccc(C5CCN(C[C@H]6CCN(c7ccc8c(c7)C(=O)N(C7CCC(=O)NC7=O)C8=O)C6)CC5)cc4)n3)C2)C1=O] |

TABLE 1-continued
Example compounds of the present invention.
| Compound Number | Structure |
|---|---|
| 45 | 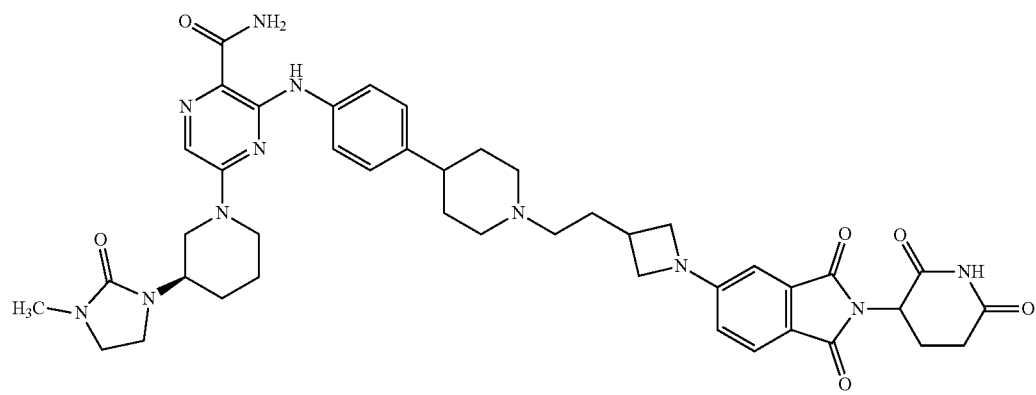 [SMILES: CN1CCN([C@@H]2CCCN(c3cnc(C(N)=O)c(Nc4ccc(C5CCN(CCC6CN(c7ccc8c(c7)C(=O)N(C7CCC(=O)NC7=O)C8=O)C6)CC5)cc4)n3)C2)C1=O] |
| 46 | 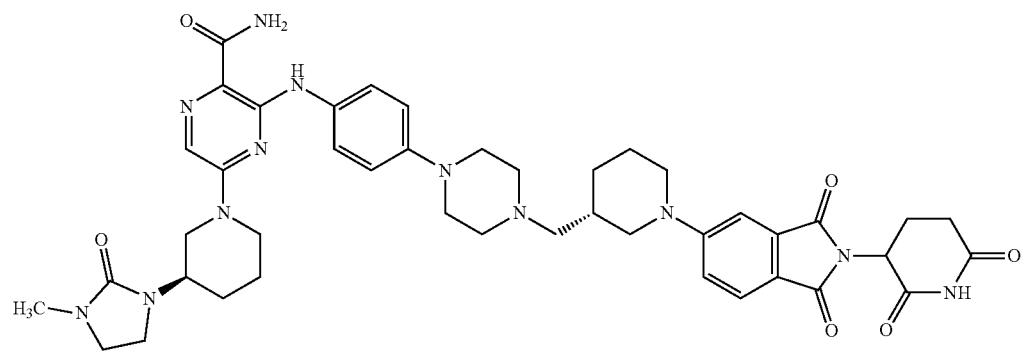 [SMILES: CN1CCN([C@@H]2CCCN(c3cnc(C(N)=O)c(Nc4ccc(N5CCN(C[C@@H]6CCCN(c7ccc8c(c7)C(=O)N(C7CCC(=O)NC7=O)C8=O)C6)CC5)cc4)n3)C2)C1=O] |
| 47 | 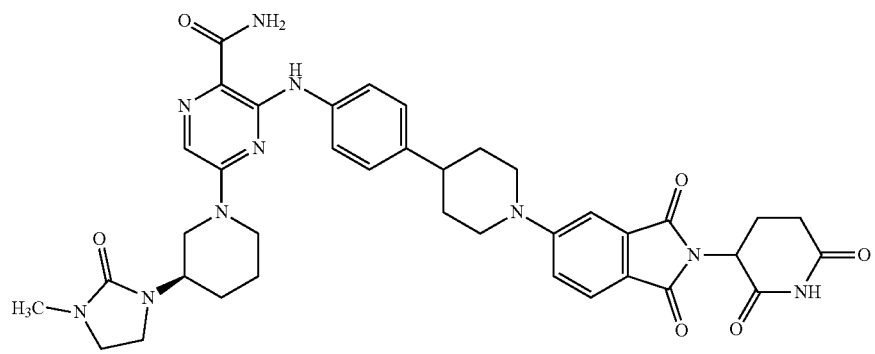 [SMILES: CN1CCN([C@@H]2CCCN(c3cnc(C(N)=O)c(Nc4ccc(C5CCN(c6ccc7c(c6)C(=O)N(C6CCC(=O)NC6=O)C7=O)CC5)cc4)n3)C2)C1=O] |
| 48 | 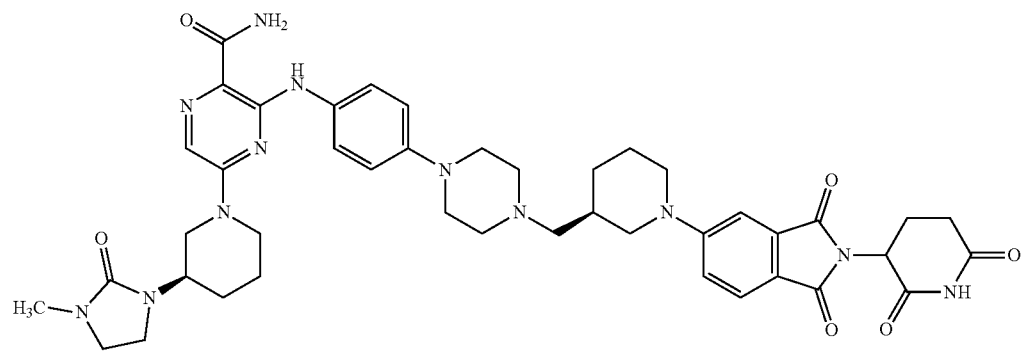 [SMILES: CN1CCN([C@@H]2CCCN(c3cnc(C(N)=O)c(Nc4ccc(N5CCN(C[C@H]6CCCN(c7ccc8c(c7)C(=O)N(C7CCC(=O)NC7=O)C8=O)C6)CC5)cc4)n3)C2)C1=O] |

TABLE 1-continued

Example compounds of the present invention.

| Compound Number | Structure |
| --- | --- |
| 49 | 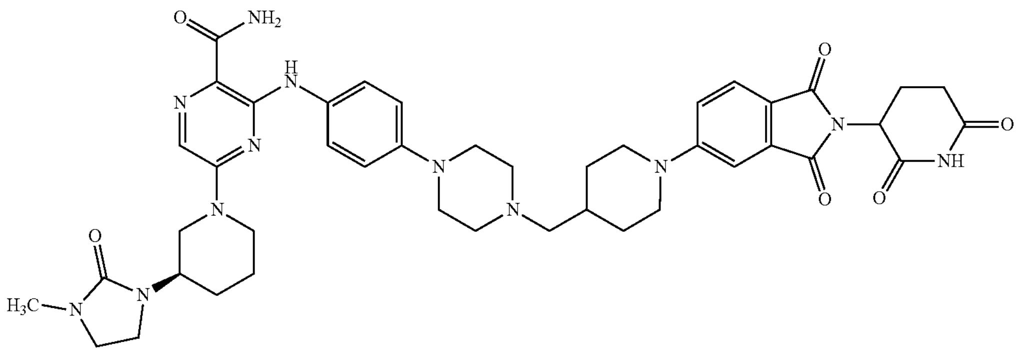 [SMILES: CN1CCN([C@@H]2CCCN(c3cnc(C(N)=O)c(Nc4ccc(N5CCN(CC6CCN(c7ccc8c(c7)C(=O)N(C7CCC(=O)NC7=O)C8=O)CC6)CC5)cc4)n3)C2)C1=O] |
| 50 | 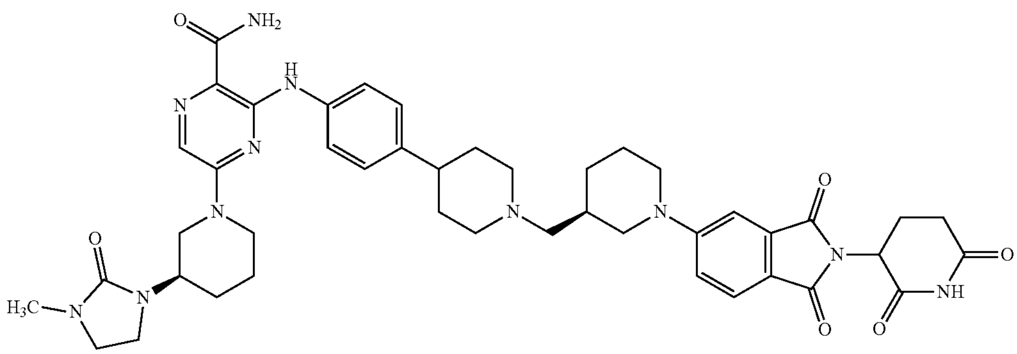 [SMILES: CN1CCN([C@@H]2CCCN(c3cnc(C(N)=O)c(Nc4ccc(C5CCN(C[C@H]6CCCN(c7ccc8c(c7)C(=O)N(C7CCC(=O)NC7=O)C8=O)C6)CC5)cc4)n3)C2)C1=O] |
| 51 | 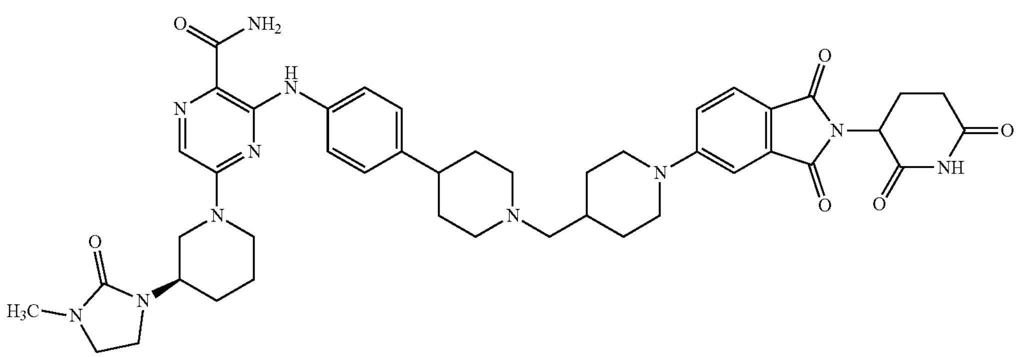 |
| 52 | 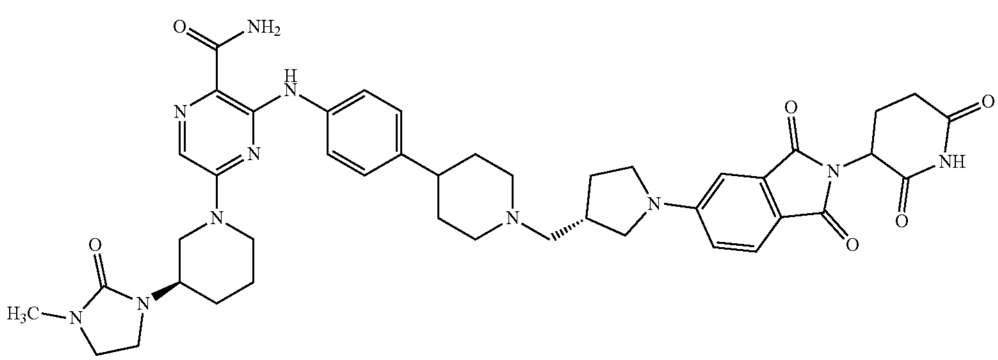 [SMILES: CN1CCN([C@@H]2CCCN(c3cnc(C(N)=O)c(Nc4ccc(C5CCN(C[C@@H]6CCN(c7ccc8c(c7)C(=O)N(C7CCC(=O)NC7=O)C8=O)C6)CC5)cc4)n3)C2)C1=O] |

TABLE 1-continued

Example compounds of the present invention.

| Compound Number | Structure |
| --- | --- |
| 53 | 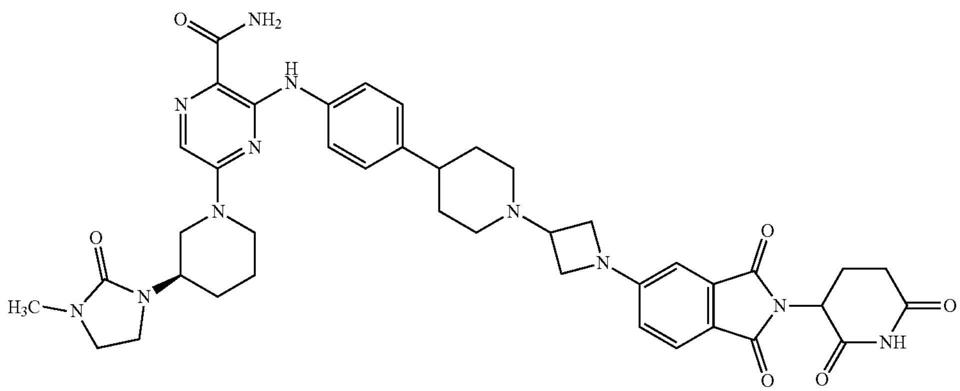 [SMILES: CN1CCN([C@@H]2CCCN(c3cnc(C(N)=O)c(Nc4ccc(C5CCN(C6CN(c7ccc8c(c7)C(=O)N(C7CCC(=O)NC7=O)C8=O)C6)CC5)cc4)n3)C2)C1=O] |
| 54 | 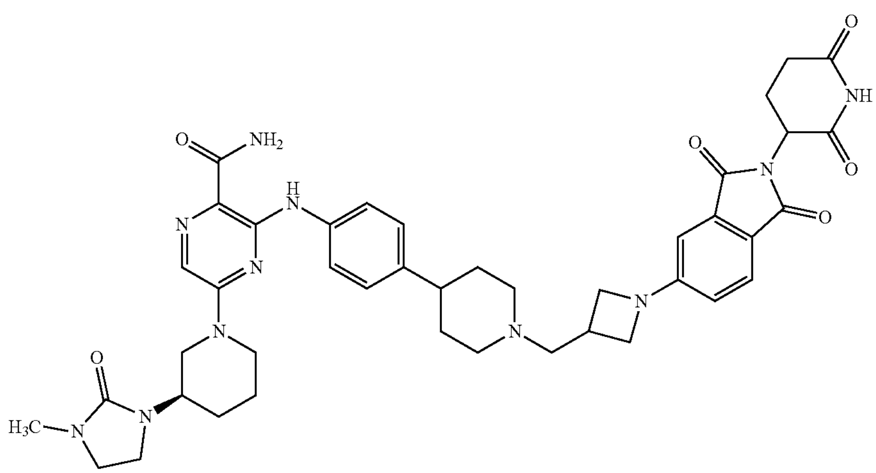 [SMILES: CN1CCN([C@@H]2CCCN(c3cnc(C(N)=O)c(Nc4ccc(C5CCN(CC6CN(c7ccc8c(c7)C(=O)N(C7CCC(=O)NC7=O)C8=O)C6)CC5)cc4)n3)C2)C1=O] |
| 55 | 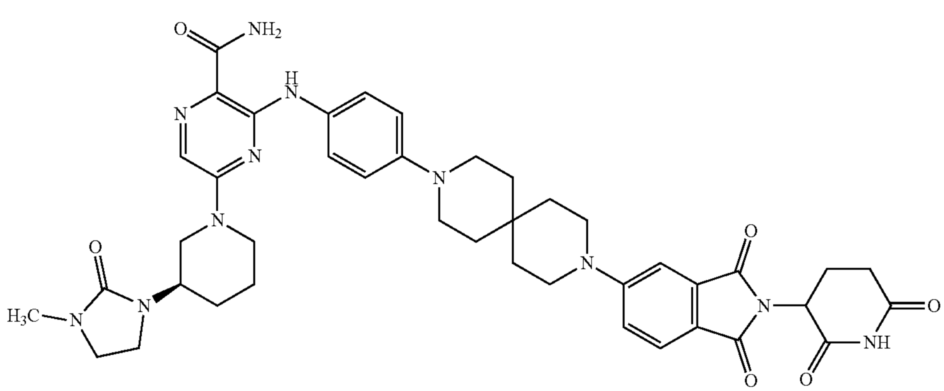 [SMILES: CN1CCN([C@@H]2CCCN(c3cnc(C(N)=O)c(Nc4ccc(N5CCC6(CC5)CCN(c5ccc7c(c5)C(=O)N(C5CCC(=O)NC5=O)C7=O)CC6)cc4)n3)C2)C1=O] |

TABLE 1-continued

Example compounds of the present invention.

| Compound Number | Structure |
|---|---|
| 56 | 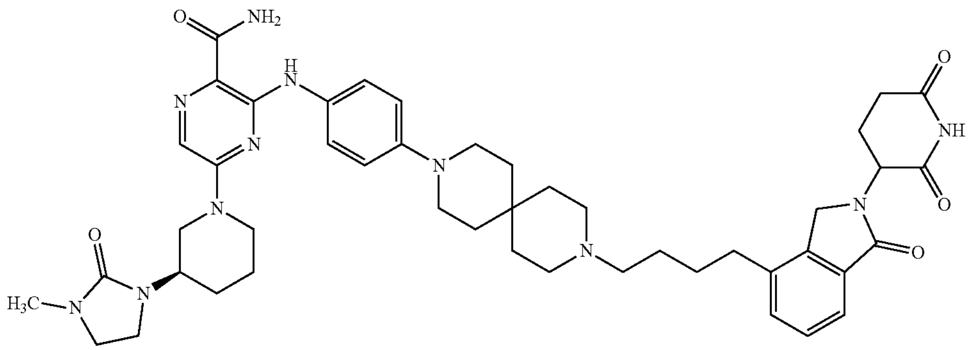 [SMILES: CN1CCN([C@@H]2CCCN(c3cnc(C(N)=O)c(Nc4ccc(N5CCC6(CCN(CCCCc7cccc8c7CN(C7CCC(=O)NC7=O)C8=O)CC6)CC5)cc4)n3)C2)C1=O] |
| 57 | 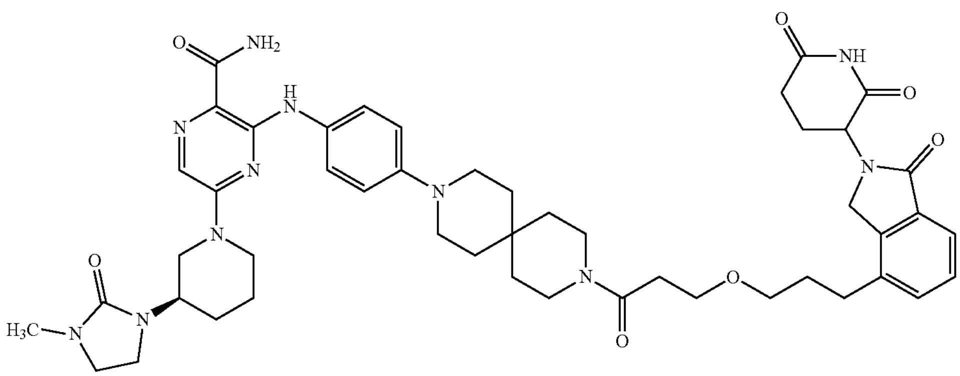 [SMILES: CN1CCN([C@@H]2CCCN(c3cnc(C(N)=O)c(Nc4ccc(N5CCC6(CCN(C(=O)CCOCCCc7cccc8c7CN(C7CCC(=O)NC7=O)C8=O)CC6)CC5)cc4)n3)C2)C1=O] |
| 58 | 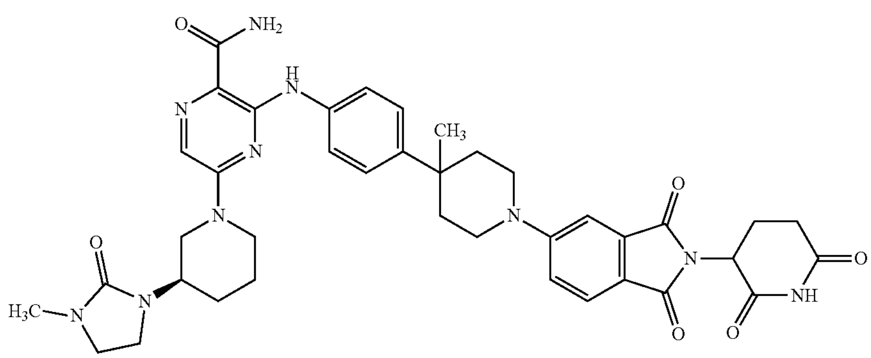 [SMILES: CN1CCN([C@@H]2CCCN(c3cnc(C(N)=O)c(Nc4ccc(C5(C)CCN(c6ccc7c(c6)C(=O)N(C6CCC(=O)NC6=O)C7=O)CC5)cc4)n3)C2)C1=O] |
| 59 | 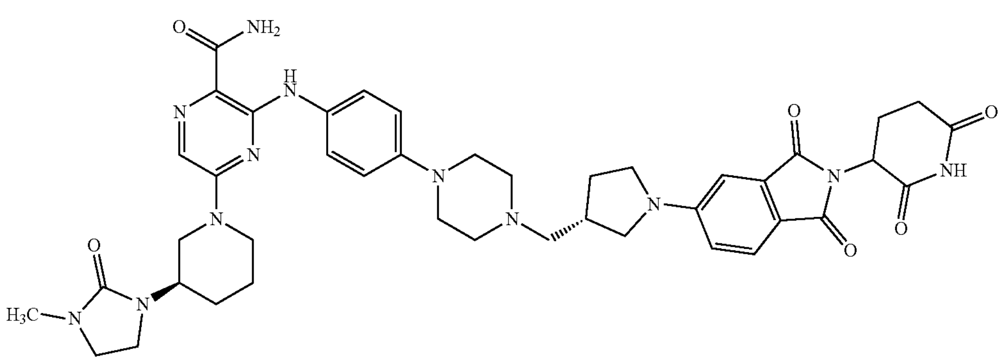 [SMILES: CN1CCN([C@@H]2CCCN(c3cnc(C(N)=O)c(Nc4ccc(N5CCN(C[C@@H]6CCN(c7ccc8c(c7)C(=O)N(C7CCC(=O)NC7=O)C8=O)C6)CC5)cc4)n3)C2)C1=O] |

TABLE 1-continued
Example compounds of the present invention.
| Compound Number | Structure |
|---|---|
| 60 | 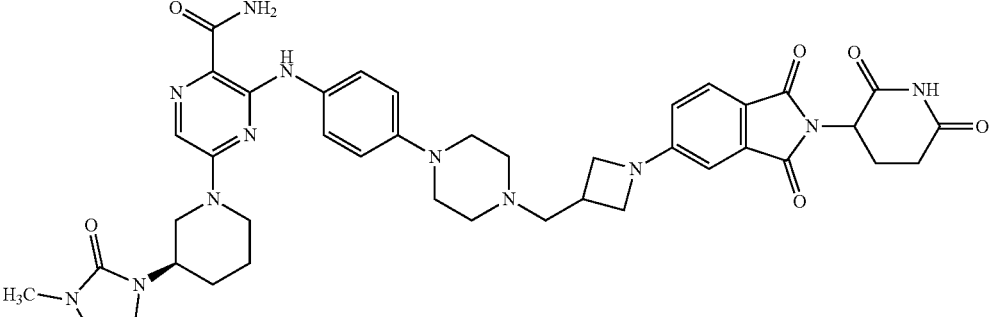 |
| 61 | 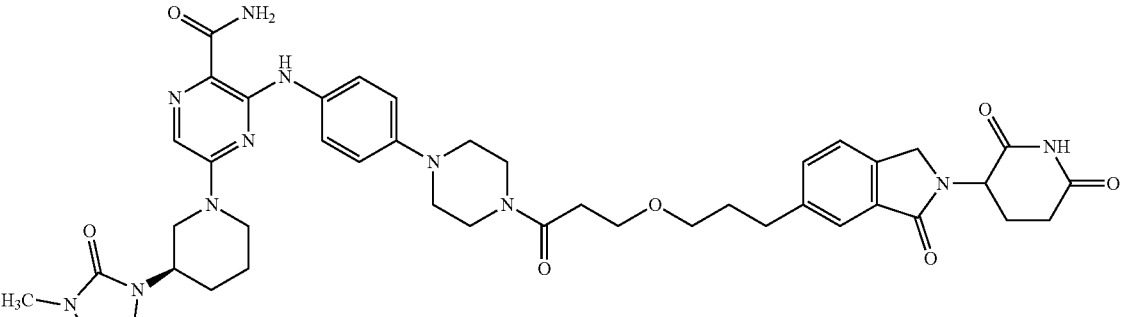 |
| 62 | 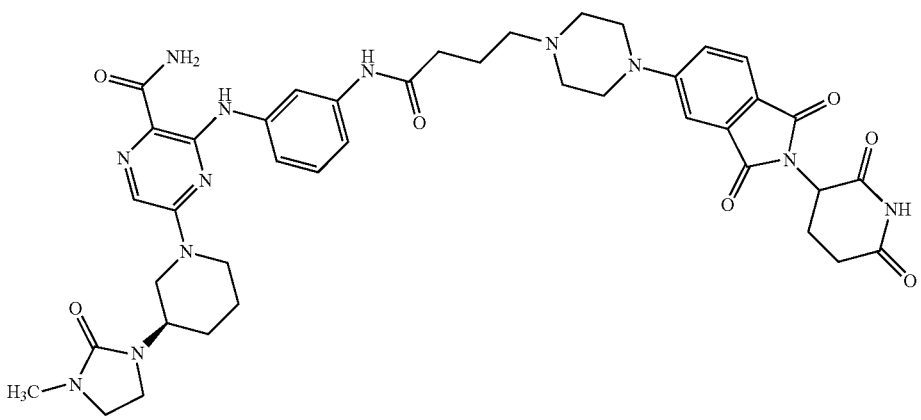 [SMILES: CN1CCN([C@@H]2CCCN(c3cnc(C(N)=O)c(Nc4cccc(NC(=O)CCCN5CCN(c6ccc7c(c6)C(=O)N(C6CCC(=O)NC6=O)C7=O)CC5)c4)n3)C2)C1=O] |
| 63 | 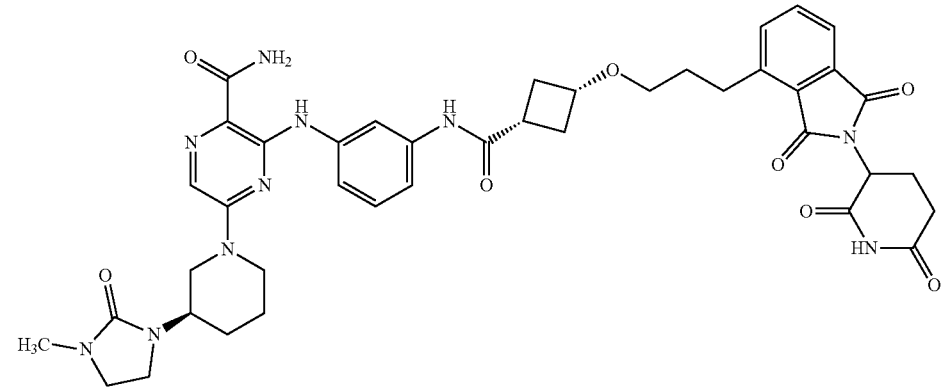 [SMILES: CN1CCN([C@@H]2CCCN(c3cnc(C(N)=O)c(Nc4cccc(NC(=O)[C@H]5C[C@@H](OCCCc6cccc7c6C(=O)N(C6CCC(=O)NC6=O)C7=O)C5)c4)n3)C2)C1=O] |

TABLE 1-continued
Example compounds of the present invention.
| Compound Number | Structure |
|---|---|
| 64 | 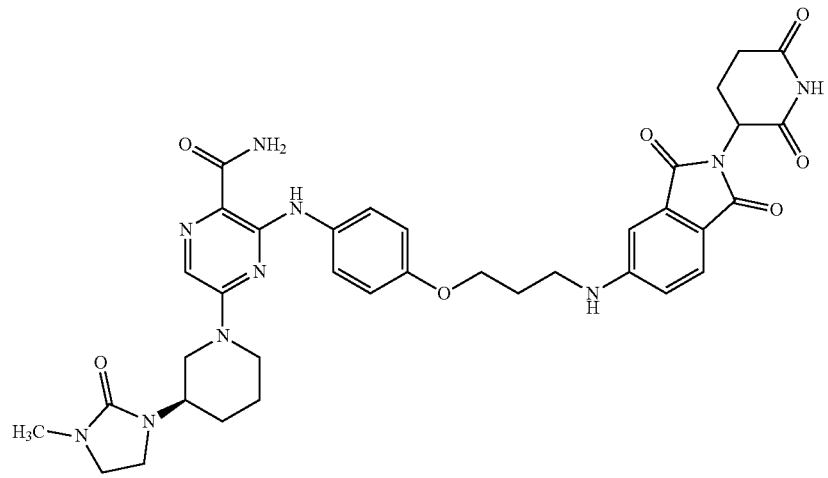 [SMILES: CN1CCN([C@@H]2CCCN(c3cnc(C(N)=O)c(Nc4ccc(OCCCNc5ccc6c(c5)C(=O)N(C5CCC(=O)NC5=O)C6=O)cc4)n3)C2)C1=O] |
| 65 | 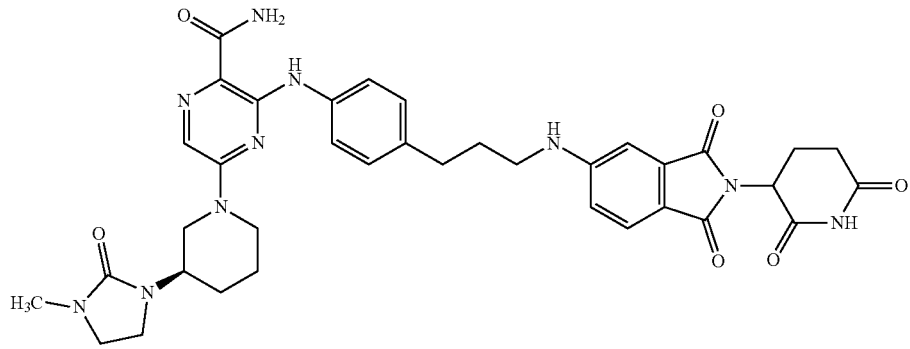 [SMILES: CN1CCN([C@@H]2CCCN(c3cnc(C(N)=O)c(Nc4ccc(CCCNc5ccc6c(c5)C(=O)N(C5CCC(=O)NC5=O)C6=O)cc4)n3)C2)C1=O] |
| 66 | 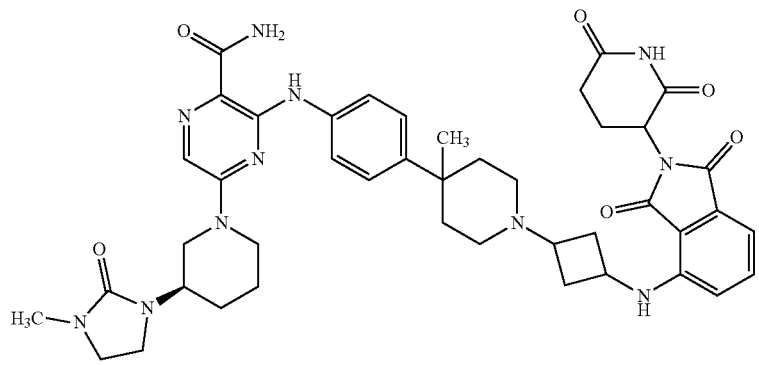 [SMILES: CN1CCN([C@@H]2CCCN(c3cnc(C(N)=O)c(Nc4ccc(C5(C)CCN(C6CC(Nc7cccc8c7C(=O)N(C7CCC(=O)NC7=O)C8=O)C6)CC5)cc4)n3)C2)C1=O] |

TABLE 1-continued

Example compounds of the present invention.

| Compound Number | Structure |
|---|---|
| 67 | 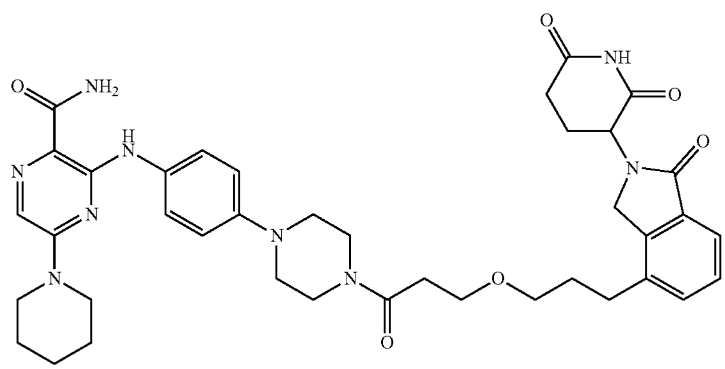 [SMILES: NC(=O)c1ncc(N2CCCCC2)nc1Nc1ccc(N2CCN(C(=O)CCOCCCc3cccc4c3CN(C3CCC(=O)NC3=O)C4=O)CC2)cc1] |
| 68 | 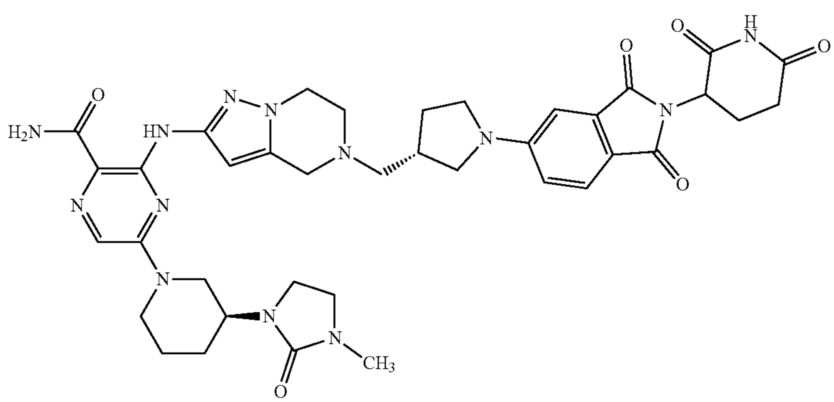 [SMILES: CN1CCN([C@H]2CCCN(c3cnc(C(N)=O)c(Nc4cc5n(n4)CCN(C[C@@H]4CCN(c6ccc7c(c6)C(=O)N(C6CCC(=O)NC6=O)C7=O)C4)C5)n3)C2)C1=O] |
| 69 | 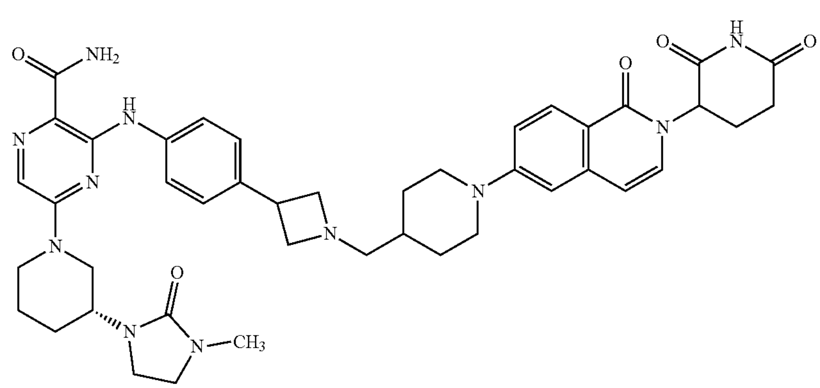 [SMILES: CN1CCN([C@@H]2CCCN(c3cnc(C(N)=O)c(Nc4ccc(C5CN(CC6CCN(c7ccc8c(=O)n(C9CCC(=O)NC9=O)ccc8c7)CC6)C5)cc4)n3)C2)C1=O] |

TABLE 1-continued
Example compounds of the present invention.
| Compound Number | Structure |
|---|---|
| 70 | 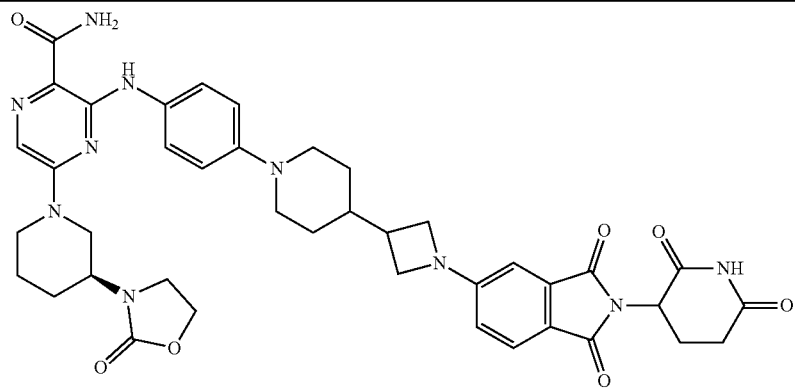 |
| 71 | 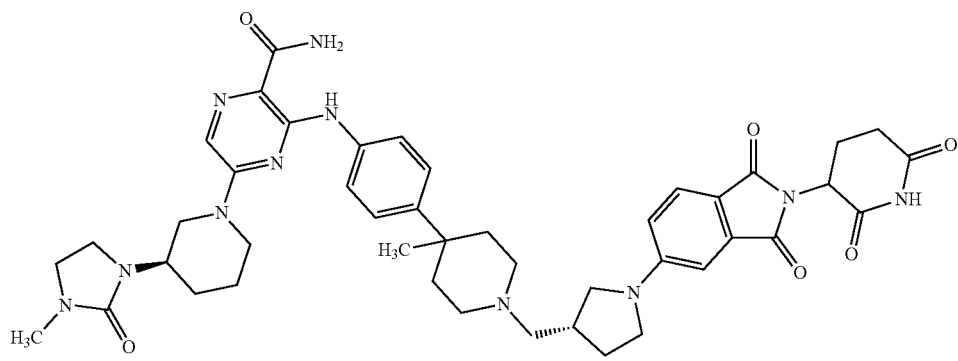 [SMILES: CN1CCN([C@@H]2CCCN(c3cnc(C(N)=O)c(Nc4ccc(C5(C)CCN(C[C@H]6CCN(c7ccc8c(c7)C(=O)N(C7CCC(=O)NC7=O)C8=O)C6)CC5)cc4)n3)C2)C1=O] |
| 72 | 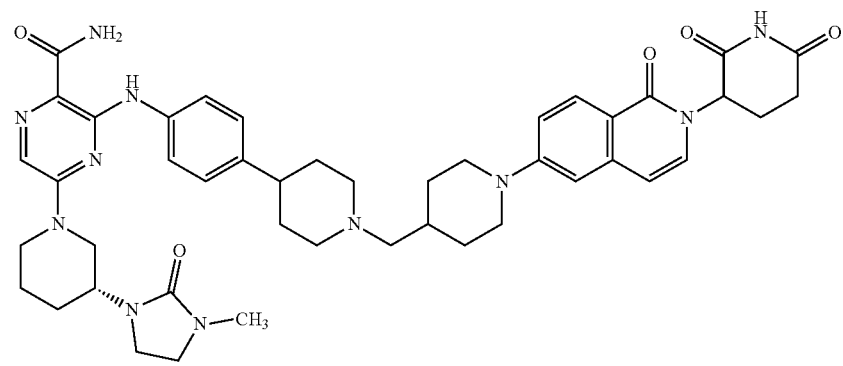 [SMILES: CN1CCN([C@@H]2CCCN(c3cnc(C(N)=O)c(Nc4ccc(C5CCN(CC6CCN(c7ccc8c(=O)n(C9CCC(=O)NC9=O)ccc8c7)CC6)CC5)cc4)n3)C2)C1=O] |
| 73 | 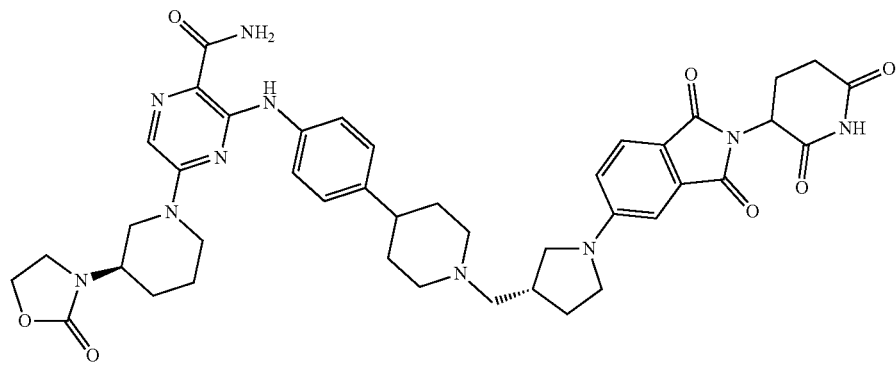 [SMILES: NC(=O)c1ncc(N2CCC[C@@H](N3CCOC3=O)C2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued
Example compounds of the present invention.
| Compound Number | Structure |
|---|---|
| 74 | 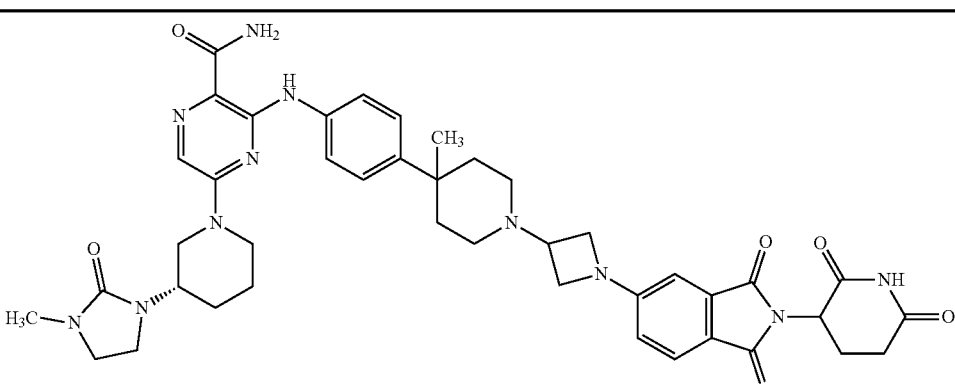 |
| 75 | 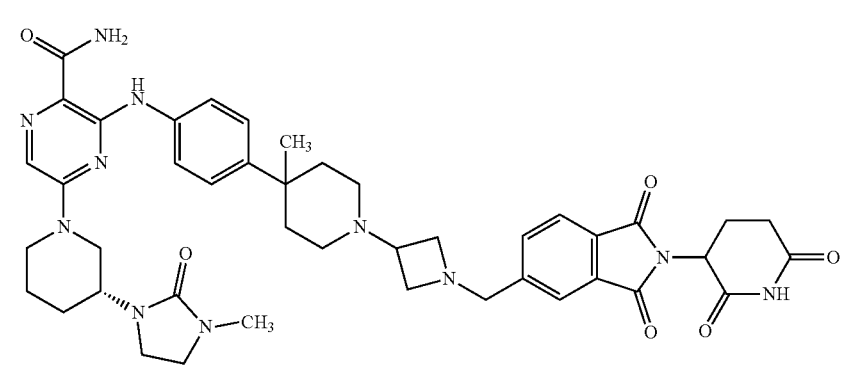 [SMILES: CN1CCN([C@@H]2CCCN(c3cnc(C(N)=O)c(Nc4ccc(C5(C)CCN(C6CN(Cc7ccc8c(c7)C(=O)N(C7CCC(=O)NC7=O)C8=O)C6)CC5)cc4)n3)C2)C1=O] |
| 76 | 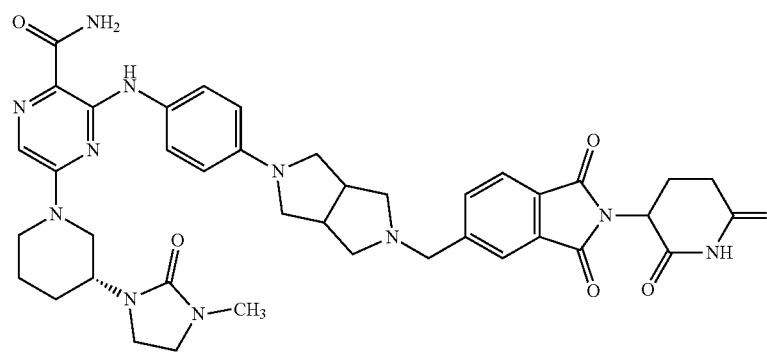 |
| 77 | 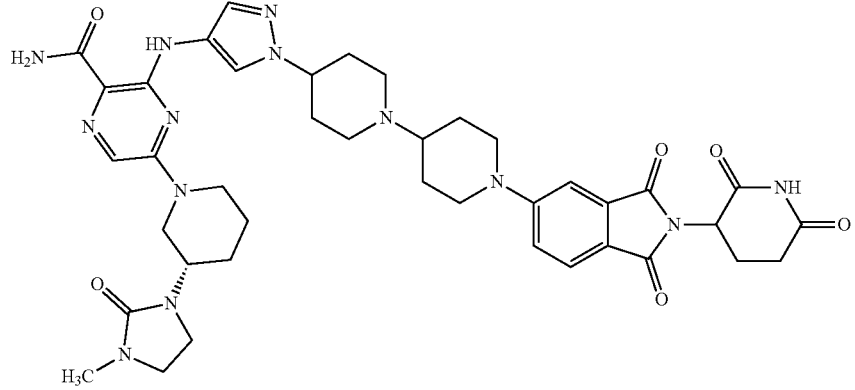 [SMILES: CN1CCN([C@H]2CCCN(c3cnc(C(N)=O)c(Nc4cnn(C5CCN(C6CCN(c7ccc8c(c7)C(=O)N(C7CCC(=O)NC7=O)C8=O)CC6)CC5)c4)n3)C2)C1=O] |

TABLE 1-continued

Example compounds of the present invention.

| Compound Number | Structure |
|---|---|
| 78 | 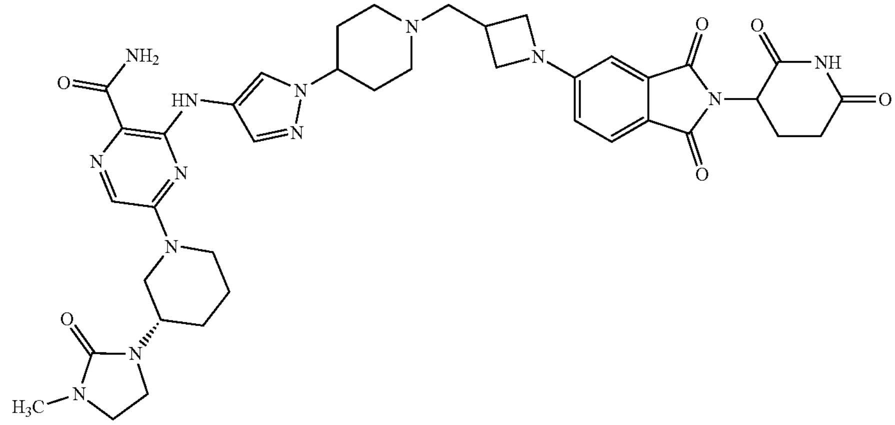 [SMILES: CN1CCN([C@H]2CCCN(c3cnc(C(N)=O)c(Nc4cnn(C5CCN(CC6CN(c7ccc8c(c7)C(=O)N(C7CCC(=O)NC7=O)C8=O)C6)CC5)c4)n3)C2)C1=O] |
| 79 | 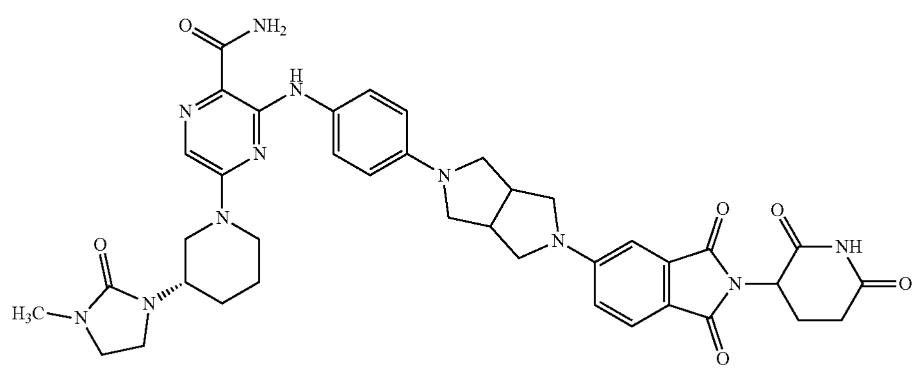 [SMILES: CN1CCN([C@H]2CCCN(c3cnc(C(N)=O)c(Nc4ccc(N5CC6CN(c7ccc8c(c7)C(=O)N(C7CCC(=O)NC7=O)C8=O)CC6C5)cc4)n3)C2)C1=O] |
| 80 | 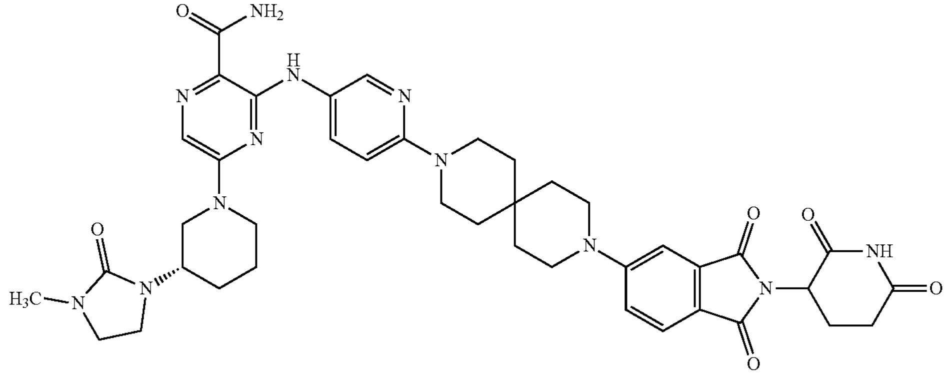 [SMILES: CN1CCN([C@H]2CCCN(c3cnc(C(N)=O)c(Nc4ccc(N5CCC6(CCN(c7ccc8c(c7)C(=O)N(C7CCC(=O)NC7=O)C8=O)CC6)CC5)nc4)n3)C2)C1=O] |

TABLE 1-continued
Example compounds of the present invention.
| Compound Number | Structure |
|---|---|
| 81 | 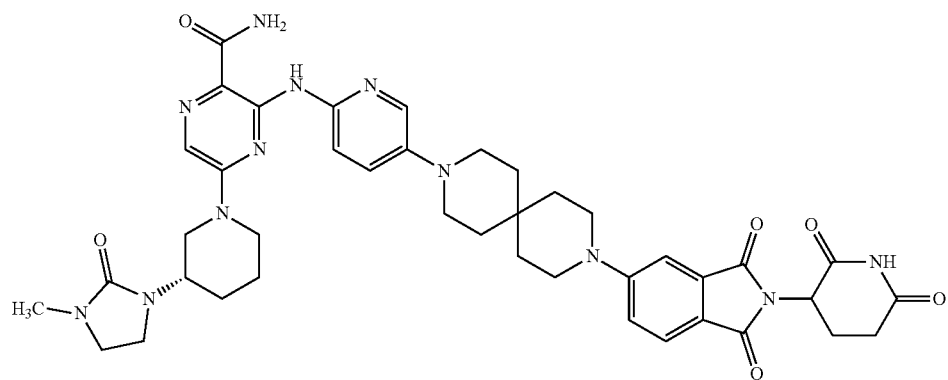 [SMILES: CN1CCN([C@H]2CCCN(c3cnc(C(N)=O)c(Nc4ccc(N5CCC6(CC5)CCN(c5ccc7c(c5)C(=O)N(C5CCC(=O)NC5=O)C7=O)CC6)cn4)n3)C2)C1=O] |
| 82 | 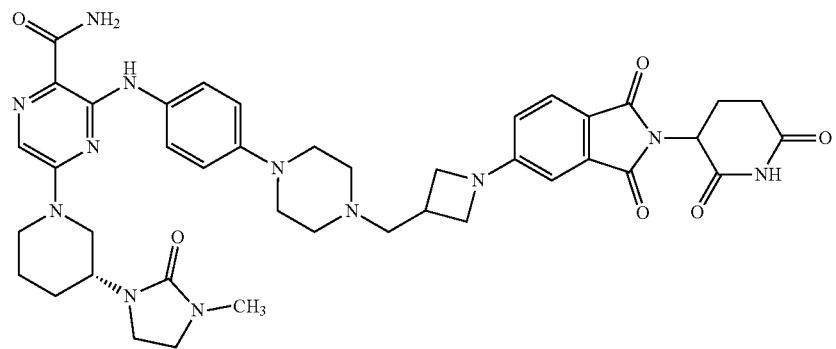 [SMILES: CN1CCN([C@@H]2CCCN(c3cnc(C(N)=O)c(Nc4ccc(N5CCN(CC6CN(c7ccc8c(c7)C(=O)N(C7CCC(=O)NC7=O)C8=O)C6)CC5)cc4)n3)C2)C1=O] |
| 83 | 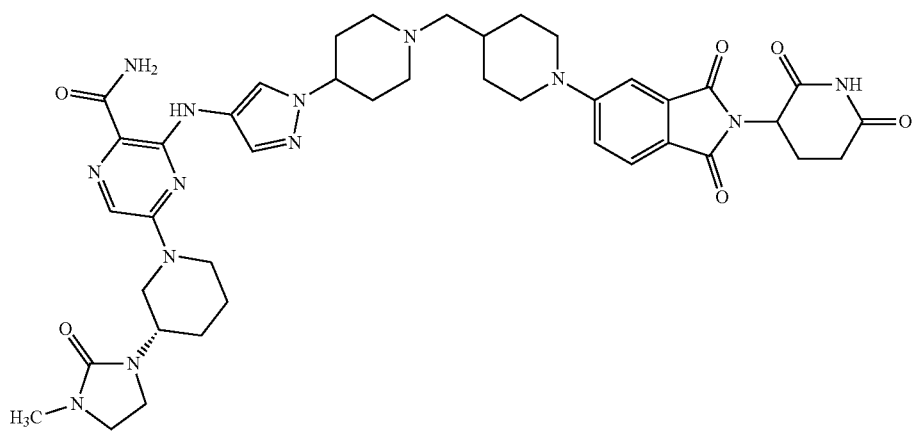 [SMILES: CN1CCN([C@H]2CCCN(c3cnc(C(N)=O)c(Nc4cnn(C5CCN(CC6CCN(c7ccc8c(c7)C(=O)N(C7CCC(=O)NC7=O)C8=O)CC6)CC5)c4)n3)C2)C1=O] |

TABLE 1-continued

Example compounds of the present invention.

| Compound Number | Structure |
|---|---|
| 84 | 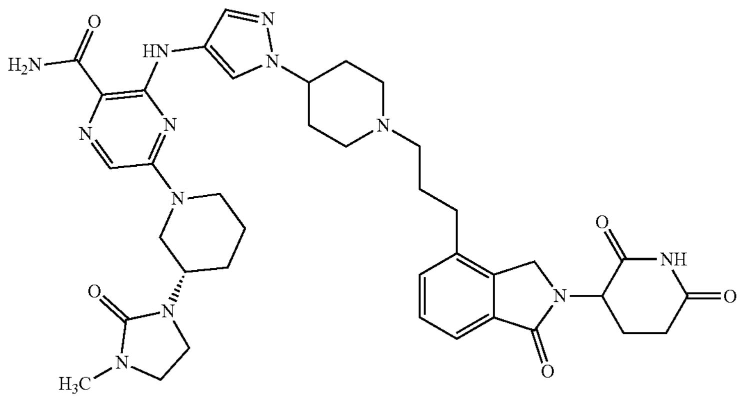 [SMILES: CN1CCN([C@H]2CCCN(c3cnc(C(N)=O)c(Nc4cnn(C5CCN(CCCc6cccc7c6CN(C6CCC(=O)NC6=O)C7=O)CC5)c4)n3)C2)C1=O] |
| 85 | 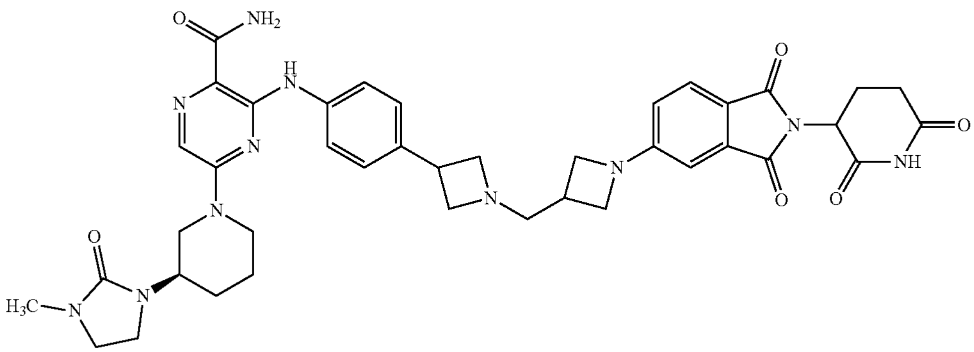 [SMILES: CN1CCN([C@@H]2CCCN(c3cnc(C(N)=O)c(Nc4ccc(C5CN(CC6CN(c7ccc8c(c7)C(=O)N(C7CCC(=O)NC7=O)C8=O)C6)C5)cc4)n3)C2)C1=O] |
| 86 | 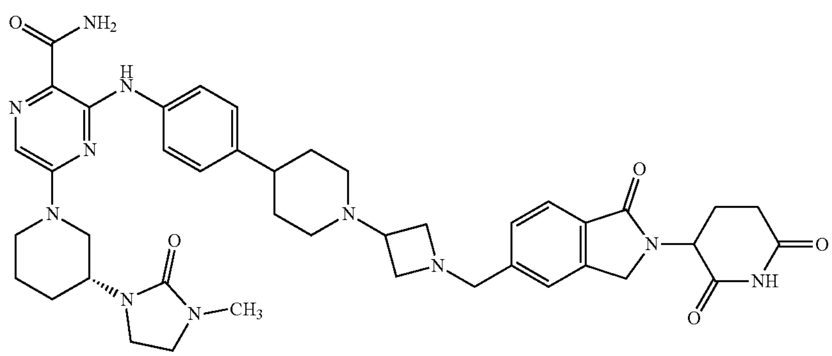 [SMILES: CN1CCN([C@@H]2CCCN(c3cnc(C(N)=O)c(Nc4ccc(C5CCN(C6CN(Cc7ccc8c(c7)CN(C7CCC(=O)NC7=O)C8=O)C6)CC5)cc4)n3)C2)C1=O] |
| 87 | 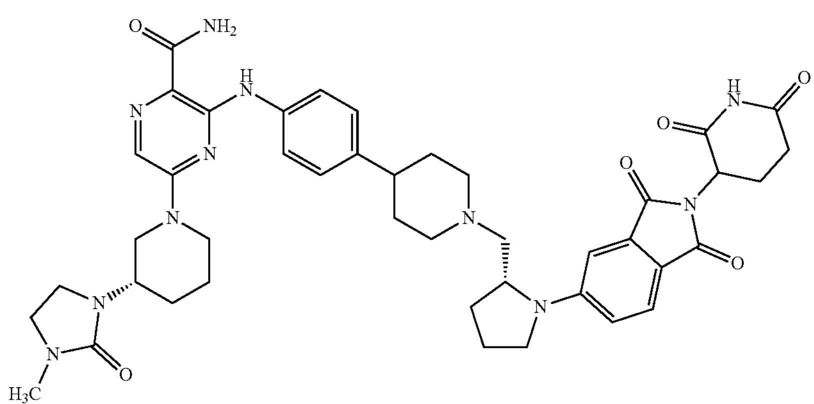 [SMILES: CN1CCN([C@H]2CCCN(c3cnc(C(N)=O)c(Nc4ccc(C5CCN(C[C@H]6CCCN6c6ccc7c(c6)C(=O)N(C6CCC(=O)NC6=O)C7=O)CC5)cc4)n3)C2)C1=O] |

TABLE 1-continued
Example compounds of the present invention.
| Compound Number | Structure |
|---|---|
| 88 | 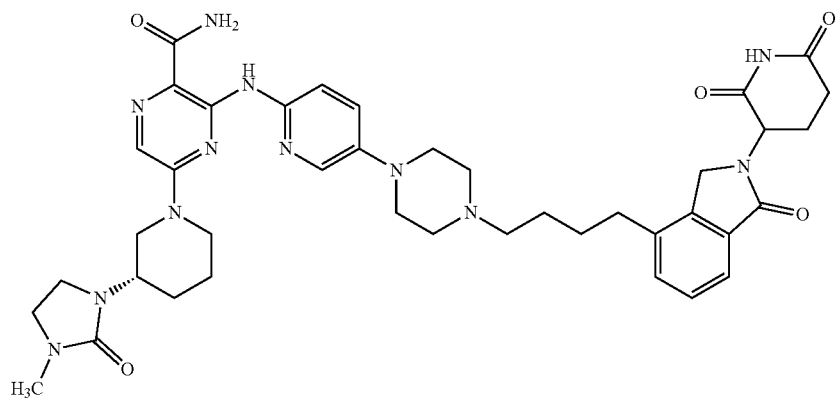 [SMILES: CN1CCN([C@H]2CCCN(c3cnc(C(N)=O)c(Nc4ccc(N5CCN(CCCCc6cccc7c6CN(C6CCC(=O)NC6=O)C7=O)CC5)cn4)n3)C2)C1=O] |
| 89 | 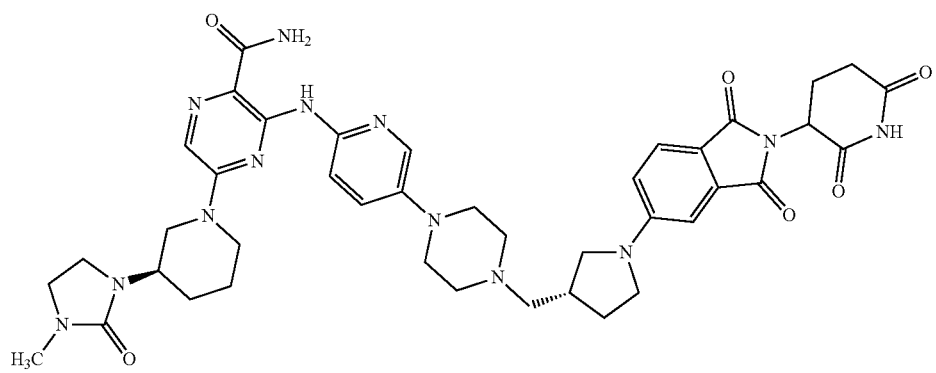 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)cn4)n3)C2)C1=O] |
| 90 | 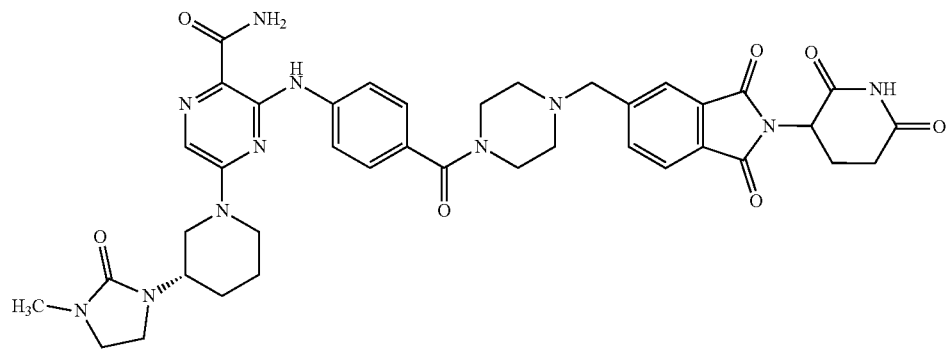 [SMILES: CN1CCN([C@H]2CCCN(c3cnc(C(N)=O)c(Nc4ccc(C(=O)N5CCN(Cc6ccc7c(c6)C(=O)N(C6CCC(=O)NC6=O)C7=O)CC5)cc4)n3)C2)C1=O] |
| 91 | 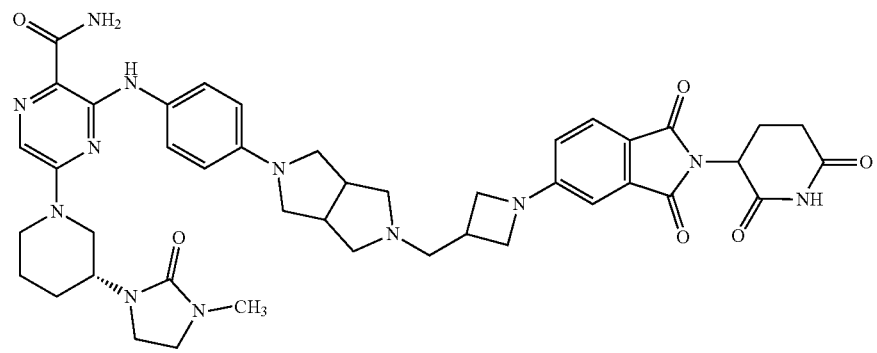 [SMILES: CN1CCN([C@@H]2CCCN(c3cnc(C(N)=O)c(Nc4ccc(N5CC6CN(CC7CN(c8ccc9c(c8)C(=O)N(C8CCC(=O)NC8=O)C9=O)C7)CC6C5)cc4)n3)C2)C1=O] |

TABLE 1-continued
Example compounds of the present invention.
| Compound Number | Structure |
|---|---|
| 92 | 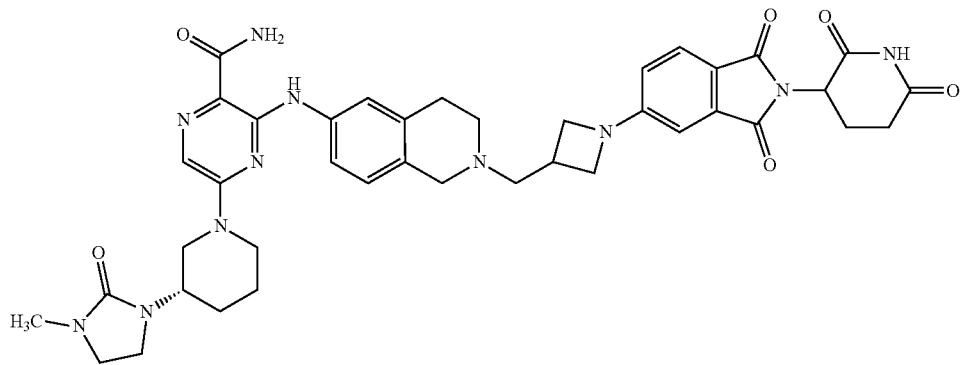 [SMILES: CN1CCN([C@H]2CCCN(c3cnc(C(N)=O)c(Nc4ccc5c(c4)CCN(CC4CN(c6ccc7c(c6)C(=O)N(C6CCC(=O)NC6=O)C7=O)C4)C5)n3)C2)C1=O] |
| 93 | 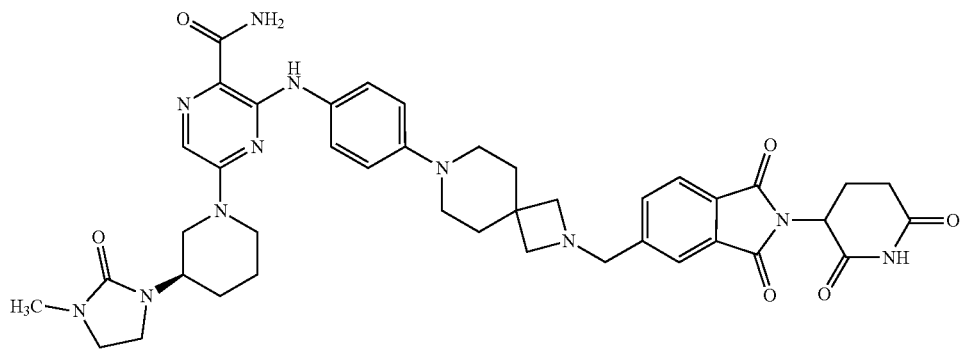 [SMILES: CN1CCN([C@@H]2CCCN(c3cnc(C(N)=O)c(Nc4ccc(N5CCC6(CC5)CN(Cc5ccc7c(c5)C(=O)N(C5CCC(=O)NC5=O)C7=O)C6)cc4)n3)C2)C1=O] |
| 94 | 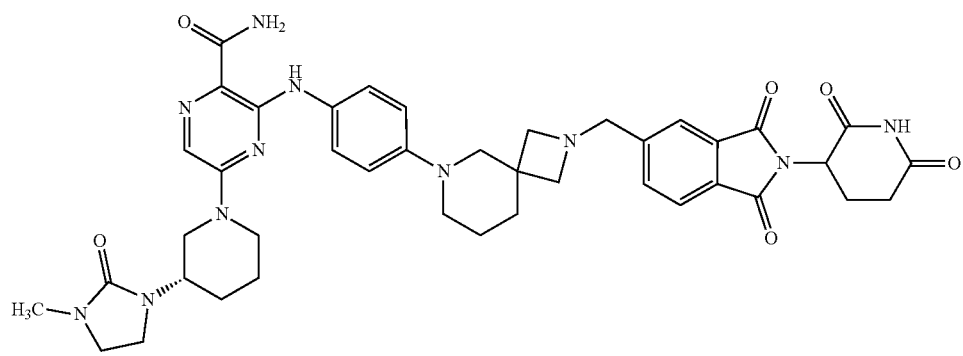 [SMILES: CN1CCN([C@H]2CCCN(c3cnc(C(N)=O)c(Nc4ccc(N5CCCC6(CN(Cc7ccc8c(c7)C(=O)N(C7CCC(=O)NC7=O)C8=O)C6)C5)cc4)n3)C2)C1=O] |
| 95 | 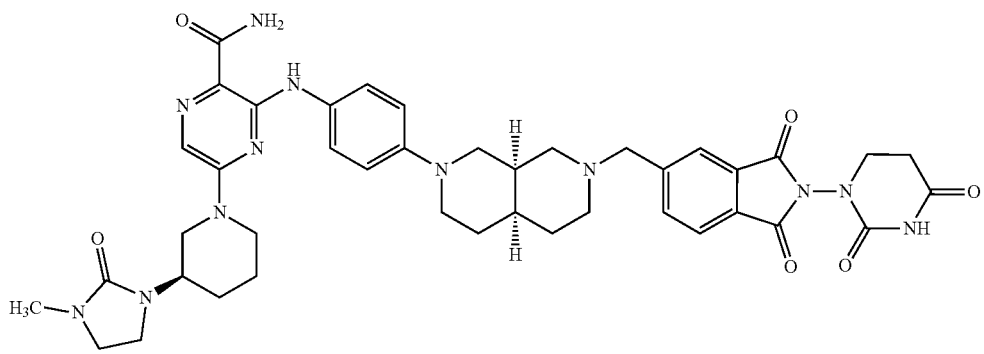 [SMILES: CN1CCN([C@@H]2CCCN(c3cnc(C(N)=O)c(Nc4ccc(N5CC[C@@H]6CCN(Cc7ccc8c(c7)C(=O)N(N7CCC(=O)NC7=O)C8=O)C[C@@H]6C5)cc4)n3)C2)C1=O] |

TABLE 1-continued
Example compounds of the present invention.
| Compound Number | Structure |
|---|---|
| 96 | 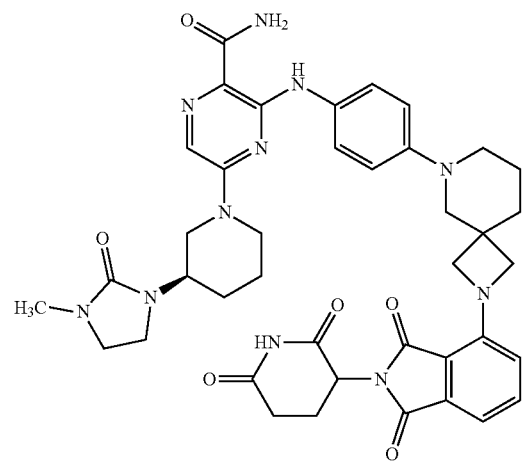 [SMILES: CN1CCN([C@@H]2CCCN(c3cnc(C(N)=O)c(Nc4ccc(N5CCCC6(C5)CN(c5cccc7c5C(=O)N(C5CCC(=O)NC5=O)C7=O)C6)cc4)n3)C2)C1=O] |
| 97 | 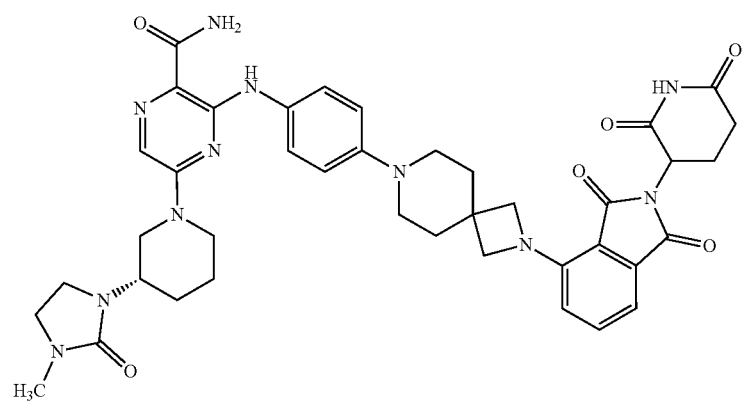 [SMILES: CN1CCN([C@H]2CCCN(c3cnc(C(N)=O)c(Nc4ccc(N5CCC6(CC5)CN(c5cccc7c5C(=O)N(C5CCC(=O)NC5=O)C7=O)C6)cc4)n3)C2)C1=O] |
| 98 | 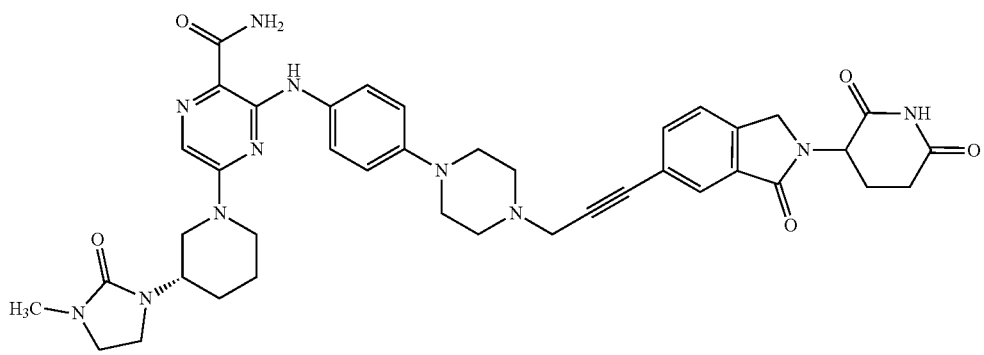 [SMILES: CN1CCN([C@H]2CCCN(c3cnc(C(N)=O)c(Nc4ccc(N5CCN(CC#Cc6ccc7c(c6)C(=O)N(C6CCC(=O)NC6=O)C7)CC5)cc4)n3)C2)C1=O] |

TABLE 1-continued

Example compounds of the present invention.

| Compound Number | Structure |
|---|---|
| 99 | (structure) |
| 100 | (structure) |
| 101 | (structure) |
| 102 | (structure) |

TABLE 1-continued
Example compounds of the present invention.
| Compound Number | Structure |
|---|---|
| 103 | 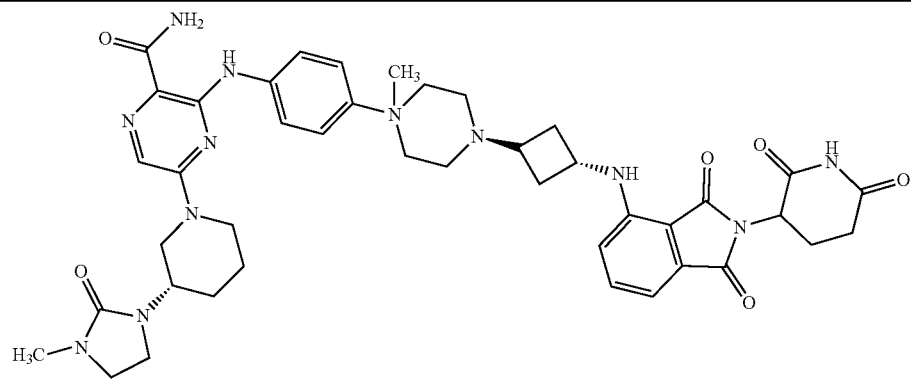 |
| 104 | 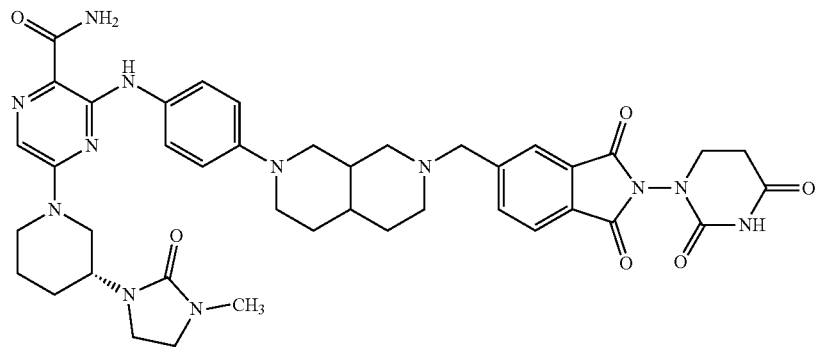 [SMILES: CN1CCN([C@@H]2CCCN(c3cnc(C(N)=O)c(Nc4ccc(N5CCC6CCN(Cc7ccc8c(c7)C(=O)N(N7CCC(=O)NC7=O)C8=O)CC6C5)cc4)n3)C2)C1=O] |
| 105 | 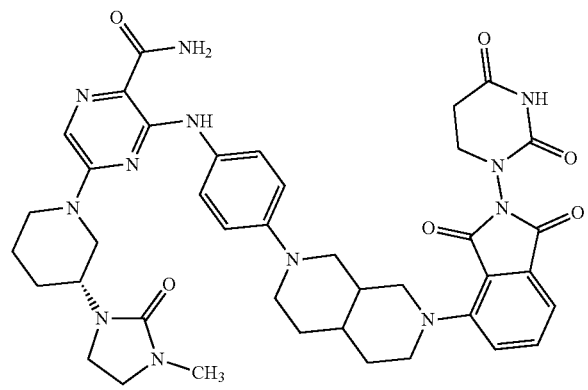 [SMILES: CN1CCN([C@@H]2CCCN(c3cnc(C(N)=O)c(Nc4ccc(N5CCC6CCN(c7cccc8c7C(=O)N(N7CCC(=O)NC7=O)C8=O)CC6C5)cc4)n3)C2)C1=O] |
| 106 | 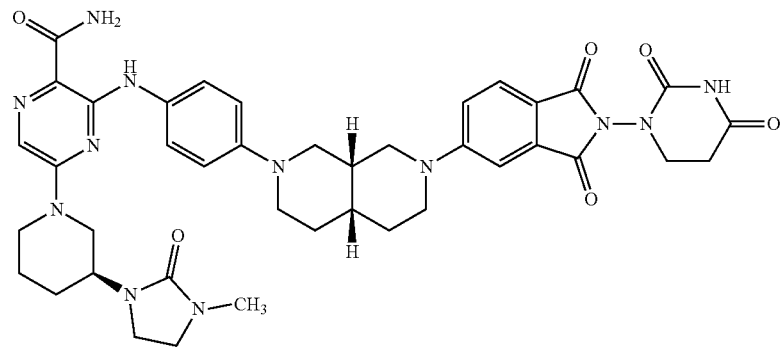 [SMILES: CN1CCN([C@H]2CCCN(c3cnc(C(N)=O)c(Nc4ccc(N5CC[C@H]6CCN(c7ccc8c(c7)C(=O)N(N7CCC(=O)NC7=O)C8=O)C[C@H]6C5)cc4)n3)C2)C1=O] |

TABLE 1-continued
Example compounds of the present invention.
| Compound Number | Structure |
|---|---|
| 107 | 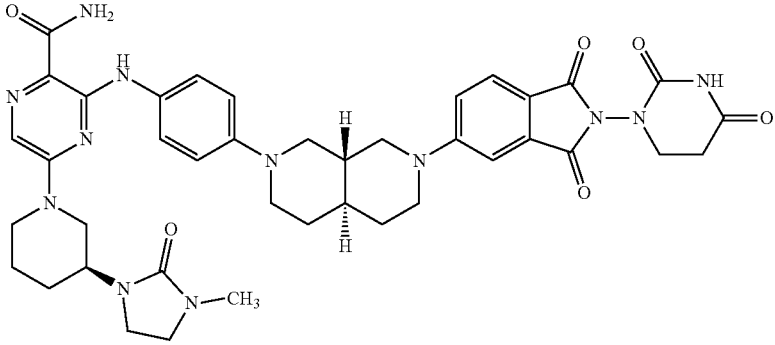 [SMILES: CN1CCN([C@H]2CCCN(c3cnc(C(N)=O)c(Nc4ccc(N5CC[C@@H]6CCN(c7ccc8c(c7)C(=O)N(N7CCC(=O)NC7=O)C8=O)C[C@H]6C5)cc4)n3)C2)C1=O] |
| 108 | 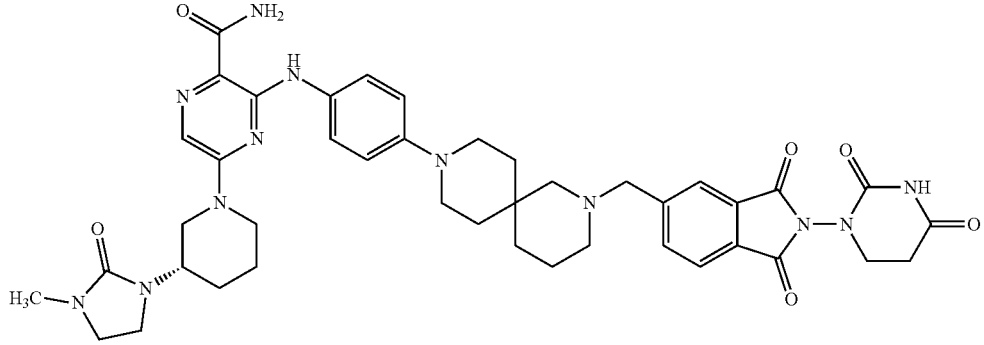 [SMILES: CN1CCN([C@H]2CCCN(c3cnc(C(N)=O)c(Nc4ccc(N5CCC6(CCCN(Cc7ccc8c(c7)C(=O)N(N7CCC(=O)NC7=O)C8=O)C6)CC5)cc4)n3)C2)C1=O] |
| 109 | 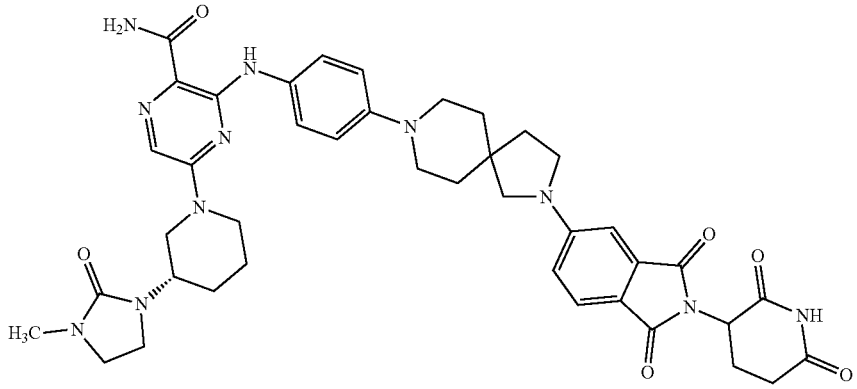 [SMILES: CN1CCN([C@H]2CCCN(c3cnc(C(N)=O)c(Nc4ccc(N5CCC6(CC5)CCN(c5ccc7c(c5)C(=O)N(C5CCC(=O)NC5=O)C7=O)C6)cc4)n3)C2)C1=O] |
| 110 | 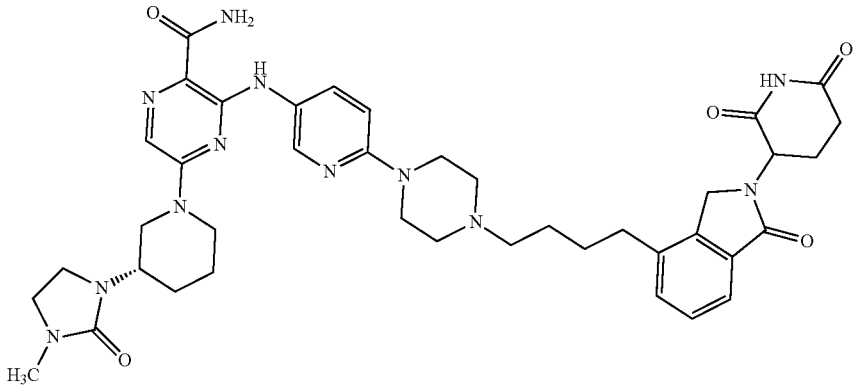 [SMILES: CN1CCN([C@H]2CCCN(c3cnc(C(N)=O)c(Nc4ccc(N5CCN(CCCCc6cccc7c6CN(C6CCC(=O)NC6=O)C7=O)CC5)nc4)n3)C2)C1=O] |

TABLE 1-continued
Example compounds of the present invention.
| Compound Number | Structure |
|---|---|
| 111 | 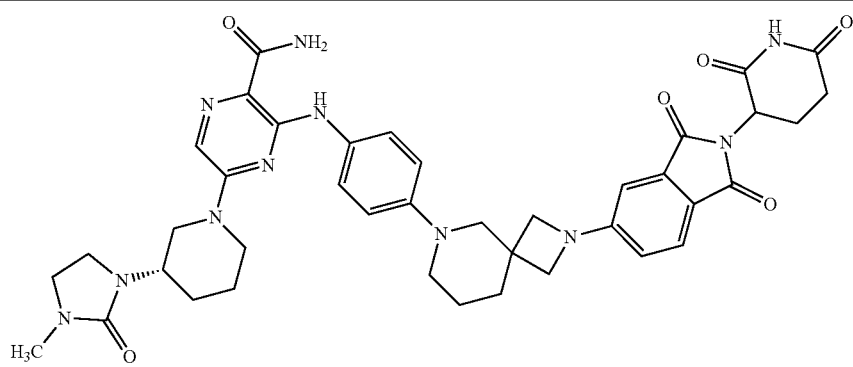 |
| 112 | 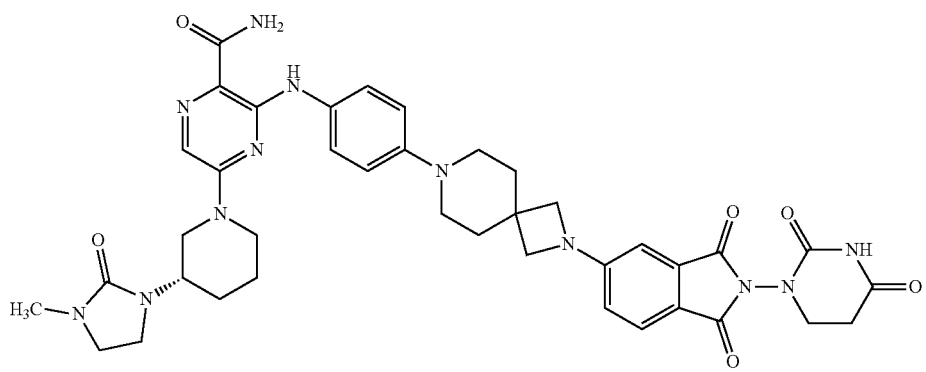 [SMILES: CN1CCN([C@H]2CCCN(c3cnc(C(N)=O)c(Nc4ccc(N5CCC6(CC5)CN(c5ccc7c(c5)C(=O)N(N5CCC(=O)NC5=O)C7=O)C6)cc4)n3)C2)C1=O] |
| 113 | 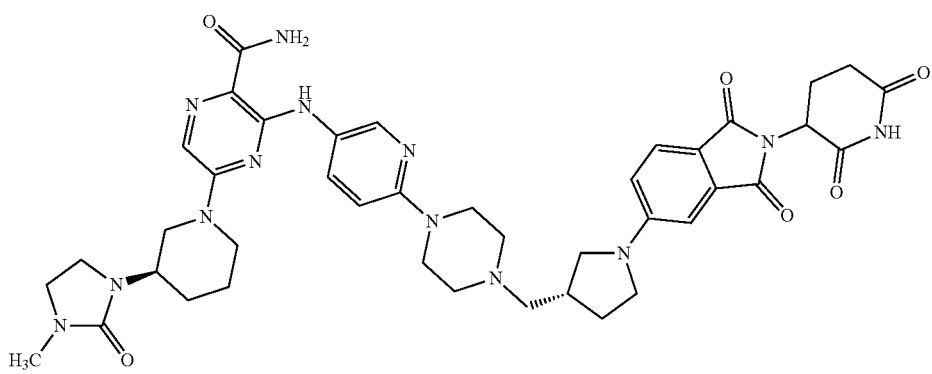 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)nc4)n3)C2)C1=O] |
| 114 | 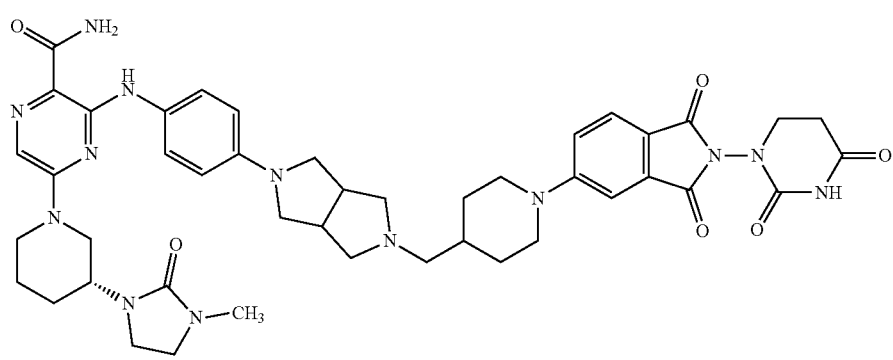 [SMILES: CN1CCN([C@@H]2CCCN(c3cnc(C(N)=O)c(Nc4ccc(N5CC6CN(CC7CCN(c8ccc9c(c8)C(=O)N(N8CCC(=O)NC8=O)C9=O)CC7)CC6C5)cc4)n3)C2)C1=O] |

US 11,479,556 B1
271                                                                 272
TABLE 1-continued
Example compounds of the present invention.
| Compound Number | Structure |
|---|---|
| 115 | 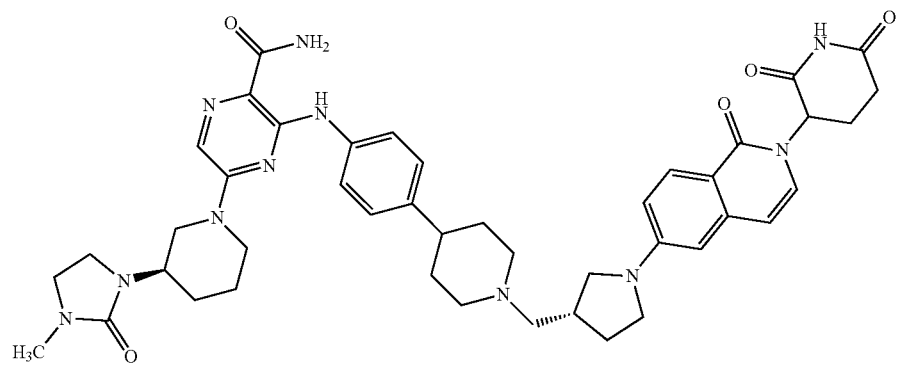 [SMILES: CN1CCN([C@@H]2CCCN(c3cnc(C(N)=O)c(Nc4ccc(C5CCN(C[C@H]6CCN(c7ccc8c(=O)n(C9CCC(=O)NC9=O)ccc8c7)C6)CC5)cc4)n3)C2)C1=O] |
| 116 | 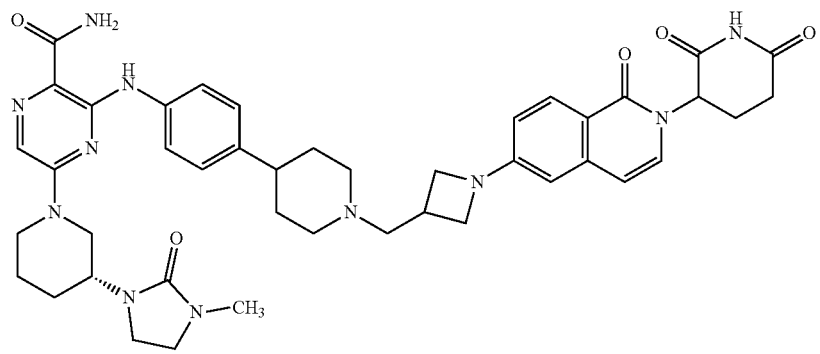 [SMILES: CN1CCN([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |
| 117 | 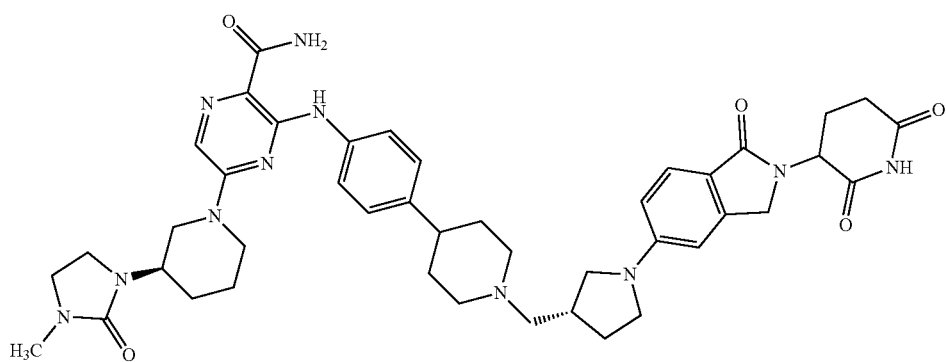 [SMILES: CN1CCN([C@@H]2CCCN(c3cnc(C(N)=O)c(Nc4ccc(C5CCN(C[C@H]6CCN(c7ccc8c(c7)CN(C7CCC(=O)NC7=O)C8=O)C6)CC5)cc4)n3)C2)C1=O] |
| 118 | 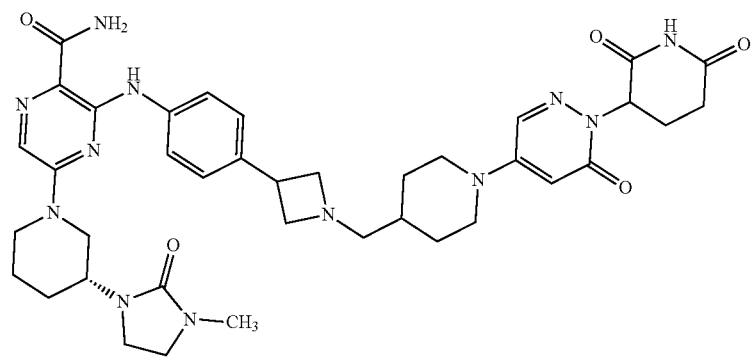 [SMILES: CN1CCN([C@@H]2CCCN(c3cnc(C(N)=O)c(Nc4ccc(C5CN(CC6CCN(c7cnn(C8CCC(=O)NC8=O)c(=O)c7)CC6)C5)cc4)n3)C2)C1=O] |

TABLE 1-continued

Example compounds of the present invention.

| Compound Number | Structure |
|---|---|
| 119 | 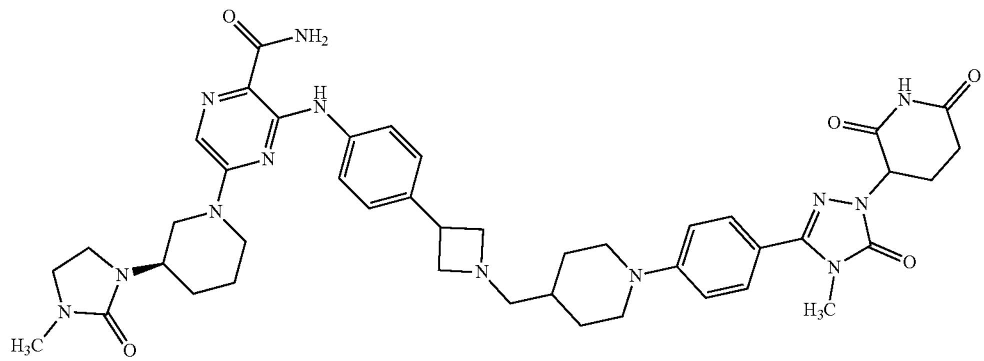 [SMILES: CN1CCN([C@@H]2CCCN(c3cnc(C(N)=O)c(Nc4ccc(C5CN(CC6CCN(c7ccc(-c8nn(C9CCC(=O)NC9=O)c(=O)n8C)cc7)CC6)C5)cc4)n3)C2)C1=O] |
| 120 | 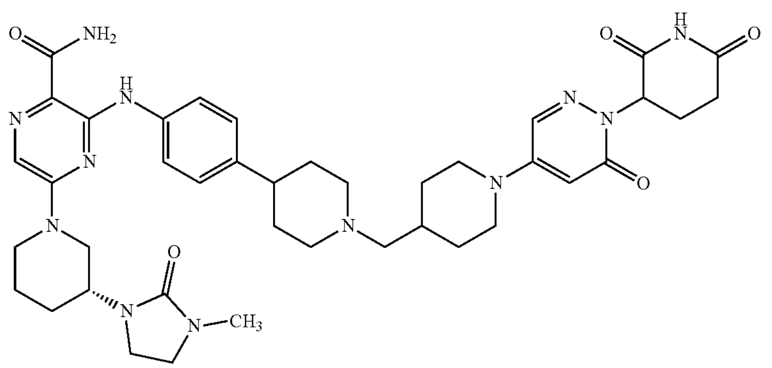 [SMILES: CN1CCN([C@@H]2CCCN(c3cnc(C(N)=O)c(Nc4ccc(C5CCN(CC6CCN(c7cnn(C8CCC(=O)NC8=O)c(=O)c7)CC6)CC5)cc4)n3)C2)C1=O] |
| 121 | 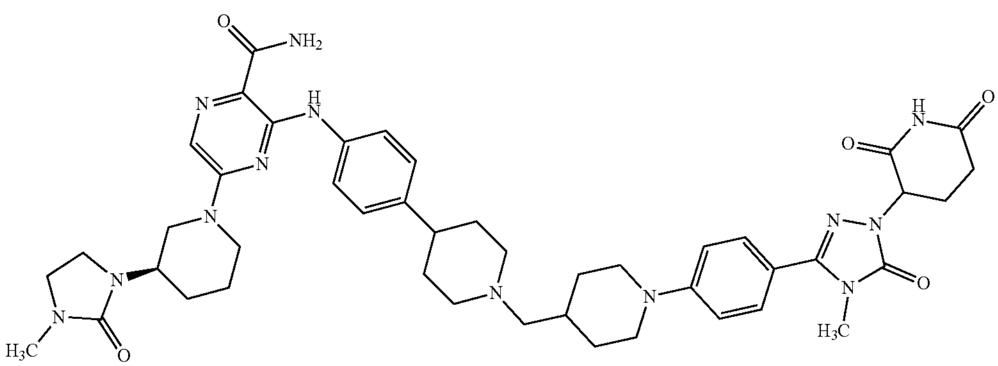 [SMILES: CN1CCN([C@@H]2CCCN(c3cnc(C(N)=O)c(Nc4ccc(C5CCN(CC6CCN(c7ccc(-c8nn(C9CCC(=O)NC9=O)c(=O)n8C)cc7)CC6)CC5)cc4)n3)C2)C1=O] |
| 122 | 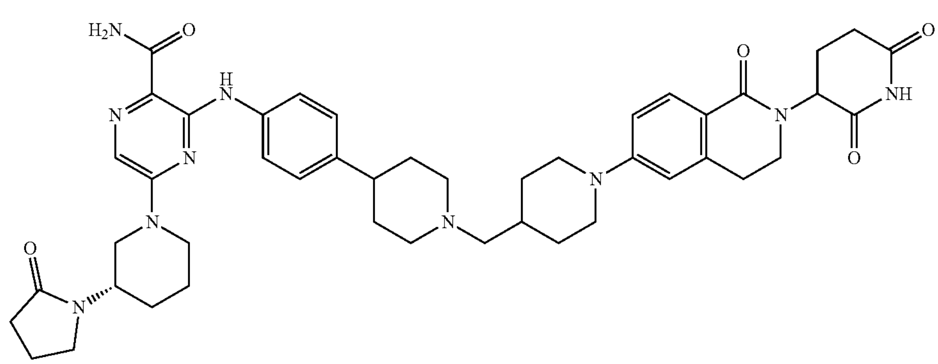 [SMILES: NC(=O)c1ncc(N2CCC[C@H](N3CCCC3=O)C2)nc1Nc1ccc(C2CCN(CC3CCN(c4ccc5c(c4)CCN(C4CCC(=O)NC4=O)C5=O)CC3)CC2)cc1] |

TABLE 1-continued
Example compounds of the present invention.
| Compound Number | Structure |
|---|---|
| 123 | 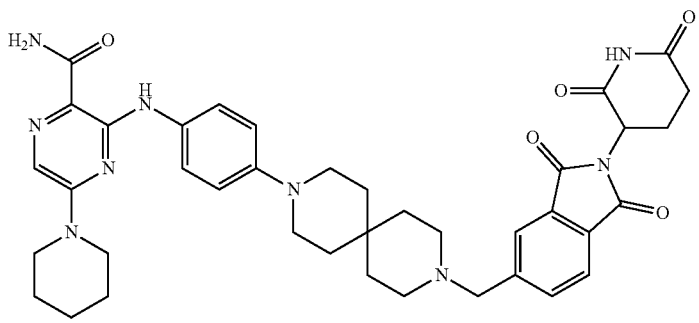 |
| 124 | 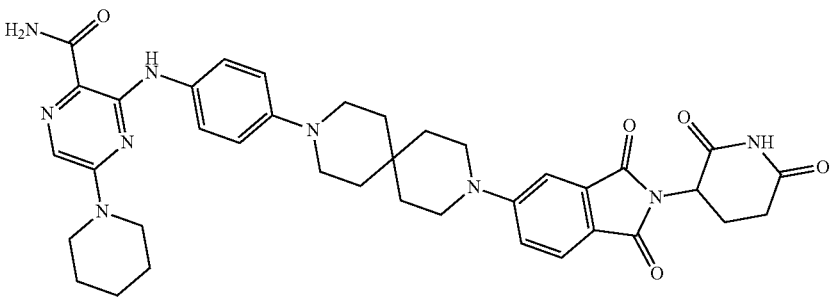 [SMILES: NC(=O)c1ncc(N2CCCCC2)nc1Nc1ccc(N2CCC3(CC2)CCN(c2ccc4c(c2)C(=O)N(C2CCC(=O)NC2=O)C4=O)CC3)cc1] |
| 125 | 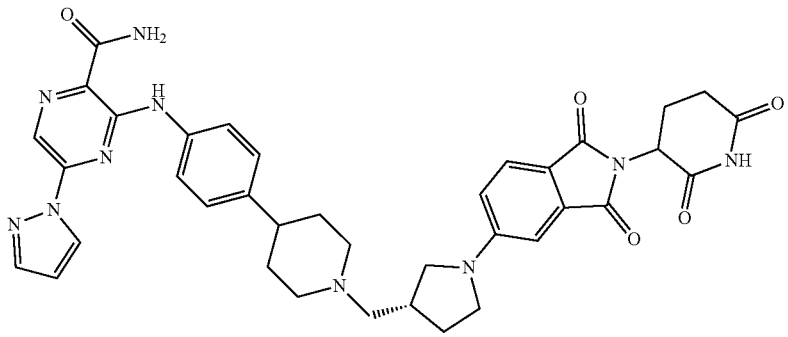 [SMILES: NC(=O)c1ncc(-n2cccn2)nc1Nc1ccc(C2CCN(C[C@H]3CCN(c4ccc5c(c4)C(=O)N(C4CCC(=O)NC4=O)C5=O)C3)CC2)cc1] |
| 126 | 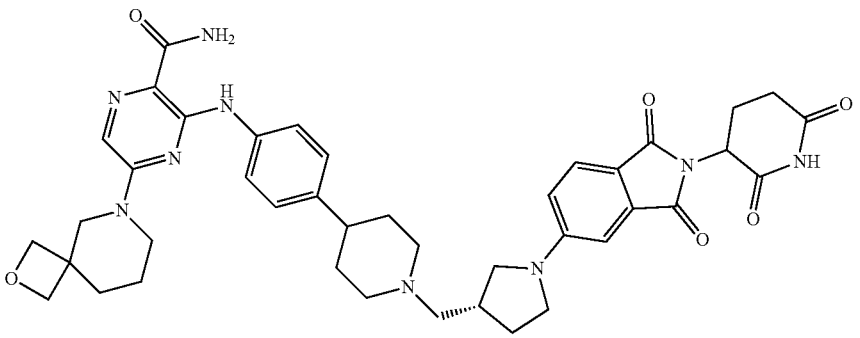 [SMILES: NC(=O)c1ncc(N2CCCC3(COC3)C2)nc1Nc1ccc(C2CCN(C[C@H]3CCN(c4ccc5c(c4)C(=O)N(C4CCC(=O)NC4=O)C5=O)C3)CC2)cc1] |

US 11,479,556 B1
277 278
TABLE 1-continued
Example compounds of the present invention.
| Compound Number | Structure |
|---|---|
| 127 | 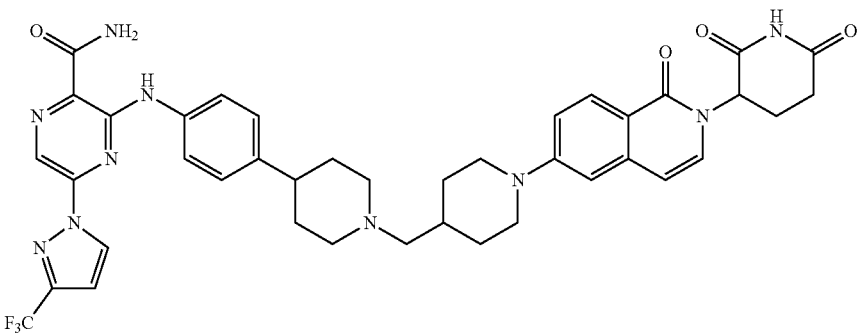 [SMILES: NC(=O)c1ncc(-n2ccc(C(F)(F)F)n2)nc1Nc1ccc(C2CCN(CC3CCN(c4ccc5c(=O)n(C6CCC(=O)NC6=O)ccc5c4)CC3)CC2)cc1] |
| 128 | 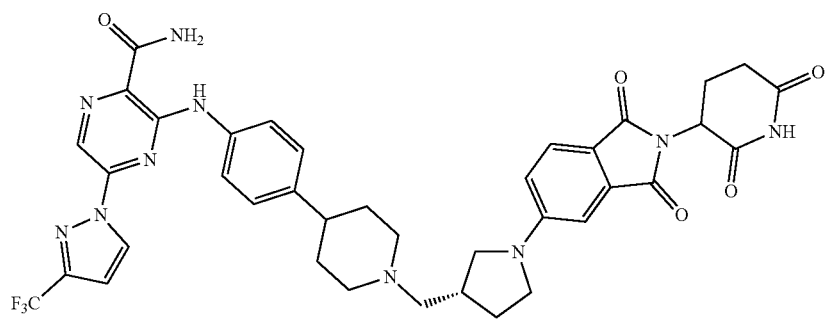 [SMILES: NC(=O)c1ncc(-n2ccc(C(F)(F)F)n2)nc1Nc1ccc(C2CCN(C[C@H]3CCN(c4ccc5c(c4)C(=O)N(C4CCC(=O)NC4=O)C5=O)C3)CC2)cc1] |
| 129 | 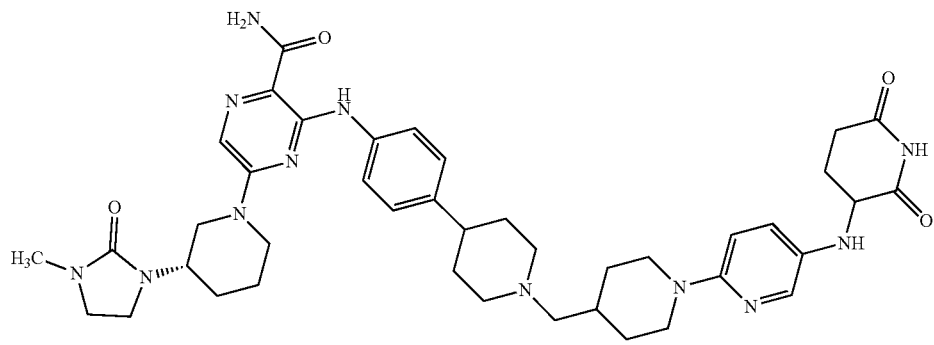 [SMILES: CN1CCN([C@H]2CCCN(c3cnc(C(N)=O)c(Nc4ccc(C5CCN(CC6CCN(c7ccc(NC8CCC(=O)NC8=O)cn7)CC6)CC5)cc4)n3)C2)C1=O] |
| 130 | 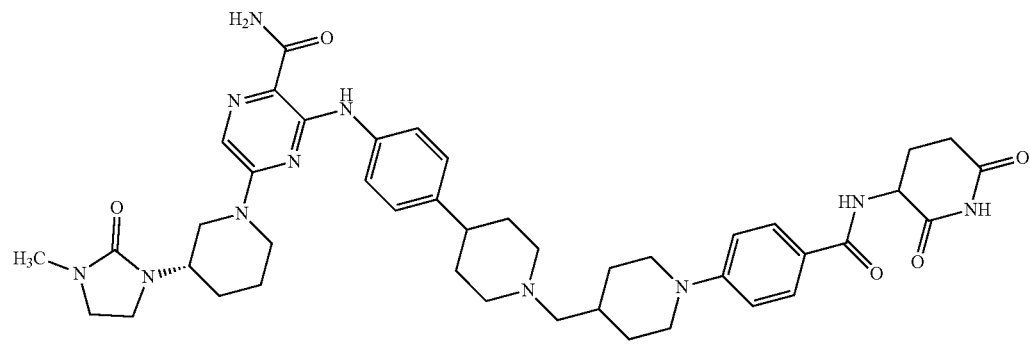 [SMILES: CN1CCN([C@H]2CCCN(c3cnc(C(N)=O)c(Nc4ccc(C5CCN(CC6CCN(c7ccc(C(=O)NC8CCC(=O)NC8=O)cc7)CC6)CC5)cc4)n3)C2)C1=O] |

TABLE 1-continued
Example compounds of the present invention.
| Compound Number | Structure |
|---|---|
| 131 | 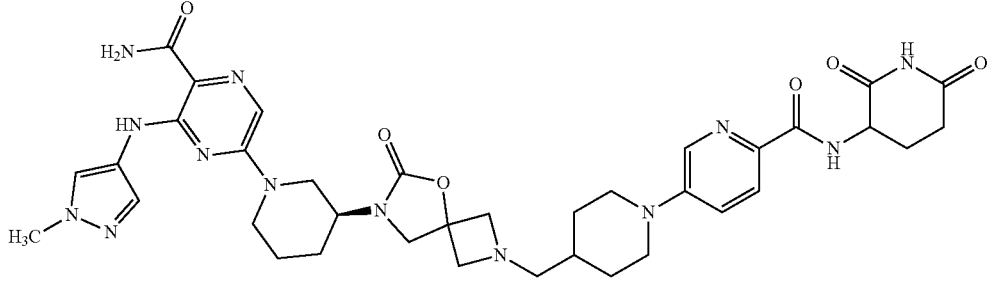 [SMILES: Cn1cc(Nc2nc(N3CCC[C@H](N4CC5(CN(CC6CCN(c7ccc(C(=O)NC8CCC(=O)NC8=O)nc7)CC6)C5)OC4=O)C3)cnc2C(N)=O)cn1] |
| 132 | 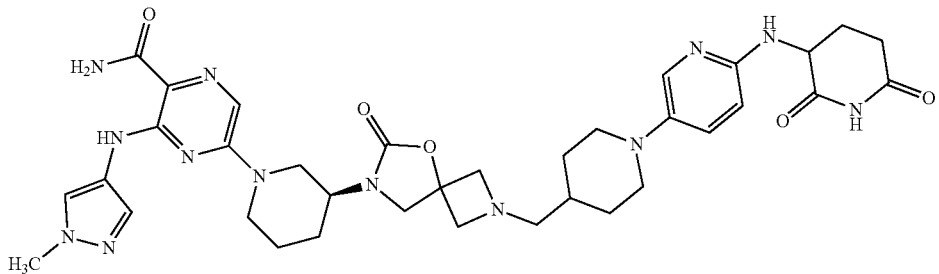 [SMILES: Cn1cc(Nc2nc(N3CCC[C@H](N4CC5(CN(CC6CCN(c7ccc(NC8CCC(=O)NC8=O)nc7)CC6)C5)OC4=O)C3)cnc2C(N)=O)cn1] |
| 133 | 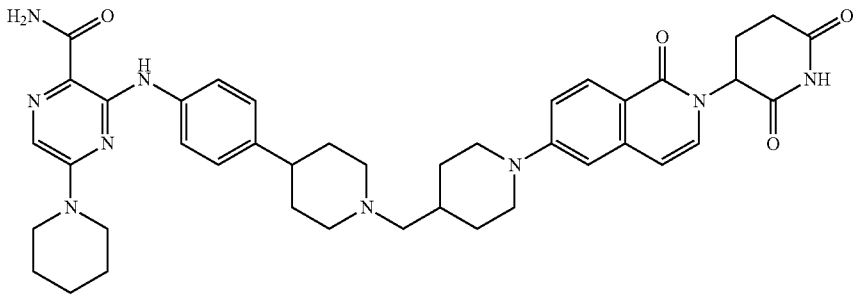 [SMILES: NC(=O)c1ncc(N2CCCCC2)nc1Nc1ccc(C2CCN(CC3CCN(c4ccc5c(=O)n(C6CCC(=O)NC6=O)ccc5c4)CC3)CC2)cc1] |
| 134 | 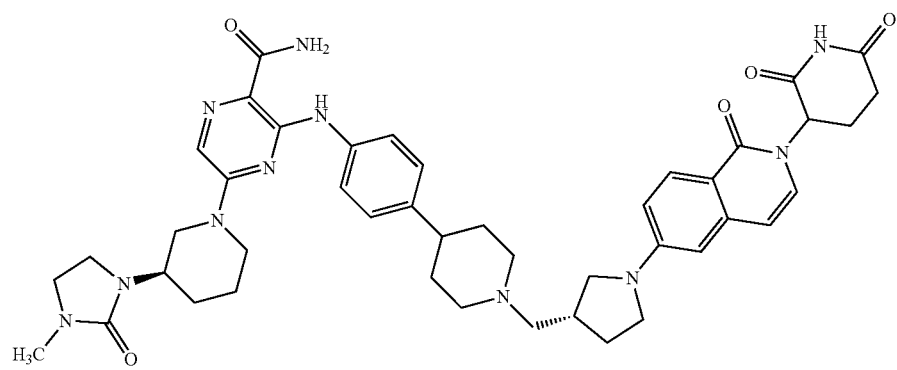 [SMILES: CN1CCN([C@@H]2CCCN(c3cnc(C(N)=O)c(Nc4ccc(C5CCN(C[C@H]6CCN(c7ccc8c(=O)n(C9CCC(=O)NC9=O)ccc8c7)C6)CC5)cc4)n3)C2)C1=O] |

TABLE 1-continued

Example compounds of the present invention.

| Compound Number | Structure |
|---|---|
| 135 | 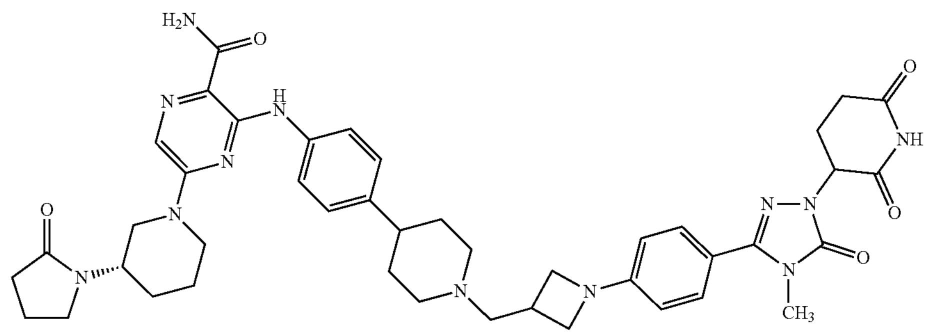 [SMILES: Cn1c(-c2ccc(N3CC(CN4CCC(c5ccc(Nc6nc(N7CCC[C@H](N8CCCC8=O)C7)cnc6C(N)=O)cc5)CC4)C3)cc2)nn(C2CCC(=O)NC2=O)c1=O] |
| 136 | 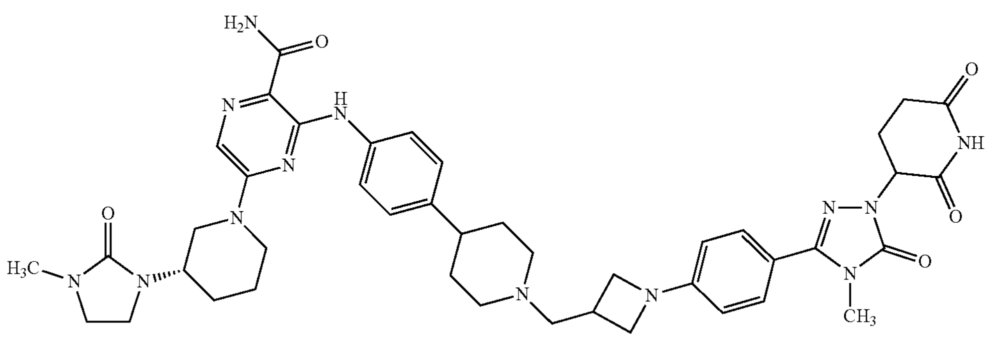 [SMILES: CN1CCN([C@H]2CCCN(c3cnc(C(N)=O)c(Nc4ccc(C5CCN(CC6CN(c7ccc(-c8nn(C9CCC(=O)NC9=O)c(=O)n8C)cc7)C6)CC5)cc4)n3)C2)C1=O] |
| 137 | 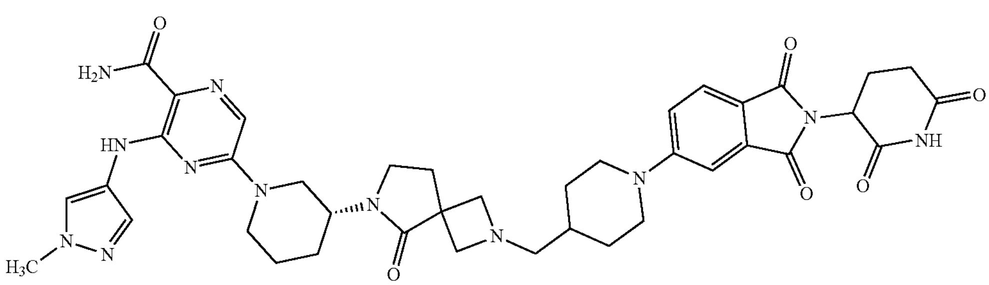 [SMILES: Cn1cc(Nc2nc(N3CCC[C@@H](N4CCC5(CN(CC6CCN(c7ccc8c(c7)C(=O)N(C7CCC(=O)NC7=O)C8=O)CC6)C5)C4=O)C3)cnc2C(N)=O)cn1] |
| 138 | 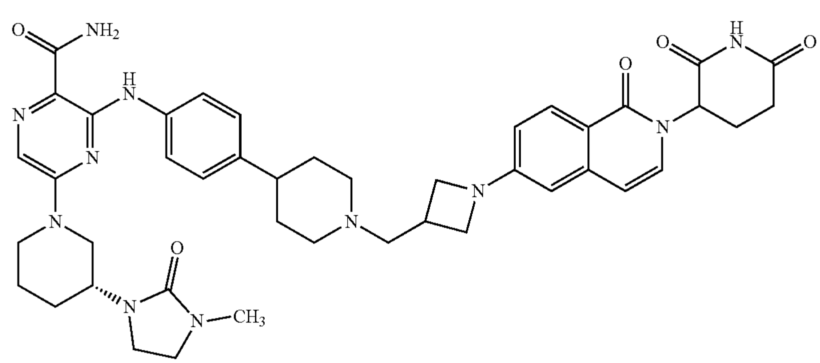 [SMILES: CN1CCN([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |

TABLE 1-continued
Example compounds of the present invention.
| Compound Number | Structure |
|---|---|
| 139 | 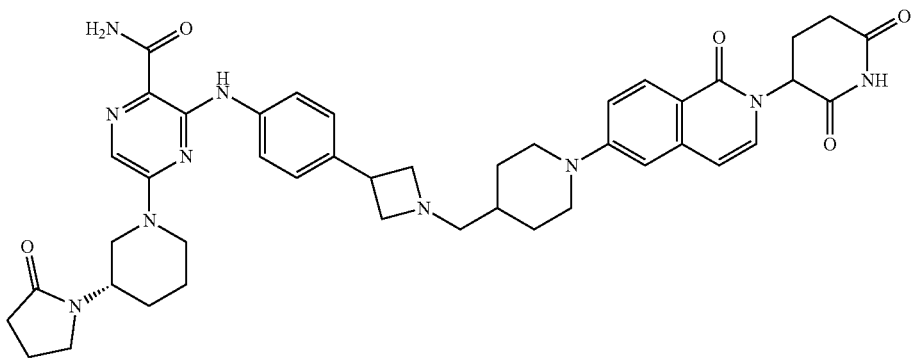 [SMILES: NC(=O)c1ncc(N2CCC[C@H](N3CCCC3=O)C2)nc1Nc1ccc(C2CN(CC3CCN(c4ccc5c(=O)n(C6CCC(=O)NC6=O)ccc5c4)CC3)C2)cc1] |
| 140 | 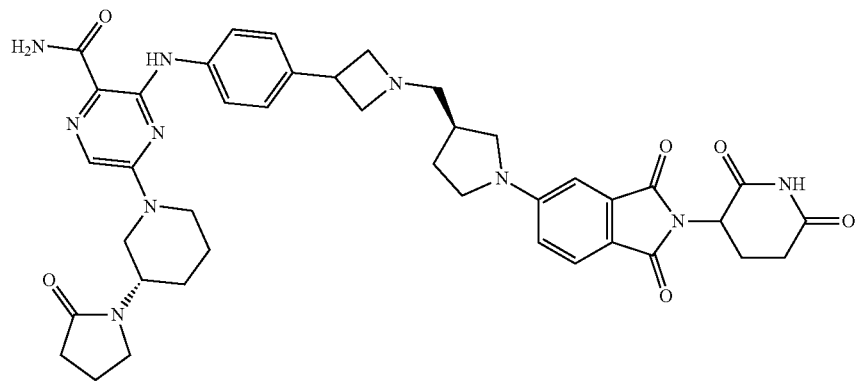 [SMILES: NC(=O)c1ncc(N2CCC[C@H](N3CCCC3=O)C2)nc1Nc1ccc(C2CN(C[C@@H]3CCN(c4ccc5c(c4)C(=O)N(C4CCC(=O)NC4=O)C5=O)C3)C2)cc1] |
| 141 | 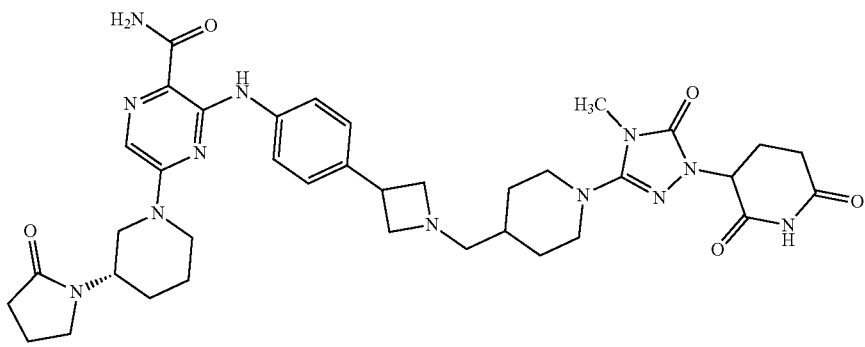 [SMILES: Cn1c(N2CCC(CN3CC(c4ccc(Nc5nc(N6CCC[C@H](N7CCCC7=O)C6)cnc5C(N)=O)cc4)C3)CC2)nn(C2CCC(=O)NC2=O)c1=O] |
| 142 | 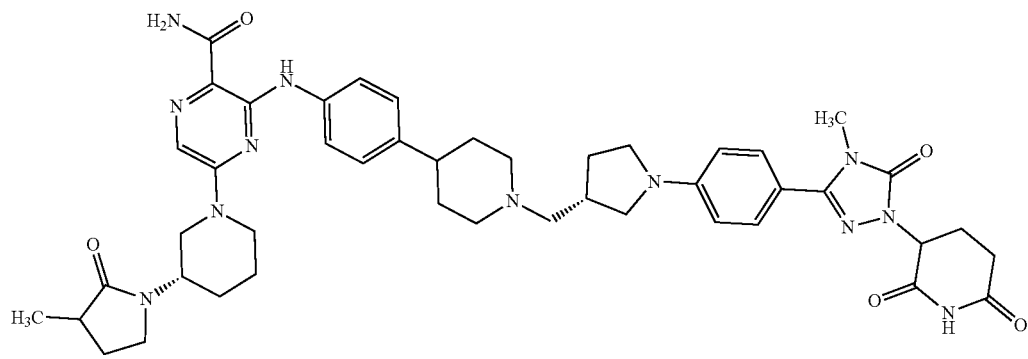 [SMILES: CC1CCN([C@H]2CCCN(c3cnc(C(N)=O)c(Nc4ccc(C5CCN(C[C@@H]6CCN(c7ccc(-c8nn(C9CCC(=O)NC9=O)c(=O)n8C)cc7)C6)CC5)cc4)n3)C2)C1=O] |

TABLE 1-continued
Example compounds of the present invention.
| Compound Number | Structure |
|---|---|
| 143 | 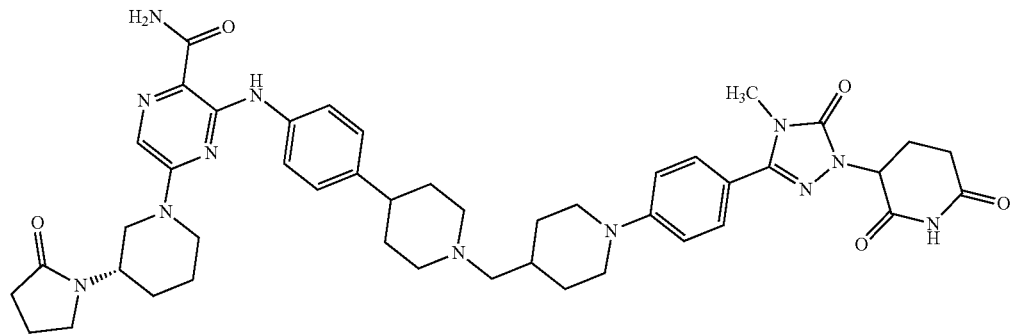 [SMILES: Cn1c(-c2ccc(N3CCC(CN4CCC(c5ccc(Nc6nc(N7CCC[C@H](N8CCCC8=O)C7)cnc6C(N)=O)cc5)CC4)CC3)cc2)nn(C2CCC(=O)NC2=O)c1=O] |
| 144 | 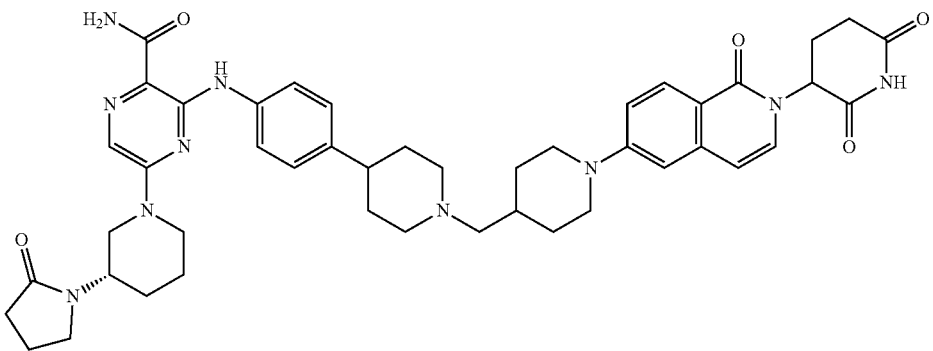 [SMILES: NC(=O)c1ncc(N2CCC[C@H](N3CCCC3=O)C2)nc1Nc1ccc(C2CCN(CC3CCN(c4ccc5c(=O)n(C6CCC(=O)NC6=O)ccc5c4)CC3)CC2)cc1] |
| 145 | 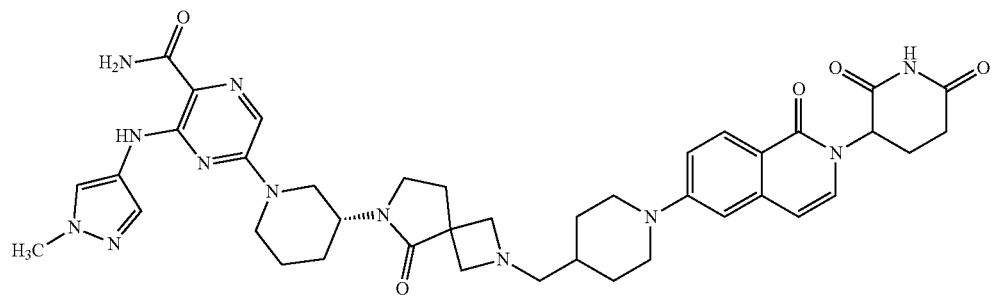 [SMILES: Cn1cc(Nc2nc(N3CCC[C@@H](N4CCC5(CN(CC6CCN(c7ccc8c(=O)n(C9CCC(=O)NC9=O)ccc8c7)CC6)C5)C4=O)C3)cnc2C(N)=O)cn1] |
| 146 | 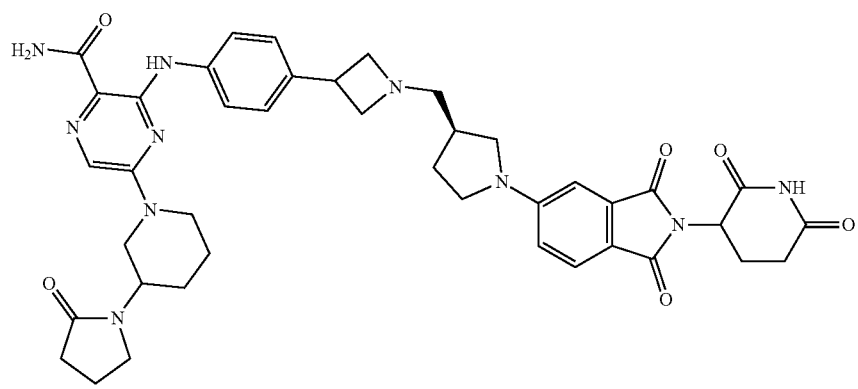 |

TABLE 1-continued

Example compounds of the present invention.

| Compound Number | Structure |
|---|---|
| 147 | 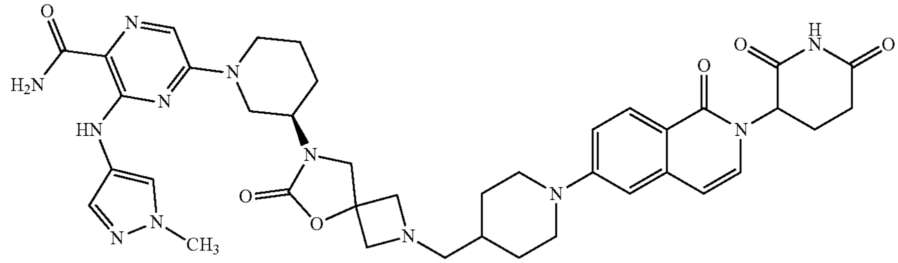 [SMILES: Cn1cc(Nc2nc(N3CCC[C@@H](N4CC5(CN(CC6CCN(c7ccc8c(=O)n(C9CCC(=O)NC9=O)ccc8c7)CC6)C5)OC4=O)C3)cnc2C(N)=O)cn1] |
| 148 | 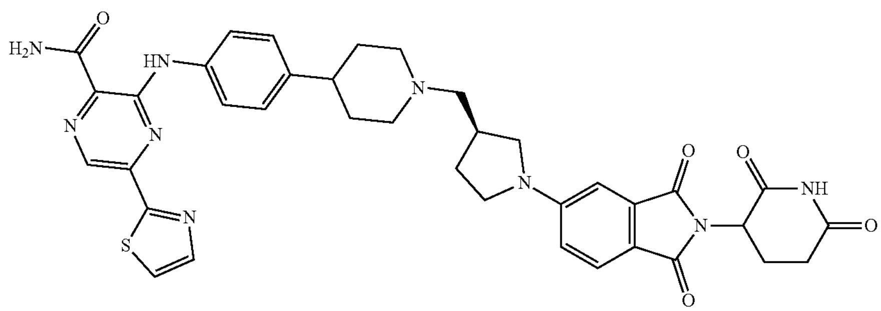 [SMILES: NC(=O)c1ncc(-c2nccs2)nc1Nc1ccc(C2CCN(C[C@@H]3CCN(c4ccc5c(c4)C(=O)N(C4CCC(=O)NC4=O)C5=O)C3)CC2)cc1] |
| 149 | 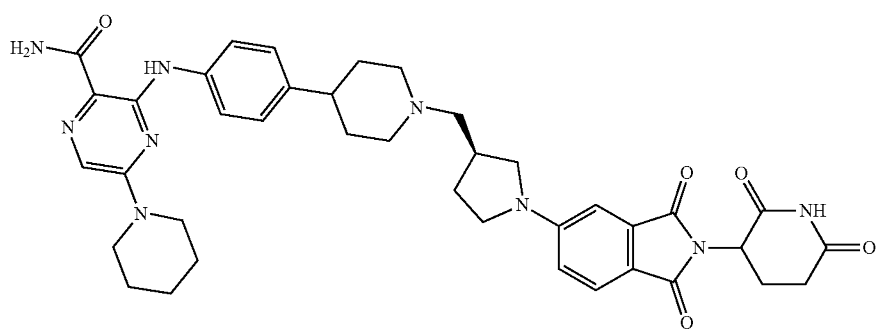 [SMILES: NC(=O)c1ncc(N2CCCCC2)nc1Nc1ccc(C2CCN(C[C@@H]3CCN(c4ccc5c(c4)C(=O)N(C4CCC(=O)NC4=O)C5=O)C3)CC2)cc1] |
| 150 | 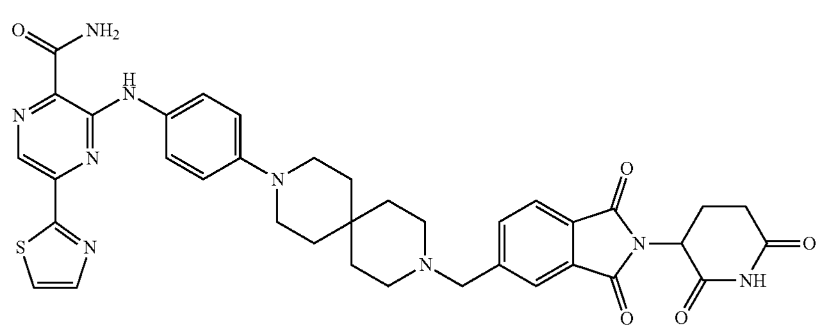 [SMILES: NC(=O)c1ncc(-c2nccs2)nc1Nc1ccc(N2CCC3(CCN(Cc4ccc5c(c4)C(=O)N(C4CCC(=O)NC4=O)C5=O)CC3)CC2)cc1] |

TABLE 1-continued
Example compounds of the present invention.
| Compound Number | Structure |
| --- | --- |
| 151 | 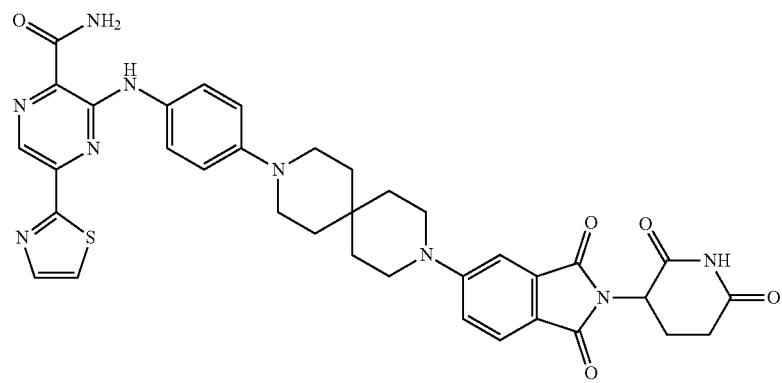 [SMILES: NC(=O)c1ncc(-c2nccs2)nc1Nc1ccc(N2CCC3(CC2)CCN(c2ccc4c(c2)C(=O)N(C2CCC(=O)NC2=O)C4=O)CC3)cc1] |
| 152 | 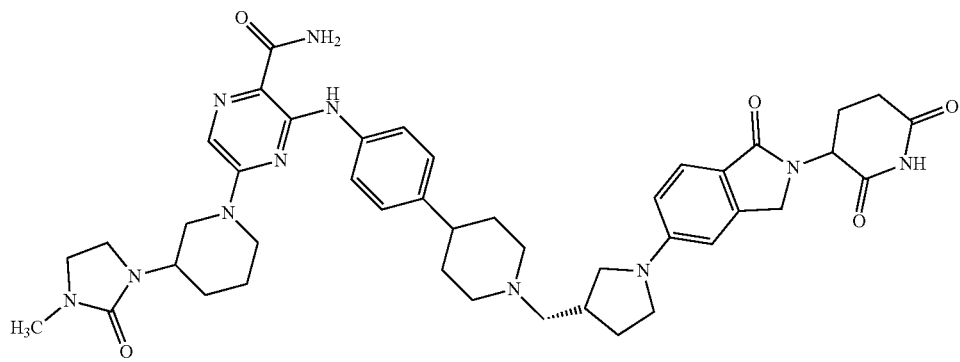 |
| 153 | 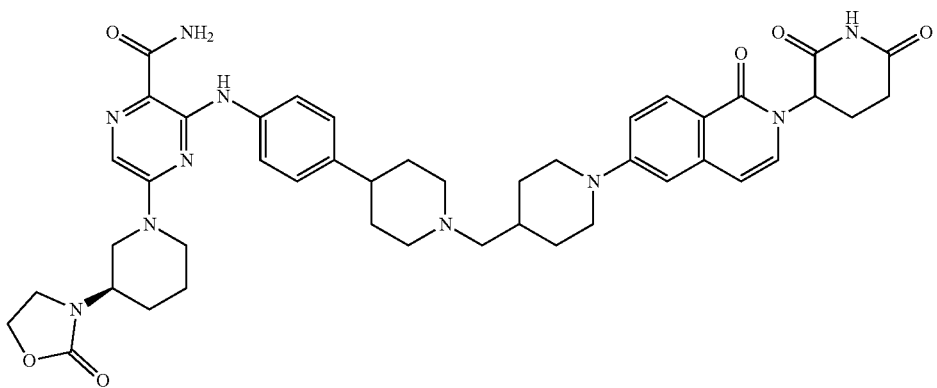 |

TABLE 1-continued

Example compounds of the present invention.

| Compound Number | Structure |
|---|---|
| 154 | 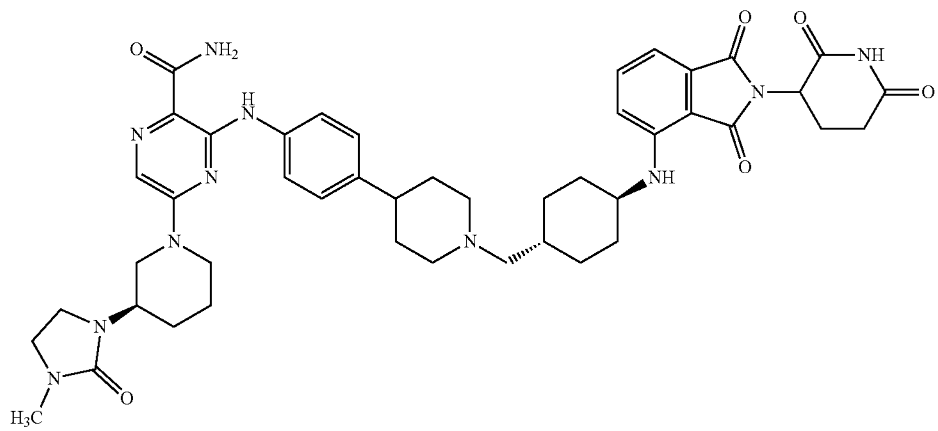 [SMILES: CN1CCN([C@@H]2CCCN(c3cnc(C(N)=O)c(Nc4ccc(C5CCN(C[C@H]6CC[C@H](Nc7cccc8c7C(=O)N(C7CCC(=O)NC7=O)C8=O)CC6)CC5)cc4)n3)C2)C1=O] |
| 155 | 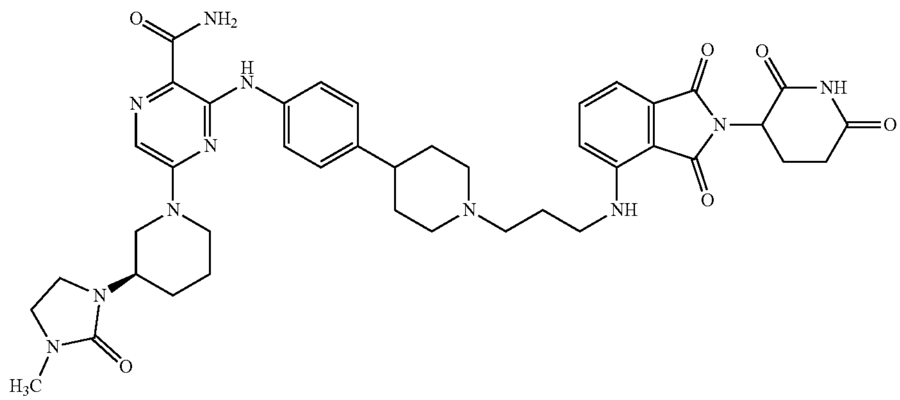 [SMILES: CN1CCN([C@@H]2CCCN(c3cnc(C(N)=O)c(Nc4ccc(C5CCN(CCCNc6cccc7c6C(=O)N(C6CCC(=O)NC6=O)C7=O)CC5)cc4)n3)C2)C1=O] |
| 156 | 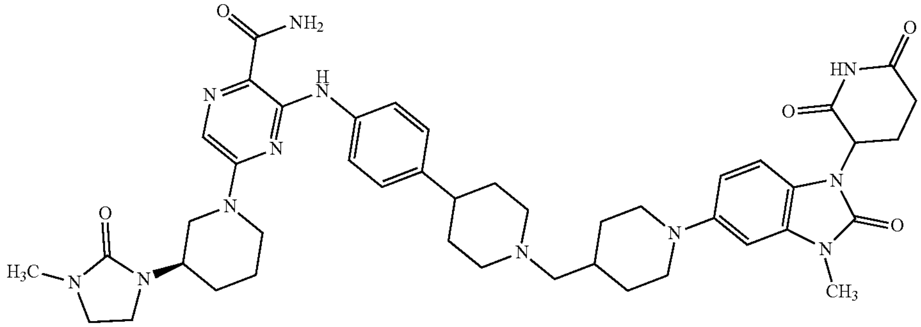 [SMILES: CN1CCN([C@@H]2CCCN(c3cnc(C(N)=O)c(Nc4ccc(C5CCN(CC6CCN(c7ccc8c(c7)n(C)c(=O)n8C7CCC(=O)NC7=O)CC6)CC5)cc4)n3)C2)C1=O] |
| 157 | 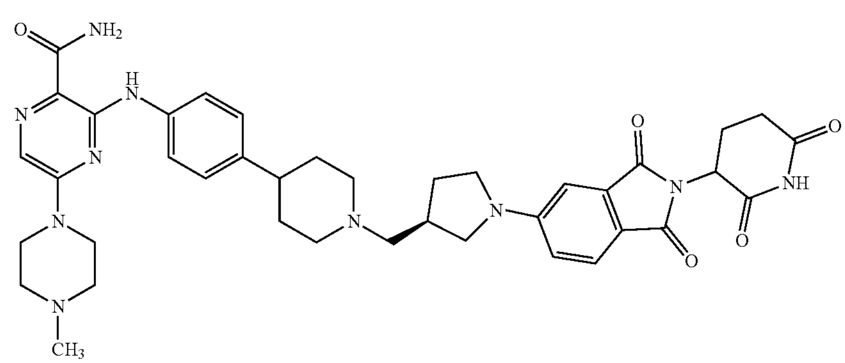 [SMILES: CN1CCN(c2cnc(C(N)=O)c(Nc3ccc(C4CCN(C[C@H]5CCN(c6ccc7c(c6)C(=O)N(C6CCC(=O)NC6=O)C7=O)C5)CC4)cc3)n2)CC1] |

TABLE 1-continued

Example compounds of the present invention.

| Compound Number | Structure |
|---|---|
| 158 | 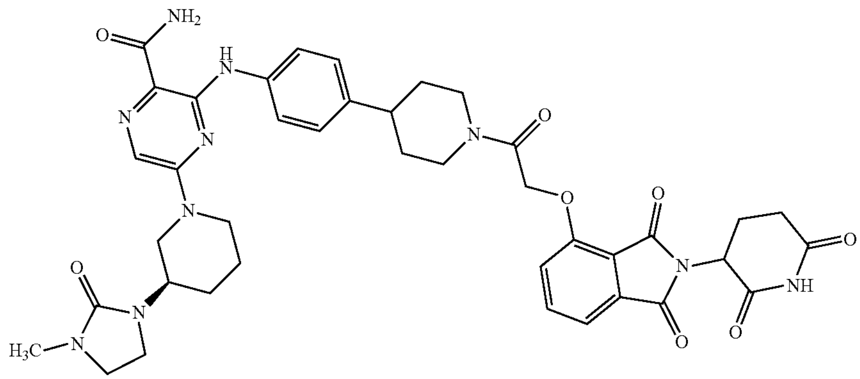 [SMILES: CN1CCN([C@@H]2CCCN(c3cnc(C(N)=O)c(Nc4ccc(C5CCN(C(=O)COc6cccc7c6C(=O)N(C6CCC(=O)NC6=O)C7=O)CC5)cc4)n3)C2)C1=O] |
| 159 | 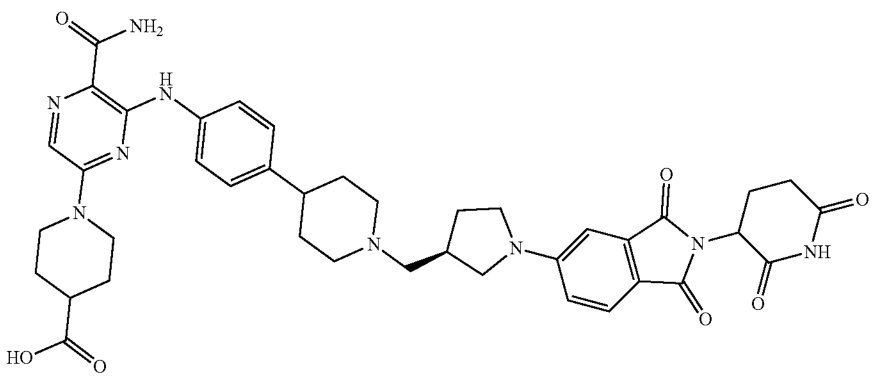 [SMILES: NC(=O)c1ncc(N2CCC(C(=O)O)CC2)nc1Nc1ccc(C2CCN(C[C@H]3CCN(c4ccc5c(c4)C(=O)N(C4CCC(=O)NC4=O)C5=O)C3)CC2)cc1] |
| 160 | 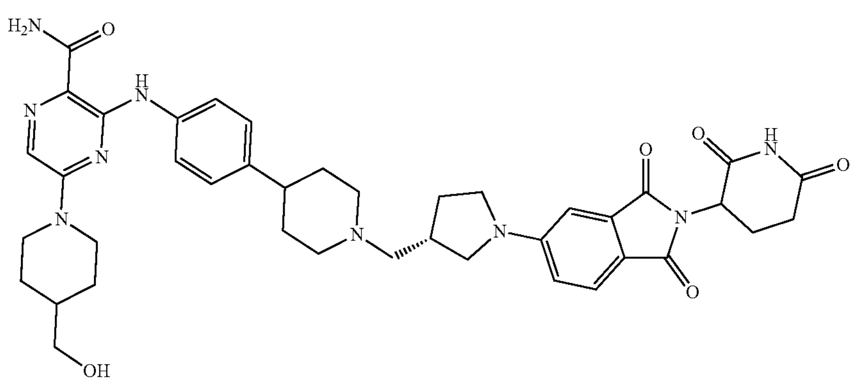 [SMILES: NC(=O)c1ncc(N2CCC(CO)CC2)nc1Nc1ccc(C2CCN(C[C@@H]3CCN(c4ccc5c(c4)C(=O)N(C4CCC(=O)NC4=O)C5=O)C3)CC2)cc1] |
| 161 | 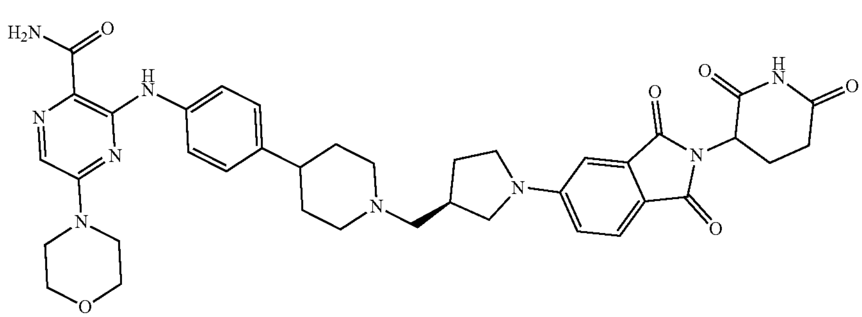 [SMILES: NC(=O)c1ncc(N2CCOCC2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued
Example compounds of the present invention.
| Compound Number | Structure |
| --- | --- |
| 162 | 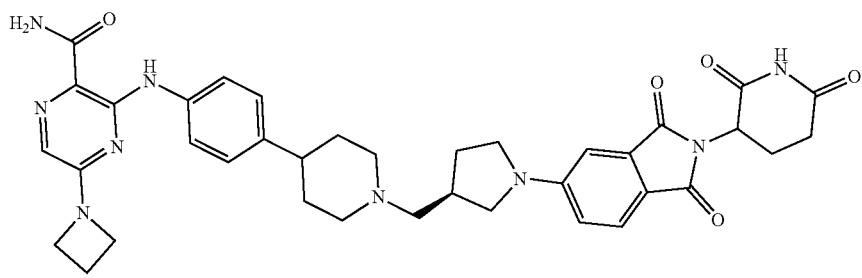 [SMILES: NC(=O)c1ncc(N2CCC2)nc1Nc1ccc(C2CCN(C[C@H]3CCN(c4ccc5c(c4)C(=O)N(C4CCC(=O)NC4=O)C5=O)C3)CC2)cc1] |
| 163 | 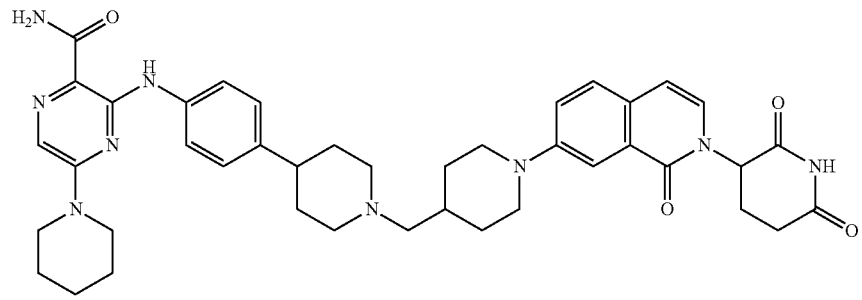 [SMILES: NC(=O)c1ncc(N2CCCCC2)nc1Nc1ccc(C2CCN(CC3CCN(c4ccc5ccn(C6CCC(=O)NC6=O)c(=O)c5c4)CC3)CC2)cc1] |
| 164 | 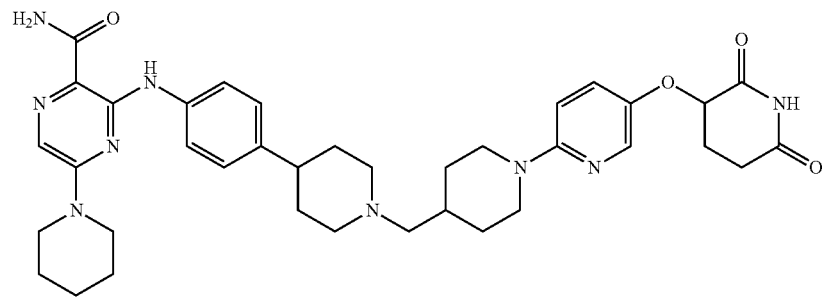 [SMILES: NC(=O)c1ncc(N2CCCCC2)nc1Nc1ccc(C2CCN(CC3CCN(c4ccc(OC5CCC(=O)NC5=O)cn4)CC3)CC2)cc1] |
| 165 | 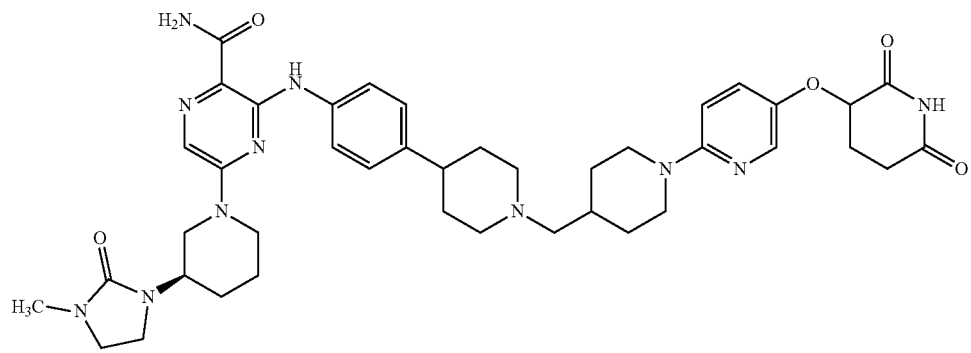 [SMILES: CN1CCN([C@@H]2CCCN(c3cnc(C(N)=O)c(Nc4ccc(C5CCN(CC6CCN(c7ccc(OC8CCC(=O)NC8=O)cn7)CC6)CC5)cc4)n3)C2)C1=O] |

TABLE 1-continued

Example compounds of the present invention.

| Compound Number | Structure |
|---|---|
| 166 | 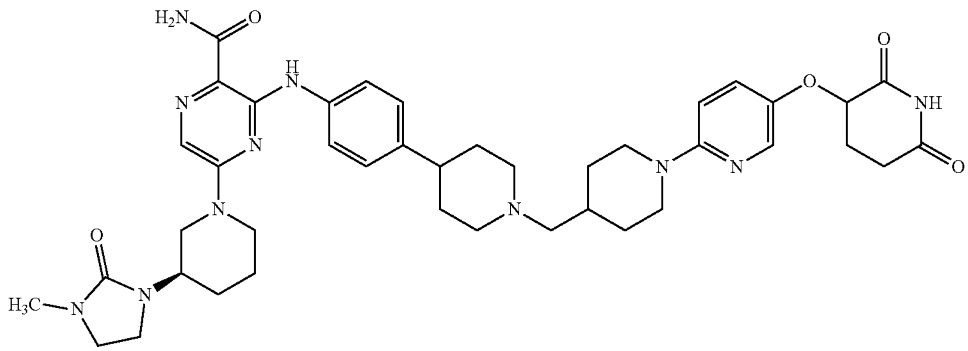 [SMILES: CN1CCN([C@@H]2CCCN(c3cnc(C(N)=O)c(Nc4ccc(C5CCN(CC6CCN(c7ccc(OC8CCC(=O)NC8=O)cn7)CC6)CC5)cc4)n3)C2)C1=O] |
| 167 | 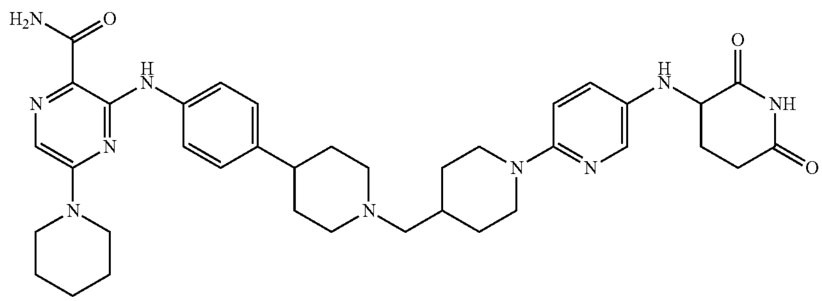 [SMILES: NC(=O)c1ncc(N2CCCCC2)nc1Nc1ccc(C2CCN(CC3CCN(c4ccc(NC5CCC(=O)NC5=O)cn4)CC3)CC2)cc1] |
| 168 | 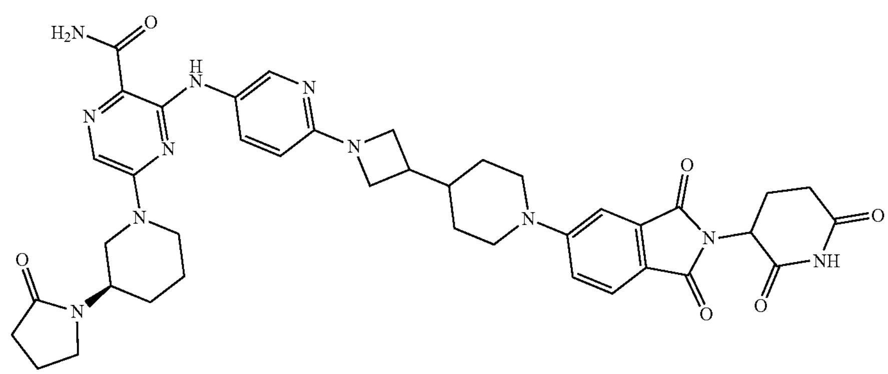 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)nc1] |
| 169 | 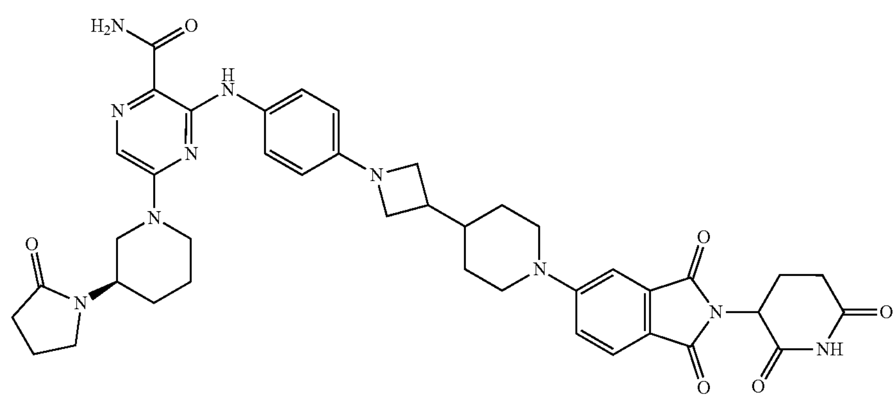 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)cc1] |

TABLE 1-continued

Example compounds of the present invention.

| Compound Number | Structure |
| --- | --- |
| 170 | 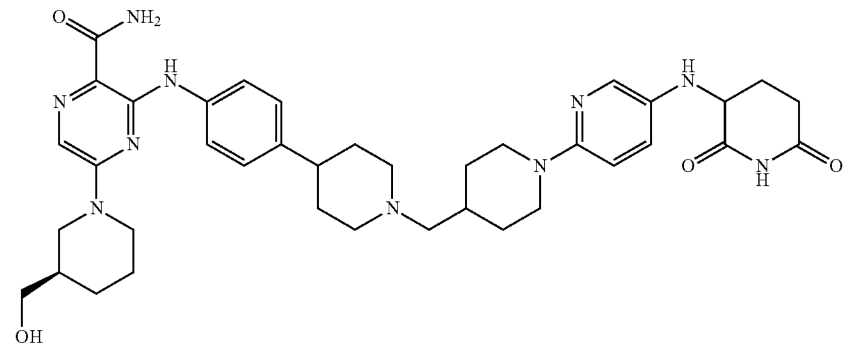 [SMILES: NC(=O)c1ncc(N2CCC[C@@H](CO)C2)nc1Nc1ccc(C2CCN(CC3CCN(c4ccc(NC5CCC(=O)NC5=O)cn4)CC3)CC2)cc1] |
| 171 | 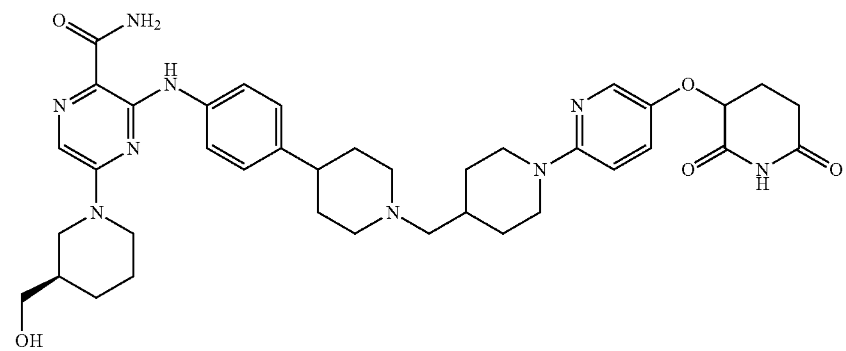 [SMILES: NC(=O)c1ncc(N2CCC[C@@H](CO)C2)nc1Nc1ccc(C2CCN(CC3CCN(c4ccc(OC5CCC(=O)NC5=O)cn4)CC3)CC2)cc1] |
| 172 | 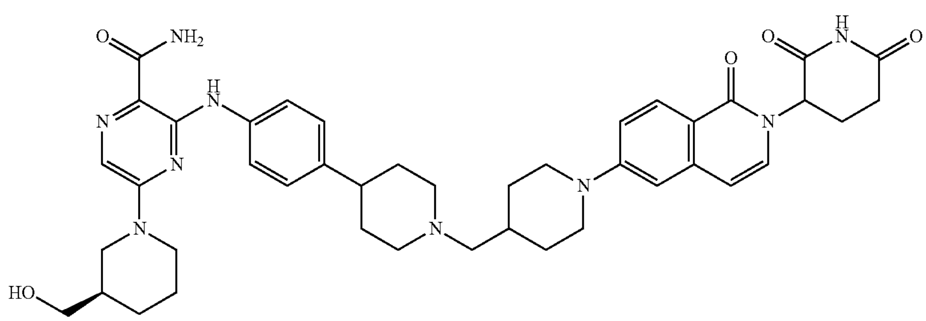 [SMILES: NC(=O)c1ncc(N2CCC[C@@H](CO)C2)nc1Nc1ccc(C2CCN(CC3CCN(c4ccc5c(=O)n(C6CCC(=O)NC6=O)ccc5c4)CC3)CC2)cc1] |
| 173 | 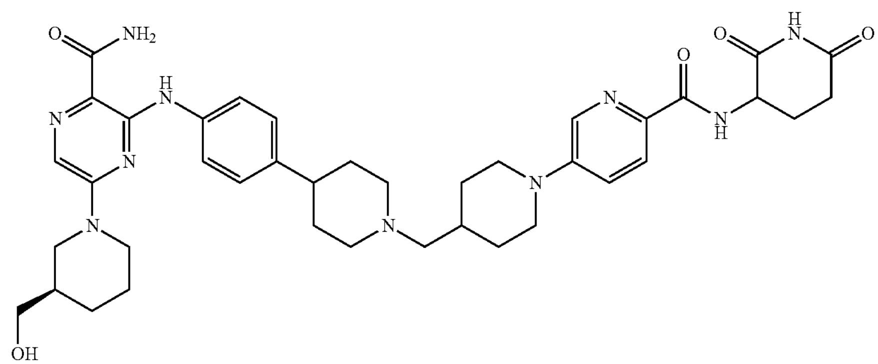 [SMILES: NC(=O)c1ncc(N2CCC[C@@H](CO)C2)nc1Nc1ccc(C2CCN(CC3CCN(c4ccc(C(=O)NC5CCC(=O)NC5=O)nc4)CC3)CC2)cc1] |

TABLE 1-continued
Example compounds of the present invention.
| Compound Number | Structure |
|---|---|
| 174 | 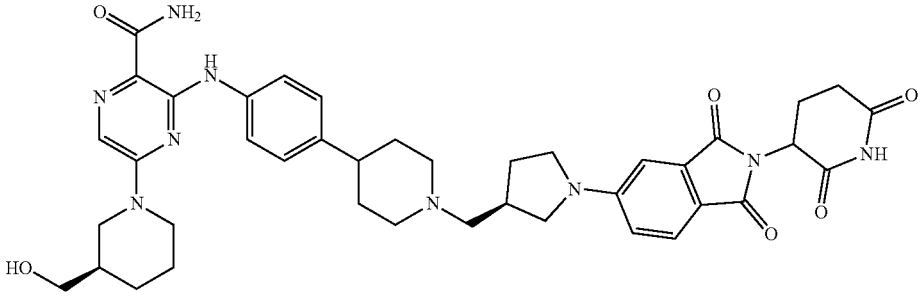 [SMILES: NC(=O)c1ncc(N2CCC[C@@H](CO)C2)nc1Nc1ccc(C2CCN(C[C@H]3CCN(c4ccc5c(c4)C(=O)N(C4CCC(=O)NC4=O)C5=O)C3)CC2)cc1] |
| 175 | 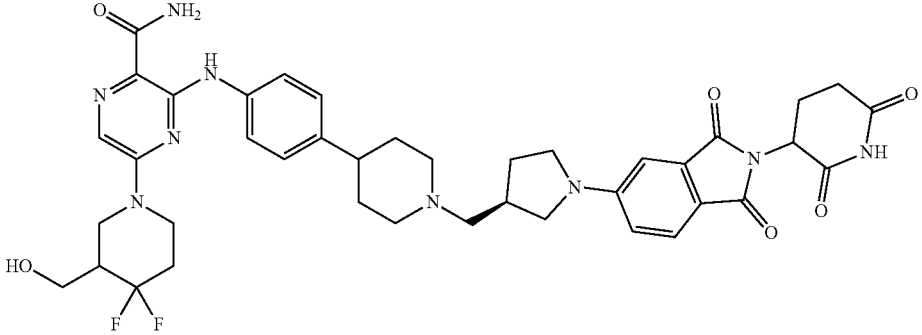 [SMILES: NC(=O)c1ncc(N2CCC(F)(F)C(CO)C2)nc1Nc1ccc(C2CCN(C[C@H]3CCN(c4ccc5c(c4)C(=O)N(C4CCC(=O)NC4=O)C5=O)C3)CC2)cc1] |
| 176 | 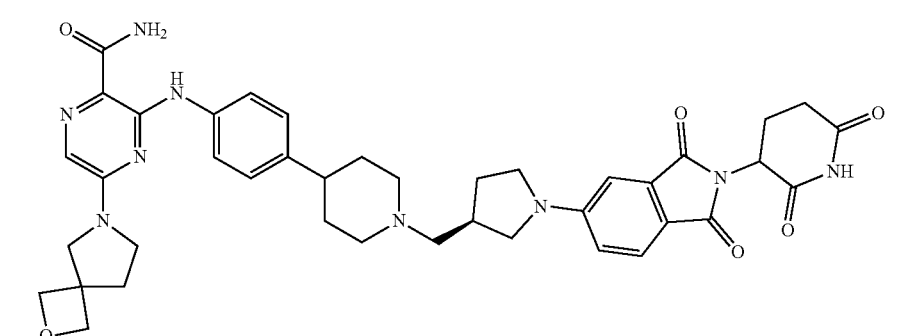 |
| 177 | 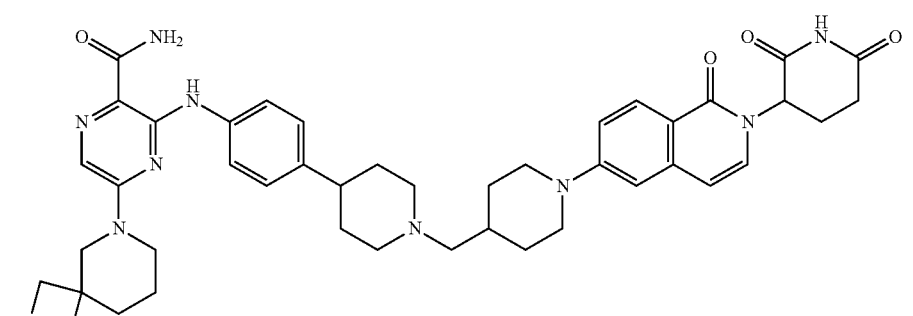 |

TABLE 1-continued

Example compounds of the present invention.

| Compound Number | Structure |
|---|---|
| 178 | 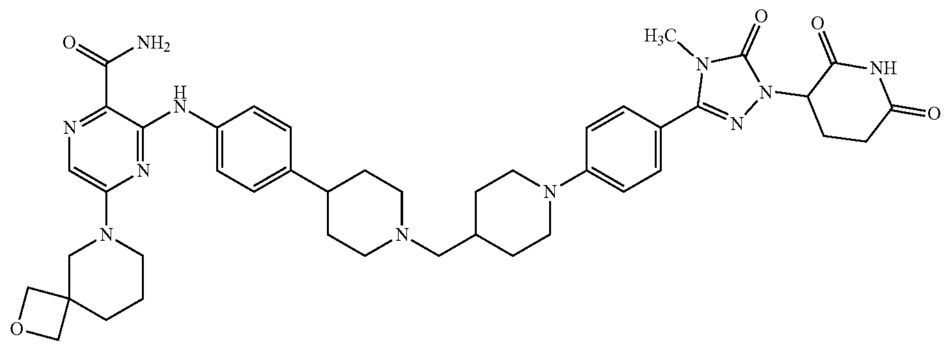 [SMILES: Cn1c(-c2ccc(N3CCC(CN4CCC(c5ccc(Nc6nc(N7CCCC8(COC8)C7)cnc6C(N)=O)cc5)CC4)CC3)cc2)nn(C2CCC(=O)NC2=O)c1=O] |
| 179 | 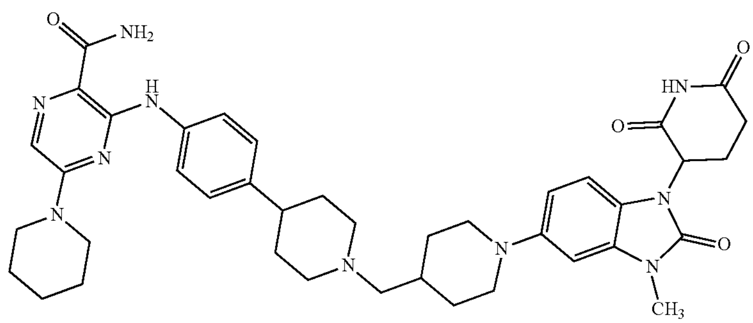 [SMILES: Cn1c(=O)n(C2CCC(=O)NC2=O)c2ccc(N3CCC(CN4CCC(c5ccc(Nc6nc(N7CCCCC7)cnc6C(N)=O)cc5)CC4)CC3)cc21] |
| 180 | 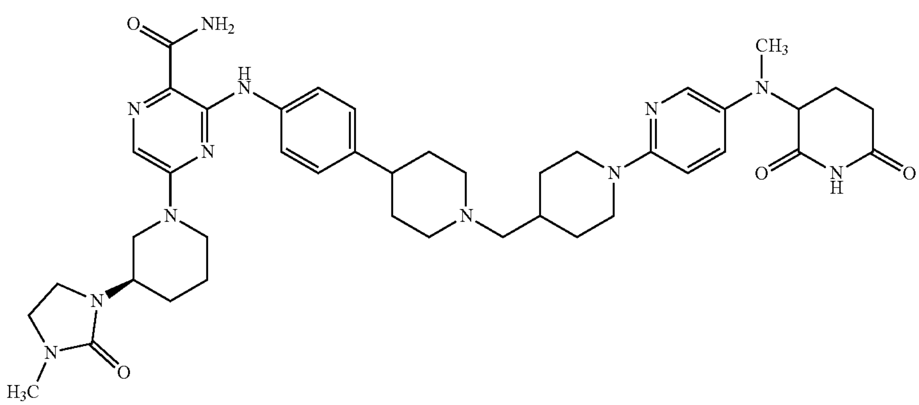 [SMILES: CN1CCN([C@@H]2CCCN(c3cnc(C(N)=O)c(Nc4ccc(C5CCN(CC6CCN(c7ccc(N(C)C8CCC(=O)NC8=O)cn7)CC6)CC5)cc4)n3)C2)C1=O] |
| 181 | 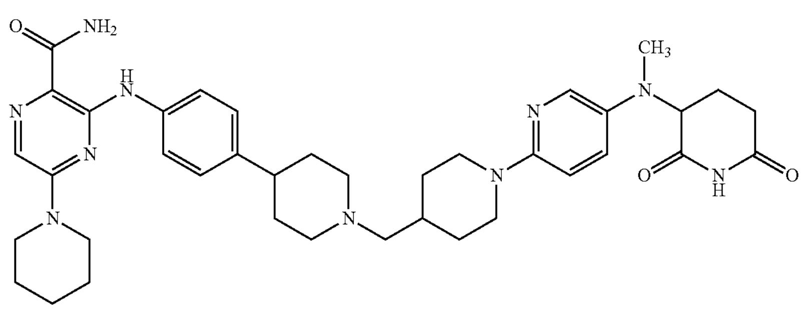 [SMILES: CN(c1ccc(N2CCC(CN3CCC(c4ccc(Nc5nc(N6CCCCC6)cnc5C(N)=O)cc4)CC3)CC2)nc1)C1CCC(=O)NC1=O] |

TABLE 1-continued

Example compounds of the present invention.

| Compound Number | Structure |
|---|---|
| 182 | 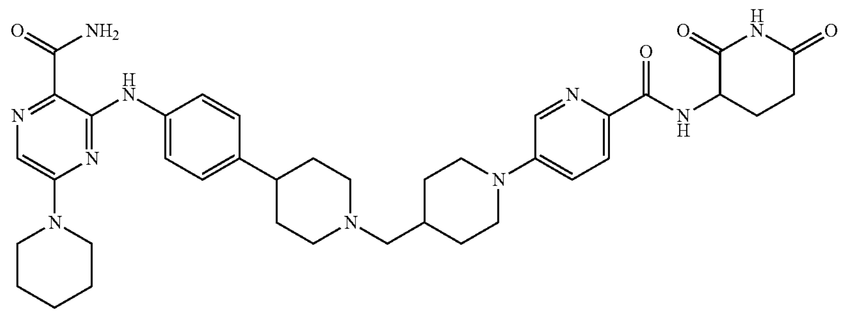 [SMILES: NC(=O)c1ncc(N2CCCCC2)nc1Nc1ccc(C2CCN(CC3CCN(c4ccc(C(=O)NC5CCC(=O)NC5=O)nc4)CC3)CC2)cc1] |
| 183 | 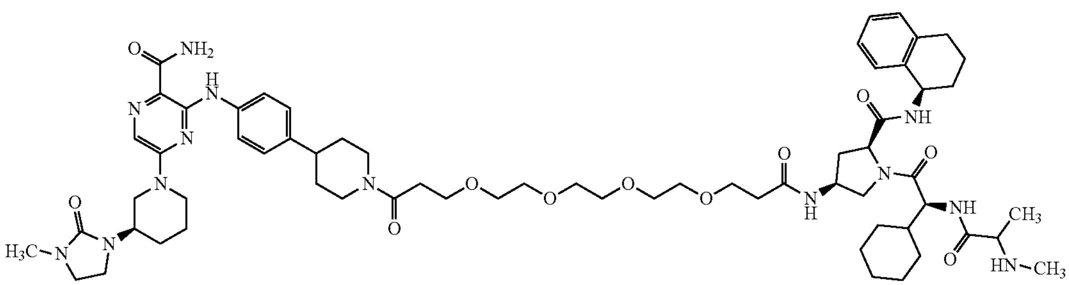 |
| 184 | 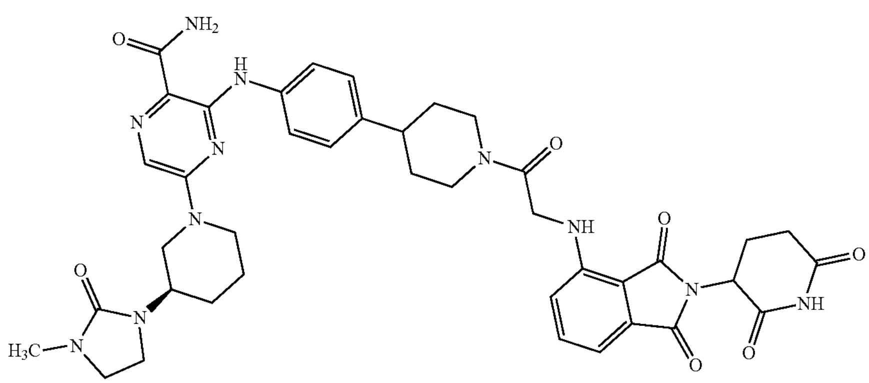 [SMILES: CN1CCN([C@@H]2CCCN(c3cnc(C(N)=O)c(Nc4ccc(C5CCN(C(=O)CNc6cccc7c6C(=O)N(C6CCC(=O)NC6=O)C7=O)CC5)cc4)n3)C2)C1=O] |
| 185 | 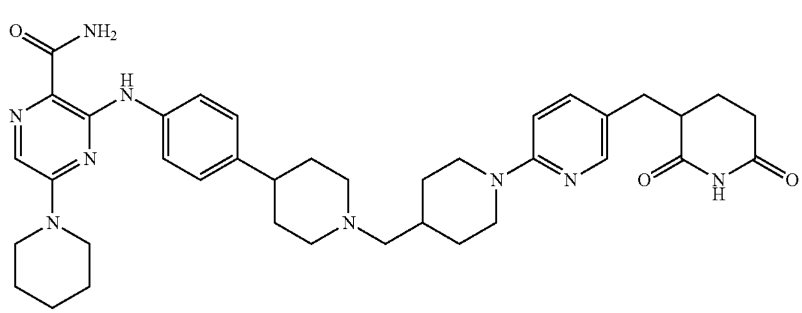 [SMILES: NC(=O)c1ncc(N2CCCCC2)nc1Nc1ccc(C2CCN(CC3CCN(c4ccc(CC5CCC(=O)NC5=O)cn4)CC3)CC2)cc1] |

TABLE 1-continued
Example compounds of the present invention.
| Compound Number | Structure |
|---|---|
| 186 | 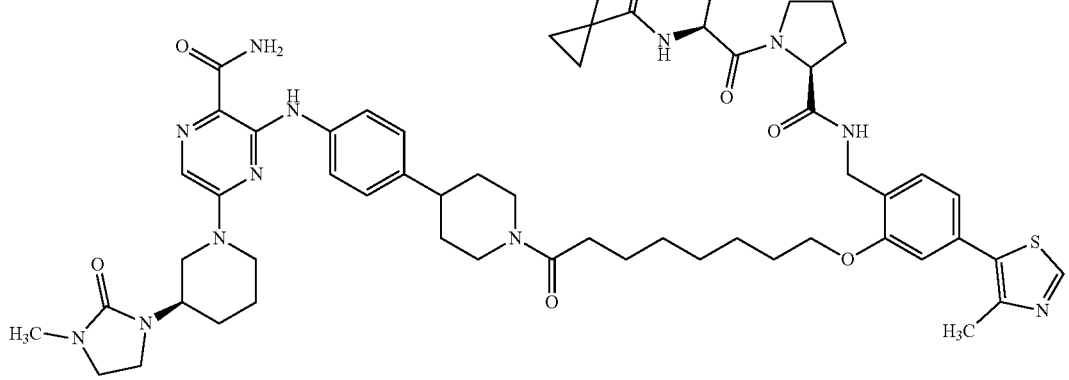 |
| 187 | 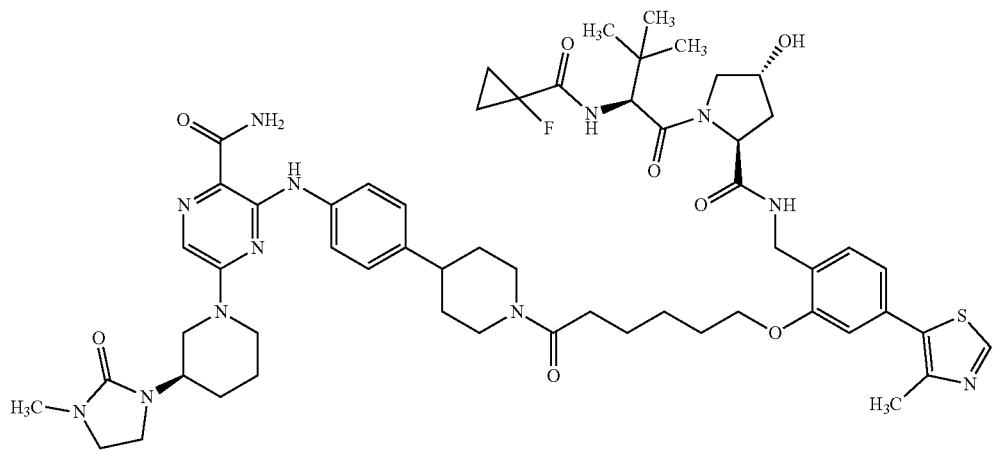 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCC(=O)N2CCC(c3ccc(Nc4nc(N5CCC[C@@H](N6CCN(C)C6=O)C5)cnc4C(N)=O)cc3)CC2)c1] |
| 188 | 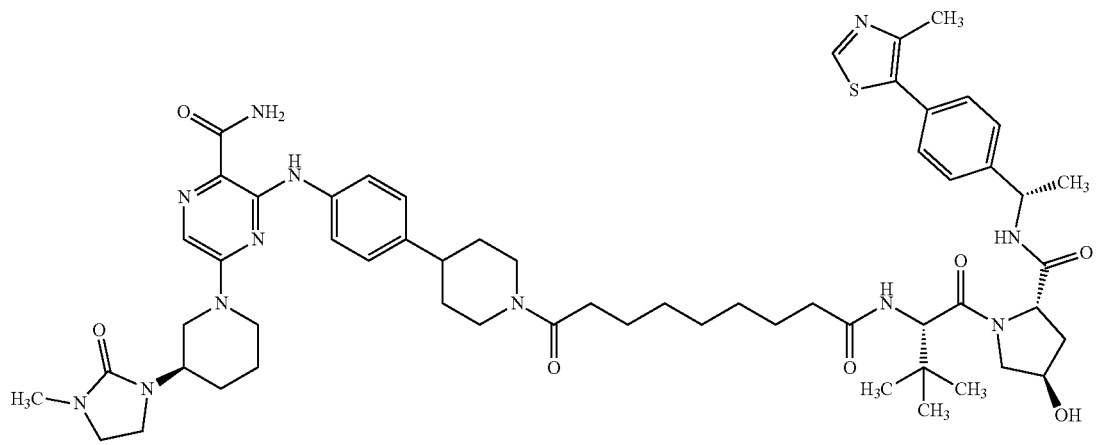 [SMILES: Cc1ncsc1-c1ccc([C@H](C)NC(=O)[C@@H]2C[C@@H](O)CN2C(=O)[C@@H](NC(=O)CCCCCCCC(=O)N2CCC(c3ccc(Nc4nc(N5CCC[C@@H](N6CCN(C)C6=O)C5)cnc4C(N)=O)cc3)CC2)C(C)(C)C)cc1] |

… TABLE 1-continued
Example compounds of the present invention.
| Compound Number | Structure |
|---|---|
| 189 | 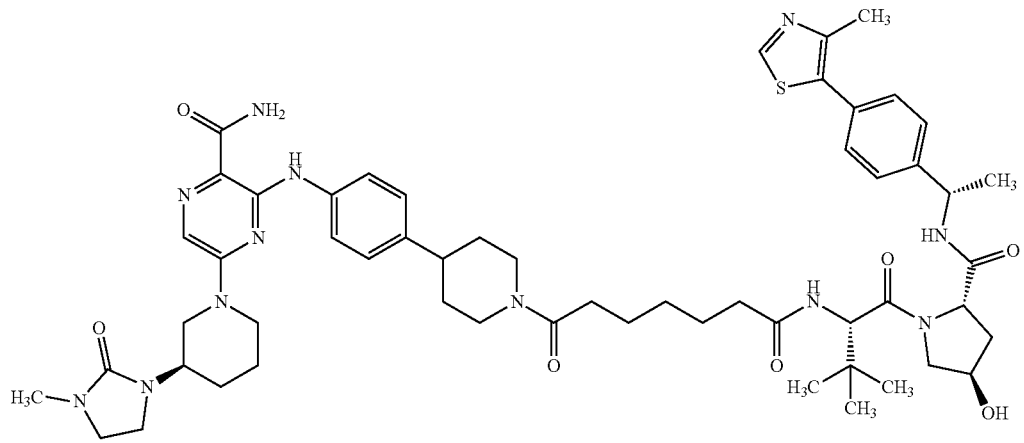 [SMILES: Cc1ncsc1-c1ccc([C@H](C)NC(=O)[C@@H]2C[C@@H](O)CN2C(=O)[C@@H](NC(=O)CCCCCC(=O)N2CCC(c3ccc(Nc4nc(N5CCC[C@@H](N6CCN(C)C6=O)C5)cnc4C(N)=O)cc3)CC2)C(C)(C)C)cc1] |
| 190 | 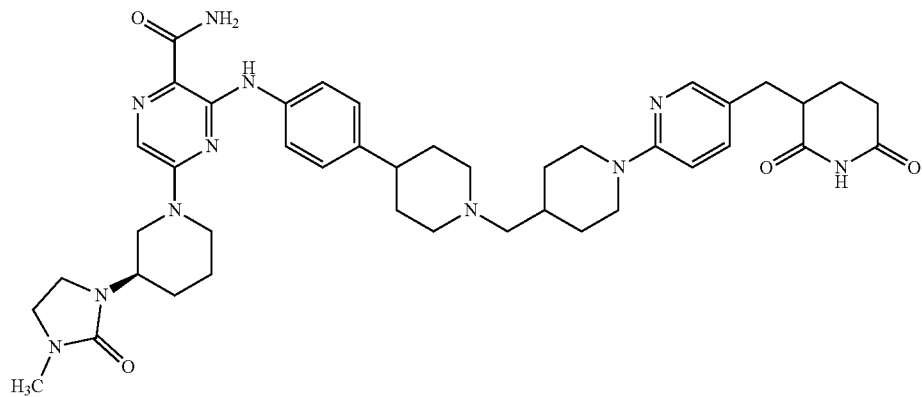 [SMILES: CN1CCN([C@@H]2CCCN(c3cnc(C(N)=O)c(Nc4ccc(C5CCN(CC6CCN(c7ccc(CC8CCC(=O)NC8=O)cn7)CC6)CC5)cc4)n3)C2)C1=O] |
| 191 | 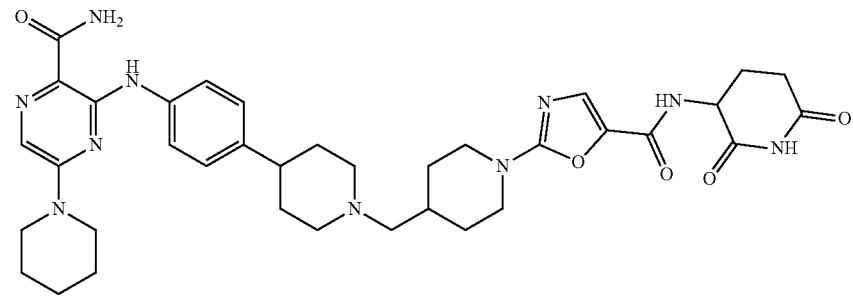 [SMILES: NC(=O)c1ncc(N2CCCCC2)nc1Nc1ccc(C2CCN(CC3CCN(c4ncc(C(=O)NC5CCC(=O)NC5=O)o4)CC3)CC2)cc1] |

TABLE 1-continued

Example compounds of the present invention.

| Compound Number | Structure |
|---|---|
| 192 | 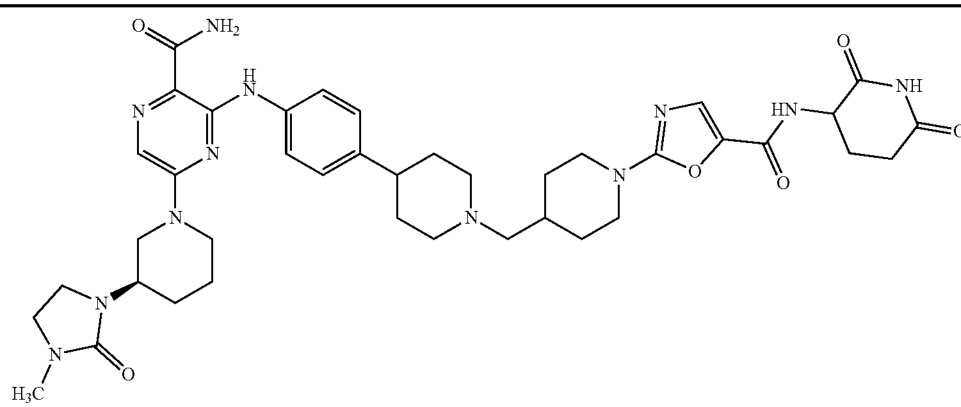 |
| 193 | 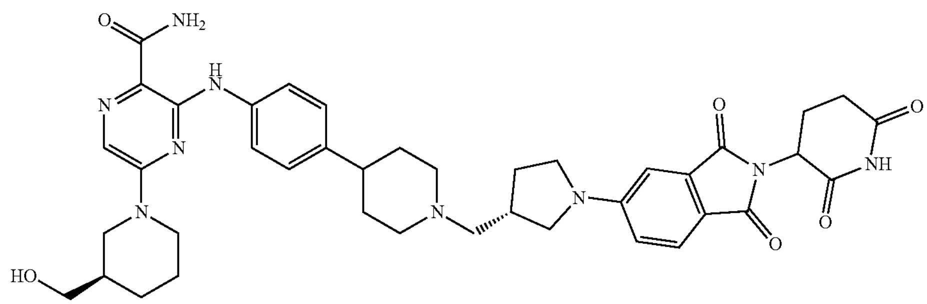 [SMILES: NC(=O)c1ncc(N2CCC[C@@H](CO)C2)nc1Nc1ccc(C2CCN(C[C@@H]3CCN(c4ccc5c(c4)C(=O)N(C4CCC(=O)NC4=O)C5=O)C3)CC2)cc1] |

III. USES, FORMULATIONS, AND ADMINISTRATION

A. Pharmaceutical Compositions

The compounds described herein can be formulated into pharmaceutical compositions that further comprise a pharmaceutically acceptable carrier, diluent, adjuvant or vehicle. In one embodiment, the present invention provides a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

According to another embodiment, the invention provides a composition comprising a compound of this invention or a pharmaceutically acceptable salt thereof and a pharmaceutically acceptable carrier, adjuvant, or vehicle. Pharmaceutical compositions of this invention comprise a therapeutically effective amount of a compound of Formula (A), (B), (C), (D), (E), (F), (G), (H), (J), (K), (M), (I) (II) (III) and/or (X) wherein a "therapeutically effective amount" is an amount that is (a) effective to measurably degrade BTK (or reduce the amount of BTK) in a biological sample or in a patient, or (b) effective in treating and/or ameliorating a disease or disorder that is mediated by BTK.

The term "patient," as used herein, means an animal, preferably a mammal, and most preferably a human.

It also will be appreciated that certain of the compounds of the present invention can exist in free form for treatment, or where appropriate, as a pharmaceutically acceptable derivative (e.g., a salt) thereof. According to the present invention, a pharmaceutically acceptable derivative includes, but is not limited to, pharmaceutically acceptable prodrugs, salts, esters, salts of such esters, or any other adduct or derivative that upon administration to a patient in need is capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

A pharmaceutically acceptable carrier may contain inert ingredients that do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, the use of such conventional carrier medium is contemplated to be within the scope of this invention. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful, uncomfortable, or risky. Side effects include, but are not limited to, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials that can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents. Preservatives and antioxidants can also be present in the composition, according to the judgment of the formulator.

As used herein, the term "measurably degrade," means a measurable reduction in (a) BTK activity, between a sample comprising a compound of this invention and a BTK and an equivalent sample comprising a BTK in the absence of said compound, or (b) the concentration of the BTK in a sample over time.

The compositions of the present invention may be administered orally, parenterally, by inhalation spray, topically, rectally, nasally, buccally, vaginally or via an implanted reservoir. As used herein, the term "parenteral" includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation also may be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions also may contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers that are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents also may be added.

Alternatively, the pharmaceutically acceptable compositions of this invention may be administered in the form of suppositories for rectal or vaginal administration. These can be prepared by mixing the agent with a suitable non-irritating excipient that is solid at room temperature but liquid at rectal temperature and therefore will melt in the rectum or vaginal cavity to release the drug. Such materials include cocoa butter, polyethylene glycol or a suppository wax that is solid at ambient temperature but liquid at body temperature and therefore melt in the rectum or vaginal cavity and release the active compound.

The pharmaceutically acceptable compositions of this invention also may be administered topically, especially when the target of treatment includes areas or organs readily accessible by topical application, including diseases of the eye, skin, or lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches also may be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention also may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions also can include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation also may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations also are prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also may comprise buffering agents.

Solid compositions of a similar type also may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Solid dosage forms optionally may contain opacifying agents. These solid dosage forms also can be of a composition such that they release the active ingredient(s) only, or preferentially, in a certain part of the intestinal tract, optionally, in a delayed manner. Examples of embedding compositions that can be used include polymeric substances and waxes. Solid compositions of a similar type also may be employed as fillers in soft and hard-filled gelatin capsules using such excipients as lactose or milk sugar as well as high molecular weight polethylene glycols and the like.

The active compounds also can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also may comprise, as is normal practice, additional substances other than inert diluents, e.g., tableting lubricants and other tableting aids such a magnesium stearate and microcrystalline cellulose. In the case of capsules, tablets and pills, the dosage forms also may comprise buffering agents. They may optionally contain opacifying agents and also can be of a composition such that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops also are contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers also can be used to increase the flux of the compound across the skin. The rate can be controlled by either providing a rate controlling membrane or by dispersing the compound in a polymer matrix or gel.

The compounds of the invention preferably are formulated in dosage unit form for ease of administration and uniformity of dosage. As used herein, the phrase "dosage unit form" refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration, and other factors. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, also may be present in the compositions of this invention. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this invention to treat proliferative diseases and cancer. Examples of known chemotherapeutic agents include, but are not limited to, PI3K inhibitors (e.g., idelalisib and copanlisib), BCL-2 inhibitors (e.g., venetoclax), BTK inhibitors (e.g., ibrutinib and acalabrutinib), etoposide, CD20 antibodies (e.g., rituximab, ocrelizumab, obinutuzumab, ofatumumab, ibritumomab tiuxetan, tositumomab, and ublituximab), aletuzumab, bendamustine, cladribine, doxorubicin, chlorambucil, prednisone, midostaurin, lenalidomide, pomalidomide, checkpoint inhibitors (e.g., ipilimumab, nivolumab, pembolizumab, atezolizumab, avelumab, durvalumab), engineered cell therapy (e.g., CAR-T therapy—Kymriah®, Yescarta®), Gleevec™, adriamycin, dexamethasone, vincristine, cyclophosphamide, fluorouracil, topotecan, taxol, interferons, and platinum derivatives.

And, in some instances, radiation therapy is administered during the treatment course wherein a compound of the present invention (or a pharmaceutically acceptable salt thereof) is administered to a patient in need thereof.

Other examples of agents with which the inhibitors of this invention also may be combined include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine;

agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

B. Uses of the Compounds and Compositions.

The bifunctional compounds of the present invention are useful for degrading BTK in biological samples or in patients via a ubiquitin proteolytic pathway. Thus, an embodiment of the present invention provides a method of treating a BTK-mediated disease or disorder. As used herein, the term "BTK-mediated disease or disorder" means any disease, disorder, or other deleterious condition in which a BTK is known to play a role. In some instances, a BTK-mediated disease or disorder is a proliferative disorder or an autoimmune disorder. Examples of proliferative disorders include cancer.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders (e.g., mantle cell lymphoma, Waldenström's macroglobulinemia, Marginal zone lymphoma, and Follicular lymphoma); Skin: malilymphgnant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma.

Examples of autoimmune disorders include uticaria, graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Baló disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, evans syndrome, fibromyalgia, fibrosing alveolitis, giant cell arteritis (temporal arteritis), giant cell myocarditis, glomerulonephritis, goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenic purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

IV. EXAMPLES

Additional embodiments are disclosed in further detail in the following examples, which are not in any way intended to limit the scope of the claims.

PRELIMINARY SYNTHESIS

Step 1: Synthesis of 2-(2,6-dioxopiperidin-3-yl)-5-fluoroisoindoline-1,3-dione

A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol) and NaOAc (4.2 g, 51.17 mmol) in HOAc (50 mL) was stirred at 120° C. for 5 h before concentrating under vacuum. The residue was washed with water and the solid was collected by filtration. The crude product was washed with water twice and ethyl acetate twice and dried to afford 2-(2,6-dioxopiperidin-3-yl)-5-fluoroisoindoline-1,3-dione (7.7 g, 92%) as a light brown solid. $^1$H NMR (300 MHz, DMSO-$d_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H). F NMR (300 MHz, DMSO-$d_6$) δ −102.078.

Step 2: Amine Displacement of Aryl Fluoride

To a solution of 2-(2,6-dioxopiperidin-3-yl)-5-fluoro-2,3-dihydro-1H-isoindole-1,3-dione (1.0 g, 3.62 mmol) in N-Methyl pyrrolidone (10 mL) were added the amine (3.60 mmol) and DIEA (1.4 g, 10.83 mmol). The resulting solution was stirred at 80° C. for 16 h. The reaction mixture was cooled down to room temperature and purified by reverse phase flash chromatography to afford the corresponding final product.

Step 3: Alcohol Oxidation to Aldehyde

To a mixture of alcohol (1.06 mmol) in CH$_2$Cl$_2$ (10 mL) was added Dess-Martin periodinane (2.12 mmol). The mixture was allowed to stir at room temperature for 1 h. The mixture was purified by column chromatography to afford the desired aldehyde.

Example 1: Synthesis of 5-[(3R)-3-(3-methyl-2-oxoimidazolidin-1-yl)piperidin-1-yl]-3-{[4-(piperazin-1-yl)phenyl]amino}pyrazine-2-carboxamide Step 1: tert-butyl (3R)-3-{[(2-chloroethyl)carbamoyl]amino}piperidine-1-carboxylate

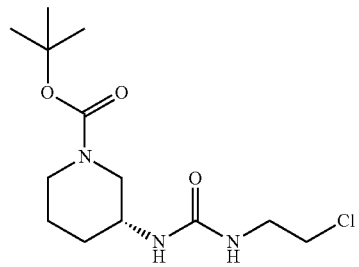 [SMILES: CC(C)(C)OC(=O)N1CCC[C@@H](NC(=O)NCCCl)C1]

To a mixture of tert-butyl (3R)-3-aminopiperidine-1-carboxylate (25.0 g, 125 mmol) and triethylamine (34.8 mL, 25.3 g, 250 mmol) in DCM (250 mL) was added 1-chloro-2-isocyanatoethane (12.8 mL, 15.8 g, 150 mmol) over 25 minutes. A mild exotherm was observed. After 4 hours, 100 mL water was added. The layers were separated. The organic layer was dried over Na$_2$SO$_4$ and concentrated. The mixture was dissolved in ethyl acetate and filtered through 1000 cc of silica gel in a 2000 mL buchner funnel eluted with ethyl acetate. The resulting solution was concentrated in vacuo to provide tert-butyl (3R)-3-{[(2-chloroethyl)carbamoyl]amino}piperidine-1-carboxylate (40.6 g, quant) which was used without further purification. LCMS: C$_{13}$H$_{24}$ClN$_3$O$_3$ requires 305, found: m/z=306 [M+H]$^+$.

Step 2: tert-butyl (3R)-3-(2-oxoimidazolidin-1-yl)piperidine-1-carboxylate

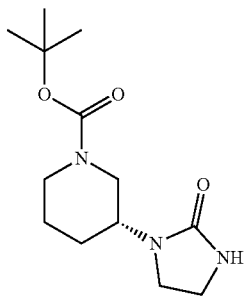 [SMILES: CC(C)(C)OC(=O)N1CCC[C@@H](N2CCNC2=O)C1]

To an ice cooled mixture of tert-butyl (3R)-3-{[(2-chloroethyl)carbamoyl]amino}piperidine-1-carboxylate (40.3 g, 132 mmol) in THF (400 mL) was added 60% sodium hydride (10.6 g, 264 mmol) in portions. The cooling bath was allowed to melt and the reaction was stirred at room temp overnight. Another portion of 60% sodium hydride (5.65 g, 141 mmol) was added, causing gas evolution. After ten minutes, a mild exotherm was observed. After 2 hours, the reaction was quenched by the addition of 75 mL water. The layers were separated. The aqueous layer was extracted with two 50 mL portions of DCM. The combined organic layers were washed with brine, dried over anhydrous Na$_2$SO$_4$, and concentrated in vacuo. The resulting material was partitioned between acetonitrile and hexanes. The acetonitrile layer was concentrated in vacuo to provide tert-butyl (3R)-3-(2-oxoimidazolidin-1-yl)piperidine-1-carboxylate (33.9 g, 95.4%). LCMS: C$_{13}$H$_{23}$N$_3$O$_3$ requires 269, found: m/z=270 [M+H]$^+$.

Step 3: tert-butyl (3R)-3-(2-oxoimidazolidin-1-yl)piperidine-1-carboxylate

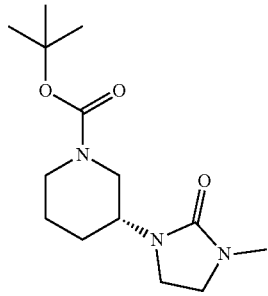 [SMILES: CN1CCN([C@@H]2CCCN(C(=O)OC(C)(C)C)C2)C1=O]

To an ice cooled mixture of tert-butyl (3R)-3-(2-oxoimidazolidin-1-yl)piperidine-1-carboxylate (33.8 g, 126 mmol) in THF (300 mL) was added 60% sodium hydride (10.1 g, 251 mmol) in portions. After 5 minutes, the cooling bath was removed and gas evolution was observed for 1 hour. The mixture was cooled in an ice bath. Methyl iodide (11.7 mL, 26.7 g, 188 mmol) was added over 5 minutes. The cooling bath was allowed to expire. After stirring for 16 hours at room temperature, the reaction was quenched with 75 mL water. The layers were separated. The organic layer was washed with brine. The combined aqueous layers were extracted twice with DCM. The combined organic layers were dried over anhydrous Na$_2$SO$_4$ and concentrated. The resulting material was partitioned between acetonitrile and hexane. The acetonitrile layer was filtered and concentrated in vacuo to provide tert-butyl (3R)-3-(3-methyl-2-oxoimidazolidin-1-yl)piperidine-1-carboxylate (38.4 g, quant) which was used crude without further purification. LCMS: C$_{14}$H$_{25}$N$_3$O$_3$ requires 283, found: m/z=306 [M+Na]$^+$.

Step 4: 1-methyl-3-[(3R)-piperidin-3-yl]imidazolidin-2-one hydrochloride

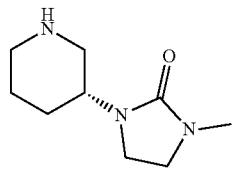

Tert-butyl (3R)-3-(3-methyl-2-oxoimidazolidin-1-yl)piperidine-1-carboxylate (35.1 g, 124 mmol) was stirred in hydrogen chloride 4M solution in dioxane (310 mL, 1.24 mol) for 2 hours. The mixture was concentrated in vacuo to provide 1-methyl-3-[(3R)-piperidin-3-yl]imidazolidin-2-one hydrochloride (35.0 g, quant) which was used crude without further purification. LCMS: C$_9$H$_{17}$N$_3$O requires 183, found: m/z=184 [M+H]$^+$.

Step 5: 3-chloro-5-[(3R)-3-(3-methyl-2-oxoimidazolidin-1-yl)piperidin-1-yl]pyrazine-2-carbonitrile

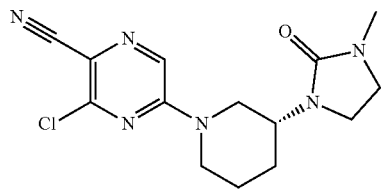 [SMILES: CN1CCN([C@@H]2CCCN(c3cnc(C#N)c(Cl)n3)C2)C1=O]

3,5-dichloropyrazine-2-carbonitrile (21.6 g, 124 mmol) was added to an ice cooled mixture of 1-methyl-3-[(3R)-piperidin-3-yl]imidazolidin-2-one hydrochloride (27.2 g, 1 24 mmol) and N,N-diisopropylethylamine (86.3 mL, 495 mmol) in DMF (300 mL). After 15 minutes, the cooling bath was removed. After stirring for 16 hours, the mixture was diluted with 800 mL water. The mixture was extracted with ethyl acetate. The organic layer was washed twice with water and washed once with brine. The organic layer was dried over anhydrous Na$_2$SO$_4$ and concentrated in vacuo. The crude residue was purified by flash chromatography on a 330 g silica gel column eluted with 0 to 3% MeOH/DCM gradient to provide 3-chloro-5-[(3R)-3-(3-methyl-2-oxoimidazolidin-1-yl)piperidin-1-yl]pyrazine-2-carbonitrile (22.1 g, 55.6%). LCMS: C14H17ClN6O requires 320, found: m/z=320 [M+H]$^+$.

325

Step 6: tert-butyl 4-[4-({3-cyano-6-[(3R)-3-(3-methyl-2-oxoimidazolidin-1-yl)piperidin-1-yl]pyrazin-2-yl}amino)phenyl]piperazine-1-carboxylate

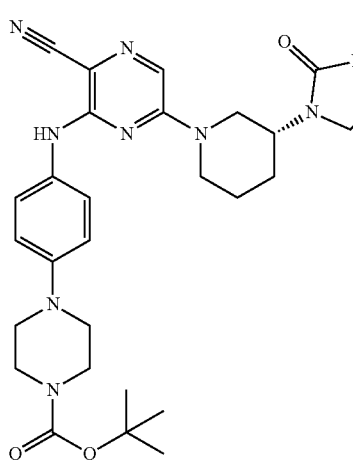

3-chloro-5-[(3R)-3-(3-methyl-2-oxoimidazolidin-1-yl)piperidin-1-yl]pyrazine-2-carbonitrile (9.57 g, 29.8 mmol), tert-butyl 4-(4-aminophenyl)piperazine-1-carboxylate (8.27 g, 29.8 mmol), and cesium carbonate (29.2 g, 89.5 mmol) were deposited in a 200 mL round bottom flask with dioxane (75 mL). A vacuum was pulled on the flask until the mixture bubbled and the headspace was backfilled with argon for 5 cycles. BINAP (1.86 g, 2.98 mmol) and palladium (II) acetate (670 mg, 2.98 mmol) were added. A vacuum was pulled on the flask and the headspace was backfilled with argon for 5 cycles. The mixture was heated at 100° C. for 3 hours. The mixture was filtered. The solid was washed with DCM. The resulting solution was concentrated in vacuo. The crude residue was purified by flash chromatography on a 330 g silica gel column eluted with 0 to 5% MeOH/DCM gradient to provide tert-butyl 4-[4-({3-cyano-6-[(3R)-3-(3-methyl-2-oxoimidazolidin-1-yl)piperidin-1-yl]pyrazin-2-yl}amino)phenyl]piperazine-1-carboxylate (8.81 g, 52.6%). LCMS: $C_{29}H_{39}N_9O_3$ requires 561, found: m/z=584 [M+Na]$^+$.

326

Step 7: tert-butyl 4-[4-({3-carbamoyl-6-[(3R)-3-(3-methyl-2-oxoimidazolidin-1-yl)piperidin-1-yl]pyrazin-2-yl}amino)phenyl]piperazine-1-carboxylate

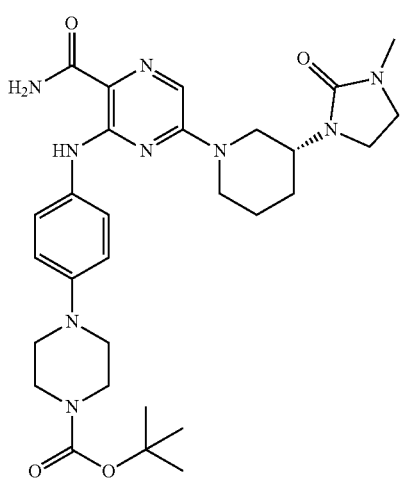 [SMILES: CN1CCN([C@@H]2CCCN(c3cnc(C(N)=O)c(Nc4ccc(N5CCN(C(=O)OC(C)(C)C)CC5)cc4)n3)C2)C1=O]

To a homogeneous solution of tert-butyl 4-[4-({3-cyano-6-[(3R)-3-(3-methyl-2-oxoimidazolidin-1-yl)piperidin-1-yl]pyrazin-2-yl}amino)phenyl]piperazine-1-carboxylate (8.23 g, 14.7 mmol) in DMSO (80 mL) and MeOH (160 mL) was added cesium carbonate (4.77 g, 14.7 mmol). The mixture was cooled in an ice bath. Hydrogen peroxide 30% solution (22.0 mL, 213 mmol) was added in 2 portions. After 5 minutes, the ice bath was removed. After 2 hours at room temperature, the mixture was cooled in an ice bath. 70 mL acetonitrile was added. The ice bath was removed. After 15 minutes, the volatiles were removed in vacuo and the mixture was diluted with 1 L of ethyl acetate. The mixture was washed with three potions of water then washed with brine. The organic layer was dried over anhydrous $Na_2SO_4$ and concentrated in vacuo. The crude residue was purified by flash chromatography on a 220 g silica gel column eluted with 0 to 10% MeOH/EtOAc gradient to provide tert-butyl 4-[4-({3-carbamoyl-6-[(3R)-3-(3-methyl-2-oxoimidazolidin-1-yl)piperidin-1-yl]pyrazin-2-yl}amino)phenyl]piperazine-1-carboxylate (7.23 g, 85.1%). LCMS: $C_{29}H_{41}N_9O_4$ requires 579, found m/z=580 [M+H]$^+$.

Step 8: 5-[(3R)-3-(3-methyl-2-oxoimidazolidin-1-yl)piperidin-1-yl]3-{[4-(piperazin-1-yl)phenyl]amino}pyrazine-2-carboxamide trifluoroacetate

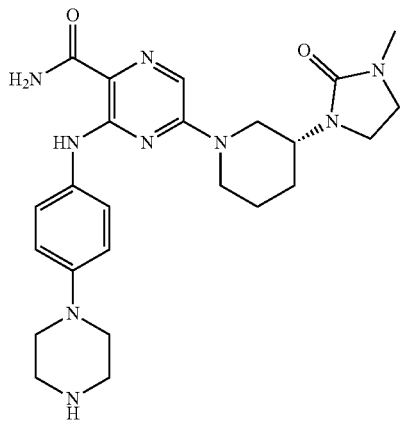

Tert-butyl 4-[4-({3-carbamoyl-6-[(3R)-3-(3-methyl-2-oxoimidazolidin-1-yl)piperidin-1-yl]pyrazin-2-yl}amino)phenyl]piperazine-1-carboxylate (2.65 g, 4.57 mmol) was stirred in DCM (15 mL) and TFA (15 mL). After 30 minutes, the mixture was concentrated to provide 5-[(3R)-3-(3-methyl-2-oxoimidazolidin-1-yl)piperidin-1-yl]-3-{[4-(piperazin-1-yl)phenyl]amino}pyrazine-2-carboxamide trifluoroacetate (2.71 g, 100%). LCMS: $C_{24}H_{33}N_9O_2$ requires 479, found m/z=480 [M+H]$^+$.

Step 9: tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate

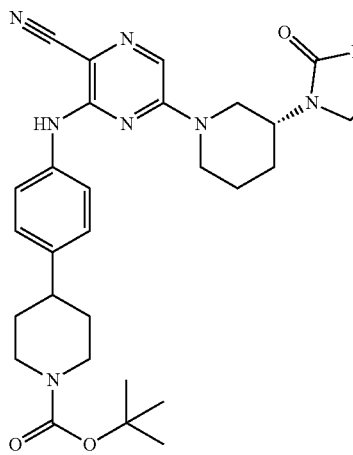

A mixture of 3-chloro-5-[(3R)-3-(3-methyl-2-oxoimidazolidin-1-yl)piperidin-1-yl]pyrazine-2-carbonitrile (244 mg, 0.76 mmol), tert-butyl 4-(4-aminophenyl)piperidine-1-carboxylate (211 mg, 0.76 mmol), Pd(OAc)$_2$ (56.4 mg, 0.25 mmol), BINAP (156.3 mg, 0.25 mmol) and Cs$_2$CO$_3$ (7434 mg, 2.28 mmol) was degassed and backfilled with N$_2$ 5 times. The mixture was allowed to stir at 100° C. for 90 min. The mixture was filtered through celite washing with MeOH/EtOAc, concentrated and purified by MPLC (0-100% EtOAc in CH$_2$Cl$_2$) to afford tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate (259 mg, 60.7%). LCMS: $C_{30}H_{40}N_8O_3$ requires 560, found m/z=561 [M+H]$^+$.

Step 10: tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate

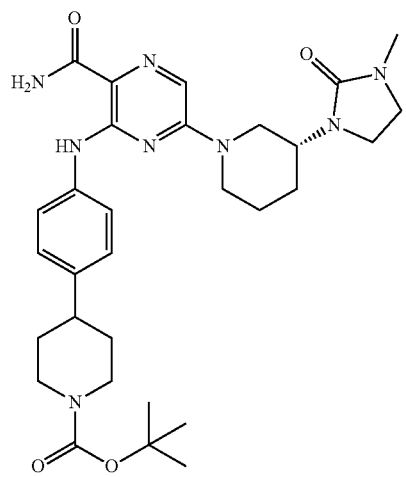

H$_2$O$_2$ (30% in water, 2.50 mL, 0.24 mmol) was added to a mixture of tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate (259 mg, 0.46 mmol), Cs$_2$CO$_3$ (150.5 mg, 0.46 mmol), MeOH (9 mL) and DMSO (0.5 mL). The mixture was allowed to stir at rt for 30 min. The mixture was concentrated, EtOAc was added and the organic phase was washed with H$_2$O and brine. The organic layer was dried with MgSO$_4$, filtered, concentrated and purified by MPLC (0-10% MeOH in CH$_2$Cl$_2$) to afford tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate (252 mg, 94%). LCMS: $C_{30}H_{42}N_8O_4$ requires 578, found m/z=579 [M+H]$^+$.

Step 11: 5-[(3R)-3-(3-methyl-2-oxoimidazolidin-1-yl)piperidin-1-yl]-3-{[4-(piperidin-4-yl)phenyl]amino}pyrazine-2-carboxamide

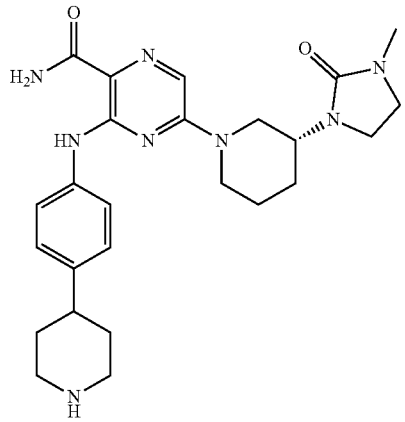 [SMILES: CN1CCN([C@@H]2CCCN(c3cnc(C(N)=O)c(Nc4ccc(C5CCNCC5)cc4)n3)C2)C1=O]

A mixture of tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate (252 mg, 0.44 mmol), hydrogen chloride (4M in dioxane, 2.72 mL, 10.89 mmol) and THF (2 mL) was allowed to stir at r.t. for 2 h. The volatiles were removed to afford 5-[(3R)-3-(3-methyl-2-oxoimidazolidin-1-yl)piperidin-1-yl]-3-{[4-(piperidin-4-yl)phenyl]amino}pyrazine-2-carboxamide (209 mg, quant).

Example 2: 5-[(3R)-3-(3-methyl-2-oxoimidazolidin-1-yl)piperidin-1-yl]-3-{[4-(4-methylpiperidin-4-yl)phenyl]amino}pyrazine-2-carboxamide Step 1: ethyl 4-hydroxy-4-methylpiperidine-1-carboxylate

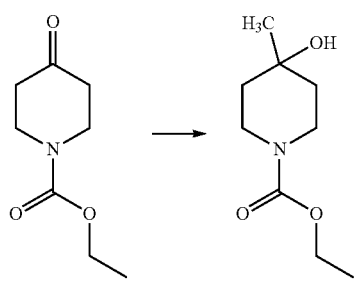

A solution of ethyl 4-oxopiperidine-1-carboxylate (10.00 g, 58.41 mmol) in diethyl ether (100.00 mL) was cooled to −30° C., chloro(methyl)magnesium (23.40 mL, 5.24 g, 70.10 mmol) (3M solution in THF) was added. The resulting mixture was stirred at 0° C. for 2 hrs, and TLC showed no starting material. The reaction was quenched with 50 mL ammonium chloride solution and a white solid precipitated. The solid was filtered and washed with DCM. The aqueous layer of the combined solution was separated and washed twice with DCM. The combined organic solution was dried over $Na_2SO_4$ and concentrated. The crude product was purified by ISCO silica gel column (40 g) using 0-100% EtOAc/Hexanes. Isolated ethyl 4-hydroxy-4-methylpiperidine-1-carboxylate (8.7 g 79.5% yield). $^1$H NMR (500 MHz, Chloroform-d) δ 4.13 (q, J=7.1 Hz, 2H), 3.78 (s, 2H), 3.28 (dt, J=14.2, 7.6 Hz, 2H), 1.56 (d, J=5.3 Hz, 4H), 1.29-1.22 (m, 6H).

Step 2: ethyl 4-(4-bromophenyl)-4-methylpiperidine-1-carboxylate

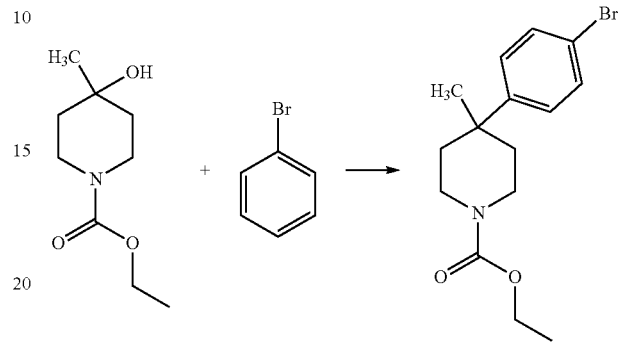

Ethyl 4-hydroxy-4-methylpiperidine-1-carboxylate (3.08 g, 16.45 mmol) in bromobenzene (25.83 g, 164.50 mmol), cooled to 0° C., trifluoromethanesulfonic acid (24.69 g, 164.50 mmol) was added. The resulting mixture was stirred at r.t. for 3 hrs. The solution was poured into ice, basified with 1N NaOH solution and extracted with DCM three times. The combined organic layers were washed with brine, dried over $Na_2SO_4$, concentrated. The crude oil was purified by ISCO silica gel column (40 g) using EtOAc/hexane (0-50%), obtained ethyl 4-(4-bromophenyl)-4-methylpiperidine-1-carboxylate (4.3 g, 80.1% yield). $^1$H NMR (500 MHz, Chloroform-d) δ 7.48-7.43 (m, 2H), 7.23-7.17 (m, 2H), 4.12 (q, J=7.1 Hz, 2H), 3.56-3.48 (m, 2H), 3.46-3.38 (m, 2H), 2.03 (br, 2H), 1.68 (br, 2H), 1.28-1.21 (m, 6H). LCMS: $C_{15}H_{20}BrNO_2$ requires: 325, found: m/z=326 [M+H]$^+$.

Step 3: 4-(4-bromophenyl)-4-methylpiperidine

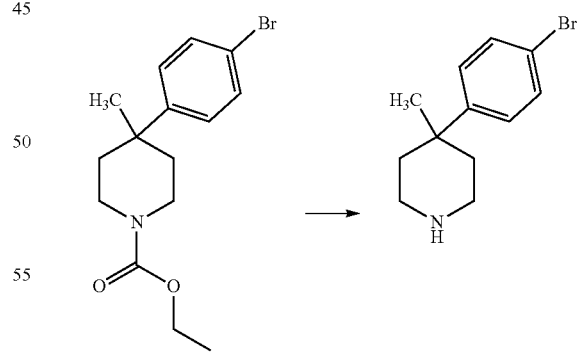

To a solution of ethyl 4-(4-bromophenyl)-4-methylpiperidine-1-carboxylate (7.00 g, 21.46 mmol) in EtOH (75 mL) was added potassium hydroxide (24.08 g, 429.14 mmol), the solution was heated at 80° C. overnight. LCMS showed no starting material left. The solvent was evaporated by reduced pressure, the residue was dissolved in DCM (50 mL), washed by water (20 mL). The aqueous layer was extracted with DCM (20 mL×5), and the combined organic layers were washed with brine, dried over Na$_2$SO$_4$, and concentrated to give 5.45 g of 4-(4-bromophenyl)-4-methylpiperidine as crude product in quantitative yield, which was used directly to the next step without further purification. LCMS: C$_{12}$H$_{16}$BrN requires: 253, found: m/z=254 [M+H]$^+$.

Step 4: tert-butyl 4-(4-bromophenyl)-4-methylpiperidine-1-carboxylate

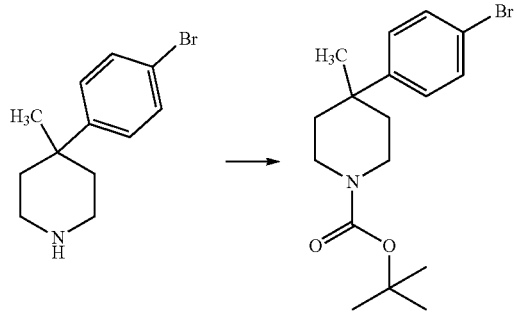 [SMILES: CC1(c2ccc(Br)cc2)CCNCC1 ; CC(C)(C)OC(=O)N1CCC(C)(c2ccc(Br)cc2)CC1]

4-(4-bromophenyl)-4-methylpiperidine (5.40 g, 21.25 mmol) was dissolved in dichloromethane (75.00 mL), di-tert-butyl dicarbonate (7.42 g, 33.99 mmol) was added slowly, and the reaction was stirred at r.t. for 1 h. The reaction solution was washed with water followed by brine, dried over Na$_2$SO$_4$, and concentrated. ISCO silica gel column purification, obtained tert-butyl 4-(4-bromophenyl)-4-methylpiperidine-1-carboxylate (7.4 g, 98.3% yield). $^1$H NMR (500 MHz, Chloroform-d) δ 7.48-7.42 (m, 2H), 7.27-7.16 (m, 2H), 3.47 (ddd, J=11.8, 7.8, 3.6 Hz, 2H), 3.41-3.33 (m, 2H), 2.00 (br, 2H), 1.71-1.62 (m, 2H), 1.45 (s, 9H), 1.23 (s, 3H) LCMS: C$_{12}$H$_{16}$BrN requires: 253, found: m/z=254 [M+H]$^+$.

Step 5: tert-butyl 4-(4-aminophenyl)-4-methylpiperidine-1-carboxylate

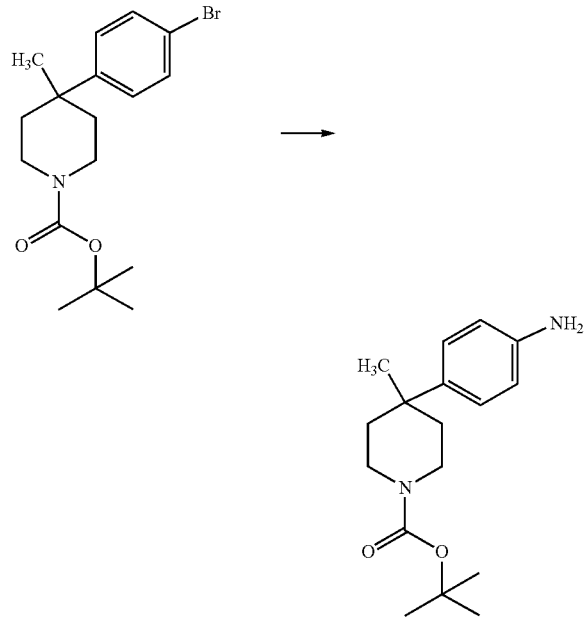

Tert-butyl 4-(4-bromophenyl)-4-methylpiperidine-1-carboxylate (2.60 g, 7.34 mmol), {[1,1'-biphenyl]-2-yl}dicyclohexylphosphane (65.00 mg, 0.19 mmol), Pd$_2$(dba)$_3$ (68.00 mg, 0.07 mmol) and LiHMDS (14.70 mL, 2.46 g, 14.68 mmol) in 15 mL anhydrous THF, the solution was bubbled with nitrogen gas and stirred at 65° C. overnight under N$_2$ protection. TLC showed no starting material left. The reaction mixture was diluted with DCM, washed by water and brine, dried over Na$_2$SO$_4$, concentrated. The crude product was purified by ISCO silica gel column using 0-60% EtOAc/hexane, obtained tert-butyl 4-(4-aminophenyl)-4-methylpiperidine-1-carboxylate (1.42 g, 66.6% yield). $^1$H NMR (500 MHz, Chloroform-d) δ 7.14-7.08 (m, 2H), 6.70-6.64 (m, 2H), 3.58 (s, 2H), 3.49-3.44 (m, 2H), 3.39-3.31 (m, 2H), 2.00 (br, 2H), 1.64-1.58 (m, 2H) 1.45 (s, 9H), 1.20 (s, 3H) LCMS: C$_{17}$H$_{26}$N$_2$O$_2$ requires: 290, found: m/z=291 [M+H]$^+$.

Step 6: tert-butyl 4-[4-({3-cyano-6-[(3R)-3-(3-methyl-2-oxoimidazolidin-1-yl)piperidin-1-yl]pyrazin-2-yl}amino)phenyl]-4-methylpiperidine-1-carboxylate

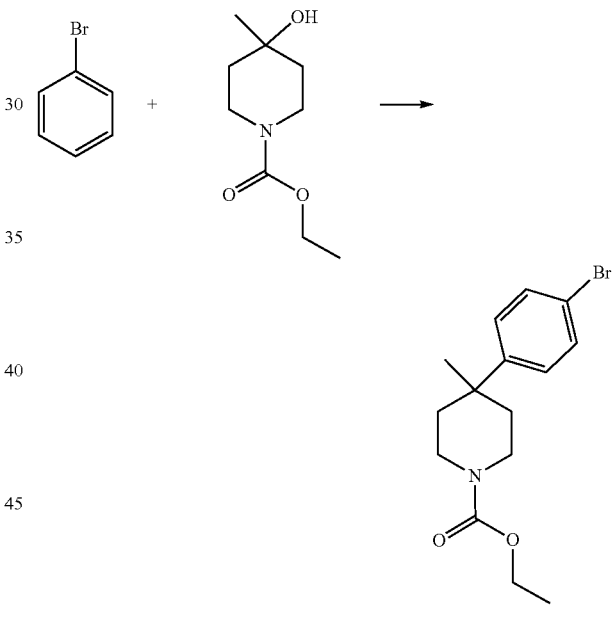

Tert-butyl 4-(4-aminophenyl)-4-methylpiperidine-1-carboxylate (0.64 g, 2.19 mmol), 3-chloro-5-[(3R)-3-(3-methyl-2-oxoimidazolidin-1-yl)piperidin-1-yl]pyrazine-2-carbonitrile (0.61 g, 1.90 mmol), cesium carbonate (1.86 g, 5.70 mmol), palladium acetate (140.89 mg, 0.63 mmol), and [2'-(diphenylphosphanyl)-[1,1'-binaphthalen]-2-yl]diphenylphosphane BINAP (390.76 mg, 0.63 mmol) in 30 mL dioxane, the solution was bubbled with nitrogen gas and heated at 115° C. for 2 hours under nitrogen protection. The reaction mixture was cooled to r.t., diluted with 250 mL EtOAc and filtered. The filtrate was concentrated and purified by ISCO silica gel column using EtOAc/DCM (0-100%), obtained tert-butyl 4-[4-({3-cyano-6-[(3R)-3-(3-methyl-2-oxoimidazolidin-1-yl)piperidin-1-yl]pyrazin-2-yl}amino)phenyl]-4-methylpiperidine-1-carboxylate (1.09 g, 100% yield). LCMS: C$_{31}$H$_{42}$N$_8$O$_3$ requires: 574, found: m/z=575 [M+H]$^+$.

Step 7: tert-butyl 4-[4-({3-carbamoyl-6-[(3R)-3-(3-methyl-2-oxoimidazolidin-1-yl)piperidin-1-yl]pyrazin-2-yl}amino)phenyl]-4-methylpiperidine-1-carboxylate

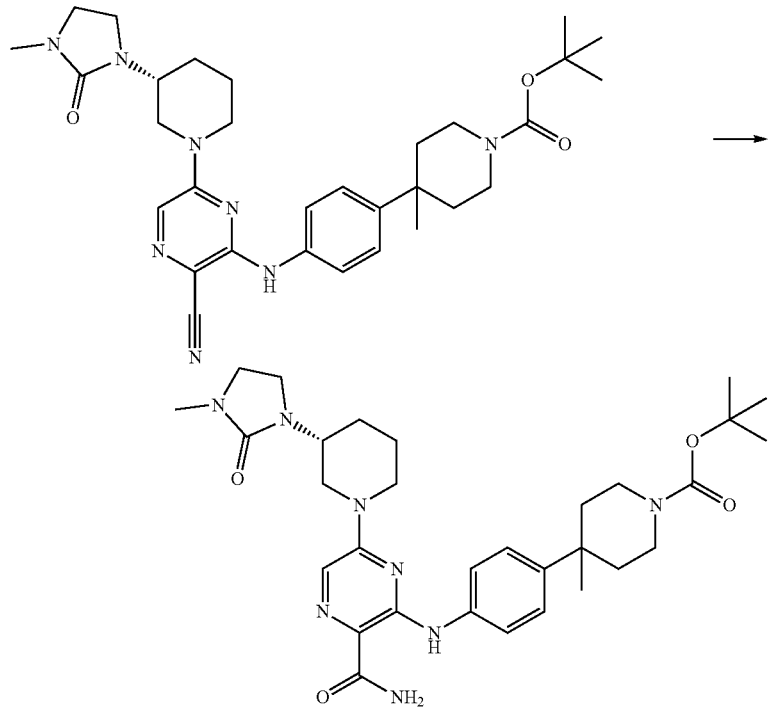

Tert-butyl 4-[4-({3-cyano-6-[(3R)-3-(3-methyl-2-oxoimidazolidin-1-yl)piperidin-1-yl]pyrazin-2-yl}amino)phenyl]-4-methylpiperidine-1-carboxylate (1.09 g, 1.9 mmol) was dissolved in methanol (25.00 mL) and DMSO (5.00 mL), cesium carbonate (325 mg, 1.0 mmol) was added, and then 30% $H_2O_2$ solution (2.31 g, 3 mL, 20.36 mmol) was added. Stirred at room temperature for 30 min. LCMS showed no starting material left. 10 mL acetonitrile was added, stirred for 5 min, evaporated all the solvent. The residue was dissolved in 200 mL EtOAc, washed with water three times, dried over $Na_2SO_4$, concentrated. ISCO silica gel column (24 g) purification using 30-100% EtOAc/Hexane, followed by 0-10% MeOH/DCM. Obtained tert-butyl 4-[4-({3-carbamoyl-6-[(3R)-3-(3-methyl-2-oxoimidazolidin-1-yl)piperidin-1-yl]pyrazin-2-yl}amino)phenyl]-4-methylpiperidine-1-carboxylate (1.00 g, 82.9% yield). $^1$H NMR (500 MHz, Chloroform-d) δ 10.84 (s, 1H), 7.60 (d, J=8.8 Hz, 2H), 7.49 (s, 1H), 7.26 (d, J=8.8 Hz, 2H), 5.18 (s, 1H), 4.36 (t, J=11.6 Hz, 2H), 3.81 (m, 1H), 3.49 (br, 2H), 3.43-3.26 (m, 5H), 3.08 (t, J=11.7 Hz, 1H), 2.98-2.92 (m, 1H), 2.82 (s, 3H), 2.05 (d, J=9.1 Hz, 2H), 2.02-1.97 (m, 1H), 1.90 (dt, J=13.3, 3.3 Hz, 1H), 1.76 (td, J=11.7, 3.5 Hz, 1H), 1.82-1.65 (m, 3H), 1.45 (s, 9H), 1.25 (s, 3H). LCMS: $C_{31}H_{44}N_8O_4$ requires: 592, found: m/z=593 [M+H]$^+$.

Step 8: 5-[(3R)-3-(3-methyl-2-oxoimidazolidin-1-yl)piperidin-1-yl]-3-{[4-(4-methylpiperidin-4-yl)phenyl]amino}pyrazine-2-carboxamide

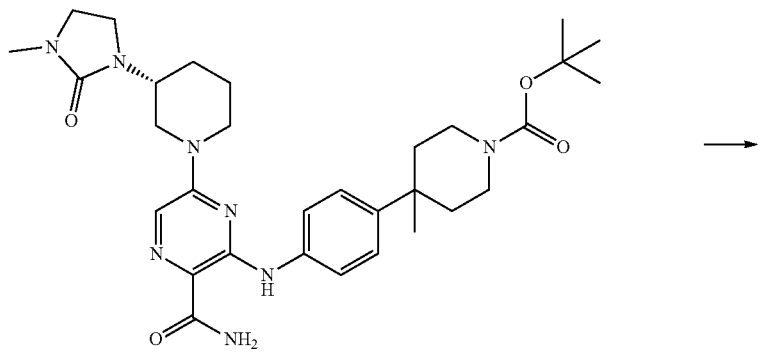

-continued

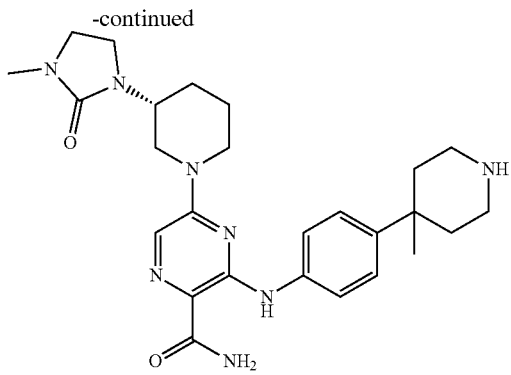

Tert-butyl 4-[4-({3-carbamoyl-6-[(3R)-3-(3-methyl-2-oxoimidazolidin-1-yl)piperidin-1-yl]pyrazin-2-yl}amino)phenyl]-4-methylpiperidine-1-carboxylate (200.00 mg, 0.34 mmol) was dissolved in 4N HCl in dioxane (2 mL), stirred at r.t. for 30 min, evaporated solvent to give 5-[(3R)-3-(3-methyl-2-oxoimidazolidin-1-yl)piperidin-1-yl]-3-{[4-(4-methylpiperidin-4-yl)phenyl]amino}pyrazine-2-carboxamide as crude product in quantitative yield, which was used directly to the next step without further purification. LCMS: $C_{26}H_{36}N_8O_2$ requires: 492, found: m/z=493 [M+H]$^+$.

Example 3: Synthesis of 3-{[4-(azetidin-3-yl)phenyl]amino}-5-[(3R)-3-(3-methyl-2-oxoimidazolidin-1-yl)piperidin-1-yl]pyrazine-2-carboxamide Step 1: tert-butyl 3-[4-({3-cyano-6-[(3R)-3-(3-methyl-2-oxoimidazolidin-1-yl)piperidin-1-yl]pyrazin-2-yl}amino)phenyl]azetidine-1-carboxylate

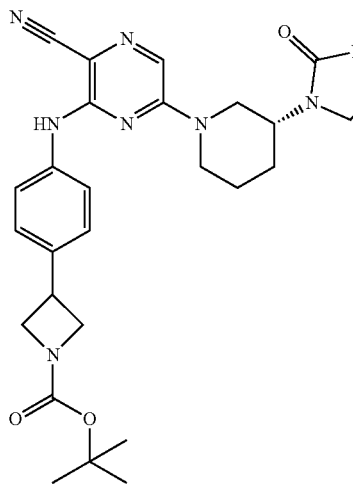

3-chloro-5-[(3R)-3-(3-methyl-2-oxoimidazolidin-1-yl)piperidin-1-yl]pyrazine-2-carbonitrile (207 mg, 0.65 mmol), tert-butyl 3-(4-aminophenyl)azetidine-1-carboxylate (160 mg, 0.65 mmol), and cesium carbonate (847 mg, 2.60 mmol) were deposited in a vial with dioxane (5 mL). A vacuum was pulled on the vial until the mixture bubbled then the headspace was backfilled with argon for 5 cycles. BINAP (80.4 mg, 0.13 mmol) and palladium (II) acetate (29.0 mg, 0.13 mmol) were added. A vacuum was pulled on the vial and the headspace was backfilled with argon for 5 cycles. The mixture was heated at 90° C. overnight. The mixture was diluted with water and extracted twice with DCM. The combined organic layers were dried over anhydrous $Na_2SO_4$ and concentrated in vacuo. The crude residue was purified by flash chromatography on a 24 g silica gel column eluted with 0 to 10% MeOH/ethyl acetate gradient to provide tert-butyl 3-[4-({3-cyano-6-[(3R)-3-(3-methyl-2-oxoimidazolidin-1-yl)piperidin-1-yl]pyrazin-2-yl}amino)phenyl]azetidine-1-carboxylate (257 mg, 74.8%). LCMS: $C_{28}H_{36}N_8O_3$ requires 532, found: m/z=533 [M+H]$^+$.

Step 2: tert-butyl 3-[4-({3-carbamoyl-6-[(3R)-3-(3-methyl-2-oxoimidazolidin-1-yl)piperidin-1-yl]pyrazin-2-yl}amino)phenyl]azetidine-1-carboxylate

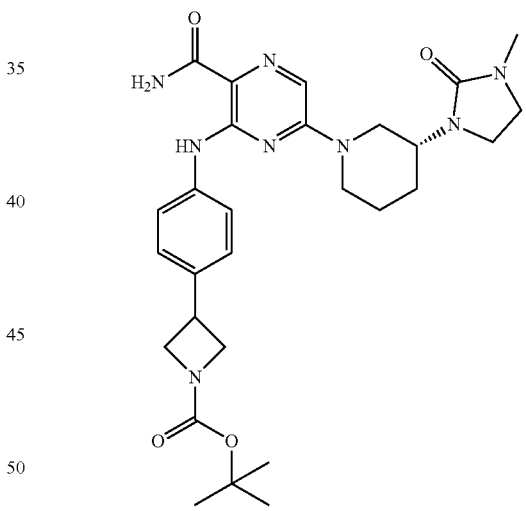

Tert-butyl 3-[4-({3-cyano-6-[(3R)-3-(3-methyl-2-oxoimidazolidin-1-yl)piperidin-1-yl]pyrazin-2-yl}amino)phenyl]azetidine-1-carboxylate (257 mg, 0.48 mmol) was dissolved in MeOH (6 mL) and DMSO (3 mL). Cesium carbonate (157 mg, 0.48 mmol) was added followed by 1.5 mL 35% $H_2O_2$. After 3 hours, 4 mL ACN was added. After 20 minutes, the mixture was diluted with ethyl acetate and washed 3× with water. The organic layer was dried over $Na_2SO_4$ and concentrated in vacuo. The crude residue was purified by flash chromatography on a 24 g silica gel column eluted with 0 to 10% MeOH/ethyl acetate gradient to provide tert-butyl 3-[4-({3-carbamoyl-6-[(3R)-3-(3-methyl-2-oxoimidazolidin-1-yl)piperidin-1-yl]pyrazin-2-yl}amino)phenyl]azetidine-1-carboxylate (261 mg, 98.2%). LCMS: $C_{28}H_{38}N_8O_4$ requires 550, found m/z=551 [M+H]$^+$.

337

Step 3: 3-{[4-(azetidin-3-yl)phenyl]amino}-5-[(3R)-3-(3-methyl-2-oxoimidazolidin-1-yl)piperidin-1-yl]pyrazine-2-carboxamide

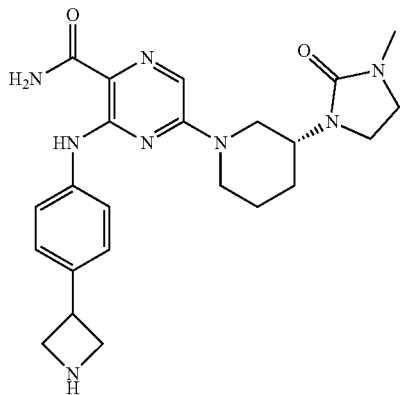 [SMILES: CN1CCN([C@@H]2CCCN(c3cnc(C(N)=O)c(Nc4ccc(C5CNC5)cc4)n3)C2)C1=O]

338

Tert-butyl 3-[4-({3-carbamoyl-6-[(3R)-3-(3-methyl-2-oxoimidazolidin-1-yl)piperidin-1-yl]pyrazin-2-yl}amino)phenyl]azetidine-1-carboxylate (261.00 mg, 0.47 mmol) was stirred in DCM (1 mL) and TFA (1 mL) for 15 minutes and was concentrated in vacuo then lyophilized to provide 3-{[4-(azetidin-3-yl)phenyl]amino}-5-[(3R)-3-(3-methyl-2-oxoimidazolidin-1-yl)piperidin-1-yl]pyrazine-2-carboxamide (265 mg, 100%). LCMS: $C_{23}H_{30}N_8O_2$ requires 451, found: m/z=451 [M+H]$^+$.

Example 4: Synthesis of (R)-3-((4-(2,6-diazaspiro[3.3]heptan-2-yl)phenyl)amino)-5-(3-(3-methyl-2-oxoimidazolidin-1-yl)piperidin-1-yl)pyrazine-2-carboxamide

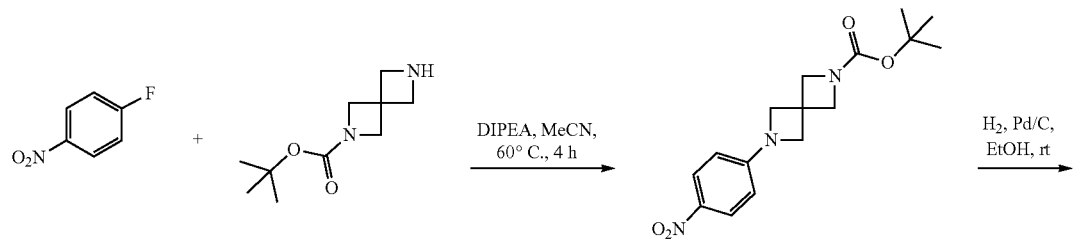

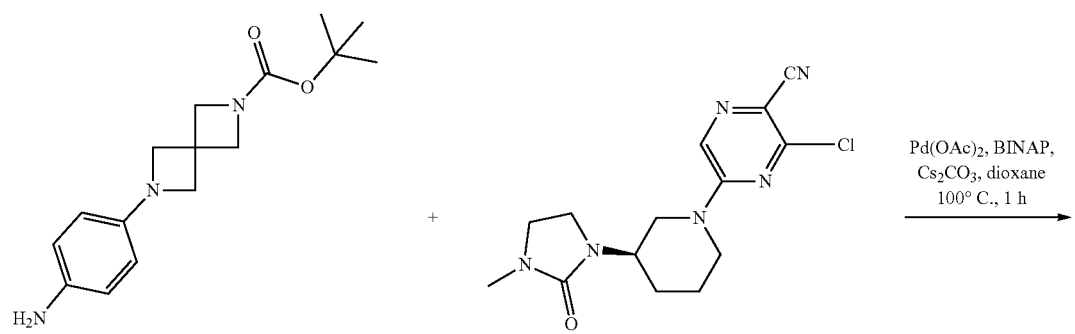

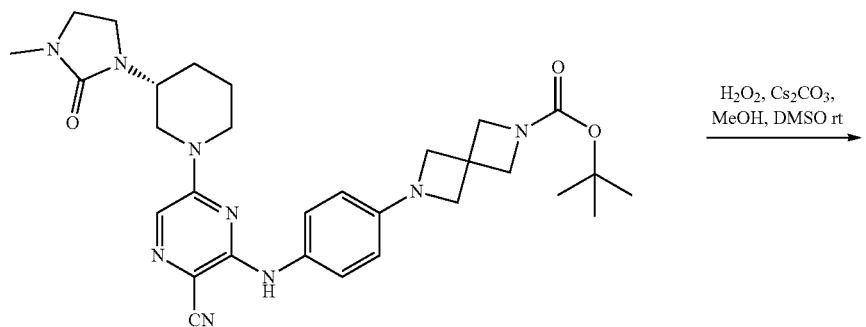

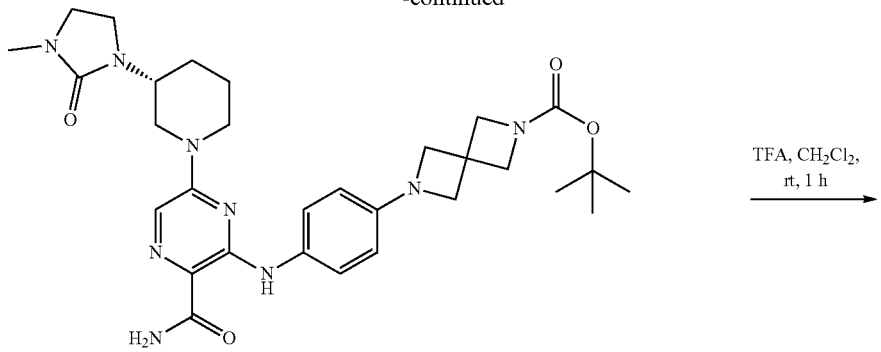

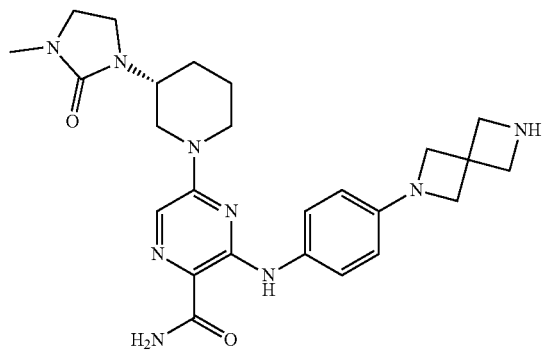

Step 1: tert-butyl 6-(4-nitrophenyl)-2,6-diazaspiro[3.3]heptane-2-carboxylate A mixture of tert-butyl 2,6-diazaspiro[3.3]heptane-2-carboxylate (515 mg, 2.60 mmol), MeCN (2 mL), ethylbis(propan-2-yl)amine (1.81 mL, 10.4 mmol) and 4-fluoronitrobenzene (367 mg, 2.60 mmol) was allowed to stir at 60° C. for 4 h. EtOAc and $H_2O$ were added. The organic layer was dried with $MgSO_4$, filtered, concentrated and purified by MPLC (0-50% EtOAc in hexanes) to afford tert-butyl 6-(4-nitrophenyl)-2,6-diazaspiro[3.3]heptane-2-carboxylate (491 mg, 59.2%). LCMS: $C_{16}H_{21}N_3O_4$ requires 319, found: m/z=320 [M+H]$^+$.

Step 2: tert-butyl 6-(4-aminophenyl)-2,6-diazaspiro[3.3]heptane-2-carboxylate A mixture of Pd/C (16 mg, 0.15 mmol), EtOH (15 mL), tert-butyl 6-(4-nitrophenyl)-2,6-diazaspiro[3.3]heptane-2-carboxylate (491 mg, 1.54 mmol) was evacuated and backfilled with $H_2$ 5 times. The mixture was allowed to stir at r.t. for 2 h. The mixture was filtered through celite washing with EtOAc/MeOH, concentrated to afford tert-butyl 6-(4-aminophenyl)-2,6-diazaspiro[3.3]heptane-2-carboxylate (439 mg, 98.7%). LCMS: $C_{16}H_{23}N_3O_2$ requires 289, found: m/z=290 [M+H]$^+$.

Step 3: tert-butyl (R)-6-(4-((3-cyano-6-(3-(3-methyl-2-oxoimidazolidin-1-yl)piperidin-1-yl)pyrazin-2-yl)amino)phenyl)-2,6-diazaspiro[3.3]heptane-2-carboxylate A mixture of tert-butyl 6-(4-aminophenyl)-2,6-diazaspiro[3.3]heptane-2-carboxylate (245 mg, 0.85 mmol), 3-chloro-5-[(3R)-3-(3-methyl-2-oxoimidazolidin-1-yl)piperidin-1-yl]pyrazine-2-carbonitrile (272 mg, 0.85 mmol), Pd(OAc)$_2$ (62.8 mg, 0.28 mmol), [2'-(diphenylphosphanyl)-[1,1'-binaphthalen]-2-yl]diphenylphosphane (174 mg, 0.28 mmol) and cesium carbonate (829 mg, 2.54 mmol) was degassed and backfilled with $N_2$ 5 times. Dioxane (4 mL) was added. The mixture was allowed to stir at 100° C. for 90 min. The mixture was filtered through celite washing with MeOH/EtOAc, concentrated and purified by MPLC (0-100% EtOAc in $CH_2Cl_2$) to afford tert-butyl 6-[4-({3-cyano-6-[(3R)-3-(3-methyl-2-oxoimidazolidin-1-yl)piperidin-1-yl]pyrazin-2-yl}amino)phenyl]-2,6-diazaspiro[3.3]heptane-2-carboxylate (272 mg, 55.9%). LCMS: $C_{30}H_{39}N_9O_3$ requires 573, found: m/z=574 [M+H]$^+$.

Step 4: tert-butyl (R)-6-(4-((3-carbamoyl-6-(3-(3-methyl-2-oxoimidazolidin-1-yl)piperidin-1-yl)pyrazin-2-yl)amino)phenyl)-2,6-diazaspiro[3.3]heptane-2-carboxylate $H_2O_2$ (30% in $H_2O$, 0.80 mL, 0.08 mmol) was added to a mixture of tert-butyl 6-[4-({3-cyano-6-[(3R)-3-(3-methyl-2-oxoimidazolidin-1-yl)piperidin-1-yl]pyrazin-2-yl}amino)phenyl]-2,6-diazaspiro[3.3]heptane-2-carboxylate (272 mg, 0.47 mmol), cesium carbonate (154 mg, 0.47 mmol), MeOH (10 mL) and DMSO (0.5 mL). The mixture was allowed to stir at r.t. for 30 min. The mixture was concentrated. EtOAc was added and the organic phase was washed with $H_2O$ and brine. The organic layer was dried with $MgSO_4$, filtered, concentrated and purified by MPLC (0-10% MeOH in $CH_2Cl_2$) to afford tert-butyl 6-[4-({3-carbamoyl-6-[(3R)-3-(3-methyl-2-oxoimidazolidin-1-yl)piperidin-1-yl]pyrazin-2-yl}amino)phenyl]-2,6-diazaspiro[3.3]heptane-2-carboxylate (142 mg, 50.6%). LCMS: $C_{30}H_{41}N_9O_4$ requires 591, found: m/z=592 [M+H]$^+$.

341

Step 5: (R)-3-((4-(2,6-diazaspiro[3.3]heptan-2-yl)phenyl)amino)-5-(3-(3-methyl-2-oxoimidazolidin-1-yl)piperidin-1-yl)pyrazine-2-carboxamide A mixture of tert-butyl 6-[4-({3-carbamoyl-6-[(3R)-3-(3-methyl-2-oxoimidazolidin-1-yl)piperidin-1-yl]pyrazin-2-yl}amino)phenyl]-2,6-diazaspiro[3.3]heptane-2-carboxylate (142 mg, 0.24 mmol), CH$_2$Cl$_2$ (2 mL) and TFA (0.4 mL) was allowed to stir at r.t. for 1 h. The volatiles were removed to afford 3-[(4-{2,6-diazaspiro[3.3]heptan-2-yl}phenyl)

342 amino]-5-[(3R)-3-(3-methyl-2-oxoimidazolidin-1-yl)piperidin-1-yl]pyrazine-2-carboxamide (117 mg, 99.2%). LCMS: C$_{25}$H$_{33}$N$_9$O$_2$ requires 491, found: m/z=492 [M+H]$^+$.

Example 5: Synthesis of (R)-3-((4-(3,9-diazaspiro[5.5]undecan-3-yl)phenyl)amino)-5-(3-(3-methyl-2-oxoimidazolidin-1-yl)piperidin-1-yl)pyrazine-2-carboxamide

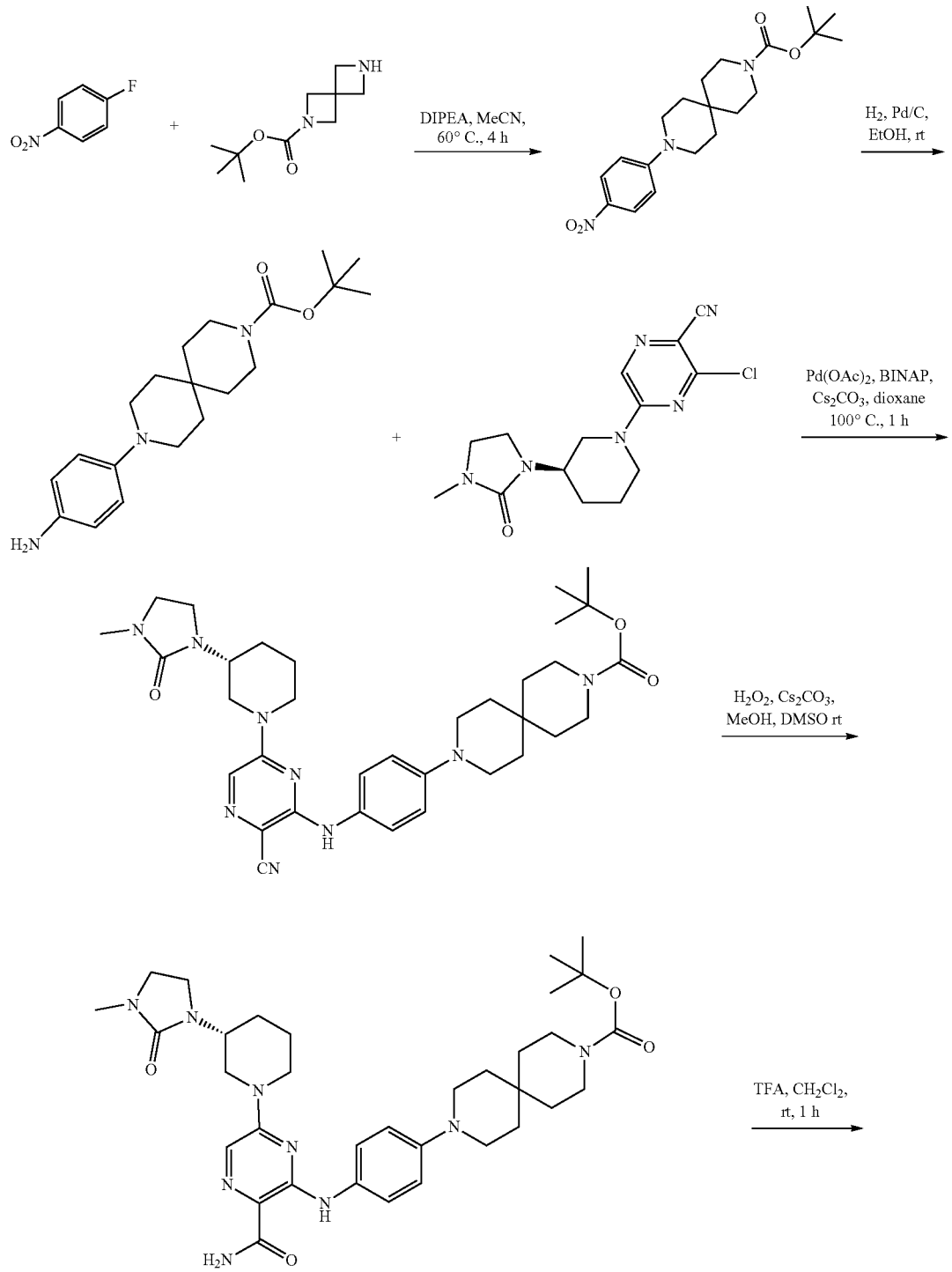

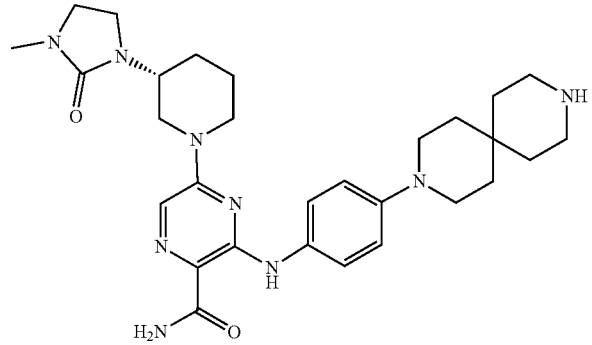

Step 1: tert-butyl 9-(4-nitrophenyl)-3,9-diazaspiro[5.5]undecane-3-carboxylate A mixture of 4-fluoronitrobenzene (554.7 mg, 3.93 mmol), DMF (20 mL), ethylbis(propan-2-yl)amine (2.74 mL, 15.7 mmol) and tert-butyl 3,9-diazaspiro[5.5]undecane-3-carboxylate (1000 mg, 3.93 mmol) was allowed to stir at 90° C. overnight. EtOAc and $H_2O$ were added. The organic layer was dried with $MgSO_4$, filtered, concentrated and purified by MPLC (0-50% EtOAc in hexanes) to afford tert-butyl 9-(4-nitrophenyl)-3,9-diazaspiro[5.5]undecane-3-carboxylate (1287.00 mg, 87.2%). $C_{20}H_{29}N_3O_4$ requires 375, found: m/z=376 $[M+H]^+$.

Step 2: tert-butyl 9-(4-aminophenyl)-3,9-diazaspiro[5.5]undecane-3-carboxylate A mixture of tert-butyl 9-(4-nitrophenyl)-3,9-diazaspiro[5.5]undecane-3-carboxylate (1.29 g, 3.43 mmol), Pd/C (36 mg, 0.34 mmol), EtOH (30 mL) was evacuated and backfilled with $H_2$ 5 times. The mixture was allowed to stir at r.t. for 2 h. The mixture was filtered through celite washing with EtOAc/MeOH, concentrated to afford tert-butyl 9-(4-aminophenyl)-3,9-diazaspiro[5.5]undecane-3-carboxylate (871 mg, 73.5%). LCMS: $C_{20}H_{31}N_3O_2$ requires 345, found: m/z=346 $[M+H]^+$.

Step 3: tert-butyl (R)-9-(4-((3-cyano-6-(3-(3-methyl-2-oxoimidazolidin-1-yl)piperidin-1-yl)pyrazin-2-yl)amino)phenyl)-3,9-diazaspiro[5.5]undecane-3-carboxylate A mixture of tert-butyl 9-(4-aminophenyl)-3,9-diazaspiro[5.5]undecane-3-carboxylate (162.6 mg, 0.47 mmol), 3-chloro-5-[(3R)-3-(3-methyl-2-oxoimidazolidin-1-yl)piperidin-1-yl]pyrazine-2-carbonitrile (151 mg, 0.47 mmol), Pd(OAc)$_2$ (34.9 mg, 0.16 mmol), [2'-(diphenylphosphanyl)-[1,1'-binaphthalen]-2-yl]diphenylphosphane (96.7 mg, 0.16 mmol) and cesium carbonate (460 mg, 1.41 mmol) was degassed and backfilled with $N_2$ 5 times. The mixture was allowed to stir at 100° C. for 90 min. The mixture was filtered through celite washing with MeOH/EtOAc, concentrated and purified by MPLC (0-100% EtOAc in $CH_2Cl_2$) to afford tert-butyl 9-[4-({3-cyano-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (204 mg, 68.8%). LCMS: $C_{34}H_{47}N_9O_3$ requires 629, found: m/z=630 $[M+H]^+$.

Step 4: tert-butyl (R)-9-(4-((3-carbamoyl-6-(3-(3-methyl-2-oxoimidazolidin-1-yl)piperidin-1-yl)pyrazin-2-yl)amino)phenyl)-3,9-diazaspiro[5.5]undecane-3-carboxylate $H_2O_2$ (30% in $H_2O$, 0.55 mL, 0.00 g, 0.05 mmol) was added to a mixture of tert-butyl 9-[4-({3-cyano-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (204 mg, 0.32 mmol), cesium carbonate (106 mg, 0.32 mmol), MeOH (6 mL) and DMSO (0.3 mL). The mixture was allowed to stir at r.t. for 30 min. The mixture was concentrated. EtOAc was added and the organic phase was washed with $H_2O$ and brine. The organic layer was dried with $MgSO_4$, filtered, concentrated and purified by MPLC (0-10% MeOH in $CH_2Cl_2$) to afford tert-butyl 9-[4-({3-carbamoyl-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (95.00 mg, 45%). LCMS: $C_{34}H_{49}N_9O_4$ requires 647, found: m/z=648 $[M+H]^+$.

Step 5: (R)-3-((4-(3,9-diazaspiro[5.5]undecan-3-yl)phenyl)amino)-5-(3-(3-methyl-2-oxoimidazolidin-1-yl)piperidin-1-yl)pyrazine-2-carboxamide A mixture of tert-butyl 9-[4-({3-carbamoyl-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (25 mg, 0.04 mmol), $CH_2Cl_2$ (1 mL) and TFA (0.2 mL) was allowed to stir at r.t. for 1 h. The volatiles were removed to afford 3-[(4-{3,9-diazaspiro[5.5]undecan-3-yl}phenyl)amino]-5-[(3R)-3-(3-methyl-2-oxoimidazolidin-1-yl)piperidin-1-yl]pyrazine-2-carboxamide (21.00 mg, 99.4%). LCMS: $C_{29}H_{41}N_9O_2$ requires 547, found: m/z=548 $[M+H]^+$.

Example 6: Synthesis of (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide

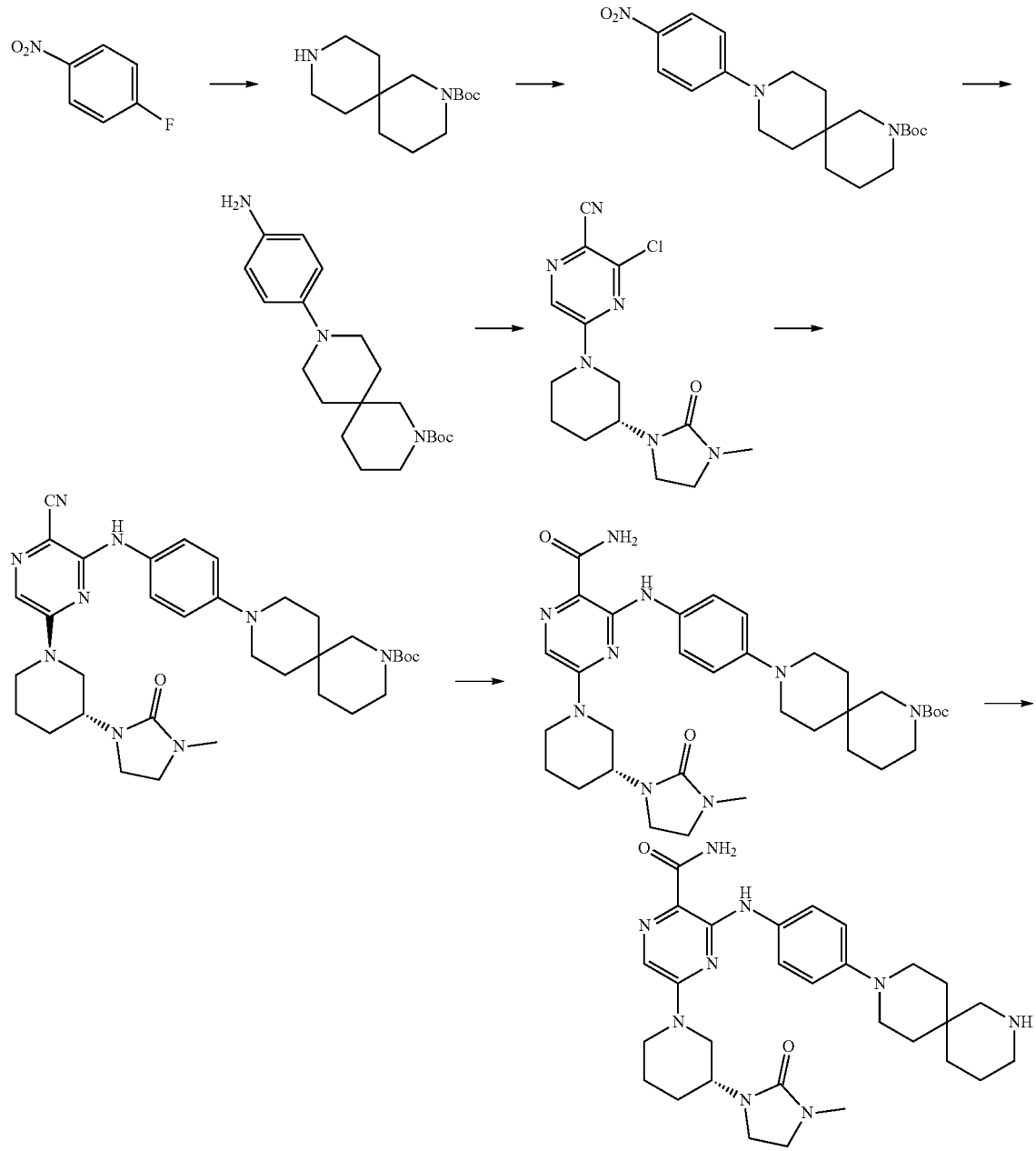

Step 1: tert-butyl 9-(4-nitrophenyl)-2,9-diazaspiro[5.5]undecane-2-carboxylate

Para-fluoronitrobenzene (1 eq) and spirocyclic amine (1 eq) were combined in DMF, followed by addition of potassium carbonate (2 eq). The reaction mixture was stirred at 65° C. for 5 h, then cooled to room temperature. The reaction mixture was then partitioned between ethyl acetate and water, and the organic layer was separated, dried over magnesium sulfate, and filtered. This solution was concentrated to afford tert-butyl 9-(4-nitrophenyl)-2,9-diazaspiro[5.5]undecane-2-carboxylate. LCMS $C_{20}H_{29}N_3O_4$ requires: 375.5, found: m/z=376.6 [M+H]$^+$.

Step 2: tert-butyl 9-(4-aminophenyl)-2,9-diazaspiro[5.5]undecane-2-carboxylate

The crude material from step 1 of this Example 6 was dissolved in ethanol and water (10:1). Ammonium chloride (3.5 eq) and iron (3 eq) were added, followed by vigorous stirring and heating to 90° C. for 4h. The reaction was then filtered with Celite while still hot, and the Celite was further washed with ethyl acetate. The resulting solution was partitioned between ethyl acetate and water. The water layer was separated and re-extracted with ethyl acetate. The combined organic layers were washed with brine, dried over magnesium sulfate, and concentrated. Silica gel chromatography provided tert-butyl 9-(4-aminophenyl)-2,9-diazaspiro[5.5]undecane-2-carboxylate (52% over 2 steps). LCMS $C_{20}H_{31}N_3O_2$ requires: 345.59, found: m/z=346.5 [M+H]$^+$.

Step 3: tert-butyl (R)-9-(4-((3-cyano-6-(3-(3-methyl-2-oxoimidazolidin-1-yl)piperidin-1-yl)pyrazin-2-yl)amino)phenyl)-2,9-diazaspiro[5.5]undecane-2-carboxylate Chloropyrimidine intermediate (R)-3-chloro-5-(3-(3-methyl-2-oxoimidazolidin-1-yl)piperidin-1-yl)pyrazine-2-carbonitrile, tert-butyl 9-(4-aminophenyl)-2,9-diazaspiro[5.5]undecane-2-carboxylate, Pd(OAc)$_2$ (0.15 eq), BINAP (0.15 eq), and cesium carbonate (2 eq) were combined in a microwave tube, followed by addition of dioxane (0.25 M). Nitrogen was bubbled through for 30 seconds, followed by capping. Heating to 9 0° C., followed by maintaining that temperature for 3 h provided a dark reaction mixture which was monitored by LCMS. The reaction was then cooled, and filtered through Celite, washing with ethyl acetate/methanol. The crude material was loaded onto silica and chromatographed (silica, 0-10% methanol in DCM), to provide tert-butyl (R)-9-(4-((3-cyano-6-(3-(3-methyl-2-oxoimidazolidin-1-yl)piperidin-1-yl)pyrazin-2-yl)amino)phenyl)-2,9-diazaspiro[5.5]undecane-2-carboxylate (40%). LCMS $C_{34}H_{47}N_9O_3$ requires: 629.81, found: m/z=630.7 [M+H]$^+$.

Step 4: tert-butyl (R)-9-(4-((3-carbamoyl-6-(3-(3-methyl-2-oxoimidazolidin-1-yl)piperidin-1-yl)pyrazin-2-yl)amino)phenyl)-2,9-diazaspiro[5.5]undecane-2-carboxylate This material was then dissolved in methanol/DMSO (10:1) and a pellet of NaOH was added. The reaction was stirred for 5 minutes, followed by addition of 35% peroxide solution (2 mL of solution per mmol of reactant). This reaction mixture was stirred for 3 h, then partitioned between ethyl acetate and water. The organic layer was separated and dried over magnesium sulfate. Chromatography (0-10% methanol in DCM) provided (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide (90% yield). LCMS $C_{34}H_{49}N_9O_4$ requires: 647.8, found: m/z=648.7[M+H]$^+$.

Step 5: (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide was dissolved in DCM:TFA (5:1 ratio, 0.2M) and the reaction was stirred for 4 h. The reaction mixture was concentrated by rotary evaporator, followed by suspension in diethyl ether. This suspension was sonicated, followed by concentration by rotary evaporator and further drying for 16 h to afford (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide. LCMS $C_{29}H_4N_9O_2$ requires: 547.7, found: m/z=548.6 [M+H]$^+$.

Example 7: Synthesis of (R)-5-(3-(3-methyl-2-oxoimidazolidin-1-yl)piperidin-1-yl)-3-((1,2,3,4-tetrahydroisoquinolin-6-yl)amino)pyrazine-2-carboxamide

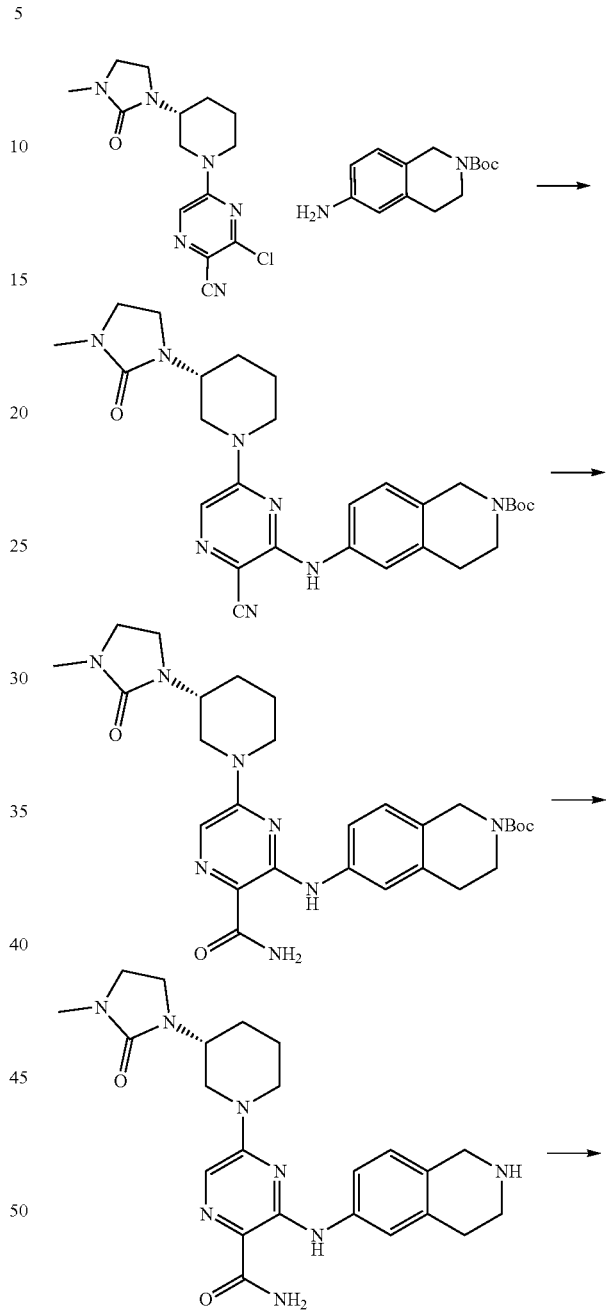

Step 1: tert-butyl (R)-6-((3-cyano-6-(3-(3-methyl-2-oxoimidazolidin-1-yl)piperidin-1-yl)pyrazin-2-yl)amino)-3,4-dihydroisoquinoline-2(1H)-carboxylate (R)-3-chloro-5-(3-(3-methyl-2-oxoimidazolidin-1-yl)piperidin-1-yl)pyrazine-2-carbonitrile, aniline, Pd(OAc)$_2$ (0.15 eq), BINAP (0.15 eq), and cesium carbonate (2 eq) were combined in a microwave tube, followed by addition of dioxane (0.25 M). Nitrogen was bubbled through for 30 seconds, followed by capping. Heating to 90° C., followed by maintaining that temperature for 3 h provided a dark reaction mixture which was monitored by LCMS. The reaction was then cooled, and filtered through Celite, washing with ethyl acetate/methanol. The crude material was loaded onto silica and chromatographed (silica, 0-10% methanol in DCM), to provide tert-butyl (R)-6-((3-cyano-6-(3-(3-methyl-2-oxoimidazolidin-1-yl)piperidin-1-yl)pyrazin-2-yl)amino)-3,4-dihydroisoquinoline-2(1H)-carboxylate. LCMS $C_{28}H_{36}N_8O_3$ requires: 532.7, found: m/z=533.5 [M+H]$^+$.

Step 2: tert-butyl (R)-6-((3-carbamoyl-6-(3-(3-methyl-2-oxoimidazolidin-1-yl)piperidin-1-yl)pyrazin-2-yl)amino)-3,4-dihydroisoquinoline-2(1H)-carboxylate Tert-butyl (R)-6-((3-cyano-6-(3-(3-methyl-2-oxoimidazolidin-1-yl)piperidin-1-yl)pyrazin-2-yl)amino)-3,4-dihydroisoquinoline-2(1H)-carboxylate was dissolved in methanol/DMSO (10:1) and a pellet of NaOH was added. The reaction was stirred for 5 minutes, followed by addition of 35% peroxide solution (2 mL of solution per mmol of reactant). This reaction mixture was stirred for 3 h, then partitioned between ethyl acetate and water. The organic layer was separated and dried over magnesium sulfate. Chromatography (0-10% methanol in DCM) provided tert-butyl (R)-6-((3-carbamoyl-6-(3-(3-methyl-2-oxoimidazolidin-1-yl)piperidin-1-yl)pyrazin-2-yl)amino)-3,4-dihydroisoquinoline-2(1H)-carboxylate (18% over 2 steps). LCMS $C_{28}H_{38}N_8O_4$ requires: 550.7, found: m/z=551.7 [M+H]$^+$.

Step 3: (R)-5-(3-(3-methyl-2-oxoimidazolidin-1-yl)piperidin-1-yl)-3-((1,2,3,4-tetrahydroisoquinolin-6-yl)amino)pyrazine-2-carboxamide Tert-butyl (R)-6-((3-carbamoyl-6-(3-(3-methyl-2-oxoimidazolidin-1-yl)piperidin-1-yl)pyrazin-2-yl)amino)-3,4-dihydroisoquinoline-2(1H)-carboxylate was dissolved in DCM:TFA (5:1 ratio, 0.2M) and the reaction was stirred for 4 h. The reaction mixture was concentrated by rotary evaporator, followed by suspension in diethyl ether. This suspension was sonicated, followed by concentration by rotary evaporator and further drying for 16 h, then used in the next step. LCMS $C_{23}H_{30}N_8O_2$ requires: 450.5, found: m/z=451 [M+H]$^+$.

Example 8: Synthesis of (R)-3-((2-(azetidin-3-yl)-1,2,3,4-tetrahydroisoquinolin-6-yl)amino)-5-(3-(3-methyl-2-oxoimidazolidin-1-yl)piperidin-1-yl)pyrazine-2-carboxamide

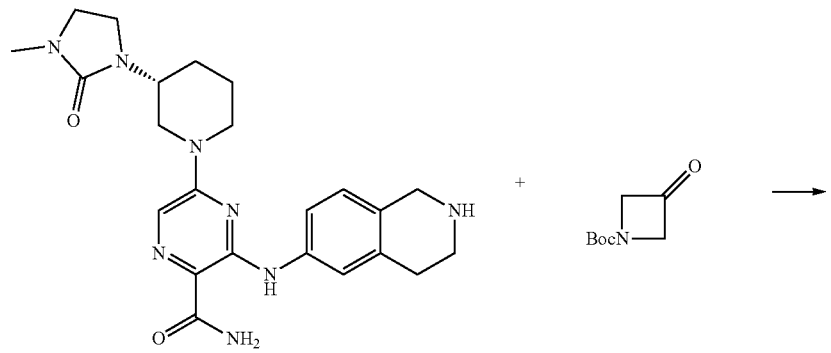

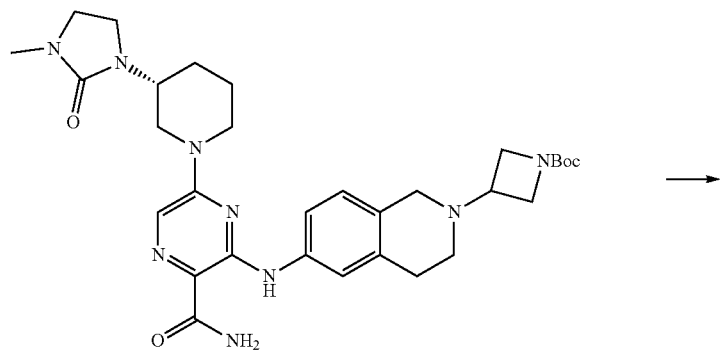

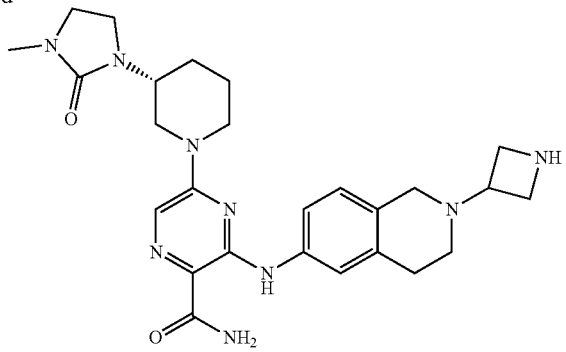

Step 1: tert-butyl (R)-3-(6-((3-carbamoyl-6-(3-(3-methyl-2-oxoimidazolidin-1-yl)piperidin-1-yl)pyrazin-2-yl)amino)-3,4-dihydroisoquinolin-2(1H)-yl)azetidine-1-carboxylate (R)-5-(3-(3-methyl-2-oxoimidazolidin-1-yl)piperidin-1-yl)-3-((1,2,3,4-tetrahydroisoquinolin-6-yl)amino)pyrazine-2-carboxamide was combined with tert-butyl 3-oxoazetidine-1-carboxylate (1 equiv) and stirred in a solution of DCE and TEA (10:1, 0.1M) for 5 minutes. Sodium triacetoxyborohydride (5 equiv.) was then added, and the reaction was stirred at room temperature for 5 h. The reaction was then partitioned between ethyl acetate and water. The organic layer was separated, washed with brine, dried over magnesium sulfate, and filtered to afford tert-butyl (R)-3-(6-((3-carbamoyl-6-(3-(3-methyl-2-oxoimidazolidin-1-yl)piperidin-1-yl)pyrazin-2-yl)amino)-3,4-dihydroisoquinolin-2(1H)-yl)azetidine-1-carboxylate (90% yield). LCMS $C_{31}H_{43}N_9O_4$ requires: 605, found: m/z=606 [M+H]$^+$.

Step 2: (R)-3-((2-(azetidin-3-yl)-1,2,3,4-tetrahydroisoquinolin-6-yl)amino)-5-(3-(3-methyl-2-oxoimidazolidin-1-yl)piperidin-1-yl)pyrazine-2-carboxamide Tert-butyl (R)-3-(6-((3-carbamoyl-6-(3-(3-methyl-2-oxoimidazolidin-1-yl)piperidin-1-yl)pyrazin-2-yl)amino)-3,4-dihydroisoquinolin-2(1H)-yl)azetidine-1-carboxylate was dissolved in DCM:TFA (5:1 ratio, 0.2M) and the reaction was stirred for 4 h. The reaction mixture was concentrated followed by suspension in diethyl ether. This suspension was sonicated, followed by concentration and drying for 16 h to afford (R)-3-((2-(azetidin-3-yl)-1,2,3,4-tetrahydroisoquinolin-6-yl)amino)-5-(3-(3-methyl-2-oxoimidazolidin-1-yl)piperidin-1-yl)pyrazine-2-carboxamide (95% yield). LCMS $C_{26}H_{35}N_9O_2$ requires: 505, found: m/z=506 [M+H]$^+$.

Example 9: Synthesis of (R)-3-((4-(1-(azetidin-3-yl)piperidin-4-yl)phenyl)amino)-5-(3-(3-methyl-2-oxoimidazolidin-1-yl)piperidin-1-yl)pyrazine-2-carboxamide

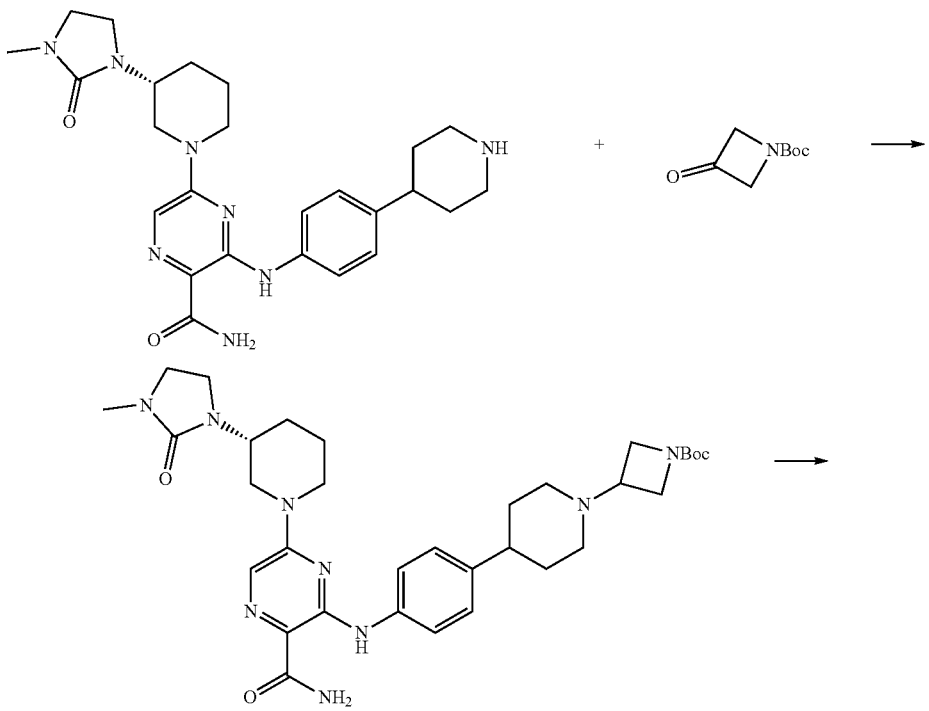

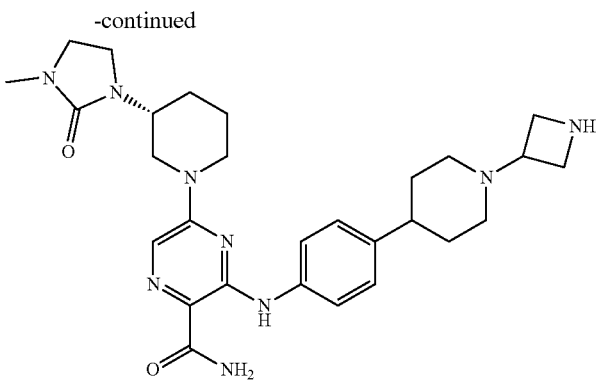

The amine intermediate was combined with tert-butyl 3-oxoazetidine-1-carboxylate (1 equiv.) and stirred in a solution of DCE and TEA (10:1, 0.1M) for 5 min. Sodium triacetoxyborohydride (5 equiv.) was then added, and the reaction was stirred at room temperature for 5 h. The reaction was then partitioned between ethyl acetate and water. The organic layer was separated, washed with brine, then dried over magnesium sulfate and filtered. The crude intermediate was then dissolved in DCM:TFA (5:1 ratio, 0.2M) and the reaction was stirred for 4 h. The reaction mixture was concentrated by rotary evaporator, followed by suspension in diethyl ether. This suspension was sonicated, followed by concentration by rotary evaporator and further drying for 16 h to afford tert-butyl 3-oxoazetidine-1-carboxylate (95% over 2 steps). LCMS $C_{41}H_{47}N_{11}O_6$ requires: 789.9, found: m/z=790.7 $[M+H]^+$.

Example 10: Synthesis of (R)-3-((3-aminophenyl)amino)-5-(3-(3-methyl-2-oxoimidazolidin-1-yl)piperidin-1-yl)pyrazine-2-carboxamide Step 1: tert-butyl (R)-(3-((3-cyano-6-(3-(3-methyl-2-oxoimidazolidin-1-yl)piperidin-1-yl)pyrazin-2-yl)amino)phenyl)carbamate (R)-3-chloro-5-(3-(3-methyl-2-oxoimidazolidin-1-yl)piperidin-1-yl)pyrazine-2-carbonitrile, tert-butyl (3-aminophenyl)carbamate (1 equiv.), $Pd(OAc)_2$ (0.15 equiv.), BINAP (0.15 equiv.), and cesium carbonate (2 equiv.) were combined in a microwave tube, followed by addition of dioxane (0.25 M). Nitrogen was bubbled through for 30 seconds, followed by capping. The mixture was allowed to stir at 90° C. for 3 h. The reaction was then cooled, and filtered through Celite, washing with ethyl acetate/methanol. The crude material was purified by MPLC (0-10% MeOH in $CH_2Cl_2$) to afford tert-butyl (R)-(3-((3-cyano-6-(3-(3-methyl-2-oxoimidazolidin-1-yl)piperidin-1-yl)pyrazin-2-yl)amino)phenyl)carbamate (45% yield). LCMS $C_{25}H_{32}N_8O_3$ requires: 492.6, found: m/z=493.6 $[M+H]^+$.

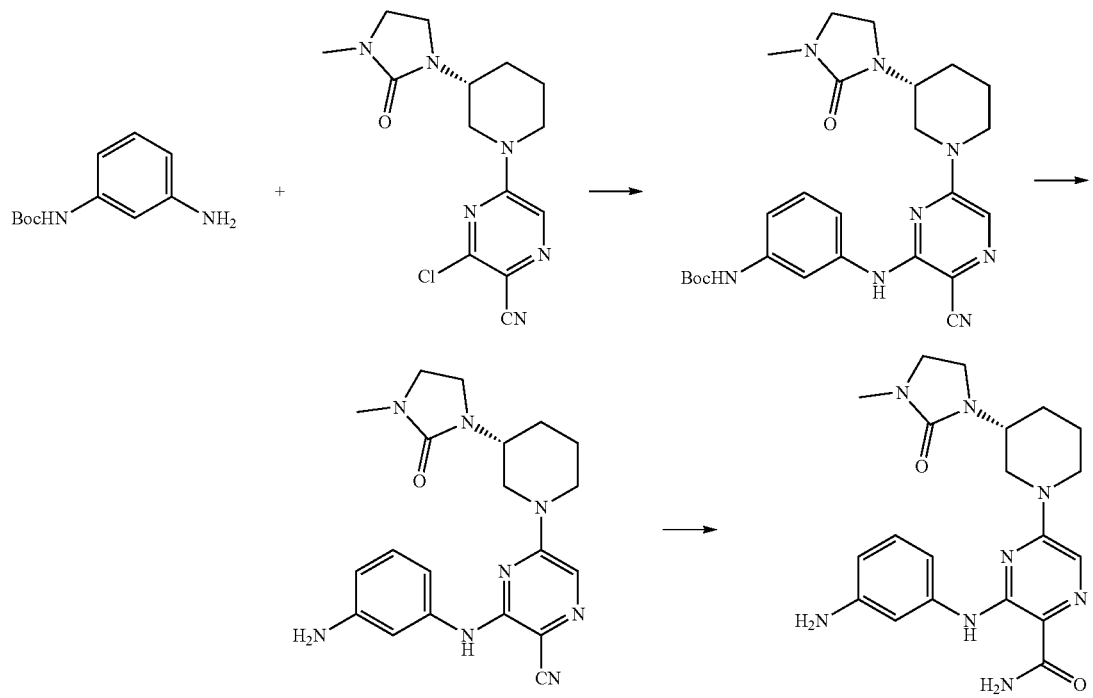

Step 2: (R)-3-((3-aminophenyl)amino)-5-(3-(3-methyl-2-oxoimidazolidin-1-yl)piperidin-1-yl)pyrazine-2-carbonitrile Tert-butyl (R)-(3-((3-cyano-6-(3-(3-methyl-2-oxoimidazolidin-1-yl)piperidin-1-yl)pyrazin-2-yl)amino)phenyl)carbamate was dissolved in DCM:TFA (5:1 ratio, 0.2M) and the reaction was stirred for 4 h. The reaction mixture was concentrated by rotary evaporator, followed by suspension in diethyl ether. This suspension was sonicated, followed by concentration by rotary evaporator and further drying for 16 h to afford (R)-3-((3-aminophenyl)amino)-5-(3-(3-methyl-2-oxoimidazolidin-1-yl)piperidin-1-yl)pyrazine-2-carbonitrile (100% crude yield). LCMS $C_{20}H_{24}N_8O$ requires: 392.5, found: m/z=393.5 [M+H]$^+$.

Step 3: (R)-3-((3-aminophenyl)amino)-5-(3-(3-methyl-2-oxoimidazolidin-1-yl)piperidin-1-yl)pyrazine-2-carboxamide (R)-3-((3-aminophenyl)amino)-5-(3-(3-methyl-2-oxoimidazolidin-1-yl)piperidin-1-yl)pyrazine-2-carbonitrile was dissolved in methanol/DMSO (10:1) and a pellet of NaOH was added. The reaction was stirred for 5 min, followed by addition of 35% peroxide solution (2 mL of solution per mmol of reactant). This reaction mixture was stirred for 3 h, then partitioned between ethyl acetate and water. The organic layer was separated, dried over magnesium sulfate and concentrated under vacuum, and purified by MPLC (0-10% methanol in DCM) to provide (R)-3-((3-aminophenyl)amino)-5-(3-(3-methyl-2-oxoimidazolidin-1-yl)piperidin-1-yl)pyrazine-2-carboxamide. LCMS $C_{20}H_{26}N_8O_2$ requires: 410.5, found: m/z=411.5 [M+H]$^+$.

Example 11: Synthesis of (R)-3-((4-(3-aminopropoxy)phenyl)amino)-5-(3-(3-methyl-2-oxoimidazolidin-1-yl)piperidin-1-yl)pyrazine-2-carboxamide

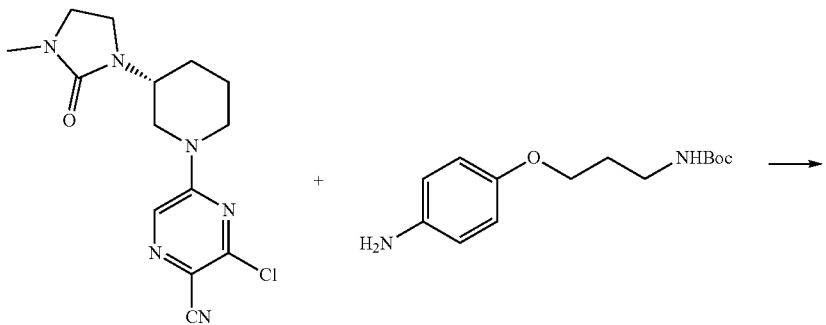

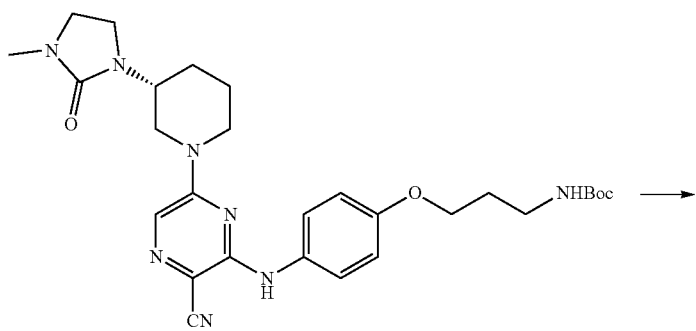

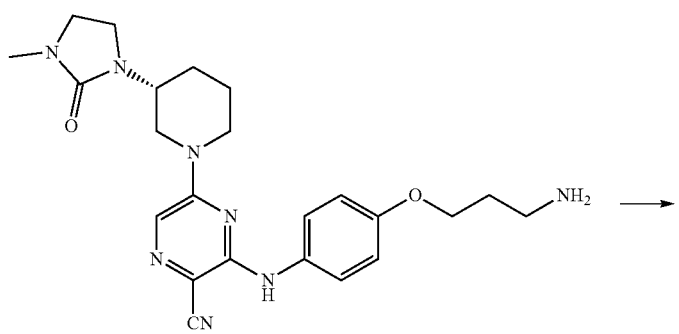

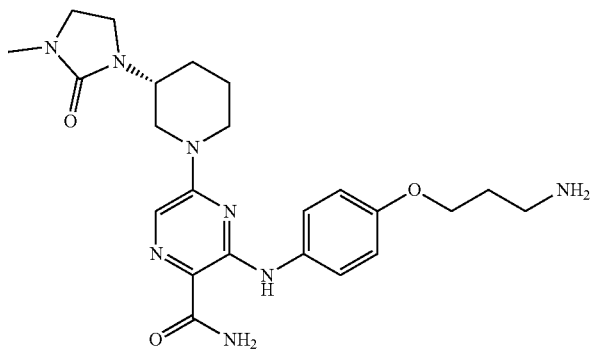

Step 1: tert-butyl (R)-(3-(4-((3-cyano-6-(3-(3-methyl-2-oxoimidazolidin-1-yl)piperidin-1-yl)pyrazin-2-yl)amino)phenoxy)propyl)carbamate (R)-3-chloro-5-(3-(3-methyl-2-oxoimidazolidin-1-yl)piperidin-1-yl)pyrazine-2-carbonitrile, tert-butyl (3-(4-aminophenoxy)propyl)carbamate (1 equiv), Pd(OAc)$_2$ (0.15 equiv), BINAP (0.15 equiv), and cesium carbonate (2 equiv) were combined in a microwave tube, followed by addition of dioxane (0.25 M). Nitrogen was bubbled through for 30 seconds, followed by capping. The mixture was allowed to stir at 90° C. for 3 h. The reaction was then cooled, and filtered through Celite, washing with ethyl acetate/methanol. The crude material was purified by MPLC (0-10% MeOH in CH$_2$Cl$_2$) to afford tert-butyl (R)-(3-(4-((3-cyano-6-(3-(3-methyl-2-oxoimidazolidin-1-yl)piperidin-1-yl)pyrazin-2-yl)amino)phenoxy)propyl)carbamate (52% yield). LCMS C$_{28}$H$_{38}$N$_8$O$_4$ requires: 550, found: m/z=551.7 [M+H]$^+$.

Step 2: (R)-3-((4-(3-aminopropoxy)phenyl)amino)-5-(3-(3-methyl-2-oxoimidazolidin-1-yl)piperidin-1-yl)pyrazine-2-carbonitrile Tert-butyl (R)-(3-(4-((3-cyano-6-(3-(3-methyl-2-oxoimidazolidin-1-yl)piperidin-1-yl)pyrazin-2-yl)amino)phenoxy)propyl)carbamate was dissolved in DCM:TFA (5:1 ratio, 0.2M) and the reaction was stirred for 4 h. The reaction mixture was concentrated by rotary evaporator, followed by suspension in diethyl ether. This suspension was sonicated, followed by concentration by rotary evaporator and further drying for 16 h to afford (R)-3-((4-(3-aminopropoxy)phenyl)amino)-5-(3-(3-methyl-2-oxoimidazolidin-1-yl)piperidin-1-yl)pyrazine-2-carbonitrile (100% crude yield). LCMS C$_{23}$H$_{30}$N$_8$O$_2$ requires: 450.6, found: m/z=451.6 [M+H]$^+$.

Step 3: (R)-3-((4-(3-aminopropoxy)phenyl)amino)-5-(3-(3-methyl-2-oxoimidazolidin-1-yl)piperidin-1-yl)pyrazine-2-carboxamide (R)-3-((4-(3-aminopropoxy)phenyl)amino)-5-(3-(3-methyl-2-oxoimidazolidin-1-yl)piperidin-1-yl)pyrazine-2-carbonitrile was dissolved in methanol/DMSO (10:1) and a pellet of NaOH was added. The reaction was stirred for 5 minutes, followed by addition of 35% peroxide solution (2 mL of solution per mmol of reactant). This reaction mixture was stirred for 3h, then partitioned between ethyl acetate and water. The organic layer was separated, dried over magnesium sulfate and concentrated under vacuum, and purified by MPLC (0-10% methanol in DCM) to provide (R)-3-((4-(3-aminopropoxy)phenyl)amino)-5-(3-(3-methyl-2-oxoimidazolidin-1-yl)piperidin-1-yl)pyrazine-2-carboxamide (77% yield). LCMS C$_{23}$H$_{32}$N$_8$O$_3$ requires: 468.6, found: m/z=469.6 [M+H]$^+$.

Example 12: General Synthetic Scheme for Examples 12A-12G

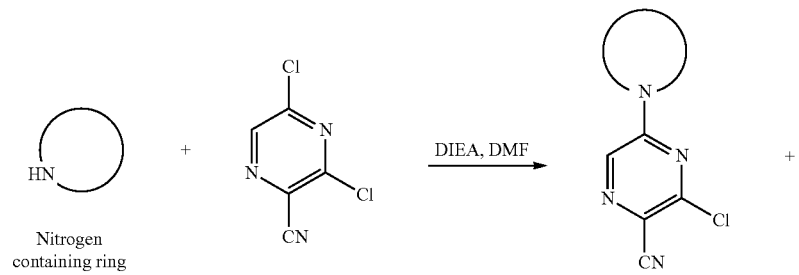

Formula P$^1$

-continued

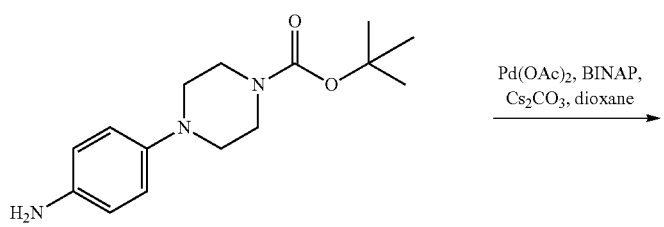

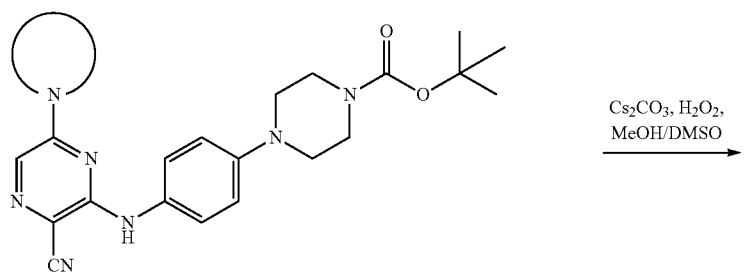

Formula P²

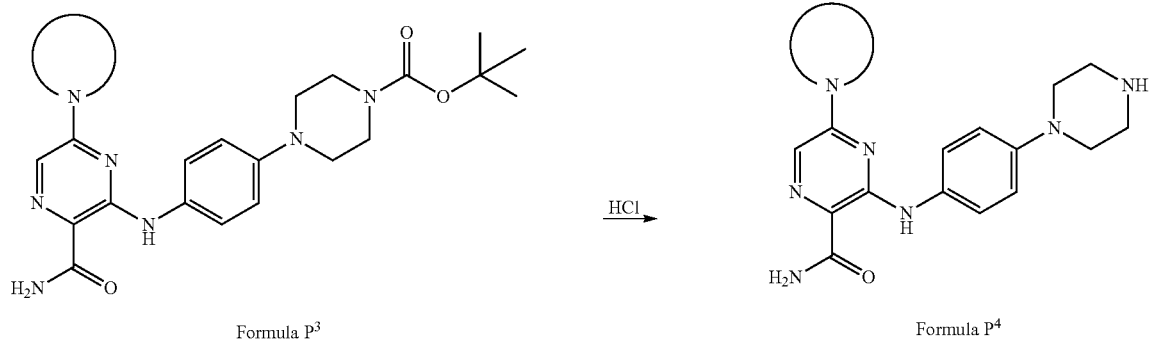

Formula P³  Formula P⁴

Step 1: Coupling of a Nitrogen Containing Ring to Provide a Compound of Formula P¹

In a typical synthesis, a mixture of 3,5-dichloropyrazine-2-carbonitrile (~1 eq.), a cyclic compound containing a ring nitrogen (~1 eq.), ethylbis(propan-2-yl)amine (~2 eq.) and a polar aprotic solvent such as DMF was allowed to stir at r.t. for 2 h. An organic solvent such as EtOAc was then added to the reaction mixture, and then washed with water. The organic layer was dried with MgSO₄, filtered, concentrated and purified by a procedure such as crystallization or MPLC (0-100% EtOAc in hexanes) to afford the purified product.

Step 2: Coupling of the Aniline Derivative to Provide a Compound of Formula P²

In a typical synthesis, a mixture of a compound of Formula P¹ (~1 eq.), tert-butyl 4-(4-aminophenyl)piperazine-1-carboxylate (~1 eq.), Pd(OAc)₂ (~0.3 eq.), BINAP (~0.3 eq.) and Cs₂CO₃ (~3 eq.) was degassed and backfilled with N₂ 5 times. The mixture was allowed to stir at about 100° C. for about 90 min. The mixture was filtered, e.g. filtered through celite, the cake was washed with a solvent system such as MeOH/EtOAc. The crude product was then concentrated and purified using a technique such as crystallization or MPLC.

Step 3: Conversion of the Cyano Group to Acetamide to Produce a Compound of Formula P³

H₂O₂ (30% in water; ~0.17 eq.) was added to a mixture of a compound of Formula P² (~1 eq.), Cs₂CO₃ (~1 eq.), and a mixture of 36:1 MeOH:DMSO as the solvent. The mixture was allowed to stir at r.t. for about 30 min. The mixture was concentrated and diluted with an organic solvent such as EtOAc, and the organic phase was washed with water, and then brine. The organic layer was further dried with MgSO₄, filtered, concentrated and purified using a technique such as crystallization or MPLC.

Step 4: Removal of the BOC Group to Provide a Compound of Formula P⁴

In a typical synthesis, a mixture of a compound of Formula P³ was dissolved in a 2.5:1 mixture of 4M hydrogen chloride in dioxane to THF, and was allowed to stir at r.t. for 2 h. The volatiles were removed to afford the product.

Example 12A: Synthesis of 3-((4-(piperazin-1-yl)phenyl)amino)-5-(piperidin-1-yl)pyrazine-2-carboxamide

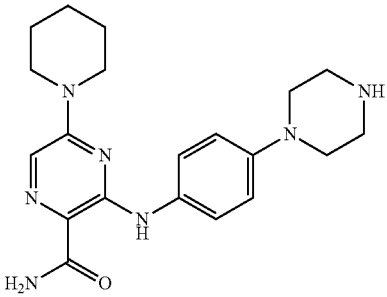 [SMILES: NC(=O)c1ncc(N2CCCCC2)nc1Nc1ccc(N2CCNCC2)cc1]

Step 1: 3-chloro-5-(piperidin-1-yl)pyrazine-2-carbonitrile

A mixture of 3,5-dichloropyrazine-2-carbonitrile (850 mg, 4.89 mmol), piperidine (0.48 mL, 4.89 mmol), ethylbis(propan-2-yl)amine (1.70 mL, 9.77 mmol) and DMF (20 mL) was allowed to stir at r.t. for 2 h. EtOAc and H2O were added. The organic layer was dried with $MgSO_4$, filtered, concentrated and purified by MPLC (0-100% EtOAc in hexanes) to afford 3-chloro-5-(piperidin-1-yl)pyrazine-2-carbonitrile (1079.6 mg, 99.2%). LCMS: $C_{10}H_{11}ClN_4$ requires: 222, found: m/z=223 $[M+H]^+$.

Step 2: tert-butyl 4-(4-{[3-cyano-6-(piperidin-1-yl)pyrazin-2-yl]amino}phenyl)piperazine-1-carboxylate A mixture of 3-chloro-5-(piperidin-1-yl)pyrazine-2-carbonitrile (534 mg, 2.40 mmol), tert-butyl 4-(4-aminophenyl)piperazine-1-carboxylate (665 mg, 2.40 mmol), $Pd(OAc)_2$ (177 mg, 0.79 mmol), BINAP (493 mg, 0.79 mmol) and $Cs_2CO_3$ (2345 mg, 7.20 mmol) was degassed and backfilled with $N_2$ 5 times. The mixture was allowed to stir at 100° C. for 90 min. The mixture was filtered through celite washing with MeOH/EtOAc, concentrated and purified by MPLC (0-100% EtOAc in $CH_2Cl_2$) to afford tert-butyl 4-(4-{[3-cyano-6-(piperidin-1-yl)pyrazin-2-yl]amino}phenyl)piperazine-1-carboxylate (833 mg, 74.9%). LCMS: $C_{25}H_{33}N_7O_2$ requires: 463, found: m/z=464 $[M+H]^+$.

Step 3: tert-butyl 4-(4-((3-carbamoyl-6-(piperidin-1-yl)pyrazin-2-yl)amino)phenyl)piperazine-1-carboxylate $H_2O_2$ (30% in water, 3.03 mL, 0.30 mmol) was added to a mixture of tert-butyl 4-(4-{[3-cyano-6-(piperidin-1-yl)pyrazin-2-yl]amino}phenyl)piperazine-1-carboxylate (833 mg, 1.80 mmol), $Cs_2CO_3$ (586 mg, 1.80 mmol), MeOH (35 mL) and DMSO (1 mL). The mixture was allowed to stir at r.t. for 30 min. The mixture was concentrated. EtOAc was added and the organic phase was washed with $H_2O$ and brine. The organic layer was dried with $MgSO_4$, filtered, concentrated and purified by MPLC (0-10% MeOH in $CH_2Cl_2$) to afford tert-butyl 4-(4-((3-carbamoyl-6-(piperidin-1-yl)pyrazin-2-yl)amino)phenyl)piperazine-1-carboxylate (809 mg, 93.5%). LCMS: $C_{25}H_{35}N_7O_3$ requires: 481, found: m/z=482 $[M+H]^+$.

Step 4: 3-{[4-(piperazin-1-yl)phenyl]amino}-5-(piperidin-1-yl)pyrazine-2-carboxamide A mixture of tert-butyl 4-(4-{[3-carbamoyl-6-(piperidin-1-yl)pyrazin-2-yl]amino}phenyl)piperazine-1-carboxylate (20 mg, 0.04 mmol), hydrogen chloride (4M in dioxane, 0.26 mL, 1.04 mmol) and THF (0.1 mL) was allowed to stir at r.t. for 2 h. The volatiles were removed to afford 3-{[4-(piperazin-1-yl)phenyl]amino}-5-(piperidin-1-yl)pyrazine-2-carboxamide (15 mg, 95%). LCMS: $C_{20}H_{27}N7O$ requires: 381, found: m/z=382 $[M+H]^+$.

Example 12B: Synthesis of (R)-5-(3-(hydroxymethyl)piperidin-1-yl)-3-((4-(piperidin-4-yl)phenyl)amino)pyrazine-2-carboxamide

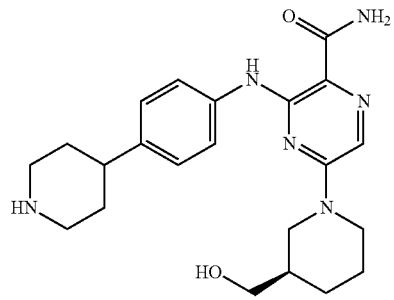 [SMILES: NC(=O)c1ncc(N2CCC[C@@H](CO)C2)nc1Nc1ccc(C2CCNCC2)cc1]

Step 1

(R)-3-chloro-5-(3-(hydroxymethyl)piperidin-1-yl)pyrazine-2-carbonitrile using (R)-piperidin-3-ylmethanol as the amine. LCMS $C_{11}H_{13}ClN_4O$ requires: 252 found: m/z=253 $[M+H]^+$.

Step 2 tert-butyl (R)-4-(4-((3-cyano-6-(3-(hydroxymethyl)piperidin-1-yl)pyrazin-2-yl)amino)phenyl)piperidine-1-carboxylate. LCMS: $C_{27}H_{36}N_6O_3$ requires: 492 found: m/z=493 $[M+H]^+$.

Step 3 tert-butyl (R)-4-(4-((3-carbamoyl-6-(3-(hydroxymethyl)piperidin-1-yl)pyrazin-2-yl)amino)phenyl)piperidine-1-carboxylate. LCMS $C_{27}H_{38}N_6O_4$ requires: 510 found: m/z=511 $[M+H]^+$.

Step 4

(R)-5-(3-(hydroxymethyl)piperidin-1-yl)-3-((4-(piperidin-4-yl)phenyl)amino)pyrazine-2-carboxamide. LCMS $C_{22}H_{30}N_6O_2$ requires: 410 found: m/z=411 $[M+H]^+$.

Example 12C: Synthesis of 5-(4,4-difluoro-3-(hydroxymethyl)piperidin-1-yl)-3-((4-(piperidin-4-yl)phenyl)amino)pyrazine-2-carboxamide

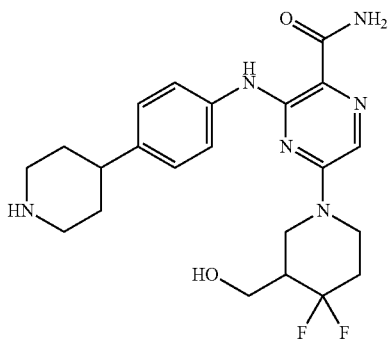 [SMILES: NC(=O)c1ncc(N2CCC(F)(F)C(CO)C2)nc1Nc1ccc(C2CCNCC2)cc1]

Step 1

3-chloro-5-(4,4-difluoro-3-(hydroxymethyl)piperidin-1-yl)pyrazine-2-carbonitrile using (4,4-difluoropiperidin-3-yl)methanol as the amine. LCMS $C_{11}H_{11}ClF_2N_4O$ requires: 288 found: m/z=289 [M+H]$^+$.

Step 2 tert-butyl 4-(4-((3-cyano-6-(4,4-difluoro-3-(hydroxymethyl)piperidin-1-yl)pyrazin-2-yl)amino)phenyl)piperidine-1-carboxylate. LCMS $C_{27}H_{34}F_2N_6O_3$ requires: 528 found: m/z=529 [M+H]$^+$.

Step 3 tert-butyl 4-(4-((3-carbamoyl-6-(4,4-difluoro-3-(hydroxymethyl)piperidin-1-yl)pyrazin-2-yl)amino)phenyl)piperidine-1-carboxylate. LCMS $C_{27}H_{36}F_2N_6O_4$ requires: 546 found: m/z=547 [M+H]$^+$.

Step 4

5-(4,4-difluoro-3-(hydroxymethyl)piperidin-1-yl)-3-((4-(piperidin-4-yl)phenyl)amino)pyrazine-2-carboxamide. LCMS $C_{22}H_{28}F_2N_6O_2$ requires: 446 found: m/z=447 [M+H]$^+$.

Example 12D: Synthesis of 3-((4-(piperidin-4-yl)phenyl)amino)-5-(2-oxa-6-azaspiro[3.5]nonan-6-yl)pyrazine-2-carboxamide

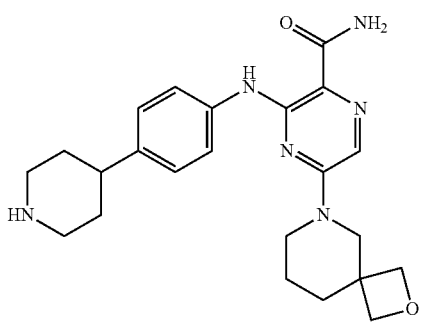 [SMILES: NC(=O)c1ncc(N2CCCC3(COC3)C2)nc1Nc1ccc(C2CCNCC2)cc1]

Step 1

3-chloro-5-(2-oxa-6-azaspiro[3.5]nonan-6-yl)pyrazine-2-carbonitrile using 2-oxa-6-azaspiro[3.5]nonane as the amine. LCMS $C_{12}H_{13}ClN_4O$ requires: 264 found: m/z=265 [M+H]$^+$.

Step 2 tert-butyl 4-(4-((3-cyano-6-(2-oxa-6-azaspiro[3.5]nonan-6-yl)pyrazin-2-yl)amino)phenyl)piperidine-1-carboxylate. LCMS $C_{28}H_{36}N_6O_3$ requires: 504 found: m/z=505 [M+H]$^+$.

Step 3 tert-butyl 4-(4-((3-carbamoyl-6-(2-oxa-6-azaspiro[3.5]nonan-6-yl)pyrazin-2-yl)amino)phenyl)piperidine-1-carboxylate. LCMS $C_{28}H_{38}N_6O_4$ requires: 522 found: m/z=523 [M+H]$^+$.

Step 4

3-((4-(piperidin-4-yl)phenyl)amino)-5-(2-oxa-6-azaspiro[3.5]nonan-6-yl)pyrazine-2-carboxamide. LCMS $C_{23}H_{30}N_6O_2$ requires: 422 found: m/z=423 [M+H]$^+$.

Example 12E: Synthesis of 3-((4-(piperidin-4-yl)phenyl)amino)-5-(2-oxa-6-azaspiro[3.4]octan-6-yl)pyrazine-2-carboxamide

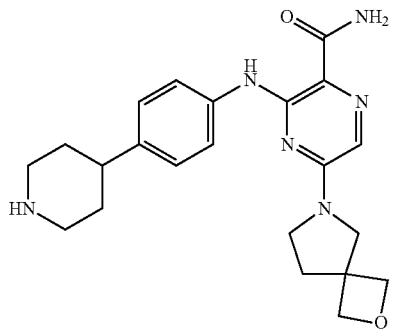 [SMILES: NC(=O)c1ncc(N2CCC3(COC3)C2)nc1Nc1ccc(C2CCNCC2)cc1]

Step 1

3-chloro-5-(2-oxa-6-azaspiro[3.4]octan-6-yl)pyrazine-2-carbonitrile using 2-oxa-6-azaspiro[3.4]octane as the amine. LCMS $C_{11}H_{11}ClN_4O$ requires: 250 found: m/z=251 [M+H]$^+$.

Step 2 tert-butyl 4-(4-((3-cyano-6-(2-oxa-6-azaspiro[3.4]octan-6-yl)pyrazin-2-yl)amino)phenyl)piperidine-1-carboxylate. LCMS $C_{27}H_{34}N_6O_3$ requires: 490 found: m/z=491 [M+H]$^+$.

Step 3 tert-butyl 4-(4-((3-carbamoyl-6-(2-oxa-6-azaspiro[3.4]octan-6-yl)pyrazin-2-yl)amino)phenyl)piperidine-1-carboxylate. LCMS $C_{27}H_{36}N_6O_4$ requires: 508 found: m/z=509 [M+H]$^+$.

Step 4

3-((4-(piperidin-4-yl)phenyl)amino)-5-(2-oxa-6-azaspiro[3.4]octan-6-yl)pyrazine-2-carboxamide. LCMS $C_{22}H_{28}N_6O_2$ requires: 408 found: m/z=409 [M+H]$^+$.

Example 12F: Synthesis of 3-((4-(piperidin-4-yl)phenyl)amino)-5-(1H-pyrazol-1-yl)pyrazine-2-carboxamide

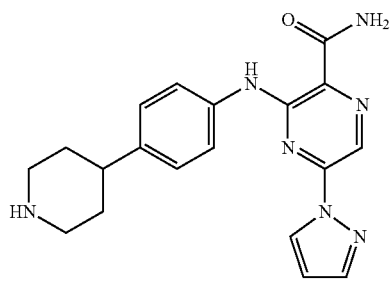 [SMILES: NC(=O)c1ncc(-n2cccn2)nc1Nc1ccc(C2CCNCC2)cc1]

Step 1

3-chloro-5-(1H-pyrazol-1-yl)pyrazine-2-carbonitrile using pyrazole as the amine. LCMS $C_8H_4ClN_5$ requires: 205 found: m/z=206 [M+H]$^+$.

Step 2 tert-butyl 4-(4-((3-cyano-6-(1H-pyrazol-1-yl)pyrazin-2-yl)amino)phenyl)piperidine-1-carboxylate. LCMS $C_{24}H_{27}N_7O_2$ requires: 445 found: m/z=446 [M+H]$^+$.

Step 3 tert-butyl 4-(4-((3-carbamoyl-6-(1H-pyrazol-1-yl)pyrazin-2-yl)amino)phenyl)piperidine-1-carboxylate. LCMS $C_{24}H_{29}N_7O_3$ requires: 463 found: m/z=464 [M+H]$^+$.

Step 4

3-((4-(piperidin-4-yl)phenyl)amino)-5-(1H-pyrazol-1-yl)pyrazine-2-carboxamide. LCMS $C_{19}H_{21}N_7O$ requires: 363 found: m/z=364 [M+H]$^+$.

Example 12G: Synthesis of 3-((4-(piperidin-4-yl)phenyl)amino)-5-(3-(trifluoromethyl)-1H-pyrazol-1-yl)pyrazine-2-carboxamide

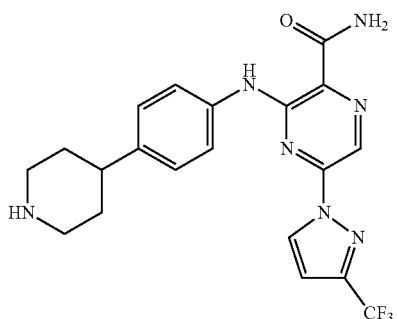

Step 1

3-chloro-5-(3-(trifluoromethyl)-1H-pyrazol-1-yl)pyrazine-2-carbonitrile using 3-trifluoromethylpyrazole as the amine. LCMS $C_9H_3ClF_3N_5$ requires: 273 found: m/z=274 [M+H]$^+$.

Step 2 tert-butyl 4-(4-((3-cyano-6-(3-(trifluoromethyl)-1H-pyrazol-1-yl)pyrazin-2-yl)amino)phenyl)piperidine-1-carboxylate. LCMS $C_{25}H_{26}F_3N_7O_2$ requires: 513 found: m/z=514 [M+H]$^+$.

Step 3 tert-butyl 4-(4-((3-carbamoyl-6-(3-(trifluoromethyl)-1H-pyrazol-1-yl)pyrazin-2-yl)amino)phenyl)piperidine-1-carboxylate. LCMS $C_{25}H_{28}F_3N_7O_3$ requires: 531 found: m/z=532 [M+H]$^+$.

Step 4

3-((4-(piperidin-4-yl)phenyl)amino)-5-(3-(trifluoromethyl)-1H-pyrazol-1-yl)pyrazine-2-carboxamide. LCMS $C_{20}H_{20}F_3N_7O$ requires: 431 found: m/z=432 [M+H]$^+$.

Example 13: Synthesis of (R)-4-((3-carbamoyl-6-(3-(3-methyl-2-oxoimidazolidin-1-yl)piperidin-1-yl)pyrazin-2-yl)amino)benzoic acid

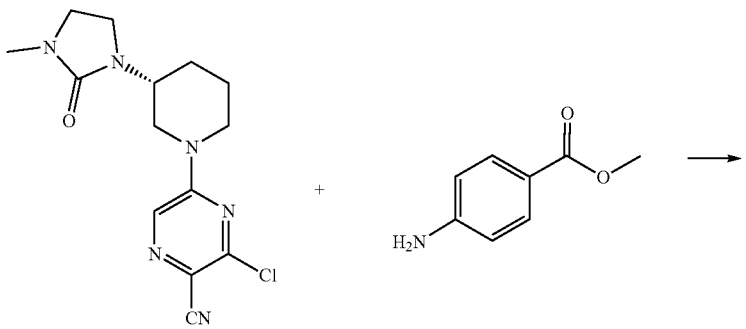

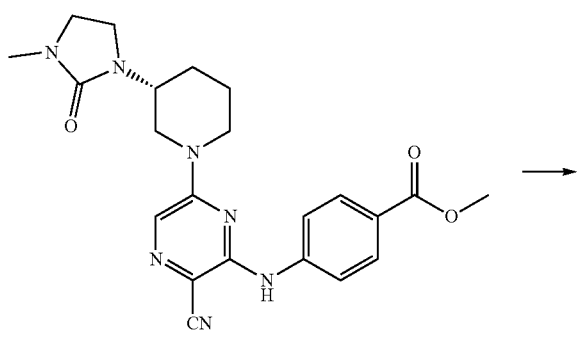
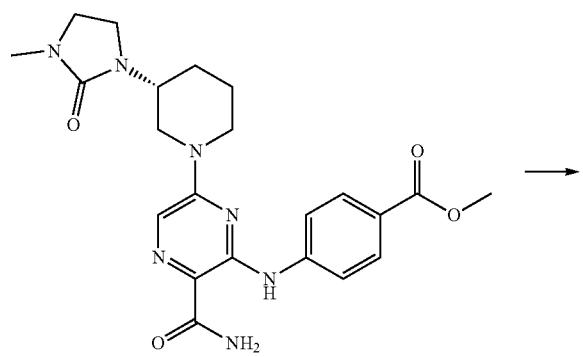

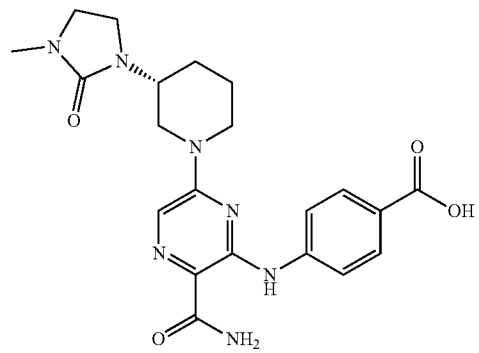

Step 1: methyl (R)-4-((3-cyano-6-(3-(3-methyl-2-oxoimidazolidin-1-yl)piperidin-1-yl)pyrazin-2-yl)amino)benzoate (R)-3-chloro-5-(3-(3-methyl-2-oxoimidazolidin-1-yl)piperidin-1-yl)pyrazine-2-carbonitrile, methyl 4-aminobenzoate (1 equiv.), Pd(OAc)$_2$ (0.15 equiv.), BINAP (0.15 equiv.), and cesium carbonate (2 equiv.) were combined in a microwave tube, followed by addition of dioxane (0.25 M). Nitrogen was bubbled through for 30 seconds, followed by capping. The mixture was allowed to stir at 90° C. for 3 h. The reaction was then cooled, and filtered through Celite, washing with ethyl acetate/methanol. The crude material was purified by MPLC (0-10% MeOH in CH$_2$Cl$_2$) to afford methyl (R)-4-((3-cyano-6-(3-(3-methyl-2-oxoimidazolidin-1-yl)piperidin-1-yl)pyrazin-2-yl)amino)benzoate (74% yield). LCMS C$_{22}$H$_{25}$N$_7$O$_3$ requires: 435.5, found: m/z=436.6 [M+H]$^+$.

Step 2: methyl (R)-4-((3-carbamoyl-6-(3-(3-methyl-2-oxoimidazolidin-1-yl)piperidin-1-yl)pyrazin-2-yl)amino)benzoate Methyl (R)-4-((3-cyano-6-(3-(3-methyl-2-oxoimidazolidin-1-yl)piperidin-1-yl)pyrazin-2-yl)amino)benzoate was dissolved in methanol/DMSO (10:1) and a pellet of NaOH was added. The reaction was stirred for 5 min, followed by addition of 35% peroxide solution (2 mL of solution per mmol of reactant). This reaction mixture was stirred for 3 h, then partitioned between ethyl acetate and water. The organic layer was separated and dried over magnesium sulfate. Chromatography (0-10% methanol in DCM) provided methyl (R)-4-((3-carbamoyl-6-(3-(3-methyl-2-oxoimidazolidin-1-yl)piperidin-1-yl)pyrazin-2-yl)amino)benzoate in 48% yield. LCMS C$_{22}$H$_{27}$N$_7$O$_4$ requires: 453.5, found: m/z=454.6 [M+H]$^+$.

Step 3: (R)-4-((3-carbamoyl-6-(3-(3-methyl-2-oxoimidazolidin-1-yl)piperidin-1-yl)pyrazin-2-yl)amino)benzoic acid Starting material was dissolved in THF (0.1 M) followed by addition of 2N LiOH (aq, 25% by volume of THF). The reaction was stirred at 80° C. for 4 h. The reaction was then poured into ethyl acetate/2N HCl in a separatory funnel. The organic layer was separated, and the aqueous layer was further extracted with methylene chloride/methanol (10%). Both organic layers were dried over magnesium sulfate, filtered, and concentrated to provide (R)-4-((3-carbamoyl-6-(3-(3-methyl-2-oxoimidazolidin-1-yl)piperidin-1-yl)pyrazin-2-yl)amino)benzoic acid (88% yield) with no further purification. LCMS C$_{21}$H$_{25}$N$_7$O$_4$ requires: 439.5, found: m/z=440.6 [M+H]$^+$.

Example 14: General Procedure A

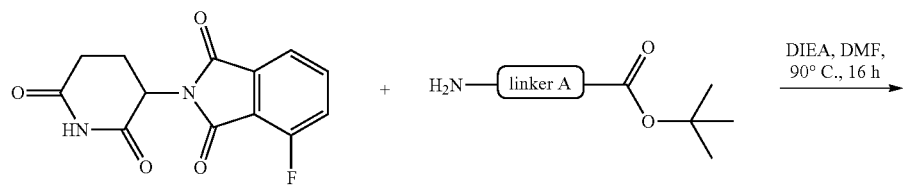

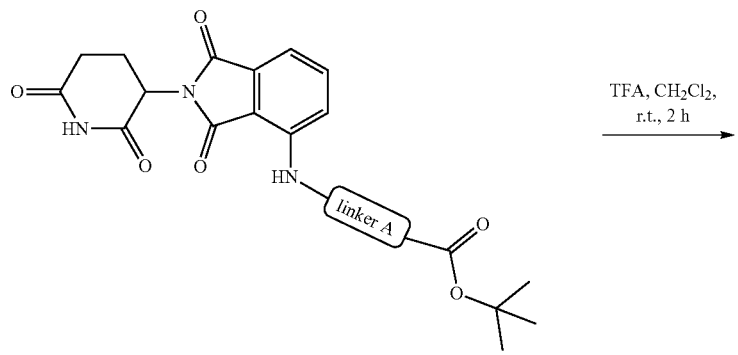

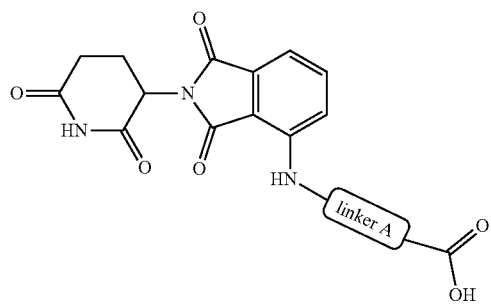

As used in General Procedure A, "linker A" is —$X^2$—$X^3$—$X^4$—$X^5$—, wherein each of $X^2$, $X^3$, $X^4$, and $X^5$ are defined above for the compound of Formula (A).

Step 1

A mixture of 2-(2,6-dioxopiperidin-3-yl)-4-fluoro-2,3-dihydro-1H-isoindole-1,3-dione (0.26 mmol), aminoester (0.26 mmol), ethylbis(propan-2-yl)amine (0.52 mmol) and DMF (1 mL) was allowed to stir at 90° C. overnight. The mixture was cooled and purified by HPLC (5-95% MeCN in H$_2$O with 0.1% TFA) to afford the tert-butylester intermediate.

Step 2

A mixture of tert-butyl 4-{[2-(2,6-dioxopiperidin-3-yl)-1,3-dioxo-2,3-dihydro-1H-isoindol-4-yl]amino}butanoate (0.10 mmol), CH$_2$Cl$_2$ (1 mL), and TFA (1 mL) was allowed to stir at r.t. for 2 h. The mixture was concentrated to afford the carboxylic acid product.

Example 14A: Synthesis of 3-(2-((2-(2,6-dioxopiperidin-3-yl)-1,3-dioxoisoindolin-4-yl)amino)ethoxy)propanoic acid

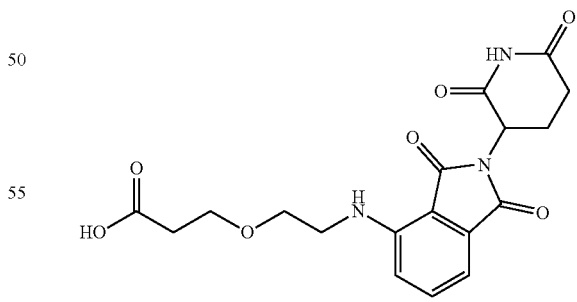

Step 1 Product tert-butyl 3-[2-[[2-(2,6-dioxo-3-piperidyl)-1,3-dioxo-isoindolin-4-yl]amino]ethoxy]propanoate (1.8 g, 51.9%). LCMS; C$_{22}$H$_{27}$N$_3$O$_7$ requires: 445, found: m/z=468 [M+Na]$^+$.

Step 2 Product

3-[2-[[2-(2,6-dioxo-3-piperidyl)-1,3-dioxo-isoindolin-4-yl]amino]ethoxy]propanoic acid (526.8 mg, 32%). LCMS; $C_{18}H_{19}N_3O_7$ requires: 389, found: m/z=390 $[M+H]^+$.

Example 14B: Synthesis of 3-(2-(2-(2-((2-(2,6-dioxopiperidin-3-yl)-1,3-dioxoisoindolin-4-yl)amino)ethoxy)ethoxy)ethoxy)propanoic acid

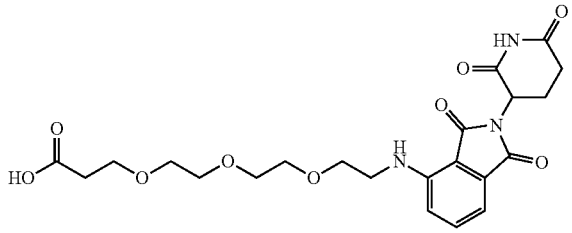 [SMILES: O=C(O)CCOCCOCCOCCNc1cccc2c1C(=O)N(C1CCC(=O)NC1=O)C2=O]

Step 1 Product tert-butyl 3-[2-[2-[2-[[2-(2,6-dioxo-3-piperidyl)-1,3-dioxoisoindolin-4-yl]amino]ethoxy]ethoxy]ethoxy]propanoate (1.6 g, 41%). LCMS; $C_{26}H_{35}N_3O_9$ requires: 533, found: m/z=534 $[M+H]^+$.

Step 2 Product

3-[2-[2-[2-[[2-(2,6-dioxo-3-piperidyl)-1,3-dioxo-isoindolin-4-yl]amino]ethoxy]ethoxy]ethoxy]propanoic acid (1.2 g, 73.62%). LCMS; $C_{22}H_{27}N_3O_9$ requires: 477, found: m/z=478 $[M+H]^+$.

Example 14C: Synthesis of trans-4-((2-(2,6-dioxopiperidin-3-yl)-1,3-dioxoisoindolin-4-yl)amino)cyclohexane-1-carboxylic acid

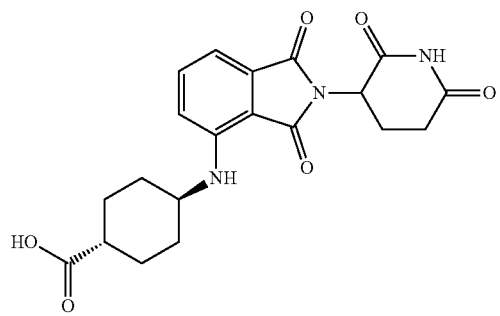 [SMILES: O=C1CCC(N2C(=O)c3cccc(N[C@H]4CC[C@H](C(=O)O)CC4)c3C2=O)C(=O)N1]

Step 1 Product trans-tert-butyl 4-((2-(2,6-dioxopiperidin-3-yl)-1,3-dioxoisoindolin-4-yl)amino)cyclohexane-1-carboxylate (43.40 mg, 47.0%).

Step 2 Product trans-4-((2-(2,6-dioxopiperidin-3-yl)-1,3-dioxoisoindolin-4-yl)amino)cyclohexane-1-carboxylic acid (38 mg, 99%).

Example 14D: Synthesis of 3-(3-((2-(2,6-dioxopiperidin-3-yl)-1-oxoisoindolin-4-yl)amino)-3-oxopropoxy)propanoic acid

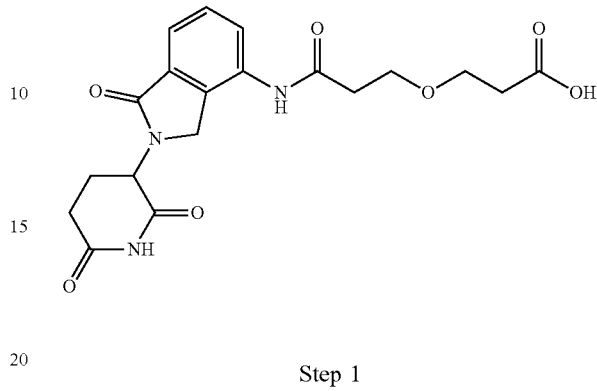

Step 1

A mixture of lenalidomide (270 mg, 1.04 mmol), 3-[3-(tert-butoxy)-3-oxopropoxy]propanoic acid (250 mg, 1.15 mmol), HATU (515 mg, 1.35 mmol), ethylbis(propan-2-yl)amine (0.73 mL, 4.17 mmol) and DMF (5 mL) was allowed to stir at rt for 6 h. EtOAc and $H_2O$ were added. The organic layer was dried with $MgSO_4$, filtered, concentrated and purified by MPLC (20-100% EtOAc in hexanes) to afford tert-butyl 3-(2-{[2-(2,6-dioxopiperidin-3-yl)-1-oxo-3H-isoindol-4-yl]carbamoyl}ethoxy)propanoate (307 mg, 64%). LCMS: $C_{23}H_{29}N_3O_7$ requires: 459, found: m/z=460 $[M+H]^+$.

Step 2

A mixture of tert-butyl 3-(2-{[2-(2,6-dioxopiperidin-3-yl)-1-oxo-3H-isoindol-4-yl]carbamoyl}ethoxy)propanoate (307 mg, 0.67 mmol), $CH_2Cl_2$ (5 mL), and TFA (1 mL) was allowed to stir at r.t. for 2 h. The mixture was concentrated to afford 3-(3-((2-(2,6-dioxopiperidin-3-yl)-1-oxoisoindolin-4-yl)amino)-3-oxopropoxy)propanoic acid (269 mg, 99%). LCMS: $C_{19}H_{21}N_3O_7$ requires: 403, found: m/z=404 $[M+H]^+$.

Example 15: General Procedure B

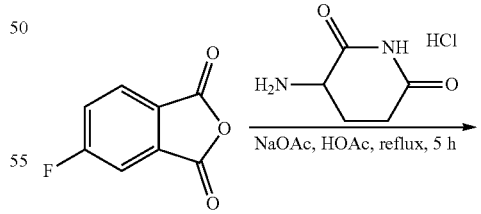

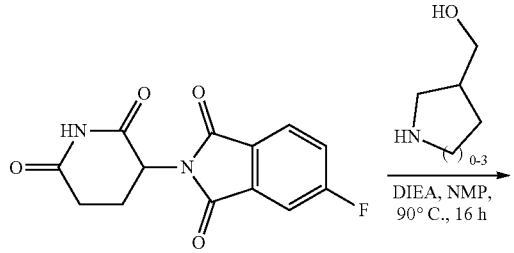

373

-continued

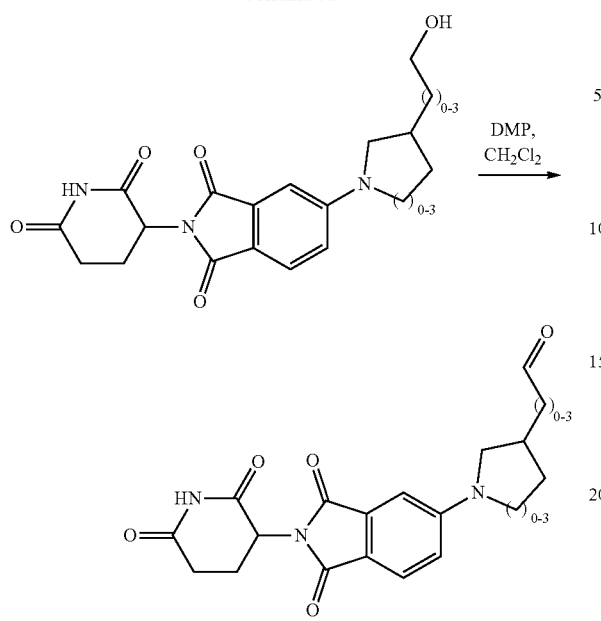

Step 1: 2-(2,6-dioxopiperidin-3-yl)-5-fluoroisoindoline-1,3-dione

A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol) and NaOAc (4.2 g, 51.17 mmol) in HOAc (50 mL) was stirred at 120° C. for 5 h before concentrated under vacuum. The residue was washed with water and the solid was collected by filtration. The crude product was washed with water twice and ethyl acetate twice and dried under oven to afford 2-(2,6-dioxopiperidin-3-yl)-5-fluoroisoindoline-1,3-dione (7.7 g, 92%) as a light brown solid. $^1$H NMR (300 MHz, DMSO-$d_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H). F NMR (300 MHz, DMSO-$d_6$) δ −102.078.

Step 2: Amine Displacement of Aryl Fluoride

To a solution of 2-(2,6-dioxopiperidin-3-yl)-5-fluoro-2,3-dihydro-1H-isoindole-1,3-dione (1.0 g, 3.62 mmol) in N-Methyl pyrrolidone (10 mL) were added the amine (3.60 mmol) and DIEA (1.4 g, 10.83 mmol). The resulting solution was stirred at 80° C. for 16 h. The reaction mixture was cooled down to room temperature and purified by reverse phase flash chromatography to afford the corresponding final product.

Step 3: Alcohol Oxidation to the Aldehyde

To a mixture of the alcohol (1.06 mmol) in CH$_2$Cl$_2$ (10 mL) was added Dess-Martin periodinane (2.12 mmol). The mixture was allowed to stir at room temperature for 1 h. The mixture was purified by column chromatography to afford the desired aldehyde.

374

Example 15A: Synthesis of 2-(1-(2-(2,6-dioxopiperidin-3-yl)-1,3-dioxoisoindolin-5-yl)piperidin-4-yl)acetaldehyde

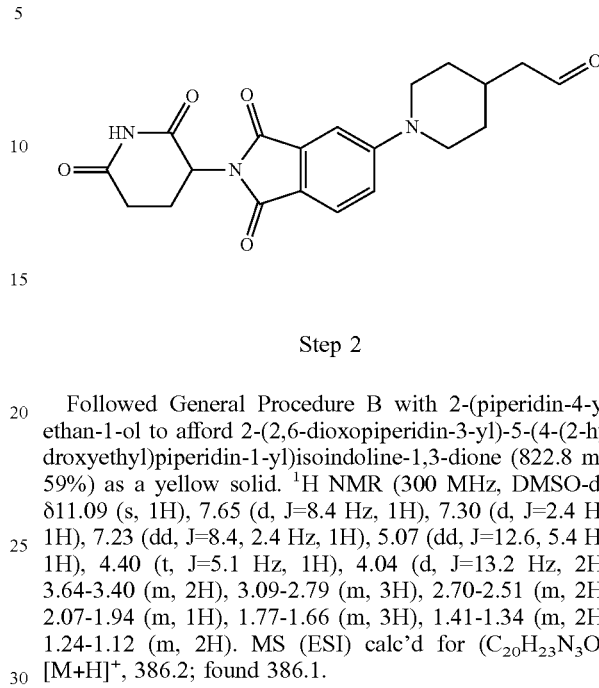

Step 2

Followed General Procedure B with 2-(piperidin-4-yl)ethan-1-ol to afford 2-(2,6-dioxopiperidin-3-yl)-5-(4-(2-hydroxyethyl)piperidin-1-yl)isoindoline-1,3-dione (822.8 mg, 59%) as a yellow solid. $^1$H NMR (300 MHz, DMSO-$d_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.40 (t, J=5.1 Hz, 1H), 4.04 (d, J=13.2 Hz, 2H), 3.64-3.40 (m, 2H), 3.09-2.79 (m, 3H), 2.70-2.51 (m, 2H), 2.07-1.94 (m, 1H), 1.77-1.66 (m, 3H), 1.41-1.34 (m, 2H), 1.24-1.12 (m, 2H). MS (ESI) calc'd for (C$_{20}$H$_{23}$N$_3$O$_5$) [M+H]$^+$, 386.2; found 386.1.

Step 3

2-(1-(2-(2,6-dioxopiperidin-3-yl)-1,3-dioxoisoindolin-5-yl)piperidin-4-yl)acetaldehyde LCMS C$_{20}$H$_{21}$N$_3$O$_5$ requires: 383, found: m/z=384 [M+H]$^+$.

Example 15B: Synthesis of 1-(2-(2,6-dioxopiperidin-3-yl)-1,3-dioxoisoindolin-5-yl)azetidine-3-carbaldehyde

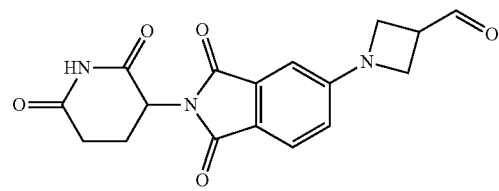 [SMILES: O=CC1CN(c2ccc3c(c2)C(=O)N(C2CCC(=O)NC2=O)C3=O)C1]

Step 2

Followed General Procedure B with azetidin-3-ylmethanol hydrochloride to afford 2-(2,6-dioxopiperidin-3-yl)-5-(3-(hydroxymethyl)azetidin-1-yl)isoindoline-1,3-dione (1.85 g, 68%) as a yellow solid. $^1$H NMR (400 MHz, DMSO-$d_6$) δ 11.09 (s, 1H), 7.63 (d, J=8.4 Hz, 1H), 6.76 (d, J=2.0 Hz, 1H), 6.62 (dd, J=8.4, 2.0 Hz, 1H), 5.06 (dd, J=12.4, 5.2 Hz, 1H), 4.86 (t, J=5.2 Hz, 1H), 4.05 (t, J=8.4 Hz, 2H), 3.77 (dd, J=8.4, 5.2 Hz, 2H), 3.60 (t, J=5.2 Hz, 2H), 3.00-2.81 (m, 2H), 2.65-2.53 (m, 2H), 2.06-1.96 (m, 1H). MS (ESI) calc'd for (C$_{17}$H$_{17}$N$_3$O$_5$) [M+H]$^+$, 344.1; found 344.4.

Step 3

1-(2-(2,6-dioxopiperidin-3-yl)-1,3-dioxoisoindolin-5-yl) azetidine-3-carbaldehyde LCMS $C_{17}H_{15}N_3O_5$ requires: 341, found: m/z=343 $[M+H]^+$.

Example 15C: Synthesis of 2-(1-(2-(2,6-dioxopiperidin-3-yl)-1,3-dioxoisoindolin-5-yl)azetidin-3-yl) acetaldehyde

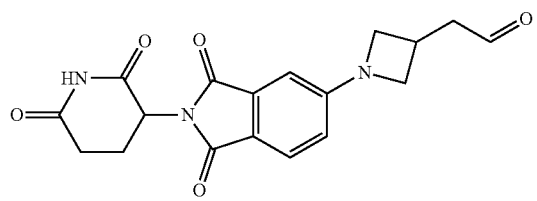 [SMILES: O=CCC1CN(c2ccc3c(c2)C(=O)N(C2CCC(=O)NC2=O)C3=O)C1]

Step 2

Followed General Procedure B with 2-(azetidin-3-yl) ethan-1-ol hydrochloride to afford 2-(2,6-dioxopiperidin-3-yl)-5-(3-(2-hydroxyethyl)azetidin-1-yl)isoindoline-1,3-dione (584.5 mg, 30%) as a yellow solid. $^1$H NMR (300 MHz, DMSO-$d_6$) δ 11.09 (s, 1H), 7.63 (d, J=8.4 Hz, 1H), 6.75 (d, J=2.1 Hz, 1H), 6.62 (dd, J=8.4, 2.1 Hz, 1H), 5.06 (dd, J=12.6, 5.4 Hz, 1H), 4.51 (t, J=5.1 Hz, 1H), 4.14 (t, J=8.1 Hz, 2H), 3.71-3.67 (m, 2H), 3.47-3.40 (m, 2H), 2.99-2.75 (m, 2H), 2.61-2.58 (m, 1H), 2.52-2.46 (m, 1H), 2.10-1.95 (m, 1H), 1.82-1.76 (m, 2H). MS (ESI) calc'd for $(C_{18}H_{19}N_3O_5)$ $[M+H]^+$, 358.1; found 358.4.

Step 3

2-(1-(2-(2,6-dioxopiperidin-3-yl)-1,3-dioxoisoindolin-5-yl)azetidin-3-yl)acetaldehyde LCMS $C_{18}H_{17}N_3O_5$ requires: 355, found: m/z=356 $[M+H]^+$.

Example 15D: Synthesis of (3R)-1-(2-(2,6-dioxopiperidin-3-yl)-1,3-dioxoisoindolin-5-yl)piperidine-3-carbaldehyde

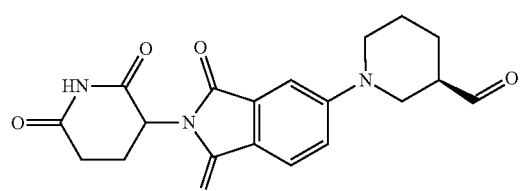

Step 2

Followed General Procedure B with (R)-piperidin-3-yl-methanol hydrochloride to afford 2-(2,6-dioxopiperidin-3-yl)-5-((R)-3-(hydroxymethyl)piperidin-1-yl)isoindoline-1,3-dione (916.3 mg, 45%) as a yellow solid. $^1$H NMR (400 MHz, DMSO-$d_6$/D$_2$O) δ 7.62 (d, J=8.4 Hz, 1H), 7.22 (d, J=2.4 Hz, 1H), 7.16 (dd, J=8.4, 2.4 Hz, 1H), 4.99 (dd, J=12.8, 5.2 Hz, 1H), 3.98-3.76 (m, 2H), 3.42-3.22 (m, 2H), 3.08-2.90 (m, 1H), 2.89-2.71 (m, 2H), 2.61-2.43 (m, 2H), 2.02-1.99 (m, 1H), 1.73-1.69 (m, 3H), 1.49-1.40 (m, 1H), 1.26-1.18 (m, 1H). MS (ESI) calc'd for $(C_{19}H_{21}N_3O_5)$ $[M+H]^+$, 372.1; found 372.4.

Step 3

(3R)-1-(2-(2,6-dioxopiperidin-3-yl)-1,3-dioxoisoindolin-5-yl)piperidine-3-carbaldehyde LCMS $C_{19}H_{19}N_3O_5$ requires: 369, found: m/z=370 $[M+H]^+$.

Example 15E: Synthesis of (3S)-1-(2-(2,6-dioxopiperidin-3-yl)-1,3-dioxoisoindolin-5-yl)piperidine-3-carbaldehyde

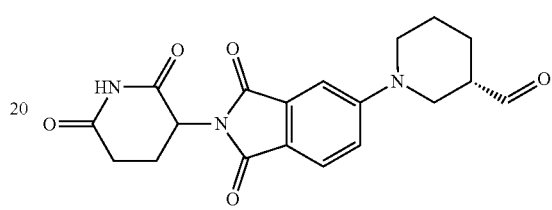

Step 2

Followed General Procedure B with (S)-piperidin-3-yl-methanol hydrochloride to afford 2-(2,6-dioxopiperidin-3-yl)-5-((S)-3-(hydroxymethyl)piperidin-1-yl)isoindoline-1, 3-dione (493.1 mg, 73%) as a yellow solid. $^1$H NMR (300 MHz, DMSO-$d_6$/D$_2$O) δ 7.65 (d, J=8.4 Hz, 1H), 7.26 (d, J=2.1 Hz, 1H), 7.19 (dd, J=8.4, 2.1 Hz, 1H), 5.04 (dd, J=12.9, 5.4 Hz, 1H), 4.00-3.90 (m, 2H), 3.38-3.32 (m, 2H), 3.13-2.71 (m, 3H), 2.67-2.44 (m, 2H), 2.03-1.98 (m, 1H), 1.76-1.67 (m, 3H), 1.57-1.38 (m, 1H), 1.34-1.10 (m, 1H). MS (ESI) calc'd for $(C_{19}H_{21}N_3O_5)$ $[M+H]^+$, 372.1; found 372.1.

Step 3

(3S)-1-(2-(2,6-dioxopiperidin-3-yl)-1,3-dioxoisoindolin-5-yl)piperidine-3-carbaldehyde LCMS $C_{19}H_{19}N_3O_5$ requires: 369, found: m/z=370 $[M+H]^+$.

Example 15F: Synthesis of (3R)-1-(2-(2,6-dioxopiperidin-3-yl)-1,3-dioxoisoindolin-5-yl)pyrrolidine-3-carbaldehyde

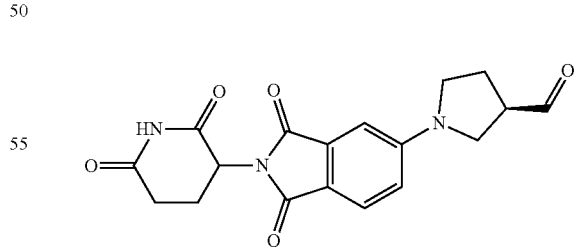

Step 2

Followed General Procedure B with (R)-pyrrolidin-3-ylmethanol to afford 2-(2,6-dioxopiperidin-3-yl)-5-((R)-3-(hydroxymethyl)pyrrolidin-1-yl)isoindoline-1,3-dione (480.6 mg, 74%) as a yellow solid. $^1$H NMR (300 MHz, DMSO-$d_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (s, 1H), 3.65-3.36 (m, 5H), 3.22-3.17 (m, 1H), 2.95-2.83 (m, 1H), 2.67-2.44 (m, 3H), 2.11-1.89 (m, 2H), 1.87-1.78 (m, 1H). MS (ESI) calc'd for ($C_{18}H_{19}N_3O_5$) [M+H]$^+$, 358.1; found 358.1.

Step 3

(3R)-1-(2-(2,6-dioxopiperidin-3-yl)-1,3-dioxoisoindolin-5-yl)pyrrolidine-3-carbaldehyde LCMS $C_{18}H_{17}N_3O_5$ requires: 355, found: m/z=356 [M+H]$^+$.

Example 15G: Synthesis of (3S)-1-(2-(2,6-dioxopiperidin-3-yl)-1,3-dioxoisoindolin-5-yl)pyrrolidine-3-carbaldehyde

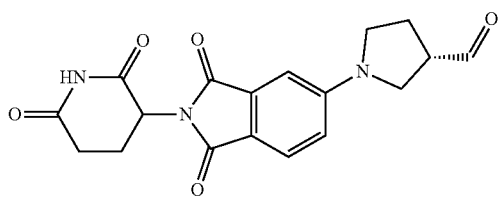 [SMILES: O=C[C@H]1CCN(c2ccc3c(c2)C(=O)N(C2CCC(=O)NC2=O)C3=O)C1]

Step 2

Followed General Procedure B with (S)-pyrrolidin-3-ylmethanol to afford 2-(2,6-dioxopiperidin-3-yl)-5-((S)-3-(hydroxymethyl)pyrrolidin-1-yl)isoindoline-1,3-dione (643.1 mg, 33%) as a yellow solid. $^1$H NMR (300 MHz, DMSO-$d_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (t, J=5.4 Hz, 1H), 3.59-3.41 (m, 5H), 3.22-3.17 (m, 1H), 2.95-2.83 (m, 1H), 2.67-2.44 (m, 3H), 2.12-1.88 (m, 2H), 1.87-1.76 (m, 1H). MS (ESI) calc'd for ($C_{18}H_{19}N_3O_5$) [M+H]$^+$, 358.1; found 358.1.

Step 3

(3S)-1-(2-(2,6-dioxopiperidin-3-yl)-1,3-dioxoisoindolin-5-yl)pyrrolidine-3-carbaldehyde LCMS $C_{18}H_{17}N_3O_5$ requires: 355, found: m/z=356 [M+H]$^+$.

Example 15H: Synthesis of 2-(2,6-dioxopiperidin-3-yl)-5-((1R,5S,6r)-6-(hydroxymethyl)-3-aza-bicyclo[3.1.0]hexan-3-yl)isoindoline-1,3-dione

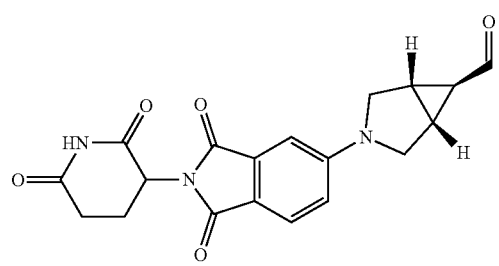 [SMILES: O=C[C@@H]1[C@H]2CN(c3ccc4c(c3)C(=O)N(C3CCC(=O)NC3=O)C4=O)C[C@@H]12]

Step 2

Followed General Procedure B with ((1R,5S,6r)-3-azabicyclo[3.1.0]hexan-6-yl)methanol to afford 2-(2,6-dioxopiperidin-3-yl)-5-(((1R,5S,6r)-6-(hydroxymethyl)-3-aza-bicyclo[3.1.0]hexan-3-yl)isoindoline-1,3-dione (315.8 mg, 21%) as a yellow solid. $^1$H NMR (300 MHz, DMSO-$d_6$) δ 11.08 (s, 1H), 7.63 (d, J=8.4 Hz, 1H), 6.92 (d, J=2.1 Hz, 1H), 6.82 (dd, J=8.4, 2.1 Hz, 1H), 5.06 (dd, J=12.6, 5.4 Hz, 1H), 4.59 (t, J=5.4 Hz, 1H), 3.64-3.60 (m, 2H), 3.50-3.35 (m, 4H), 3.00-2.76 (m, 1H), 2.58-2.44 (m, 2H), 2.07-1.91 (m, 1H), 1.69 (s, 2H), 0.86-0.79 (m, 1H). MS (ESI) calc'd for ($C_{19}H_{19}N_3O_5$) [M+H]$^+$, 370.1; found 370.1.

Step 3

(1R,5S,6r)-3-(2-(2,6-dioxopiperidin-3-yl)-1,3-dioxoisoindolin-5-yl)-3-azabicyclo[3.1.0]hexane-6-carbaldehyde LCMS $C_{19}H_{17}N_3O_5$ requires: 367, found: m/z=368 [M+H]$^+$.

Example 16: General Procedure C

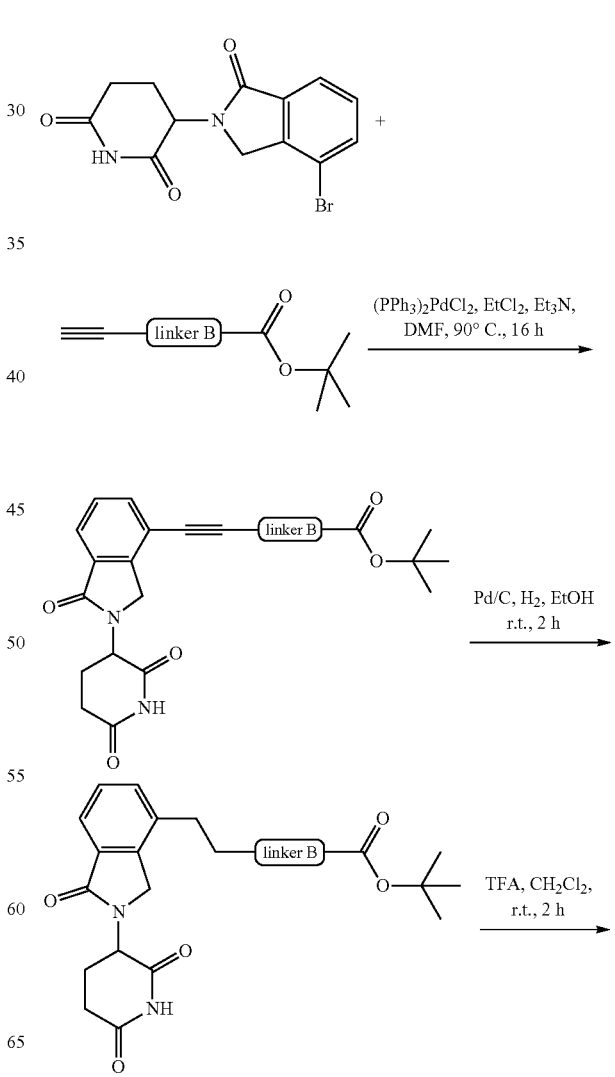

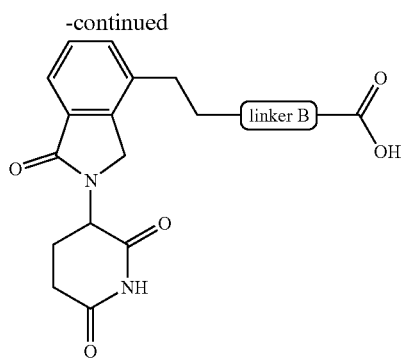

As used in General Procedure B, "linker B" is —(CH$_2$—CH$_2$—O)$_x$—, wherein x is an integer from 1 to 3.

Step 1

A mixture of 3-(4-bromo-1-oxo-2,3-dihydro-1H-isoindol-2-yl)piperidine-2,6-dione (2.52 mmol), (PPh$_3$)$_2$PdCl$_2$ (0.15 mmol), CuI (0.25 mmol), alkyne ester (5.04 mmol) were added to a vial. The vial was evacuated and backfilled with N$_2$ 5 times. DMF and triethylamine (30.3 mmol) were added and the mixture was allowed to stir at 90° C. overnight. The mixture was filtered through celite, washing with MeOH and EtOAc. EtOAc and saturated aqueous NaCl were added. The organic layer was dried with MgSO$_4$, filtered, concentrated and purified by reverse phase MPLC (5-100% MeCN in H2O on C18 column) to afford the product.

Step 2

A mixture of disubstituted alkyne (0.81 mmol), Pd/C 10 wt % (0.08 mmol) and EtOH were mixed in a flask. The flask was evacuated and backfilled with H$_2$ 5 times and allowed to stir at r.t. for 2 h. The mixture was filtered through celite washing with MeOH and EtOAc, concentrated and carried to the next step.

Step 3

A mixture of tert-butylester (0.81 mmol), CH$_2$Cl$_2$ (2 mL), and TFA (2 mL) was allowed to stir at r.t. for 2 h. The mixture was concentrated to afford the carboxylic acid product.

Example 16A: Synthesis of 3-(3-(2-(2,6-dioxopiperidin-3-yl)-1-oxoisoindolin-4-yl)propoxy)propanoic acid

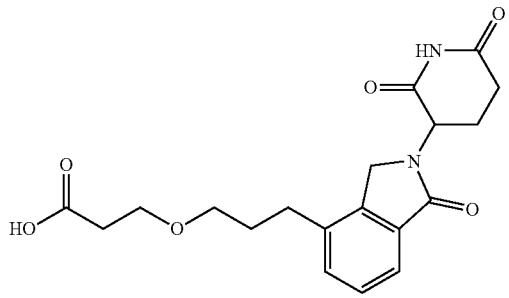 [SMILES: O=C(O)CCOCCCc1cccc2c1CN(C1CCC(=O)NC1=O)C2=O]

Step 1 Product tert-butyl 3-((3-(2-(2,6-dioxopiperidin-3-yl)-1-oxoisoindolin-4-yl)prop-2-yn-1-yl)oxy)propanoate (347 mg, 32.3%). LCMS: C$_{23}$H$_{26}$N$_2$O$_6$ requires: 426, found: m/z=427 [M+H]$^+$.

Step 2 Product tert-butyl 3-(3-(2-(2,6-dioxopiperidin-3-yl)-1-oxoisoindolin-4-yl)propoxy)propanoate (350 mg, 99%). LCMS: C$_{23}$H$_{30}$N$_2$O$_6$ requires: 430, found: m/z=431 [M+H]$^+$.

Step 3 Product 3-(3-(2-(2,6-dioxopiperidin-3-yl)-1-oxoisoindolin-4-yl)propoxy)propanoic acid (304 mg, 99%). LCMS: C$_{19}$H$_{22}$N$_2$O$_6$ requires: 374, found: m/z=375 [M+H]$^+$.

Example 17: Synthesis of (1s,3s)-3-(3-(2-(2,6-dioxopiperidin-3-yl)-1-oxoisoindolin-4-yl)propoxy)cyclobutane-1-carboxylic acid

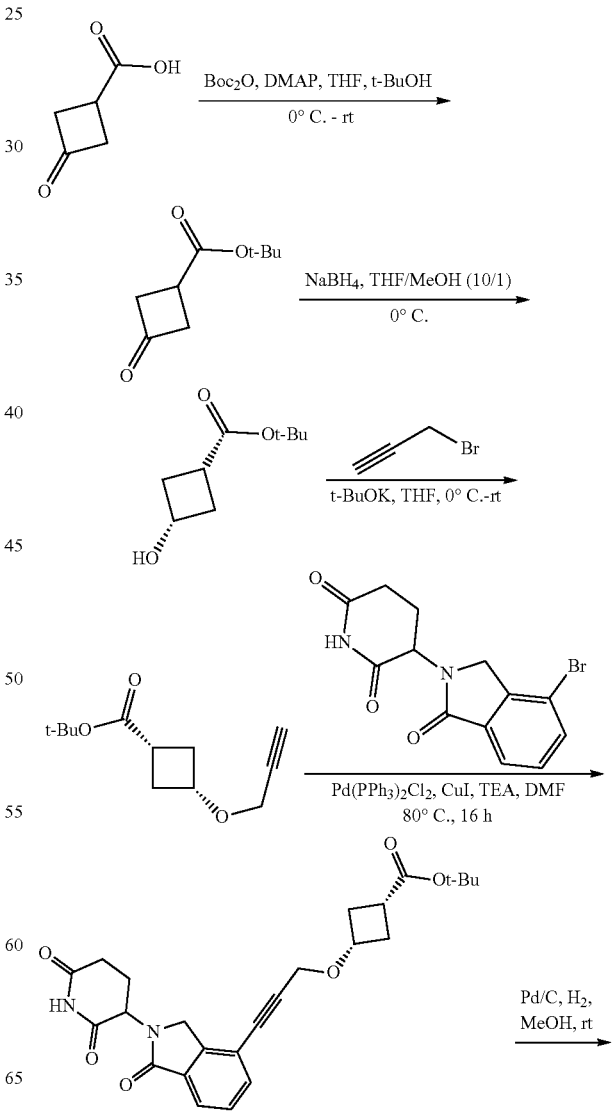

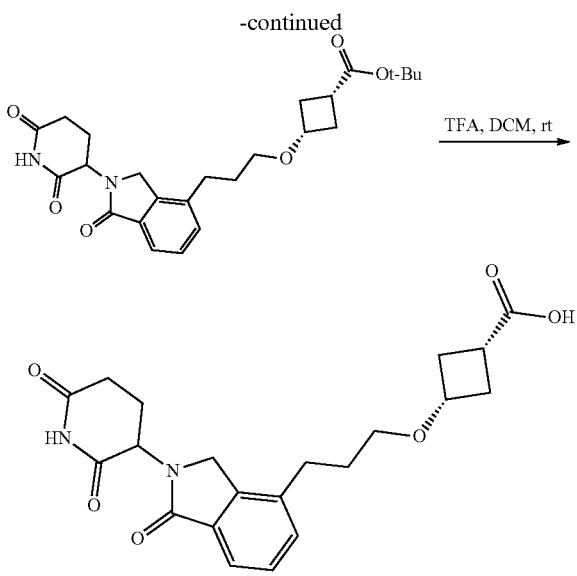

Step 1: tert-butyl 3-oxocyclobutane-1-carboxylate

To a solution of 3-oxocyclobutane-1-carboxylic acid (5.0 g, 43.82 mmol) and DMAP (2.7 g, 21.91 mmol) in t-BuOH (20 mL) and THF (20 mL) was added a solution of Boc$_2$O (14.3 g, 65.73 mmol) in THF (10 mL) dropwise at 0° C. under nitrogen atmosphere. The mixture was stirred at room temperature for 16 h. The reaction was quenched by the addition of water and extracted with ethyl acetate. The combined organic layer was washed with brine, dried over anhydrous Na$_2$SO$_4$ and concentrated under vacuum. The residue was purified by flash column chromatography with 0~15% ethyl acetate in petroleum ether to afford tert-butyl 3-oxocyclobutane-1-carboxylate (6.2 g, 83%) as colorless oil. MS (ESI) calc'd for (C$_9$H$_{14}$O$_3$) [M+1]$^+$, 171.1; found, 171.2. $^1$H NMR (300 MHz, Chloroform-d) δ 3.39-2.98 (m, 5H), 1.44 (s, 9H).

Step 2: tert-butyl (1s,3s)-3-hydroxycyclobutane-1-carboxylate

To a solution of tert-butyl 3-oxocyclobutane-1-carboxylate (5.1 g, 29.96 mmol) in THF (50 mL) and MeOH (5 mL) was added NaBH$_4$ (566.8 mg, 14.98 mmol) in portions at 0° C. under nitrogen atmosphere. The resulting mixture was stirred at 0° C. for 30 min. The reaction was then quenched by the addition of ice water and extracted with ethyl acetate. The combined organic layer was washed with brine, dried over anhydrous Na$_2$SO$_4$ and concentrated under vacuum to afford tert-butyl (1s,3s)-3-hydroxycyclobutane-1-carboxylate (4.8 g, 93%) as a light yellow oil, which was used for the next step without further purification. MS (ESI) calc'd for (C$_9$H$_{16}$O$_3$) [M+1]$^+$, 173.1; found, 173.0. $^1$H NMR (300 MHz, Chloroform-d) δ 4.20-4.07 (m, 1H), 2.61-2.43 (m, 3H), 2.30 (s, 1H), 2.17-2.20 (m, 2H), 1.43 (s, 9H).

Step 3: tert-butyl (1s,3s)-3-(prop-2-yn-1-yloxy)cyclobutane-1-carboxylate

To a solution of tert-butyl (1s,3s)-3-hydroxycyclobutane-1-carboxylate (5.0 g, 29.03 mmol) and 3-bromoprop-1-yne (3.8 g, 31.94 mmol) in THF was added t-BuOK (32 mL, 1 M in THF, 32.0 mmol) dropwise at 0° C. under nitrogen atmosphere. The mixture was stirred at room temperature for 16 h. The reaction was then quenched by the addition of ice water and extracted with ethyl acetate. The combined organic layer was washed with brine, dried over anhydrous Na$_2$SO$_4$ and concentrated under vacuum. The residue was purified by flash column chromatography with 0~20% ethyl acetate in petroleum ether to afford tert-butyl (1s,3s)-3-(prop-2-yn-1-yloxy)cyclobutane-1-carboxylate (3.2 g, 52%) as a light yellow oil. MS (ESI) calc'd for (C$_{12}$H$_{18}$O$_3$) [M+1]$^+$, 211.1; found, 211.3. $^1$H NMR (300 MHz, Chloroform-d) δ 4.17-3.99 (m, 3H), 2.63-2.43 (m, 3H), 2.29-2.11 (m, 2H), 2.04 (s, 1H), 1.44 (s, 9H).

Step 4: tert-butyl (1s,3s)-3-((3-(2-(2,6-dioxopiperidin-3-yl)-1-oxoisoindolin-4-yl)prop-2-yn-1-yl)oxy)cyclobutane-1-carboxylate A mixture of 3-(4-bromo-1-oxoisoindolin-2-yl)piperidine-2,6-dione (3.3 g, 10.21 mmol), tert-butyl (1s,3s)-3-(prop-2-yn-1-yloxy)cyclobutane-1-carboxylate (3.2 g, 15.32 mmol), Pd(PPh$_3$)$_2$Cl$_2$ (1.1 g, 1.53 mmol) and CuI (486.2 mg, 2.55 mmol) in triethylamine (30 mL) and DMF (30 mL) was stirred at 80° C. for 16 h under nitrogen atmosphere. After cooled down to room temperature, the reaction was diluted with saturated NH$_4$Cl aqueous solution and then extracted with ethyl acetate. The combined organic layer was washed with brine, dried over anhydrous Na$_2$SO$_4$ and concentrated under vacuum. The residue was purified by flash column chromatography with 0~10% ethyl acetate in methanol to afford tert-butyl (1s,3s)-3-((3-(2-(2,6-dioxopiperidin-3-yl)-1-oxoisoindolin-4-yl)prop-2-yn-1-yl)oxy)cyclobutane-1-carboxylate (1.5 g, 27%) as a light yellow solid. MS (ESI) calc'd for (C$_{25}$H$_{28}$N$_2$O$_6$) [M+1]$^+$, 453.2; found, 453.3.

Step 5: tert-butyl (1s,3s)-3-(3-(2-(2,6-dioxopiperidin-3-yl)-1-oxoisoindolin-4-yl)propoxy)cyclobutane-1-carboxylate To a solution of tert-butyl (1s,3s)-3-((3-(2-(2,6-dioxopiperidin-3-yl)-1-oxoisoindolin-4-yl)prop-2-yn-1-yl)oxy)cyclobutane-1-carboxylate (1.5 g, 2.75 mmol) in MeOH (20 mL) was added Pd/C (10%, 200 mg) under nitrogen atmosphere. The mixture was stirred at room temperature for 16 h under hydrogen atmosphere (2 atm). The solid was filtered out through a Celite pad and the filtrate was concentrated under vacuum. The residue was purified by reverse phase flash column chromatography with 10~70% acetonitrile in water to afford tert-butyl (1s,3s)-3-(3-(2-(2,6-dioxopiperidin-3-yl)-1-oxoisoindolin-4-yl)propoxy)cyclobutane-1-carboxylate (650 mg, 43%) as a light yellow solid. MS (ESI) calc'd for (C$_{25}$H$_{32}$N$_2$O$_6$) [M+1]$^+$, 457.2; found, 457.3.

Step 6: (1s,3s)-3-(3-(2-(2,6-dioxopiperidin-3-yl)-1-oxoisoindolin-4-yl)propoxy)cyclobutane-1-carboxylic acid A mixture of tert-butyl (1s,3s)-3-(3-(2-(2,6-dioxopiperidin-3-yl)-1-oxoisoindolin-4-yl)propoxy)cyclobutane-1-carboxylate (1.2 g, 2.63 mmol) in TFA (4 mL) and DCM (12 mL) was stirred at room temperature for 2 h before concentrated under vacuum. The residue was purified by reverse phase flash column chromatography to afford (1s,3s)-3-(3-(2-(2,6-dioxopiperidin-3-yl)-1-oxoisoindolin-4-yl)propoxy)cyclobutane-1-carboxylic acid (968.7 mg, 92%). MS (ESI) calc'd for (C$_{21}$H$_{24}$N$_2$O$_6$) [M+1]$^+$, 401.2; found, 400.8. $^1$H NMR (300 MHz, DMSO-d$_6$) δ 12.12 (s, 1H), 10.97 (s, 1H), 7.59-7.53 (m, 1H), 7.48-7.41 (m, 2H), 5.15-5.09 (m, 1H), 4.45 (d, J=17.1 Hz, 1H), 4.29 (d, J=17.1 Hz, 1H), 3.89-3.69 (m, 1H), 3.27 (t, J=6.3 Hz, 2H), 2.97-2.85 (m, 1H), 2.77-2.51 (m, 4H), 2.46-2.28 (m, 3H), 2.14-1.73 (m, 3H), 1.86-1.73 (m, 2H).

Example 18: Synthesis of 3-(4-bromo-1-oxoisoindolin-2-yl)piperidine-2,6-dione

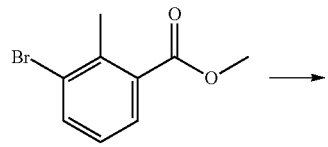

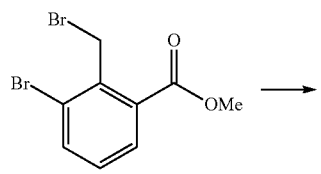

Step 1: methyl 3-bromo-2-(bromomethyl)benzoate

To a solution of methyl 3-bromo-2-methyl-benzoate (50 g, 218.27 mmol, 1 eq), NBS (46.62 g, 261.93 mmol, 1.2 eq) in CHCl$_3$ (400 mL) was added AIBN (3.58 g, 21.83 mmol, 0.1 equiv.). The mixture was stirred at 70° C. for 12 h. The reaction mixture was concentrated in vacuum, diluted with DCM (400 mL), washed with H$_2$O (100 mL) and brine (100 mL), extracted with DCM (100 mL), and washed with brine (50 mL) again. The organic phase was combined, dried over Na$_2$SO$_4$, and concentrated in vacuum. The residue was purified by flash silica gel chromatography (Petroleum ether/Ethyl acetate=100/1) to yield 3-bromo-2-(bromomethyl) benzoate (63 g, 204.57 mmol, 93.72% yield) as a light yellow solid.

Step 2: 3-(4-bromo-1-oxo-isoindolin-2-yl)piperidine-2,6-dione

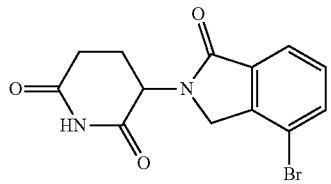 [SMILES: O=C1CCC(N2Cc3c(Br)cccc3C2=O)C(=O)N1]

To a solution of methyl 3-bromo-2-(bromomethyl)benzoate (88.2 g, 286.39 mmol, 1 eq) in ACN (600 mL) was added DIEA (49.23 g, 380.91 mmol, 66.35 mL, 1.33 equiv.) and 3-aminopiperidine-2,6-dione hydrochloride (51.01 g, 309.94 mmol, 1.08 eq). The mixture was stirred at 80° C. for 16 hr. The reaction mixture was filtered. The filter cake was triturated by a mixture solution (EtOAc:H$_2$O=100 mL:200 mL) to yield 3-(4-bromo-1-oxo-isoindolin-2-yl)piperidine-2,6-dione (56.5 g, 174.85 mmol, 61.05% yield) as a purple powder.

Example 19: Synthesis of 2-(4-(3-(2-(2,6-dioxopiperidin-3-yl)-1-oxoisoindolin-4-yl)propyl)piperazin-1-yl)acetic acid

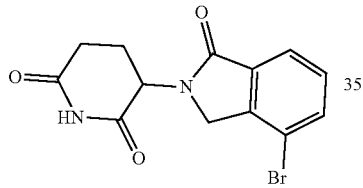

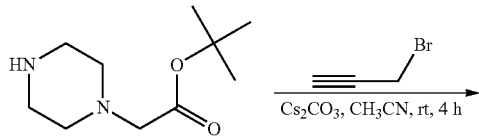

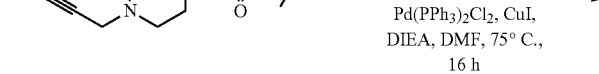

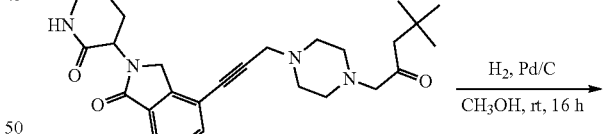

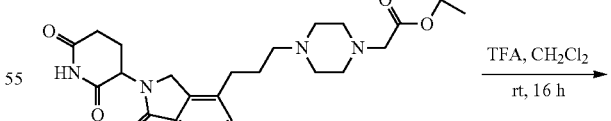

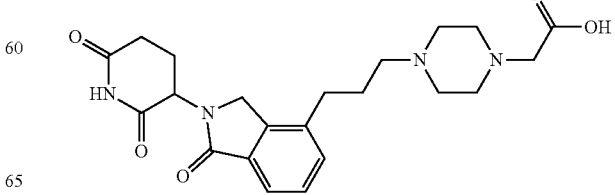

Step 1: tert-butyl 2-(4-(prop-2-ynyl)piperazin-1-yl) acetate

To a solution of tert-butyl 2-(piperazin-1-yl)acetate (1.5 g, 7.49 mmol) in acetonitrile (50 mL) were added 3-bromoprop-1-yne (892.5 mg, 7.50 mmol) and $Cs_2CO_3$ (2.4 g, 7.50 mmol). The resulting solution was stirred at room temperature for 4 h. The solids were filtered out and the filtrate was evaporated under vacuum. The residue was purified by phase flash column chromatography with 0~30% ethyl acetate in petroleum ether to afford tert-butyl 2-(4-(prop-2-ynyl)piperazin-1-yl)acetate (1.1 g, 62%) as a yellow oil. MS (ESI) calculated for $(C_{13}H_{22}N_2O_2)$ $[M+H]^+$, 239.2; found, 239.1.

Step 2: tert-butyl 2-(4-(3-(2-(2,6-dioxopiperidin-3-yl)-1-oxoisoindolin-4-yl)prop-2-ynyl)piperazin-1-yl) acetate To a degassed solution of 3-(4-bromo-1-oxoisoindolin-2-yl)piperidine-2,6-dione (1.5 g, 4.64 mmol) in N,N-dimethylformamide (30 mL) were added tert-butyl 2-(4-(prop-2-ynyl)piperazin-1-yl)acetate (1.5 g, 6.29 mmol), $Pd(PPh_3)_2Cl_2$ (489.0 mg, 0.70 mmol), DIEA (20 mL) and CuI (221.7 mg, 1.16 mmol). The resulting solution was stirred at 75° C. for 16 h under nitrogen. The reaction was quenched by the addition of water, and then extracted with ethyl acetate. The combined organic layer was washed with brine, dried over anhydrous sodium sulfate and filtered. The filtrate was evaporated under vacuum. The residue was purified by flash column chromatography with 0-10% methanol in dichloromethane to afford tert-butyl 2-(4-(3-(2-(2,6-dioxopiperidin-3-yl)-1-oxoisoindolin-4-yl)prop-2-ynyl)piperazin-1-yl) acetate (1.5 g, 68%) as a yellow solid. MS (ESI) calculated for $(C_{26}H_{32}N_4O_5)$ $[M+H]^+$, 481.2; found, 481.1.

Step 3: tert-butyl 2-(4-(3-(2-(2,6-dioxopiperidin-3-yl)-1-oxoisoindolin-4-yl)propyl)piperazin-1-yl)acetate To a solution of tert-butyl 2-(4-(3-(2-(2,6-dioxopiperidin-3-yl)-1-oxoisoindolin-4-yl)prop-2-ynyl)piperazin-1-yl)acetate (2.2 g, 4.58 mmol) in methanol (50 mL) was added Pd/C (dry, 0.44 g). The resulting solution was stirred at room temperature for 16 h under hydrogen (2 atm). The solids were filtered out. The filtrate was evaporated under vacuum to afford tert-butyl 2-(4-(3-(2-(2,6-dioxopiperidin-3-yl)-1-oxoisoindolin-4-yl)propyl)piperazin-1-yl)acetate (1.4 g, crude) as a yellow oil, which was used in the next step without further purification. MS (ESI) calculated for $(C_{26}H_{36}N_4O_5)$ $[M+H]^+$, 485.3; found, 485.2.

Step 4: 2-(4-(3-(2-(2,6-dioxopiperidin-3-yl)-1-oxoisoindolin-4-yl)propyl)piperazin-1-yl)acetic acid TFA Salt To a solution of tert-butyl 2-(4-(3-(2-(2,6-dioxopiperidin-3-yl)-1-oxoisoindolin-4-yl)propyl)piperazin-1-yl)acetate (1.4 g, 2.89 mmol) in dichloromethane (20 mL) was added trifluoroacetic acid (20 mL). The resulting solution was stirred at room temperature for 16 h before concentrated under vacuum. The residue was purified by HPLC (MeCN/$H_2O$ with TFA) to afford 2-(4-(3-(2-(2,6-dioxopiperidin-3-yl)-1-oxoisoindolin-4-yl)propyl)piperazin-1-yl)acetic acid TFA salt (434.3 mg, 35%) as a yellow solid. MS (ESI) calculated for $(C_{22}H_{28}N_4O_5)$ $[M+H]^+$, 429.2; found, 429.0. $^1$H NMR (300 MHz, DMSO-$d_6$) δ 11.08 (s, 1H), 7.60-7.65 (m, 1H), 7.52-7.47 (m, 2H), 5.20-5.13 (m, 1H), 4.52-4.46 (m, 1H), 4.35-4.29 (m, 1H), 3.51 (s, 3H), 3.47-2.84 (m, 9H), 2.72-2.50 (m, 4H), 2.49-2.31 (m, 1H), 2.05-1.97 (m, 3H).

Example 20: Synthesis of 2-(4-(2-(2-(2,6-dioxopiperidin-3-yl)-1-oxoisoindolin-4-yl)ethyl)piperazin-1-yl)acetic acid

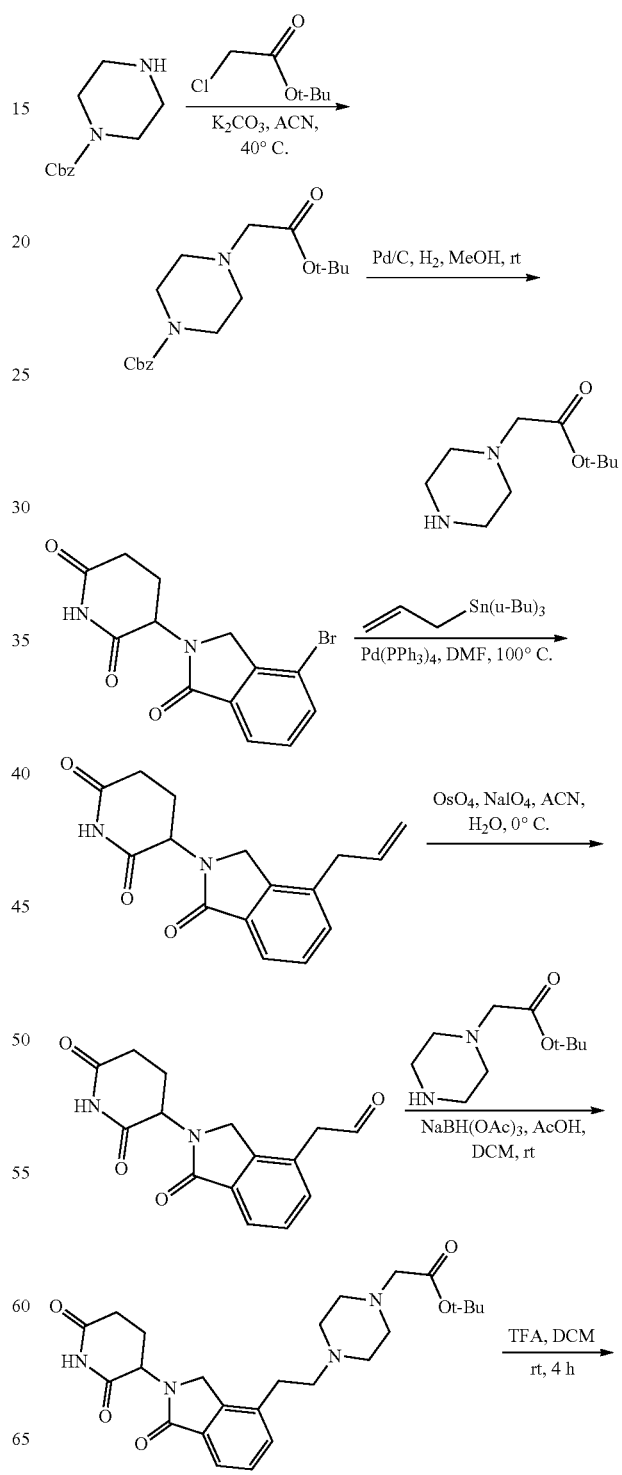

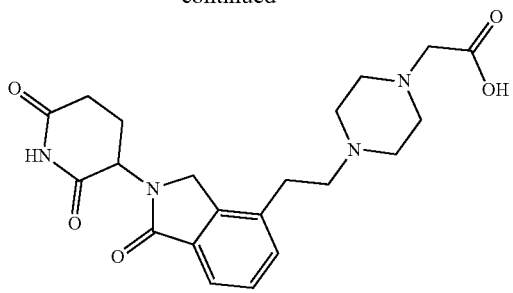

Step 1: benzyl 4-(2-(tert-butoxy)-2-oxoethyl)piperazine-1-carboxylate

To a solution of benzyl piperazine-1-carboxylate (10.0 g, 45.4 mmol) and $K_2CO_3$ (12.6 g, 90.8 mmol) in acetonitrile (150 mL) was added tert-butyl 2-chloroacetate (7.5 g, 49.9 mmol). The resulting solution was stirred at 40° C. for 16 h under nitrogen atmosphere. The solids were filtered out and the filtrate was concentrated under vacuum. The residue was purified by flash column chromatography with 0~50% ethyl acetate in petroleum ether to afford benzyl 4-(2-(tert-butoxy)-2-oxoethyl)piperazine-1-carboxylate (9.6 g, 63%) as a light yellow oil. MS (ESI) calculated for $(C_{18}H_{26}N_2O_4)$ $[M+H]^+$, 335.2; found, 335.3.

Step 2: tert-butyl 2-(piperazin-1-yl)acetate

To a solution of benzyl 4-(2-(tert-butoxy)-2-oxoethyl)piperazine-1-carboxylate (9.6 g, 28.7 mmol) in methanol (100 mL) was added Pd/C (10%, 2.0 g) under nitrogen atmosphere. The mixture was stirred at room temperature for 16 h under hydrogen atmosphere (2 atm). The solids were filtered out and the filtrate was concentrated under vacuum to afford tert-butyl 2-(piperazin-1-yl)acetate (6.2 g, crude) as a light yellow oil, which was used in the next step without further purification. MS (ESI) calculated for $(C_{10}H_{20}N_2O_2)$ $[M+H]^+$, 201.2; found, 201.0.

Step 3: 3-(4-allyl-1-oxoisoindolin-2-yl)piperidine-2,6-dione

A degassed mixture of 3-(4-bromo-1-oxo-2,3-dihydro-1H-isoindol-2-yl)piperidine-2,6-dione (10.0 g, 30.9 mmol), allyltributylstannane (15.4 g, 46.4 mmol) and $Pd(PPh_3)_4$ (3.6 g, 3.1 mmol) in DMF (80 mL) was stirred at 100° C. for 16 h under nitrogen atmosphere. When the reaction was completed by LCMS, the resulting mixture was diluted with water and extracted with ethyl acetate. The combined organic layer was washed with brine, dried over anhydrous $Na_2SO_4$, filtered and concentrated under vacuum. The residue was purified by flash column chromatography with 0~10% methanol in dichloromethane to afford 3-(4-allyl-1-oxoisoindolin-2-yl)piperidine-2,6-dione (7.0 g, 79%) as a white solid. MS (ESI) calculated for $(C_{16}H_{16}N_2O_3)$ $[M+H]^+$, 285.1; found, 285.2. $^1$H NMR (400 MHz, DMSO-$d_6$) δ 10.99 (s, 1H), 7.62-7.60 (m, 1H), 7.52-7.27 (m, 2H), 6.02-5.92 (m, 1H), 5.16-5.09 (m, 3H), 4.45 (d, J=17.2 Hz, 1H), 4.30 (d, J=17.2 Hz, 1H), 3.46-3.44 (m, 2H), 2.97-2.86 (m, 1H), 2.70-2.57 (m, 1H), 2.04-1.99 (m, 1H), 1.68-1.55 (m, 1H).

Step 4: 2-(2-(2,6-dioxopiperidin-3-yl)-1-oxoisoindolin-4-yl)acetaldehyde

A mixture of 3-(4-allyl-1-oxoisoindolin-2-yl)piperidine-2,6-dione (7.0 g, 24.6 mmol), $OsO_4$ (625 mg, 2.5 mmol) and $NaIO_4$ (10.5 g, 49.2 mmol) in MeCN (60 mL) and $H_2O$ (20 mL) was stirred at 0° C. for 6 h. When the reaction was completed, the resulting mixture was diluted with water and extracted with ethyl acetate. The combined organic layer was washed with brine, dried over anhydrous $Na_2SO_4$, filtered and concentrated under vacuum to afford 2-(2-(2,6-dioxopiperidin-3-yl)-1-oxoisoindolin-4-yl)acetaldehyde (4.0 g, crude) as a brown solid, which was used in the next step without further purification. MS (ESI) calculated for $(C_{15}H_{14}N_2O_4)$ $[M+H]^+$, 287.1; found, 287.2.

Step 5: tert-butyl 2-(4-(2-(2-(2,6-dioxopiperidin-3-yl)-1-oxoisoindolin-4-yl)ethyl)piperazin-1-yl)acetate A mixture of 2-[2-(2,6-dioxopiperidin-3-yl)-1-oxo-2,3-dihydro-1H-isoindol-4-yl]acetaldehyde (4.0 g, 13.9 mmol), tert-butyl 2-(piperazin-1-yl)acetate (3.4 g, 16.8 mmol), AcOH (1 mL) and $NaBH(OAc)_3$ (5.9 g, 27.9 mmol) in dichloromethane (50 mL) was stirred at room temperature for 16 h. The resulting mixture was diluted with water and extracted with ethyl acetate. The combined organic layer was washed with brine, dried over anhydrous $Na_2SO_4$, filtered and concentrated under vacuum. The crude residue was purified by reverse phase flash column chromatography with 10~50% acetonitrile in water to afford tert-butyl 2-(4-(2-(2-(2,6-dioxopiperidin-3-yl)-1-oxoisoindolin-4-yl)ethyl)piperazin-1-yl)acetate (2.5 g, 22% over two steps) as a light brown syrup. MS (ESI) calculated for $(C_{25}H_{34}N_4O_5)$ $[M+H]^+$, 471.2; found, 471.0.

Step 6: 2-(4-(2-(2-(2,6-dioxopiperidin-3-yl)-1-oxoisoindolin-4-yl)ethyl)piperazin-1-yl)acetic acid TFA Salt To a solution of tert-butyl 2-(4-(2-(2-(2,6-dioxopiperidin-3-yl)-1-oxoisoindolin-4-yl)ethyl)piperazin-1-yl)acetate (2.5 g, 5.3 mmol) in dichloromethane (20 mL) was added trifluoroacetic acid (20 mL). The resulting mixture was stirred at room temperature for 16 h before concentrated under vacuum. The residue was purified by reverse phase flash column chromatography with 5~30% acetonitrile in water to afford 2-(4-(2-(2-(2,6-dioxopiperidin-3-yl)-1-oxoisoindolin-4-yl)ethyl)piperazin-1-yl)acetic acid (1.7214 g, 78%) as a light brown solid. MS (ESI) calculated for $(C_{21}H_{26}N_4O_5)$ $[M+H]^+$, 415.2; found, 415.4. $^1$H NMR (300 MHz, DMSO-$d_6$) δ 11.08 (s, 1H), 7.66-7.62 (m, 1H), 7.54-7.47 (m, 2H), 5.14-5.08 (m, 1H), 4.54-4.48 (m, 1H), 4.40-4.31 (m, 1H), 3.76 (s, 2H), 3.60-3.10 (m, 10H), 3.10-2.78 (m, 3H), 2.68-2.54 (m, 1H), 2.40-2.31 (m, 1H), 2.10-1.94 (m, 1H).

Example 21: Synthesis of 2-(4-(3-(2-(2,6-dioxopiperidin-3-yl)-1,3-dioxoisoindolin-4-yl)propyl)piperazin-1-yl)acetic acid

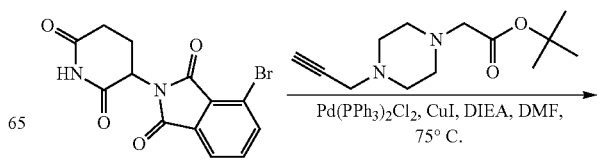

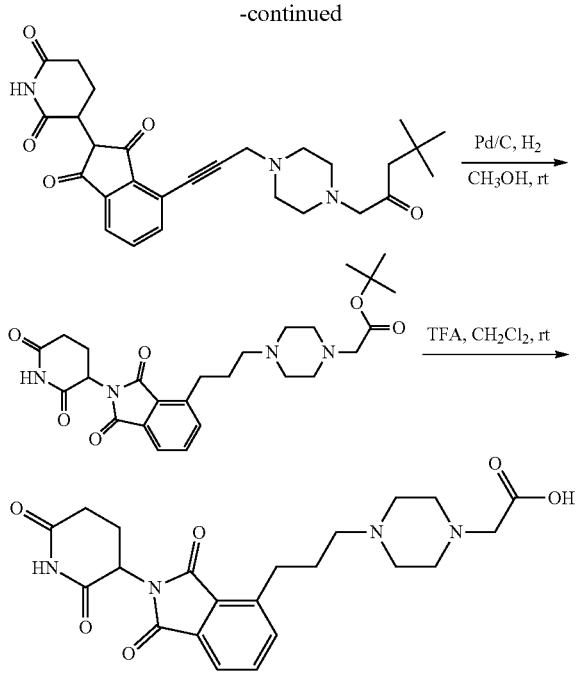

Step 1: tert-butyl 2-(4-(3-(2-(2,6-dioxopiperidin-3-yl)-1,3-dioxoisoindolin-4-yl)prop-2-yn-1-yl)piperazin-1-yl)acetate To a degassed solution of 4-bromo-2-(2,6-dioxopiperidin-3-yl)isoindoline-1,3-dione (1.3 g, 3.86 mmol) in N,N-dimethylformamide (18 mL) were added tert-butyl 2-(4-(prop-2-ynyl)piperazin-1-yl)acetate (1.4 g, 5.57 mmol), Pd(PPh$_3$)$_2$Cl$_2$ (423.3 mg, 0.60 mmol), DIEA (12 mL) and CuI (251.1 mg, 1.32 mmol). The resulting solution was stirred at 75° C. for 4 h under nitrogen. The reaction was quenched by the addition of water, and then extracted with ethyl acetate. The combined organic layer was washed with brine, dried over anhydrous sodium sulfate and filtered. The filtrate was evaporated under vacuum. The residue was purified by flash column chromatography with 0~10% methanol in dichloromethane to afford tert-butyl 2-(4-(3-(2-(2,6-dioxopiperidin-3-yl)-1,3-dioxoisoindolin-4-yl)prop-2-yn-1-yl)piperazin-1-yl)acetate (2.5 g, 70%) as a yellow solid. MS (ESI) calculated for (C$_{26}$H$_{30}$N$_4$O$_6$) [M+H]$^+$, 495.2; found, 495.1.

Step 2: tert-butyl 2-(4-(3-(2-(2,6-dioxopiperidin-3-yl)-1,3-dioxoisoindolin-4-yl)propyl)piperazin-1-yl)acetate To a solution of tert-butyl 2-(4-(3-(2-(2,6-dioxopiperidin-3-yl)-1,3-dioxoisoindolin-4-yl)prop-2-ynyl)piperazin-1-yl)acetate (2.1 g, 4.25 mmol) in methanol (50 mL) was added Pd/C (dry, 0.42 g). The resulting solution was stirred at room temperature for 16 h under hydrogen (2 atm). The solids were filtered out and the filtrate was evaporated under vacuum to afford tert-butyl 2-(4-(3-(2-(2,6-dioxopiperidin-3-yl)-1,3-dioxoisoindolin-4-yl)propyl)piperazin-1-yl)acetate (1.6 g, crude) as a yellow solid, which was used in the next step without further purification. MS (ESI) calculated for (C$_{26}$H$_{34}$N$_4$O$_6$) [M+H]$^+$, 499.2; found, 499.0.

Step 3: 2-(4-(3-(2-(2,6-dioxopiperidin-3-yl)-1,3-dioxoisoindolin-4-yl)propyl)piperazin-1-yl)acetic acid TFA Salt To a solution of tert-butyl 2-(4-(3-(2-(2,6-dioxopiperidin-3-yl)-1,3-dioxoisoindolin-4-yl)propyl)piperazin-1-yl)acetate (2.1 g, 4.21 mmol) in dichloromethane (20 mL) was added trifluoroacetic acid (20 mL). The resulting solution was stirred at room temperature for 4 h before concentrated under vacuum. The residue was purified by Pre-HPLC with the following conditions: [Column: XSelect CSH Prep C18 OBD Column, 5 um, 19*150 mm; Mobile Phase A: Water (0.05% TFA), Mobile Phase B: ACN; Flow rate: 25 mL/min; Gradient: 5% B to 20% B in 7 min; 254/220 nm] to afford 2-(4-(3-(2-(2,6-dioxopiperidin-3-yl)-1,3-dioxoisoindolin-4-yl)propyl)piperazin-1-yl)acetic acid TFA salt (398.0 mg, 21%) as a yellow solid. MS (ESI) calculated for (C$_{22}$H$_{26}$N$_4$O$_6$) [M+H]$^+$, 443.2; found, 442.9. $^1$H NMR (300 MHz, DMSO-d$_6$) δ 11.15 (s, 1H), 7.95-7.73 (m, 3H), 5.17-5.11 (m, 1H), 3.74-3.29 (m, 3H), 3.25-2.73 (m, 11H), 2.64 (s, 1H), 2.60-2.52 (m, 1H), 2.46-2.45 (m, 1H), 2.11-1.92 (m, 3H).

Example 22: General Procedure D

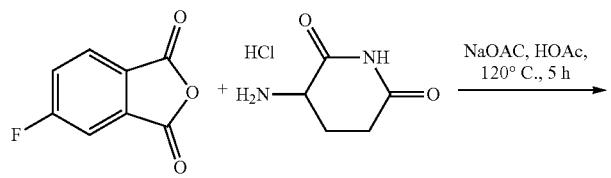

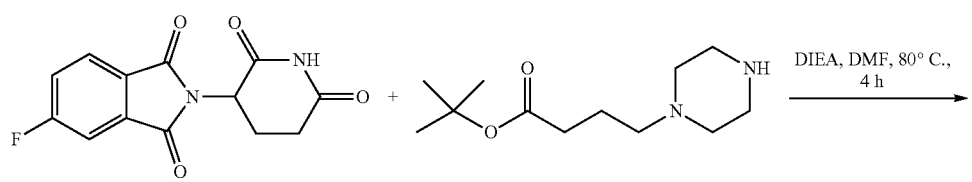

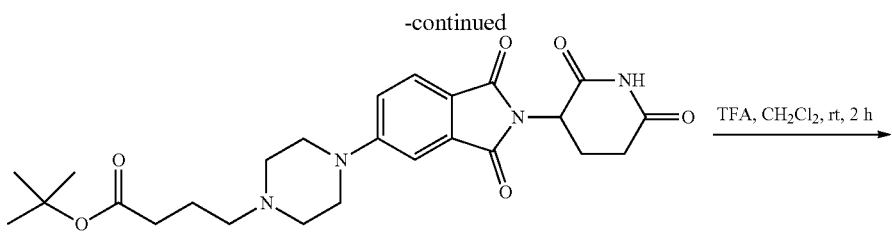

Step 1

To a solution of fluoro-benzofuran-1,3-dione (27.16 mmol) in HOAc (50 mL) were added sodium acetate (46.17 mmol) and 3-aminopiperidine-2,6-dione hydrochloride (38.02 mmol). The reaction mixture was stirred at 120° C. for 5 h. The mixture was cooled to room temperature and diluted with water. The solids were collected by filtration and dried to afford the fluoroimide intermediate.

Step 2

To a solution of fluoroimide (0.68 mmol) in DMF (30 mL) was added tert-butyl 4-(piperazin-1-yl)butanoate (0.68 mmol) and N-ethyl-N-isopropylpropan-2-amine (1.4 mmol). The reaction mixture was stirred at 80° C. for 4 h. The resulting mixture was cooled to room temperature and diluted with water. The aqueous phase was extracted with ethyl acetate. The combined organic layer was washed with brine and water, dried over anhydrous sodium sulfate, filtered and concentrated under vacuum to afford the tert-butyl ester intermediate (3.3 g, crude) which was used in the next step without further purification.

Step 3

To a solution of the tert-butyl ester intermediate (6.57 mmol) in dichloromethane (20 mL) was added trifluoroacetic acid (10 mL). The reaction mixture was stirred at room temperature for 2 h. The solvent was removed under vacuum. The residue was purified by reverse phase flash column chromatography (20-80% acetonitrile in water) to afford the acid product (38% over 2 steps).

Example 22A: Synthesis of 4-(4-(2-(2,6-dioxopiperidin-3-yl)-1,3-dioxoisoindolin-5-yl)piperazin-1-yl)butanoic acid

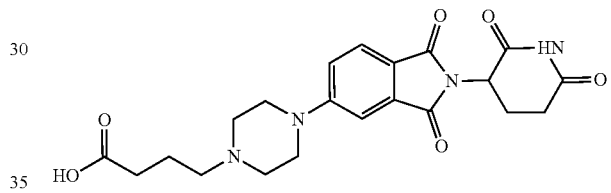

Step 1 Product 2-(2,6-dioxopiperidin-3-yl)-5-fluoroisoindoline-1,3-dione (3.0 g, 50%). LCMS: $C_{13}H_9FN_2O_4$ requires: 276, found: m/z=277 [M+H]$^+$.

Step 2 Product tert-butyl 4-(4-(2-(2,6-dioxopiperidin-3-yl)-1,3-dioxoisoindolin-5-yl)piperazin-1-yl)butanoate (4.4 g, 84%). LCMS: $C_{25}H_{32}N_4O_6$ requires: 484, found: m/z=485 [M+H]$^+$.

Step 3 Product 4-(4-(2-(2,6-dioxopiperidin-3-yl)-1,3-dioxoisoindolin-5-yl)piperazin-1-yl)butanoic acid TFA salt (3.35 g, 56%). LCMS: $C_{21}H_{24}N_4O_6$ requires: 428, found: m/z=429 [M+H]$^+$.

Example 23: General Procedure E

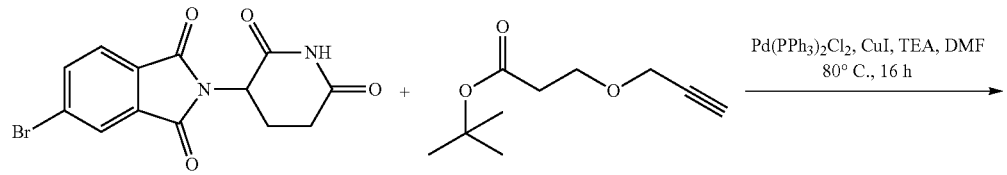

-continued

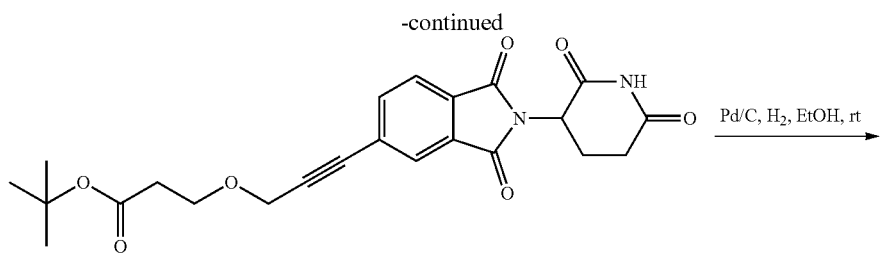

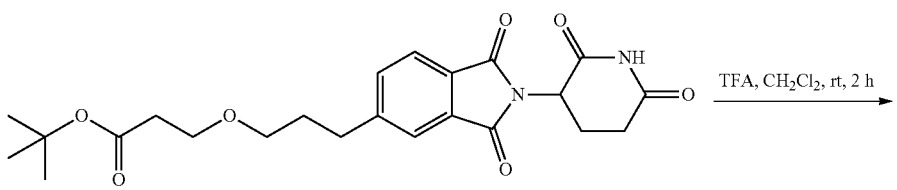

Step 1

5-bromo-2-(2,6-dioxopiperidin-3-yl)isoindole-1,3-dione (347 mg, 1.03 mmol), (PPh₃)₃PdCl₂ (43.4 mg, 0.06 mmol), CuI (19.6 mg, 0.10 mmol) were added to a vial. The vial was evacuated and backfilled with N₂ 5 times. DMF (0.00 g, 1.03 mmol), tert-butyl 3-(prop-2-yn-1-yloxy)propanoate (190 mg, 1.03 mmol) and triethylamine (1.72 mL, 12.4 mmol) were added and the mixture was allowed to stir at 90° C. overnight. The mixture was filtered through SiO₂ washing with EtOAc/MeOH, concentrated and purified by HPLC (5-95% MeCN in H₂O with 0.1% TFA) to afford tert-butyl 3-({3-[2-(2,6-dioxopiperidin-3-yl)-1,3-dioxoisoindol-5-yl]prop-2-yn-1-yl}oxy)propanoate (173 mg, 38.2%).

Step 2

A mixture of tert-butyl 3-({3-[2-(2,6-dioxopiperidin-3-yl)-1,3-dioxoisoindol-5-yl]prop-2-yn-1-yl}oxy)propanoate (173 mg, 0.39 mmol), Pd/C 10 wt % (4.0 mg, 0.04 mmol) and EtOH (5 mL) were mixed in a flask. The flask was evacuated and backfilled with H₂ 5 times and allowed to stir at r.t. for 2 h. The mixture was filtered through celite washing with MeOH and EtOAc, concentrated and carried to the next step.

Step 3

A mixture of tert-butyl 3-{3-[2-(2,6-dioxopiperidin-3-yl)-1,3-dioxoisoindol-5-yl]propoxy}propanoate (174 mg, 0.39 mmol), CH₂Cl₂ (3 mL) and trifluoroacetic acid (1 mL) was allowed to stir at r.t. for 2 h. The volatiles were removed to afford 3-{3-[2-(2,6-dioxopiperidin-3-yl)-1,3-dioxoisoindol-5-yl]propoxy}propanoic acid (151 mg, 99.3%).

Example No. 24: General Procedure F

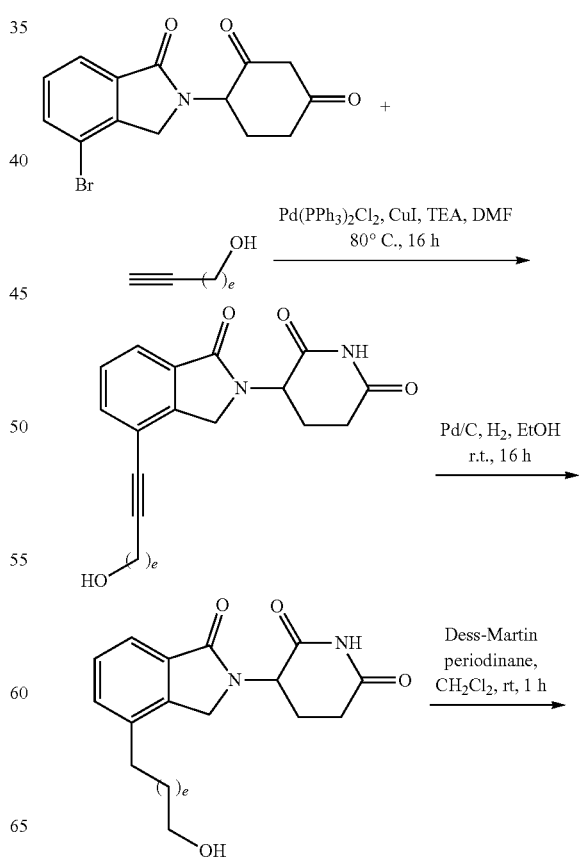

395
-continued

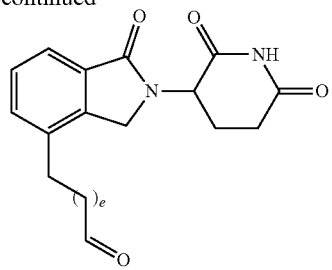

e is C$_{1-6}$ alkylidene chain.

Step 1

3-(4-bromo-1-oxo-2,3-dihydro-1H-isoindol-2-yl)piperidine-2,6-dione (1.79 mmol), (PPh$_3$)$_2$PdCl$_2$ (0.11 mmol), CuI (0.15 mmol) were added to a vial. The vial was evacuated and backfilled with N$_2$ 5 times. DMF (5 mL), alkyne (4.37 mmol) and triethylamine (18.05 mmol) were added and the mixture was allowed to stir at 90° C. overnight. The mixture was filtered through celite and purified by HPLC (5-95% MeCN in H$_2$O with 0.1% TFA) to afford the aryl alkyne (58%).

Step 2

A mixture of aryl alkyne (1.04 mmol), Pd/C 10 wt % (0.12 mmol) and EtOH (015 mL) were mixed in a flask. The flask was evacuated and backfilled with H$_2$ 5 times and allowed to stir at r.t. for 16 h. The mixture was filtered through celite washing with MeOH and EtOAc and concentrated to afford the alkyl alcohol (74%).

Step 3

Dess-Martin periodinane (1.54 mmol) was added to a mixture of the alkyl alcohol (0.77 mmol) and CH$_2$Cl$_2$ (10 mL). The mixture was allowed to stir at r.t. for 1 h. CH$_2$Cl$_2$ and aqueous Na$_2$SO$_3$ were added. The organic layer was dried with MgSO$_4$, filtered, concentrated and purified by MPLC (20-100% EtOAc in hexanes) to afford the aldehyde.

Example 24A: Synthesis of 3-(2-(2,6-dioxopiperidin-3-yl)-1-oxoisoindolin-4-yl)propanal

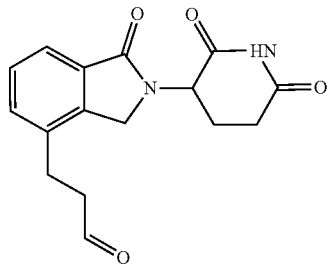 [SMILES: O=CCCc1cccc2c1CN(C1CCC(=O)NC1=O)C2=O]

Step 1 Product 3-(4-(3-hydroxyprop-1-yn-1-yl)-1-oxoisoindolin-2-yl)piperidine-2,6-dione (127.6 mg, 23.1%). LCMS; C$_{16}$H$_{14}$N$_2$O$_4$ requires: 298, found: m/z=299 [M+H]$^+$.

396

Step 2 Product 3-(4-(3-hydroxypropyl)-1-oxoisoindolin-2-yl)piperidine-2,6-dione (129 mg, 99%). LCMS; C$_{16}$H$_{18}$N$_2$O$_4$ requires: 302, found: m/z=303 [M+H]$^+$.

Step 3 Product 3-(2-(2,6-dioxopiperidin-3-yl)-1-oxoisoindolin-4-yl)propanal (29 mg, 99%). LCMS; C$_{16}$H$_{16}$N$_2$O$_4$ requires: 300, found: m/z=301 [M+H]$^+$.

Example 24B: Synthesis of 4-(2-(2,6-dioxopiperidin-3-yl)-1-oxoisoindolin-4-yl)butanal

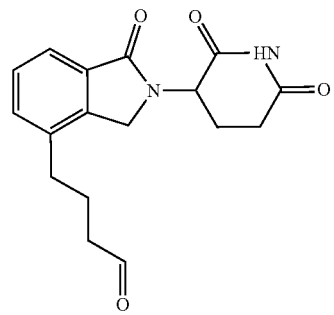 [SMILES: O=CCCCc1cccc2c1CN(C1CCC(=O)NC1=O)C2=O]

Step 1 Product 3-(4-(4-hydroxybut-1-yn-1-yl)-1-oxoisoindolin-2-yl)piperidine-2,6-dione (325 mg, 58.1%). LCMS; C$_{17}$H$_{16}$N$_2$O$_4$ requires: 312, found: m/z=313 [M+H]$^+$.

Step 2 Product 3-(4-(4-hydroxybutyl)-1-oxoisoindolin-2-yl)piperidine-2,6-dione (244 mg, 74.1%). LCMS; C$_{17}$H$_{20}$N$_2$O$_4$ requires: 316, found: m/z=317 [M+H]$^+$.

Step 3 Product 4-(2-(2,6-dioxopiperidin-3-yl)-1-oxoisoindolin-4-yl)butanal (178 mg, 73.4%). LCMS; C$_{17}$H$_{18}$N$_2$O$_4$ requires: 314, found: m/z=315 [M+H]$^+$.

Example 25: Synthesis of 2-(3-(2-(2,6-dioxopiperidin-3-yl)-1,3-dioxoisoindolin-4-yl)propoxy)acetaldehyde

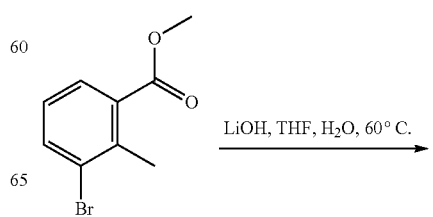

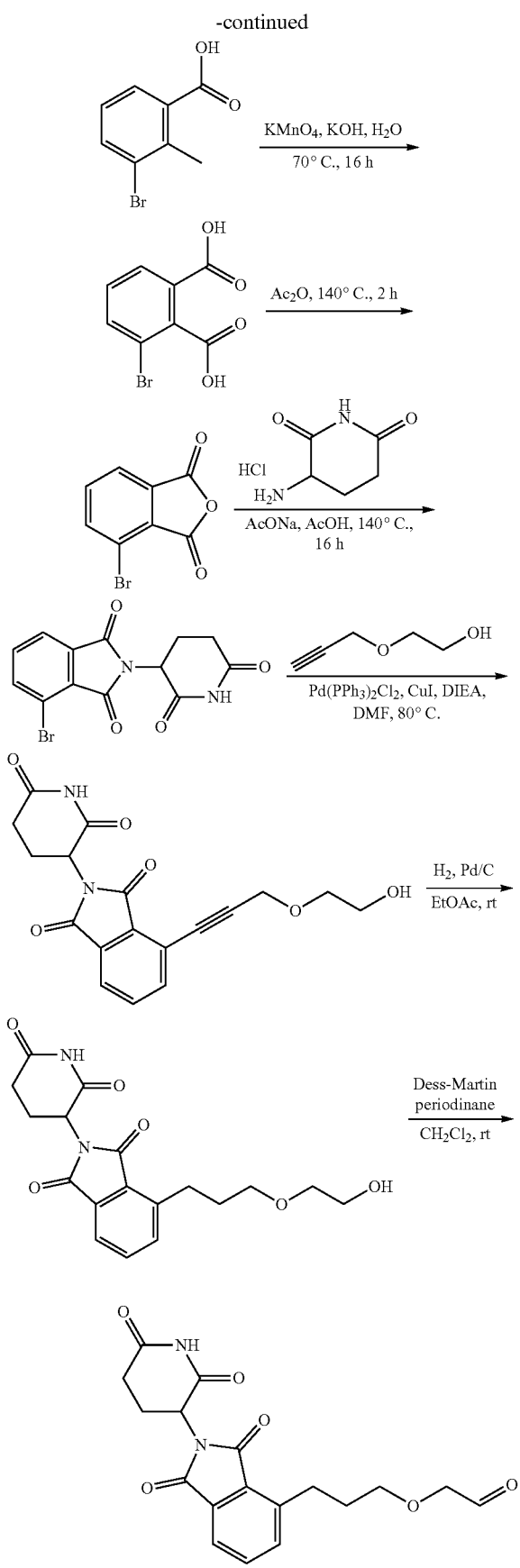

Step 1: 3-bromo-2-methylbenzoic acid

A mixture of methyl 3-bromo-2-methylbenzoate (35.0 g, 152.79 mmol) and LiOH (10.9 g, 453.79 mmol) in THF (300 mL) and H$_2$O (50 mL) was stirred at 60° C. for 16 h and then concentrated under vacuum. The residue was diluted with water (80 mL) and the mixture was then acidified to pH 4 with 2N HCl. The precipitated solids were collected by filtration and washed with water. The solids were dried under vacuum to afford 3-bromo-2-methylbenzoic acid (30 g, 91%) as a white solid. MS (ESI) calculated for (C$_8$H$_7$BrO$_2$) [M+H]$^+$, 214.9, 216.9; found, 215.0, 217.0.

Step 2: 3-bromophthalic acid

To a solution of KOH (78.3 g, 1395.58 mmol) in H$_2$O (2.5 L) was added 3-bromo-2-methylbenzoic acid (50.0 g, 232.51 mmol) at room temperature. The mixture was stirred for 5 min and then to the mixture was added KMnO$_4$ (73.5 g, 465.02 mmol). The resulting mixture was stirred at 70° C. for 16 h. The mixture was cooled to room temperature and then diluted with ethanol (1.0 L). The resulting mixture was stirred for another 30 min before filtration. The filtrate was acidified to pH 4 with HCl (3 N) and extracted with ethyl acetate (1 L×3). The combined organic layers were washed with brine, dried over anhydrous Na$_2$SO$_4$, filtered and concentrated under vacuum to afford 3-bromophthalic acid (55 g, 96%) as an off-white solid. MS (ESI) calculated for (C$_8$H$_5$BrO$_4$) [M+H]$^+$, 244.9, 246.9; found, 245.1, 247.1.

Step 3: 4-bromoisobenzofuran-1,3-dione

A mixture of 3-bromophthalic acid (55.0 g, crude) in Ac$_2$O (500 mL) was stirred at 140° C. for 2 h before concentrated under vacuum. The residue was purified by trituration with ethyl acetate/petroleum ether (1/5) to afford 4-bromoisobenzofuran-1,3-dione (45 g, crude) as a light yellow solid. MS (ESI) calculated for (C$_8$H$_3$BrO$_3$) [M+H]$^+$, 226.9, 228.9; found, 227.1, 229.1.

Step 4: tert-butyl 3-bromo-5-methyl-1H-pyrazolo[4,3-b]pyridine-1-carboxylate

A mixture of 4-bromoisobenzofuran-1,3-dione (15.0 g, 66.08 mmol), 3-aminopiperidine-2,6-dione hydrochloride (15.2 g, 92.50 mmol) and NaOAc (9.2 g, 112.33 mmol) in AcOH (200 mL) was stirred at 140° C. for 8 h under nitrogen atmosphere. The mixture was cooled to room temperature. The solids were collected by filtration and then washed with water and ethyl acetate. The solids was dried under vacuum to afford 4-bromo-2-(2,6-dioxopiperidin-3-yl)isoindoline-1,3-dione (20 g, 89%) as an off-white solid. MS (ESI) calculated for (C$_{13}$H$_9$BrN$_2$O$_4$) [M+H]$^+$, 336.9, 338.9.

Step 5: 2-(2,6-dioxopiperidin-3-yl)-4-(3-(2-hydroxyethoxy)prop-1-yn-1-yl)isoindoline-1,3-dione To a degassed solution of 4-bromo-2-(2,6-dioxopiperidin-3-yl)isoindoline-1,3-dione (10.0 g, 29.66 mmol) in dry N,N-dimethylformamide (160 mL) were added [1,1'-Bis(diphenylphosphino)ferrocene]dichloropalladium (II) dichloromethane adduct (3.1 g, 4.44 mmol), copper(I) iodide (1.4 g, 7.36 mmol), N-ethyl-N-isopropylpropan-2-amine (100 mL) and 2-(prop-2-yn-1-yloxy)ethan-1-ol (4.4 g, 44.34 mmol). The resulting mixture was stirred at 80° C. for 16 h under nitrogen. The reaction mixture was diluted with water and extracted with ethyl acetate. The combined organic layer was washed with water and brine, dried over anhydrous sodium sulfate, filtered and concentrated under vacuum. The residue was purified by flash column chromatography with 0~100% ethyl acetate in petroleum ether to afford 2-(2,6-dioxopiperidin-3-yl)-4-(3-(2-hydroxyethoxy)prop-1-yn-1-yl)isoindoline-1,3-dione (3.0 g, 28%) as a gray solid. MS (ESI) calc'd for ($C_{18}H_{16}N_2O_6$) [M+H]$^+$, 357.1; found, 357.0.

Step 6: 2-(2,6-dioxopiperidin-3-yl)-4-(3-(2-hydroxyethoxy)propyl)isoindoline-1,3-dione A mixture of 2-(2,6-dioxopiperidin-3-yl)-4-(3-(2-hydroxyethoxy)prop-1-yn-1-yl)isoindoline-1,3-dione (2.8 g, 7.87 mmol) and Palladium/C (0.7 g, 10%) in ethyl acetate (50 mL) was stirred at room temperature for 16 h under $H_2$. The solids were filtered. The filtrate was concentrated under vacuum to afford the crude product. The residue was purified by reversed phase flash column chromatography with 5~50% acetonitrile in water to afford 2-(2,6-dioxopiperidin-3-yl)-4-(3-(2-hydroxyethoxy)propyl)isoindoline-1,3-dione (882.2 mg, 31%) as a white solid. MS (ESI) calc'd for ($C_{18}H_{20}N_2O_6$) [M+H]$^+$, 361.1; found, 361.1.

Step 7: 2-(3-(2-(2,6-dioxopiperidin-3-yl)-1,3-dioxoisoindolin-4-yl)propoxy)acetaldehyde 1,1-bis(acetyloxy)-3-oxo-3H-1lambda5,2-benziodaoxol-1-yl acetate (90 mg, 0.21 mmol) was added to a mixture of 3-[4-(3-hydroxypropyl)-1-oxo-2,3-dihydro-1H-isoindol-2-yl]piperidine-2,6-dione (32 mg, 0.11 mmol) and $CH_2Cl_2$ (1 mL). The mixture was allowed to stir at r.t. for 1 h. The mixture was purified by MPLC (10-100% EtOAc in hexanes) to afford 2-(3-(2-(2,6-dioxopiperidin-3-yl)-1,3-dioxoisoindolin-4-yl)propoxy)acetaldehyde (35 mg, 97%).

Example 26: Synthesis of 4-(5-(2-(2,6-dioxopiperidin-3-yl)-1-oxoisoindolin-4-ylamino)-1,3,4-oxadiazol-2-yl)butanoic acid

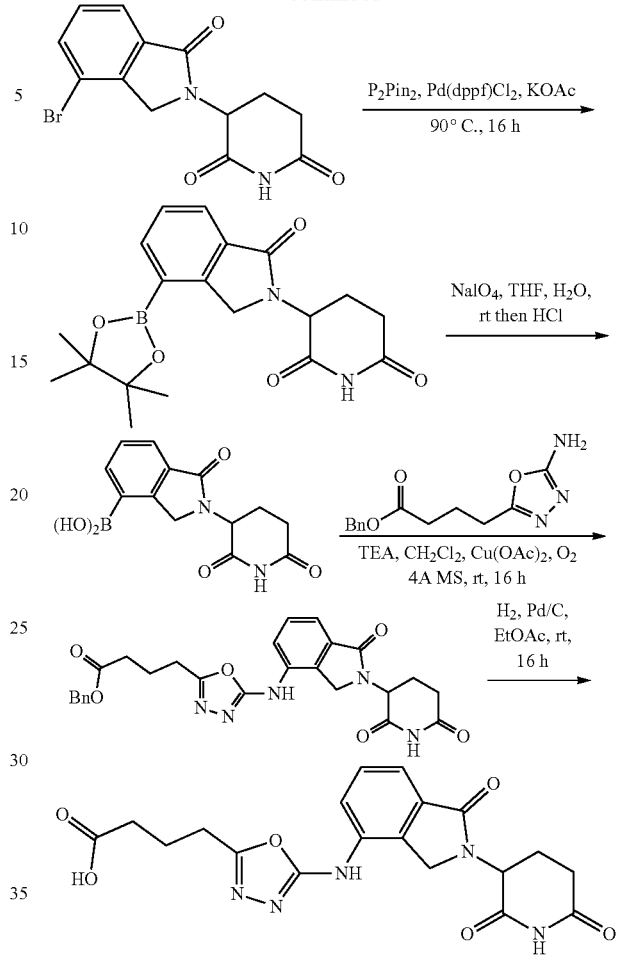

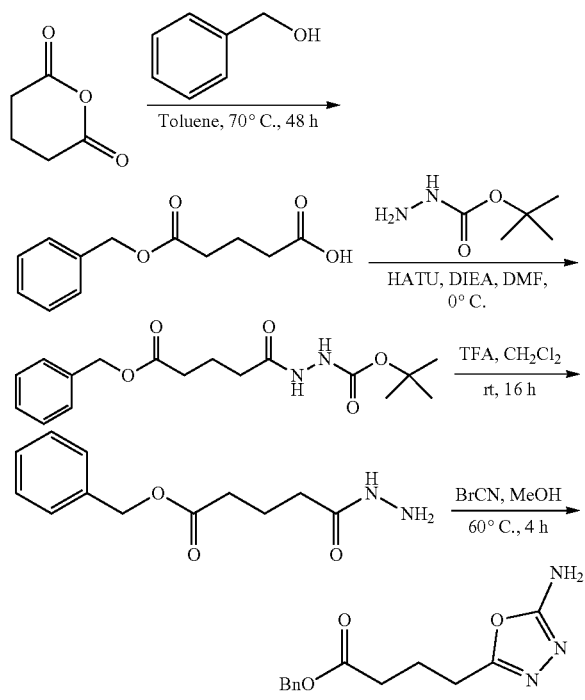

Step 1: 5-(benzyloxy)-5-oxopentanoic acid

To a solution of dihydro-3H-pyran-2,6-dione (50.0 g, 438.21 mmol) in toluene (500 mL) was added phenylmethanol (52.1 g, 482.40 mmol). The resulting solution was stirred at 70° C. for 48 h. After the reaction was completed, the resulting mixture was concentrated under vacuum to afford 5-(benzyloxy)-5-oxopentanoic acid (90 g, crude) as colorless oil, which was used for the next step without further purification. MS (ESI) calculated for ($C_{12}H_{14}O_4$) [M+H]$^+$, 223.1; found, 223.0.

Step 2: tert-butyl 2-(5-(benzyloxy)-5-oxopentanoyl)hydrazinecarboxylate

To a solution of 5-(benzyloxy)-5-oxopentanoic acid (20.0 g, 89.99 mmol) in DMF (500 mL) were added tert-butyl hydrazinecarboxylate (11.9 g, 89.99 mmol), DIEA (58.1 g, 449.96 mmol) and HATU (68.4 g, 179.99 mmol). The mixture was stirred at 0° C. for 1.5 h. After the reaction was completed, the resulting mixture was diluted with ethyl acetate. The organic phase was washed with water and brine, dried over anhydrous sodium sulfate and filtered. The filtrate was concentrated under vacuum. The residue was purified by silica gel flash column chromatography with 0~50% ethyl acetate in petroleum ether to afford tert-butyl 2-(5-(benzyloxy)-5-oxopentanoyl)hydrazinecarboxylate (28.0 g, 92%) as yellow oil. MS (ESI) calculated for ($C_{17}H_{24}N_2O_5$) [M+H]$^+$, 337.2; found [M+Na]$^+$, 359.2.

Step 3: benzyl 5-hydrazinyl-5-oxopentanoate

To a solution of tert-butyl 2-(5-(benzyloxy)-5-oxopentanoyl)hydrazinecarboxylate (18.0 g, 54.05 mmol) in $CH_2Cl_2$ (100 mL) was added TFA (50 mL). The mixture was stirred at room temperature for 16 h. After the reaction was completed, the reaction solution was concentrated under vacuum. The residue was dissolved in saturated $NaHCO_3$ aqueous solution and extracted with dichloromethane. The combined organic phase was washed with water and brine, dried over anhydrous sodium sulfate and filtered. The filtrate was concentrated under vacuum to afford benzyl 5-hydrazinyl-5-oxopentanoate (12.0 g, crude) as yellow oil, which was used for the next step without further purification. MS (ESI) calculated for ($C_{12}H_{16}N_2O_3$) [M+H]$^+$, 237.1; found, 237.1.

Step 4: benzyl 4-(5-amino-1,3,4-oxadiazol-2-yl)butanoate

To a solution of benzyl 5-hydrazinyl-5-oxopentanoate (13.5 g, 57.14 mmol) in MeOH (200 mL) was added carbononitridic bromide (7.3 g, 68.56 mmol). The mixture was stirred at 60° C. for 4 h. After the reaction was completed, the mixture was concentrated under vacuum. The residue was dissolved in saturated $NaHCO_3$ aqueous solution and extracted with dichloromethane. The combined organic phase was washed with water and brine, dried over anhydrous sodium sulfate and filtered. The filtrate was concentrated under vacuum. The residue was purified by silica gel flash column chromatography with 0~100% ethyl acetate in petroleum ether to afford benzyl 4-(5-amino-1,3,4-oxadiazol-2-yl)butanoate (8.0 g, 53%) as a white solid. MS (ESI) calculated for ($C_{13}H_{15}N_3O_3$) [M+H]$^+$, 262.1; found, 262.1.

Step 5: 3-(1-oxo-4-(4,4,5,5-tetramethyl-1,3,2-dioxaborolan-2-yl)isoindolin-2-yl)piperidine-2,6-dione To a degassed solution of 3-(4-bromo-1-oxoisoindolin-2-yl)piperidine-2,6-dione (1.0 g, 3.09 mmol) in dioxane (10 mL) were added 4,4,5,5-tetramethyl-2-(4,4,5,5-tetramethyl-1,3,2-dioxaborolan-2-yl)-1,3,2-dioxaborolane (1.57 g, 6.19 mmol), Pd(dppf)Cl$_2$ (226 mg, 0.31 mmol) and KOAc (607 mg, 6.19 mmol). The mixture was stirred at 90° C. for 16 h under nitrogen. After the reaction was completed, the solid was filtered. The filtrate was concentrated under vacuum. The residue was purified by silica gel flash column chromatography with 0-100% ethyl acetate in petroleum ether to afford 3-(1-oxo-4-(4,4,5,5-tetramethyl-1,3,2-dioxaborolan-2-yl)-isoindolin-2-yl)piperidine-2,6-dione (1.2 g, 83%) as a yellow solid. MS (ESI) calculated for ($C_{19}H_{23}BN_2O_5$) [M+H]$^+$, 370.2; found, 370.1.

Step 6: 2-(2,6-dioxopiperidin-3-yl)-1-oxoisoindolin-4-ylboronic acid

To a solution of 3-[1-oxo-4-(4,4,5,5-tetramethyl-1,3,2-dioxaborolan-2-yl)-2,3-dihydro-1H-isoindol-2-yl]piperidine-2,6-dione (1.0 g, 2.75 mmol) in THF (48 mL) and $H_2O$ (12 mL) was added $NaIO_4$ (2.1 g, 10.00 mmol). The mixture was stirred at room temperature for 30 min. Then 1N HCl (1.9 mL, 1.90 mmol) was added to the above mixture and stirred at room temperature for another 4 h. After the reaction was completed, the solid was filtered. The filtrate was concentrated under vacuum. The residue was purified by reverse phase FC with 5~60% MeCN in $H_2O$ to afford 2-(2,6-dioxopiperidin-3-yl)-1-oxoisoindolin-4-ylboronic acid (410 mg, 51%) as an off-white solid. MS (ESI) calculated for ($C_{13}H_{13}BN_2O_5$) [M+H]$^+$, 289.1; found, 289.1

Step 7: benzyl 4-(5-(2-(2,6-dioxopiperidin-3-yl)-1-oxoisoindolin-4-ylamino)-1,3,4-oxadi-azol-2-yl) butanoate To a solution of 2-(2,6-dioxopiperidin-3-yl)-1-oxoisoindolin-4-ylboronic acid (310 mg, 1.07 mmol) in $CH_2Cl_2$ (6 mL) were added benzyl 4-(5-amino-1,3,4-oxadiazol-2-yl) butanoate (525 mg, 2.01 mmol), Cu(OAc)$_2$ (224 mg, 1.24 mmol), TEA (1.5 mL) and 4A MS (100 mg). The mixture was stirred at room temperature for 16 h under oxygen. After the reaction was completed, the solid was filtered. The filtrate was concentrated under vacuum. The residue was purified by reverse phase FC with 5~65% MeCN in $H_2O$ to afford benzyl 4-(5-(2-(2,6-dioxopiperidin-3-yl)-1-oxoisoindolin-4-ylamino)-1,3,4-oxadiazol-2-yl)butanoate (370 mg, 68%) as a yellow solid. MS (ESI) calculated for ($C_{26}H_{25}N_5O_6$) [M+H]$^+$, 504.2; found, 504.4.

Step 8: 4-(5-(2-(2,6-dioxopiperidin-3-yl)-1-oxoisoindolin-4-ylamino)-1,3,4-oxadiazol-2-yl)-butanoic acid To a solution of benzyl 4-(5-(2-(2,6-dioxopiperidin-3-yl)-1-oxoisoindolin-4-ylamino)-1,3,4-oxadiazol-2-yl)butanoate (360 mg, 0.71 mmol) in ethyl acetate (5 mL) was added Pd/C (dry, 50 mg). The mixture was stirred at room temperature for 16 h under hydrogen. After the reaction was completed, the solid was filtered out. The filtrate was concentrated under vacuum. The residue was purified by reverse phase FC with 5~55% MeCN in $H_2O$ and then further purified by prep-HPLC with the following conditions: [Column: Sunfire prep C18 column 30*150, 5 um; Mobile Phase A:, Mobile Phase B: ACN; Flow rate: 60 mL/min; Gradient: 10% B to 26% B in 7 min; 254 nm] to afford 4-(5-(2-(2,6-dioxopiperidin-3-yl)-1-oxoisoindolin-4-ylamino)-1,3,4-oxadiazol-2-yl)-butanoic acid (25 mg, 8%) as a white solid. MS (ESI) calculated for ($C_{19}H_{19}N_5O_6$) [M+H]$^+$, 414.1; found, 414.4. $^1$H NMR (400 MHz, DMSO-d$_6$) δ 12.17 (s, 1H), 11.04 (s, 1H), 10.23 (s, 1H), 8.17-8.13 (m, 1H), 7.54 (t, J=7.6 Hz, 1H), 7.42 (d, J=7.6 Hz, 1H), 5.17-5.12 (m, 1H), 4.63-4.28 (m, 2H), 2.97-2.91 (m, 1H), 2.84-2.79 (m, 2H), 2.66-2.59 (m, 1H), 2.41-2.24 (m, 3H), 2.13-2.00 (m, 1H), 1.96-1.85 (m, 2H).

Example 27: General Procedure G

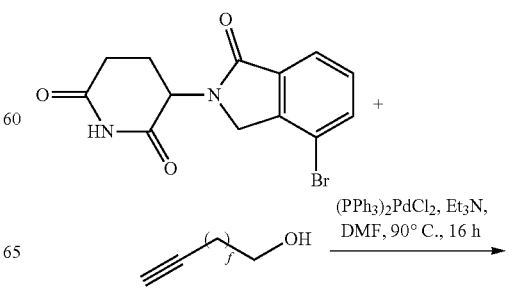

-continued

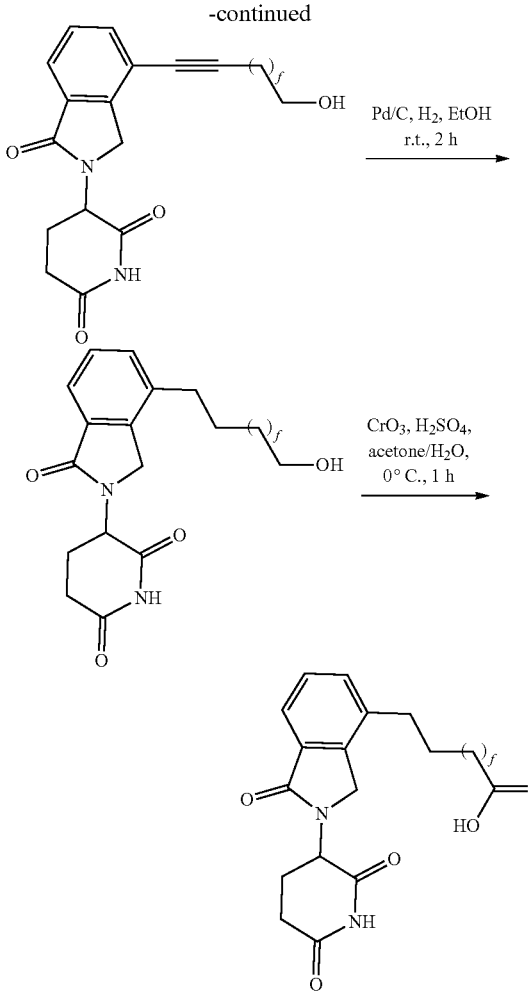

f is C$_{1-5}$ alkylidene chain.

Step 1

3-(4-Bromo-1-oxoisoindolin-2-yl)piperidine-2,6-dione (4.6 mmol), copper iodide (177 mg) and bis-triphenylphosphine-palladium dichloride (326 mg) were evacuated and flushed with nitrogen 3 times. DMF (5 mL), triethylamine (6.5 mL) and the alkyne (27.9 mmol) were added and the vial was flushed with nitrogen, sealed and heated to 80° C. for 20 h. The mixture was cooled to room temperature and was diluted with DCM/ethyl acetate (1:1, 20 mL) and the solid was filtered over a pad of Celite. The solid was stirred with acetonitrile for 16 h. The solids were filtered and concentrated to give the disubstituted alkyne product.

Step 2

The disubstituted alkyne (2.2 mmol) was dissolved in methanol (40 mL). Palladium over charcoal (10%, 235 mg) was added and the flask was filled with hydrogen at 65 psi for 3 h. The mixture was filtered over Celite and washed with methanol to give the alcohol product.

Step 3

Chromic acid (360 mg, 3.6 mmol) was added to 3 M sulfuric acid (3 mL) to make a solution of chromium oxidant (Jones' reagent). The alcohol (1.2 mmol) was suspend in acetone (2.5 mL) and 3 M sulfuric acid (0.5 mL) and the suspension was cooled to 0° C. The Jones' reagent was slowly added to the alcohol suspension and allowed to stir for 1 h. The mixture was poured into of iced water (20 mL) and the solid was filtered and washed with water. The aqueous solution was extracted with (2×20 mL) EtOAc, washed with brine and concentrated. The organic fractions were combined with the solid and the mixture was purified by flash column chromatography (0-25% methanol in DCM) to afford the acid product.

Example 27A: Synthesis of 5-(2-(2,6-dioxopiperidin-3-yl)-1-oxoisoindolin-4-yl)pentanoic acid

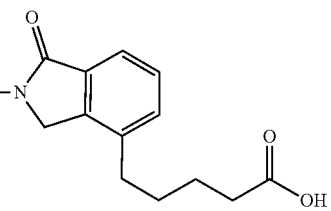

Step 1 Product 3-(4-(5-hydroxypent-1-yn-1-yl)-1-oxoisoindolin-2-yl)piperidine-2,6-dione (325 mg, 58%). LCMS; C$_{18}$H$_{18}$N$_2$O$_4$ requires: 326, found: m/z=349 [M+Na]$^+$.

Step 2 Product 3-(4-(5-hydroxypentyl)-1-oxoisoindolin-2-yl)piperidine-2,6-dione (160 mg, 99%). LCMS; C$_{18}$H$_{22}$N$_2$O$_4$ requires: 330, found: m/z=353 [M+Na]$^+$.

Step 3 Product 5-(2-(2,6-dioxopiperidin-3-yl)-1-oxoisoindolin-4-yl)pentanoic acid (74 mg, 60%). LCMS; C$_{18}$H$_{20}$N$_2$O$_5$ requires: 344, found: m/z=367 [M+Na]$^+$.

Example 28: Synthesis of 3-(3-(2-(2,6-dioxopiperidin-3-yl)-3-oxoisoindolin-5-yl)propoxy)propanoic acid

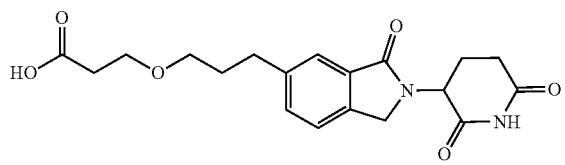 [SMILES: O=C(O)CCOCCCc1ccc2c(c1)C(=O)N(C1CCC(=O)NC1=O)C2]

Step 1: methyl 5-bromo-2-(bromomethyl)benzoate

To a solution of methyl 5-bromo-2-methylbenzoate (24.5 g, 107.4 mmol) in CCl$_4$ (300 mL) were added NBS (17.1 g, 96.7 mmol) and BPO (4.8 g, 19.8 mmol). The mixture was stirred at 80° C. for 16 h under N$_2$. The resulting mixture was cooled down to room temperature and then filtered. The filtrate was concentrated under vacuum and the residue was purified by silica gel flash column chromatography with 0~5% ethyl acetate in petroleum ether to afford methyl 5-bromo-2-(bromomethyl)benzoate (23.5 g, 76%) as yellow oil. 1H NMR (300 MHz, DMSO-$d_6$) δ 7.98 (d, J=2.1 Hz, 1H), 7.81 (dd, J=8.4, 2.1 Hz, 1H), 7.56 (d, J=8.4 Hz, 1H), 4.98 (s, 2H), 3.88 (s, 3H).

Step 2: 3-(6-bromo-1-oxoisoindolin-2-yl)piperidine-2,6-dione

To a mixture of methyl 5-bromo-2-(bromomethyl)benzoate (23.5 g, 76.8 mmol) in MeCN (250 mL) were added 3-aminopiperidine-2,6-dione hydrochloride (19.0 g, 115.8 mmol) and TEA (31.0 g, 306.9 mmol). The mixture was stirred at 80° C. for 16 h. The resulting mixture was cooled down to room temperature and then filtered. The filtrate was concentrated under vacuum and the crude residue was purified by trituration with methanol and acetonitrile to afford 3-(6-bromo-1-oxoisoindolin-2-yl)piperidine-2,6-dione (5.8 g, 23%) as a dark blue solid. $^1$H NMR (300 MHz, DMSO-$d_6$) δ 11.01 (s, 1H), 7.91-7.78 (m, 2H), 7.61 (d, J=8.1 Hz, 1H), 5.13 (dd, J=13.2, 5.1 Hz, 1H), 4.46 (d, J=17.7 Hz, 1H), 4.32 (d, J=17.7 Hz, 1H), 2.98-2.86 (m, 1H), 2.67-2.54 (m, 1H), 2.47-2.33 (m, 1H), 2.08-1.99 (m, 1H). MS (ESI) calc'd for ($C_{13}H_{11}BrN_2O_3$) [M+H]$^+$, 323.0/325.0; found 322.9/324.9.

Step 3: tert-butyl 3-((3-(2-(2,6-dioxopiperidin-3-yl)-3-oxoisoindolin-5-yl)prop-2-yn-1-yl)oxy)propanoate 3-(6-bromo-1-oxo-3H-isoindol-2-yl)piperidine-2,6-dione (511 mg, 1.58 mmol), (PPh$_3$)$_2$PdCl$_2$ (66.6 mg, 0.09 mmol), CuI (30.1 mg, 0.16 mmol) were added to a vial. The vial was evacuated and backfilled with N$_2$ 5 times. DMF (5 mL), tert-butyl 3-(prop-2-yn-1-yloxy)propanoate (437 mg, 2.37 mmol) and triethylamine (2.64 mL, 19.0 mmol) were added and the mixture was allowed to stir at 90° C. overnight. The mixture was filtered through celite washing with MeOH and EtOAc. The volatiles were removed under vacuum. EtOAc and H$_2$O were added. The organic layer as washed with brine, dried with MgSO$_4$, filtered, concentrated and purified by MPLC (0-10% MeOH in CH$_2$Cl$_2$) to afford tert-butyl 3-({3-[2-(2,6-dioxopiperidin-3-yl)-3-oxo-1H-isoindol-5-yl]prop-2-yn-1-yl}oxy)propanoate (107 mg, 15.9%). LCMS; $C_{23}H_{26}N_2O_6$ requires: 426, found: m/z=427 [M+H]$^+$.

Step 4: tert-butyl 3-(3-(2-(2,6-dioxopiperidin-3-yl)-3-oxoisoindolin-5-yl)propoxy)propanoate A mixture of tert-butyl 3-({3-[2-(2,6-dioxopiperidin-3-yl)-3-oxo-1H-isoindol-5-yl]prop-2-yn-1-yl}oxy)propanoate (107 mg, 0.25 mmol), Pd/C 10 wt % (2.5 mg, 0.03 mmol) and EtOH (4 mL) were mixed in a flask. The flask was evacuated and backfilled with H$_2$ 5 times and allowed to stir at r.t. for 2h. The mixture was filtered through celite washing with MeOH and EtOAc, concentrated and carried to the next step. LCMS; $C_{23}H_{30}N_2O_6$ requires: 430, found: m/z=431 [M+H]$^+$.

Step 5: 3-(3-(2-(2,6-dioxopiperidin-3-yl)-3-oxoisoindolin-5-yl)propoxy)propanoic acid A mixture of tert-butyl 3-{3-[2-(2,6-dioxopiperidin-3-yl)-3-oxo-1H-isoindol-5-yl]propoxy}propanoate (106 mg, 0.25 mmol), CH$_2$Cl$_2$ (2 mL) and trifluoroacetic acid (0.4 mL) was allowed to stir at r.t. for 2 h. The volatiles were removed to afford 3-{3-[2-(2,6-dioxopiperidin-3-yl)-3-oxo-1H-isoindol-5-yl]propoxy}propanoic acid (60 mg, 65.1% over 2 steps). LCMS; $C_{19}H_{22}N_2O_6$ requires: 374, found: m/z=375 [M+H]$^+$.

Example 29: Synthesis of 4-((2-(2-(2-(2-aminoethoxy)ethoxy)ethoxy)ethyl)amino)-2-(2,6-dioxopiperidin-3-yl)isoindoline-1,3-dione

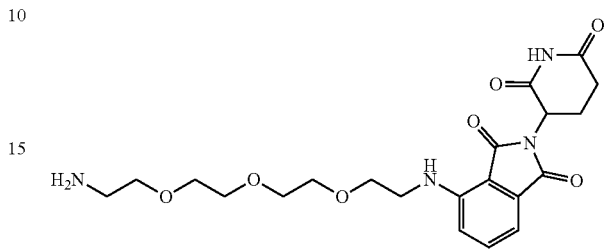

Step 1

A solution of tert-butyl N-[2-[2-[2-(2-aminoethoxy)ethoxy]ethoxy]ethyl]carbamate (3 g, 10.26 mmol, 1 eq), i-Pr$_2$NEt (2.65 g, 20.52 mmol, 3.57 mL, 2 eq) and 2-(2,6-dioxo-3-piperidyl)-4-fluoro-isoindoline-1,3-dione (2.89 g, 10.26 mmol, 1 eq) in DMSO (40 mL) was stirred at 90° C. for 6 h. The reaction mixture was diluted with H$_2$O (60 mL) and extracted with EtOAc. The combined organic layer was washed with brine, dried over Na$_2$SO$_4$, and concentrated under reduced pressure. The residue was purified by reverse MPLC column (0.1% FA in H$_2$O). tert-butyl N-[2-[2-[2-[2-[[2-(2,6-dioxo-3-piperidyl)-1,3-dioxo-isoindolin-4-yl]amino]ethoxy]ethoxy]ethoxy]ethyl]carbamate (2.9 g, 5.29 mmol, 51.5%) was obtained as a blue oil. LCMS: $C_{26}H_{36}N_4O_9$ requires: 548, found: m/z=549 [M+H]$^+$.

Step 2

A solution of tert-butyl N-[2-[2-[2-[2-[[2-(2,6-dioxo-3-piperidyl)-1,3-dioxo-isoindolin-4-yl]amino]ethoxy]ethoxy]ethoxy]ethyl]carbamate (2.9 g, 5.29 mmol, 1 equiv.) and HCl (4 M in dioxane, 30 mL, 22.7 equiv.) was stirred at 25° C. for 2 h under N$_2$. The reaction mixture was concentrated under reduced pressure. The residue was purified by HPLC (1-30% MeCN in H$_2$O with 0.05% HCl). 4-[2-[2-[2-(2-aminoethoxy)ethoxy]ethoxy]ethylamino]-2-(2,6-dioxo-3-piperidyl)isoindoline-1,3-dione (1.1 g, 2.07 mmol, 39.1%, 2HCl) was obtained as a yellow solid. LCMS: $C_{21}H_{28}N_4O_7$ requires: 448, found: m/z=449 [M+H]$^+$.

Example 30: Synthesis of 3-[4-[3-[2-[2-(2-aminoethoxy)ethoxy]ethoxy]propyl]-1-oxo-isoindolin-2-yl]piperidine-2,6-dione

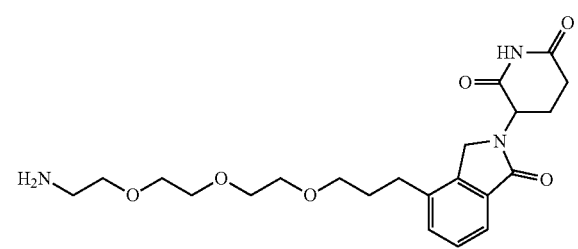 [SMILES: NCCOCCOCCOCCCc1cccc2c1CN(C1CCC(=O)NC1=O)C2=O]

Step 1

A mixture of 3-(4-bromo-1-oxo-2,3-dihydro-1H-isoindol-2-yl)piperidine-2,6-dione (2.52 mmol), (PPh$_3$)$_2$PdCl$_2$ (0.15 mmol), CuI (0.25 mmol), alkyne (5.04 mmol) were added to a vial. The vial was evacuated and backfilled with N$_2$ 5 times. DMF and triethylamine (30.3 mmol) were added and the mixture was allowed to stir at 90° C. overnight. The mixture was filtered through celite, washing with MeOH and EtOAc. EtOAc and saturated aqueous NaCl were added. The organic layer was dried with MgSO$_4$, filtered, concentrated and purified by reverse phase MPLC (5-100% MeCN in H2O on C18 column) to afford the product.

Step 2

A mixture of disubstituted alkyne (0.81 mmol), Pd/C 10 wt % (0.08 mmol) and EtOH were mixed in a flask. The flask was evacuated and backfilled with H$_2$ 5 times and allowed to stir at r.t. for 2h. The mixture was filtered through celite washing with MeOH and EtOAc, concentrated and carried to the next step.

Step 3

A mixture of tert-butylcarbamate (0.81 mmol), CH$_2$Cl$_2$ (2 mL), and TFA (2 mL) was allowed to stir at r.t. for 2 h. The mixture was concentrated to afford the amine product.

Step 1 Product tert-butyl N-[2-[2-[2-[3-[2-(2,6-dioxo-3-piperidyl)-1-oxo-isoindolin-4-yl]prop-2-ynoxy]ethoxy]ethoxy]ethyl]carbamate (1.45 g, 58.1%). LCMS: C$_{27}$H$_{35}$N$_3$O$_8$ requires: 529, found: m/z=552 [M+Na]$^+$.

Step 2 Product tert-butyl N-[2-[2-[2-[3-[2-(2,6-dioxo-3-piperidyl)-1-oxo-isoindolin-4-yl]propoxy]ethoxy]ethoxy]ethyl]carbamate (960 mg, 92.75%). LCMS: C$_{27}$H$_{39}$N$_3$O$_8$ requires: 533, found: m/z=556 [M+Na]$^+$.

Step 3 Product

3-[4-[3-[2-[2-(2-aminoethoxy)ethoxy]ethoxy]propyl]-1-oxo-isoindolin-2-yl]piperidine-2,6-dione (576.82 mg, 74.15%). LCMS: C$_{22}$H$_{31}$N$_3$O$_6$ requires: 433, found: m/z=434 [M+H]$^+$.

Example 31: Synthesis of 5-[(3R)-3-(3-methyl-2-oxoimidazolidin-1-yl)piperidin-1-yl]-3-{[4-(piperazin-1-yl)phenyl]amino}pyrazine-2-carboxamide Step 1: 2-(2,6-dioxopiperidin-3-yl)-5-[(2S)-2-(hydroxymethyl)pyrrolidin-1-yl]isoindole-1,3-dione

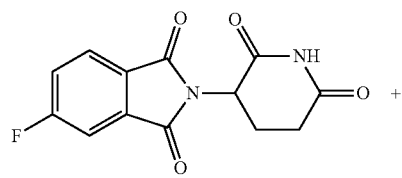 +

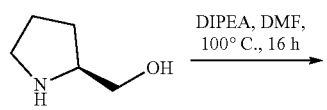

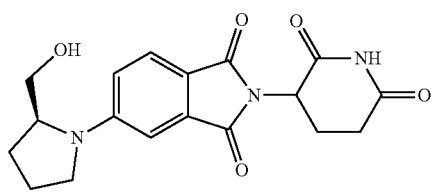

A mixture of 2-(2,6-dioxopiperidin-3-yl)-5-fluoroisoindole-1,3-dione (373 mg, 1.35 mmol), DMF (8 mL), ethylbis(propan-2-yl)amine (0.94 mL, 5.40 mmol) and prolinol (137 mg, 1.35 mmol) was allowed to stir at 90° C. for 16 h. CH$_2$Cl$_2$ and H$_2$O were added. The organic layer was dried with MgSO$_4$, filtered, concentrated and purified by MPLC (0-10% MeOH in CH$_2$Cl$_2$) to afford 2-(2,6-dioxopiperidin-3-yl)-5-[(2S)-2-(hydroxymethyl)pyrrolidin-1-yl]isoindole-1,3-dione (386.00 mg, 80.0%).

Step 2: (2S)-1-[2-(2,6-dioxopiperidin-3-yl)-1-oxo-3H-isoindol-5-yl]pyrrolidine-2-carbaldehyde

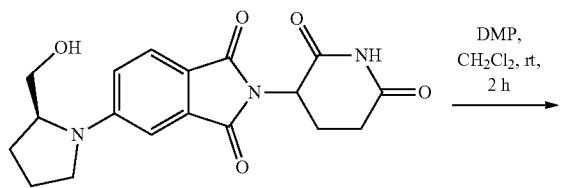

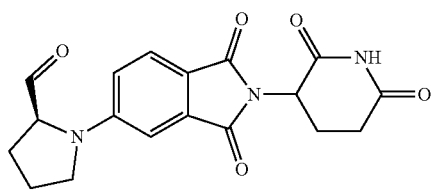

1,1-bis(acetyloxy)-3-oxo-1lambda5,2-benziodaoxol-1-yl acetate (548 mg, 1.29 mmol) was added to a mixture of 3-{5-[(2S)-2-(hydroxymethyl)pyrrolidin-1-yl]-1-oxo-3H-isoindol-2-yl}piperidine-2,6-dione (222 mg, 0.65 mmol) and CH$_2$Cl$_2$ (10 mL). The mixture was allowed to stir at rt for 1 h. The mixture was purified by MPLC (10-100% EtOAc in hexanes) to afford (2S)-1-[2-(2,6-dioxopiperidin-3-yl)-1-oxo-3H-isoindol-5-yl]pyrrolidine-2-carbaldehyde (67 mg, 30%).

Example 32: Synthesis of 5-[(3R)-3-(3-methyl-2-oxoimidazolidin-1-yl)piperidin-1-yl]-3-{[6-(piperazin-1-yl)pyridin-3-yl]amino}pyrazine-2-carboxamide

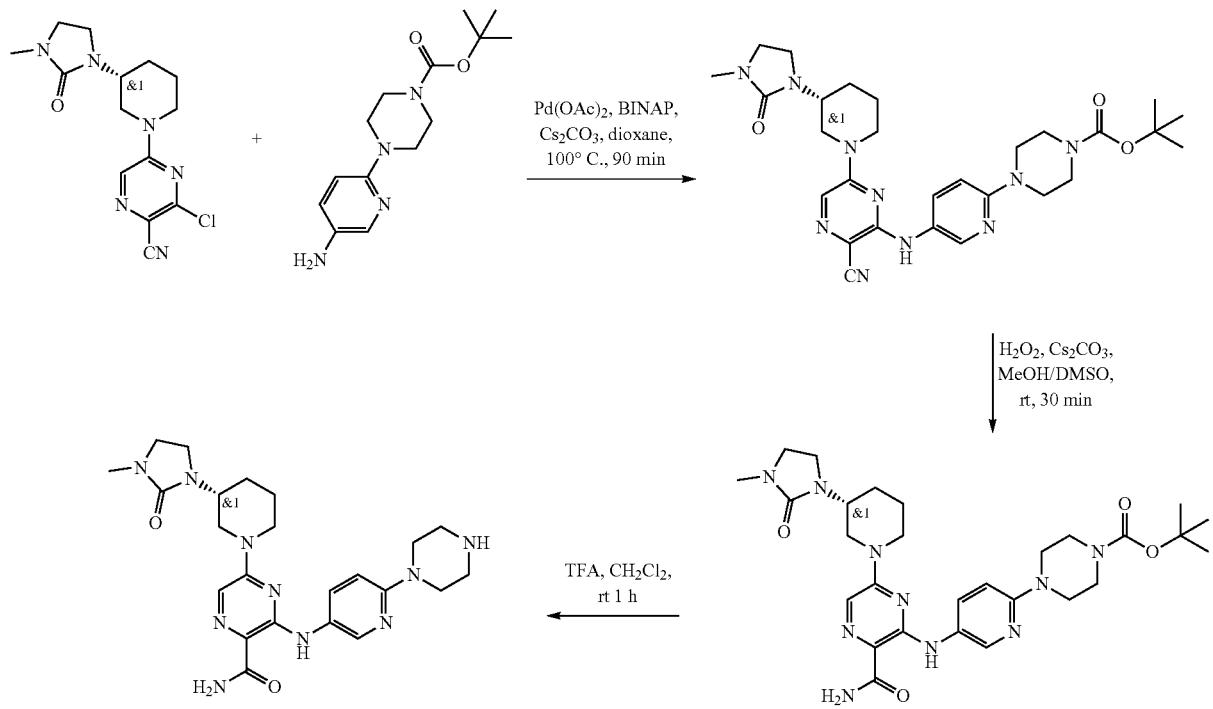

Step 1: tert-butyl 4-[5-({3-cyano-6-[(3R)-3-(3-methyl-2-oxoimidazolidin-1-yl)piperidin-1-yl]pyrazin-2-yl}amino)pyridin-2-yl]piperazine-1-carboxylate A mixture of 3-chloro-5-[(3R)-3-(3-methyl-2-oxoimidazolidin-1-yl)piperidin-1-yl]pyrazine-2-carbonitrile (322 mg, 1.00 mmol), tert-butyl 4-(5-aminopyridin-2-yl)piperazine-1-carboxylate (293 mg, 1.05 mmol), (acetyloxy)palladio acetate (74 mg, 0.33 mmol), [2'-(diphenylphosphanyl)-[1,1'-binaphthalen]-2-yl]diphenylphosphane (206.27 mg, 0.33 mmol) and Cs$_2$CO$_3$ (981 mg, 3.01 mmol) was degassed and backfilled with N$_2$ 5 times. The mixture was allowed to stir at 100° C. for 90 min. The mixture was filtered through Celite washing with MeOH/EtOAc, concentrated and purified by MPLC (0-100% EtOAc in CH$_2$Cl$_2$) to afford tert-butyl 4-[5-({3-cyano-6-[(3R)-3-(3-methyl-2-oxoimidazolidin-1-yl)piperidin-1-yl]pyrazin-2-yl}amino)pyridin-2-yl]piperazine-1-carboxylate (0.2920 g, 51.7%).

Step 2: tert-butyl 4-[5-({3-carbamoyl-6-[(3R)-3-(3-methyl-2-oxoimidazolidin-1-yl)piperidin-1-yl]pyrazin-2-yl}amino)pyridin-2-yl]piperazine-1-carboxylate H$_2$O$_2$ (30% in water, 0.88 mL, 0.09 mmol) was added to a mixture of rac-tert-butyl 4-[5-({3-cyano-6-[(3R)-3-(3-methyl-2-oxoimidazolidin-1-yl)piperidin-1-yl]pyrazin-2-yl}amino)pyridin-2-yl]piperazine-1-carboxylate (292 mg, 0.52 mmol), Cs$_2$CO$_3$ (169 mg, 0.52 mmol), DMSO (0.5 mL) and MeOH (10 mL). The mixture was allowed to stir at rt for 30 min. The mixture was concentrated. EtOAc was added and the organic phase was washed with H$_2$O and brine. The organic layer was dried with MgSO$_4$, filtered, concentrated and purified by MPLC (0-10% MeOH in CH$_2$Cl$_2$) to afford tert-butyl 4-[5-({3-carbamoyl-6-[(3R)-3-(3-methyl-2-oxoimidazolidin-1-yl)piperidin-1-yl]pyrazin-2-yl}amino)pyridin-2-yl]piperazine-1-carboxylate (0.279 g, 92.6%).

Step 3: 5-[(3R)-3-(3-methyl-2-oxoimidazolidin-1-yl)piperidin-1-yl]-3-{[6-(piperazin-1-yl)pyridin-3-yl]amino}pyrazine-2-carboxamide A mixture of tert-butyl 4-[5-({3-carbamoyl-6-[(3R)-3-(3-methyl-2-oxoimidazolidin-1-yl)piperidin-1-yl]pyrazin-2-yl}amino)pyridin-2-yl]piperazine-1-carboxylate (279 mg, 0.48 mmol), CH$_2$Cl$_2$ (5 mL) and TFA (1 mL) was allowed to stir at rt for 2 h. The volatiles were removed. The mixture was filtered through a NaHCO$_3$ cartridge, concentrated and purified by reverse phase MPLC (5-90% MeCN in H2O) to afford 5-[(3R)-3-(3-methyl-2-oxoimidazolidin-1-yl)piperidin-1-yl]-3-{[6-(piperazin-1-yl)pyridin-3-yl]amino}pyrazine-2-carboxamide (0.085 g, 37%).

Example 33: Synthesis of 1-(2-(2,6-dioxopiperidin-3-yl)-1-oxoisoindolin-5-yl)azetidine-3-carbaldehyde

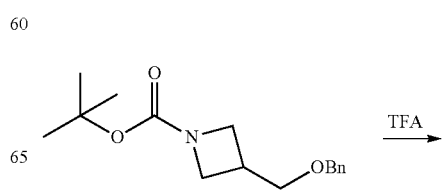

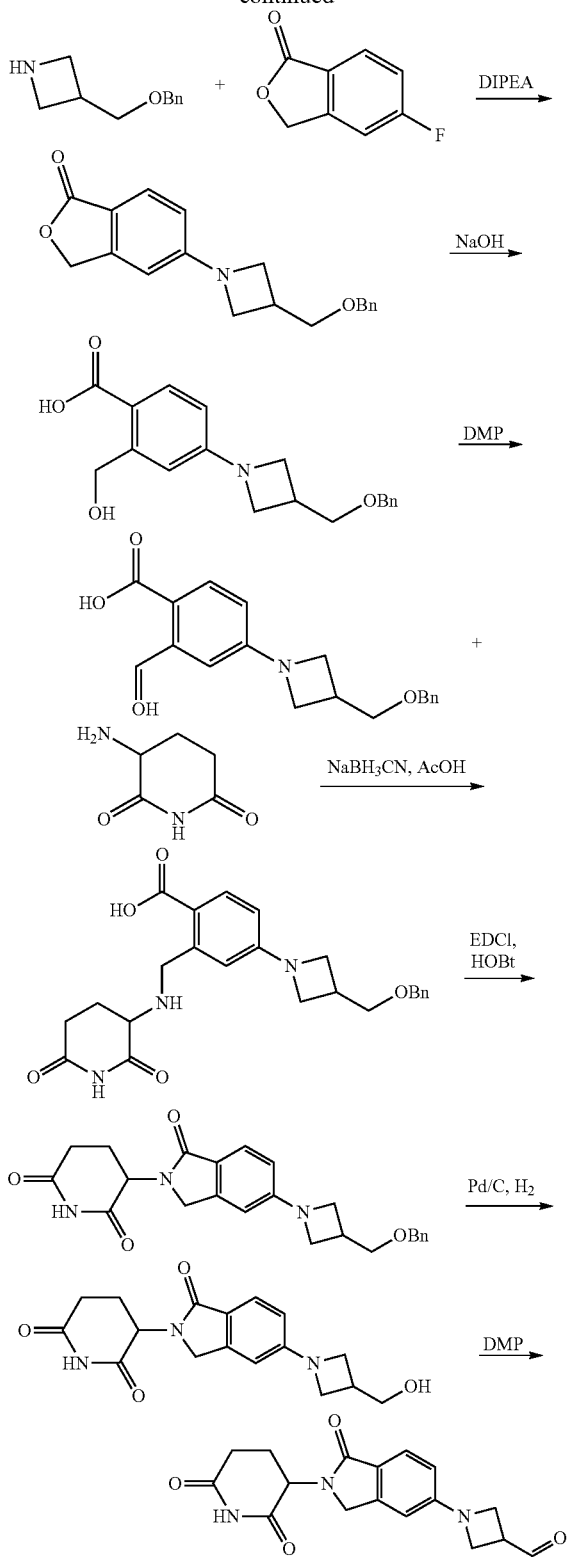

Step 1

TFA (1 mL) was added to a solution of tert-butyl 3-[(benzyloxy)methyl]azetidine-1-carboxylate (1 g, 3.62 mmol, 1.1 eq) in CH$_2$Cl$_2$ (1 mL). After stirring for 30 mins, the reaction mixture was concentrated under reduced pressure, and carried to the next step.

Step 2

5-fluoro-3H-2-benzofuran-1-one (500 mg, 3.29 mmol, 1 eq) and i-Pr$_2$NEt (2.86 mL, 16.4 mmol, 5 eq) were added sequentially to a solution of crude amine in NMP (4 mL). After stirring at 100° C. for 16 hrs, the reaction was quenched with H$_2$O. The resulting mixture was extracted with EtOAc, dried over Na$_2$SO$_4$, concentrated under reduced pressure. MPLC (0-30% EtOAc in hexanes) afforded the desired product (848 mg, 2.74 mmol, 83% yield). LCMS: C$_{19}$H$_{19}$NO$_3$ requires: 309, found: m/z=310 [M+H]$^+$.

Step 3

A solution of NaOH (439 mg, 11 mmol, 4 eq) in H$_2$O (1.8 mL) was added to a solution of 5-{3-[(benzyloxy)methyl]azetidin-1-yl}-3H-2-benzofuran-1-one (848 mg, 2.74 mmol, 1 eq.) in MeOH (3.4 mL) and THF (3.4 mL). After stirring for 1 hr, the volatile was removed. The resulting mixture was diluted with H$_2$O, extracted with EtOAc. The aqueous phase was acidified with aqueous 1.5 N HCl to pH 6, extracted with EtOAc, dried over Na$_2$SO$_4$, concentrated under reduced pressure, and carried to the next step. (659 mg, 2.01 mmol, 73% yield). LCMS: C$_{19}$H$_{21}$NO$_4$ requires: 327, found: m/z=328 [M+H]$^+$.

Step 4

Dess-Martin periodinane (774 mg, 1.83 mmol, 1.1 eq) was added to a solution of 4-{3-[(benzyloxy)methyl]azetidin-1-yl}-2-(hydroxymethyl)benzoic acid (543 mg, 1.66 mmol, 1 eq) in CH$_2$Cl$_2$ (8.3 mL). After stirring for 1 hr, the reaction was quenched with an equal mixture of saturated aqueous NaHCO$_3$ and 10 wt. % aqueous Na$_2$S$_2$O$_3$. After stirring for 30 min, the resulting mixture was extracted with CH$_2$Cl$_2$, dried over Na$_2$SO$_4$, and concentrated under reduced pressure. MPLC (0-5% MeOH in CH$_2$Cl$_2$) afforded the desired product (435 mg, 1.34 mmol, 81% yield). LCMS: C$_{19}$H$_{19}$NO$_4$ requires: 325, found: m/z=326 [M+H]$^+$.

Step 5

NaOAc (203 mg, 2.48 mmol, 1.5 eq.) and NaBH$_3$CN (311 mg, 4.94 mmol, 3 eq.) were added sequentially to a solution of 3-aminopiperidine-2,6-dione hydrochloride (407 mg, 2.48 mmol, 1.5 eq.) and 4-(3-((benzyloxy)methyl)azetidin-1-yl)-2-formylbenzoic acid (536 mg, 1.65 mmol, 1 eq.) in MeOH (8.2 mL). After stirring for 30 mins, the reaction mixture was concentrated under reduced pressure. Reverse phase MPLC (0-70% MeCN in H$_2$O) afforded the desired product (600 mg, 1.37 mmol, 83% yield). LCMS: C$_{24}$H$_{27}$N$_3$O$_5$ requires: 437, found: m/z=438 [M+H]$^+$.

Step 6

A mixture of 4-(3-((benzyloxy)methyl)azetidin-1-yl)-2-(((2,6-dioxopiperidin-3-yl)amino)methyl)benzoic acid (331 mg, 0.76 mmol, 1 eq), EDCI (176 mg, 1.13 mmol, 1.5 eq), HOBt (174 mg, 1.13 mmol, 1.5 eq) Et$_3$N (316 μL, 2.27 mmol, 3 eq) in CH$_2$Cl$_2$ was allowed to stir at r.t. for 16 hrs. The reaction mixture was washed with H$_2$O and saturated aqueous NaHCO$_3$, and concentrated under reduced pressure.

MPLC (0-3% MeOH in CH$_2$Cl$_2$) afforded the desired product (254 mg, 0.61 mmol, 80% yield). LCMS: C$_{24}$H$_{25}$N$_3$O$_4$ requires: 419, found: m/z=420 [M+H]$^+$.

Step 7

A solution of 3-(5-(3-(hydroxymethyl)azetidin-1-yl)-1-oxoisoindolin-2-yl)piperidine-2,6-dione (100 mg, 0.24 mmol, 1 eq.) in an equal mixture of CH$_2$Cl$_2$ (5 mL) and EtOH (5 mL) was stirred with Pd/C (20 mg, 20 wt. %) under a balloon of H$_2$. After stirring for 16 hrs, the reaction mixture was filtered through Celite, concentrated under reduced pressure, and carried to the next step (79 mg, 0.24 mmol, quantitative). LCMS: C$_{17}$H$_{19}$N$_3$O$_4$ requires: 329, found: m/z=330 [M+H]$^+$.

Step 8

Prepared using general procedure starting from 3-(5-(3-(hydroxymethyl)azetidin-1-yl)-1-oxoisoindolin-2-yl)piperidine-2,6-dione (60 mg, 0.16 mmol) to afford the desired product (23.9 mg, 0.08 mmol, 46%). LCMS: C$_{17}$H$_{17}$N$_3$O$_4$ requires: 327, found: m/z=328 [M+H]$^+$.

Example 34: Synthesis of (R)-5-(3-(3-methyl-2-oxoimidazolidin-1-yl)piperidin-1-yl)-3-((1-(piperidin-4-yl)-1H-pyrazol-4-yl)amino)pyrazine-2-carboxamide

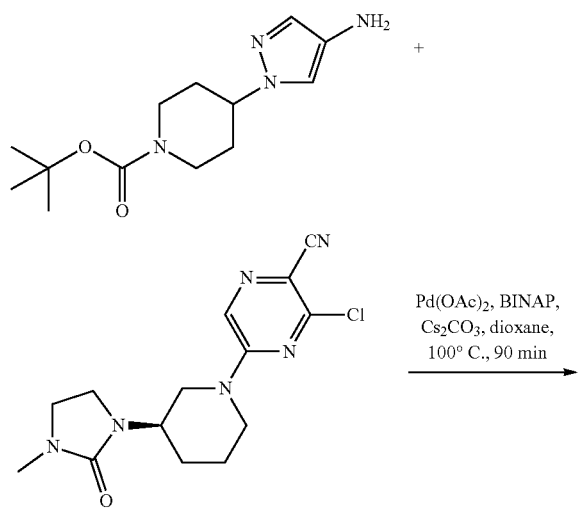

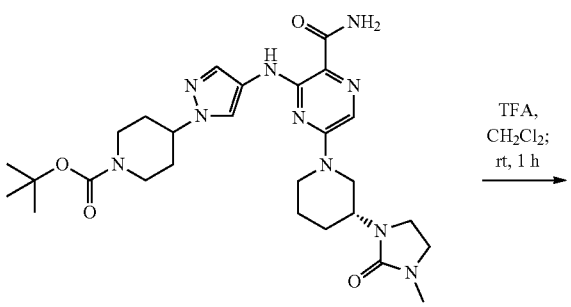

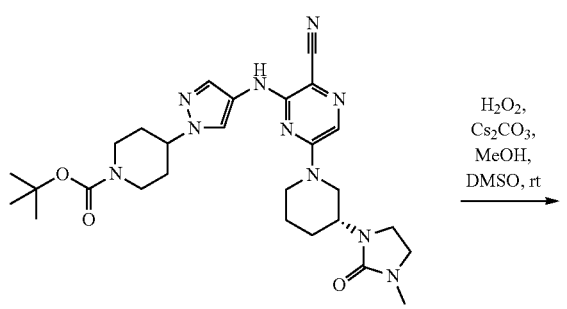

Prepared in a similar fashion as 5-[(3R)-3-(3-methyl-2-oxoimidazolidin-1-yl)piperidin-1-yl]-3-{[4-(piperazin-1-yl)phenyl]amino}pyrazine-2-carboxamide as described in Example 32.

Step 1

Obtained tert-butyl 4-[4-({3-cyano-6-[(3R)-3-(3-methyl-2-oxoimidazolidin-1-yl)piperidin-1-yl]pyrazin-2-yl}amino)pyrazol-1-yl]piperidine-1-carboxylate (1.45 g, 2.63 mmol, 85%). LCMS: C$_{27}$H$_{38}$N$_{10}$O$_3$ requires: 550, found: m/z=551 [M+H]$^+$.

Step 2

Obtained tert-butyl (R)-4-(4-((3-carbamoyl-6-(3-(3-methyl-2-oxoimidazolidin-1-yl)piperidin-1-yl)pyrazin-2-yl)amino)-1H-pyrazol-1-yl)piperidine-1-carboxylate (1.19 g, 2.09 mmol, 80%). LCMS: C$_{27}$H$_{40}$N$_{10}$O$_4$ requires: 569, found: m/z=570 [M+H]$^+$.

Step 3

Obtained (R)-5-(3-(3-methyl-2-oxoimidazolidin-1-yl)piperidin-1-yl)-3-((1-(piperidin-4-yl)-1H-pyrazol-4-yl)amino)pyrazine-2-carboxamide (106 mg, 0.23 mmol, quantitative). LCMS: $C_{22}H_{32}N_{10}O_2$ requires: 468, found: m/z=469 $[M+H]^+$.

Example 35: Synthesis of 3-(2-(2,6-dioxopiperidin-3-yl)-3-oxoisoindolin-5-yl)propiolaldehyde

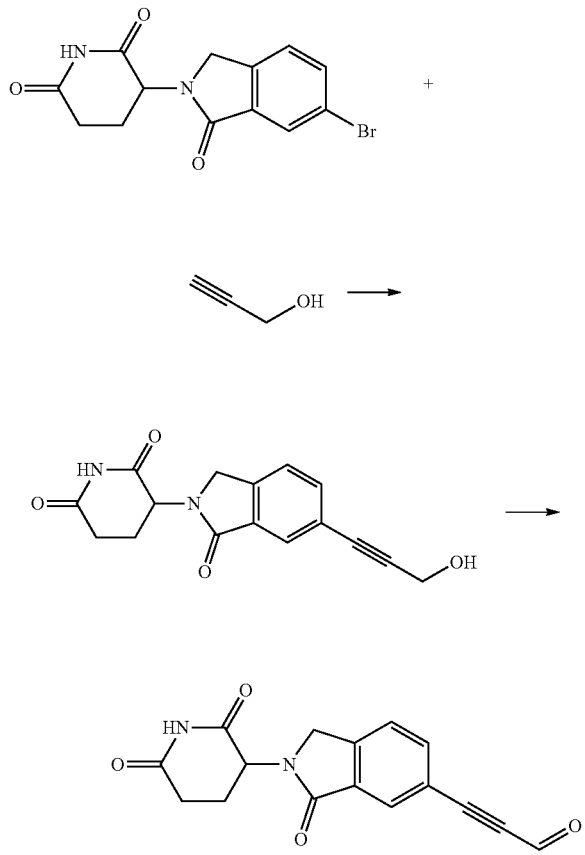

Step 1

Prepared in a similar fashion as tert-butyl 3-({3-[2-(2,6-dioxopiperidin-3-yl)-1,3-dioxoisoindol-5-yl]prop-2-yn-1-yl}oxy)propanoate to afford 3-(6-(3-hydroxyprop-1-yn-1-yl)-1-oxoisoindolin-2-yl)piperidine-2,6-dione (30.7 mg, 0.1 mmol, 11.1%). LCMS: $C_{16}H_{14}N_2O_4$ requires: 298, found: m/z=299 $[M+H]^+$.

Step 2

Prepared in a similar fashion as 1-(2-(2,6-dioxopiperidin-3-yl)-1,3-dioxoisoindolin-5-yl)piperidine-4-carbaldehyde to afford 3-(2-(2,6-dioxopiperidin-3-yl)-3-oxoisoindolin-5-yl)propiolaldehyde. LCMS: $C_{16}H_{12}N_2O_4$ requires: 296, found: m/z=297 $[M+H]^+$.

Example 36: Synthesis of 3-((4-(1-((1s,3s)-3-aminocyclobutyl)-4-methylpiperidin-4-yl)phenyl)amino)-5-(3-(3-methyl-2-oxoimidazolidin-1-yl)piperidin-1-yl)pyrazine-2-carboxamide and 3-((4-(1-((1r,3r)-3-aminocyclobutyl)-4-methylpiperidin-4-yl)phenyl)amino)-5-(3-(3-methyl-2-oxoimidazolidin-1-yl)piperidin-1-yl)pyrazine-2-carboxamide Step 1: tert-butyl ((1s,3s)-3-(4-(4-((3-carbamoyl-6-(3-(3-methyl-2-oxoimidazolidin-1-yl)piperidin-1-yl)pyrazin-2-yl)amino)phenyl)-4-methylpiperidin-1-yl)cyclobutyl)carbamate and tert-butyl ((1r,3r)-3-(4-(4-((3-carbamoyl-6-(3-(3-methyl-2-oxoimidazolidin-1-yl)piperidin-1-yl)pyrazin-2-yl)amino)phenyl)-4-methylpiperidin-1-yl)cyclobutyl)carbamate

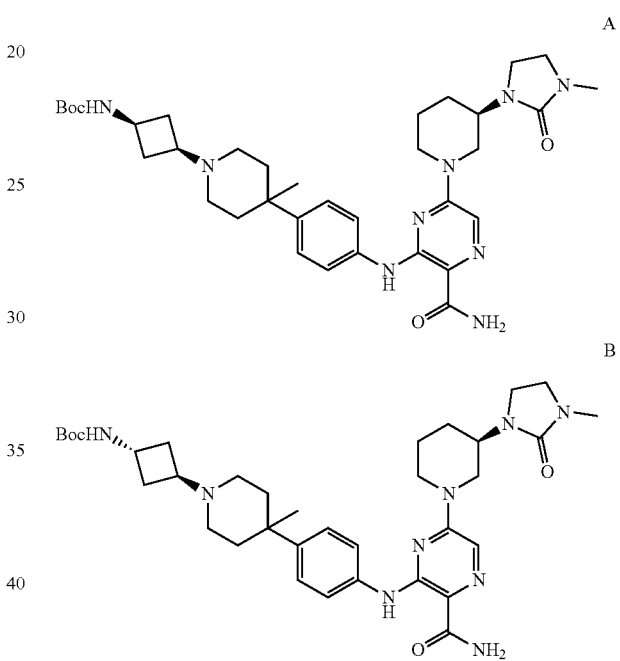

i-Pr₂NEt (115 μL, 0.66 mmol) and tert-butyl N-(3-oxocyclobutyl)carbamate (44 mg, 0.24 mmol) was add to a suspension of 5-[(3R)-3-(3-methyl-2-oxoimidazolidin-1-yl)piperidin-1-yl]-3-{[4-(4-methylpiperidin-4-yl)phenyl]amino}pyrazine-2-carboxamide trifluoroacetic acid (80 mg, 0.13 mmol) in DCE (2 mL). After stirring at RT for 30 min, NaBH(OAc)₃ (37 mg, 0.17 mmol) was added. After stirring at RT overnight, additional NaBH(OAc)₃ (25 mg, 0.12 mmol) was added. After stirring for 3-4 hrs, additional tert-butyl N-(3-oxocyclobutyl)carbamate (10 mg, 0.054 mmol) and NaBH(OAc)₃ was added. After stirring at RT overnight, the yellow reaction mixture was diluted with DCM (50 mL), washed with water, dried over Na₂SO₄, filtered, and concentrated to give a crude yellow liquid. MPLC (0-10% MeOH in DCM) gave separation of two isomers:

Isomer-A (26 mg as a yellow film, 30%). ¹H NMR (500 MHz, CDCl₃) δ 10.92 (s, 1H), 7.64 (d, J=8.4 Hz, 2H), 7.52 (s, 1H), 7.48-7.41 (m, 1H), 7.29 (s, 0H), 7.25 (d, J=8.4 Hz, 2H), 5.40-5.16 (m, 2H), 4.38 (dd, J=26.0, 12.8 Hz, 2H), 3.96 (d, J=11.6 Hz, 1H), 3.91-3.79 (m, 1H), 3.51 (s, 1H), 2.84 (s, 3H), 1.44 (s, 10H), 1.27 (s, 4H). LCMS: $C_{35}H_{50}N_9O_4$ requires: 660, found: m/z=662 $[M+H]^+$.

Isomer-B (17 mg of a yellow film, 20%). $^1$H NMR (500 MHz, CDCl$_3$) δ 10.87 (s, 1H), 7.65-7.57 (m, 2H), 7.51 (s, 1H), 7.45 (s, 1H), 7.27 (dd, J=9.7, 2.9 Hz, 2H), 5.29 (s, 1H), 4.80 (s, 1H), 4.37 (d, J=13.3 Hz, 2H), 4.05 (s, 1H), 3.93-3.78 (m, 1H), 3.50 (s, 3H), 3.41 (dd, J=7.5, 5.8 Hz, 1H), 3.38-3.27 (m, 3H), 3.11 (dd, J=12.8, 10.5 Hz, 1H), 3.03-2.93 (m, 2H), 2.84 (s, 3H), 2.44 (t, J=52.0 Hz, 5H), 2.20 (s, 2H), 2.12-1.98 (m, 0H), 1.97-1.63 (m, 2H), 1.24 (s, 3H). LCMS: C$_{35}$H$_{50}$N$_9$O$_4$ requires: 660, found: m/z=662 [M+H]$^+$.

Step 2: 3-((4-(1-((1s,3s)-3-aminocyclobutyl)-4-methylpiperidin-4-yl)phenyl)amino)-5-(3-(3-methyl-2-oxoimidazolidin-1-yl)piperidin-1-yl)pyrazine-2-carboxamide and 3-((4-(1-((1r,3r)-3-aminocyclobutyl)-4-methylpiperidin-4-yl)phenyl)amino)-5-(3-(3-methyl-2-oxoimidazolidin-1-yl)piperidin-1-yl)pyrazine-2-carboxamide

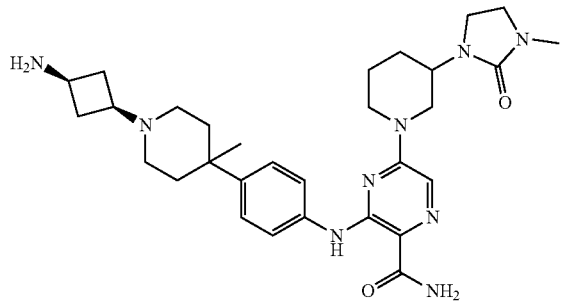

A

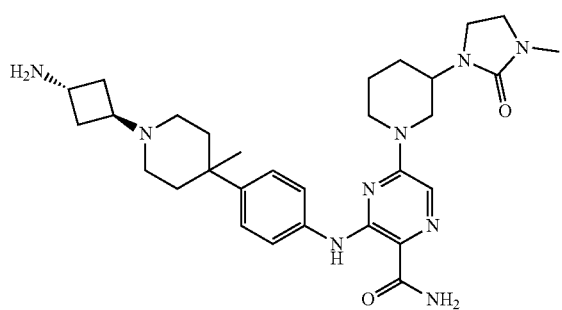

B

To a solution of tert-butyl N-[(1R,3R)-3-{4-[4-({3-carbamoyl-6-[(3R)-3-(3-methyl-2-oxoimidazolidin-1-yl)piperidin-1-yl]pyrazin-2-yl}amino)phenyl]-4-methylpiperidin-1-yl}cyclobutyl]carbamate (17 mg, 0.03 mmol) in DCM (1 mL) was added trifluoroacetic acid (65.38 μL, 0.10 g, 0.85 mmol). After stirring for 30 min at RT, the reaction mixture was concentrated, re-dissolved in DCM and re-concentrated.

Example 37: Synthesis of tert-butyl 7-(4-nitrophenyl)-2,7-diazaspiro[3.5]nonane-2-carboxylate

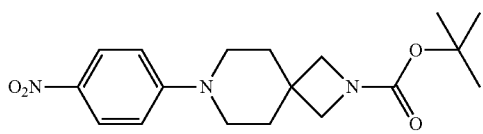 [SMILES: CC(C)(C)OC(=O)N1CC2(CCN(c3ccc([N+](=O)[O-])cc3)CC2)C1]

Tert-butyl 2,7-diazaspiro[3.5]nonane-2-carboxylate (419 mg, 1.85 mmol), 4-fluoronitrobenzene (261 mg, 1.85 mmol) and potassium carbonate (511 mg, 3.70 mmol) were stirred in DMF (5.00 mL) at 90° C. overnight. 30 mL water was added. The resulting solid was filtered and washed with water then air dried overnight to provide tert-butyl 7-(4-nitrophenyl)-2,7-diazaspiro[3.5]nonane-2-carboxylate (606 mg, 94.2%). LCMS: C$_{18}$H$_{25}$N$_3$O$_4$ requires 347, found: m/z=348 [M+H]$^+$.

Example 38: Synthesis of tert-butyl 7-(4-aminophenyl)-2,7-diazaspiro[3.5]nonane-2-carboxylate

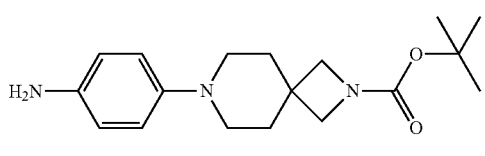

Tert-butyl 7-(4-nitrophenyl)-2,7-diazaspiro[3.5]nonane-2-carboxylate (606 mg, 1.74 mmol) and 10% Pd/C (50 mg, mmol) were stirred in EtOH (3.00 mL) and ethyl acetate (3.00 mL) under a balloon of H$_2$. After 2 hours, 10% Pd/C (50 mg, mmol) was added. The mixture stirred under a balloon of H$_2$ overnight then was filtered through a plug of celite and concentrated to provide tert-butyl 7-(4-aminophenyl)-2,7-diazaspiro[3.5]nonane-2-carboxylate (545 mg, 98.4%). LCMS: C$_{18}$H$_{27}$N$_3$O$_2$ requires 317, found: m/z=318 [M+H]$^+$.

Example 39: Synthesis of tert-butyl 7-[4-({3-cyano-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate

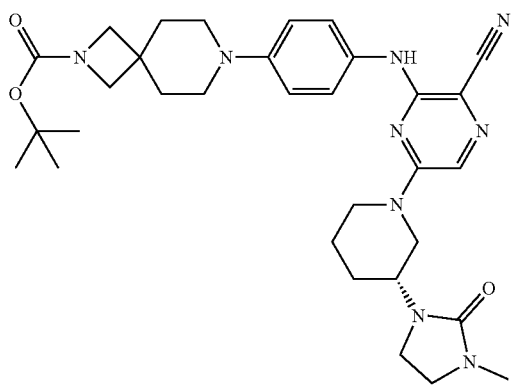 [SMILES: CN1CCN([C@@H]2CCCN(c3cnc(C#N)c(Nc4ccc(N5CCC6(CC5)CN(C(=O)OC(C)(C)C)C6)cc4)n3)C2)C1=O]

3-Chloro-5-[(3R)-3-(3-methyl-2-oxoimidazolidin-1-yl)piperidin-1-yl]pyrazine-2-carbonitrile (209 mg, 0.65 mmol), tert-butyl 7-(4-aminophenyl)-2,7-diazaspiro[3.5]nonane-2-carboxylate (207 mg, 0.65 mmol), and cesium carbonate (0.85 g, 2.61 mmol) were deposited in a vial with dioxane (6.00 mL). A vacuum was pulled on the vial until the mixture bubbled and the headspace was backfilled with argon 5 times. Palladium (II) acetate (29 mg, 0.13 mmol) and BINAP (81 mg, 0.13 mmol) were added. A vacuum was pulled on the vial and the headspace was backfilled with argon for 5 cycles. The mixture was heated at 90° C. overnight. Water was added and the mixture was extracted twice with DCM. The combined organic layers were concentrated then purified by flash chromatography on a 24 g column eluted with 0 to 10% MeOH/ethyl acetate to provide tert-butyl 7-[4-({3-cyano-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate (258 mg, 65.8%). LCMS: $C_{32}H_{43}N_9O_3$ requires 601, found: m/z=602 $[M+H]^+$.

Example 40: Synthesis of tert-butyl 7-[4-({3-carbamoyl-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate

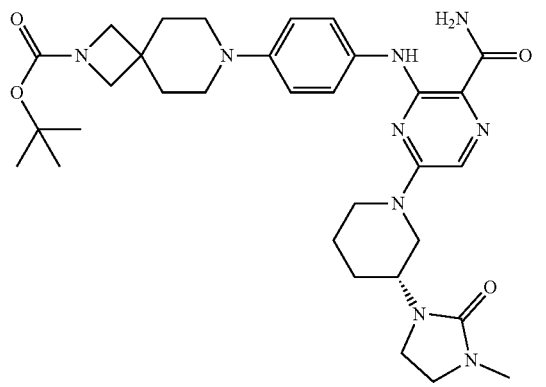 [SMILES: CN1CCN([C@@H]2CCCN(c3cnc(C(N)=O)c(Nc4ccc(N5CCC6(CC5)CN(C(=O)OC(C)(C)C)C6)cc4)n3)C2)C1=O]

Tert-butyl 7-[4-({3-cyano-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate (258 mg, 0.43 mmol) was dissolved in MeOH (6.00 mL) and DMSO (3.00 mL). Cesium carbonate (140 mg, 0.43 mmol) and 1 mL 35% $H_2O_2$ were added. After 1 hour, 3 mL ACN was added. After 5 minutes, the mixture got hot. Water and ethyl acetate were added. The organic layer was washed with 2 more portions of water. The organic layer was dried over $Na_2SO_4$ and concentrated to provide tert-butyl 7-[4-({3-carbamoyl-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate (267 mg, 100%). LCMS: $C_{32}H_{45}N_9O_4$ requires 619, found: m/z=620 $[M+H]^+$.

Example 41: Synthesis of 3-[(4-{2,7-diazaspiro[3.5]nonan-7-yl}phenyl)amino]-5-[(3R)-3-(3-methyl-2-oxoimidazolidin-1-yl)piperidin-1-yl]pyrazine-2-carboxamide

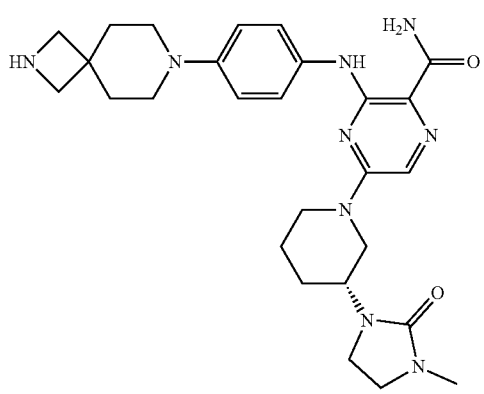 [SMILES: CN1CCN([C@@H]2CCCN(c3cnc(C(N)=O)c(Nc4ccc(N5CCC6(CC5)CNC6)cc4)n3)C2)C1=O]

Tert-butyl 7-[4-({3-carbamoyl-6-[(3R)-3-(3-methyl-2-oxoimidazolidin-1-yl)piperidin-1-yl]pyrazin-2-yl}amino)phenyl]-2,7-diazaspiro[3.5]nonane-2-carboxylate (267 mg, 0.43 mmol) was stirred in DCM (2.00 mL) and TFA (2.00 mL) for 15 minutes. The mixture was concentrated to provide 3-[(4-{2,7-diazaspiro[3.5]nonan-7-yl}phenyl)amino]-5-[(3R)-3-(3-methyl-2-oxoimidazolidin-1-yl)piperidin-1-yl]pyrazine-2-carboxamide (223 mg, 100%). LCMS: $C_{27}H_{37}N_9O_2$ requires 519, found: m/z=520 $[M+H]^+$.

Example 42: Synthesis of 3-[(4-{2,6-diazaspiro[3.5]nonan-6-yl}phenyl)amino]-5-[(3R)-3-(3-methyl-2-oxoimidazolidin-1-yl)piperidin-1-yl]pyrazine-2-carboxamide

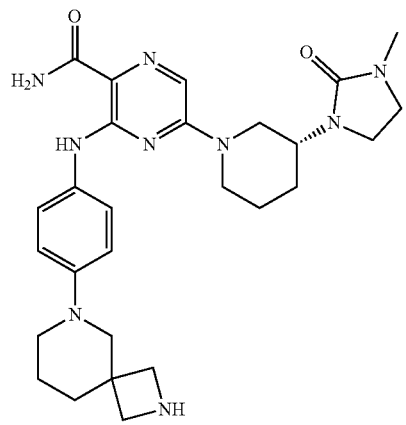 [SMILES: CN1CCN([C@@H]2CCCN(c3cnc(C(N)=O)c(Nc4ccc(N5CCCC6(CNC6)C5)cc4)n3)C2)C1=O]

3-[(4-{2,6-diazaspiro[3.5]nonan-6-yl}phenyl)amino]-5-[(3R)-3-(3-methyl-2-oxoimidazolidin-1-yl)piperidin-1-yl]pyrazine-2-carboxamide was made in an analogous fashion to 3-[(4-{2,7-diazaspiro[3.5]nonan-7-yl}phenyl)amino]-5-[(3R)-3-(3-methyl-2-oxoimidazolidin-1-yl)piperidin-1-yl]pyrazine-2-carboxamide starting with tert-butyl 2,6-diazaspiro[3.5]nonane-2-carboxylate (428 mg, 1.89 mmol). LCMS: $C_{27}H_{37}N_9O_2$ requires 519, found: m/z=520 $[M+H]^+$.

Example 43: Synthesis of tert-butyl 4-[6-({3-cyano-6-[(3R)-3-(3-methyl-2-oxoimidazolidin-1-yl)piperidin-1-yl]pyrazin-2-yl}amino)pyridin-3-yl]piperazine-1-carboxylate

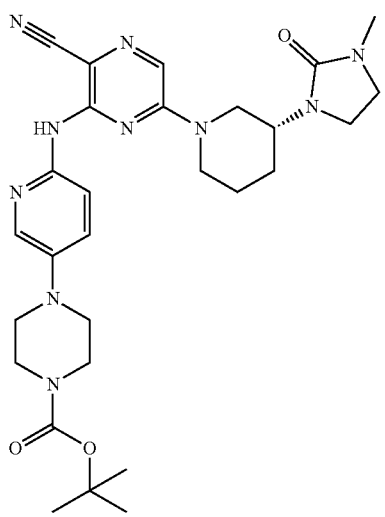 [SMILES: CN1CCN([C@@H]2CCCN(c3cnc(C#N)c(Nc4ccc(N5CCN(C(=O)OC(C)(C)C)CC5)cn4)n3)C2)C1=O]

3-Chloro-5-[(3R)-3-(3-methyl-2-oxoimidazolidin-1-yl)piperidin-1-yl]pyrazine-2-carbonitrile (218 mg, 0.68 mmol), tert-butyl 4-(6-aminopyridin-3-yl)piperazine-1-carboxylate (284 mg, 1.02 mmol), and cesium carbonate (886 mg, 2.72 mmol) were deposited in a vial with dioxane (5.00 mL). A vacuum was pulled on the vial and the headspace was backfilled with argon for 5 cycles. Palladium (II) acetate (31 mg, 0.14 mmol) and BINAP (85 mg, 0.14 mmol) were added. A vacuum was pulled and the headspace was backfilled with argon for 5 cycles. The mixture was next heated at 90° C. overnight. The mixture was cooled, diluted with DCM, filtered, and concentrated. The crude residue was purified by flash chromatography on a 24 g column eluted with 0 to 10% MeOH/DCM to provide tert-butyl 4-[6-({3-cyano-6-[(3R)-3-(3-methyl-2-oxoimidazolidin-1-yl)piperidin-1-yl]pyrazin-2-yl}amino)pyridin-3-yl]piperazine-1-carboxylate (282 mg, 73.7%). LCMS: $C_{28}H_{38}N_{10}O_3$ requires 562, found: m/z=563 [M+H]$^+$.

Example 44: Synthesis of tert-butyl 4-[6-({3-carbamoyl-6-[(3R)-3-(3-methyl-2-oxoimidazolidin-1-yl)piperidin-1-yl]pyrazin-2-yl}amino)pyridin-3-yl]piperazine-1-carboxylate

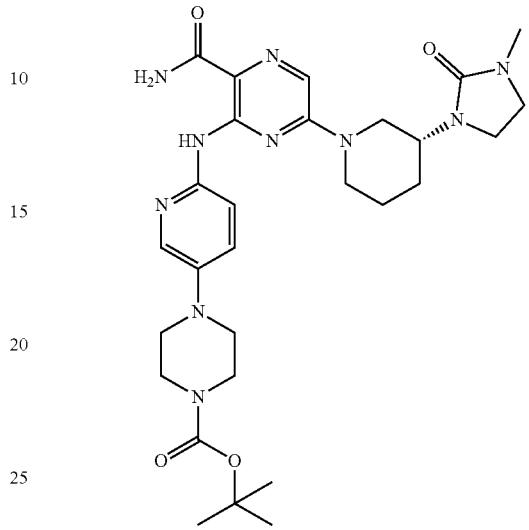

To a mixture of tert-butyl 4-[6-({3-cyano-6-[(3R)-3-(3-methyl-2-oxoimidazolidin-1-yl)piperidin-1-yl]pyrazin-2-yl}amino)pyridin-3-yl]piperazine-1-carboxylate (280 mg, 0.50 mmol) and cesium carbonate (162 mg, 0.50 mmol) in MeOH (6.00 mL) and DMSO (3.00 mL) was added 1 mL 35% hydrogen peroxide. After 5 hours, 3 mL acetonitrile was added. After 5 minutes, the mixture became hot. The mixture was transferred to a separatory funnel with ethyl acetate and was washed with water 3×. The organic layer was dried over Na$_2$SO$_4$ and concentrated. The crude residue was purified on a 24 g flash column eluted with 0 to 20% MeOH/ethyl acetate to provide tert-butyl 4-[6-({3-carbamoyl-6-[(3R)-3-(3-methyl-2-oxoimidazolidin-1-yl)piperidin-1-yl]pyrazin-2-yl}amino)pyridin-3-yl]piperazine-1-carboxylate (191 mg, 66.1%). LCMS: $C_{28}H_{40}N_{10}O_4$ requires 580, found: m/z=581 [M+H]$^+$.

Example 45: 5-[(3R)-3-(3-methyl-2-oxoimidazolidin-1-yl)piperidin-1-yl]-3-{[5-(piperazin-1-yl)pyridin-2-yl]amino}pyrazine-2-carboxamide

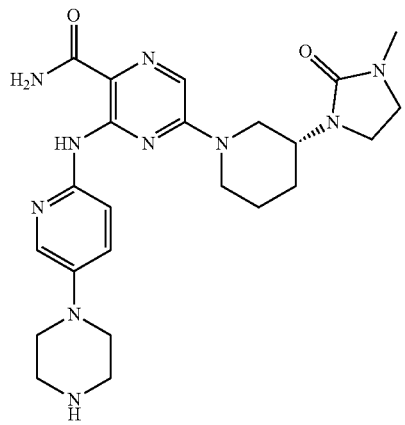

To tert-butyl 4-[6-({3-carbamoyl-6-[(3R)-3-(3-methyl-2-oxoimidazolidin-1-yl)piperidin-1-yl]pyrazin-2-yl}amino)pyridin-3-yl]piperazine-1-carboxylate (40 mg, 0.07 mmol) was added 4M hydrogen chloride solution in dioxane (1.00 mL, 0.15 g, 4.00 mmol) and DCM (1.00 mL). After 20 minutes, the mixture was concentrated to provide 5-[(3R)-3-(3-methyl-2-oxoimidazolidin-1-yl)piperidin-1-yl]-3-{[5-(piperazin-1-yl)pyridin-2-yl]amino}pyrazine-2-carboxamide (33 mg, 100%). LCMS: $C_{23}H_{32}N_{10}O_2$ requires 480, found: m/z=481 [M+H]$^+$.

Example 46: Synthesis of tert-butyl 2-({3-cyano-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate

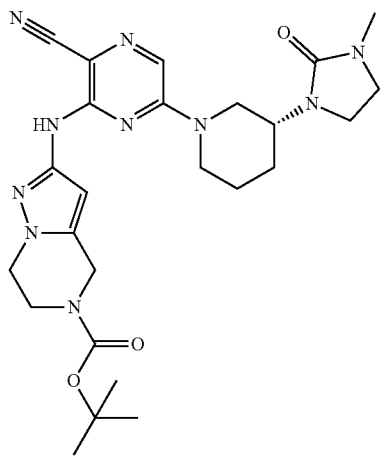 [SMILES: CN1CCN([C@@H]2CCCN(c3cnc(C#N)c(Nc4cc5n(n4)CCN(C(=O)OC(C)(C)C)C5)n3)C2)C1=O]

3-chloro-5-[(3R)-3-(3-methyl-2-oxoimidazolidin-1-yl)piperidin-1-yl]pyrazine-2-carbonitrile (299 mg, 0.93 mmol), tert-butyl 2-amino-4H,6H,7H-pyrazolo[1,5-a]pyrazine-5-carboxylate (222 mg, 0.93 mmol), and cesium carbonate (1.21 g, 3.73 mmol) were deposited in a vial with dioxane (6.00 mL). A vacuum was pulled on the vial until the mixture bubbled then the headspace was backfilled with argon for 5 cycles. BINAP (116 mg, 0.19 mmol) and palladium (II) acetate (42 mg, 0.19 mmol) were added. A vacuum was pulled on the vial until the mixture bubbled then the headspace was backfilled with argon for 5 cycles. The mixture was heated at 90° C. overnight. The mixture was diluted with DCM and filtered. The resulting solution was concentrated and purified by flash chromatography on a 40 g column eluted with 0 to 10% MeOH/ethyl acetate to provide tert-butyl 2-({3-cyano-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate (0.285 g, 58.5%). LCMS: $C_{25}H_{34}N_{10}O_3$ requires 522 found: m/z=523 [M+H]$^+$.

Example 47: Synthesis of tert-butyl 2-({3-carbamoyl-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate

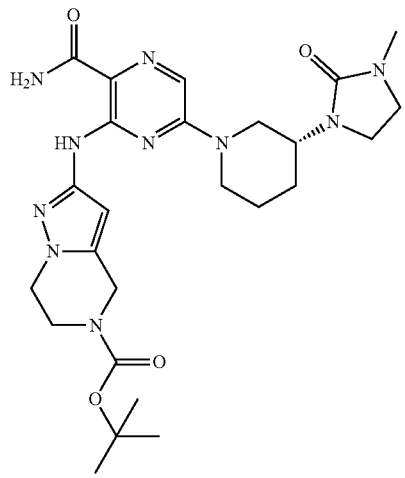 [SMILES: CN1CCN([C@@H]2CCCN(c3cnc(C(N)=O)c(Nc4cc5n(n4)CCN(C(=O)OC(C)(C)C)C5)n3)C2)C1=O]

To a mixture of tert-butyl 2-({3-cyano-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate (285 mg, 0.55 mmol) in MeOH (6.00 mL) and DMSO (3.00 mL) was added cesium carbonate (178 mg, 0.55 mmol) followed by 35% hydrogen peroxide (0.10 mL, 0.04 g, 1.09 mmol). After 40 minutes, the reaction was quenched with 3 mL acetonitrile. The mixture was transferred to a separatory funnel with ethyl acetate and was washed twice with water. The organic layer was dried over $Na_2SO_4$ and concentrated to provide tert-butyl 2-({3-carbamoyl-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate (0.295 g, 100%). LCMS: $C_{25}H_{36}N_{10}O_4$ requires 540, found: m/z=541 [M+H]$^+$.

Example 48: Synthesis of 5-[(3R)-3-(3-methyl-2-oxoimidazolidin-1-yl)piperidin-1-yl]-3-{4H,5H,6H,7H-pyrazolo[1,5-a]pyrazin-2-ylamino}pyrazine-2-carboxamide

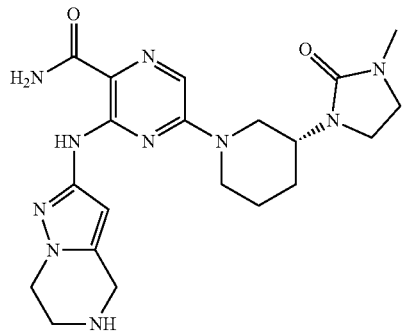 [SMILES: CN1CCN([C@@H]2CCCN(c3cnc(C(N)=O)c(Nc4cc5n(n4)CCNC5)n3)C2)C1=O]

tert-butyl 2-({3-carbamoyl-6-[(3R)-3-(3-methyl-2-oxoimidazolidin-1-yl)piperidin-1-yl]pyrazin-2-yl}amino)-4H,6H,7H-pyrazolo[1,5-a]pyrazine-5-carboxylate (24 mg, 0.04 mmol) was stirred in DCM (1.00 mL) and TFA (1.00 mL) for 20 minutes. The mixture was concentrated to provide 5-[(3R)-3-(3-methyl-2-oxoimidazolidin-1-yl)piperidin-1-yl]-3-{4H,5H,6H,7H-pyrazolo[1,5-a]pyrazin-2-ylamino}pyrazine-2-carboxamide (0.020 g, 100%). LCMS: $C_{20}H_{28}N_{10}O_2$ requires 440, found: m/z=441 [M+H]$^+$.

Example 49: Synthesis of 5-((R)-3-(3-methyl-2-oxoimidazolidin-1-yl)piperidin-1-yl)-3-((4-(octahydro-2,7-naphthyridin-2(1H)-yl)phenyl)amino)pyrazine-2-carboxamide

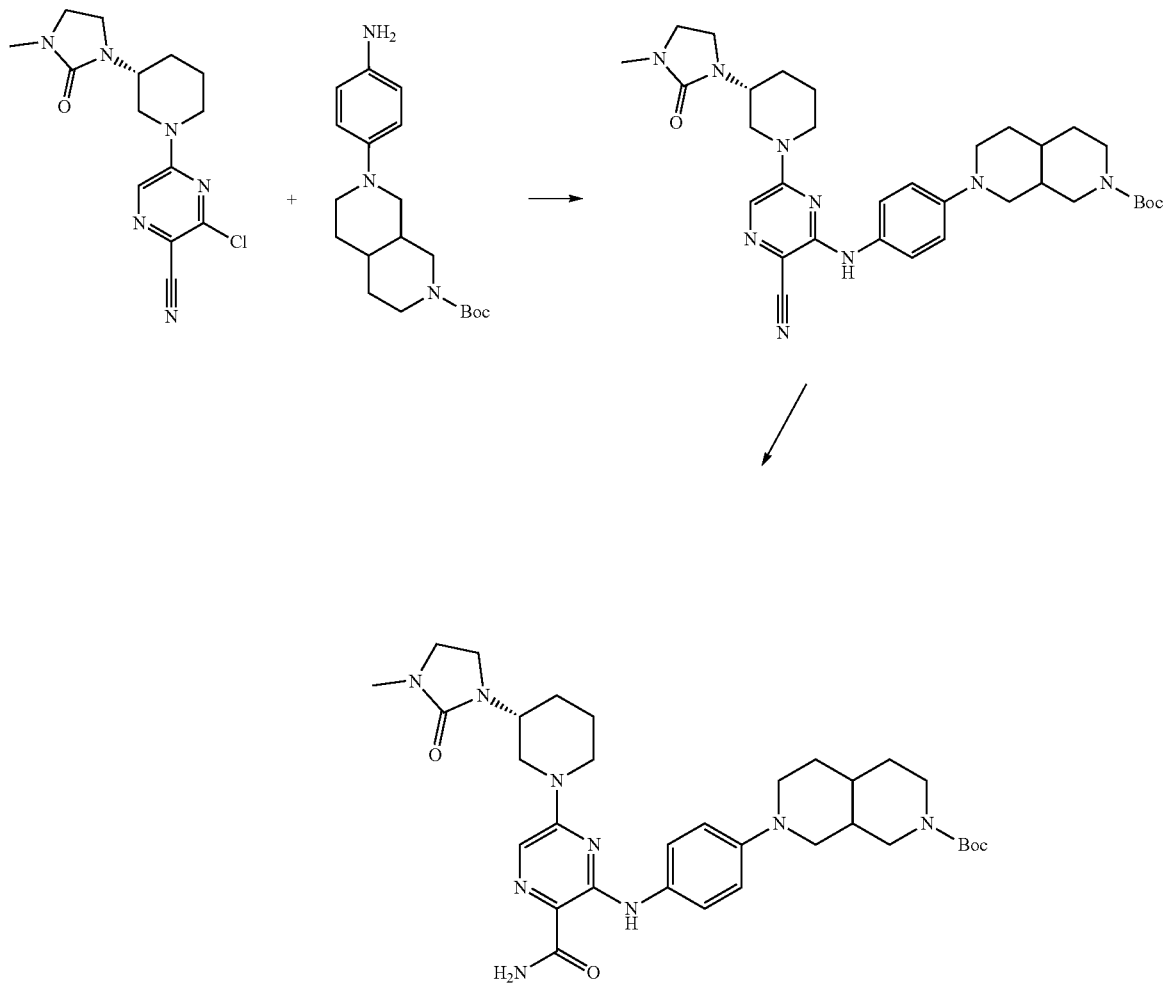

Step 1

Under argon, Pd(OAc)$_2$ (105 mg, 0.47 mmol) was added to a degassed dioxane (10.00 mL) solution containing cesium carbonate (1523.56 mg, 4.68 mmol), tert-butyl 7-(4-aminophenyl)-octahydro-2,7-naphthyridine-2-carboxylate (517 mg, 1.56 mmol), BINAP (291 mg, 0.47 mmol), and 3-chloro-5-[(3R)-3-(3-methyl-2-oxoimidazolidin-1-yl)piperidin-1-yl]pyrazine-2-carbonitrile (500 mg, 1.56 mmol). The mixture was then stirred at 100 deg. C for 16h. The mixture was then partition with water and ethyl acetate, dried over sodium sulfate, and concentrated. The resulting residue was then purified by reverse phase preparative HPLC (Waters 5 mM CSH C18 column, 50×50 mm), eluting with solvent with acetonitrile in water with 0.1% TFA, using a 10-95% gradient over 9 min. The desired fractions were combined and concentrated to give product. This material was dissolved in a MeOH/DMSO solution (2 mL) 10:1 with one NaOH pellet. After 2 min. a 30% aqueous hydrogen peroxide solution (0.5 mL) was added and the reaction continued stirring at room temp for 1 h. The reaction was quenched with the addition of ACN. After concentration the crude reaction mixture was then purified by reverse phase preparative HPLC (Waters 5 mM CSH C18 column, 50×50 mm), eluting with solvent with acetonitrile in water with 0.1% TFA, using a 10-95% gradient over 9 min. The desired fractions were combined and concentrated to give product. LCMS $C_{25}H_{34}N_6O_3$ requires 633, found: m/z=634 [M+H]$^+$.

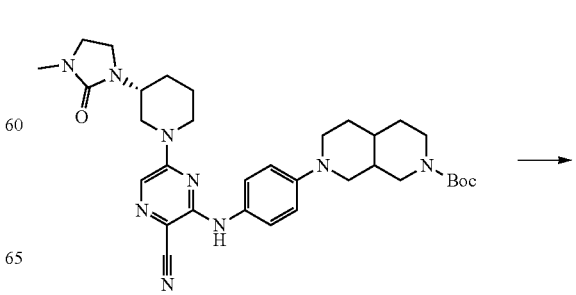

427
-continued

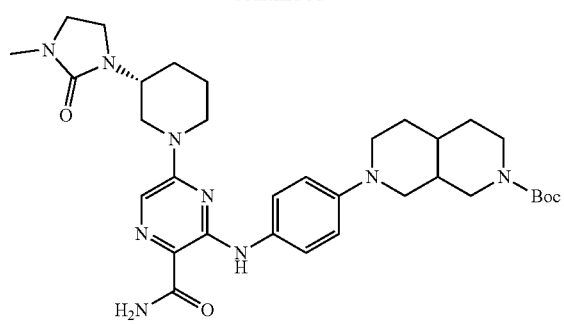

Step 2

Tert-butyl 7-[4-({3-carbamoyl-6-[(3R)-3-(3-methyl-2-oxoimidazolidin-1-yl)piperidin-1-yl]pyrazin-2-yl}amino)phenyl]-octahydro-2,7-naphthyridine-2-carboxylate (240 mg, 0.38 mmol) was dissolved in 1/1 DCM/TFA solution 2 mL and stirred at room temp for 1 h. The reaction was then concentrated. This material was used in the next step without further purification.

Example 50A: Synthesis of (R)-3-((6-(3,9-diazaspiro[5.5]undecan-3-yl)pyridin-3-yl)amino)-5-(3-(3-methyl-2-oxoimidazolidin-1-yl)piperidin-1-yl)pyrazine-2-carboxamide

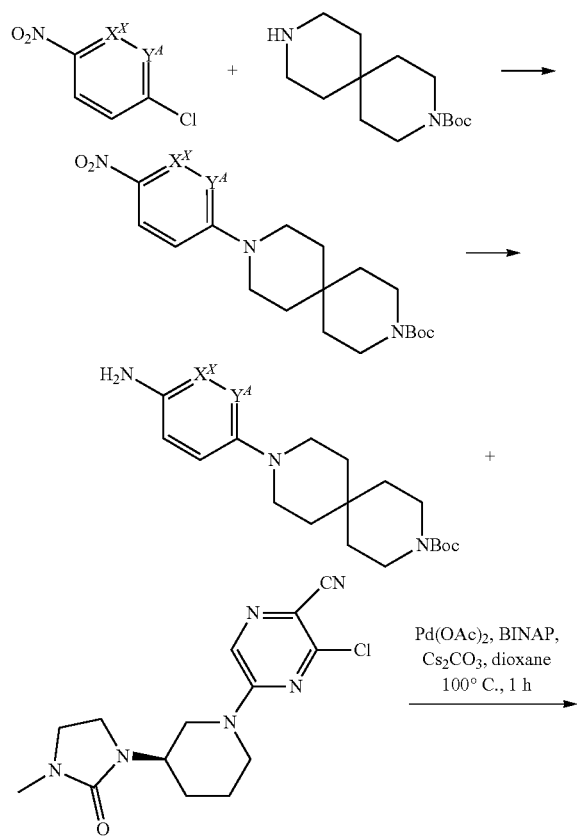

428
-continued

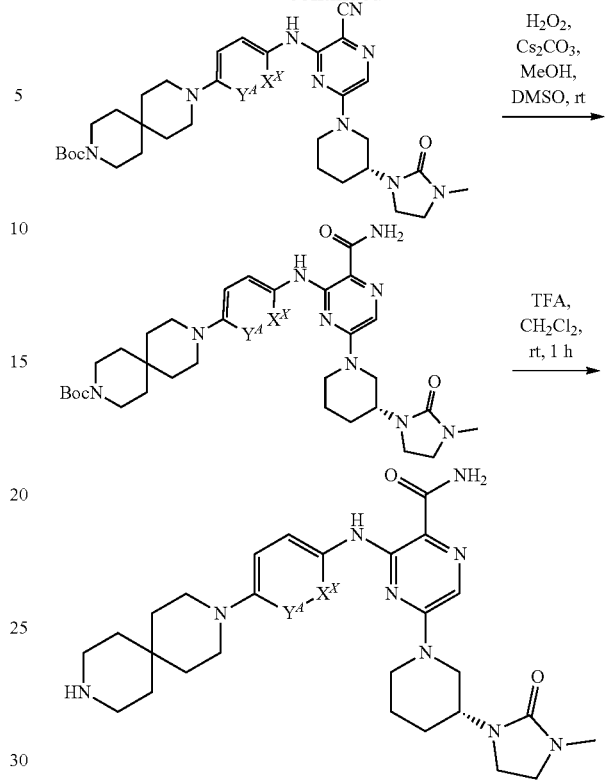

wherein $X^X$ and $Y^A$ are each independently CH or N.

Step 1

2-Chloro-5-nitropyridine (1 eq; $Y^A$ is N and $X^X$ is CH) and tert-butyl 3,9-diazaspiro[5.5]undecane-3-carboxylate (1 eq) were combined in DMF:DIEA solution (10:1 ratio, 0.1M). The reaction mixture was stirred at 70° C. for 16 h, then cooled to room temperature. The reaction mixture was then partitioned between ethyl acetate and water, and the organic layer was separated, dried over magnesium sulfate, and filtered. This solution was concentrated onto silica gel and chromatographed by silica (0-100% ethyl acetate in hexane) to afford tert-butyl 9-(5-nitropyridin-2-yl)-3,9-diazaspiro[5.5]undecane-3-carboxylate (90%). LCMS $C_{19}H_{28}N_4O_4$ requires: 376.5 found: m/z=377.4 [M+H]$^+$.

Step 2

The purified material from step 1 was dissolved in ethanol and water (10:1). Ammonium chloride (3.5 eq) and iron (3 eq) were added, followed by vigorous stirring and heating to 90° C. for 9h. The reaction was then filtered with Celite while still hot, and the Celite was further washed with ethyl acetate. The resulting solution was partitioned between ethyl acetate and water. The water layer was separated and re-extracted with ethyl acetate. The combined organic layers were washed with brine, dried over magnesium sulfate, and concentrated. Silica gel chromatography provided tert-butyl 9-(5-aminopyridin-2-yl)-3,9-diazaspiro [5.5]undecane-3-carboxylate (85%). LCMS $C_{19}H_{30}N_4O_2$ requires: 346.5, found: m/z=347.4 [M+H]$^+$.

Step 3

Pd(OAc)$_2$ (73 mg) was added to a degassed dioxane (10.00 mL) solution containing cesium carbonate (1.78 g), tert-butyl 9-(5-aminopyridin-2-yl)-3,9-diazaspiro [5.5]undecane-3-carboxylate (1.134 g), BINAP (200 mg), and 3-chloro-5-[(3R)-3-(3-methyl-2-oxoimidazolidin-1-yl)piperidin-1-yl]pyrazine-2-carbonitrile (700 mg). The mixture was then stirred at 100° C. for 4 h. The mixture was filtered and purified by MPLC (0-10% MeOH in $CH_2Cl_2$) to afford tert-butyl (R)-9-(5-((3-cyano-6-(3-(3-methyl-2-oxoimidazolidin-1-yl)piperidin-1-yl)pyrazin-2-yl)amino)pyridin-2-yl)-3,9-diazaspiro[5.5]undecane-3-carboxylate (800 mg). LCMS $C_{33}H_{46}N_{10}O_3$ requires: 630, found: m/z=631 $[M+H]^+$.

Step 4

Starting material was dissolved in methanol/DMSO, followed by addition of 3 pellets of NaOH (solid). The reaction was stirred for 1 minute before addition of 5 mL of 30% aq hydrogen peroxide solution. The reaction was stirred for 1 h. The reaction mixture was then partitioned between ethyl acetate and water. The organic layer was separated, and washed with water, then brine. The mixture was purified by MPLC (0-10% MeOH in $CH_2Cl_2$) to afford tert-butyl (R)-9-(5-((3-carbamoyl-6-(3-(3-methyl-2-oxoimidazolidin-1-yl)piperidin-1-yl)pyrazin-2-yl)amino)pyridin-2-yl)-3,9-diazaspiro[5.5]undecane-3-carboxylate (750 mg, 91%). LCMS $C_{33}H_{48}N_{10}O_4$ requires: 648, found: m/z=649 $[M+H]^+$.

Step 5

A mixture of TFA (2 mL), $CH_2Cl_2$ (15 mL) and tert-butyl (R)-9-(5-((3-carbamoyl-6-(3-(3-methyl-2-oxoimidazolidin-1-yl)piperidin-1-yl)pyrazin-2-yl)amino)pyridin-2-yl)-3,9-diazaspiro[5.5]undecane-3-carboxylate (750 mg) was allowed to stir at rt for 1 h. The volatiles were removed and the material was carried to the next step. LCMS $C_{28}H_{40}N_{10}O_2$ requires: 548, found: m/z=549 $[M+H]^+$.

Example 50B: Synthesis of (R)-3-((5-(3,9-diazaspiro[5.5]undecan-3-yl)pyridin-2-yl)amino)-5-(3-(3-methyl-2-oxoimidazolidin-1-yl)piperidin-1-yl)pyrazine-2-carboxamide The title compound was synthesized using the procedure in Example 50A, but substituting 5-Chloro-2-nitropyridine, wherein $Y^A$ is CH and $X^X$ is N, for 2-chloro-5-nitropyridine. LCMS $C_{28}H_{40}N_{10}O_2$ requires: 548, found: m/z=549 $[M+H]^+$.

Example 51: Synthesis of 3-((4-(hexahydropyrrolo[3,4-c]pyrrol-2(1H)-yl)phenyl)amino)-5-((R)-3-(3-methyl-2-oxoimidazolidin-1-yl)piperidin-1-yl)pyrazine-2-carboxamide

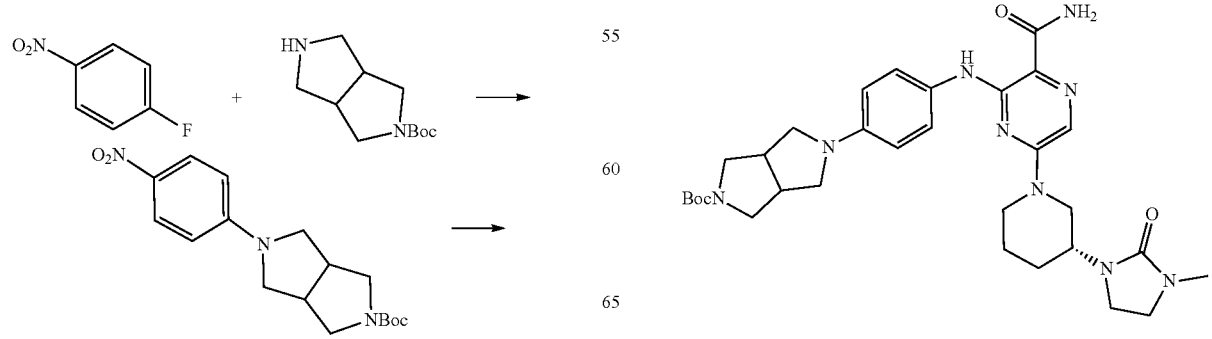

Steps 1-5

Para-fluoronitrobenzene (1 eq) and amine (1 eq) were combined in DMF, followed by addition of potassium carbonate (2 eq). The reaction mixture was stirred at 90° C. for 3h, then cooled to room temperature. The reaction mixture was then partitioned between ethyl acetate and water, and the organic layer was separated, dried over magnesium sulfate, and filtered. The crude material from was dissolved in ethanol and water (10:1). Ammonium chloride (3.5 eq) and iron (3 eq) were added, followed by vigorous stirring and heating to 90° C. for 5h. The reaction was then filtered with Celite, and the Celite was further washed with ethyl acetate. The resulting solution was partitioned between ethyl acetate and water. The water layer was separated and re-extracted with ethyl acetate. The combined organic layers were washed with brine, dried over magnesium sulfate, and concentrated to provide tert-butyl 5-(4-aminophenyl)-hexahydropyrrolo[3,4-c]pyrrole-2-carboxylate (37% over 2 steps). LCMS $C_{17}H_{25}N_3O_2$ requires: 303.4, found: m/z=304.3 [M+H]$^+$. tert-butyl 5-(4-aminophenyl)-hexahydropyrrolo[3,4-c]pyrrole-2-carboxylate was carried forward to 3-((4-(hexahydropyrrolo[3,4-c]pyrrol-2(1H)-yl)phenyl)amino)-5-((R)-3-(3-methyl-2-oxoimidazolidin-1-yl)piperidin-1-yl)pyrazine-2-carboxamide in a similar fashion as 5-[(3R)-3-(3-methyl-2-oxoimidazolidin-1-yl)piperidin-1-yl]-3-{[5-(piperazin-1-yl)pyridin-2-yl]amino}pyrazine-2-carboxamide.

Example 52: Synthesis of 3-[(4-{1-[(1-{4-[1-(2,6-dioxopiperidin-3-yl)-4-methyl-5-oxo-1,2,4-triazol-3-yl]phenyl}azetidin-3-yl)methyl]piperidin-4-yl}phenyl)amino]-5-[(3R)-3-(3-methyl-2-oxoimidazolidin-1-yl)piperidin-1-yl]Pyrazine-2-carboxamide To a mixture of 5-[(3R)-3-(3-methyl-2-oxoimidazolidin-1-yl)piperidin-1-yl]-3-{[4-(piperidin-4-yl)phenyl]amino}pyrazine-2-carboxamide (60 mg, 0.13 mmol) in DCE (1.00 mL) was added N,N-diisopropylethylamine (0.27 mL, 1.5 mmol), 1-{4-[1-(2,6-dioxopiperidin-3-yl)-4-methyl-5-oxo-1,2,4-triazol-3-yl]phenyl}azetidine-3-carbaldehyde (55 mg, 0.15 mmol), and sodium triacetoxyborohydride (80 mg, 0.38 mmol). After 90 minutes, water was added and the mixture was extracted twice with DCM. The combined organic layers were concentrated then purified by preparative TLC eluted with 10% MeOH/DCM to provide 3-[(4-{1-[(1-{4-[1-(2,6-dioxopiperidin-3-yl)-4-methyl-5-oxo-1,2,4-triazol-3-yl]phenyl}azetidin-3-yl)methyl]piperidin-4-yl}phenyl)amino]-5-[(3R)-3-(3-methyl-2-oxoimidazolidin-1-yl)piperidin-1-yl]pyrazine-2-carboxamide (0.034 g, 29%).

Example 53: Synthesis of 3-[(4-{1-[(1-{4-[1-(2,6-dioxopiperidin-3-yl)-4-methyl-5-oxo-1,2,4-triazol-3-yl]phenyl}azetidin-3-yl)methyl]piperidin-4-yl}phenyl)amino]-5-[(3R)-3-(2-oxopyrrolidin-1-yl)piperidin-1-yl]pyrazine-2-carboxamide To a mixture of 5-[(3R)-3-(2-oxopyrrolidin-1-yl)piperidin-1-yl]-3-{[4-(piperidin-4-yl)phenyl]amino}pyrazine-2-carboxamide (16.2 mg, 0.04 mmol) in DCE (1.00 mL) was added N,N-diisopropylethylamine (0.06 mL, 0.42 mmol). 1-{4-[1-(2,6-dioxopiperidin-3-yl)-4-methyl-5-oxo-1,2,4-triazol-3-yl]phenyl}azetidine-3-carbaldehyde (12.9 mg, 0.04 mmol) was added followed by sodium triacetoxyborohydride (22 mg, 0.10 mmol). After 90 minutes, water was added and the mixture was extracted twice with DCM. The combined organic layers were purified by prep TLC eluted with 10% MeOH/DCM to provide 3-[(4-{1-[(1-{4-[1-(2,6-dioxopiperidin-3-yl)-4-methyl-5-oxo-1,2,4-triazol-3-yl]phenyl}azetidin-3-yl)methyl]piperidin-4-yl}phenyl)amino]-5-[(3R)-3-(2-oxopyrrolidin-1-yl)piperidin-1-yl]pyrazine-2-carboxamide (0.0094 g, 31%).

Example 54: Synthesis of 2-(2,6-dioxopiperidin-3-yl)-5-(4-{[4-(4-{[4-methyl-3-oxo-6-(1,3-thiazol-2-yl)pyrazin-2-yl]amino}phenyl)piperidin-1-yl]methyl}piperidin-1-yl)isoindole-1,3-dione To a mixture of 1-methyl-3-{[4-(piperidin-4-yl)phenyl]amino}-5-(1,3-thiazol-2-yl)pyrazin-2-one (24 mg, 0.065 mmol) and 1-[2-(2,6-dioxopiperidin-3-yl)-1,3-dioxoisoindol-5-yl]piperidine-4-carbaldehyde (24 mg, 0.065 mmol) in 1,2-dichloroethane (1.0 mL) was added sodium triacetoxyborohydride (41 mg, 0.20 mmol). After 30 minutes, additional portions of 1-[2-(2,6-dioxopiperidin-3-yl)-1,3-dioxoisoindol-5-yl]piperidine-4-carbaldehyde (24 mg, 0.065 mmol) and sodium triacetoxyborohydride (41 mg, 0.20 mmol) were added. After 30 more minutes, water was added and the mixture was extracted twice with dichloromethane. The combined organic layers were concentrated then purified by preparative TLC eluted with 10% MeOH/DCM to provide 2-(2,6-dioxopiperidin-3-yl)-5-(4-{[4-(4-{[4-methyl-3-oxo-6-(1,3-thiazol-2-yl)pyrazin-2-yl]amino}phenyl)piperidin-1-yl]methyl}piperidin-1-yl)isoindole-1,3-dione (0.017 g, 35%).

Example 55: Synthesis of (R)-3-((4-(3-aminopropoxy)phenyl)amino)-5-(3-(3-methyl-2-oxoimidazolidin-1-yl)piperidin-1-yl)pyrazine-2-carbonitrile

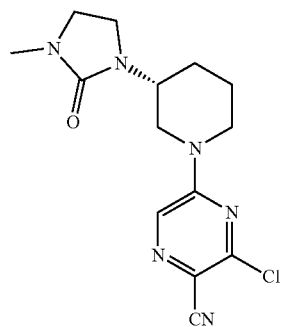
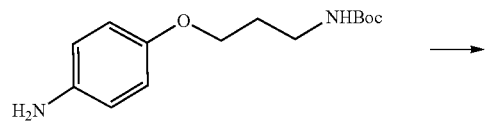

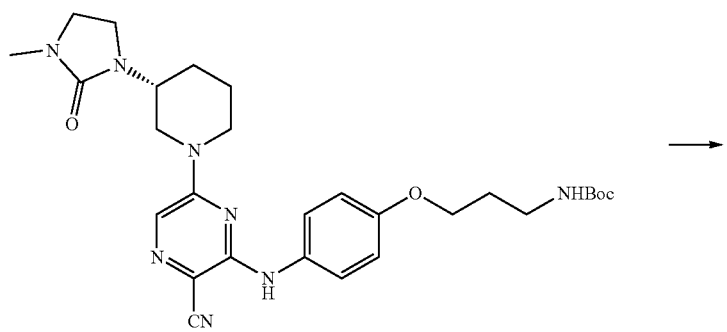

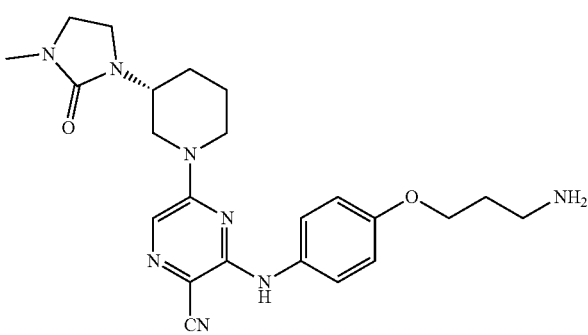

Step 1

(R)-3-chloro-5-(3-(3-methyl-2-oxoimidazolidin-1-yl)piperidin-1-yl)pyrazine-2-carbonitrile, the aniline compound, Pd(OAc)$_2$ (0.15 eq), BINAP (0.15 eq), and cesium carbonate (2 eq) were combined in a microwave tube, followed by addition of dioxane (0.25 M). Nitrogen was bubbled through for 30 seconds, followed by capping. Heating to 90° C., followed by maintaining that temperature for 3 h provided a dark reaction mixture which was monitored by LCMS. The reaction was then cooled, and filtered through Celite, washing with ethyl acetate/methanol. The crude material was loaded onto silica and chromatographed (silica, 0-10% methanol in DCM), to provide the desired intermediate compound in 52% yield. Obtained tert-butyl (R)-(3-(4-((3-cyano-6-(3-(3-methyl-2-oxoimidazolidin-1-yl)piperidin-1-yl)pyrazin-2-yl)amino)phenoxy)propyl)carbamate. LCMS $C_{28}H_{38}N_8O_4$ requires: 550, found: m/z=551.7 [M+H]$^+$.

Step 2

The intermediate from step 1 was dissolved in DCM:TFA (5:1 ratio, 0.2M) and the reaction was stirred for 4 h. The reaction mixture was concentrated by rotary evaporator, followed by chromatography (0-20% methanol in DCM) to provide desired amine in 92% yield. Obtained (R)-3-((4-(3-aminopropoxy)phenyl)amino)-5-(3-(3-methyl-2-oxoimidazolidin-1-yl)piperidin-1-yl)pyrazine-2-carbonitrile. LCMS $C_{23}H_{30}N_8O_2$ requires: 450.6, found: m/z=451.6 [M+H]$^+$.

Example 56: Synthesis of (R)-4-((3-carbamoyl-6-(3-(3-methyl-2-oxoimidazolidin-1-yl)piperidin-1-yl)pyrazin-2-yl)amino)benzoic acid

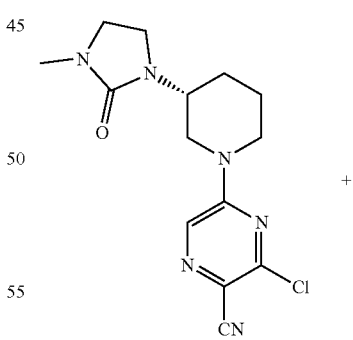

+

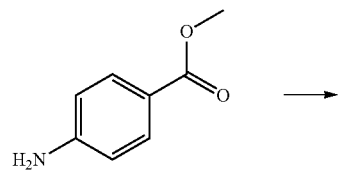

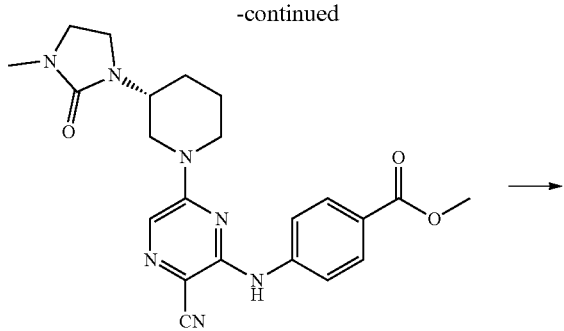

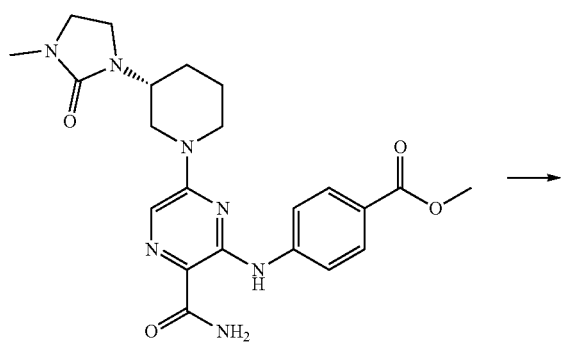

Step 1

(R)-3-chloro-5-(3-(3-methyl-2-oxoimidazolidin-1-yl)piperidin-1-yl)pyrazine-2-carbonitrile, the aniline compound, Pd(OAc)$_2$ (0.15 eq), BINAP (0.15 eq), and cesium carbonate (2 eq) were combined in a microwave tube, followed by addition of dioxane (0.25 M). Nitrogen was bubbled through for 30 seconds, followed by capping. Heating to 90° C., followed by maintaining that temperature for 3 h provided a dark reaction mixture which was monitored by LCMS. The reaction was then cooled, and filtered through Celite, washing with ethyl acetate/methanol. The crude material was loaded onto silica and chromatographed (silica, 0-10% methanol in DCM), to provide the desired intermediate compound in 74% yield. Obtained methyl (R)-4-((3-cyano-6-(3-(3-methyl-2-oxoimidazolidin-1-yl)piperidin-1-yl) pyrazin-2-yl)amino)benzoate. LCMS C$_{22}$H$_{25}$N$_7$O$_3$ requires: 435.5, found: m/z=436.6 [M+H]$^+$.

Step 2

This material was then dissolved in methanol/DMSO (10:1) and a pellet of NaOH was added. The reaction was stirred for 5 minutes, followed by addition of 35% peroxide solution (2 mL of solution per mmol of reactant). This reaction mixture was stirred for 3 h, then partitioned between ethyl acetate and water. The organic layer was separated, and dried over magnesium sulfate. Chromatography (0-10% methanol in DCM) provided desired product in 48% yield. Obtained methyl (R)-4-((3-carbamoyl-6-(3-(3-methyl-2-oxoimidazolidin-1-yl)piperidin-1-yl)pyrazin-2-yl)amino)benzoate. LCMS C$_{22}$H$_{27}$N$_7$O$_4$ requires: 453.5, found: m/z=454.6 [M+H]$^+$.

Step 3

Starting material was dissolved in THF (0.1 M) followed by addition of 2N LiOH (aq, 25% by volume of THF). The reaction was stirred at 80° C. for 4 h. The reaction was then poured into ethyl acetate/2N HCl in a separatory funnel. The organic layer was separated, and the aqueous layer was further extracted with methylene chloride/methanol (10%). Both organic layers were dried over magnesium sulfate and filtered, followed by concentration by rotory evaporator, to provide desired carboxylic acid in 88% with no further purification. Obtained (R)-4-((3-carbamoyl-6-(3-(3-methyl-2-oxoimidazolidin-1-yl)piperidin-1-yl)pyrazin-2-yl)amino) benzoic acid. LCMS C$_{21}$H$_{25}$N$_7$O$_4$ requires: 439.5, found: m/z=440.6 [M+H]$^+$.

Example 57: General Strategy for Ring Attachment

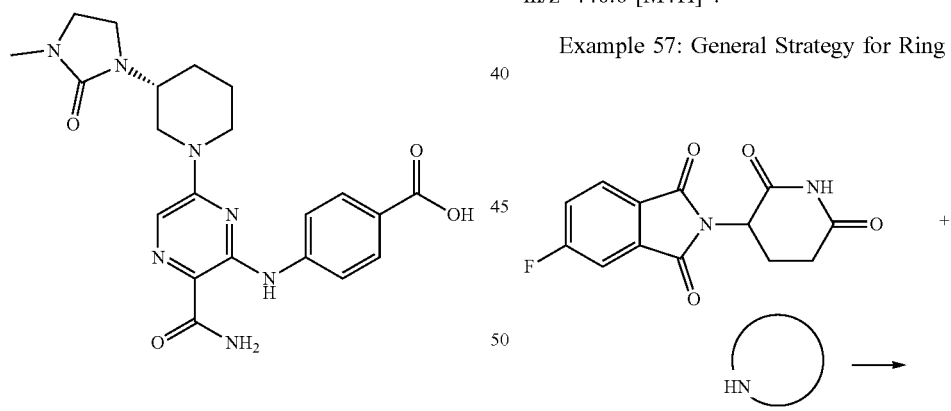

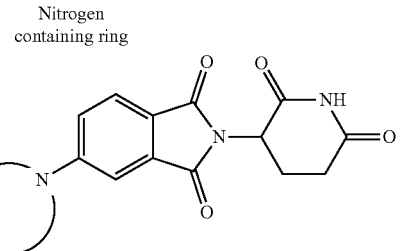

In a typical procedure, to a mixture of 2-(2,6-dioxopiperidin-3-yl)-5-fluoroisoindole-1,3-dione (~1 eq.) and a cyclic compound containing a ring nitrogen (~1 eq.) in a polar aprotic solvent such as N-methyl-2 pyrrolidinone (NMP), DMF, or DMSO, was added an organic base such as N,N-diisopropylethylamine (~3 eq.). The resulting mixture was heated at a temperature ranging from about 50 to about 120° C. (e.g. 90° C.) for a time period of about 2 hours to about 24 hours (e.g. 16 hours). The mixture was diluted with an organic solvent such as ethyl acetate and washed with water. The organic layer was 1) dried using a simple procedure such as washing with brine and pouring over anhydrous $Na_2SO_4$, and then 2) concentrated in vacuo to provide a crude product that could be further purified using methods such as crystallization or flash chromatography.

Example 57A: Synthesis of 2-(2,6-dioxopiperidin-3-yl)-5-(4-oxopiperidin-1-yl)isoindole-1,3-dione

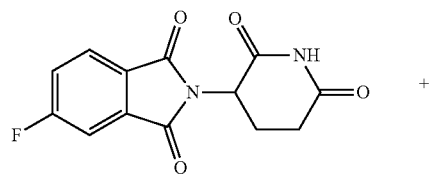

+


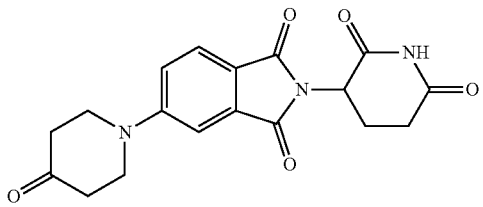

To a mixture of 2-(2,6-dioxopiperidin-3-yl)-5-fluoroisoindole-1,3-dione (500 mg, 1.81 mmol) and 4-piperidinone hydrochloride (245 mg, 1.81 mmol) in 3 mL NMP was added N,N-diisopropylethylamine (703 mg, 5.43 mmol). The mixture was heated at 90° C. for 16 h. The mixture was diluted with ethyl acetate and washed with 2 portions of water. The organic layer was washed with brine, dried over anhydrous $Na_2SO_4$, and concentrated in vacuo. The crude residue was purified by flash chromatography eluted with 10 to 100% ethyl acetate/hexanes gradient to provide 2-(2,6-dioxopiperidin-3-yl)-5-(4-oxopiperidin-1-yl)isoindole-1,3-dione (131 mg, 20.4%). LCMS: $C_{18}H_{17}N_3O_5$ requires 355, found: m/z=356 $[M+H]^+$.

Example 58: Synthesis of 3-{[4-(1-{1-[2-(2,6-dioxopiperidin-3-yl)-1,3-dioxoisoindol-5-yl]piperidin-4-yl}azetidin-3-yl)phenyl]amino}-5-[(3R)-3-(3-methyl-2-oxoimidazolidin-1-yl)piperidin-1-yl]pyrazine-2-carboxamide

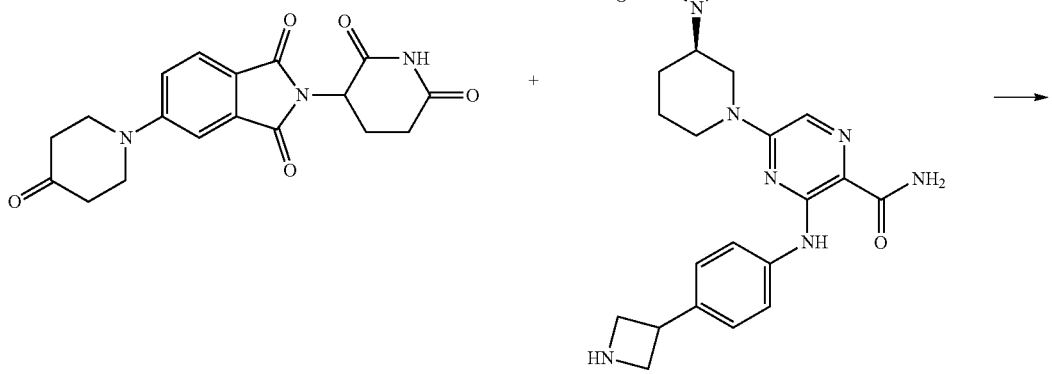

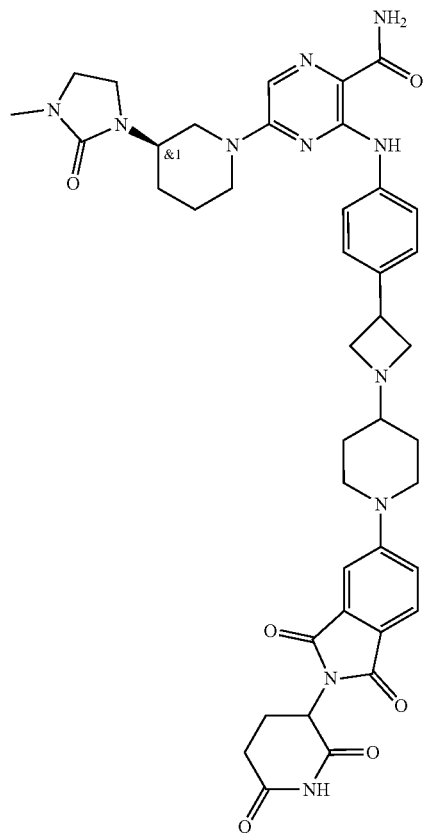

Followed general procedure 2 starting from 3-{[4-(azetidin-3-yl)phenyl]amino}-5-[(3R)-3-(3-methyl-2-oxoimidazolidin-1-yl)piperidin-1-yl]pyrazine-2-carboxamide (55.0 mg, 0.12 mmol) and 2-(2,6-dioxopiperidin-3-yl)-5-(4-oxopiperidin-1-yl)isoindole-1,3-dione (43.4 mg, 0.12 mmol) to afford 3-{[4-(1-{1-[2-(2,6-dioxopiperidin-3-yl)-1,3-dioxoisoindol-5-yl]piperidin-4-yl}azetidin-3-yl)phenyl]amino}-5-[(3R)-3-(3-methyl-2-oxoimidazolidin-1-yl)piperidin-1-yl]pyrazine-2-carboxamide (9.50 mg, 9.9%). $^1$H NMR (500 MHz, DMSO-$d_6$) δ 11.26 (s, 1H), 11.08 (s, 1H), 7.77 (d, J=2.9 Hz, 1H), 7.70-7.64 (m, 2H), 7.55 (d, J=8.3 Hz, 2H), 7.37-7.29 (m, 2H), 7.30-7.23 (m, 3H), 5.08 (dd, J=12.8, 5.4 Hz, 1H), 4.40 (d, J=12.6 Hz, 1H), 4.30 (d, J=13.6 Hz, 1H), 3.88 (dt, J=13.5, 4.5 Hz, 2H), 3.67-3.49 (m, 4H), 3.41-3.22 (m, 2H), 3.16 (ddd, J=13.0, 9.8, 3.1 Hz, 2H), 3.10-2.83 (m, 5H), 2.72 (s, 3H), 2.65-2.53 (m, 2H), 2.42-2.33 (m, 1H), 2.08-1.96 (m, 1H), 1.86-1.71 (m, 6H), 1.60-1.50 (m, 1H), 1.33-1.22 (m, 3H). LCMS: $C_{41}H_{47}N_{11}O_6$ requires 789, found: m/z=790 [M+H]$^+$.

Example 59: Synthesis of (R)-3-((4-(2,8-diazaspiro[4.5]decan-8-yl)phenyl)amino)-5-(3-(3-methyl-2-oxoimidazolidin-1-yl)piperidin-1-yl)pyrazine-2-carboxamide

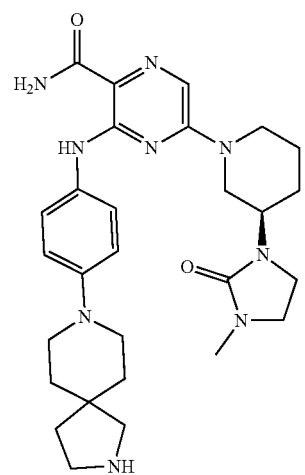 [SMILES: CN1CCN([C@@H]2CCCN(c3cnc(C(N)=O)c(Nc4ccc(N5CCC6(CCNC6)CC5)cc4)n3)C2)C1=O]

(R)-3-((4-(2,8-diazaspiro[4.5]decan-8-yl)phenyl)amino)-5-(3-(3-methyl-2-oxoimidazolidin-1-yl)piperidin-1-yl)pyrazine-2-carboxamide was made in an analogous fashion to (R)-3-((4-(2,9-diazaspiro[5.5]undecan-9-yl)phenyl)amino)-5-(3-(3-methyl-2-oxoimidazolidin-1-yl)piperidin-1-yl)pyrazine-2-carboxamide starting with tert-butyl 2,8-diazaspiro[4.5]decane-2-carboxylate (see Example 6). LCMS: $C_{28}H_{39}N_9O_2$ requires 519, found: m/z=520 $[M+H]^+$.

Example 60: Synthesis of 5-morpholino-3-[4-(4-piperidyl)anilino]pyrazine-2-carboxamide

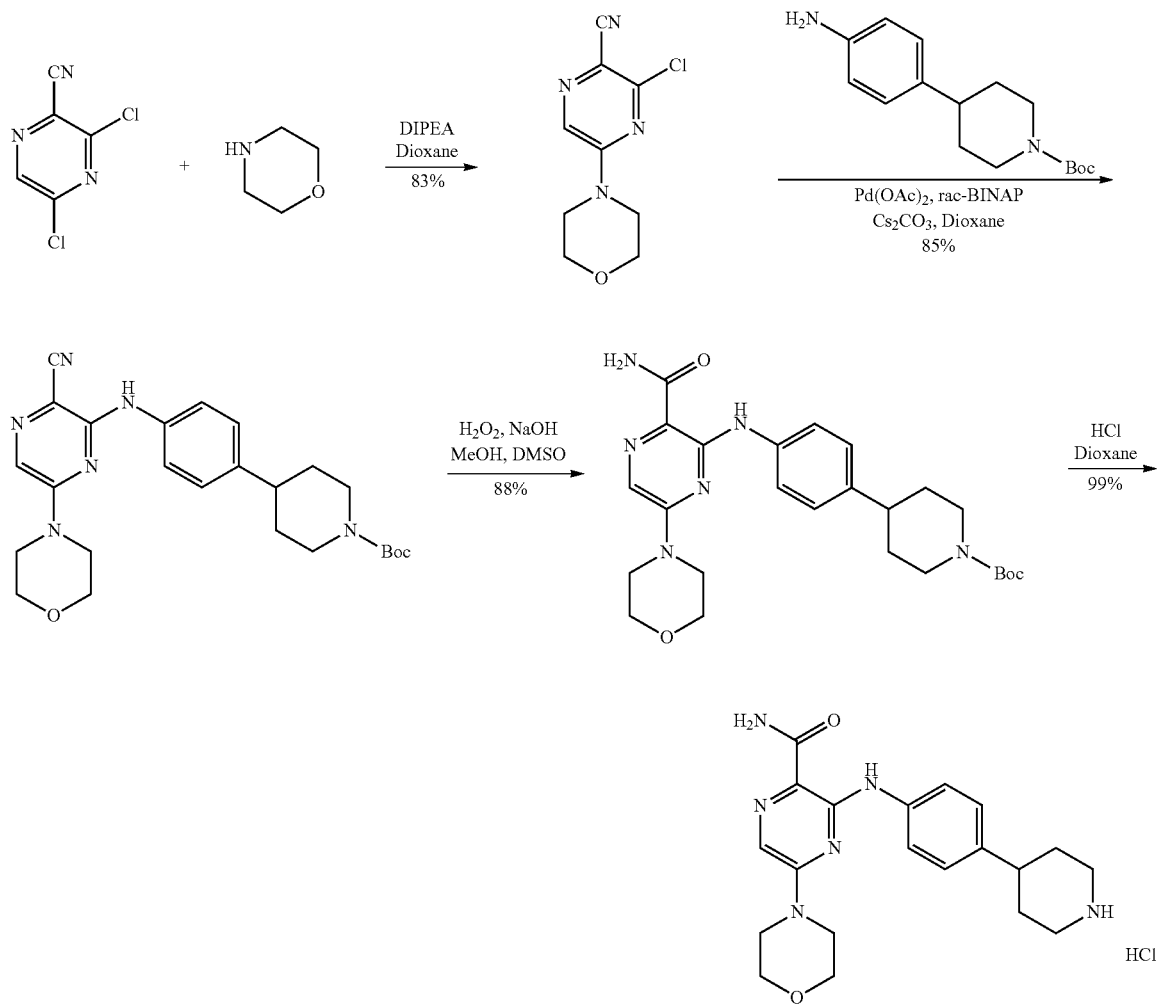

Step 1:
3-chloro-5-morpholino-pyrazine-2-carbonitrile

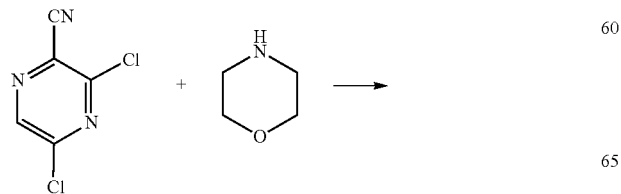

-continued

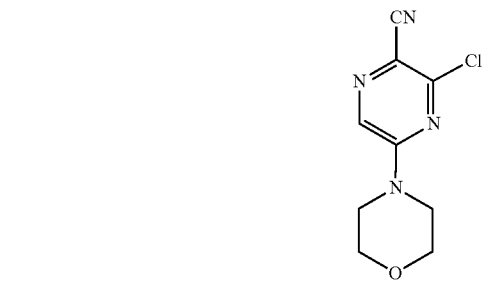

To a solution of morpholine (2.65 mL, 30.4 mmol) and 3,5-dichloropyrazine-2-carbonitrile 1 (6.2 g, 35.5 mmol) in anhydrous DMF (40.0 mL) at rt, was added DIPEA (6.4 mL, 36.5 mmol). The reaction solution was stirred at rt for 4 h. The mixture was diluted with water (100 mL) and EtOAc (100 mL). The layers were separated, and the aqueous layer was extracted with EtOAc (3×20 mL). The combined organic layers were washed with water (2×20 mL) and brine (3×20 mL), then dried ($Na_2SO_4$), filtered and concentrated under reduced pressure to afford title compound (5.7 g, 83%) as a solid. MS (ESI) [M+H]+ 225.1.

Step 2: Tert-butyl 4-[4-[(3-cyano-6-morpholino-pyrazin-2-yl)amino]phenyl]piperidine-1-carboxylate

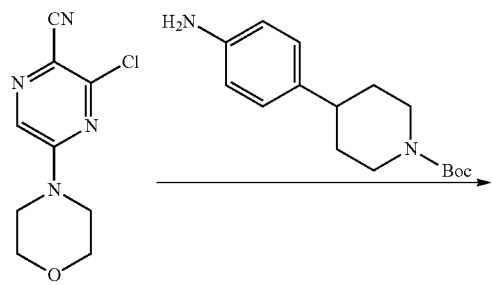

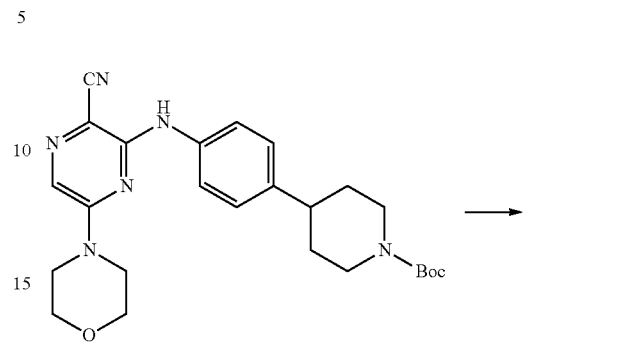

The mixture of 3-chloro-5-morpholino-pyrazine-2-carbonitrile (4.06 g, 18.1 mmol), tert-butyl 4-(4-aminophenyl)piperidine-1-carboxylate (5.0 g, 18.1 mmol), rac-BINAP (1.13 g, 1.81 mmol) and $Cs_2CO_3$ (17.7 g, 54.3 mmol) in anhydrous dioxane (60.0 mL) was degassed with $N_2$ for 10 min. Pd(OAc)$_2$ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated under reduced pressure. The material was suspended in MeOH (50 mL) and sonicated for 2 min. The resulting solid filtered and dried to afford the title compound (7.1 g, 85%) as a solid. MS (ESI) [M−Boc+H]+ 365.3.

Step 3: Tert-butyl 4-[4-[(3-carbamoyl-6-morpholino-pyrazin-2-yl)amino]phenyl]piperidine-1-carboxylate

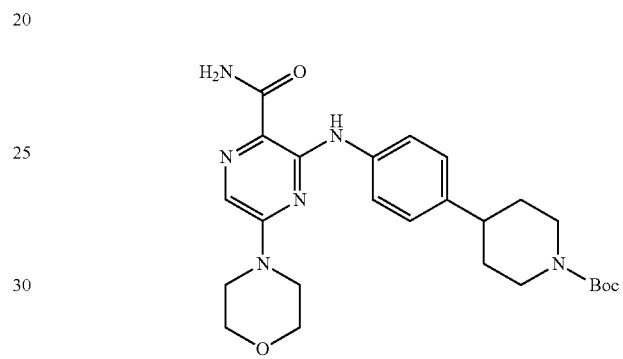

To a solution of tert-butyl 4-[4-[(3-cyano-6-morpholino-pyrazin-2-yl)amino]phenyl]piperidine-1-carboxylate (7.1 g, 15.3 mmol) in MeOH (100.0 mL) and DMSO (10.0 mL) at rt, was added NaOH (4 M in water, 7.64 mL 30.6 mmol) followed by $H_2O_2$ (30% in water, 6.93 mL, 61.1 mmol). The reaction mixture was stirred at for 3.5 h. The mixture was diluted with acetonitrile (10 mL) and EtOAc (100 mL). The layers were separated, and the aqueous layer was extracted with EtOAc (3×50 mL). The combined organic layers were washed brine (2×30 mL), then dried ($Na_2SO_4$), filtered and concentrated under reduced pressure to afford the title compound as a solid (6.51 g, 88%). MS (ESI) [M−H]− 481.4.

Step 4: 5-morpholino-3-[4-(4-piperidyl)anilino]pyrazine-2-carboxamide hydrochloride

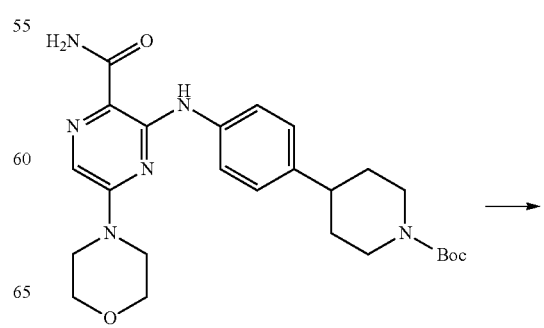

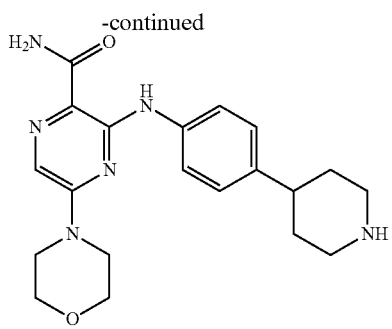

To a solution of tert-butyl 4-[4-[(3-carbamoyl-6-morpholino-pyrazin-2-yl)amino]phenyl]piperidine-1-carboxylate (6.51 g, 13.5 mmol) in anhydrous DCM (20.0 mL) at rt, was added HCl (35.0 mL, 140 mmol, 4 M in dioxane) and the reaction mixture was stirred at rt for 2 h. The resulting solid was filtered, washed with acetonitrile (100 mL) and DCM (100 mL), then dried under reduced pressure to afford title compound (5.6 g, 99%) as a yellow solid. $^1$H NMR (400 MHz, DMSO) δ 11.35 (s, 1H), 9.13-8.93 (m, 2H), 7.91-7.71 (m, 1H), 7.67 (s, 1H), 7.55 (d, J=8.6 Hz, 2H), 7.49-7.29 (m, 1H), 7.17 (d, J=8.6 Hz, 2H), 3.76-3.69 (m, 4H), 3.67-3.61 (m, 4H), 3.33 (d, J=12.7 Hz, 2H), 3.02-2.90 (m, 2H), 2.84-2.73 (m, 1H), 1.94-1.81 (m, 4H). MS (ESI) [M+H]$^+$ 383.2.

Example 61: 5-(4-methylpiperazin-1-yl)-3-[4-(4-piperidyl)anilino]pyrazine-2-carboxamide

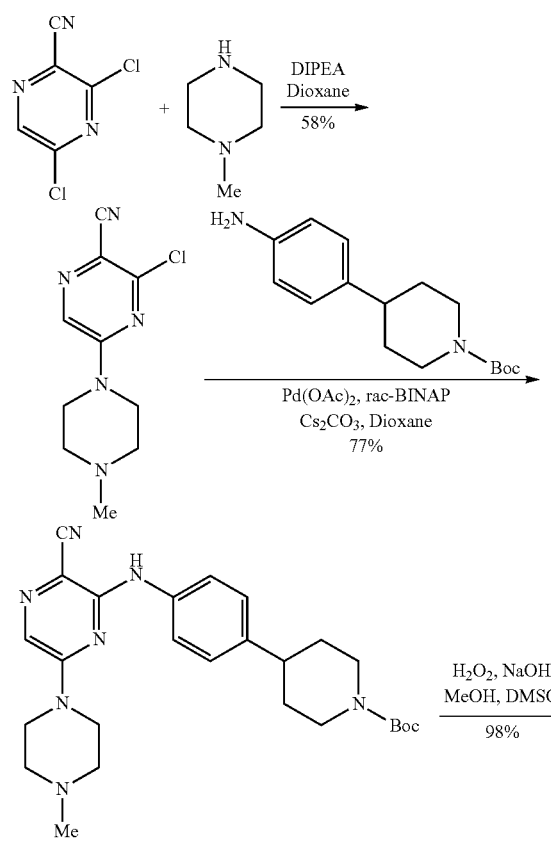

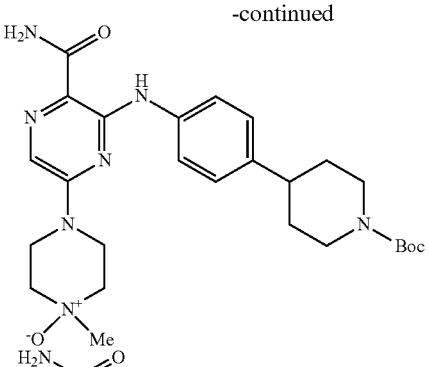

Step 1: 3-chloro-5-(4-methylpiperazin-1-yl)pyrazine-2-carbonitrile

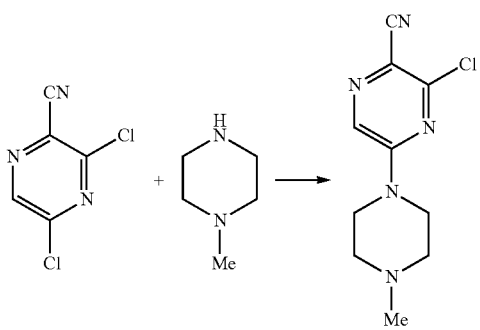 [SMILES: N#Cc1ncc(Cl)nc1Cl ; CN1CCNCC1 ; CN1CCN(c2cnc(C#N)c(Cl)n2)CC1]

To a solution of 1-methylpiperazine (3.3 mL, 30.0 mmol) and 3,5-dichloropyrazine-2-carbonitrile (6.1 g, 34.9 mmol) in anhydrous DMF (40 mL) at rt, was added DIPEA (6.26 mL, 35.9 mmol) and the reaction mixture was stirred at rt for 4 h. The mixture was diluted with water (100 mL) and EtOAc (100 mL). The layers were separated, and the aqueous layer was extracted with EtOAc (3×20 mL). The combined organic layers were washed with water (2×20 mL) and brine (3×20 mL), then dried (Na₂SO₄), filtered and concentrated under reduced pressure to afford the title compound (4.1 g, 58%) as a solid. MS (ESI) [M+H]⁺ 238.1.

Step 2: Tert-butyl 4-[4-[[3-cyano-6-(4-methylpiperazin-1-yl)pyrazin-2-yl]amino]phenyl]piperidine-1-carboxylate

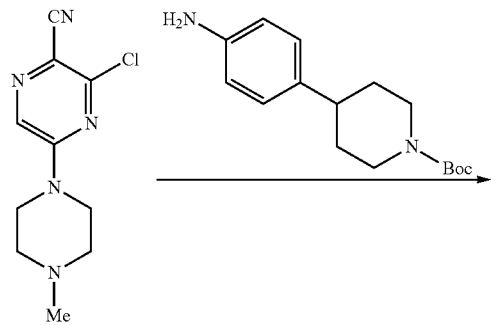

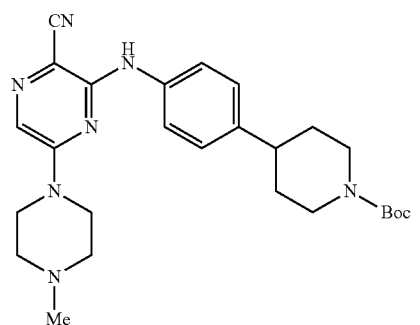

A mixture of 3-chloro-5-(4-methylpiperazin-1-yl)pyrazine-2-carbonitrile (4.1 g, 17.2 mmol), tert-butyl 1-(4-aminophenyl)piperidine-4-carboxylate (5.0 g, 18.1 mmol), rac-BINAP (1.13 g, 1.81 mmol), and Cs₂CO₃ (17.7 g, 54.3 mmol) in anhydrous dioxane (60.0 mL) was degassed with N₂ for 10 min. Pd(OAc)₂ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated under reduced pressure. The material was suspended in MeOH (50 mL) and sonicated for 2 min. The resulting solid filtered and dried under reduced pressure to afford the title compound (6.68 g, 77%) as a solid. MS (ESI) [M−Boc+2H]⁺ 378.3.

Step 3: Tert-butyl 4-[4-[[3-carbamoyl-6-(4-methyl-4-oxido-piperazin-4-ium-1-yl)pyrazin-2-yl]amino]phenyl]piperidine-1-carboxylate

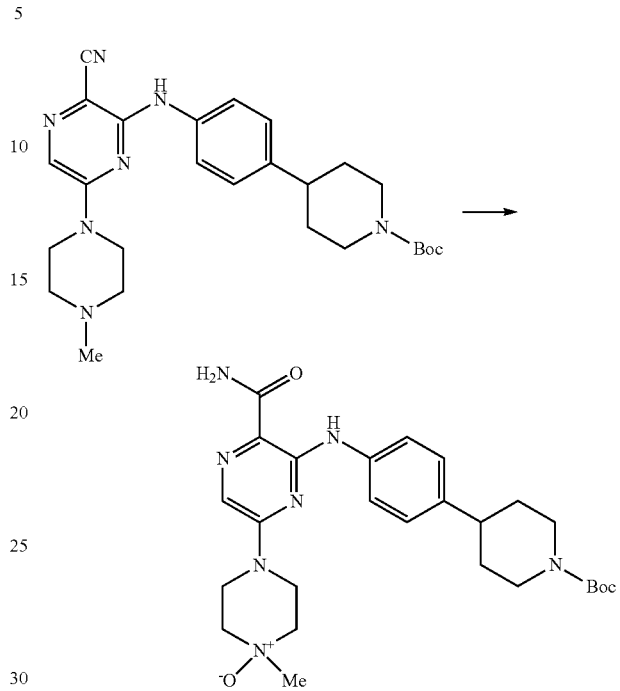

To a suspension of tert-butyl 4-[4-[[3-cyano-6-(4-methylpiperazin-1-yl)pyrazin-2-yl]amino]phenyl]piperidine-1-carboxylate (6.80 g, 14.2 mmol) in MeOH (100.0 mL) and DMSO (10.0 mL) at rt, was added aqueous NaOH (4 M in water, 7.1 mL 28.5 mmol), followed by H₂O₂ (30% in water, 6.5 mL, 57.3 mmol) at rt. The reaction mixture was stirred at for 3.5 h. The mixture was diluted with cold water (50 mL). The resulting solid was filtered and washed with water (50 mL) and cold MeOH (40 mL) to afford the title compound (7.10 g, 98%) as a solid. ¹H NMR (400 MHz, DMSO) δ 11.30 (s, 1H), 7.82-7.73 (m, 1H), 7.67 (s, 1H), 7.51 (d, J=8.6 Hz, 2H), 7.41-7.31 (m, 1H), 7.18 (d, J=8.5 Hz, 2H), 4.13-3.98 (m, 2H), 3.73-3.58 (m, 4H), 2.90-2.71 (m, 2H), 2.69-2.57 (m, 1H), 2.46-2.35 (m, 4H), 2.22 (s, 3H), 1.79-1.67 (m, 2H), 1.52-1.43 (m, 2H), 1.42 (s, 9H). MS (ESI) [M−H]⁺ 510.5.

Step 4: Tert-butyl 4-[4-[[3-carbamoyl-6-(4-methylpiperazin-1-yl)pyrazin-2-yl]amino]phenyl]piperidine-1-carboxylate

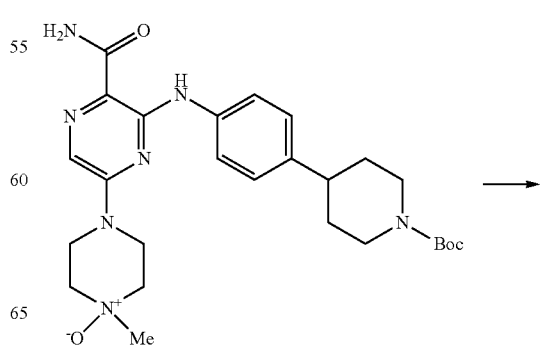

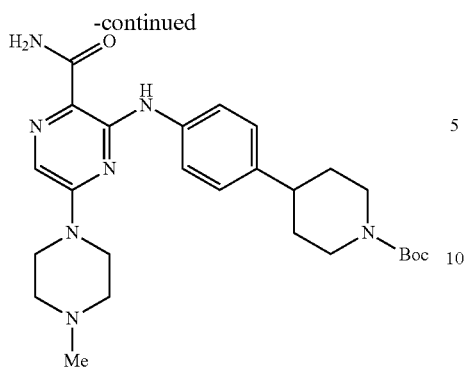

To solution of tert-butyl 4-[4-[[3-carbamoyl-6-(4-methyl-4-oxido-piperazin-4-ium-1-yl)pyrazin-2-yl]amino]phenyl]piperidine-1-carboxylate (4.50 g, 8.80 mmol) in anhydrous DMF (50.0 mL) at rt, was added trimethylphosphane (44.0 mL, 44.0 mmol, 1.0 M in THF) and the resulting mixture was heated at 80° C. for 4 h. The mixture was diluted with EtOAc (100 mL) and water (200 mL). The layers were separated, and the aqueous layer was extracted with EtOAc (3×50 mL). The combined organic layers were washed with brine (3×50 mL), then dried ($Na_2SO_4$), filtered and concentrated under reduced pressure to afford title compound (2.20 g, 51%) as a solid. MS (ESI) [M−H]⁻ 494.5.

Step 5: 5-(4-methylpiperazin-1-yl)-3-[4-(4-piperidyl)anilino]pyrazine-2-carboxamide dihydrochloride

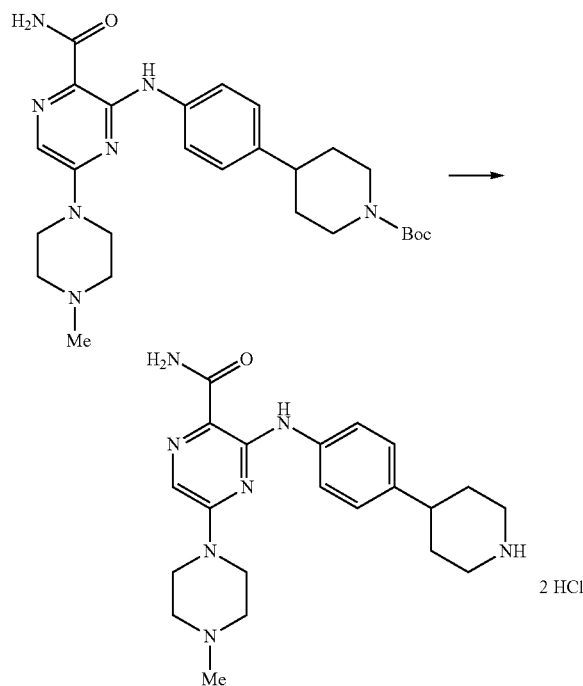

To a solution of tert-butyl 4-[4-[[3-carbamoyl-6-(4-methylpiperazin-1-yl pyrazin-2-yl]amino]phenyl]piperidine-1-carboxylate (2.60 g, 5.25 mmol) in anhydrous DCM (40.0 mL) at rt, was added HCl (15.0 mL, 60.0 mmol, 4.0 M in dioxane) and the resulting suspension was stirred at rt for 1 h. The resulting solid was filtered, washed with DCM (100 mL) and dried under reduced pressure to afford the title compound (2.35 g, 96%) as a yellow-orange solid. ¹H NMR (500 MHz, DMSO) δ 11.55-11.40 (m, 1H), 11.38 (s, 1H), 9.21-8.99 (m, 2H), 7.96-7.85 (m, 1H), 7.78 (s, 1H), 7.55 (d, J=8.4 Hz, 2H), 7.51-7.42 (m, 1H), 7.20 (d, J=8.4 Hz, 2H), 4.49 (d, J=14.3 Hz, 2H), 3.55-3.44 (m, 4H), 3.39-3.29 (m, 2H), 3.20-3.06 (m, 2H), 3.04-2.90 (m, 2H), 2.85-2.72 (m, 4H), 1.97-1.79 (m, 4H). MS (ESI) [M+H]⁺ 396.3.

Example 62: Synthesis of 5-[4-(hydroxymethyl)-1-piperidyl]-3-[4-(4-piperidyl)anilino]pyrazine-2-carboxamide

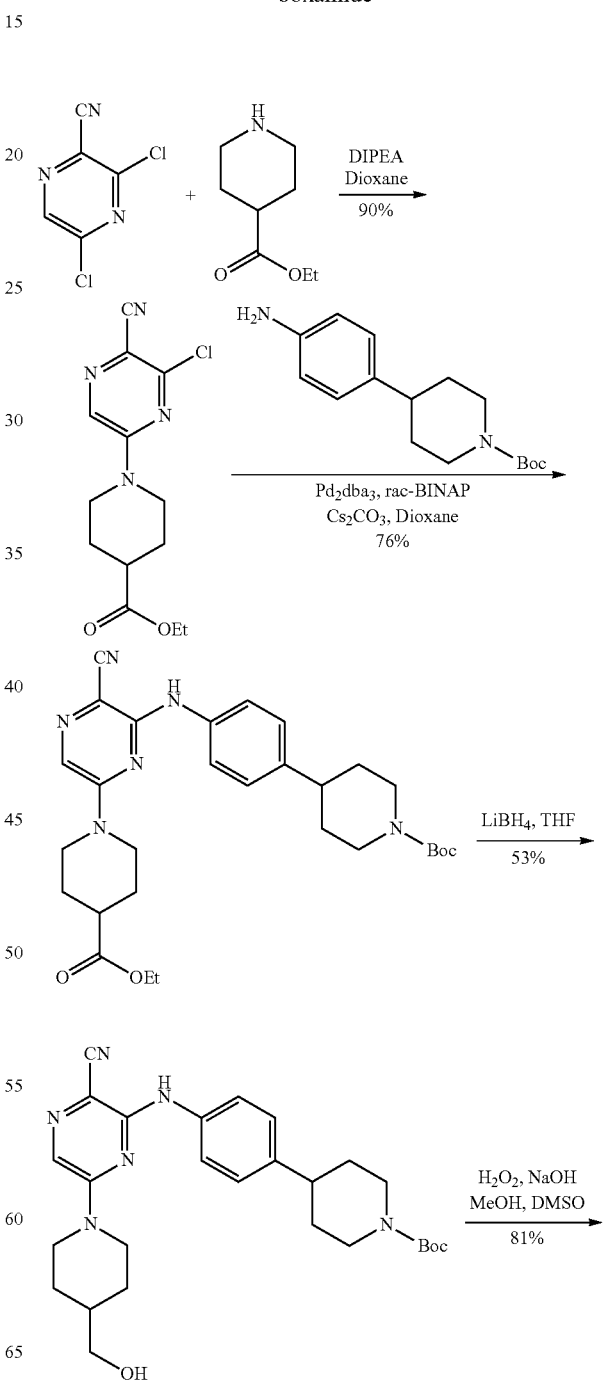

-continued

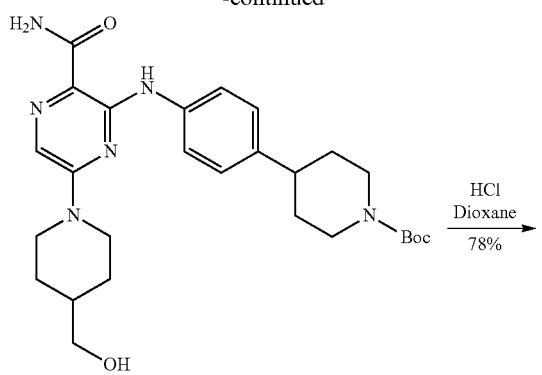

Step 2: Tert-butyl 4-[4-[[3-cyano-6-(4-ethoxycarbonyl-1-piperidyl)pyrazin-2-yl]amino]phenyl]piperidine-1-carboxylate

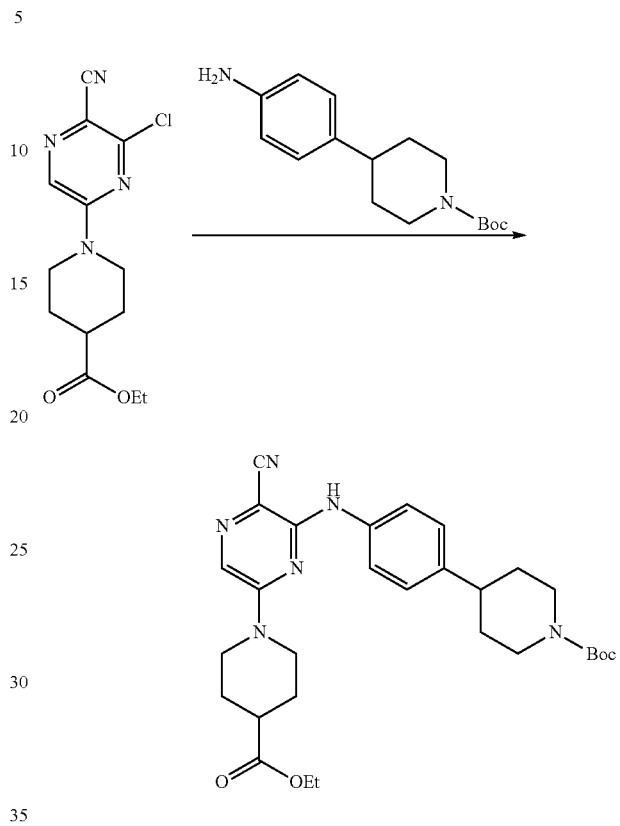

Step 1: Ethyl 1-(6-chloro-5-cyano-pyrazin-2-yl)piperidine-4-carboxylate

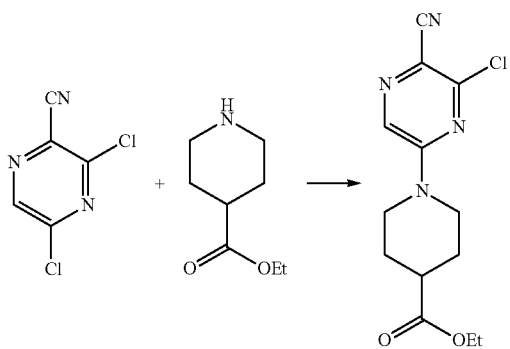 [SMILES: N#Cc1ncc(Cl)nc1Cl ; CCOC(=O)C1CCNCC1 ; CCOC(=O)C1CCN(c2cnc(C#N)c(Cl)n2)CC1]

To a solution of 3,5-dichloropyrazine-2-carbonitrile (6.96 g, 40.0 mmol) in anhydrous 1,4-dioxane (60.0 mL) at rt, was added ethyl piperidine-4-carboxylate (6.8 mL, 44 mmol) followed by DIPEA (14.0 mL, 80 mmol) and the reaction mixture was stirred for 1 h at rt. The volatiles were evaporated under reduced pressure. The material was purified by column chromatography on silica gel (dry loading, 220 g) using a gradient of 0-40% EtOAc in hexane to afford the title compound (11.8 g, 90%) as an oil. MS (ESI) [M+H]$^+$ 295.2.

To a mixture of tert-butyl 4-(4-aminophenyl)piperidine-1-carboxylate (9.95 g, 36.0 mmol), Pd$_2$DBA$_3$ (1.65 g, 1.80 mmol), rac-BINAP (2.24 g, 3.60 mmol) and Cs$_2$CO$_3$ (29.3 g, 90.0 mmol) at rt, was added a degassed solution of ethyl 1-(6-chloro-5-cyano-pyrazin-2-yl)piperidine-4-carboxylate (11.8 g, 36.0 mmol) in anhydrous 1,4-dioxane (120.0 mL). The resulting mixture was further sparged with N$_2$ for 10 min and then stirred at 90° C. for 1.5 h, and was further stirred at 60° C. for 72 h. The mixture was cooled to rt, the suspension was filtered and washed with EtOAc. The filtrate was concentrated under reduced pressure, and the residue was diluted with MeOH (50 mL). The resulting suspension was filtered, and the collected solid was washed with MeOH (20 mL) to afford the title compound (9.1 g). The filtrate was concentrated under reduced pressure, then diluted with MeOH (25 mL). The resulting suspension was filtered, and the collected solid was washed with MeOH (10 mL) to afford the title compound (2.7 g). The filtrate was concentrated under reduced pressure and the material was purified by column chromatography on silica gel (dry loading, 120 g) using a gradient of 0-50% EtOAc in hexane to afford crude title compound. The material was diluted with MeOH (20 mL). The resulting suspension was filtered, and the collected solid was washed with MeOH (10 mL) to afford the title compound (2.9 g, total of 14.7 g, 76%) as a yellow solid. $^1$H NMR (400 MHz, DMSO) δ 8.94 (s, 1H), 7.84 (s, 1H), 7.46 (d, J=8.6 Hz, 2H), 7.16 (d, J=8.7 Hz, 2H), 4.27-4.16 (m, 2H), 4.12-4.01 (m, 4H), 3.17-3.08 (m, 2H), 2.86-2.58 (m, 4H), 1.95-1.84 (m, 2H), 1.78-1.70 (m, 2H), 1.60-1.38 (m, 13H), 1.18 (t, J=7.1 Hz, 3H). MS (ESI) [M−Boc+2H]$^+$ 435.4.

Step 3: Tert-butyl 4-[4-[[3-cyano-6-[4-(hydroxymethyl)-1-piperidyl]pyrazin-2-yl]amino]phenyl]piperidine-1-carboxylate

Step 4: Tert-butyl 4-[4-[[3-carbamoyl-6-[4-(hydroxymethyl)-1-piperidyl]pyrazin-2-yl]amino]phenyl]piperidine-1-carboxylate

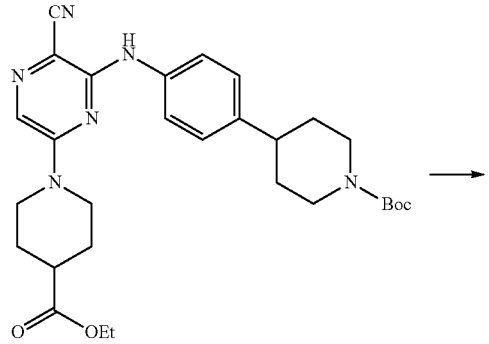

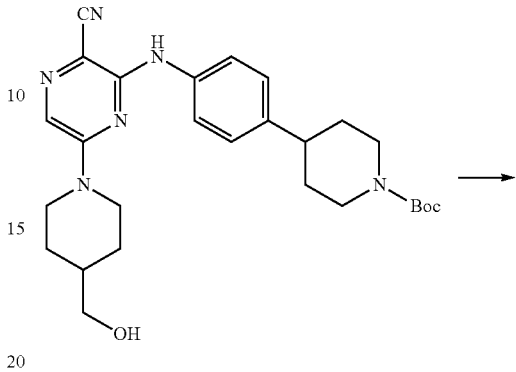

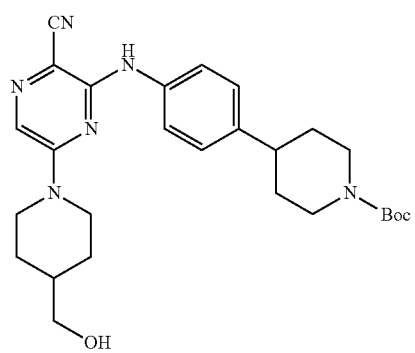

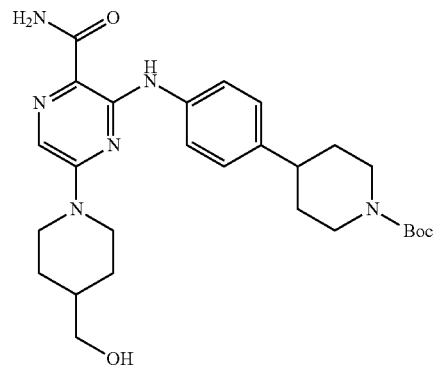

To a solution of tert-butyl 4-[4-[[3-cyano-6-(4-ethoxycarbonyl-1-piperidyl)pyrazin-2-yl]amino]phenyl]piperidine-1-carboxylate (6.95 g, 13.0 mmol) in anhydrous THF (65 mL) at 0° C., was added LiBH$_4$ (2.0 M in THF, 13.0 mL, 26 mmol) and the resulting mixture was stirred at rt for 60 h. The mixture was diluted with EtOAc (65 mL) and saturated NH$_4$Cl (20 mL) and water (50 mL) [Note: caution: hydrogen evolution]. The layers were separated, and the aqueous phase was extracted with EtOAc (2×100 mL). The combined organic layers were washed with brine (50 mL), then dried (MgSO$_4$), filtered and concentrated under reduced pressure. The material was purified by column chromatography on silica gel (dry loading, 120 g) using a gradient of 0-65% EtOAc in hexane to afford the title compound (3.4 g, 53%) as a solid. $^1$H NMR (500 MHz, DMSO) δ 8.90 (s, 1H), 7.83 (s, 1H), 7.47 (d, J=8.7 Hz, 2H), 7.15 (d, J=8.7 Hz, 2H), 4.48 (t, J=5.3 Hz, 1H), 4.34 (d, J=13.2 Hz, 2H), 4.12-4.01 (m, 2H), 3.26 (t, J=5.7 Hz, 2H), 2.94 (t, J=12.5 Hz, 2H), 2.78 (s, 2H), 2.63 (tt, J=12.3, 3.5 Hz, 1H), 1.77-1.65 (m, 5H), 1.51-1.43 (m, 2H), 1.41 (s, 9H), 1.11 (qd, J=12.0, 11.2, 3.4 Hz, 2H). MS (ESI) [M−Boc+2H]$^+$ 393.3.

To a solution of tert-butyl 4-[4-[[3-cyano-6-[4-(hydroxymethyl)-1-piperidyl]pyrazin-2-yl]amino]phenyl]piperidine-1-carboxylate (3.40 g, 6.90 mmol) in MeOH (50.0 mL) and DMSO (5.0 mL) at rt, was added KOH (426 mg, 7.59 mmol) followed by 30% aqueous H$_2$O$_2$ (0.85 mL, 8.3 mmol). The resulting mixture was stirred at rt for 4 h, and then cooled to 0° C. MeCN (2.0 mL) was added dropwise and the resulting mixture was then concentrated under reduced pressure. The residue was diluted with EtOAc (100 mL) and water (50 mL). The layers were separated, and the aqueous layer was extracted with EtOAc (2×50 mL). The combined organic layers were washed with water (50 mL) and brine (50 mL), then dried (MgSO$_4$), filtered and concentrated under reduced pressure to afford the title compound (2.84 g, 81%) as a solid. $^1$H NMR (500 MHz, DMSO) δ 11.29 (s, 1H), 7.73 (d, J=3.2 Hz, 1H), 7.66 (s, 1H), 7.52 (d, J=8.7 Hz, 2H), 7.31 (d, J=3.0 Hz, 1H), 7.17 (d, J=8.7 Hz, 2H), 4.49 (t, J=5.4 Hz, 1H), 4.40 (d, J=13.1 Hz, 2H), 4.11-4.01 (m, 2H), 3.28 (t, J=5.8 Hz, 2H), 2.98 (td, J=13.0, 2.6 Hz, 2H), 2.90-2.67 (m, 2H), 2.62 (tt, J=11.7, 3.3 Hz, 1H), 1.80-1.66 (m, 5H), 1.51-1.43 (m, 2H), 1.41 (s, 9H), 1.20-1.12 (m, 2H). MS (ESI) [M−H]$^−$ 509.5.

455

Step 5: 5-[4-(hydroxymethyl)-1-piperidyl]-3-[4-(4-piperidyl)anilino]pyrazine-2-carboxamide; hydrochloride

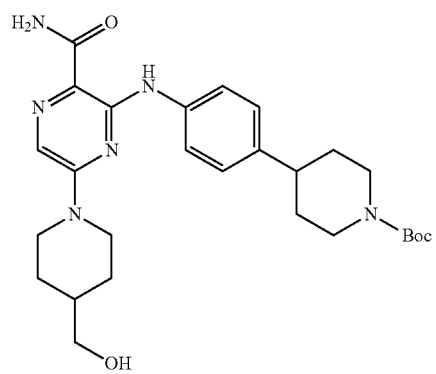

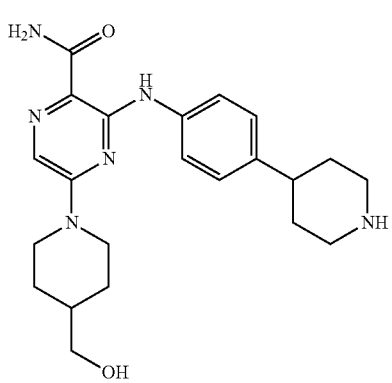

To a solution of tert-butyl 4-[4-[[3-carbamoyl-6-[4-(hydroxymethyl)-1-piperidyl]pyrazin-2-yl]amino]phenyl]piperidine-1-carboxylate (2.84 g, 5.56 mmol) in anhydrous 1,4-dioxane (30 mL) at rt, HCl (4 M in dioxane, 11 mL, 44 mmol) was added, and the resulting mixture was stirred for 1 h at rt. Additional HCl (4 M in dioxane, 11 mL, 44 mmol) was added, and the resulting mixture was stirred for 4 h at rt. The resulting suspension was diluted with Et$_2$O (100 mL). The resulting solid was filtered and washed with MeCN (25 mL), DCM (25 mL) and Et$_2$O (25 mL). The solid was suspended in MeOH (50 mL) and stirred for 30 min and then Et$_2$O (100 mL) was added. The resulting suspension was filtered, and the solid was washed with Et$_2$O (25 mL) and the dried under reduced pressure to afford the title compound (2.19 g, 78%) of as a bright yellow solid. $^1$H NMR (500 MHz, DMSO) δ 11.31 (s, 1H), 9.23-9.13 (m, 1H), 9.13-9.02 (m, 1H), 7.67 (s, 1H), 7.56 (d, J=8.7 Hz, 2H), 7.30 (s, 2H), 7.16 (d, J=8.7 Hz, 2H), 4.40 (d, J=13.2 Hz, 2H), 3.32 (d, J=12.5 Hz, 2H), 3.27 (d, J=6.1 Hz, 2H), 3.03-2.91 (m, 4H), 2.84-2.73 (m, 1H), 1.93-1.82 (m, 4H), 1.79-1.65 (m, 3H), 1.23-1.11 (m, 2H). *The —OH signal was not observed. MS (ESI) [M+H]$^+$ 411.3.

456

Example 63: Synthesis of 1-[5-carbamoyl-6-[4-(4-piperidyl)anilino]pyrazin-2-yl]piperidine-4-carboxylic acid

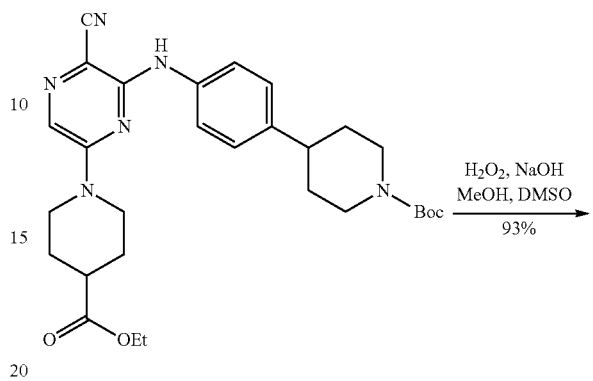

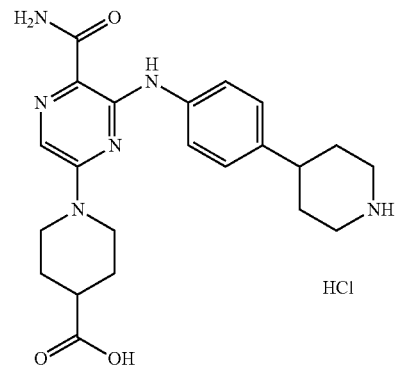

457

Step 1: 1-[6-[4-(1-tert-butoxycarbonyl-4-piperidyl)anilino]-5-carbamoyl-pyrazin-2-yl]piperidine-4-carboxylic acid

458

Step 2: 1-[5-carbamoyl-6-[4-(4-piperidyl)anilino]pyrazin-2-yl]piperidine-4-carboxylic acid hydrochloride

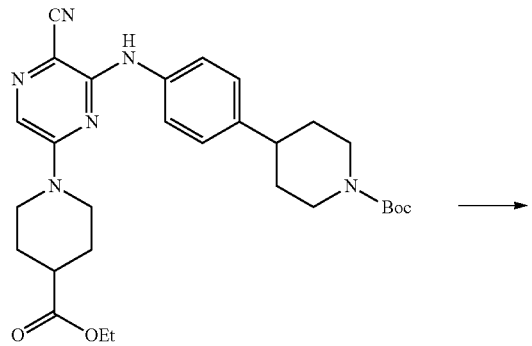

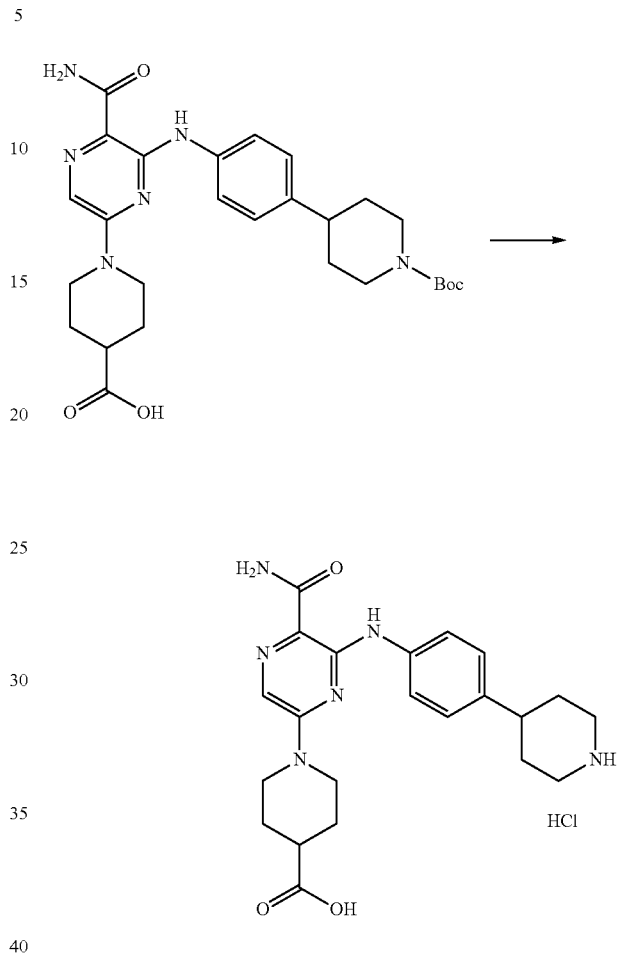

To a solution of tert-butyl 4-[4-[[3-cyano-6-(4-ethoxycarbonyl-1-piperidyl)pyrazin-2-yl]amino]phenyl]piperidine-1-carboxylate in MeOH (75.0 mL) and DMSO (5.0 mL) at rt, was added KOH (1.41 g, 25.1 mmol) followed by 30% aq. $H_2O_2$ (1.3 mL, 13 mmol). The resulting mixture was stirred at rt 2 h, and then additional KOH (512 mg, 9.13 mmol) and 30% aq. $H_2O_2$ (0.70 mL, 6.9 mmol) were added. The reaction mixture was stirred for 2 h at rt. The mixture was cooled to 0° C., and MeCN (2.0 mL) was added dropwise. The volatiles were evaporated under reduced pressure, and the residue was diluted with water (50 mL). 2 M aqueous $NaHSO_4$ (50 mL) was then added, and the resulting suspension was filtered. The collected solid was washed with water (3×50 mL) and dried under reduced pressure to afford title compound (5.56 g, 93%) as a solid. $^1$H NMR (500 MHz, DMSO) δ 11.85 (s, 1H), 11.29 (s, 1H), 7.75 (d, J=2.5 Hz, 1H), 7.68 (s, 1H), 7.52 (d, J=8.7 Hz, 2H), 7.33 (d, J=2.8 Hz, 1H), 7.19 (d, J=8.5 Hz, 2H), 4.27 (d, J=13.7 Hz, 2H), 4.06 (d, J=9.8 Hz, 2H), 3.16 (t, J=10.9 Hz, 2H), 2.79 (s, 2H), 2.68-2.56 (m, 2H), 2.01-1.88 (m, 2H), 1.75 (d, J=12.5 Hz, 2H), 1.62-1.53 (m, 2H), 1.51-1.43 (m, 2H), 1.41 (s, 9H). MS (ESI) [M−H]$^−$ 523.5.

To a solution of 1-[6-[4-(1-tert-butoxycarbonyl-4-piperidyl)anilino]-5-carbamoyl-pyrazin-2-yl]piperidine-4-carboxylic acid (5.56 g, 10.6 mmol) in anhydrous 1,4-dioxane (50.0 mL) at rt, was added HCl (4 M in dioxane, 21 mL, 84 mmol) and the resulting mixture was stirred for 1 h at rt. Additional HCl (4 M in dioxane, 21 mL, 84 mmol) was added, and the resulting mixture was further stirred for 4 h at rt. The resulting suspension was diluted with $Et_2O$ (100 mL). The resulting solid was filtered and washed with MeCN (50 mL), DCM (50 mL) and $Et_2O$ (50 mL). The solid was suspended in MeOH (100 mL) and stirred for 30 min and then $Et_2O$ (100 mL) was added. The resulting suspension was filtered, and the solid was washed with $Et_2O$ (50 mL) and then dried under reduced pressure to afford the title compound (5.17 g, 99%) as a bright yellow solid. $^1$H NMR (500 MHz, DMSO) δ 11.32 (s, 1H), 9.19-9.09 (m, 1H), 9.00 (d, J=10.4 Hz, 1H), 7.85 (s, 1H), 7.69 (s, 1H), 7.55 (d, J=8.7 Hz, 2H), 7.34 (s, 1H), 7.18 (d, J=8.7 Hz, 2H), 4.27 (d, J=13.1 Hz, 2H), 3.32 (d, J=12.5 Hz, 2H), 3.21-3.12 (m, 2H), 3.02-2.90 (m, 2H), 2.84-2.74 (m, 1H), 2.65-2.56 (m, 1H), 1.99-1.78 (m, 6H), 1.64-1.53 (m, 2H). *The —COOH signal was not observed. MS (ESI) [M+H]$^+$ 425.3.

Example 64: Synthesis of 3-((4-(piperidin-4-yl)phenyl)amino)-5-(pyrrolidin-1-yl)pyrazine 2-carboxamide

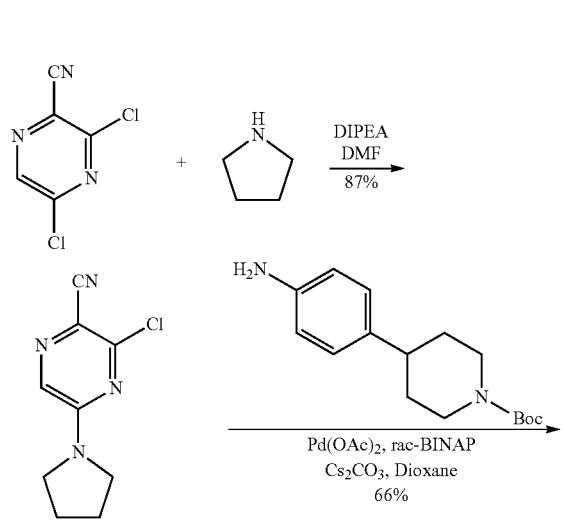

Step 1: 3-chloro-5-pyrrolidin-1-yl-pyrazine-2-carbonitrile

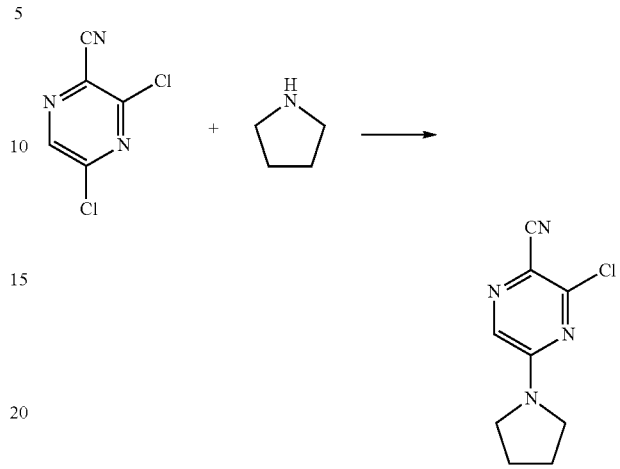

To a solution of pyrrolidine (1.52 mL, 18.2 mmol) and 3,5-dichloropyrazine-2-carbonitrile (3.17 g, 18.2 mmol) in anhydrous DMF (20.0 mL) at rt, was added DIPEA (3.81 mL, 21.9 mmol). The resulting solution was stirred at rt for 1 h. The mixture was diluted with water (100 mL) and the resulting solid was collected by filtration then dried under reduced pressure to afford title compound (3.3 g, 87%) as a solid. MS (ESI) [M+H]$^+$ 209.1.

Step 2: Tert-butyl 4-[4-[(3-cyano-6-pyrrolidin-1-yl-pyrazin-2-yl)amino]phenyl]piperidine-1-carboxylate

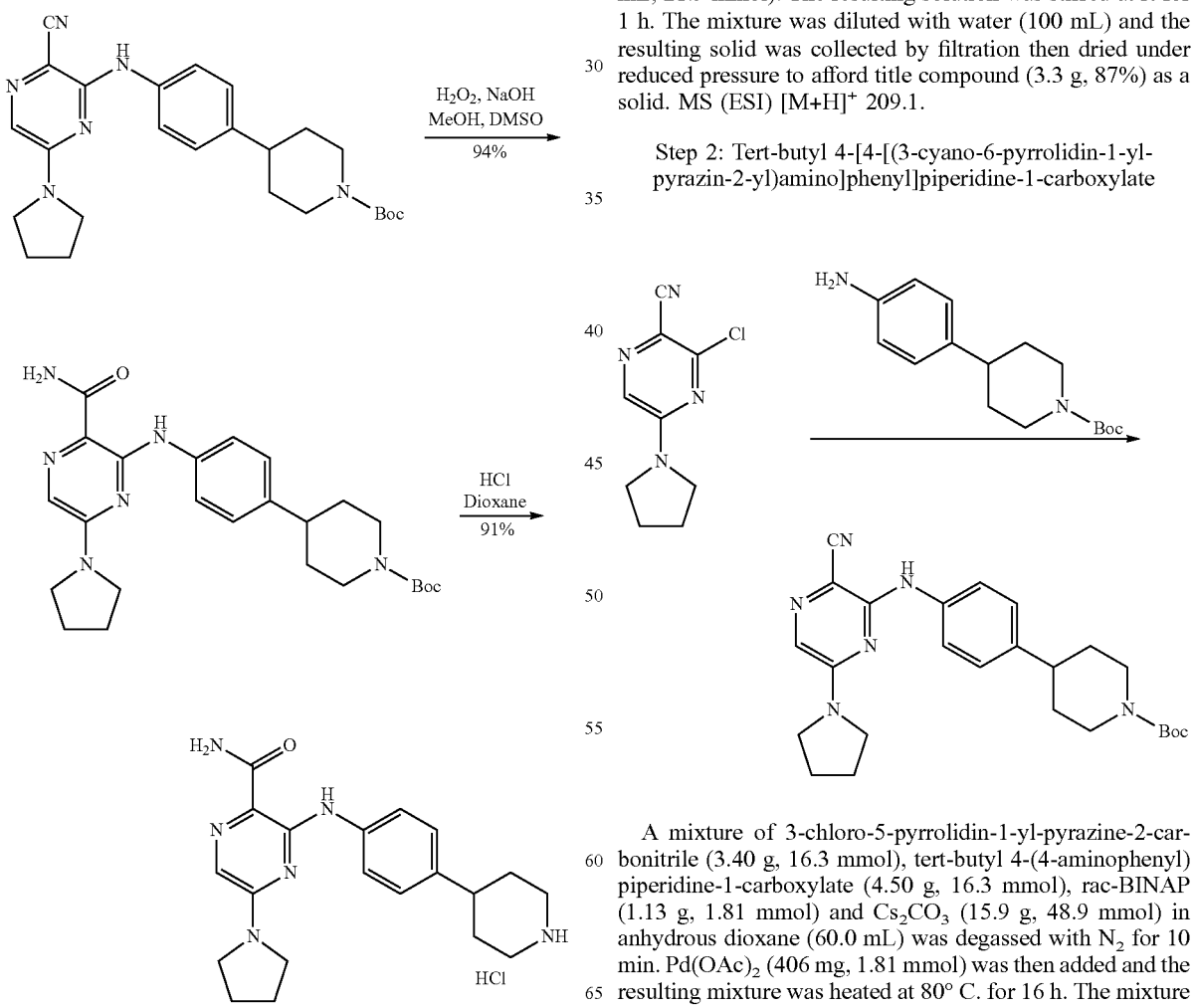

A mixture of 3-chloro-5-pyrrolidin-1-yl-pyrazine-2-carbonitrile (3.40 g, 16.3 mmol), tert-butyl 4-(4-aminophenyl)piperidine-1-carboxylate (4.50 g, 16.3 mmol), rac-BINAP (1.13 g, 1.81 mmol) and Cs$_2$CO$_3$ (15.9 g, 48.9 mmol) in anhydrous dioxane (60.0 mL) was degassed with N$_2$ for 10 min. Pd(OAc)$_2$ (406 mg, 1.81 mmol) was then added and the resulting mixture was heated at 80° C. for 16 h. The mixture was cooled to rt, the suspension was filtered on Celite and was washed with DCM (100 mL). The filtrate was concentrated reduced pressure. The material was suspended in MeOH (50 mL) and sonicated for 2 min. The resulting solid was filtered and dried under reduced pressure to afford the title compound (4.80 g, 66%) as a solid. ¹H NMR (400 MHz, DMSO) δ 8.83 (s, 1H), 7.59 (d, J=8.7 Hz, 2H), 7.50 (s, 1H), 7.15 (d, J=8.6 Hz, 2H), 4.13-3.96 (m, 2H), 3.52-3.42 (m, 4H), 2.88-2.70 (m, 2H), 2.67-2.58 (m, 1H), 2.01-1.84 (m, 4H), 1.79-1.68 (m, 2H), 1.52-1.42 (m, 2H), 1.41 (s, 9H). MS (ESI) [M−Boc+2H]⁺ 349.3.

Step 3: Tert-butyl 4-[4-[(3-carbamoyl-6-pyrrolidin-1-yl-pyrazin-2-yl)amino]phenyl]piperidine-1-carboxylate

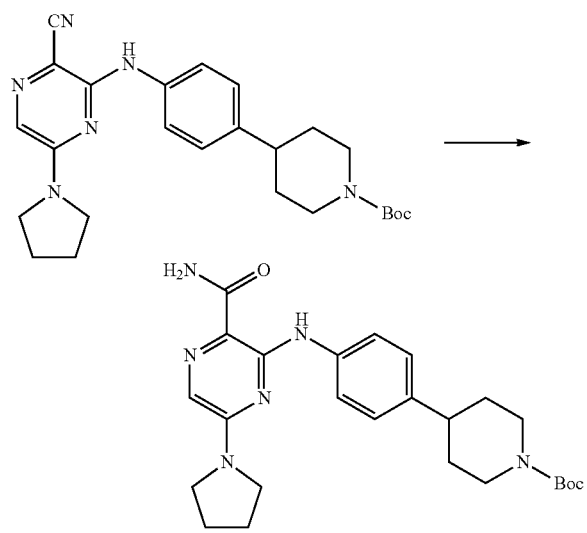

To a solution of tert-butyl 4-[4-[(3-cyano-6-pyrrolidin-1-yl-pyrazin-2-yl)amino]phenyl]piperidine-1-carboxylate (4.80 g, 10.7 mmol) in MeOH (100.0 mL) and DMSO (10.0 mL) at rt, was added NaOH (4 M in water, 5.35 mL 21.4 mmol) followed by H₂O₂ (30% in water, 4.85 mL, 42.8 mmol) at rt. The reaction mixture was stirred at for 18 h, and then water (100 mL) was added. The resulting solid was filtered and dried under reduced pressure to afford the title compound (4.70 g, 94%) as a solid. ¹H NMR (500 MHz, DMSO) δ 11.40 (s, 1H), 7.75-7.71 (m, 1H), 7.64 (d, J=8.6 Hz, 2H), 7.35 (s, 1H), 7.31-7.25 (m, 1H), 7.18 (d, J=8.6 Hz, 2H), 4.15-4.01 (m, 2H), 3.59-3.49 (m, 4H), 2.95-2.70 (m, 2H), 2.67-2.59 (m, 1H), 2.04-1.93 (m, 4H), 1.79-1.72 (m, 2H), 1.51-1.44 (m, 2H), 1.42 (s, 9H).

Step 4: 3-[4-(4-piperidyl)anilino]-5-pyrrolidin-1-yl-pyrazine-2-carboxamide hydrochloride

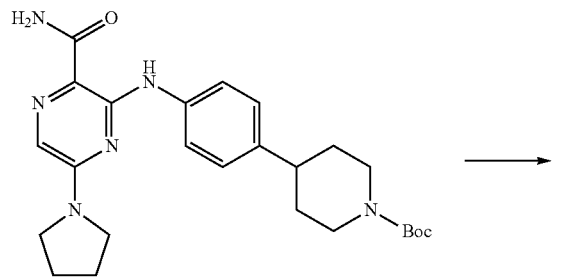

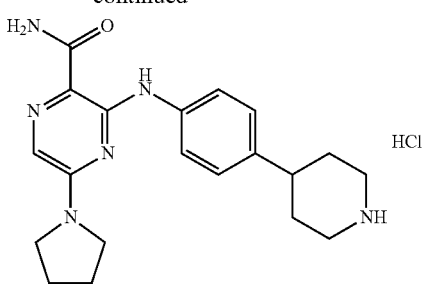

To a solution of tert-butyl 4-[4-[(3-carbamoyl-6-pyrrolidin-1-yl-pyrazin-2-yl)amino]phenyl]piperidine-1-carboxylate (4.80 g, 10.3 mmol) in DCM (75 mL) and MeOH (25 mL) at rt, was added HCl (20.0 mL, 80.0 mmol, 4.0 M in dioxane) and the resulting mixture was stirred at rt for 2 h. The suspension was filtered, washed with DCM and then dried under reduced pressure to afford title compound (3.78 g, 91%) as yellow-orange solid. ¹H NMR (400 MHz, DMSO) δ 11.42 (s, 1H), 8.97-8.76 (m, 2H), 7.82-7.59 (m, 1H), 7.68 (d, J=8.5 Hz, 2H), 7.35 (s, 1H), 7.33-7.19 (m, 1H), 7.16 (d, J=8.5 Hz, 2H), 3.56-3.47 (m, 4H), 3.38-3.30 (m, 2H), 3.03-2.90 (m, 2H), 2.83-2.73 (m, 1H), 2.03-1.96 (m, 4H), 1.92-1.77 (m, 4H). MS (ESI) [M+H]⁺ 367.2.

Example 65: Synthesis of (S)-1-(4-(4-methylthiazol-5-yl)phenyl)ethan-1-amine hydrogen chloride [Intermediate 1]

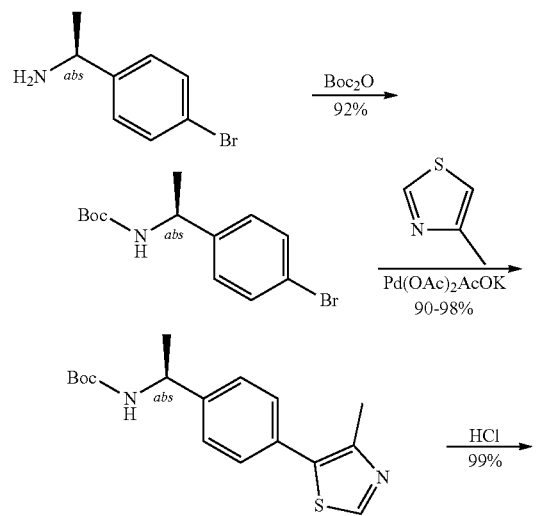

(S)-1-(4-(4-methylthiazol-5-yl)phenyl)ethan-1-amine hydrogen chloride [Intermediate 1]

Step 1: Tert-butyl N-[(1S)-1-(4-bromophenyl)ethyl] carbamate

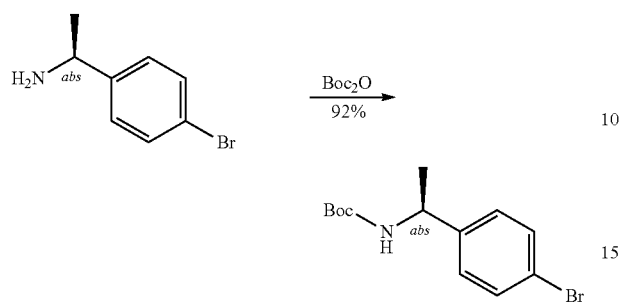

To a solution of (1S)-1-(4-bromophenyl)ethanamine (25.0 g, 125 mmol) and BOC anhydride (32.7 g, 150 mmol) in DCM (250 mL) at 0° C., TEA (34.8 mL, 250 mmol) was added. The reaction mixture was stirred at 0° C. for 15 min and then 18 h at rt. The mixture was diluted with water (250 mL) and the layers were separated. The aqueous layer was extracted with EtOAc (2×100 mL). The combined organic layers were washed with brine (100 mL) then dried (Na$_2$SO$_4$), filtered, and concentrated under reduced pressure. The resulting solid was triturated with hexanes (400 mL), filtered and washed with hexanes (500 mL) to afford the title compound as a solid (34.5 g, 92%). MS (ESI) [M−tBu]$^+$ 244.0, 246.0.

Step 2: Tert-butyl N-[(1S)-1-[4-(4-methylthiazol-5-yl)phenyl]ethyl]carbamate

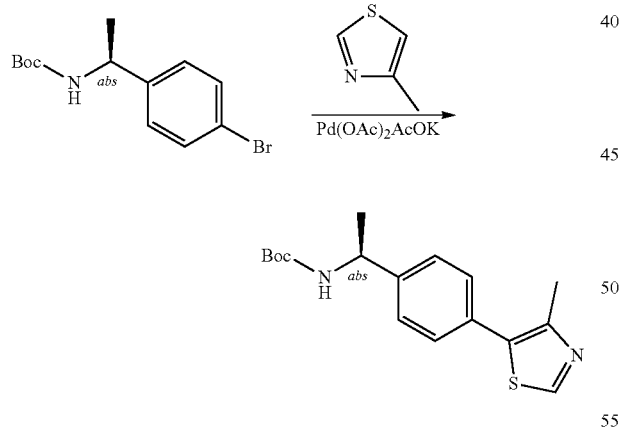

A mixture of tert-butyl N-[(1S)-1-(4-bromophenyl)ethyl]carbamate (15.0 g, 50.0 mmol), potassium acetate (9.81 g, 100 mmol) and Pd(OAc)$_2$ (112 mg, 0.50 mmol) in DMA (100 mL) at rt, was added 4-methylthiazole (9.10 mL, 100 mmol). The mixture was purged with nitrogen and put under vacuum (3× cycle) and then stirred at 120° C. for 2 h. The mixture was cooled to rt and diluted with water (250 mL). The resulting solid was filtered and washed with water (500 mL). The solid was dried in a vacuum oven at 65° C. for 18 h to afford the title compound 15.6 g, 98%). MS (ESI) [M+H]$^+$ 319.2.

Step 3: (1S)-1-[4-(4-methylthiazol-5-yl)phenyl]ethanamine hydrochloride [Intermediate 1]

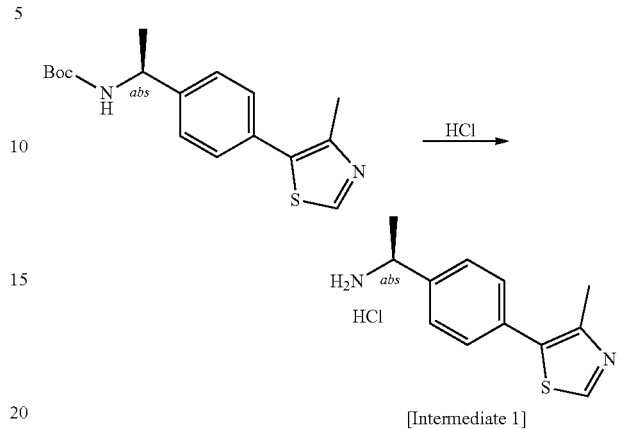

[Intermediate 1]

To a solution of tert-butyl N-[(1S)-1-[4-(4-methylthiazol-5-yl)phenyl]ethyl]carbamate (17.4 g, 54.6 mmol) in DCM (200 mL) at 0° C., was added HCl (4M in dioxane, 200 mL, 800 mmol) and the mixture was warmed to rt and stirred for 3 h. The mixture was diluted with ether (50 mL) and the resulting solid was filtered. The solid was washed with ether (500 mL) and dried to afford the title compound as a solid (15.0 g, quant). $^1$H NMR (400 MHz, DMSO) δ 9.11 (s, 1H), 8.69 (br s, 3H), 7.67-7.62 (m, 2H), 7.58-7.53 (m, 2H), 4.44 (dt, J=11.9, 5.9 Hz, 1H), 2.47 (s, 3H), 1.55 (d, J=6.8 Hz, 3H). MS (ESI) [M+H]$^+$ 202.2.

Example 66: Synthesis of (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride [Intermediate 2]

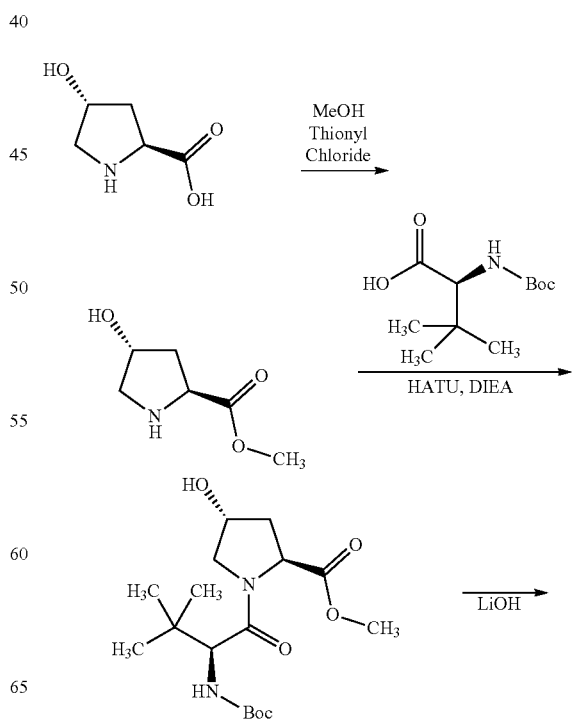

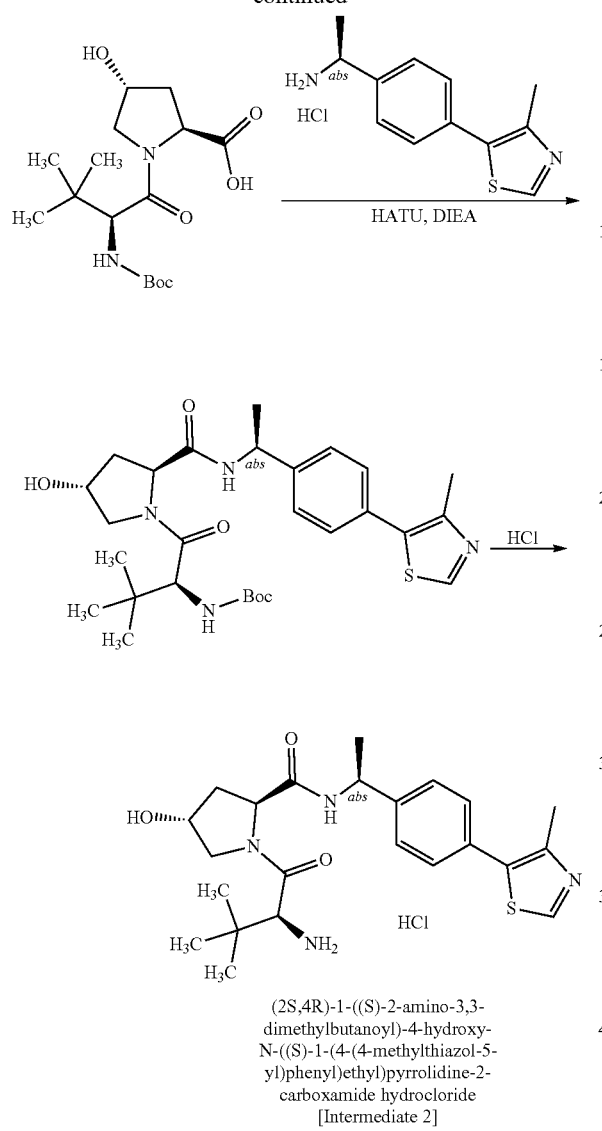

Step 1: methyl (2S,4R)-4-hydroxypyrrolidine-2-carboxylate

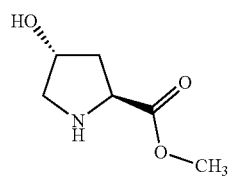

To a solution of (2S,4R)-4-hydroxypyrrolidine-2-carboxylic acid (10.0 g, 76.3 mmol) in MeOH (300 mL) at 0° C., was added SOCl$_2$ (10.0 mL, 137 mmol) under nitrogen. The mixture was warmed to rt and stirred for 18 h. The volatiles were evaporated under reduced pressure to afford the title compound, which was used in the next step without further purification.

Step 2: methyl (2S,4R)-1-((S)-2-((tert-butoxycarbonyl)amino)-3,3-dimethylbutanoyl)-4-hydroxypyrrolidine-2-carboxylate

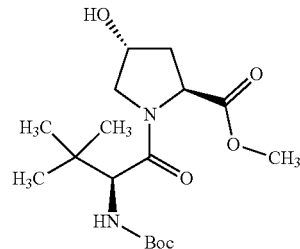 [SMILES: COC(=O)[C@@H]1C[C@@H](O)CN1C(=O)[C@@H](NC(=O)OC(C)(C)C)C(C)(C)C]

To a solution of methyl (2S,4R)-4-hydroxypyrrolidine-2-carboxylate in DCM (250 mL) at rt, were sequentially added (2R)-2-[(tert-butoxycarbonylamino)methyl]-3,3-dimethyl-butanoic acid (18.7 g, 80.9 mmol) and HATU (43.5 g, 114 mmol). The mixture was cooled to 0° C. and then DIEA (65 mL, 380 mmol) was slowly added over 15 min. The reaction mixture was warmed to rt and stirred for 20 h. The mixture was diluted with 5% citric acid (400 mL) and DCM (200 mL) and the layers were separated. The aqueous layer was extracted with DCM (300 mL). The combined organic layers were washed with 1M NaOH (2×200 mL) and brine (200 mL), then dried (Na$_2$SO$_4$), filtered and concentrated under reduce pressure to afford the title compound, which was used in the next step without further purification. MS (ESI) [M-BOC]$^+$259.3.

Step 3: (2S,4R)-1-((S)-2-((tert-butoxycarbonyl)amino)-3,3-dimethylbutanoyl)-4-hydroxypyrrolidine-2-carboxylic acid

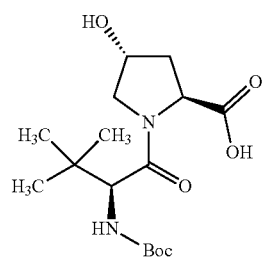 [SMILES: CC(C)(C)OC(=O)N[C@H](C(=O)N1C[C@H](O)C[C@H]1C(=O)O)C(C)(C)C]

To a solution of methyl (2S,4R)-1-[(2S)-2-(tert-butoxycarbonylamino)-3,3-dimethyl-butanoyl]-4-hydroxy-pyrrolidine-2-carboxylate (27.4 g, 76.4 mmol) in MeOH (372 mL) and THF (372 mL) at rt, was added lithium hydroxide monohydrate (7.40 g, 176 mmol) and the mixture was stirred at rt for 48 h. The volatiles were evaporated under reduced pressure. The residue was diluted with 1M NaOH (300 mL) and washed with ether (250 mL). The aqueous layer was acidified to pH 4 and extracted with EtOAc (2×300 mL). The pH was then adjusted to 1 and the mixture was extracted with EtOAc (3×300 mL). The combined organic layers were washed with brine (300 mL), then dried (Na$_2$SO$_4$), filtered and reduced under reduced pressure to afford title compound as a foam (31 g), which was used in the next step without further purification. MS (ESI) [M–tBu]$^+$289.1.

Step 4: Tert-butyl N-[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]carbamate

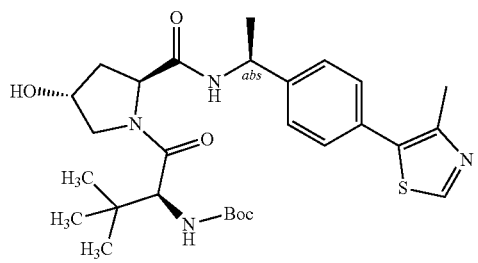 [SMILES: Cc1ncsc1-c1ccc([C@H](C)NC(=O)[C@@H]2C[C@@H](O)CN2C(=O)[C@@H](NC(=O)OC(C)(C)C)C(C)(C)C)cc1]

To a mixture of (2S,4R)-1-[(2S)-2-(tert-butoxycarbonylamino)-3,3-dimethyl-butanoyl]-4-hydroxy-pyrrolidine-2-carboxylic acid (27.3 g, 79.2 mmol), (1S)-1-[4-(4-methylthiazol-5-yl)phenyl]ethanamine hydrochloride (20.2 g, 79.2 mmol) and HATU (45.2 g, 119 mmol) in DCM (775 mL) at 0° C., was slowly added DIEA (68.0 mL, 396 mmol) and the mixture was stirred for 20 h. The mixture was then diluted with 5% citric acid (500 mL) and the layers were separated. The organic layer was washed with 1M NaOH (2×300 mL) and brine (300 mL) then dried (Na$_2$SO$_4$), filtered and concentrated under reduced pressure. The resulting solid was dissolved into minimal amount of MeOH and then water was added until precipitation is observed. The resulting solid were filtered, washed with ether (400 mL) and then dried in a vacuum oven at 60° C. to afford the title compound as a solid (34 g, 79%). MS (ESI) [M+H]$^+$ 545.3.

Step 5: (2S,4R)-1-[(2S)-2-amino-3,3-dimethyl-butanoyl]-4-hydroxy-N-[(1S)-1-[4-(4-methylthiazol-5-yl)phenyl]ethyl]pyrrolidine-2-carboxamide hydrochloride

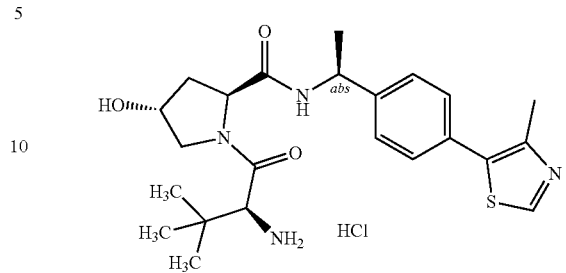

To a solution of tert-butyl N-[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]carbamate (34.0 g, 62.0 mmol) in DCM (200 mL) at 0° C., was added an HCl solution (4M in dioxane, 200 mL, 800 mmol) and the mixture was warmed to rt and stirred for 15 min. The mixture was diluted with MeOH (150 mL) and the mixture was stirred for 30 min. The volatiles were evaporated under reduced pressure and coevaporated with PhMe (2×100 mL) to afford the title compound as a solid (30.6 g, 92%, contains 9% PhMe by weight). $^1$H NMR (500 MHz, DMSO) δ 9.04 (s, 1H), 8.59 (d, J=7.8 Hz, 1H), 8.09 (d, J=4.3 Hz, 3H), 7.47-7.43 (m, 2H), 7.42-7.37 (m, 2H), 4.93 (p, J=7.0 Hz, 1H), 4.55 (t, J=8.4 Hz, 1H), 4.33 (br s, 1H), 3.91 (q, J=5.7 Hz, 1H), 3.73 (d, J=10.6 Hz, 1H), 3.50 (dd, J=10.9, 3.9 Hz, 1H), 2.70 (s, 1H), 2.47 (s, 3H), 2.12 (dd, J=12.9, 7.7 Hz, 1H), 1.81-1.72 (m, 1H), 1.39 (d, J=7.0 Hz, 3H), 1.03 (s, 9H). MS (ESI) [M+H]$^+$ 445.2.

Example 67: Synthesis of 3-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)propanoic acid

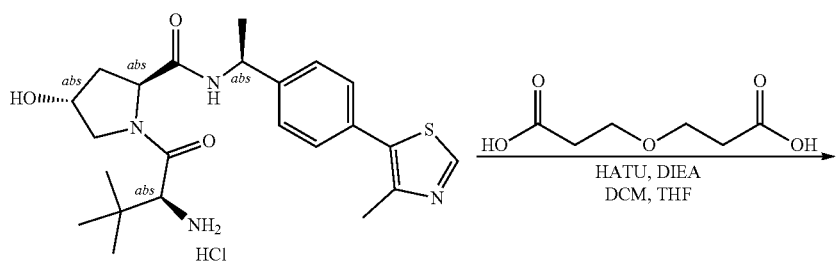

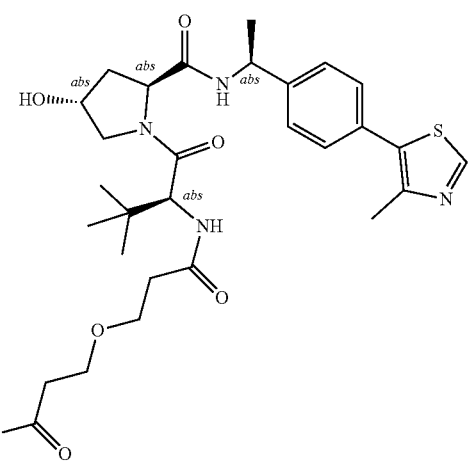

To a solution of 3-(2-carboxyethoxy)propanoic acid (1.5 g, 9.4 mmol) and HATU (2.6 g, 6.9 mmol) in DCM (30 mL) was slowly added DIEA (5.3 mL, 31 mmol) and the solution was stirred for 5 min at rt. To the mixture was added Intermediate 2 (3.0 g, 6.2 mmol) and the reaction mixture was stirred for 30 min. The mixture was diluted with 1M NaOH (5.0 mL) and stirred for 5 min. The mixture was then acidified to pH 5 using 5% citric acid. The layers were separated, and the aqueous layer was extracted with EtOAc (7×50 mL) and DCM (3×50 mL). The combined organic layers were dried (Na$_2$SO$_4$), filtered and concentrated under reduced pressure. The material was purified by reverse phase chromatography on C18 using a 10-30% gradient of MeCN and water (contains 0.1% ammonium formate/formic acid) to afford 3-(3-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)propanoic acid as a solid (1.28 g, 35%). $^1$H NMR (500 MHz, DMSO) δ 8.99 (s, 1H), 8.39 (d, J=7.8 Hz, 1H), 7.87 (d, J=9.3 Hz, 1H), 7.47-7.41 (m, 2H), 7.39 (s, 2H), 4.92 (p, J=7.0 Hz, 1H), 4.53 (d, J=9.4 Hz, 1H), 4.44 (t, J=8.0 Hz, 1H), 4.28 (s, 1H), 3.65-3.49 (m, 6H), 2.46 (s, 3H), 2.37 (t, J=6.7 Hz, 2H), 2.39-2.31 (m, 1H), 2.05-1.99 (m, 1H), 1.80 (ddd, J=12.9, 8.4, 4.7 Hz, 1H), 1.37 (t, J=8.2 Hz, 3H), 0.94 (s, 9H). MS (ESI) [M+H]$^+$ 589.3.

Example 68: Synthesis of 3-[2-[2-[2-[2-[3-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-3-oxo-propoxy]ethoxy]ethoxy]ethoxy]ethoxy]propanoic acid

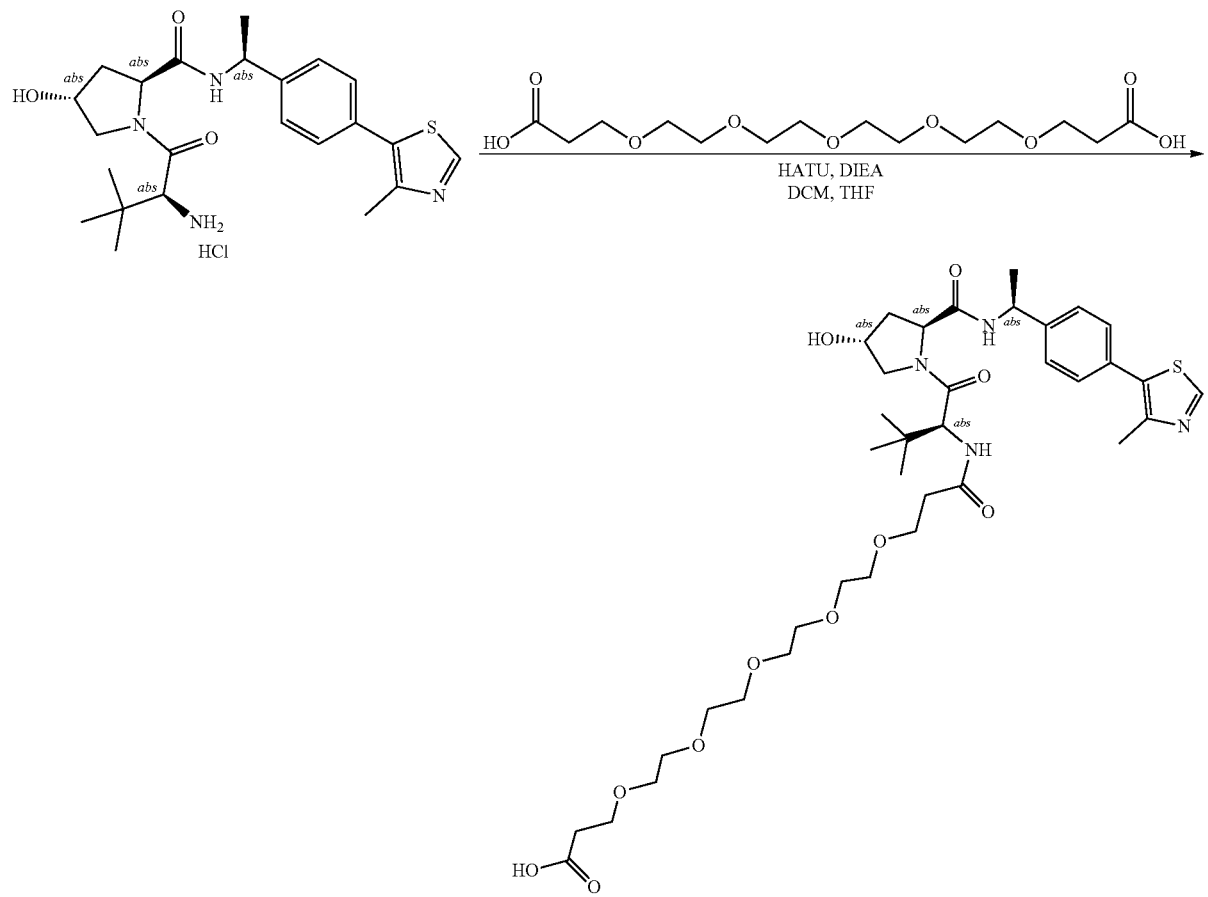

To a solution of 3-[2-[2-[2-[2-(2-carboxyethoxy)ethoxy]ethoxy]ethoxy]ethoxy]propanoic acid (2.0 g, 5.9 mmol) and HATU (1.65 g, 4.34 mmol) in DCM (20 mL) was slowly added DIEA (3.38 mL, 19.7 mmol) and the solution was stirred for 5 min at rt. To the mixture was added Intermediate 2 (1.9 g, 4.0 mmol) and the reaction mixture was stirred for 30 min. The mixture was diluted with 1M NaOH (10 mL) and stirred for 5 min. The mixture was then acidified to pH 5 using 5% citric acid and the layers were separated. The aqueous layer was extracted with EtOAc (7×50 mL) and DCM (3×50 mL). The combined organic layers were dried (Na$_2$SO$_4$), filtered and concentrated under reduced pressure. The material was purified by reverse phase chromatography on C18 using a 10-30% gradient of ACN and water (contains 0.1% ammonium formate/formic acid) to afford (S)-21-((2S, 4R)-4-hydroxy-2-(((S)-1-(4-(4-methylthiazol-5-yl)phenyl)ethyl)carbamoyl)pyrrolidine-1-carbonyl)-22,22-dimethyl-19-oxo-4,7,10,13,16-pentaoxa-20-azatricosanoic acid as a solid (1.38 g, 46%). $^1$H NMR (500 MHz, DMSO) δ 8.99 (s, 1H), 8.43 (s, 1H), 8.39 (d, J=7.4 Hz, 1H), 7.87 (d, J=9.1 Hz, 1H), 7.46-7.42 (m, 2H), 7.41-7.36 (m, 2H), 4.98-4.84 (m, 1H), 4.53 (d, J=9.7 Hz, 1H), 4.43 (t, J=7.7 Hz, 1H), 4.30-4.26 (m, 1H), 3.60 (dd, J=11.9, 5.5 Hz, 6H), 3.54-3.41 (m, 16H), 2.57-2.53 (m, 1H), 2.46 (s, 3H), 2.42 (t, J=6.9 Hz, 2H), 2.36-2.31 (m, 1H), 2.05-1.98 (m, 1H), 1.83-1.76 (m, 1H), 1.38 (d, J=7.1 Hz, 3H), 0.94 (s, 9H). MS (ESI) [M+H]$^+$ 765.4.

Example 69: Synthesis of 7-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-7-oxo-heptanoic acid

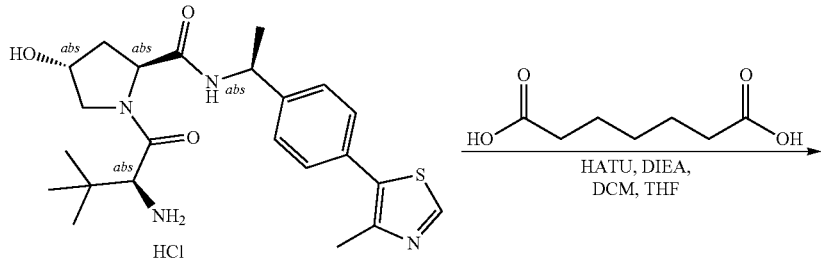

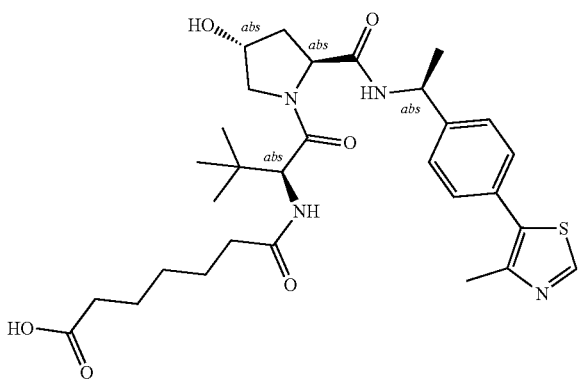

To a solution of Intermediate 2 (1.75 g, 3.64 mmol), heptanedioic acid (874 mg, 5.46 mmol) and HATU (1.94 g, 5.09 mmol) in DCM (70.0 mL) at 0° C., was added DIEA (3.11 mL, 18.2 mmol) and the reaction mixture was stirred for 2 h. The mixture was diluted with 1M NaOH (50 mL) and stirred for 1 h. The layers were separated, and the organic layer was extracted with 1M NaOH (2×30 mL). The combined aqueous layers were acidified to pH 5-6 and extracted with EtOAc (5×50 mL). The combined organic layers were dried (Na$_2$SO$_4$), filtered and concentrated under reduced pressure. The material was further purified by reverse phase chromatography on C18 using a 10-60% gradient of MeCN and water (contains 0.1% ammonium formate/formic acid) to afford 7-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-7-oxoheptanoic acid as a solid (0.924 g, 43%). $^1$H NMR (500 MHz, DMSO) δ 8.99 (s, 1H), 8.37 (d, J=7.8 Hz, 1H), 7.79 (d, J=9.3 Hz, 1H), 7.46-7.41 (m, 2H), 7.40-7.36 (m, 2H), 4.92 (p, J=7.0 Hz, 1H), 4.52 (d, J=9.4 Hz, 1H), 4.43 (t, J=8.1 Hz, 1H), 4.30-4.26 (m, 1H), 3.65-3.57 (m, 2H), 3.46-3.33 (m, 1H), 2.46 (s, 3H), 2.28-2.20 (m, 1H), 2.18 (t, J=7.4 Hz, 2H), 2.15-2.06 (m, 1H), 2.04-1.97 (m, 1H), 1.80 (ddd, J=12.9, 8.5, 4.7 Hz, 1H), 1.54-1.42 (m, 4H), 1.38 (d, J=7.0 Hz, 3H), 1.28-1.20 (m, 2H), 0.94 (s, 9H). MS (ESI) [M+H]$^+$ 587.3.

Example 70: 9-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-9-oxo-nonanoic acid

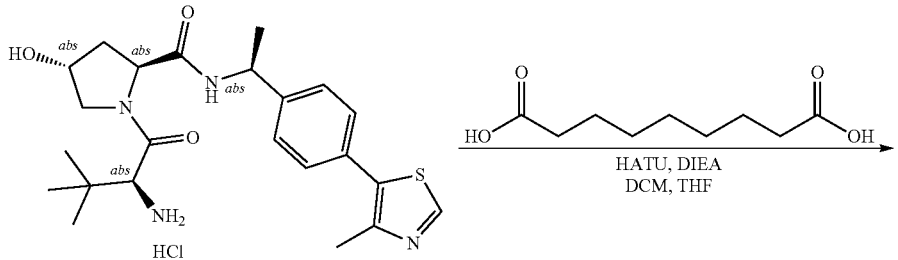

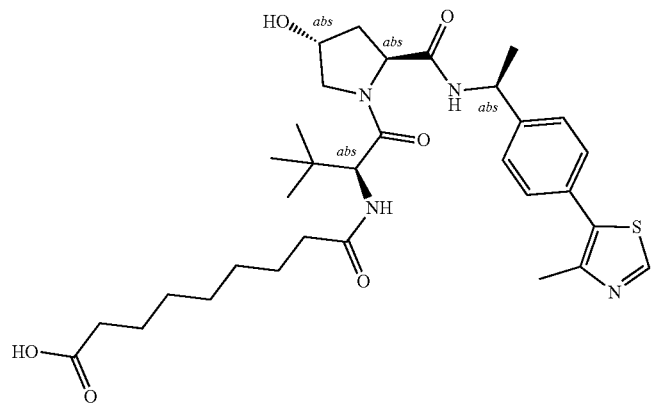

To a solution of Intermediate 2 (2.0 g, 4.2 mmol), nonanedioic acid (1.2 g, 6.2 mmol) and HATU (2.1 g, 5.4 mmol) in DCM (20 mL) and THF (20 mL) at 0° C., was added DIEA (3.56 mL, 20.8 mmol) and the reaction mixture was stirred for 2 h. The mixture was diluted with 1M NaOH (50 mL) and stirred for 1 h. The mixture was acidified to pH 5 and the aqueous layer was extracted with EtOAc (5×50 mL). The combined organic layers were dried (Na$_2$SO$_4$), filtered and concentrated under reduced pressure. The material was purified by reverse phase chromatography on C18 using a 10-40% gradient of MeCN and water (contains 0.1% ammonium formate/formic acid) to afford 9-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-9-oxononanoic acid as a solid (1.00 g, 39%). $^1$H NMR (500 MHz, DMSO) δ 8.99 (s, 1H), 8.37 (d, J=7.8 Hz, 1H), 7.78 (d, J=9.3 Hz, 1H), 7.47-7.42 (m, 2H), 7.40-7.36 (m, 2H), 5.10 (br s, 1H), 4.97-4.88 (m, 1H), 4.52 (d, J=9.3 Hz, 1H), 4.43 (t, J=8.0 Hz, 1H), 4.33-4.24 (m, 1H), 3.66-3.54 (m, 2H), 2.46 (s, 3H), 2.28-2.22 (m, 1H), 2.19 (t, J=7.4 Hz, 2H), 2.14-2.07 (m, 1H), 2.04-1.98 (m, 1H), 1.83-1.76 (m, 1H), 1.54-1.41 (m, 4H), 1.38 (d, J=7.0 Hz, 3H), 1.31-1.19 (m, 6H), 0.94 (s, 9H). MS (ESI) [M+H]$^+$ 615.7.

Example 71: 11-[[(1S)-1-[(2S,4R)-4-hydroxy-2-[[(1S)-1-[4-(4-methylthiazol-5-yl)phenyl]ethyl]carbamoyl]pyrrolidine-1-carbonyl]-2,2-dimethyl-propyl]amino]-11-oxo-undecanoic acid

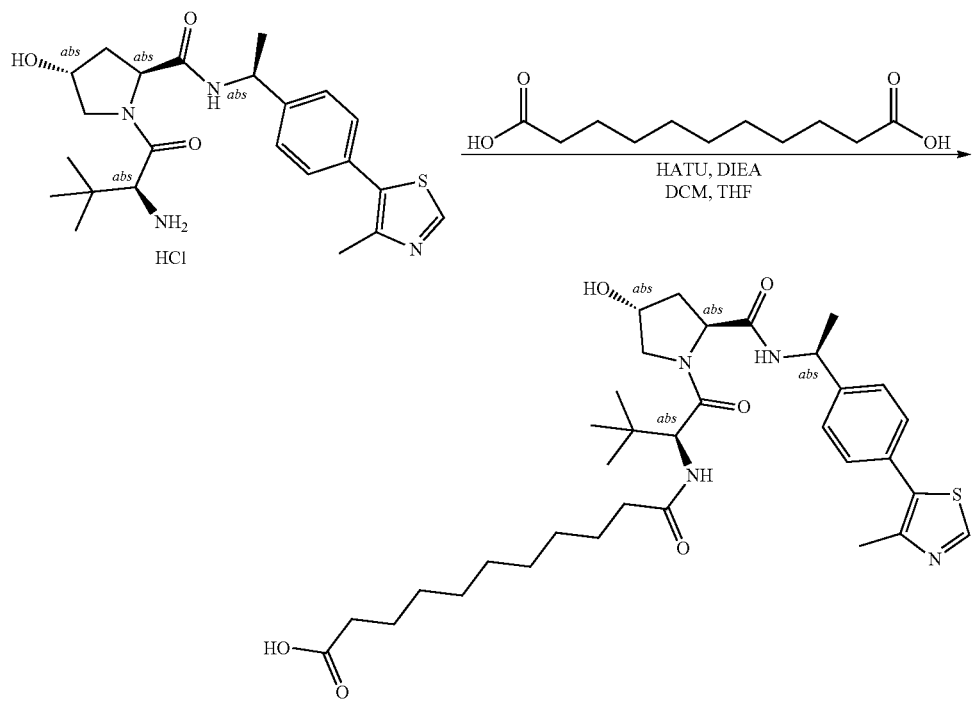

To a solution of Intermediate 2 (2.0 g, 4.2 mmol), undecanedioic acid (1.4 g, 6.2 mmol) and HATU (2.4 g, 6.2 mmol) in DCM (20 mL) and THF (20 mL) at 0° C., was added DIEA (3.56 mL, 20.8 mmol) and the reaction mixture was stirred for 2 h. The mixture was diluted with 1M NaOH (50 mL) and stirred for 1 h. The mixture was acidified to pH 5 and the aqueous layer was extracted with EtOAc (5×50 mL). The combined organic layers were dried (Na$_2$SO$_4$), filtered and concentrated under reduced pressure. The material was purified by reverse phase chromatography on C18 using a 10-40% gradient of MeCN and water (contains 0.1% ammonium formate/formic acid) to afford 11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoic acid as a solid (832 mg, 31%). $^1$H NMR (500 MHz, DMSO) δ 8.99 (s, 1H), 8.37 (d, J=7.8 Hz, 1H), 7.77 (d, J=9.4 Hz, 1H), 7.46-7.42 (m, 2H), 7.41-7.36 (m, 2H), 5.09 (br s, 1H), 4.95-4.88 (m, 1H), 4.52 (d, J=9.4 Hz, 1H), 4.43 (t, J=8.0 Hz, 1H), 4.31-4.25 (m, 1H), 3.67-3.54 (m, 2H), 2.46 (s, 3H), 2.30-2.21 (m, 1H), 2.19 (t, J=7.4 Hz, 2H), 2.14-2.06 (m, 1H), 2.04-1.98 (m, 1H), 1.80 (ddd, J=12.9, 8.4, 4.6 Hz, 1H), 1.54-1.42 (m, 4H), 1.38 (d, J=7.0 Hz, 3H), 1.30-1.18 (m, 10H), 0.94 (s, 9H). MS (ESI) [M+H]$^+$ 643.4.

Example 72: Preparation of 3-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)propanoic acid

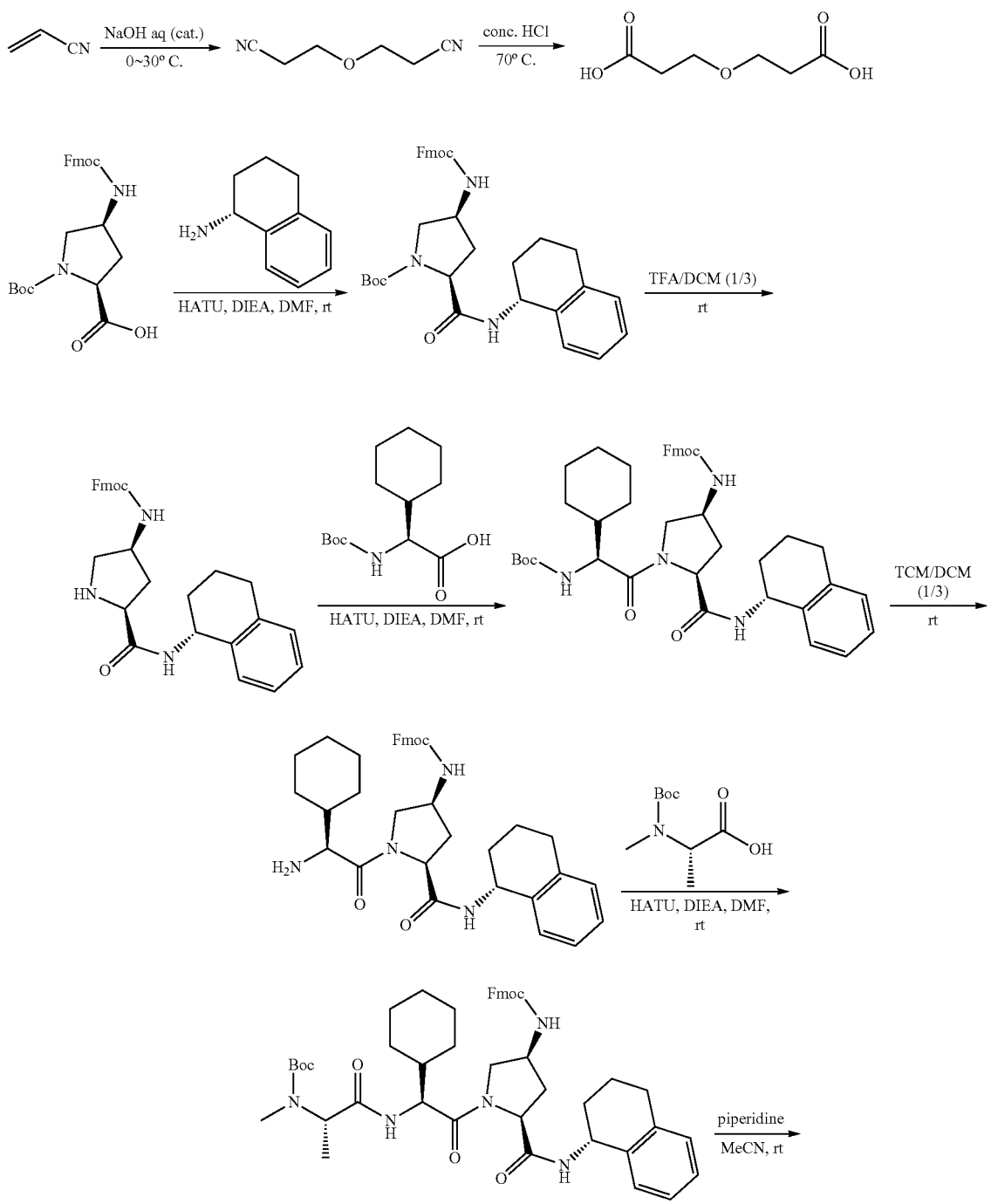

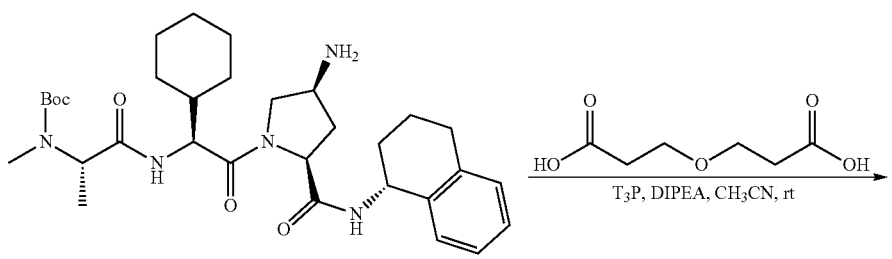

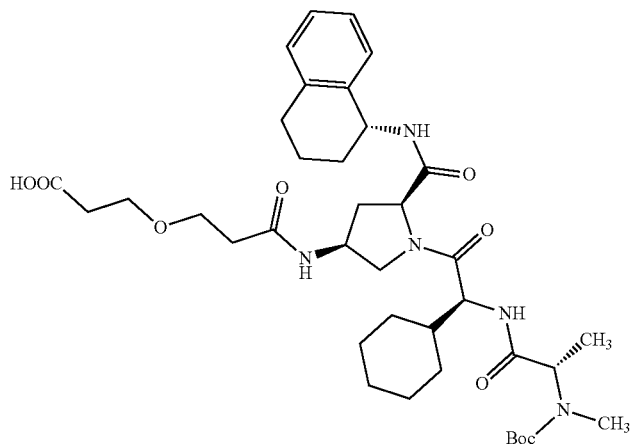 [SMILES: C[C@@H](C(=O)N[C@H](C(=O)N1C[C@@H](NC(=O)CCOCCC(=O)O)C[C@H]1C(=O)N[C@@H]1CCCc2ccccc21)C1CCCCC1)N(C)C(=O)OC(C)(C)C]

Step 1: 3,3'-oxydipropanenitrile

To a stirred solution of NaOH aqueous (3 mL, 40% wt) was added acrylonitrile (17.5 g, 330 mmol) dropwise at 0° C. The solution was stirred at 30° C. for 16 h. When the reaction was completed, the reaction was diluted with 100 mL H$_2$O and neutralized to pH 7 by HCl (2 N). The aqueous solution was extracted with ethyl acetate (100 mL×3). The combined organic solution was dried over anhydrous Na$_2$SO$_4$ and concentrated to give 3,3'-oxydipropanenitrile (4.1 g, crude) as yellow oil, which was used for the next step without further purification. $^1$H NMR (300 MHz, Chloroform-d) δ 3.74 (t, J=6.3 Hz, 4H), 2.65 (t, J=6.3 Hz, 4H).

Step 2: 3,3'-oxydipropionic acid

A mixture of 3,3'-oxydipropanenitrile (4.1 g, 33 mmol) and concentrated HCl (38 mL) was stirred at 70° C. for 16 h. After cooled to room temperature, the solids were filtered and the filtrate was concentrated under vacuum. The crude residue was purified by flash column chromatography with 30~100% ethyl acetate in petroleum ether to afford 3,3'-oxydipropionic acid (3.2 g, 12% over 2 steps) as yellow oil. $^1$H NMR (400 MHz, DMSO-d$_6$) δ 12.20 (s, 2H), 3.62-3.55 (m, 4H), 2.42-2.40 (m, 4H).

Step 3: (2S,4S)-tert-butyl 4-(((9H-fluoren-9-yl)methoxy)carbonylamino)-2-((R)-1,2,3,4-tetrahydronaphthalen-1-ylcarbamoyl)pyrrolidine-1-carboxylate To a solution of (2S,4S)-4-(((9H-fluoren-9-yl)methoxy)carbonylamino)-1-(tert-butoxycarbonyl)pyrrolidine-2-carboxylic acid (10 g, 22.2 mmol), (R)-1,2,3,4-tetrahydronaphthalen-1-amine (3.26 g, 22.2 mmol) and DIEA (14.28 g, 111 mmol) in DMF (100 mL) was added HATU (9.26 g, 24.4 mmol). The solution was stirred at room temperature for 3 h. The reaction was quenched by the addition of 200 mL H$_2$O and then extracted with ethyl acetate (200 mL×3). The combined organic layer was washed with brine, dried over anhydrous Na$_2$SO$_4$ and concentrated under vacuum. The crude residue was purified by flash column chromatography with 10~50% ethyl acetate in petroleum ether to afford (2S,4S)-tert-butyl 4-(((9H-fluoren-9-yl)methoxy)carbonylamino)-2-((R)-1,2,3,4-tetrahydronaphthalen-1-ylcarbamoyl)pyrrolidine-1-carboxylate (12.0 g, 93%) as a white solid. MS (ESI) calculated for (C$_{35}$H$_{39}$N$_3$O$_5$) [M+H]$^+$, 582.3; found, 582.0.

Step 4: (9H-fluoren-9-yl)methyl ((3S,5S)-5-(((R)-1,2,3,4-tetrahydronaphthalen-1-yl)carbamoyl)pyrrolidin-3-yl)carbamate TFA salt To a stirred solution of (2S,4S)-tert-butyl 4-(((9H-fluoren-9-yl)methoxy)carbonylamino)-2-((R)-1,2,3,4-tetrahydronaphthalen-1-ylcarbamoyl)pyrrolidine-1-carboxylate (12 g, 26.54 mmol) in DCM (120 mL) was added TFA (40 mL) at room temperature. The resulting mixture was stirred at room temperature overnight. The solvent was removed under vacuum to afford (9H-fluoren-9-yl)methyl ((3S,5S)-5-(((R)-1,2,3,4-tetrahydronaphthalen-1-yl)carbamoyl)pyrrolidin-3-yl)carbamate TFA salt (13 g, crude) as yellow oil, which was used for the next step without further purification. MS (ESI) calculated for ($C_{30}H_{31}N_3O_3$) [M+H]$^+$, 482.2; found, 482.0.

Step 5: 9H-fluoren-9-ylmethyl N-[(3S,5S)-1-[(2S)-2-[[(tert-butoxy)carbonyl]amino]-2-cyclohexylacetyl]-5-[[(1R)-1,2,3,4-tetrahydronaphthalen-1-yl]carbamoyl]pyrrolidin-3-yl]carbamate To a stirred solution of (9H-fluoren-9-yl)methyl (3S,5S)-5-((R)-1,2,3,4-tetrahydronaphthalen-1-ylcarbamoyl)pyrrolidin-3-ylcarbamate TFA salt (13 g, 27.0 mmol), DIEA (17.44 g, 135 mmol) and (S)-2-(tert-butoxycarbonylamino)-2-cyclohexylacetic acid (6.95 g, 27.0 mmol) in DMF (150 mL) was added HATU (12.33 g, 32.4 mmol). The resulting mixture was stirred at room temperature for 4 h. The reaction was quenched by the addition of 200 mL H$_2$O and extracted with ethyl acetate (200 mL×3). The combined organic layer was washed with brine, dried over anhydrous Na$_2$SO$_4$ and concentrated under vacuum. The crude residue was purified by flash column chromatography with 10~40% ethyl acetate in petroleum ether to afford 9H-fluoren-9-ylmethyl N-[(3S,5S)-1-[(2S)-2-[[(tert-butoxy)carbonyl]amino]-2-cyclohexylacetyl]-5-[[(1R)-1,2,3,4-tetrahydronaphthalen-1-yl]carbamoyl]pyrrolidin-3-yl]carbamate (5.2 g, 27%) as colorless oil. MS (ESI) calculated for ($C_{43}H_{52}N_4O_6$) [M+H]$^+$, 721.4; found, 721.0.

Step 6: (9H-fluoren-9-yl)methyl (3S,5S)-1-((S)-2-amino-2-cyclohexylacetyl)-5-((R)-1,2,3,4-tetrahydronaphthalen-1-ylcarbamoyl)pyrrolidin-3-ylcarbamate TFA Salt To a stirred solution of 9H-fluoren-9-ylmethyl N-[(3S,5S)-1-[(2S)-2-[[(tert-butoxy)carbonyl]amino]-2-cyclohexylacetyl]-5-[[(1R)-1,2,3,4-tetrahydronaphthalen-1-yl]carbamoyl]pyrrolidin-3-yl]carbamate (5.2 g, 7.22 mmol) in DCM (90 mL) was added TFA (30 mL). The solution was stirred at room temperature overnight. The solvents were removed under vacuum to afford (9H-fluoren-9-yl)methyl (3S,5S)-1-((S)-2-amino-2-cyclohexylacetyl)-5-((R)-1,2,3,4-tetrahydronaphthalen-1-ylcarbamoyl)pyrrolidin-3-ylcarbamate TFA salt (4.48 g, crude) as yellow oil. MS (ESI) calculated for ($C_{38}H_{44}N_4O_4$) [M+H]$^+$, 621.3; found, 621.0.

Step 7: 9H-fluoren-9-ylmethyl N-[(3S,5S)-1-[(2S)-2-[(2S)-2-[[(tert-butoxy)carbonyl](methyl)amino]propanamido]-2-cyclohexylacetyl]-5-[[(1R)-1,2,3,4-tetrahydronaphthalen-1-yl]carbamoyl]pyrrolidin-3-yl]carbamate To a stirred solution of (9H-fluoren-9-yl)methyl (3S,5S)-1-((S)-2-amino-2-cyclohexylacetyl)-5-((R)-1,2,3,4-tetrahydronaphthalen-1-ylcarbamoyl)pyrrolidin-3-ylcarbamate (4.48 g, 7.22 mmol), DIEA (4.66 g, 36.1 mmol) and (S)-2-(tert-butoxycarbonyl(methyl)amino)propanoic acid (1.46 g, 7.22 mmol) in DMF (50 mL) was added HATU (3.3 g, 8.68 mmol). The resulting mixture was stirred at room temperature for 3 h. The reaction was quenched by the addition of 100 mL H$_2$O and extracted with ethyl acetate (100 mL×3). The combined organic layer was washed with brine, dried over anhydrous Na$_2$SO$_4$ and concentrated under vacuum. The crude residue was purified by flash column chromatography with 20-60% ethyl acetate in petroleum ether to afford 9H-fluoren-9-ylmethyl N-[(3S,5S)-1-[(2S)-2-[(2S)-2-[[(tert-butoxy)carbonyl](methyl)amino]propanamido]-2-cyclohexylacetyl]-5-[[(1R)-1,2,3,4-tetrahydronaphthalen-1-yl]carbamoyl]pyrrolidin-3-yl]carbamate (5.2 g, 89%) as colorless oil. MS (ESI) calculated for ($C_{47}H_{59}N_5O_7$) [M+H]$^+$, 806.4; found, 806.0.

Step 8: tert-butyl (S)-1-((S)-2-((2S,4S)-4-amino-2-((R)-1,2,3,4-tetrahydronaphthalen-1-ylcarbamoyl)pyrrolidin-1-yl)-1-cyclohexyl-2-oxoethylamino)-1-oxopropan-2-yl(methyl)carbamate To a stirred solution of 9H-fluoren-9-ylmethyl N-[(3S,5S)-1-[(2S)-2-[(2S)-2-[[(tert-butoxy)carbonyl](methyl)amino]propanamido]-2-cyclohexylacetyl]-5-[[(1R)-1,2,3,4-tetrahydronaphthalen-1-yl]carbamoyl]pyrrolidin-3-yl]carbamate (5.2 g, 6.46 mmol) in acetonitrile (80 mL) was added piperidine (5.2 mL). The mixture was stirred at room temperature for 1 h. The solids were filtered out by filtration and the filtrate was concentrated under vacuum. The crude residue was purified by reverse phase flash column chromatography with 5~95% acetonitrile in water to afford tert-butyl (S)-1-((S)-2-((2S,4S)-4-amino-2-((R)-1,2,3,4-tetrahydronaphthalen-1-ylcarbamoyl)pyrrolidin-1-yl)-1-cyclohexyl-2-oxoethylamino)-1-oxopropan-2-yl(methyl)carbamate (3.1656 g, 84%) as a white solid. $^1$H NMR (300 MHz, DMSO-d6) δ 8.45-8.12 (m, 1H), 7.71 (m, 1H), 7.39-6.99 (m, 4H), 4.94-4.91 (m, 1H), 4.61-4.45 (m, 1H), 4.34-4.19 (m, 2H), 3.90-3.88 (m, 1H), 3.29-3.16 (m, 1H), 2.75-2.72 (m, 5H), 2.50-2.27 (m, 1H), 2.01-1.82 (m, 4H), 1.81-1.50 (m, 9H), 1.41 (s, 9H), 1.29-0.85 (m, 9H). MS (ESI) calculated for ($C_{32}H_{49}N_5O_5$) [M+H]$^+$, 584.4; found, 584.4.

Step 9: 3-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)propanoic acid To a stirred solution of tert-butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (1.5 g, 2.57 mmol), 3,3'-oxydipropionic acid (2.78 g, 12.86 mmol) and DIEA (1.65 g, 12.86 mmol) in acetonitrile (30 mL) was added T$_3$P (12.3 g, 10.28 mmol, 50% in ethyl acetate) under nitrogen. The solution was stirred at 20° C. for 16 h. When the reaction was completed, the reaction was quenched by the addition of 50 mL H$_2$O and the aqueous solution was extracted with ethyl acetate (50 mL×3). The combined organic layer was washed with brine, dried over anhydrous Na$_2$SO$_4$ and concentrated under vacuum. The crude residue was purified by reverse phase flash column chromatography with 5~50% acetonitrile in water to afford 3-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)propanoic acid (1.0929 g, 58%) as a white solid. $^1$H NMR (400 MHz, Methanol-d$_4$) δ 7.48-7.36 (m, 1H), 7.23-7.03 (m, 3H), 5.07-5.06 (m, 1H), 4.63-4.30 (m, 4H), 4.21-4.18 (m, 1H), 3.72-3.67 (m, 4H), 3.55-3.51 (m, 1H), 2.91 (s, 3H), 2.91-2.73 (m, 2H), 2.67-2.41 (m, 5H), 2.04-1.61 (m, 11H), 1.49 (s, 9H), 1.38-1.00 (m, 8H). MS (ESI) calculated for ($C_{38}H_{57}N_5O_9$) [M+H]$^+$, 728.4; found, 728.7.

Example 73: 3-(2-(2-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)ethoxy)ethoxy)propanoic acid

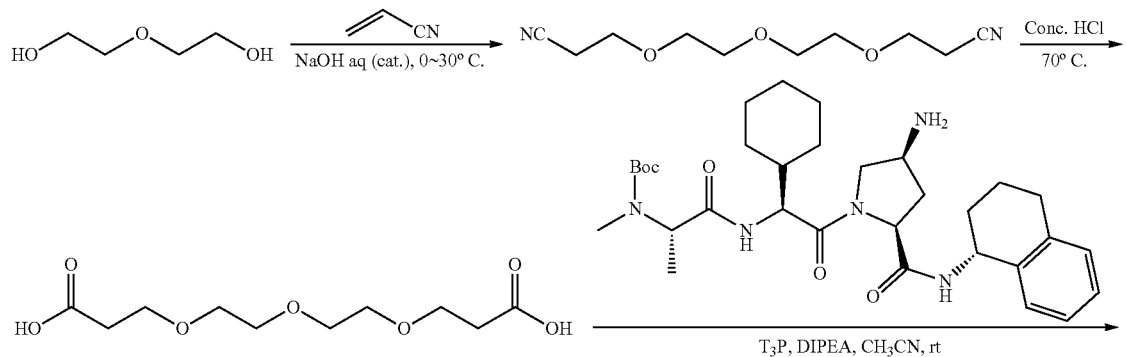

Step 1: 3,3'-((oxybis(ethane-2,1-diyl))bis(oxy))dipropanenitrile

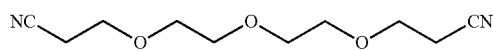 [SMILES: N#CCCOCCOCCOCCC#N]

To a stirred solution of 2,2'-oxybis(ethan-1-ol) (15 g, 141 mmol) and NaOH aqueous (1.7 mL, 40% wt) was added acrylonitrile (17.25 g, 325 mmol) dropwise at 0° C. The solution was stirred at 30° C. for 16 h. When the reaction was completed, the reaction was diluted with 100 mL H$_2$O and neutralized to pH 7 by HCl (2 N). The aqueous solution was extracted with ethyl acetate. The combined organic layer was dried over anhydrous Na$_2$SO$_4$ and concentrated under vacuum to afford 3,3'-((oxybis(ethane-2,1-diyl))bis(oxy))dipropanenitrile (26 g, crude) as yellow oil, which was used for the next step without further purification. $^1$H NMR (300 MHz, Chloroform-d) δ 3.72 (t, J=6.3 Hz, 4H), 3.67 (s, 8H), 2.62 (t, J=6.3 Hz, 4H).

Step 2: 3,3'-((oxybis(ethane-2,1-diyl))bis(oxy))dipropionic acid

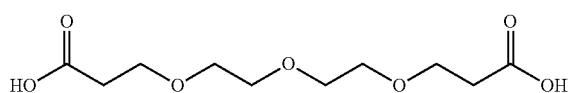 [SMILES: O=C(O)CCOCCOCCOCCC(=O)O]

A mixture of 3,3'-((oxybis(ethane-2,1-diyl))bis(oxy))dipropanenitrile (26 g, 123 mmol) and concentrated HCl (140 mL) was stirred at 70° C. overnight. After cooled to room temperature, the solids were filtered out by filtration and the filtrate was concentrated under vacuum. The crude residue was purified by flash column chromatography with 30~100% ethyl acetate in petroleum ether to afford 3,3'-((oxybis(ethane-2,1-diyl))bis(oxy))dipropionic acid (20.9 g, 70% over 2 steps) as yellow oil. $^1$H NMR (400 MHz, DMSO-d6) δ 12.16 (s, 2H), 3.61-3.57 (m, 4H), 3.51-3.47 (m, 8H), 2.44 (t, J=6.3 Hz, 4H).

Step 3: 3-(2-(2-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)ethoxy)ethoxy)propanoic acid

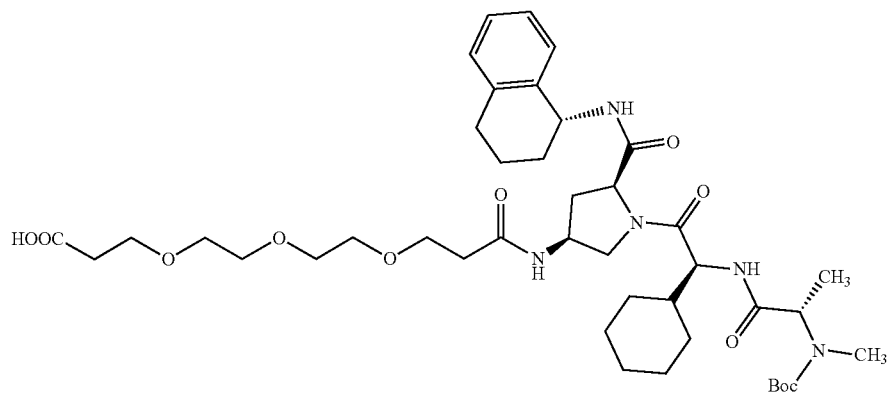 [SMILES: C[C@@H](C(=O)N[C@H](C(=O)N1C[C@@H](NC(=O)CCOCCOCCOCCC(=O)O)C[C@H]1C(=O)N[C@@H]1CCCc2ccccc21)C1CCCCC1)N(C)C(=O)OC(C)(C)C]

To a stirred solution of tert-butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (1.0 g, 1.71 mmol), 3,3'-((oxybis(ethane-2,1-diyl))bis(oxy))dipropionic acid (1.15 g, 3.43 mmol) and DIEA (1.1 g, 8.57 mmol) in acetonitrile (20 mL), was added $T_3P$ (8.66 g, 6.86 mmol, 50% in EtOAc) under nitrogen. The resulting mixture was stirred at room temperature for 16 h. When the reaction was completed, the reaction was quenched by the addition of 50 mL $H_2O$. The aqueous solution was extracted with ethyl acetate. The combined organic layer was washed with brine, dried over anhydrous $Na_2SO_4$ and concentrated under vacuum. The residue was purified by pre-HPLC with the following conditions: [(Column: X Bridge Prep OBD C18 Column 30×150 mm 5 um; Mobile Phase A: Water (10 mmol/L $NH_4HCO_3$), Mobile Phase B: ACN; Flow rate: 60 mL/min; Gradient: 28% B to 44% B in 7 min; 254/220 nm] to afford 3-(2-(2-(3-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-3-oxopropoxy)ethoxy)ethoxy)propanoic acid (215.4 mg, 15%) as a white solid. $^1$H NMR (300 MHz, DMSO-$d_6$) δ 8.39 (d, J=8.7 Hz, 1H), 8.22 (d, J=7.5 Hz, 1H), 7.80-7.70 (m, 1H), 7.32 (d, J=7.2 Hz, 1H), 7.22-6.98 (m, 3H), 4.94-4.92 (m, 1H), 4.51-4.49 (m, 1H), 4.28-4.26 (m, 3H), 4.09 (t, J=8.7 Hz, 1H), 3.60-3.58 (m, 4H), 3.49 (s, 8H), 2.75-2.73 (m, 5H), 2.35-2.31 (m, 5H), 1.99-1.50 (m, 11H), 1.40 (s, 9H), 1.30-0.82 (m, 9H). MS (ESI) calculated for ($C_{42}H_{65}N_5O_{11}$) [M+H]$^+$, 816.5; found, 816.5.

Example 74: (S)-2-((S)-2-((tert-butoxycarbonyl)(methyl)amino) propanamido)-2-cyclohexylacetic acid

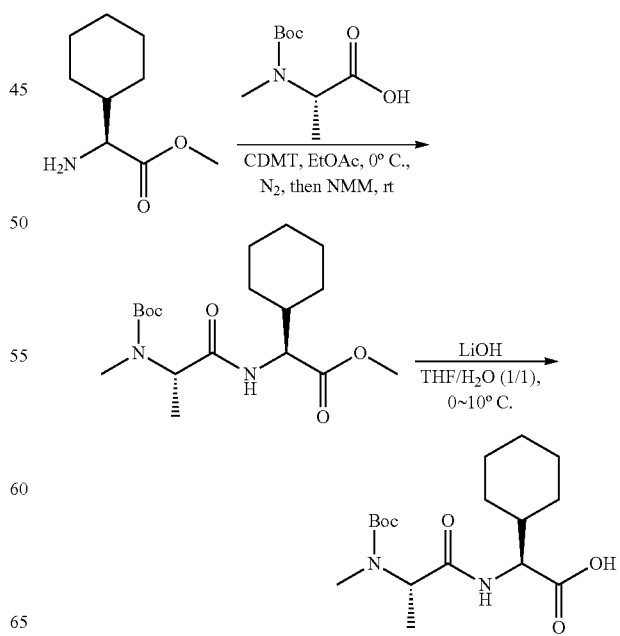

Step 1: methyl (S)-2-((S)-2-((tert-butoxycarbonyl)(methyl)amino)propanamido)-2-cyclohexylacetate

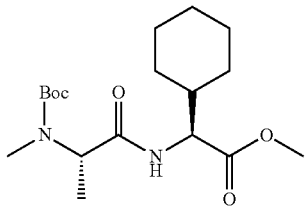

A solution of (S)-methyl-2-amino cyclohexyl acetate hydrochloride (70.0 g, 0.34 mol) and (S)-2-(tert-butoxycarbonyl(methyl)amino)propanoic acid (69.0 g, 0.34 mol) in ethyl acetate (300 mL) was treated with 2-chloro-4,6-dimethoxy-1,3,5-triazine (CDMT) (64.7 g, 0.37 mol) under nitrogen. The reaction mixture was cooled to 0° C. and treated with N-methylmorpholine (85.8 g, 0.85 mol). The reaction mixture was warmed to room temperature and stirred for 4 h. The solid precipitate was filtered out and rinsed with ethyl acetate. The filtrate was washed with saturated NaHCO$_3$ aqueous solution and then 10% citric acid and brine, dried over anhydrous sodium sulfate and concentrated under vacuum to afford methyl (S)-2-((S)-2-((tert-butoxycarbonyl)(methyl)amino)propanamido)-2-cyclohexylacetate (85.0 g, 71%) as an off-white solid. MS (ESI) calculated for (C$_{18}$H$_{32}$N$_2$O$_5$) [M+H]$^+$, 357.2; found, 357.0.

Step 2: (S)-2-((S)-2-((tert-butoxycarbonyl)(methyl)amino)propanamido)-2-cyclohexylacetic acid

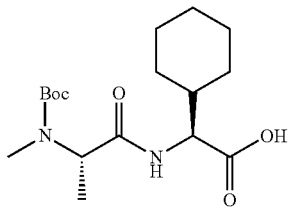 [SMILES: C[C@@H](C(=O)N[C@H](C(=O)O)C1CCCCC1)N(C)C(=O)OC(C)(C)C]

To a solution of methyl (S)-2-((S)-2-((tert-butoxycarbonyl)(methyl)amino) propanamido)-2-cyclohexylacetate (85.0 g, 0.24 mol) in THE (1.2 L) was added a solution of LiOH—H$_2$O (25.2 g, 0.60 mol) in water (1.2 L) maintained the temperature at 0~10° C. under nitrogen. The resulting mixture was stirred at 0~10° C. for 3 h. The organic solvent was removed under vacuum and the pH value of aqueous phase was adjusted to ~3 by citric acid. The mixture was extracted with ethyl acetate twice. The combined organic layer was washed with brine, dried over anhydrous sodium sulfate and concentrated under vacuum to afford (S)-2-((S)-2-((tert-butoxycarbonyl)(methyl)amino)propanamido)-2-cyclohexylacetic acid (100 g, crude) as colorless oil, which was used for the next step without further purification. MS (ESI) calculated for (C$_{17}$H$_{30}$N$_2$O$_5$) [M−H]$^−$, 341.2; found, 341.0.

Example 75: tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate

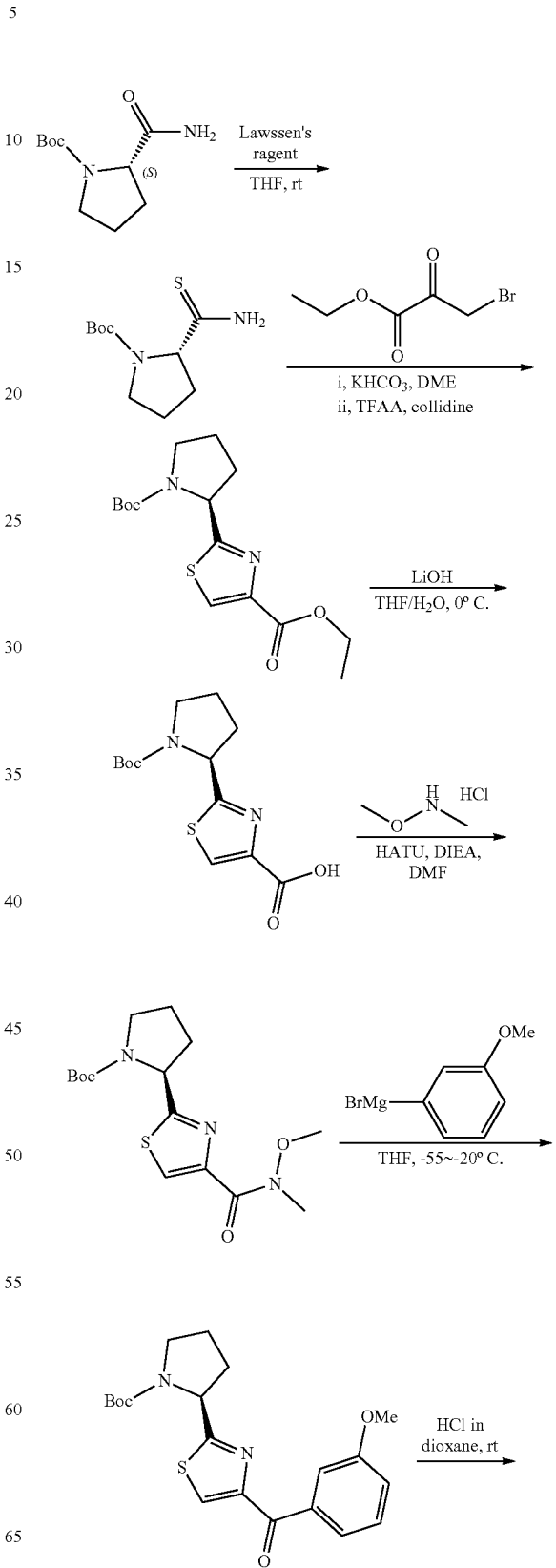

-continued

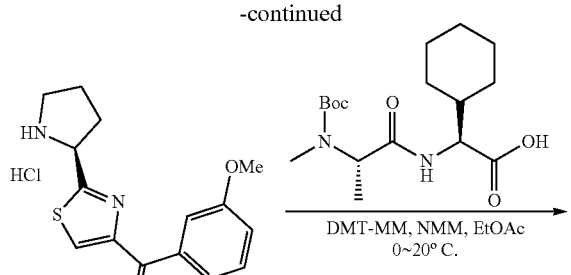

DMT-MM, NMM, EtOAc
0~20° C.

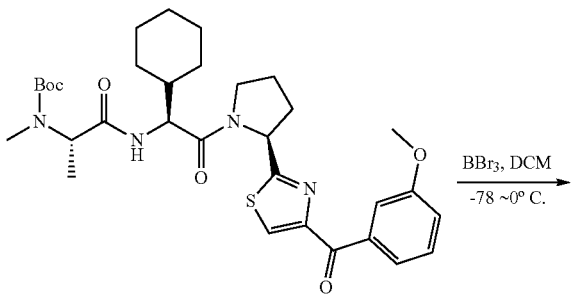

BBr₃, DCM
−78 ~0° C.

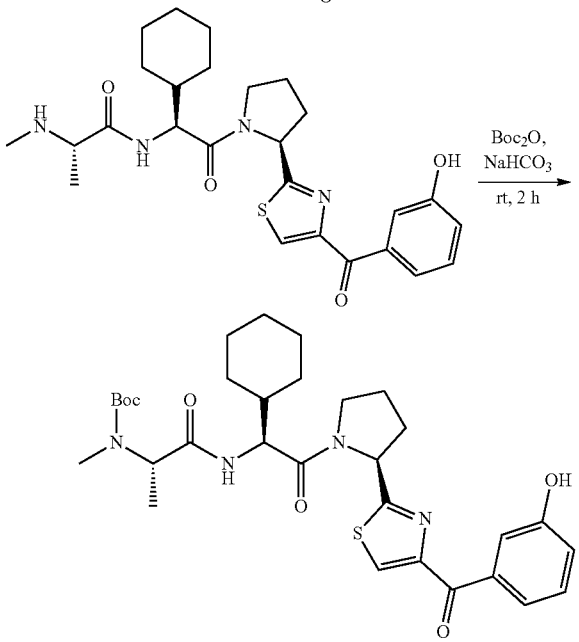

Boc₂O, NaHCO₃
rt, 2 h

Step 1: tert-butyl (S)-2-carbamothioylpyrrolidine-1-carboxylate

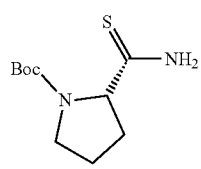

To a solution of tert-butyl (2S)-2-carbamoylpyrrolidine-1-carboxylate (100 g, 466.72 mmol) in tetrahydrofuran (1.2 L) was added lawesson's reagent (113 g, 279.70 mmol). The resulting mixture was stirred at room temperature for 16 h. The mixture was then diluted with saturated NaHCO₃ aqueous solution and extracted with ethyl acetate. The combined organic layer was washed with brine, dried over anhydrous sodium sulfate and concentrated under vacuum to afford tert-butyl (S)-2-carbamothioylpyrrolidine-1-carboxylate (110 g, crude) as a white solid, which was used for the next step without further purification. MS (ESI) calculated for $(C_{10}H_{18}N_2O_2S)$ $[M+H]^+$, 231.1; found, 231.0.

Step 2: ethyl (S)-2-(1-(tert-butoxycarbonyl)pyrrolidin-2-yl)thiazole-4-carboxylate

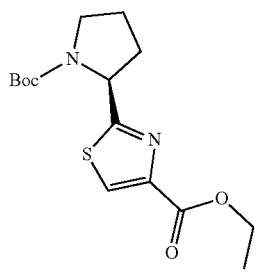 [SMILES: CCOC(=O)c1csc([C@@H]2CCCN2C(=O)OC(C)(C)C)n1]

To a mixture of tert-butyl (S)-2-carbamothioylpyrrolidine-1-carboxylate (100.0 g, 0.44 mol) and potassium bicarbonate (348.0 g, 3.48 mol) in dimethoxyethane (1.5 L) was added ethyl 3-bromo-2-oxopropanoate (253.1 g, 1.30 mol) dropwise at room temperature. The resulting mixture was stirred at room temperature for 1 h and then cooled to 0° C. And then trifluoroacetic acid (365.4 g, 1.74 mol) and collidine (298.2 g, 2.78 mol) were added dropwise to the above solution at 0° C. The resulting mixture was stirred at room temperature for 8 h. The reaction was quenched by the addition of water and the aqueous phase was extracted with dichloromethane. The combined organic layer was washed with HCl (0.5 N) and brine, dried over anhydrous sodium sulfate and concentrated under vacuum. The crude residue was purified by flash column chromatography with 10-30% ethyl acetate in petroleum ether to afford ethyl (S)-2-(1-(tert-butoxycarbonyl)pyrrolidin-2-yl)thiazole-4-carboxylate (51.5 g, 34% over two steps) as a brown solid. MS (ESI) calculated for $(C_{15}H_{22}N_2O_4S)$ $[M+H]^+$, 327.1; found, 327.0.

Step 3: (S)-2-(1-(tert-butoxycarbonyl)pyrrolidin-2-yl)thiazole-4-carboxylic acid

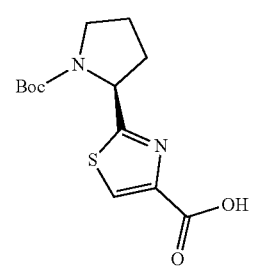 [SMILES: CC(C)(C)OC(=O)N1CCC[C@H]1c1nc(C(=O)O)cs1]

To a mixture of ethyl (S)-2-(1-(tert-butoxycarbonyl)pyrrolidin-2-yl)thiazole-4-carboxylate (51.5 g, 0.16 mol) in THF (300 mL) and water (200 mL) was added a solution of lithium hydroxide hydrate (26.5 g, 0.63 mol) in water (100 mL) dropwise at 0° C. The resulting mixture was stirred at 0° C. for 5 h. The organic layer was removed under vacuum.

The residue was diluted with 200 mL of water and the pH value was adjusted to 3 by HCl (6 N). The solution was extracted with ethyl acetate. The combined organic layer was washed with brine, dried over anhydrous sodium sulfate and concentrated under vacuum to afford (S)-2-(1-(tert-butoxycarbonyl)pyrrolidin-2-yl)thiazole-4-carboxylic acid (45.0 g, 95%) as a light brown solid. MS (ESI) calculated for $(C_{13}H_{18}N_2O_4S)$ [M−H]$^−$, 297.1; found, 297.0.

Step 4: tert-butyl (S)-2-(4-(methoxy(methyl)carbamoyl)thiazol-2-yl)pyrrolidine-1-carboxylate

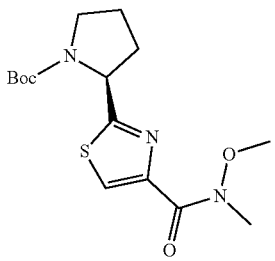 [SMILES: CON(C)C(=O)c1csc([C@@H]2CCCN2C(=O)OC(C)(C)C)n1]

A mixture of (S)-2-(1-(tert-butoxycarbonyl)pyrrolidin-2-yl)thiazole-4-carboxylic acid (90.0 g, 0.30 mol), methoxy(methyl)amine hydrogen chloride (43.6 g, 0.45 mol), HATU (114.0 g, 0.30 mol) and DIEA (96.7 g, 0.75 mol) in DMF (500 mL) was stirred at room temperature for 16 h. The mixture was diluted with water and the aqueous phase was extracted with ethyl acetate. The combined organic layer was washed with brine, dried over anhydrous sodium sulfate and concentrated under vacuum. The crude residue was purified by flash column chromatography with 40-80% ethyl acetate in petroleum ether to afford tert-butyl (S)-2-(4-(methoxy(methyl)carbamoyl)thiazol-2-yl)pyrrolidine-1-carboxylate (60.0 g, 59%) as a light yellow oil. MS (ESI) calculated for $(C_{15}H_{23}N_3O_4S)$ [M+H]$^+$, 342.1; found, 342.0.

Step 5: tert-butyl (S)-2-(4-(3-methoxybenzoyl)thiazol-2-yl)pyrrolidine-1-carboxylate

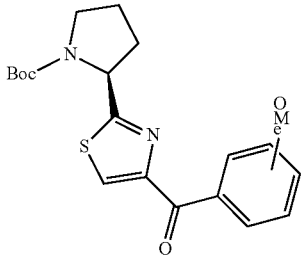

To a solution of tert-butyl (S)-2-(4-(methoxy(methyl)carbamoyl)thiazol-2-yl)pyrrolidine-1-carboxylate (30.0 g, 88.0 mmol) in anhydrous THF (300 mL) was added (3-methoxyphenyl)magnesium bromide (1M in THF, 530 mL, 0.53 mol) dropwise at −55° C. under nitrogen. The resulting mixture was stirred for 4 h below −20° C. The reaction was then quenched by the addition of saturated NH$_4$Cl aqueous solution at 0° C. cautiously. The mixture was extracted with ethyl acetate. The combined organic layer was washed with brine, dried over anhydrous sodium sulfate and concentrated under vacuum. The crude residue was purified by flash column chromatography with 10~50% ethyl acetate in petroleum ether to afford tert-butyl (S)-2-(4-(3-methoxybenzoyl)thiazol-2-yl)pyrrolidine-1-carboxylate (24 g, 70%) as light yellow oil. MS (ESI) calculated for $(C_{20}H_{24}N_2O_4S)$ [M+H]$^+$, 389.1; found, 389.0.

Step 6: (S)-(3-methoxyphenyl)(2-(pyrrolidin-2-yl)thiazol-4-yl)methanone HCl Salt

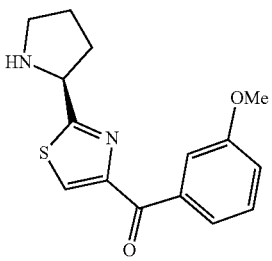 [SMILES: COc1cccc(C(=O)c2csc([C@@H]3CCCN3)n2)c1]

A mixture of tert-butyl (S)-2-(4-(3-methoxybenzoyl)thiazol-2-yl)pyrrolidine-1-carboxylate (24 g, 61.8 mmol) in HCl (4 M in dioxane, 200 mL) was stirred at room temperature for 2 h. The solvent was removed under vacuum to afford (S)-(3-methoxyphenyl)(2-(pyrrolidin-2-yl)thiazol-4-yl)methanone HCl salt (26 g, crude) as yellow oil, which was used for the next step without further purification. MS (ESI) calculated for $(C_{20}H_{16}N_2O_2S)$ [M+H]$^+$, 289.1; found, 289.0.

Step 7: tert-butyl ((S)-1-(((S)-1-cyclohexyl-2-((S)-2-(4-(3-methoxybenzoyl)thiazol-2-yl)pyrrolidin-1-yl)-2-oxoethyl)amino)-1-oxopropan-2-yl)(methyl)carbamate

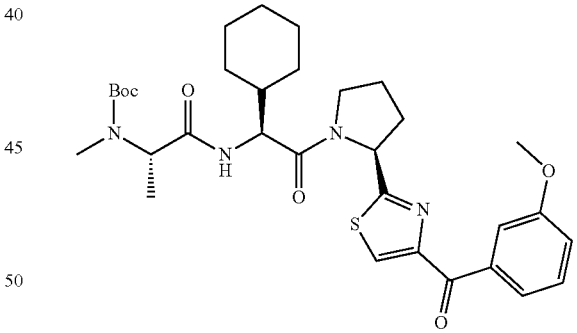

To a solution of 4-[(3-methoxyphenyl)carbonyl]-2-[(2S)-pyrrolidin-2-yl]-1,3-thiazole (25 g, 86.70 mmol) and (2S)-2-[(2S)-2-[[(tert-butoxy)carbonyl](methyl)amino]propanamido]-2-cyclohexylacetic acid (29.7 g, 86.73 mmol) in ethyl acetate (400 mL) were added 4-(4,6-dmethoxy-1,3,5-triazine-2-yl)-4-methyl morpholinium chloride (DMT-MM) (26.35 g, 95.47 mmol) and 4-methylmorpholine (21.9 g, 216.83 mmol) at 0° C. The resulting mixture was stirred at room temperature for 3 h. The reaction was then quenched by the addition of water and the aqueous phase was extracted with ethyl acetate. The combined organic layer was washed with brine, dried over anhydrous sodium sulfate and concentrated under vacuum. The crude residue was purified by flash column chromatography with 0~30% ethyl acetate in petroleum ether to afford tert-butyl ((S)-1-(((S)-1-cyclohexyl-2-((S)-2-(4-(3-methoxybenzoyl)thiazol-2-yl)pyrrolidin-1-yl)-2-oxoethyl)amino)-1-oxopropan-2-yl)(methyl)carbamate (24 g, 46%) as light yellow oil. MS (ESI) calculated for ($C_{32}H_{44}N_4O_6S$) [M+H]$^+$, 613.3; found, 613.0.

Step 8: (S)—N—((S)-1-cyclohexyl-2-((S)-2-(4-(3-hydroxybenzoyl)thiazol-2-yl)pyrrolidin-1-yl)-2-oxoethyl)-2-(methylamino)propanamide

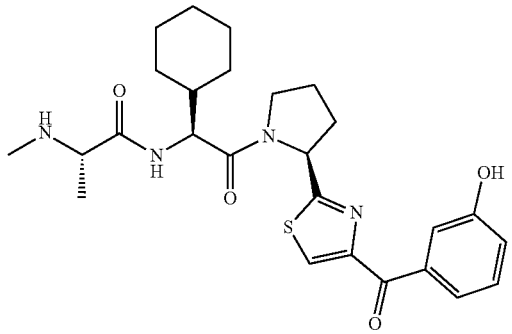 [SMILES: CN[C@@H](C)C(=O)N[C@H](C(=O)N1CCC[C@H]1c1nc(C(=O)c2cccc(O)c2)cs1)C1CCCCC1]

To a solution of tert-butyl ((S)-1-(((S)-1-cyclohexyl-2-((S)-2-(4-(3-methoxybenzoyl)thiazol-2-yl)pyrrolidin-1-yl)-2-oxoethyl)amino)-1-oxopropan-2-yl)(methyl)carbamate (9.0 g, 14.69 mmol) in dichloromethane (120 mL) was added BBr$_3$ (10.9 g, 44.1 mmol) dropwise at −78° C. The resulting mixture was stirred below 0° C. for 4 h under nitrogen. The reaction was then quenched by the addition of water cautiously and the aqueous phase was extracted with dichloromethane. The combined organic layer was washed with brine, dried over anhydrous sodium sulfate and concentrated under vacuum to afford (S)—N—((S)-1-cyclohexyl-2-((S)-2-(4-(3-hydroxybenzoyl)thiazol-2-yl)pyrrolidin-1-yl)-2-oxoethyl)-2-(methylamino)propanamide (9 g, crude) as light brown oil, which was used for the next step without further purification. MS (ESI) calculated for ($C_{26}H_{34}N_4O_4S$) [M+H]$^+$, 499.2; found, 499.0.

Step 9: tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate

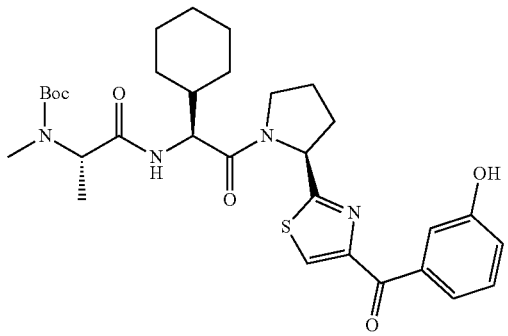 [SMILES: C[C@@H](C(=O)N[C@H](C(=O)N1CCC[C@H]1c1nc(C(=O)c2cccc(O)c2)cs1)C1CCCCC1)N(C)C(=O)OC(C)(C)C]

To a solution of (S)—N—((S)-1-cyclohexyl-2-((S)-2-(4-(3-hydroxybenzoyl)thiazol-2-yl)pyrrolidin-1-yl)-2-oxoethyl)-2-(methylamino)propanamide (10 g, 20.05 mmol) and sodium bicarbonate (3.6 g, 43.21 mmol) in dioxane (120 mL) was added a solution of Boc$_2$O (5.6 g, 25.48 mmol) in dioxane (30 mL) dropwise at 0° C. The mixture was stirred at room temperature for 2 h. The reaction was diluted with water and the aqueous phase was extracted with ethyl acetate. The combined organic layer was washed with brine, dried over anhydrous sodium sulfate and concentrated under vacuum. The crude residue was purified by flash column chromatography with 10~50% ethyl acetate in petroleum ether to afford tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (5.2 g, 59% over 2 steps) as light yellow oil. MS (ESI) calculated for ($C_{31}H_{42}N_4O_6S$) [M+H]$^+$, 599.3; found, 599.3. $^1$H NMR (300 MHz, Chloroform-d) δ 8.60 (br, 1H), 8.09 (d, J=2.0 Hz, 1H), 7.78-7.54 (m, 2H), 7.38-7.34 (m, 1H), 7.11-7.08 (m, 1H), 6.79 (br, 1H), 5.68-5.47 (m, 1H), 4.85-4.64 (m, 2H), 4.00-3.59 (m, 2H), 2.80 (s, 3H), 2.58-2.09 (m, 4H), 1.87-1.58 (m, 6H), 1.50 (s, 9H), 1.36 (d, J=7.1 Hz, 3H), 1.18-0.81 (m, 5H).

Example 76: Synthesis of 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoic acid

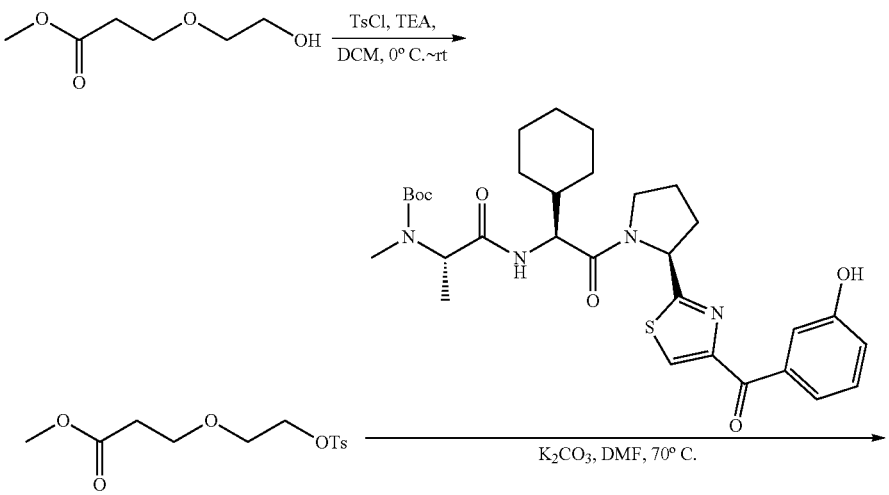

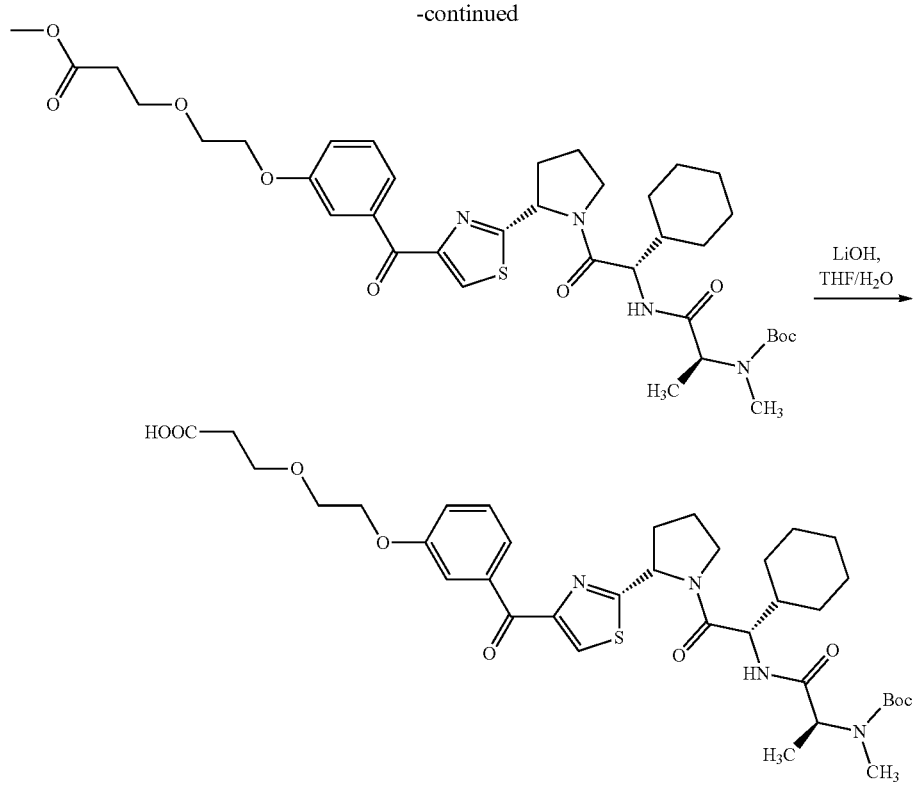

Step 1: methyl 3-[2-[(4-methylbenzenesulfonyl)oxy]ethoxy]propanoate

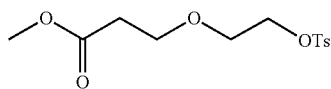 [SMILES: COC(=O)CCOCCOS(=O)(=O)c1ccc(C)cc1]

To a solution of methyl 3-(2-hydroxyethoxy)propanoate (1.00 g, 6.7 mmol) in dichloromethane (15 mL) was added triethylamine (1.72 g, 13.2 mmol) and p-TsCl (1.54 g, 8.1 mmol) at room temperature. The mixture was stirred at room temperature for 16 h. The reaction mixture was quenched by the addition of water and the aqueous phase was extracted with dichloromethane. The combined organic layer was washed with brine, dried over anhydrous sodium sulfate, filtered and concentrated under vacuum. The residue was purified by flash column chromatography with 0~50% ethyl acetate in petroleum ether to afford methyl 3-[2-[(4-methylbenzenesulfonyl)oxy]ethoxy]propanoate (1.05 g, 51%) as yellow oil. MS (ESI) calculated for ($C_{13}H_{18}O_6S$) [M+H]$^+$, 303.1; found, 303.0.

Step 2: methyl 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoate

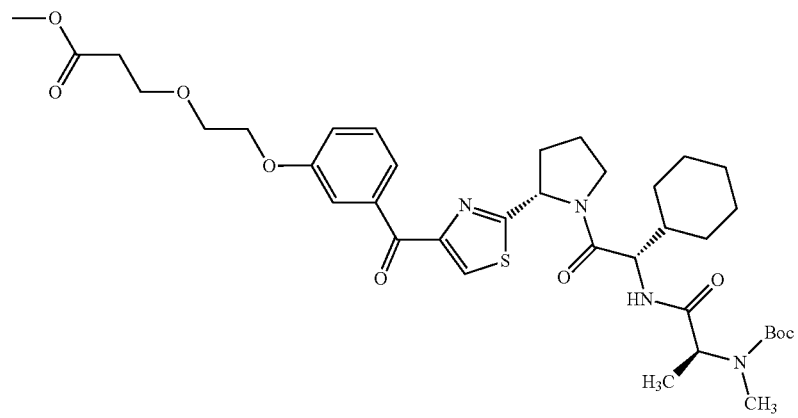

To a solution of methyl 3-[2-[(4-methylbenzenesulfonyl)oxy]ethoxy]propanoate (1.05 g, 3.5 mmol) in N,N-dimethylformamide (10 mL) was added tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.32 g, 2.2 mmol) and potassium carbonate (607 mg, 4.4 mmol). The mixture was stirred at 70° C. for 16 h. After cooled to room temperature, the reaction mixture was diluted with water and the aqueous phase was extracted with ethyl acetate. The combined organic layer was washed with brine, dried over anhydrous sodium sulfate, filtered and concentrated under vacuum. The residue was purified by flash column chromatography with 0~50% ethyl acetate in petroleum ether to afford methyl 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoate (1.0 g, 62%) as light yellow oil. MS (ESI) calculated for $(C_{36}H_{50}N_4O_9S)$ $[M+H]^+$, 715.3; found, 715.0.

Step 3: 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoic acid

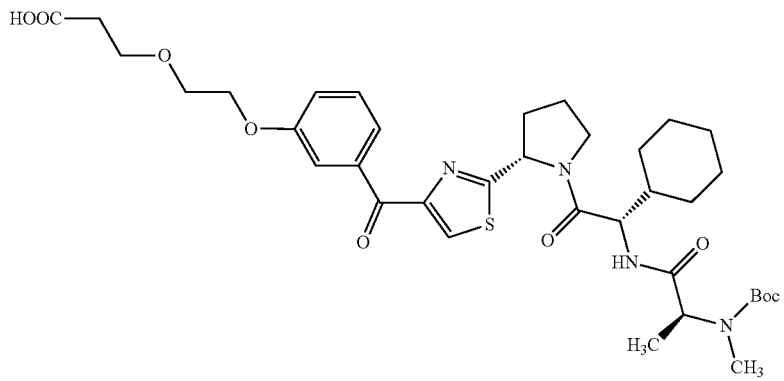

To a solution of 3-(2-(3-(2-((S)-1-((S)-2-((S)-2-((tert-butoxycarbonyl)(methyl)amino) propanamido)-2-cyclohexylacetyl)pyrrolidin-2-yl)thiazole-4-carbonyl)phenoxy) ethoxy) propanoic acid (1.0 g, 1.37 mmol) in tetrahydrofuran (5 mL) and H₂O (5 mL) was added lithium hydroxide hydrate (115 mg, 2.75 mmol). The mixture was stirred at room temperature for 5 h. The reaction mixture was diluted with water and adjusted the pH to ~3 by HCl (2 N). The mixture was extracted with ethyl acetate. The combined organic layer was washed with brine, dried over anhydrous sodium sulfate and concentrated under vacuum. The crude residue was purified by reverse phase flash column chromatography with 5~55% acetonitrile in water to afford 3-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)propanoic acid (733.9 mg, 75%) as a white solid. $^1$H NMR (300 MHz, Methanol-d4) δ 8.33 (s, 1H), 7.77-7.65 (m, 2H), 7.52-7.39 (m, 1H), 7.26-7.24 (m, 1H), 5.70-5.46 (m, 1H), 4.71-4.42 (m, 2H), 4.28-4.16 (m, 2H), 4.05-3.72 (m, 6H), 2.80 (s, 3H), 2.49 (t, J=7.2 Hz, 2H), 2.44-2.03 (m, 4H), 1.89-1.55 (m, 6H), 1.49 (s, 9H), 1.37-1.35 (m, 3H), 1.30-0.95 (m, 5H). MS (ESI) calculated for $(C_{36}H_{50}N_4O_9S)$ $[M+H]^+$, 715.3; found, 715.5.

Preparation of 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy)propanoic acid

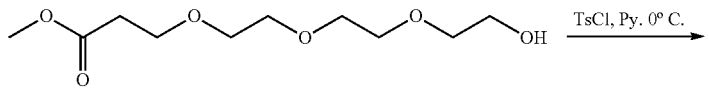

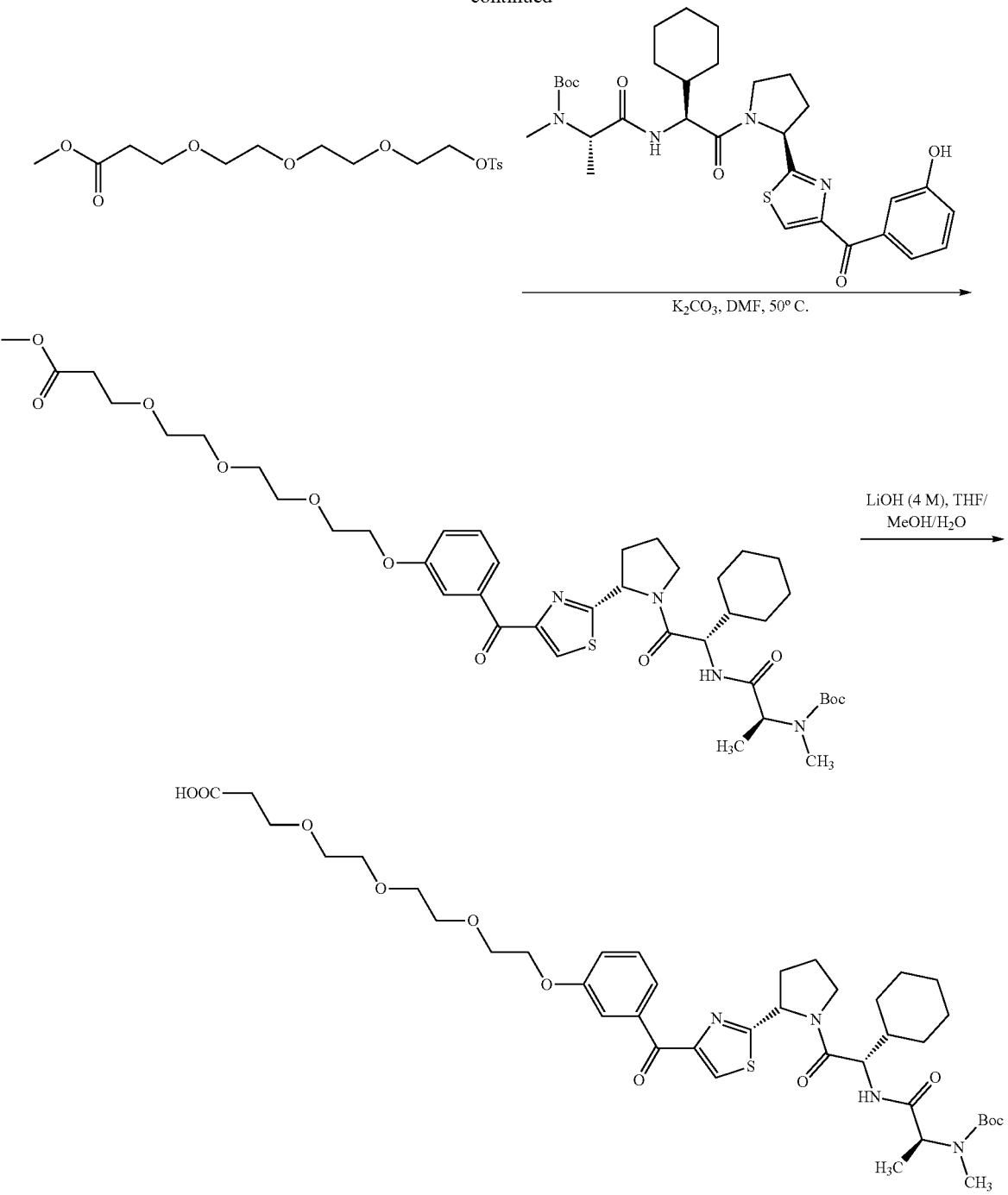

Step 1: methyl 3-(2-(2-(2-(tosyloxy)ethoxy)ethoxy)ethoxy)propanoate

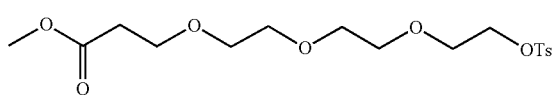 [SMILES: COC(=O)CCOCCOCCOCCOS(=O)(=O)c1ccc(C)cc1]

To a solution of methyl 3-(2-(2-(2-hydroxyethoxy)ethoxy)ethoxy)propanoate (1 g, 4.23 mmol) in pyridine (10 mL) was added p-TsCl (1.2 g, 6.29 mmol). The mixture was stirred at room temperature for 16 h. The reaction mixture was diluted with water and the aqueous phase was extracted with ethyl acetate. The combined organic layer was washed with brine, dried over anhydrous sodium sulfate, filtered and concentrated under vacuum. The residue was purified by flash column chromatography with 0~50% ethyl acetate in petroleum ether to afford methyl 3-(2-(2-(2-(tosyloxy)ethoxy)ethoxy)ethoxy)propanoate (1.0 g, 60%) as light yellow oil. MS (ESI) calculated for ($C_{17}H_{26}O_8S$) [M+H]$^+$, 391.1; found, 391.0.

Step 2: methyl 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy)propanoate

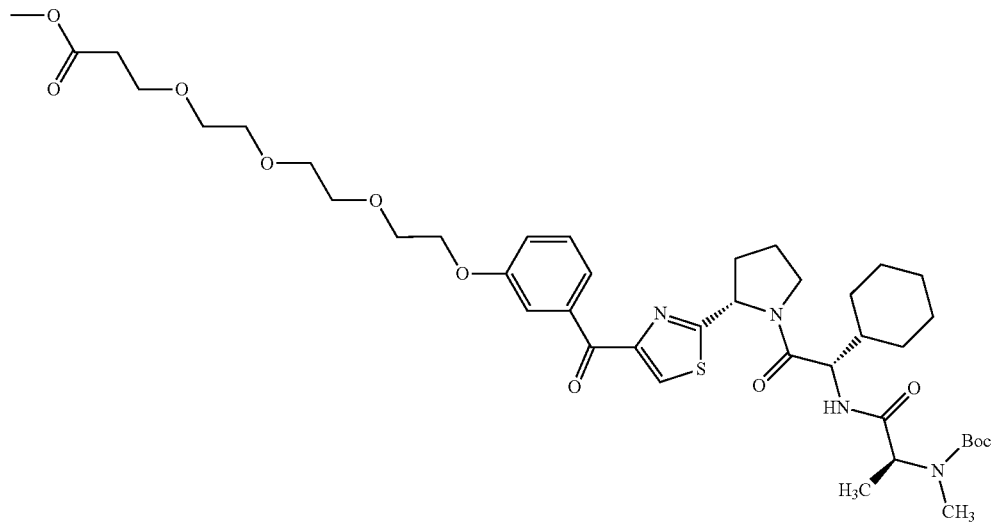

To a solution of methyl 3-(2-(2-(2-(tosyloxy)ethoxy)ethoxy)ethoxy)propanoate (1.0 g, 2.56 mmol) in N,N-dimethylformamide (10 mL) was added tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.2 g, 2.00 mmol) and potassium carbonate (400 mg, 2.89 mmol). The mixture was stirred at 50° C. for 16 h. The reaction mixture was then diluted with water and the aqueous phase was extracted with ethyl acetate. The combined organic layer was washed with brine, dried over anhydrous sodium sulfate, filtered and concentrated under vacuum. The crude residue was purified by flash column chromatography with 10~60% ethyl acetate in petroleum ether to afford methyl 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy)propanoate (1.0 g, 61%) as a light yellow solid. MS (ESI) calculated for ($C_{41}H_{60}N_4O_{11}S$) [M+H]$^+$, 817.4; found, 817.0.

Step 3: 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy)propanoic acid

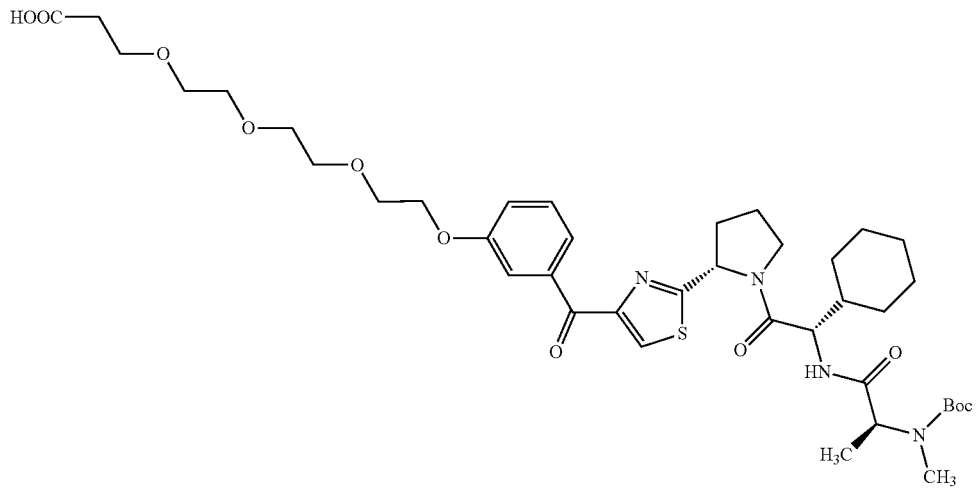

To a solution of methyl 3-(2-[2-[2-(3-[2-[(2S)-1-[(2S)-2-[(2S)-2-[[(tert-butoxy)carbonyl](methyl)amino]propanamido]-2-cyclohexylacetyl]pyrrolidin-2-yl]-1,3-thiazole-4-carbonyl]phenoxy)ethoxy]ethoxy]ethoxy)propanoate (1.0 g, 1.22 mmol) in tetrahydrofuran (4 mL) and MeOH (4 mL) was added lithium hydroxide solution (4 M, 2 mL). The resulting mixture was stirred at room temperature for 6 h. The mixture was diluted with water and adjusted the pH to ~3 by HCl (2 N). The aqueous phase was extracted with ethyl acetate. The combined organic layer was dried over anhydrous sodium sulfate, filtered and concentrated under vacuum. The residue was purified by flash column chromatography with 10~80% acetonitrile in water to afford 3-(2-(2-(2-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)ethoxy)ethoxy)ethoxy)propanoic acid (573.3 mg, 58%) as a white solid. $^1$H NMR (300 MHz, Methanol-d4) δ 8.35 (s, 1H), 7.79-7.71 (m, 2H), 7.47-7.44 (m, 1H), 7.28-7.26 (m, 1H), 5.73-5.46 (m, 1H), 4.69-4.35 (m, 2H), 4.28-4.18 (m, 2H), 4.05-3.86 (m, 4H), 3.78-3.56 (m, 10H), 2.88 (s, 3H), 2.54 (t, J=6.3 Hz, 2H), 2.47-2.11 (m, 4H), 1.86-1.53 (m, 6H), 1.48 (s, 9H), 1.36 (d, J=7.2 Hz, 3H), 1.28-0.99 (m, 5H). MS (ESI) calculated for ($C_{40}H_{58}N_4O_{11}S$) [M+H]$^+$, 803.4; found, 803.7.

Example 77: Synthesis of 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oic acid

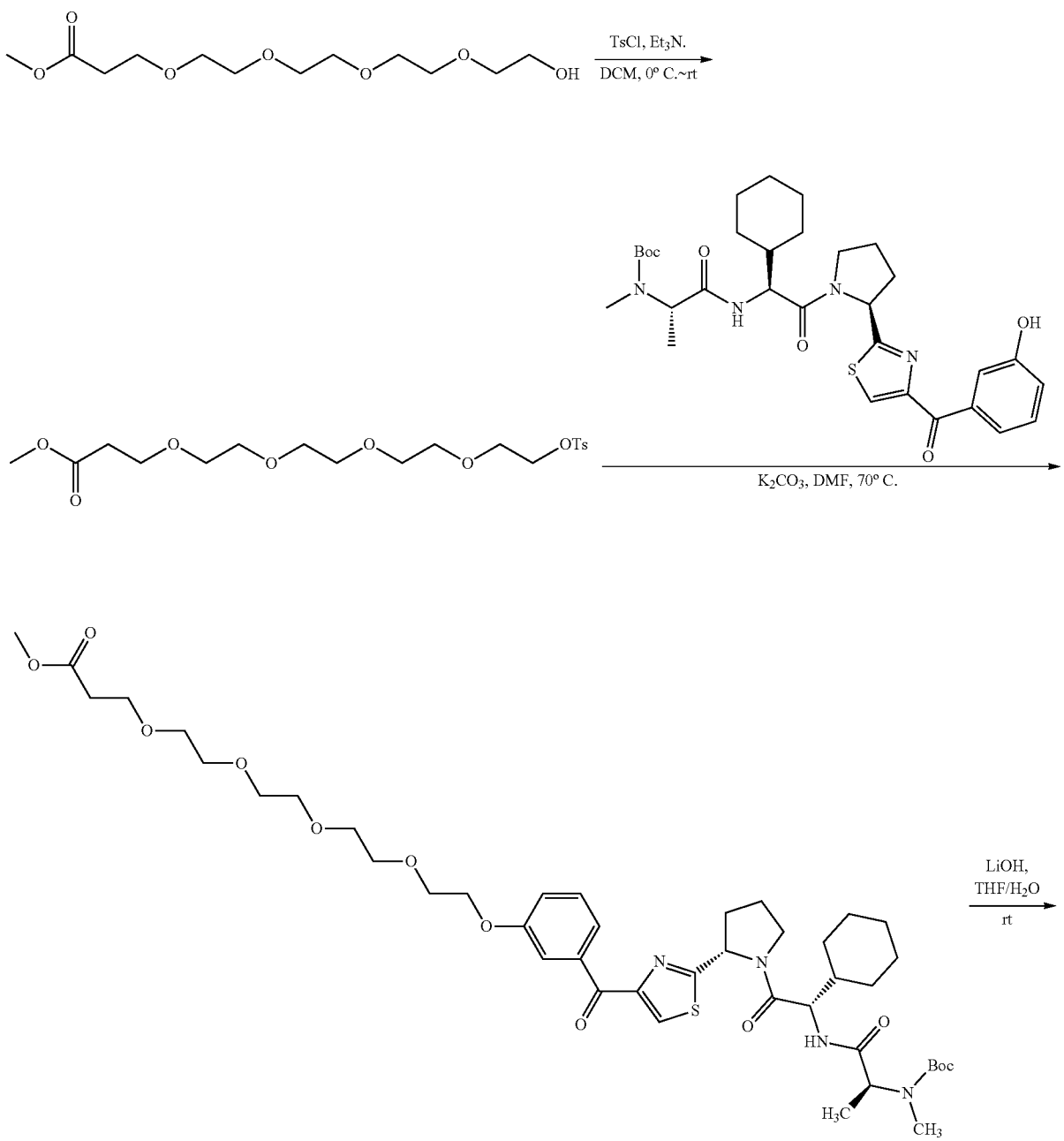

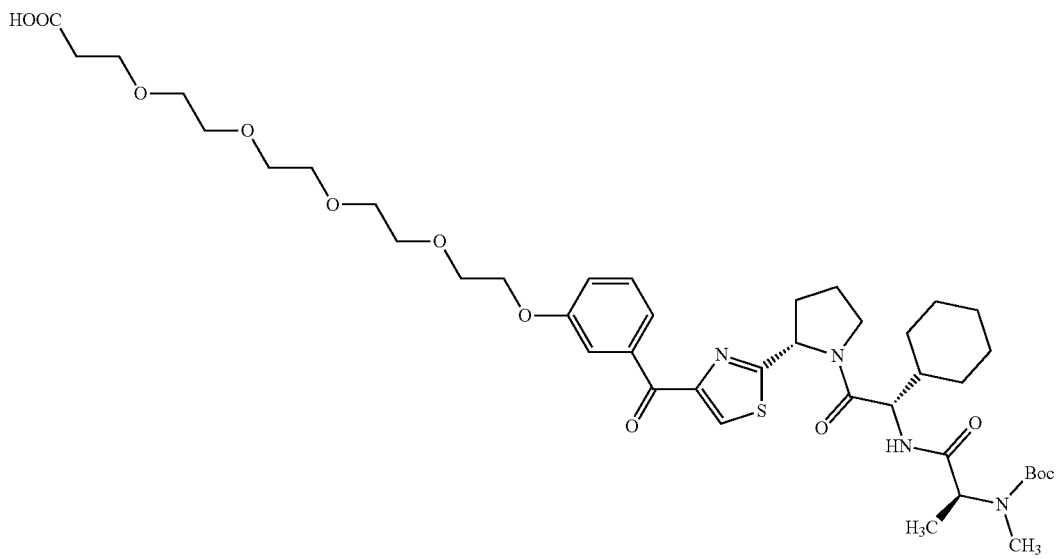 [SMILES: C[C@@H](C(=O)N[C@H](C(=O)N1CCC[C@H]1c1nc(C(=O)c2cccc(OCCOCCOCCOCCOCCC(=O)O)c2)cs1)C1CCCCC1)N(C)C(=O)OC(C)(C)C]

Step 1: methyl 1-[(4-methylbenzenesulfonyl)oxy]-3,6,9,12-tetraoxapentadecan-15-oate

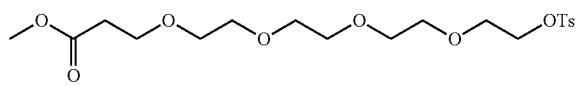 [SMILES: COC(=O)CCOCCOCCOCCOCCOS(=O)(=O)c1ccc(C)cc1]

To a solution of methyl 1-hydroxy-3,6,9,12-tetraoxapentadecan-15-oate (970 mg, 3.46 mmol) in dichloromethane (20 mL) was added triethylamine (700 mg, 6.93 mmol) and p-TsCl (990 mg, 5.19 mmol). The mixture was stirred at room temperature for 16 h. The reaction mixture was diluted with water and the aqueous phase was extracted with ethyl acetate. The combined organic layer was washed with brine, dried over anhydrous sodium sulfate, filtered and concentrated under vacuum. The residue was purified by flash column chromatography with 0~50% ethyl acetate in petroleum ether to afford methyl 1-[(4-methylbenzenesulfonyl)oxy]-3,6,9,12-tetraoxapentadecan-15-oate (1.28 g, 85%) as light yellow oil. MS (ESI) calculated for ($C_{19}H_{30}O_9S$) [M+H]$^+$, 435.2; found, 435.0.

Step 2: methyl 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oate

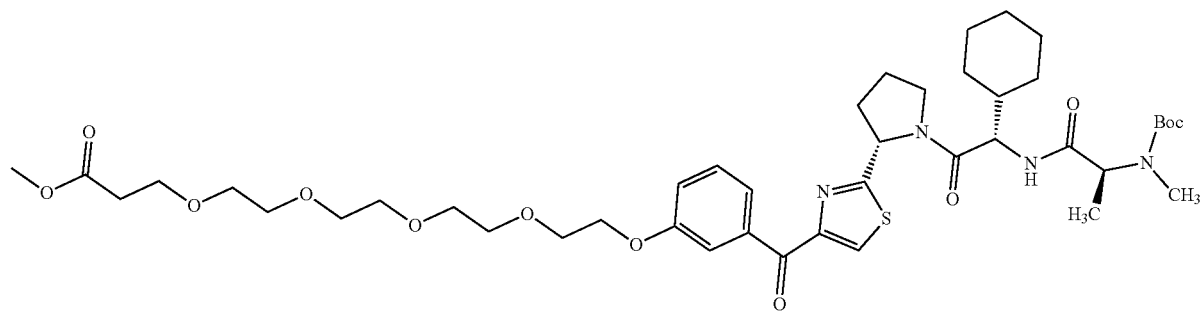

To a solution of methyl 1-[(4-methylbenzenesulfonyl)oxy]-3,6,9,12-tetraoxapentadecan-15-oate (1.28 g, 2.95 mmol) in N,N-dimethylformamide (10 mL) was added tert-butyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.17 g, 1.96 mmol) and potassium carbonate (370 mg, 2.68 mmol). The mixture was stirred at 50° C. for 16 h. The reaction mixture was then diluted with water and the aqueous phase was extracted with ethyl acetate. The combined organic layer was washed with brine, dried over anhydrous sodium sulfate, filtered and concentrated under vacuum. The residue was purified by flash column chromatography with 0~50% ethyl acetate in petroleum ether to afford methyl 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oate (1.2 g, 60%) as light yellow oil. MS (ESI) calculated for $(C_{43}H_{64}N_4O_{12}S)$ $[M+H]^+$, 861.4; found, 861.0.

Step 3: 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oic acid

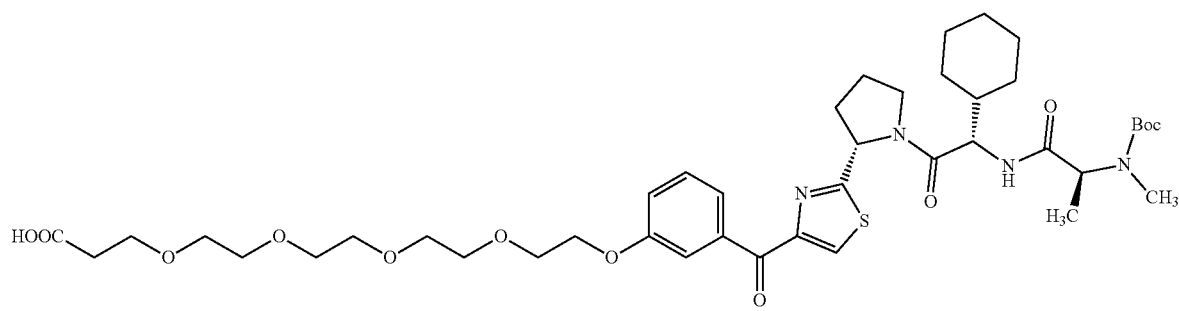 [SMILES: C[C@@H](C(=O)N[C@H](C(=O)N1CCC[C@H]1c1nc(C(=O)c2cccc(OCCOCCOCCOCCOCCC(=O)O)c2)cs1)C1CCCCC1)N(C)C(=O)OC(C)(C)C]

To a solution of 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oate (1.2 g, 1.39 mmol) in tetrahydrofuran (10 mL) and $H_2O$ (10 mL) was added lithium hydroxide hydrate (140 mg, 3.33 mmol). The mixture was stirred at room temperature for 16 h. The reaction mixture was diluted with water and the pH was adjusted to ~3 by HCl (2 N). The aqueous phase was extracted with ethyl acetate. The combined organic layer was washed with brine, dried over anhydrous sodium sulfate, filtered and concentrated under vacuum. The residue was purified by flash column chromatography with 10~80% acetonitrile in water to afford 1-(3-(2-((S)-1-((S)-2-((S)-2-((tert-butoxycarbonyl)(methyl)amino)propanamido)-2-cyclohexylacetyl)pyrrolidin-2-yl)thiazole-4-carbonyl)phenoxy)-3,6,9,12-tetraoxapentadecan-15-oic acid (805.2 mg, 68%) as a white solid. $^1$H NMR (300 MHz, Methanol-$d_4$) δ 8.35 (s, 1H), 7.80-7.69 (m, 2H), 7.50-7.42 (m, 1H), 7.26-7.23 (m, 1H), 5.50-5.45 (m, 1H), 4.56-4.53 (m, 2H), 4.32-4.16 (m, 2H), 4.05-3.85 (m, 4H), 3.77-3.66 (m, 6H), 3.66-3.56 (m, 8H), 2.80 (s, 3H), 2.45 (t, J=7.2 Hz, 2H), 2.41-2.08 (m, 3H), 1.88-1.55 (m, 6H), 1.49 (s, 9H), 1.36 (d, J=7.2 Hz, 3H), 1.08-1.04 (m, 6H). MS (ESI) calculated for $(C_{42}H_{62}N_4O_{12}S)$ $[M+H]^+$, 847.4; found, 847.8.

Example 78: 16-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-16-oxo-4,7,10,13-tetraoxahexadecanoic acid

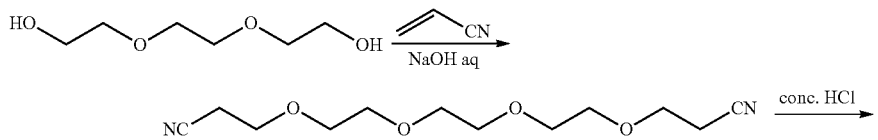

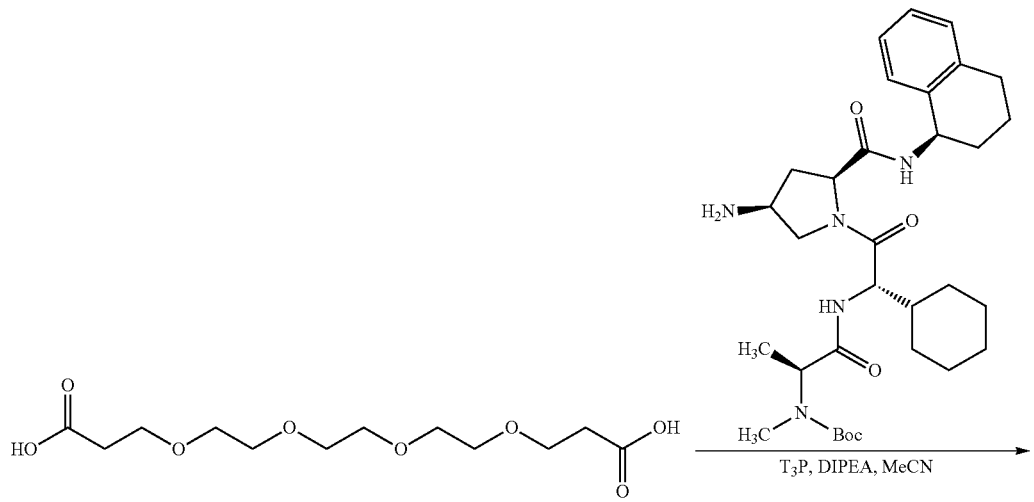

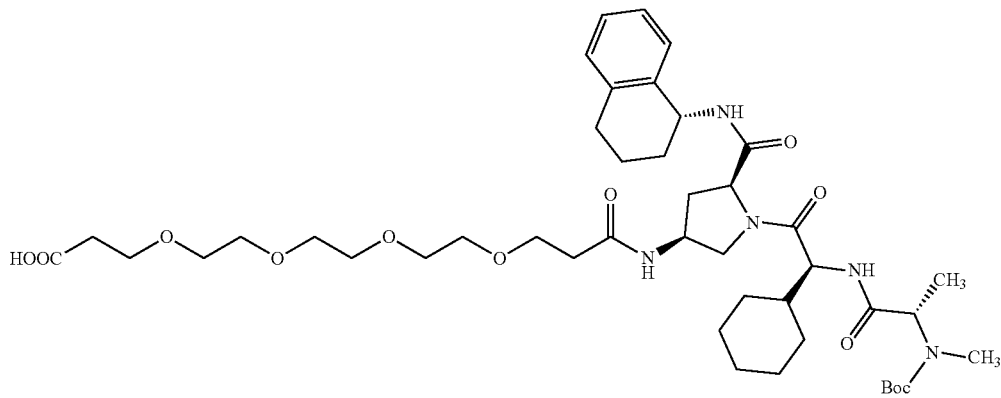

Step 1: 4,7,10,13-tetraoxahexadecanedinitrile

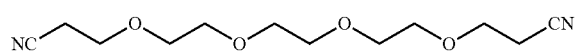 [SMILES: N#CCCOCCOCCOCCOCCC#N]

To a stirred solution of 2,2'-(ethane-1,2-diylbis(oxy))bis(ethan-1-ol) (15 g, 99.90 mmol) and NaOH aqueous (1.2 mL, 40% wt) was added acrylonitrile (12.2 g, 230 mmol) dropwise at 0° C. The solution was stirred at 30° C. for 16 h. When the reaction was complete, the reaction was quenched by the addition of 100 mL H$_2$O, neutralized to pH 7 by HCl (1 N). The aqueous solution was extracted with ethyl acetate (100 mL×3). The combined organic solution was dried over Na$_2$SO$_4$ and concentrated to afford 4,7,10,13-tetraoxahexadecanedinitrile (15 g, 59%) as yellow oil. $^1$H NMR (300 MHz, Chloroform-d) δ 3.72 (t, J=6.3 Hz, 4H), 3.69-3.62 (m, 12H), 2.62 (t, J=6.3 Hz, 4H).

Step 2: 4,7,10,13-tetraoxahexadecanedioic acid

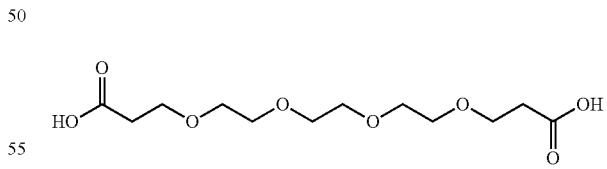

Concentrated HCl (68 mL) was added to 4,7,10,13-tetraoxahexadecanedinitrile (15 g, 58.60 mmol). The solution was stirred at 70° C. overnight. When the reaction was completed, the mixture was filtered, and the filtrate was concentrated to afford the residue, which was purified by flash column chromatography with 30~100% ethyl acetate in petroleum ether to afford 4,7,10,13-tetraoxahexadecanedioic acid (10.0 g, crude) as yellow oil. $^1$H NMR (400 MHz, DMSO-d$_6$) δ 12.18 (s, 2H), 3.60 (t, J=6.4 Hz, 4H), 3.51-3.48 (m, 12H), 2.44 (t, J=6.4 Hz, 4H).

Step 3: 16-(((3S,5S)-1-((S)-2-((S)-2-((tert-butoxy-carbonyl)(methyl)amino)propanamido)-2-cyclohexy-lacetyl)-5-(((R)-1,2,3,4-tetrahydronaphthalen-1-yl)carbamoyl)pyrrolidin-3-yl)amino)-16-oxo-4,7,10,13-tetraoxahexadecanoic acid

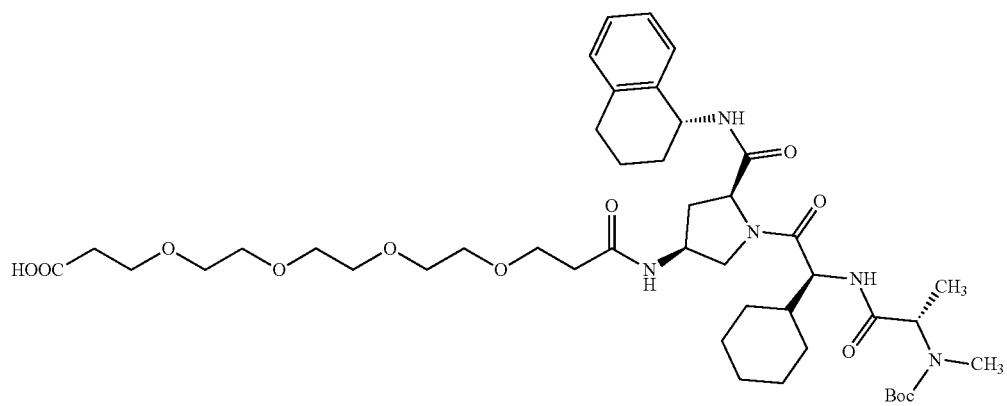 [SMILES: C[C@@H](C(=O)N[C@H](C(=O)N1C[C@@H](NC(=O)CCOCCOCCOCCOCCC(=O)O)C[C@H]1C(=O)N[C@@H]1CCCc2ccccc21)C1CCCCC1)N(C)C(=O)OC(C)(C)C]

To a stirred solution of tert-butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (1.5 g, 2.57 mmol), 4,7,10,13-tetraoxahexadecanedioic acid (5.0 g, 12.90 mmol) and DIEA (1.7 g, 12.86 mmol) in acetonitrile (30 mL) under nitrogen was added $T_3P$ (6.5 g, 10.28 mmol). The solution was stirred at 20° C. for 16 h. When the reaction was completed, the reaction was quenched by the addition of 50 mL $H_2O$. The aqueous solution was extracted with ethyl acetate (30 mL×3). The combined organic solution was dried over $Na_2SO_4$ to give the residue which was purified by reverse phase FC with 5~50% acetonitrile in $H_2O$ to afford 16-(((3S,5S)-1-((S)-2-((S)-2-((tert-butoxycarbonyl)(methyl)amino)propanamido)-2-cyclohexylacetyl)-5-(((R)-1,2,3,4-tetrahydronaphthalen-1-yl)carbamoyl)pyrrolidin-3- yl)amino)-16-oxo-4,7,10,13-tetraoxahexadecanoic acid (511.2 mg, 23%) as white solid. ¹H NMR (400 MHz, Methanol-d₄) δ 7.44-7.38 (m, 1H), 7.21-7.12 (m, 2H), 7.12-7.06 (m, 1H), 5.06 (t, J=6.0 Hz, 1H), 4.67-4.38 (m, 4H), 4.22-4.18 (m, 1H), 3.74-3.70 (m, 4H), 3.68-3.59 (m, 11H), 3.55-3.50 (m, 1H), 2.91-2.73 (m, 5H), 2.60-2.41 (m, 5H), 1.93-1.83 (m, 6H), 1.82-1.66 (m, 5H), 1.49 (s, 9H), 1.39-0.98 (m, 9H). MS (ESI) calculated for (C₄₄H₆₉N₅O₁₂) [M+1]⁺, 860.7; found, 860.7.

Example 79: General Procedures for CTM Syntheses Using Coupling Chemistry

General Coupling 1:

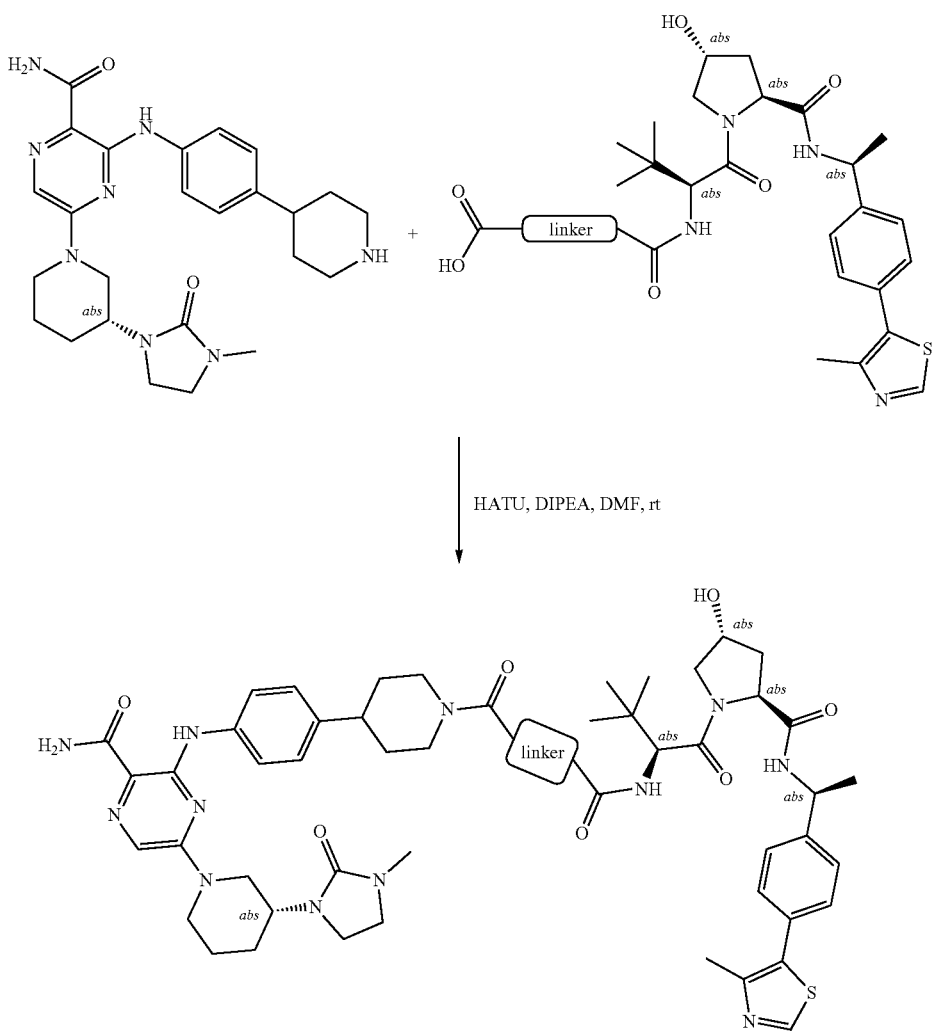

In a typical procedure, a mixture of amine (1 equiv), acid (1.1 equiv), HATU (1.2 equiv), DIPEA (3 equiv) and DMF (0.2 M) was allowed to stir at room temperature for 1 hour. The mixture was purified by HPLC (5-95% MeCN in H₂O with 0.1% TFA) to afford the desired product.

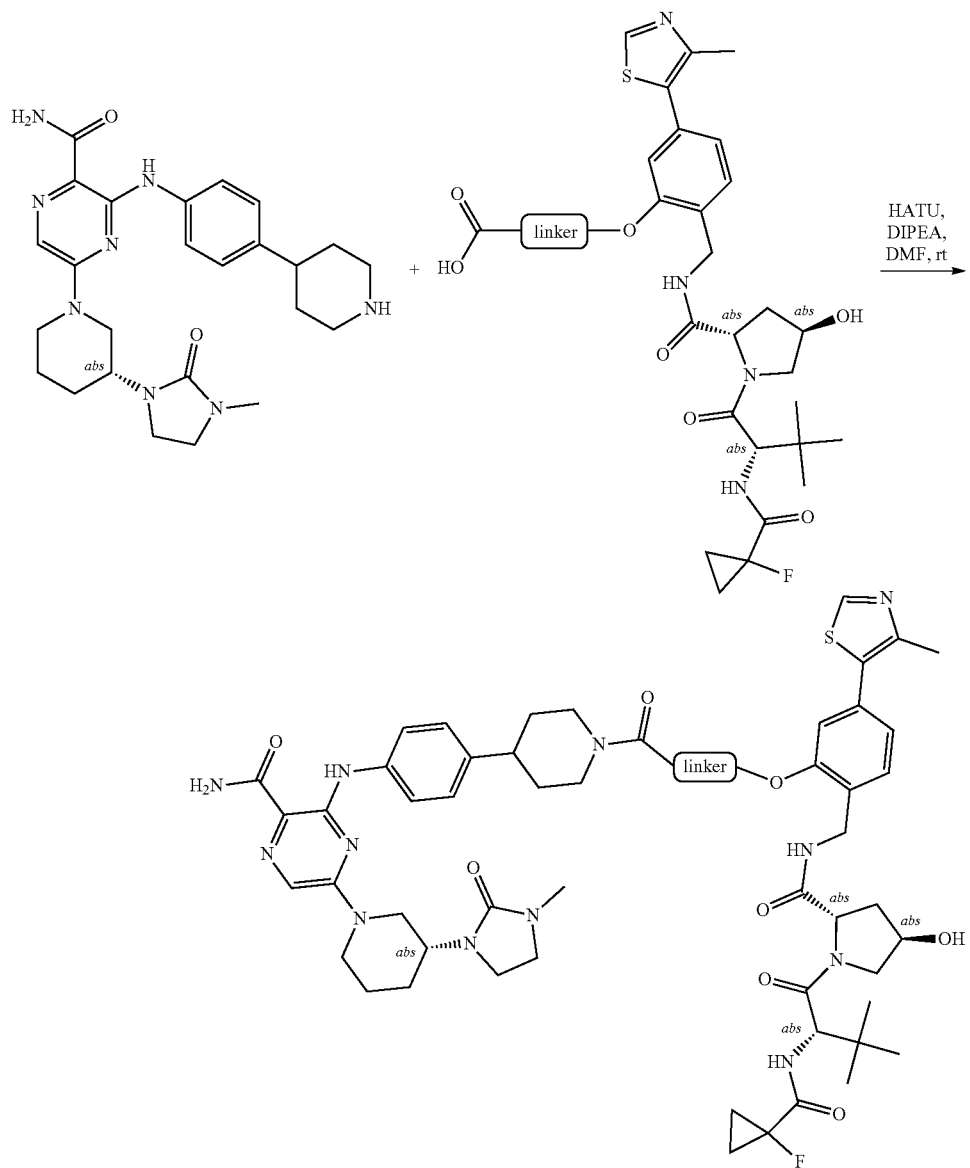
In a typical procedure, a mixture of amine (1 equiv), acid (1.1 equiv), HATU (1.2 equiv), DIPEA (3 equiv) and DMF (0.2 M) was allowed to stir at room temperature for 1 hour. The mixture was purified by HPLC (5-95% MeCN in H$_2$O with 0.1% TFA) to afford the desired product
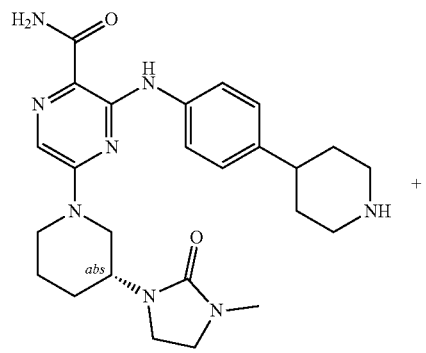
+

-continued

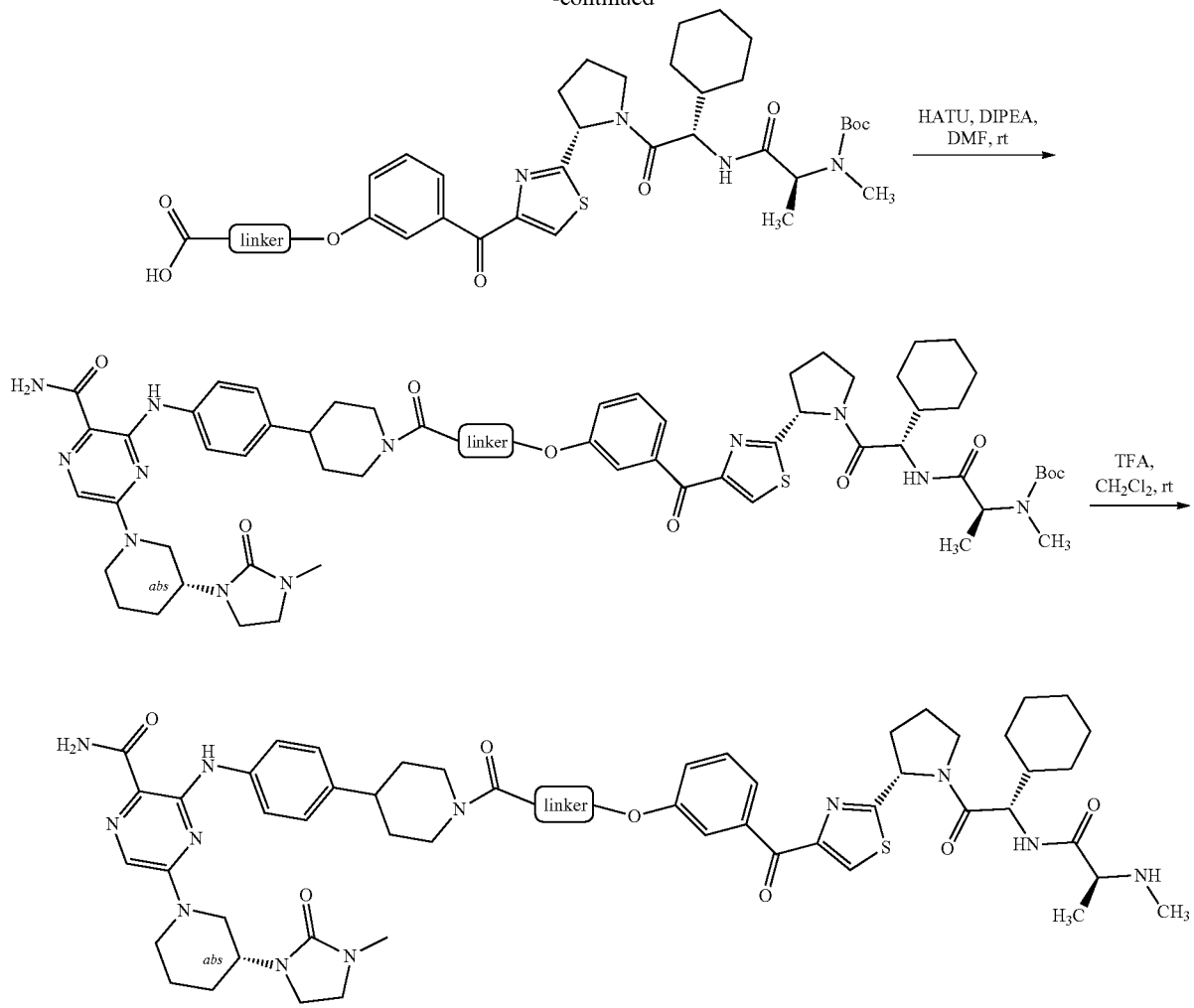

In a typical procedure, a mixture of amine (1 equiv), acid (1.1 equiv), HATU (1.2 equiv), DIPEA (3 equiv) and DMF (0.2 M) was allowed to stir at room temperature for 1 hour. EtOAc and $H_2O$ were added. The organic layer was dried with MgSO4, filtered, concentrated and carried to the next step.

TFA (20 equiv) and $CH_2Cl_2$ (0.1 M) were added and the mixture was allowed to stir at room temperature for 1 h. The volatiles were removed and the mixture was purified by HPLC (5-95% MeCN in $H_2O$ with 0.1% TFA) to afford the desired product.

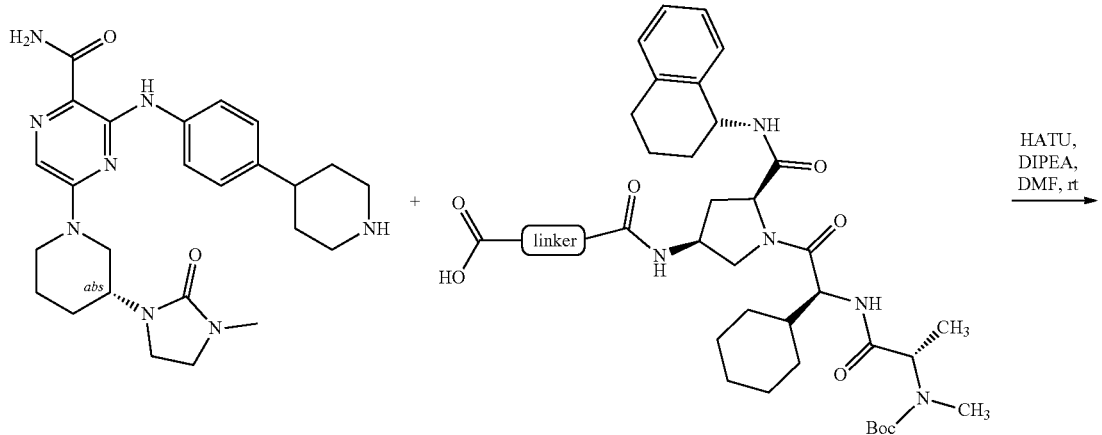

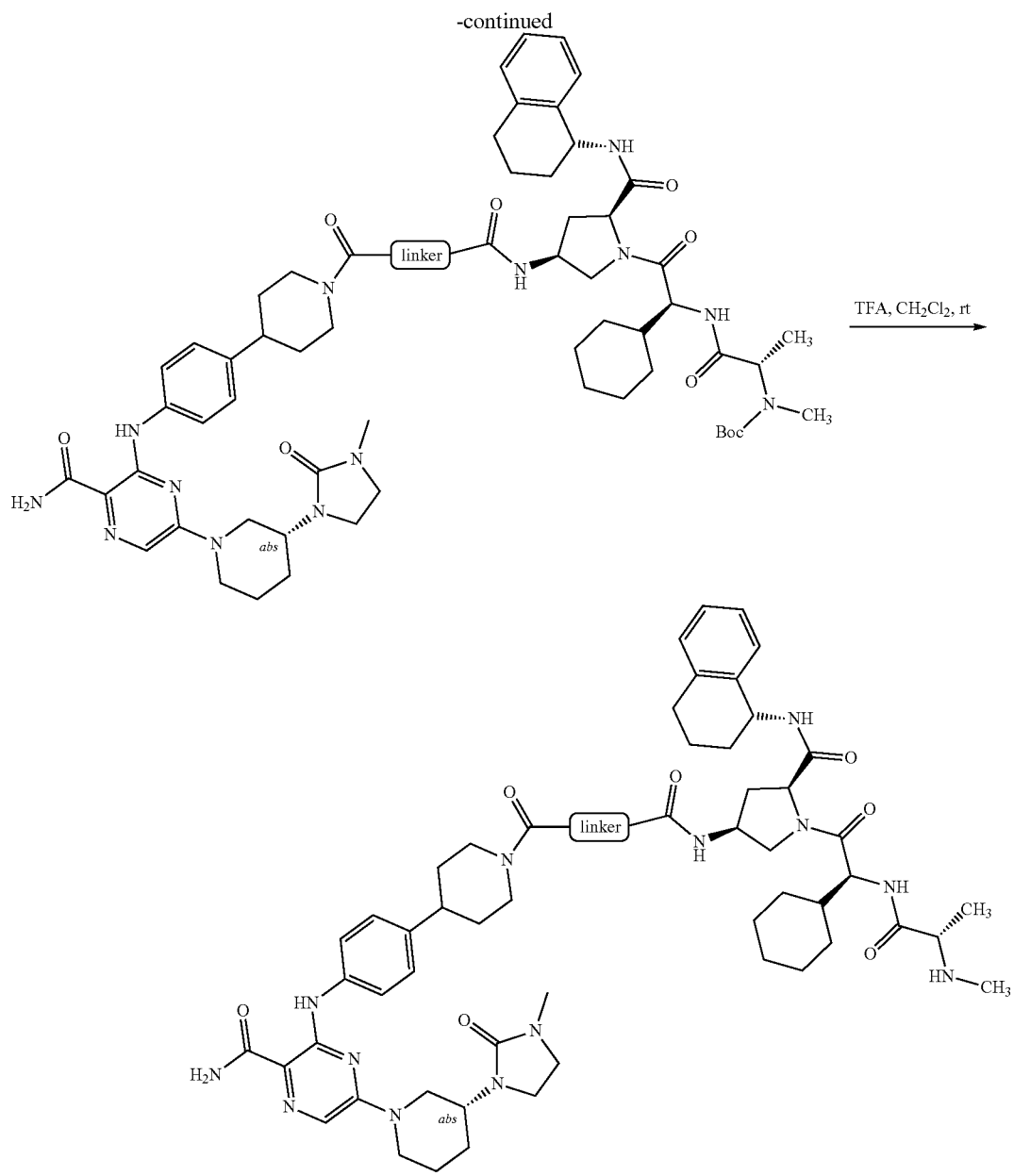

A mixture of amine (1 equiv), acid (1.1 equiv), HATU (1.2 equiv), DIPEA (3 equiv) and DMF (0.2 M) was allowed to stir at room temperature for 1 hour. EtOAc and H₂O were added. The organic layer was dried with MgSO4, filtered, concentrated and carried to the next step.

TFA (20 equiv) and CH$_2$Cl$_2$ (0.1 M) were added and the mixture was allowed to stir at room temperature for 1 h. The volatiles were removed and the mixture was purified by HPLC (5-95% MeCN in H$_2$O with 0.1% TFA) to afford the desired product.

Physical Data for Example Compounds of Table 1.

The $^1$H NMR spectra and mass spectrometry (LCMS) data were obtained for the example compounds reported in Table 1. These experimental data are provided in Table 2.

TABLE 2

Physical Data for the Example Compounds of Table 1.

| Compound No. | $^1$H NMR | Mass Spec (LCMS) |
|---|---|---|
| 1 | $^1$H NMR (500 MHz, DMSO-d$_6$) δ 11.24 (d, J = 13.2 Hz, 1H), 11.09 (s, 1H), 7.78 (s, 1H), 7.74-7.63 (m, 0H), 7.68 (s, 1H), 7.60 (t, J = 7.8 Hz, 1H), 7.57-7.47 (m, 3H), 7.35 (s, 1H), 7.23 (d, J = 8.1 Hz, 2H), 7.16 (dd, J = 16.8, 8.4 Hz, 2H), 7.05 (d, J = 7.0 Hz, | LCMS: C$_{35}$H$_{38}$N$_{10}$O$_6$ requires: 694, found: m/z = 695 [M + H]$^+$. |

TABLE 2-continued

Physical Data for the Example Compounds of Table 1.

| Compound No. | $^1$H NMR | Mass Spec (LCMS) |
|---|---|---|
| | 1H), 6.58 (d, J = 6.3 Hz, 1H), 5.05 (dd, J = 12.8, 5.4 Hz, 1H), 4.33 (s, 3H), 3.55 (d, J = 6.8 Hz, 2H), 3.25 (s, 1H), 3.18 (s, 2H), 2.98 (d, J = 12.7 Hz, 1H), 2.92-2.83 (m, 3H), 2.76-2.67 (m, 4H), 2.61 (s, 1H), 2.48 (s, 10H), 2.06-1.99 (m, 1H), 1.83 (d, J = 12.1 Hz, 4H), 1.77 (s, 1H), 1.57 (d, J = 11.3 Hz, 2H), 1.38 (d, J = 7.4 Hz, 1H), 1.31-1.23 (m, 2H). | |
| 2 | $^1$H NMR (500 MHz, Acetonitrile-d$_3$) δ 11.25 (s, 1H), 9.03 (s, 1H), 7.67-7.61 (m, 2H), 7.58 (dd, J = 8.8, 1.3 Hz, 2H), 7.49 (d, J = 1.0 Hz, 1H), 7.45 (s, 2H), 7.42-7.32 (m, 2H), 6.94 (t, J = 5.9 Hz, 1H), 6.87 (dd, J = 16.7, 7.8 Hz, 2H), 6.31 (s, 1H), 5.82 (s, 1H), 5.54 (dd, J = 6.1, 2.3 Hz, 5H), 5.48 (dd, J = 6.0, 2.1 Hz, 4H), 5.34 (dd, J = 6.0, 2.1 Hz, 2H), 4.84 (ddd, J = 12.3, 5.4, 3.4 Hz, 1H), 4.30 (d, J = 12.9 Hz, 1H), 4.20 (t, J = 7.1 Hz, 1H), 3.76 (dddd, J = 15.7, 13.2, 8.1, 6.0 Hz, 25H), 3.65-3.41 (m, 16H), 3.41 (q, J = 5.4 Hz, 2H), 3.32-3.13 (m, 6H), 2.96 (t, J = 11.8 Hz, 1H), 2.88 (t, J = 12.9 Hz, 1H), 2.72-2.60 (m, 1H), 2.63-2.50 (m, 2H), 2.05-1.73 (m, 19H), 1.81 (s, 13H), 1.76-1.52 (m, 24H), 1.19 (s, 1H), 1.09 (d, J = 18.8 Hz, 1H). | LCMS C$_{43}$H$_{54}$N$_{10}$O$_9$ requires: 855, found: m/z = 856 [M + H]$^+$. |
| 3 | $^1$H NMR (500 MHz, DMSO-d$_6$) δ 11.49 (s, 1H), 11.02 (s, 1H), 8.24 (t, J = 5.6 Hz, 1H), 7.80-7.70 (m, 3H), 7.67 (s, 1H), 7.58 (dd, J = 9.1, 2.5 Hz, 2H), 7.53-7.45 (m, 1H), 7.36 (d, J = 2.9 Hz, 1H), 7.08-7.00 (m, 1H), 7.00-6.90 (m, 1H), 6.55-6.45 (m, 1H), 4.98 (dd, J = 12.7, 5.4 Hz, 1H), 4.26 (s, 2H), 3.53 (dt, J = 10.7, 4.9 Hz, 5H), 3.19 (dd, J = 9.3, 7.3 Hz, 3H), 3.03 (t, J = 11.8 Hz, 2H), 2.92 (t, J = 12.6 Hz, 2H), 2.81 (ddd, J = 17.0, 13.8, 5.5 Hz, 1H), 2.64 (s, 3H), 2.47 (s, 2H), 2.02-1.91 (m, 1H), 1.80-1.59 (m, 4H), 1.51 (d, J = 12.6 Hz, 1H). | LCMS C$_{42}$H$_{51}$N$_{11}$O$_{10}$ requires: 870, found: m/z = 871 [M + H]$^+$. |
| 4 | $^1$H NMR (500 MHz, DMSO-d$_6$) δ 11.02 (s, 1H), 10.98 (s, 1H), 9.77 (s, 1H), 8.01 (t, J = 5.7 Hz, 1H), 7.77-7.57 (m, 3H), 7.55 (s, 1H), 7.41 (d, J = 9.0 Hz, 4H), 7.30-7.14 (m, 3H), 6.79 (d, J = 8.6 Hz, 2H), 5.09-4.88 (m, 1H), 4.41-4.02 (m, 5H), 3.88 (t, J = 6.3 Hz, 3H), 3.70-3.44 (m, 7H), 3.16 (ddt, J = 22.1, 14.8, 8.7 Hz, 11H), 3.08-3.00 (m, 5H), 3.00-2.77 (m, 5H), 2.64 (s, 4H), 2.15 (t, J = 7.0 Hz, 3H), 1.96 (dt, J = 12.3, 5.7 Hz, 2H), 1.89-1.62 (m, 9H), 1.54-1.40 (m, 1H). | LCMS C$_{44}$H$_{54}$N$_{12}$O$_8$ requires: 879, found: m/z = 880 [M + H]$^+$. |
| 5 | $^1$H NMR (500 MHz, DMSO-d$_6$) δ 11.04 (s, 1H), 10.96 (s, 1H), 7.78 (t, J = 5.6 Hz, 1H), 7.74-7.64 (m, 3H), 7.62 (dd, J = 6.9, 2.0 Hz, 1H), 7.55 (s, 1H), 7.44-7.33 (m, 2H), 7.22 (s, 1H), 6.85-6.72 (m, 2H), 5.06 (dd, J = 12.8, 5.4 Hz, 1H), 4.23 (dd, J = 33.8, 12.8 Hz, 2H), 3.86 (t, J = 6.3 Hz, 3H), 3.34-3.07 (m, 10H), 3.05-2.75 (m, 6H), 2.63 (s, 3H), 2.58-2.46 (m, 3H), 2.38 (ddd, J = 9.8, 7.7, 2.1 Hz, 2H), 2.20 (ddd, J = 8.4, 6.5, 4.4 Hz, 2H), 1.98 (ddt, J = 15.2, 9.4, 3.3 Hz, 2H), 1.87 (qd, J = 8.4, 2.7 Hz, 2H), 1.80-1.66 (m, 7H), 1.47 (d, J = 11.3 Hz, 1H). | LCMS C$_{44}$H$_{56}$N$_{12}$O$_7$ requires: 865, found: m/z = 866 [M + H]$^+$. |
| 6 | $^1$H NMR (500 MHz, DMSO-d$_6$) δ 10.96 (s, 1H), 10.92 (s, 1H), 7.82 (t, J = 5.6 Hz, 1H), 7.65 (s, 1H), 7.55 (s, 1H), 7.50 (dd, J = 6.2, 2.4 Hz, 1H), 7.43-7.31 (m, 4H), 7.22 (s, 1H), 6.87-6.72 (m, 2H), 5.05 (dd, J = 13.3, 5.2 Hz, 1H), 4.46-4.11 (m, 4H), 3.86 (t, J = 6.3 Hz, 2H), 3.28-3.07 (m, 8H), 3.01-2.79 (m, 3H), 2.62 (d, J = 1.8 Hz, 3H), 2.56 (dd, J = 9.6, 6.7 Hz, 3H), 2.34 (dd, J = 13.2, 4.5 Hz, 3H), 2.05 (t, J = 7.4 Hz, 2H), 1.94 (dd, J = 12.9, 6.1 Hz, 1H), 1.82-1.65 (m, 7H), 1.54-1.40 (m, 1H). | LCMS C$_{40}$H$_{48}$N$_{10}$O$_7$ requires: 781, found: m/z = 782 [M + H]$^+$. |
| 7 | $^1$H NMR (500 MHz, DMSO-d$_6$) δ 11.17 (s, 1H), 10.95 (s, 1H), 10.14 (s, 1H), 8.09 (d, J = 8.1 Hz, 1H), 7.69 (s, 1H), 7.60 (s, 1H), 7.47 (t, J = 8.7 Hz, 3H), 7.35 (d, J = 7.5 Hz, 2H), 7.24 (t, J = 10.8 Hz, 3H), 5.07 (dd, J = 13.3, 5.1 Hz, 1H), 4.46-4.15 (m, 4H), 3.47-3.33 (m, 1H), 3.33-3.12 (m, 5H), 3.01-2.77 (m, 3H), 2.74 (t, J = 7.4 Hz, 2H), 2.63 (d, J = 1.7 Hz, 3H), 2.60-2.51 (m, 1H), 2.33-2.15 (m, 1H), 2.05-1.40 (m, 9H), 1.15 (s, 3H). | LCMS: C$_{45}$H$_{53}$N$_{13}$O$_7$ requires: 887, found: m/z = 888 [M + H]$^+$. |

TABLE 2-continued

Physical Data for the Example Compounds of Table 1.

| Compound No. | $^1$H NMR | Mass Spec (LCMS) |
|---|---|---|
| 8 | $^1$H NMR (500 MHz, DMSO-d$_6$) δ 11.49 (s, 1H), 11.01 (s, 1H), 8.26 (t, J = 5.7 Hz, 1H), 7.78-7.70 (m, 3H), 7.67 (s, 1H), 7.58 (d, J = 8.7 Hz, 2H), 7.50 (dd, J = 8.6, 7.1 Hz, 1H), 7.36 (s, 1H), 7.05 (d, J = 8.6 Hz, 1H), 6.94 (d, J = 7.0 Hz, 1H), 6.51 (s, 1H), 4.98 (dd, J = 12.8, 5.5 Hz, 1H), 4.27 (s, 2H), 3.31-3.14 (m, 6H), 3.03 (t, J = 11.8 Hz, 1H), 2.92 (t, J = 12.1 Hz, 1H), 2.81 (ddd, J = 16.8, 13.8, 5.4 Hz, 1H), 2.63 (s, 3H), 1.95 (ddt, J = 12.9, 5.4, 3.3 Hz, 1H), 1.80-1.66 (m, 3H), 1.58-1.48 (m, 6H). | LCMS C$_{38}$H$_{43}$N$_{11}$O$_7$ requires: 766, found: m/z = 767 [M + H]$^+$. |
| 9 | $^1$H NMR (500 MHz, DMSO-d$_6$) δ 11.50 (s, 1H), 10.91 (s, 1H), 8.21 (t, J = 5.6 Hz, 1H), 7.77 (s, 1H), 7.74-7.66 (m, 3H), 7.61-7.55 (m, 2H), 7.50 (d, J = 7.6 Hz, 1H), 7.44 (d, J = 7.6 Hz, 1H), 7.38-7.31 (m, 2H), 5.05 (dd, J = 13.3, 5.1 Hz, 1H), 4.42 (dd, J = 17.1, 1.8 Hz, 1H), 4.32-4.24 (m, 3H), 3.68-3.54 (m, 1H), 3.44 (t, J = 6.1 Hz, 1H), 3.36-3.14 (m, 4H), 3.04 (t, J = 11.7 Hz, 1H), 2.93 (t, J = 12.1 Hz, 1H), 2.90-2.77 (m, 3H), 2.63 (s, 3H), 2.52 (d, J = 18.9 Hz, 1H), 2.38-2.29 (m, 1H), 1.92 (ddd, J = 12.2, 6.2, 3.7 Hz, 1H), 1.73 (dtd, J = 18.4, 11.8, 10.7, 5.3 Hz, 3H), 1.51 (d, J = 11.6 Hz, 1H). | LCMS C$_{38}$H$_{44}$N$_{10}$O$_7$ requires: 753, found: m/z = 754 [M + H]$^+$. |
| 10 | $^1$H NMR (500 MHz, DMSO-d$_6$) δ 11.30-11.13 (m, 1H), 11.04 (s, 1H), 7.72 (dd, J = 7.7, 2.2 Hz, 1H), 7.68 (d, J = 6.6 Hz, 1H), 7.59 (d, J = 3.6 Hz, 2H), 7.50-7.43 (m, 2H), 7.31-7.15 (m, 3H), 5.11-5.00 (m, 1H), 4.26 (dd, J = 50.5, 13.4 Hz, 2H), 3.63-3.08 (m, 9H), 3.00-2.76 (m, 2H), 2.72 (t, J = 7.6 Hz, 2H), 2.63 (d, J = 1.2 Hz, 2H), 2.60-2.45 (m, 3H), 2.05-1.39 (m, 11H), 1.14 (s, 3H). | LCMS: C$_{45}$H$_{54}$N$_{10}$O$_8$ requires: 862, found: m/z = 863 [M + H]$^+$. |
| 11 | $^1$H NMR (500 MHz, DMSO-d$_6$) δ 11.31-11.16 (m, 1H), 11.02 (s, 1H), 9.61 (s, 1H), 7.70 (d, J = 8.3 Hz, 2H), 7.61 (d, J = 7.0 Hz, 1H), 7.53-7.47 (m, 2H), 7.42 (d, J = 2.2 Hz, 1H), 7.33-7.19 (m, 4H), 5.03 (dd, J = 12.8, 5.5 Hz, 1H), 4.41-4.06 (m, 4H), 3.60-3.33 (m, 4H), 3.33-3.02 (m, 11H), 3.01-2.73 (m, 3H), 2.64 (d, J = 2.5 Hz, 3H), 2.62-2.46 (m, 2H), 2.02-1.41 (m, 12H), 1.16 (d, J = 1.8 Hz, 3H). | LCMS: C$_{47}$H$_{58}$N$_{12}$O$_7$ requires: 902, found: m/z = 903 [M + H]$^+$. |
| 12 | $^1$H NMR (500 MHz, DMSO-d$_6$) δ 10.98 (d, J = 6.3 Hz, 2H), 7.66 (s, 1H), 7.61-7.54 (m, 2H), 7.45 (d, J = 6.9 Hz, 2H), 7.43-7.38 (m, 2H), 7.22 (s, 1H), 6.89-6.84 (m, 2H), 5.10 (dd, J = 13.3, 5.2 Hz, 1H), 4.45 (d, J = 17.0 Hz, 1H), 4.36-4.14 (m, 3H), 3.61-3.44 (m, 5H), 3.34-3.14 (m, 4H), 3.11-2.80 (m, 9H), 2.64 (s, 3H), 2.61-2.53 (m, 1H), 2.33-2.24 (m, 1H), 2.04-1.91 (m, 1H), 1.80-1.64 (m, 4H), 1.48 (d, J = 12.8 Hz, 1H). | LCMS: C$_{45}$H$_{57}$N$_{13}$O$_6$ requires: 875, found: m/z = 876 [M + H]$^+$. |
| 13 | $^1$H NMR (500 MHz, DMSO-d$_6$) δ 11.24 (dd, J = 42.3, 5.8 Hz, 1H), 10.96 (s, 1H), 7.71 (s, 1H), 7.62 (d, J = 7.0 Hz, 1H), 7.57 (d, J = 6.5 Hz, 1H), 7.53-7.49 (m, 2H), 7.44 (d, J = 7.9 Hz, 2H), 7.31-7.20 (m, 3H), 5.10 (dd, J = 13.3, 5.1 Hz, 1H), 4.44 (d, J = 17.1 Hz, 1H), 4.37-4.18 (m, 2H), 3.34-3.10 (m, 4H), 3.04-2.78 (m, 4H), 2.67-2.53 (m, 4H), 2.29 (p, J = 1.9 Hz, 1H), 1.94 (d, J = 33.6 Hz, 3H), 1.82-1.40 (m, 7H), 1.17 (d, J = 1.9 Hz, 3H). | LCMS: C$_{47}$H$_{60}$N$_{12}$O$_6$ requires: 888, found: m/z = 889 [M + H]$^+$. |
| 14 | $^1$H NMR (500 MHz, DMSO-d$_6$) δ 11.22 (d, J = 56.8 Hz, 1H), 10.94 (s, 1H), 9.73 (s, 1H), 7.77-7.66 (m, 2H), 7.60 (d, J = 5.3 Hz, 1H), 7.44 (ddd, J = 20.1, 15.6, 8.0 Hz, 4H), 7.25 (d, J = 13.9 Hz, 1H), 7.23-7.16 (m, 2H), 5.07 (dd, J = 13.3, 5.1 Hz, 1H), 4.38-4.15 (m, 5H), 3.63 (t, J = 6.3 Hz, 2H), 3.60-3.48 (m, 2H), 3.39 (d, J = 8.8 Hz, 1H), 3.35-3.11 (m, 5H), 3.01-2.77 (m, 3H), 2.63 (s, 3H), 2.60-2.47 (m, 4H), 2.34-2.20 (m, 1H), 2.01-1.85 (m, 1H), 1.85-1.63 (m, 3H), 1.60-1.39 (m, 0H), 1.10 (d, J = 3.3 Hz, 3H). | LCMS: C$_{45}$H$_{55}$N$_{11}$O$_8$ requires: 877, found: m/z = 878 [M + H]$^+$. |

TABLE 2-continued

Physical Data for the Example Compounds of Table 1.

| Compound No. | ¹H NMR | Mass Spec (LCMS) |
|---|---|---|
| 15 | ¹H NMR (500 MHz, Methanol-$d_4$) δ 7.71 (dd, J = 7.2, 1.5 Hz, 1H), 7.60 (s, 1H), 7.58-7.51 (m, 4H), 7.01-6.95 (m, 2H), 5.20 (dd, J = 13.3, 5.2 Hz, 1H), 4.59-4.45 (m, 2H), 4.36 (dd, J = 33.5, 12.9 Hz, 2H), 3.83-3.60 (m, 3H), 3.52-3.32 (m, 6H), 3.12 (dd, J = 12.8, 10.6 Hz, 1H), 3.05-2.88 (m, 4H), 2.87-2.81 (m, 2H), 2.78 (d, J = 8.1 Hz, 4H), 2.65 (s, 1H), 2.51 (dd, J = 13.2, 4.6 Hz, 1H), 2.24-2.11 (m, 4H), 2.03-1.79 (m, 4H). | LCMS: $C_{40}H_{49}N_{11}O_5$ requires: 763, found: m/z = 764 $[M + H]^+$. |
| 16 | ¹H NMR (500 MHz, Methanol-$d_4$) δ 7.73-7.51 (m, 4H), 7.49-7.45 (m, 1H), 7.35-7.27 (m, 2H), 5.18 (ddd, J = 19.2, 13.4, 5.2 Hz, 1H), 4.43 (ddd, J = 53.8, 36.6, 16.1 Hz, 4H), 3.83-3.70 (m, 1H), 3.60-3.32 (m, 3H), 3.16-2.69 (m, 9H), 2.67-2.38 (m, 2H), 2.26-1.55 (m, 9H), 1.39 (s, 1H), 1.25 (s, 2H). | LCMS: $C_{42}H_{52}N_{10}O_5$ requires: 776, found: m/z = 777 $[M + H]^+$. |
| 17 | ¹H NMR (500 MHz, DMSO-$d_6$) δ 10.91 (d, J = 6.2 Hz, 2H), 7.64 (d, J = 2.8 Hz, 1H), 7.53 (s, 1H), 7.50 (dd, J = 5.8, 2.8 Hz, 1H), 7.43-7.37 (m, 2H), 7.37-7.32 (m, 2H), 7.20 (d, J = 2.9 Hz, 1H), 6.82-6.76 (m, 2H), 5.06 (dd, J = 13.3, 5.1 Hz, 1H), 4.40 (d, J = 17.1 Hz, 1H), 4.33-4.14 (m, 3H), 3.58-3.49 (m, 3H), 3.04-2.79 (m, 8H), 2.65-2.47 (m, 7H), 2.33-2.24 (m, 2H), 2.15 (t, J = 7.4 Hz, 1H), 1.94 (dd, J = 11.4, 6.0 Hz, 1H), 1.80-1.65 (m, 6H), 1.63-1.36 (m, 5H), 1.17 (s, 3H). | LCMS: $C_{41}H_{51}N_{11}O_5$ requires: 777, found: m/z = 778 $[M + H]^+$. |
| 18 | ¹H NMR (500 MHz, DMSO-$d_6$) δ 11.20 (d, J = 16.7 Hz, 1H), 11.05 (d, J = 6.4 Hz, 2H), 9.15 (d, J = 83.4 Hz, 1H), 7.77-7.57 (m, 6H), 7.54-7.38 (m, 3H), 7.31-7.14 (m, 4H), 5.05 (dt, J = 12.7, 5.2 Hz, 2H), 4.37-4.01 (m, 3H), 3.09-2.72 (m, 8H), 2.62 (s, 4H), 2.07-1.63 (m, 12H), 1.28-1.04 (m, 5H). | LCMS: $C_{44}H_{54}N_{10}O_7$ requires: 834, found: m/z = 835 $[M + H]^+$. |
| 19 | ¹H NMR (500 MHz, DMSO-$d_6$) δ 10.99 (d, J = 30.5 Hz, 1H), 7.65 (s, 1H), 7.58-7.47 (m, 2H), 7.37 (dd, J = 8.8, 4.4 Hz, 2H), 7.22 (s, 1H), 7.07 (d, J = 8.7 Hz, 1H), 6.97 (d, J = 7.1 Hz, 1H), 6.82 (d, J = 8.8 Hz, 2H), 6.52 (s, 1H), 4.98 (dd, J = 13.0, 5.4 Hz, 1H), 4.24 (dd, J = 28.7, 12.9 Hz, 2H), 3.68-3.45 (m, 23H), 3.40 (d, J = 5.1 Hz, 2H), 3.31-3.13 (m, 3H), 3.05-2.71 (m, 7H), 2.63 (d, J = 1.6 Hz, 2H), 2.60-2.53 (m, 2H), 1.93 (dd, J = 12.8, 5.9 Hz, 1H), 1.79-1.62 (m, 2H), 1.48 (d, J = 12.9 Hz, 1H). | LCMS: $C_{42}H_{50}N_{12}O_8$ requires: 850, found: m/z = 851 $[M + H]^+$. |
| 20 | ¹H NMR (500 MHz, DMSO-$d_6$) δ 11.20 (d, J = 6.4 Hz, 1H), 10.95 (s, 1H), 7.71 (s, 1H), 7.61 (s, 1H), 7.52 (ddd, J = 21.3, 6.8, 2.8 Hz, 3H), 7.43 (d, J = 3.6 Hz, 2H), 7.30-7.21 (m, 3H), 5.09 (dd, J = 13.3, 5.2 Hz, 1H), 4.41 (d, J = 17.0 Hz, 1H), 4.24 (dd, J = 16.1, 10.8 Hz, 2H), 3.32-3.11 (m, 4H), 3.08-2.79 (m, 4H), 2.67-2.51 (m, 8H), 2.34-2.24 (m, 1H), 2.04-1.82 (m, 5H), 1.81-1.41 (m, 8H), 1.16 (d, J = 2.0 Hz, 3H). | LCMS: $C_{48}H_{62}N_{12}O_6$ requires: 902, found: m/z = 903 $[M + H]^+$. |
| 21 | ¹H NMR (500 MHz, DMSO-$d_6$) δ 11.14 (s, 1H), 10.91 (s, 1H), 7.68 (d, J = 2.8 Hz, 1H), 7.60 (d, J = 4.8 Hz, 1H), 7.52-7.43 (m, 3H), 7.38 (d, J = 4.4 Hz, 2H), 7.26 (d, J = 2.8 Hz, 1H), 7.19 (d, J = 8.4 Hz, 2H), 5.06 (dd, J = 13.3, 5.1 Hz, 1H), 4.38 (d, J = 17.1 Hz, 1H), 4.22 (dd, J = 15.5, 10.4 Hz, 3H), 3.60-3.47 (m, 1H), 3.21-3.11 (m, 2H), 3.05-2.73 (m, 3H), 2.65-2.48 (m, 6H), 2.37-2.10 (m, 4H), 1.98-1.83 (m, 3H), 1.82-1.30 (m, 11H), 1.07 (s, 3H). | LCMS: $C_{43}H_{54}N_{10}O_5$ requires: 790, found: m/z = 791 $[M + H]^+$. |
| 22 | ¹H NMR (500 MHz, DMSO-$d_6$) δ 11.20 (d, J = 6.5 Hz, 1H), 11.06 (s, 1H), 7.77-7.65 (m, 4H), 7.61 (s, 1H), 7.50 (dd, J = 8.8, 2.4 Hz, 2H), 7.30-7.21 (m, 3H), 5.06 (dd, J = 12.8, 5.5 Hz, 1H), 4.27 (dd, J = 46.1, 13.1 Hz, 2H), 3.59-3.15 (m, 8H), 3.07-2.77 (m, 7H), 2.68-2.47 (m, 5H), 2.07-1.83 (m, 6H), 1.81-1.41 (m, 6H), 1.16 (d, J = 1.9 Hz, 3H). | LCMS: $C_{48}H_{60}N_{12}O_7$ requires: 916, found: m/z = 917 $[M + H]^+$. |
| 23 | ¹H NMR (500 MHz, DMSO-$d_6$) δ 11.13 (d, J = 4.1 Hz, 1H), 10.92 (s, 1H), 7.69 (s, 1H), 7.59 (s, 1H), 7.50 (dd, J = 6.2, 2.4 Hz, 1H), 7.46-7.37 (m, 4H), 7.26 (s, 1H), 7.07 (d, J = 8.4 Hz, 2H), 5.07 (dd, J = 13.3, 5.2 Hz, 1H), 4.43 (dd, J = 25.5, 15.3 Hz, 2H), 4.34-4.18 (m, 2H), 3.89 (d, J = 13.4 Hz, 1H), 3.31-3.11 (m, 4H), 3.06-2.79 (m, 4H), 2.70-2.46 (m, 8H), 2.40-2.21 (m, 3H), 2.00-1.89 (m, 1H), 1.83-1.18 (m, 12H). | LCMS: $C_{43}H_{52}N_{10}O_6$ requires: 804, found: m/z = 805 $[M + H]^+$. |

TABLE 2-continued

Physical Data for the Example Compounds of Table 1.

| Compound No. | $^1$H NMR | Mass Spec (LCMS) |
|---|---|---|
| 24 | $^1$H NMR (500 MHz, DMSO-d$_6$) δ 11.21 (d, J = 4.4 Hz, 1H), 11.09 (s, 1H), 7.76 (s, 1H), 7.66 (s, 1H), 7.58 (dd, J = 8.6, 7.1 Hz, 1H), 7.50 (d, J = 8.2 Hz, 2H), 7.33 (s, 1H), 7.19-7.11 (m, 3H), 7.04 (d, J = 7.0 Hz, 1H), 6.60 (s, 1H), 5.06 (dd, J = 12.7, 5.4 Hz, 1H), 4.53 (d, J = 12.8 Hz, 1H), 4.32 (dd, J = 32.0, 12.9 Hz, 2H), 3.98 (d, J = 13.4 Hz, 1H), 3.68-3.48 (m, 11H), 3.38-3.16 (m, 4H), 3.10-2.82 (m, 4H), 2.70 (s, 3H), 2.63-2.53 (m, 3H), 2.08-1.97 (m, 1H), 1.86-1.68 (m, 5H), 1.63-1.28 (m, 3H). | LCMS: $C_{47}H_{59}N_{11}O_{10}$ requires: 937, found: m/z = 938 [M + H]$^+$. |
| 25 | $^1$H NMR (500 MHz, DMSO-d$_6$) δ 11.13 (d, J = 2.7 Hz, 1H), 11.02 (s, 1H), 7.68 (s, 1H), 7.59 (s, 1H), 7.51 (dd, J = 8.5, 7.1 Hz, 1H), 7.44-7.38 (m, 2H), 7.26 (s, 1H), 7.07 (dd, J = 8.6, 6.7 Hz, 3H), 6.97 (d, J = 7.0 Hz, 1H), 6.53 (s, 1H), 4.97 (dd, J = 12.9, 5.4 Hz, 1H), 4.45 (d, J = 12.9 Hz, 1H), 4.34-4.14 (m, 2H), 3.91 (d, J = 13.4 Hz, 1H), 3.63 (t, J = 6.6 Hz, 2H), 3.58-3.44 (m, 8H), 3.44-3.34 (m, 3H), 3.29-3.09 (m, 4H), 3.04-2.75 (m, 4H), 2.62 (s, 4H), 1.92 (qd, J = 6.9, 4.2, 3.5 Hz, 1H), 1.78-1.20 (m, 7H). | LCMS: $C_{43}H_{51}N_{11}O_8$ requires: 849, found: m/z = 850 [M + H]$^+$. |
| 26 | $^1$H NMR (500 MHz, DMSO-d$_6$) δ 11.17 (d, J = 5.1 Hz, 1H), 10.92 (s, 1H), 7.69 (s, 1H), 7.60 (s, 1H), 7.52-7.45 (m, 3H), 7.40-7.36 (m, 2H), 7.30-7.18 (m, 3H), 5.06 (dd, J = 13.3, 5.1 Hz, 1H), 4.45-4.16 (m, 4H), 3.32-3.11 (m, 5H), 3.01-2.80 (m, 3H), 2.68-2.50 (m, 6H), 2.38-2.20 (m, 3H), 1.98-1.63 (m, 4H), 1.61-1.40 (m, 8H), 1.13 (s, 3H). | LCMS: $C_{44}H_{54}N_{10}O_6$ requires: 818, found: m/z = 819 [M + H]$^+$. |
| 27 | $^1$H NMR (500 MHz, DMSO-d$_6$) δ 11.17 (d, J = 4.1 Hz, 1H), 11.02 (s, 1H), 7.69 (s, 1H), 7.59 (s, 1H), 7.53-7.45 (m, 3H), 7.31-7.18 (m, 3H), 7.05 (d, J = 8.6 Hz, 1H), 6.96 (d, J = 7.0 Hz, 1H), 6.52 (s, 1H), 4.98 (dd, J = 12.8, 5.4 Hz, 1H), 4.27 (dd, J = 52.2, 13.5 Hz, 2H), 3.32-3.11 (m, 4H), 2.99-2.75 (m, 3H), 2.63 (d, J = 1.2 Hz, 2H), 2.60-2.45 (m, 4H), 2.02-1.43 (m, 10H), 1.13 (s, 3H). | LCMS: $C_{48}H_{61}N_{11}O_{10}$ requires: 951, found: m/z = 952 [M + H]$^+$. |
| 28 | $^1$H NMR (500 MHz, DMSO-d$_6$) δ 11.16 (d, J = 2.7 Hz, 1H), 11.02 (s, 1H), 7.69 (s, 1H), 7.60 (s, 1H), 7.51-7.43 (m, 4H), 7.26 (s, 1H), 7.22-7.18 (m, 2H), 7.05 (d, J = 8.6 Hz, 1H), 6.96 (d, J = 7.0 Hz, 1H), 6.50 (t, J = 5.8 Hz, 1H), 4.98 (dd, J = 12.7, 5.4 Hz, 1H), 4.27 (dd, J = 49.9, 13.2 Hz, 2H), 3.29-3.13 (m, 4H), 2.99-2.75 (m, 3H), 2.63 (s, 3H), 2.59-2.47 (m, 3H), 2.00-1.43 (m, 7H), 1.12 (s, 3H). | LCMS: $C_{44}H_{53}N_{11}O_8$ requires: 863, found: m/z = 864 [M + H]$^+$. |
| 29 | $^1$H NMR (500 MHz, DMSO-d$_6$) δ 11.08 (s, 1H), 7.77 (s, 1H), 7.70-7.62 (m, 4H), 7.57 (s, 1H), 7.39 (s, 2H), 7.33 (d, J = 16.2 Hz, 3H), 5.07 (dd, J = 12.8, 5.4 Hz, 2H), 4.36 (d, J = 12.3 Hz, 2H), 4.30 (d, J = 13.3 Hz, 2H), 3.62 (s, 4H), 3.05 (s, 2H), 3.01-2.85 (m, 6H), 2.67 (s, 6H), 2.41 (s, 3H), 2.05-1.99 (m, 2H), 1.83 (d, J = 11.8 Hz, 5H), 1.77 (d, J = 9.7 Hz, 3H), 1.69 (s, 5H), 1.58 (s, 3H), 1.25 (s, 1H). | LCMS $C_{42}H_{49}N_{11}O_6$ requires: 804, found: m/z = 805 [M + H]$^+$. |
| 30 | $^1$H NMR (500 MHz, DMSO-d$_6$) δ 11.44 (s, 1H), 11.09 (d, J = 10.0 Hz, 1H), 10.81 (s, 1H), 7.83 (s, 1H), 7.79-7.63 (m, 3H), 7.41 (s, 2H), 7.16 (d, J = 8.2 Hz, 1H), 6.93 (s, 1H), 6.84-6.73 (m, 1H), 5.08 (ddd, J = 15.5, 10.1, 5.4 Hz, 1H), 4.65-4.02 (m, 10H), 3.28 (dd, J = 9.9, 7.2 Hz, 3H), 3.10 (d, J = 15.2 Hz, 5H), 3.04-2.74 (m, 4H), 2.71 (s, 4H), 2.60 (d, J = 19.6 Hz, 2H), 2.04 (dq, J = 11.9, 6.0, 4.8 Hz, 1H), 1.81 (td, J = 18.8, 16.1, 10.1 Hz, 3H), 1.59 (d, J = 11.5 Hz, 1H). | LCMS: $C_{39}H_{43}N_{11}O_6$ expected: 761.8. Found [M + H]: 762.7 |
| 31 | $^1$H NMR (500 MHz, DMSO-d$_6$) δ 11.44 (d, J = 9.7 Hz, 1H), 11.09 (s, 1H), 9.58 (s, 1H), 7.83 (s, 1H), 7.80-7.62 (m, 3H), 7.51-7.25 (m, 4H), 7.16 (d, J = 8.5 Hz, 1H), 5.08 (dd, J = 12.8, 5.4 Hz, 1H), 4.58 (d, J = 15.3 Hz, 1H), 4.43-4.22 (m, 3H), 4.13 (d, J = 13.2 Hz, 2H), 3.10-2.85 (m, 8H), 2.70 (d, J = 2.7 Hz, 4H), 2.15-1.68 (m, 7H), 1.59 (d, J = 12.4 Hz, 1H), 1.31 (qd, J = 17.9, 16.1, 8.7 Hz, 2H). | LCMS $C_{42}H_{49}N_{11}O_6$ requires: 804, found: m/z = 805 [M + H]$^+$. |
| 32 | $^1$H NMR (500 MHz, DMSO-d$_6$) δ 11.20 (s, 1H), 11.07 (s, 1H), 7.76 (s, 1H), 7.67 (t, J = 4.3 Hz, 2H), 7.52 (d, J = 8.3 Hz, 2H), 7.32 (d, J = 21.4 Hz, 2H), 7.21 (t, J = 8.3 Hz, 3H), 5.06 (dd, J = 12.9, 5.4 Hz, 1H), 4.44-4.25 (m, 2H), 3.89 (s, 3H), 3.62 (d, J = | LCMS: $C_{44}H_{53}N_{11}O_6$ requires: 831, found: m/z = 832 [M + H]$^+$. |

TABLE 2-continued

Physical Data for the Example Compounds of Table 1.

| Compound No. | $^1$H NMR | Mass Spec (LCMS) |
|---|---|---|
| | 11.2 Hz, 1H), 3.10-2.81 (m, 6H), 2.73 (s, 3H), 2.69-2.57 (m, 2H), 2.41-2.26 (m, 1H), 2.22-1.45 (m, 19H), 1.26 (d, J = 17.1 Hz, 4H). | |
| 33 | $^1$H NMR (500 MHz, DMSO-d$_6$) δ 11.01 (s, 1H), 10.91 (s, 1H), 7.70 (s, 1H), 7.61-7.54 (m, 2H), 7.50-7.44 (m, 2H), 7.40-7.34 (m, 2H), 7.26 (d, J = 2.8 Hz, 1H), 6.38 (d, J = 8.7 Hz, 2H), 5.15 (dd, J = 13.3, 5.2 Hz, 1H), 4.48 (d, J = 17.1 Hz, 1H), 4.41-4.19 (m, 3H), 3.81 (s, 4H), 3.60 (d, J = 5.6 Hz, 1H), 3.24 (s, 4H), 2.96 (dt, J = 36.5, 13.5 Hz, 4H), 2.72 (s, 3H), 2.65 (dd, J = 9.7, 5.5 Hz, 3H), 2.39-2.30 (m, 2H), 2.07-1.99 (m, 1H), 1.87-1.70 (m, 3H), 1.62 (t, J = 7.5 Hz, 2H), 1.24 (d, J = 9.4 Hz, 1H). | LCMS: $C_{41}H_{49}N_{11}O_5$ requires: 775, found: m/z = 776 [M + H]$^+$. |
| 34 | $^1$H NMR (500 MHz, DMSO-d$_6$) δ 11.08 (s, 1H), 10.94 (s, 1H), 7.73-7.65 (m, 2H), 7.60 (s, 1H), 7.41 (d, J = 8.7 Hz, 2H), 7.27 (d, J = 3.0 Hz, 1H), 6.84 (d, J = 2.0 Hz, 1H), 6.70 (dd, J = 8.4, 2.1 Hz, 1H), 6.44 (d, J = 8.6 Hz, 2H), 5.07 (dd, J = 12.8, 5.4 Hz, 1H), 4.37 (d, J = 12.4 Hz, 1H), 4.26 (s, 4H), 3.99 (s, 4H), 3.05-2.83 (m, 3H), 2.73 (s, 3H), 2.67-2.55 (m, 2H), 2.08-1.97 (m, 1H), 1.91-1.69 (m, 3H), 1.56 (d, J = 12.9 Hz, 1H). | LCMS: $C_{38}H_{41}N_{11}O_6$ requires: 747, found: m/z = 748 [M + H]$^+$. |
| 35 | $^1$H NMR (500 MHz, DMSO-d$_6$) δ 11.27 (s, 1H), 11.07 (s, 1H), 7.77 (d, J = 2.8 Hz, 1H), 7.70-7.62 (m, 2H), 7.55 (d, J = 8.5 Hz, 2H), 7.35 (d, J = 2.8 Hz, 1H), 7.27 (d, J = 8.5 Hz, 2H), 6.91 (d, J = 2.2 Hz, 1H), 6.83 (dd, J = 8.6, 2.2 Hz, 1H), 5.06 (dd, J = 12.9, 5.4 Hz, 1H), 4.39 (d, J = 12.4 Hz, 1H), 4.30 (d, J = 13.3 Hz, 1H), 3.76-3.44 (m, 6H), 3.44-3.19 (m, 5H), 3.18-2.83 (m, 6H), 2.73 (s, 3H), 2.66-2.30 (m, 5H), 2.20-1.96 (m, 2H), 1.91-1.68 (m, 4H), 1.61-1.54 (m, 1H). | LCMS: $C_{41}H_{47}N_{11}O_6$ requires 789, found: m/z = 790 [M + H]$^+$. |
| 36 | $^1$H NMR (500 MHz, DMSO-d$_6$) δ 11.28 (s, 1H), 11.01 (s, 1H), 7.78 (d, J = 2.8 Hz, 1H), 7.68 (s, 1H), 7.62-7.53 (m, 3H), 7.50-7.46 (m, 2H), 7.36 (d, J = 2.9 Hz, 1H), 7.27 (d, J = 8.1 Hz, 2H), 5.15 (dd, J = 13.3, 5.1 Hz, 1H), 4.48 (d, J = 17.1 Hz, 1H), 4.34 (dd, J = 24.1, 12.5 Hz, 3H), 3.69-3.54 (m, 1H), 3.42-3.19 (m, 4H), 3.09-2.88 (m, 3H), 2.76-2.23 (m, 14H), 2.06-1.99 (m, 1H), 1.89-1.72 (m, 3H), 1.69-1.54 (m, 3H), 1.48-1.32 (m, 2H). | LCMS: $C_{40}H_{48}N_{10}O_5$ requires 748, found: m/z = 749 [M + H]$^+$. |
| 37 | $^1$H NMR (500 MHz, DMSO-d$_6$) δ 11.26 (s, 1H), 11.08 (s, 1H), 7.77 (d, J = 2.9 Hz, 1H), 7.70-7.64 (m, 2H), 7.55 (d, J = 8.3 Hz, 2H), 7.37-7.29 (m, 2H), 7.30-7.23 (m, 3H), 5.08 (dd, J = 12.8, 5.4 Hz, 1H), 4.40 (d, J = 12.6 Hz, 1H), 4.30 (d, J = 13.6 Hz, 1H), 3.88 (dt, J = 13.5, 4.5 Hz, 2H), 3.67-3.49 (m, 4H), 3.41-3.22 (m, 2H), 3.16 (ddd, J = 13.0, 9.8, 3.1 Hz, 2H), 3.10-2.83 (m, 5H), 2.72 (s, 3H), 2.65-2.53 (m, 2H), 2.42-2.33 (m, 1H), 2.08-1.96 (m, 1H), 1.86-1.71 (m, 6H), 1.60-1.50 (m, 1H), 1.33-1.22 (m, 3H). | LCMS: $C_{41}H_{47}N_{11}O_6$ requires 789, found: m/z = 790 [M + H]$^+$. |
| 38 | $^1$H NMR (500 MHz, DMSO-d$_6$) δ 11.06 (s, 1H), 10.99 (s, 1H), 7.71 (d, J = 3.0 Hz, 1H), 7.65-7.58 (m, 2H), 7.42 (d, J = 8.8 Hz, 2H), 7.27 (d, J = 2.9 Hz, 1H), 6.94-6.86 (m, 2H), 6.89-6.79 (m, 2H), 5.05 (dd, J = 12.9, 5.4 Hz, 1H), 4.35 (d, J = 12.1 Hz, 1H), 4.27 (d, J = 13.4 Hz, 1H), 3.68 (d, J = 10.3 Hz, 2H), 3.60 (ddt, J = 10.9, 7.8, 4.3 Hz, 1H), 3.46 (d, J = 9.4 Hz, 2H), 3.38-3.33 (m, 2H), 3.30-3.17 (m, 3H), 3.08 (t, J = 4.7 Hz, 4H), 3.05-2.82 (m, 3H), 2.70 (s, 3H), 2.65-2.53 (m, 5H), 2.48-2.44 (m, 1H), 2.35 (d, J = 6.8 Hz, 2H), 2.01 (ddt, J = 12.5, 7.3, 4.4 Hz, 1H), 1.80 (s, 2H), 1.74 (td, J = 12.2, 4.1 Hz, 1H), 1.66 (s, 1H), 1.56 (s, 1H), 0.76 (tt, J = 6.5, 3.3 Hz, 1H). | LCMS: $C_{43}H_{50}N_{12}O_6$ requires: 830, found: m/z = 831 [M + H]$^+$. |
| 39 | $^1$H NMR (500 MHz, DMSO-d$_6$) δ 11.20 (s, 1H), 11.06 (s, 1H), 7.75 (s, 1H), 7.67-7.60 (m, 2H), 7.50 (d, J = 8.2 Hz, 2H), 7.33 (s, 1H), 7.16 (d, J = 8.2 Hz, 2H), 6.92 (s, 1H), 6.82 (d, J = 8.3 Hz, 1H), 5.05 (dd, J = 12.9, 5.4 Hz, 1H), 4.31 (dd, J = 31.1, 12.9 Hz, 2H), 3.67 (d, J = 10.2 Hz, 2H), 3.61 (tt, J = 10.1, 4.1 Hz, 1H), 3.46 (d, J = 9.5 Hz, 2H), 3.36 (d, J = 8.3 Hz, 1H), 3.29-3.24 (m, 3H), 3.12-2.83 | LCMS: $C_{44}H_{51}N_{11}O_6$ requires: 829, found: m/z = 830 [M + H]$^+$. |

TABLE 2-continued

Physical Data for the Example Compounds of Table 1.

| Compound No. | $^1$H NMR | Mass Spec (LCMS) |
|---|---|---|
| | (m, 5H), 2.71 (s, 3H), 2.56 (td, J = 14.9, 14.4, 4.1 Hz, 2H), 2.42 (d, J = 11.9 Hz, 1H), 2.36 (s, 3H), 2.09 (s, 2H), 2.00 (dt, J = 12.0, 5.3 Hz, 1H), 1.85-1.70 (m, 4H), 1.70-1.51 (m, 5H), 0.75 (s, 1H). | |
| 40 | $^1$H NMR (500 MHz, DMSO-d$_6$) δ 11.07 (s, 1H), 10.98 (s, 1H), 7.70 (d, J = 2.9 Hz, 1H), 7.67-7.58 (m, 2H), 7.42 (d, J = 8.8 Hz, 2H), 7.33-7.20 (m, 3H), 6.87 (d, J = 8.8 Hz, 2H), 5.06 (dd, J = 12.8, 5.4 Hz, 1H), 4.35 (d, J = 12.5 Hz, 1H), 4.27 (d, J = 13.3 Hz, 1H), 4.04 (d, J = 13.1 Hz, 2H), 3.60 (ddt, J = 11.1, 8.4, 4.3 Hz, 1H), 3.35 (dd, J = 9.9, 5.9 Hz, 2H), 3.30-3.21 (m, 5H), 3.09-2.98 (m, 4H), 3.00-2.82 (m, 4H), 2.70 (s, 3H), 2.65-2.53 (m, 3H), 2.37 (t, J = 7.4 Hz, 2H), 2.01 (ddt, J = 11.3, 6.3, 4.0 Hz, 1H), 1.84-1.70 (m, 5H), 1.64 (s, 2H), 1.43 (q, J = 7.2 Hz, 2H), 1.26-1.15 (m, 3H). | LCMS: $C_{44}H_{54}N_{12}O_6$ requires: 846, found: m/z = 847 [M + H]$^+$. |
| 41 | $^1$H NMR (500 MHz, DMSO-d$_6$) δ 11.19 (s, 1H), 11.07 (s, 1H), 7.75 (d, J = 2.9 Hz, 1H), 7.65 (d, J = 7.7 Hz, 2H), 7.49 (d, J = 8.3 Hz, 2H), 7.34-7.28 (m, 2H), 7.23 (d, J = 8.9 Hz, 2H), 7.15 (d, J = 8.2 Hz, 2H), 5.06 (dd, J = 12.8, 5.4 Hz, 1H), 4.35 (d, J = 12.4 Hz, 1H), 4.28 (d, J = 13.3 Hz, 1H), 4.04 (d, J = 13.0 Hz, 2H), 3.62 (dq, J = 11.0, 6.3, 5.1 Hz, 1H), 3.38-3.35 (m, 2H), 3.28-3.22 (m, 4H), 3.06-2.93 (m, 5H), 2.95-2.84 (m, 2H), 2.71 (s, 3H), 2.65-2.53 (m, 2H), 2.46-2.35 (m, 3H), 2.00 (s, 2H), 1.86-1.71 (m, 6H), 1.60 (p, J = 10.6, 9.1 Hz, 4H), 1.43 (t, J = 7.6 Hz, 2H), 1.20 (qd, J = 12.5, 3.9 Hz, 2H). | LCMS: $C_{45}H_{55}N_{11}O_6$ requires: 845, found: m/z = 846 [M + H]$^+$. |
| 42 | $^1$H NMR (500 MHz, DMSO-d$_6$) δ 11.07 (s, 1H), 11.00 (s, 1H), 7.72 (d, J = 2.9 Hz, 1H), 7.68-7.60 (m, 2H), 7.44 (d, J = 8.8 Hz, 2H), 7.29 (d, J = 2.9 Hz, 1H), 6.94-6.87 (m, 3H), 6.83 (dd, J = 8.6, 2.2 Hz, 1H), 5.06 (dd, J = 12.9, 5.4 Hz, 1H), 4.36 (d, J = 12.3 Hz, 1H), 4.28 (d, J = 13.3 Hz, 1H), 3.65-3.55 (m, 1H), 3.54-3.48 (m, 1H), 3.47-3.20 (m, 5H), 3.17 (dd, J = 10.3, 6.9 Hz, 1H), 3.13-3.07 (m, 4H), 3.06-2.83 (m, 3H), 2.76-2.31 (m, 14H), 2.20-2.12 (m, 1H), 2.07-1.98 (m, 1H), 1.87-1.70 (m, 3H), 1.59-1.50 (m, 1H). | LCMS: $C_{42}H_{50}N_{12}O_6$ requires: 818, found: m/z = 819 [M + H]$^+$. |
| 43 | $^1$H NMR (500 MHz, DMSO-d$_6$) δ 11.07 (s, 1H), 10.99 (s, 1H), 7.72 (d, J = 2.8 Hz, 1H), 7.67-7.60 (m, 2H), 7.43 (d, J = 8.9 Hz, 2H), 7.31-7.26 (m, 1H), 6.89 (d, J = 9.0 Hz, 2H), 6.77 (d, J = 2.1 Hz, 1H), 6.64 (dd, J = 8.3, 2.1 Hz, 1H), 5.06 (dd, J = 12.8, 5.4 Hz, 1H), 4.36 (d, J = 12.6 Hz, 1H), 4.28 (d, J = 13.3 Hz, 1H), 4.16 (t, J = 8.2 Hz, 2H), 3.71 (dd, J = 8.3, 5.7 Hz, 2H), 3.66-3.58 (m, 1H), 3.39-3.20 (m, 4H), 3.12-2.78 (m, 8H), 2.71 (s, 3H), 2.65-2.41 (m, 5H), 2.38-2.32 (m, 2H), 2.07-1.94 (m, 1H), 1.90-1.70 (m, 6H), 1.59-1.53 (m, 1H). | LCMS: $C_{42}H_{50}N_{12}O_6$ requires 818, found: m/z = 819 [M + H]$^+$. |
| 44 | $^1$H NMR (500 MHz, DMSO-d$_6$) δ 11.19 (s, 1H), 11.07 (s, 1H), 7.76 (d, J = 2.8 Hz, 1H), 7.70-7.63 (m, 2H), 7.51 (d, J = 8.5 Hz, 2H), 7.34 (d, J = 2.7 Hz, 1H), 7.18 (d, J = 8.5 Hz, 2H), 6.91 (d, J = 2.2 Hz, 1H), 6.83 (dd, J = 8.6, 2.2 Hz, 1H), 5.07 (dd, J = 12.9, 5.4 Hz, 1H), 4.38 (d, J = 12.3 Hz, 1H), 4.30 (d, J = 13.2 Hz, 1H), 3.69-3.47 (m, 2H), 3.33 (s, 4H), 3.18 (dd, J = 10.3, 6.8 Hz, 1H), 3.10-2.82 (m, 3H), 2.75 (s, 3H), 2.51 (p, J = 1.8 Hz, 9H), 2.19-1.97 (m, 4H), 1.90-1.47 (m, 10H). | LCMS: $C_{43}H_{51}N_{11}O_6$ requires: 817, found: m/z = 818 [M + H]$^+$. |
| 45 | $^1$H NMR (500 MHz, DMSO-d$_6$) δ 11.20 (s, 1H), 11.07 (s, 1H), 7.76 (d, J = 2.7 Hz, 1H), 7.69-7.62 (m, 2H), 7.57-7.48 (m, 2H), 7.34 (d, J = 2.9 Hz, 1H), 7.17 (d, J = 8.5 Hz, 2H), 6.77 (d, J = 2.1 Hz, 1H), 6.64 (dd, J = 8.4, 2.1 Hz, 1H), 5.05 (dd, J = 13.0, 5.3 Hz, 1H), 4.37 (d, J = 12.3 Hz, 1H), 4.30 (d, J = 13.2 Hz, 1H), 4.16 (t, J = 8.2 Hz, 2H), 3.70 (dd, J = 8.4, 5.7 Hz, 2H), 3.67-3.57 (m, 1H), 3.40-3.23 (m, 4H), 3.10-2.75 (m, 5H), 2.73 (s, 3H), 2.66-2.36 (m, 6H), 2.33 (t, J = 7.1 Hz, 2H), 2.05-1.94 (m, 3H), 1.88-1.69 (m, 7H), 1.67-1.56 (m, 1H). | LCMS: $C_{43}H_{51}N_{11}O_6$ requires: 817, found: m/z = 818 [M + H]$^+$. |

TABLE 2-continued

Physical Data for the Example Compounds of Table 1.

| Compound No. | ¹H NMR | Mass Spec (LCMS) |
|---|---|---|
| 46 | ¹H NMR (500 MHz, DMSO-d₆) δ 11.08 (s, 1H), 10.99 (s, 1H), 7.74-7.70 (m, 1H), 7.67 (d, J = 8.5 Hz, 1H), 7.62 (s, 1H), 7.44 (d, J = 8.5 Hz, 2H), 7.29 (d, J = 4.4 Hz, 2H), 7.22 (dd, J = 8.6, 2.3 Hz, 1H), 6.90 (d, J = 8.5 Hz, 2H), 5.07 (dd, J = 13.0, 5.3 Hz, 1H), 4.32 (dd, J = 41.4, 13.0 Hz, 2H), 3.89 (dd, J = 24.1, 13.2 Hz, 2H), 3.62 (dd, J = 12.1, 7.9 Hz, 1H), 3.27 (dt, J = 17.7, 7.6 Hz, 2H), 3.12 (t, J = 4.9 Hz, 5H), 3.06-2.81 (m, 4H), 2.70 (s, 3H), 2.40-2.29 (m, 1H), 2.18 (dd, J = 12.2, 5.8 Hz, 1H), 2.08-1.45 (m, 7H). | LCMS: $C_{43}H_{52}N_{12}O_6$ requires: 832, found: m/z = 833 $[M + H]^+$. |
| 47 | ¹H NMR (500 MHz, DMSO-d₆) δ 11.22 (s, 1H), 11.09 (s, 1H), 7.76 (d, J = 2.7 Hz, 1H), 7.74-7.63 (m, 2H), 7.52 (d, J = 8.5 Hz, 2H), 7.43-7.27 (m, 3H), 7.16 (d, J = 8.3 Hz, 2H), 5.09 (dd, J = 13.0, 5.4 Hz, 1H), 4.42-4.17 (m, 4H), 3.60 (d, J = 11.1 Hz, 1H), 3.26-3.16 (m, 3H), 3.16-3.04 (m, 2H), 3.04-2.78 (m, 5H), 2.61 (s, 5H), 2.07-1.98 (m, 1H), 1.91-1.71 (m, 5H), 1.71-1.46 (m, 3H). | LCMS $C_{38}H_{42}N_{10}O_6$ requires: 735, found: m/z = 736 $[M + H]^+$. |
| 48 | ¹H NMR (500 MHz, DMSO-d₆) δ 11.10 (d, J = 8.5 Hz, 2H), 9.37 (s, 1H), 7.82-7.66 (m, 2H), 7.65 (s, 1H), 7.60-7.46 (m, 2H), 7.41 (d, J = 2.3 Hz, 1H), 7.39-7.27 (m, 2H), 6.98 (d, J = 8.7 Hz, 2H), 5.09 (dd, J = 12.7, 5.4 Hz, 1H), 4.33 (dd, J = 26.6, 12.8 Hz, 2H), 4.02 (dd, J = 63.9, 12.6 Hz, 2H), 3.73 (t, J = 13.8 Hz, 4H), 3.33-3.07 (m, 10H), 3.07-2.77 (m, 7H), 2.72 (s, 3H), 2.18 (d, J = 10.2 Hz, 1H), 2.10-1.96 (m, 1H), 1.96-1.88 (m, 1H), 1.86-1.76 (m, 4H), 1.69-1.53 (m, 2H), 1.34 (q, J = 11.7 Hz, 1H). | LCMS $C_{43}H_{52}N_{12}O_6$ requires: 833, found: m/z = 833.3 $[M + H]^+$. |
| 49 | ¹H NMR (500 MHz, DMSO-d₆) δ 11.08 (s, 1H), 11.00 (s, 1H), 7.72 (s, 1H), 7.66 (d, J = 8.6 Hz, 1H), 7.62 (s, 1H), 7.46-7.37 (m, 2H), 7.32 (d, J = 2.3 Hz, 1H), 7.31-7.22 (m, 2H), 6.92-6.86 (m, 2H), 5.77 (s, 1H), 5.07 (dd, J = 12.9, 5.4 Hz, 1H), 4.36 (d, J = 12.4 Hz, 1H), 4.28 (d, J = 13.0 Hz, 1H), 4.06 (d, J = 13.2 Hz, 2H), 3.62 (s, 1H), 3.42-3.32 (m, 4H), 3.28 (dd, J = 13.1, 7.0 Hz, 2H), 3.08 (s, 3H), 3.06-2.85 (m, 4H), 2.71 (s, 3H), 2.63-2.54 (m, 2H), 2.21 (d, J = 7.0 Hz, 2H), 2.02 (d, J = 12.2 Hz, 1H), 1.83 (d, J = 13.2 Hz, 8H), 1.56 (d, J = 12.2 Hz, 1H), 1.21 (dd, J = 24.7, 13.6 Hz, 2H), 1.10 (t, J = 7.0 Hz, 4H). | LCMS $C_{43}H_{52}N_{12}O_6$ requires: 833, found: m/z = 833.6 $[M + H]^+$. |
| 50 | ¹H NMR (500 MHz, DMSO-d₆) δ 11.20 (s, 1H), 11.07 (s, 1H), 7.77 (s, 1H), 7.67 (t, J = 4.3 Hz, 2H), 7.52 (d, J = 8.1 Hz, 2H), 7.32 (d, J = 24.4 Hz, 2H), 7.21 (t, J = 9.3 Hz, 3H), 5.07 (dd, J = 12.9, 5.4 Hz, 1H), 4.34 (dd, J = 40.2, 12.9 Hz, 2H), 3.90 (s, 2H), 3.62 (d, J = 10.6 Hz, 2H), 3.07-2.78 (m, 10H), 2.73 (s, 4H), 1.88-1.65 (m, 11H), 1.57 (d, J = 20.1 Hz, 2H), 1.28 (d, J = 11.0 Hz, 2H). | LCMS $C_{44}H_{53}N_{11}O_6$ requires: 832, found: m/z = 833 $[M + H]^+$. |
| 51 | ¹H NMR (500 MHz, DMSO-d₆) δ 11.20 (s, 1H), 11.08 (s, 1H), 7.76 (s, 1H), 7.71-7.61 (m, 2H), 7.54-7.48 (m, 2H), 7.37-7.30 (m, 2H), 7.25 (dd, J = 8.9, 2.4 Hz, 1H), 7.18 (d, J = 8.5 Hz, 2H), 5.08 (dd, J = 12.8, 5.4 Hz, 1H), 4.34 (dd, J = 39.9, 12.8 Hz, 2H), 4.06 (d, J = 13.1 Hz, 2H), 3.62 (d, J = 11.3 Hz, 1H), 3.11-2.80 (m, 8H), 2.73 (s, 4H), 2.69-2.55 (m, 3H), 2.20 (s, 2H), 2.09-1.96 (m, 3H), 1.88-1.70 (m, 9H), 1.70-1.48 (m, 4H), 1.17 (d, J = 12.6 Hz, 2H). | LCMS $C_{44}H_{53}N_{11}O_6$ requires: 832, found: m/z = 833 $[M + H]^+$. |
| 52 | ¹H NMR (500 MHz, DMSO-d₆) δ 11.19 (s, 1H), 11.08 (s, 1H), 7.76 (d, J = 2.8 Hz, 1H), 7.66 (d, J = 9.5 Hz, 2H), 7.51 (d, J = 8.2 Hz, 2H), 7.34 (d, J = 3.0 Hz, 1H), 7.18 (d, J = 8.2 Hz, 2H), 6.91 (d, J = 2.2 Hz, 1H), 6.82 (dd, J = 8.5, 2.2 Hz, 1H), 5.07 (dd, J = 12.9, 5.4 Hz, 1H), 4.38 (d, J = 12.5 Hz, 1H), 4.29 (d, J = 13.3 Hz, 1H), 3.57 (dddd, J = 38.9, 22.7, 9.5, 5.5 Hz, 4H), 3.17 (dd, J = 10.4, 6.7 Hz, 2H), 3.11-2.82 (m, 6H), 2.75 (s, 3H), 2.68-2.56 (m, 3H), 2.44-2.34 (m, 3H), 2.20-2.05 (m, 2H), 1.91-1.46 (m, 10H). | LCMS $C_{43}H_{51}N_{11}O_6$ requires: 818, found: m/z = 819 $[M + H]^+$. |

TABLE 2-continued

Physical Data for the Example Compounds of Table 1.

| Compound No. | $^1$H NMR | Mass Spec (LCMS) |
|---|---|---|
| 53 | $^1$H NMR (500 MHz, DMSO-d$_6$) δ 11.30 (s, 1H), 11.10 (s, 1H), 10.08 (s, 1H), 7.86-7.74 (m, 2H), 7.69 (s, 1H), 7.58 (d, J = 8.3 Hz, 2H), 7.36 (s, 1H), 7.19 (d, J = 8.2 Hz, 2H), 6.95 (s, 1H), 6.80 (d, J = 8.3 Hz, 1H), 5.09 (dd, J = 12.8, 5.3 Hz, 1H), 4.36 (d, J = 44.5 Hz, 7H), 2.73 (s, 3H), 2.08 (d, J = 37.7 Hz, 3H), 1.90-1.72 (m, 6H), 1.58 (d, J = 13.4 Hz, 1H). | LCMS C$_{41}$H$_{47}$N$_{11}$O$_6$ requires: 790, found: m/z = 791 [M + H]$^+$. |
| 54 | $^1$H NMR (500 MHz, DMSO-d$_6$) δ 11.20 (s, 1H), 11.08 (s, 1H), 7.81-7.72 (m, 1H), 7.69-7.61 (m, 2H), 7.51 (d, J = 8.2 Hz, 2H), 7.34 (d, J = 2.8 Hz, 1H), 7.18 (d, J = 8.5 Hz, 2H), 6.79 (d, J = 2.1 Hz, 1H), 6.66 (dd, J = 8.3, 2.1 Hz, 1H), 5.07 (dd, J = 12.8, 5.4 Hz, 1H), 4.33 (dd, J = 34.4, 12.7 Hz, 2H), 4.16 (t, J = 8.2 Hz, 2H), 3.81-3.68 (m, 2H), 3.63 (t, J = 10.9 Hz, 1H), 3.09-2.82 (m, 7H), 2.73 (s, 3H), 2.68-2.59 (m, 4H), 2.05 (ddd, J = 20.5, 11.7, 8.1 Hz, 3H), 1.92-1.71 (m, 6H), 1.60 (q, J = 12.2 Hz, 4H). | LCMS C$_{42}$H$_{49}$N$_{11}$O$_6$ requires: 804, found: m/z = 805 [M + H]$^+$. |
| 55 | $^1$H NMR (500 MHz, DMSO-d$_6$) δ 11.09 (s, 2H), 7.81 (s, 2H), 7.75-7.59 (m, 4H), 7.43-7.32 (m, 4H), 7.27 (dd, J = 8.7, 2.3 Hz, 2H), 5.08 (dd, J = 12.8, 5.4 Hz, 2H), 4.34 (dd, J = 24.7, 13.0 Hz, 5H), 3.58 (dt, J = 52.0, 4.9 Hz, 9H), 3.43-3.20 (m, 8H), 3.14-2.81 (m, 6H), 2.72 (s, 5H), 2.67-2.54 (m, 3H), 2.03 (ddd, J = 12.6, 5.7, 3.1 Hz, 2H), 1.92-1.48 (m, 30H). | LCMS: C$_{42}$H$_{49}$N$_{11}$O$_6$ requires: 803, found: m/z = 804 [M + H]$^+$. |
| 56 | $^1$H NMR (500 MHz, DMSO-d$_6$) δ 11.13 (s, 2H), 11.03 (s, 1H), 9.00 (s, 1H), 7.76 (s, 1H), 7.70-7.59 (m, 2H), 7.56-7.46 (m, 4H), 7.32 (s, 1H), 5.17 (dd, J = 13.3, 5.1 Hz, 1H), 4.55-4.24 (m, 4H), 3.63 (dq, J = 11.2, 5.3, 4.6 Hz, 1H), 3.43-2.88 (m, 18H), 2.71 (s, 5H), 2.67-2.59 (m, 1H), 2.44-2.33 (m, 1H), 2.04 (ddd, J = 7.4, 5.3, 2.4 Hz, 1H), 1.92-1.42 (m, 17H). | LCMS: C$_{46}$H$_{59}$N$_{11}$O$_5$ requires: 845, found: m/z = 846 [M + H]$^+$. |
| 57 | $^1$H NMR (500 MHz, DMSO-d$_6$) δ 11.00 (s, 2H), 7.76 (d, J = 48.5 Hz, 6H), 7.59 (dd, J = 5.1, 3.5 Hz, 2H), 7.48 (d, J = 3.4 Hz, 4H), 5.16 (dd, J = 13.3, 5.2 Hz, 2H), 4.53-4.26 (m, 6H), 3.61 (q, J = 6.2 Hz, 5H), 3.53-3.19 (m, 22H), 3.13-2.87 (m, 5H), 2.77-2.55 (m, 15H), 2.09-1.28 (m, 34H). | LCMS: C$_{48}$H$_{61}$N$_{11}$O$_7$ requires: 903, found: m/z = 904 [M + H]$^+$. |
| 58 | $^1$H NMR (500 MHz, DMSO-d$_6$) δ 11.25 (s, 1H), 11.08 (s, 1H), 7.97 (s, 1H), 7.83-7.72 (m, 1H), 7.67 (d, J = 9.2 Hz, 2H), 7.57 (d, J = 8.4 Hz, 2H), 7.34 (d, J = 7.5 Hz, 4H), 7.26 (dd, J = 8.6, 2.4 Hz, 1H), 5.07 (dd, J = 12.9, 5.4 Hz, 1H), 4.35 (dd, J = 56.3, 12.9 Hz, 2H), 3.70-3.52 (m, 4H), 3.00 (dt, J = 26.6, 12.2 Hz, 3H), 2.90 (s, 7H), 2.73 (d, J = 12.7 Hz, 9H), 2.15-1.95 (m, 4H), 1.79 (dt, J = 20.2, 13.5 Hz, 6H), 1.69-1.46 (m, 2H). | LCMS C$_{39}$H$_{44}$N$_{10}$O$_6$ requires: 749, found: m/z = 750 [M + H]$^+$. |
| 59 | $^1$H NMR (500 MHz, DMSO-d$_6$) δ 11.09 (d, J = 14.6 Hz, 2H), 9.46 (s, 1H), 7.83-7.68 (m, 2H), 7.64 (s, 1H), 7.51 (d, J = 8.8 Hz, 2H), 7.30 (s, 1H), 7.02-6.91 (m, 3H), 6.85 (dd, J = 8.7, 2.2 Hz, 1H), 5.06 (dd, J = 12.8, 5.4 Hz, 1H), 4.31 (dd, J = 26.3, 12.6 Hz, 2H), 3.86-3.54 (m, 12H), 3.34-3.15 (m, 13H), 3.13-2.81 (m, 9H), 2.71 (s, 4H), 2.59 (d, J = 18.6 Hz, 3H), 2.07-1.95 (m, 1H), 1.90-1.75 (m, 5H), 1.67-1.51 (m, 1H). | LCMS C$_{42}$H$_{50}$N$_{12}$O$_6$ requires: 819, found: m/z = 820 [M + H]$^+$. |
| 60 | $^1$H NMR (500 MHz, DMSO-d$_6$) δ 11.09 (d, J = 12.6 Hz, 2H), 9.71 (s, 1H), 7.74 (s, 1H), 7.69 (d, J = 8.2 Hz, 1H), 7.64 (s, 1H), 7.51 (d, J = 8.9 Hz, 2H), 7.30 (s, 1H), 6.97 (d, J = 8.9 Hz, 2H), 6.83 (d, J = 2.1 Hz, 1H), 6.70 (dd, J = 8.4, 2.1 Hz, 1H), 5.07 (dd, J = 12.8, 5.5 Hz, 1H), 4.27 (t, J = 8.2 Hz, 4H), 3.87 (dd, J = 8.5, 5.7 Hz, 3H), 3.39-3.17 (m, 11H), 3.12-2.81 (m, 7H), 2.71 (s, 4H), 2.67-2.57 (m, 2H), 2.02 (dq, J = 9.7, 4.5, 4.0 Hz, 1H), 1.88-1.73 (m, 3H), 1.64-1.50 (m, 1H). | LCMS C$_{41}$H$_{48}$N$_{12}$O$_6$ requires: 805, found: m/z = 806 [M + H]$^+$. |
| 61 | $^1$H NMR (500 MHz, DMSO-d$_6$) δ 10.94 (d, J = 33.3 Hz, 2H), 7.65 (s, 1H), 7.55 (d, J = 2.2 Hz, 1H), 7.48 (d, J = 1.4 Hz, 1H), 7.45-7.35 (m, 4H), 7.22 (s, 1H), 6.86 (d, J = 8.3 Hz, 2H), 5.03 (dd, J = 13.3, 5.1 Hz, 1H), 4.39-4.12 (m, 5H), 3.55 (t, J = 6.4 Hz, 8H), 3.36-3.13 (m, 6H), 3.09-2.77 (m, 7H), 2.72-2.49 (m, 7H), 1.98-1.36 (m, 9H). | LCMS: C$_{43}$H$_{53}$N$_{11}$O$_7$ requires: 835, found: m/z = 836 [M + H]$^+$. |

TABLE 2-continued

Physical Data for the Example Compounds of Table 1.

| Compound No. | $^1$H NMR | Mass Spec (LCMS) |
|---|---|---|
| 62 | $^1$H NMR (500 MHz, Methanol-d$_4$) δ 7.89 (q, J = 2.2 Hz, 1H), 7.75 (d, J = 8.5 Hz, 1H), 7.61 (s, 1H), 7.51-7.39 (m, 2H), 7.34 (dd, J = 8.4, 2.4 Hz, 1H), 7.23 (t, J = 8.1 Hz, 1H), 7.12-7.01 (m, 1H), 5.09 (dd, J = 12.4, 5.5 Hz, 1H), 4.34 (dd, J = 38.9, 13.0 Hz, 3H), 4.17 (s, 1H), 3.79-3.68 (m, 2H), 3.46-3.34 (m, 6H), 3.03 (t, J = 12.2 Hz, 2H), 2.86 (ddd, J = 17.9, 14.2, 5.3 Hz, 2H), 2.77 (s, 4H), 2.75-2.69 (m, 1H), 2.66 (t, J = 6.5 Hz, 2H), 2.13 (tt, J = 10.2, 5.9 Hz, 3H), 1.96-1.80 (m, 3H), 1.66 (q, J = 12.6, 11.9 Hz, 1H). | LCMS C$_{41}$H$_{48}$N$_{12}$O$_7$ requires: 821, found: m/z = 822 [M + H]$^+$. |
| 63 | $^1$H NMR (500 MHz, Methanol-d$_4$) δ 8.00 (d, J = 18.8 Hz, 1H), 7.79-7.70 (m, 2H), 7.70-7.57 (m, 2H), 7.28 (ddd, J = 8.1, 2.1, 1.1 Hz, 1H), 7.20 (t, J = 8.0 Hz, 1H), 7.14-7.02 (m, 1H), 5.12 (ddd, J = 12.6, 5.5, 1.4 Hz, 1H), 4.38 (dd, J = 40.7, 13.3 Hz, 2H), 3.92 (p, J = 7.6 Hz, 1H), 3.72 (ddd, J = 14.8, 10.5, 4.0 Hz, 1H), 3.41 (ddt, J = 10.2, 7.1, 3.0 Hz, 4H), 3.35-3.25 (m, 31H), 3.18 (dd, J = 9.2, 6.1 Hz, 4H), 3.01 (t, J = 12.1 Hz, 1H), 2.89-2.78 (m, 1H), 2.79-2.66 (m, 6H), 2.47 (dt, J = 13.8, 6.7 Hz, 2H), 2.31-2.07 (m, 3H), 2.01-1.86 (m, 4H), 1.81 (qd, J = 12.8, 11.7, 4.8 Hz, 1H), 1.67 (dt, J = 16.0, 11.9 Hz, 1H). | LCMS C$_{41}$H$_{46}$N$_{10}$O$_8$ requires: 807, found: m/z = 808 [M + H]$^+$. |
| 64 | $^1$H NMR (500 MHz, DMSO-d$_6$) δ 11.11-10.93 (m, 2H), 7.66 (s, 1H), 7.56 (s, 1H), 7.50 (d, J = 8.3 Hz, 1H), 7.41 (dd, J = 8.9, 1.8 Hz, 3H), 7.19 (d, J = 42.2 Hz, 2H), 6.92 (d, J = 2.1 Hz, 1H), 6.89-6.74 (m, 4H), 4.96 (dd, J = 12.7, 5.4 Hz, 1H), 4.23 (dd, J = 36.2, 13.0 Hz, 3H), 3.93 (dt, J = 45.1, 6.2 Hz, 3H), 3.22-3.10 (m, 6H), 3.02-2.67 (m, 5H), 2.62 (d, J = 10.8 Hz, 5H), 2.07-1.86 (m, 4H), 1.83-1.62 (m, 5H). | LCMS C$_{36}$H$_{40}$N$_{10}$O$_7$ requires: 725, found: m/z = 726 [M + H]$^+$. |
| 65 | $^1$H NMR (500 MHz, DMSO-d$_6$) δ 11.14 (s, 1H), 10.99 (s, 1H), 7.69 (s, 1H), 7.59 (s, 1H), 7.49 (d, J = 8.3 Hz, 1H), 7.48-7.42 (m, 2H), 7.26 (s, 1H), 7.09 (t, J = 12.2 Hz, 3H), 6.88 (d, J = 2.1 Hz, 1H), 6.77 (dd, J = 8.3, 2.1 Hz, 1H), 4.96 (dd, J = 12.8, 5.4 Hz, 1H), 4.24 (dd, J = 28.7, 12.7 Hz, 2H), 3.18-3.09 (m, 5H), 3.02-2.76 (m, 4H), 2.59 (s, 5H), 1.98-1.87 (m, 1H), 1.87-1.63 (m, 6H), 1.48 (d, J = 12.4 Hz, 1H). | LCMS C$_{36}$H$_{40}$N$_{10}$O$_6$ requires: 709, found: m/z = 710 [M + H]$^+$. |
| 66 | $^1$H NMR (500 MHz, DMSO-d$_6$) δ 11.25 (d, J = 22.6 Hz, 1H), 11.03 (d, J = 23.2 Hz, 1H), 7.72 (s, 1H), 7.67-7.44 (m, 4H), 7.33-7.19 (m, 3H), 7.07 (dd, J = 17.4, 7.1 Hz, 1H), 6.84 (dd, J = 28.1, 8.6 Hz, 1H), 6.63 (d, J = 5.3 Hz, 1H), 6.60-6.31 (m, 2H), 4.99 (ddd, J = 23.5, 12.9, 5.5 Hz, 1H), 4.27 (d, J = 24.4 Hz, 2H), 4.15-3.89 (m, 2H), 3.83 (s, 1H), 3.07-2.69 (m, 6H), 2.64 (d, J = 10.6 Hz, 5H), 2.21 (s, 2H), 2.09-1.87 (m, 3H), 1.73 (q, J = 14.5, 13.9 Hz, 4H), 1.51 (d, J = 10.3 Hz, 1H), 1.25 (s, 2H), 1.12 (s, 2H). | LCMS C$_{43}$H$_{51}$N$_{11}$O$_6$ requires: 818, found: m/z = 819 [M + H]$^+$. |
| 67 | $^1$H NMR (500 MHz, DMSO-d$_6$) δ 11.15 (s, 1H), 11.00 (s, 1H), 7.71 (s, 1H), 7.64 (d, J = 2.5 Hz, 1H), 7.58 (dd, J = 5.5, 3.2 Hz, 1H), 7.54-7.42 (m, 4H), 7.29 (s, 1H), 6.99 (s, 2H), 5.15 (dd, J = 13.3, 5.1 Hz, 1H), 4.54-4.23 (m, 2H), 3.64 (dt, J = 22.8, 5.9 Hz, 11H), 3.39 (t, J = 6.2 Hz, 2H), 3.10 (d, J = 31.4 Hz, 4H), 2.93 (ddd, J = 17.1, 13.7, 5.4 Hz, 1H), 2.66 (dt, J = 32.6, 6.8 Hz, 5H), 2.02 (dtd, J = 12.8, 5.3, 2.3 Hz, 1H), 1.84 (td, J = 7.6, 6.8, 3.3 Hz, 2H), 1.73-1.45 (m, 6H). | LCMS: C$_{39}$H$_{47}$N$_9$O$_6$ requires: 737, found: m/z = 738 [M + H]$^+$. |
| 68 | $^1$H NMR (500 MHz, DMSO-d$_6$) δ 11.28 (s, 1H), 11.07 (s, 1H), 7.73 (d, J = 2.9 Hz, 1H), 7.67-7.61 (m, 2H), 7.33 (d, J = 2.9 Hz, 1H), 6.93 (d, J = 2.1 Hz, 1H), 6.84 (dd, J = 8.6, 2.2 Hz, 1H), 6.43 (s, 1H), 5.05 (dd, J = 12.9, 5.4 Hz, 1H), 4.45 (d, J = 12.3 Hz, 1H), 4.28 (d, J = 13.2 Hz, 1H), 3.98 (t, J = 5.5 Hz, 2H), 3.75-3.48 (m, 6H), 3.43 (dt, J = 10.1, 7.5 Hz, 1H), 3.27-3.14 (m, 3H), 3.04-2.83 (m, 5H), 2.76-2.54 (m, 8H), 2.23-2.13 (m, 1H), 2.06-1.97 (m, 1H), 1.86-1.69 (m, 5H), 1.58-1.51 (m, 1H). | LCMS: C$_{38}$H$_{45}$N$_{13}$O$_6$ requires 779, found: m/z = 780 [M + H]$^+$ |

TABLE 2-continued

Physical Data for the Example Compounds of Table 1.

| Compound No. | ¹H NMR | Mass Spec (LCMS) |
|---|---|---|
| 69 | ¹H NMR (500 MHz, Acetonitrile-d3) δ 11.23 (d, J = 5.8 Hz, 1H), 10.34 (s, 1H), 8.86 (s, 1H), 8.10 (d, J = 9.0 Hz, 1H), 7.69 (dd, J = 8.8, 2.7 Hz, 2H), 7.60 (s, 1H), 7.50-7.36 (m, 2H), 7.31 (d, J = 8.4 Hz, 2H), 7.16 (dd, J = 9.1, 2.4 Hz, 1H), 7.06 (d, J = 7.5 Hz, 1H), 6.94 (d, J = 2.4 Hz, 1H), 6.47 (d, J = 7.5 Hz, 1H), 5.85 (s, 1H), 4.67-4.27 (m, 4H), 4.27-4.14 (m, 2H), 4.03 (dd, J = 31.8, 11.0 Hz, 4H), 3.82-3.68 (m, 1H), 3.52-3.20 (m, 6H), 3.15 (t, J = 6.5 Hz, 2H), 3.13-2.99 (m, 3H), 2.99-2.86 (m, 4H), 2.26-2.13 (m, 2H), 1.92-1.75 (m, 7H), 1.75-1.58 (m, 2H), 1.46-1.29 (m, 3H). | LCMS: $C_{43}H_{51}N_{11}O_5$ requires: 802, found: m/z = 802.7 [M + H]+ |
| 70 | ¹H NMR (500 MHz, Acetonitrile-d₃) δ 11.08 (s, 1H), 8.89 (s, 1H), 7.65 (d, J = 8.3 Hz, 1H), 7.60-7.52 (m, 3H), 7.50-7.37 (m, 1H), 7.23 (d, J = 8.3, Hz, 2H), 6.82 (d, J = 2.1 Hz, 1H), 6.66 (dd, J = 8.3, 2.2 Hz, 1H), 5.81 (s, 1H), 4.96 (dd, J = 12.3, 5.4 Hz, 1H), 4.47 (d, J = 13.0 Hz, 1H), 4.31 (t, J = 8.0 Hz, 3H), 4.16 (t, J = 7.7 Hz, 2H), 3.90 (dd, J = 8.4, 5.2 Hz, 2H), 3.83-3.52 (m, 3H), 3.38 (p, J = 6.1 Hz, 1H), 3.19-2.92 (m, 4H), 2.84-2.61 (m, 3H), 2.61-2.53 (m, 1H), 2.16 (s, 27H), 2.07-2.00 (m, 3H), 1.90-1.77 (m, 5H), 1.70 (tt, J = 12.9, 6.6 Hz, 3H). | LCMS: $C_{40}H_{44}N_{10}O_7$ requires: 776.9, found: m/z = 777.6 [M + H]⁺ |
| 71 | ¹H NMR (500 MHz, DMSO-d₆) δ 11.23 (s, 1H), 11.07 (s, 1H), 7.74-7.60 (m, 3H), 7.55 (d, J = 8.2 Hz, 3H), 7.30 (d, J = 8.3 Hz, 3H), 6.90 (d, J = 2.1 Hz, 1H), 6.87-6.77 (m, 1H), 5.06 (dd, J = 12.9, 5.4 Hz, 1H), 4.36 (dd, J = 59.2, 13.0 Hz, 3H), 3.70-3.61 (m, 2H), 3.55 (t, J = 8.8 Hz, 4H), 3.46-3.37 (m, 5H), 3.14 (t, J = 8.5 Hz, 2H), 3.10-2.81 (m, 5H), 2.73 (s, 4H), 2.39 (d, J = 62.2 Hz, 8H), 2.19-1.95 (m, 7H), 1.95-1.67 (m, 9H), 1.58 (d, J = 10.3 Hz, 2H), 1.19 (s, 4H). | LCMS: $C_{44}H_{53}N_{11}O_6$ requires: 832, found: m/z = 832.7 [M + H]⁺. |
| 72 | ¹H NMR (500 MHz, DMSO-d₆) δ 11.30 (d, J = 6.9 Hz, 1H), 11.01 (s, 1H), 8.89 (s, 1H), 8.00 (d, J = 8.9 Hz, 1H), 7.80 (s, 1H), 7.69 (s, 1H), 7.58 (d, J = 8.1 Hz, 2H), 7.36 (s, 1H), 7.29 (t, J = 8.3 Hz, 1H), 7.21 (t, J = 9.1 Hz, 3H), 7.00 (s, 1H), 6.49 (d, J = 7.5 Hz, 1H), 4.31 (d, J = 18.7 Hz, 2H), 4.03 (d, J = 12.9 Hz, 2H), 3.64 (s, 4H), 3.08 (d, J = 11.3 Hz, 6H), 2.94 (t, J = 12.9 Hz, 6H), 2.73 (s, 3H), 2.62 (d, J = 14.2 Hz, 3H), 2.11-1.69 (m, 11H), 1.59 (d, J = 12.2 Hz, 1H), 1.43-1.25 (m, 2H). | LCMS: $C_{45}H_{55}N_{11}O_5$ requires: 830, found: m/z = 830.7 [M + H]⁺ |
| 73 | ¹H NMR (500 MHz, DMSO-d₆) δ 11.26 (s, 1H), 11.08 (s, 1H), 7.84-7.75 (m, 1H), 7.75-7.59 (m, 2H), 7.51 (d, J = 8.2 Hz, 2H), 7.40-7.31 (m, 1H), 7.19 (d, J = 8.2 Hz, 2H), 6.98-6.75 (m, 2H), 5.06 (dd, J = 12.9, 5.4 Hz, 1H), 4.41 (d, J = 12.8 Hz, 1H), 4.31 (t, J = 8.0 Hz, 3H), 3.61 (dt, J = 15.9, 8.2 Hz, 7H), 3.16 (d, J = 10.7 Hz, 6H), 3.02 (dt, J = 20.5, 10.8 Hz, 4H), 2.92-2.85 (m, 1H), 2.64 (d, J = 28.8 Hz, 3H), 2.40 (d, J = 7.5 Hz, 3H), 2.15 (d, J = 6.9 Hz, 1H), 2.14-1.97 (m, 4H), 1.83 (ddd, J = 43.1, 32.8, 8.9 Hz, 7H), 1.63 (dd, J = 30.3, 13.7 Hz, 4H). | LCMS: $C_{42}H_{48}N_{10}O_7$ requires: 804.9, found: m/z = 805.5 [M + H]⁺ |
| 74 | ¹H NMR (500 MHz, DMSO-d₆) δ 11.34 (d, J = 33.7 Hz, 1H), 11.10 (s, 1H), 10.14 (d, J = 31.6 Hz, 1H), 7.89-7.53 (m, 5H), 7.35 (d, J = 12.0 Hz, 3H), 6.93 (d, J = 11.3 Hz, 1H), 6.78 (t, J = 11.2 Hz, 1H), 5.09 (dd, J = 12.8, 5.4 Hz, 1H), 4.31 (t, J = 46.0 Hz, 8H), 3.15-2.77 (m, 4H), 2.72 (s, 4H), 2.04 (dt, J = 32.2, 10.9 Hz, 3H), 1.82 (q, J = 13.1 Hz, 4H), 1.58 (d, J = 12.2 Hz, 1H), 1.30 (dd, J = 80.8, 21.9 Hz, 4H). | LCMS: $C_{42}H_{49}N_{11}O_6$ requires: 803.9, found: m/z = 804.7 [M + H]⁺ |
| 75 | ¹H NMR (500 MHz, DMSO-d₆) δ 11.32 (s, 1H), 11.15 (s, 1H), 8.07-7.84 (m, 3H), 7.80 (s, 1H), 7.69 (s, 1H), 7.60 (d, J = 8.3 Hz, 2H), 7.39-7.22 (m, 3H), 5.18 (dd, J = 12.8, 5.4 Hz, 1H), 4.35 (dd, J = 32.7, 13.3 Hz, 4H), 3.41-3.23 (m, 8H), 3.17-2.85 (m, 7H), 2.71 (s, 4H), 2.63 (d, J = 22.5 Hz, 2H), 2.13-2.03 (m, 2H), 1.82 (dd, J = 28.5, 10.7 Hz, 6H), 1.67-1.52 (m, 1H), 1.24 (s, 3H). | LCMS: $C_{43}H_{51}N_{11}O_6$ requires: 818, found: m/z = 818.7 [M + H]⁺ |

TABLE 2-continued

Physical Data for the Example Compounds of Table 1.

| Compound No. | $^1$H NMR | Mass Spec (LCMS) |
|---|---|---|
| 76 | $^1$H NMR (500 MHz, DMSO-d$_6$) δ 11.13 (s, 1H), 10.91 (s, 1H), 7.96-7.78 (m, 3H), 7.70 (d, J = 2.9 Hz, 1H), 7.60 (s, 1H), 7.46-7.35 (m, 2H), 7.26 (d, J = 2.9 Hz, 1H), 6.63 (d, J = 8.9 Hz, 2H), 5.15 (dd, J = 12.8, 5.4 Hz, 1H), 4.32 (dd, J = 41.0, 12.7 Hz, 2H), 3.78 (s, 2H), 3.70-3.50 (m, 2H), 3.24 (dd, J = 11.8, 5.2 Hz, 3H), 3.11-2.84 (m, 8H), 2.70 (d, J = 10.6 Hz, 5H), 2.61 (dd, J = 18.3, 3.3 Hz, 3H), 2.45 (d, J = 9.1 Hz, 3H), 2.13-1.94 (m, 1H), 1.87-1.68 (m, 3H), 1.55 (d, J = 11.2 Hz, 1H). | LCMS: $C_{40}H_{45}N_{11}O_6$ requires: 775.9, found: m/z = 776.6 $[M + H]^+$ |
| 77 | $^1$H NMR (500 MHz, DMSO-d$_6$) δ 11.08 (s, 1H), 10.85 (s, 1H), 7.97 (s, 1H), 7.73-7.64 (m, 2H), 7.60 (s, 1H), 7.53 (s, 1H), 7.34 (d, J = 2.3 Hz, 1H), 7.31-7.21 (m, 2H), 5.08 (dd, J = 12.8, 5.4 Hz, 1H), 4.34 (dd, J = 50.4, 13.0 Hz, 2H), 4.16-3.99 (m, 3H), 3.60 (dt, J = 10.4, 5.8 Hz, 1H), 3.13-2.80 (m, 7H), 2.72-2.56 (m, 5H), 2.39-2.23 (m, 3H), 2.01 (dd, J = 20.0, 10.3 Hz, 3H), 1.94-1.69 (m, 8H), 1.54 (dd, J = 24.9, 12.3 Hz, 3H). | LCMS: $C_{40}H_{49}N_{13}O_6$ requires: 807, found: m/z = 808 $[M + H]^+$. |
| 78 | $^1$H NMR (500 MHz, DMSO-d$_6$) δ 11.08 (s, 1H), 10.86 (s, 1H), 7.98 (s, 1H), 7.74-7.68 (m, 1H), 7.65 (d, J = 8.3 Hz, 1H), 7.61 (s, 1H), 7.56 (s, 1H), 7.29 (d, J = 2.9 Hz, 1H), 6.80 (d, J = 2.1 Hz, 1H), 6.67 (dd, J = 8.4, 2.1 Hz, 1H), 5.06 (dd, J = 12.7, 5.4 Hz, 1H), 4.34 (dd, J = 46.2, 13.0 Hz, 2H), 4.16 (s, 3H), 3.79-3.54 (m, 3H), 3.14-2.81 (m, 4H), 2.76-2.56 (m, 5H), 2.24-1.69 (m, 10H), 1.57 (d, J = 12.8 Hz, 1H). | LCMS: $C_{39}H_{47}N_{13}O_6$ requires: 793, found: m/z = 794 $[M + H]^+$. |
| 79 | $^1$H NMR (500 MHz, DMSO-d$_6$) δ 11.07 (s, 1H), 10.87 (s, 1H), 7.80-7.64 (m, 2H), 7.58 (s, 1H), 7.39 (d, J = 8.5 Hz, 2H), 7.25 (s, 1H), 6.97 (d, J = 2.1 Hz, 1H), 6.87 (dd, J = 8.6, 2.2 Hz, 1H), 6.55 (d, J = 8.7 Hz, 2H), 5.06 (dd, J = 12.9, 5.3 Hz, 1H), 4.30 (dd, J = 39.1, 12.9 Hz, 2H), 3.75 (d, J = 4.5 Hz, 2H), 3.42 (d, J = 10.7 Hz, 4H), 3.35-3.15 (m, 11H), 3.09-2.83 (m, 4H), 2.69 (s, 4H), 2.02 (qd, J = 7.5, 6.9, 3.9 Hz, 1H), 1.87-1.71 (m, 3H), 1.60-1.47 (m, 1H). | LCMS: $C_{39}H_{43}N_{11}O_6$ requires: 761.8, found: m/z = 762.5 $[M + H]^+$ |
| 80 | $^1$H NMR (500 MHz, DMSO-d$_6$) δ 11.09 (s, 1H), 10.86 (s, 1H), 8.19 (d, J = 2.6 Hz, 1H), 7.88 (dd, J = 9.0, 2.7 Hz, 1H), 7.77-7.58 (m, 3H), 7.40-7.16 (m, 3H), 6.79 (d, J = 9.1 Hz, 1H), 5.08 (dd, J = 12.9, 5.4 Hz, 1H), 4.27 (d, J = 11.3 Hz, 2H), 3.68-3.37 (m, 10H), 3.37-3.22 (m, 8H), 3.18 (d, J = 4.5 Hz, 2H), 3.03 (t, J = 11.8 Hz, 1H), 2.99-2.83 (m, 2H), 2.70 (s, 3H), 2.59 (td, J = 14.4, 3.9 Hz, 3H), 2.07-1.98 (m, 1H), 1.79 (q, J = 13.4, 10.1 Hz, 3H), 1.59 (dt, J = 17.9, 5.7 Hz, 9H). | LCMS: $C_{41}H_{48}N_{12}O_6$ requires: 804.9, found: m/z = 805.7 $[M + H]^+$ |
| 81 | $^1$H NMR (500 MHz, Methanol-d$_4$) δ 8.16 (dd, J = 9.8, 3.2 Hz, 1H), 8.12-7.99 (m, 2H), 7.85-7.65 (m, 2H), 7.37 (d, J = 2.4 Hz, 1H), 7.24 (dd, J = 8.8, 2.6 Hz, 1H), 5.09 (dd, J = 12.4, 5.5 Hz, 2H), 4.59 (d, J = 13.3 Hz, 1H), 4.35 (d, J = 13.6 Hz, 1H), 3.82 (q, J = 11.2, 9.1 Hz, 1H), 3.65-3.50 (m, 5H), 3.16 (dt, J = 16.2, 12.9 Hz, 2H), 2.95-2.80 (m, 4H), 2.82-2.64 (m, 2H), 2.20-1.93 (m, 4H), 1.93-1.54 (m, 9H). | LCMS: $C_{41}H_{48}N_{12}O_6$ requires: 804.9, found: m/z = 805.6 $[M + H]^+$ |
| 82 | $^1$H NMR (500 MHz, CD$_3$CN) δ 10.95 (s, 1H), 8.80 (s, 1H), 7.60-7.51 (m, 4H), 7.40 (s, 1H), 6.97 (d, J = 8.8 Hz, 2H), 6.53 (d, J = 10.0 Hz, 2H), 5.79 (s, 1H), 5.04 (dd, J = 13.4, 5.1 Hz, 1H), 4.47-4.41 (m, 1H), 4.29 (dt, J = 22.6, 16.5 Hz, 3H), 4.19 (t, J = 7.8 Hz, 2H), 3.80-3.75 (m, 2H), 3.71 (ddt, J = 11.3, 8.3, 4.1 Hz, 1H), 3.59 (br, 2H), 3.48 (d, J = 7.1 Hz, 2H), 3.44-3.23 (m, 4H), 3.16 (br, 2H), 3.08-2.94 (m, 2H), 2.84 (ddd, J = 18.4, 13.5, 5.4 Hz, 1H), 2.77 (s, 2H), 2.76-2.74 (m, 1H), 2.40 (dp, J = 13.5, 5.4, 5.0 Hz, 2H), 2.11 (ddd, J = 12.8, 7.6, 5.0 Hz, 1H), 1.94-1.77 (m, 4H), 1.71-1.61 (m, 1H). | LCMS: $C_{41}H_{50}N_{12}O_5$ requires: 790, found: m/z = 791 $[M + H]^+$. |
| 83 | $^1$H NMR (500 MHz, DMSO-d$_6$) δ 11.08 (s, 1H), 10.85 (s, 1H), 7.98 (s, 1H), 7.73-7.64 (m, 2H), 7.60 (s, 1H), 7.55 (s, 1H), 7.36-7.21 (m, 3H), 5.07 (dd, J = 12.8, 5.4 Hz, 1H), 4.34 (dd, J = 49.6, 13.1 Hz, 2H), 4.07 (t, J = 11.4 Hz, 3H), 3.61 (dt, J = 10.6, 6.0 Hz, 1H), 3.16-2.81 (m, 8H), 2.73-2.56 | LCMS: $C_{41}H_{51}N_{13}O_6$ requires: 821, found: m/z = 822 $[M + H]^+$. |

TABLE 2-continued

Physical Data for the Example Compounds of Table 1.

| Compound No. | $^1$H NMR | Mass Spec (LCMS) |
|---|---|---|
| | (m, 4H), 2.19 (d, J = 6.8 Hz, 2H), 2.12-1.71 (m, 14H), 1.27-1.09 (m, 2H). | |
| 84 | $^1$H NMR (500 MHz, DMSO-d$_6$) δ 10.99 (s, 1H), 10.85 (s, 1H), 7.97 (s, 1H), 7.70 (d, J = 2.9 Hz, 1H), 7.63-7.56 (m, 2H), 7.54 (s, 1H), 7.52-7.45 (m, 2H), 7.29 (d, J = 2.8 Hz, 1H), 5.15 (dd, J = 13.3, 5.1 Hz, 1H), 4.51 (d, J = 17.1 Hz, 1H), 4.34 (dt, J = 28.7, 13.7 Hz, 3H), 4.08 (td, J = 11.0, 5.5 Hz, 1H), 3.60 (tt, J = 10.3, 4.8 Hz, 1H), 3.25 (t, J = 7.2 Hz, 2H), 3.14-2.85 (m, 6H), 2.74-2.57 (m, 6H), 2.41-2.24 (m, 2H), 2.11-1.67 (m, 14H). | LCMS: C$_{38}$H$_{48}$N$_{12}$O$_5$ requires: 752, found: m/z = 753 [M + H]$^+$. |
| 85 | $^1$H NMR (500 MHz, DMSO-d$_6$) δ 11.26 (s, 1H), 11.08 (s, 1H), 7.77 (d, J = 2.7 Hz, 1H), 7.70-7.62 (m, 2H), 7.57-7.51 (m, 2H), 7.35 (d, J = 2.8 Hz, 1H), 7.28-7.23 (m, 2H), 6.78 (d, J = 2.1 Hz, 1H), 6.65 (dd, J = 8.4, 2.1 Hz, 1H), 5.09-4.96 (m, 1H), 4.39 (d, J = 12.4 Hz, 1H), 4.30 (d, J = 13.3 Hz, 1H), 4.11 (t, J = 8.0 Hz, 2H), 3.76-3.54 (m, 5H), 3.45-3.17 (m, 3H), 3.13-2.93 (m, 4H), 2.92-2.68 (m, 6H), 2.66-2.20 (m, 3H), 2.04-1.98 (m, 1H), 1.87-1.72 (m, 3H), 1.61-1.51 (m, 1H), 1.40-1.07 (m, 2H). | LCMS: C$_{40}$H$_{45}$N$_{11}$O$_6$ requires 775, found: m/z = 776 [M + H]$^+$ |
| 86 | $^1$H NMR (500 MHz, DMSO-d$_6$) δ 11.22 (s, 1H), 11.00 (s, 1H), 7.83-7.63 (m, 3H), 7.52 (q, J = 21.0, 15.4 Hz, 4H), 7.42-7.30 (m, 1H), 7.17 (d, J = 8.2 Hz, 2H), 5.13 (dd, J = 13.4, 5.1 Hz, 1H), 4.46 (d, J = 17.2 Hz, 1H), 4.40-4.27 (m, 3H), 3.67-3.57 (m, 2H), 3.40 (d, J = 7.0 Hz, 9H), 3.18 (d, J = 5.2 Hz, 1H), 3.08 (d, J = 14.6 Hz, 3H), 3.04-2.77 (m, 7H), 2.73 (d, J = 6.1 Hz, 4H), 2.66-2.58 (m, 2H), 2.46-2.32 (m, 2H), 2.08-1.94 (m, 2H), 1.94-1.70 (m, 7H), 1.58 (d, J = 15.9 Hz, 3H), 1.19 (t, J = 7.2 Hz, 3H). | LCMS: C$_{42}$H$_{51}$N$_{11}$O$_5$ requires: 789.9, found: m/z = 790.7 [M + H]$^+$ |
| 87 | $^1$H NMR (500 MHz, DMSO-d$_6$) δ 11.19 (s, 1H), 11.08 (s, 1H), 7.76 (d, J = 2.8 Hz, 1H), 7.69-7.64 (m, 2H), 7.54-7.48 (m, 2H), 7.34 (d, J = 2.9 Hz, 1H), 7.18 (d, J = 8.2 Hz, 2H), 7.04 (d, J = 9.6 Hz, 1H), 6.89 (d, J = 8.7 Hz, 1H), 5.06 (dd, J = 12.8, 5.4 Hz, 1H), 4.34 (dd, J = 41.1, 12.8 Hz, 2H), 4.16 (s, 1H), 3.69-3.49 (m, 2H), 3.19 (s, 1H), 3.11-2.83 (m, 4H), 2.73 (s, 3H), 2.68-2.55 (m, 2H), 2.46-2.29 (m, 2H), 2.25-1.93 (m, 7H), 1.90-1.49 (m, 7H), 1.25 (s, 2H). | LCMS: C$_{43}$H$_{51}$N$_{11}$O$_6$ requires: 817, found: m/z = 818 [M + H]$^+$. |
| 88 | $^1$H NMR (500 MHz, DMSO-d$_6$) δ 11.44 (s, 1H), 11.00 (s, 1H), 8.08 (d, J = 9.0 Hz, 1H), 7.98 (d, J = 3.0 Hz, 1H), 7.77 (d, J = 2.7 Hz, 1H), 7.71 (s, 1H), 7.62-7.54 (m, 1H), 7.51-7.44 (m, 2H), 7.38-7.31 (m, 2H), 5.14 (dd, J = 13.3, 5.2 Hz, 1H), 4.48 (d, J = 17.1 Hz, 1H), 4.42-4.28 (m, 3H), 3.68-3.59 (m, 1H), 3.44-3.21 (m, 5H), 3.13-2.87 (m, 7H), 2.72-2.66 (m, 5H), 2.65-2.56 (m, 1H), 2.55-2.40 (m, 5H), 2.39-2.32 (m, 2H), 2.07-1.98 (m, 1H), 1.88-1.72 (m, 3H), 1.72-1.46 (m, 4H). | LCMS: C$_{40}$H$_{50}$N$_{12}$O$_5$ requires 778, found: m/z = 779 [M + H]$^+$. |
| 89 | $^1$H NMR (500 MHz, DMSO-d$_6$) δ 11.45 (s, 1H), 11.07 (s, 1H), 8.09 (d, J = 9.1 Hz, 1H), 8.01 (d, J = 3.0 Hz, 1H), 7.77 (d, J = 2.8 Hz, 1H), 7.71 (s, 1H), 7.65 (d, J = 8.4 Hz, 1H), 7.40-7.33 (m, 2H), 6.92 (d, J = 2.2 Hz, 1H), 6.83 (dd, J = 8.6, 2.2 Hz, 1H), 5.03 (d, J = 11.0 Hz, 1H), 4.40 (d, J = 12.5 Hz, 1H), 4.31 (d, J = 13.3 Hz, 1H), 3.67-3.56 (m, 2H), 3.54-3.50 (m, 1H), 3.47-3.22 (m, 6H), 3.21-2.93 (m, 7H), 2.87 (t, J = 14.0 Hz, 1H), 2.75-2.32 (m, 12H), 2.20-2.13 (m, 1H), 2.04-1.97 (m, 1H), 1.90-1.73 (m, 3H), 1.65-1.49 (m, 2H). | LCMS: C$_{41}$H$_{49}$N$_{13}$O$_6$ requires 819, found: m/z = 820 [M + H]$^+$ |
| 90 | $^1$H NMR (500 MHz, DMSO-d$_6$) δ 11.58 (s, 1H), 11.16 (s, 1H), 8.02 (d, J = 50.3 Hz, 3H), 7.86 (s, 1H), 7.76 (s, 1H), 7.69 (d, J = 8.1 Hz, 2H), 7.44 (d, J = 7.0 Hz, 3H), 5.20 (dd, J = 12.8, 5.5 Hz, 1H), 4.35 (dd, J = 28.1, 12.6 Hz, 3H), 3.17-2.80 (m, 6H), 2.70 (s, 3H), 2.14-2.00 (m, 1H), 1.82 (q, J = 11.2, 9.6 Hz, 3H), 1.59 (d, J = 12.0 Hz, 1H). | LCMS: C$_{39}$H$_{43}$N$_{11}$O$_7$ requires: 777.8, found: m/z = 778.6 [M + H]$^+$ |

TABLE 2-continued

Physical Data for the Example Compounds of Table 1.

| Compound No. | $^1$H NMR | Mass Spec (LCMS) |
|---|---|---|
| 91 | $^1$H NMR (500 MHz, DMSO-d$_6$) δ 11.07 (s, 1H), 10.90 (s, 1H), 7.75-7.67 (m, 1H), 7.67-7.58 (m, 2H), 7.39 (d, J = 8.8 Hz, 2H), 7.26 (d, J = 2.6 Hz, 1H), 6.77 (d, J = 2.1 Hz, 1H), 6.68-6.59 (m, 3H), 5.77 (s, 1H), 5.05 (dd, J = 12.7, 5.5 Hz, 1H), 4.32 (dd, J = 42.2, 13.2 Hz, 2H), 4.13 (t, J = 8.2 Hz, 2H), 3.75-3.57 (m, 3H), 3.38 (dd, J = 14.1, 7.1 Hz, 3H), 3.08-2.77 (m, 8H), 2.70 (d, J = 14.7 Hz, 9H), 2.44-2.28 (m, 8H), 2.12-1.93 (m, 2H), 1.89-1.67 (m, 4H), 1.56 (d, J = 12.1 Hz, 1H). | LCMS: $C_{43}H_{50}N_{12}O_6$ requires: 831, found: m/z = 831.7 $[M + H]^+$ |
| 92 | $^1$H NMR (500 MHz, DMSO-d$_6$) δ 11.24 (s, 1H), 11.08 (s, 1H), 7.78 (s, 1H), 7.67 (q, J = 10.7, 8.1 Hz, 2H), 7.57 (s, 1H), 7.36 (s, 1H), 7.16 (d, J = 8.2 Hz, 1H), 6.98 (d, J = 8.4 Hz, 1H), 6.80 (s, 1H), 6.66 (d, J = 8.4 Hz, 1H), 5.07 (dd, J = 12.9, 5.5 Hz, 1H), 4.34 (dd, J = 43.8, 11.9 Hz, 2H), 4.17 (t, J = 8.4 Hz, 2H), 3.75 (t, J = 6.8 Hz, 2H), 3.64 (d, J = 11.4 Hz, 1H), 3.55 (s, 2H), 3.08 (dd, J = 24.9, 13.1 Hz, 2H), 3.03-2.85 (m, 3H), 2.77 (t, J = 6.3 Hz, 3H), 2.70 (s, 5H), 2.11-1.96 (m, 1H), 1.81 (q, J = 21.3, 17.4 Hz, 3H), 1.59 (d, J = 14.4 Hz, 1H). | LCMS: $C_{40}H_{45}N_{11}O_6$ requires: 775.9, found: m/z = 776.7 $[M + H]^+$ |
| 93 | $^1$H NMR (500 MHz, DMSO-d$_6$) δ 11.13 (s, 1H), 10.97 (s, 1H), 7.92-7.81 (m, 2H), 7.83-7.77 (m, 2H), 7.71 (d, J = 3.0 Hz, 1H), 7.61 (s, 1H), 7.41 (d, J = 8.9 Hz, 2H), 7.28 (d, J = 2.9 Hz, 1H), 6.88 (d, J = 8.9 Hz, 2H), 5.15 (dd, J = 12.8, 5.4 Hz, 1H), 4.70 (s, 1H), 4.36 (d, J = 12.5 Hz, 1H), 4.27 (d, J = 13.4 Hz, 1H), 3.81 (s, 2H), 3.69-3.55 (m, 1H), 3.41-3.20 (m, 2H), 3.10-2.84 (m, 11H), 2.71 (s, 3H), 2.65-2.52 (m, 2H), 2.10-2.03 (m, 1H), 1.85-1.71 (m, 7H), 1.57-1.53 (m, 1H). | LCMS: $C_{41}H_{47}N_{11}O_6$ requires 789, found: m/z = 790 $[M + H]^+$ |
| 94 | $^1$H NMR (500 MHz, DMSO-d$_6$) δ 11.12 (s, 1H), 11.02 (s, 1H), 7.88 (d, J = 7.5 Hz, 1H), 7.83-7.77 (m, 2H), 7.72 (d, J = 2.9 Hz, 1H), 7.62 (s, 1H), 7.48-7.42 (m, 2H), 7.29 (d, J = 3.1 Hz, 1H), 6.91 (d, J = 8.9 Hz, 2H), 5.11 (s, 1H), 4.41 (d, J = 12.2 Hz, 1H), 4.28 (d, J = 13.5 Hz, 1H), 3.82 (s, 2H), 3.65-3.61 (m, 1H), 3.33-3.21 (m, 3H), 3.19-3.09 (m, 4H), 3.05-2.80 (m, 7H), 2.72 (s, 3H), 2.67-2.53 (m, 2H), 2.10-2.00 (m, 1H), 1.89-1.48 (m, 9H). | LCMS: $C_{41}H_{47}N_{11}O_6$ requires 789, found: m/z = 790 $[M + H]^+$ |
| 95 | Stereoisomer 1: $^1$H NMR (500 MHz, Methanol-d$_4$) δ 8.08 (s, 1H), 7.99 (q, J = 7.2, 5.2 Hz, 2H), 7.62 (d, J = 92.6 Hz, 4H), 7.00 (s, 1H), 5.19 (dd, J = 12.6, 5.4 Hz, 1H), 4.55 (s, 2H), 4.40 (d, J = 14.2 Hz, 2H), 3.77 (dq, J = 10.4, 5.4, 4.2 Hz, 1H), 3.61 (s, 2H), 3.50 (dt, J = 10.2, 7.5 Hz, 2H), 3.45-3.39 (m, 2H), 3.41-3.34 (m, 4H), 3.12 (s, 2H), 3.00 (t J = 12.8 Hz, 1H), 2.90 (ddd, J = 18.5, 14.0, 5.3 Hz, 2H), 2.80 (s, 3H), 2.79-2.77 (m, 1H), 2.77-2.70 (m, 2H), 2.39-2.05 (m, 5H), 1.90 (dt, J = 30.1, 12.7 Hz, 4H), 1.75-1.59 (m, 2H). Stereoisomer 2: $^1$H NMR (500 MHz, Methanol-d$_4$) δ 8.10 (s, 1H), 8.05 (d, J = 7.7 Hz, 1H), 8.01 (d, J = 7.5 Hz, 1H), 7.95-7.81 (m, 2H), 7.63 (s, 2H), 7.17 (s, 1H), 5.18 (ddd, J = 25.3, 12.6, 5.5 Hz, 2H), 4.66-4.49 (m, 2H), 4.44 (d, J = 12.6 Hz, 1H), 4.35 (d, J = 13.7 Hz, 1H), 3.65 (d, J = 12.6 Hz, 1H), 3.53-3.40 (m, 4H), 3.13 (t, J = 11.8 Hz, 3H), 3.03 (t, J = 12.8 Hz, 2H), 2.98-2.83 (m, 3H), 2.83-2.69 (m, 7H), 2.06 (d, J = 12.9 Hz, 2H), 1.93 (d, J = 23.4 Hz, 3H), 1.90-1.80 (m, 1H), 1.64 (d, J = 34.6 Hz, 4H). | Stereoisomer 1: LCMS: $C_{42}H_{49}N_{11}O_6$ requires 804, found: m/z = 804.6 $[M + H]^+$ Stereoisomer 2: LCMS: $C_{42}H_{49}N_{11}O_6$ requires 804, found: m/z = 804.7 $[M + H]^+$ |
| 96 | $^1$H NMR (500 MHz, DMSO-d$_6$) δ 11.08-11.01 (m, 2H), 7.72 (d, J = 2.8 Hz, 1H), 7.64-7.54 (m, 2H), 7.45 (d, J = 8.8 Hz, 2H), 7.29 (d, J = 2.8 Hz, 1H), 7.12 (d, J = 6.9 Hz, 1H), 6.95 (d, J = 8.9 Hz, 2H), 6.83 (d, J = 8.5 Hz, 1H), 5.05 (dd, J = 12.8, 5.4 Hz, 1H), 4.39 (d, J = 12.4 Hz, 1H), 4.27 (d, J = 13.4 Hz, 1H), 4.09-3.87 (m, 4H), 3.66-3.56 (m, 1H), 3.26-3.13 (m, 5H), 3.02-2.83 (m, 5H), 2.65 (s, 3H), 2.62-2.52 (m, 2H), 2.06-1.95 (m, 1H), 1.87-1.63 (m, 8H), 1.58-1.52 (m, 1H). | LCMS: $C_{40}H_{45}N_{11}O_6$ requires 775, found: m/z = 776 $[M + H]^+$ |
| 97 | $^1$H NMR (500 MHz, DMSO-d$_6$) δ 11.07 (s, 1H), 11.00 (s, 1H), 7.72 (d, J = 2.8 Hz, 1H), 7.64-7.54 (m, 2H), 7.46-7.41 (m, 2H), 7.29 (d, J = 3.0 Hz, 1H), 7.12 (d, J = 6.9 Hz, 1H), 6.92 (d, J = 8.9 Hz, | LCMS: $C_{40}H_{45}N_{11}O_6$ requires 775, found: m/z = 776 $[M + H]^+$ |

TABLE 2-continued

Physical Data for the Example Compounds of Table 1.

| Compound No. | $^1$H NMR | Mass Spec (LCMS) |
|---|---|---|
| | 2H), 6.81 (d, J = 8.5 Hz, 1H), 5.05 (dd, J = 12.7, 5.5 Hz, 1H), 4.37 (d, J = 12.4 Hz, 1H), 4.28 (d, J = 13.3 Hz, 1H), 4.00 (s, 4H), 3.64-3.60 (m, 1H), 3.33 (s, 4H), 3.15-2.81 (m, 7H), 2.72 (s, 3H), 2.67-2.40 (m, 2H), 2.05-1.71 (m, 8H), 1.60-1.53 (m, 1H). | |
| 98 | $^1$H NMR (500 MHz, CD$_3$CN) δ 10.84 (s, 1H), 10.17 (s, 1H), 7.78 (s, 1H), 7.66 (d, J = 7.8 Hz, 1H), 7.54 (d, J = 7.9 Hz, 1H), 7.50 (s, 1H), 7.46 (d, J = 8.6 Hz, 2H), 7.41 (s, 1H), 6.91 (d, J = 8.5 Hz, 2H), 6.22 (s, 1H), 5.06 (dd, J = 13.5, 5.2 Hz, 1H), 4.39 (q, J = 17.3 Hz, 3H), 4.24 (d, J = 13.8 Hz, 1H), 3.65 (d, J = 11.9 Hz, 1H), 3.57 (s, 2H), 3.39-3.20 (m, 5H), 3.16 (s, 4H), 2.95 (dt, J = 23.8, 12.3 Hz, 2H), 2.84-2.67 (m, 4H), 2.38-2.27 (m, 3H), 2.10 (dd, J = 13.5, 7.1 Hz, 1H), 1.90-1.74 (m, 5H), 1.61 (q, J = 12.5 Hz, 1H). | LCMS: C$_{40}$H$_{45}$N$_{11}$O$_5$ requires: 759, found: m/z = 760 [M + H]$^+$. |
| 99 | $^1$H NMR (500 MHz, CD$_3$CN) δ 10.81 (s, 1H), 8.83 (d, J = 40 Hz, 1H), 7.73 (d, J = 7.4 Hz, 1H), 7.65 (d, J = 7.6 Hz, 1H), 7.54-7.44 (m, 4H), 7.36 (s, 1H), 6.94-6.87 (m, 2H), 5.72 (s, 1H), 5.07 (dd, J = 13.3, 5.2 Hz, 1H), 4.49-4.33 (m, 3H), ), 4.24 (s, 1H), 3.68 (s, 1H), 3.63 (d, J = 2.6 Hz, 2H), 3.37-3.22 (m, 5H), 3.17 (t, J = 4.9 Hz, 4H), 3.03-2.90 (m, 2H), 2.85-2.61 (m, 4H), 2.45-2.37 (m, 3H), 2.09 (s, 1H), 1.87-1.76 (m, 5H), 1.64 (s, 1H). | LCMS: C$_{40}$H$_{45}$N$_{11}$O$_5$ requires: 759, found: m/z = 760 [M + H]$^+$. |
| 100 | $^1$H NMR (500 MHz, Acetonitrile-d$_3$) δ 11.12 (s, 1H), 10.62 (s, 1H), 8.96 (s, 1H), 8.10 (s, 1H), 8.05-7.91 (m, 2H), 7.68-7.51 (m, 3H), 7.42 (s, 1H), 7.19 (d, J = 8.3 Hz, 2H), 5.81 (s, 1H), 5.07 (dd, J = 12.4, 5.4 Hz, 1H), 4.41 (d, J = 13.4 Hz, 3H), 4.30 (d, J = 13.7 Hz, 1H), 3.78-3.61 (m, 1H), 3.56 (d, J = 12.2 Hz, 2H), 3.46-3.23 (m, 5H), 3.16-2.95 (m, 5H), 2.86-2.72 (m, 8H), 2.22-2.15 (m, 3H), 1.92-1.76 (m, 5H), 1.66 (d, J = 13.1 Hz, 2H). | LCMS: C$_{39}$H$_{44}$N$_{10}$O$_6$ requires: 748.9, found: m/z = 749.6 [M + H]$^+$ |
| 101 | $^1$H NMR (500 MHz, DMSO-d$_6$) δ 11.19 (s, 1H), 11.12 (s, 1H), 7.87 (d, J = 7.6 Hz, 1H), 7.83-7.77 (m, 2H), 7.75 (d, J = 2.7 Hz, 1H), 7.66 (s, 1H), 7.49 (d, J = 8.4 Hz, 2H), 7.32 (s, 1H), 7.15 (d, J = 8.3 Hz, 2H), 5.14 (dd, J = 12.8, 5.4 Hz, 1H), 4.34 (d, J = 13.2 Hz, 1H), 4.28 (d, J = 13.2 Hz, 1H), 3.77 (s, 2H), 3.60 (dq, J = 10.4, 5.6, 4.1 Hz, 1H), 3.42 (d, J = 5.5 Hz, 2H), 3.37-3.32 (m, 1H), 3.30-3.18 (m, 2H), 3.04 (t, J = 11.8 Hz, 1H), 2.99-2.83 (m, 5H), 2.80 (d, J = 10.6 Hz, 2H), 2.71 (s, 3H), 2.63 (dt, J = 6.8, 2.4 Hz, 1H), 2.59-2.55 (m, 1H), 2.44-2.32 (m, 1H), 2.12-1.97 (m, 1H), 1.95-1.67 (m, 8H), 1.58 (q, J = 12.0, 11.5 Hz, 3H). | LCMS: C$_{42}$H$_{49}$N$_{11}$O$_6$ requires: 813, found: m/z = 814 [M + H]$^+$. |
| 102 | $^1$H NMR (500 MHz, CD$_3$CN) δ 11.17 (s, 1H), 11.12 (s, 1H), 10.71 (s, 2H), 8.91 (s, 2H), 7.74-7.55 (m, 6H), 7.44 (s, 2H), 7.34 (dd, J = 11.6, 8.5 Hz, 3H), 7.18-7.08 (m, 2H), 7.03-6.99 (m, 1H), 6.94 (d, J = 8.6 Hz, 1H), 6.48-6.33 (m, 2H), 5.83 (s, 2H), 4.96 (dd, J = 12.4, 5.4 Hz, 2H), 4.48 (s, 2H), 4.32 (d, J = 12.8 Hz, 2H), 4.08-3.86 (m, 1H), 3.73 (s, 0H), 3.57-3.17 (m, 5H), 3.04 (dt, J = 25.2, 11.9 Hz, 4H), 2.81 (d, J = 15.0 Hz, 0H), 2.74-2.63 (m, 3H), 2.48 (d, J = 53.6 Hz, 1H), 1.68 (d, J = 12.7 Hz, 2H), 1.38 (s, 2H), 1.24 (s, 3H). | LCMS: C$_{43}$H$_{51}$N$_{11}$O$_6$ requires: 817, found: m/z = 818 [M + H]$^+$. |
| 103 | $^1$H NMR (500 MHz, CD$_3$CN) δ 11.14 (d, J = 13.1 Hz, 1H), 8.93 (s, 1H), 7.72-7.55 (m, 4H), 7.43 (s, 1H), 7.33 (dd, J = 17.9, 8.6 Hz, 2H), 7.14 (dd, J = 14.5, 7.1 Hz, 1H), 6.87 (dd, J = 22.9, 8.5 Hz, 1H), 6.46 (s, 0H), 6.36 (d, J = 5.2 Hz, 0H), 5.82 (s, 1H), 5.05-4.87 (m, 1H), 4.48 (s, 1H), 4.33 (s, 0H), 3.72 (s, 2H), 3.52-3.22 (m, 5H), 3.14-2.85 (m, 3H), 2.83-2.63 (m, 5H), 2.53 (t, J = 7.6 Hz, 1H), 1.37 (s, 1H), 1.25 (d, J = 7.2 Hz, 2H). | LCMS: C$_{43}$H$_{51}$N$_{11}$O$_6$ requires: 817, found: m/z = 818 [M + H]$^+$. |
| 104 | Stereoisomer 2: $^1$H NMR (500 MHz, Methanol-d$_4$) δ 8.10 (s, 1H), 8.05 (d, J = 7.7 Hz, 1H), 8.01 (d, J = 7.5 Hz, 1H), 7.95-7.81 (m, 2H), 7.63 (s, 2H), 7.17 (s, 1H), 5.18 (ddd, J = 25.3, 12.6, 5.5 Hz, 2H), 4.66-4.49 (m, 2H), 4.44 (d, J = 12.6 Hz, 1H), 4.35 (d, J = 13.7 Hz, 1H), 3.65 (d, J = 12.6 Hz, 1H), 3.53-3.40 (m, 4H), 3.13 (t, J = 11.8 Hz, 3H), 3.03 (t, J = 12.8 Hz, 2H), 2.98-2.83 (m, 3H), 2.83-2.69 (m, | LCMS: C$_{42}$H$_{49}$N$_{11}$O$_6$ requires 804, found: m/z = 804.7 [M + H]$^+$ |

TABLE 2-continued

Physical Data for the Example Compounds of Table 1.

| Compound No. | $^1$H NMR | Mass Spec (LCMS) |
|---|---|---|
| | 7H), 2.06 (d, J = 12.9 Hz, 2H), 1.93 (d, J = 23.4 Hz, 3H), 1.90-1.80 (m, 1H), 1.64 (d, J = 34.6 Hz, 4H). | |
| 105 | $^1$H NMR (500 MHz, Methanol-d$_4$) δ 7.82 (ddd, J = 8.1, 6.2, 3.9 Hz, 2H), 7.75-7.65 (m, 2H), 7.60 (dd, J = 16.5, 8.8 Hz, 2H), 7.47-7.32 (m, 2H), 5.20-5.00 (m, 1H), 4.36 (dt, J = 50.2, 13.1 Hz, 2H), 4.15 (q, J = 13.1, 11.1 Hz, 1H), 4.03-3.63 (m, 5H), 3.57 (d, J = 13.3 Hz, 1H), 3.54-3.36 (m, 3H), 3.36-3.30 (m, 4H), 3.02 (d, J = 14.6 Hz, 3H), 2.81-2.63 (m, 5H), 2.58 (d, J = 12.2 Hz, 1H), 2.24-2.00 (m, 3H), 2.01-1.79 (m, 3H), 1.71 (d, J = 37.4 Hz, 2H). | LCMS: $C_{41}H_{47}N_{11}O_6$ requires 790, found: m/z = 790.7 [M + H]$^+$ |
| 106 | Stereoisomer 2: $^1$H NMR (500 MHz, Methanol-d$_4$) δ 7.83 (dd, J = 9.2, 3.1 Hz, 2H), 7.72 (d, J = 2.0 Hz, 1H), 7.69 (dd, J = 8.6, 2.5 Hz, 1H), 7.56 (dd, J = 9.1, 3.2 Hz, 2H), 7.41 (d, J = 2.3 Hz, 1H), 7.28 (dd, J = 8.5, 2.4 Hz, 1H), 5.08 (ddd, J = 12.6, 5.6, 2.7 Hz, 1H), 4.45 (d, J = 12.9 Hz, 1H), 4.34 (d, J = 13.8 Hz, 1H), 4.07 (s, 1H), 3.97 (s, 1H), 3.76 (dd, J = 24.2, 12.2 Hz, 5H), 3.56 (d, J = 12.2 Hz, 1H), 3.52-3.39 (m, 4H), 3.18-2.99 (m, 5H), 2.91-2.82 (m, 2H), 2.80-2.76 (m, 2H), 2.74 (dd, J = 5.5, 3.2 Hz, 4H), 2.71 (s, 1H), 2.58 (s, 1H), 2.29 (s, 3H), 2.09 (dd, J = 22.6, 14.0 Hz, 3H), 1.94 (s, 5H), 1.72 (s, 3H). | LCMS: $C_{41}H_{47}N_{11}O_6$ requires 790, found: m/z = 790.7 [M + H]$^+$ |
| 107 | Stereoisomer 1: $^1$H NMR (500 MHz, Methanol-d$_4$) δ 7.88 (d, J = 8.7 Hz, 2H), 7.75 (s, 1H), 7.72 (d, J = 8.6 Hz, 1H), 7.58 (d, J = 8.8 Hz, 2H), 7.43 (d, J = 2.2 Hz, 1H), 7.33-7.28 (m, 1H), 5.10 (dd, J = 12.4, 5.5 Hz, 1H), 4.47 (d, J = 12.7 Hz, 1H), 4.39 (d, J = 14.1 Hz, 1H), 4.21 (d, J = 13.5 Hz, 1H), 4.07 (d, J = 12.9 Hz, 1H), 3.83-3.65 (m, 4H), 3.56-3.49 (m, 1H), 3.46 (t, J = 7.9 Hz, 2H), 3.40 (t, J = 7.8 Hz, 2H), 3.18-3.04 (m, 5H), 2.93-2.87 (m, 1H), 2.84 (s, 4H), 2.81-2.67 (m, 4H), 2.18-2.06 (m, 2H), 1.96 (t, J = 10.2 Hz, 4H), 1.91-1.85 (m, 2H), 1.51 (d, J = 12.8 Hz, 2H), 0.92 (t, J = 6.7 Hz, 3H). | LCMS: $C_{41}H_{47}N_{11}O_6$ requires 790, found: m/z = 790.5 [M + H]$^+$ |
| 108 | $^1$H NMR (500 MHz, DMSO-d$_6$) δ 11.17 (d, J = 7.9 Hz, 2H), 9.41 (s, 1H), 8.17 (s, 1H), 8.13-7.97 (m, 2H), 7.77 (s, 1H), 7.67 (s, 1H), 7.55 (d, J = 8.3 Hz, 2H), 7.34 (s, 1H), 7.14 (s, 2H), 5.19 (td, J = 13.1, 5.9 Hz, 1H), 4.54 (d, J = 48.5 Hz, 3H), 4.33 (dd, J = 28.6, 12.0 Hz, 4H), 3.45-3.12 (m, 9H), 3.12-2.76 (m, 6H), 2.71 (s, 3H), 2.26-1.99 (m, 2H), 1.99-1.73 (m, 7H), 1.58 (dd, J = 17.8, 9.0 Hz, 3H), 1.44-1.23 (m, 1H). | LCMS: $C_{43}H_{51}N_{11}O_6$ requires: 818, found: m/z = 818.7 [M + H]$^+$ |
| 109 | $^1$H NMR (500 MHz, DMSO-d$_6$) δ 11.07 (s, 1H), 10.99 (s, 1H), 7.72 (d, J = 2.7 Hz, 1H), 7.66 (d, J = 8.4 Hz, 1H), 7.62 (s, 1H), 7.44 (d, J = 8.6 Hz, 2H), 7.29 (d, J = 2.8 Hz, 1H), 6.97 (d, J = 2.1 Hz, 1H), 6.93 (d, J = 8.7 Hz, 2H), 6.85 (dd, J = 8.7, 2.2 Hz, 1H), 5.06 (dd, J = 12.7, 5.3 Hz, 1H), 4.44-4.21 (m, 2H), 3.70-3.48 (m, 3H), 3.29-3.07 (m, 3H), 3.06-2.80 (m, 2H), 2.74-2.60 (m, 6H), 2.07-1.91 (m, 3H), 1.87-1.44 (m, 10H). | LCMS: $C_{41}H_{47}N_{11}O_6$ requires: 789, found: m/z = 790 [M + H]$^+$ |
| 110 | $^1$H NMR (500 MHz, DMSO-d$_6$) δ 11.00 (s, 1H), 10.87 (s, 1H), 8.20 (d, J = 2.7 Hz, 1H), 7.88 (dd, J = 9.1, 2.8 Hz, 1H), 7.73 (s, 1H), 7.64 (s, 1H), 7.61-7.54 (m, 1H), 7.51-7.44 (m, 2H), 7.31 (d, J = 2.8 Hz, 1H), 6.77 (d, J = 9.1 Hz, 1H), 5.14 (dd, J = 13.3, 5.1 Hz, 1H), 4.48 (d, J = 17.2 Hz, 1H), 4.37-4.24 (m, 3H), 3.63-3.51 (m, 1H), 3.48-3.14 (m, 7H), 3.03 (t, J = 11.7 Hz, 1H), 2.97-2.87 (m, 2H), 2.74-2.22 (m, 13H), 2.05-1.99 (m, 1H), 1.82-1.77 (m, 3H), 1.69-1.61 (m, 2H), 1.57-1.49 (m, 4H). | LCMS: $C_{40}H_{50}N_{12}O_5$ requires 778, found: m/z = 779 [M + H]$^+$ |
| 111 | $^1$H NMR (500 MHz, DMSO-d$_6$) δ 11.16-10.96 (m, 2H), 7.72 (d, J = 2.9 Hz, 1H), 7.69-7.60 (m, 2H), 7.48-7.42 (m, 2H), 7.29 (d, J = 2.9 Hz, 1H), 6.99-6.92 (m, 2H), 6.83 (d, J = 2.1 Hz, 1H), 6.70 (dd, J = 8.4, 2.1 Hz, 1H), 5.08-5.01 (m, 1H), 4.38 (d, J = 12.5 Hz, 1H), 4.27 (d, J = 13.1 Hz, 1H), 3.85 (d, J = 9.0 Hz, 2H), 3.79 (d, J = 8.4 Hz, 2H), 3.63-3.59 (m, 1H), 3.26-3.16 (m, 3H), 3.03-2.82 (m, 5H), 2.65 (s, 3H), 2.61-2.35 (m, 4H), 2.05-1.98 (m, 1H), 1.86-1.63 (m, 8H), 1.60-1.48 (m, 1H). | LCMS: $C_{40}H_{45}N_{11}O_6$ requires: 775, found: m/z = 776 [M + H]$^+$ |

TABLE 2-continued

Physical Data for the Example Compounds of Table 1.

| Compound No. | ¹H NMR | Mass Spec (LCMS) |
|---|---|---|
| 112 | ¹H NMR (500 MHz, DMSO-d₆) δ 11.08 (s, 1H), 11.00 (s, 1H), 7.72 (d, J = 3.0 Hz, 1H), 7.69-7.60 (m, 2H), 7.47-7.41 (m, 2H), 7.29 (s, 1H), 6.96-6.90 (m, 2H), 6.81 (d, J = 2.1 Hz, 1H), 6.68 (dd, J = 8.4, 2.1 Hz, 1H), 5.05 (dd, J = 13.0, 5.4 Hz, 1H), 4.37 (d, J = 12.5 Hz, 1H), 4.28 (d, J = 13.5 Hz, 1H), 3.84 (s, 4H), 3.40-3.18 (m, 3H), 3.11 (t, J = 5.4 Hz, 4H), 3.06-2.83 (m, 3H), 2.72 (s, 3H), 2.65-2.34 (m, 3H), 2.05-1.98 (m, 1H), 1.91 (t, J = 5.4 Hz, 4H), 1.86-1.70 (m, 4H), 1.59-1.52 (m, 1H). | LCMS: $C_{40}H_{45}N_{11}O_6$ requires 775, found: m/z = 776 [M + H]⁺ |
| 113 | ¹H NMR (500 MHz, DMSO-d₆) δ 11.07 (s, 1H), 10.88 (s, 1H), 8.21 (s, 1H), 7.90 (d, J = 8.7 Hz, 1H), 7.77-7.70 (m, 1H), 7.69-7.59 (m, 2H), 7.31 (s, 1H), 6.92 (s, 1H), 6.87-6.75 (m, 2H), 5.07 (dd, J = 12.9, 5.4 Hz, 1H), 4.28 (d, J = 12.9 Hz, 2H), 3.67-3.38 (m, 7H), 3.31-3.13 (m, 3H), 3.10-2.81 (m, 3H), 2.73-2.56 (m, 5H), 2.24-1.96 (m, 2H), 1.80 (q, J = 14.0, 9.8 Hz, 5H), 1.55 (d, J = 13.2 Hz, 1H). | LCMS: $C_{41}H_{49}N_{13}O_6$ requires: 819, found: m/z = 820 [M + H]⁺. |
| 114 | ¹H NMR (500 MHz, DMSO-d₆) δ 11.09 (s, 1H), 10.98 (s, 1H), 9.46 (s, 1H), 7.78-7.64 (m, 2H), 7.61 (s, 1H), 7.45 (dd, J = 9.1, 3.8 Hz, 2H), 7.37 (s, 1H), 7.29 (d, J = 4.4 Hz, 2H), 6.70 (dd, J = 17.3, 8.6 Hz, 2H), 5.13-4.95 (m, 1H), 4.48-4.22 (m, 3H), 4.11 (d, J = 13.3 Hz, 2H), 3.99 (s, 2H), 3.01 (d, J = 10.9 Hz, 9H), 2.73 (d, J = 4.6 Hz, 4H), 2.62 (s, 4H), 2.11-1.93 (m, 3H), 1.82 (d, J = 11.0 Hz, 5H), 1.64-1.50 (m, 1H), 1.30-1.23 (m, 3H). | LCMS: $C_{45}H_{54}N_{12}O_6$ requires: 859, found: m/z = 858.7 [M + H]⁺ |
| 115 | ¹H NMR (500 MHz, DMSO-d₆) δ 11.20 (s, 1H), 10.99 (s, 1H), 7.98 (d, J = 9.2 Hz, 1H), 7.77 (s, 1H), 7.67 (s, 1H), 7.52 (d, J = 8.2 Hz, 2H), 7.34 (s, 1H), 7.21 (dd, J = 18.5, 7.8 Hz, 3H), 6.79 (d, J = 9.1 Hz, 1H), 6.58-6.44 (m, 2H), 4.50-4.23 (m, 3H), 4.04 (q, J = 7.1 Hz, 6H), 3.21-2.93 (m, 9H), 2.75 (s, 6H), 2.64 (d, J = 19.4 Hz, 7H), 2.40 (d, J = 7.9 Hz, 4H), 2.10 (t, J = 15.1 Hz, 5H), 1.88-1.53 (m, 12H). | LCMS: $C_{44}H_{53}N_{11}O_5$ requires: 816, found: m/z = 816.9 [M + H]⁺ |
| 116 | ¹H NMR (500 MHz, DMSO-d₆) δ 11.30 (s, 1H), 11.00 (s, 1H), 8.02 (d, J = 8.9 Hz, 1H), 7.79 (s, 1H), 7.69 (d, J = 3.0 Hz, 1H), 7.58 (d, J = 8.1 Hz, 2H), 7.36 (s, 1H), 7.28 (d, J = 7.4 Hz, 1H), 7.19 (d, J = 8.3 Hz, 3H), 6.65 (dd, J = 8.8, 2.3 Hz, 1H), 6.53 (s, 1H), 6.47 (d, J = 7.7 Hz, 2H), 4.42-4.15 (m, 4H), 3.80 (d, J = 7.5 Hz, 2H), 3.69-3.47 (m, 4H), 3.04 (dd, J = 61.3, 12.4 Hz, 5H), 2.82-2.57 (m, 6H), 1.92 (d, J = 95.5 Hz, 8H), 1.25 (s, 5H). | LCMS: $C_{43}H_{51}N_{11}O_5$ requires: 801, found: m/z = 802 [M + H]⁺ |
| 117 | ¹H NMR (500 MHz, Acetonitrile-d₃) δ 10.99 (s, 1H), 8.76 (s, 1H), 7.58-7.48 (m, 4H), 7.36 (d, J = 20.8 Hz, 1H), 7.19 (d, J = 8.1 Hz, 2H), 6.64 (d, J = 7.8 Hz, 2H), 5.76 (s, 1H), 5.08-4.88 (m, 2H), 4.42 (s, 1H), 4.35-4.11 (m, 3H), 3.69 (s, 1H), 3.59 (s, 1H), 3.52 (s, 0H), 3.48 (d, J = 8.2 Hz, 0H), 3.46-3.39 (m, 1H), 3.39-3.24 (m, 2H), 3.15-3.05 (m, 1H), 2.99 (dt, J = 24.0, 12.3 Hz, 3H), 2.87 (s, 1H), 2.77 (s, 3H), 2.72 (s, 0H), 2.71-2.58 (m, 2H), 2.48 (s, 1H), 2.40 (d, J = 7.8 Hz, 2H), 1.87 (s, 2H), 1.79 (d, J = 11.0 Hz, 4H), 1.69 (s, 8H), 1.27 (s, 2H), 1.15-1.04 (m, 0H), 0.84 (d, J = 6.6 Hz, 1H). | LCMS: $C_{43}H_{51}N_{11}O_5$ requires: 803, found: m/z = 804 [M + H]⁺ |
| 118 | ¹H NMR (500 MHz, Acetonitrile-d₃) δ 11.23 (d, J = 5.4 Hz, 1H), 8.80 (s, 1H), 7.84 (d, J = 2.8 Hz, 1H), 7.73-7.66 (m, 2H), 7.60 (s, 1H), 7.48-7.35 (m, 2H), 7.30 (d, J = 8.5 Hz, 2H), 5.84 (t, J = 2.7 Hz, 2H), 5.57 (dd, J = 12.3, 5.4 Hz, 1H), 4.61 (s, 2H), 4.56-4.30 (m, 3H), 4.28-4.08 (m, 2H), 4.08-3.93 (m, 2H), 3.91 (d, J = 13.5 Hz, 2H), 3.77-3.63 (m, 1H), 3.45-3.15 (m, 6H), 3.15-2.88 (m, 7H), 2.63-2.49 (m, 6H), 2.14 (ddt, J = 10.5, 5.5, 2.8 Hz, 2H), 1.89-1.74 (m, 5H), 1.74-1.57 (m, 2H), 1.51-1.19 (m, 3H). | LCMS: $C_{38}H_{48}N_{12}O_5$ requires: 752, found: m/z = 753 [M + H]⁺ |
| 119 | ¹H NMR (500 MHz, Acetonitrile-d₃) δ 11.23 (d, J = 6.0 Hz, 1H), 9.50 (s, 1H), 8.85 (s, 1H), 7.70 (dd, J = 8.6, 4.5 Hz, 2H), 7.61 (s, 1H), 7.57-7.48 (m, 2H), 7.45 (s, 1H), 7.37 (d, J = 8.3 Hz, 1H), 7.35-7.28 (m, 2H), 7.07 (dd, J = 9.0, 2.0 Hz, 2H), 5.85 (s, 1H), 5.04 (dd, J = 12.4, 5.2 Hz, 1H), 4.61 (q, J = 8.2, 7.2 Hz, 2H), 4.56-4.40 (m, 3H), 4.40-3.98 (m, 5H), 3.88 (d, J = 12.8 Hz, 2H), 3.74-3.67 (m, 1H), 3.43- | LCMS: $C_{43}H_{53}N_{13}O_5$ requires: 831, found: m/z = 832 [M + H]⁺ |

TABLE 2-continued

Physical Data for the Example Compounds of Table 1.

| Compound No. | $^1$H NMR | Mass Spec (LCMS) |
|---|---|---|
| | 3.35 (m, 2H), 3.35-3.26 (m, 7H), 3.17 (t, J = 6.5 Hz, 3H), 3.13-2.95 (m, 6H), 2.93-2.81 (m, 5H), 2.60 (qd, J = 12.6, 5.5 Hz, 3H), 2.23 (dtd, J = 13.6, 5.2, 3.5 Hz, 1H), 1.91-1.78 (m, 6H), 1.74-1.59 (m, 2H), 1.49-1.37 (m, 2H). | |
| 120 | $^1$H NMR (500 MHz, Acetonitrile-d$_3$) δ 11.13 (s, 1H), 9.75 (s, 1H), 8.80 (s, 1H), 7.85 (d, J = 2.9 Hz, 1H), 7.71-7.54 (m, 3H), 7.43 (s, 1H), 7.22 (t, J = 9.5 Hz, 2H), 5.89-5.72 (m, 2H), 5.57 (dd, J = 12.2, 5.3 Hz, 1H), 4.37 (dd, J = 50.3, 13.4 Hz, 3H), 3.92 (d, J = 13.4 Hz, 3H), 3.69 (dd, J = 12.1, 8.5 Hz, 4H), 3.58-3.16 (m, 7H), 3.16-3.03 (m, 2H), 3.03-2.87 (m, 9H), 2.88-2.82 (m, 2H), 2.71 (dd, J = 15.5, 6.1 Hz, 2H), 2.59 (qd, J = 12.9, 4.9 Hz, 5H), 2.24-2.03 (m, 10H), 1.95-1.80 (m, 8H), 1.68 (t, J = 12.1 Hz, 2H), 1.37 (q, J = 12.6 Hz, 3H). | LCMS: $C_{40}H_{52}N_{12}O_5$ requires: 780, found: m/z = 781 [M + H]$^+$ |
| 121 | $^1$H NMR (500 MHz, Methanol-d$_4$) δ 7.63 (s, 1H), 7.60-7.49 (m, 4H), 7.20 (d, J = 8.3 Hz, 2H), 7.09 (d, J = 8.6 Hz, 2H), 5.19 (dd, J = 12.6, 5.3 Hz, 2H), 4.41 (dd, J = 37.5, 13.0 Hz, 2H), 3.91 (d, J = 12.7 Hz, 2H), 3.84-3.70 (m, 1H), 3.54-3.40 (m, 6H), 3.40-3.36 (m, 3H), 3.20-3.06 (m, 4H), 3.02 (t, J = 12.5 Hz, 2H), 2.96-2.86 (m, 2H), 2.77-2.49 (m, 3H), 2.41 (d, J = 6.7 Hz, 2H), 2.28-2.18 (m, 2H), 2.01-1.77 (m, 10H), 1.69 (dd, J = 27.1, 14.7 Hz, 2H), 1.47-1.32 (m, 3H). | LCMS: $C_{40}H_{52}N_{12}O_5$ requires: 859, found: m/z = 860 [M + H]$^+$ |
| 122 | $^1$H NMR (500 MHz, CD$_3$CN) δ 11.09 (s, 1H), 10.21 (s, 1H), 8.71 (s, 1H), 7.77 (d, J = 8.7 Hz, 1H), 7.60-7.53 (m, 3H), 7.40 (s, 1H), 7.19 (d, J = 8.3 Hz, 2H), 6.86 (dd, J = 8.9, 2.5 Hz, 1H), 6.74 (d, J = 2.6 Hz, 1H), 5.80 (s, 1H), 5.15 (s, 1H), 4.37 (d, J = 12.7 Hz, 1H), 4.29 (d, J = 13.6 Hz, 1H), 3.97-3.86 (m, 3H), 3.64 (d, J = 12.3 Hz, 2H), 3.43 (tdd, J = 21.4, 11.4, 5.2 Hz, 4H), 3.09-2.63 (m, 12H), 2.50 (s, 1H), 2.42-2.10 (m, 8H), 2.04-1.97 (m, 3H), 1.89-1.79 (m, 6H), 1.71-1.60 (m, 1H), 1.37 (q, J = 11.0, 10.5 Hz, 2H). | LCMS: $C_{45}H_{56}N_{10}O_5$ requires: 816, found: m/z = 817 [M + H]$^+$ |
| 123 | $^1$H NMR (500 MHz, DMSO-d$_6$) δ 11.26 (s, 1H), 11.17 (s, 1H), 9.55 (s, 1H), 8.17-8.03 (m, 2H), 7.98 (d, J = 7.7 Hz, 1H), 7.75 (s, 1H), 7.68 (s, 1H), 7.57 (s, 1H), 7.32 (s, 1H), 7.17 (s, 1H), 5.21 (dd, J = 13.0, 5.4 Hz, 1H), 4.57 (d, J = 4.9 Hz, 2H), 3.33-3.03 (m, 8H), 2.92 (ddd, J = 18.4, 13.9, 5.4 Hz, 1H), 2.74-2.58 (m, 1H), 2.14-2.03 (m, 1H), 1.88 (d, J = 44.4 Hz, 3H), 1.76-1.45 (m, 11H). | LCMS: $C_{39}H_{45}N_9O_5$ requires: 719.8, found: m/z = 720.6 [M + H]$^+$ |
| 124 | $^1$H NMR (500 MHz, DMSO-d$_6$) δ 11.46 (s, 1H), 11.09 (s, 1H), 7.79 (s, 1H), 7.75-7.65 (m, 3H), 7.37 (d, J = 9.2 Hz, 2H), 7.28 (d, J = 8.7 Hz, 1H), 5.08 (dd, J = 12.7, 5.4 Hz, 1H), 2.90 (ddd, J = 18.4, 13.9, 5.4 Hz, 1H), 2.60 (d, J = 18.7 Hz, 2H), 2.03 (dt, J = 11.3, 5.2 Hz, 1H), 1.83 (s, 4H), 1.65 (dq, J = 33.5, 5.5 Hz, 10H). | LCMS: $C_{38}H_{43}N_9O_5$ requires: 705.8, found: m/z = 706.7 [M + H]$^+$ |
| 125 | $^1$H NMR (500 MHz, Acetonitrile-d$_3$) δ 11.34 (s, 1H), 11.16 (s, 1H), 8.89 (s, 1H), 8.57 (s, 1H), 8.51 (d, J = 2.7 Hz, 1H), 7.87 (s, 1H), 7.76 (s, 1H), 7.69 (dd, J = 21.8, 8.3 Hz, 3H), 7.34 (d, J = 8.3 Hz, 2H), 6.98 (d, J = 2.2 Hz, 1H), 6.83 (dd, J = 8.5, 2.1 Hz, 1H), 6.62 (t, J = 2.1 Hz, 1H), 6.28 (s, 1H), 4.96 (dd, J = 12.0, 5.4 Hz, 1H), 3.90-3.65 (m, 3H), 3.65-3.53 (m, 1H), 3.47 (q, J = 8.7 Hz, 1H), 3.31 (t, J = 9.0 Hz, 3H), 3.12-2.83 (m, 4H), 2.83-2.62 (m, 3H), 2.53 (s, 1H). | LCMS: $C_{37}H_{38}N_{10}O_5$ requires: 702.8, found: m/z = 703.7 [M + H]$^+$ |
| 126 | $^1$H NMR (500 MHz, DMSO-d$_6$) δ 11.36 (d, J = 6.8 Hz, 1H), 11.09 (s, 1H), 9.08 (d, J = 10.7 Hz, 1H), 7.78 (d, J = 7.6 Hz, 2H), 7.71 (d, J = 8.4 Hz, 1H), 7.66 (d, J = 8.2 Hz, 2H), 7.36 (d, J = 11.7 Hz, 1H), 7.24 (d, J = 8.2 Hz, 2H), 6.97 (d, J = 2.1 Hz, 1H), 6.87 (dd, J = 8.6, 2.2 Hz, 1H), 5.08 (dd, J = 12.7, 5.5 Hz, 1H), 4.32 (s, 4H), 3.98 (s, 2H), 3.83-3.65 (m, 5H), 3.13 (t, J = 10.9 Hz, 3H), 2.88 (ddt, J = 24.4, 16.0, 12.6 Hz, 4H), 2.63-2.55 (m, 3H), 2.31 (dd, J = 12.3, 6.9 Hz, 1H), 2.04 (q, J = 9.5, 5.9 Hz, 3H), 1.92 (h, J = 7.9, 5.9 Hz, 4H), 1.58 (q, J = 7.4, 6.0 Hz, 2H). | LCMS: $C_{41}H_{47}N_9O_6$ requires: 761.9, found: m/z = 762.8 [M + H]$^+$ |

TABLE 2-continued

Physical Data for the Example Compounds of Table 1.

| Compound No. | $^1$H NMR | Mass Spec (LCMS) |
|---|---|---|
| 127 | $^1$H NMR (500 MHz, DMSO-d$_6$) δ 11.61 (s, 1H), 11.01 (s, 1H), 8.90 (s, 1H), 8.72 (d, J = 2.6 Hz, 1H), 8.51 (d, J = 16.4 Hz, 2H), 8.10-7.96 (m, 2H), 7.72 (d, J = 8.2 Hz, 2H), 7.37 -7.18 (m, 5H), 7.00 (d, J = 2.3 Hz, 1H), 6.49 (d, J = 7.5 Hz, 1H), 4.04 (d, J = 12.9 Hz, 2H), 3.09 (q, J = 6.5 Hz, 5H), 3.01-2.79 (m, 6H), 2.03 (tdd, J = 22.6, 13.7, 10.1 Hz, 6H), 1.88 (d, J = 13.2 Hz, 3H), 1.33 (qd, J = 15.6, 15.1, 5.7 Hz, 2H). | LCMS: $C_{40}H_{41}N_{10}F_3O_4$ requires: 782.8, found: m/z = 783.8 [M + H]$^+$ |
| 128 | $^1$H NMR (500 MHz, DMSO-d$_6$) δ 11.26 (s, 1H), 11.08 (s, 1H), 7.84-7.75 (m, 1H), 7.75-7.59 (m, 2H), 7.51 (d, J = 8.2 Hz, 2H), 7.40-7.31 (m, 1H), 7.19 (d, J = 8.2 Hz, 2H), 6.98 -6.75 (m, 2H), 5.06 (dd, J = 12.9, 5.4 Hz, 1H), 4.41 (d, J = 12.8 Hz, 1H), 4.31 (t, J = 8.0 Hz, 3H), 3.61 (dt, J = 15.9, 8.2 Hz, 7H), 3.16 (d, J = 10.7 Hz, 6H), 3.02 (dt, J = 20.5, 10.8 Hz, 4H), 2.92-2.85 (m, 1H), 2.64 (d, J = 28.8 Hz, 3H), 2.40 (d, J = 7.5 Hz, 3H), 2.15 (d, J = 6.9 Hz, 1H), 2.14-1.97 (m, 4H), 1.83 (ddd, J = 43.1, 32.8, 8.9 Hz, 7H), 1.63 (dd, J = 30.3, 13.7 Hz, 4H). | LCMS: $C_{38}H_{37}N_1F_3O_5$ requires: 770.8, found: m/z = 771.8 [M + H]$^+$ |
| 129 | $^1$H NMR (500 MHz, DMSO-d$_6$) δ 11.28 (s, 1H), 10.77 (s, 1H), 8.81 (s, 1H), 7.78 (s, 1H), 7.68 (s, 2H), 7.56 (d, J = 8.0 Hz, 2H), 7.35 (s, 1H), 7.18 (d, J = 8.2 Hz, 2H), 7.05 (s, 1H), 6.73 (s, 1H), 6.52 (s, 1H), 5.41 (s, 1H), 4.31 (s, 2H), 4.20 (s, 1H), 4.05 (d, J = 12.5 Hz, 2H), 3.62 (d, J = 11.3 Hz, 4H), 3.30-3.20 (m, 2H), 3.06 (d, J = 14.2 Hz, 5H), 2.96 (d, J = 12.4 Hz, 1H), 2.77 (s, 2H), 2.71 (d, J = 3.6 Hz, 3H), 2.66 (d, J = 16.1 Hz, 2H), 2.60 (s, 0H), 2.09 (s, 1H), 1.98 (s, 2H), 1.90 (d, J = 18.1 Hz, 2H), 1.79 (d, J = 15.6 Hz, 6H), 1.57 (d, J = 13.8 Hz, 2H), 1.26 (d, J = 13.6 Hz, 3H). | LCMS: $C_{41}H_{54}N_{12}O_4$ requires: 778, found: m/z = 779 [M + H]$^+$ |
| 130 | $^1$H NMR (500 MHz, DMSO-d$_6$) δ 11.18 (s, 1H), 10.84 (s, 1H), 8.69 (d, J = 8.3 Hz, 1H), 8.31 (s, 1H), 7.84 (d, J = 8.9 Hz, 1H), 7.75 (s, 1H), 7.66 (s, 1H), 7.49 (d, J = 7.9 Hz, 2H), 7.40 (d, J = 9.0 Hz, 1H), 7.32 (s, 1H), 7.19-7.13 (m, 2H), 5.75 (s, 1H), 4.74 (s, 1H), 4.35 (s, 1H), 4.28 (d, J = 13.1 Hz, 1H), 3.94 (d, J = 12.5 Hz, 2H), 3.62 (s, 1H), 3.27 (d, J = 7.7 Hz, 2H), 3.07-2.96 (m, 1H), 2.97-2.91 (m, 3H), 2.86 (t, J = 12.5 Hz, 2H), 2.81-2.74 (m, 1H), 2.72 (s, 3H), 2.42 (s, 1H), 2.18 (d, J = 5.8 Hz, 3H), 2.02-1.93 (m, 4H), 1.85-1.78 (m, 5H), 1.77-1.71 (m, 3H), 1.63-1.59 (m, 3H), 1.25-1.16 (m, 3H). | LCMS: $C_{42}H_{54}N_{12}O_5$ requires: 806, found: m/z = 807 [M + H]$^+$ |
| 131 | $^1$H NMR (500 MHz, Acetonitrile-d$_3$) δ 11.17 (s, 1H), 10.73 (s, 1H), 8.75 (s, 1H), 8.33-8.17 (m, 2H), 7.91 (d, J = 8.8 Hz, 1H), 7.84 (s, 1H), 7.53-7.41 (m, 2H), 7.40-7.24 (m, 2H), 5.76 (s, 1H), 4.72 (ddd, J = 13.1, 7.8, 5.5 Hz, 1H), 4.59 (d, J = 45.9 Hz, 4H), 4.31-4.08 (m, 3H), 3.93 (d, J = 13.1 Hz, 3H), 3.84 (s, 3H), 3.77-3.70 (m, 1H), 3.14 (d, J = 49.4 Hz, 6H), 2.89 (t, J = 12.1 Hz, 2H), 2.75 (ddd, J = 18.5, 13.4, 5.5 Hz, 1H), 2.67 (s, 1H), 2.33-2.22 (m, 1H), 2.13 (qd, J = 13.4, 5.2 Hz, 1H), 2.00 (d, J = 11.5 Hz, 1H), 1.92-1.72 (m, 2H), 1.67 (t, J = 12.5 Hz, 1H), 1.45-1.30 (m, 2H). | LCMS: $C_{36}H_{45}N_{13}O_6$ requires: 755, found: m/z = 756 [M + H]$^+$ |
| 132 | $^1$H NMR (500 MHz, Acetonitrile-d$_3$) δ 12.38 (s, 1H), 10.72 (s, 1H), 8.73 (s, 1H), 7.84 (s, 1H), 7.54 (dd, J = 9.6, 2.9 Hz, 1H), 7.47 (s, 1H), 7.45 (s, 1H), 7.43 (d, J = 2.8 Hz, 1H), 7.34 (s, 1H), 7.08 (d, J = 9.7 Hz, 1H), 5.76 (s, 1H), 4.54 (d, J = 11.6 Hz, 2H), 4.18 (d, J = 14.2 Hz, 1H), 4.13 (dd, J = 12.1, 4.9 Hz, 1H), 3.99 (d, J = 13.4 Hz, 2H), 3.90 (s, 2H), 3.83 (s, 3H), 3.72 (dq, J = 11.0, 5.4, 4.7 Hz, 1H), 3.16 (s, 2H), 3.13-2.99 (m, 4H), 2.77-2.64 (m, 3H), 2.31-2.21 (m, 3H), 1.99 (dd, J = 12.0, 5.5 Hz, 3H), 1.92-1.83 (m, 3H), 1.83-1.72 (m, 1H), 1.66 (dd, J = 17.1, 8.3 Hz, 1H), 1.35 (qd, J = 12.3, 4.0 Hz, 2H). | LCMS: $C_{35}H_{45}N_{13}O_5$ requires: 727, found: m/z = 728 [M + H]$^+$ |
| 133 | $^1$H NMR (500 MHz, Acetonitrile-d$_3$) δ 11.14 (s, 1H), 9.42 (s, 1H), 8.82 (s, 1H), 8.07 (d, J = 9.1 Hz, 1H), 7.61 (d, J = 8.3 Hz, 2H), 7.54 (s, 1H), 7.38 (s, 1H), 7.20 (d, J = 8.1 Hz, 2H), 7.17-7.11 (m, 1H), 7.03 (d, J = 7.4 Hz, 1H), 6.92 (d, J = 2.7 Hz, 1H), 6.45 (d, J = 7.5 Hz, 1H), 5.79-5.75 (m, 1H), 5.23 (s, 1H), 3.97 (d, J = 12.9 Hz, 2H), 3.72-3.63 (m, | LCMS: $C_{41}H_{59}N_9O_4$ requires: 731, found: m/z = 732 [M + H]$^+$ |

TABLE 2-continued

Physical Data for the Example Compounds of Table 1.

| Compound No. | $^1$H NMR | Mass Spec (LCMS) |
|---|---|---|
| | 6H), 3.16-3.12 (m, 1H), 3.00-2.88 (m, 5H), 2.82-2.73 (m, 0H), 2.14 (s, 4H), 2.13-2.06 (m, 1H), 2.03 (d, J = 14.6 Hz, 2H), 1.71 (d, J = 7.0 Hz, 2H), 1.64 (d, J = 7.0 Hz, 5H), 1.40 (d, J = 12.5 Hz, 2H), 1.32 (dd, J = 10.7, 6.4 Hz, 3H). | |
| 134 | $^1$H NMR (500 MHz, DMSO-d$_6$) δ 11.20 (s, 1H), 10.99 (s, 1H), 7.98 (d, J = 9.2 Hz, 1H), 7.77 (s, 1H), 7.67 (s, 1H), 7.52 (d, J = 8.2 Hz, 2H), 7.34 (s, 1H), 7.21 (dd, J = 18.5, 7.8 Hz, 3H), 6.79 (d, J = 9.1 Hz, 1H), 6.58-6.44 (m, 2H), 4.50-4.23 (m, 3H), 4.04 (q, J = 7.1 Hz, 6H), 3.21-2.93 (m, 9H), 2.75 (s, 6H), 2.64 (d, J = 19.4 Hz, 7H), 2.40 (d, J = 7.9 Hz, 4H), 2.10 (t, J = 15.1 Hz, 5H), 1.88-1.53 (m, 12H). | LCMS: C$_{41}$H$_{59}$N$_9$O$_4$ requires: 815, found: m/z = 816 [M + H]$^+$ |
| 135 | $^1$H NMR (500 MHz, DMSO-d$_6$) δ 11.22 (s, 1H), 11.03 (s, 1H), 7.80-7.75 (m, 1H), 7.68 (s, 1H), 7.49 (dd, J = 8.6, 2.7 Hz, 4H), 7.37-7.33 (m, 1H), 7.17 (d, J = 8.2 Hz, 2H), 6.52 (d, J = 8.5 Hz, 2H), 5.18 (dd, J = 12.6, 5.3 Hz, 1H), 4.31 (d, J = 12.7 Hz, 2H), 4.03 (t, J = 7.6 Hz, 2H), 3.89-3.85 (m, 1H), 3.60-3.54 (m, 2H), 3.45-3.37 (m, 2H), 3.30 (s, 3H), 3.10 (t, J = 11.8 Hz, 1H), 3.05-2.82 (m, 5H), 2.51 (p, J = 1.7 Hz, 5H), 2.34-2.25 (m, 2H), 2.17-2.01 (m, 3H), 2.01-1.93 (m, 2H), 1.87-1.72 (m, 5H), 1.70-1.52 (m, 3H). | LCMS: C$_{43}$H$_{52}$N$_{12}$O$_5$ requires 816, found: m/z = 817 [M + H]$^+$ |
| 136 | $^1$H NMR (500 MHz, DMSO-d$_6$) δ 11.20 (s, 1H), 11.03 (s, 1H), 7.79-7.74 (m, 1H), 7.67 (s, 1H), 7.53-7.45 (m, 4H), 7.36-7.32 (m, 1H), 7.17 (d, J = 8.2 Hz, 2H), 6.54-6.48 (m, 2H), 5.18 (dd, J = 12.7, 5.2 Hz, 1H), 4.37 (d, J = 12.4 Hz, 1H), 4.30 (d, J = 13.3 Hz, 1H), 4.02 (t, J = 7.6 Hz, 2H), 3.67-3.53 (m, 3H), 3.31 (d, J = 13.5 Hz, 8H), 3.09-2.79 (m, 6H), 2.73 (s, 3H), 2.65-2.58 (m, 3H), 2.51-2.39 (m, 1H), 2.14-2.02 (m, 2H), 1.89-1.70 (m, 5H), 1.61 (dq, J = 23.4, 12.0 Hz, 4H). | LCMS: C$_{43}$H$_{53}$N$_{13}$O$_5$ requires 832, found: m/z = 832 [M + H]$^+$ |
| 137 | $^1$H NMR (500 MHz, Acetonitrile-d$_3$) δ 10.70 (s, 1H), 10.54 (s, 1H), 8.88 (s, 1H), 7.74 (s, 1H), 7.70-7.59 (m, 1H), 7.56 (s, 1H), 7.48 (d, J = 5.3 Hz, 1H), 7.34 (s, 1H), 7.30 (s, 1H), 7.16 (d, J = 8.6 Hz, 1H), 5.83-5.69 (m, 1H), 4.93 (dd, J = 12.3, 5.4 Hz, 1H), 4.54-4.37 (m, 1H), 4.30 (s, 1H), 4.22 (d, J = 13.3 Hz, 1H), 4.14 (dd, J = 11.1, 5.2 Hz, 1H), 4.09-3.97 (m, 3H), 3.95 (d, J = 10.1 Hz, 1H), 3.83 (d, J = 9.4 Hz, 3H), 3.47-3.28 (m, 2H), 3.25-3.12 (m, 2H), 3.06 (dt, J = 19.7, 12.2 Hz, 2H), 2.97 (t, J = 12.6 Hz, 2H), 2.85-2.61 (m, 3H), 2.38 (dt, J = 23.8, 7.2 Hz, 2H), 2.19-2.02 (m, 1H), 1.91-1.73 (m, 6H), 1.66 (d, J = 13.0 Hz, 1H), 1.47-1.24 (m, 2H). | LCMS: C$_{39}$H$_{46}$N$_{12}$O$_6$ requires 778, found: m/z = 779 [M + H]$^+$ |
| 138 | $^1$H NMR (500 MHz, DMSO-d$_6$) δ 11.30 (s, 1H), 11.00 (s, 1H), 8.02 (d, J = 8.9 Hz, 1H), 7.79 (s, 1H), 7.69 (d, J = 3.0 Hz, 1H), 7.58 (d, J = 8.1 Hz, 2H), 7.36 (s, 1H), 7.28 (d, J = 7.4 Hz, 1H), 7.19 (d, J = 8.3 Hz, 3H), 6.65 (dd, J = 8.8, 2.3 Hz, 1H), 6.53 (s, 1H), 6.47 (d, J = 7.7 Hz, 2H), 4.42-4.15 (m, 4H), 3.80 (d, J = 7.5 Hz, 2H), 3.69-3.47 (m, 4H), 3.04 (dd, J = 61.3, 12.4 Hz, 5H), 2.82-2.57 (m, 6H), 1.92 (d, J = 95.5 Hz, 8H), 1.25 (s, 5H). | LCMS: C$_{43}$H$_{51}$N$_{11}$O$_5$ requires 801, found: m/z = 802 [M + H]$^+$ |
| 139 | $^1$H NMR (500 MHz, DMSO-d$_6$) δ 11.22 (s, 1H), 10.98 (s, 1H), 7.96 (d, J = 9.0 Hz, 1H), 7.77 (s, 1H), 7.67 (s, 1H), 7.51 (d, J = 8.0 Hz, 2H), 7.35 (s, 1H), 7.25 (d, J = 7.8 Hz, 3H), 7.15 (d, J = 9.3 Hz, 1H), 6.94 (s, 1H), 6.46 (d, J = 7.5 Hz, 1H), 4.35-4.27 (m, 2H), 3.95 (d, J = 12.7 Hz, 2H), 3.86 (d, J = 10.1 Hz, 1H), 3.61 (d, J = 6.7 Hz, 2H), 3.55 (t, J = 7.7 Hz, 1H), 3.40 (q, J = 7.3 Hz, 2H), 3.04 (td, J = 23.5, 20.0, 12.5 Hz, 4H), 2.84 (t, J = 12.6 Hz, 3H), 2.61 (t, J = 14.6 Hz, 2H), 2.34 (d, J = 7.2 Hz, 3H), 2.28 (q, J = 11.6, 9.9 Hz, 2H), 1.96 (dh, J = 17.4, 9.5, 8.4 Hz, 3H), 1.79 (d, J = 13.1 Hz, 4H), 1.56 (d, J = 12.1 Hz, 2H), 1.21 (q, J = 12.8, 12.4 Hz, 3H). | LCMS: C$_{43}$H$_{50}$N$_{10}$O$_5$ requires: 786, found: m/z = 787 [M + H]$^+$ |
| 140 | $^1$H NMR (500 MHz, CD$_3$CN) δ 11.06 (s, 1H), 8.88 (s, 1H), 7.63-7.52 (m, 4H), 7.40 (s, 1H), 7.28 (d, J = 8.1 Hz, 2H), 6.92 (s, 1H), 6.77 (d, J = 8.5 Hz, 1H), 5.79 (s, 1H), 4.92 (q, J = 5.4 Hz, 1H), 4.38 (d, J = 12.8 Hz, 1H), 4.29 (d, J = 13.5 Hz, 1H), 3.95 (d, J = 12.4 Hz, 1H), 3.77 (s, 2H), 3.66 (s, 1H), 3.56 (d, J = | LCMS: C$_{41}$H$_{46}$N$_{10}$O$_6$ requires: 774, found: m/z = 775 [M + H]$^+$ |

TABLE 2-continued

Physical Data for the Example Compounds of Table 1.

| Compound No. | ¹H NMR | Mass Spec (LCMS) |
|---|---|---|
| | 8.9 Hz, 1H), 3.49 (d, J = 8.3 Hz, 1H), 3.40 (dt, J = 17.0, 7.8 Hz, 3H), 3.29-3.20 (m, 2H), 3.17 (d, J = 8.8 Hz, 1H), 3.02 (dt, J = 27.3, 12.5 Hz, 2H), 2.81-2.58 (m, 5H), 2.43 (s, 1H), 2.30 (d, J = 8.8 Hz, 2H), 2.11 (m, 1H), 1.99 (d, J = 8.5 Hz, 2H), 1.86 (d, J = 9.8 Hz, 3H), 1.81 (s, 1H), 1.78 (d, J = 10.4 Hz, 1H), 1.66 (s, 1H). | |
| 141 | ¹H NMR (500 MHz, CD$_3$CN) δ 11.05 (s, 1H), 8.83 (s, 1H), 7.55 (d, J = 9.8 Hz, 3H), 7.48 (d, J = 8.5 Hz, 2H), 7.40 (s, 1H), 7.28 (d, J = 8.2 Hz, 2H), 7.00 (d, J = 8.6 Hz, 2H), 5.79 (s, 1H), 5.00 (d, J = 12.4 Hz, 1H), 4.39 (d, J = 13.0 Hz, 1H), 4.29 (d, J = 13.8 Hz, 1H), 3.93 (d, J = 11.2 Hz, 1H), 3.82 (d, J = 12.7 Hz, 2H), 3.68 (s, 2H), 3.61 (s, 1H), 3.42 (dt, J = 25.7, 8.7 Hz, 2H), 3.30 (s, 3H), 3.14 (s, 2H), 3.01 (dt, J = 26.3, 12.4 Hz, 2H), 2.83-2.69 (m, 4H), 2.58 (q, J = 14.1 Hz, 1H), 2.41 (d, J = 6.7 Hz, 2H), 2.30 (d, J = 8.7 Hz, 2H), 2.21 (m, 1H), 2.00 (d, J = 8.0 Hz, 3H), 1.83 (d, J = 13.7 Hz, 4H), 1.67 (t, J = 13.1 Hz, 1H), 1.55 (d, J = 12.7 Hz, 1H), 1.28 (q, J = 13.4, 13.0 Hz, 2H). | LCMS: C$_{43}$H$_{52}$N$_{12}$O$_5$ requires: 816, found: m/z = 817 [M + H]⁺ |
| 142 | ¹H NMR (500 MHz, DMSO-d$_6$) δ 11.23 (d, J = 46.5 Hz, 1H), 11.02 (s, 1H), 7.76 (s, 1H), 7.66 (s, 1H), 7.50 (s, 4H), 7.33 (s, 1H), 7.17 (d, J = 8.3 Hz, 2H), 6.62 (d, J = 8.3 Hz, 2H), 5.17 (dd, J = 12.7, 5.3 Hz, 1H), 4.45-4.18 (m, 2H), 3.61 (d, J = 10.8 Hz, 1H), 3.41 (d, J = 29.2 Hz, 3H), 3.16-2.92 (m, 5H), 2.88 (ddd, J = 17.8, 13.3, 5.4 Hz, 1H), 2.73 (s, 3H), 2.61 (d, J = 17.5 Hz, 4H), 2.48-2.40 (m, 4H), 2.36 (s, 1H), 2.17-1.91 (m, 5H), 1.79 (dd, J = 30.2, 12.0 Hz, 7H), 1.70-1.46 (m, 5H). | LCMS: C$_{44}$H$_{55}$N$_{13}$O$_5$ requires: 845, found: m/z = 846 [M + H]⁺ |
| 143 | ¹H NMR (500 MHz, CD$_3$CN) δ 11.09 (s, 1H), 8.83 (s, 1H), 7.58 (d, J = 8.3 Hz, 2H), 7.55 (s, 1H), 7.51 (d, J = 8.4 Hz, 2H), 7.40 (s, 1H), 7.18 (d, J = 8.1 Hz, 2H), 7.04 (d, J = 8.5 Hz, 2H), 5.81 (s, 1H), 5.01 (dd, J = 12.4, 5.2 Hz, 1H), 4.40-4.33 (m, 1H), 4.29 (d, J = 13.5 Hz, 1H), 3.94 (dt, J = 10.7, 6.2 Hz, 1H), 3.86 (d, J = 12.7 Hz, 2H), 3.66 (d, J = 12.2 Hz, 2H), 3.42 (dq, J = 29.1, 8.3 Hz, 2H), 3.31 (s, 3H), 3.09-2.94 (m, 6H), 2.90-2.74 (m, 4H), 2.58 (qd, J = 12.7, 5.6 Hz, 3H), 2.32 (dt, J = 9.5, 4.7 Hz, 2H), 2.21 (dt, J = 13.3, 4.7 Hz, 1H), 2.14-1.97 (m, 6H), 1.92-1.79 (m, 4H), 1.66 (d, J = 11.6 Hz, 1H), 1.41 (qd, J = 12.2, 3.9 Hz, 2H). | LCMS: C$_{45}$H$_{56}$N$_{12}$O$_5$ requires: 844, found: m/z = 845 [M + H]⁺ |
| 144 | ¹H NMR (500 MHz, CD$_3$CN) δ 11.09 (s, 1H), 9.05 (s, 1H), 8.83 (s, 1H), 8.08 (d, J = 9.0 Hz, 1H), 7.63-7.53 (m, 3H), 7.40 (s, 1H), 7.16 (dd, J = 20.0, 8.6 Hz, 3H), 7.03 (d, J = 7.4 Hz, 1H), 6.92 (s, 1H), 6.45 (d, J = 7.5 Hz, 1H), 5.81 (s, 1H), 5.24 (s, 1H), 4.37 (d, J = 11.7 Hz, 1H), 4.29 (d, J = 13.6 Hz, 1H), 4.01-3.90 (m, 3H), 3.66 (d, J = 12.2 Hz, 2H), 3.42 (dq, J = 28.9, 8.0 Hz, 2H), 3.10-2.88 (m, 8H), 2.88-2.50 (m, 7H), 2.32 (td, J = 7.9, 3.3 Hz, 2H), 2.20-1.96 (m, 7H), 1.92-1.79 (m, 6H), 1.66 (d, J = 13.0 Hz, 1H), 1.46-1.35 (m, 2H). | LCMS: C$_{45}$H$_{54}$N$_{10}$O$_5$ requires: 814, found: m/z = 815 [M + H]⁺ |
| 145 | ¹H NMR (500 MHz, Acetonitrile-d$_3$) δ 10.73 (d, J = 22.4 Hz, 2H), 8.84 (s, 1H), 8.06 (d, J = 8.9 Hz, 1H), 7.74 (s, 1H), 7.66-7.52 (m, 1H), 7.48 (d, J = 4.8 Hz, 1H), 7.35 (s, 1H), 7.12 (dd, J = 9.2, 2.4 Hz, 1H), 7.03 (d, J = 7.4 Hz, 1H), 6.90 (d, J = 2.5 Hz, 1H), 6.44 (d, J = 7.4 Hz, 1H), 5.76 (s, 1H), 5.23 (s, 1H), 4.55 (dd, J = 52.9, 11.5 Hz, 1H), 4.43 (d, J = 14.0 Hz, 1H), 4.31 (s, 2H), 4.23 (d, J = 13.3 Hz, 1H), 4.14 (dd, J = 11.2, 5.0 Hz, 1H), 4.08-4.00 (m, 1H), 3.95 (d, J = 12.6 Hz, 4H), 3.83 (d, J = 7.7 Hz, 3H), 3.38 (dq, J = 31.6, 8.2 Hz, 2H), 3.25-3.12 (m, 2H), 3.06 (dt, J = 22.9, 11.9 Hz, 2H), 2.88 (t, J = 12.6 Hz, 2H), 2.82-2.61 (m, 2H), 2.43-2.28 (m, 2H), 2.18-2.09 (m, 1H), 1.85 (dd, J = 23.8, 14.3 Hz, 4H), 1.66 (d, J = 12.6 Hz, 1H), 1.46-1.25 (m, 2H). | LCMS: C$_{40}$H$_{48}$N$_{12}$O$_5$ requires: 776, found: m/z = 777 [M + H]⁺ |
| 146 | ¹H NMR (500 MHz, CD$_3$CN) δ 11.09 (s, 1H), 9.86 (s, 1H), 8.88 (s, 1H), 7.64 (d, J = 8.4 Hz, 1H), 7.58 (d, J = 8.2 Hz, 2H), 7.54 (s, 1H), 7.40 (s, 1H), 7.18 (d, J = 8.2 Hz, 2H), 6.94 (d, J = 2.3 Hz, 1H), 6.79 (dd, J = 8.6, 2.3 Hz, 1H), 5.81 (s, 1H), 4.93 (dd, J = | LCMS: C$_{43}$H$_{50}$N$_{10}$O$_6$ requires: 802, found: m/z = 803 [M + H]⁺ |

TABLE 2-continued

Physical Data for the Example Compounds of Table 1.

| Compound No. | ¹H NMR | Mass Spec (LCMS) |
|---|---|---|
| | 12.2, 5.4 Hz, 1H), 4.40-4.34 (m, 1H), 4.29 (d, J = 13.6 Hz, 1H), 3.94 (tt, J = 10.3, 4.5 Hz, 1H), 3.72 (ddd, J = 33.4, 15.6, 9.9 Hz, 3H), 3.55 (td, J = 9.5, 8.6, 3.3 Hz, 1H), 3.48-3.34 (m, 3H), 3.29-3.18 (m, 3H), 3.02 (dt, J = 31.3, 12.1 Hz, 4H), 2.93-2.63 (m, 4H), 2.32 (td, J = 8.1, 3.4 Hz, 3H), 2.16-1.96 (m, 6H), 1.86 (qd, J = 12.9, 6.4 Hz, 4H), 1.71-1.61 (m, 1H). | |
| 147 | ¹H NMR (500 MHz, Acetonitrile-d₃) δ 11.15 (s, 1H), 10.73 (s, 1H), 8.82 (s, 1H), 8.07 (d, J = 9.0 Hz, 1H), 7.84 (s, 1H), 7.47 (d, J = 6.3 Hz, 2H), 7.35 (s, 1H), 7.13 (dd, J= 9.2, 2.4 Hz, 1H), 7.03 (d, J = 7.4 Hz, 1H), 6.91 (d, J = 2.4 Hz, 1H), 6.45 (d, J = 7.4 Hz, 1H), 5.76 (s, 1H), 5.23 (s, 1H), 4.59 (d, J = 42.9 Hz, 3H), 4.22 (d, J = 21.2 Hz, 3H), 4.03-3.86 (m, 3H), 3.84 (s, 3H), 3.74 (d, J = 11.5 Hz, 1H), 3.14 (d, J = 49.3 Hz, 6H), 2.89 (t, J = 12.4 Hz, 2H), 2.83-2.69 (m, 2H), 2.14 (dd, J = 9.6, 4.6 Hz, 1H), 2.00 (d, J = 13.8 Hz, 1H), 1.89 (d, J = 13.4 Hz, 1H), 1.79 (dd, J = 18.5, 6.3 Hz, 2H), 1.67 (t, J = 12.9 Hz, 2H), 1.44-1.29 (m, 2H). | LCMS: $C_{39}H_{46}N_{12}O_6$ requires: 778, found: m/z = 779 $[M + H]^+$ |
| 148 | ¹H NMR (500 MHz, DMSO-d₆) δ 11.50 (s, 1H), 11.07 (s, 1H), 9.02 (s, 1H), 8.68 (s, 1H), 8.54 (s, 1H), 8.14 (d, J = 3.1 Hz, 1H), 8.09-8.03 (m, 2H), 7.77 (d, J = 8.1 Hz, 2H), 7.70 (d, J = 8.2 Hz, 1H), 7.31 (d, J = 8.3 Hz, 2H), 6.95 (s, 1H), 6.89-6.83 (m, 1H), 5.06 (dd, J = 12.7, 5.4 Hz, 1H), 3.76 (dd, J = 18.8, 9.5 Hz, 1H), 3.68 (d, J = 17.4 Hz, 2H), 3.58 (t, J = 9.6 Hz, 2H), 3.25 (dd, J = 10.3, 8.2 Hz, 1H), 3.15 (d, J = 13.2 Hz, 2H), 2.94-2.83 (m, 3H), 2.59 (d, J = 16.0 Hz, 1H), 2.39 (s, 1H), 2.29 (s, 2H), 2.09 (d, J = 13.1 Hz, 2H), 2.01 (dd, J = 12.5, 6.3 Hz, 1H), 1.89 (dt, J = 32.7, 11.1 Hz, 3H). | LCMS: $C_{37}H_{37}N_9O_5S$ requires: 719, found: m/z = 720 $[M + H]^+$ |
| 149 | ¹H NMR (500 MHz, DMSO-d₆) δ 11.28 (s, 1H), 11.06 (s, 1H), 7.73 (d, J = 2.8 Hz, 1H), 7.66 (s, 1H), 7.64 (d, J = 8.4 Hz, 1H), 7.55-7.48 (m, 2H), 7.31 (d, J = 2.9 Hz, 1H), 7.20 (s, 1H), 7.18 (s, 1H), 6.90 (d, J = 2.2 Hz, 1H), 6.82 (dd, J = 8.6, 2.2 Hz, 1H), 5.05 (dd, J = 12.9, 5.4 Hz, 1H), 3.67 (t, J = 5.5 Hz, 4H), 3.56 (dd, J = 10.3, 7.2 Hz, 1H), 3.54-3.46 (m, 1H), 3.40 (dt, J = 10.3, 7.5 Hz, 1H), 3.15 (dd, J = 10.4, 6.8 Hz, 1H), 3.04 (d, J = 10.9 Hz, 1H), 2.97 (d, J = 11.0 Hz, 1H), 2.88 (ddd, J = 17.4, 14.1, 5.5 Hz, 1H), 2.67-2.57 (m, 2H), 2.59-2.51 (m, 1H), 2.50-2.40 (m, 1H), 2.37 (d, J = 7.6 Hz, 2H), 2.18-2.08 (m, 1H), 2.09-1.96 (m, 3H), 1.82-1.71 (m, 3H), 1.71-1.61 (m, 4H), 1.64-1.54 (m, 4H). | LCMS: $C_{39}H_{45}N_9O_5$ requires: 719, found: m/z = 720 $[M + H]^+$ |
| 150 | ¹H NMR (500 MHz, DMSO-d₆) δ 11.33 (s, 1H), 11.17 (s, 1H), 9.47 (s, 1H), 8.63 (s, 1H), 8.50 (s, 1H), 8.29-7.93 (m, 6H), 7.76-7.58 (m, 2H), 7.12 (s, 2H), 5.21 (dd, J = 12.9, 5.5 Hz, 1H), 4.57 (d, J = 5.2 Hz, 2H), 3.38-3.01 (m, 9H), 2.92 (ddd, J = 17.7, 13.9, 5.4 Hz, 1H), 2.64 (d, J = 18.1 Hz, 2H), 2.19-2.05 (m, 1H), 1.87 (d, J = 57.7 Hz, 5H), 1.56 (d, J = 11.3 Hz, 5H). | LCMS: $C_{37}H_{37}N_9O_5S$ requires: 719.8, found: m/z = 720.3 $[M + H]^+$ |
| 151 | ¹H NMR (500 MHz, DMSO-d₆) δ 11.09 (s, 1H), 8.65 (s, 1H), 8.52 (s, 1H), 8.14 (d, J = 3.2 Hz, 1H), 8.05 (d, J = 19.0 Hz, 2H), 7.68 (d, J = 8.5 Hz, 2H), 7.35 (s, 1H), 7.27 (d, J = 8.6 Hz, 1H), 5.08 (dd, J = 12.7, 5.5 Hz, 1H), 2.99-2.77 (m, 1H), 2.62 (s, 3H), 2.13-1.97 (m, 1H), 1.68 (d, J = 42.6 Hz, 7H). | LCMS: $C_{36}H_{35}N_9O_5S$ requires: 705.8, found: m/z = 706.3 $[M + H]^+$ |
| 152 | ¹H NMR (500 MHz, Acetonitrile-d₃) δ 10.99 (s, 1H), 8.76 (s, 1H), 7.58-7.48 (m, 4H), 7.36 (d, J = 20.8 Hz, 1H), 7.19 (d, J = 8.1 Hz, 2H), 6.64 (d, J = 7.8 Hz, 2H), 5.76 (s, 1H), 5.08-4.88 (m, 2H), 4.42 (s, 1H), 4.35-4.11 (m, 3H), 3.69 (s, 1H), 3.59 (s, 1H), 3.52 (s, 0H), 3.48 (d, J = 8.2 Hz, 0H), 3.46-3.39 (m, 1H), 3.39-3.24 (m, 2H), 3.15-3.05 (m, 1H), 2.99 (dt, J = 24.0, 12.3 Hz, 3H), 2.87 (s, 1H), 2.77 (s, 3H), 2.72 (s, 0H), 2.71-2.58 (m, 2H), 2.48 (s, 1H), 2.40 (d, J = 7.8 Hz, 2H), 1.87 (s, 2H), 1.79 (d, J = 11.0 Hz, 4H), 1.69 (s, 8H), 1.27 (s, 2H), 1.15-1.04 (m, 0H), 0.84 (d, J = 6.6 Hz, 1H). | LCMS: $C_{43}H_{53}N_{11}O_5$ requires: 803, found: m/z = 804 $[M + H]^+$ |

TABLE 2-continued

Physical Data for the Example Compounds of Table 1.

| Compound No. | ¹H NMR | Mass Spec (LCMS) |
|---|---|---|
| 153 | ¹H NMR (500 MHz, DMSO-$d_6$) δ 11.37 (d, J = 80.3 Hz, 2H), 11.09 (s, 1H), 8.75-8.48 (m, 2H), 8.20-7.98 (m, 2H), 7.93-7.61 (m, 3H), 7.47-7.13 (m, 2H), 5.08 (dd, J = 12.8, 5.4 Hz, 1H), 3.47 (m 27H), 2.90 (ddd, J = 16.8, 13.8, 5.4 Hz, 1H), 2.10-1.93 (m, 1H), 1.72 (d, J = 53.4 Hz, 8H). | LCMS: $C_{44}H_{52}N_{10}O_6$ requires: 816, found: m/z = 817 [M + H]⁺ |
| 154 | ¹H NMR (500 MHz, Acetonitrile-$d_3$) δ 11.12 (s, 1H), 9.79 (s, 1H), 8.92 (s, 1H), 7.68-7.50 (m, 4H), 7.43 (s, 1H), 7.21 (d, J = 8.2 Hz, 2H), 7.08 (dd, J = 21.8, 7.8 Hz, 2H), 6.17 (s, 1H), 5.84 (s, 1H), 4.96 (dd, J = 12.4, 5.3 Hz, 1H), 4.36 (d, J = 48.4, 13.3 Hz, 2H), 3.68 (t, J = 14.8 Hz, 3H), 3.52 (s, 1H), 3.46-3.22 (m, 3H), 3.16-2.89 (m, 5H), 2.88-2.62 (m, 6H), 2.19-2.01 (m, 5H), 1.68 (t, J = 12.6 Hz, 1H), 1.46-1.12 (m, 4H). | LCMS: $C_{45}H_{55}N_{11}O_6$ requires: 845, found: m/z = 846 [M + H]⁺. |
| 155 | ¹H NMR (500 MHz, Acetonitrile-$d_3$) δ 11.11 (s, 1H), 10.44 (s, 1H), 8.93 (s, 1H), 7.66-7.52 (m, 4H), 7.43 (s, 1H), 7.20 (d, J = 8.2 Hz, 2H), 7.10 (d, J = 7.7 Hz, 2H), 6.47 (s, 1H), 5.83 (s, 1H), 4.97 (dd, J = 12.5, 5.4 Hz, 1H), 4.42 (d, J = 12.6 Hz, 1H), 4.31 (d, J = 13.6 Hz, 1H), 3.66 (dd, J = 31.4, 11.6 Hz, 2H), 3.52-3.22 (m, 8H), 3.22-2.89 (m, 5H), 2.89-2.64 (m, 9H), 2.19-2.04 (m, 6H), 1.93-1.56 (m, 4H). | LCMS: $C_{41}H_{49}N_{11}O_6$ requires: 791, found: m/z = 792 [M + H]⁺. |
| 156 | ¹H NMR (500 MHz, DMSO-$d_6$) δ 11.20 (s, 1H), 11.07 (s, 1H), 7.77 (s, 1H), 7.67 (s, 1H), 7.51 (d, J = 8.3 Hz, 2H), 7.36-7.31 (m, 1H), 7.18 (d, J = 8.2 Hz, 2H), 6.94 (d, J = 8.6 Hz, 1H), 6.86-6.79 (m, 1H), 6.65 (dd, J = 8.7, 2.2 Hz, 1H), 5.30 (dd, J = 12.9, 5.4 Hz, 1H), 4.34 (dd, J = 39.6, 12.9 Hz, 2H), 3.67-3.54 (m, 4H), 3.33 (s, 2H), 3.12-2.84 (m, 6H), 2.77-2.58 (m, 7H), 2.29-2.14 (m, 2H), 2.05-1.92 (m, 3H), 1.88-1.49 (m, 14H), 1.33-1.23 (m, 3H). | LCMS: $C_{44}H_{56}N_{12}O_5$ requires 832, found: m/z = 833 [M + H]⁺. |
| 157 | ¹H NMR (500 MHz, Acetonitrile-$d_3$) δ 8.92 (s, 1H), 7.67-7.52 (m, 4H), 7.22 (d, J = 8.4 Hz, 2H), 7.10 (d, J = 7.2 Hz, 1H), 7.03 (d, J = 8.5 Hz, 1H), 5.04-4.93 (m, 1H), 4.76-4.63 (m, 1H), 4.41 (d, J = 12.9 Hz, 1H), 4.27 (d, J = 13.4 Hz, 1H), 4.22-4.09 (m, 2H), 4.07-3.91 (m, 1H), 3.71 (t, J = 10.8 Hz, 1H), 3.48-3.16 (m, 4H), 3.06 (dt, J = 33.2, 12.3 Hz, 1H), 2.91-2.70 (m, 6H), 2.19-2.07 (m, 1H), 1.93-1.40 (m, 8H). | LCMS: $C_{40}H_{45}N_{11}O_7$ requires: 791, found: m/z = 792 [M + H]⁺. |
| 158 | ¹H NMR (500 MHz, Acetonitrile-$d_3$) δ 9.07 (d, J = 22.0 Hz, 1H), 7.75 (t, J = 7.9 Hz, 1H), 7.58-7.44 (m, 4H), 7.31 (d, J = 8.5 Hz, 1H), 7.21 (d, J = 8.2 Hz, 2H), 5.21-4.92 (m, 3H), 4.59 (d, J = 13.3 Hz, 1H), 4.32-4.24 (m, 1H), 4.17 (d, J = 13.5 Hz, 1H), 3.94 (d, J = 13.6 Hz, 1H), 3.72 (tt, J = 10.0, 4.0 Hz, 1H), 3.48-3.29 (m, 4H), 3.29-3.01 (m, 3H), 2.20-2.07 (m, 1H), 2.02-1.43 (m, 9H). | LCMS: $C_{40}H_{44}N_{10}O_8$ requires: 792, found: m/z = 793 [M + H]⁺. |
| 159 | ¹H NMR (500 MHz, Acetonitrile-$d_3$) δ 11.17 (s, 1H), 10.21 (s, 1H), 8.89 (s, 1H), 7.74-7.55 (m, 4H), 7.43 (s, 1H), 7.25 (d, J = 8.2 Hz, 2H), 6.98 (d, J = 2.2 Hz, 1H), 6.83 (dd, J = 8.5, 2.3 Hz, 1H), 5.88-5.77 (m, 1H), 4.96 (dd, J = 12.1, 5.3 Hz, 1H), 4.35 (d, J = 13.5 Hz, 2H), 3.85-3.67 (m, 3H), 3.58 (d, J = 8.8 Hz, 1H), 3.47 (q, J = 9.4, 8.7 Hz, 1H), 3.35-3.15 (m, 5H), 3.12-2.57 (m, 8H), 1.70 (td, J = 14.5, 7.4 Hz, 2H). | LCMS: $C_{40}H_{45}N_9O_7$ requires: 763, found: m/z = 764 [M + H]⁺. |
| 160 | ¹H NMR (500 MHz, Acetonitrile-$d_3$) δ 11.17 (s, 1H), 8.89 (s, 1H), 7.66 (dd, J = 13.4, 8.3 Hz, 3H), 7.59 (d, J = 3.8 Hz, 1H), 7.41 (s, 1H), 7.24 (d, J = 8.1 Hz, 2H), 6.98 (d, J = 2.3 Hz, 1H), 6.83 (dd, J = 8.6, 2.2 Hz, 1H), 5.80 (s, 1H), 4.96 (dd, J = 12.1, 5.3 Hz, 1H), 4.47 (d, J = 12.3 Hz, 3H), 3.88-3.65 (m, 3H), 3.59 (t, J = 8.7 Hz, 1H), 3.52-3.18 (m, 5H), 3.10-2.62 (m, 8H), 1.38-1.16 (m, 2H). | LCMS: $C_{40}H_{47}N_9O_6$ requires: 749, found: m/z = 750 [M + H]⁺. |

TABLE 2-continued

Physical Data for the Example Compounds of Table 1.

| Compound No. | $^1$H NMR | Mass Spec (LCMS) |
|---|---|---|
| 161 | $^1$H NMR (500 MHz, Acetonitrile-d$_3$) δ 11.19 (s, 1H), 10.26 (s, 1H), 8.90 (s, 1H), 7.71-7.60 (m, 3H), 7.55 (s, 1H), 7.46 (s, 1H), 7.24 (d, J = 8.4 Hz, 2H), 6.97 (d, J = 2.3 Hz, 1H), 6.82 (dd, J = 8.5, 2.3 Hz, 1H), 5.87 (s, 1H), 4.96 (dd, J = 12.2, 5.4 Hz, 1H), 3.86-3.63 (m, 10H), 3.58 (td, J = 9.5, 8.4, 3.3 Hz, 1H), 3.47 (q, J = 9.2, 8.7 Hz, 1H), 3.34-3.17 (m, 3H), 3.11-2.62 (m, 6H), 2.20-2.00 (m, 4H). | LCMS: C$_{38}$H$_{43}$N$_9$O$_6$ requires: 721, found: m/z = 722 [M + H]$^+$. |
| 162 | $^1$H NMR (500 MHz, Acetonitrile-d$_3$) δ 11.28 (s, 1H), 10.26 (s, 1H), 8.89 (s, 1H), 7.73 (d, J = 8.5 Hz, 2H), 7.67 (d, J = 8.4 Hz, 1H), 7.42 (s, 1H), 7.26-7.19 (m, 2H), 7.15 (s, 1H), 6.98 (d, J = 2.3 Hz, 1H), 6.82 (dd, J = 8.5, 2.3 Hz, 1H), 5.79 (s, 1H), 4.96 (dd, J = 12.1, 5.4 Hz, 1H), 4.22 (t, J = 7.5 Hz, 4H), 3.87-3.66 (m, 4H), 3.63-3.54 (m, 1H), 3.53-3.17 (m, 5H), 3.11-2.64 (m, 7H), 2.49 (p, J = 7.5 Hz, 2H). | LCMS: C$_{37}$H$_{41}$N$_9$O$_5$ requires: 691, found: m/z = 692 [M + H]$^+$. |
| 163 | $^1$H NMR (500 MHz, DMSO-d$_6$) δ 11.33 (s, 1H), 11.01 (s, 1H), 8.82 (s, 1H), 7.75 (s, 1H), 7.68 (s, 1H), 7.61-7.50 (m, 5H), 7.33 (s, 1H), 7.20 (dd, J = 7.6, 2.3 Hz, 3H), 6.57 (d, J = 7.3 Hz, 1H), 3.87 (d, J = 12.6 Hz, 2H), 3.68 (t, J = 5.5 Hz, 5H), 3.66-3.60 (m, 2H), 3.07 (q, J = 6.0, 5.5 Hz, 3H), 2.82 (dt, J = 23.4, 12.1 Hz, 4H), 2.67-2.58 (m, 3H), 2.38-2.35 (m, 1H), 2.11-1.83 (m, 5H), 1.69-1.63 (m, 2H), 1.59 (p, J = 5.8 Hz, 4H), 1.37 (q, J = 12.0 Hz, 2H). | LCMS: C$_{41}$H$_{49}$N$_9$O$_4$ requires: 732, found: m/z = 733 [M + H]$^+$. |
| 164 | $^1$H NMR (500 MHz, DMSO-d$_6$) δ 11.33 (s, 1H), 10.93 (s, 1H), 8.89 (s, 1H), 7.91 (d, J = 3.1 Hz, 1H), 7.75 (s, 1H), 7.68 (s, 1H), 7.58 (d, J = 8.5 Hz, 2H), 7.46-7.40 (m, 1H), 7.32 (d, J = 5.2 Hz, 1H), 7.20 (d, J = 8.4 Hz, 2H), 6.93 (d, J = 9.3 Hz, 1H), 5.04 (dd, J = 10.7, 5.0 Hz, 1H), 4.18 (d, J = 13.0 Hz, 2H), 3.68 (t, J = 5.4 Hz, 4H), 3.62 (d, J = 12.0 Hz, 2H), 3.04 (t, J = 6.3 Hz, 4H), 2.81 (dt, J = 20.5, 12.0 Hz, 3H), 2.64 (qt, J = 12.6, 5.9 Hz, 2H), 2.21 (dq, J = 12.9, 4.9 Hz, 1H), 2.12 (ddt, J = 13.1, 11.1, 5.6 Hz, 2H), 1.97 (q, J = 13.6, 12.5 Hz, 3H), 1.82 (d, J = 13.3 Hz, 2H), 1.69-1.63 (m, 2H), 1.59 (t, J = 5.7 Hz, 4H), 1.25 (q, J = 12.3, 11.5 Hz, 2H). | LCMS: C$_{37}$H$_{47}$N$_9$O$_4$ requires: 682, found: m/z = 683 [M + H]$^+$. |
| 165 | $^1$H NMR (500 MHz, DMSO-d$_6$) δ 11.28 (d, J = 7.6 Hz, 1H), 10.94 (s, 1H), 8.93 (s, 1H), 7.91 (d, J = 3.0 Hz, 1H), 7.78 (s, 1H), 7.68 (d, J = 2.2 Hz, 1H), 7.56 (d, J = 8.0 Hz, 2H), 7.46 (d, J = 9.2 Hz, 1H), 7.35 (s, 1H), 7.16 (dd, J = 13.4, 8.1 Hz, 2H), 6.96 (d, J = 9.3 Hz, 1H), 5.05 (dd, J = 10.7, 5.0 Hz, 1H), 4.30 (d, J = 20.5 Hz, 2H), 4.18 (d, J = 12.9 Hz, 2H), 3.62 (d, J = 11.5 Hz, 3H), 3.34 (tt, J = 15.5, 8.8 Hz, 2H), 3.26 (t, J = 7.8 Hz, 2H), 3.12-3.01 (m, 4H), 2.97 (t, J = 12.4 Hz, 2H), 2.85 (t, J = 12.4 Hz, 1H), 2.77 (d, J = 12.4 Hz, 1H), 2.71 (s, 3H), 2.65 (dt, J = 13.7, 5.3 Hz, 2H), 2.21 (dd, J = 11.6, 6.4 Hz, 1H), 2.17-2.08 (m, 2H), 2.03-1.87 (m, 4H), 1.82 (d, J = 12.4 Hz, 4H), 1.76 (s, 1H), 1.57 (d, J = 12.6 Hz, 1H), 1.26 (q, J = 12.3, 11.9 Hz, 2H). | LCMS: C$_{41}$H$_{53}$N$_{11}$O$_5$ requires: 780, found: m/z = 781 [M + H]$^+$. |
| 166 | $^1$H NMR (500 MHz, CD$_3$CN) δ 11.10 (s, 1H), 9.12 (s, 1H), 8.80 (s, 1H), 7.81 (d, J = 9.5 Hz, 1H), 7.59 (d, J = 8.0 Hz, 2H), 7.55 (s, 1H), 7.41 (s, 1H), 7.37 (s, 1H), 7.19 (d, J = 7.9 Hz, 2H), 6.96 (d, J = 9.7 Hz, 1H), 5.81 (s, 1H), 4.51 (dd, J = 12.3, 5.1 Hz, 1H), 4.39 (d, J = 12.9 Hz, 1H), 4.29 (d, J = 13.7 Hz, 1H), 3.71-3.62 (m, 3H), 3.52 (d, J = 11.9 Hz, 2H), 3.42-3.33 (m, 1H), 3.35-3.28 (m, 1H), 3.27 (dd, J = 10.5, 6.9 Hz, 2H), 3.06 (t, J = 11.7 Hz, 1H), 2.98 (dd, J = 15.5, 9.8 Hz, 4H), 2.82 (s, 3H), 2.75 (d, J = 1.7 Hz, 4H), 2.75-2.65 (m, 3H), 2.27 (dd, J = 13.0, 4.9 Hz, 1H), 2.19-2.10 (m, 1H), 2.10-2.03 (m, 3H), 1.97-1.89 (m, 3H), 1.88 (s, 1H), 1.80 (dd, J = 24.4, 12.9 Hz, 2H), 1.64 (d, J = 12.5 Hz, 1H), 1.43 (d, J = 12.7 Hz, 2H). | LCMS: C$_{41}$H$_{54}$N$_{12}$O$_4$ requires: 779, found: m/z = 780 [M + H]$^+$. |
| 167 | $^1$H NMR (500 MHz, CD$_3$CN) δ 11.13 (s, 1H), 9.63 (s, 1H), 8.79 (s, 1H), 7.81 (d, J = 9.7 Hz, 1H), 7.61 (d, J = 8.3 Hz, 2H), 7.54 (d, J = 2.5 Hz, 1H), 7.37 (s, 2H), 7.19 (d, J = 7.9 Hz, 2H), 6.95 (d, J = 9.7 Hz, 1H), 5.78 (s, 1H), 4.52 (dd, J = 12.5, 4.8 Hz, 1H), 3.72-3.62 (m, 6H), 3.52 (d, J = 11.7 Hz, 2H), 2.98 | LCMS: C$_{37}$H$_{48}$N$_{10}$O$_3$ requires: 681, found: m/z = 682 [M + H]$^+$. |

TABLE 2-continued

Physical Data for the Example Compounds of Table 1.

| Compound No. | $^1$H NMR | Mass Spec (LCMS) |
|---|---|---|
| | (d, J = 12.3 Hz, 3H), 2.81 (d, J = 13.0 Hz, 2H), 2.71 (q, J = 12.0, 10.8 Hz, 5H), 2.28 (d, J = 12.6 Hz, 1H), 2.12 (dt, J = 25.4, 11.2 Hz, 3H), 2.02 (d, J = 14.9 Hz, 3H), 1.92 (s, 1H), 1.70 (s, 2H), 1.64 (s, 4H), 1.43 (d, J = 12.7 Hz, 2H). | |
| 168 | $^1$H NMR (500 MHz, CD$_3$CN) δ 10.70 (s, 1H), 8.86 (s, 1H), 7.63 (d, J = 8.4 Hz, 1H), 7.46 (s, 1H), 7.38 (s, 2H), 7.35 (s, 1H), 7.30 (d, J = 2.4 Hz, 1H), 7.19-7.14 (m, 1H), 6.41 (s, 2H), 5.71 (s, 1H), 4.93 (dd, J = 12.2, 5.4 Hz, 1H), 4.34 (d, J = 12.8 Hz, 1H), 4.26 (d, J = 13.4 Hz, 1H), 4.04 (d, J = 13.1 Hz, 2H), 3.90 (s, 1H), 3.54 (s, 2H), 3.42 (q, J = 7.8 Hz, 1H), 3.37 (q, J = 8.4, 7.7 Hz, 1H), 2.97 (p, J = 13.0, 12.5 Hz, 4H), 2.72 (td, J = 18.2, 11.1 Hz, 3H), 2.29 (t, J = 8.1 Hz, 2H), 2.02-1.95 (m, 2H), 1.82 (d, J = 13.7 Hz, 6H), 1.64 (s, 2H), 1.25 (d, J = 22.7 Hz, 4H), 0.85 (s, 1H). | LCMS: $C_{40}H_{45}N_{11}O_6$ requires: 776, found: m/z = 777 [M + H]$^+$. |
| 169 | $^1$H NMR (500 MHz, CD$_3$CN) δ 10.70 (s, 1H), 8.86 (s, 1H), 7.63 (d, J = 8.4 Hz, 1H), 7.46 (s, 1H), 7.38 (s, 2H), 7.35 (s, 1H), 7.30 (d, J = 2.4 Hz, 1H), 7.19-7.14 (m, 1H), 6.41 (s, 2H), 5.71 (s, 1H), 4.93 (dd, J = 12.2, 5.4 Hz, 1H), 4.34 (d, J = 12.8 Hz, 1H), 4.26 (d, J = 13.4 Hz, 1H), 4.04 (d, J = 13.1 Hz, 2H), 3.90 (s, 1H), 3.54 (s, 2H), 3.42 (q, J = 7.8 Hz, 1H), 3.37 (q, J = 8.4, 7.7 Hz, 1H), 2.97 (p, J = 13.0, 12.5 Hz, 4H), 2.72 (td, J = 18.2, 11.1 Hz, 3H), 2.50 (s, 0H), 2.29 (t, J = 8.1 Hz, 2H), 2.02-1.95 (m, 2H), 1.82 (d, J = 13.7 Hz, 6H), 1.64 (s, 1H), 1.25 (d, J = 22.7 Hz, 4H), 0.85 (s, 1H). | LCMS: $C_{41}H_{46}N_{10}O_6$ requires: 775, found: m/z = 776 [M + H]$^+$. |
| 170 | $^1$H NMR (500 MHz, DMSO-d$_6$) δ 11.36 (s, 1H), 10.85 (s, 1H), 8.98 (s, 1H), 7.77 (s, 1H), 7.68 (s, 1H), 7.64 (d, J = 8.2 Hz, 2H), 7.58-7.40 (m, 2H), 7.34 (s, 1H), 7.20 (d, J = 8.4 Hz, 2H), 4.47 (d, J = 13.1 Hz, 1H), 4.34 (s, 2H), 4.25 (d, J = 13.3 Hz, 2H), 4.04 (d, J = 12.9 Hz, 4H), 3.64 (d, J = 12.0 Hz, 6H), 3.53-3.25 (m, 6H), 3.14-3.01 (m, 6H), 2.92-2.67 (m, 5H), 2.20-2.04 (m, 3H), 2.04-1.85 (m, 7H), 1.85-1.61 (m, 4H), 1.49 (dd, J = 17.1, 8.4 Hz, 1H), 1.31 (q, J = 11.9, 11.5 Hz, 3H). | LCMS: $C_{38}H_{50}N_{10}O_4$ requires: 710.9, found: m/z = 711.7 [M + H]$^+$ |
| 171 | $^1$H NMR (500 MHz, Acetonitrile-d$_3$) δ 11.14 (s, 1H), 9.39 (s, 1H), 8.77 (s, 1H), 7.92 (d, J = 3.1 Hz, 1H), 7.67 (d, J = 8.1 Hz, 2H), 7.58 (s, 1H), 7.56-7.47 (m, 1H), 7.41 (s, 1H), 7.24 (d, J = 8.2 Hz, 2H), 6.95 (d, J = 9.6 Hz, 1H), 5.79 (s, 1H), 4.87 (dd, J = 10.4, 5.0 Hz, 1H), 4.56 (d, J = 13.1 Hz, 1H), 4.21 (t, J = 17.6 Hz, 4H), 3.68 (d, J = 12.1 Hz, 3H), 3.51 (dd, J = 10.7, 5.1 Hz, 2H), 3.42 (dd, J = 10.6, 7.7 Hz, 2H), 3.26-3.07 (m, 3H), 3.00 (d, J = 13.1 Hz, 9H), 2.85 (t, J = 11.8 Hz, 4H), 2.79-2.66 (m, 5H), 2.05 (d, J = 14.4 Hz, 4H), 1.82 (d, J = 33.6 Hz, 6H), 1.58 (d, J = 11.5 Hz, 3H), 1.36 (td, J = 23.5, 13.1 Hz, 5H). | LCMS: $C_{38}H_{49}N_9O_5$ requires: 711.9, found: m/z = 712.8 [M + H]$^+$ |
| 172 | $^1$H NMR (500 MHz, DMSO-d$_6$) δ 11.35 (s, 1H), 11.00 (s, 1H), 8.90 (s, 1H), 8.05-7.94 (m, 1H), 7.83-7.71 (m, 1H), 7.71-7.58 (m, 3H), 7.40-7.24 (m, 2H), 7.24-7.15 (m, 3H), 7.00 (d, J = 2.4 Hz, 1H), 6.48 (d, J = 7.5 Hz, 1H), 4.47 (d, J = 13.3 Hz, 1H), 4.25 (d, J = 13.4 Hz, 1H), 4.03 (d, J = 12.8 Hz, 3H), 3.63 (s, 7H), 3.39-3.30 (m, 3H), 3.15-3.01 (m, 5H), 3.01-2.68 (m, 5H), 2.61 (d, J = 14.2 Hz, 2H), 2.15 (s, 1H), 2.08-1.90 (m, 5H), 1.87 (d, J = 12.8 Hz, 2H), 1.83-1.65 (m, 3H), 1.48 (t, J = 12.5 Hz, 1H), 1.39-1.31 (m, 2H), 1.28 (dd, J = 17.7, 6.5 Hz, 1H). | LCMS: $C_{42}H_{51}N_9O_5$ requires: 761.9, found: m/z = 762.8 [M + H]$^+$ |
| 173 | $^1$H NMR (500 MHz, DMSO-d$_6$) δ 11.35 (s, 1H), 10.86 (s, 1H), 9.02 (s, 1H), 8.71 (d, J = 8.2 Hz, 1H), 8.36 (d, J = 2.6 Hz, 1H), 7.88 (d, J = 8.7 Hz, 1H), 7.76 (s, 1H), 7.73-7.55 (m, 3H), 7.46 (dd, J = 9.0, 2.6 Hz, 1H), 7.32 (d, J = 17.4 Hz, 1H), 7.20 (d, J = 8.1 Hz, 2H), 4.84-4.69 (m, 1H), 4.46 (d, J = 13.2 Hz, 1H), 4.25 (d, J = 13.4 Hz, 1H), 4.01 (d, J = 12.8 Hz, 3H), 3.45-3.24 (m, 4H), 3.22-3.02 (m, 5H), 2.93 (t, J = 12.4 Hz, 3H), 2.81 (qd, J = 14.0, 12.4, 4.6 Hz, 3H), 2.19 (qd, J = 15.0, 14.0, 5.3 Hz, 2H), 2.09-1.82 (m, 8H), 1.75 (dd, J = 38.7, 21.6 Hz, | LCMS: $C_{39}H_{50}N_{10}O_5$ requires: 738.9, found: m/z = 739.8 [M + H]$^+$ |

TABLE 2-continued

Physical Data for the Example Compounds of Table 1.

| Compound No. | $^1$H NMR | Mass Spec (LCMS) |
|---|---|---|
| | 3H), 1.61-1.42 (m, 1H), 1.34 (dt, J = 16.9, 10.8 Hz, 3H). | |
| 174 | $^1$H NMR (500 MHz, Acetonitrile-d$_3$) δ 11.13 (s, 1H), 10.49 (s, 1H), 8.89 (s, 1H), 7.67 (dd, J = 8.4, 3.7 Hz, 3H), 7.58 (s, 1H), 7.40 (s, 1H), 7.25 (d, J = 8.4 Hz, 2H), 6.98 (d, J = 2.3 Hz, 1H), 6.87-6.80 (m, 1H), 5.79 (s, 1H), 4.96 (dd, J = 12.1, 5.4 Hz, 1H), 4.58 (d, J = 13.0 Hz, 1H), 4.24 (d, J = 13.5 Hz, 1H), 3.90-3.64 (m, 4H), 3.64-3.41 (m, 6H), 3.34-3.21 (m, 4H), 3.14 (t, J = 12.7 Hz, 2H), 2.94 (d, J = 16.1 Hz, 5H), 2.89-2.67 (m, 8H), 1.79 (s, 5H), 1.59 (d, J = 12.4 Hz, 1H), 1.42-1.29 (m, 2H). | LCMS: C$_{40}$H$_{47}$N$_9$O$_6$ requires: 749.9, found: m/z = 750.9 [M + H]$^+$ |
| 175 | $^1$H NMR (500 MHz, DMSO-d$_6$) δ 11.33 (s, 1H), 11.08 (s, 1H), 7.93-7.81 (m, 1H), 7.74 (s, 1H), 7.66 (d, J = 8.4 Hz, 1H), 7.58 (d, J = 8.2 Hz, 2H), 7.46-7.34 (m, 1H), 7.21 (d, J = 8.2 Hz, 2H), 6.93 (d, J = 2.1 Hz, 1H), 6.84 (dd, J = 8.5, 2.1 Hz, 1H), 5.07 (dd, J = 13.0, 5.4 Hz, 1H), 4.94 (t, J = 5.3 Hz, 1H), 4.53 (d, J = 13.6 Hz, 1H), 4.20 (d, J = 14.0 Hz, 1H), 3.82 (dt, J = 11.0, 4.2 Hz, 1H), 3.59 (t, J = 8.8 Hz, 1H), 3.55-3.39 (m, 6H), 3.29-3.23 (m, 1H), 3.18 (dd, J = 9.9, 6.4 Hz, 1H), 3.07 (d, J = 10.6 Hz, 1H), 2.99 (d, J = 10.8 Hz, 1H), 2.90 (ddd, J = 17.4, 14.1, 5.6 Hz, 1H), 2.71-2.60 (m, 3H), 2.40 (d, J = 7.7 Hz, 3H), 2.25-2.14 (m, 3H), 2.08-1.98 (m, 3H), 1.86-1.60 (m, 5H). | LCMS: C$_{40}$H$_{45}$N$_9$O$_6$F$_2$ requires: 785.9, found: m/z = 786.8 [M + H]$^+$ |
| 176 | $^1$H NMR (500 MHz, DMSO-d$_6$) δ 11.47 (d, J = 10.1 Hz, 1H), 11.09 (s, 1H), 9.10 (s, 1H), 7.79 (s, 1H), 7.71 (d, J = 8.2 Hz, 3H), 7.36 (d, J = 23.8 Hz, 2H), 7.24 (d, J = 8.2 Hz, 2H), 6.98 (d, J = 2.1 Hz, 1H), 6.87 (dd, J = 8.5, 2.2 Hz, 1H), 5.08 (dd, J = 12.8, 5.5 Hz, 1H), 4.60 (dd, J = 35.6, 6.2 Hz, 4H), 3.83 (s, 2H), 3.78 (dd, J = 10.2, 7.3 Hz, 1H), 3.70 (t, J = 15.4 Hz, 3H), 3.65-3.53 (m, 5H), 3.15 (dd, J = 20.9, 10.6 Hz, 2H), 2.97-2.75 (m, 4H), 2.62 (d, J = 3.4 Hz, 2H), 2.31 (t, J = 7.3 Hz, 3H), 2.14-2.01 (m, 3H), 2.01-1.83 (m, 4H). | LCMS: C$_{40}$H$_{45}$N$_9$O$_6$ requires: 747.9, found: m/z = 748.8 [M + H]$^+$ |
| 177 | $^1$H NMR (500 MHz, DMSO-d$_6$) δ 11.35 (d, J = 5.9 Hz, 1H), 11.00 (s, 1H), 8.88 (s, 1H), 8.00 (d, J = 9.0 Hz, 1H), 7.78 (d, J = 7.5 Hz, 2H), 7.65 (d, J = 8.4 Hz, 2H), 7.35 (d, J = 14.5 Hz, 1H), 7.28 (d, J = 7.5 Hz, 1H), 7.23 (d, J = 7.7 Hz, 3H), 7.00 (s, 1H), 6.48 (d, J = 7.5 Hz, 1H), 4.32 (s, 4H), 4.00 (q, J = 11.5, 10.1 Hz, 6H), 3.83-3.39 (m, 23H), 3.13-3.00 (m, 4H), 2.93 (t, J = 12.4 Hz, 3H), 2.81 (t, J = 10.4 Hz, 1H), 2.61 (d, J = 14.3 Hz, 2H), 2.15 (s, 1H), 2.08-1.82 (m, 9H), 1.58 (d, J = 9.5 Hz, 2H), 1.33 (q, J = 12.0 Hz, 2H). | LCMS: C$_{43}$H$_{51}$N$_9$O$_5$ requires: 773.9, found: m/z = 774.9 [M + H]$^+$ |
| 178 | $^1$H NMR (500 MHz, Acetonitrile-d$_3$) δ 11.11 (s, 1H), 8.92 (s, 1H), 8.06 (s, 1H), 7.76-7.59 (m, 5H), 7.37-7.17 (m, 4H), 5.06 (dd, J = 12.4, 5.3 Hz, 5H), 4.37 (s, 4H), 3.99 (s, 2H), 3.85 (d, J = 12.7 Hz, 2H), 3.69 (d, J = 12.4 Hz, 2H), 3.61 (t, J = 5.6 Hz, 2H), 3.35 (s, 3H), 3.08 (p, J = 8.1, 6.9 Hz, 6H), 2.93-2.72 (m, 3H), 2.61 (qd, J = 12.6, 5.5 Hz, 1H), 2.24 (dtd, J = 13.7, 5.3, 3.6 Hz, 2H), 2.10 (dp, J = 10.6, 5.2, 4.5 Hz, 4H), 1.70-1.53 (m, 4H). | LCMS: C$_{44}$H$_{52}$N$_{10}$O$_6$ requires: 804.0, found: m/z = 804.8 [M + H]$^+$ |
| 179 | $^1$H NMR (500 MHz, DMSO-d$_6$) δ 11.29 (s, 1H), 11.07 (s, 1H), 7.74 (d, J = 2.9 Hz, 1H), 7.67 (s, 1H), 7.53 (d, J = 8.2 Hz, 2H), 7.32 (d, J = 2.9 Hz, 1H), 7.20 (d, J = 8.2 Hz, 2H), 6.94 (d, J = 8.5 Hz, 1H), 6.83 (d, J = 2.1 Hz, 1H), 6.65 (dd, J = 8.7, 2.2 Hz, 1H), 5.30 (dd, J = 12.8, 5.4 Hz, 1H), 3.69 (t, J = 5.4 Hz, 4H), 3.60 (d, J = 11.8 Hz, 2H), 3.32 (s, 3H), 3.03-2.82 (m, 3H), 2.74-2.59 (m, 4H), 2.50-2.42 (m, 1H), 2.21 (d, J = 7.1 Hz, 2H), 2.03-1.95 (m, 3H), 1.86-1.72 (m, 4H), 1.71-1.56 (m, 9H), 1.33-1.22 (m, 2H). | LCMS: C$_{40}$H$_{50}$N$_{10}$O$_4$ requires 734, found: m/z = 735 [M + H]$^+$. |
| 180 | $^1$H NMR (500 MHz, DMSO-d$_6$) δ 11.19 (s, 1H), 10.75 (s, 1H), 7.83-7.74 (m, 2H), 7.67 (s, 1H), 7.50 (d, J = 8.2 Hz, 2H), 7.34 (d, J = 2.9 Hz, 1H), 7.24-7.15 (m, 3H), 6.75 (d, J = 9.2 Hz, 1H), 4.67 (dd, J = 12.5, 4.8 Hz, 1H), 4.38 (d, J = 12.3 Hz, 1H), 4.30 (d, J = 13.4 Hz, 1H), 4.08 (d, J = 12.5 Hz, 2H), 3.67-3.59 (m, 1H), 3.31-3.24 (m, 3H), 3.10- | LCMS: C$_{42}$H$_{56}$N$_{12}$O$_4$ requires 792, found: m/z = 793 [M + H]$^+$. |

TABLE 2-continued

Physical Data for the Example Compounds of Table 1.

| Compound No. | $^1$H NMR | Mass Spec (LCMS) |
|---|---|---|
| | 2.90 (m, 4H), 2.85-2.60 (m, 11H), 2.30-2.22 (m, 1H), 2.18 (d, J = 6.9 Hz, 2H), 1.98 (t, J = 11.4 Hz, 2H), 1.93-1.50 (m, 13H), 1.19-1.08 (m, 2H). | |
| 181 | $^1$H NMR (500 MHz, DMSO-d$_6$) δ 11.29 (s, 1H), 10.75 (s, 1H), 7.81 (d, J = 3.2 Hz, 1H), 7.74 (d, J = 2.8 Hz, 1H), 7.67 (s, 1H), 7.53 (d, J = 8.2 Hz, 2H), 7.32 (d, J = 2.8 Hz, 1H), 7.24-7.17 (m, 3H), 6.74 (d, J = 9.1 Hz, 1H), 4.67 (dd, J = 12.6, 4.9 Hz, 1H), 4.08 (d, J = 12.6 Hz, 2H), 3.72-3.66 (m, 4H), 2.95 (d, J = 10.9 Hz, 2H), 2.80 (ddd, J = 18.1, 13.5, 5.4 Hz, 1H), 2.72-2.61 (m, 6H), 2.26 (qd, J = 12.7, 4.3 Hz, 1H), 2.18 (d, J = 7.0 Hz, 2H), 2.02-1.93 (m, 2H), 1.92-1.86 (m, 1H), 1.81-1.71 (m, 5H), 1.71-1.57 (m, 9H), 1.13 (dt, J = 12.6, 9.3 Hz, 2H). | LCMS: $C_{38}H_{50}N_{10}O_3$ requires 694, found: m/z = 695 [M + H]$^+$. |
| 182 | $^1$H NMR (500 MHz, DMSO-d$_6$) δ 11.29 (s, 1H), 10.85 (s, 1H), 8.74-8.68 (m, 1H), 8.32 (s, 1H), 7.85 (d, J = 9.3 Hz, 1H), 7.74 (s, 1H), 7.68 (s, 1H), 7.53 (d, J = 8.1 Hz, 2H), 7.42 (d, J = 8.9 Hz, 1H), 7.32 (s, 1H), 7.20 (d, J = 8.1 Hz, 2H), 4.75 (s, 1H), 3.96 (d, J = 12.7 Hz, 2H), 3.69 (s, 3H), 3.21-3.16 (m, 1H), 2.96 (d, J = 10.6 Hz, 2H), 2.88 (t, J = 12.6 Hz, 2H), 2.79 (d, J = 15.1 Hz, 1H), 2.19 (s, 3H), 2.03-1.95 (m, 3H), 1.83 (d, J = 12.9 Hz, 3H), 1.76 (d, J = 12.4 Hz, 3H), 1.67 (s, 3H), 1.61 (s, 5H), 1.27-1.18 (m, 3H). | LCMS: $C_{38}H_{48}N_{10}O_4$ requires 708, found: m/z = 709 |
| 183 | $^1$H NMR (500 MHz, Acetonitrile-d$_3$) δ 11.00 (s, 1H), 9.26 (s, 1H), 7.74 (dd, J = 15.7, 8.0 Hz, 1H), 7.64-7.37 (m, 6H), 7.27 (d, J = 7.5 Hz, 1H), 7.22-7.02 (m, 6H), 6.02 (s, 1H), 5.12-4.95 (m, 1H), 4.66 (d, J = 13.5 Hz, 1H), 4.57-4.35 (m, 5H), 4.29 (d, J = 13.7 Hz, 1H), 4.04 (d, J = 13.6 Hz, 1H), 3.99-3.85 (m, 2H), 3.72 (dt, J = 23.0, 6.3 Hz, 5H), 3.44-3.23 (m, 4H), 3.21-2.90 (m, 3H), 2.71-2.49 (m, 6H), 1.92-1.45 (m, 9H), 1.44-1.35 (m, 3H), 1.31-0.95 (m, 6H).⁻ | LCMS: $C_{64}H_{93}N_{13}O_{11}$ requires 1219, found: m/z = 1220 [M + H]$^+$. |
| 184 | $^1$H NMR (500 MHz, Acetonitrile-d$_3$) δ 8.92 (s, 1H), 7.67-7.52 (m, 4H), 7.22 (d, J = 8.4 Hz, 2H), 7.10 (d, J = 7.2 Hz, 1H), 7.03 (d, J = 8.5 Hz, 1H), 5.04-4.93 (m, 1H), 4.76-4.63 (m, 1H), 4.41 (d, J = 12.9 Hz, 1H), 4.27 (d, J = 13.4 Hz, 1H), 4.22-4.09 (m, 2H), 4.07-3.91 (m, 1H), 3.71 (t, J = 10.8 Hz, 1H), 3.48-3.16 (m, 4H), 3.06 (dt, J = 33.2, 12.3 Hz, 1H), 2.91-2.70 (m, 6H), 2.19-2.07 (m, 1H), 1.93-1.40 (m, 8H). | LCMS: $C_{40}H_{45}N_{11}O_7$ requires: 791, found: m/z = 792 [M + H]$^+$. |
| 185 | $^1$H NMR (500 MHz, DMSO-d$_6$) δ 11.29 (s, 1H), 10.67 (s, 1H), 7.95 (d, J = 2.5 Hz, 1H), 7.74 (d, J = 2.9 Hz, 1H), 7.67 (s, 1H), 7.53 (d, J = 8.3 Hz, 2H), 7.38 (dd, J = 8.7, 2.5 Hz, 1H), 7.32 (d, J = 2.8 Hz, 1H), 7.20 (d, J = 8.3 Hz, 2H), 6.76 (d, J = 8.8 Hz, 1H), 4.23 (d, J = 12.8 Hz, 2H), 3.69 (t, J = 5.4 Hz, 4H), 3.06-2.96 (m, 1H), 2.98-2.92 (m, 2H), 2.78-2.67 (m, 3H), 2.60-2.32 (m, 4H), 2.17 (d, J = 6.6 Hz, 2H), 2.02-1.93 (m, 2H), 1.82-1.44 (m, 15H), 1.14-1.05 (m, 2H). | LCMS $C_{38}H_{49}N_9O_3$ requires: 679, found: 680 [M + H]$^+$. |
| 186 | $^1$H NMR (500 MHz, Acetonitrile-d$_3$) δ 11.01 (s, 1H), 9.17 (d, J = 3.4 Hz, 1H), 7.57 (s, 1H), 7.51 (dd, J = 14.1, 8.1 Hz, 4H), 7.28 (d, J = 9.5 Hz, 1H), 7.16 (d, J = 8.2 Hz, 2H), 7.13-7.05 (m, 1H), 7.01 (t, J = 6.9 Hz, 2H), 5.88 (d, J = 10.3 Hz, 1H), 4.66 (d, J = 9.6 Hz, 2H), 4.55 (t, J = 8.1 Hz, 1H), 4.51-4.40 (m, 3H), 4.38-4.22 (m, 2H), 4.16-3.97 (m, 3H), 3.82-3.67 (m, 3H), 3.50-3.07 (m, 3H), 2.68-2.31 (m, 5H), 2.12 (d, J = 10.1 Hz, 2H), 1.93-1.77 (m, 6H), 1.64 (dt, J = 48.0, 7.5 Hz, 3H), 1.41-1.16 (m, 5H), 0.99 (s, 8H). | LCMS: $C_{59}H_{79}FN_{12}O_8S$ requires 1134, found: m/z = 1135 [M + H]$^+$. |

TABLE 2-continued

Physical Data for the Example Compounds of Table 1.

| Compound No. | $^1$H NMR | Mass Spec (LCMS) |
| --- | --- | --- |
| 187 | $^1$H NMR (500 MHz, Acetonitrile-d$_3$) δ 11.01 (s, 1H), 9.17 (d, J = 3.4 Hz, 1H), 7.57 (s, 1H), 7.51 (dd, J = 14.1, 8.1 Hz, 4H), 7.28 (d, J = 9.5 Hz, 1H), 7.16 (d, J = 8.2 Hz, 2H), 7.13-7.05 (m, 1H), 7.01 (t, J = 6.9 Hz, 2H), 5.88 (d, J = 10.3 Hz, 1H), 4.66 (d, J = 9.6 Hz, 2H), 4.55 (t, J = 8.1 Hz, 1H), 4.51-4.40 (m, 3H), 4.38-4.22 (m, 2H), 4.16-3.97 (m, 3H), 3.82-3.67 (m, 3H), 3.50-3.07 (m, 3H), 2.68-2.31 (m, 5H), 2.12 (d, J = 10.1 Hz, 2H), 1.93-1.77 (m, 6H), 1.64 (dt, J = 48.0, 7.5 Hz, 3H), 1.41-1.16 (m, 5H), 0.99 (s, 8H). | LCMS: $C_{57}H_{75}FN_{12}O_8S$ requires 1106, found: m/z = 1107 $[M + H]^+$. |
| 188 | $^1$H NMR (500 MHz, Acetonitrile-d$_3$) δ 11.02 (s, 1H), 8.84 (s, 1H), 7.56 (d, J = 7.0 Hz, 3H), 7.49-7.31 (m, 6H), 7.19 (d, J = 8.0 Hz, 2H), 6.67 (d, J = 9.1 Hz, 1H), 5.85 (s, 1H), 4.97 (q, J = 7.2 Hz, 1H), 4.64 (d, J = 13.4 Hz, 1H), 4.57 (d, J = 9.0 Hz, 1H), 4.55-4.35 (m, 3H), 4.27 (d, J = 13.7 Hz, 1H), 4.02 (d, J = 14.0 Hz, 1H), 3.84 (d, J = 11.1 Hz, 1H), 3.76-3.61 (m, 1H), 3.45-3.24 (m, 4H), 2.77 (s, 4H), 2.62 (t, J = 12.7 Hz, 1H), 2.49 (s, 3H), 2.38 (s, 2H), 2.23 (td, J = 7.1, 3.1 Hz, 2H), 2.17-2.07 (m, 1H), 2.03-1.93 (m, 27H), 1.93-1.77 (m, 2H), 1.73-1.41 (m, 11H), 1.34 (d, J = 8.4 Hz, 7H), 1.01 (s, 10H). | LCMS: $C_{57}H_{78}N_{12}O_7S$ requires: 1075, found: m/z = 1076 $[M + H]^+$. |
| 189 | $^1$H NMR (500 MHz, Acetonitrile-d$_3$) δ 11.00 (s, 1H), 9.07 (s, 1H), 7.58-7.49 (m, 3H), 7.44 (s, 5H), 7.28 (s, 1H), 7.23-7.14 (m, 2H), 6.77 (d, J = 8.9 Hz, 1H), 5.92 (s, 1H), 4.97 (p, J = 7.1 Hz, 1H), 4.65 (d, J = 13.3 Hz, 1H), 4.58 (d, J = 8.9 Hz, 1H), 4.55-4.35 (m, 3H), 4.26 (d, J = 13.5 Hz, 1H), 4.02 (d, J = 13.6 Hz, 1H), 3.86 (d, J = 11.1 Hz, 1H), 3.78-3.62 (m, 2H), 3.06-2.91 (m, 1H), 2.77 (s, 4H), 2.64 (t, J = 12.8 Hz, 1H), 2.50 (s, 3H), 2.39 (d, J = 7.5 Hz, 2H), 2.25 (tp, J = 13.1, 6.6, 6.1 Hz, 2H), 1.99 (s, 13H), 1.94-1.73 (m, 4H), 1.71-1.25 (m, 11H), 1.01 (s, 10H). | LCMS: $C_{55}H_{74}N_{12}O_7S$ requires 1046, found: m/z = 1047 $[M + H]^+$. |
| 190 | $^1$H NMR (500 MHz, DMSO-d$_6$) δ 11.19 (s, 1H), 10.67 (s, 1H), 7.95 (d, J = 2.4 Hz, 1H), 7.76 (d, J = 2.9 Hz, 1H), 7.67 (s, 1H), 7.50 (d, J = 8.3 Hz, 2H), 7.41-7.31 (m, 2H), 7.17 (d, J = 8.3 Hz, 2H), 6.77 (d, J = 8.7 Hz, 1H), 4.38 (d, J = 12.2 Hz, 1H), 4.33-4.20 (m, 3H), 3.67-3.53 (m, 1H), 3.32-3.23 (m, 3H), 3.10-2.89 (m, 6H), 2.81-2.62 (m, 6H), 2.51 (p, J = 1.8 Hz, 6H), 2.17 (d, J = 6.7 Hz, 2H), 2.02-1.94 (m, 2H), 1.89-1.46 (m, 14H), 1.27-1.19 (m, 7H), 1.15-1.05 (m, 2H). | LCMS: $C_{42}H_{55}N_{11}O_4$ requires: 777, found: m/z = 778 $[M + H]^+$. |
| 191 | $^1$H NMR (500 MHz, Acetonitrile-d$_3$) δ 11.13 (s, 1H), 9.92 (s, 1H), 8.73 (s, 1H), 7.61 (d, J = 8.4 Hz, 2H), 7.54 (s, 1H), 7.39 (d, J = 9.1 Hz, 2H), 7.20 (d, J = 8.4 Hz, 2H), 7.04 (d, J = 8.3 Hz, 1H), 5.76 (s, 1H), 4.71 (q, J = 8.5 Hz, 1H), 4.17 (d, J = 13.1 Hz, 2H), 3.72-3.62 (m, 7H), 3.07 (t, J = 12.8 Hz, 2H), 2.96 (q, J = 10.8, 8.5 Hz, 4H), 2.76-2.60 (m, 2H), 2.19-2.10 (m, 5H), 2.01 (d, J = 14.0 Hz, 2H), 1.70 (q, J = 6.0, 5.4 Hz, 2H), 1.64 (p, J = 5.8 Hz, 5H), 1.35 (q, J = 12.0 Hz, 2H). | LCMS: $C_{36}H_{46}N_{10}O_5$ requires: 698, found: m/z = 699 $[M + H]^+$. |
| 192 | $^1$H NMR (500 MHz, Acetonitrile-d$_3$) δ 11.10 (s, 1H), 9.54 (s, 1H), 8.74 (s, 1H), 7.59 (d, J = 8.4 Hz, 2H), 7.55 (s, 1H), 7.40 (s, 2H), 7.19 (d, J = 8.4 Hz, 2H), 7.04 (d, J = 8.1 Hz, 1H), 5.80 (s, 1H), 4.71 (q, J = 8.5 Hz, 1H), 4.39 (d, J = 13.1 Hz, 1H), 4.29 (d, J = 13.7 Hz, 1H), 4.18 (d, J = 13.5 Hz, 2H), 3.70-3.63 (m, 4H), 3.42-3.23 (m, 4H), 3.15-3.01 (m, 4H), 3.02-2.93 (m, 6H), 2.86-2.78 (m, 1H), 2.75 (s, 3H), 2.72-2.59 (m, 2H), 2.20-2.00 (m, 6H), 1.87-1.75 (m, 2H), 1.32 (dd, J = 28.8, 16.0 Hz, 3H). | LCMS: $C_{40}H_{52}N_{12}O_6$ requires: 796, found: m/z = 797 $[M + H]^+$. |
| 193 | $^1$H NMR (500 MHz, Acetonitrile-d$_3$) δ 11.13 (s, 1H), 10.41 (s, 1H), 8.89 (s, 1H), 7.67 (dd, J = 8.4, 3.7 Hz, 4H), 7.58 (s, 1H), 7.50-7.36 (m, 1H), 7.25 (d, J = 8.2 Hz, 2H), 6.98 (d, J = 2.3 Hz, 1H), 6.82 (dd, J = 8.6, 2.3 Hz, 1H), 5.79 (s, 1H), 4.96 (dd, J = 12.1, 5.4 Hz, 1H), 4.58 (d, J = 13.4 Hz, 1H), 4.24 (d, J = 13.7 Hz, 1H), 3.85-3.65 (m, 4H), 3.58 (d, J = 8.1 Hz, 2H), 3.54-3.38 (m, 4H), 3.30 (t, J = 9.1 | LCMS: $C_{40}H_{47}N_9O_6$ requires: 749, found: m/z = 750 $[M + H]^+$. |

TABLE 2-continued

Physical Data for the Example Compounds of Table 1.

| Compound No. | ¹H NMR | Mass Spec (LCMS) |
|---|---|---|
| | Hz, 2H), 3.14 (t, J = 12.0 Hz, 2H), 2.98 (d, J = 41.7 Hz, 5H), 2.90-2.68 (m, 8H), 1.80 (d, J = 19.1 Hz, 5H), 1.59 (d, J = 11.7 Hz, 2H), 1.48-1.27 (m, 2H). | |

Example 66: BTK Degradation Assay

Cell Culture

TMD8 cells were obtained from Tokyo Medical and Dental University and were grown in alpha-MEM (Fisher 12571063) supplemented with 10% heat-inactivated FBS (Corning Premium Fetal Bovine Serum from Fisher, MT35015CV).

Cellular BTK HTRF Assay

Compounds of the present invention were added to 50,000 TMD8 cells in round-bottom 96 well plates with a final DMSO concentration of <0.200 and were incubated at 37° C. 5% $CO_2$ for four hours. BTK levels were determined using Cisbio Total-BTK HTRF (Homologous Time-Resolved Fluorescence) kit (63ADK064PEG) according to manufacturer's protocol. Briefly, cells were incubated in 1× supplied lysis buffer for 30 minutes. In an opaque white low volume 96 well plate (Cisbio, 66PL96005), cell lysate was combined with two different specific BTK antibodies, one conjugated with $Eu^{3+}$-Cryptate FRET donor and one conjugated with d2 FRET acceptor. Assay controls include wells containing cell lysate with only the $Eu^{3+}$-Cryptate FRET donor antibody and wells containing both HTRF antibodies and lysis buffer without cells or control lysate provided by Cisbio. HTRF ratio was calculated as (acceptor signal at 665 nm/donor signal at 620 nm)×$10^4$. Background HTRF levels were determined from the control well containing the donor, but no acceptor, antibody. Background HTRF levels were subtracted from all samples. Readouts were reported as HTRF levels relative to HTRF levels of DMSO-treated cells. Four-parameter non-linear regressions were performed in GraphPad Prism 7.02 to obtain $DC_{50}$ values. $DC_{50}$ values are provided in Table 3, wherein A<5.0 nM, 5.0 nM≤B≤15 nM, and 15 nM<C.

TABLE 3

BTK degradation activity.

| Compound No. | Cellular BTK HTRF TMD8: $DC_{50}$ |
|---|---|
| 1 | — |
| 2 | C |
| 3 | C |
| 4 | C |
| 5 | C |
| 6 | C |
| 7 | C |
| 8 | B |
| 9 | C |
| 10 | B |
| 11 | A |
| 12 | B |
| 13 | B |
| 14 | C |
| 15 | A |
| 16 | B |
| 17 | A |

TABLE 3-continued

BTK degradation activity.

| Compound No. | Cellular BTK HTRF TMD8: $DC_{50}$ |
|---|---|
| 18 | B |
| 19 | B |
| 20 | A |
| 21 | B |
| 22 | B |
| 23 | B |
| 24 | B |
| 25 | B |
| 26 | B |
| 27 | B |
| 28 | B |
| 29 | A |
| 30 | B |
| 31 | A |
| 32 | A |
| 33 | A |
| 34 | A |
| 35 | A |
| 36 | B |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | B |
| 59 | A |
| 60 | A |
| 61 | A |
| 62 | C |
| 63 | C |
| 64 | C |
| 65 | C |
| 66 | A |
| 67 | C |
| 68 | — |
| 69 | A |
| 70 | A |
| 71 | A |
| 72 | A |
| 73 | A |
| 74 | A |
| 75 | A |
| 76 | B |
| 77 | A |

TABLE 3-continued

BTK degradation activity.

| Compound No. | Cellular BTK HTRF TMD8: $DC_{50}$ |
|---|---|
| 78 | A |
| 79 | C |
| 80 | A |
| 81 | C |
| 82 | A |
| 83 | A |
| 84 | C |
| 85 | A |
| 86 | A |
| 87 | A |
| 88 | C |
| 89 | B |
| 90 | B |
| 91 | A |
| 92 | B |
| 93 | A |
| 94 | A |
| 95 | B |
| 96 | C |
| 97 | C |
| 98 | A |
| 99 | A |
| 100 | C |
| 101 | A |
| 102 | A |
| 103 | A |
| 104 | B |
| 105 | C |
| 106 | B |
| 107 | C |
| 108 | B |
| 109 | A |
| 110 | A |
| 111 | B |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | B |
| 124 | C |
| 125 | A |
| 126 | A |
| 127 | C |
| 128 | C |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | B |
| 151 | C |
| 152 | A |
| 153 | A |
| 154 | A |
| 155 | A |
| 156 | A |
| 157 | B |
| 158 | B |
| 159 | B |
| 160 | A |
| 161 | B |
| 162 | A |
| 163 | A |
| 164 | B |
| 165 | B |
| 166 | A |
| 167 | C |
| 168 | A |
| 169 | A |
| 170 | A |
| 171 | A |
| 172 | A |
| 173 | A |
| 174 | A |
| 175 | A |
| 176 | A |
| 177 | A |
| 178 | B |
| 179 | A |
| 180 | C |
| 181 | B |
| 182 | A |
| 183 | C |
| 184 | B |
| 185 | C |
| 186 | C |
| 187 | C |
| 188 | C |
| 189 | C |
| 190 | B |
| 191 | B |
| 192 | A |
| 193 | A |

Example 67: Aiolos Degradation Assay

Flow Cytometry Assays.

Frozen human peripheral blood mononuclear cells (PBMCs) were thawed and treated with DMSO or compound for 24 hours and then fixed and permeabilized using a Foxp3/Transcription Factor Fixation/Permeabilization Kit (eBioscience, 00-5523). Cells were stained with fluorophore-conjugated antibodies against CD20 (Biolegend 302330), CD3 (BD Pharmingen 552127), and Aiolos (Biolegend 371106). An additional set of DMSO-treated PBMCs was stained for CD20, CD3, and an AlexaFluor 647-conjugated mouse IgG1 isotype control antibody (Biolegend 400136). Stained cells were analyzed using an Attune NxT Acoustic Focusing Flow Cytometer (Thermo-Fisher A29004), and data was analyzed using FlowJo (v10.5.3) and GraphPad Prism (v7.00) software. Single lymphocytes were gated for B cells (CD20+CD3−) and T cells (CD3+CD20−), and the geometric mean fluorescence intensity (MFI) of Aiolos was calculated for each population. The MFI of the isotype control was calculated for each population and used to quantify background staining. Percent Aiolos degradation was calculated for each compound-treated sample using the following equation:

$$\% \text{ degradation} = 100 \times \frac{(\text{Sample } MFI - \text{Isotope } MFI)}{(DMSO \ MFI - \text{Isotope } MFI)}$$

Four-parameter non-linear regressions were performed in GraphPad Prism 7.02 to obtain $DC_{50}$ values. Aiolos T Cell $DC_{50}$ values are provided in Table 4, wherein A<10.0 nM, 10.0 nM≤B≤1000 nM, and 1000 nM<C.

TABLE 4

Aiolos degradation activity.

| Compound No. | Aiolos T Cell $DC_{50}$ (nM) |
| --- | --- |
| 14 | C |
| 17 | B |
| 25 | A |
| 29 | C |
| 30 | A |
| 31 | B |
| 34 | B |
| 37 | B |
| 38 | B |
| 51 | B |
| 53 | B |
| 61 | C |
| 64 | B |
| 75 | C |
| 78 | B |
| 92 | A |
| 99 | C |
| 123 | C |
| 155 | B |
| 156 | A |
| 157 | C |
| 166 | C |

Example 68: Mouse BTK Degradation Assay with Oral Dosing

A method of determining the pharmacodynamic profile of compounds of the present invention (experimental compound) was performed by dosing either CD-1 or BALB/c mice with the compound. The experimental compound was prepared in a suitable formulation and was administered via oral gavage (PO) at a suitable dose level and frequency as informed by prior pharmacokinetic and tolerability studies. Following administration of the experimental compound, BTK levels in blood or splenocytes are measured using flow cytometry or HTRF. For assessment of BTK levels via flow cytometry, either whole blood or spleen were first treated with ACK RBC lysis buffer to facilitate lysing of red blood cells. Remaining cells were then stained with fluorophore-conjugated antibodies against CD45, TCR beta and CD45R (B220). Cell pellets were washed with 1×PBS and fixed and permeabilized for 24 hrs with Foxp3/Transcription Factor Fixation/Permeabilization Kit. Cells were then stained intracellularly with unconjugated BTK antibody and detected with a fluorophore-conjugated secondary antibody. Stained cells were run on an Attune NxT Acoustic Focusing Flow Cytometer (Thermo-Fisher A29004), and data was analyzed using FlowJo (v10.5.3) and GraphPad Prism (v7.00) software. Lymphocytes were gated for B cells defined as CD45+ TCR beta– B220+ and T cells as CD45+ TCR beta+ B220–. The BTK geometric mean fluorescence intensity (MFI) was calculated for B and T cells. Percent BTK degradation for each experimental compound treated sample was calculated using the equation described below:

$$\% \text{ degradation} = 100 \times \frac{(\text{Treated } Smpl \text{ B Cell } BTK \ MFI - \text{Treated } Smpl \text{ T Cell } BTK \ MFI)}{(Veh. \text{ B Cell } BTK \ MFI - Veh. \text{ T Cell } BTK \ MFI)}$$

Experimental compounds, i.e., compounds of the present invention, which demonstrated significant BTK degradation upon oral dosage are summarized in Table 5.

TABLE 5

Oral bioavailability in mouse model.

| Compound No. | Oral Bioavailability |
| --- | --- |
| 44 | Yes |
| 70 | Yes |
| 71 | Yes |
| 72 | Yes |
| 73 | Yes |
| 74 | Yes |
| 131 | Yes |
| 150 | Yes |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (A)

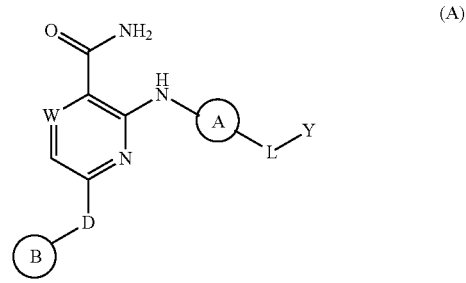

or a pharmaceutically acceptable salt thereof, wherein
W is CH or N;
D is a bond or —NH—;
Ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S, wherein ring A is optionally and independently substituted with up to 3 substituents selected from halo, —CN, —COOH, $NH_2$, and optionally substituted $C_{1-6}$ alkyl;
Ring B is a phenyl, a 5-6 membered heteroaryl, a 4-6 membered heterocycloalkyl, or a 8-10 membered spiro bicyclic heterocycle, wherein ring B is optionally substituted, and wherein the heteroaryl and heterocycloalkyl of ring B has 1-3 heteroatoms independently selected from N, O, or S;

L is —X¹—X²—X³—X⁴—X⁵—;

X¹ is a bond, —C(O)—N(R)—, —N(R)—C(O)—, —(O—CH₂—CH₂)ₘ—, —O(C₆H₄)—, —(O—CH₂—CH₂—CH₂)ₘ—, —C₁₋₅ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of X¹ is optionally substituted with —CH₃;

X² is a bond, —(O—CH₂—CH₂)ₙ—, —(CH₂—CH₂—O)ₙ—, —N(R)—C(O)—, —N(R)—, —C(O)—, —C₁₋₅ alkyl-, 4-6 membered monocyclic cycloalkyl, or 4-6 membered monocyclic heterocycloalkyl having 1-2 heteroatoms independently selected from N, O, or S;

X³ is a bond, —C₁₋₈ alkyl-, —C≡C—, 4-6 membered cycloalkyl, —N(R)—, —N(R)—C(O)—, —(O—CH₂—CH₂)ₚ—, —(CH₂—CH₂—O)ₚ—, 4-6 membered heterocycloalkyl having 1-2 heteroatoms independently selected from N, O, or S wherein the heterocycloalkyl is optionally substituted with —CH₃;

X⁴ is a bond, —CH₂—CH₂—N(R)—, —N(R)—, —C₁₋₄ alkyl-, —(O—CH₂—CH₂—CH₂)ₘ—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S;

X⁵ is a bond, —C₁₋₄ alkyl-, —N(R)—, —O—, —C(O)—, or —C(O)—N(R)—;

each R is independently —H or —C₁₋₃ alkyl; and each of m, n, and p is independently an integer from 1 to 3; and Y is

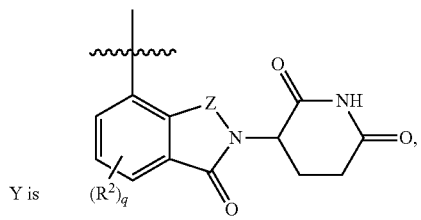

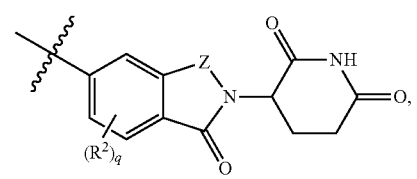

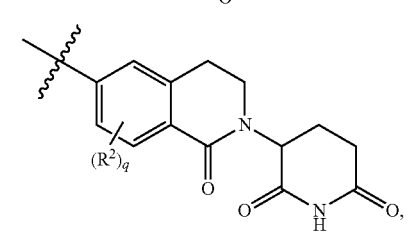

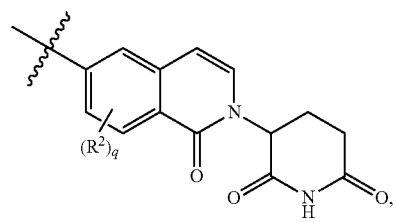

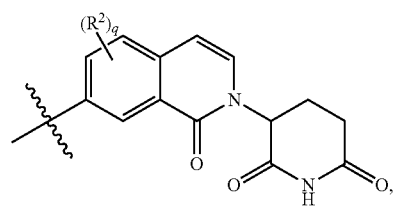

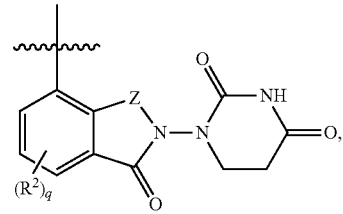

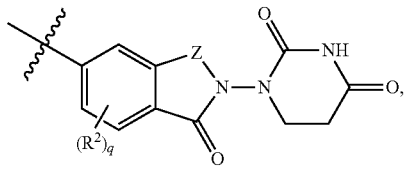

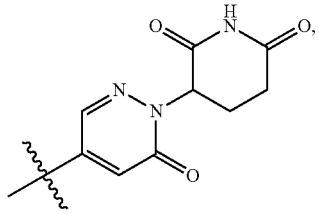

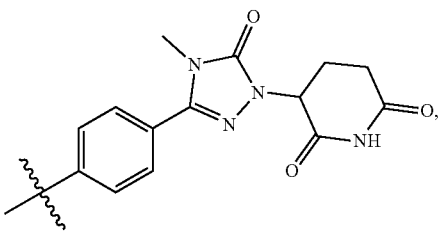

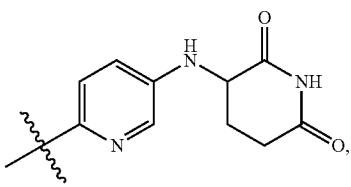

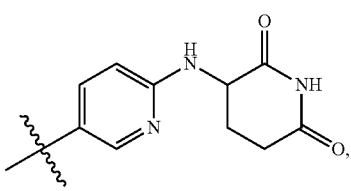

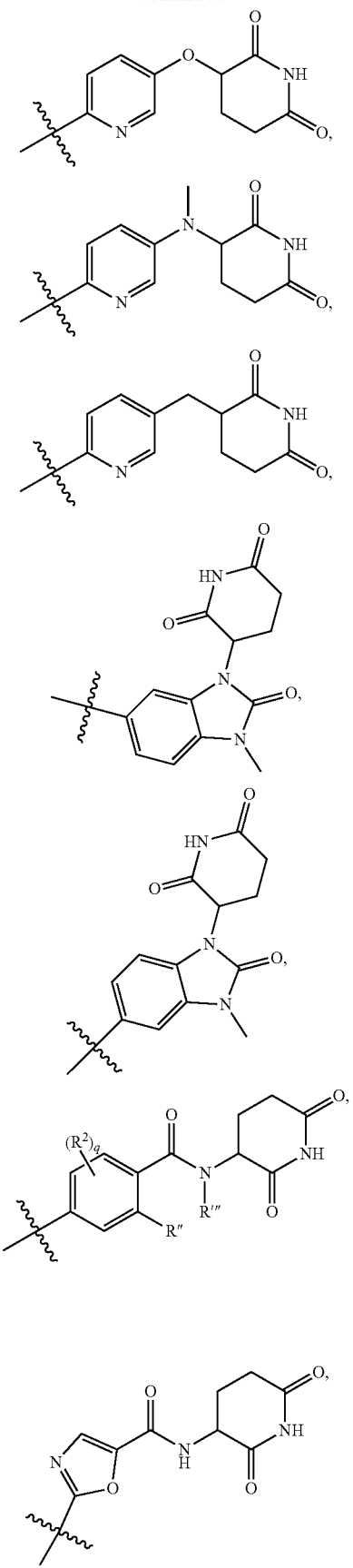
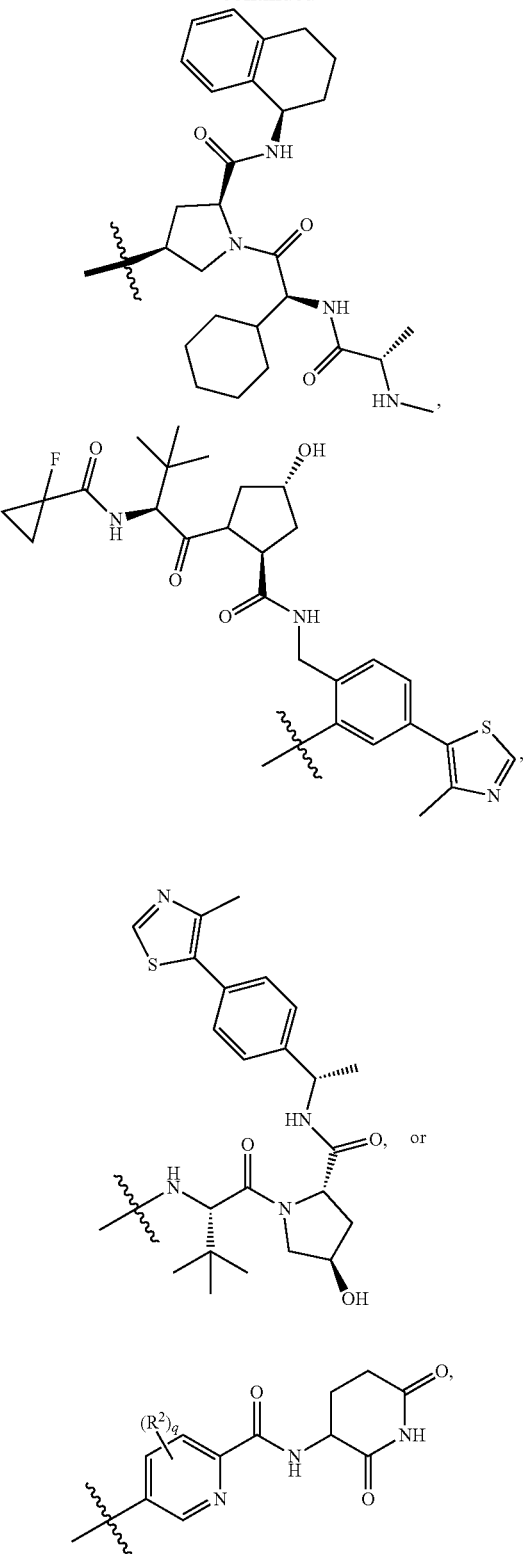
wherein
each R² is independently halo, —CN, or C₁₋₄ alkyl, wherein each C₁₋₄ alkyl is optionally and independently substituted with up to three instances of halo, —CN, —COOH, —COONH₂, —NH₂, or —CF₃;

each R'' and R''' are independently H or, together with the atoms to which they are attached, form a 5-6 membered partially unsaturated or fully unsaturated benzofuzed heterocycle;

each Z is —C(R$^4$)$_2$— or —C(O)—;

each R$^A$ is independently —H or —C$_{1-4}$ alkyl; and q is 0, 1, or 2.

2. The compound or pharmaceutically acceptable salt of claim 1, wherein ring B is an optionally substituted 5-6 membered heterocycloalkyl having 1-2 nitrogen atoms.

3. The compound or pharmaceutically acceptable salt of claim 1, wherein ring B is an optionally substituted 5-6 membered heteroaryl having 1-2 heteroatoms independently selected from N and S.

4. The compound or pharmaceutically acceptable salt of claim 1, wherein ring B is

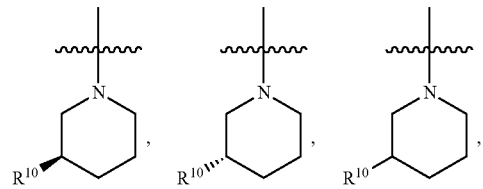

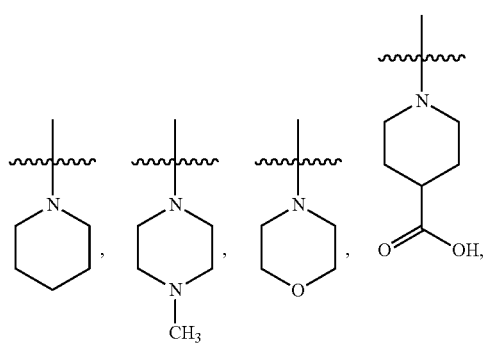

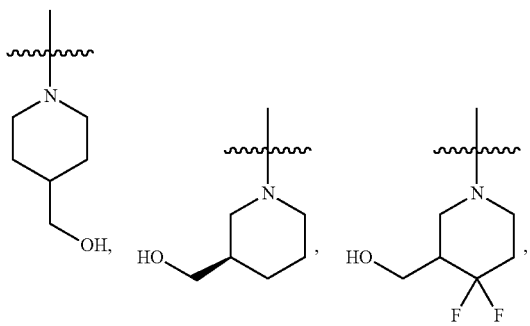

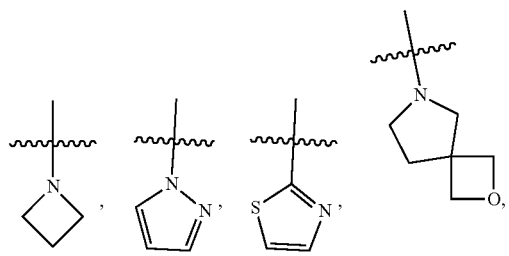

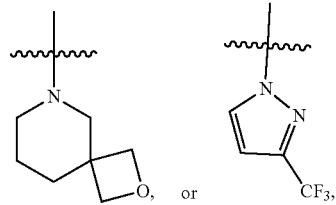

wherein R$^{10}$ is

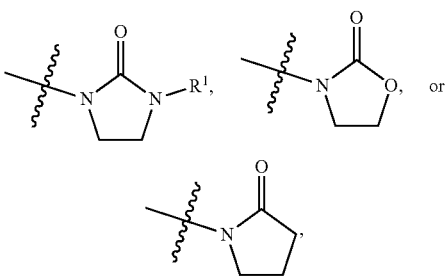

and wherein R$^1$ is a C$_{1-4}$ alkyl group.

5. The compound or pharmaceutically acceptable salt of claim 1, wherein ring B is

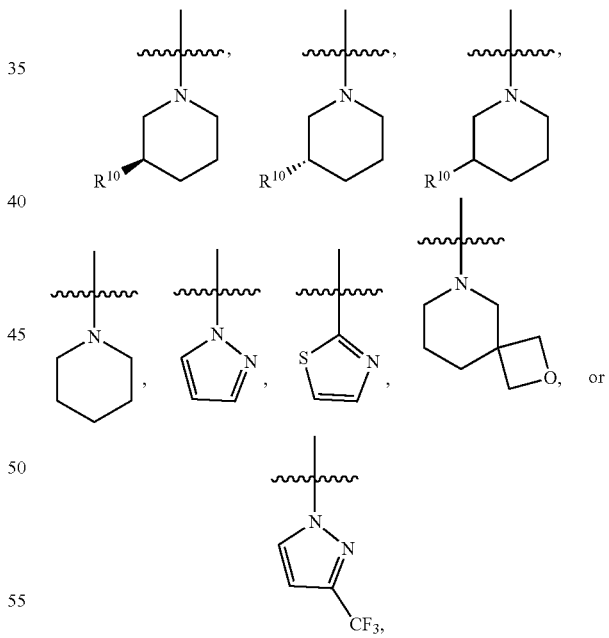

wherein R$^{10}$ is

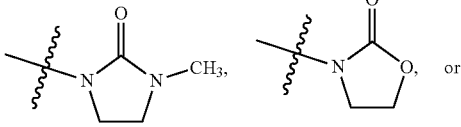

-continued

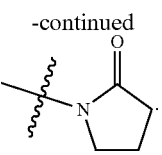

6. The compound or pharmaceutically acceptable salt of claim 4, wherein ring B is

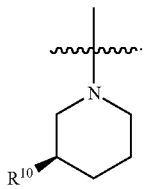

7. The compound or pharmaceutically acceptable salt of claim 4, wherein $R^{10}$ is

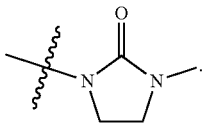

8. The compound or pharmaceutically acceptable salt of claim 4, wherein ring A is

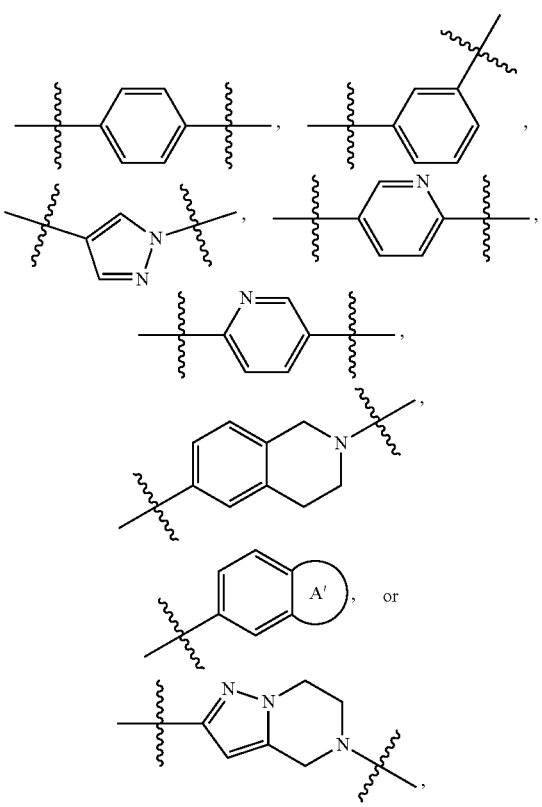

or wherein ring A' together with the phenyl ring to which it is fused form a 9-10 membered bicyclic aryl or a 9-10 membered bicyclic heteroaryl wherein the bicyclic heteroaryl has 1-3 heteroatoms independently selected from N, O, or S.

9. The compound or pharmaceutically acceptable salt of claim 1, wherein ring A is

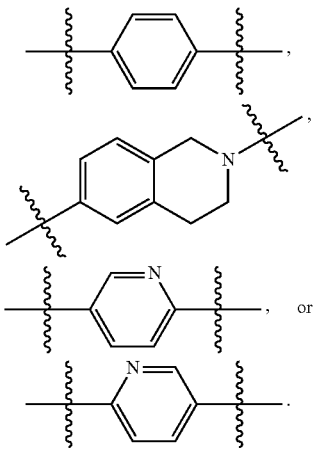

10. The compound or pharmaceutically acceptable salt of claim 1, or a pharmaceutically acceptable salt thereof, wherein at least one of $X^1$, $X^2$, and $X^5$ is —N(R)—, —C(O)—N(R)—, or —CH$_2$—.

11. The compound or pharmaceutically acceptable salt of claim 1, wherein $X^1$ is —C(O)—N(R)—.

12. The compound or pharmaceutically acceptable salt of claim 1, or a pharmaceutically acceptable salt thereof, wherein $X^2$ is —(O—CH$_2$—CH$_2$)$_n$—, —(CH$_2$—CH$_2$—O)$_n$—, or —C$_{1-5}$ alkyl-.

13. The compound or pharmaceutically acceptable salt of claim 1, wherein $X^3$ is a bond, —C≡C—, —C$_{1-4}$ alkyl-, or —N(R)—.

14. The compound or pharmaceutically acceptable salt of claim 1, wherein $X^4$ is a bond, —CH$_2$—, or —N(R)—.

15. The compound or pharmaceutically acceptable salt of claim 1, wherein $X^5$ is a bond.

16. The compound or pharmaceutically acceptable salt of claim 1, wherein $X^1$ is —(O—CH$_2$—CH$_2$—CH$_2$)$_m$—, m is 1, and $X^2$ is —C(O)—N(R)—.

17. The compound or pharmaceutically acceptable salt of claim 1, wherein $X^1$ is —CH$_2$—, —C(O)—,

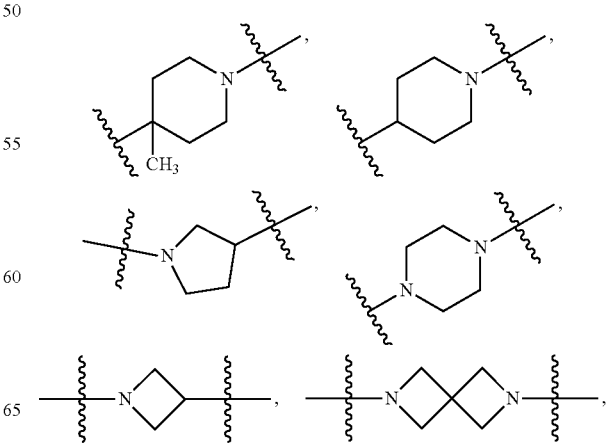

-continued

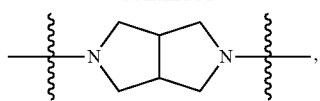

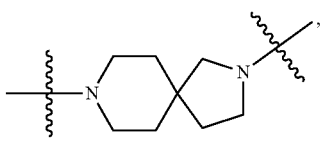

-continued

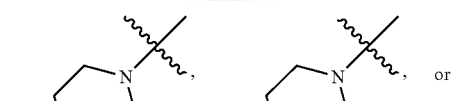

19. The compound or pharmaceutically acceptable salt of claim 1, wherein $X^3$ is bond, —$C_{1-4}$ alkyl-, 4-6 membered cycloalkyl, or —N(R)—.

20. The compound or pharmaceutically acceptable salt of claim 1, wherein $X^3$ is a bond, —$C_{1-4}$ alkyl-, —NH—,

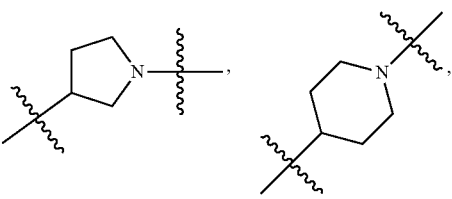

or —C≡C—.

21. The compound or pharmaceutically acceptable salt of claim 1, wherein $X^4$ is a bond,

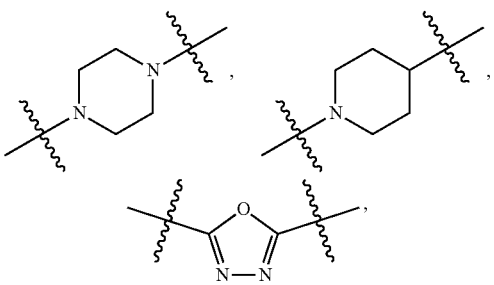

—$C_{1-4}$ alkyl-, —$CH_2$—$CH_2$—N(R)—, or —N(R)—.

22. The compound or pharmaceutically acceptable salt of claim 1, wherein $X^5$ is a bond, —$C_{1-4}$ alkyl-, —N(R)—, or —C(O)—N(R)—.

18. The compound or pharmaceutically acceptable salt of claim 1, wherein $X^2$ is a bond, —C(O)—, —$C_{1-5}$ alkyl-,

23. The compound or pharmaceutically acceptable salt of claim 1, wherein L is
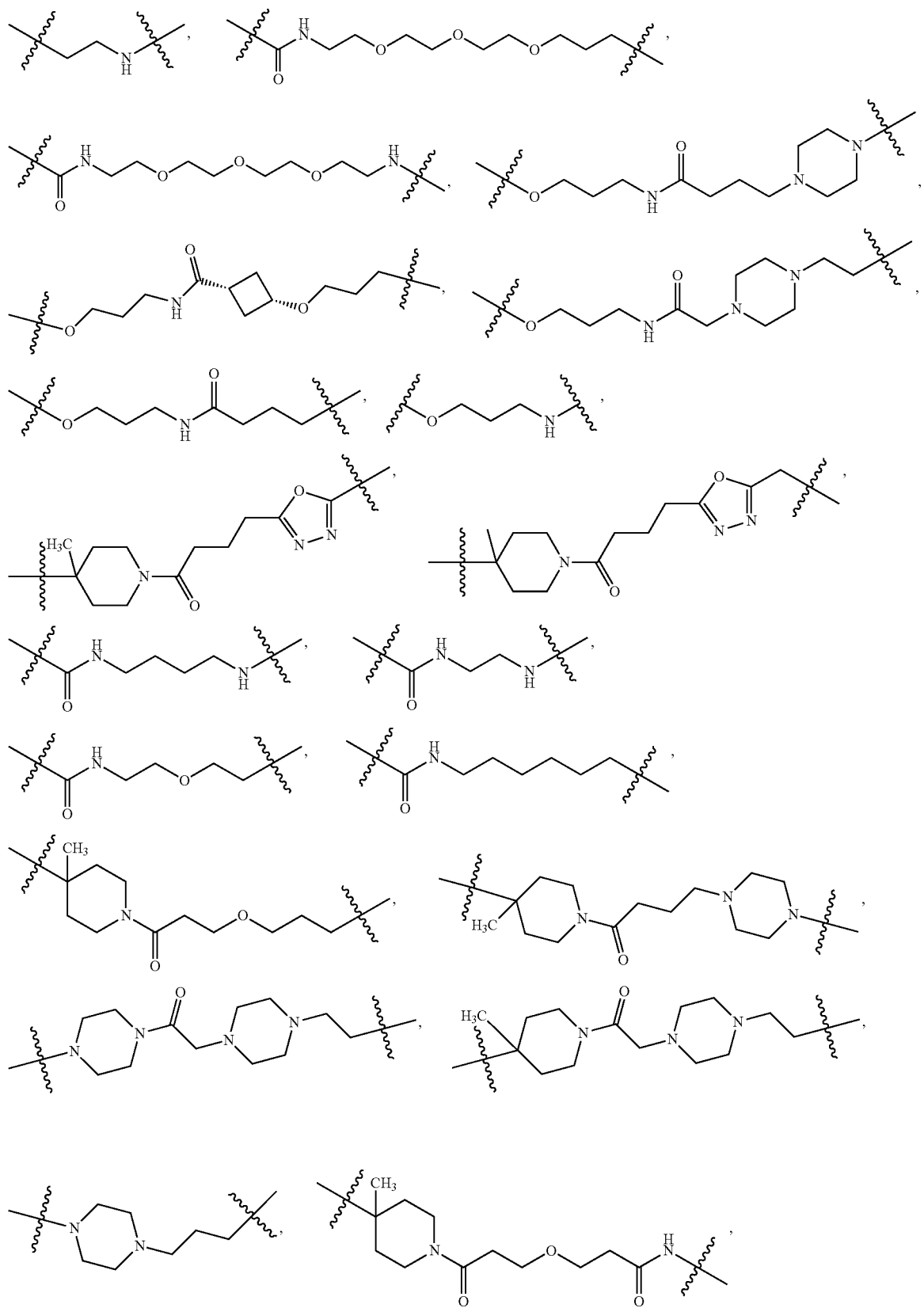

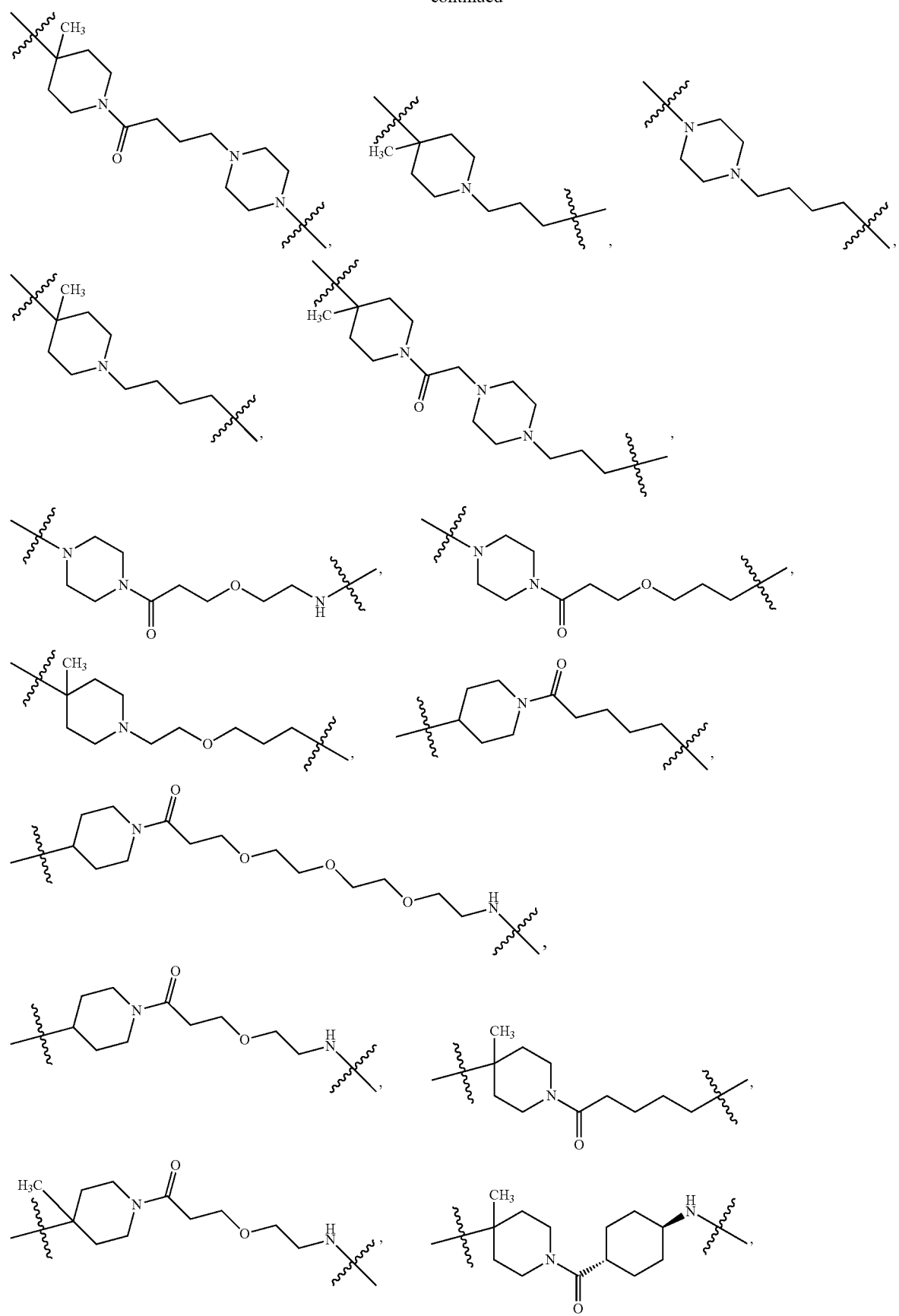

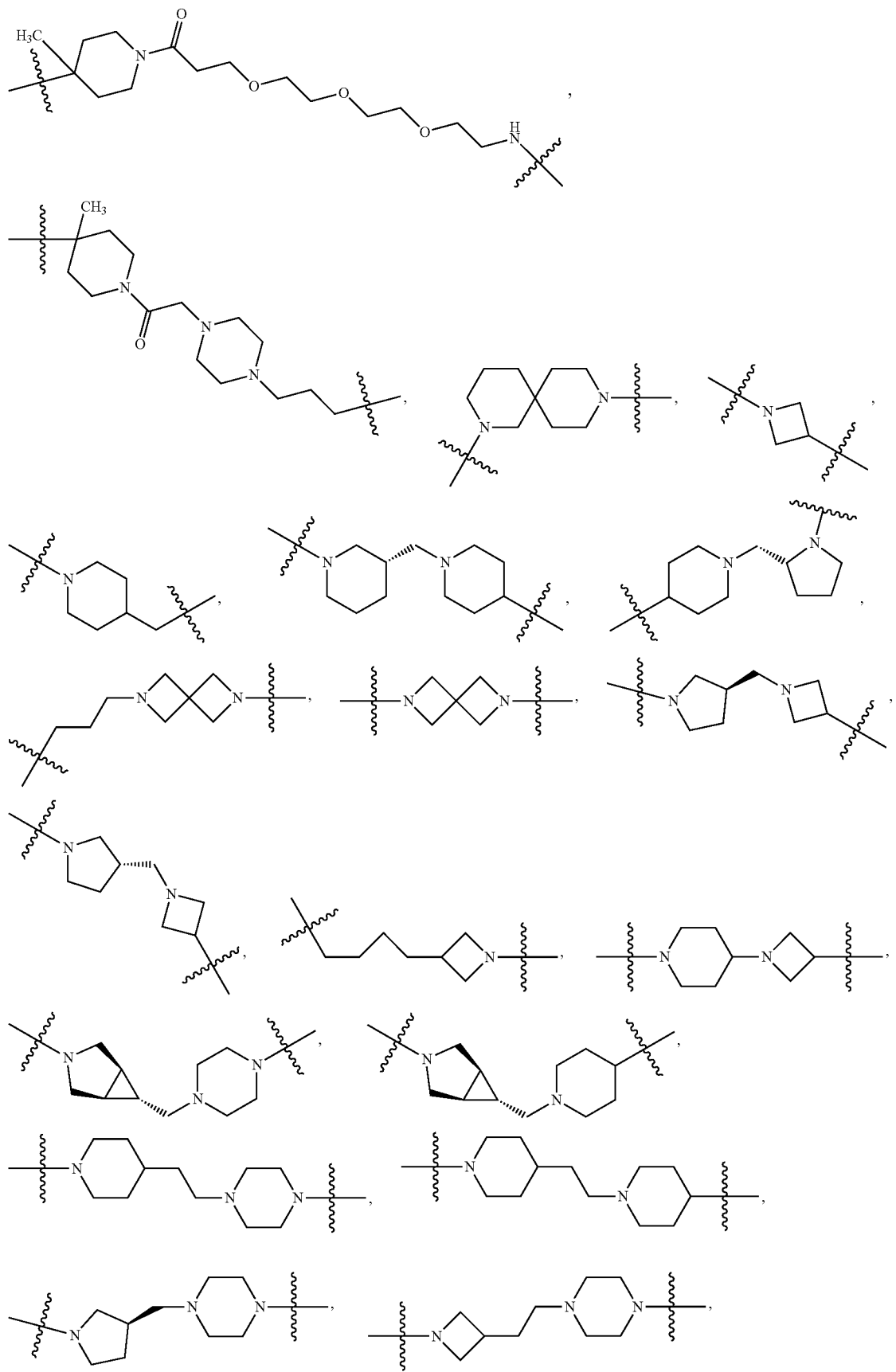

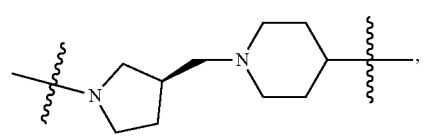
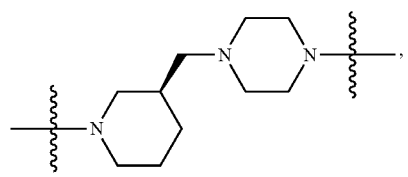
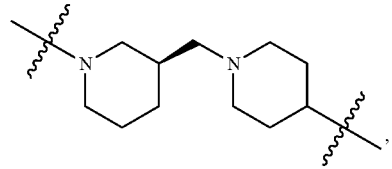
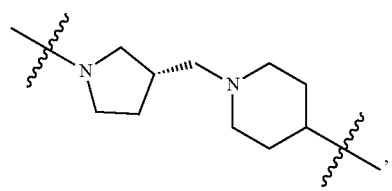
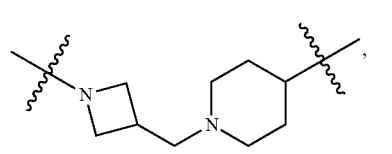
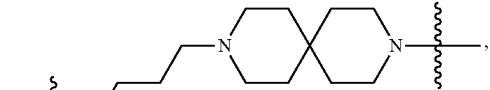
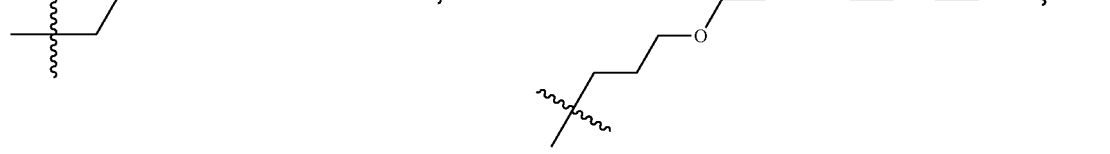
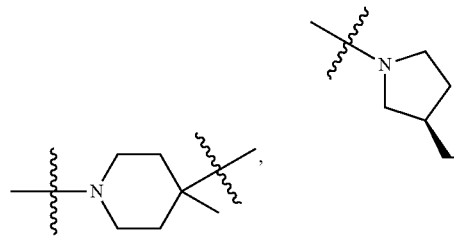
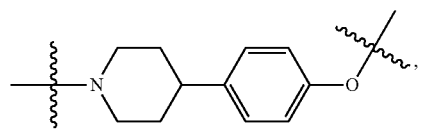
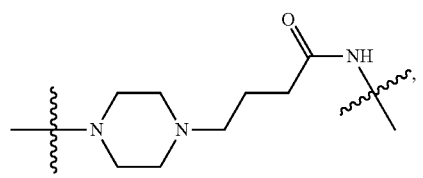
-continued
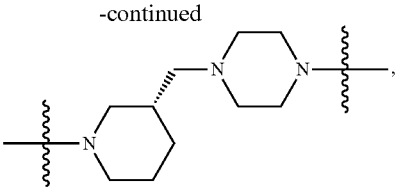
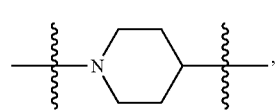
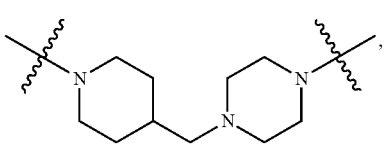
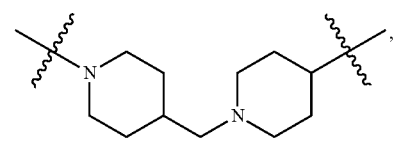
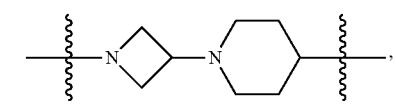
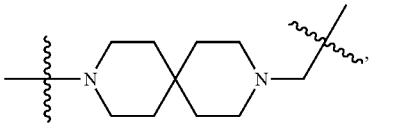
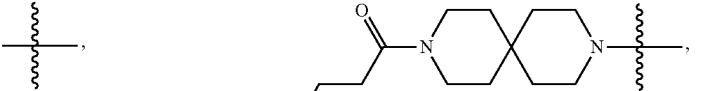
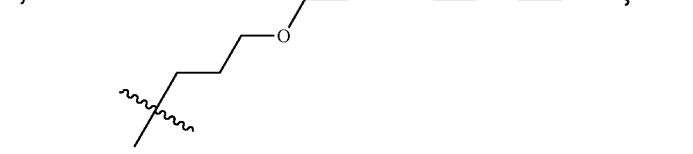
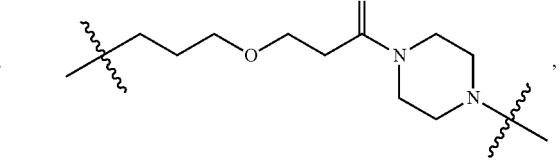
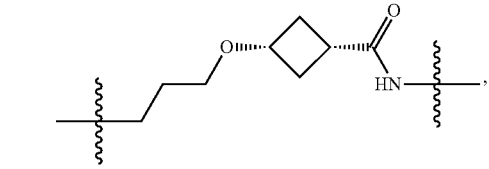

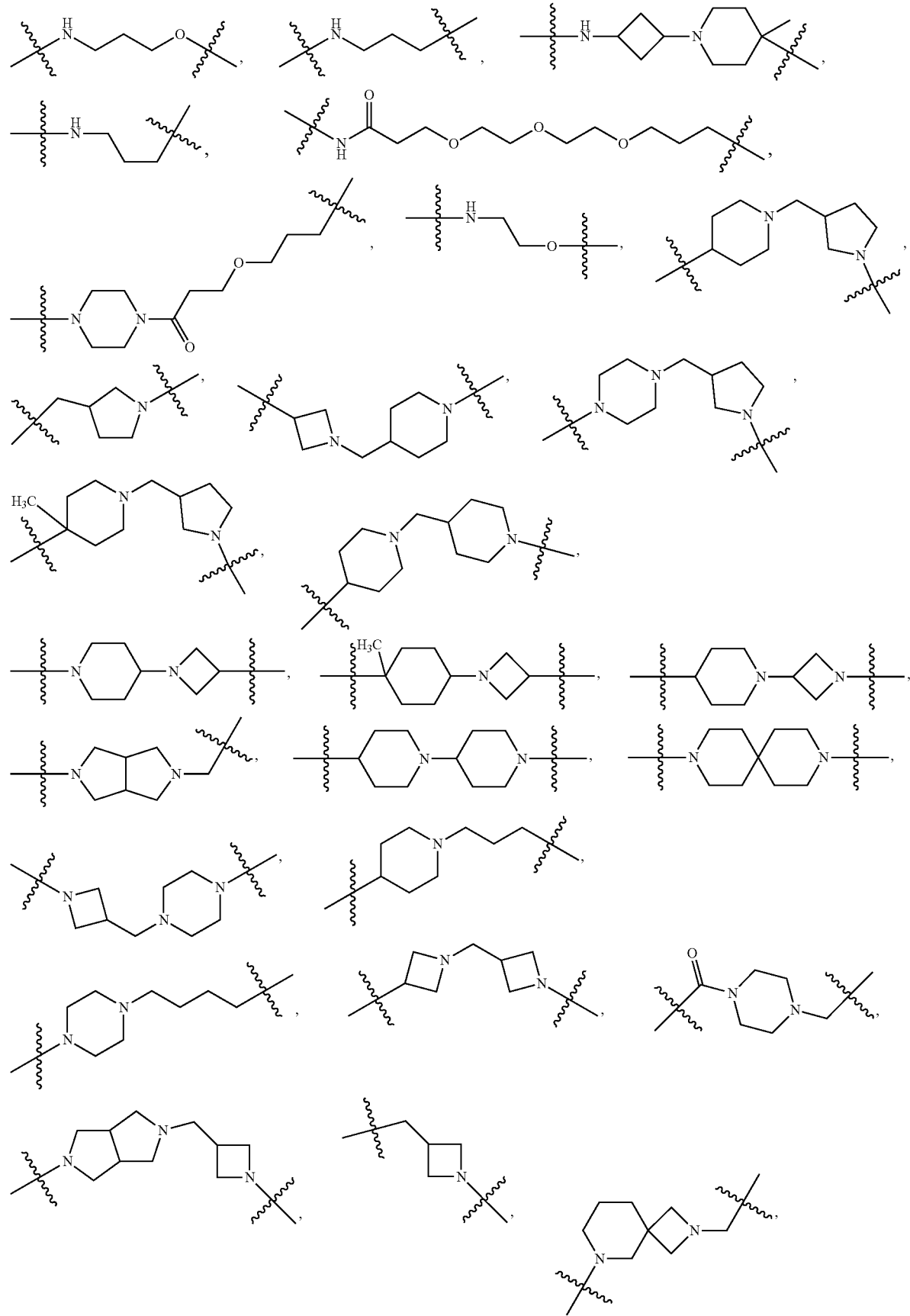

-continued
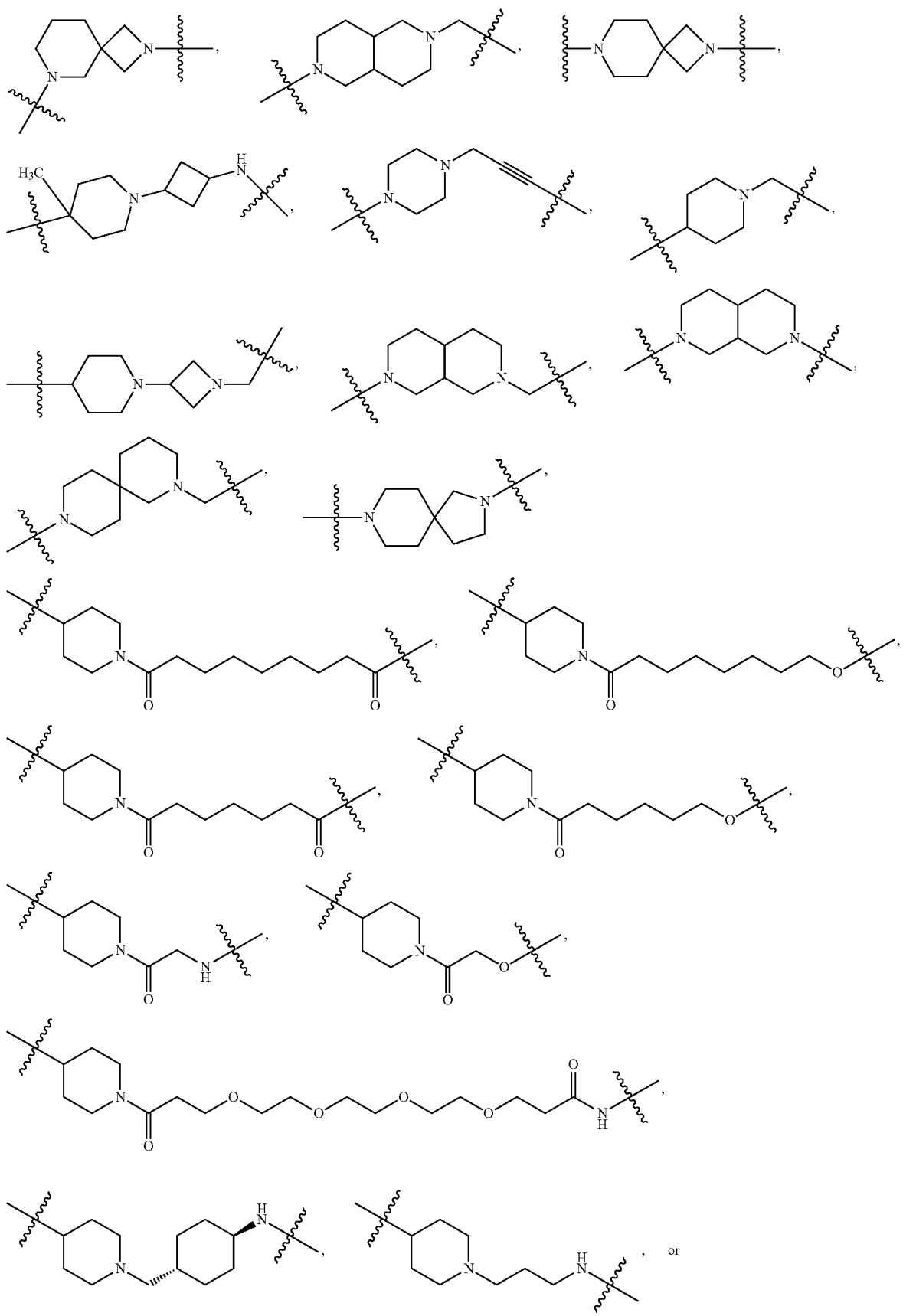

601
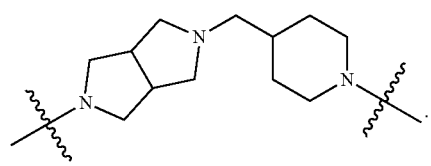
24. The compound or pharmaceutically acceptable salt of claim 1, wherein Y is
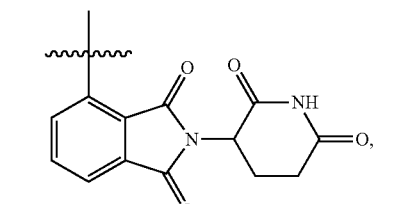
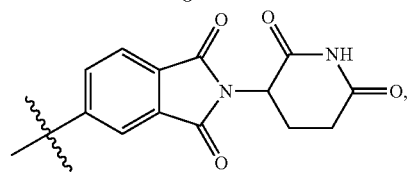
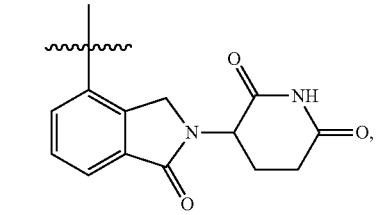
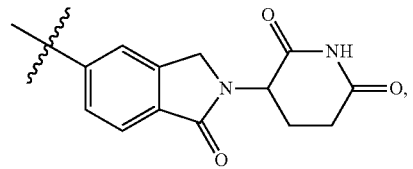
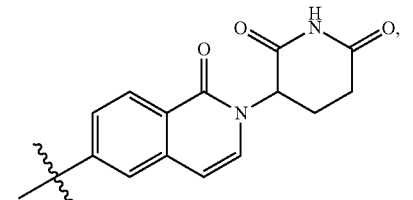
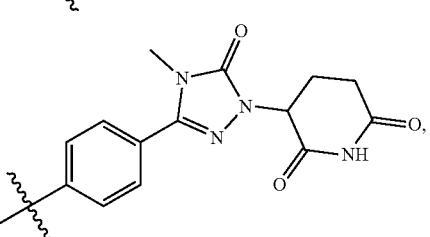
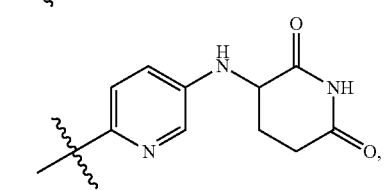
602
-continued
-continued
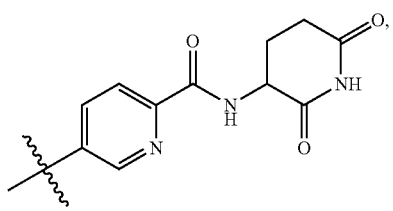
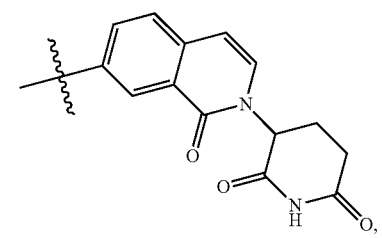
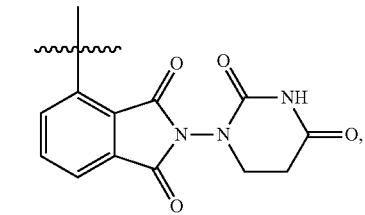
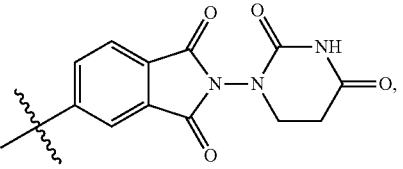
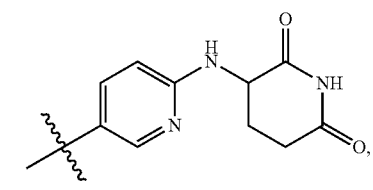
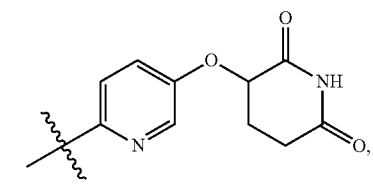
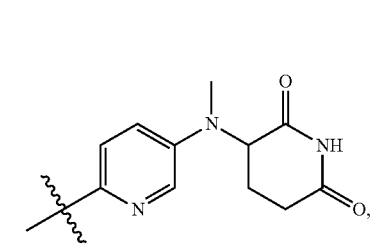

-continued

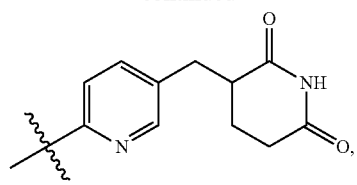

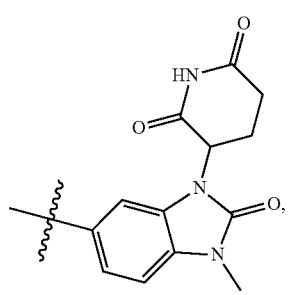

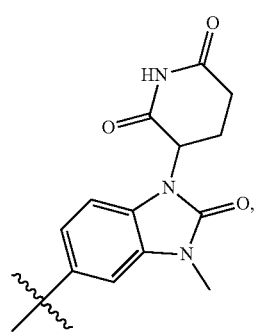

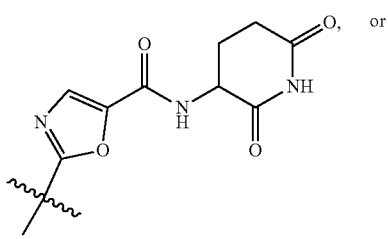

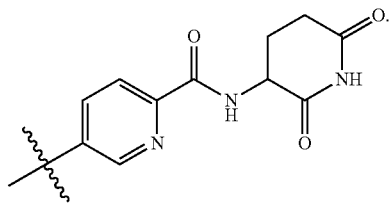

25. The compound or pharmaceutically acceptable salt of claim 1, wherein W is N.

26. The compound or pharmaceutically acceptable salt of claim 1, wherein D is a bond.

27. The compound or pharmaceutically acceptable salt of claim 1, wherein the compound of Formula (A) is a compound of Formula (B)

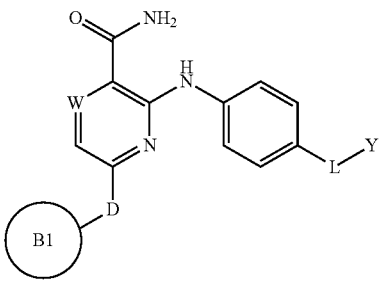

or a pharmaceutically acceptable salt thereof, wherein

W is CH or N;

D is a bond or —NH—;

Ring B1 is a 4-6 membered, fully saturated, partially unsaturated, or fully unsaturated monocyclic heterocycle or a 8-10 membered, fully saturated, spiro bicyclic heterocycle, wherein ring B1 has 1-3 heteroatoms independently selected from N, O, or S, and is optionally substituted with 1-3 groups selected from halo, —CH$_3$, —CF$_3$, —C(O)OH, —CH$_2$OH, or a 5 membered heterocycloalkyl optionally substituted with oxo and having 1-2 heteroatoms independently selected from N or O;

L is —X$^1$—X$^2$—X$^3$—;

X$^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of X$^1$ is optionally substituted with —CH$_3$;

X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S;

X$^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$;

each R is independently —H or —C$_{1-3}$ alkyl;

each of m, n, and p is independently an integer from 1 to 3; and

Y is

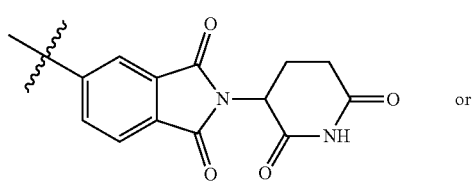 or

605

-continued

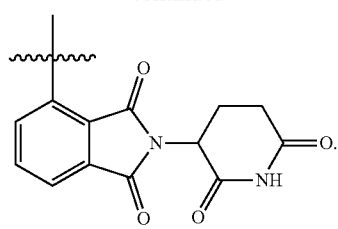

28. The compound or pharmaceutically acceptable salt of claim 27, wherein ring B1 is

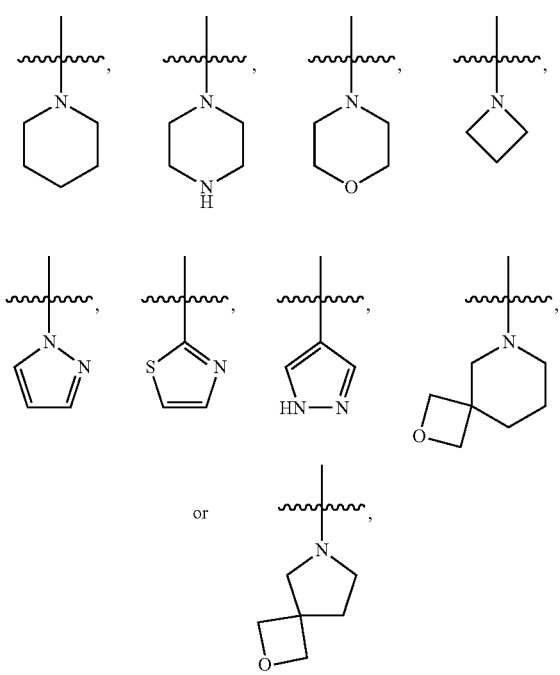

or and ring B1 is optionally substituted 1-3 groups selected from —CH$_3$, —CH$_2$OH, —C(O)OH, —CF$_3$, —F,

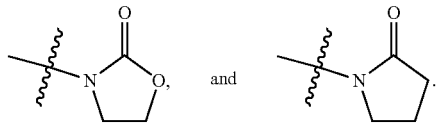 [SMILES: *N1CCOC1=O ; *N1CCCC1=O] and

29. The compound or pharmaceutically acceptable salt of claim 27, wherein ring B1 is

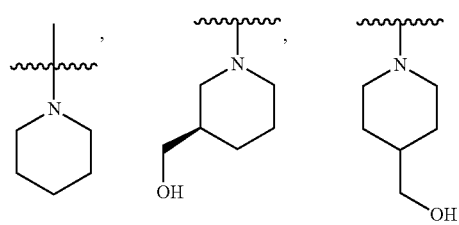

606

-continued

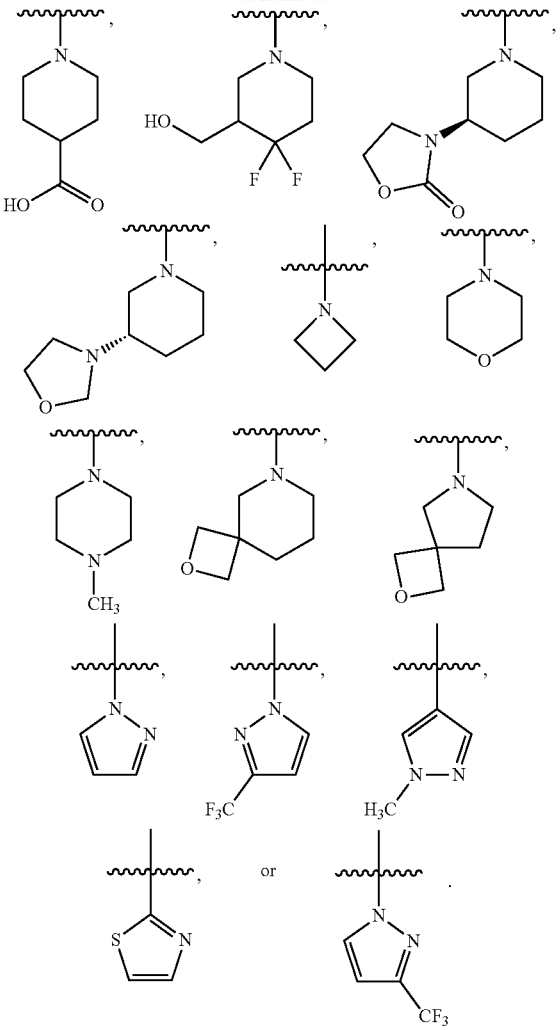

30. The compound or pharmaceutically acceptable salt of claim 27, wherein ring B1 is or 31. The compound or pharmaceutically acceptable salt of claim 27, wherein X$^1$ is

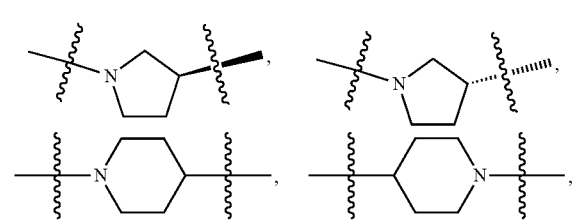

32. The compound or pharmaceutically acceptable salt of claim 27, wherein $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S.

33. The compound or pharmaceutically acceptable salt of claim 27, wherein $X^2$ is a bond, —$C_{1-3}$ alkyl-, —C(O)—,

34. The compound or pharmaceutically acceptable salt of claim 27, wherein $X^3$ is a bond, —$C_{1-4}$ alkyl-, —N(R)—, —(O—CH$_2$—CH$_2$)$_p$—, —(CH$_2$—CH$_2$—O)$_p$—, or a 4-6 membered heterocycloalkyl having 1-2 heteroatoms independently selected from N, O, or S wherein the heterocycloalkyl is optionally substituted with —CH$_3$.

35. The compound or pharmaceutically acceptable salt of claim 27, wherein $X^3$ is a bond,

36. The compound or pharmaceutically acceptable salt of claim 27, wherein L is

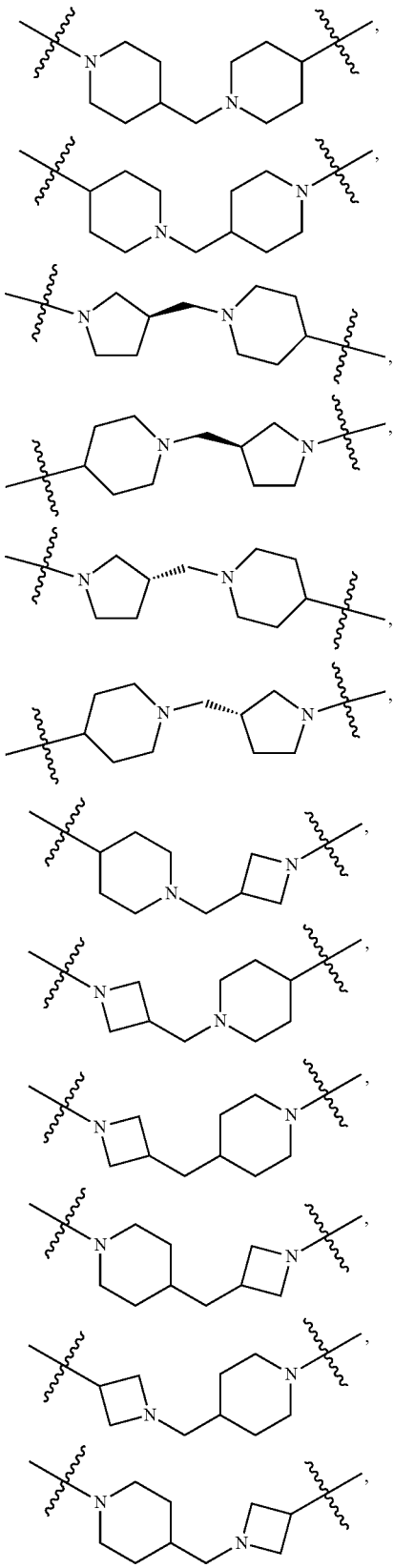

-continued

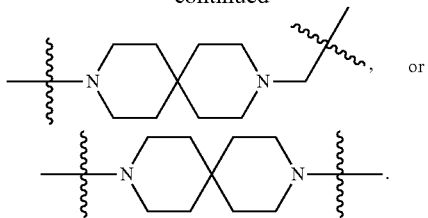

37. The compound or pharmaceutically acceptable salt of claim 27, wherein W is N and D is a bond.

38. The compound or pharmaceutically acceptable salt of claim 1, wherein the compound of Formula (A) is a compound of Formula (C)

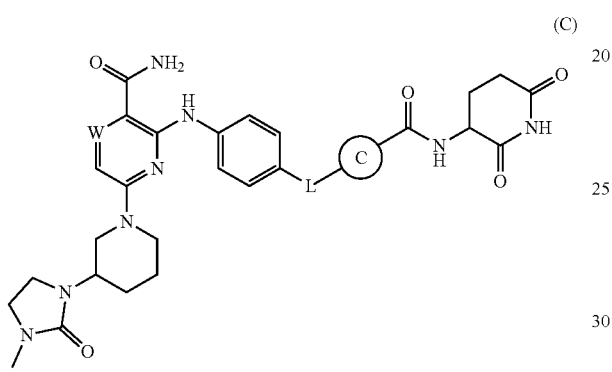

(C)

or a pharmaceutically acceptable salt thereof, wherein
W is CH or N;
Ring C is phenyl or a saturated, partially unsaturated, or fully unsaturated 5-6 membered monocyclic heterocycle having 1-2 heteroatoms independently selected from N, O, or S, wherein each of the phenyl and heterocycle of ring C is optionally substituted;
L is —$X^1$—$X^2$—$X^3$—;
$X^1$ is —C(O)—N(R)—, —N(R)—C(O)—, —(O—CH$_2$—CH$_2$)$_m$—, —O—(C$_6$H$_4$)—, —(O—CH$_2$—CH$_2$—CH$_2$)$_m$—, —C$_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the bicyclic heterocycloalkyl and the monocyclic heterocycloalkyl of $X^1$ is optionally substituted with —CH$_3$;
$X^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S;
$X^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$;
each R is independently —H or —C$_{1-3}$ alkyl; and
each of m, n, and p is independently an integer from 1 to 3.

39. The compound or pharmaceutically acceptable salt of claim 38, wherein ring C is

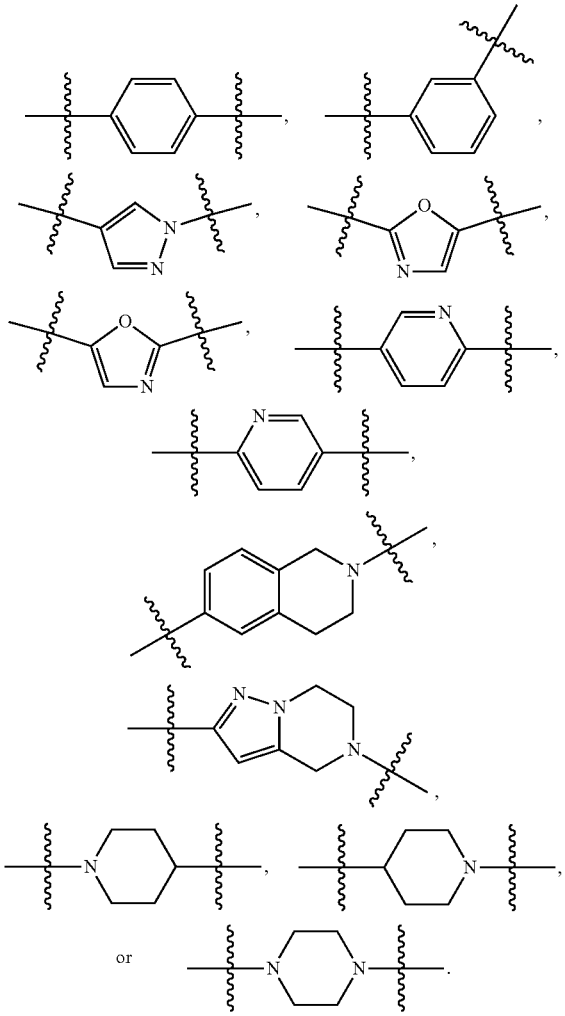

40. The compound or pharmaceutically acceptable salt of claim 38, wherein ring C is

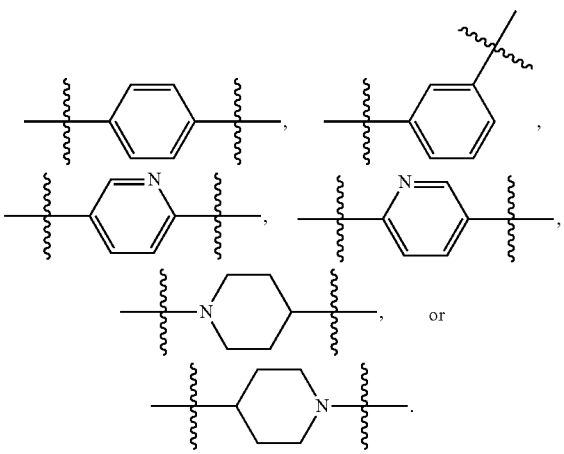

41. The compound or pharmaceutically acceptable salt of claim 38, wherein $X^1$ is a 4-6 membered monocyclic heterocycloalkyl having 1-2 heteroatoms independently selected from N, O, or S.

42. The compound or pharmaceutically acceptable salt of claim 38, wherein $X^1$ is

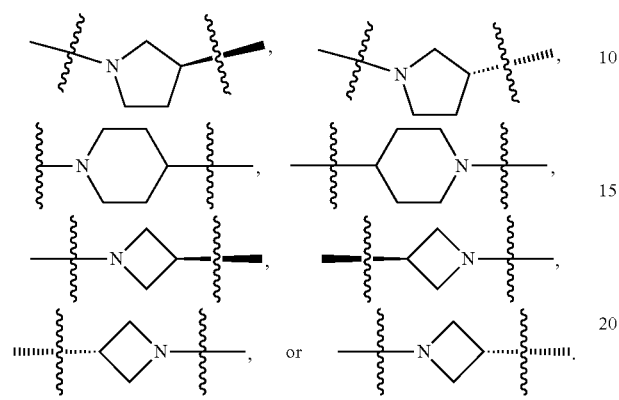

43. The compound or pharmaceutically acceptable salt of claim 38, wherein $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S.

44. The compound or pharmaceutically acceptable salt of claim 38, wherein $X^2$ is a bond or —$C_{1-3}$ alkyl-.

45. The compound or pharmaceutically acceptable salt of claim 38, wherein $X^3$ is a 4-6 membered cycloalkyl, —N(R)—, or a 4-6 membered heterocycloalkyl having 1-2 heteroatoms independently selected from N, O, or S wherein the heterocycloalkyl is optionally substituted with —$CH_3$.

46. The compound or pharmaceutically acceptable salt of claim 38, wherein $X^3$ is

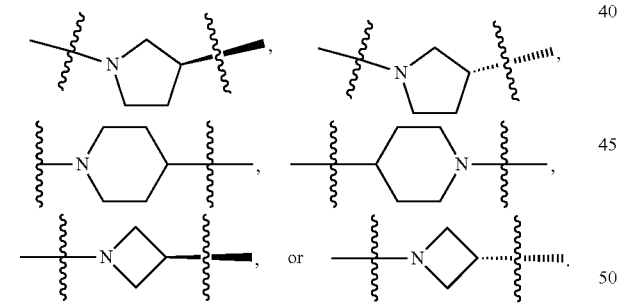

47. The compound or pharmaceutically acceptable salt of claim 38, wherein L is

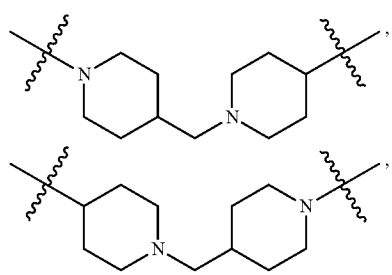

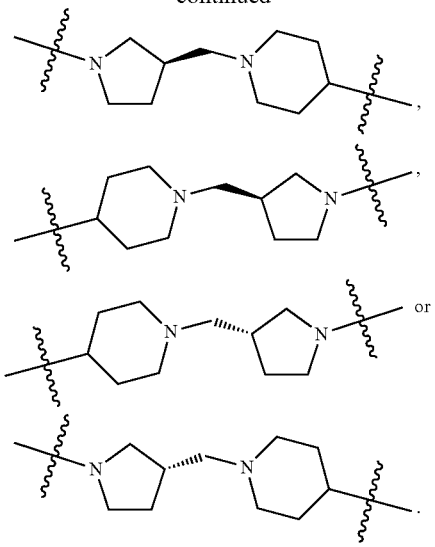

48. The compound or pharmaceutically acceptable salt of claim 1, wherein the compound of Formula (A) is a compound of Formula (D)

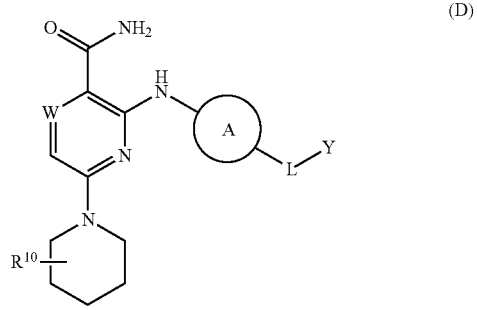

or a pharmaceutically acceptable salt thereof, wherein
W is CH or N;
Ring A is

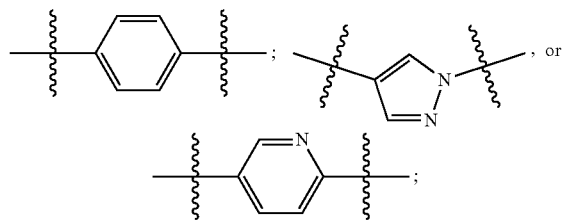

L is —$X^1$—$X^2$—$X^3$—;
 $X^1$ is —$C_{1-5}$ alkyl- or 4-6 membered monocyclic heterocycloalkyl having 1-2 heteroatoms independently selected from N, O, or S wherein the monocyclic heterocycloalkyl of $X^1$ is optionally substituted with —$CH_3$;
 $X^2$ is a bond, —$C_{1-5}$ alkyl-, or 4-6 membered monocyclic heterocycloalkyl having 1-2 heteroatoms independently selected from N, O, or S wherein the monocyclic heterocycloalkyl of $X^1$ is optionally substituted with —$CH_3$;

X³ is a bond, —C₁₋₄ alkyl-, 4-6 membered monocyclic cycloalkyl, or 4-6 membered heterocycloalkyl having 1-2 heteroatoms independently selected from N, O, or S wherein the heterocycloalkyl is optionally substituted with —CH₃;

Y is

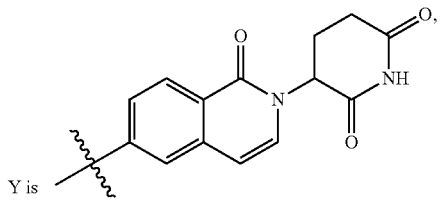

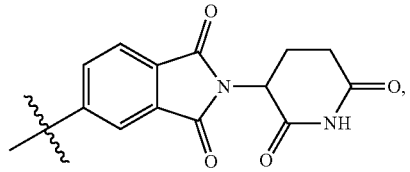

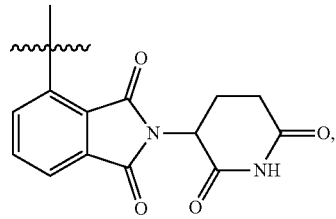

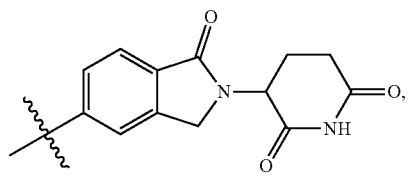

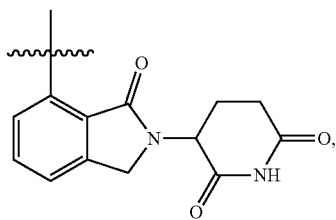

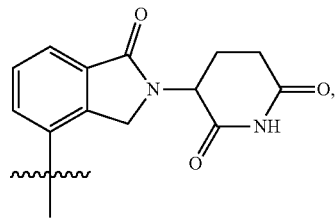

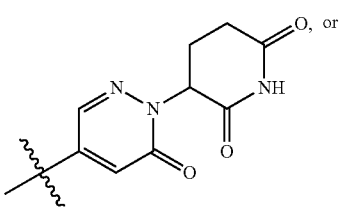

-continued

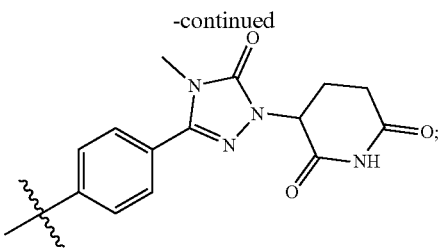

and
R¹⁰ is halo, —C₁₋₅ alkyl, -3-6 membered cycloalkyl, 5-6 membered heterocycloalkyl, —CN, —OH, —CF₃, —C(O)OH, —CH₂OH, —CH₂CH₂OH,

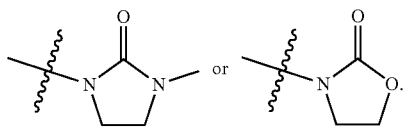

49. The compound or pharmaceutically acceptable salt of claim 1, wherein the compound of Formula (D) is a compound of Formula (D-1)

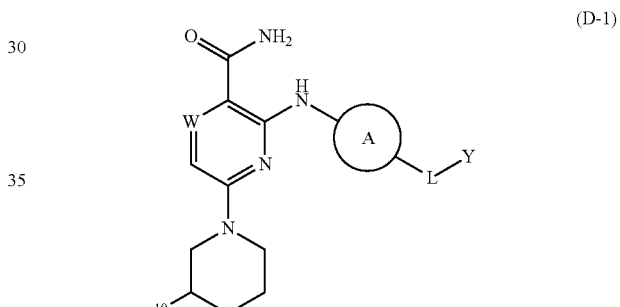

(D-1)

or a pharmaceutically acceptable salt thereof, wherein
W is CH or N;
Ring A is

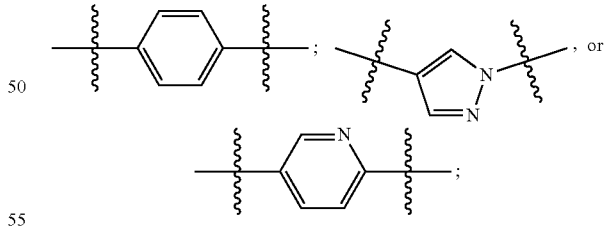

L is —X¹—X²—X³—;
X¹ is —C₁₋₅ alkyl- or 4-6 membered monocyclic heterocycloalkyl having 1-2 heteroatoms independently selected from N, O, or S wherein the monocyclic heterocycloalkyl of X¹ is optionally substituted with —CH₃;
X² is a bond, —C₁₋₅ alkyl-, or 4-6 membered monocyclic heterocycloalkyl having 1-2 heteroatoms independently selected from N, O, or S wherein the monocyclic heterocycloalkyl of X¹ is optionally substituted with —CH₃;

$X^3$ is a bond, —$C_{1-4}$ alkyl-, 4-6 membered monocyclic cycloalkyl, or 4-6 membered heterocycloalkyl having 1-2 heteroatoms independently selected from N, O, or S wherein the heterocycloalkyl is optionally substituted with —$CH_3$;

Y is 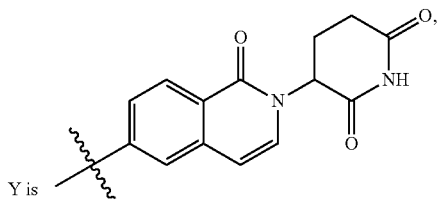

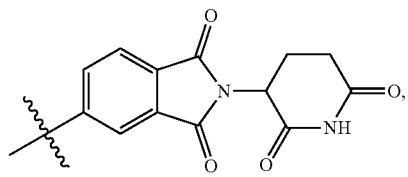

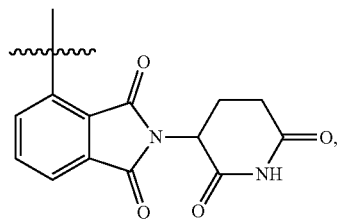

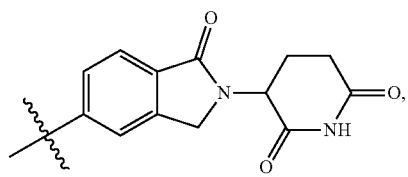

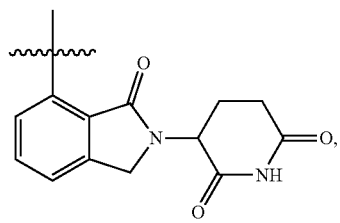

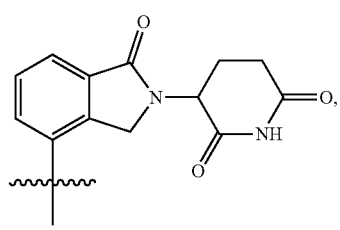

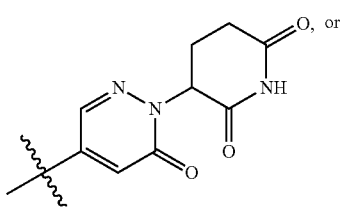

-continued

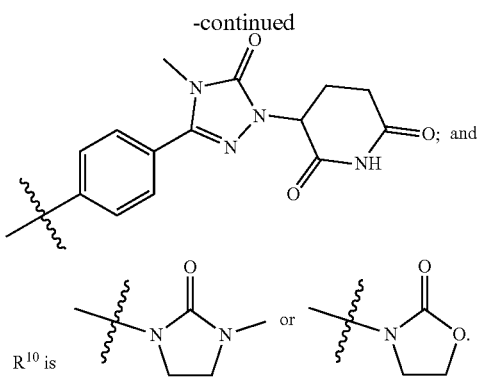

$R^{10}$ is 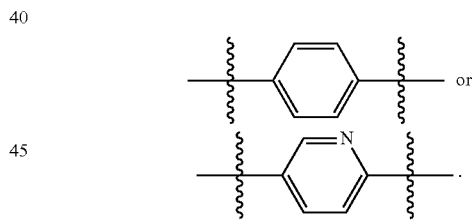

50. The compound or pharmaceutically acceptable salt of claim 48, wherein the compound of Formula (D) is a compound of Formula (D-2):

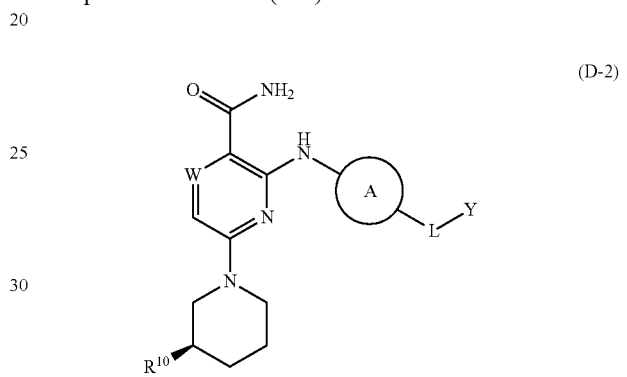

(D-2)

or a pharmaceutically acceptable salt thereof.

51. The compound or pharmaceutically acceptable salt of claim 48, wherein ring A is or

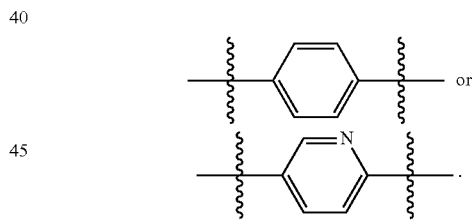

52. The compound or pharmaceutically acceptable salt of claim 48, wherein $X^1$ is a 4-6 membered monocyclic heterocycloalkyl having 1-2 heteroatoms independently selected from N, O, or S wherein the monocyclic heterocycloalkyl of $X^1$ is optionally substituted with —$CH_3$.

53. The compound or pharmaceutically acceptable salt of claim 48, wherein $X^1$ is

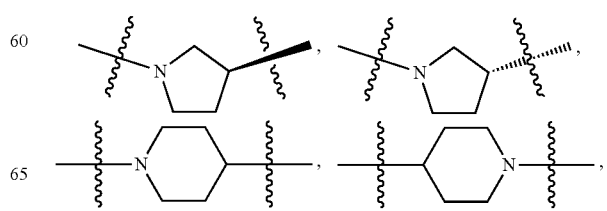

-continued

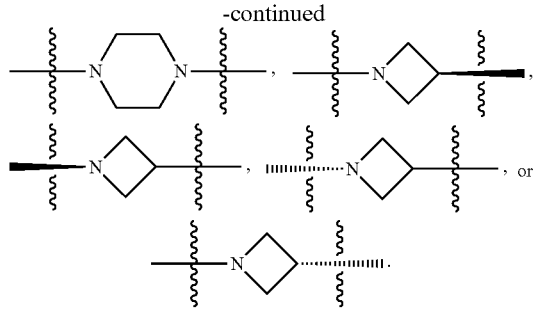

54. The compound or pharmaceutically acceptable salt of claim 48, wherein $X^2$ is a bond, —$C_{1-5}$ alkyl-, 4-6 membered monocyclic cycloalkyl, or 4-6 membered monocyclic heterocycloalkyl having 1-2 heteroatoms independently selected from N, O, or S.

55. The compound or pharmaceutically acceptable salt of claim 48, wherein $X^2$ is a bond or —$C_{1-4}$ alkyl-.

56. The compound or pharmaceutically acceptable salt of claim 48, wherein $X^3$ is a bond, a 4-6 membered monocyclic cycloalkyl, or 4-6 membered monocyclic heterocycloalkyl having 1-2 heteroatoms independently selected from N, O, or S.

57. The compound or pharmaceutically acceptable salt of claim 48, wherein $X^3$ is

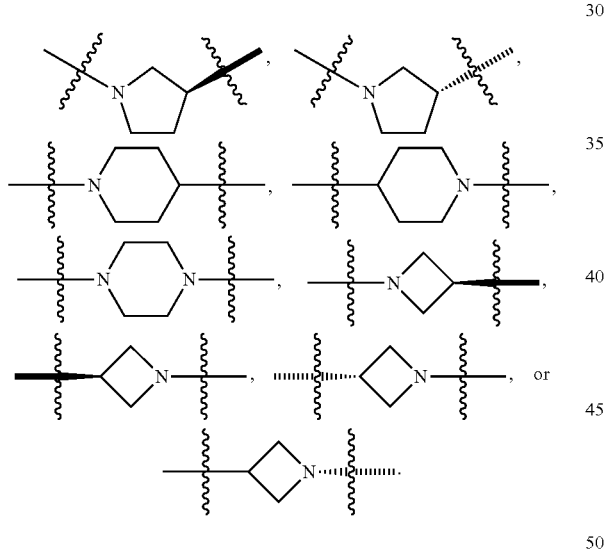

58. The compound or pharmaceutically acceptable salt of claim 48, wherein L is

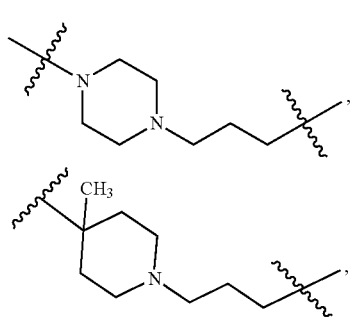

-continued

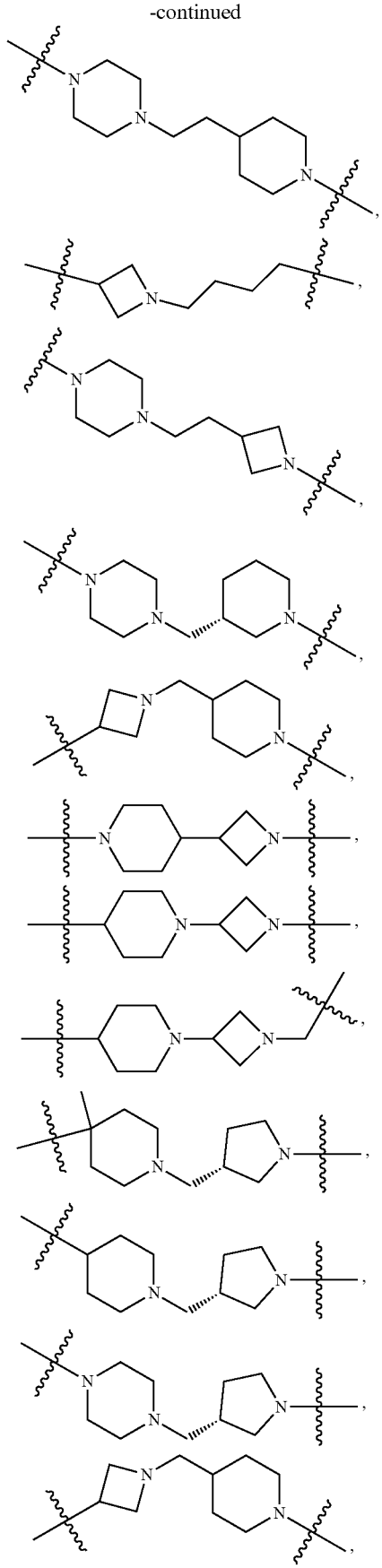

-continued

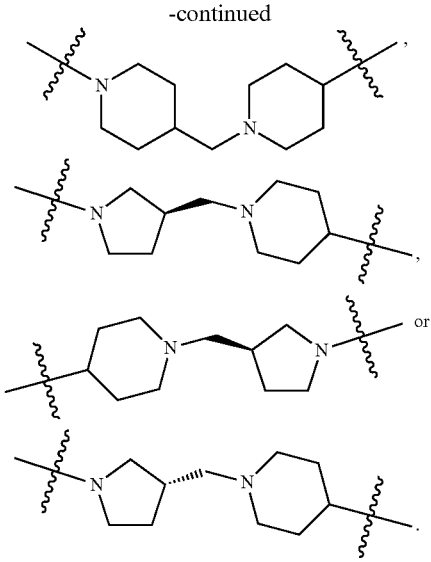

59. The compound or pharmaceutically acceptable salt of claim 48, wherein $R^{10}$ is

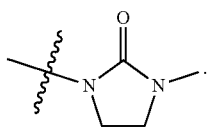 [SMILES: *N1CCN(C)C1=O]

60. The compound or pharmaceutically acceptable salt of claim 48, wherein $R^{10}$ is

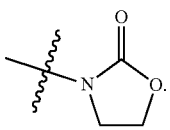 [SMILES: *N1CCOC1=O]

61. The compound or pharmaceutically acceptable salt of claim 1, wherein the compound of Formula (A) is a compound of Formula (E)

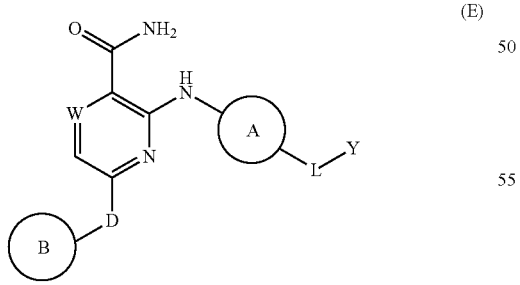

(E)

or a pharmaceutically acceptable salt thereof, wherein
D is a bond or —NH—;
W is N or CH;
Ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of ring A each possess 1-3 heteroatoms independently selected from N, O, or S;
Ring B is an optionally substituted 5-6 membered saturated, partially unsaturated, or fully unsaturated monocyclic heterocycle, or an optionally substituted 8-10 membered spiro bicyclic heterocycle, wherein ring B has 1-3 heteroatoms independently selected from N, O, or S;
L is —$X^1$—$X^2$—$X^3$—$X^4$—$X^5$—;
$X^1$ is a bond, —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$, —C$_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —CH$_3$;
$X^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having 1-2 heteroatoms independently selected from N, O, or S;
$X^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having 1-2 heteroatoms independently selected from N, O, or S wherein the heterocycloalkyl is optionally substituted with —CH$_3$;
$X^4$ is a bond, —CH$_2$—CH$_2$—N(R)—, —N(R)—, —C$_{1-4}$ alkyl-, —(O—CH$_2$—CH$_2$—CH$_2$)$_m$—, a 5-6 membered saturated, partially unsaturated, or fully unsaturated carbocycle, or a 5-6 membered saturated, partially unsaturated, or fully unsaturated heterocycle having 1-3 heteroatoms independently selected from N, O, or S;
$X^5$ is a bond, —N(R)—, or —C(O)—N(R)—;
each R is independently —H or —C$_{1-3}$ alkyl;
each of m, n, and p is independently an integer from 1 to 3; and Y is

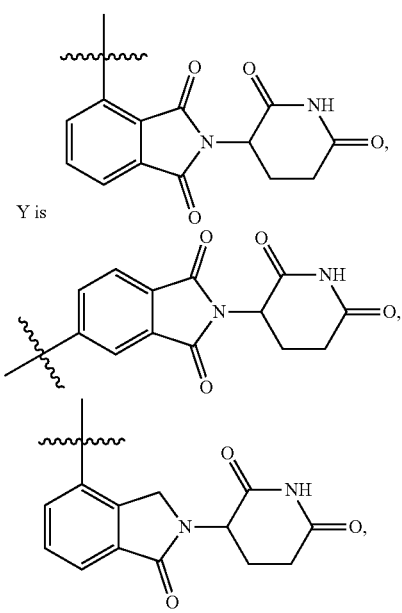

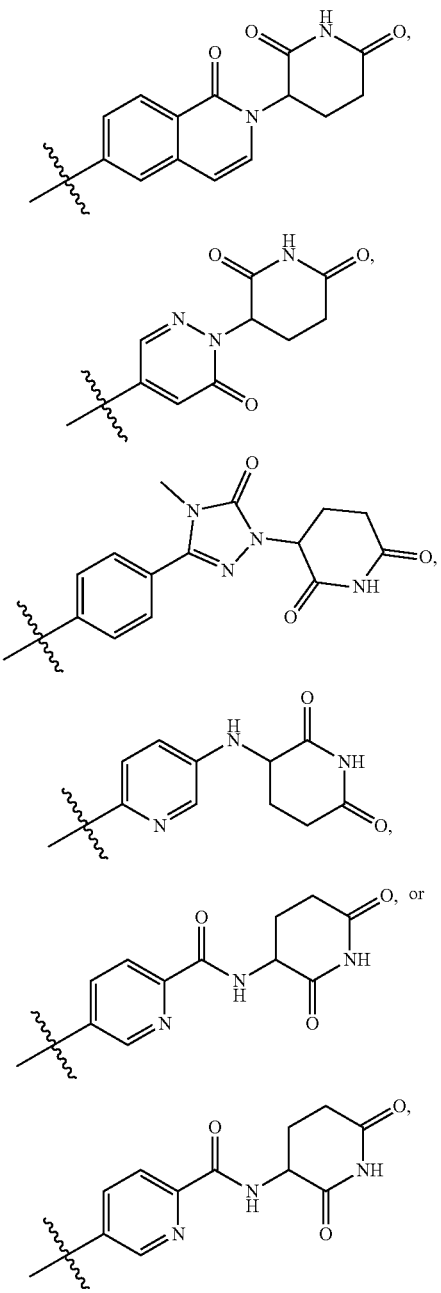
wherein at least one of $X^1$, $X^2$, $X^3$, $X^4$, and $X^5$ has a nitrogen atom, and Y is directly bonded to L at a nitrogen atom of $X^1$, $X^2$, $X^3$, $X^4$, or $X^5$.
62. The compound or pharmaceutically acceptable salt of claim 61, wherein ring B is
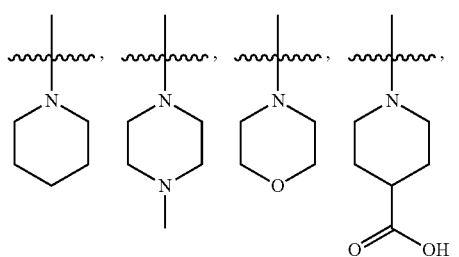
and wherein $R^1$ is a $C_{1-4}$ alkyl group.

63. The compound or pharmaceutically acceptable salt of claim 61, wherein ring B is

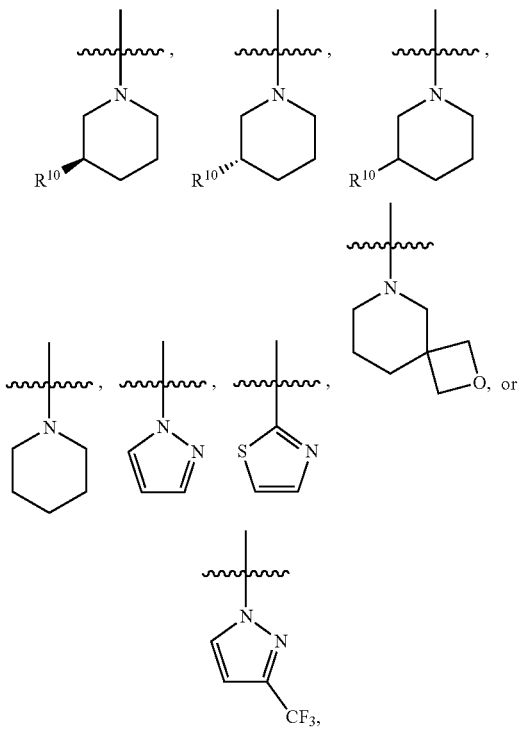

wherein $R^{10}$ is

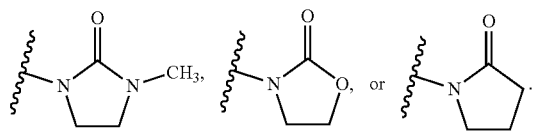 [SMILES: *N1CCN(C)C1=O ; *N1CCOC1=O ; *N1CCCC1=O]

64. The compound or pharmaceutically acceptable salt of claim 61, wherein ring B is

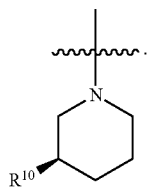

65. The compound or pharmaceutically acceptable salt of claim 61, wherein $R^{10}$ is

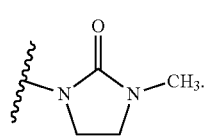

66. The compound or pharmaceutically acceptable salt of claim 61, wherein ring A is

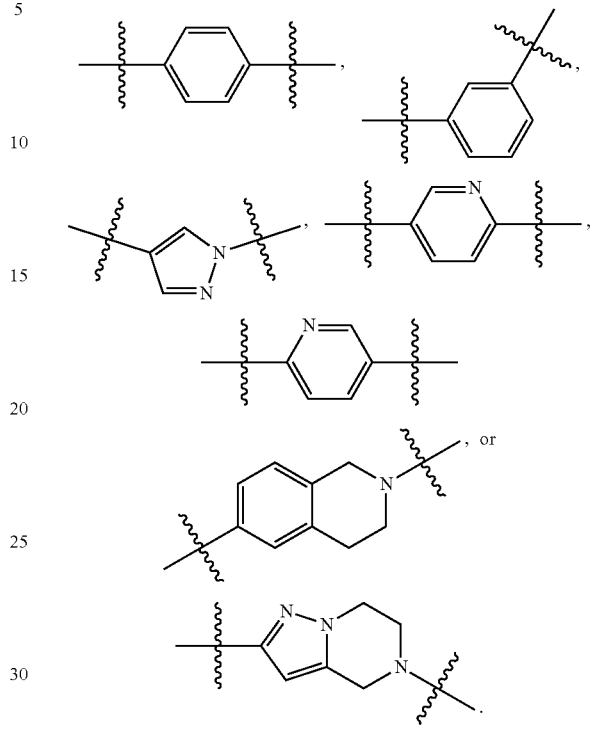

67. The compound or pharmaceutically acceptable salt of claim 61, wherein $X^5$ is —N(R)—.

68. The compound or pharmaceutically acceptable salt of claim 61, wherein $X^5$ is —C(O)—N(R)—.

69. The compound or pharmaceutically acceptable salt of claim 61, wherein $X^5$ is a bond.

70. The compound or pharmaceutically acceptable salt of claim 61, wherein L is

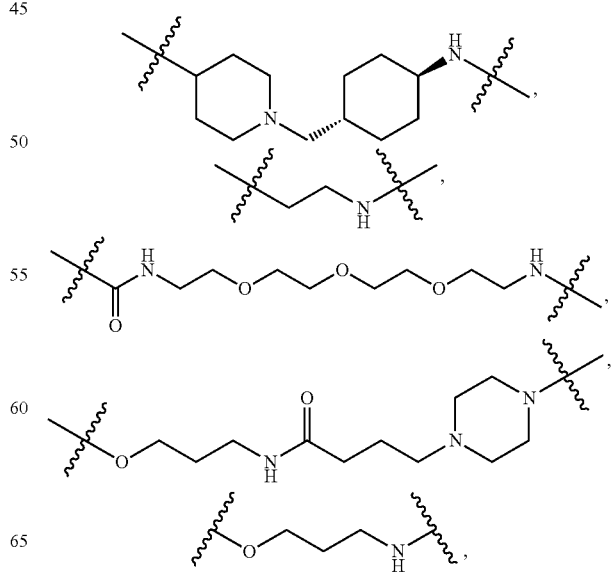

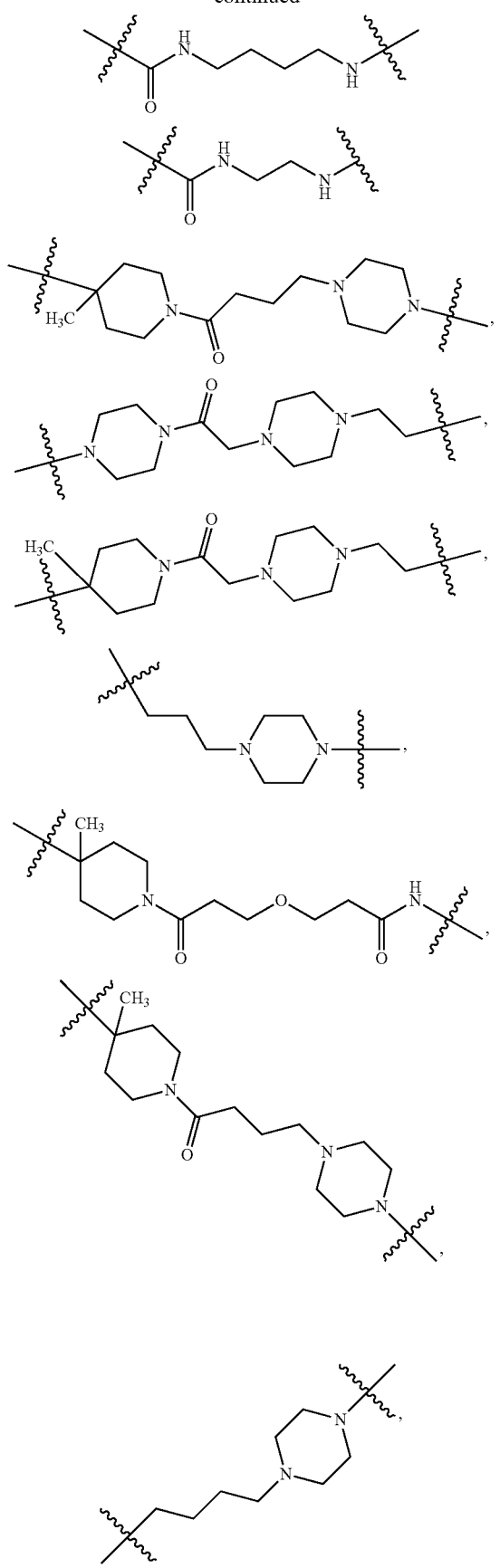
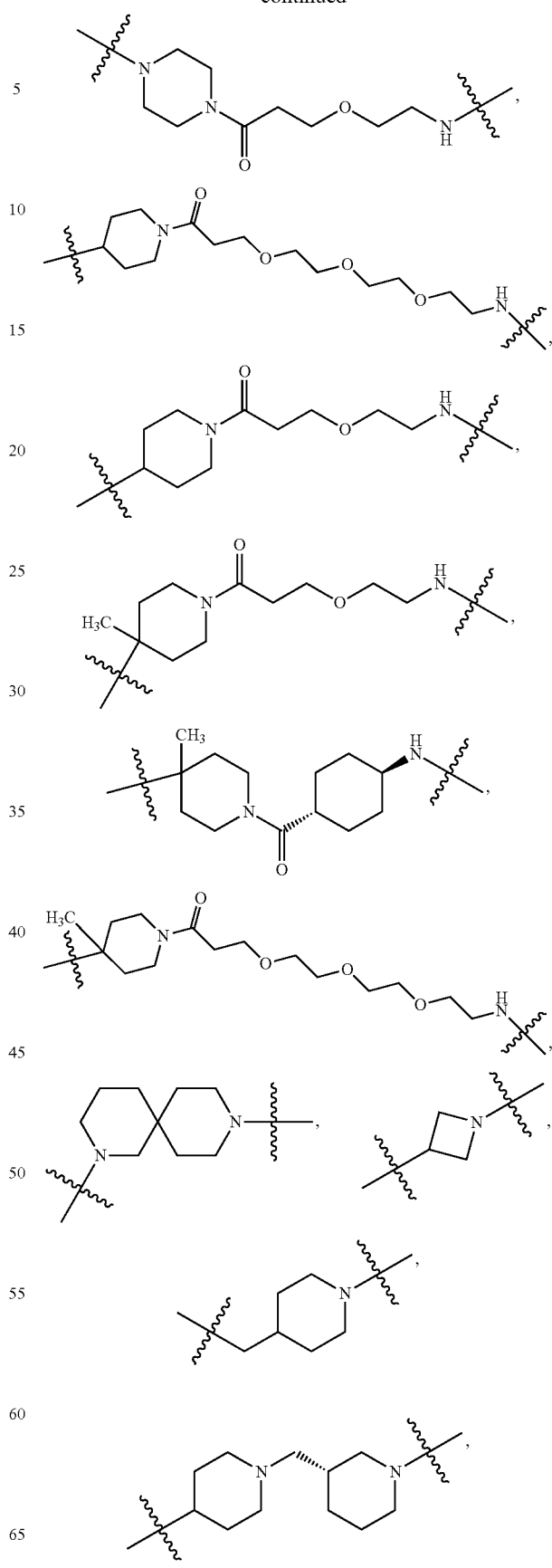

627
-continued
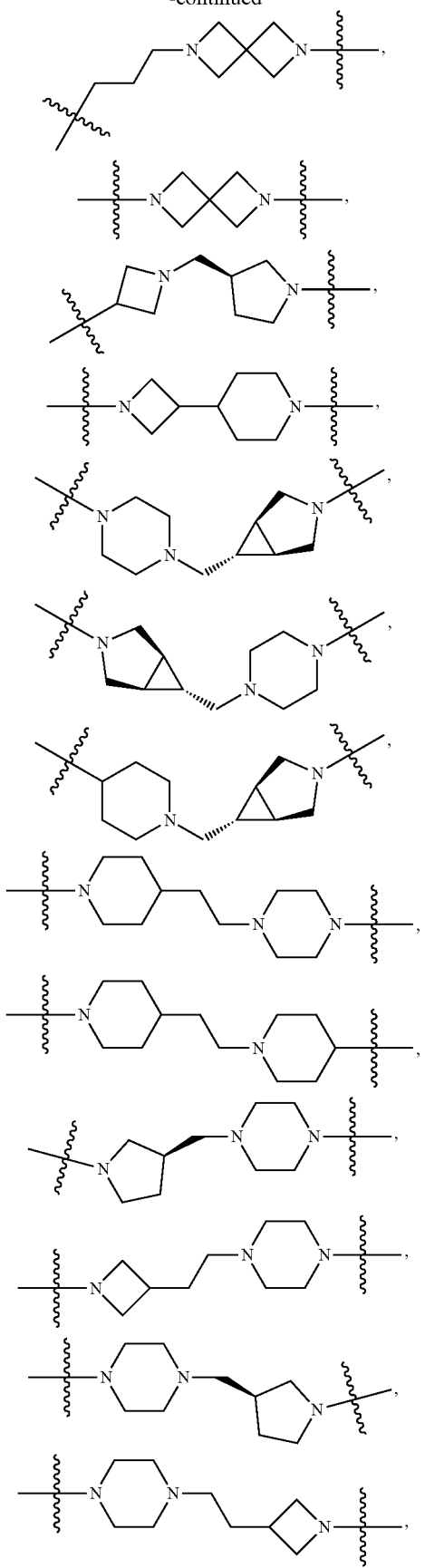
628
-continued
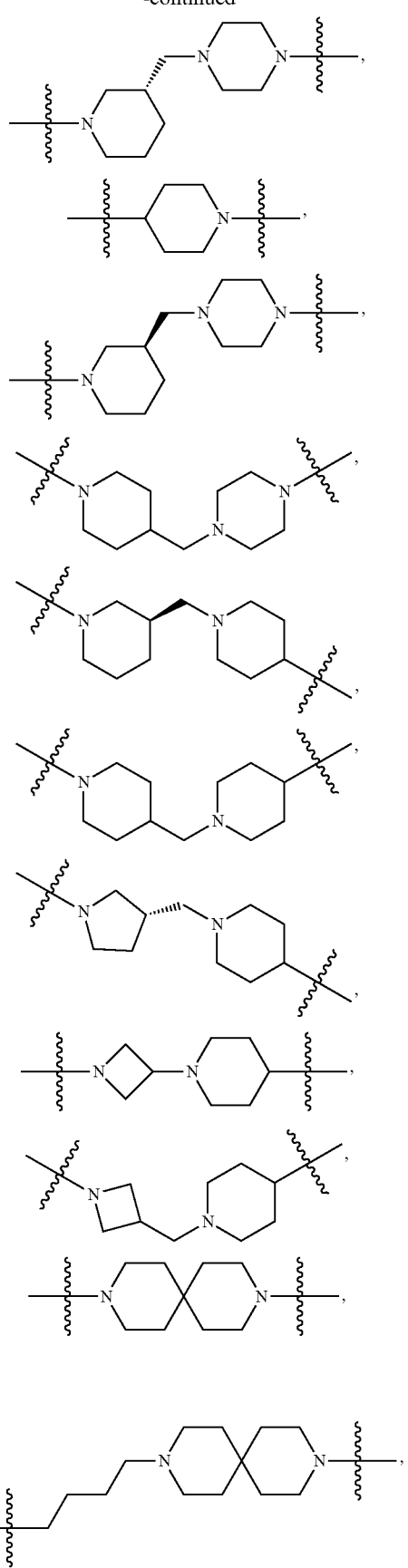

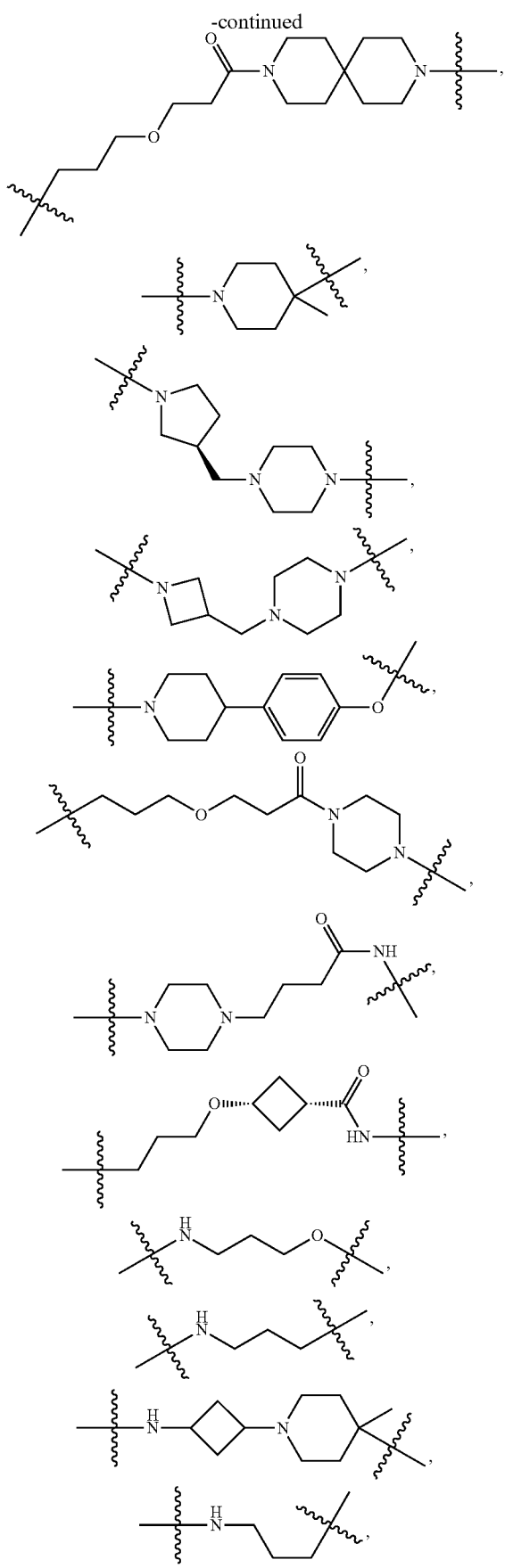
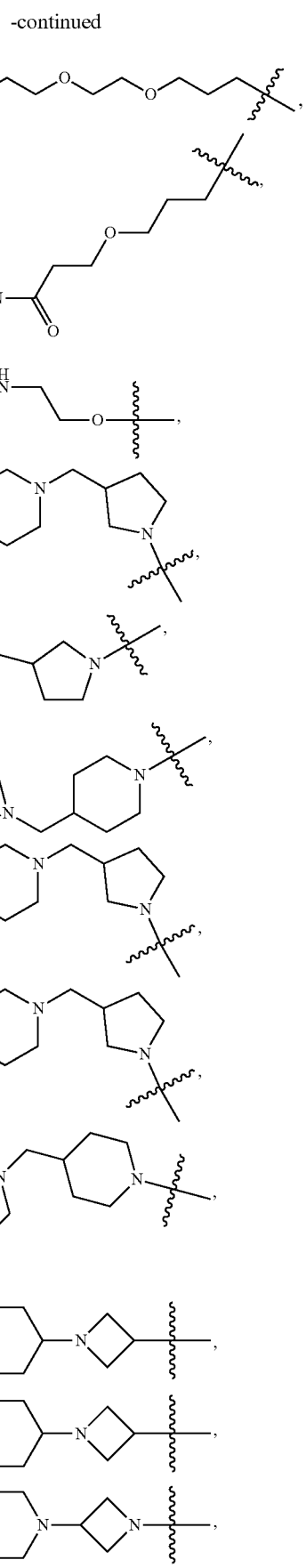

631
-continued
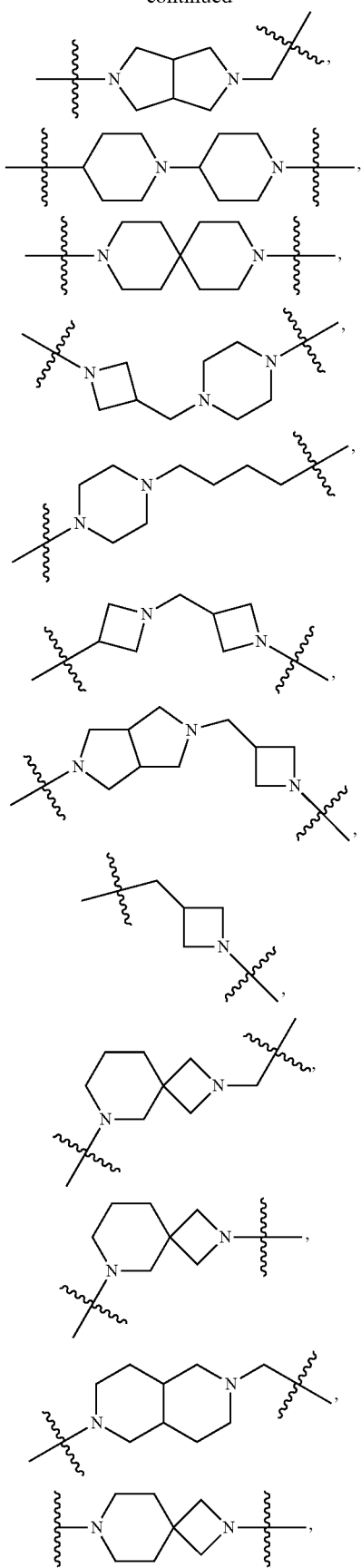
632
-continued
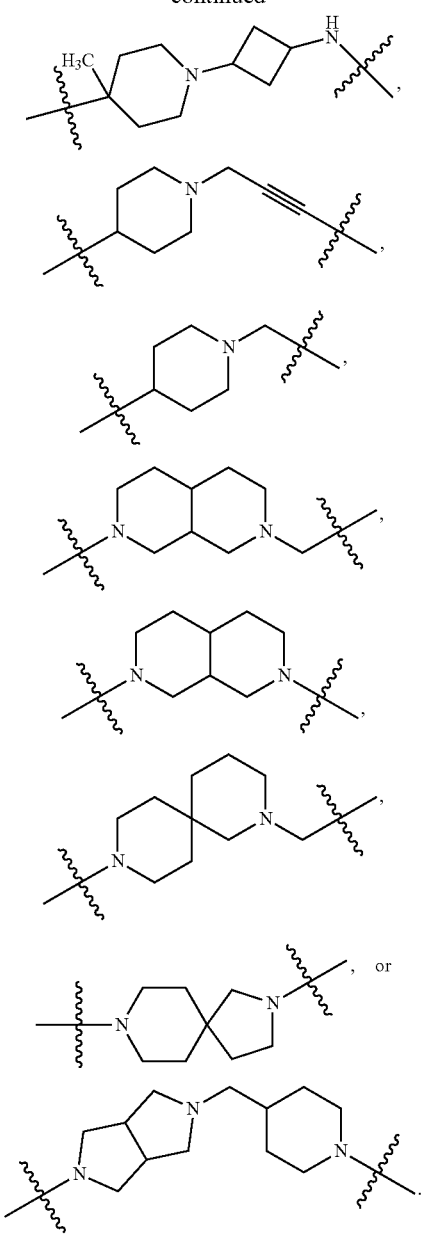
71. The compound or pharmaceutically acceptable salt of claim 61, wherein Y is
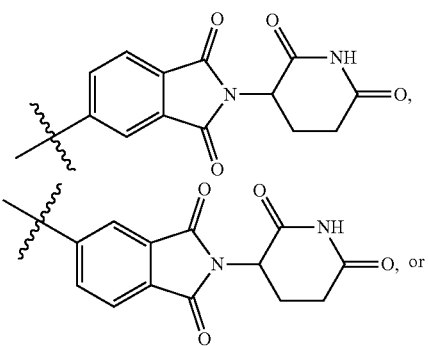

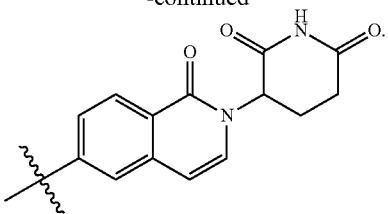

72. The compound or pharmaceutically acceptable salt of claim 1, wherein the compound of Formula (A) is a compound of Formula (F)

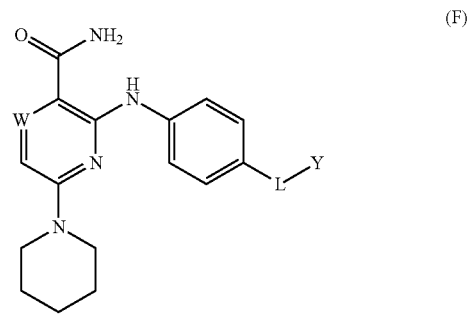

(F)

or a pharmaceutically acceptable salt thereof, wherein
W is CH or N;
L is —$X^1$—$X^2$—$X^3$—;
$X^1$ is —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having 1-3 heteroatoms independently selected from N, O, or S, or 4-6 membered monocyclic heterocycloalkyl having 1-2 heteroatoms independently selected from N, O, or S, wherein each of the monocyclic and bicyclic heterocycloalkyl of $X^1$ is optionally substituted with —$CH_3$;
$X^2$ is a bond, —$C_{1-5}$ alkyl-, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having 1-2 heteroatoms independently selected from N, O, or S;
$X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having 1-2 heteroatoms independently selected from N, O, or S wherein the heterocycloalkyl is optionally substituted with —$CH_3$;
each R is independently —H or —$C_{1-3}$ alkyl;
each of m, n, and p is independently an integer from 1 to 3; and
Y is

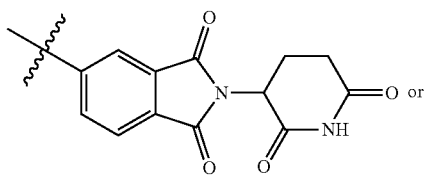

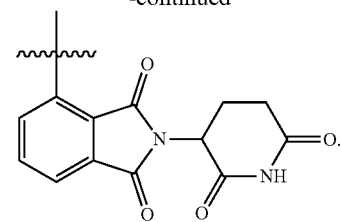

73. The compound or pharmaceutically acceptable salt of claim 72, wherein W is N.
74. The compound or pharmaceutically acceptable salt of claim 72, wherein Y is

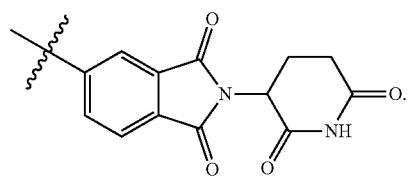 [SMILES: *c1ccc2c(c1)C(=O)N(C1CCC(=O)NC1=O)C2=O]

75. The compound or pharmaceutically acceptable salt of claim 72, wherein $X^1$ is a 4-6 membered monocyclic heterocycloalkyl having 1-2 heteroatoms independently selected from N, O, or S, wherein each of the monocyclic heterocycloalkyl of $X^1$ is optionally substituted with —$CH_3$.
76. The compound or pharmaceutically acceptable salt of claim 72, wherein $X^1$ is

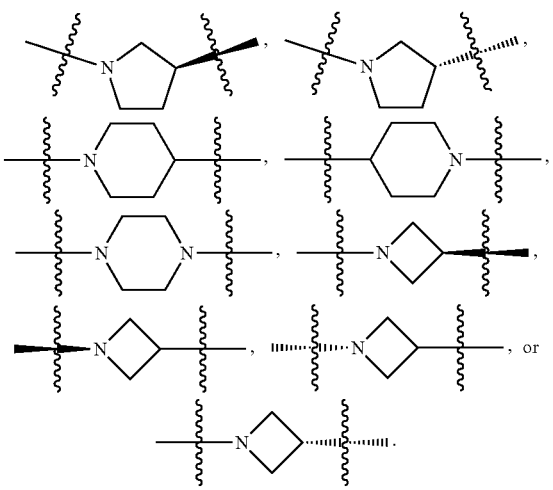

77. The compound or pharmaceutically acceptable salt of claim 72, wherein $X^1$ is

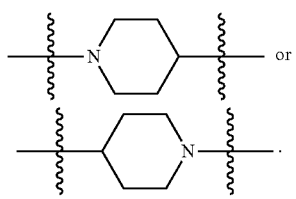

78. The compound or pharmaceutically acceptable salt of claim 72, wherein $X^2$ is a bond or —$C_{1-5}$ alkyl-.

79. The compound or pharmaceutically acceptable salt of claim 72, wherein X³ is a 4-6 membered monocyclic heterocycloalkyl having 1-2 heteroatoms independently selected from N, O, or S.

80. The compound or pharmaceutically acceptable salt of claim 72, wherein X³ is

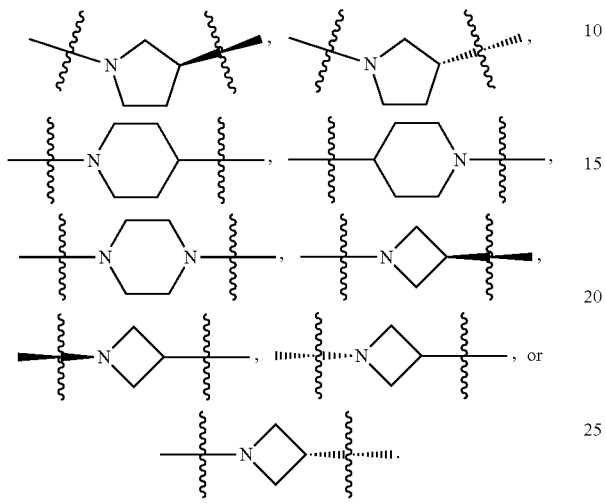

81. The compound or pharmaceutically acceptable salt of claim 72, wherein X³ is or

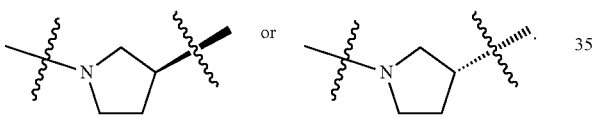

82. The compound or pharmaceutically acceptable salt of claim 72, wherein L is

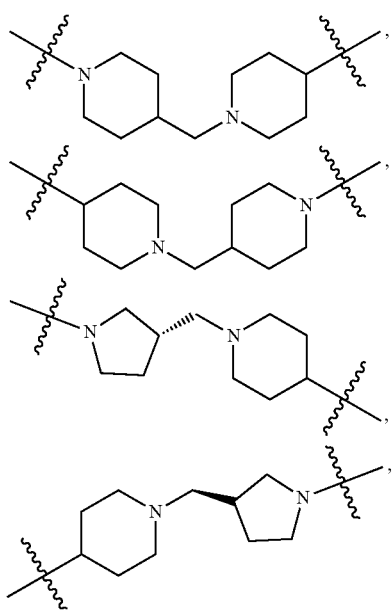

-continued

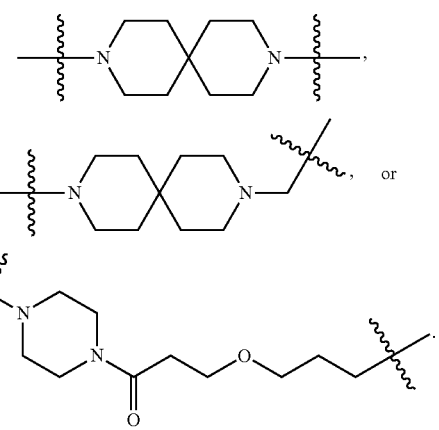

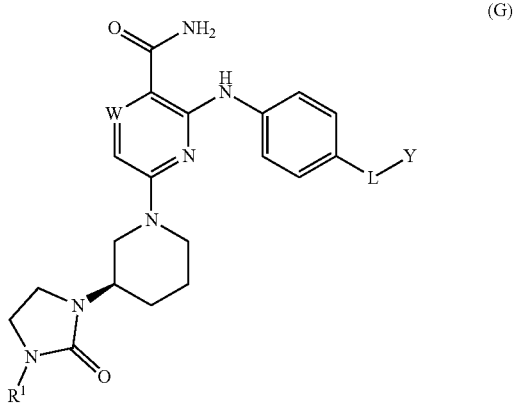

83. The compound or pharmaceutically acceptable salt of claim 1, wherein the compound of Formula (A) is a compound of Formula (G)

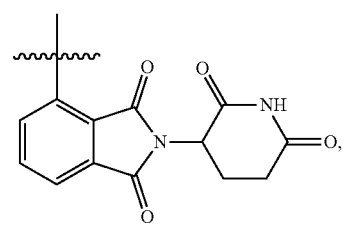

(G)

or a pharmaceutically acceptable salt thereof.

84. The compound or pharmaceutically acceptable salt of claim 83, wherein R¹ is methyl.

85. The compound or pharmaceutically acceptable salt of claim 83, wherein Y is

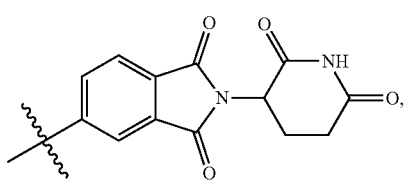

-continued

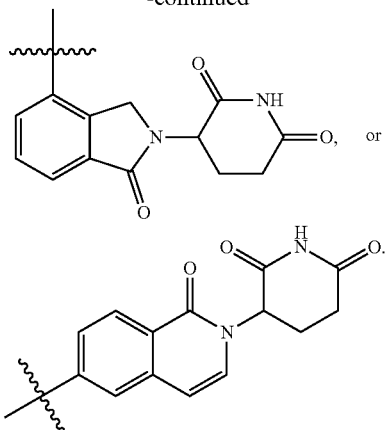

O, or

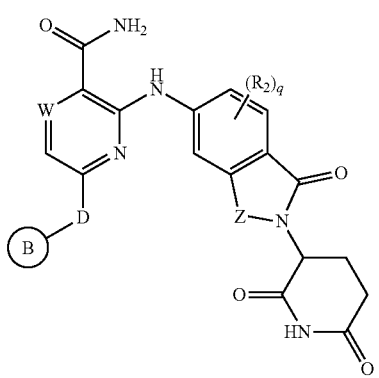

86. The compound or pharmaceutically acceptable salt of claim 83, wherein W is N.

87. The compound or pharmaceutically acceptable salt of claim 1, wherein the compound of Formula (A) is a compound of Formula (H)

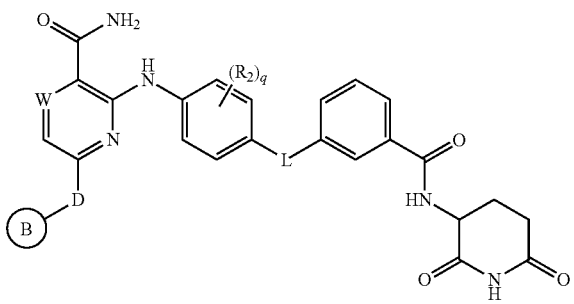
(H)

or a pharmaceutically acceptable salt thereof.

88. The compound or pharmaceutically acceptable salt of claim 1, wherein q is 0.

89. The compound or pharmaceutically acceptable salt of claim 1, wherein the compound of Formula (A) is a compound of Formula (J)

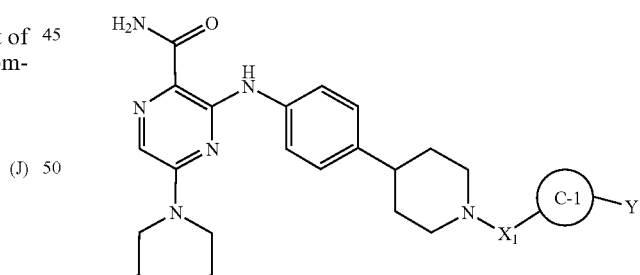
(J)

or a pharmaceutically acceptable salt thereof.

90. The compound or pharmaceutically acceptable salt of claim 1, wherein the compound of Formula (A) is a compound of Formula (K)

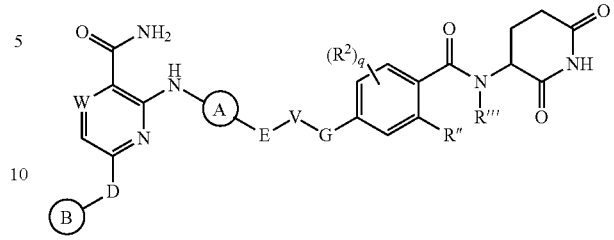
(K)

or a pharmaceutically acceptable salt thereof, wherein

Ring A is

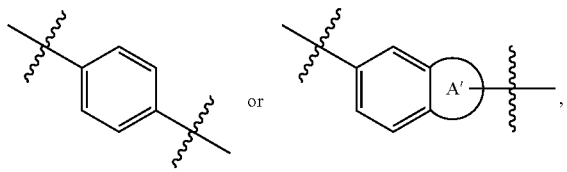

wherein ring A is optionally and independently substituted with up to 3 substituents selected from halo, CN, carboxyl, $NH_2$, and optionally substituted $C_{1-6}$ alkyl;

V is a bond or —$CH_2$—; and

E and G are each independently a 5-6 membered heterocycloalkyl, wherein each heterocycloalkyl contains at least one nitrogen atom.

91. The compound or pharmaceutically acceptable salt of claim 90, wherein D is a bond and W is a nitrogen atom.

92. The compound of pharmaceutically acceptable salt of claim 1, wherein the compound of Formula (A) is a compound of Formula (M)

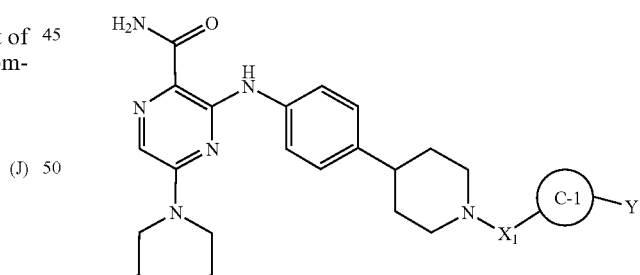
(M)

or a pharmaceutically acceptable salt thereof, wherein $R^{104}$ is —H,

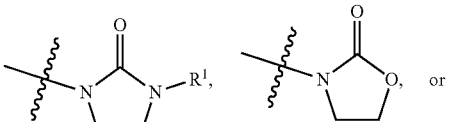

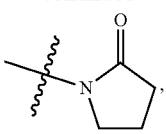

wherein $R^1$ is $C_{1-4}$ alkyl;

$X^1$ is —$C_{1-5}$ alkyl-;

Ring C-1 is a 5-6 membered heterocycloalkyl having 1 nitrogen atom; and

Y is

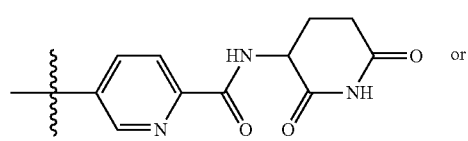

93. The compound or pharmaceutically acceptable salt of claim 92, wherein $R^{10.4}$ is —H or

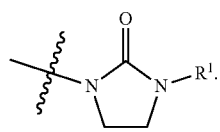

94. The compound or pharmaceutically acceptable salt of claim 92, wherein $R^{10.4}$ is

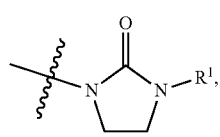

and $R^1$ is methyl, ethyl, propyl, iso-propyl, butyl, sec-butyl, or iso-butyl.

95. The compound or pharmaceutically acceptable salt of claim 92, wherein $R^1$ is methyl.

96. The compound or pharmaceutically acceptable salt of claim 92, wherein $X^1$ is methylene, ethylene, or propylene.

97. The compound or pharmaceutically acceptable salt of claim 92, wherein $X^1$ is methylene.

98. The compound or pharmaceutically acceptable salt of claim 92, wherein ring C-1 is

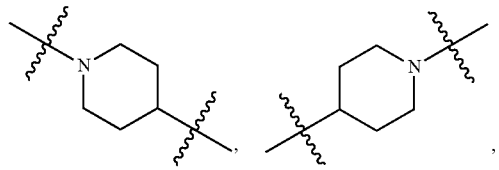

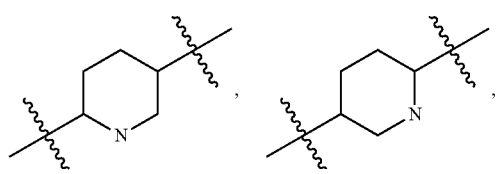

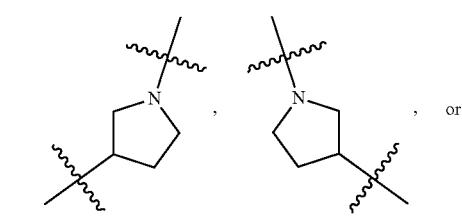

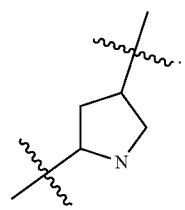

99. The compound or pharmaceutically acceptable salt of claim 92, wherein ring C-1 is

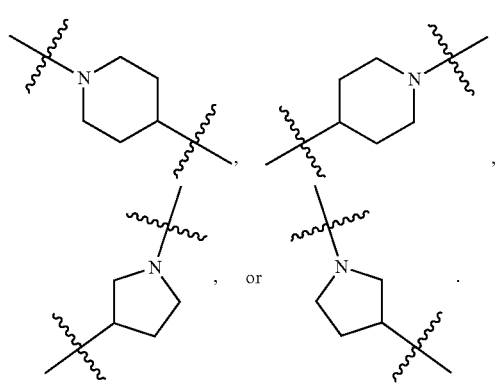

100. A compound selected from Table 1, or a pharmaceutically acceptable salt thereof
TABLE 1
| Compound Number | Structure |
|---|---|
| 1 | 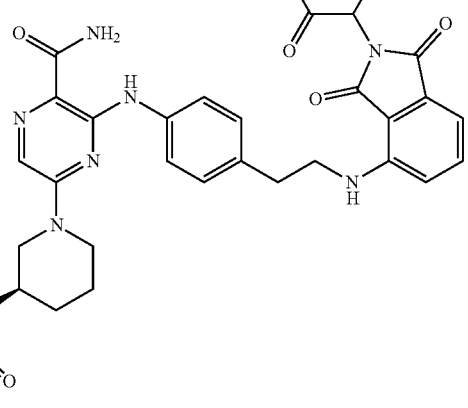 |
| 2 | 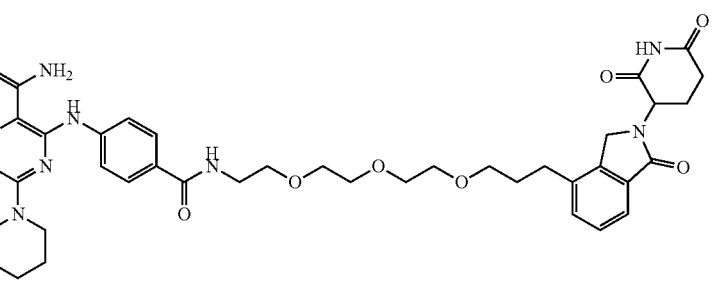 |
| 3 | 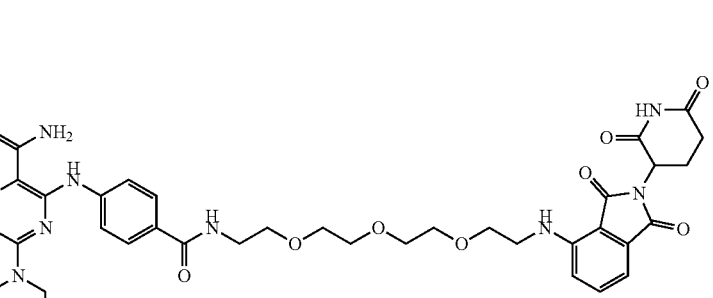 |
| 4 | 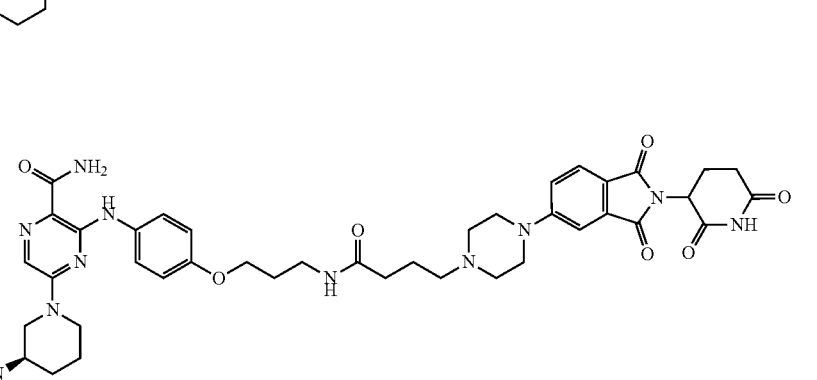 |

TABLE 1-continued
| Compound Number | Structure |
|---|---|
| 5 | 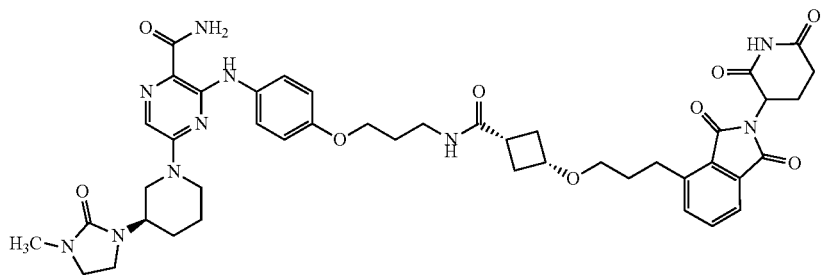 |
| 6 | 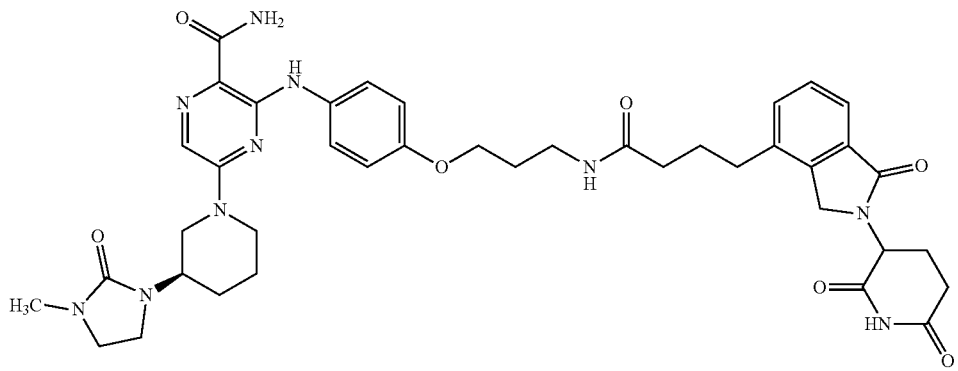 |
| 7 | 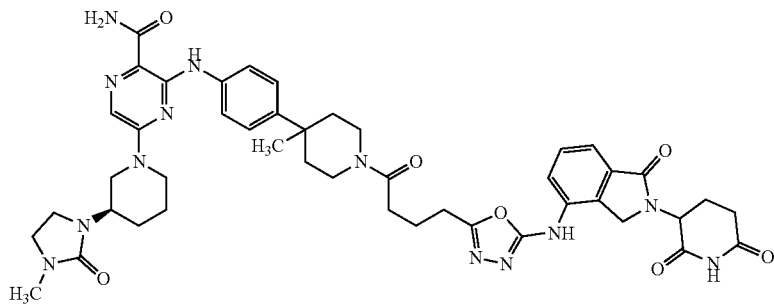 |
| 8 | 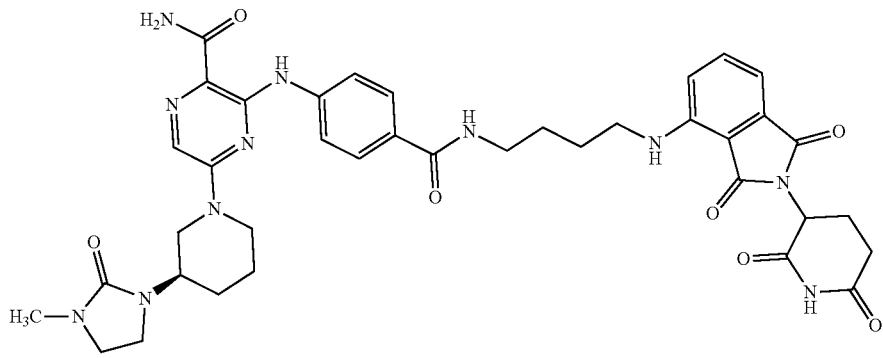 |

TABLE 1-continued
| Compound Number | Structure |
|---|---|
| 9 | 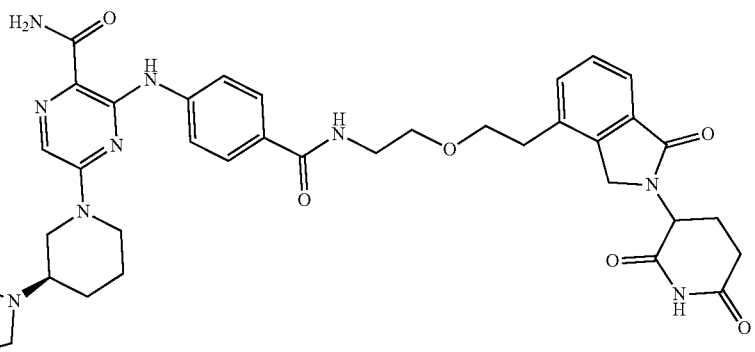 |
| 10 | 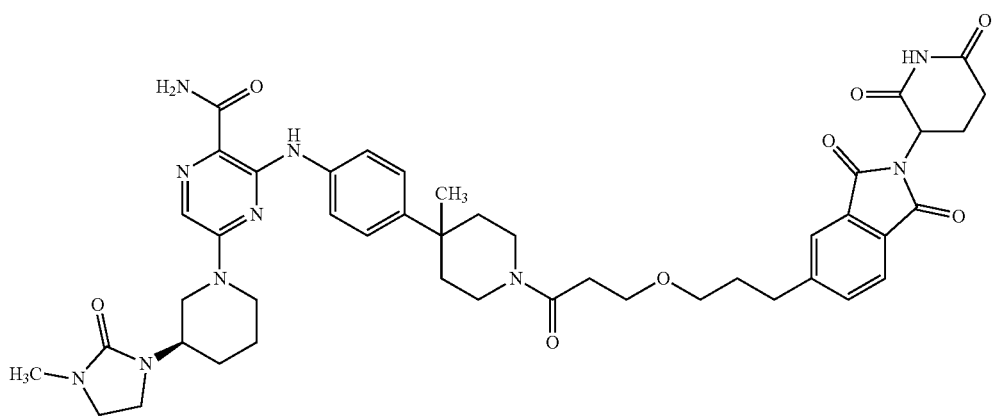 |
| 11 | 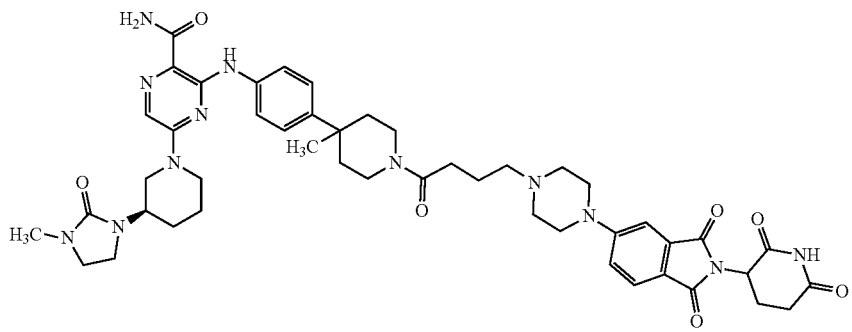 |
| 12 | 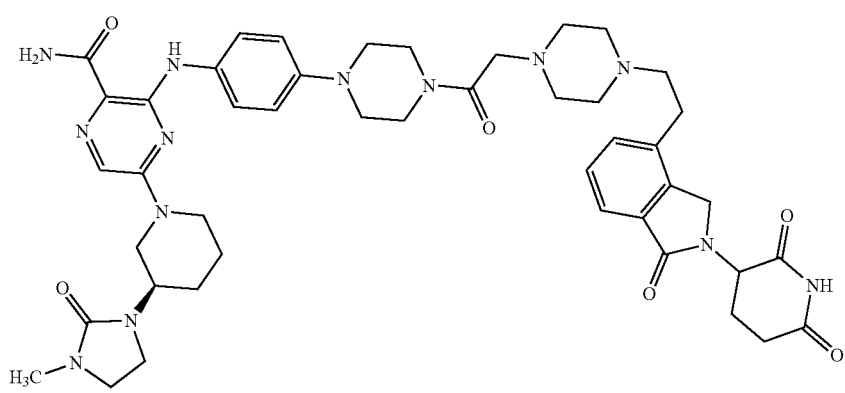 |

TABLE 1-continued
| Compound Number | Structure |
|---|---|
| 13 | 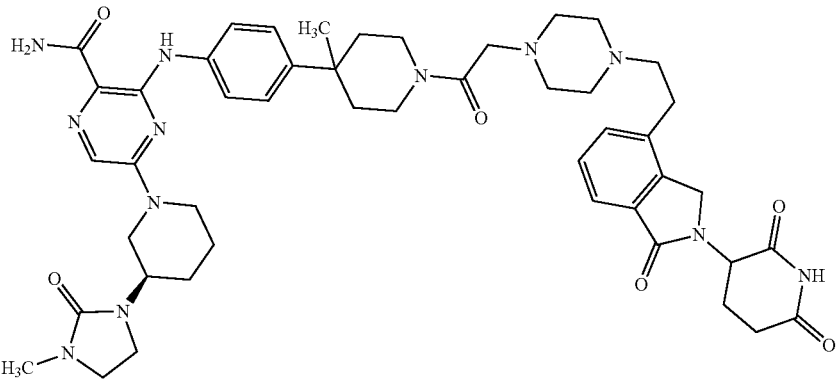 |
| 14 | 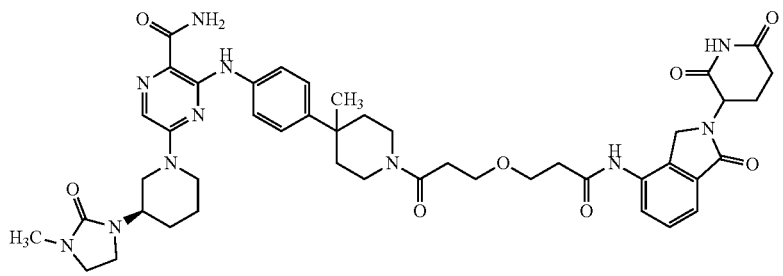 |
| 15 | 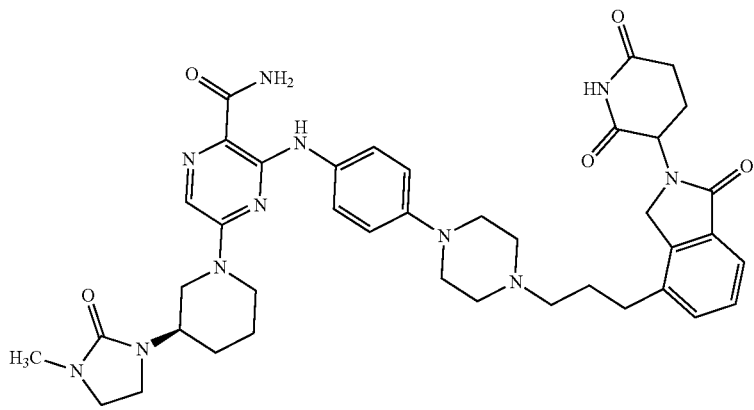 |
| 16 | 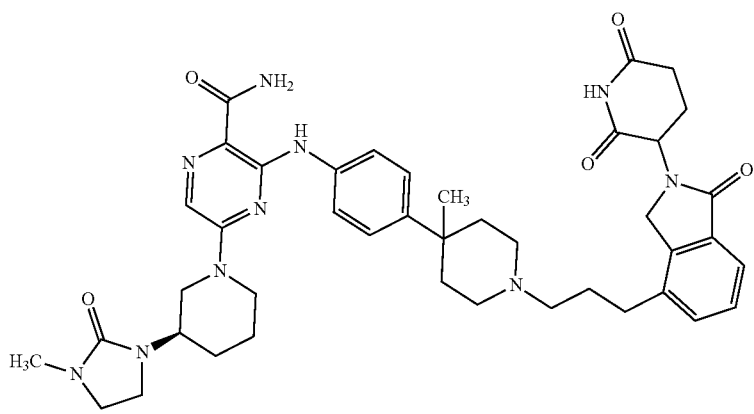 |

TABLE 1-continued
Compound Number | Structure
17 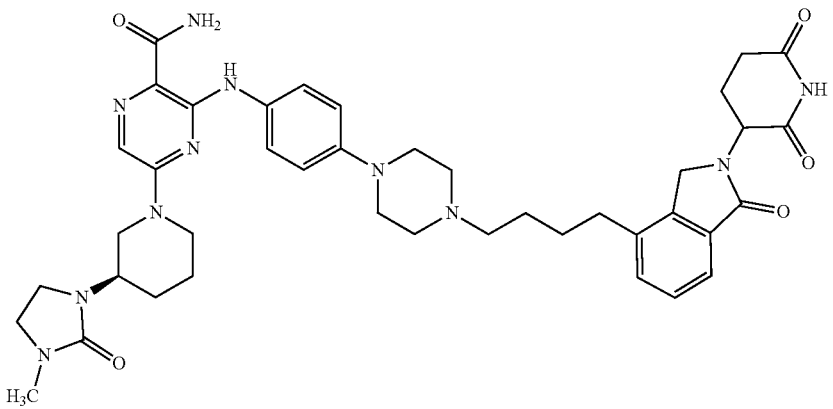
18 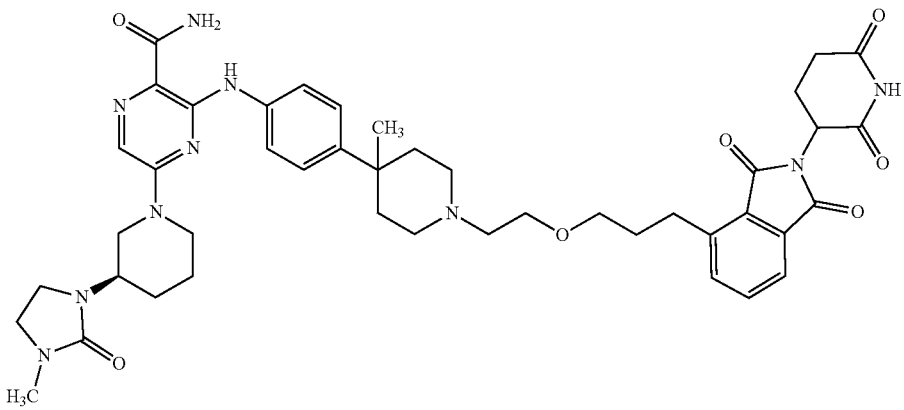
19 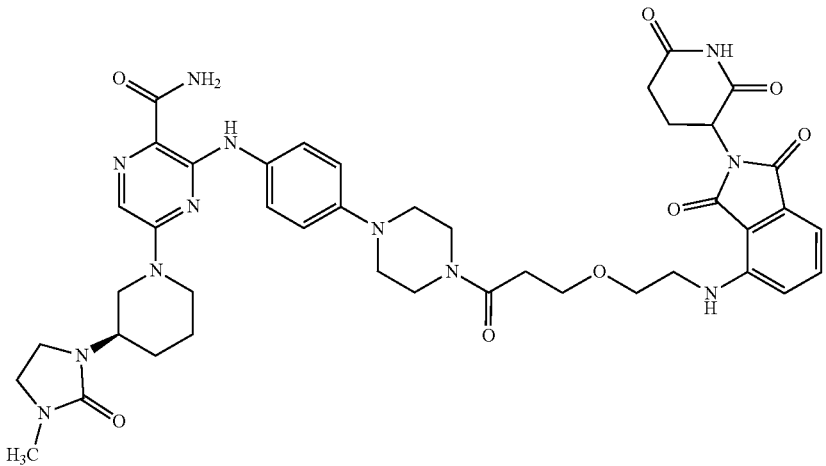

TABLE 1-continued
| Compound Number | Structure |
|---|---|
| 20 | 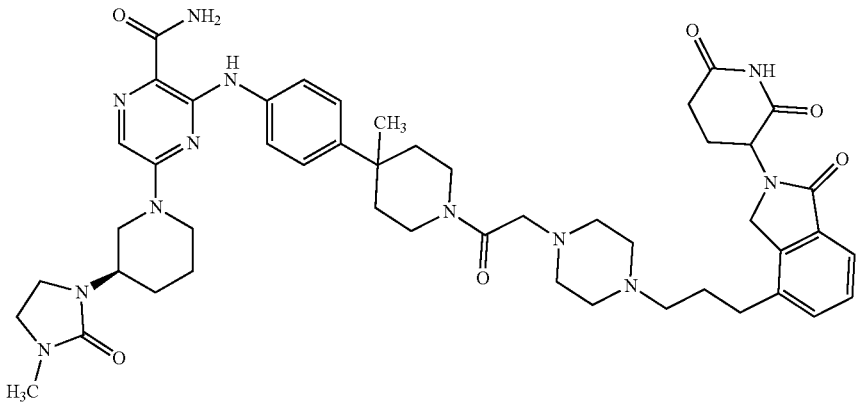 |
| 21 | 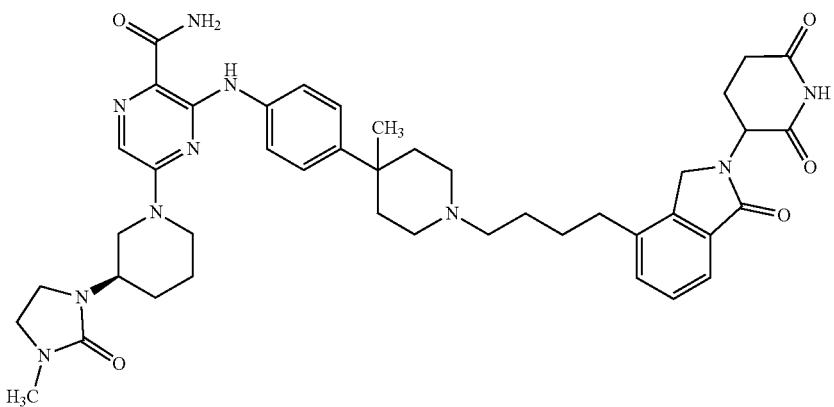 |
| 22 | 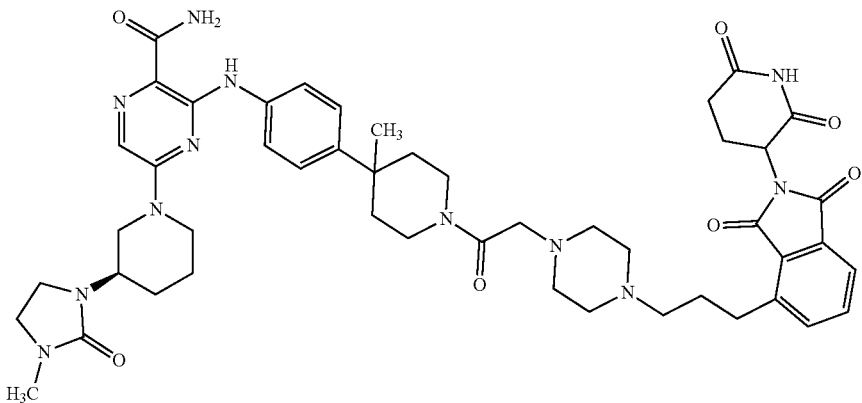 |

TABLE 1-continued
| Compound Number | Structure |
| --- | --- |
| 23 | 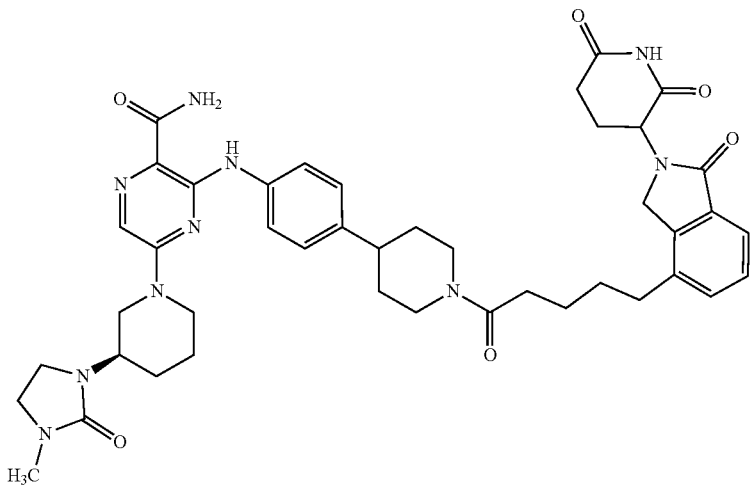 |
| 24 | 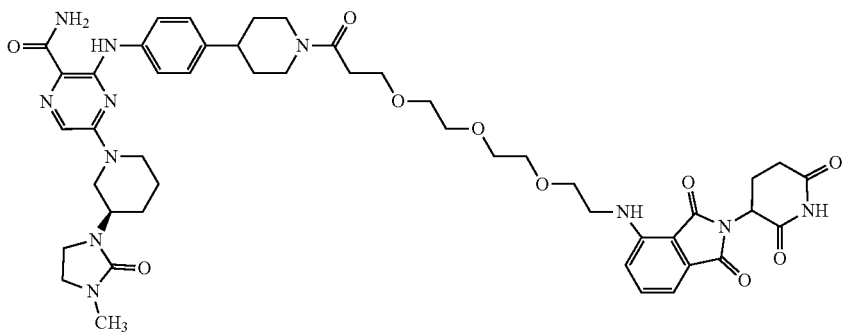 [SMILES: CN1CCN([C@@H]2CCCN(c3cnc(C(N)=O)c(Nc4ccc(C5CCN(C(=O)CCOCCOCCOCCNc6cccc7c6C(=O)N(C6CCC(=O)NC6=O)C7=O)CC5)cc4)n3)C2)C1=O] |
| 25 | 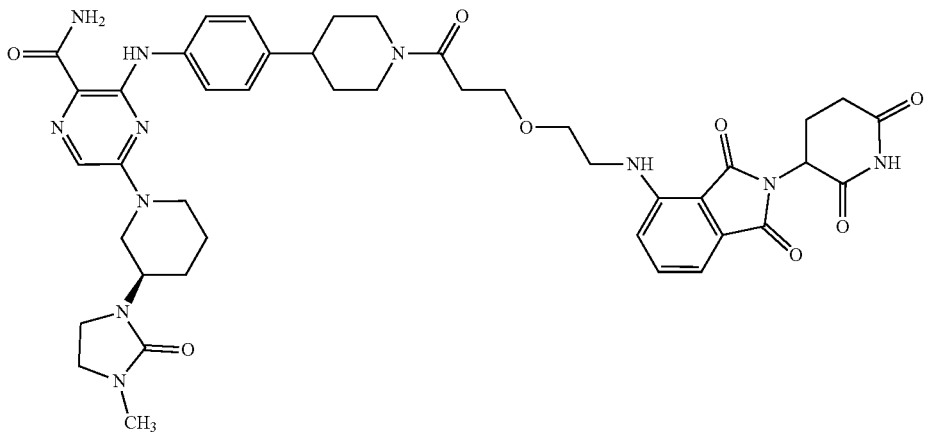 [SMILES: CN1CCN([C@@H]2CCCN(c3cnc(C(N)=O)c(Nc4ccc(C5CCN(C(=O)CCOCCNc6cccc7c6C(=O)N(C6CCC(=O)NC6=O)C7=O)CC5)cc4)n3)C2)C1=O] |

TABLE 1-continued
| Compound Number | Structure |
|---|---|
| 26 | 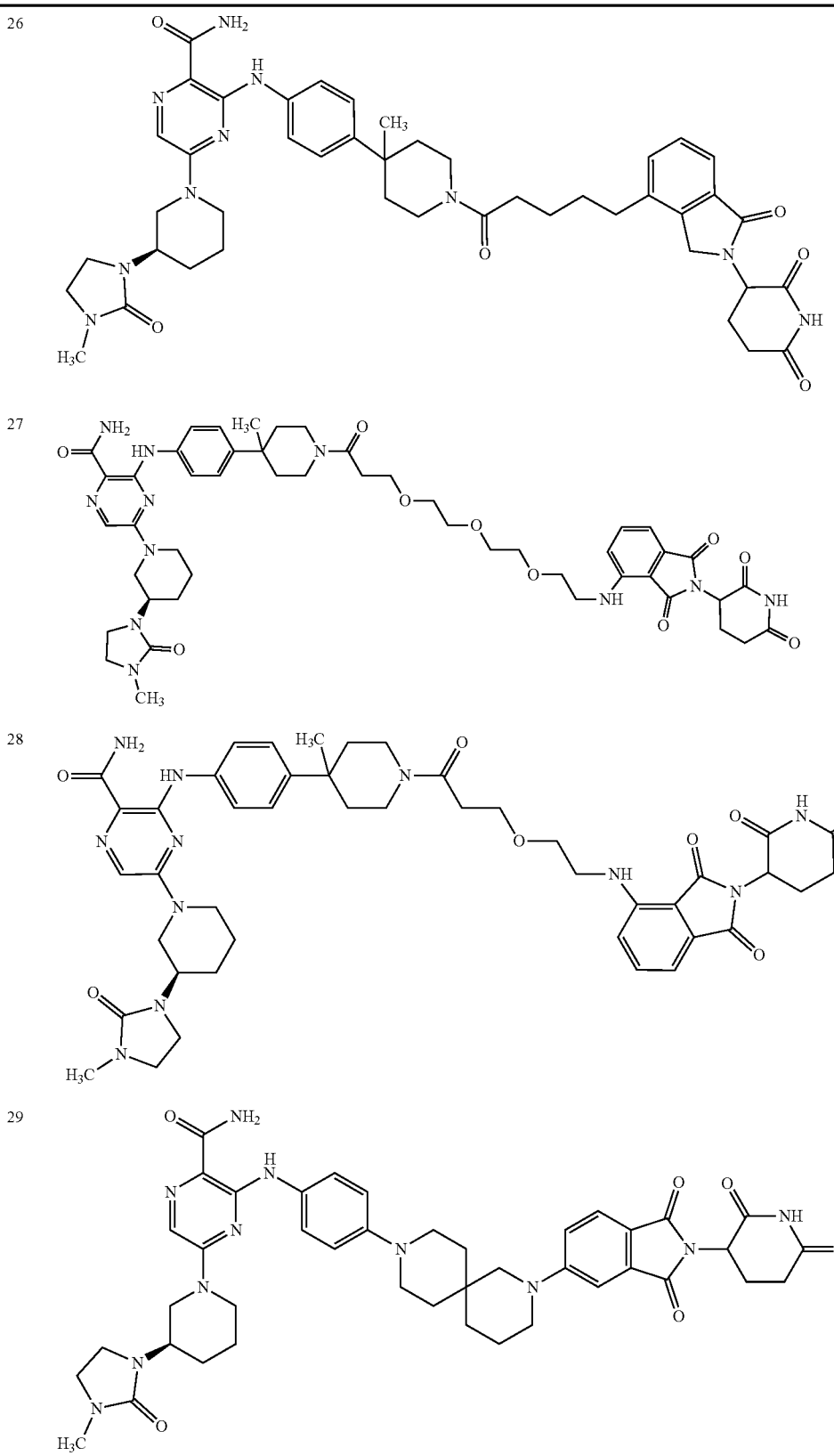 |
| 27 | 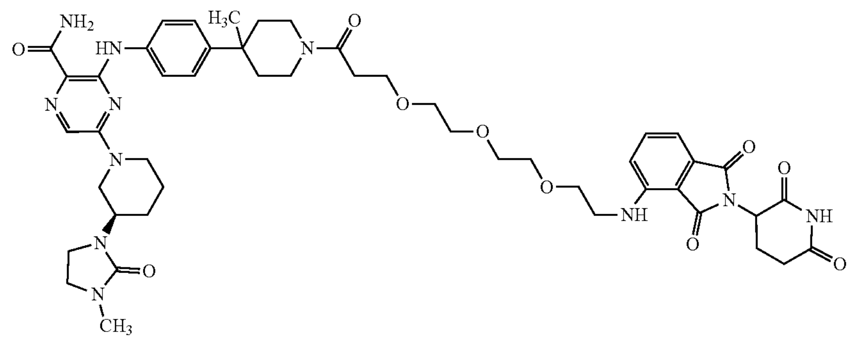 [SMILES: CN1CCN([C@@H]2CCCN(c3cnc(C(N)=O)c(Nc4ccc(C5(C)CCN(C(=O)CCOCCOCCOCCNc6cccc7c6C(=O)N(C6CCC(=O)NC6=O)C7=O)CC5)cc4)n3)C2)C1=O] |
| 28 | 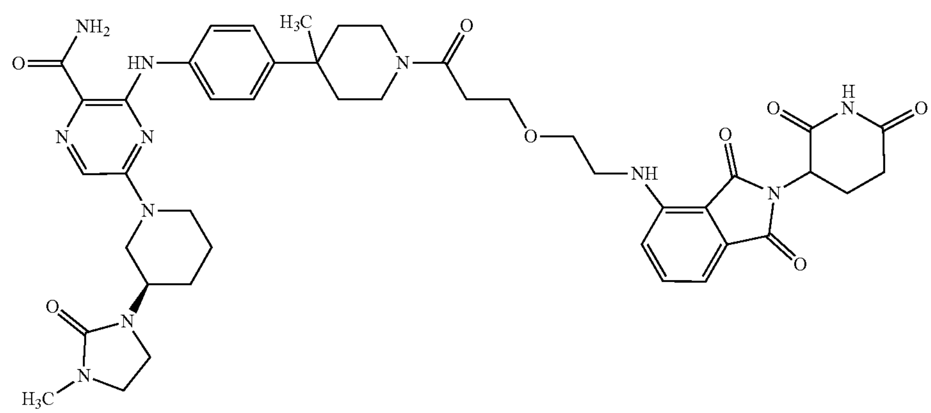 |
| 29 | 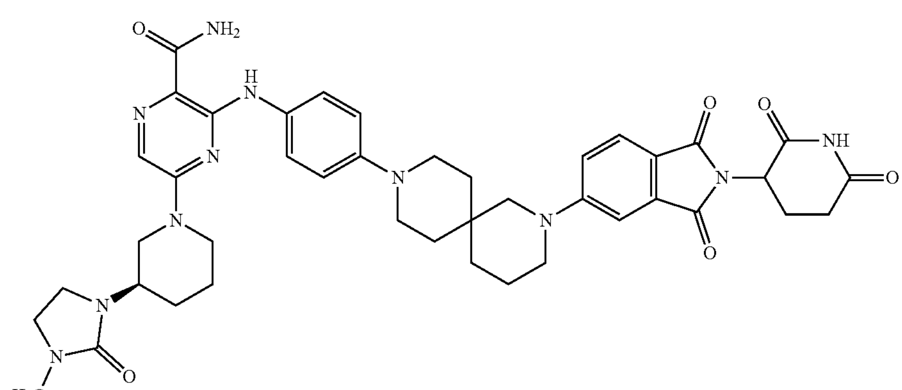 |

TABLE 1-continued
Compound Number | Structure
30 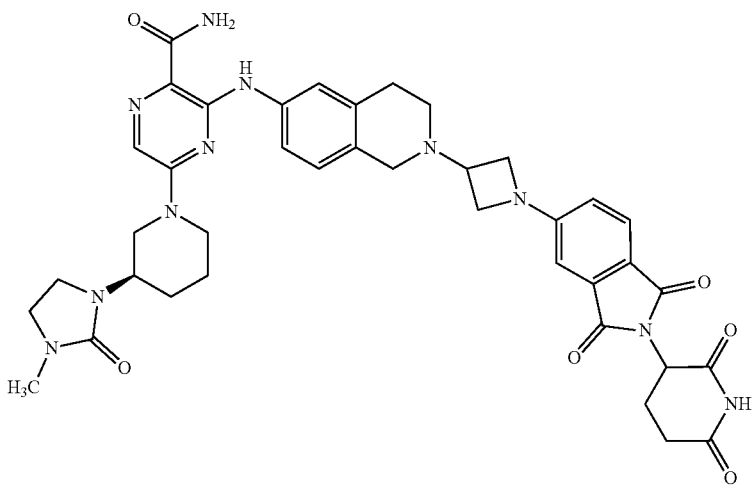
31 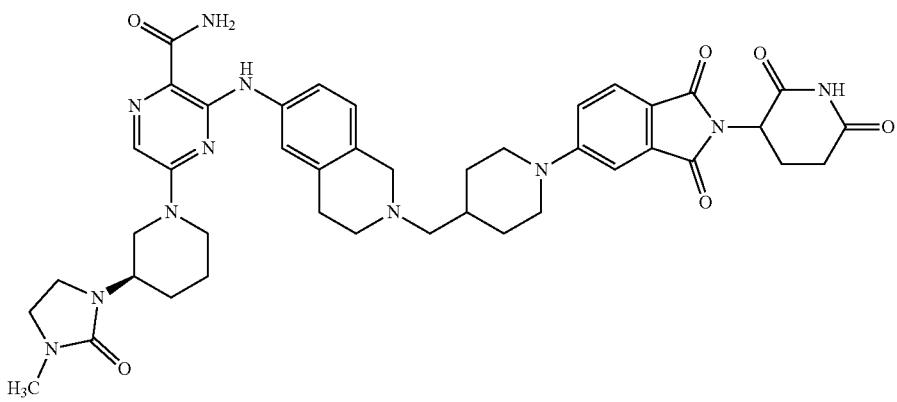
32 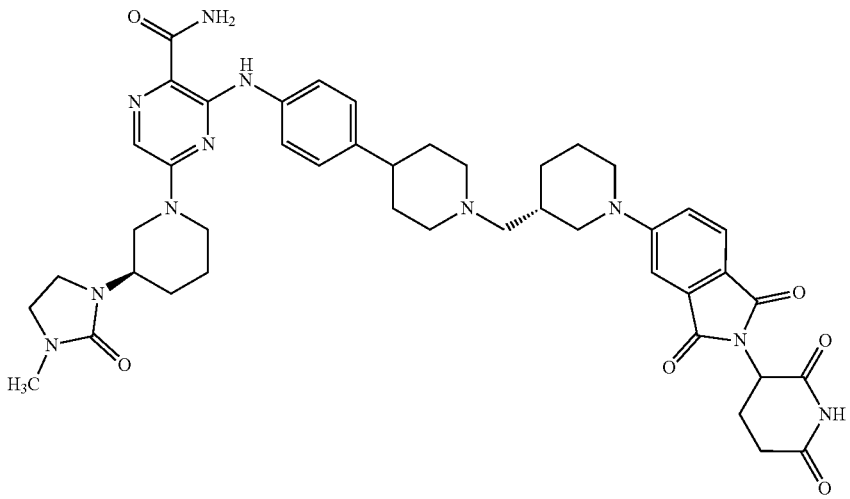

TABLE 1-continued
| Compound Number | Structure |
|---|---|
| 33 | 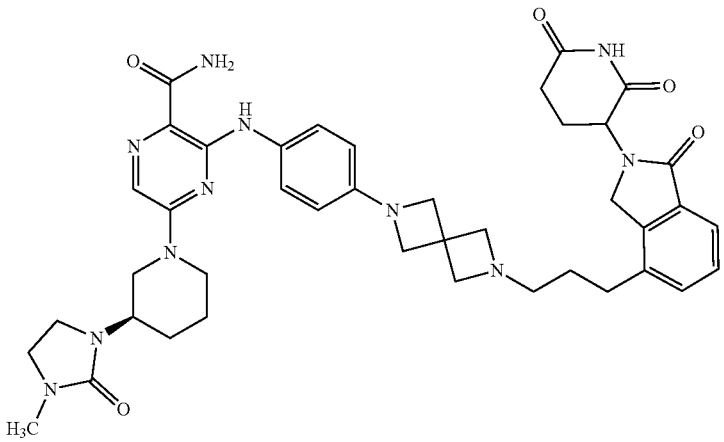 |
| 34 | 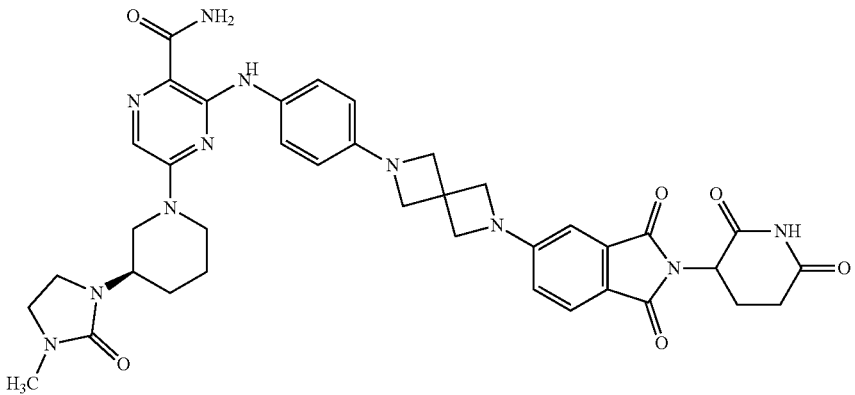 |
| 35 | 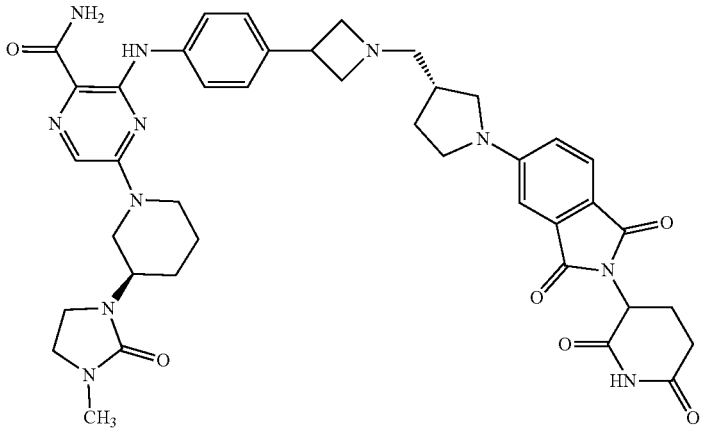 [SMILES: CN1CCN([C@@H]2CCCN(c3cnc(C(N)=O)c(Nc4ccc(C5CN(C[C@H]6CCN(c7ccc8c(c7)C(=O)N(C7CCC(=O)NC7=O)C8=O)C6)C5)cc4)n3)C2)C1=O] |

TABLE 1-continued
| Compound Number | Structure |
|---|---|
| 36 | 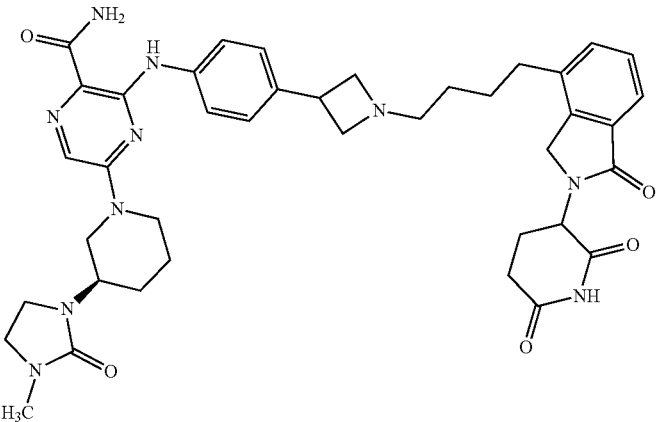 |
| 37 | 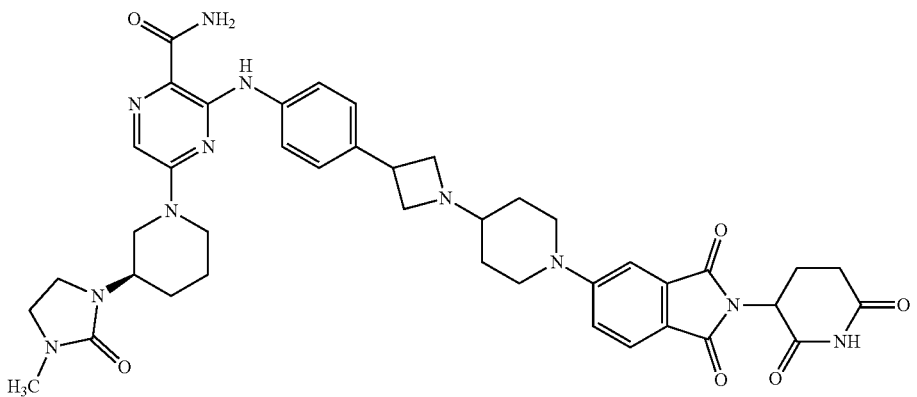 |
| 38 | 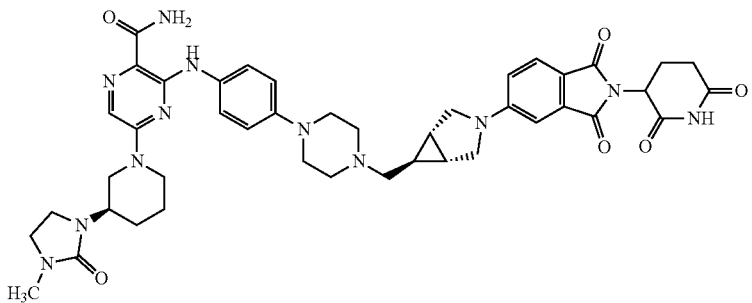 |
| 39 | 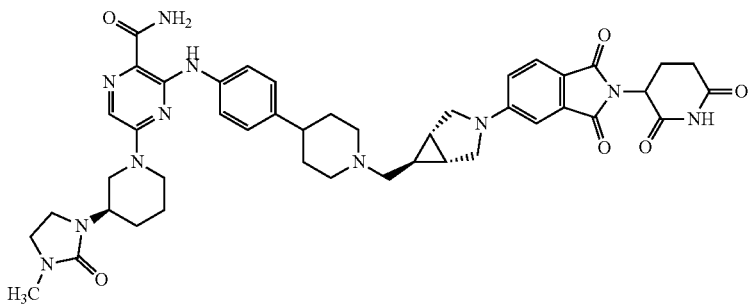 |

TABLE 1-continued
| Compound Number | Structure |
|---|---|
| 40 | 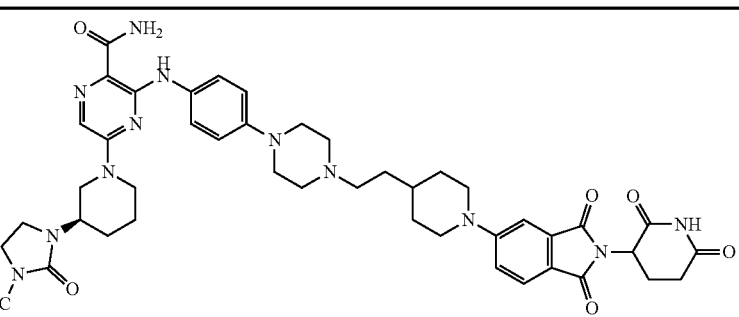 |
| 41 | 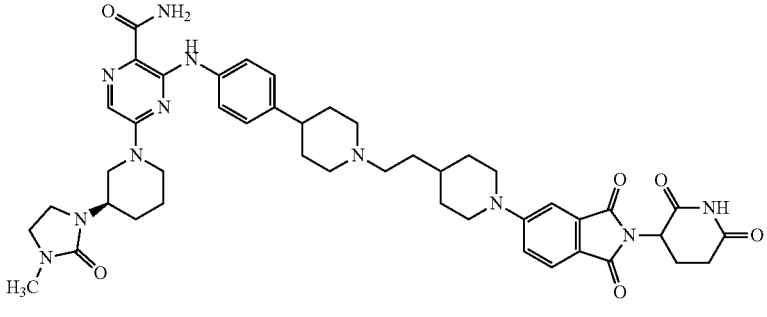 |
| 42 | 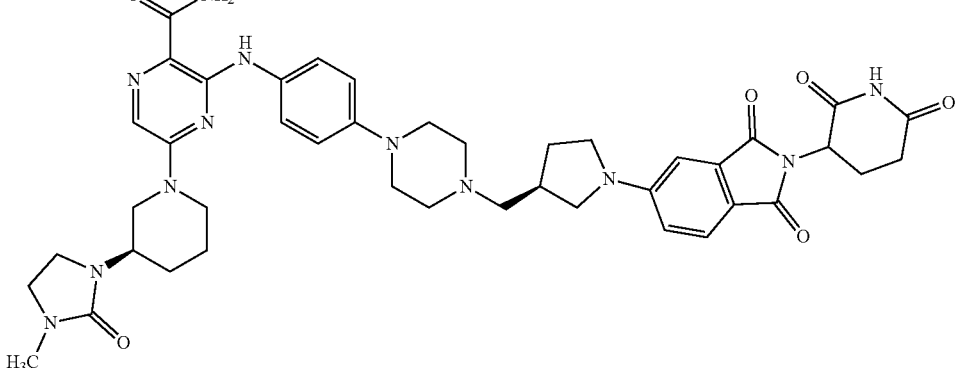 |
| 43 | 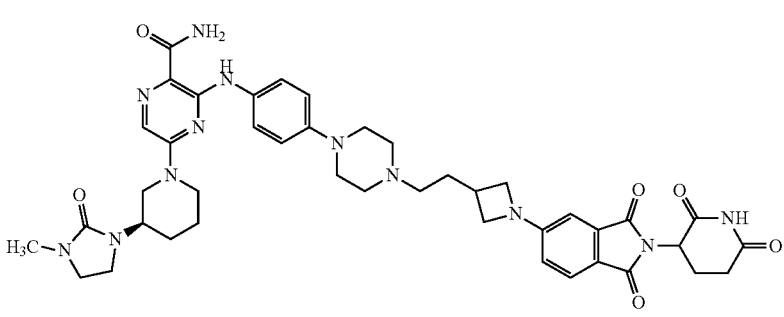 |
| 44 | 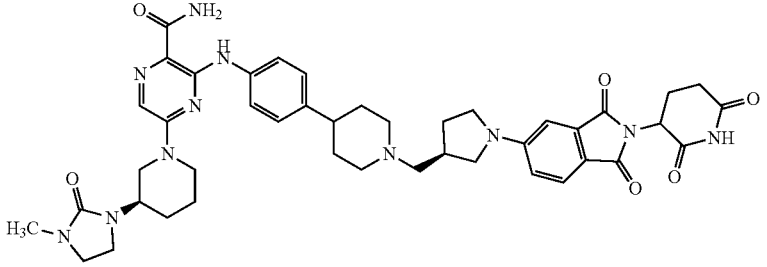 |

US 11,479,556 B1
TABLE 1-continued
| Compound Number | Structure |
|---|---|
| 45 | 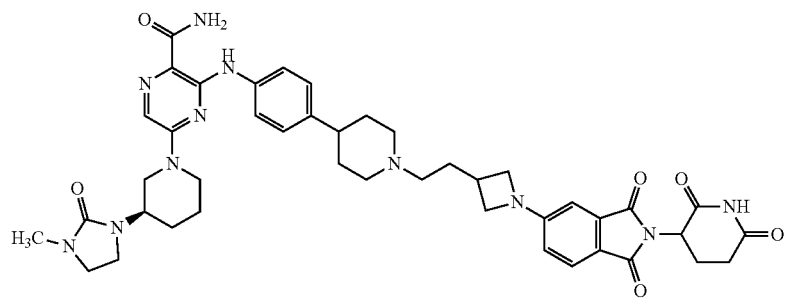 |
| 46 | 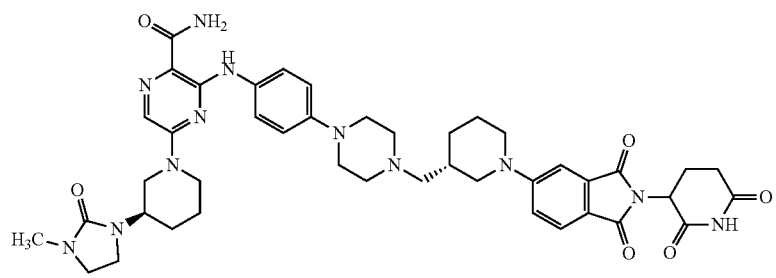 |
| 47 | 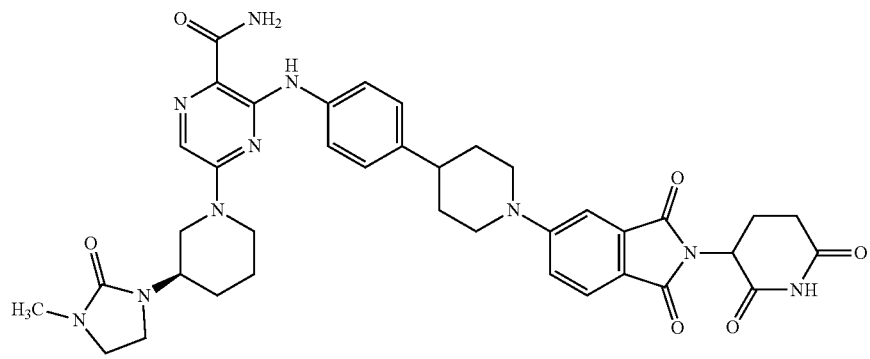 |
| 48 | 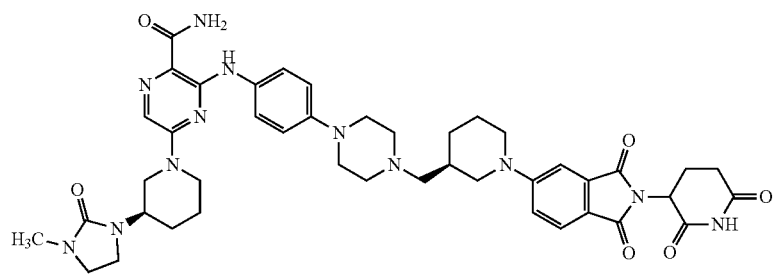 |
| 49 | 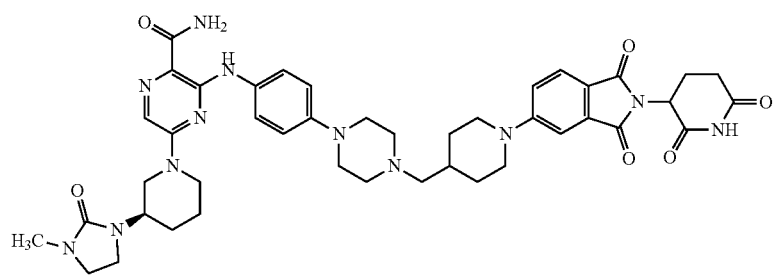 |

TABLE 1-continued
| Compound Number | Structure |
|---|---|
| 50 | 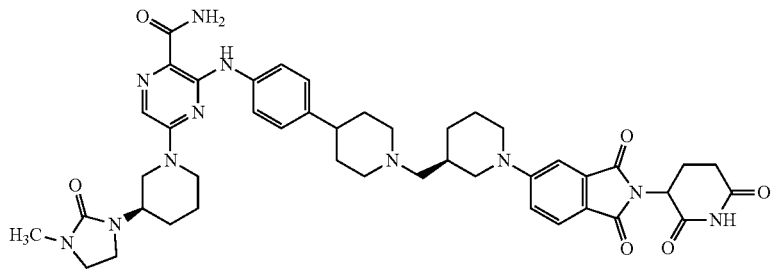 |
| 51 | 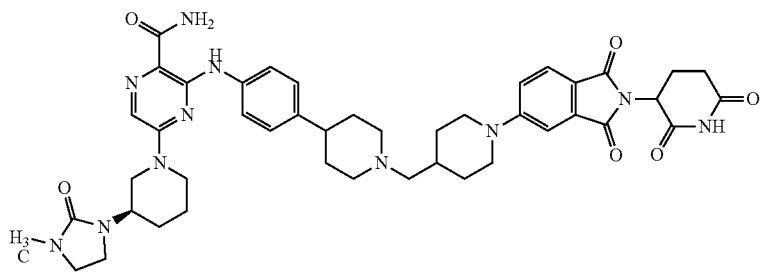 |
| 52 | 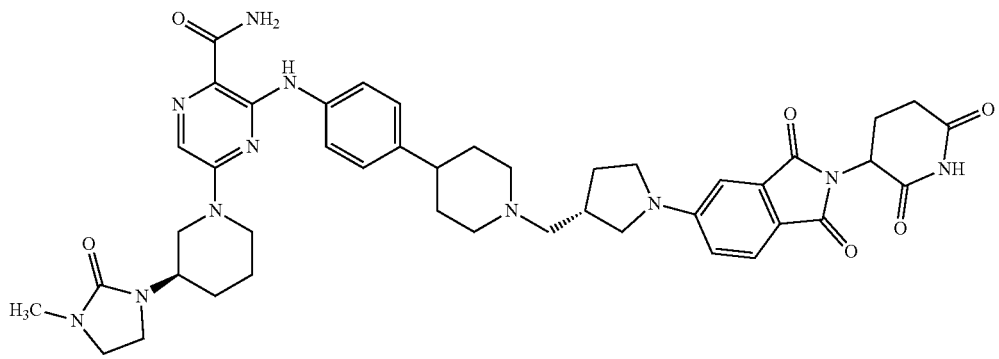 |
| 53 | 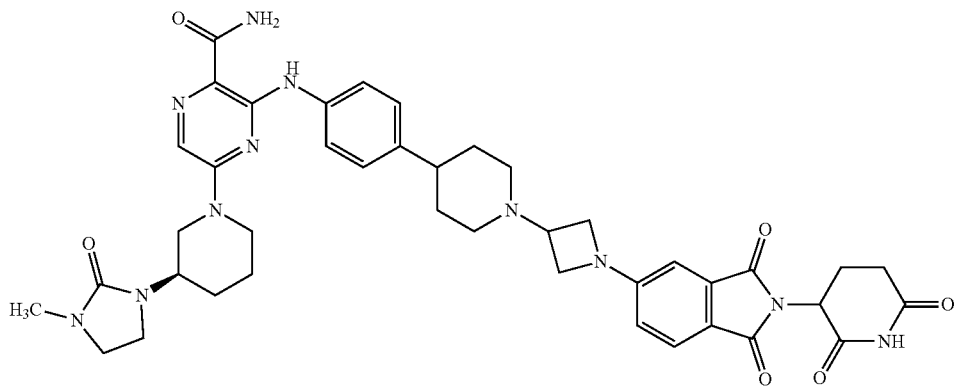 |

TABLE 1-continued
| Compound Number | Structure |
|---|---|
| 54 | 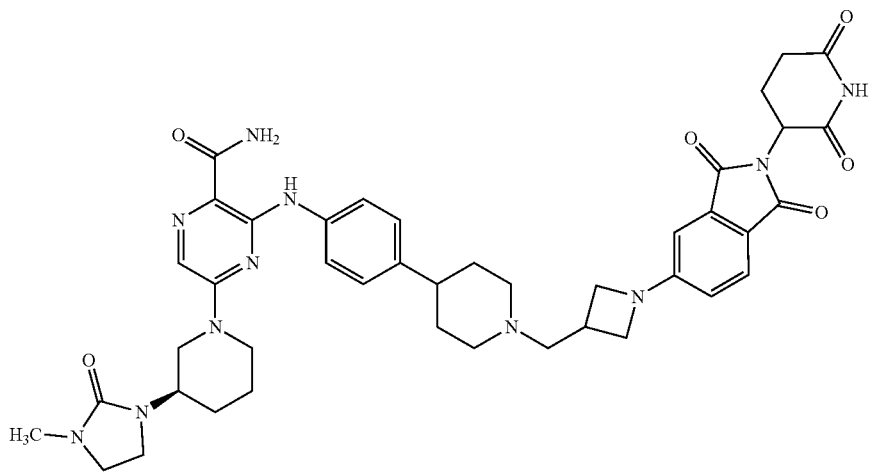 |
| 55 | 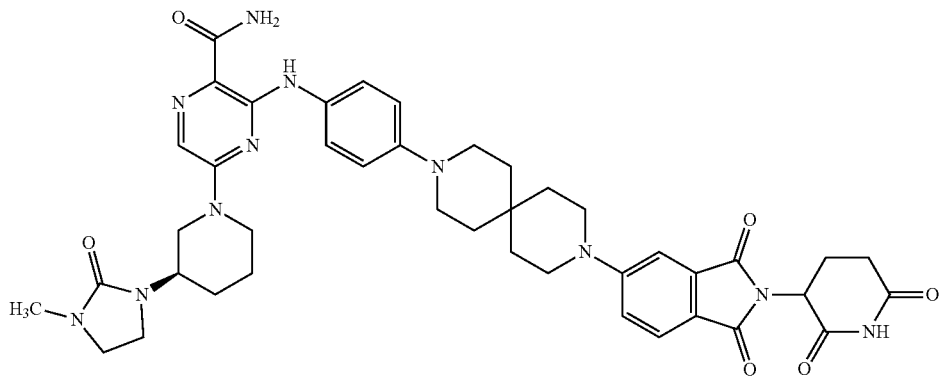 |
| 56 | 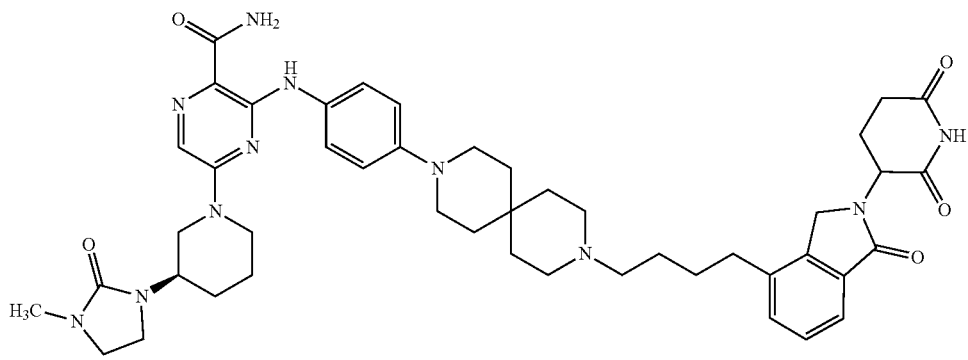 |
| 57 | 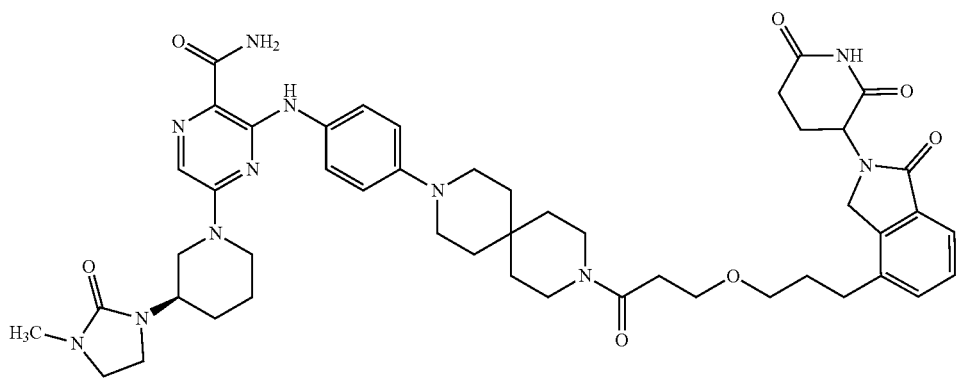 |

TABLE 1-continued

| Compound Number | Structure |
|---|---|
| 58 | 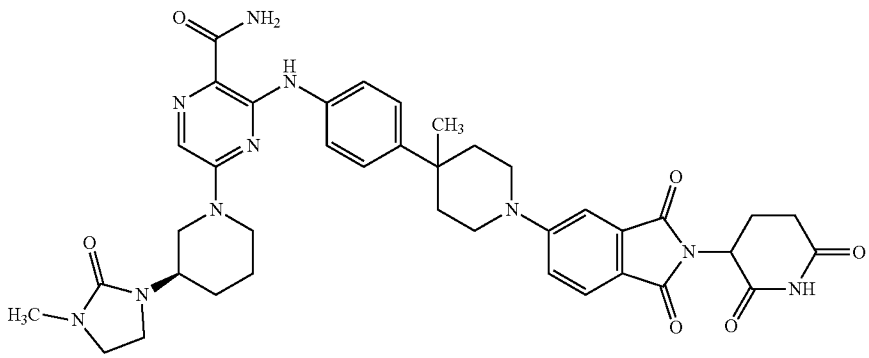 |
| 59 | 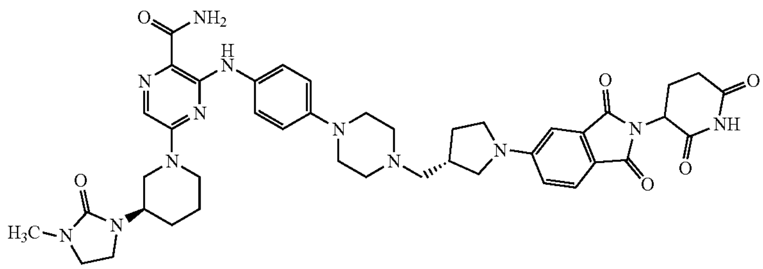 [SMILES: CN1CCN([C@@H]2CCCN(c3cnc(C(N)=O)c(Nc4ccc(N5CCN(C[C@@H]6CCN(c7ccc8c(c7)C(=O)N(C7CCC(=O)NC7=O)C8=O)C6)CC5)cc4)n3)C2)C1=O] |
| 60 | 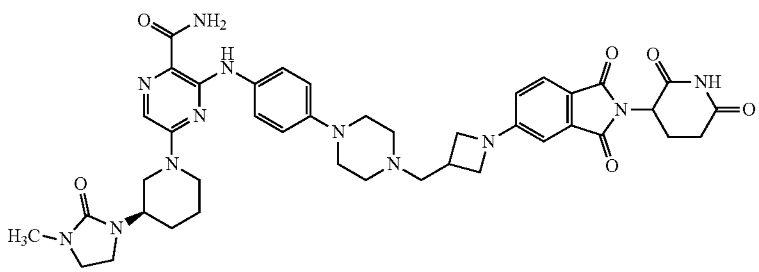 [SMILES: CN1CCN([C@@H]2CCCN(c3cnc(C(N)=O)c(Nc4ccc(N5CCN(CC6CN(c7ccc8c(c7)C(=O)N(C7CCC(=O)NC7=O)C8=O)C6)CC5)cc4)n3)C2)C1=O] |
| 61 | 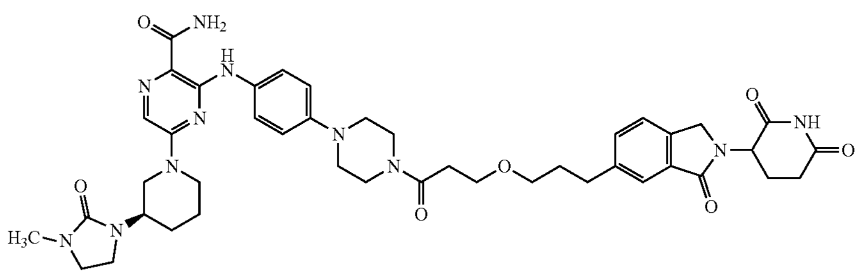 [SMILES: CN1CCN([C@@H]2CCCN(c3cnc(C(N)=O)c(Nc4ccc(N5CCN(C(=O)CCOCCCc6ccc7c(c6)C(=O)N(C6CCC(=O)NC6=O)C7)CC5)cc4)n3)C2)C1=O] |
| 62 | 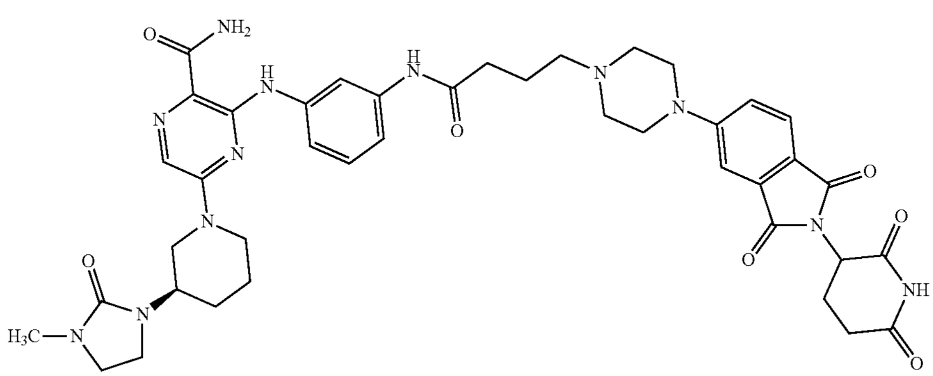 [SMILES: CN1CCN([C@@H]2CCCN(c3cnc(C(N)=O)c(Nc4cccc(NC(=O)CCCN5CCN(c6ccc7c(c6)C(=O)N(C6CCC(=O)NC6=O)C7=O)CC5)c4)n3)C2)C1=O] |

TABLE 1-continued
| Compound Number | Structure |
|---|---|
| 63 | 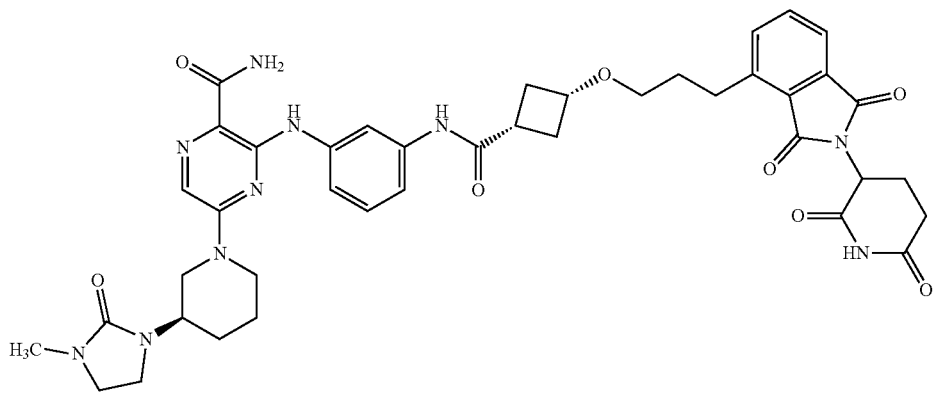 [SMILES: CN1CCN([C@@H]2CCCN(c3cnc(C(N)=O)c(Nc4cccc(NC(=O)[C@H]5C[C@@H](OCCCc6cccc7c6C(=O)N(C6CCC(=O)NC6=O)C7=O)C5)c4)n3)C2)C1=O] |
| 64 | 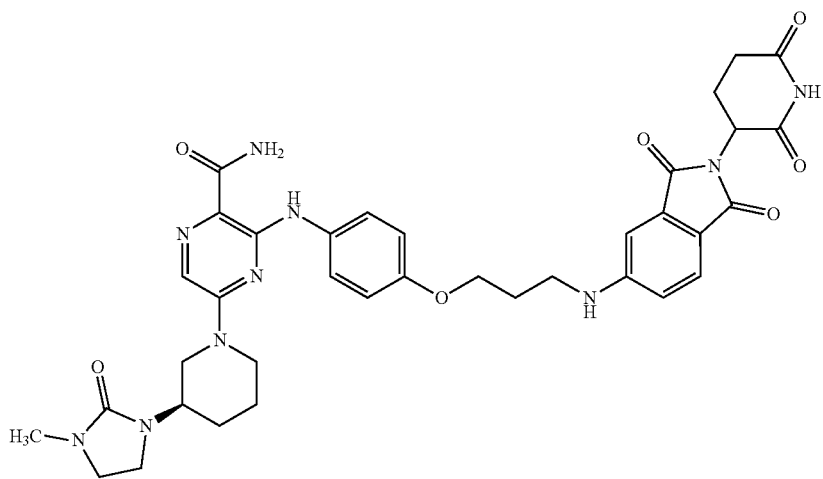 [SMILES: CN1CCN([C@@H]2CCCN(c3cnc(C(N)=O)c(Nc4ccc(OCCCNc5ccc6c(c5)C(=O)N(C5CCC(=O)NC5=O)C6=O)cc4)n3)C2)C1=O] |
| 65 | 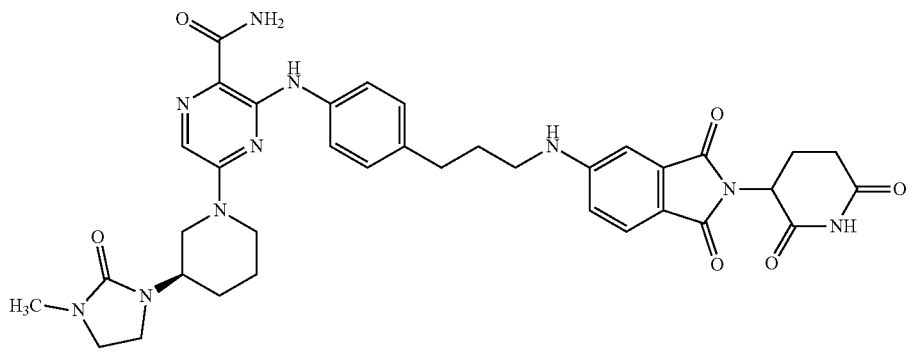 [SMILES: CN1CCN([C@@H]2CCCN(c3cnc(C(N)=O)c(Nc4ccc(CCCNc5ccc6c(c5)C(=O)N(C5CCC(=O)NC5=O)C6=O)cc4)n3)C2)C1=O] |
| 66 | 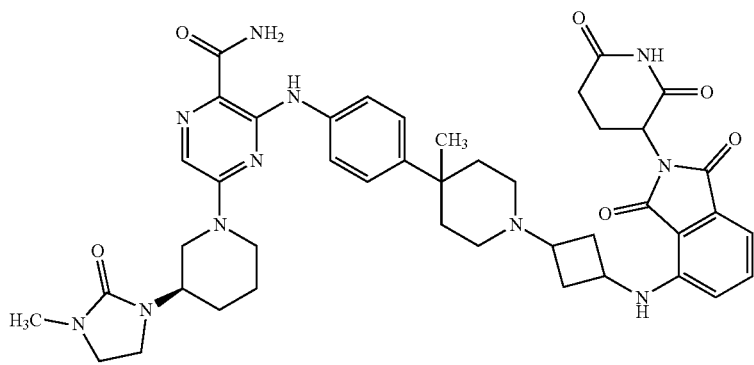 [SMILES: CN1CCN([C@@H]2CCCN(c3cnc(C(N)=O)c(Nc4ccc(C5(C)CCN(C6CC(Nc7cccc8c7C(=O)N(C7CCC(=O)NC7=O)C8=O)C6)CC5)cc4)n3)C2)C1=O] |

| Compound Number | Structure |
|---|---|
| 67 | 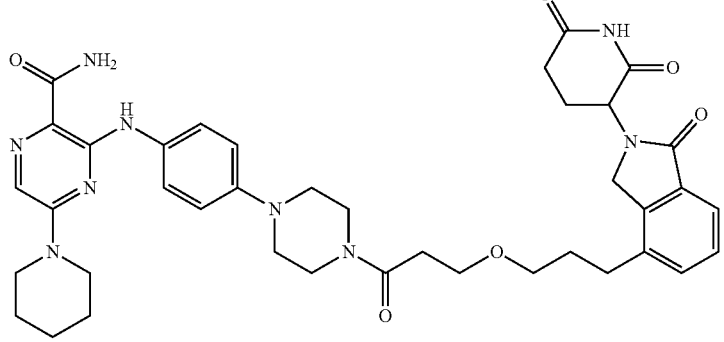 |
| 68 | 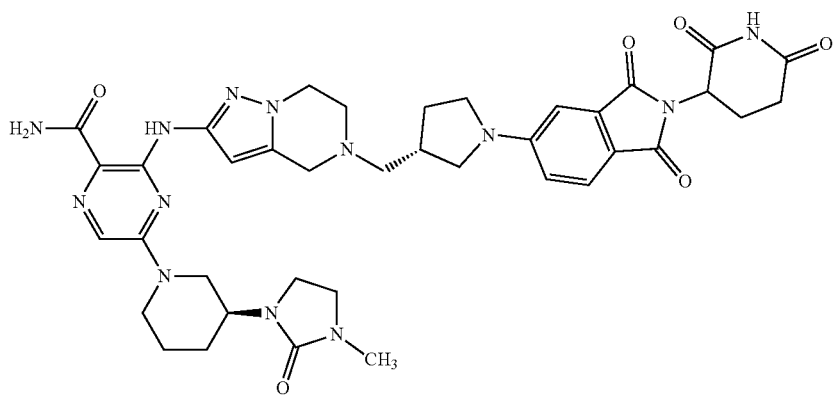 [SMILES: CN1CCN([C@H]2CCCN(c3cnc(C(N)=O)c(Nc4cc5n(n4)CCN(C[C@@H]4CCN(c6ccc7c(c6)C(=O)N(C6CCC(=O)NC6=O)C7=O)C4)C5)n3)C2)C1=O] |
| 69 | 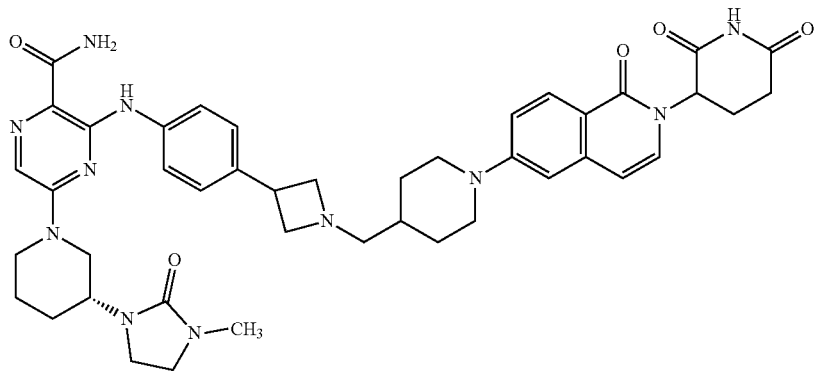 [SMILES: CN1CCN([C@@H]2CCCN(c3cnc(C(N)=O)c(Nc4ccc(C5CN(CC6CCN(c7ccc8c(=O)n(C9CCC(=O)NC9=O)ccc8c7)CC6)C5)cc4)n3)C2)C1=O] |
| 70 | 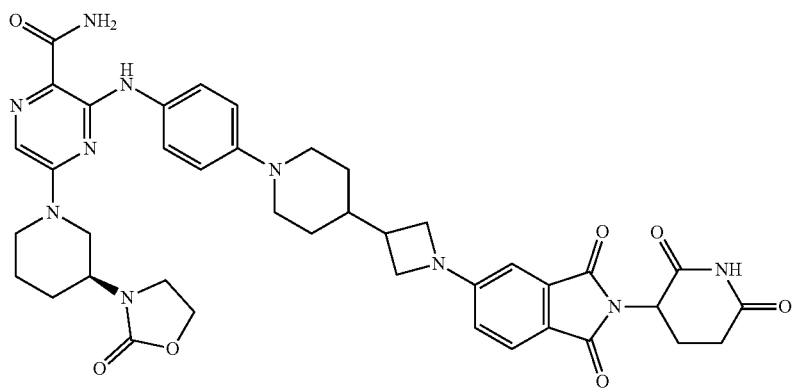 [SMILES: NC(=O)c1ncc(N2CCC[C@H](N3CCOC3=O)C2)nc1Nc1ccc(N2CCC(C3CN(c4ccc5c(c4)C(=O)N(C4CCC(=O)NC4=O)C5=O)C3)CC2)cc1] |

TABLE 1-continued
| Compound Number | Structure |
|---|---|
| 71 | 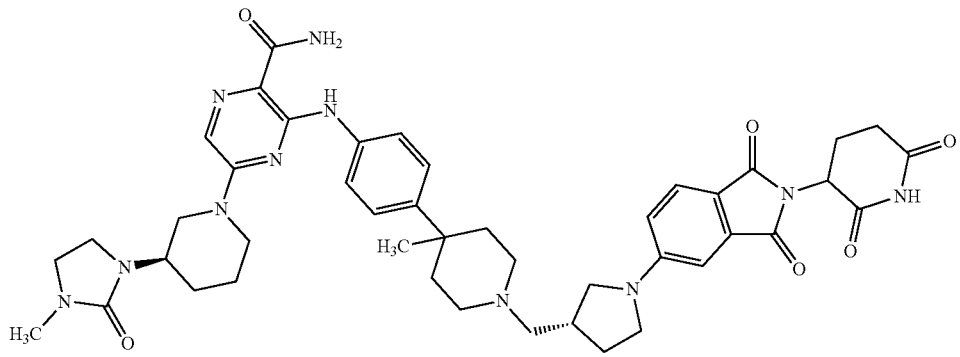 [SMILES: CN1CCN([C@@H]2CCCN(c3cnc(C(N)=O)c(Nc4ccc(C5(C)CCN(C[C@H]6CCN(c7ccc8c(c7)C(=O)N(C7CCC(=O)NC7=O)C8=O)C6)CC5)cc4)n3)C2)C1=O] |
| 72 | 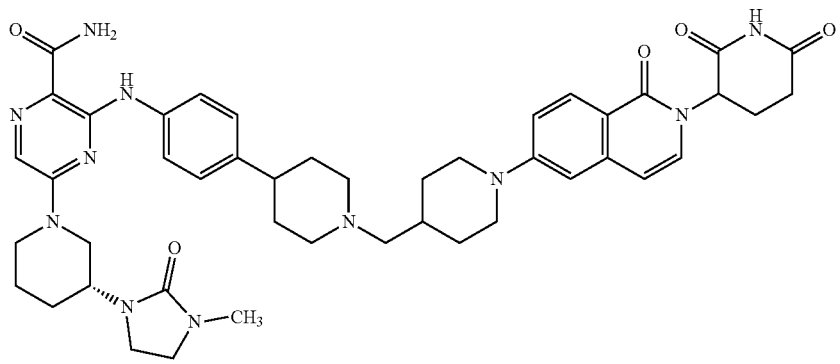 [SMILES: CN1CCN([C@@H]2CCCN(c3cnc(C(N)=O)c(Nc4ccc(C5CCN(CC6CCN(c7ccc8c(=O)n(C9CCC(=O)NC9=O)ccc8c7)CC6)CC5)cc4)n3)C2)C1=O] |
| 73 | 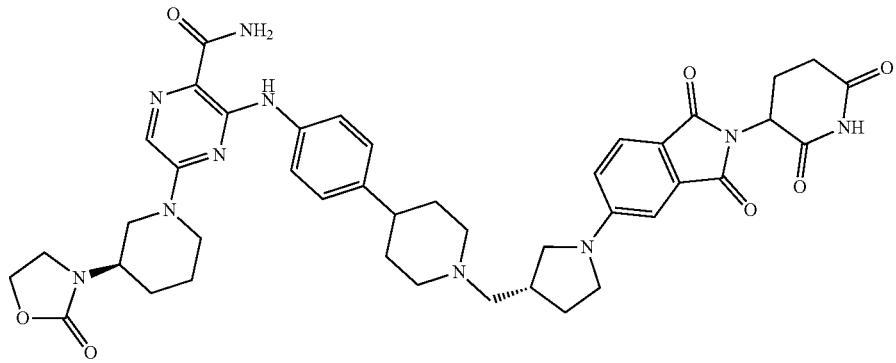 [SMILES: NC(=O)c1ncc(N2CCC[C@@H](N3CCOC3=O)C2)nc1Nc1ccc(C2CCN(C[C@H]3CCN(c4ccc5c(c4)C(=O)N(C4CCC(=O)NC4=O)C5=O)C3)CC2)cc1] |
| 74 | 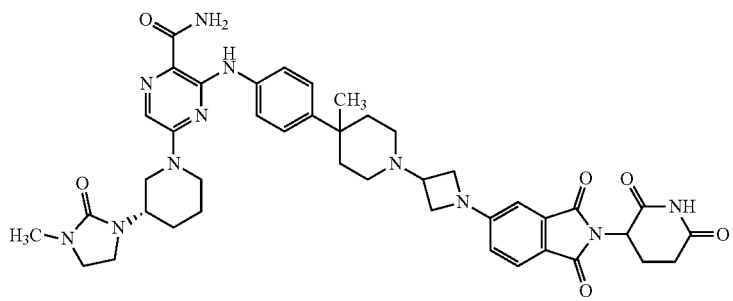 [SMILES: CN1CCN([C@H]2CCCN(c3cnc(C(N)=O)c(Nc4ccc(C5(C)CCN(C6CN(c7ccc8c(c7)C(=O)N(C7CCC(=O)NC7=O)C8=O)C6)CC5)cc4)n3)C2)C1=O] |

TABLE 1-continued

| Compound Number | Structure |
|---|---|
| 75 | 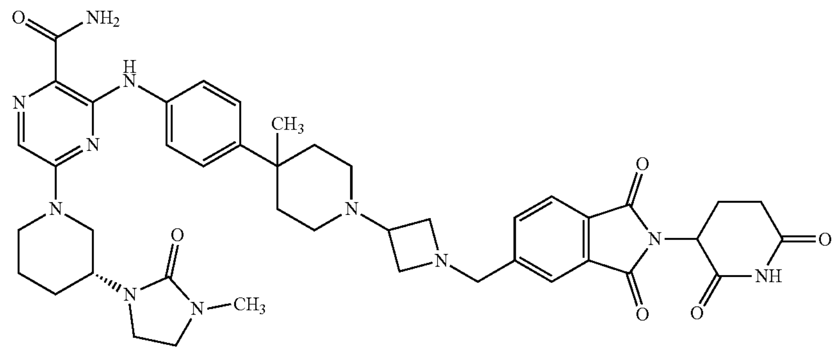 [SMILES: CN1CCN([C@@H]2CCCN(c3cnc(C(N)=O)c(Nc4ccc(C5(C)CCN(C6CN(Cc7ccc8c(c7)C(=O)N(C7CCC(=O)NC7=O)C8=O)C6)CC5)cc4)n3)C2)C1=O] |
| 76 | 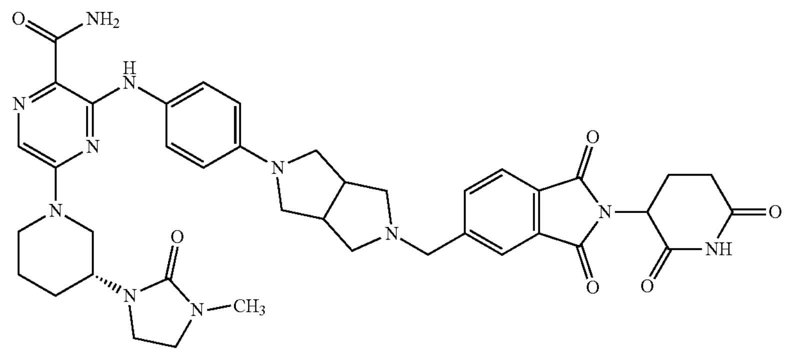 [SMILES: CN1CCN([C@@H]2CCCN(c3cnc(C(N)=O)c(Nc4ccc(N5CC6CN(Cc7ccc8c(c7)C(=O)N(C7CCC(=O)NC7=O)C8=O)CC6C5)cc4)n3)C2)C1=O] |
| 77 | 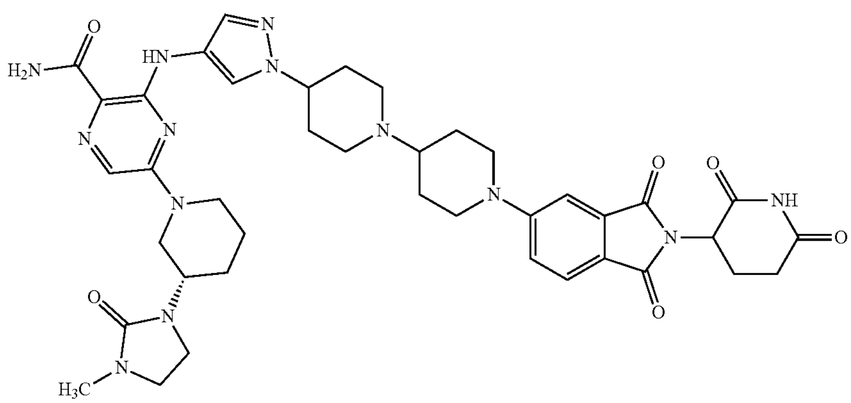 [SMILES: CN1CCN([C@H]2CCCN(c3cnc(C(N)=O)c(Nc4cnn(C5CCN(C6CCN(c7ccc8c(c7)C(=O)N(C7CCC(=O)NC7=O)C8=O)CC6)CC5)c4)n3)C2)C1=O] |
| 78 | 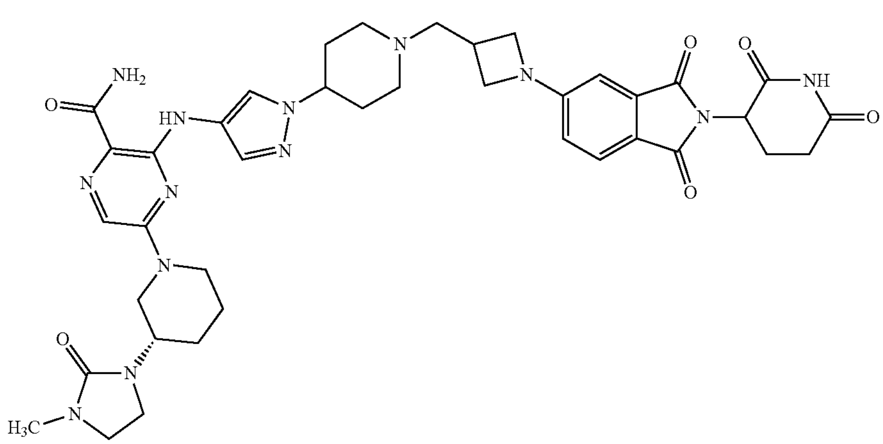 [SMILES: CN1CCN([C@H]2CCCN(c3cnc(C(N)=O)c(Nc4cnn(C5CCN(CC6CN(c7ccc8c(c7)C(=O)N(C7CCC(=O)NC7=O)C8=O)C6)CC5)c4)n3)C2)C1=O] |

TABLE 1-continued
| Compound Number | Structure |
|---|---|
| 79 | 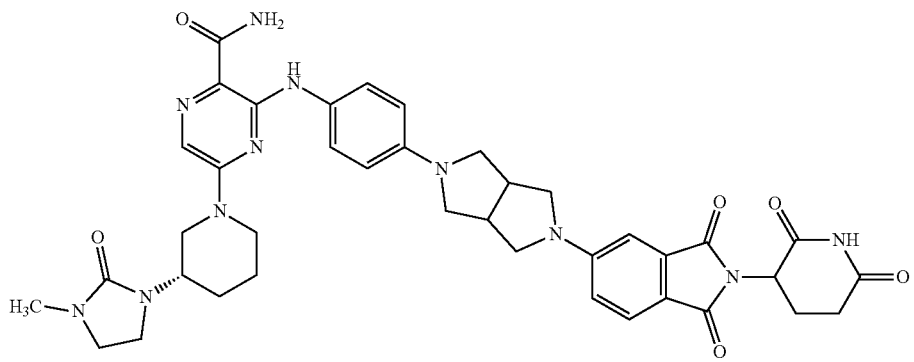 [SMILES: CN1CCN([C@H]2CCCN(c3cnc(C(N)=O)c(Nc4ccc(N5CC6CN(c7ccc8c(c7)C(=O)N(C7CCC(=O)NC7=O)C8=O)CC6C5)cc4)n3)C2)C1=O] |
| 80 | 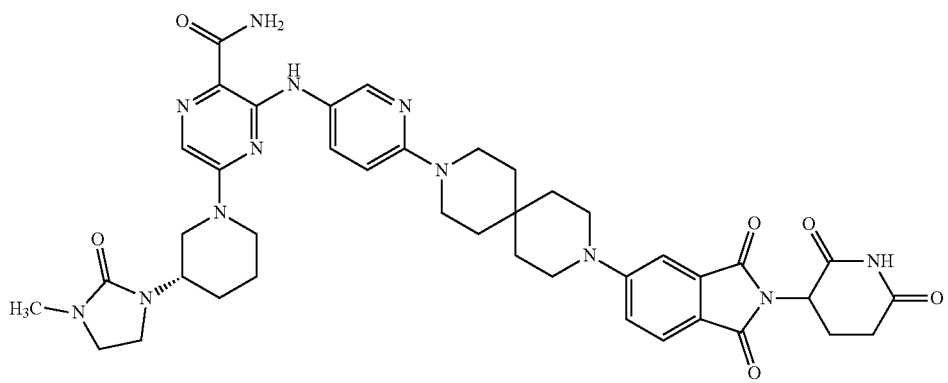 [SMILES: CN1CCN([C@H]2CCCN(c3cnc(C(N)=O)c(Nc4ccc(N5CCC6(CCN(c7ccc8c(c7)C(=O)N(C7CCC(=O)NC7=O)C8=O)CC6)CC5)nc4)n3)C2)C1=O] |
| 81 | 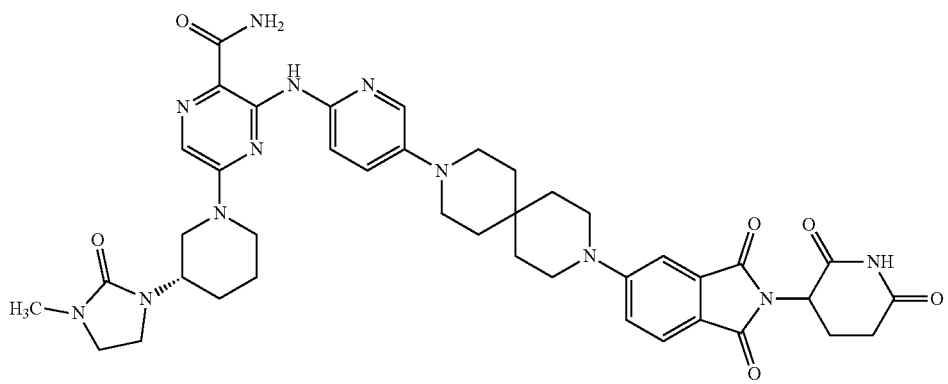 |
| 82 | 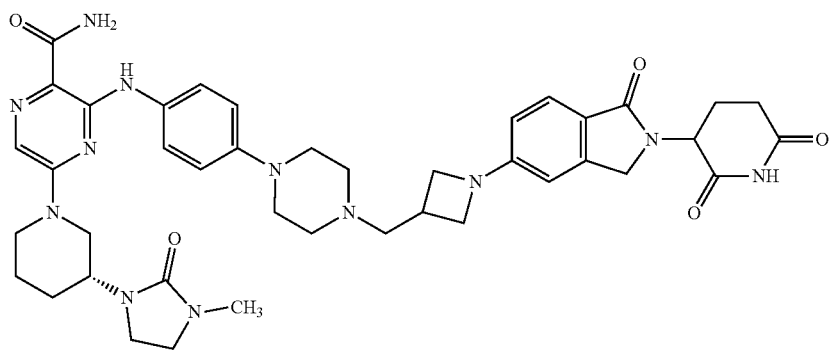 [SMILES: CN1CCN([C@@H]2CCCN(c3cnc(C(N)=O)c(Nc4ccc(N5CCN(CC6CN(c7ccc8c(c7)CN(C7CCC(=O)NC7=O)C8=O)C6)CC5)cc4)n3)C2)C1=O] |

TABLE 1-continued
| Compound Number | Structure |
|---|---|
| 83 | 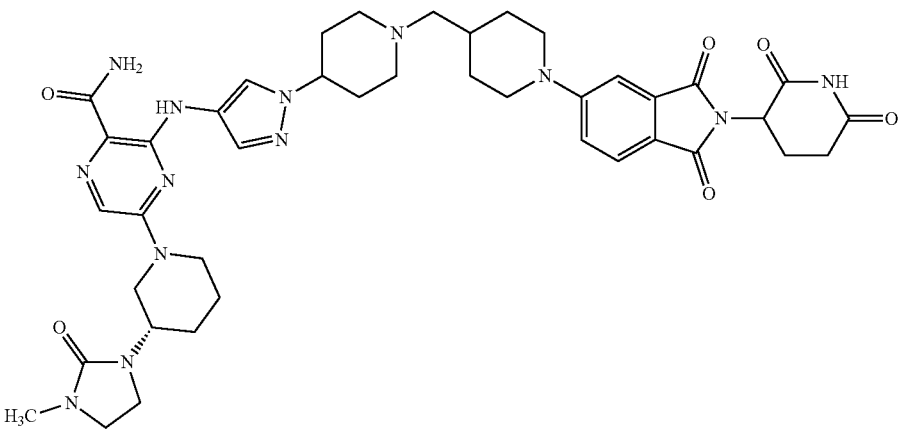 [SMILES: CN1CCN([C@H]2CCCN(c3cnc(C(N)=O)c(Nc4cnn(C5CCN(CC6CCN(c7ccc8c(c7)C(=O)N(C7CCC(=O)NC7=O)C8=O)CC6)CC5)c4)n3)C2)C1=O] |
| 84 | 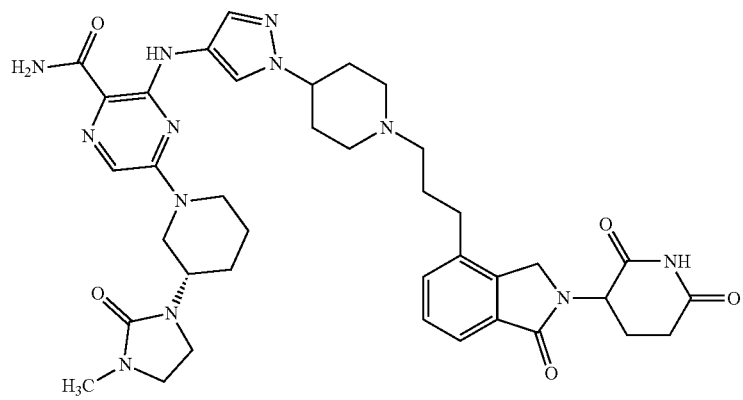 [SMILES: CN1CCN([C@H]2CCCN(c3cnc(C(N)=O)c(Nc4cnn(C5CCN(CCCc6cccc7c6CN(C6CCC(=O)NC6=O)C7=O)CC5)c4)n3)C2)C1=O] |
| 85 | 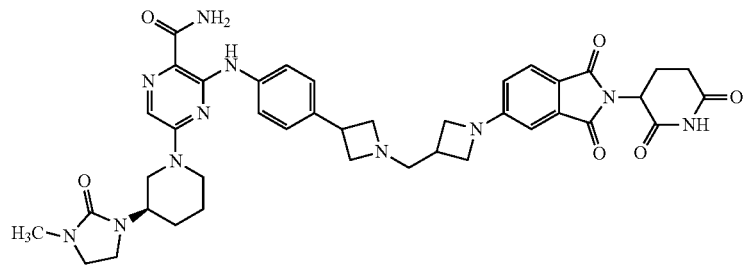 [SMILES: CN1CCN([C@@H]2CCCN(c3cnc(C(N)=O)c(Nc4ccc(C5CN(CC6CN(c7ccc8c(c7)C(=O)N(C7CCC(=O)NC7=O)C8=O)C6)C5)cc4)n3)C2)C1=O] |
| 86 | 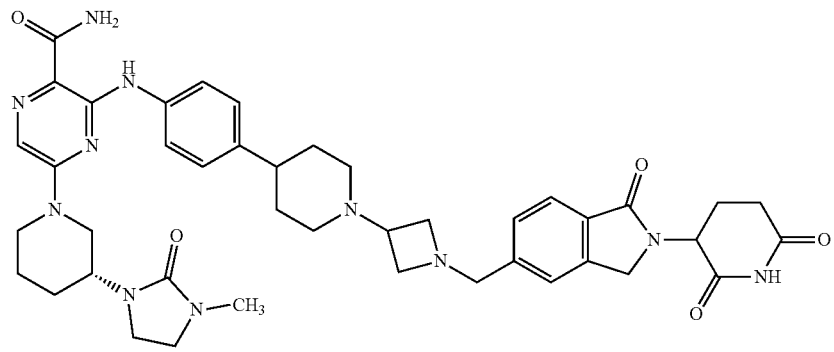 [SMILES: CN1CCN([C@@H]2CCCN(c3cnc(C(N)=O)c(Nc4ccc(C5CCN(C6CN(Cc7ccc8c(c7)CN(C7CCC(=O)NC7=O)C8=O)C6)CC5)cc4)n3)C2)C1=O] |

TABLE 1-continued
| Compound Number | Structure |
|---|---|
| 87 | 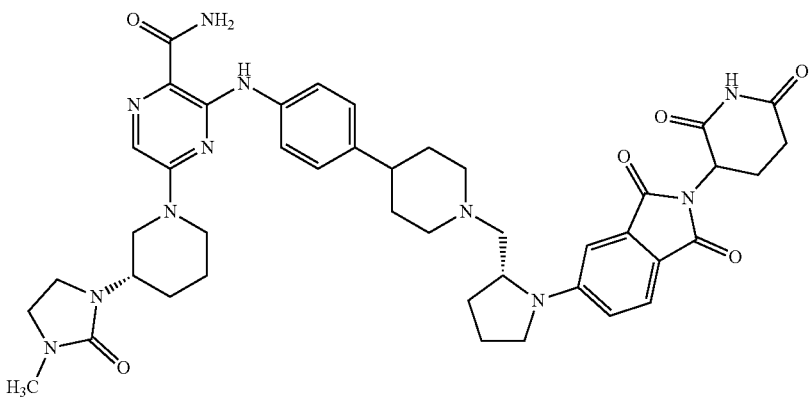 [SMILES: CN1CCN([C@H]2CCCN(c3cnc(C(N)=O)c(Nc4ccc(C5CCN(C[C@H]6CCCN6c6ccc7c(c6)C(=O)N(C6CCC(=O)NC6=O)C7=O)CC5)cc4)n3)C2)C1=O] |
| 88 | 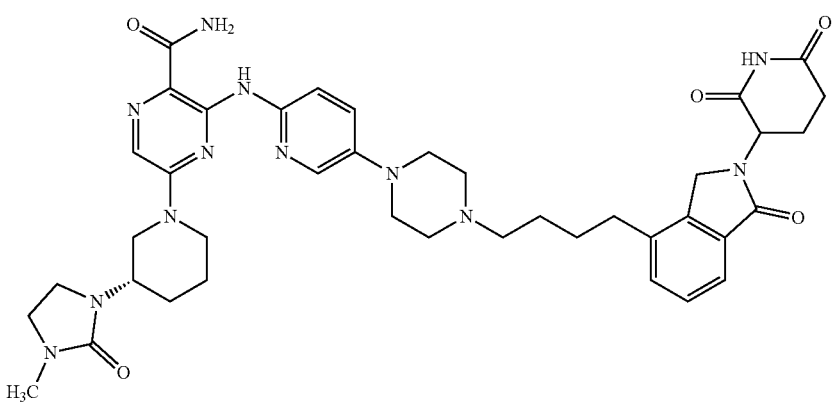 [SMILES: CN1CCN([C@H]2CCCN(c3cnc(C(N)=O)c(Nc4ccc(N5CCN(CCCCc6cccc7c6CN(C6CCC(=O)NC6=O)C7=O)CC5)cn4)n3)C2)C1=O] |
| 89 | 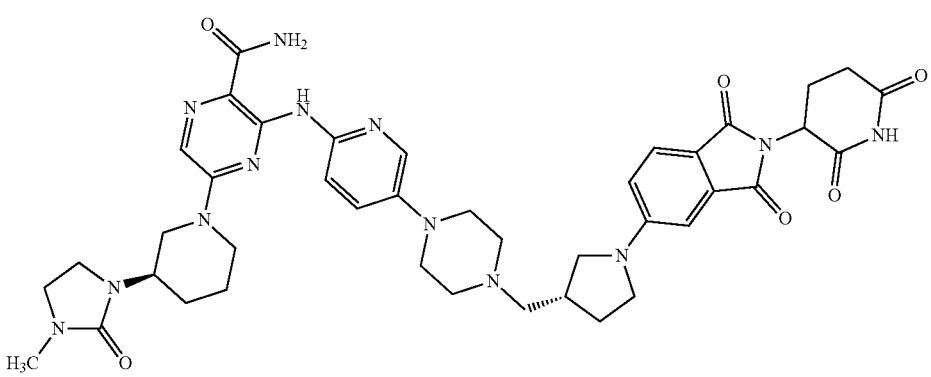 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)cn4)n3)C2)C1=O] |
| 90 | 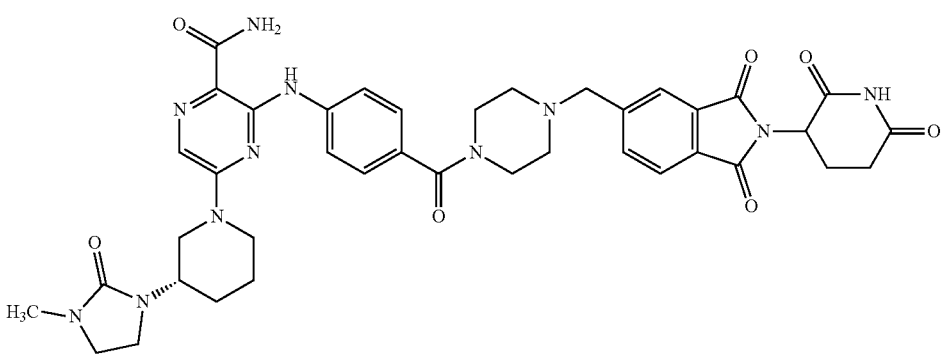 [SMILES: CN1CCN([C@H]2CCCN(c3cnc(C(N)=O)c(Nc4ccc(C(=O)N5CCN(Cc6ccc7c(c6)C(=O)N(C6CCC(=O)NC6=O)C7=O)CC5)cc4)n3)C2)C1=O] |

TABLE 1-continued
| Compound Number | Structure |
|---|---|
| 91 | 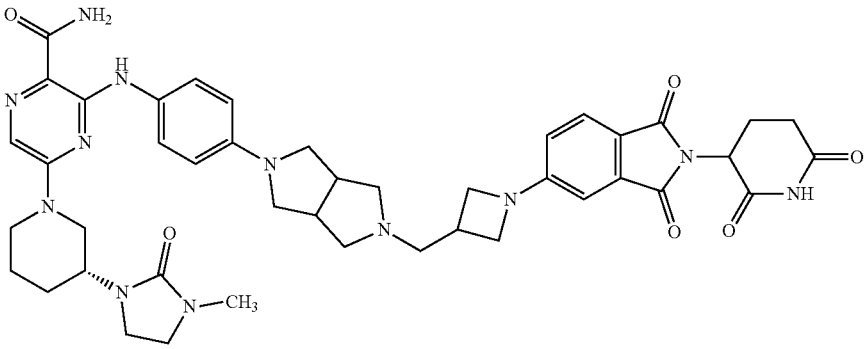 [SMILES: CN1CCN([C@@H]2CCCN(c3cnc(C(N)=O)c(Nc4ccc(N5CC6CN(CC7CN(c8ccc9c(c8)C(=O)N(C8CCC(=O)NC8=O)C9=O)C7)CC6C5)cc4)n3)C2)C1=O] |
| 92 | 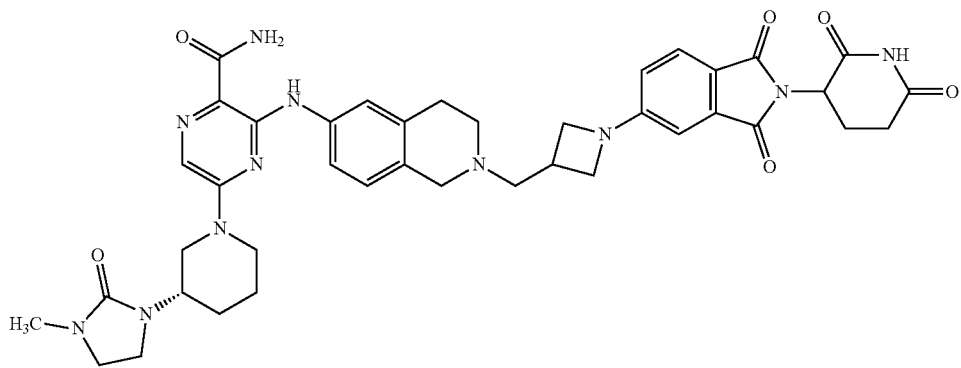 [SMILES: CN1CCN([C@H]2CCCN(c3cnc(C(N)=O)c(Nc4ccc5c(c4)CCN(CC4CN(c6ccc7c(c6)C(=O)N(C6CCC(=O)NC6=O)C7=O)C4)C5)n3)C2)C1=O] |
| 93 | 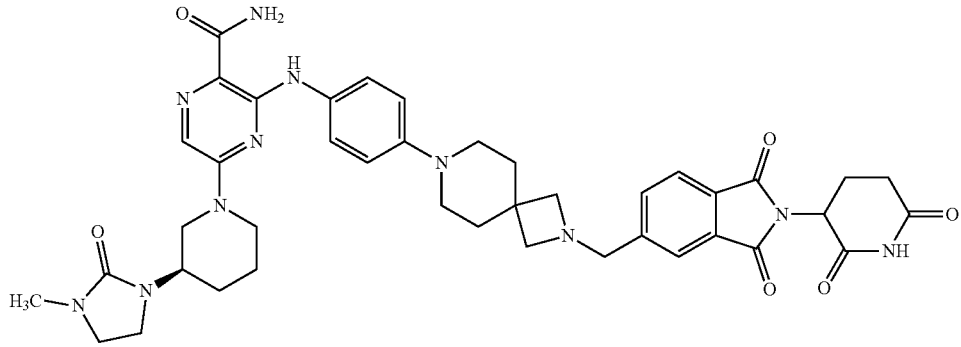 [SMILES: CN1CCN([C@@H]2CCCN(c3cnc(C(N)=O)c(Nc4ccc(N5CCC6(CC5)CN(Cc5ccc7c(c5)C(=O)N(C5CCC(=O)NC5=O)C7=O)C6)cc4)n3)C2)C1=O] |
| 94 | 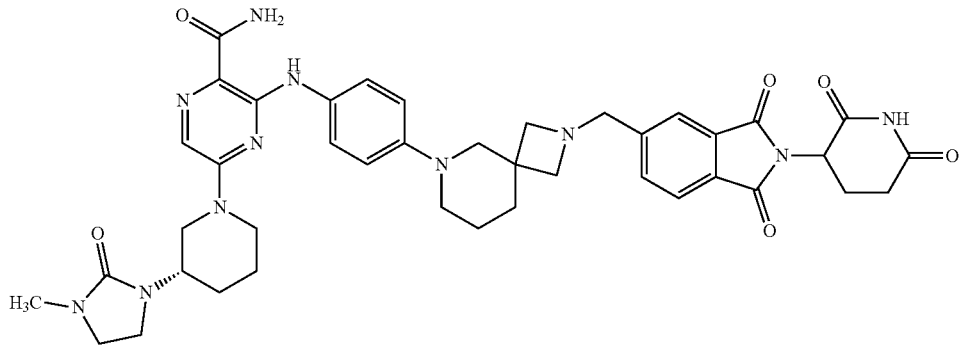 [SMILES: CN1CCN([C@H]2CCCN(c3cnc(C(N)=O)c(Nc4ccc(N5CCCC6(CN(Cc7ccc8c(c7)C(=O)N(C7CCC(=O)NC7=O)C8=O)C6)C5)cc4)n3)C2)C1=O] |

TABLE 1-continued
| Compound Number | Structure |
|---|---|
| 95 | 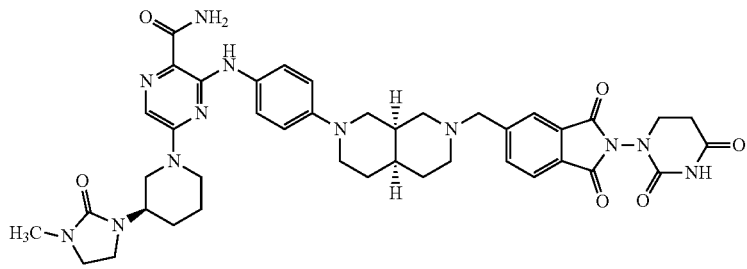 [SMILES: CN1CCN([C@@H]2CCCN(c3cnc(C(N)=O)c(Nc4ccc(N5CC[C@@H]6CCN(Cc7ccc8c(c7)C(=O)N(N7CCC(=O)NC7=O)C8=O)C[C@@H]6C5)cc4)n3)C2)C1=O] |
| 96 | 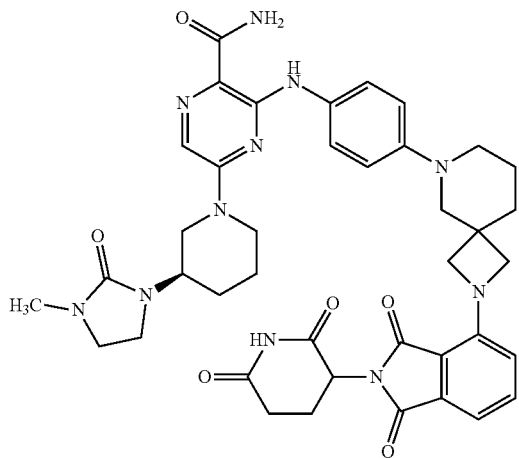 [SMILES: CN1CCN([C@@H]2CCCN(c3cnc(C(N)=O)c(Nc4ccc(N5CCCC6(C5)CN(c5cccc7c5C(=O)N(C5CCC(=O)NC5=O)C7=O)C6)cc4)n3)C2)C1=O] |
| 97 | 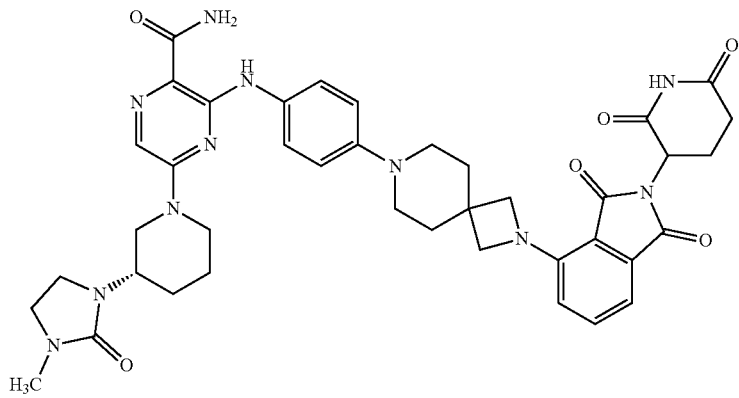 [SMILES: CN1CCN([C@H]2CCCN(c3cnc(C(N)=O)c(Nc4ccc(N5CCC6(CC5)CN(c5cccc7c5C(=O)N(C5CCC(=O)NC5=O)C7=O)C6)cc4)n3)C2)C1=O] |
| 98 | 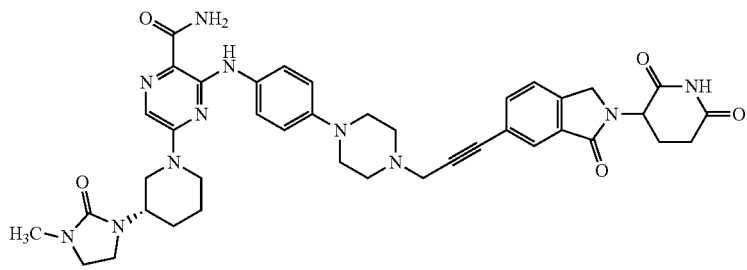 [SMILES: CN1CCN([C@H]2CCCN(c3cnc(C(N)=O)c(Nc4ccc(N5CCN(CC#Cc6ccc7c(c6)C(=O)N(C6CCC(=O)NC6=O)C7)CC5)cc4)n3)C2)C1=O] |

TABLE 1-continued
| Compound Number | Structure |
|---|---|
| 99 | 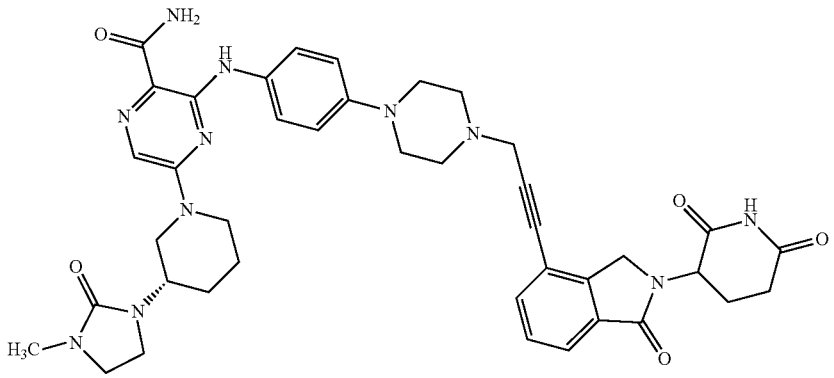 [SMILES: CN1CCN([C@H]2CCCN(c3cnc(C(N)=O)c(Nc4ccc(N5CCN(CC#Cc6cccc7c6CN(C6CCC(=O)NC6=O)C7=O)CC5)cc4)n3)C2)C1=O] |
| 100 | 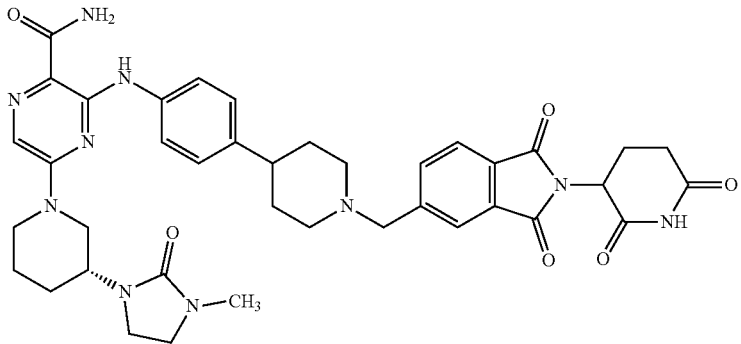 [SMILES: CN1CCN([C@@H]2CCCN(c3cnc(C(N)=O)c(Nc4ccc(C5CCN(Cc6ccc7c(c6)C(=O)N(C6CCC(=O)NC6=O)C7=O)CC5)cc4)n3)C2)C1=O] |
| 101 | 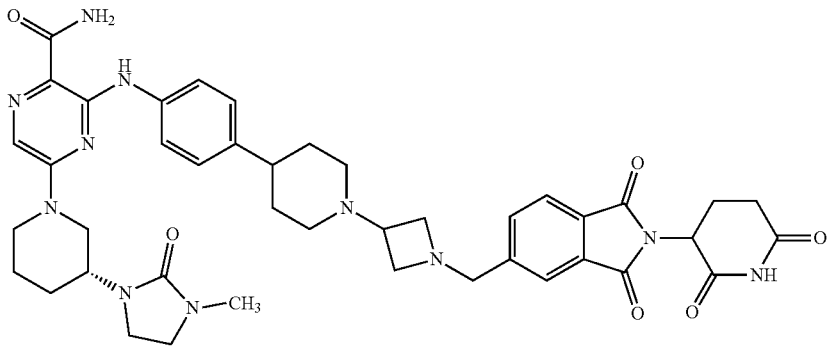 [SMILES: CN1CCN([C@@H]2CCCN(c3cnc(C(N)=O)c(Nc4ccc(C5CCN(C6CN(Cc7ccc8c(c7)C(=O)N(C7CCC(=O)NC7=O)C8=O)C6)CC5)cc4)n3)C2)C1=O] |
| 102 | 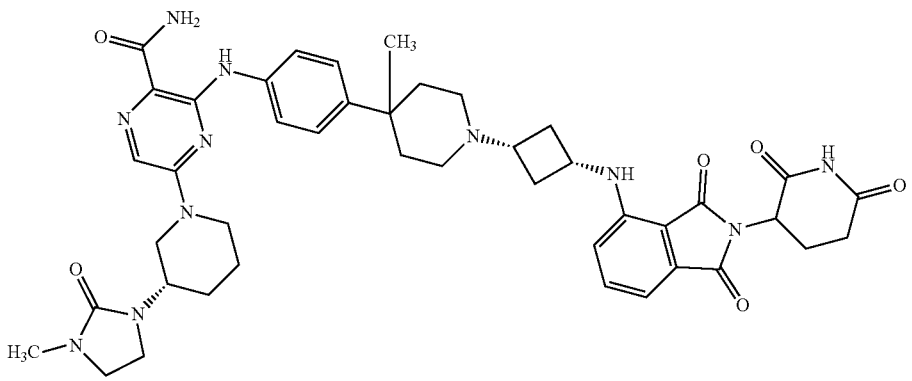 [SMILES: CN1CCN([C@H]2CCCN(c3cnc(C(N)=O)c(Nc4ccc(C5(C)CCN([C@H]6C[C@@H](Nc7cccc8c7C(=O)N(C7CCC(=O)NC7=O)C8=O)C6)CC5)cc4)n3)C2)C1=O] |

TABLE 1-continued
| Compound Number | Structure |
|---|---|
| 103 | 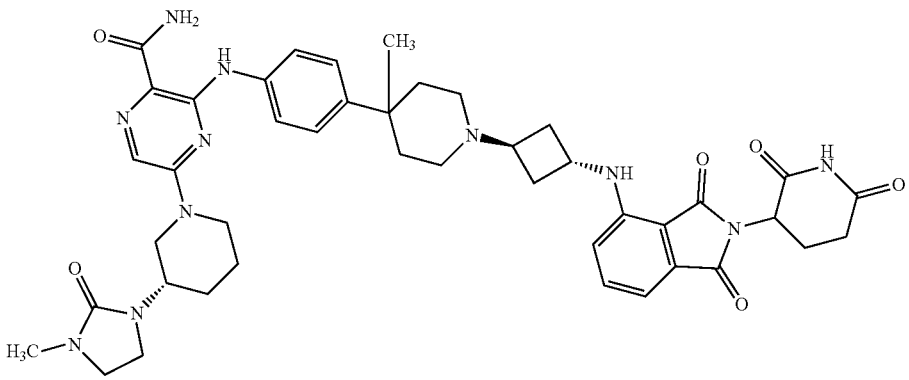 [SMILES: CN1CCN([C@H]2CCCN(c3cnc(C(N)=O)c(Nc4ccc(C5(C)CCN([C@H]6C[C@H](Nc7cccc8c7C(=O)N(C7CCC(=O)NC7=O)C8=O)C6)CC5)cc4)n3)C2)C1=O] |
| 104 | 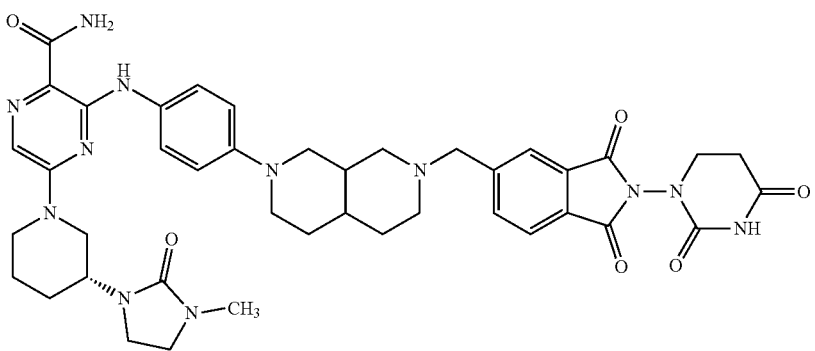 [SMILES: CN1CCN([C@@H]2CCCN(c3cnc(C(N)=O)c(Nc4ccc(N5CCC6CCN(Cc7ccc8c(c7)C(=O)N(N7CCC(=O)NC7=O)C8=O)CC6C5)cc4)n3)C2)C1=O] |
| 105 | 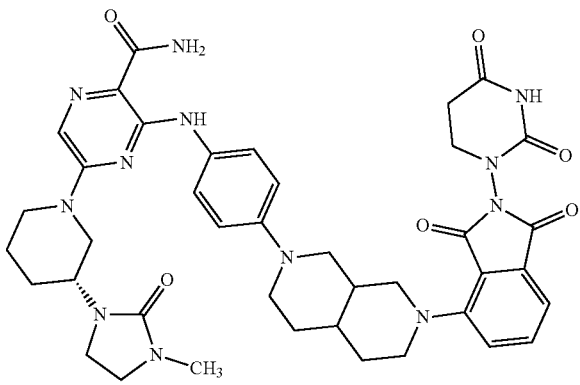 [SMILES: CN1CCN([C@@H]2CCCN(c3cnc(C(N)=O)c(Nc4ccc(N5CCC6CCN(c7cccc8c7C(=O)N(N7CCC(=O)NC7=O)C8=O)CC6C5)cc4)n3)C2)C1=O] |
| 106 | 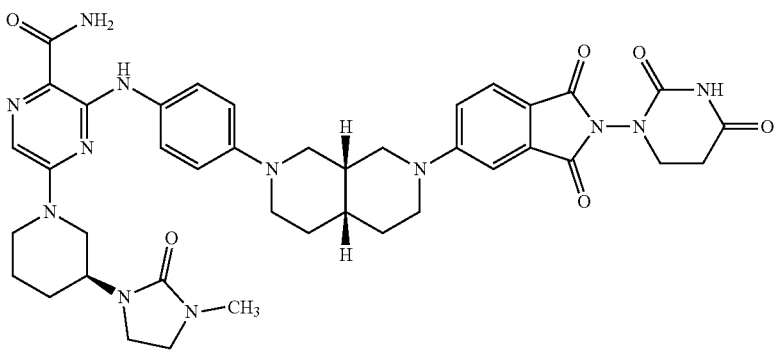 [SMILES: CN1CCN([C@H]2CCCN(c3cnc(C(N)=O)c(Nc4ccc(N5CC[C@H]6CCN(c7ccc8c(c7)C(=O)N(N7CCC(=O)NC7=O)C8=O)C[C@H]6C5)cc4)n3)C2)C1=O] |

TABLE 1-continued
| Compound Number | Structure |
|---|---|
| 107 | 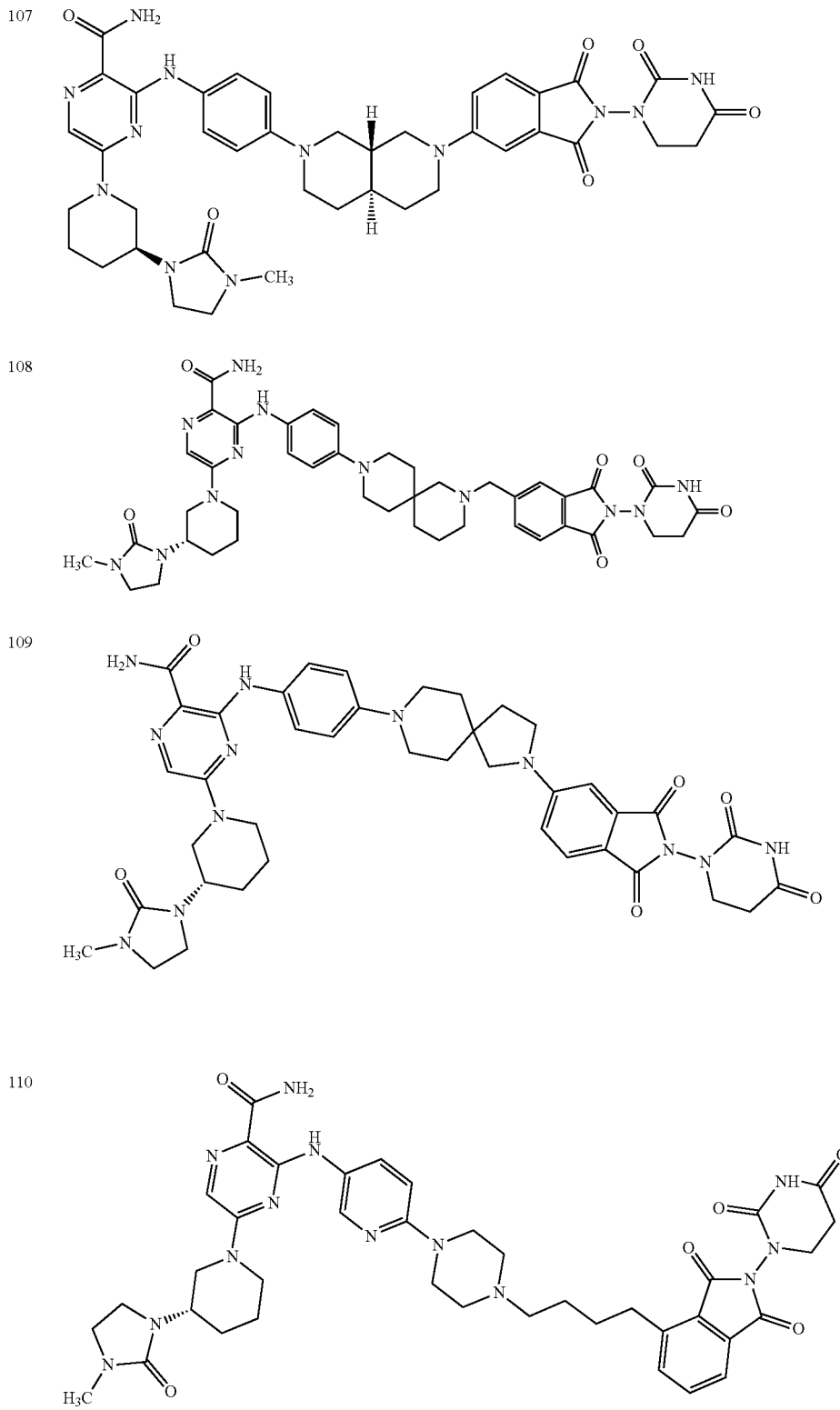 |
| 108 | 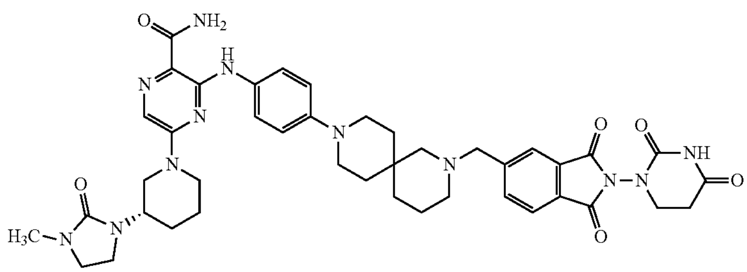 [SMILES: CN1CCN([C@H]2CCCN(c3cnc(C(N)=O)c(Nc4ccc(N5CCC6(CCCN(Cc7ccc8c(c7)C(=O)N(N7CCC(=O)NC7=O)C8=O)C6)CC5)cc4)n3)C2)C1=O] |
| 109 | 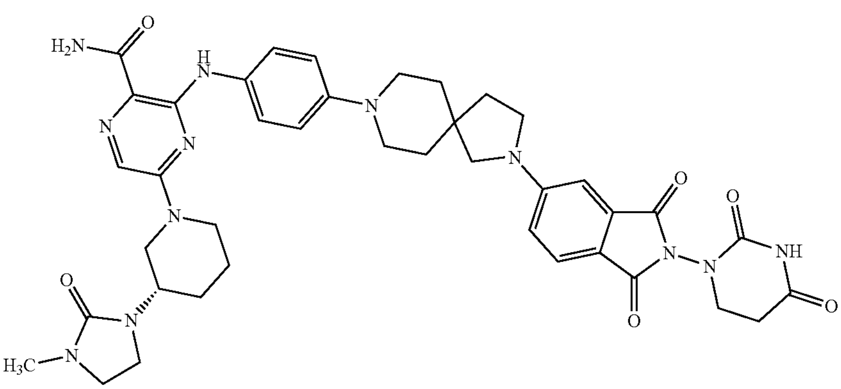 [SMILES: CN1CCN([C@H]2CCCN(c3cnc(C(N)=O)c(Nc4ccc(N5CCC6(CC5)CCN(c5ccc7c(c5)C(=O)N(N5CCC(=O)NC5=O)C7=O)C6)cc4)n3)C2)C1=O] |
| 110 | 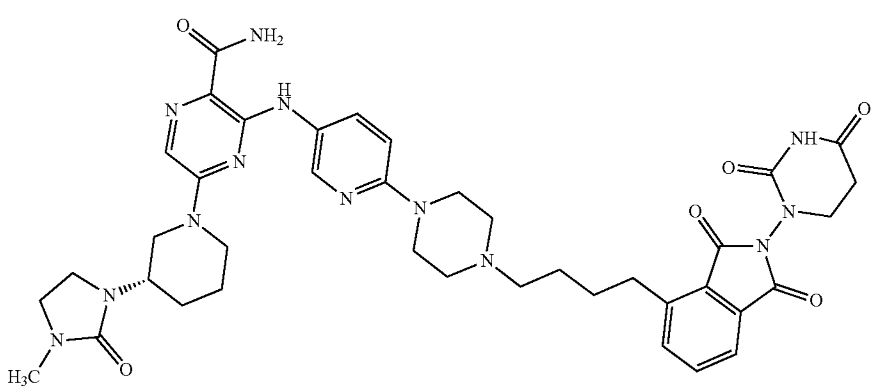 [SMILES: CN1CCN([C@H]2CCCN(c3cnc(C(N)=O)c(Nc4ccc(N5CCN(CCCCc6cccc7c6C(=O)N(N6CCC(=O)NC6=O)C7=O)CC5)nc4)n3)C2)C1=O] |

TABLE 1-continued
| Compound Number | Structure |
|---|---|
| 111 | 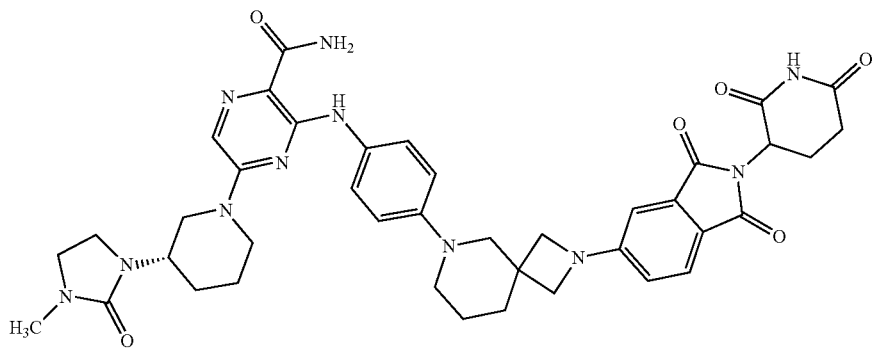 [SMILES: CN1CCN([C@H]2CCCN(c3cnc(C(N)=O)c(Nc4ccc(N5CCCC6(C5)CN(c5ccc7c(c5)C(=O)N(C5CCC(=O)NC5=O)C7=O)C6)cc4)n3)C2)C1=O] |
| 112 | 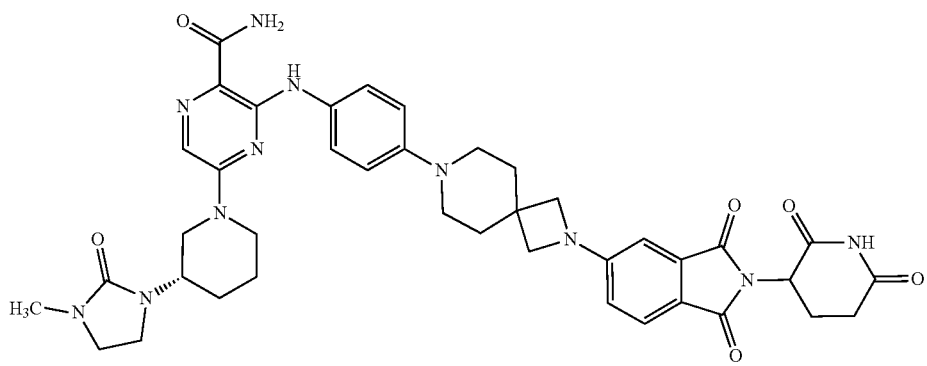 [SMILES: CN1CCN([C@H]2CCCN(c3cnc(C(N)=O)c(Nc4ccc(N5CCC6(CC5)CN(c5ccc7c(c5)C(=O)N(C5CCC(=O)NC5=O)C7=O)C6)cc4)n3)C2)C1=O] |
| 113 | 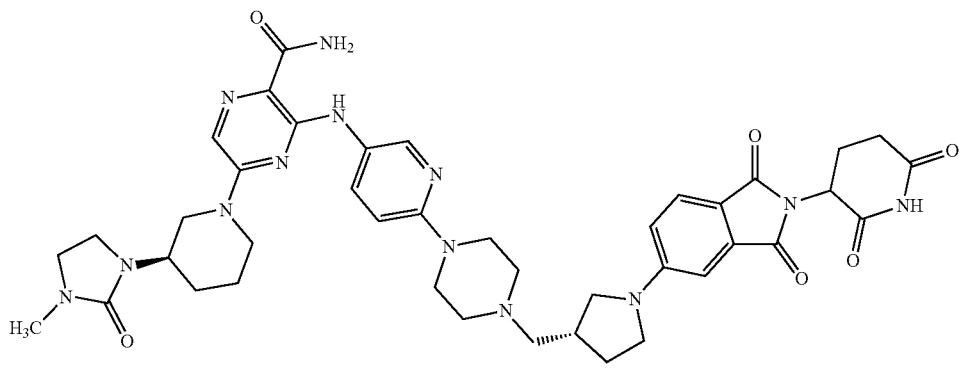 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)nc4)n3)C2)C1=O] |
| 114 | 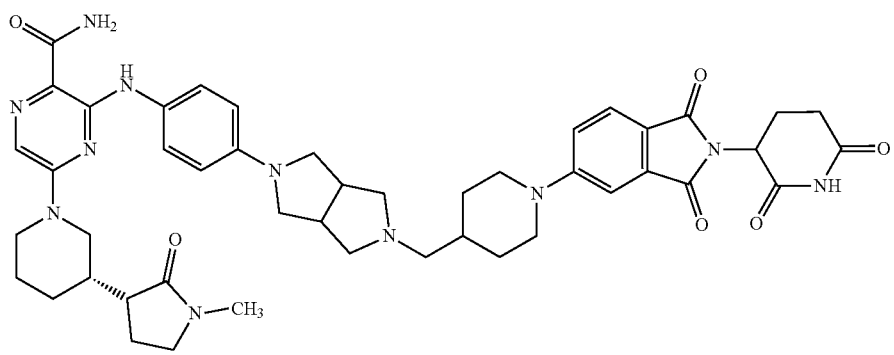 [SMILES: CN1CCC([C@@H]2CCCN(c3cnc(C(N)=O)c(Nc4ccc(N5CC6CN(CC7CCN(c8ccc9c(c8)C(=O)N(C8CCC(=O)NC8=O)C9=O)CC7)CC6C5)cc4)n3)C2)C1=O] |

TABLE 1-continued
| Compound Number | Structure |
|---|---|
| 115 | 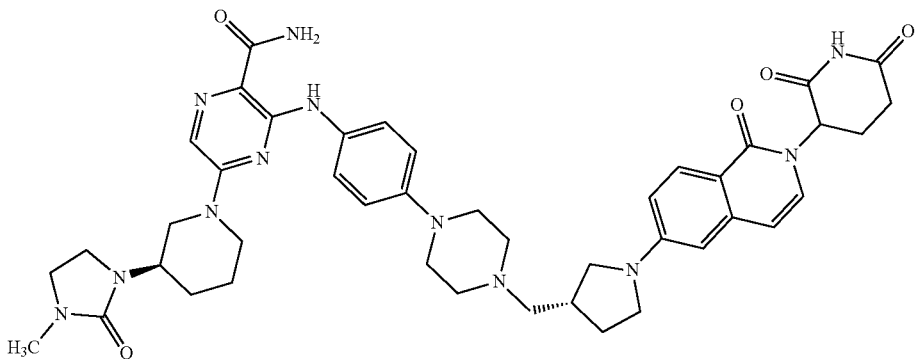 [SMILES: CN1CCN([C@@H]2CCCN(c3cnc(C(N)=O)c(Nc4ccc(N5CCN(C[C@H]6CCN(c7ccc8c(=O)n(C9CCC(=O)NC9=O)ccc8c7)C6)CC5)cc4)n3)C2)C1=O] |
| 116 | 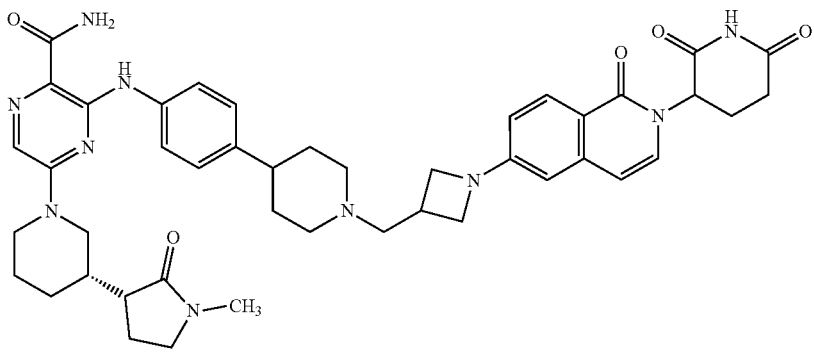 [SMILES: CN1CCC([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |
| 117 | 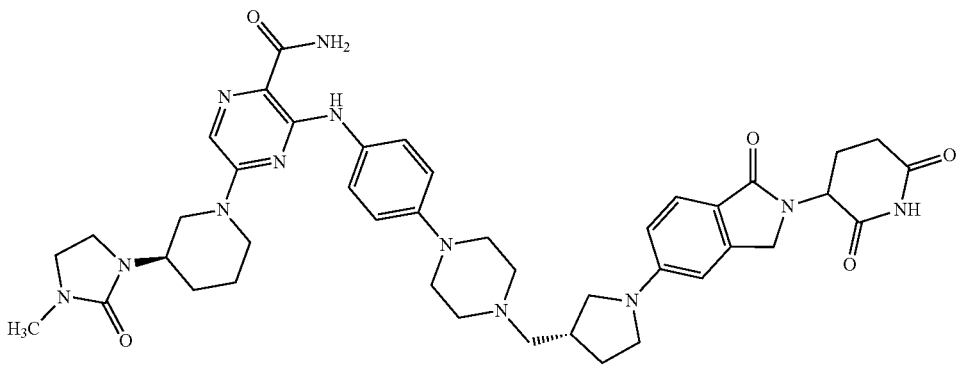 [SMILES: CN1CCN([C@@H]2CCCN(c3cnc(C(N)=O)c(Nc4ccc(N5CCN(C[C@H]6CCN(c7ccc8c(c7)CN(C7CCC(=O)NC7=O)C8=O)C6)CC5)cc4)n3)C2)C1=O] |
| 118 | 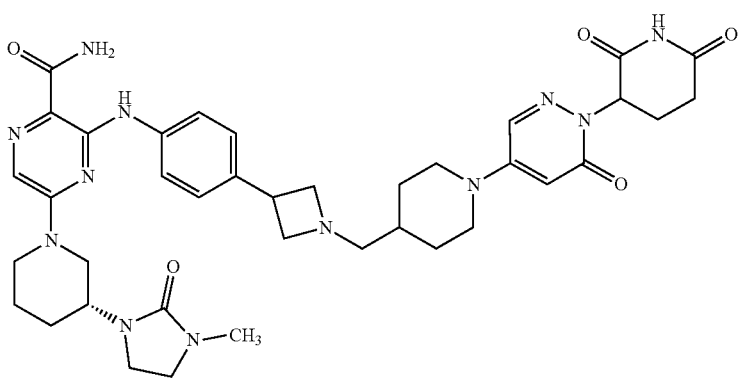 [SMILES: CN1CCN([C@@H]2CCCN(c3cnc(C(N)=O)c(Nc4ccc(C5CN(CC6CCN(c7cnn(C8CCC(=O)NC8=O)c(=O)c7)CC6)C5)cc4)n3)C2)C1=O] |

TABLE 1-continued
| Compound Number | Structure |
|---|---|
| 119 | 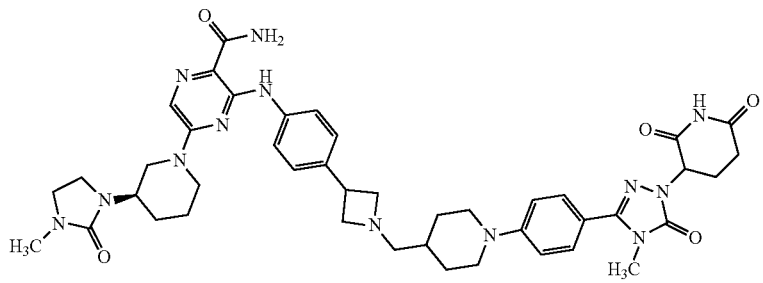 [SMILES: CN1CCN([C@@H]2CCCN(c3cnc(C(N)=O)c(Nc4ccc(C5CN(CC6CCN(c7ccc(-c8nn(C9CCC(=O)NC9=O)c(=O)n8C)cc7)CC6)C5)cc4)n3)C2)C1=O] |
| 120 | 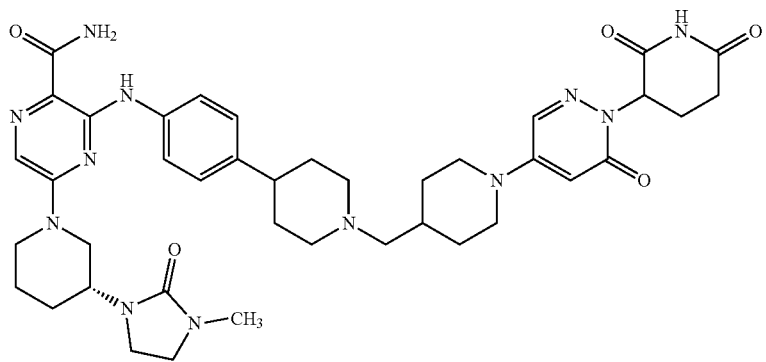 [SMILES: CN1CCN([C@@H]2CCCN(c3cnc(C(N)=O)c(Nc4ccc(C5CCN(CC6CCN(c7cnn(C8CCC(=O)NC8=O)c(=O)c7)CC6)CC5)cc4)n3)C2)C1=O] |
| 121 | 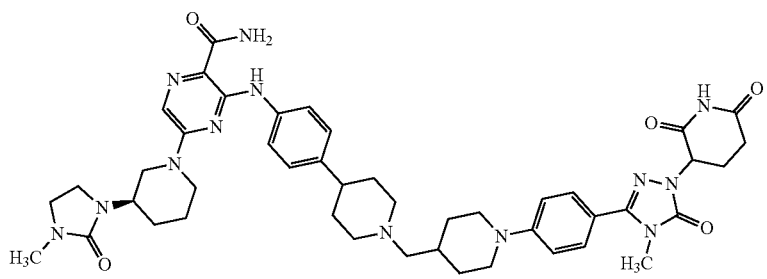 [SMILES: CN1CCN([C@@H]2CCCN(c3cnc(C(N)=O)c(Nc4ccc(C5CCN(CC6CCN(c7ccc(-c8nn(C9CCC(=O)NC9=O)c(=O)n8C)cc7)CC6)CC5)cc4)n3)C2)C1=O] |
| 122 | 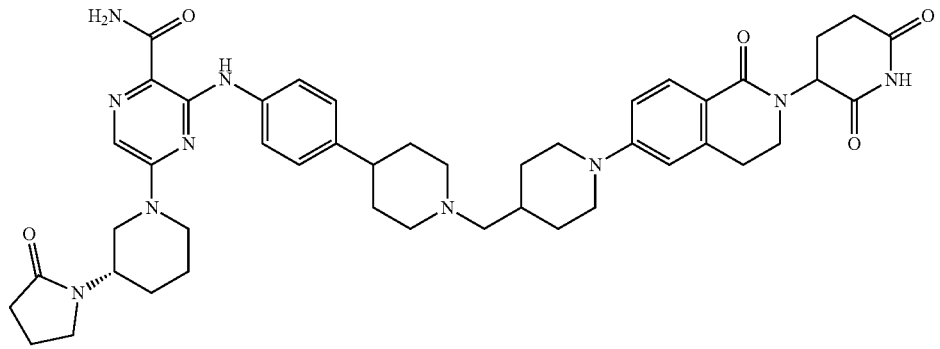 [SMILES: NC(=O)c1ncc(N2CCC[C@H](N3CCCC3=O)C2)nc1Nc1ccc(C2CCN(CC3CCN(c4ccc5c(c4)CCN(C4CCC(=O)NC4=O)C5=O)CC3)CC2)cc1] |

TABLE 1-continued
| Compound Number | Structure |
|---|---|
| 123 | 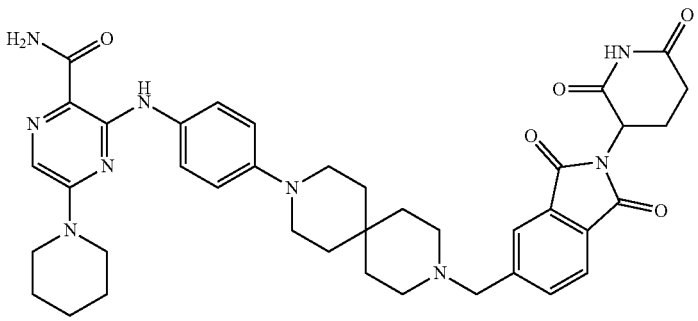 [SMILES: NC(=O)c1ncc(N2CCCCC2)nc1Nc1ccc(N2CCC3(CCN(Cc4ccc5c(c4)C(=O)N(C4CCC(=O)NC4=O)C5=O)CC3)CC2)cc1] |
| 124 | 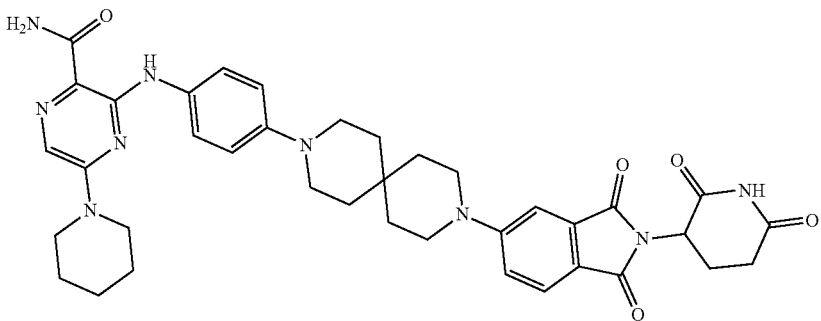 [SMILES: NC(=O)c1ncc(N2CCCCC2)nc1Nc1ccc(N2CCC3(CC2)CCN(c2ccc4c(c2)C(=O)N(C2CCC(=O)NC2=O)C4=O)CC3)cc1] |
| 125 | 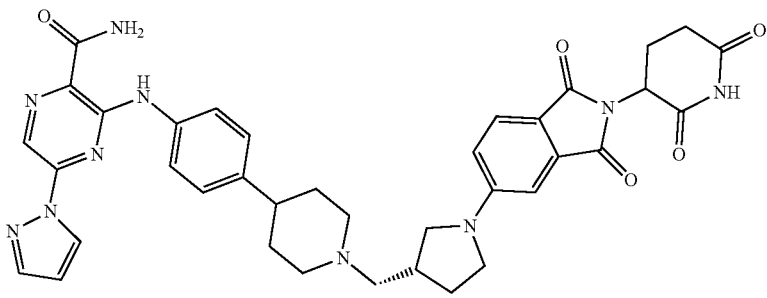 |
| 126 | 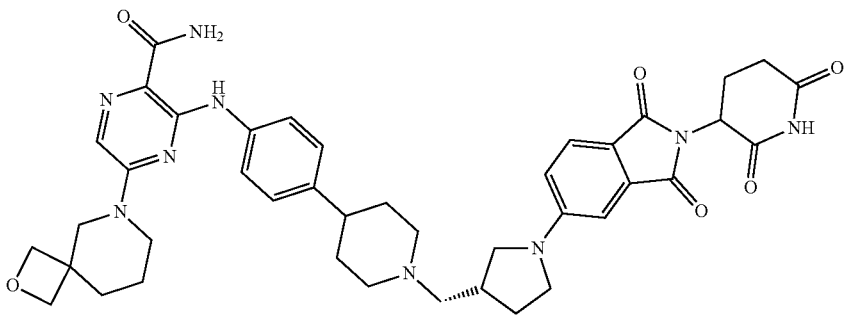 |

TABLE 1-continued

| Compound Number | Structure |
| --- | --- |
| 127 | 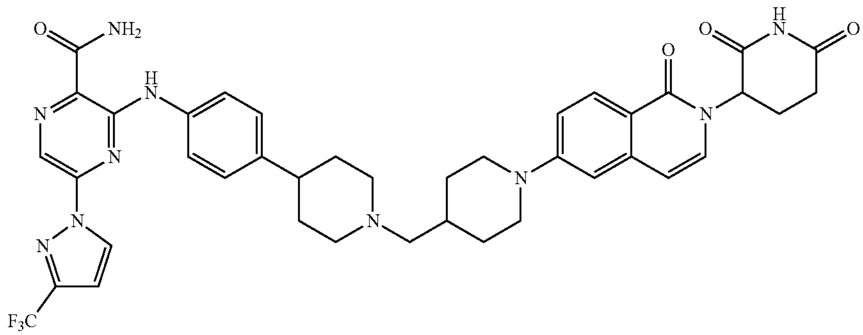 [SMILES: NC(=O)c1ncc(-n2ccc(C(F)(F)F)n2)nc1Nc1ccc(C2CCN(CC3CCN(c4ccc5c(=O)n(C6CCC(=O)NC6=O)ccc5c4)CC3)CC2)cc1] |
| 128 | 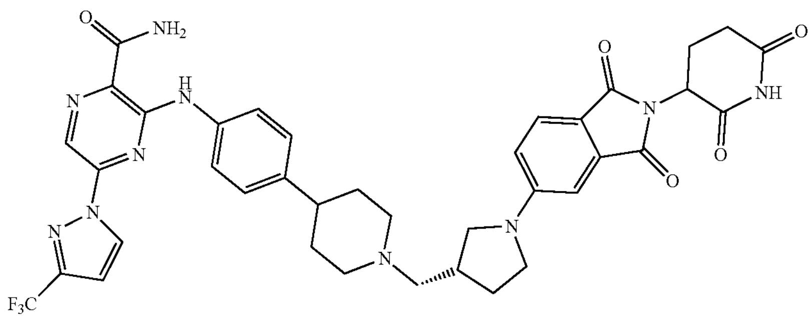 |
| 129 | 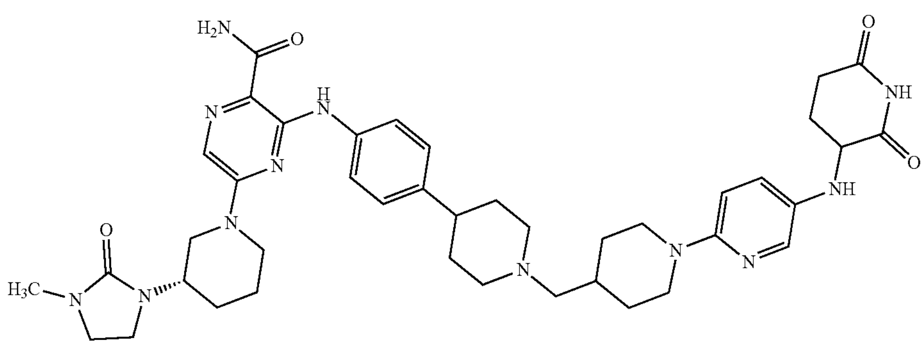 [SMILES: CN1CCN([C@H]2CCCN(c3cnc(C(N)=O)c(Nc4ccc(C5CCN(CC6CCN(c7ccc(NC8CCC(=O)NC8=O)cn7)CC6)CC5)cc4)n3)C2)C1=O] |
| 130 | 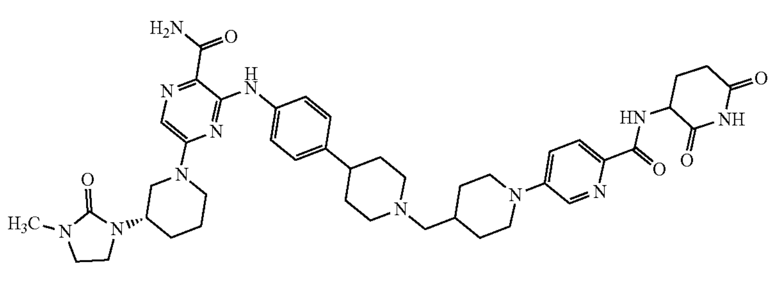 [SMILES: CN1CCN([C@H]2CCCN(c3cnc(C(N)=O)c(Nc4ccc(C5CCN(CC6CCN(c7ccc(C(=O)NC8CCC(=O)NC8=O)nc7)CC6)CC5)cc4)n3)C2)C1=O] |
| 131 | 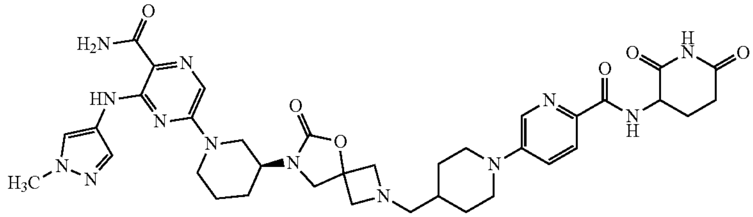 [SMILES: Cn1cc(Nc2nc(N3CCC[C@H](N4CC5(CN(CC6CCN(c7ccc(C(=O)NC8CCC(=O)NC8=O)nc7)CC6)C5)OC4=O)C3)cnc2C(N)=O)cn1] |

TABLE 1-continued
| Compound Number | Structure |
|---|---|
| 132 | 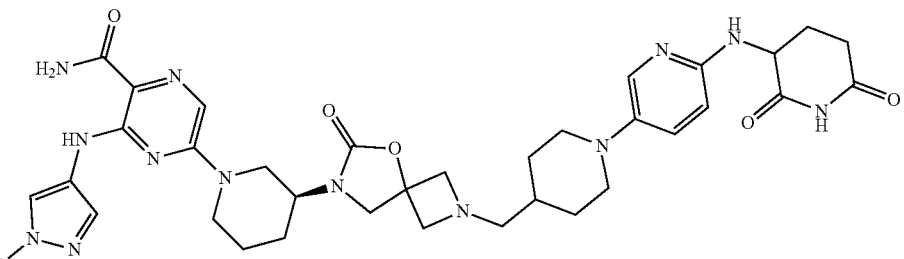 |
| 133 | 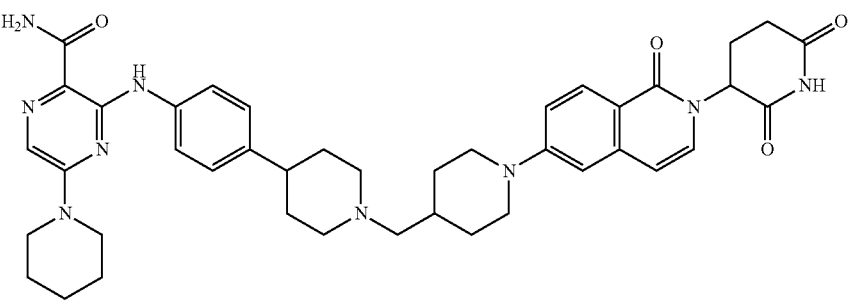 [SMILES: NC(=O)c1ncc(N2CCCCC2)nc1Nc1ccc(C2CCN(CC3CCN(c4ccc5c(=O)n(C6CCC(=O)NC6=O)ccc5c4)CC3)CC2)cc1] |
| 134 | 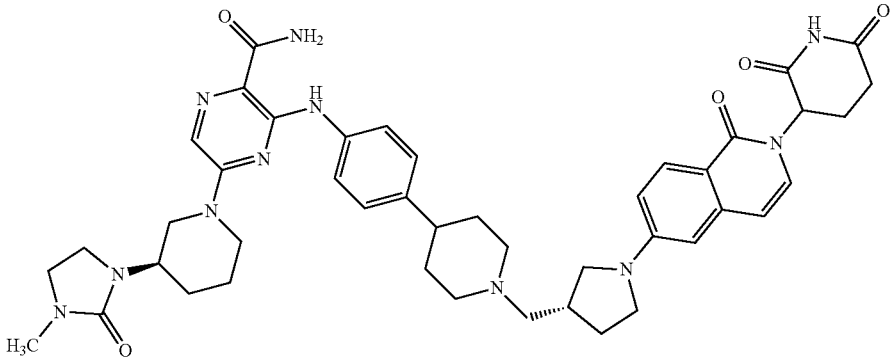 [SMILES: CN1CCN([C@@H]2CCCN(c3cnc(C(N)=O)c(Nc4ccc(C5CCN(C[C@H]6CCN(c7ccc8c(=O)n(C9CCC(=O)NC9=O)ccc8c7)C6)CC5)cc4)n3)C2)C1=O] |
| 135 | 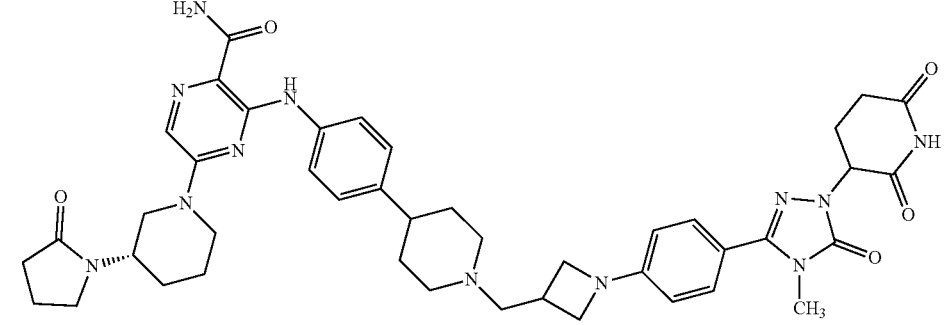 [SMILES: Cn1c(-c2ccc(N3CC(CN4CCC(c5ccc(Nc6nc(N7CCC[C@H](N8CCCC8=O)C7)cnc6C(N)=O)cc5)CC4)C3)cc2)nn(C2CCC(=O)NC2=O)c1=O] |
| 136 | 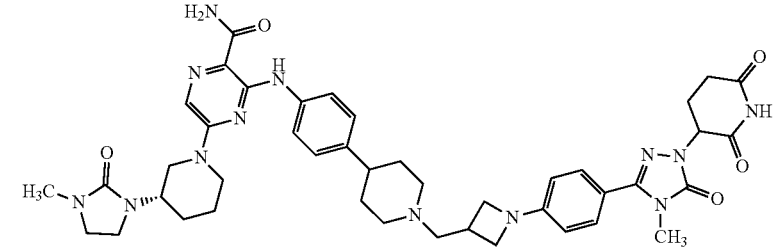 [SMILES: CN1CCN([C@H]2CCCN(c3cnc(C(N)=O)c(Nc4ccc(C5CCN(CC6CN(c7ccc(-c8nn(C9CCC(=O)NC9=O)c(=O)n8C)cc7)C6)CC5)cc4)n3)C2)C1=O] |

TABLE 1-continued

| Compound Number | Structure |
|---|---|
| 137 | 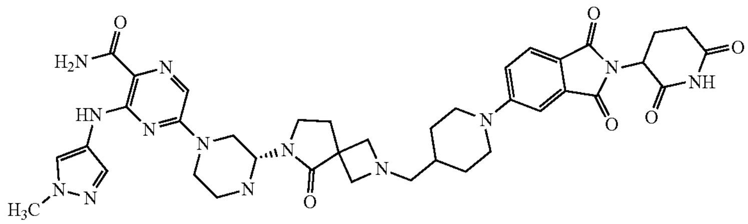 [SMILES: Cn1cc(Nc2nc(N3CCN[C@@H](N4CCC5(CN(CC6CCN(c7ccc8c(c7)C(=O)N(C7CCC(=O)NC7=O)C8=O)CC6)C5)C4=O)C3)cnc2C(N)=O)cn1] |
| 138 | 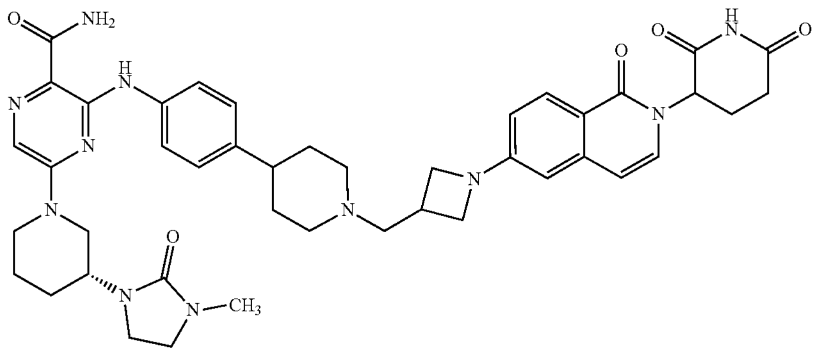 [SMILES: CN1CCN([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |
| 139 | 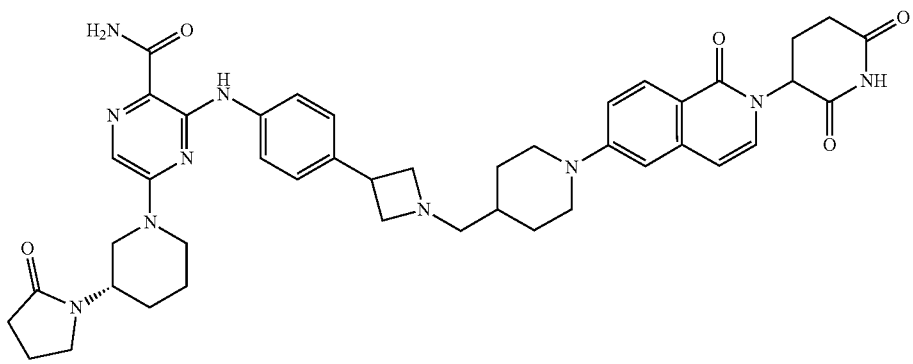 [SMILES: NC(=O)c1ncc(N2CCC[C@H](N3CCCC3=O)C2)nc1Nc1ccc(C2CN(CC3CCN(c4ccc5c(=O)n(C6CCC(=O)NC6=O)ccc5c4)CC3)C2)cc1] |
| 140 | 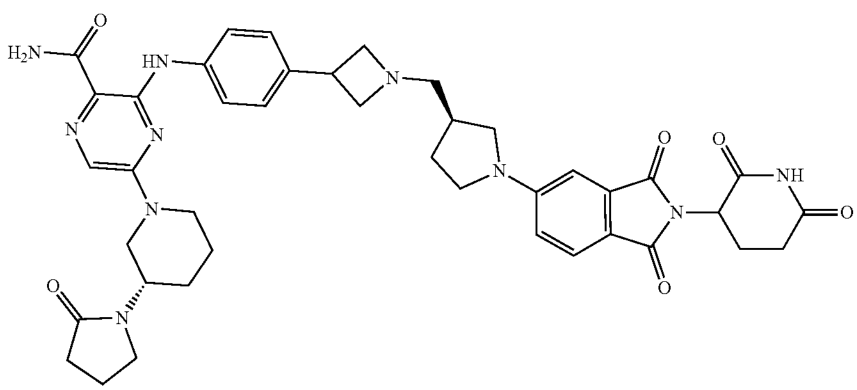 [SMILES: NC(=O)c1ncc(N2CCC[C@H](N3CCCC3=O)C2)nc1Nc1ccc(C2CN(C[C@@H]3CCN(c4ccc5c(c4)C(=O)N(C4CCC(=O)NC4=O)C5=O)C3)C2)cc1] |
| 141 | 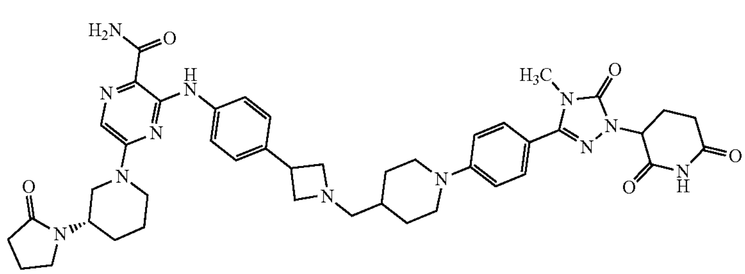 [SMILES: Cn1c(-c2ccc(N3CCC(CN4CC(c5ccc(Nc6nc(N7CCC[C@H](N8CCCC8=O)C7)cnc6C(N)=O)cc5)C4)CC3)cc2)nn(C2CCC(=O)NC2=O)c1=O] |

TABLE 1-continued

| Compound Number | Structure |
|---|---|
| 142 | 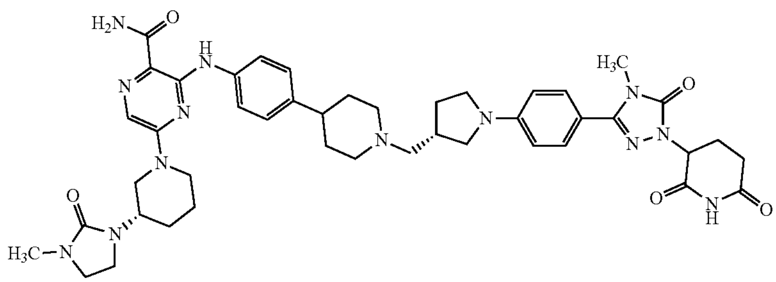 [SMILES: CN1CCN([C@H]2CCCN(c3cnc(C(N)=O)c(Nc4ccc(C5CCN(C[C@@H]6CCN(c7ccc(-c8nn(C9CCC(=O)NC9=O)c(=O)n8C)cc7)C6)CC5)cc4)n3)C2)C1=O] |
| 143 | 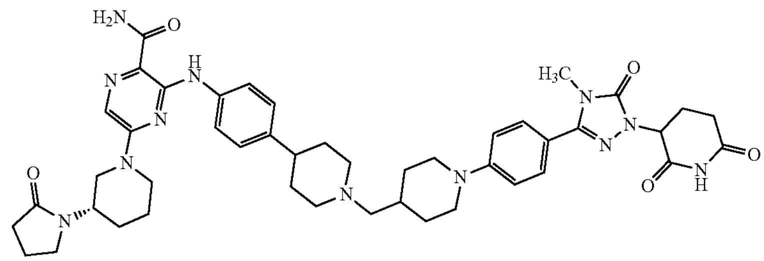 [SMILES: Cn1c(-c2ccc(N3CCC(CN4CCC(c5ccc(Nc6nc(N7CCC[C@H](N8CCCC8=O)C7)cnc6C(N)=O)cc5)CC4)CC3)cc2)nn(C2CCC(=O)NC2=O)c1=O] |
| 144 | 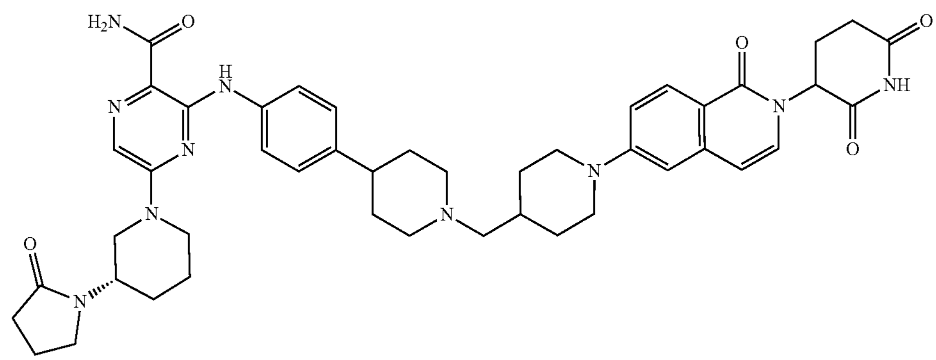 [SMILES: NC(=O)c1ncc(N2CCC[C@H](N3CCCC3=O)C2)nc1Nc1ccc(C2CCN(CC3CCN(c4ccc5c(=O)n(C6CCC(=O)NC6=O)ccc5c4)CC3)CC2)cc1] |
| 145 | 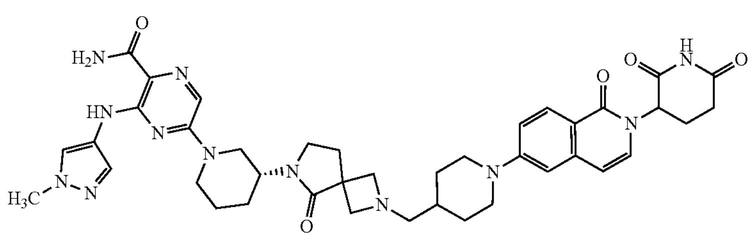 [SMILES: Cn1cc(Nc2nc(N3CCC[C@@H](N4CCC5(CN(CC6CCN(c7ccc8c(=O)n(C9CCC(=O)NC9=O)ccc8c7)CC6)C5)C4=O)C3)cnc2C(N)=O)cn1] |
| 146 | 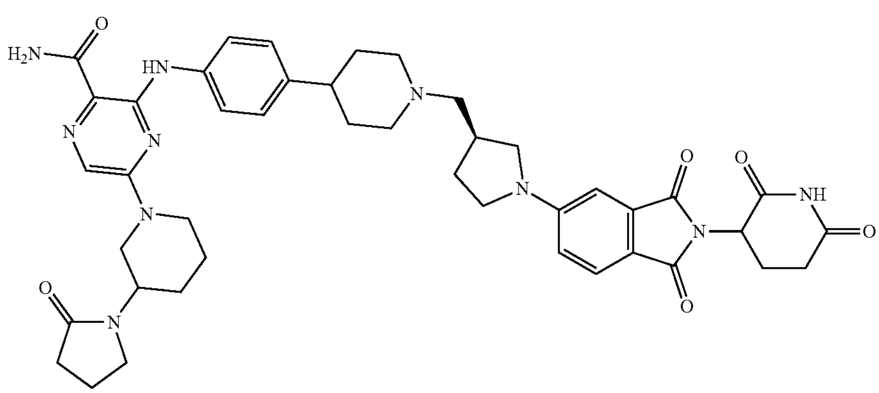 [SMILES: NC(=O)c1ncc(N2CCCC(N3CCCC3=O)C2)nc1Nc1ccc(C2CCN(C[C@@H]3CCN(c4ccc5c(c4)C(=O)N(C4CCC(=O)NC4=O)C5=O)C3)CC2)cc1] |

TABLE 1-continued
| Compound Number | Structure |
|---|---|
| 147 | 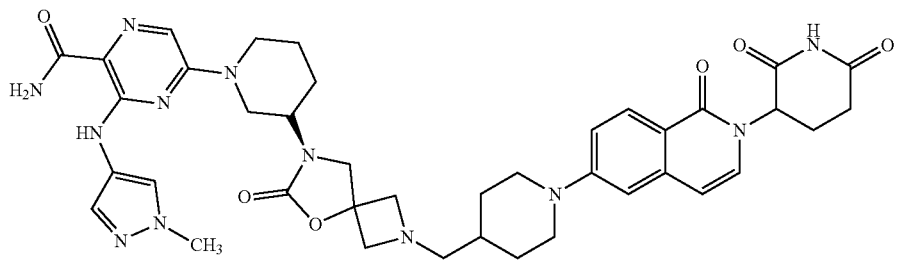 |
| 148 | 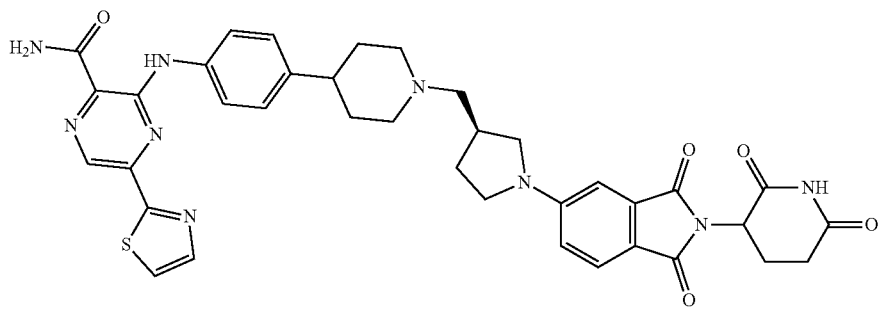 [SMILES: NC(=O)c1ncc(-c2nccs2)nc1Nc1ccc(C2CCN(C[C@@H]3CCN(c4ccc5c(c4)C(=O)N(C4CCC(=O)NC4=O)C5=O)C3)CC2)cc1] |
| 149 | 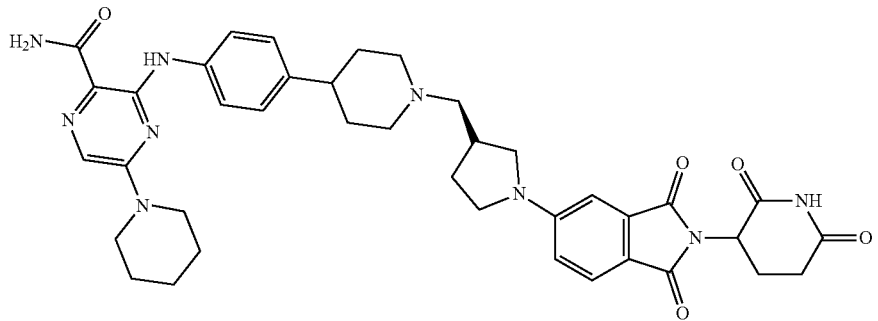 |
| 150 | 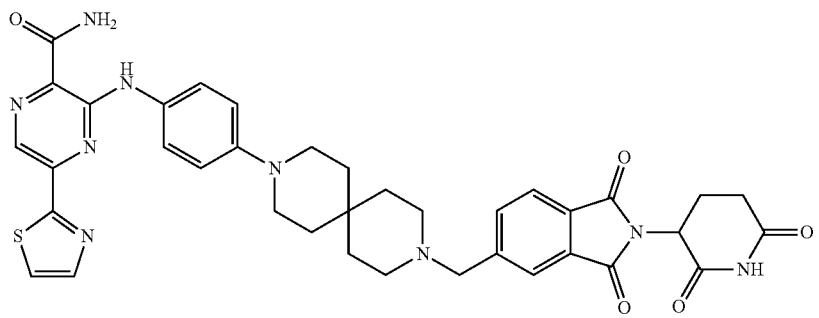 [SMILES: NC(=O)c1ncc(-c2nccs2)nc1Nc1ccc(N2CCC3(CCN(Cc4ccc5c(c4)C(=O)N(C4CCC(=O)NC4=O)C5=O)CC3)CC2)cc1] |

TABLE 1-continued

| Compound Number | Structure |
|---|---|
| 151 | 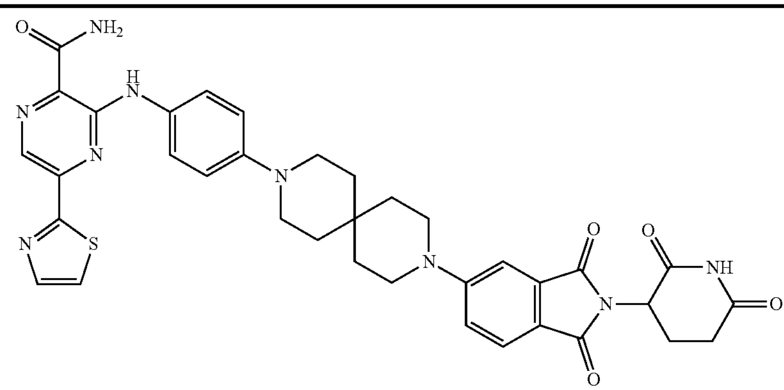 |
| 152 | 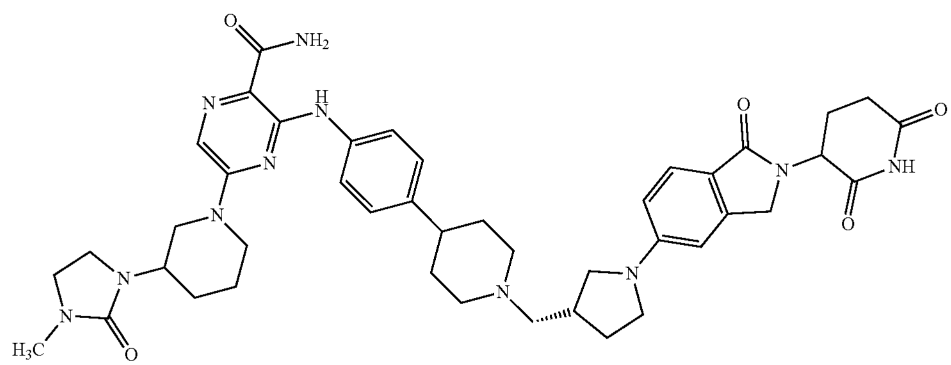 |
| 153 | 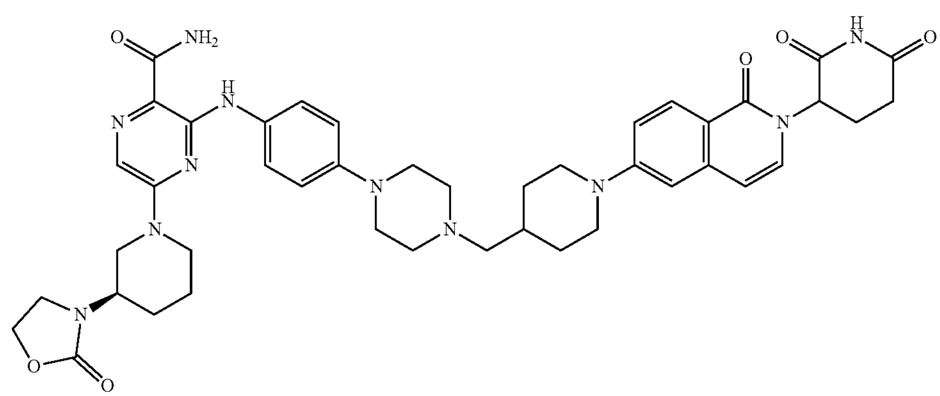 |
| 154 | 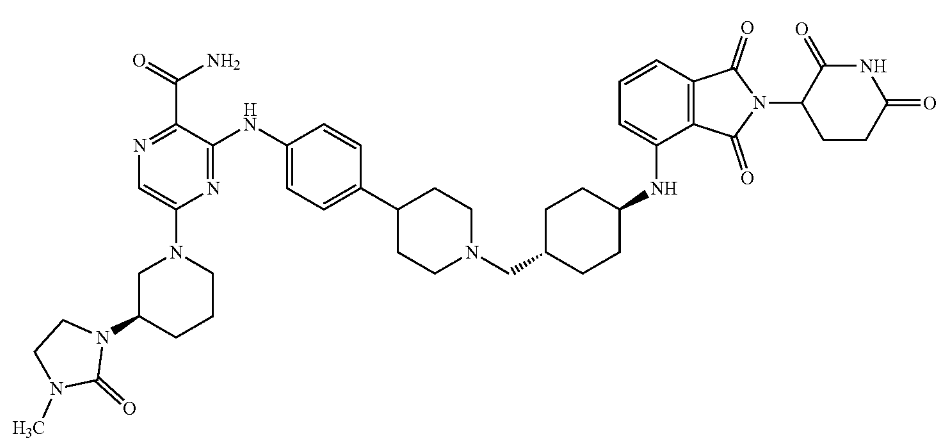 [SMILES: CN1CCN([C@@H]2CCCN(c3cnc(C(N)=O)c(Nc4ccc(C5CCN(C[C@H]6CC[C@H](Nc7cccc8c7C(=O)N(C7CCC(=O)NC7=O)C8=O)CC6)CC5)cc4)n3)C2)C1=O] |

TABLE 1-continued
| Compound Number | Structure |
|---|---|
| 155 | 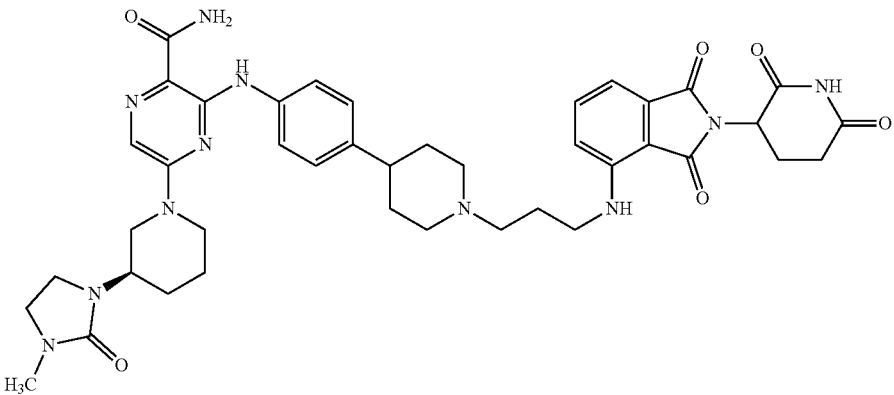 [SMILES: CN1CCN([C@@H]2CCCN(c3cnc(C(N)=O)c(Nc4ccc(C5CCN(CCCNc6cccc7c6C(=O)N(C6CCC(=O)NC6=O)C7=O)CC5)cc4)n3)C2)C1=O] |
| 156 | 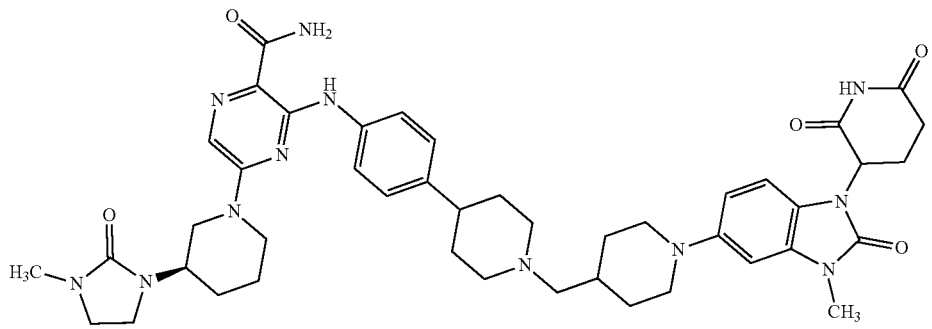 [SMILES: CN1CCN([C@@H]2CCCN(c3cnc(C(N)=O)c(Nc4ccc(C5CCN(CC6CCN(c7ccc8c(c7)n(C)c(=O)n8C7CCC(=O)NC7=O)CC6)CC5)cc4)n3)C2)C1=O] |
| 157 | 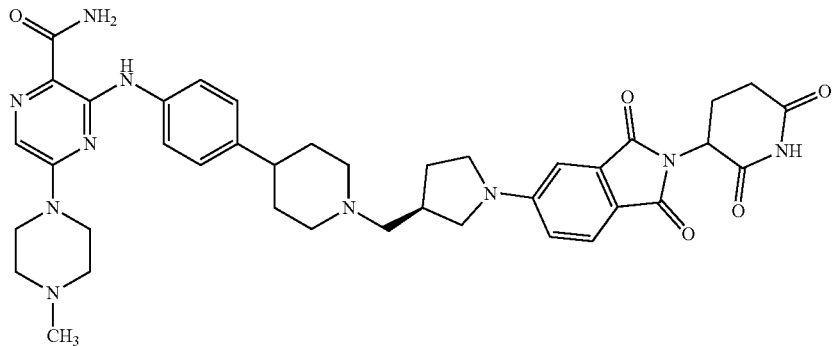 [SMILES: CN1CCN(c2cnc(C(N)=O)c(Nc3ccc(C4CCN(C[C@H]5CCN(c6ccc7c(c6)C(=O)N(C6CCC(=O)NC6=O)C7=O)C5)CC4)cc3)n2)CC1] |
| 158 | 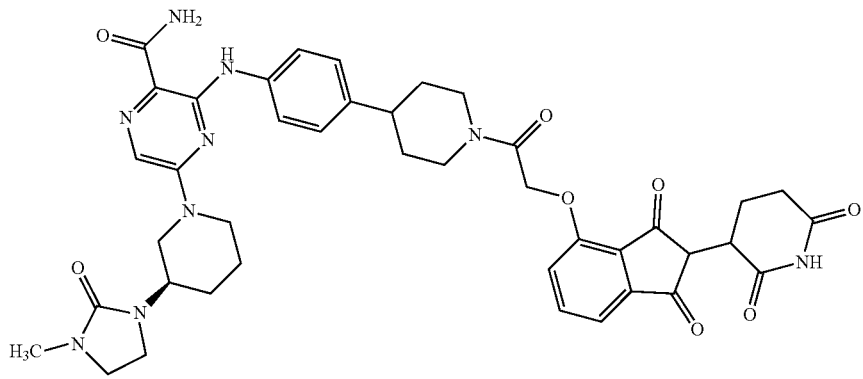 [SMILES: CN1CCN([C@@H]2CCCN(c3cnc(C(N)=O)c(Nc4ccc(C5CCN(C(=O)COc6cccc7c6C(=O)C(C6CCC(=O)NC6=O)C7=O)CC5)cc4)n3)C2)C1=O] |

TABLE 1-continued
| Compound Number | Structure |
|---|---|
| 159 | 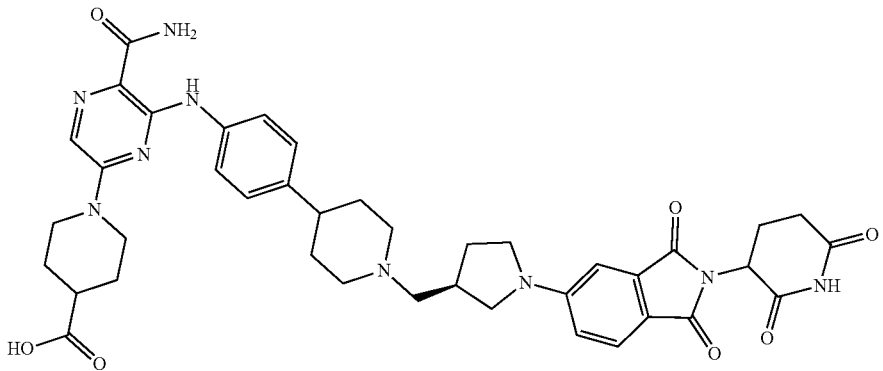 [SMILES: NC(=O)c1ncc(N2CCC(C(=O)O)CC2)nc1Nc1ccc(C2CCN(C[C@H]3CCN(c4ccc5c(c4)C(=O)N(C4CCC(=O)NC4=O)C5=O)C3)CC2)cc1] |
| 160 | 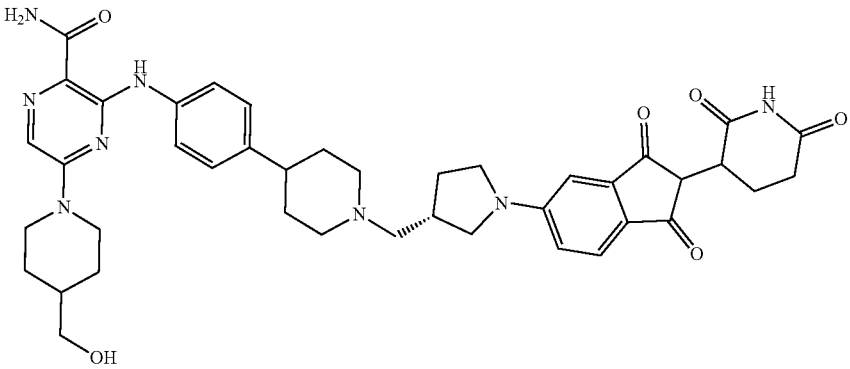 [SMILES: NC(=O)c1ncc(N2CCC(CO)CC2)nc1Nc1ccc(C2CCN(C[C@@H]3CCN(c4ccc5c(c4)C(=O)C(C4CCC(=O)NC4=O)C5=O)C3)CC2)cc1] |
| 161 | 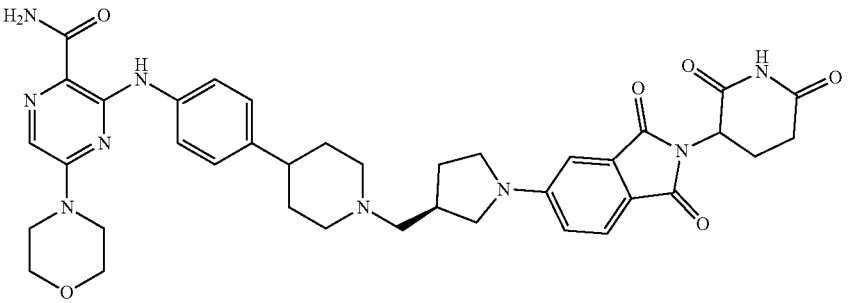 [SMILES: NC(=O)c1ncc(N2CCOCC2)nc1Nc1ccc(C2CCN(C[C@H]3CCN(c4ccc5c(c4)C(=O)N(C4CCC(=O)NC4=O)C5=O)C3)CC2)cc1] |
| 162 | 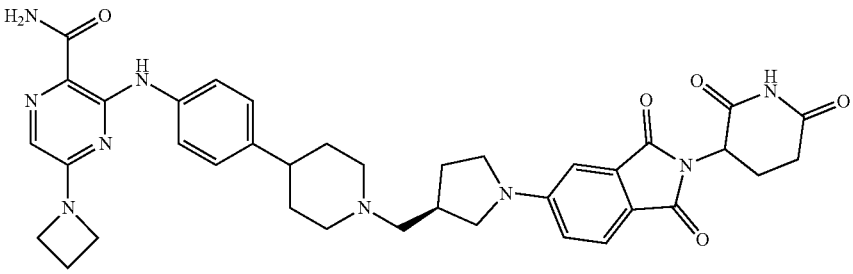 [SMILES: NC(=O)c1ncc(N2CCC2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued

| Compound Number | Structure |
|---|---|
| 163 | 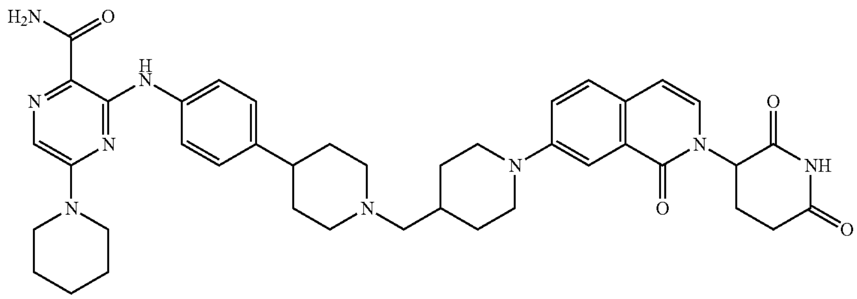 [SMILES: NC(=O)c1ncc(N2CCCCC2)nc1Nc1ccc(C2CCN(CC3CCN(c4ccc5ccn(C6CCC(=O)NC6=O)c(=O)c5c4)CC3)CC2)cc1] |
| 164 | 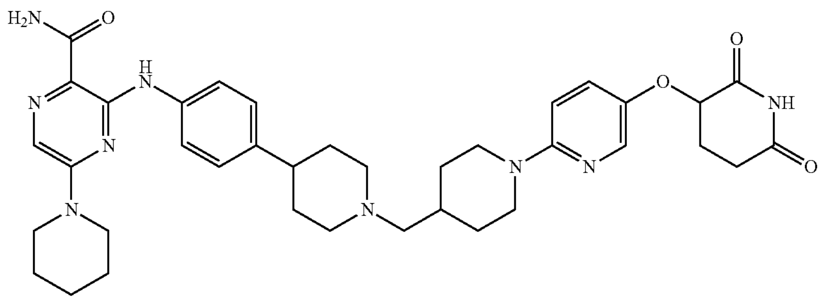 [SMILES: NC(=O)c1ncc(N2CCCCC2)nc1Nc1ccc(C2CCN(CC3CCN(c4ccc(OC5CCC(=O)NC5=O)cn4)CC3)CC2)cc1] |
| 165 | 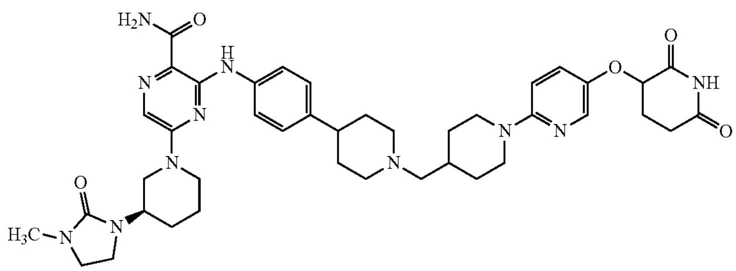 [SMILES: CN1CCN([C@@H]2CCCN(c3cnc(C(N)=O)c(Nc4ccc(C5CCN(CC6CCN(c7ccc(OC8CCC(=O)NC8=O)cn7)CC6)CC5)cc4)n3)C2)C1=O] |
| 166 | 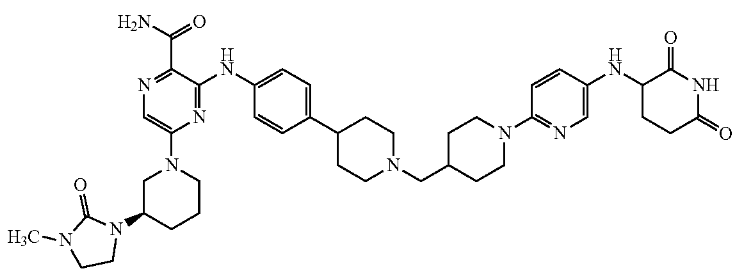 [SMILES: CN1CCN([C@@H]2CCCN(c3cnc(C(N)=O)c(Nc4ccc(C5CCN(CC6CCN(c7ccc(NC8CCC(=O)NC8=O)cn7)CC6)CC5)cc4)n3)C2)C1=O] |
| 167 | 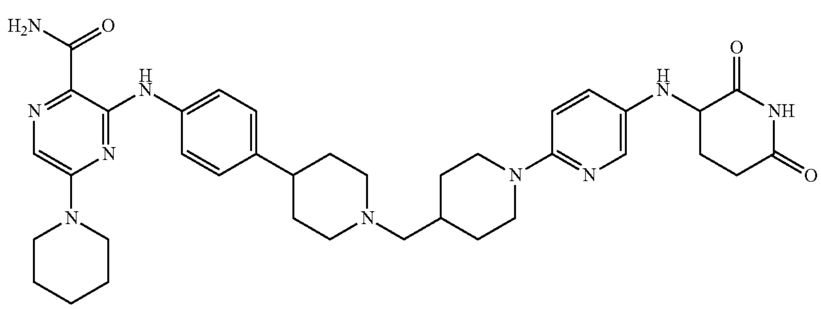 [SMILES: NC(=O)c1ncc(N2CCCCC2)nc1Nc1ccc(C2CCN(CC3CCN(c4ccc(NC5CCC(=O)NC5=O)cn4)CC3)CC2)cc1] |

TABLE 1-continued
| Compound Number | Structure |
|---|---|
| 168 | 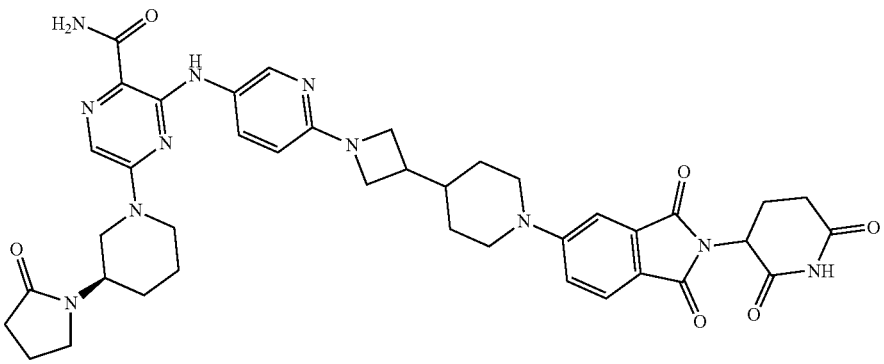 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)nc1] |
| 169 | 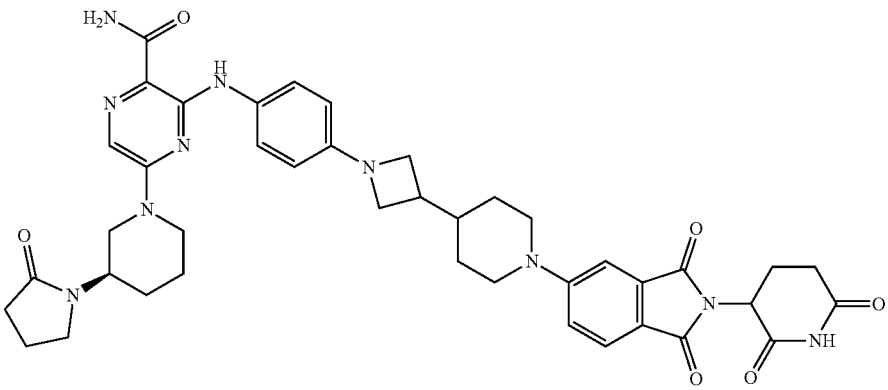 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)cc1] |
| 170 | 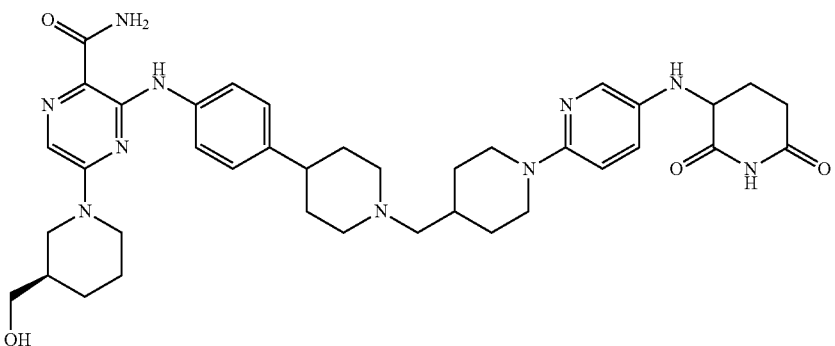 [SMILES: NC(=O)c1ncc(N2CCC[C@@H](CO)C2)nc1Nc1ccc(C2CCN(CC3CCN(c4ccc(NC5CCC(=O)NC5=O)cn4)CC3)CC2)cc1] |
| 171 | 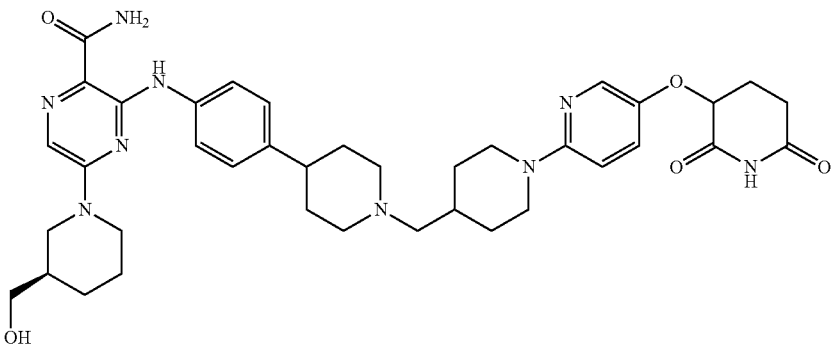 [SMILES: NC(=O)c1ncc(N2CCC[C@@H](CO)C2)nc1Nc1ccc(C2CCN(CC3CCN(c4ccc(OC5CCC(=O)NC5=O)cn4)CC3)CC2)cc1] |

TABLE 1-continued
| Compound Number | Structure |
|---|---|
| 172 | 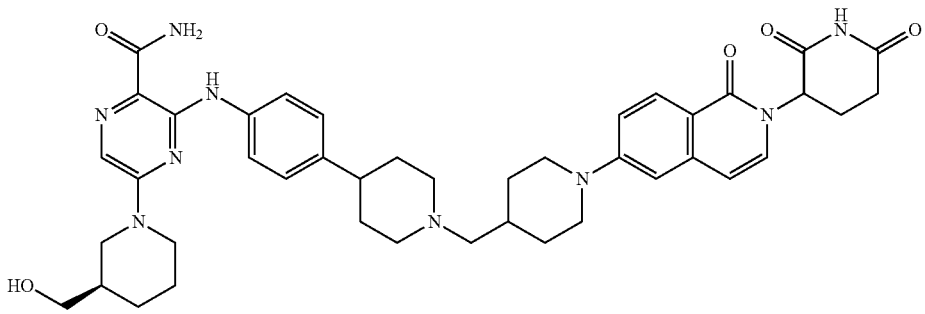 [SMILES: NC(=O)c1ncc(N2CCC[C@@H](CO)C2)nc1Nc1ccc(C2CCN(CC3CCN(c4ccc5c(=O)n(C6CCC(=O)NC6=O)ccc5c4)CC3)CC2)cc1] |
| 173 | 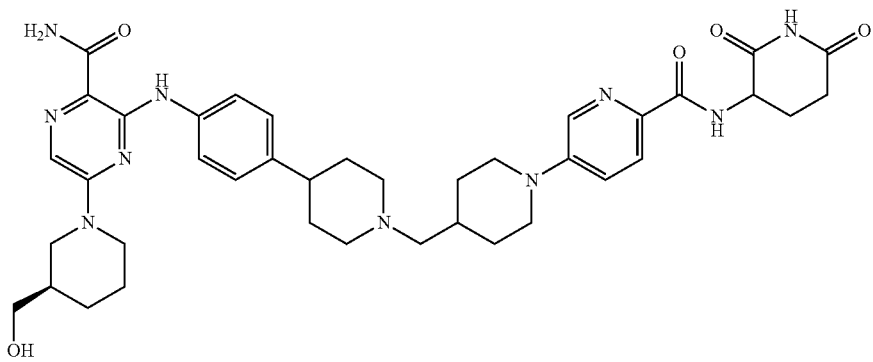 [SMILES: NC(=O)c1ncc(N2CCC[C@@H](CO)C2)nc1Nc1ccc(C2CCN(CC3CCN(c4ccc(C(=O)NC5CCC(=O)NC5=O)nc4)CC3)CC2)cc1] |
| 174 | 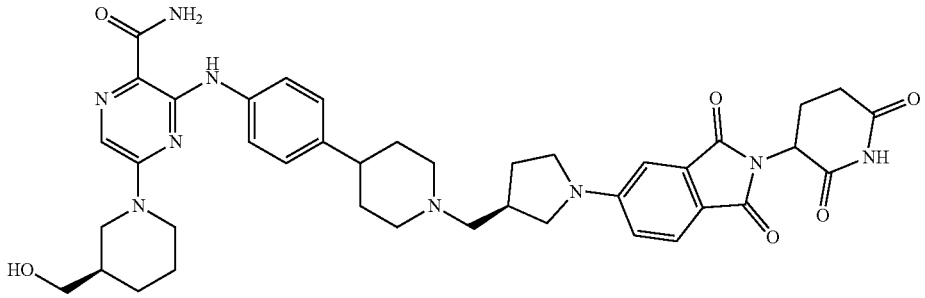 [SMILES: NC(=O)c1ncc(N2CCC[C@@H](CO)C2)nc1Nc1ccc(C2CCN(C[C@H]3CCN(c4ccc5c(c4)C(=O)N(C4CCC(=O)NC4=O)C5=O)C3)CC2)cc1] |
| 175 | 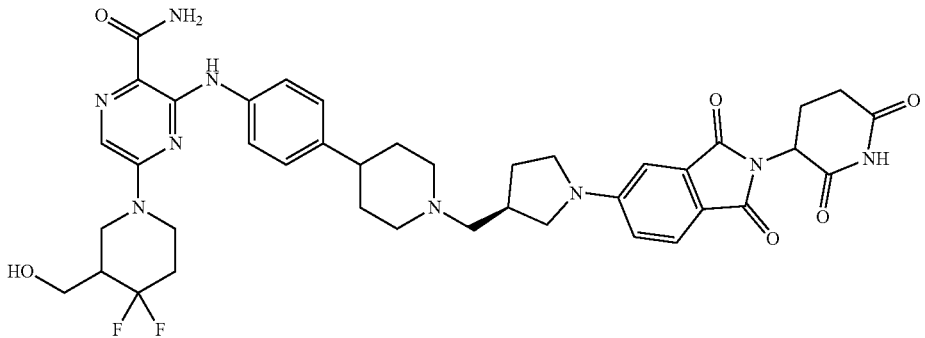 [SMILES: NC(=O)c1ncc(N2CCC(F)(F)C(CO)C2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued
| Compound Number | Structure |
|---|---|
| 176 | 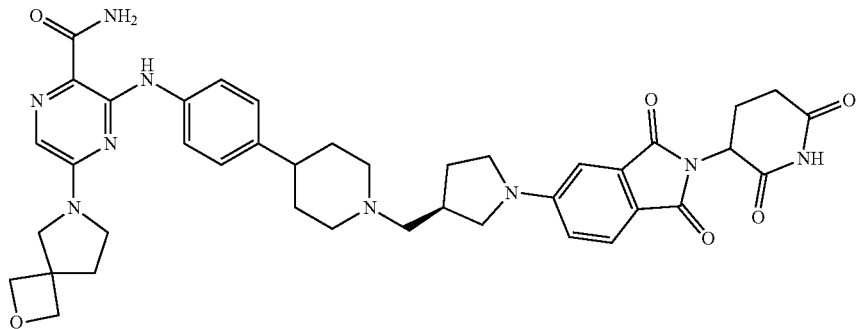 [SMILES: NC(=O)c1ncc(N2CCC3(COC3)C2)nc1Nc1ccc(C2CCN(C[C@H]3CCN(c4ccc5c(c4)C(=O)N(C4CCC(=O)NC4=O)C5=O)C3)CC2)cc1] |
| 177 | 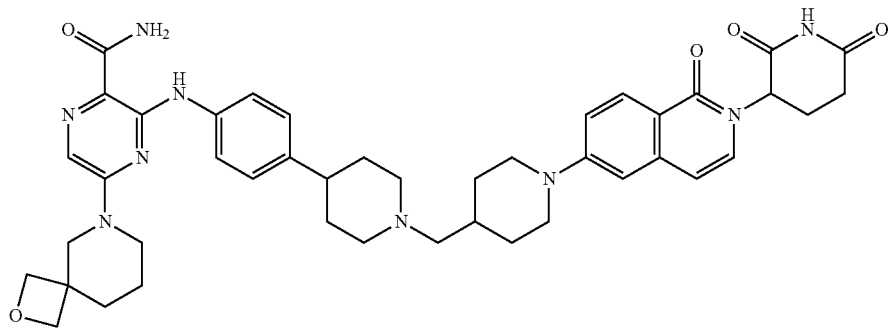 |
| 178 | 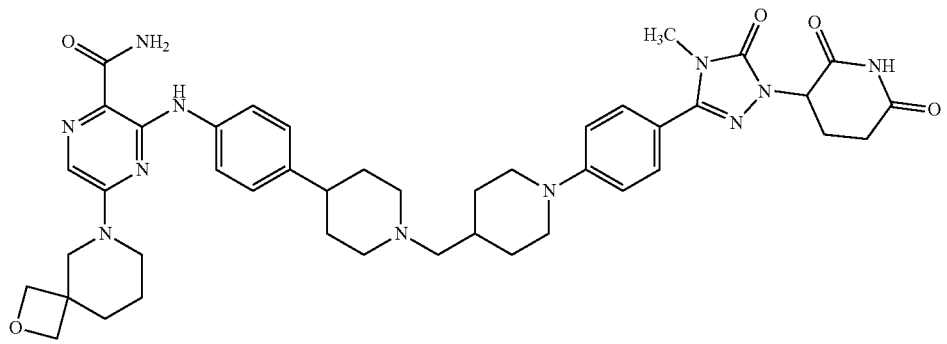 [SMILES: Cn1c(-c2ccc(N3CCC(CN4CCC(c5ccc(Nc6nc(N7CCCC8(COC8)C7)cnc6C(N)=O)cc5)CC4)CC3)cc2)nn(C2CCC(=O)NC2=O)c1=O] |
| 179 | 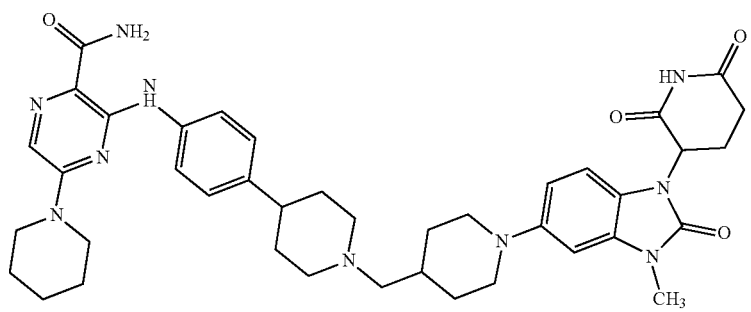 [SMILES: Cn1c(=O)n(C2CCC(=O)NC2=O)c2ccc(N3CCC(CN4CCC(c5ccc(Nc6nc(N7CCCCC7)cnc6C(N)=O)cc5)CC4)CC3)cc21] |

TABLE 1-continued
| Compound Number | Structure |
|---|---|
| 180 | 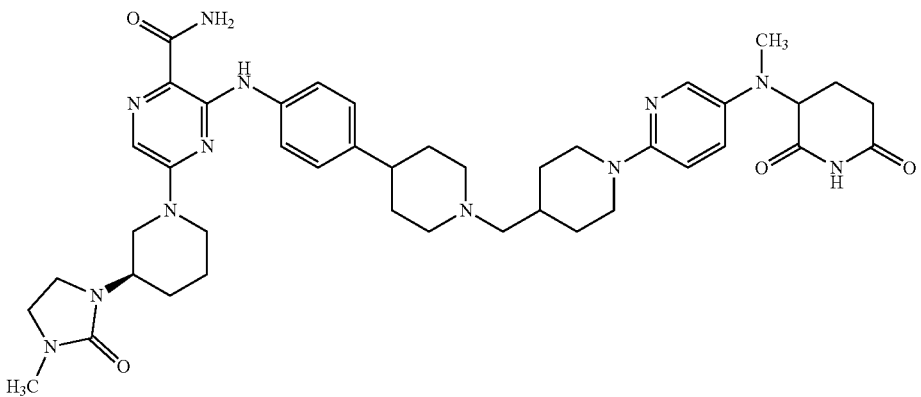 [SMILES: CN1CCN([C@@H]2CCCN(c3cnc(C(N)=O)c(Nc4ccc(C5CCN(CC6CCN(c7ccc(N(C)C8CCC(=O)NC8=O)cn7)CC6)CC5)cc4)n3)C2)C1=O] |
| 181 | 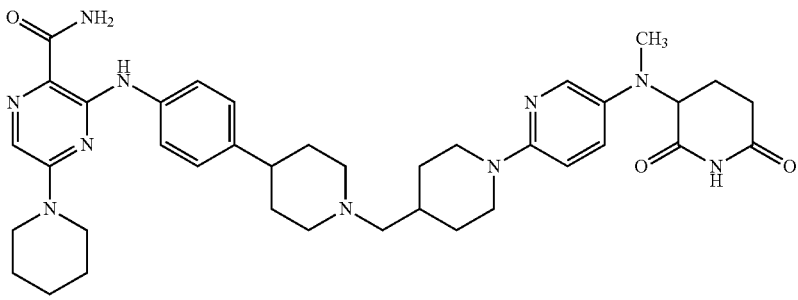 [SMILES: CN(c1ccc(N2CCC(CN3CCC(c4ccc(Nc5nc(N6CCCCC6)cnc5C(N)=O)cc4)CC3)CC2)nc1)C1CCC(=O)NC1=O] |
| 182 | 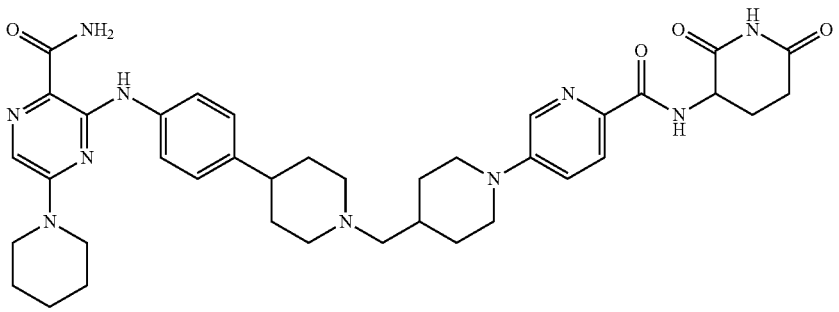 [SMILES: NC(=O)c1ncc(N2CCCCC2)nc1Nc1ccc(C2CCN(CC3CCN(c4ccc(C(=O)NC5CCC(=O)NC5=O)nc4)CC3)CC2)cc1] |
| 183 | 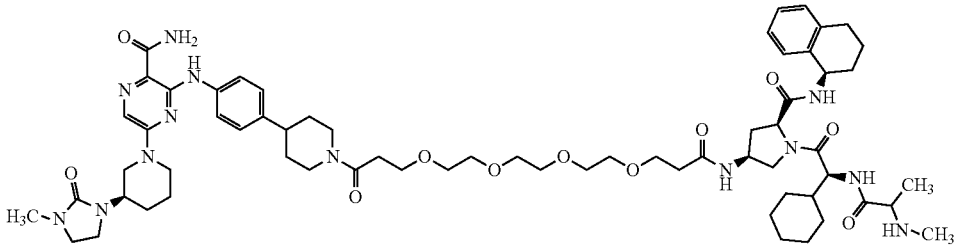 |

TABLE 1-continued
| Compound Number | Structure |
|---|---|
| 184 | 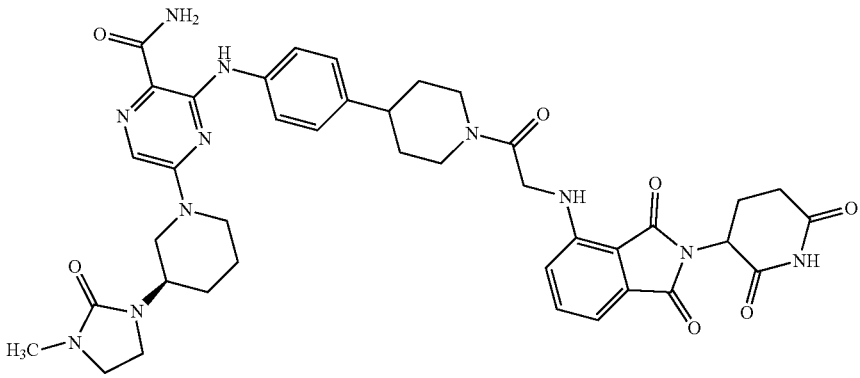 |
| 185 | 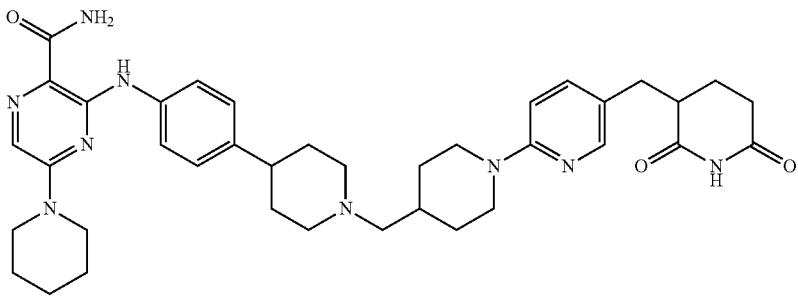 [SMILES: NC(=O)c1ncc(N2CCCCC2)nc1Nc1ccc(C2CCN(CC3CCN(c4ccc(CC5CCC(=O)NC5=O)cn4)CC3)CC2)cc1] |
| 186 | 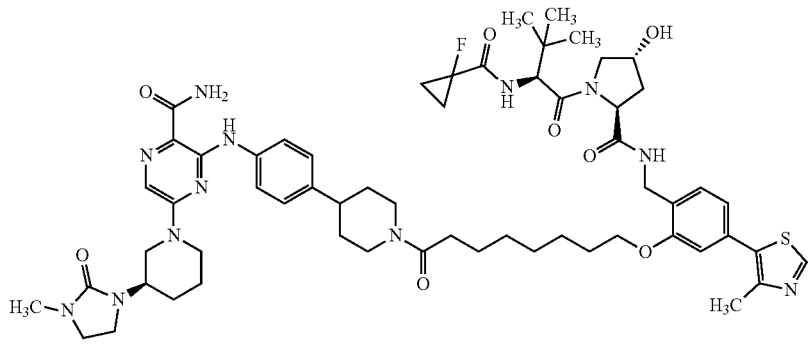 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCC(=O)N2CCC(c3ccc(Nc4nc(N5CCC[C@@H](N6CCN(C)C6=O)C5)cnc4C(N)=O)cc3)CC2)c1] |
| 187 | 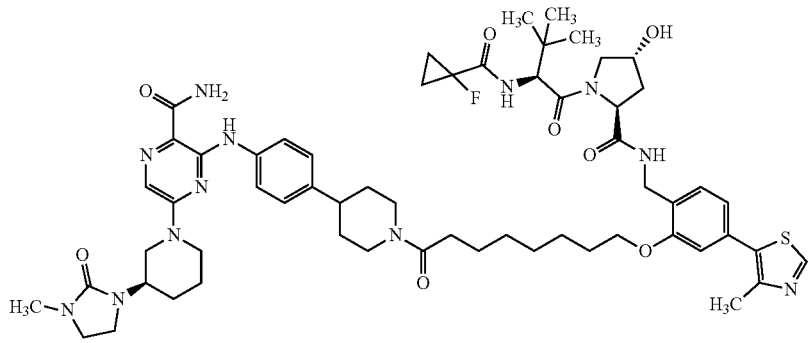 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCCCC(=O)N2CCC(c3ccc(Nc4nc(N5CCC[C@@H](N6CCN(C)C6=O)C5)cnc4C(N)=O)cc3)CC2)c1] |

| Compound Number | Structure |
|---|---|
| 188 | 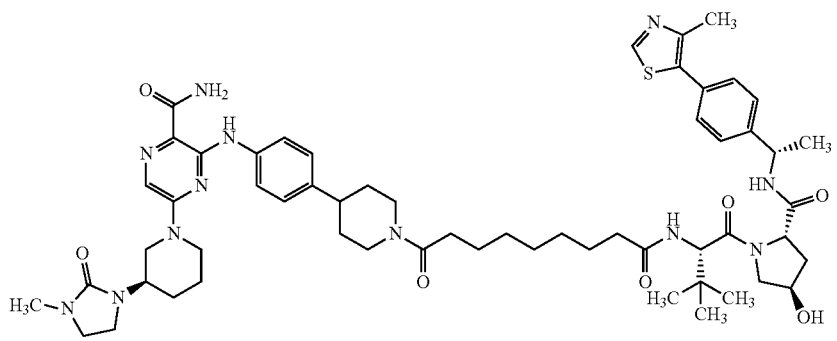 [SMILES: Cc1ncsc1-c1ccc([C@H](C)NC(=O)[C@@H]2C[C@@H](O)CN2C(=O)[C@@H](NC(=O)CCCCCCCC(=O)N2CCC(c3ccc(Nc4nc(N5CCC[C@@H](N6CCN(C)C6=O)C5)cnc4C(N)=O)cc3)CC2)C(C)(C)C)cc1] |
| 189 | 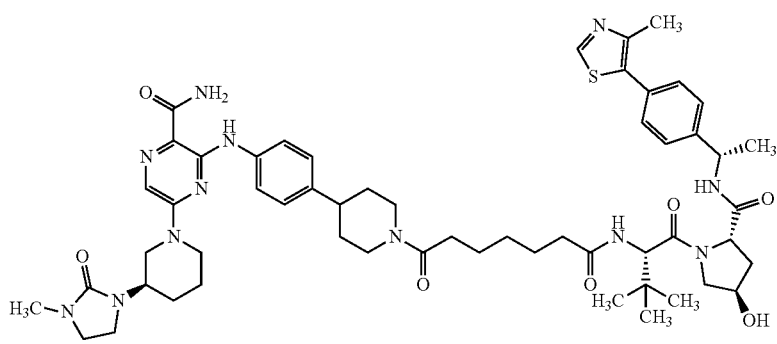 [SMILES: Cc1ncsc1-c1ccc([C@H](C)NC(=O)[C@@H]2C[C@@H](O)CN2C(=O)[C@@H](NC(=O)CCCCCC(=O)N2CCC(c3ccc(Nc4nc(N5CCC[C@@H](N6CCN(C)C6=O)C5)cnc4C(N)=O)cc3)CC2)C(C)(C)C)cc1] |
| 190 | 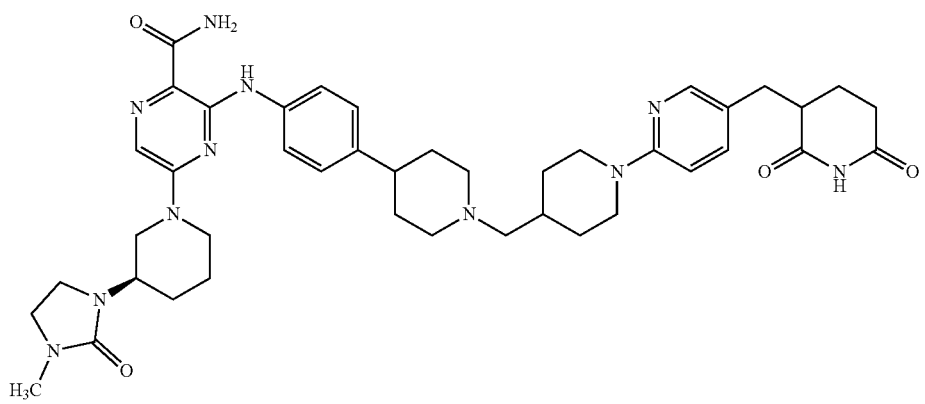 [SMILES: CN1CCN([C@@H]2CCCN(c3cnc(C(N)=O)c(Nc4ccc(C5CCN(CC6CCN(c7ccc(CC8CCC(=O)NC8=O)cn7)CC6)CC5)cc4)n3)C2)C1=O] |
| 191 | 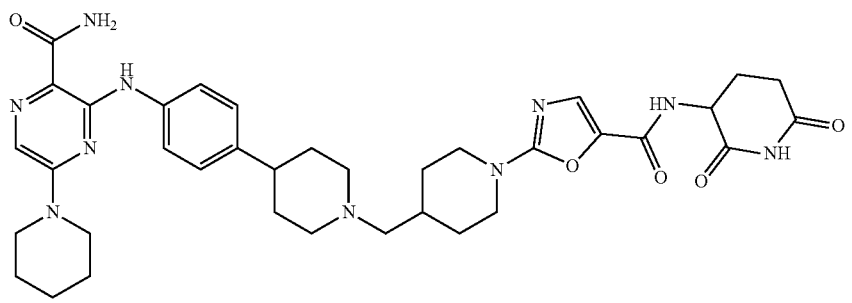 [SMILES: NC(=O)c1ncc(N2CCCCC2)nc1Nc1ccc(C2CCN(CC3CCN(c4ncc(C(=O)NC5CCC(=O)NC5=O)o4)CC3)CC2)cc1] |

TABLE 1-continued

| Compound Number | Structure |
|---|---|
| 192 | 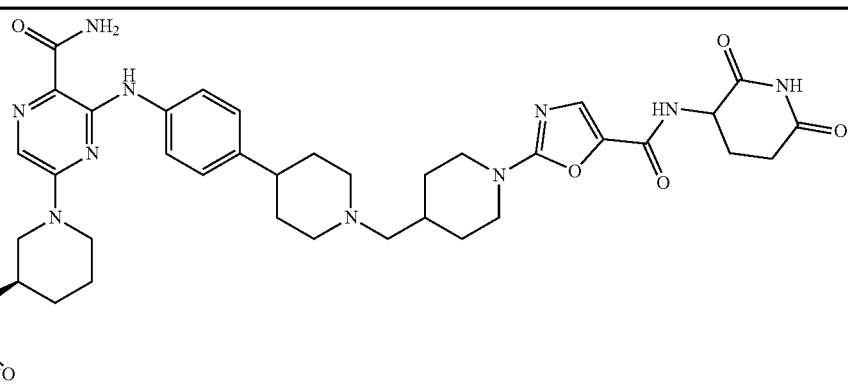 |
| 193 | 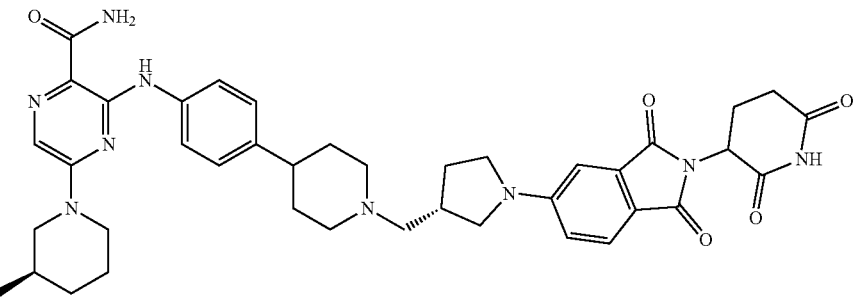 |

101. A pharmaceutical composition comprising a compound or pharmaceutically acceptable salt of a compound of claim 1 and a pharmaceutically acceptable carrier, vehicle, or adjuvant.

102. A method of treating a disease or disorder mediated by degrading Bruton's tyrosine kinase, comprising administering to a patient or biological sample a compound or pharmaceutically acceptable salt of a compound of claim 1.

103. The method of claim 102, wherein the disease or disorder is cancer.

104. The method of claim 103, wherein the cancer is a hematological cancer selected from myeloid leukemia (acute and chronic), acute lymphoblastic leukemia, chronic lymphocytic leukemia, myeloproliferative diseases, multiple myeloma, myelodysplastic syndrome, Hodgkin's disease, non-Hodgkin's lymphoma (malignant lymphoma) hairy cell, mantle cell lymphoma, Waldenström's macroglobulinemia, marginal zone lymphoma, and follicular lymphoma.

105. The method of claim 102, wherein the disease or disorder is an autoimmune disease.

106. The method of claim 105, wherein the autoimmune disease is selected from uticaria, graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Baló disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, evans syndrome, fibromyalgia, fibrosing alveolitis, giant cell arteritis (temporal arteritis), giant cell myocarditis, glomerulonephritis, goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenic purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

* * * * *